US009073890B2

(12) United States Patent
Suzuki et al.

(10) Patent No.: US 9,073,890 B2
(45) Date of Patent: Jul. 7, 2015

(54) THERAPEUTIC COMPOUNDS AND RELATED METHODS OF USE

(75) Inventors: Masaki Suzuki, Osaka (JP); Kazumi Kondo, Osaka (JP); Muneaki Kurimura, Osaka (JP); Krishna Reddy Valluru, Hyderabad (IN); Akira Takahashi, Osaka (JP); Takeshi Kuroda, Osaka (JP); Haruka Takahashi, Osaka (JP); Tae Fukushima, Osaka (JP); Shin Miyamura, Osaka (JP); Indranath Ghosh, Belmont, MA (US); Abhishek Dogra, Somerville, MA (US); Geraldine Harriman, Charlestown, RI (US); Amy Elder, Arlington, MA (US); Satoshi Shimizu, Osaka (JP); Kevin J. Hodgetts, Natick, MA (US); Jason S. Newcom, Norfolk, MA (US)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 24 days.

(21) Appl. No.: 13/520,018

(22) PCT Filed: Dec. 30, 2010

(86) PCT No.: PCT/US2010/062555

§ 371 (c)(1),
(2), (4) Date: Sep. 25, 2012

(87) PCT Pub. No.: WO2011/082337

PCT Pub. Date: Jul. 7, 2011

(65) Prior Publication Data

US 2013/0053341 A1 Feb. 28, 2013

Related U.S. Application Data

(60) Provisional application No. 61/291,544, filed on Dec. 31, 2009, provisional application No. 61/291,550, filed on Dec. 31, 2009, provisional application No. 61/291,554, filed on Dec. 31, 2009.

(51) Int. Cl.

| | |
|---|---|
| *A01N 43/90* | (2006.01) |
| *A61K 31/519* | (2006.01) |
| *A01N 43/54* | (2006.01) |
| *A61K 31/517* | (2006.01) |
| *C07D 491/00* | (2006.01) |
| *C07D 495/00* | (2006.01) |
| *C07D 401/00* | (2006.01) |
| *C07D 403/00* | (2006.01) |
| *C07D 413/00* | (2006.01) |
| *C07D 417/00* | (2006.01) |
| *C07D 419/00* | (2006.01) |
| *C07D 401/04* | (2006.01) |
| *C07D 401/14* | (2006.01) |
| *C07D 403/04* | (2006.01) |
| *C07D 405/14* | (2006.01) |
| *C07D 409/14* | (2006.01) |
| *C07D 413/14* | (2006.01) |
| *C07D 417/14* | (2006.01) |
| *C07D 487/04* | (2006.01) |
| *C07D 495/04* | (2006.01) |

(52) U.S. Cl.
CPC ............ *C07D 401/04* (2013.01); *C07D 401/14* (2013.01); *C07D 403/04* (2013.01); *C07D 405/14* (2013.01); *C07D 409/14* (2013.01); *C07D 413/14* (2013.01); *C07D 417/14* (2013.01); *C07D 487/04* (2013.01); *C07D 495/04* (2013.01)

(58) Field of Classification Search
None
See application file for complete search history.

(56) References Cited

U.S. PATENT DOCUMENTS

| | | | |
|---|---|---|---|
| 5,439,895 | A | 8/1995 | Lee et al. |
| 2002/0025968 | A1 | 2/2002 | Pamukcu et al. |
| 2009/0143399 | A1 | 6/2009 | Hurley et al. |

FOREIGN PATENT DOCUMENTS

| | | | |
|---|---|---|---|
| JP | H06192235 | A | 7/1994 |
| WO | 02/062767 | A1 | 8/2002 |
| WO | 03062209 | A2 | 7/2003 |
| WO | 03/000188 | A3 | 12/2003 |
| WO | 2004054582 | A1 | 7/2004 |
| WO | 2004065392 | A1 | 8/2004 |
| WO | 2004078733 | A1 | 9/2004 |
| WO | 2005/042501 | A1 | 5/2005 |
| WO | 2005/055813 | A2 | 6/2005 |
| WO | 2005/055813 | A3 | 9/2005 |
| WO | 2005099711 | A1 | 10/2005 |
| WO | 2006/058201 | A3 | 7/2007 |
| WO | 2007/104560 | A1 | 9/2007 |
| WO | 2008092862 | A1 | 8/2008 |
| WO | 2008116910 | A1 | 10/2008 |

(Continued)

OTHER PUBLICATIONS

Lafferty, et. al., Journal of Organic Chemistry (1967), 32(5), 1591-6.*
Alvestad, et al., "Tyrosine Dephosphorylation and Ethanol Inhibition of N-Methyl-d-aspartate Receptor Function", J Biol Chem, 278 (13): 11020 (2003).
Baum, et al, "A STEP forward in neural function and degeneration", Commun Integr Biol, 3 (5): 419 (2010).

(Continued)

*Primary Examiner* — Jeffrey H Murray
(74) *Attorney, Agent, or Firm* — Lando & Anastasi, LLP

(57) ABSTRACT

Compounds, pharmaceutical compositions containing the compounds, and methods of using the compounds to treat a disorder, e.g., schizophrenia and cognitive deficit, in a subject are described herein. The compounds disclosed herein include quinoline and quinazoline-containing compounds that modulate striatal-enriched tyrosine phosphatase (STEP) activity.

7 Claims, No Drawings

(56) References Cited

FOREIGN PATENT DOCUMENTS

| | | | |
|---|---|---|---|
| WO | 2008/009078 | A3 | 12/2008 |
| WO | 2009/000085 | A1 | 12/2008 |
| WO | 2007/133773 | A3 | 1/2009 |
| WO | 2009097446 | A1 | 8/2009 |

OTHER PUBLICATIONS

Berge, et al. "Pharmaceutical Salts", J. Pharm. Sci. 66: 1-19 (1977).

Braithwaite, et al., "Synaptic Plasticity: One STEP at a time", Trends Neurosci, 29 (8): 452 (2006).

Choi, et al, "Status epilepticus-induced somatostatinergic hilar interneuron degeneration is regulated by striatal enriched protein tyrosine phosphatase", J Neurosci, 27 (11): 2999 (2007).

Czarnik, "Encoding methods for combinatorial chemistry", Curr. Opin. Chem. Bio. 1, 60 (1997).

Engel, et al., "The extracellular signal-regulated kinase pathway contributes to the control of behavioral excitement", Mol Psychiatry, 14 (4): 448 (2009).

Falls, et al., "Extinction of fear-potentiated startle: blockade by infusion of an NMDA antagonist into the amygdala", J Neurosci, 12 (3): 854 (1992).

Fox, et al., "Tyrosine dephosphorylation is required for Bak activation in apoptosis." EMBO J, 29 (22): 3853 (2010).

Gladding, et al, "Investigating the molecular mechanisms underlying increased extrasynaptic NMDA receptor localisation in a mouse model of Huntington Disease" Abstracts of the Society for Neuroscience Meetings (2010).

Goebel-Goody, et al., "Loss of striatal-enriched protein tyrosine phosphatase (STEP) reverses deficits in a fragile x syndrome mouse model", Abstracts of the Society for Neuroscience Meetings (2010).

Hansen, et al., Tweaking Agonist Efficacy at N-Methyl-D-aspartete Receptors by Site-Directed Mutagenesis, Mol Pharmacol 68, pp. 1510-1523, p. 1512-1522 (2005).

Hynd, et al., "Differential expression of N-methyl-D-aspartate receptor NR2 isoforms in Alzheimer's disease", J Neurochem, 90 (4): 913 (2004).

International Search Report and Written Opinion for PCT/US2010/62555 mailed Mar. 11, 2011.

Lahti, et al., "Subanesthetic doses of ketamine stimulate psychosis in schizophrenia", Neuropsychopharmacology, 13 (1): 9 (1995).

Machado-Vieira al.,"The role of lithium in the treatment of bipolar disorder: convergent evidence for neurotrophic effects as a unifying hypothesis", Bipolar Disord, 11 Suppl 2:92 (2009).

Machado-Vieira, et al., "Ketamine and the next generation of antidepressants with a rapid onset of action", Pharmacol Ther, 123 (2): 143 (2009).

Milnerwood, et al, "Early increase in extrasynaptic NMDA receptor signaling and expression contributes to phenotype onset in Huntington's disease mice" Neuron, 65 (2): 178 (2010).

Miserendino, et al., "Blocking of acquisition but not expression of conditioned fear-potentiated startle by NMDA antagonists in the amygdala.", Nature, 345 (6277): 716 (1990).

Snyder, et al., "Regulation of NMDA receptor trafficking by amyloid-beta.", Nat Neurosci, 8 (8): 1051 (2005).

Wan, et al., "The scope and mechanism of phosphonium-mediated S(N)Ar reactions in heterocyclic amides and ureas", J. Org. Chem., 72, 10194-10210, (2007).

Xu J, et al., "Inhibition of pyk2 signaling by striatal-enriched tyrosine phosphatase (STEP)", Abstracts of the Society for Neuroscience Meetings (2010).

Xu, et at, "Extrasynaptic NMDA receptors couple preferentially to excitotoxicity via calpain-mediated cleavage of STEP.", J Neurosci, 29 (29): 9330 (2009).

Zhang, et al., "Genetic reduction of striatal-enriched tyrosine phosphatase (STEP) reverses cognitive and cellular deficits in an Alzheimer's disease mouse model", Proc Natl Acad Sci USA, 107 (44): 19014 (2010).

Zhang, et al., "The tyrosine phosphatase STEP mediates AMPA receptor endocytosis after metabotropic glutamate receptor stimulation.", J Neurosci, 28 (42): 10561 (2008).

Current Chemical Genomics, vol. 3, 2009, pp. 42-49.

Bioorganic & Medicinal Chemistry Letters, vol. 19, No. 8, Apr. 15, 2009, pp. 2277-2281.

Supplementary European Search Report dated May 8, 2013 for EP Patent Application No. 10841742.9.

First Examination Report dated Sep. 23, 2014 for New Zealand Patent Application No. 630775.

* cited by examiner

THERAPEUTIC COMPOUNDS AND RELATED METHODS OF USE

RELATED APPLICATIONS

This application claims priority to U.S. Provisional Application Ser. Nos. 61/291,544, entitled "Therapeutic Compounds and Related Methods of Use" filed on Dec. 31, 2009; 61/291,550, entitled "Therapeutic Compounds and Related Methods of Use" filed on Dec. 31, 2009; and 61/291,554, entitled "Therapeutic Compounds and Related Methods of Use" filed on Dec. 31, 2009, all of which are herein incorporated by reference in their entireties.

BACKGROUND OF INVENTION

Tyrosine phosphorylation of synaptic receptors and signaling molecules regulates synaptic activity. A number of protein tyrosine phosphatases specifically expressed within the brain have been identified, including STEP (for STriatal-Enriched tyrosine Phosphatase, also known as PTPN5). Recent evidence suggests that STEP plays an important role in synaptic plasticity, for review see (Braithwaite S P. et al., (2006), Trends Neurosci, 29 (8): 452; Baum M L, et al., (2010), Commun Integr Biol, 3 (5): 419) STEP is specifically expressed within neurons of the central nervous system. As its name indicates, the highest expression level is within the striatum. However, more recent work has found that it is expressed at lower levels in multiple brain regions including the neocortex, amygdala, hippocampus, and embryonic spinal cord.

Four groups of proteins that STEP regulates have been identified: the mitogen-activated protein kinases (MAPKs), the tyrosine kinase Fyn, the N-methyl-D-aspartate (NMDA) receptor complex (specifically the NR2B subunit) and AMPA receptors (specifically, GluR2, (Zhang Y, et al., (2008), J Neurosci, 28 (42): 10561)). Three additional new substrates for STEP have also been recently discovered; proline-rich tyrosine kinase 2 (Pyk2; Xu J, et al., (2010), Abstracts of the Society for Neuroscience Meetings), the fragile X mental retardation protein (FMRP) (Goebel-Goody S M, et al., (2010), Abstracts of the Society for Neuroscience Meetings) and the cell-death mediator Bak (Fox J L, et al., (2010), EMBO J, 29 (22): 3853). Tyrosine phosphorylation of one member of the MAPK family, the extracellular signal regulated kinase (ERK), is necessary for the expression and maintenance of synaptic plasticity in many brain regions, and disruption of the ERK pathway leads to a disruption of learning and memory. One of the functions of these src and Pyk2 kinases is to phosphorylate NMDA receptors, thereby modulating their channel conductance properties and facilitating their movement toward the surface of neuronal plasma membranes. Pyk2 and Fyn tyrosine kinases are activated by phosphorylation on tyrosine residues. NR2B phosphorylation on Tyrosine 1452 inhibits the receptor endocytosis. STEP acts as direct or indirect brake of NMDAR mediated signaling by either respectively dephosphorylating NR2B or its associated kinases, Pyk2 and Fyn. Activation of AMPA, NMDA receptors and MAPKs are required for the induction of several forms of long-term potentiation (LTP) and long-term depression (LTD). Hippocampal LTP is increased in transgenic mice model of Alzheimer lacking STEP (Zhang Y, et al., (2010), Proc Natl Acad Sci USA, 107 (44): 19014). NR2B and AMPA receptor surface expression is increased in STEP KO mice. AMPA receptor endocytosis in group I metabotropic glutamate receptor I (mGluR) mediated LTD is mediated by a tyrosine phosphatase. AMPA receptor endocytosis induced by activation of group I mGLuR is blocked in STEP KO mice suggesting that STEP might also control mGluR mediated LTD.

Compounds that inhibit STEP activity should mimic the effects observed with the STEP KO and may be useful for treating conditions mediated by abnormal NMDA-receptor (NMDA-Rs) and/or MAP kinase pathway signaling. Both may mediate cognition, learning and memory, neurogenesis, and may also affect neuronal plasticity, pain perception, mood and anxiety, and neuroendocrine regulation.

Modulation of NMDA-Rs:

STEP decreases the tyrosine phosphorylation level of NMDA-Rs. Less phosphorylated NMDA-Rs have lower conductance states and thus will allow less current and fewer ions to pass. The NMDA-Rs will therefore be functionally less active (Alvestad K M, et al., (2003), J Biol Chem, 278 (13): 11020), which can lead to schizophrenic symptoms. Hypofunction of NMDA-Rs has been liked to schizophrenia. For example, phencyclidine, ketamine, and other noncompetitive antagonists at NMDA-type glutamate receptors can exacerbate symptoms in patients (Lahti A C, et al., (1995), Neuropsychopharmacology, 13 (1): 9) and may produce a range of psychotic symptoms in volunteers that are similar to those of schizophrenic patients. NMDA-R hypofunction is also linked to psychosis and drug addiction (Javitt D C and Zukin S R, (1991), Am J Psychiatry, 148 (10): 1301). Chronic treatment of atypical antipsychotic clozapine and risperidone in mice result in significant increase of phosphorylation of ERK, NR2B and Pyk2 on tyrosine residues recognized by STEP (Carry N C, et al., (2010), Abstracts of the Society for Neuroscience Meetings). Treatment of these anti-psychotics also enhances cAMP and STEP phosphorylation. Since PKA mediated phosphorylation of STEP is know to inactivate STEP, these results suggest that STEP inhibition mediates the beneficial effect of antipsychotic drugs. Recent studies have linked abnormal NMDA-R activity and expression of STEP to the cognitive decline observed in Alzheimer's disease or transgenic mice expressing mutant APP (Tg2576 mice) (Snyder E M, et al., (2005), Nat Neurosci, 8 (8): 1051; Hynd M R, et al., (2004), J Neurochem, 90 (4): 913; Kurup P, et al., (2010), Channels (Austin), 4 (5)). More specifically, STEP KO mice are less susceptible to PCP-induced hyperlocomotion and PCP-induced cognitive deficits in the object recognition tasks (Carty N C, et al., (2010), Abstracts of the Society for Neuroscience Meetings). Compared to the Tg2576 mice expressing STEP, Tg2576 lacking STEP gene showed rescue in their deficits in hyppocampal LTP and in different behavioral cognitive tasks. Altogether, these results suggest that STEP inhibitors might represent a novel class of drugs that can treat both positive symptoms and cognitive deficit associated with schizophrenia.

Medications that modulate glutamatergic neurotransmission via NMDA-Rs may be also effective in treatment for mood and anxiety disorders. Administration of NMDA-R antagonists has anxiolytic effects in rodent models of anxiety (Falls W A, et al., (1992), J Neurosci, 12 (3): 854; Miserendino M J, et al., (1990), Nature, 345 (6277): 716). NMDA-Rs antagonist like ketamine has been shown to be effective in drug-resistant unipolar depression (Machado-Vieira R, et al., (2009), Pharmacol Ther, 123 (2): 143).

Abnormal balance between the activity of NMDA receptors at synaptic (prosurvival linked to ERK activation) and extrasynaptic (proapoptotic linked to p38 activation) sites has been proposed in cellular and mouse model of Huntington Disease (HD) (Milnerwood A J, et al., Neuron, 65 (2): 178). YAC128 mouse model (containing high number of glutanmine repeat on huntingtin) of HD showed an increased activity of extrasynaptic NMDA receptors (NR2B subunit) and require p38 and caspase-6 cleavage activation. In YAC128 mice, NR2B synaptic expression is associated with high STEP expression and activity and a reduction in NR2B expression and phosphorylation (Gladding C M, et al., (2010), Abstracts of the Society for Neuroscience Meetings). Extrasynaptic NMDA receptors couple preferentially to excitotoxicity via calpain-mediated cleavage of STEP and activation of p38 (Xu J, et al., (2009), J Neurosci, 29 (29): 9330). Inhibiting STEP activity might therefore shift the balance toward the NMDA receptor/ERK synaptic prosurvival signaling pathway.

Modulation of ERK Pathway:

STEP inhibition may translate into activation of ERK1/2 kinases, for example, in the central nervous system (CNS). Activation of the ERK pathway in the CNS can mediate neurotrophic pathways involved in cellular resilience. ERK signaling directly affects Bak phosphorylation through inhibition of STEP to promote cell survival (Fox J L, et al., (2010), EMBO J, 29 (22): 3853). BDNF and other neurotrophins can block apoptosis and increase cell survival of different type of CNS neurons in vitro and in vivo via stimulation of the ERK pathway. Mood stabilizers effective in bipolar disorder like valproate and lithium may be potent activators of ERK activity. This effect on ERK activation is believed to be responsible for the neurotrophic effects of mood stabilizers observed in vitro or in brains of treated patients with bipolar disorder, for review see (Engel S R, et al., (2009), Mol Psychiatry, 14 (4): 448; Chen G and Manji H K, (2006), Curr Opin Psychiatry, 19 (3): 313; Machado-Vieira R, et al., (2009), Bipolar Disord, 11 Suppl 2 92). In vivo disruption of STEP activity was shown to activate MAPK pathway, leading to significant rescue from neuronal cell death after pilocarpine-induced status epilepticus (Choi Y S, et al., (2007), J Neurosci, 27 (11): 2999). Increasing cellular resilience could therefore limit or reduce neuronal loss in several neurologic disorders. Recent work has suggested a positive role for STEP inhibition in fragile X syndrome (FXS). This disorder results from the mutation of fmr1 gene coding for the fragile X mental retardation protein (FMRP). STEP binds to FMRP and its expression is dysregulated in FXS. FMR KO mice model displayed audiogenic seizures. FMR KO mice lacking STEP gene show a significant reduction of these seizures (Goebel-Goody S M, et al., (2010), Abstracts of the Society for Neuroscience Meetings), suggesting that STEP modulators might be therapeutic approach for FXS.

Various substituted heterocyclic compounds are disclosed in the art. For example, WO 02/062767 discloses quinazoline derivatives; WO 03/000188 discloses quinazolines and uses thereof; WO 2005/042501 discloses norepinephrine reuptake inhibitors for the treatment of central nervous system disorders; WO2006/058201 discloses heterocyclic and bicyclic compounds, compositions and methods; WO 2007/104560 discloses substituted 4-amino-quinazoline derivatives as regulators of metabotropic glutamate receptors and their use for producing drugs; WO 2007/133773 discloses CDKI pathway inhibitors; WO 2008/009078 discloses 4,6-DL- and 2,4,6-trisubstituted quinazoline derivatives useful for treating viral infections; WO 2009/000085 discloses quinoline and quinazoline derivatives useful as modulators of gated ion channels; US 2009/0143399 discloses protein kinase inhibitors; and Japan Publication Number 2007-084494A discloses substituted bicyclic compounds.

SUMMARY OF INVENTION

Described herein are compounds, pharmaceutical compositions containing the compounds, and methods of using the compounds to treat a disorder, e.g., schizophrenia or cognitive deficit, in a subject. The compounds disclosed herein include quinoline- and quinazoline-containing compounds that modulate (e.g., inhibit) the activity of STEP.

The present invention provides therapeutic compounds, pharmaceutical composition comprising said compounds, use of said compounds and method for treating or preventing a disorder as described in items 1 to 42 below.

Item 1. A compound of formula (I):

(I)

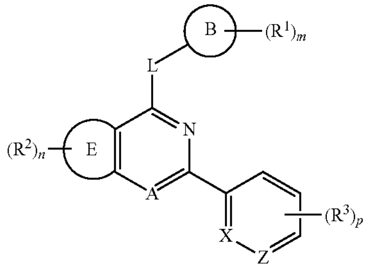

or a salt thereof, wherein:

A is $CR^4$ or N;

B is aryl, cyclyl or a 5- or 6-membered heteroaryl;

m is 0, 1, 2, 3, 4 or 5;

E is aryl or a 5-membered heteroaryl;

n is 0, 1, 2, 3 or 4;

when E is aryl, n is 0, 1, 2, 3 or 4; and when E is a 5-membered heteroaryl, n is 0, 1, 2 or 3;

L is $NR^5$, S, O or a direct bond;

one of X and Z is N and the other is CH;

p is 0, 1, 2, 3 or 4;

each $R^1$, $R^2$ and $R^3$ is independently $C_1$-$C_8$ alkyl, $C_2$-$C_8$ alkenyl, $C_2$-$C_8$ alkynyl, aryl, heteroaryl, cyclyl, heterocyclyl, arylalkyl, heteroarylalkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silyloxyalkynyl, silylalkoxy, silylalkoxyalkyl, —CN, oxo, $—NO_2$, $—C(O)OR^a$, $—C(Y)NR^bR^{b'}$, $—NR^cC(Y)R^{c'}$, $—NR^bR^{b'}$, $—OC(O)NR^bR^{b'}$, $—NR^cC(O)OR^{c'}$, $—SO_2NR^bR^{b'}$, $—NR^cSO_2R^{c'}$, $NR^cC(Y)NR^bR^{b'}$, $—OR^d$, $—SR^{d'}$, $—C(Y)R^c$ or $—S(O)_qR^f$, each of which is optionally substituted with 1-3 $R^6$; wherein two $R^1$, together with the atoms to which they are attached, may form an optionally substituted cyclyl, heterocyclyl, aryl or heteroaryl ring;

$R^4$ is hydrogen, $C_1$-$C_8$ alkyl, $C_2$-$C_8$ alkenyl, $C_2$-$C_8$ alkynyl, aryl, heteroaryl, cyclyl, heterocyclyl, arylalkyl, heteroarylalkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy, silylalkoxyalkyl, —CN, $—NO_2$, $—C(O)OR^a$, $—C(Y)NR^bR^{b'}$, $—NR^cC(Y)R^{c'}$, $NR^bR^{b'}$, $—OC(O)NR^bR^{b'}$, $—NR^cC(O)OR^{c'}$, $SO_2NR^bR^{b'}$, $—NR^cSO_2R^{c'}$, $—NR^cC(Y)NR^bR^{b'}$, $—OR^d$, $—SR^{d'}$, $—C(Y)R^e$ or $—S(O)_qR^f$, each of which is optionally substituted with 1-3 $R^6$;

$R^5$ is hydrogen; or when m is not 0, $R^5$ and one $R^1$ may be taken together with the atoms to which they are attached to form an optionally substituted heteroaryl or heterocyclyl ring;

each $R^6$ is independently $C_1$-$C_8$ alkyl, $C_2$-$C_8$ alkenyl, $C_2$-$C_8$ alkynyl, aryl, heteroaryl, cyclyl, heterocyclyl, arylalkyl, heteroarylalkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy, silylalkoxyalkyl, oxo, thioxo, —CN, $—NO_2$, $—C(O)OR^a$, $—C(Y)NR^bR^{b'}$, $—NR^cC(Y)R^{c'}$, $—NR^bR^{b'}$, $—OC(O)NR^bR^{b'}$, $—NR^cC(O)OR^{c'}$, $—SO_2NR^bR^{b'}$, $—NR^cSO_2R^c$, $—NR^cC(Y)NR^bR^{b'}$, $—OR^d$, $—SR^{d'}$, $—C(Y)R^c$ or $—S(O)_qR^f$, each of which is optionally substituted with 1-3 $R^7$;

each $R^7$ is independently $C_1$-$C_8$ alkyl, $C_2$-$C_8$ alkenyl, $C_2$-$C_8$ alkynyl, aryl, heteroaryl, cyclyl, heterocyclyl, arylalkyl, heteroarylalkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy, silylalkoxyalkyl, oxo, thioxo, —CN, $—NO_2$, $—C(O)OR^a$, $—C(Y)NR^bR^{b'}$, $—NR^cC(Y)R^{c'}$, $—NR^bR^{b'}$, $—OC(O)NR^bR^{b'}$, $—NR^cC(O)OR^{c'}$, $—SO_2NR^bR^{b'}$, $—NR^cC(Y)R^{c'}$, $—NR^cC(Y)NR^bR^{b'}$, $—OR^d$, $—SR^{d'}$, $—C(Y)R^c$ or $—S(O)_qR^f$, each of which is optionally substituted with 1-3 $R^9$;

each $R^9$ is independently $C_1$-$C_8$ alkyl, $C_2$-$C_8$ alkenyl, $C_2$-$C_8$ alkynyl, aryl, heteroaryl, cyclyl, heterocyclyl, arylalkyl, heteroarylalkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy, silylalkoxyalkyl, oxo, thioxo, —CN, $—NO_2$, $—C(O)OR^a—C(Y)NR^bR^{b'}$, $—NR^cC(Y)R^{c'}$, $—NR^bR^{b'}$, $—OC(O)NR^bR^{b'}$, $—NR^cC(O)OR^{c'}$, $—SO_2NR^bR^{b'}$, $—NR^cSO_2R^{c'}$, $—NR^cC(Y)NR^bR^{b'}$, $—OR^d$, $—SR^{d'}$, $—C(Y)R^c$ or $—S(O)_qR^f$;

Y is O or S;

q is 1 or 2 and each $R^a$, $R^b$, $R^{b'}$, $R^c$, $R^{c'}$, $R^d$, $R^{d'}$, $R^e$ and $R^f$ is independently hydrogen, $C_1$-$C_8$ alkyl, $C_2$-$C_8$ alkenyl, $C_2$-$C_8$ alkynyl, acyl, aryl, heteroaryl, cyclyl, heterocyclyl, arylalkyl, heteroarylalkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy or silylalkoxyalkyl;

wherein when B is phenyl, two $R^1$ are not taken together to form a pyrazole ring; and when B is phenyl, $R^2$ is not

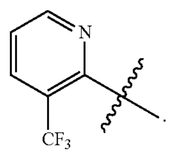 [SMILES: *c1ncccc1C(F)(F)F]

a compound of formula (II):

(II)

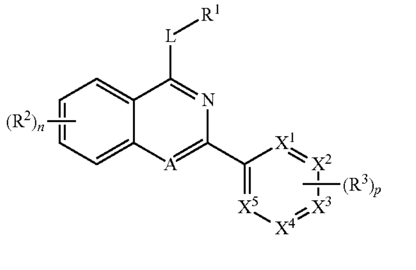

or a salt thereof, wherein:

L is $CR^4R^5$, O, C(O), $NR^6C(O)$ or $NR^7$;

A is N;

each $X^1$, $X^2$, $X^3$, $X^4$ and $X^5$ is independently CH or N, provided that at least two of $X^1$, $X^2$, $X^3$, $X^4$ and $X^5$ are N;

n is 0, 1, 2, 3 or 4;

p is 0, 1, 2 or 3;

$R^1$ is $C_1$-$C_8$ alkyl, $C_2$-$C_8$ alkenyl, $C_2$-$C_5$ alkynyl, aryl, heteroaryl, cyclyl, heterocyclyl, arylalkyl, heteroarylalkyl, cyclylalkyl or heterocyclylalkyl, each of which is optionally substituted with 1-5 $R^9$; wherein $R^1$ or $R^9$ is optionally taken together with one of $R^4$, $R^5$, $R^6$ or $R^7$, and the atoms to which they are attached, to form a cyclyl, heterocyclyl, aryl or heteroaryl ring that is optionally substituted with 1-3 $R^{10}$;

each $R^2$ and $R^3$ is independently hydrogen, $C_1$-$C_8$ alkyl, $C_2$-$C_8$ alkenyl, $C_2$-$C_8$ alkynyl, aryl, heteroaryl, cyclyl, heterocyclyl, arylalkyl, heteroarylalkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy, silylalkoxyalkyl, —CN, $—NO_2$, $—C(O)OR^a$, $—C(Y)NR^bR^{b'}$, $—NR^cC(Y)R^{c'}$, $—NR^bR^{b'}$, $—OC(O)NR^bR^{b'}$, $—NR^cC(O)OR^{c'}$, $—SO_2NR^bR^{b'}$, $—NR^cSO_2R^{c'}$, $—NR^cC(Y)NR^bR^{b'}$, $—OR^d$, $—SR^{d'}$, $—C(Y)R^e$ or $—S(O)_qR^f$; each of which is optionally substituted with 1-3 $R^{11}$;

each $R^4$, $R^5$, $R^6$ and $R^7$ is independently hydrogen, $C_1$-$C_8$ alkyl, $C_2$-$C_8$ alkenyl, $C_2$-$C_8$ alkynyl, aryl, heteroaryl, cyclyl, heterocyclyl, arylalkyl, heteroarylalkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy, silylalkoxyalkyl, —CN, $—NO_2$, $—C(O)OR^a$, $—C(Y)NR^bR^{b'}$, $—NR^cC(Y)R^{c'}$, $—NR^bR^{b'}$, $—OC(O)NR^bR^{b'}$, $—NR^cC(O)OR^{c'}$, $—SO_2NR^bR^{b'}$, $—NR^cSO_2R^{c'}$, $—NR^cC(Y)NR^bR^{b'}$, $—OR^d$, $—SR^{d'}$, $—C(Y)R^e$ or $—S(O)_qR^f$;

each $R^9$, $R^{10}$ and $R^{11}$ is independently $C_1$-$C_8$ alkyl, $C_2$-$C_8$ alkenyl, $C_2$-$C_8$ alkynyl, aryl, heteroaryl, cyclyl, heterocyclyl, arylalkyl, heteroarylalkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy, silylalkoxyalkyl, oxo, thioxo, —CN, $—NO_2$, $—C(O)OR^a$, $—C(Y)NR^bR^{b'}$, $—NR^cC(Y)R^{c'}$, $—NR^bR^{b'}$, $—OC(O)NR^bR^{b'}$, $—NR^cC(O)OR^{c'}$, $—SO_2NR^bR^{b'}$, $—NR^cSO_2R^{c'}$, $—NR^cC(Y)NR^bR^{b'}$, $—OR^d$, $—SR^{d'}$, $—C(Y)R^e$ or $—S(O)_qR^f$, each of which is optionally substituted with 1-3 $R^{12}$;

wherein, two $R^9$, two $R^{10}$ or two $R^{11}$ is optionally taken together with the atoms to which they are attached to form an optionally substituted cyclyl, heterocyclyl, aryl or heteroaryl ring;

$R^{12}$ is $—OR^d$;

Y is O or S;

q is 1 or 2 and each $R^a$, $R^b$, $R^{b'}$, $R^c$, $R^{c'}$, $R^d$, $R^{d'}$, $R^e$, $R^{e'}$ and $R^f$ is independently hydrogen, $C_1$-$C_8$ alkyl, $C_2$-$C_8$ alkenyl, $C_2$-$C_8$ alkynyl, acyl, cyclyl, heterocyclyl, aryl, heteroaryl, cyclylalkyl, heterocyclylalkyl, arylalkyl or heteroarylalkyl and a compound of formula (III):

(III)

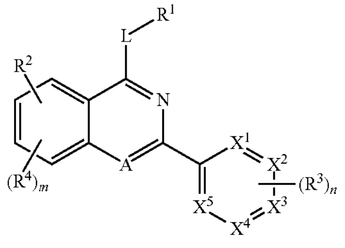

or a salt thereof, wherein:

A is CH or N;

L is O, a direct bond or $NR^6$;

one of $X^1$, $X^2$, $X^3$, $X^4$ and $X^5$ is N and the others are CH;

m is 1, or 3;

n is 1, 2, 3 or 4;

$R^1$ is hydrogen, $C_1$-$C_8$ alkyl, $C_2$-$C_8$ alkenyl, $C_2$-$C_8$ alkynyl, alkoxyalkyl, hydroxyalkyl, heteroaryl, heteroarylalkyl, arylalkyl, —C(Y)$R^e$, cyclyl, cyclylalkyl or heterocyclyl, each of which is optionally substituted with 1-3 $R^7$;

$R^2$ is aryl or heteroaryl, each of which is optionally substituted with 1-5 $R^9$;

each $R^3$ or $R^4$ is independently hydrogen, $C_1$-$C_8$ alkyl, $C_2$-$C_8$ alkenyl, $C_2$-$C_8$ alkynyl, aryl, heteroaryl, cyclyl, heterocyclyl, arylalkyl, heteroarylalkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy, silylalkoxyalkyl, —CN, —$NO_2$, —C(O)$OR^a$, —C(Y)$NR^bR^{b'}$, —$NR^cC(Y)R^{c'}$, —$NR^bR^{b'}$, —OC(O)$NR^bR^{b'}$, —$NR^cC(O)OR^{c'}$, —$SO_2NR^bR^{b'}$, —$NR^cSO_2R^{c'}$, —$NR^cC(Y)NR^bR^{b'}$, —$OR^d$, —$SR^{d'}$, —C(Y)$R^e$ or —$S(O)_qR^f$, each of which is optionally substituted with 1-3 $R^{10}$;

$R^6$ is hydrogen, $C_1$-$C_8$ alkyl, $C_2$-$C_8$ alkenyl, $C_2$-$C_8$ alkynyl, cyclyl or heterocyclyl, each of which is optionally substituted with 1-3 $R^{11}$;

each $R^7$, $R^9$ and $R^{10}$ is independently $C_1$-$C_8$ alkyl, $C_2$-$C_8$ alkenyl, $C_1$-$C_8$ alkynyl, aryl, hetero aryl, cyclyl, heterocyclyl, arylalkyl, heteroarylalkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy, silylalkoxyalkyl, oxo, thioxo, —CN, —$NO_2$, —C(O)$OR^a$, —C(Y)$NR^bR^{b'}$, —$NR^cC(Y)R^{c'}$, —$NR^bR^{b'}$, —OC(O)$NR^bR^{b'}$, —$NR^cC(O)OR^{c'}$, —$SO_2NR^bR^{b'}$, —$NR^cSO_2R^{c'}$, —$NR^cC(Y)NR^bR^{b'}$, —$OR^d$, —$SR^{d'}$, —C(Y)$R^e$ or —$S(O)_qR^f$, each of which is optionally substituted with 1-3 $R^{12}$; wherein two $R^7$, two $R^9$ or two $R^{10}$ are optionally be taken together with the atoms to which they are attached to form an optionally substituted cyclyl, heterocyclyl, aryl or heteroaryl ring;

each $R^{11}$ and $R^{12}$ is independently $C_1$-$C_8$ alkyl, $C_2$-$C_8$ alkenyl, $C_2$-$C_8$ alkynyl, aryl, heteroaryl, cyclyl, heterocyclyl, arylalkyl, heteroarylalkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy, silylalkoxyalkyl, oxo, thioxo, —CN, —$NO_2$, —C(O)$OR^a$, —C(Y)$NR^bR^{b'}$, —$NR^cC(Y)R^{c'}$, —$NR^bR^{b'}$, —OC(O)$NR^bR^{b'}$, —$NR^cC(O)OR^{c'}$, —$SO_2NR^bR^{b'}$, —$NR^cSO_2R^{c'}$, —$NR^cC(Y)NR^bR^{b'}$, —$OR^d$, —$SR^{d'}$, —C(Y)$R^e$ or —$S(O)_qR^f$, each of which is optionally substituted with 1-3 $R^{13}$;

$R^{13}$ is independently $C_1$-$C_8$ alkyl, haloalkyl, halo, heterocyclyl, cyclyl, oxo or —C(Y)$NR^bR^{b'}$;

Y is independently O or S;

q is 1 or 2; and each $R^a$, $R^b$, $R^{b'}$, $R^c$, $R^{c'}$, $R^d$, $R^{d'}$, $R^e$ and $R^f$ is independently hydrogen, $C_1$-$C_8$ alkyl, $C_2$-$C_8$ alkenyl, $C_2$-$C_8$ alkynyl, acyl, haloalkyl alkoxyalkyl, alkylaminoalkyl, dialkylaminoalkyl, cyclyl, heterocyclyl, aryl, heteroaryl, cyclylalkyl, heterocyclylalkyl, arylalkyl or heteroarylalkyl;

with proviso $R^9$ is not

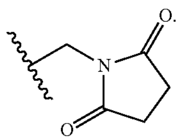 [SMILES: *CN1C(=O)CCC1=O]

Item 2. The compound according to item 1 represented by general formula (I) or a salt thereof, wherein:

A is $CR^4$ or N:

B is aryl, cyclyl or a 5- or 6-membered heteroaryl;

m is 0, 1, 2, 3, 4 or 5;

n is 0, 1, 2, 3 or 4;

E is aryl or a 5-membered heteroaryl;

when E is aryl, n is 0, 1, 2, 3 or 4; and when E is a 5-membered heteroaryl, n is 0, 1, 2 or 3;

L is $NR^5$, S, O or a direct bond:

one of X and Z is N and the other is CH;

p is 0, 1, 2, 3 or 4;

each $R^1$, $R^2$ and $R^3$ is independently $C_1$-$C_8$ alkyl, $C_2$-$C_8$ alkenyl, $C_2$-$C_8$ alkynyl, aryl, heteroaryl, cyclyl, heterocyclyl, arylalkyl, heteroarylalkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silyloxyalkynyl, silylalkoxy, silylalkoxyalkyl, —CN, oxo, —$NO_2$, —C(O)$OR^a$, —C(Y)$NR^bR^{b'}$, —$NR^cC(Y)R^{c'}$, —$NR^bR^{b'}$, —OC(O)$NR^bR^{b'}$, —$NR^cC(O)OR^{c'}$, —$SO_2NR^bR^{b'}$, —$NR^cSO_2R^{c'}$, —$NR^cC(Y)NR^bR^{b'}$, —$OR^d$, —$SR^{d'}$, —C(Y)$R^e$ or —$S(O)_qR^f$, each of which is optionally substituted with 1-3 $R^6$; wherein two $R^1$, together with the atoms to which they are attached, may form an optionally substituted cyclyl, heterocyclyl, aryl or heteroaryl ring;

$R^4$ is hydrogen, $C_1$-$C_8$ alkyl, $C_2$-$C_8$ alkenyl, $C_2$-$C_8$ alkynyl, aryl, heteroaryl, cyclyl, heterocyclyl, arylalkyl, heteroarylalkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy, silylalkoxyalkyl, —CN, —$NO_2$, —C(O)$OR^a$, —C(Y)$NR^bR^{b'}$, —$NR^cC(Y)R^{c'}$, —$NR^bR^{b'}$, —OC(O)$NR^bR^{b'}$, —$NR^cC(O)OR^{c'}$, —$SO_2NR^bR^{b'}$, —$NR^cSO_2R^{c'}$, —$NR^cC(Y)NR^bR^{b'}$, —$OR^d$, —$SR^{d'}$, —C(Y)$R^e$ or —$S(O)_qR^f$, each of which is optionally substituted with 1-3 $R^6$;

$R^5$ is hydrogen; or when m is not 0, $R^5$ and one $R^1$ may be taken together with the atoms to which they are attached to form an optionally substituted heteroaryl or heterocyclyl ring;

each $R^6$ is independently $C_1$-$C_8$ alkyl, $C_2$-$C_8$ alkenyl, $C_2$-$C_8$ alkynyl, aryl, heteroaryl, cyclyl, heterocyclyl, arylalkyl, heteroarylalkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy, silylalkoxyalkyl, oxo, thioxo, —CN, —$NO_2$, —C(O)$OR^a$, —C(Y)$NR^bR^{b'}$, —$NR^cC(Y)R^{c'}$, —$NR^bR^b$, —OC(O)$NR^bR^{b'}$, —$NR^cC(O)OR^{c'}$, —$SO_2NR^bR^{b'}$, —$NR^cSO_2R^{c'}$, —$NR^cC(Y)NR^bR^{b'}$, —$OR^d$, —$SR^{d'}$, —C(Y)$R^e$ or —$S(O)_qR^f$, each of which is optionally substituted with 1-3 $R^7$;

each $R^7$ is independently $C_1$-$C_8$ alkyl, $C_2$-$C_8$ alkenyl, $C_2$-$C_8$ alkynyl, aryl, heteroaryl, cyclyl, heterocyclyl, arylalkyl, heteroarylalkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy, silylalkoxyalkyl, oxo, thioxo, —CN, —$NO_2$, —C(O)$OR^a$, —C(Y)$NR^bR^{b'}$, —$NR^cC(Y)R^{c'}$, —$NR^bR^{b'}$, —C(O)$NR^bR^{b'}$, —$NR^cC(O)OR^{c'}$, —$SO_2NR^bR^{b'}$, —$NR^cSO_2R^{c'}$, —$NR^cC(Y)NR^bR^{b'}$, —$OR^d$, —$SR^{d'}$, —C(Y)$R^e$ or —$S(O)_qR^f$, each of which is optionally substituted with 1-3 $R^9$;

each $R^9$ is independently $C_1$-$C_8$ alkyl, $C_2$-$C_8$ alkenyl, $C_2$-$C_8$ alkynyl, aryl, heteroaryl, cyclyl, heterocyclyl, arylalkyl, heteroarylalkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy, silylalkoxyalkyl, oxo, thioxo, —CN, —$NO_2$, —C(O)$OR^a$, —C(Y)$NR^bR^{b'}$, —$NR^cC(Y)R^{c'}$, —$NR^bR^{b'}$, —OC(O)$NR^bR^{b'}$, —$NR^cC(O)OR^{c'}$, —$SO_2NR^bR^{b'}$, —$NR^cSO_2R^{c'}$, —$NR^cC(Y)NR^bR^{b'}$, —$OR^d$, —$SR^{d'}$, —C(Y)$R^e$ or —$S(O)_qR^f$;

Y is O or S;

q is 1 or 2; and each $R^a$, $R^b$, $R^{b'}$, $R^c$, $R^{c'}$, $R^d$, $R^{d'}$, $R^e$ and $R^f$ is independently hydrogen, $C_1$-$C_8$ alkyl, $C_2$-$C_8$ alkenyl, $C_2$-$C_8$ alkynyl, acyl, aryl, heteroaryl, cyclyl, heterocyclyl, arylalkyl, heteroarylalkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy or silylalkoxyalkyl;

wherein when B is phenyl, two $R^1$ are not taken together to form a pyrazole ring; and when B is phenyl, $R^2$ is not

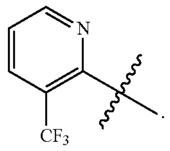

Item 3. The compound according to item 2 represented by general formula (I) or a salt thereof, wherein:

A is CH or N;

B is aryl, cyclyl or a 5- or 6-membered heteroaryl;

m is 0, 1, 2, 3 or 4;

E is aryl or a 5-membered heteroaryl;

n is 0, 1 or 2;

when E is aryl, n is 0, 1 or 2 and when E is a 5-membered heteroaryl, n is 0 or 1;

p is 0, 1 or 2;

each $R^1$, $R^2$ and $R^3$ is independently $C_1$-$C_8$ alkyl, $C_2$-$C_8$ alkynyl, aryl, heteroaryl, cyclyl, heterocyclyl, arylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silyloxyalkynyl, —CN, oxo, —$NO_2$, —C(O)$OR^a$, —C(Y)$NR^bR^{b'}$, —$NR^bR^{b'}$, —OC(O)$NR^bR^{b'}$, —$NR^c$C(Y)$R^{c'}$, —$SO_2NR^bR^{b'}$, —$OR^d$, —$SR^{d'}$, C(Y)$R^c$ or —$S(O)_qR^f$, each of which is optionally substituted with 1-3 $R^6$; wherein two $R^1$, together with the atoms to which they are attached, may form an optionally substituted cyclyl, heterocyclyl, aryl or heteroaryl ring;

each $R^6$ is independently $C_1$-$C_8$ alkyl, heterocyclyl, heterocyclylalkyl, hydroxyalkyl, halo, haloalkyl, haloalkoxy, alkoxyalkyl, oxo, —CN, —$NO_2$, —C(O)$OR^a$, —C(Y)$NR^bR^{b'}$, —$NR^c$C(Y)R, —$NR^bR^{b'}$, —$OR^d$ or —C(Y)$R^e$, each of which is optionally substituted with 1-3 $R^7$;

each $R^7$ is oxo; and each $R^a$, $R^b$, $R^{b'}$, $R^c$, $R^{c'}$, $R^d$, $R^{d'}$, $R^e$ and $R^f$ is independently hydrogen, $C_1$-$C_8$ alkyl, $C_2$-$C_8$ alkenyl, $C_2$-$C_8$ alkynyl, acyl, aryl, heteroaryl, cyclyl, heterocyclyl, arylalkyl, heteroarylalkyl, cyclylalkyl, heterocyclylalkyl, haloalkyl, dialkylaminoalkyl, hydroxyalkyl or alkoxyalkyl.

Item 4. The compound according to item 3 represented by general formula (I) or a salt thereof, wherein:

B or two R1 and B are taken together to form a group is phenyl, dihydroindenyl, dihydrobenzoxazinyl, dihydrobenzodioxinyl, chromenyl, tetrahydroquinoxalinyl, tetrahydroisoquinolinyl, tetrahydroquinolinyl, dihydroquinolinyl, quinolyl, isoquinolinyl, tetrahydroquinazolinyl, indolinyl, dihydrobenzothiazolyl, dihydrobenzimidazolyl, dihydrobenzoxazolyl, isoindolinyl, dihydroisobenzofuranyl, benzofuryl, benzothienyl, benzodioxolyl, indolyl, indazolyl, benzoimidazolyl, benzotriazolyl, benzisoxazolyl, benzoxazolyl, benzothiazolyl, benzoxadiazolyl, dihydrocyclopentathiophenyl, tetrahydrobenzothiophenyl, thienyl, thiazolyl, imidazolyl, pyrazolyl, isoxazolyl, thiadiazolyl, pyrrolyl or pyridyl;

E is phenyl, thienyl or pyrrolyl;

when E is phenyl, n is 1 or 2; and when E is thienyl, n is 0 or 1;

each $R^1$, $R^2$ and $R^3$ is independently $C_1$-$C_8$ alkyl, $C_2$-$C_8$ alkynyl, phenyl, thienyl, pyrrolyl, oxadiazolyl, pyridyl, benzodioxolyl, furyl, pyrimidinyl, oxazolyl, isoxazolyl, pyrazolyl, $C_3$-$C_8$ cycloalkyl, piperidyl, pyrrolidinyl, morpholinyl, dioxolanyl, phenylalkyl, thiomorpholinylalkyl, pyrrolidinylalkyl, morpholinylalkyl, piperidylalkyl, piperazinylalkyl, halo, haloalkyl, haloalkoxy, aminoalkyl, alkylaminoalkyl, dialkylaminoalkyl, hydroxyalkyl, alkoxyalkyl, silyloxyalkyl, silyloxyalkynyl, —CN, —$NO_2$, oxo, —C(O)$OR^a$, —C(Y)$NR^bR^{b'}$, —$NR^c$C(Y)$R^{c'}$, —$NR^bR^{b'}$, —OC(O)$NR^bR^{b'}$, —$SO_2NR^bR^{b'}$, —$OR^d$, —$SR^{d'}$, —C(Y)$R^e$ or —$S(O)_qR^f$, each of which is optionally substituted with 1-3 $R^6$;

each $R^6$ is independently $C_1$-$C_8$ alkyl, tetrahydropyranyl, morpholinyl, thiomorpholinyl, morpholinylalkyl, dialkylaminoalkyl, halo, haloalkyl, haloalkoxy, hydroxyalkyl, oxo, —CN, —$NO_2$, —C(O)$OR^a$, —$NR^c$C(Y)$R^{c'}$, —C(Y)$NR^bR^{b'}$, —$NR^bR^{b'}$, alkoxyalkyl, —$OR^d$ or —C(Y)$R^e$; and each $R^a$, $R^b$, $R^{b'}$, $R^c$, $R^{c'}$, $R^d$, $R^{d'}$, $R^e$ and $R^f$ is independently hydrogen, $C_1$-$C_8$ alkyl, $C_2$-$C_5$ alkenyl, $C_2$-$C_8$ alkynyl, $C_3$-$C_8$ cycloalkyl, phenyl, pyridyl, dihydroindenyl, morpholinyl, tetrahydropyranyl, piperidyl, pyrrolidinyl, piperazinyl, thiomorpholinyl, phenylalkyl, thienylalkyl, furylalkyl, pyridylalkyl, tetrahydropyranylalkyl, dihydroindenylalkyl, tetrahydrofurylalkyl, hydroxyalkyl, thiazolylalkyl, pyrazolylalkyl, morpholinylalkyl, pyrrolidinylalkyl, dialkylaminoalkyl, piperidylalkyl, benzodioxolylalkyl, dihydrobenzodioxinylalkyl, benzothienylalkyl, $C_3$-$C_8$ cycloalkylalkyl, oxazolidinylalkyl, haloalkyl or alkoxyalkyl.

Item 5. The compound according to item 3 represented by general formula (I) or a salt thereof, wherein:

B or two R1 and B are taken together to form a group is phenyl, dihydroindenyl, dihydrobenzoxazinyl, dihydrobenzodioxinyl, chromenyl, tetrahydroquinoxalinyl, tetrahydroisoquinolyl, tetrahydroquinolinyl, dihydroquinolyl, quinolyl, isoquinolyl, tetrahydroquinazolinyl, indolinyl, dihydrobenzothiazolyl, dihydrobenzimidazolyl, dihydrobenzoxazolyl, isoindolinyl, dihydroisobenzofuranyl, benzofuryl, benzothienyl, benzodioxolyl, indolyl, indazolyl, benzoimidazolyl, benzotriazolyl, benzisoxazolyl, benzoxazolyl, benzothiazolyl, benzoxadiazolyl, dihydrocyclopentathiophenyl, tetrahydrobenzothienyl, thienyl, thiazolyl, imidazolyl, pyrazolyl, isoxazolyl, thiadiazolyl, pyrrolyl or pyridyl;

E is phenyl, thienyl or pyrrolyl;

when E is phenyl, n is 0, 1 or 2; and when E is thienyl, n is 0 or 1;

each $R^1$, $R^2$ and $R^3$ is independently $C_1$-$C_8$ alkyl, $C_2$-$C_8$ alkynyl, phenyl, thienyl, pyrrolyl, oxazolyl, oxadiazolyl, pyridyl, benzodioxolyl, furyl, pyrimidinyl, isoxazolyl, pyrazolyl, $C_3$-$C_8$ cycloalkyl, piperidyl, pyrrolidinyl, morpholinyl, dioxolanyl, phenylalkyl, thiomorpholinylalkyl, pyrrolidinylalkyl, morpholinylalkyl, piperidylalkyl, piperazinylalkyl, halo, haloalkyl, haloalkoxy, aminoalkyl, alkylaminoalkyl, dialkylaminoalkyl, hydroxyalkyl, alkoxyalkyl, silyloxyalkyl, silyloxyalkynyl, —CN, —$NO_2$, oxo, —C(O)$OR^a$, —C(Y)$NR^bR^{b'}$, —$NR^bR^{b'}$, —$NR^c$C(Y)$R^{c'}$, —OC(O)$NR^bR^{b'}$, —$SO_2NR^bR^{b'}$, —$OR^d$, —$SR^{d'}$, —C(Y)$R^e$ or —$S(O)_qR^f$, each of which is optionally substituted with 1-3 $R^6$;

each $R^6$ is independently $C_1$-$C_8$ alkyl, tetrahydropyranyl, morpholinyl, thiomorpholinyl, morpholinylalkyl, dialkylaminoalkyl, halo, haloalkyl, haloalkoxy, hydroxyalkyl, oxo, —CN, —$NO_2$, —C(O)$OR^a$, —$NR^c$C(Y)$R^{c'}$, —C(Y)$NR^bR^{b'}$, —$NR^bR^{b'}$, alkoxyalkyl, —$OR^d$ or —$C(Y)R^e$, each of which is optionally substituted with 1-3 $R^7$;

$R^7$ is oxo; and each $R^a$, $R^b$, $R^{b'}$, $R^c$, $R^{c'}$, $R^d$, $R^{d'}$, $R^e$ and $R^f$ is independently hydrogen, $C_1$-$C_8$ alkyl, $C_2$-$C_8$ alkenyl, $C_2$-$C_8$ alkynyl, $C_3$-$C_8$ cycloalkyl, phenyl, pyridyl, dihydroindenyl, morpholinyl, tetrahydropyranyl, piperidyl, pyrrolidinyl, piperazinyl, thiomorpholinyl, phenylalkyl, thienylalkyl, furylalkyl, pyridylalkyl, tetrahydropyranylalkyl, dihydroindenylalkyl, tetrahydrofurylalkyl, hydroxyalkyl, thiazolylalkyl, pyrazolylalkyl, morpholinylalkyl, pyrrolidinylalkyl, dialkylaminoalkyl, piperidylalkyl, benzodioxolilalkyl, dihydrobenzodioxiyalkyl, benznylalkyl, benzothienylalkyl, $C_3$-$C_8$ cycloalkylalkyl, oxazolidinylalkyl, haloalkyl, or alkoxyalkyl.

Item 6. The compound according to item 5 represented by general formula (I) or a salt thereof, wherein:

$R^1$ is $C_1$-$C_8$ alkyl, phenyl, thienyl, pyrrolyl, oxazolyl, $C_3$-$C_8$ cycloalkyl, dioxolanyl, phenylalkyl, halo, haloalkyl, haloalkoxy, alkoxyalkyl, —CN, oxo, —$NO_2$, —$C(O)OR^a$, —$C(Y)NR^bR^{b'}$, —$NR^cC(Y)R^{c'}$, —$SO_2NR^bR^{b'}$, —$OR^d$, —$SR^{d'}$, —$C(Y)R^e$ or —$S(O)_qR^f$, each of which is optionally substituted with 1-3 $R^6$;

$R^2$ is $C_1$-$C_8$ alkyl, $C_2$-$C_8$ alkynyl, phenyl, thienyl, pyridyl, benzodioxolyl, furyl, pyrimidinyl, isoxazolyl, pyrazolyl, $C_3$-$C_8$ cycloalkyl, pyrrolidinyl, morpholinyl thiomorpholinylalkyl, pyrrolidinylalkyl, morpholinylalkyl, piperiridylalkyl, piperazinylalkyl, halo, haloalkyl, haloalkoxy, aminoalkyl, alkylaminoalkyl, dialkylaminoalkyl, hydroxyalkyl, alkoxyalkyl, silyloxyalkyl, silyloxyalkynyl, —CN, —$NO_2$, —$C(O)OR^a$, —$C(Y)NR^bR^{b'}$, —$NR^bR^{b'}$, —$OC(O)NR^bR^{b'}$, —$OR^d$ or —$C(Y)R^e$, each of which is optionally substituted with 1-3 $R^6$;

$R^3$ is $C_1$-$C_8$ alkyl, halo, haloalkyl, —$NR^bR^{b'}$ or —$OR^d$, each of which is optionally substituted with 1-3 $R^6$.

Item 7. The compound according to item 4 or 6 represented by general formula (I) or a salt thereof, wherein:

$R^1$ is $C_1$-$C_8$ alkyl, phenyl, thienyl, pyrrolyl, oxazolyl, $C_3$-$C_8$ cycloalkyl, dioxolanyl, phenylalkyl, halo, haloalkyl, haloalkoxy, alkoxyalkyl, —CN, oxo, —$NO_2$, —$C(O)OR^a$, —$C(Y)NR^bR^{b'}$, —$NR^cC(Y)R^{c'}$, —$SO_2NR^bR^{b'}$, —$OR^d$, —$SR^{d'}$, —$C(Y)R^e$ or —$S(O)_qR^f$;

$R^2$ is $C_1$-$C_8$ alkyl, $C_2$-$C_8$ alkynyl, phenyl, thienyl, pyridyl, benzodioxolyl, furyl, pyrimidinyl, isoxazolyl, pyrazolyl, $C_3$-$C_8$ cycloalkyl, piperidinyl, pyrrolidinyl, morpholinyl, thiomorpholinylalkyl, pyrrolidinylalkyl, morpholinylalkyl, piperiridinylalkyl, piperazinylalkyl, halo, haloalkyl, haloalkoxy, aminoalkyl, alkylaminoalkyl, dialkylaminoalkyl, hydroxyalkyl, alkoxyalkyl, silyloxyalkyl, silyloxyalkynyl, —CN, —$NO_2$, —$C(O)OR^a$, —$C(Y)NR^bR^{b'}$, —$NR^bR^{b'}$, —$OC(O)NR^bR^{b'}$, —$OR^d$, —$C(Y)R^e$ or —$S(O)_qR^f$;

$R^3$ is $C_1$-$C_8$ alkyl, halo, haloalkyl, —$NR^bR^{b'}$ or —$OR^d$.

Item 8. The compound according to item 7 represented by general formula (I) or a salt thereof, wherein:

B or two R1 and B are taken together to form a group is phenyl, dihydroindenyl, dihydrobenzoxazinyl, dihydrobenzodioxinyl, chromenyl, tetrahydroisoquinolyl, tetrahydroquinolinyl, dihydroquinolyl, quinolyl, tetrahydroquinazolinyl, indolinyl, dihydrobenzothiazolyl, dihydrobenzimidazolyl, dihydrobenzoxazolyl, isoindolinyl, benzofuryl, benzothienyl, benzodioxolyl, indolyl, indazolyl, benzoimidazolyl, benzotriazolyl, benzisoxazolyl, benzoxazolyl, benzothiazolyl, benzoxadiazolyl, tetrahydrobenzothienyl, thienyl, thiazolyl, imidazolyl, pyrazolyl, thiadiazolyl or pyridyl:

m is 1, 2, 3 or 4;

$R^1$ is $C_1$-$C_8$ alkyl, halo, haloalkyl, haloalkoxy, alkoxyalkyl, —CN, oxo, —$NO_2$, —$C(O)OR^a$, —$C(Y)NR^bR^{b'}$, —$NR^cC(Y)R^{c'}$, —$SO_2NR^bR^{b'}$, —$OR^d$, or —$S(O)_qR^f$;

$R^2$ is $C_1$-$C_8$ alkyl, $C_3$-$C_8$ cycloalkyl, thiomorpholinylalkyl, pyrrolidinylalkyl, morpholinylalkyl, haloalkyl, haloalkoxy, aminoalkyl, alkylaminoalkyl, dialkylaminoalkyl, hydroxyalkyl, alkoxyalkyl, silyloxyalkyl, —CN, —$NO_2$, —$C(O)OR^a$, —$C(Y)NR^bR^{b'}$, —$NR^bR^{b'}$, —$OR^d$, —$C(Y)R^e$ or —$S(O)_qR^f$;

each $R^a$, $R^b$, $R^{b'}$, $R^c$, $R^{c'}$, $R^d$, $R^{d'}$, $R^e$ and $R^f$ is independently hydrogen, $C_1$-$C_8$ alkyl, $C_2$-$C_8$ alkenyl, $C_1$-$C_8$ alkynyl, $C_3$-$C_8$ cycloalkyl, phenyl, dihydroindenyl, morpholinyl, tetrahydropyranyl, piperidyl, pyrrolidinyl, thiomorpholinyl, phenylalkyl, thienylalkyl, pyridylalkyl, tetrahydropyranylalkyl, dihydroindenylalkyl, tetrahydrofurylalkyl, hydroxyalkyl, morpholinylalkyl, pyrrolidinylalkyl, dialkylaminoalkyl, piperidylalkyl, benzodioxolilalkyl, dihydrobenzodioxinylalkyl, $C_3$-$C_8$ cycloalkylalkyl, haloalkyl or alkoxyalkyl.

Item 9. The compound according to item 1 represented by general formula (II) or a salt thereof, wherein:

L is $CR^4R^5$, O, C(O), $NR^6C(O)$ or $NR^7$;

A is N;

each $X^1$, $X^2$, $X^3$, $X^4$ and $X^5$ is independently CH or N, provided that at least two of $X^1$, $X^2$, $X^3$, $X^4$, and $X^5$ are N;

n is 0, 1, 2, 3 or 4;

p is 0, 1, 2 or 3;

$R^1$ is $C_1$-$C_8$ alkyl, $C_2$-$C_8$ alkenyl, $C_2$-$C_8$ alkynyl, aryl, heteroaryl, cyclyl, heterocyclyl, arylalkyl, heteroarylalkyl, cyclylalkyl or heterocyclylalkyl, each of which is optionally substituted with 1-5 $R^9$; wherein $R^1$ or $R^9$ is optionally taken together with one of $R^4$, $R^5$, $R^6$ or $R^7$, and the atoms to which they are attached to form a cyclyl, heterocyclyl, aryl or heteroaryl ring that is optionally substituted with 1-3 $R^{10}$;

each $R^2$ and $R^3$ is independently hydrogen, $C_1$-$C_8$ alkyl, $C_2$-$C_8$ alkenyl, $C_2$-$C_8$ alkynyl, aryl, heteroaryl, cyclyl, heterocyclyl, arylalkyl, heteroarylalkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy, silylalkoxyalkyl, —CN, —$NO_2$, —$C(O)OR^a$, —$C(Y)NR^bR^{b'}$, —$NR^cC(Y)R^{c'}$, —$NR^bR^{b'}$, —$OC(O)NR^bR^{b'}$, —$NR^cC(O)OR^{c'}$, —$SO_2NR^bR^{b'}$, —$NR^cSO_2R^{c'}$, —$NR^cC(Y)NR^bR^{b'}$, —$OR^d$, —$SR^{d'}$, —$C(Y)R^e$ or —$S(O)_qR^f$, each of which is optionally substituted with 1-3 $R^{11}$;

each $R^4$, $R^5$, $R^6$ and $R^7$ is independently hydrogen, $C_1$-$C_8$ alkyl, $C_2$-$C_8$ alkenyl, $C_2$-$C_8$ alkynyl, aryl, heteroaryl, cyclyl, heterocyclyl, arylalkyl, heteroarylalkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy, silylalkoxyalkyl, —CN, —$NO_2$, —$C(O)OR^a$, —$C(Y)NR^bR^{b'}$, —$NR^cC(Y)R^{c'}$, —$NR^bR^{b'}$, —$OC(O)NR^bR^{b'}$, —$NR^cC(O)OR^{c'}$, —$SO_2NR^bR^{b'}$, —$NR^cSO_2R^{c'}$, —$NR^cC(Y)NR^bR^{b'}$, —$OR^d$, —$SR^{d'}$, —$C(Y)R^e$ or —$S(O)_qR^f$;

each $R^9$, $R^{10}$ and $R^{11}$ is independently $C_1$-$C_8$ alkyl, $C_2$-$C_8$ alkenyl, $C_2$-$C_8$ alkynyl, aryl, heteroaryl, cyclyl, heterocyclyl, arylalkyl, heteroarylalkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy, silylalkoxyalkyl, oxo, thioxo, —CN, —$NO_2$, —$C(O)OR^a$, —$C(Y)NR^bR^{b'}$, —$NR^cC(Y)R^{c'}$, —$NR^bR^{b'}$, —$OC(O)NR^bR^{b'}$, —$NR^cC(O)OR^{c'}$, —$SO_2NR^bR^{b'}$, —$NR^cSO_2R^{c'}$, $NR^cC(Y)NR^bR^{b'}$, —$OR^d$, —$SR^{d'}$, —$C(Y)R^e$ or —$S(O)_qR^f$, each of which is optionally substituted with 1-3 $R^{12}$; wherein two $R^8$, two $R^9$, two $R^{10}$ or two $R^{11}$ is optionally taken together with the atoms to which they are attached to form an optionally substituted cyclyl, heterocyclyl, aryl or heteroaryl ring;

$R^{12}$ is —$OR^d$;

Y is O or S;

q is 1 or 2; and each $R^a$, $R^b$, $R^{b'}$, $R^c$, $R^{c'}$, $R^d$, $R^{d'}$, $R^e$, $R^{e'}$ and $R^f$ is independently hydrogen, $C_1$-$C_8$ alkyl, $C_2$-$C_8$ alkenyl, $C_2$-$C_8$ alkynyl, acyl, cyclyl, heterocyclyl, aryl, heteroaryl, cyclylalkyl, heterocyclylalkyl, arylalkyl, or heteroarylalkyl.

Item 10. The compound according to item 9 represented by general formula (II) or a salt thereof, L is $NR^7$;

n is 0, 1 or 2;

p is 0;

$R^1$ is $C_1$-$C_8$ alkyl, aryl or heteroaryl;

each $R^2$ and $R^3$ is independently hydrogen, $C_1$-$C_8$ alkyl, aryl, halo, heterocyclylalkyl, —$NR^cC(Y)R^c$, —$NR^bR^{b'}$ or —$OR^d$, each of which is optionally substituted with 1-3 $R^{11}$;

$R^7$ is hydrogen; and each $R^9$, $R^{10}$ and $R^{11}$ is independently $C_1$-$C_8$ alkyl, heterocyclyl, halo, haloalkyl, haloalkoxy, —CN, —$C(O)OR^a$, —$C(Y)NR^bR^{b'}$, —$OR^d$ or —$C(Y)R^c$;

Y is O;

each $R^a$, $R^b$, $R^{b'}$, $R^c$, $R^{c'}$, $R^d$, $R^{d'}$, $R^e$, $R^{e'}$ and $R^f$ is independently hydrogen, $C_1$-$C_8$ alkyl, cyclyl, heterocyclyl, aryl, or heteroaryl.

Item 11. The compound according to item 10 represented by general formula (II) or a salt thereof, wherein:

$R^1$ is $C_1$-$C_8$ alkyl, phenyl or benzodioxolyl;

each $R^2$ and $R^3$ is independently hydrogen, $C_1$-$C_8$ alkyl, phenyl, halo, morholinylalkyl, —$NR^cC(Y)R^c$, —$NR^bR^{b'}$ or —$OR^d$;

$R^9$ is independently $C_1$-$C_8$ alkyl, morpholinyl, tetrahydropyranyl, halo, haloalkyl, haloalkoxy, —CN, —$C(O)OR^a$, —$C(Y)NR^bR^{b'}$, —$OR^d$ or —$C(Y)R^c$; and each $R^a$, $R^b$, $R^{b'}$, $R^c$, $R^{c'}$, $R^d$, $R^{d'}$, $R^e$, $R^{e'}$ and $R^f$ is independently hydrogen, $C_1$-$C_8$ alkyl, $C_3$-$C_8$ cycloalkyl, tetrahydropyranyl, phenyl, or pyridyl.

Item 12. The compound according to item 10 represented by general formula (II) or a salt thereof, wherein:

$R^1$ is $C_1$-$C_8$ alkyl, phenyl or benzodioxolyl;

each $R^2$ and $R^3$ is independently hydrogen, $C_1$-$C_8$ alkyl, phenyl, halo, morholinylalkyl, —$NR^cC(Y)R^c$, —$NR^bR^{b'}$ or —$OR^d$, each of which is optionally substituted with 1-3 $R^{11}$;

each $R^9$, $R^{10}$ and $R^{11}$ is independently $C_1$-$C_8$ alkyl, morpholinyl, tetrahydropyranyl, halo, haloalkyl, haloalkoxy, —CN, —$C(O)OR^a$, —$C(Y)NR^bR^{b'}$, —$OR^d$ or —$C(Y)R^e$; and each $R^a$, $R^b$, $R^{b'}$, $R^c$, $R^{c'}$, $R^d$, $R^{d'}$, $R^e$, $R^{e'}$ and $R^f$ is independently hydrogen, $C_1$-$C_8$ alkyl, $C_3$-$C_8$ cycloalkyl, tetrahydropyranyl, phenyl, or pyridyl.

Item 13. The compound according to item 12 represented by general formula (II) or a salt thereof, wherein:

$R^2$ is $C_1$-$C_8$ alkyl, phenyl, halo, morholinylalkyl, —$NR^cC(Y)R^{c'}$, —$NR^bR^{b'}$ or —$OR^d$, each of which is optionally substituted with 1-3 $R^{11}$;

$R^3$ is hydrogen;

$R^9$ is halo, haloalkoxy, —CN, —$C(O)OR^a$ or —$C(Y)NR^bR^{b'}$; and $R^{11}$ is $C_1$-$C_8$ alkyl, morpholinyl, tetrahydropyranyl, halo, —CN, —$OR^d$ or —$C(Y)R^e$;

Item 14. The compound according to idem 11 or 13 represented by general formula (II) or a salt thereof, wherein:

$R^2$ is $C_1$-$C_8$ alkyl, phenyl, halo, morholinylalkyl, —$NR^cC(Y)R^{c'}$, —$NR^bR^{b'}$ or —$OR^d$;

$R^3$ is hydrogen; and $R^9$ is halo, haloalkoxy, —CN, —$C(O)OR^a$ or —$C(Y)NR^bR^{b'}$.

Item 15. The compound according to item 1 represented by general formula (III) or a salt thereof, wherein:

A is CH or N;

L is O, a direct bond or NH;

one of $X^1$, $X^2$, $X^3$, $X^4$ and $X^5$ is N and the others are CH;

m is 1, or 3:

n is 1, 2, 3 or 4;

$R^1$ is hydrogen, $C_1$-$C_8$ alkyl, $C_2$-$C_8$ alkenyl, $C_2$-$C_8$ alkynyl, alkoxyalkyl, hydroxyalkyl, heteroaryl, heteroarylalkyl, arylalkyl, —$C(Y)R^e$, cyclyl, cyclylalkyl or heterocyclyl, each of which is optionally substituted with 1-3 $R^7$;

$R^2$ is aryl or heteroaryl, each of which is optionally substituted with 1-5 $R^9$;

each $R^3$ or $R^4$ is independently hydrogen, $C_1$-$C_8$ alkyl, $C_2$-$C_8$ alkenyl, $C_2$-$C_8$ alkynyl, aryl, heteroaryl, cyclyl, heterocyclyl, arylalkyl, heteroarylalkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy, silylalkoxyalkyl, —CN, —$NO_2$, —$C(O)OR^a$, —$C(Y)NR^bR^{b'}$, —$NR^cC(Y)R^{c'}$, —$NR^bR^{b'}$, —$OC(O)NR^bR^{b'}$, —$NR^cC(O)OR^{c'}$, —$SO_2NR^bR^{b'}$, —$NR^cSO_2R^{c'}$, —$NR^cC(Y)NR^bR^{b'}$, —$OR^d$, —$SR^d$, —$C(Y)R^c$ or —$S(O)_qR^f$, each of which is optionally substituted with 1-3 $R^{10}$;

each $R^7$, $R^9$ and $R^{10}$ is independently $C_1$-$C_8$ alkyl, $C_2$-$C_8$ alkenyl, $C_2$-$C_8$ alkynyl, aryl, heteroaryl, cyclyl, heterocyclyl, arylalkyl, heteroarylalkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy, silylalkoxyalkyl, oxo, thioxo, —CN, —$NO_2$, —$C(O)OR^a$, —$C(Y)NR^bR^{b'}$, —$NR^cC(Y)R^{c'}$, $NR^bR^{b'}$, —$OC(O)NR^bR^{b'}$, —$NR^cC(O)OR^{c'}$, —$SO_2NR^bR^{b'}$, —$NR^cSO_2R^{c'}$, —$NR^cC(Y)NR^bR^{b'}$, —$OR^d$, —$SR^{d'}$, —$C(Y)R^e$ or —$S(O)_qR^f$, each of which is optionally substituted with 1-3 $R^{12}$; wherein two $R^7$ or two $R^9$ are optionally be taken together with the atoms to which they are attached to form an optionally substituted cyclyl, heterocyclyl, aryl or heteroaryl ring;

$R^{12}$ is independently $C_1$-$C_8$ alkyl, $C_2$-$C_8$ alkenyl, $C_2$-$C_8$ alkynyl, aryl, heteroaryl, cyclyl, heterocyclyl, arylalkyl, heteroarylalkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy, silylalkoxyalkyl, oxo, thioxo, —CN, —$NO_2$, —$C(O)OR^a$, —$C(Y)NR^bR^{b'}$, —$NR^cC(Y)R^{c'}$, —$NR^bR^{b'}$, —$OC(O)NR^bR^{b'}$, —$NR^cC(O)OR^{c'}$, —$SO_2NR^bR^{b'}$, —$NR^cSO_2R^{c'}$, —$NR^cC(Y)NR^bR^{b'}$, —$OR^d$, —$SR^{d'}$, —$C(Y)R^e$ or —$S(O)_qR^f$, each of which is optionally substituted with 1-3 $R^{13}$;

$R^{13}$ is independently $C_1$-$C_8$ alkyl, haloalkyl, halo, heterocyclyl, cyclyl, oxo or —$C(Y)NR^bR^{b'}$;

Y is or S;

q is 1 or 2; and each $R^a$, $R^b$, $R^{b'}$, $R^c$, $R^{c'}$, $R^d$, $R^{d'}$, $R^e$ and $R^f$ is independently hydrogen, $C_1$-$C_8$ alkyl, $C_2$-$C_8$ alkenyl, $C_2$-$C_8$ alkynyl, acyl, cyclyl, heterocyclyl, aryl, haloalkyl, alkoxyalkyl, alkylaminoalkyl, dialkylaminoalkyl, heteroaryl, cyclylalkyl, heterocyclylalkyl, arylalkyl or heteroarylalkyl.

Item 16. The compound according to item 15 represented by general formula (III) or a salt thereof, wherein:

m is 1;

n is 1;

$R^1$ is hydrogen, $C_1$-$C_8$ alkyl, $C_2$-$C_8$ alkenyl, $C_2$-$C_8$ alkynyl, heteroaryl, heterocyclyl, arylalkyl, cyclylalkyl, heteroarylalkyl, alkoxyalkyl, hydroxyalkyl or —C(O)$R^e$, each of which is optionally substituted with 1-3 $R^7$;

$R^2$ is aryl, heteroaryl or benzofuryl, each of which is optionally substituted with 1-5 $R^9$;

each $R^3$ or $R^4$ is independently hydrogen, $C_1$-$C_8$ alkyl, halo, haloalkyl or —O$R^d$;

$R^6$ is hydrogen or $C_1$-$C_8$ alkyl;

each $R^7$ and $R^9$ is independently $C_1$-$C_8$ alkyl, aryl, heteroaryl, halo, haloalkyl, haloalkoxy, hydroxyalkyl, alkoxyalkyl, oxo, —CN, —$NO_2$, —C(O)O$R^a$, —C(O)N$R^bR^{b'}$, —N$R^bR^{b'}$, —O$R^d$, —C(O)$R^e$ or —$S(O)_qR^f$, each of which is optionally substituted with 1-3 $R^{12}$;

$R^{12}$ is independently $C_1$-$C_8$ alkyl, oxo, halo, haloalkyl, —CN, —C(O)N$R^bR^{b'}$ or —C(O)$R^e$ each of which is optionally substituted with 1-3 $R^{13}$;

$R^{13}$ is independently $C_1$-$C_8$ alkyl, halo or heterocyclyl; and each $R^a$, $R^b$, $R^{b'}$, $R^c$, $R^{c'}$, $R^d$, $R^{d'}$, $R^e$ and $R^f$ is independently hydrogen, $C_1$-$C_8$ alkyl, cyclyl, heterocyclyl, arylalkyl, alkoxyalkyl, heterocyclylalkyl, heteroarylalkyl, alkylaminoalkyl, dialkylaminoalkyl or phenyl.

Item 17. The compound according to Item 16 represented by general formula (III) or a salt thereof, wherein:

$R^1$ is hydrogen, $C_1$-$C_8$ alkyl, $C_2$-$C_8$ alkenyl, $C_2$-$C_8$ alkynyl, alkoxyalkyl, hydroxyalkyl, imidazolyl, pyridylalkyl, phenylalkyl, oxazolylalkyl, thienylalkyl, thiazolidinyl isoindolyl, —C(O)$R^e$, dihydroindenyl, $C_3$-$C_8$ cycloalkyl, $C_3$-$C_8$ cycloalkylalkyl, piperidyl, morpholinyl, pyrrolidinyl, azetidinyl or piperazinyl, each of which is optionally substituted with 1-3 $R^7$;

$R^2$ is phenyl, naphthyl, benzofuryl, indazolyl, benzothienyl, pyridyl, pyrimidinyl, dihydrobenzodioxinyl, benzodioxolyl, benzoimidazolyl, isoxazolyl, pyrazolyl, indolinyl or benzoisoxazolyl, each of which is optionally substituted with 1-5 $R^9$;

each $R^3$ or $R^4$ is independently hydrogen, $C_1$-$C_8$ alkyl, halo, haloalkyl or —O$R^d$:

$R^6$ is hydrogen or $C_1$-$C_8$ alkyl;

each $R^7$ and $R^9$ is independently $C_1$-$C_8$ alkyl, phenyl, halo, haloalkyl, haloalkoxy, hydroxyalkyl, alkoxyalkyl, oxo, —CN, —$NO_2$, —C(O)O$R^a$, —C(O)N$R^bR^{b'}$, —N$R^bR^{b'}$, —O$R^d$, —C(O)$R^e$ or —$S(O)_qR^f$; and each $R^a$, $R^b$, $R^{b'}$, $R^c$, $R^{c'}$, $R^d$, $R^{d'}$, $R^e$ and $R^f$ is independently hydrogen, $C_1$-$C_8$ alkyl, $C_3$-$C_8$ cycloalkyl, pyrrolidinyl, piperidinyl, morpholinyl, piperazinyl, tetrahydropyranyl, phenylalkyl, alkoxyalkyl, morholinylalkyl, oxazolidinylalkyl, imidazolylalkyl, tetrahydropyranylalkyl, pyridylalkyl, pyrazolylalkyl, tetrazolylalkyl, thiazolylalkyl, pyrrolylalkyl, benzoxazolylalkyl, indazolylalkyl, dihydrobenzoxazinylalkyl, tetrahydrofurylalkyl, tetrahydrofuryl, alkylaminoalkyl, dialkylaminoalkyl or phenyl.

Item 18. The compound according to item 16 represented by general formula (III) or a salt thereof, wherein:

$R^1$ is hydrogen, $C_1$-$C_8$ alkyl, $C_2$-$C_8$ alkenyl, $C_2$-$C_8$ alkynyl, alkoxyalkyl, hydroxyalkyl, imidazolyl, furylalkyl, pyridylalkyl, phenylalkyl, oxazolylalkyl, thienylalkyl, thiazolidinyl, isoindolyl, —C(O)$R^e$, dihydroindenyl, $C_3$-$C_8$ cycloalkyl, $C_3$-$C_8$ cycloalkylalkyl, piperidyl, morpholinyl, pyrrolidinyl, azetidinyl or piperazinyl, each of which is optionally substituted with 1-3 $R^7$;

$R^2$ is phenyl, naphthyl, benzofuryl, indazolyl, benzothienyl, pyridyl, pyrimidinyl, dihydrobenzodioxinyl, benzodioxolyl, benzoimidazolyl, isoxazolyl, pyrazolyl, indolinyl or benzisoxazolyl, each of which is optionally substituted with 1-5 $R^9$;

each $R^3$ or $R^4$ is independently hydrogen, $C_1$-$C_8$ alkyl, halo, haloalkyl or —O$R^d$;

$R^6$ is hydrogen or $C_1$-$C_8$ alkyl;

each $R^7$ and $R^9$ is independently $C_1$-$C_8$ alkyl, phenyl, halo, haloalkyl, haloalkoxy, hydroxyalkyl, alkoxyalkyl, oxo, —CN, —$NO_2$, —C(O)O$R^a$, —C(O)N$R^bR^{b'}$, —N$R^bR^{b'}$, —O$R^d$, —C(O)$R^e$ or —$S(O)_qR^f$, each of which is optionally substituted with 1-3 $R^{12}$;

$R^{12}$ is independently $C_1$-$C_8$ alkyl, oxo, halo, haloalkyl, —CN, —C(O)N$R^bR^{b'}$ or —C(O)$R^e$, each of which is optionally substituted with 1-3 $R^{13}$;

$R^{13}$ is independently $C_1$-$C_8$ alkyl, halo or pyrrolidinyl; and each $R^a$, $R^b$, $R^{b'}$, $R^c$, $R^{c'}$, $R^d$, $R^{d'}$, $R^e$ and $R^f$ is independently hydrogen, $C_1$-$C_8$ alkyl, $C_3$-$C_8$ cycloalkyl, pyrrolidinyl, piperidyl, morpholinyl, piperazinyl, tetrahydropyranyl, phenylalkyl, alkoxyalkyl, morpholinylalkyl, oxazolidinylalkyl, imidazolylalkyl, tetrahydropyranylalkyl, pyridylalkyl, pyrazolylalkyl, tetrazolylalkyl, thiazolylalkyl, pyrrolylalkyl, benzoxazolylalkyl, indazolylalkyl, dihydrobenzoxazinylalkyl, tetrahydrofurylalkyl, tetrahydrofuryl, alkylaminoalkyl, dialkylaminoalkyl or phenyl.

Item 19. The compound according to idem 18 represented by general formula (III) or a salt thereof, wherein:

A is N;

$R^3$ is hydrogen, $C_1$-$C_8$ alkyl, halo, haloalkyl, or —O$R^d$;

$R^4$ is hydrogen, $C_1$-$C_8$ alkyl, halo, or —O$R^d$;

$R^7$ is $C_1$-$C_8$ alkyl, phenyl, halo, haloalkyl, oxo, —C(O)O$R^a$, —C(O)N$R^bR^{b'}$ or —O$R^d$ each of which is optionally substituted with 1-3 $R^{12}$;

$R^9$ is $C_1$-$C_8$ alkyl, phenyl, halo, haloalkyl, haloalkoxy, hydroxyalkyl, alkoxyalkyl, —CN, —$NO_2$, —C(O)N$R^bR^{b'}$, —C(O)O$R^a$, —N$R^bR^{b'}$, —O$R^d$, —C(O)$R^e$ or —$S(O)_qR^f$, each of which is optionally substituted with 1-3 $R^{12}$; and each $R^a$, $R^b$, $R^{b'}$, $R^c$, $R^{c'}$, $R^d$, $R^{d'}$, $R^e$ and $R^f$ is independently hydrogen, $C_1$-$C_8$ alkyl, $C_3$-$C_8$ cycloalkyl, pyrrolidinyl, piperidyl, morpholinyl, piperazinyl, tetrahydropyranyl, phenylalkyl, alkoxyalkyl, morpholinylalkyl, oxazolidinylalkyl, imidazolylalkyl, tetrahydropyranylalkyl, pyridylalkyl, pyrazolylalkyl, tetrazolylalkyl, thiazolylalkyl, pyrrolylalkyl, benzoxazolylalkyl, indazolylalkyl, tetrahydrofurylalkyl, dihydrobenzoxazinylalkyl, tetrahydrofuryl, alkylaminoalkyl, dialkylaminoalkyl or phenyl.

Item 20. The compound according to item 17 or 19 represented by general formula (III) or a salt thereof, wherein:

A is N;

$R^3$ is hydrogen, $C_1$-$C_8$ alkyl, halo, haloalkyl, or —O$R^d$;

$R^4$ is hydrogen, $C_1$-$C_8$ alkyl, halo, or —O$R^d$;

$R^7$ is $C_1$-$C_8$ alkyl, phenyl, halo, haloalkyl, oxo, —C(O)O$R^a$, —C(O)N$R^bR^{b'}$ or —O$R^d$;

$R^9$ is $C_1$-$C_8$ alkyl, phenyl, halo, haloalkyl, haloalkoxy, hydroxyalkyl, alkoxyalkyl, —CN, —$NO_2$, —C(O)N$R^bR^{b'}$, —C(O)O$R^a$, —N$R^bR^{b'}$, —O$R^d$, —C(O)$R^e$ or —$S(O)_qR^f$; and each $R^a$, $R^b$, $R^{b'}$, $R^c$, $R^{c'}$, $R^d$, $R^{d'}$, $R^e$ and $R^f$ is independently hydrogen, $C_1$-$C_8$ alkyl, $C_3$-$C_8$ cycloalkyl, pyrrolidinyl, piperidyl, morpholinyl, piperazinyl, tetrahydropyranyl, phenylalkyl, alkoxyalkyl, morpholinylalkyl, oxazolidinylalkyl, imidazolylalkyl, tetrahydropyranylalkyl, pyridylalkyl, pyrazolylalkyl, tetrazolylalkyl, thiazolylalkyl, pyrrolylalkyl, benzoxazolylalkyl, indazolylalkyl, tetrahydrofurylalkyl, tetrahydrofuryl, dihydrobenzoxazinylalkyl, alkylaminoalkyl, dialkylaminoalkyl or phenyl.

Item 21. The compound according to item 20 represented by general formula (III) or a salt thereof, wherein:

$R^1$ is hydrogen, $C_1$-$C_8$ alkyl, $C_2$-$C_8$ alkenyl, $C_2$-$C_8$ alkynyl, alkoxyalkyl, hydroxyalkyl, imidazolyl, furylalkyl, pyridylalkyl, phenylalkyl, oxazolylalkyl, thienylalkyl, isoindolyl, —C(O)$R^e$, dihydroindenyl, $C_3$-$C_8$ cycloalkyl, $C_3$-$C_8$ cycloalkylalkyl, piperidyl, morpholinyl, pyrrolidinyl, azetidinyl or piperazinyl, each of which is optionally substituted with 1-3 $R^7$;

$R^2$ is phenyl, which is optionally substituted with 1-5 $R^9$; and each $R^a$, $R^b$, $R^{b'}$, $R^c$, $R^{c'}$, $R^d$, $R^{d'}$, $R^e$ and $R^f$ is independently hydrogen, $C_1$-$C_8$ alkyl, pyrrolidinyl, morpholinyl, tetrahydropyranyl, alkoxyalkyl, morpholinylalkyl, tetrahydropyranylalkyl, pyridylalkyl, thiazolylalkyl, pyrrolylalkyl, tetrahydrofuryl, alkylaminoalkyl or phenyl.

Item 22. A pharmaceutical composition comprising the compound according to any one of items 1 to 21 or a salt thereof as an active ingredient and a pharmaceutically acceptable carrier.

Item 23. The pharmaceutical composition according to item 2 for preventing or treating central nervous system diseases.

Item 24. The pharmaceutical composition according to item 23 for treating or preventing central nervous system disorders selected from the group consisting of schizophrenia; refractory, intractable or chronic schizophrenia; emotional disturbance; psychotic disorder; mood disorder; bipolar I type disorder; bipolar II type disorder; depression; endogenous depression; major depression; melancholy and refractory depression; dysthymic disorder; cyclothymic disorder; panic attack; panic disorder; agoraphobia; social phobia; obsessive-compulsive disorder; post-traumatic stress disorder; generalized anxiety disorder; acute stress disorder; hysteria; somatization disorder; conversion disorder; pain disorder; hypochondriasis; factitious disorder; dissociative disorder; sexual dysfunction; sexual desire disorder; sexual arousal disorder; erectile dysfunction; anorexia nervosa; bulimia nervosa; sleep disorder; adjustment disorder; alcohol abuse; alcohol intoxication; drug addiction; stimulant intoxication; narcotism; anhedonia; iatrogenic anhedonia; anhedonia of a psychic or mental cause; anhedonia associated with depression; anhedonia associated with schizophrenia; delirium; cognitive impairment; cognitive impairment associated with Alzheimer's disease, Parkinson's disease and other neurodegenerative diseases; cognitive impairment caused by Alzheimer's disease; Parkinson's disease and associated neurodegenerative diseases; cognitive impairment of schizophrenia; cognitive impairment caused by refractory, intractable or chronic schizophrenia; vomiting; motion sickness: obesity; migraine; pain (ache); mental retardation; autism disorder (autism); Tourette's disorder; tic disorder; attention-deficit/hyperactivity disorder; conduct disorder; and Down's syndrome.

Item 25. A process for producing a pharmaceutical composition comprising mixing a compound of the formula (I), (II), or (III) or a salt thereof according to any one of items 1 to 21 with a pharmaceutically acceptable carrier.

Item 26. Use of a compound of the formula (I), (II) or (III) or a salt thereof according to any one of items 1 to 21 as a drug.

Item 27. Use of the compound according to any one of items 1 to 21 represented by general formula (I), (II) or (III) or a salt thereof as a STEP inhibitor.

Item 28. A method of treating a disorder that would benefit by the modulation of STEP (e.g., by activation of inhibition of STEP) in a subject, the method comprising administering to a compound of formula (I), (II) or (III) or a salt thereof according to any one of items 1 to 21.

Item 29. The method of item 28, wherein the disorder is schizophrenia.

Item 30. The method of item 28, wherein the disorder is cognitive deficit.

Item 31. The method of item 28, wherein the compound of formula (I), (II), or (III) is administered in combination with an additional therapeutic agent.

Item 32. The method of item 28, wherein the additional therapeutic agent is an atypical antipsychotic.

Item 33. The method of item 28, wherein the additional therapeutic agent is selected from the group consisting of aripiprazole, clozapine, ziprasidone, risperidone, quetiapine, olanzapine, amisulpride, asenapine, iloperidone, melperone, paliperidone, perospirone, sertindole and sulpiride.

Item 34. The method of item 28, wherein the additional therapeutic agent is a typical antipsychotic.

Item 35. The method of item 28, wherein the additional therapeutic agent is selected from the group consisting of haloperidol, molindone, loxapine, thioridazine, molindone, thiothixene, pimozide, fluphenazine, trifluoperazine, mesoridazine, chlorprothixene, chlorpromazine, perphenazine, triflupromazine and zuclopenthixol.

Item 36. A kit comprising a composition comprising a compound of formula (I), (II), or (III) or a salt thereof according to any one of items 1 to 21 and an acceptable carrier, Item 37. A kit comprising a pharmaceutical composition comprising a compound of formula (I), (II), or (III) or a salt thereof according to any one of items 1 to 21 and a pharmaceutically acceptable carrier.

Item 38. A compound of formula (IV):

(IV)

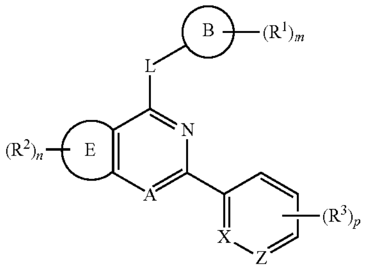

wherein:

A is CH, $CR^4$ or N;

B is aryl or a 5- or 6-membered heteroaryl:

m is 0, 1, 2, 3, 4 or 5:

E is aryl or a 5-membered heteroaryl;

when E is aryl, n is 1, 2, 3 or 4; and when E is a 5-membered heteroaryl, n is 0, 1, 2 or 3;

L is $NR^5$ or O;

one of X and Z is N and the other is CH;

p is 0, 1, 2, 3 or 4;

each $R^1$, $R^2$ and $R^3$ is independently $C_1$-$C_8$ alkyl, $C_2$-$C_8$ alkenyl, $C_2$-$C_8$ alkynyl, aryl, heteroaryl, cyclyl, heterocyclyl, aralkyl, heteroaralkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy, silylalkoxyalkyl, —CN, —$NO_2$, —C(O)$OR^a$, —C(Y)$NR^bR^{b'}$, —$NR^cC(Y)R^{c'}$, —$NR^bR^{b'}$, —OC(O)$NR^bR^{b'}$, —$NR^cC(O)OR^{c'}$, —$SO_2NR^bR^{b'}$, —$NR^cSO_2R^{c'}$, —$NR^cC(Y)NR^bR^{b'}$, —$OR^d$, —$SR^{d'}$, —C(Y)$R^e$ or —$S(O)_q R^f$, each of which may be optionally substituted with 1-3 $R^6$; wherein two $R^1$, together with the atoms to which they are attached, may form an optionally substituted cyclyl, heterocyclyl, aryl or heteroaryl ring;

$R^4$ is hydrogen, $C_1$-$C_8$ alkyl, $C_2$-$C_8$ alkenyl, $C_2$-$C_8$ alkynyl, aryl, heteroaryl, cyclyl, heterocyclyl, aralkyl, heteroaralkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy, silylalkoxyalkyl, —CN, —$NO_2$, —C(O)$OR^a$, —C(Y)$NR^bR^{b'}$, —$NR^cC(Y)R^{c'}$, —$NR^bR^{b'}$, —OC(O)$NR^bR^{b'}$, —$NR^cC(O)OR^{c'}$, —$SO_2NR^bR^{b'}$, —$NR^cSO_2R^{c'}$, —$NR^cC(Y)NR^bR^{b'}$, —$OR^d$, —$SR^{d'}$, —C(Y)$R^e$ or —$S(O)_qR^f$, each of which may be optionally substituted with 1-3 $R^6$;

$R^5$ is hydrogen; or when in is not 0, $R^5$ and 1 $R^1$ may be taken together with the atoms to which they are attached to form an optionally substituted heteroaryl or heterocyclyl ring;

each $R^6$ is independently $C_1$-$C_8$ alkyl, $C_2$-$C_8$ alkenyl, $C_1$-$C_8$ alkynyl, aryl, heteroaryl, cyclyl, heterocyclyl, aralkyl, heteroaralkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy, silylalkoxyalkyl, oxo, thiono, —CN, —$NO_2$, —C(O)$OR^a$, —C(Y)$NR^bR^{b'}$, —$NR^cC(Y)R^c$, —$NR^bR^{b'}$, —OC(O)$NR^bR^{b'}$, —$NR^cC(O)OR^{c'}$, —$SO_2NR^bR^{b'}$, —$NR^cSO_2R^{c'}$, —$NR^cC(Y)NR^bR^{b'}$, —$OR^d$, —$SR^{d'}$, —C(Y)$R^e$ or —$S(O)_qR^f$, each of which may be optionally substituted with 1-3 $R^7$;

each $R^7$ is independently $C_1$-$C_8$ alkyl, $C_2$-$C_8$ alkenyl, $C_2$-$C_8$ alkynyl, aryl, heteroaryl, cyclyl, heterocyclyl, aralkyl, heteroaralkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy, silylalkoxyalkyl, oxo, thiono, —CN, —$NO_2$, —C(O)$OR^a$, —C(Y)$NR^bR^{b'}$, —$NR^cC(Y)R^{c'}$, —$NR^bR^{b'}$, —OC(O)$NR^bR^{b'}$, —$NR^cC(O)OR^a$, —$SO_2NR^bR^{b'}$, —$NR^cSO_2R^{c'}$, —$NR^cC(Y)NR^bR^{b'}$, —$OR^d$, —$SR^{d'}$, —C(Y)$R^e$ or —$S(O)_qR^f$;

each Y is independently O or S;

q is 1 or 2; and each $R^a$, $R^b$, $R^{b'}$, $R^c$, $R^{c'}$, $R^d$, $R^{d'}$, $R^d$, $R^e$, $R^{e'}$ and $R^f$ is independently selected from hydrogen, $C_1$-$C_8$ alkyl, $C_2$-$C_8$ alkenyl, $C_2$-$C_8$ alkynyl, acyl, aryl, heteroaryl, cyclyl, heterocyclyl, aralkyl, heteroaralkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy and silylalkoxyalkyl, each of which may be optionally substituted with 1-3 $R^6$, wherein $R^b$ and $R^{b'}$, together with the atoms to which they are attached, may form an optionally substituted cyclyl or heterocyclyl ring;

or a pharmaceutically acceptable derivative or prodrug thereof, wherein when B is phenyl, two $R^1$ are not taken together to form a pyrazole ring;

when B is phenyl, $R^2$ is not

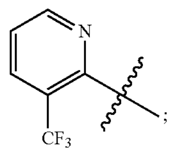

and where in the compound is not:

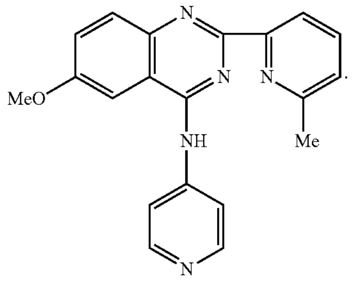 [SMILES: COc1ccc2nc(-c3cccc(C)n3)nc(Nc3ccncc3)c2c1]

Item 39. A compound of formula (IV):

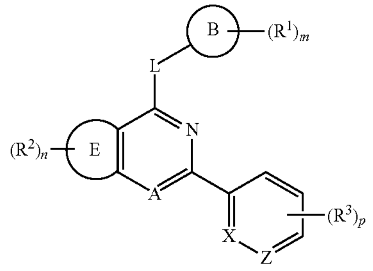

(IV)

wherein:

A is CH, $CR^4$ or N;

B is aryl or a 5-membered heteroaryl;

E is aryl or a 5-membered heteroaryl;

L is $NR^5$ or O;

one of X and Z is N and the other is CH;

m is 0, 1, 2, 3, 4 or 5;

n is 1, 2, 3 or 4;

p is, 1, 2, 3 or 4;

each $R^1$ and $R^3$ is independently $C_1$-$C_8$ alkyl, $C_2$-$C_8$ alkenyl, $C_2$-$C_8$ alkynyl, aryl, heteroaryl, cyclyl, heterocyclyl, aralkyl, heteroaralkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy, silylalkoxyalkyl, —CN, —$NO_2$, —C(O)$OR^a$, —C(Y)$NR^bR^{b'}$, —$NR^cC(Y)R^{c'}$, —$NR^bR^{b'}$, —OC(O)$NR^bR^{b'}$, —$NR^cC(O)OR^{c'}$, —$SO_2NR^bR^{b'}$, —$NR^cSO_2R^{c'}$, —$NR^cC(Y)NR^bR^{b'}$, —$OR^d$, —$SR^{d'}$, —C(Y)$R^e$ or —$S(O)_qR^f$, each of which may be optionally substituted with 1-3 $R^6$; wherein two $R^1$, together with the atoms to which they are attached, may form an optionally substituted cyclyl, heterocyclyl, or aryl ring;

each $R^2$ is independently $C_1$-$C_8$ alkyl, $C_2$-$C_8$ alkenyl, $C_2$-$C_8$ alkynyl, aryl, cyclyl, heterocyclyl, aralkyl, heteroaralkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy, silylalkoxyalkyl, —CN, —$NO_2$, —C(O)$OR^a$, —C(Y)$NR^bR^{b'}$, —$NR^cC(Y)R^{c'}$, —$NR^bR^{b'}$, —OC(O)$NR^b$ $R^{b'}$, —$NR^cC(O)OR^{c'}$, —$SO_2NR^bR^{b'}$, —$NR^cSO_2R^{c'}$, —$NR^cC(Y)NR^bR^{b'}$, —$OR^d$, —$SR^{d'}$, —$C(Y)R^e$ or —$S(O)_qR^f$, each of which may be optionally substituted with 1-3 $R^6$; wherein two $R^1$, together with the carbons to which they are attached, may form an optionally substituted cyclyl, heterocyclyl, aryl or heteroaryl ring;

$R^4$ is hydrogen, $C_1$-$C_8$ alkyl, $C_2$-$C_8$ alkenyl, $C_2$-$C_8$ alkynyl, aryl, heteroaryl, cyclyl, heterocyclyl, aralkyl, heteroaralkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy, silylalkoxyalkyl, —CN, —$NO_2$, —C(O)OR, —$C(Y)NR^bR^{b'}$, —$NR^cC(Y)R^{c'}$, —$NR^bR^{b'}$, —$OC(O)NR^bR^{b'}$, —$NR^cC(O)OR^{c'}$, —$SO_2NR^bR^{b'}$, —$NR^cSO_2R^{c'}$, —$NR^cC(Y)NR^bR^{b'}$, —$OR^d$, —$SR^{d'}$, —$C(Y)R^e$ or —$S(O)_qR^f$, each of which may be optionally substituted with 1-3 $R^6$;

$R^5$ is hydrogen; or when m is not 0, $R^5$ and 1 $R^1$ may be taken together with the atoms to which they are attached to form an optionally substituted heteroaryl or heterocyclyl ring;

each $R^6$ is independently $C_1$-$C_8$ alkyl, $C_2$-$C_8$ alkenyl, $C_1$-$C_8$ alkynyl, aryl, heteroaryl, cyclyl, heterocyclyl, aralkyl, heteroaralkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy, silylalkoxyalkyl, oxo, thiono, —CN, —$NO_2$, —$C(O)OR^a$, —$C(Y)NR^bR^{b'}$, —$NR^cC(Y)R^{c'}$, —$NR^bR^{b'}$, —$OC(O)NR^bR^{b'}$, —$NR^c(C(O)OR^{c'}$, —$SO_2NR^bR^{b'}$, —$NR^cSO_2R^{c'}$, —$NR^c(Y)NR^bR^{b'}$, —$OR^d$, —$SR^{d'}$, —$C(Y)R^e$ or —$S(O)_qR^f$, each of which may be optionally substituted with 1-3 $R^7$;

each $R^7$ is independently $C_1$-$C_8$ alkyl, $C_2$-$C_8$ alkenyl, $C_2$-$C_8$ alkynyl, aryl, heteroaryl, cyclyl, heterocyclyl, aralkyl, heteroaralkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy, silylalkoxyalkyl, oxo, thiono, —CN, —$NO_2$, —$C(O)OR^a$, —$C(Y)NR^bR^{b'}$, —$NR^cC(Y)R^{c'}$, —$NR^bR^{b'}$, —$OC(O)NR^bR^{b'}$, —$NR^cC(O)OR^{c'}$, —$SO_2NR^bR^{b'}$, —$NR^cSO_2R^{c'}$, —$NR^cC(Y)NR^bR^{b'}$, —$OR^d$, —$SR^{d'}$, —$C(Y)R^e$ or —$S(O)_qR^f$;

Y is O or S;

q is 1 or 2; and each $R^a$, $R^b$, $R^{b'}$, $R^c$, $R^{c'}$, $R^d$, $R^{d'}$, $R^e$, $R^{e'}$ and $R^f$ is independently selected from hydrogen, $C_1$-$C_8$ alkyl, $C_2$-$C_8$ alkenyl, $C_2$-$C_8$ alkynyl, acyl, cyclyl, heterocyclyl, aryl, heteroaryl, cyclylalkyl, heterocyclylalkyl, aralkyl and heteroaralkyl, each of which may be optionally further substituted with 1-3 $R^6$, wherein $R^b$ and $R^{b'}$, together with the atoms to which they are attached, may form an optionally substituted cyclyl or heterocyclyl ring;

wherein when 13 is phenyl, two $R^1$ are not taken together to form a pyrazole ring; and when B is phenyl, $R^2$ is not

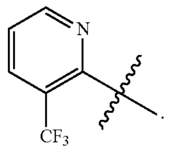

Item 40. A compound of formula (V):

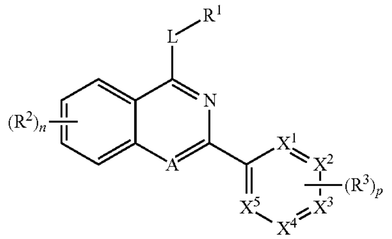

(V)

wherein:

L is $CR^4R^5$, O, C(O), $NR^6C(O)$, or $NR^7$;

A is $CR^8$, CH or N;

each $X^1$, $X^2$, $X^3$, $X^4$ and $X^5$ is independently CH or N, provided that at least two of $X^1$, $X^2$, $X^2$, $X^4$ and $X^5$ are N:

n is 0, 1, 2, 3 or 4;

p is 0, 1, 2 or 3;

$R^1$ is $C_1$-$C_8$ alkyl, $C_2$-$C_8$ alkenyl, $C_2$-$C_8$ alkynyl, aryl, heteroaryl, cyclyl, heterocyclyl, aralkyl, heteroaralkyl, cyclylalkyl or heterocyclylalkyl, each of which may be optionally substituted with 1-5 $R^9$; wherein $R^1$ or $R^9$ may optionally be taken together with one of $R^4$, $R^5$, $R^6$ or $R^7$, and the atoms to which they are attached, to form a cyclyl, heterocyclyl, aryl or heteroaryl ring that is optionally substituted with 1-3 $R^{10}$;

each $R^2$ and $R^3$ is independently $C_1$-$C_8$ alkyl, $C_2$-$C_8$ alkenyl, $C_2$-$C_8$ alkynyl, aryl, heteroaryl, cyclyl, heterocyclyl, aralkyl, heteroaralkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy, silylalkoxyalkyl, —CN, —$NO_2$, —$C(O)OR^a$, —$C(Y)NR^bR^{b'}$, —$NR^cC(Y)R^{c'}$, —$NR^bR^{b'}$, —$OC(O)NR^bR^{b'}$, —$NR^cC(O)OR^{c'}$, —$SO_2NR^bR^{b'}$, —$NR^cSO_2R^{c'}$, —$NR^cC(Y)NR^bR^{b'}$, —$OR^d$, —$SR^{d'}$, —$C(Y)R^e$ or —$S(O)_qR^f$; each of which is optionally substituted with 1-3 $R^{11}$;

each $R^4$, $R^5$, $R^6$ and $R^7$ is independently H, $C_1$-$C_8$ alkyl, $C_2$-$C_8$ alkenyl, $C_2$-$C_8$ alkynyl, aryl, heteroaryl, cyclyl, heterocyclyl, aralkyl, heteroaralkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy, silylalkoxyalkyl, —CN, —$NO_2$, —$C(O)OR^a$, —$C(Y)NR^bR^{b'}$, —$NR^cC(Y)R^{c'}$, —$NR^bR^{b'}$, —$OC(O)NR^bR^{b'}$, —$NR^cC(O)OR^{c'}$, —$SO_2NR^bR^{b'}$, —$NR^cSO_2R^{c'}$, —$NR^cC(Y)NR^bR^{b'}$, —$OR^d$, —$SR^{d'}$, —$C(Y)R^e$ or —$S(O)_qR^f$;

each $R^8$, $R^9$, $R^{10}$ and $R^{11}$ is independently $C_1$-$C_8$ alkyl, $C_2$-$C_8$ alkenyl, $C_2$-$C_8$ alkynyl, aryl, heteroaryl, cyclyl, heterocyclyl, aralkyl, heteroaralkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy, silylalkoxyalkyl, oxo, thiono, —CN, —$NO_2$, —$C(O)OR^a$, —$C(Y)NR^bR^{b'}$, —$NR^c(Y)R^{c'}$, —$NR^bR^{b'}$, —$OC(O)NR^bR^{b'}$, —$NR^cC(O)OR^{c'}$, —$SO_2NR^bR^{b'}$, —$NR^cSO_2R^{c'}$, —$NR^cC(Y)NR^bR^{b'}$, —$OR^d$, —$SR^{d'}$, —$C(Y)R^e$ or —$S(O)_qR^f$, each of which may be optionally further substituted; wherein two $R^8$, two $R^9$, two $R^{10}$ or two $R^{11}$ may optionally be taken together with the atoms to which they are attached to form an optionally substituted cyclyl, heterocyclyl, aryl or heteroaryl ring;

each Y is independently O or S;

q is 1 or 2; and each $R^a$, $R^b$, $R^{b'}$, $R^c$, $R^{c'}$, $R^d$, $R^{d'}$, $R^e$, $R^{e'}$ and $R^f$ is independently selected from hydrogen, $C_1$-$C_8$ alkyl, $C_2$-$C_8$ alkenyl, $C_2$-$C_8$ alkynyl, acyl, cyclyl, heterocyclyl, aryl, heteroaryl, cyclylalkyl, heterocyclylalkyl, aralkyl and heteroaralkyl, each of which may be optionally substituted with 1-3 $R^8$, or a pharmaceutically acceptable derivative or prodrug thereof.

Item 41. A compound of formula (VI):

(VI)

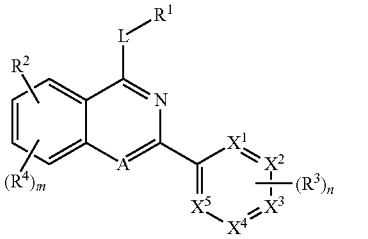

wherein:

A is $CR^5$, CH or N;

L is O or $NR^6$;

1, 2 or 3 of $X^1$, $X^2$, $X^3$, $X^4$ and $X^5$ are N and the others are CH;

m is 0, 1, 2 or 3;

n is 0, 1, 2, 3 or 4;

$R^1$ is hydrogen, $C_1$-$C_8$ alkyl, $C_2$-$C_8$ alkenyl, $C_2$-$C_8$ alkynyl, cyclyl or heterocyclyl, each of which is optionally substituted with 1-3 $R^7$; or when L is $NR^6$, $R^1$ or $R^7$ may be taken together with $R^6$ and the atoms to which they are attached to form a heterocyclyl or heteroaryl ring that is optionally substituted with 1-3 $R^8$;

$R^2$ is aryl or heteroaryl, each of which is optionally substituted with 1-5 $R^9$;

each $R^3$, $R^4$ and $R^5$ is independently $C_1$-$C_8$ alkyl, $C_2$-$C_8$ alkenyl, $C_2$-$C_8$ alkynyl, aryl, heteroaryl, cyclyl, heterocyclyl, aralkyl, heteroaralkyl, cyclylalkyl, heterocyclyalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy, silylalkoxyalkyl, —CN, —$NO_2$, —C(O)$OR^a$, —C(Y)$NR^bR^{b'}$, —$NR^cC(Y)R^{c'}$, —$NR^bR^{b'}$, —OC(O)$NR^bR^{b'}$, —$NR^cC(O)OR^{c'}$, —$SO_2NR^bR^{b'}$, —$NR^cSO_2R^{c'}$, —$NR^cC(Y)NR^bR^{b'}$, —$OR^d$, —$SR^{d'}$, —C(Y)$R^e$ or —$S(O)_qR^f$, each of which is optionally substituted with 1-3 $R^{10}$;

$R^6$ is hydrogen, $C_1$-$C_8$ alkyl, $C_2$-$C_8$ alkenyl, $C_2$-$C_8$ alkynyl, cyclyl or heterocyclyl, each of which is optionally substituted with 1-3 $R^{11}$;

each $R^7$, $R^8$, $R^9$ and $R^{10}$ is independently $C_1$-$C_8$ alkyl, $C_2$-$C_8$ alkenyl, $C_2$-$C_8$ alkynyl, aryl, heteroaryl, cyclyl, heterocyclyl, aralkyl, heteroaralkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy, silylalkoxyalkyl, oxo, thiono, —CN, —$NO_2$, —C(O)$OR^a$, —C(Y)$NR^bR^{b'}$, —$NR^cC(Y)R^{c'}$, —$NR^bR^{b'}$, —OC(O)$NR^bR^{b'}$, —$NR^cC(O)OR^{c'}$, —$SO_2NR^bR^{b'}$, —$NR^cSO_2R^{c'}$, —$NR^cC(Y)NR^bR^{b'}$, —$OR^d$, —$SR^{d'}$, —C(Y)$R^e$ or —$S(O)_qR^f$, each of which is optionally substituted with 1-3 $R^{12}$; wherein two $R^7$, two $R^8$, two $R^9$ or two $R^{10}$ may optionally be taken together with the atoms to which they are attached to form an optionally substituted cyclyl, heterocyclyl, aryl or heteroaryl ring;

each $R^{11}$ and $R^{12}$ is independently $C_1$-$C_8$ alkyl, $C_2$-$C_8$ alkenyl, $C_2$-$C_8$ alkynyl, aryl, heteroaryl, cyclyl, heterocyclyl, aralkyl, heteroaralkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy, silylalkoxyalkyl, oxo, thiono, —CN, —$NO_2$, —C(O)$OR^a$, —C(Y)$NR^bR^{b'}$, —$NR^c(Y)R^{c'}$, —$NR^bR^{b'}$, —OC(O)$NR^bR^{b'}$, —$NR^cC(O)OR^{c'}$, —$SO_2NR^bR^{b'}$, —$NR^cSO_2R^{c'}$, —$NR^cC(Y)NR^bR^{b'}$, —$OR^d$, —$SR^{d'}$, —C(Y)$R^e$ or —$S(O)_qR^f$;

each Y is independently O or S;

q is 1 or 2; and each $R^a$, $R^b$, $R^{b'}$, $R^c$, $R^{c'}$, $R^d$, $R^{d'}$, $R^e$, $R^{e'}$ and $R^f$ is independently selected from hydrogen, $C_1$-$C_8$ alkyl, $C_2$-$C_8$ alkenyl, $C_2$-$C_8$ alkynyl, acyl, cyclyl, heterocyclyl, aryl, heteroaryl, cyclylalkyl, heterocyclylalkyl, aralkyl and heteroaralkyl, each of which may be optionally substituted with 1-3 $R^7$;

or a pharmaceutically acceptable derivative or prodrug thereof, wherein when $R^1$ is cyclopropyl, $R^9$ is not:

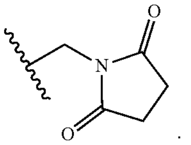 [SMILES: *CN1C(=O)CCC1=O]

Item 42. A compound of formula (VI):

(VI)

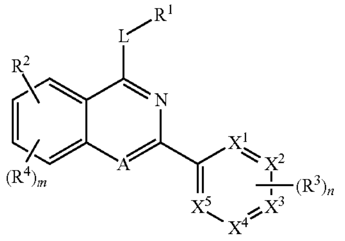

wherein:

A is $CR^5$, CH or N;

L is O or $NR^6$;

1, 2 or 3 of $X^1$, $X^2$, $X^3$, $X^4$ and $X^5$ are N and the others are CH;

m is 0, 1, 2 or 3;

n is 0, 1, 2, 3 or 4;

$R^1$ is hydrogen, $C_1$-$C_8$ alkyl, $C_2$-$C_8$ alkenyl, $C_2$-$C_8$ alkynyl, cyclyl or heterocyclyl, each of which is optionally substituted with 1-3 $R^7$; or when L is $NR^6$, $R^1$ or $R^7$ may be taken together with $R^6$ and the atoms to which they are attached to form a heterocyclyl or heteroaryl ring that is optionally substituted with 1-3 $R^8$;

$R^2$ is aryl or heteroaryl, each of which is optionally substituted with 1-5 $R^9$;

each $R^3$, $R^4$ and $R^1$ is independently $C_1$-$C_8$ alkyl, $C_2$-$C_8$ alkenyl, $C_2$-$C_8$ alkynyl, aryl, heteroaryl, cyclyl, heterocyclyl, aralkyl, heteroaralkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy, silylalkoxyalkyl, —CN, —$NO_2$, —C(O)$OR^a$, —C(Y)$NR^bR^{b'}$, —$NR^cC(Y)R^{c'}$, —$NR^bR^{b'}$, —OC(O)$NR^bR^{b'}$, —$NR^cC(O)OR^{c'}$, —$SO_2NR^bR^{b'}$, —$NR^cSO_2R^{c'}$, —$NR^cC(Y)NR^bR^{b'}$, —$OR^d$, —$SR^{d'}$, —C(Y)$R^e$ or —$S(O)_qR^f$, each of which is optionally substituted with 1-3 $R^{11}$;

$R^6$ is hydrogen, $C_1$-$C_8$ alkyl, $C_2$-$C_8$ alkenyl, $C_2$-$C_8$ alkynyl, cyclyl or heterocyclyl, each of which is optionally substituted with 1-3 $R^{11}$;

each $R^7$, $R^8$, $R^9$ and $R^{10}$ is independently $C_1$-$C_8$ alkyl, $C_2$-$C_8$ alkenyl, $C_2$-$C_8$ alkynyl, aryl, heteroaryl, cyclyl, heterocyclyl, aralkyl, heteroaralkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy, silylalkoxyalkyl, oxo, thiono, —CN, —$NO_2$, —C(O)$OR^a$, —C(Y)$NR^bR^{b'}$, —$NR^c$C(Y)$R^{c'}$, —$NR^bR^{b'}$, —OC(O)$NR^bR^{b'}$, —$NR^c$C(O)$OR^{c'}$, —$SO_2NR^bR^{b'}$, —$NR^cSO_2R^{c'}$, —$NR^c$C(Y)$NR^bR^{b'}$, —$OR^d$, —$SR^{d'}$, —C(Y)$R^e$ or —S(O)$_qR^f$, each of which is optionally substituted with 1-3 $R^{12}$; wherein two $R^7$, two $R^8$, two $R^9$ or two $R^{10}$ may optionally be taken together with the atoms to which they are attached to form an optionally substituted cyclyl, heterocyclyl, aryl or heteroaryl ring;

each $R^{11}$ and $R^{12}$ is independently $C_1$-$C_8$ alkyl, $C_2$-$C_8$ alkenyl, $C_2$-$C_8$ alkynyl, aryl, heteroaryl, cyclyl, heterocyclyl, aralkyl, heteroaralkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy, silylalkoxyalkyl, oxo, thiono, —CN, —$NO_2$, —C(O)$OR^a$, —C(Y)$NR^bR^{b'}$, —$NR^c$C(Y)$R^{c'}$, —$NR^bR^{b'}$, —OC(O)$NR^bR^{b'}$, —$NR^c$C(O)$OR^{c'}$, —$SO_2NR^bR^{b'}$, —$NR^cSO_2R^{c'}$, —$NR^c$C(Y)$NR^bR^{b'}$, —$OR^d$, —$SR^{d'}$, —C(Y)$R^e$ or —S(O)$_qR^f$;

each Y is independently O or S;

q is 1 or 2; and each $R^a$, $R^b$, $R^{b'}$, $R^c$, $R^{c'}$, $R^d$, $R^{d'}$, $R^e$, $R^{e'}$ and $R^f$ is independently selected from hydrogen, $C_1$-$C_8$ alkyl, $C_2$-$C_8$ alkenyl, $C_2$-$C_8$ alkynyl, acyl, cyclyl, heterocyclyl, aryl, heteroaryl, cyclylalkyl, heterocyclylalkyl, aralkyl and heteroaralkyl, each of which may be optionally substituted with 1-3 $R^7$;

wherein $R^9$ is not:

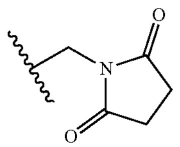

.

Compounds of Formula (I)

The following aspects and embodiments relate to compounds of formula (I).

Item 2. The compound according to item 1 represented by general formula (I) or a salt thereof, wherein:

A is $CR^4$ or N;

B is aryl, cyclyl or a 5- or 6-membered heteroaryl;

m is 0, 1, 2, 3, 4 or 5;

n is 0, 1, 2, 3 or 4;

E is aryl or a 5-membered heteroaryl;

when E is aryl, n is 0, 1, 2, 3 or 4; and when E is a 5-membered heteroaryl, n is 0, 1, 2 or 3;

L is $NR^5$, S, O or a direct bond;

one of X and Z is N and the other is CH;

p is 0, 1, 2, 3 or 4;

each $R^1$, $R^2$ and $R^3$ is independently $C_1$-$C_8$ alkyl, $C_2$-$C_8$ alkenyl, $C_2$-$C_8$ alkynyl, aryl, heteroaryl, cyclyl, heterocyclyl, arylalkyl, heteroarylalkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silyloxyalkynyl, silylalkoxy, silylalkoxyalkyl, —CN, oxo, —$NO_2$, —C(O)$OR^a$, —C(Y)$NR^bR^{b'}$, —$NR^c$C(Y)$R^{c'}$, —$NR^bR^{b'}$, —OC(O)$NR^bR^{b'}$, —$NR^c$C(O)$OR^{c'}$, —$SO_2NR^bR^{b'}$, —$NR^cSO_2R^{c'}$, —$NR^c$C(Y)$NR^bR^{b'}$, —$OR^d$, —$SR^{d'}$, —C(Y)$R^e$ or —S(O)$_qR^f$, each of which is optionally substituted with 1-3 $R^6$; wherein two $R^1$, together with the atoms to which they are attached, may form an optionally substituted cyclyl, heterocyclyl, aryl or heteroaryl ring;

$R^4$ is hydrogen, $C_1$-$C_8$ alkyl, $C_2$-$C_8$ alkenyl, $C_2$-$C_8$ alkynyl, aryl, heteroaryl, cyclyl, heterocyclyl, arylalkyl, heteroarylalkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy, silylalkoxyalkyl, —CN, —$NO_2$, C(O)$OR^a$, —C(Y)$NR^bR^{b'}$, —$NR^c$C(Y)$R^{c'}$, —$NR^bR^{b'}$, —OC(O)$NR^bR^{b'}$, —$NR^c$C(O)$OR^{c'}$, —$SO_2NR^bR^{b'}$, —$NR^cSO_2R^{c'}$, —$NR^c$C(Y)$NR^bR^{b'}$, —$OR^d$, —$SR^{d'}$, —C(Y)$R^e$ or —S(O)$_qR^f$, each of which is optionally substituted with 1-3 $R^6$;

$R^5$ is hydrogen; or when m is not 0, $R^5$ and one $R^1$ may be taken together with the atoms to which they are attached to form an optionally substituted heteroaryl or heterocyclyl ring;

each $R^6$ is independently $C_1$-$C_8$ alkyl, $C_2$-$C_8$ alkenyl, $C_2$-$C_8$ alkynyl, aryl, heteroaryl, cyclyl, heterocyclyl, arylalkyl, heteroarylalkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy, silylalkoxyalkyl, oxo, thioxo, —CN, —$NO_2$, —C(O)$OR^a$, —C(Y)$NR^bR^{b'}$, —$NR^c$C(Y)$R^{c'}$, —$NR^bR^{b'}$, —OC(O)$NR^bR^{b'}$, —$NR^c$C(O)$OR^{c'}$, —$SO_2NR^bR^{b'}$, —$NR^cSO_2R^{c'}$, —$NR^c$C(Y)$NR^bR^{b'}$, —$OR^d$, —$SR^{d'}$, —C(Y)$R^e$ or —S(O)$_qR^f$, each of which is optionally substituted with 1-3 $R^7$;

each $R^7$ is independently $C_1$-$C_8$ alkyl, $C_2$-$C_8$ alkenyl, $C_2$-$C_8$ alkynyl, aryl, heteroaryl, cyclyl, heterocyclyl, arylalkyl, heteroarylalkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy, silylalkoxyalkyl, oxo, thioxo, —CN, —$NO_2$, —C(O)$OR^a$, —C(Y)$NR^bR^{b'}$, —$NR^c$C(Y)$R^{c'}$, —$NR^bR^{b'}$, —OC(O)$NR^bR^{b'}$, —$NR^c$C(O)$OR^{c'}$, —$SO_2NR^bR^{b'}$, —$NR^cSO_2R^{c'}$, —$NR^c$C(Y)$NR^bR^{b'}$, —$OR^d$, —$SR^{d'}$, —C(Y)$R^e$ or —S(O)$_qR^f$, each of which is optionally substituted with 1-3 $R^9$;

each $R^9$ is independently $C_1$-$C_8$ alkyl, $C_2$-$C_8$ alkenyl, $C_2$-$C_8$ alkynyl, aryl, heteroaryl, cyclyl, heterocyclyl, arylalkyl, heteroarylalkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy, silylalkoxyalkyl, oxo, thioxo, —CN, —$NO_2$, —C(O)$OR^a$, —C(Y)$NR^bR^{b'}$, —$NR^c$C(Y)$R^{c'}$, —$NR^bR^{b'}$, —OC(O)$NR^bR^{b'}$, —$NR^c$C(O)$OR^{c'}$, —$SO_2NR^bR^{b'}$, —$NR^cSO_2R^{c'}$, —$NR^c$C(Y)$NR^bR^{b'}$, —$OR^d$, —$SR^{d'}$, —C(Y)$R^e$ or —S(O)$_qR^f$;

Y is O or S;

q is 1 or 2; and each $R^a$, $R^b$, $R^{b'}$, $R^c$, $R^{c'}$, $R^d$, $R^{d'}$, $R^e$ and $R^f$ is independently hydrogen, $C_1$-$C_8$ alkyl, $C_2$-$C_8$ alkenyl, $C_2$-$C_8$ alkynyl, acyl, aryl, heteroaryl, cyclyl, heterocyclyl, arylalkyl, heteroarylalkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy or silylalkoxyalkyl;

wherein when B is phenyl, two $R^1$ are not taken together to form a pyrazole ring; and when B is phenyl, $R^2$ is not

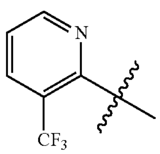

.

Item 3. The compound according to item 2 represented by general formula (I) or a salt thereof, wherein:

A is CH or N;

B is aryl, cyclyl or a 5- or 6-membered heteroaryl;

m is 0, 1, 2, 3 or 4;

E is aryl or a 5-membered heteroaryl;

n is 0, 1 or 2;

when E is aryl, n is 0, 1 or 2 and when E is a 5-membered heteroaryl, n is 0 or 1;

p is 0, 1 or 2;

each $R^1$, $R^2$ and $R^3$ is independently $C_1$-$C_8$ alkyl, $C_2$-$C_8$ alkynyl, aryl, heteroaryl, cyclyl, heterocyclyl, arylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silyloxyalkynyl, —CN, oxo, —$NO_2$, —C(O)$OR^a$, —C(Y)$NR^bR^{b'}$, —$NR^bR^{b'}$, —OC(O)$NR^bR^{b'}$, —$NR^cC(Y)R^{c'}$, —$SO_2NR^bR^{b'}$, —$OR^d$, —$SR^{d'}$, —C(Y)$R^e$ or —$S(O)_qR^f$, each of which is optionally substituted with 1-3 $R^6$; wherein two $R^1$, together with the atoms to which they are attached, may form an optionally substituted cyclyl, heterocyclyl, aryl or heteroaryl ring;

each $R^6$ is independently $C_1$-$C_8$ alkyl, heterocyclyl, heterocyclylalkyl, hydroxyalkyl, halo, haloalkyl, haloalkoxy, alkoxyalkyl, oxo, —CN, —$NO_2$, —C(O)$OR^a$, —C(Y)$NR^bR^{b'}$, —$NR^cC(Y)R^{c'}$, —$NR^bR^{b'}$, —$OR^d$ or —C(Y)$R^e$, each of which is optionally substituted with 1-3 $R^7$;

each $R^7$ is oxo; and each $R^a$, $R^b$, $R^{b'}$, $R^c$, $R^{c'}$, $R^d$, $R^{d'}$, $R^e$ and $R^f$ is independently hydrogen, $C_1$-$C_8$ alkyl, $C_2$-$C_8$ alkenyl, $C_2$-$C_8$ alkynyl, acyl, aryl, heteroaryl, cyclyl, heterocyclyl, arylalkyl, heteroarylalkyl, cyclylalkyl, heterocyclylalkyl, haloalkyl, dialkylaminoalkyl, hydroxyalkyl or alkoxyalkyl.

Item 4. The compound according to item 3 represented by general formula (I) or a salt thereof, wherein:

B or two R1 and B are taken together to form a group is phenyl, dihydroindenyl, dihydrobenzoxazinyl, dihydrobenzodioxinyl, chromenyl, tetrahydroquinoxalinyl, tetrahydroisoquinolinyl, tetrahydroquinolinyl, dihydroquinolinyl, quinolyl, isoquinolinyl, tetrahydroquinazolinyl, indolinyl, dihydrobenzothiazolyl, dihydrobenzimidazolyl, dihydrobenzoxazolyl, isoindolinyl, dihydroisobenzofuranyl, benzofuryl, benzothienyl, benzodioxolyl, indolyl, indazolyl, benzoimidazolyl, benzotriazolyl, benzisoxazolyl, benzoxazolyl, benzothiazolyl, benzoxadiazolyl, dihydrocyclopentathiophenyl, tetrahydrobenzothiophenyl, thienyl, thiazolyl, imidazolyl, pyrazolyl, isoxazolyl, thiadiazolyl, pyrrolyl or pyridyl;

E is phenyl, thienyl or pyrrolyl;

when E is phenyl, n is 1 or 2; and when E is thienyl, n is 0 or 1;

each $R^1$, $R^2$ and $R^3$ is independently $C_1$-$C_8$ alkyl, $C_2$-$C_8$ alkynyl, phenyl, thienyl, pyrrolyl, oxadiazolyl, pyridyl, benzodioxolyl, furyl, pyrimidinyl, oxazolyl, isoxazolyl, pyrazolyl, $C_3$-$C_8$ cycloalkyl, piperidyl, pyrrolidinyl, morpholinyl, dioxolanyl, phenylalkyl, thiomorpholinylalkyl, pyrrolidinylalkyl, morpholinylalkyl, piperidylalkyl, piperazinylalkyl, halo, haloalkyl, haloalkoxy, aminoalkyl, alkylaminoalkyl, dialkylaminoalkyl, hydroxyalkyl, alkoxyalkyl, silyloxyalkyl, silyloxyalkynyl, —CN, —$NO_2$, oxo, —C(O)$OR^a$, —C(Y)$NR^bR^{b'}$, —$NR^cC(Y)R^{c'}$, —$NR^bR^{b'}$, —OC(O)$NR^bR^{b'}$, —$SO_2NR^bR^{b'}$, —$OR^d$, —$SR^{d'}$, —C(Y)$R^e$ or —$S(O)_qR^f$, each of which is optionally substituted with 1-3 $R^6$;

each $R^6$ is independently $C_1$-$C_8$ alkyl, tetrahydropyranyl, morpholinyl, thiomorpholinyl, morpholinylalkyl, dialkylaminoalkyl, halo, haloalkyl, haloalkoxy, hydroxyalkyl, oxo, —CN, —$NO_2$, —C(O)$OR^a$, —$NR^cC(Y)R^{c'}$, —C(Y)$NR^bR^{b'}$, —$NR^bR^{b'}$, alkoxyalkyl, —$OR^d$ or —C(Y)$R^e$; and each $R^a$, $R^b$, $R^{b'}$, $R^c$, $R^{c'}$, $R^d$, $R^{d'}$, $R^e$ and $R^f$ is independently hydrogen, $C_1$-$C_8$ alkyl, $C_2$-$C_8$ alkenyl, $C_2$-$C_8$ alkynyl, $C_3$-$C_8$ cycloalkyl, phenyl, pyridyl, dihydroindenyl, morpholinyl, tetrahydropyranyl, piperidyl, pyrrolidinyl, piperazinyl, thiomorpholinyl, phenylalkyl, thienylalkyl, furylalkyl, pyridylalkyl, tetrahydropyranylalkyl, dihydroindenylalkyl, tetrahydrofurylalkyl, hydroxyalkyl, thiazolylalkyl, pyrazolylalkyl, morpholinylalkyl, pyrrolidinylalkyl, dialkylaminoalkyl, piperidylalkyl, benzodioxolylalkyl, dihydrobenzodioxinylalkyl, benzothienylalkyl, $C_3$-$C_8$ cycloalkylalkyl, oxazolidinylalkyl, haloalkyl, or alkoxyalkyl.

Item 5. The compound according to item 3 represented by general formula (I) or a salt thereof, wherein:

B or two R1 and B are taken together to form a group is phenyl, dihydroindenyl, dihydrobenzoxazinyl, dihydrobenzodioxinyl, chromenyl, tetrahydroquinoxalinyl, tetrahydroisoquinolyl, tetrahydroquinolinyl, dihydroquinolyl, quinolyl, isoquinolyl, tetrahydroquinazolinyl, indolinyl, dihydrobenzothiazolyl, dihydrobenzimidazolyl, dihydrobenzoxazolyl, isoindolinyl, dihydroisobenzofuranyl, benzofuryl, benzothienyl, benzodioxolyl, indolyl, indazolyl, benzoimidazolyl, benzotriazolyl, benzisoxazolyl, benzoxazolyl, benzothiazolyl, benzoxadiazolyl, dihydrocyclopentathiophenyl, tetrahydrobenzothienyl, thienyl, thiazolyl, imidazolyl, pyrazolyl, isoxazolyl, thiadiazolyl, pyrrolyl or pyridyl;

E is phenyl, thienyl or pyrrolyl;

when E is phenyl, n is 0, 1 or 2; and when E is thienyl, n is 0 or 1;

each $R^1$, $R^2$ and $R^3$ is independently $C_1$-$C_8$ alkyl, $C_2$-$C_8$ alkynyl, phenyl, thienyl, pyrrolyl, oxazolyl, oxadiazolyl, pyridyl, benzodioxolyl, furyl, pyrimidinyl, isoxazolyl, pyrazolyl, $C_3$-$C_8$ cycloalkyl, piperidyl, pyrrolidinyl, morpholinyl, dioxolanyl, phenylalkyl, thiomorpholinylalkyl, pyrrolidinylalkyl, morpholinylalkyl, piperidylalkyl, piperazinylalkyl, halo, haloalkyl, haloalkoxy, aminoalkyl, alkylaminoalkyl, dialkylaminoalkyl, hydroxyalkyl, alkoxyalkyl, silyloxyalkyl, silyloxyalkynyl, —CN, —$NO_2$, oxo, —C(O)$OR^a$, —C(Y)$NR^bR^{b'}$, —$NR^bR^{b'}$, —$NR^cC(Y)R^{c'}$, O—C(O)$NR^bR^{b'}$, $SO_2NR^bR^{b'}$, —$OR^d$, —$SR^{d'}$, —C(Y)$R^e$ or —$S(O)_qR^f$, each of which is optionally substituted with 1-3 $R^6$;

each $R^6$ is independently $C_1$-$C_8$ alkyl, tetrahydropyranyl, morpholinyl, thiomorpholinyl, morpholinylalkyl, dialkylaminoalkyl, halo, haloalkyl, haloalkoxy, hydroxyalkyl, oxo, —CN, —$NO_2$, —C(O)$OR^a$, —$NR^cC(Y)R^{c'}$, —C(Y)$NR^bR^{b'}$, —$NR^bR^{b'}$, alkoxyalkyl, —$OR^d$ or —C(Y)$R^e$, each of which is optionally substituted with 1-3 $R^7$;

$R^7$ is oxo; and each $R^a$, $R^b$, $R^{b'}$, $R^c$, $R^{c'}$, $R^d$, $R^{d'}$, $R^e$ and $R^f$ is independently hydrogen, $C_1$-$C_8$ alkyl, $C_2$-$C_8$ alkenyl, $C_2$-$C_8$ alkynyl, $C_3$-$C_8$ cycloalkyl, phenyl, pyridyl, dihydroindenyl, morpholinyl, tetrahydropyranyl, piperidyl, pyrrolidinyl, piperazinyl, thiomorpholinyl, phenylalkyl, thienylalkyl, furylalkyl, pyridylalkyl, tetrahydropyranylalkyl, dihydroindenylalkyl, tetrahydrofurylalkyl, hydroxyalkyl, thiazolylalkyl, pyrazolylalkyl, morpholinylalkyl, pyrrolidinylalkyl, dialkylaminoalkyl, piperidylalkyl, benzodioxolilalkyl, dihydrobenzodioxinylalkyl, benzothienylalkyl, $C_3$-$C_8$ cycloalkylalkyl, oxazolidinylalkyl, haloalkyl, or alkoxyalkyl.

Item 6. The compound according to item 5 represented by general formula (I) or a salt thereof, wherein:

$R^1$ is $C_1$-$C_8$ alkyl, phenyl, thienyl, pyrrolyl, oxazolyl, $C_3$-$C_8$ cycloalkyl, dioxolanyl, phenylalkyl, halo, haloalkyl, haloalkoxy, alkoxyalkyl, —CN, oxo, —$NO_2$, —C(O)OR$^a$, —C(Y)NR$^b$R$^{b'}$, —NR$^c$C(Y)R$^{c'}$, —SO$_2$NR$^b$R$^{b'}$, —OR$^d$, —SR$^{d'}$, —C(Y)R$^e$ or —S(O)$_q$R$^f$, each of which is optionally substituted with 1-3 $R^6$;

$R^2$ is $C_1$-$C_8$ alkyl, $C_2$-$C_8$ alkynyl, phenyl, thienyl, pyridyl, benzodioxolyl, furyl, pyrimidinyl, isoxazolyl, pyrazolyl, $C_3$-$C_8$ cycloalkyl, pyrrolidinyl, morpholinyl, thiomorpholinylalkyl, pyrrolidinylalkyl, morpholinylalkyl, piperiridylalkyl, piperazinylalkyl, halo, haloalkyl, haloalkoxy, aminoalkyl, alkylaminoalkyl, dialkylaminoalkyl, hydroxyalkyl, alkoxyalkyl, silyloxyalkyl, silyloxyalkynyl, —CN, —$NO_2$, —C(O)OR$^a$, —C(Y)NR$^b$R$^{b'}$, —NR$^b$R$^{b'}$, —OC(O)NR$^b$R$^{b'}$, —OR$^d$ or —C(Y)R$^e$, each of which is optionally substituted with 1-3 $R^6$;

$R^3$ is $C_1$-$C_8$ alkyl, halo, haloalkyl, —NR$^b$R$^{b'}$ or —OR$^d$, each of which is optionally substituted with 1-3 $R^6$.

Item 7. The compound according to item 4 or 6 represented by general formula (I) or a salt thereof, wherein:

$R^1$ is $C_1$-$C_8$ alkyl, phenyl, thienyl, pyrrolyl, oxazolyl, $C_3$-$C_8$ cycloalkyl, dioxolanyl, phenylalkyl, halo, haloalkyl, haloalkoxy, alkoxyalkyl, —CN, oxo, —$NO_2$, —C(O)OR$^a$, —C(Y)NR$^b$R$^{b'}$, —NR$^c$C(Y)R$^{c'}$, —SO$_2$NR$^b$R$^{b'}$, —OR$^d$, —SR$^{d'}$, —C(Y)R$^e$ or —S(O)$_q$R$^f$;

$R^2$ is $C_1$-$C_8$ alkyl, $C_2$-$C_8$ alkynyl, phenyl, thienyl, pyridyl, benzodioxolyl, furyl, pyrimidinyl, isoxazolyl, pyrazolyl, $C_3$-$C_8$ cycloalkyl, piperidinyl, pyrrolidinyl, morpholinyl, thiomorpholinylalkyl, pyrrolidinylalkyl, morpholinylalkyl, piperidinylalkyl, piperazinylalkyl, halo, haloalkyl, haloalkoxy, aminoalkyl, alkylaminoalkyl, dialkylaminoalkyl, hydroxyalkyl, alkoxyalkyl, silyloxyalkyl, silyloxyalkynyl, —CN, —$NO_2$, —C(O)OR$^a$, —C(Y)NR$^b$R$^{b'}$, —NR$^b$R$^{b'}$, —OC(O)NR$^b$R$^{b'}$, —OR$^d$, —C(Y)R$^e$ or —S(O)$_q$R$^f$;

$R^3$ is $C_1$-$C_8$ alkyl, halo, haloalkyl, —NR$^b$R$^{b'}$ or —OR$^d$.

Item 8. The compound according to item 7 represented by general formula (I) or a salt thereof, wherein:

B or two R1 and B are taken together to form a group is phenyl, dihydroindenyl, dihydrobenzoxazinyl, dihydrobenzodioxinyl, chromenyl, tetrahydroisoquinolyl, tetrahydroquinolinyl, dihydroquinolyl, quinolyl, tetrahydroquinazolinyl, indolinyl, dihydrobenzothiazolyl, dihydrobenzimidazolyl, dihydrobenzoxazolyl, isoindolinyl, benzofuryl, benzothienyl, benzodioxolyl, indolyl, indazolyl, benzoimidazolyl, benzotriazolyl, benzisoxazolyl, benzoxazolyl, benzothiazolyl, benzoxadiazolyl, tetrahydrobenzothienyl, thienyl, thiazolyl, imidazolyl, pyrazolyl, thiadiazolyl or pyridyl;

n is 1, 2, 3 or 4;

$R^1$ is $C_1$-$C_8$ alkyl, halo, haloalkyl, haloalkoxy, alkoxyalkyl, —CN, oxo, —$NO_2$, —C(O)OR$^a$, —C(Y)NR$^b$R$^{b'}$, —NR$^c$C(Y)R$^{c'}$, —SO$_2$NR$^b$R$^{b'}$, —OR$^d$, or —S(O)$_q$R$^f$;

$R^2$ is $C_1$-$C_8$ alkyl, $C_3$-$C_8$ cycloalkyl, thiomorpholinylalkyl, pyrrolidinylalkyl, morpholinylalkyl, haloalkyl, haloalkoxy, aminoalkyl, alkylaminoalkyl, dialkylaminoalkyl, hydroxyalkyl, alkoxyalkyl, silyloxyalkyl, —CN, —$NO_2$, —C(O)OR$^a$, —C(Y)NR$^b$R$^{b'}$, —NR$^b$R$^{b'}$, —OR$^d$, —C(Y)R$^e$ or —S(O)$_q$R$^f$;

each R$^a$, R$^b$, R$^{b'}$, R$^c$, R$^{c'}$, R$^d$, R$^{d'}$, R$^e$ and R$^f$ is independently hydrogen, $C_1$-$C_8$ alkyl, $C_2$-$C_8$ alkenyl, $C_2$-$C_8$ alkynyl, $C_3$-$C_8$ cycloalkyl, phenyl, dihydroindenyl, morpholinyl, tetrahydropyranyl, piperidyl, pyrrolidinyl, thiomorpholinyl, phenylalkyl, thienylalkyl, pyridylalkyl, tetrahydropyranylalkyl, dihydroindenylalkyl, tetrahydrofurylalkyl, hydroxyalkyl, morpholinylalkyl, pyrrolidinylalkyl, dialkylaminoalkyl, piperidylalkyl, benzodioxolilalkyl, dihydrobenzodioxinylalkyl, $C_3$-$C_8$ cycloalkylalkyl, haloalkyl or alkoxyalkyl.

In some embodiments, A is N. In some embodiments, A is CH. In some embodiments, A is CR$^4$.

In some embodiments, B is aryl (e.g., phenyl).

In some embodiments, m is 0.

In some embodiments, m is 1. In some embodiments, m is 2. In some embodiments, m is 3.

In some embodiments, $R^1$ is in the ortho position. In some embodiments, $R^1$ is in the meta position. In some embodiments, $R^1$ is in the para position.

In some embodiments, $R^1$ is $C_1$-$C_8$ alkyl (e.g., methyl or tert-butyl). In some embodiments, $R^1$ is heteroaryl (e.g., oxazolyl, oxadiazolyl or quinazolinyl).

In some embodiments, $R^1$ is heteroaryl substituted with 1-3 $R^6$ (e.g., 1 $R^6$).

In some embodiments, $R^1$ is oxadiazolyl substituted with 1 $R^6$. some embodiments, $R^6$ is $C_1$-$C_8$ alkyl (e.g., methyl).

In some embodiments, $R^1$ is heteroaryl substituted with 2 $R^6$. In some embodiments, $R^1$ is quinazolinyl substituted with 2 $R^6$. In some embodiments, one $R^6$ is halo (e.g., bromo) and the other is heteroaryl (e.g., pyridyl).

In some embodiments, m is 1 and $R^1$ is halo (e.g., fluoro, chloro or bromo). In some embodiments, m is 2 and each $R^1$ is halo (e.g., fluoro, chloro or bromo). In some embodiments, m is 3 and each $R^1$ is halo (e.g., fluoro, chloro or bromo). In some embodiments, $R^1$ is haloalkyl (e.g., trifluoromethyl). In some embodiments, $R^1$ is haloalkoxy (e.g., difluoromethoxy or trifluoromethoxy).

In some embodiments, $R^1$ is haloalkoxy substituted with 1 $R^6$. In some embodiments, $R^1$ is —O—CF$_2$—R$^6$. In some embodiments, $R^6$ is —C(Y)NR$^b$R$^{b'}$. In some embodiments, Y is O, R$^b$ is hydrogen and R$^{b'}$ is $C_1$-$C_8$ alkyl (e.g., methyl). In some embodiments, $R^1$ is —O—CF$_2$—CH$_2$—R$^6$. In some embodiments, $R^6$ is —OR$^d$. In some embodiments, R$^d$ is hydrogen. In some embodiments, R$^d$ is $C_1$-$C_8$ alkyl (e.g., methyl). In some embodiments, $R^6$ is —NR$^b$R$^{b'}$. In some embodiments, R$^b$ and R$^{b'}$ are each independently $C_1$-$C_8$ alkyl (e.g., R$^b$ and R$^{b'}$ are both methyl). In some embodiments, $R^6$ is heterocyclyl (e.g., morpholino).

In some embodiments, $R^1$ is aminoalkyl. In some embodiments, $R^1$ is —CH$_2$NH$_2$. In some embodiments, $R^1$ is alkylaminoalkyl. In some embodiments, $R^1$ is —CH$_2$NHCH$_2$CH$_2$CH$_3$. In some embodiments, $R^1$ is dialkylaminoalkyl. In some embodiments, $R^1$ is —CH$_2$N(CH(CH$_3$)$_2$)$_2$.

In some embodiments, $R^1$ is hydroxyalkyl. In some embodiments, $R^1$ is —CH$_2$OH.

In some embodiments, $R^1$ is —CN.

In some embodiments, $R^1$ is —$NO_2$.

In some embodiments, $R^1$ is —C(O)OR$^a$. In some embodiments, R$^a$ is hydrogen. In some embodiments, R$^a$ is $C_1$-$C_8$ alkyl (e.g., methyl or ethyl).

In some embodiments, $R^1$ is —NR$^c$C(Y)R$^{c'}$. In some embodiments, one of R$^c$ and R$^{c'}$ is hydrogen and the other is $C_1$-$C_8$ alkyl (e.g., methyl).

In some embodiments, $R^1$ is —OR$^d$. In some embodiments, R$^d$ is hydrogen. In some embodiments, R$^d$ is $C_1$-$C_8$ alkyl (e.g., methyl or ethyl).

In some embodiments, $R^1$ is —SO$_2$NR$^b$R$^{b'}$. In some embodiments, R$^b$ and R$^{b'}$ are both hydrogen.

In some embodiments, $R^1$ is —C(Y)R$^e$. In some embodiments, Y is O. In some embodiments, R$^e$ is $C_1$-$C_8$ alkyl (e.g., methyl). In some embodiments, R$^e$ is heterocyclyl (e.g., pyrrolidinyl, piperidinyl or morpholino).

In some embodiments, $R^1$ is —C(Y)NR$^b$R$^{b'}$. In some embodiments, Y is S. In some embodiments, Y is O. In some embodiments, $R^b$ and $R^{b'}$ are both hydrogen. In some embodiments, $R^b$ is hydrogen. In some embodiments, $R^b$ is hydrogen and $R^{b'}$ is aralkyl. In some embodiments, $R^b$ is hydrogen and $R^{b'}$ is optionally substituted benzyl. In some embodiments, $R^b$ is $C_1$-$C_8$ alkyl, e.g., methyl, ethyl, $C_3$ alkyl (e.g., n-propyl or isopropyl), $C_4$ alkyl (e.g., n-butyl, sec-butyl or tert-butyl), $C_5$ alkyl (e.g., n-pentyl, isopentyl or pentan-3-yl), $C_6$ alkyl (e.g., n-hexyl or 3,3-dimethylbutan-2-yl), or $C_7$ alkyl (e.g., n-heptyl or 2-heptyl).

In some embodiments, $R^{b'}$ is bicyclyl (e.g., indanyl). In some embodiments, $R^{b'}$ is heterocyclyl, e.g., a 6-membered heterocyclyl. In some embodiments, $R^{b'}$ is a 6-membered oxygen-containing heterocyclyl (e.g., tetrahydropyranyl). In some embodiments, $R^{b'}$ is a 6-membered nitrogen-containing heterocyclyl (e.g., piperidinyl).

In some embodiments, $R^{b'}$ is aralkyl. In some embodiments, the alkyl is a $C_1$-$C_8$ alkyl (e.g., $C_1$, $C_2$, $C_3$ or $C_4$ alkyl). In some embodiments, the alkyl is a straight-chain alkyl. In some embodiments, the alkyl is a branched alkyl. In some embodiments, the aryl is phenyl. In some embodiments, $R^{b'}$ is benzyl. In some embodiments, $R^{b'}$ is phenylethyl.

In some embodiments, $R^{b'}$ is heteroaralkyl. In some embodiments, the alkyl is a $C_1$-$C_8$ alkyl (e.g., $C_1$, $C_2$ or $C_3$ alkyl). In some embodiments, the alkyl is a straight-chain alkyl. In some embodiments, the alkyl is a branched alkyl. In some embodiments, the heteroaryl is pyridyl. In some embodiments, the heteroaryl is furanyl. In some embodiments, the heteroaryl is thiazolyl. In some embodiments, the heteroaryl is thienyl.

In some embodiments, $R^{b'}$ is cyclylalkyl. In some embodiments, the alkyl is a $C_1$-$C_8$ alkyl (e.g., $C_1$ alkyl). In some embodiments, the cyclyl group is cyclopropyl. In some embodiments, the cyclyl group is cyclopentyl. In some embodiments, the cyclyl group is a bicyclic group. In some embodiments, the bicyclic group is indanyl. In some embodiments, $R^{b'}$ is heterocyclylalkyl. In some embodiments, the alkyl is a $C_1$-$C_8$ alkyl (e.g., $C_1$ alkyl). In some embodiments, the heterocyclyl group is tetrahydropyranyl.

In some embodiments, $R^{b'}$ is haloalkyl (e.g., fluoroethyl, difluoroethyl, trifluoroethyl or trifluoropropyl).

In some embodiments, $R^{b'}$ is alkoxyalkyl. In some embodiments, the alkyl is a $C_1$-$C_8$ alkyl (e.g., $C_1$, $C_2$, $C_3$ or $C_4$ alkyl). In some embodiments, the alkyl is a straight-chain alkyl. In some embodiments, the alkyl is a branched alkyl. In some embodiments, the alkoxy is methoxy.

In some embodiments, $R^b$ and $R^{b'}$ are each independently $C_1$-$C_8$ alkyl (e.g., $R^b$ and $R^{b'}$ are both methyl, both ethyl, or both isopropyl).

In some embodiments, two $R^1$ and B are taken together to form a bicyclic heteroaryl or heterocyclic ring.

In some embodiments, two $R^1$ and B are taken together to form

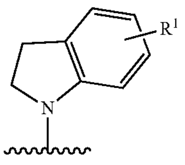

.

In some embodiments, $R^1$ is halo. In some embodiments, $R^1$ is at the 6, 7, or 8 position.

In some embodiments, two $R^1$ and B are taken together to form a group selected from:

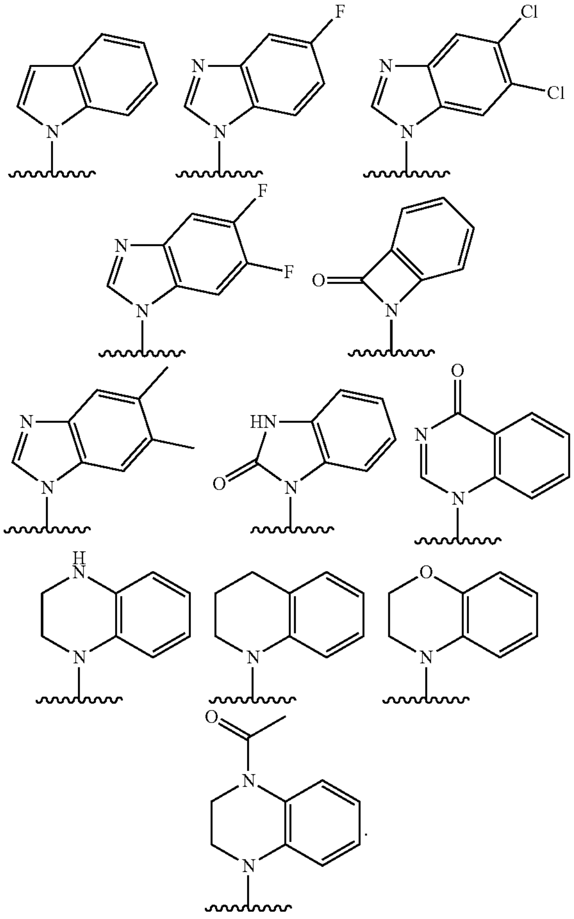

In some embodiments, $R^2$ is aryl.

In some embodiments, each $R^1$ is independently $C_1$-$C_8$ alkyl (e.g., each $R^1$ is methyl). In some embodiments, each $R^1$ is independently halo (e.g., each $R^1$ is fluoro or each $R^1$ is chloro). In some embodiments, one $R^1$ is fluoro and the other is chloro. In some embodiments, one $R^1$ is chloro and the other is bromo.

In some embodiments, each $R^1$ is independently —$OR^d$. In some embodiments, each $R^d$ is independently $C_1$-$C_8$ alkyl (e.g., each $R^d$ is methyl).

In some embodiments, one $R^1$ is halo (e.g., chloro) and the other is $C_1$-$C_8$ alkyl (e.g., methyl). In some embodiments, one $R^1$ is halo (e.g., fluoro) and the other is heterocyclylalkyl (e.g., —$CH_2$-heterocyclyl). In some embodiments, the heterocyclyl is morpholino. In some embodiments, the heterocyclyl is pyrrolidinyl. In some embodiments, the heterocyclyl is piperazinyl. In some embodiments, the piperazinyl is substituted with 1 $R^6$. In some embodiments, $R^6$ is $C_1$-$C_8$ alkyl (e.g., methyl).

In some embodiments, one $R^1$ is halo (e.g., fluoro or chloro) and the other is haloalkyl (e.g., trifluoromethyl).

In some embodiments, one $R^1$ is halo (e.g., chloro) and the other is haloalkoxy (e.g., difluoromethoxy or trifluoromethoxy).

In some embodiments, one $R^1$ is halo (e.g., chloro) and the other is —$C(O)OR^a$. In some embodiments, $R^a$ is hydrogen.

In some embodiments, one $R^1$ is halo (e.g., fluoro or chloro) and the other is —$C(Y)NR^bR^{b'}$. In some embodiments, Y is O. In some embodiments, $R^b$ and $R^{b'}$ are both hydrogen. In some embodiments, one of $R^b$ and $R^{b'}$ is hydrogen and the other is $C_1$-$C_8$ alkyl (e.g., methyl).

In some embodiments, one $R^1$ is halo (e.g., chloro) and the other is —$NR^cC(Y)R^{c'}$. In some embodiments, Y is O. In some embodiments, $R^c$ is hydrogen and $R^{c'}$ is $C_1$-$C_8$ alkyl (e.g., methyl).

In some embodiments, one $R^1$ is halo (e.g., fluoro or chloro) and the other is —$OR^d$. In some embodiments, $R^d$ is hydrogen. In some embodiments, $R^d$ is $C_1$-$C_8$ alkyl (e.g., methyl).

In some embodiments, one $R^1$ is halo (e.g., fluoro or chloro) and the other is —CN.

In some embodiments, one $R^1$ is halo (e.g., chloro) and the other is —$NO_2$.

In some embodiments, one $R^1$ is —$C(O)OR^d$ and the other is —$NO_2$. In some embodiments, $R^a$ is hydrogen.

In some embodiments, one $R^1$ is —$C(O)OR^a$ and the other is —$OR^d$. In some embodiments, each $R^a$ and $R^d$ is hydrogen.

In some embodiments, one $R^1$ is —$C(Y)NR^bR^{b'}$ and the other is haloalkyl (e.g., trifluoromethyl). In some embodiments, $R^b$ and $R^{b'}$ are both hydrogen.

In some embodiments, one $R^1$ is —$C(Y)NR^bR^{b'}$ and the other is haloalkoxy (e.g. trifluoromethoxy). In some embodiments, $R^b$ and $R^{b'}$ are both hydrogen.

In some embodiments, one $R^1$ is —$C(Y)NR^bR^{b'}$ and the other is —$S(O)_qR^f$. In some embodiments, $R^b$ and $R^{b'}$ are both hydrogen. In some embodiments, $R^f$ is $C_1$-$C_8$ alkyl (e.g., methyl).

In some embodiments, one $R^1$ is —$C(Y)NR^bR^{b'}$ and the other is —CN. In some embodiments, $R^b$ and $R^{b'}$ are both hydrogen.

In some embodiments, one $R^1$ is —$OR^d$ and the other is $C_1$-$C_8$ alkyl (e.g., methyl). In some embodiments, $R^d$ is $C_1$-$C_8$ alkyl (e.g., methyl).

In some embodiments, one $R^1$ is —$OR^d$ and the other is haloalkyl (e.g., trifluoromethyl). In some embodiments, $R^d$ is $C_1$-$C_8$ alkyl (e.g., methyl).

In some embodiments, one $R^1$ is —$OR^d$ and the other is —$C(O)OR^a$. In some embodiments, $R^d$ is $C_1$-$C_8$ alkyl (e.g., methyl). In some embodiments, $R^a$ is hydrogen. In some embodiments, $R^1$ is $C_1$-$C_8$ alkyl (e.g., methyl).

In some embodiments, one $R^1$ is —$OR^d$ and the other is —$NR^cC(O)R^{c'}$. In some embodiments, $R^d$ is $C_1$-$C_8$ alkyl (e.g., methyl). In some embodiments, $R^c$ is hydrogen and $R^{c'}$ is $C_1$-$C_8$ alkyl (e.g., methyl).

In some embodiments, one $R^1$ is haloalkyl (e.g., trifluoromethyl) and the other is —CN.

In some embodiments, two $R^1$, together with the atoms to which they are attached, are taken together to form a cyclyl ring (e.g., a substituted cyclyl ring). In some embodiments, two $R^1$, together with the atoms to which they are attached, are taken together to form a heterocyclyl ring (e.g., a substituted heterocyclyl ring). In some embodiments, two $R^1$, together with the atoms to which they are attached, are taken together to form a heteroaryl ring (e.g., a substituted heteroaryl ring).

In some embodiments, two $R^1$ and ring B are taken together to form a group selected from:

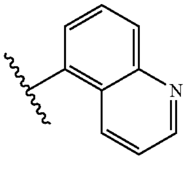
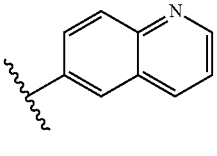

-continued

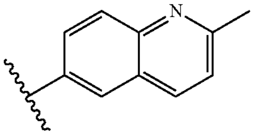
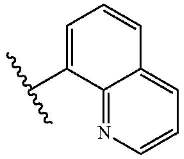
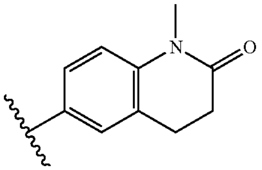
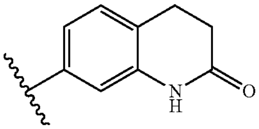
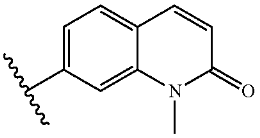
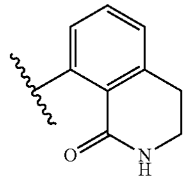
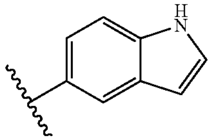
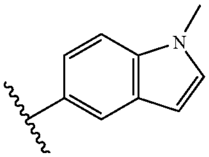
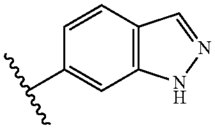
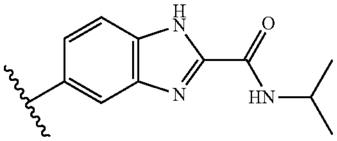
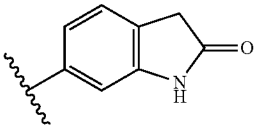
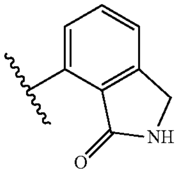
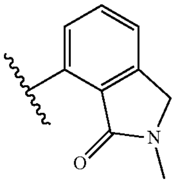
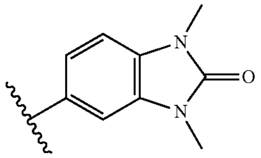
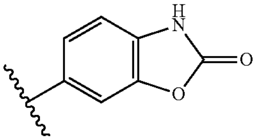
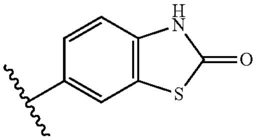
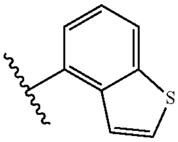
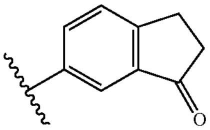
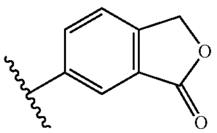
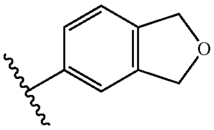

-continued

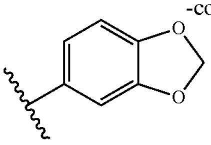

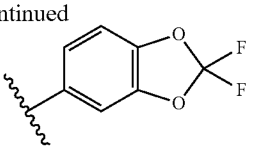

In some embodiments, $R^2$ is aryl.

In some embodiments, each $R^1$ is independently halo (e.g., all three $R^1$ are fluoro or all three $R^1$ are chloro).

In some embodiments, two $R^1$ are independently halo (e.g., both are chloro) and the other is $C_1$-$C_8$ alkyl (e.g., methyl). In some embodiments, two $R^1$ are independently halo (e.g., both are chloro) and the other is heteroaryl (e.g., pyrrolyl). In some embodiments, two $R^1$ are independently halo (e.g., both are fluoro) and the other is —C(Y)NR$^b$R$^{b'}$ (e.g., —C(O)$NH_2$). In some embodiments, two $R^1$ are independently $C_1$-$C_8$ alkyl (e.g., both are methyl) and the other is halo (e.g., chloro or bromo).

In some embodiments, one $R^1$ is $C_1$-$C_8$ alkyl (e.g., methyl), and two $R^1$, together with the atoms to which they are attached, are taken together to form a heterocyclyl ring.

In some embodiments, one $R^1$ is —OR$^d$, and two $R^1$, together with the atoms to which they are attached, are taken together to form a heterocyclyl ring. In some embodiments, $R^d$ is $C_1$-$C_8$ alkyl (e.g., methyl).

In some embodiments, three $R^1$ and ring B are taken together to form a group selected from:

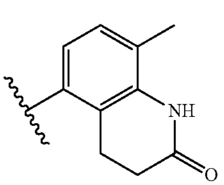

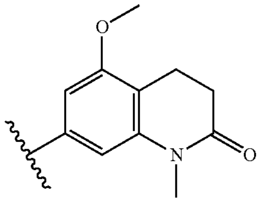

.

In some embodiments, B is a 6-membered heteroaryl.

In some embodiments, B is pyridyl. In some embodiments, B is 3-pyridyl. In some embodiments, in is 2. In some embodiments, two $R^1$, together with the atoms to which they are attached, are taken together to form an aryl ring (e.g., a phenyl ring). In some embodiments, m is 3. In some embodiments, one $R^1$ is —OR$^d$, and two $R^1$, together with the atoms to which they are attached, are taken together to form an aryl ring (e.g., a phenyl ring). In some embodiments, $R^d$ is hydrogen.

In some embodiments, B is pyrazolyl. In some embodiments, m is 2. In some embodiments, two $R^1$, together with the atoms to which they are attached, are taken together to form a cyclyl ring (e.g., a cyclohexyl ring).

In some embodiments, B is selected from:

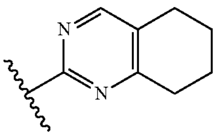

,

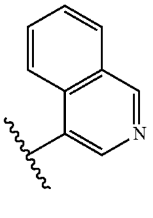

and

-continued

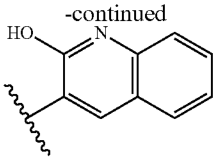

.

In some embodiments, B is a 5-membered heteroaryl (e.g., pyrazolyl).

In some embodiments, m is 1.

In some embodiments, $R^1$ is aryl (e.g., phenyl).

In some embodiments, $R^1$ is phenyl substituted with 1 $R^6$.

In some embodiments, $R^6$ is halo (e.g., chloro). In some embodiments, $R^1$ is selected from:

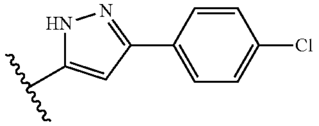

and

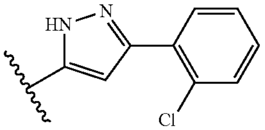

.

In some embodiments, m is 2.

In some embodiments, one $R^1$ is $C_1$-$C_8$ alkyl (e.g., methyl) and the other is aryl (e.g., phenyl). In some embodiments, the aryl is phenyl substituted with 1 $R^6$. In some embodiments, $R^6$ is halo (e.g., chloro). In some embodiments, $R^1$ is:

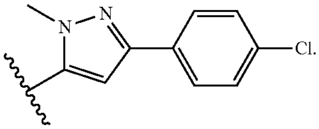 [SMILES: *c1cc(-c2ccc(Cl)cc2)nn1C]

In some embodiments, B is thienyl. In some embodiments, B is selected from:

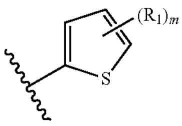

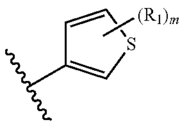

and

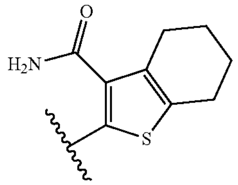

.

In some embodiments, m is 1. In some embodiments, in is 2. In some embodiments m is 2 and two $R^1$, together with the atoms to which they are attached, form an optionally substituted cyclyl, heterocyclyl, aryl or heteroaryl ring In some embodiments, $R^1$ is —C(O)OR$^a$. In some embodiments, $R^a$ is $C_1$-$C_8$ alkyl (e.g., ethyl).

In some embodiments, $R^1$ is —C(Y)NR$^b$R$^{b'}$. In some embodiments, Y is O. In some embodiments, $R^b$ and $R^{b'}$ are both hydrogen.

In some embodiments, m is 2.

In some embodiments, one $R^1$ is $C_1$-$C_8$ alkyl (e.g., methyl) and the other is —C(Y)NR$^b$R$^{b'}$. In some embodiments, Y is O. In some embodiments, $R^h$ and $R^{b'}$ are both hydrogen.

In some embodiments, B is thiazolyl.

In some embodiments, in is 1.

In some embodiments, $R^1$ is aryl (e.g., phenyl).

In some embodiments, m is 2.

In some embodiments, two $R^1$, together with the atoms to which they are attached, form an aryl ring. In some embodiments, the aryl ring is substituted with —C(Y)R$^e$. In some embodiments, Y is O. In some embodiments, $R^e$ is $C_1$-$C_8$ alkyl (e.g., methyl).

In some embodiments, B is:

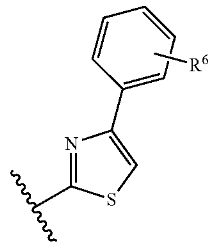

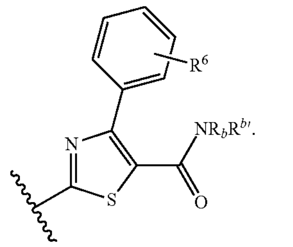

In some embodiments, B is:

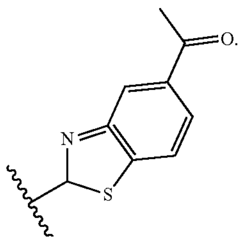

In some embodiments, E is aryl (e.g., phenyl).

In some embodiments, n is 1.

In some embodiments, $R^2$ is $C_1$-$C_8$ alkyl (e.g., methyl).

In some embodiments, $R^2$ is $C_1$-$C_8$ alkyl substituted with 1-3 $R^6$. In some embodiments, $R^2$ is $C_1$ alkyl substituted with 1 $R^6$.

In some embodiments, $R^6$ is —NR$^b$R$^{b'}$. In some embodiments, $R^b$ and $R^{b'}$ are each independently $C_1$-$C_8$ alkyl (e.g., $R^b$ and $R^{b'}$ are both methyl, or $R^b$ and $R^{b'}$ are both ethyl). In some embodiments, one of $R^b$ and $R^{b'}$ is hydrogen and the other is haloalkyl (e.g., trifluoroethyl).

In some embodiments, $R^6$ is —OR$^d$. In some embodiments, $R^d$ is cyclyl (e.g., cyclopentyl). In some embodiments, $R^d$ is heterocyclylalkyl (e.g., —$CH_2$-tetrahydropyranyl).

In some embodiments, $R^2$ is $C_2$ alkyl substituted with 1 $R^6$.

In some embodiments, $R^6$ is —C(Y)NR$^b$R$^{b'}$. In some embodiments, Y is O. In some embodiments, $R^b$ and $R^{b'}$ are both hydrogen. In some embodiments, $R^b$ and $R^{b'}$ are each independently $C_1$-$C_8$ alkyl (e.g., $R^b$ and $R^{b'}$ are both methyl). In some embodiments, one of $R^b$ and $R^{b'}$ is hydrogen and the other is $C_1$-$C_8$ alkyl (e.g., methyl).

In some embodiments, $R^6$ is —C(Y)R$^e$. In some embodiments, Y is O. In some embodiments, $R^e$ is heterocyclyl (e.g., morpholino or thiomorpholino). In some embodiments, $R^e$ is thiomorpholino substituted with 2 $R^7$. In some embodiments, each $R^7$ is oxo. In some embodiments, $R^e$ is:

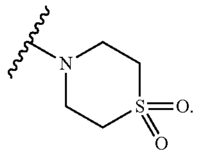 [SMILES: *N1CCS(=O)(=O)CC1]

In some embodiments, $R^2$ is $C_3$ alkyl substituted with 1 $R^6$.

In some embodiments, $R^6$ is —C(Y)NR$^b$R$^{b'}$. In some embodiments, Y is O. In some embodiments, $R^b$ and $R^{b'}$ are both hydrogen. In some embodiments, $R^b$ and $R^{b'}$ are each independently $C_1$-$C_8$ alkyl (e.g., $R^b$ and $R^{b'}$ are both methyl). In some embodiments, one of $R^b$ and $R^{b'}$ is hydrogen and the other is $C_1$-$C_8$ alkyl (e.g., methyl).

In some embodiments, $R^6$ is —NR$^c$C(Y)R$^{c'}$. In some embodiments, Y is O. In some embodiments, $R^c$ and $R^{c'}$ are each independently $C_1$-$C_8$ alkyl (e.g., $R^c$ and $R^{c'}$ are both methyl).

In some embodiments, $R^6$ is —OR$^d$. In some embodiments, $R^d$ is hydrogen. In some embodiments, $R^d$ is $C_1$-$C_8$ alkyl (e.g., methyl).

In some embodiments, $R^6$ is silyloxy (e.g., tert-butyldimethylsilyloxy).

In some embodiments, $R^6$ is —C(Y)R$^c$. In some embodiments, Y is O. In some embodiments, $R^e$ is heterocyclyl (e.g., morpholino).

In some embodiments, $R^2$ is $C_2$-$C_8$ alkynyl. In some embodiments, $R^2$ is $C_2$-$C_8$ alkynyl substituted with 1 $R^6$ (e.g., $C_3$ alkynyl substituted with 1 $R^6$). In some embodiments, $R^2$ is —C≡C—$CH_2$—$R^6$. In some embodiments, $R^6$ is —NR$^b$ R$^{b'}$. In some embodiments, $R^b$ and $R^{b'}$ are each independently $C_1$-$C_8$ alkyl (e.g., $R^b$ and $R^{b'}$ are both methyl). In some embodiments, $R^6$ is —OR$^d$. In some embodiments, $R^d$ is hydrogen. In some embodiments, $R^6$ is silyloxy (e.g., tert-butyldimethylsilyloxy). In some embodiments, $R^6$ is heterocyclyl (e.g., morpholino or thiomorpholino). In some embodiments, $R^6$ is thiomorpholino substituted with 2 $R^7$. In some embodiments, each $R^7$ is oxo. In some embodiments, $R^6$ is:

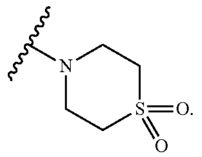 [SMILES: *N1CCS(=O)(=O)CC1]

In some embodiments, $R^2$ is aryl (e.g., phenyl). In some embodiments, $R^2$ is unsubstituted phenyl.

In some embodiments, $R^2$ is phenyl substituted with 1 $R^6$.

In some embodiments, $R^6$ is heterocyclylalkyl (e.g., —$CH_2$-morpholino). In some embodiments, $R^6$ is haloalkyl (e.g., trifluoromethyl). In some embodiments, $R^6$ is —CN. In some embodiments. $R^6$ is —OR$^d$. In some embodiments, $R^d$ is $C_1$-$C_8$ alkyl (e.g., methyl). In some embodiments, $R^6$ is —C(Y)R$^c$. In some embodiments, Y is O. In some embodiments, $R^e$ is heterocyclyl (e.g., morpholino).

In some embodiments, $R^2$ is phenyl substituted with 2 $R^6$.

In some embodiments, each $R^6$ is independently —OR$^d$. In some embodiments, each $R^d$ is $C_1$-$C_8$ alkyl (e.g., methyl). In some embodiments, one $R^6$ is halo (e.g., fluoro) and the other is $C_1$-$C_8$ alkyl (e.g., methyl). In some embodiments, one $R^6$ is —C(O)OR$^a$ and the other is —OR$^d$. In some embodiments, $R^a$ and $R^d$ are each independently $C_1$-$C_8$ alkyl (e.g., $R^a$ and $R^d$ are both methyl).

In some embodiments, $R^2$ is heteroaryl.

In some embodiments, $R^2$ is isoxazolyl. In some embodiments, $R^2$ is isoxazolyl substituted with 2 $R^6$. In some embodiments, each $R^6$ is independently $C_1$-$C_8$ alkyl (e.g., $R^6$ is methyl), In some embodiments, $R^2$ is pyrazolyl. In some embodiments, $R^2$ is pyrazolyl substituted with 1 $R^6$. In some embodiments, $R^6$ is $C_1$-$C_8$ alkyl (e.g., methyl).

In some embodiments, $R^2$ is pyridyl. In some embodiments, $R^2$ is unsubstituted pyridyl. In some embodiments, $R^1$ is pyridyl substituted with 1 $R^6$. In some embodiments, $R^6$ is halo (e.g., fluoro). In some embodiments, $R^6$ is —$NR^bR^{b'}$. In some embodiments, $R^b$ and $R^{b'}$ are each hydrogen. In some embodiments, $R^6$ is —$OR^d$. In some embodiments, $R^d$ is hydrogen. In some embodiments, $R^d$ is $C_1$-$C_8$ alkyl (e.g., methyl). In some embodiments, $R^6$ is heterocyclyl (e.g., morpholino or piperazinyl). In some embodiments, $R^6$ is piperazinyl substituted with 1 $R^7$. In some embodiments, $R^7$ is $C_1$-$C_8$ alkyl (e.g., methyl).

In some embodiments, $R^2$ is pyrimidinyl.

In some embodiments, $R^2$ is pyridazinyl.

In some embodiments, $R^2$ is cyclyl (e.g., cyclopropyl).

In some embodiments, $R^2$ is heterocyclyl (e.g., morpholino or pyrrolidinyl).

In some embodiments, $R^2$ is aralkyl (e.g., benzyl).

In some embodiments, $R^2$ is heterocyclylalkyl. In some embodiments, the alkyl is $C_1$ alkyl. In some embodiments, the alkyl is $C_2$ alkyl. In some embodiments, the alkyl is $C_3$ alkyl. In some embodiments, the heterocyclyl is piperidinyl. In some embodiments, the heterocyclyl is piperazinyl. In some embodiments, the heterocyclyl is piperazinyl substituted with 1 $R^6$. In some embodiments, $R^6$ is $C_1$-$C_8$ alkyl (e.g., methyl). In some embodiments, the heterocyclyl is pyrrolidinyl. In some embodiments, the heterocyclyl is morpholino. In some embodiments, the heterocyclyl is thiomorpholino. In some embodiments, the heterocyclyl is thiomorpholino substituted with 2 $R^6$. In some embodiments, each $R^6$ is oxo. In some embodiments, the heterocyclyl is:

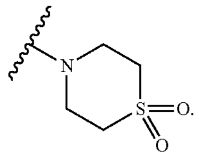 [SMILES: *N1CCS(=O)(=O)CC1]

In some embodiments, $R^2$ is halo (e.g., fluoro, chloro, bromo or iodo).

In some embodiments, $R^2$ is haloalkyl (e.g., trifluoromethyl).

In some embodiments, $R^2$ is haloalkoxy (e.g., trifluoromethoxy).

In some embodiments, $R^2$ is —CN.

In some embodiments, $R^2$ is —$NO_2$.

In some embodiments, $R^2$ is —$C(O)OR^a$. In some embodiments, $R^a$ is hydrogen. In some embodiments, $R^a$ is $C_1$-$C_8$, alkyl (e.g., methyl).

In some embodiments, $R^2$ is —$C(Y)NR^bR^{b'}$. In some embodiments, Y is O. In some embodiments, $R^b$ and $R^{b'}$ are each hydrogen. In some embodiments, $R^b$ and $R^{b'}$ are each independently $C_1$-$C_8$ alkyl (e.g., $R^b$ and $R^{b'}$ are both methyl). In some embodiments, one of $R^b$ and $R^{b'}$ is hydrogen and the other is $C_1$-$C_8$ alkyl (e.g., methyl or ethyl). In some embodiments, one of $R^b$ and $R^{b'}$ is hydrogen and the other is heterocyclylalkyl (e.g., —$CH_2$—$CH_2$-morpholino). In some embodiments, one of $R^b$ and $R^{b'}$ is hydrogen and the other is haloalkyl (e.g., trifluoroethyl).

In some embodiments, $R^2$ is —$NR^bR^{b'}$. In some embodiments, $R^b$ and $R^{b'}$ are both hydrogen. In some embodiments, $R^b$ and $R^{b'}$ are each independently $C_1$-$C_8$ alkyl (e.g., $R^b$ and $R^{b'}$ are both methyl). In some embodiments, one of $R^b$ and $R^{b'}$ is hydrogen and the other is $C_1$-$C_8$ alkyl (e.g., methyl). In some embodiments, one of $R^b$ and $R^{b'}$ is hydrogen and the other is heterocyclyl (e.g., tetrahydropyranyl). In some embodiments, one of $R^b$ and $R^{b'}$ is hydrogen and the other is heterocyclylalkyl. In some embodiments, the alkyl is $C_1$ alkyl. In some embodiments, the alkyl is $C_2$ alkyl. In some embodiments, the alkyl is $C_3$ alkyl. In some embodiments, the heterocyclyl is morpholino. In some embodiments, the heterocyclyl is pyrrolidinyl. In some embodiments, the heterocyclyl is tetrahydrofuranyl. In some embodiments, the heterocyclyl is tetrahydropyranyl. In some embodiments, one of $R^b$ and $R^{b'}$ is hydrogen and the other is hydroxyalkyl. In some embodiments, the alkyl is $C_2$ alkyl. In some embodiments, one of $R^b$ and $R^{b'}$ is hydrogen and the other is alkoxyalkyl. In some embodiments, the alkyl is $C_2$ alkyl. In some embodiments, the alkyl is $C_3$ alkyl. In some embodiments, the alkoxy is methoxy. In some embodiments, one of $R^b$ and $R^{b'}$ is hydrogen and the other is —$C(Y)R^e$. In some embodiments, Y is O. In some embodiments, $R^e$ is $C_1$-$C_8$ alkyl (e.g., methyl). In some embodiments, $R^e$ is heterocyclyl. In some embodiments, $R^e$ is tetrahydropyranyl.

In some embodiments, $R^2$ is —$OR^d$.

In some embodiments, $R^d$ is hydrogen. In some embodiments, $R^d$ is $C_1$-$C_8$ alkyl (e.g., methyl).

In some embodiments, $R^1$ is ethyl. In some embodiments, $R^d$ is $C_3$ alkyl (e.g., isopropyl or n-propyl). In some embodiments, $R^d$ is optionally substituted heteroaralkyl. In some embodiments, $R^d$ is optionally substituted pyrindinalkyl.

In some embodiments, $R^d$ is n-propyl. In some embodiments, $R^d$ is cyclyl (e.g., cyclopentyl).

In some embodiments, $R^d$ is heteroaralkyl (e.g., —$CH_2$-pyridyl).

In some embodiments, $R^d$ is heterocyclylalkyl. In some embodiments, the alkyl is $C_1$ alkyl. In some embodiments, the alkyl is $C_2$ alkyl. In some embodiments, the alkyl is $C_3$ alkyl. In some embodiments, the alkyl is $C_4$ alkyl. In some embodiments, the heterocyclyl is morpholino. In some embodiments, the heterocyclyl is piperidyl. In some embodiments, the heterocyclyl is tetrahydrofuranyl. In some embodiments, $R^d$ is cyclylalkyl (e.g., —$CH_2$-cyclobutyl).

In some embodiments, $R^d$ is alkoxyalkyl. In some embodiments, the alkyl is $C_2$ alkyl. In some embodiments, the alkyl is $C_3$ alkyl. In some embodiments, the alkoxy is methoxy.

In some embodiments, $R^d$ is dialkylaminoalkyl. In some embodiments, the alkyl is $C_2$ alkyl. In some embodiments, the alkyl is $C_3$ alkyl. In some embodiments, the dialkylamino is dimethylamino.

In some embodiments, $R^2$ is —$C(Y)R^e$. In some embodiments, Y is O. In some embodiments, $R^e$ is heterocyclyl. In some embodiments, $R^e$ is piperidyl. In some embodiments, $R^e$ is pyrrolidinyl. In some embodiments, $R^e$ is piperazinyl. In some embodiments, $R^e$ is morpholino. In some embodiments, $R^e$ is thiomorpholino.

In some embodiments, n is 2.

In some embodiments, each $R^2$ is independently halo (e.g., each $R^2$ is chloro).

In some embodiments, each $R^2$ is independently —$OR^d$.

In some embodiments, each $R^d$ is $C_1$-$C_8$ alkyl.

In some embodiments, each $R^2$ is methoxy. In some embodiments, one $R^2$ is methoxy and the other is ethoxy. In some embodiments, one $R^2$ is methoxy and the other is propoxy. In some embodiments, one $R^2$ is methoxy and the other is isopropoxy.

In some embodiments, one $R^2$ is methoxy and the other is ethoxy substituted with 1 $R^6$. In some embodiments, $R^6$ is —$NR^bR^{b'}$. In some embodiments, $R^b$ and $R^{b'}$ are each independently $C_1$-$C_8$ alkyl (e.g., $R^b$ and $R^{b'}$ are both methyl). In some embodiments, $R^6$ is —$OR^d$. In some embodiments, $R^d$ is $C_1$-$C_8$ alkyl (e.g., methyl).

In some embodiments, one $R^2$ is methoxy and the other is propoxy substituted with 1 $R^6$. In some embodiments, $R^6$ is —$OR^d$. In some embodiments, $R^d$ is $C_1$-$C_8$ alkyl (e.g., methyl).

In some embodiments, one $R^2$ is —$OR^d$ and the other is $C_1$-$C_8$ alkyl (e.g., methyl). In some embodiments, $R^2$ is $C_1$-$C_8$ alkyl (e.g., methyl or ethyl).

In some embodiments, one $R^2$ is —$OR^d$ and the other is halo (e.g., chloro). In some embodiments, $R^d$ is $C_1$-$C_8$ alkyl (e.g., methyl).

In some embodiments, one $R^2$ is —$OR^d$ and the other is —CN. In some embodiments, $R^d$ is $C_1$-$C_8$ alkyl (e.g. methyl).

In some embodiments, one $R^2$ is —$OR^d$ and the other is —$C(O)OR^a$. In some embodiments, $R^d$ and $R^a$ are both hydrogen.

In some embodiments, one $R^2$ is —$OR^d$ and the other is $C_1$-$C_8$ alkyl (e.g., methyl). In some embodiments, $R^d$ is $C_1$-$C_8$ alkyl (e.g., methyl).

In some embodiments, one $R^2$ is —$OR^d$ and the other is —$C(Y)R^e$. In some embodiments, $R^d$ is $C_1$-$C_8$ alkyl (e.g., methyl). In some embodiments, Y is O. In some embodiments, $R^e$ is heterocyclyl (e.g., morpholino).

In some embodiments, one $R^2$ is halo (e.g., chloro or bromo) and the other is $C_1$-$C_8$ alkyl (e.g., methyl).

In some embodiments, one $R^2$ is $C_1$-$C_8$ alkyl (e.g., methyl) and the other is —CN.

In some embodiments, one $R^2$ is $C_1$-$C_8$ alkyl (e.g., methyl) and the other is heteroaryl (e.g., pyridyl). In some embodiments, the pyridyl is substituted with 1 $R^6$. In some embodiments, $R^6$ is —$OR^d$. In some embodiments, $R^d$ is $C_1$-$C_8$ alkyl (e.g., methyl).

In some embodiments, one $R^2$ is $C_1$-$C_8$ alkyl (e.g., methyl) and the other is heterocyclylalkyl (e.g., —$CH_2$-morpholino).

In some embodiments, p is 0.

In some embodiments, p is 1.

In some embodiments, $R^3$ is $C_1$-$C_8$ alkyl (e.g., methyl). In some embodiments, $R^3$ is halo (e.g., chloro). In some embodiments, $R^3$ is haloalkyl (e.g., trifluoromethyl). In some embodiments $R^3$ is oxo.

In some embodiments, $R^3$ is —$OR^d$. In some embodiments, $R^d$ is hydrogen. In some embodiments, $R^d$ is $C_1$-$C_8$ alkyl (e.g., methyl).

In some embodiments, $R^3$ is —$NR^bR^{b'}$. In some embodiments, $R^b$ and $R^{b'}$ are both hydrogen. In some embodiments, one of $R^b$ and $R^{b'}$ is hydrogen and the other is $C_1$-$C_8$ alkyl (e.g., methyl).

In some embodiments, $R^3$ is heterocyclyl (e.g., piperazinyl). In some embodiments, $R^3$ is piperazinyl substituted with 1 $R^6$. In some embodiments, $R^6$ is $C_1$-$C_8$ alkyl (e.g., methyl).

In some embodiments, E is a 5-membered heteroaryl ring.

In some embodiments, E is a thiophene ring.

In some embodiments, E is a pyrrole ring.

In some embodiments, n is 1. In some embodiments, $R^2$ is $C_1$-$C_8$ alkyl (e.g., methyl). In some embodiments, E is an N-methylpyrrole ring.

In some embodiments, L is $NR^5$. In some embodiments, $R^5$ is hydrogen.

In some embodiments, L is O.

In some embodiments, the compound is:

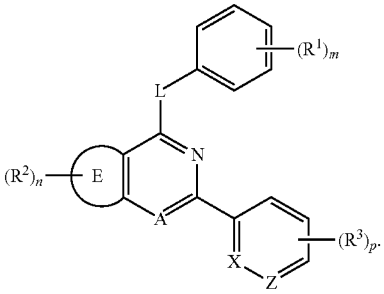

In some embodiments, $R^2$ is $C_1$-$C_4$ alkoxy. In some embodiments, $R^2$ is halo. In some embodiments, $R^1$ is —C(Y)$NR^bR^{b'}$.

In some embodiments, the compound is:

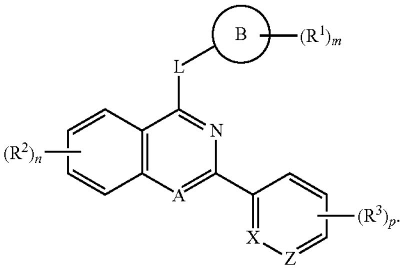

In some embodiments, $R^2$ is $C_1$-$C_4$ alkoxy. In some embodiments, $R^2$ is halo. In some embodiments, $R^1$ is —C(Y)$NR^bR^{b'}$.

In some embodiments,

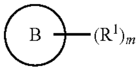 is 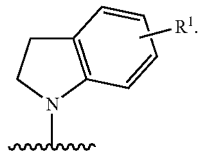

In some embodiments,

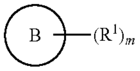 is 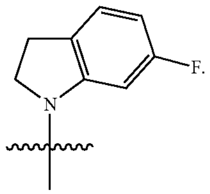

In some embodiments, L is NH, and

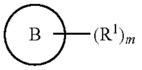

is selected from

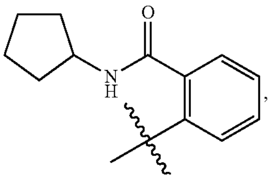
,
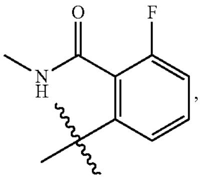
,
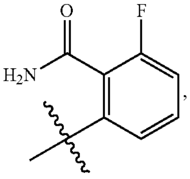
,
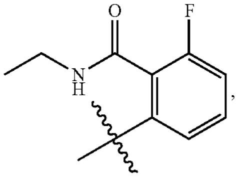
,
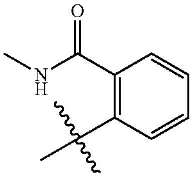
,
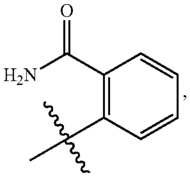
,
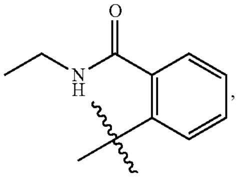
,
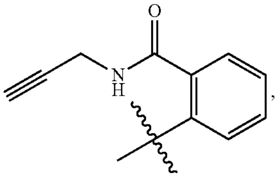
,
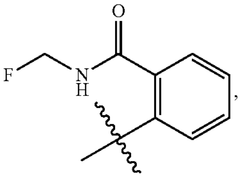
, c,
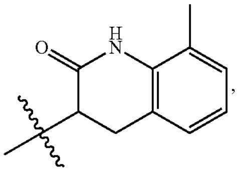
,
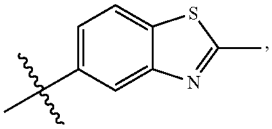
,
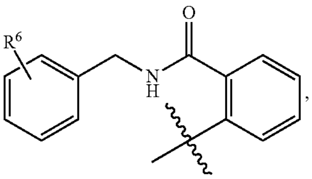
, and
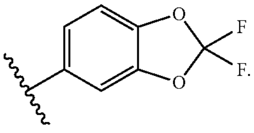

In some embodiments $R^6$ is halo.

In some embodiments, the compound is:

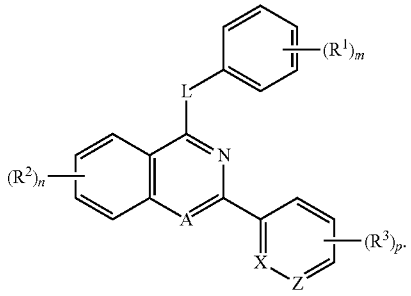

In some embodiments, $R^1$ is —C(Y)$NR^bR^{b'}$. In some embodiments, $R^1$ is halo. In some embodiments, $R^2$ is $C_1$-$C_4$ alkoxy. In some embodiments, $R^2$ is halo. In some embodiments, m is 2 and two $R^1$ are 3,4-dichloro; 3,4-difluoro, 3,5-dichloro; 3,5-difluoro; 3-chloro,4-fluoro; or 3-chloro,5-fluoro. In some embodiments, $R^2$ is —-C(O)$NR^bR^{b'}$ and $R^3$ is H. In some embodiments, $R^b$ and $R^{b'}$ are H. In some embodiments, $R^b$ and $R^{b'}$ are independently $C_1$-$C_4$ alkyl or halo-substituted $C_1$-$C_4$ alkyl. In some embodiments, $R^b$ is methyl and $R^{b'}$ is trifluoroethyl. In some embodiments, $R^1$ is $C_1$-$C_4$ alkoxy or halo-substituted $C_1$-$C_4$ alkoxy. In some embodiments, n and p are zero.

In some embodiments, the compound is:

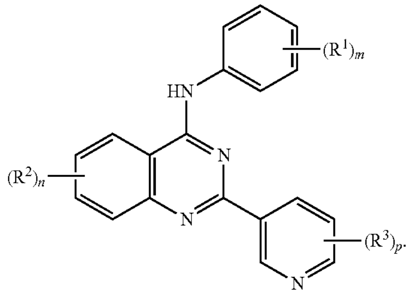

In some embodiments, $R^1$ is —C(Y)$NR^bR^{b'}$. In some embodiments, $R^1$ is halo. In some embodiments, $R^2$ is $C_1$-$C_4$ alkoxy. In some embodiments, $R^2$ is halo. In some embodiments, m is 2 and two $R^1$ are 3,4-dichloro; 3,4-difluoro, 3,5-dichloro; 3,5-difluoro; 3-chloro,4-fluoro; or 3-chloro,5-fluoro. In some embodiments, $R^2$ is —C(O)$NR^bR^{b'}$ and $R^3$ is H. In some embodiments, $R^b$ and $R^{b'}$ are H. In some embodiments, $R^b$ and $R^{b'}$ are independently $C_1$-$C_4$ alkyl or halo-substituted $C_1$-$C_4$ alkyl. In some embodiments, $R^b$ is methyl and $R^{b'}$ is trifluoroethyl. In some embodiments, $R^1$ is $C_1$-$C_4$ alkoxy or halo-substituted $C_1$-$C_4$ alkoxy. In some embodiments, n and p are zero.

In some embodiments, the compound is:

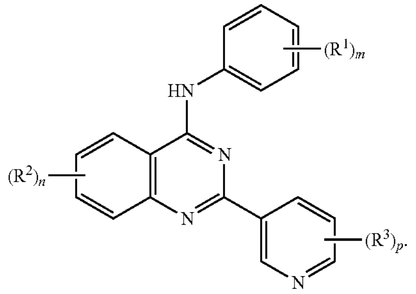

In some embodiments, $R^1$ is —C(Y)$NR^bR^{b'}$. In some embodiments, $R^1$ is halo. In some embodiments, $R^2$ is $C_1$-$C_4$ alkoxy. In some embodiments, $R^2$ is halo. In some embodiments, in is 2 and two $R^1$ are 3,4-dichloro; 3,4-difluoro, 3,5-dichloro; 3,5-difluoro; 3-chloro,4-fluoro; or 3-chloro,5-fluoro. In some embodiments, $R^2$ is —C(O)$NR^bR^{b'}$ and $R^3$ is H. In some embodiments, $R^b$ and $R^{b'}$ are H. In some embodiments, $R^b$ and $R^{b'}$ are independently $C_1$-$C_4$ alkyl or halo-substituted $C_1$-$C_4$ alkyl. In some embodiments, $R^b$ is methyl and $R^{b'}$ is trifluoroethyl. In some embodiments, $R^1$ is $C_1$-$C_4$ alkoxy or halo-substituted $C_1$-$C_4$ alkoxy. In some embodiments, n and p are zero.

In some embodiments, the compound is:

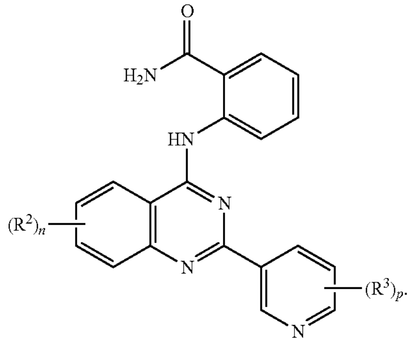

In some embodiments, $R^1$ is —C(Y)$NR^bR^{b'}$. In some embodiments, $R^1$ is halo. In some embodiments, $R^2$ is $C_1$-$C_4$ alkoxy. In some embodiments, $R^2$ is halo. In some embodiments, m is 2 and two $R^1$ are 3,4-dichloro; 3,4-difluoro, 3,5-dichloro; 3,5-difluoro; 3-chloro,4-fluoro; or 3-chloro,5-fluoro. In some embodiments, $R^2$ is —C(O)$NR^bR^{b'}$ and $R^3$ is H. In some embodiments, $R^b$ and $R^{b'}$ are H. In some embodiments, $R^b$ and $R^{b'}$ are independently $C_1$-$C_4$ alkyl or halo-substituted $C_1$-$C_4$ alkyl. In some embodiments, $R^b$ is methyl and $R^{b'}$ is trifluoroethyl. In some embodiments, $R^1$ is $C_1$-$C_4$ alkoxy or halo-substituted $C_1$-$C_4$ alkoxy. In some embodiments, n and p are zero.

Compounds of Formula (II)

The following aspects and embodiments relate to compounds of formula (II).

Item 9. The compound according to item 1 represented by general formula (II) or a salt thereof, wherein:

L is $CR^4R^5$, O, C(O), $NR^6$C(O) or $NR^7$;

A is N;

each $X^1$, $X^2$, $X^3$, X and $X^5$ is independently CH or N, provided that at least two of $X^1$, $X^2$, $X^3$, $X^4$ and $X^5$ are N;

n is 0, 1, 2, 3 or 4;

p is 0, 1, 2 or 3

$R^1$ is $C_1$-$C_8$ alkyl, $C_2$-$C_8$ alkenyl, $C_2$-$C_8$ alkynyl, aryl, heteroaryl, cyclyl, heterocyclyl, arylalkyl, heteroarylalkyl, cyclylalkyl or heterocyclylalkyl, each of which is optionally substituted with 1-5 $R^9$; wherein $R^1$ or $R^9$ is optionally taken together with one of $R^4$, $R^5$, $R^6$ or $R^7$, and the atoms to which they are attached to form a cyclyl, heterocyclyl, aryl or heteroaryl ring that is optionally substituted with 1-3 $R^{10}$;

each $R^2$ and $R^3$ is independently hydrogen, $C_1$-$C_8$ alkyl, $C_2$-$C_8$ alkenyl, $C_2$-$C_8$ alkynyl, aryl, heteroaryl, cyclyl, heterocyclyl, arylalkyl, heteroarylalkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy, silylalkoxyalkyl, —CN, —$NO_2$, —C(O)$OR^a$, —C(Y)$NR^bR^{b'}$, —$NR^c$C(Y)$R^{c'}$, —$NR^bR^{b'}$, —OC(O)$NR^bR^{b'}$, —$NR^c$C(O)$OR^{c'}$, —$SO_2NR^bR^{b'}$, —$NR^cSO_2R^{c'}$, —$NR^c$C(Y)$NR^bR^{b'}$, —$OR^d$, —$SR^{d'}$, —C(Y)$R^e$ or —$S(O)_qR^f$, each of which is optionally substituted with 1-3 $R^{11}$;

each $R^4$, $R^5$, $R^6$ and $R^7$ is independently hydrogen, $C_1$-$C_8$ alkyl, $C_2$-$C_8$ alkenyl, $C_2$-$C_8$ alkynyl, aryl, heteroaryl, cyclyl, heterocyclyl, arylalkyl, heteroarylalkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy, silylalkoxyalkyl, —CN, —$NO_2$, —C(O)$OR^a$, —C(Y)$NR^bR^{b'}$, —$NR^c$C(Y)$R^{c'}$, —$NR^bR^{b'}$, —OC(O)$NR^bR^{b'}$, —$NR^c$C(O)$OR^{c'}$, —$SO_2NR^bR^{b'}$, —$NR^cSO_2R^{c'}$, —$NR^c$C(Y)$NR^bR^{b'}$, —$OR^d$, —$SR^{d'}$, —C(Y)$R^e$ or —$S(O)_qR^f$;

each $R^9$, $R^{10}$ and $R^{11}$ is independently $C_1$-$C_8$ alkyl, $C_2$-$C_8$ alkenyl, $C_2$-$C_8$ alkynyl, aryl, heteroaryl, cyclyl, heterocyclyl, arylalkyl, heteroarylalkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy, silylalkoxyalkyl, oxo, thioxo, —CN, —$NO_2$, —C(O)OR, —C(Y)$NR^bR^{b'}$, —$NR^c$C(Y)$R^{c'}$, —$NR^b$ $R^{b'}$, —OC(O)$NR^bR^{b'}$, —$NR^c$C(O)$OR^{c'}$, —$SO_2NR^bR^{b'}$, —$NR^cSO_2R^{c'}$, —$NR^c$C(Y)$NR^bR^{b'}$, —$OR^d$, —$SR^{d'}$, —C(Y) $R^e$ or —$S(O)_qR^f$, each of which is optionally substituted with 1-3 $R^{12}$; wherein two $R^8$, two $R^9$, two $R^{10}$ or two $R^{11}$ is optionally taken together with the atoms to which they are attached to form an optionally substituted cyclyl, heterocyclyl, aryl or heteroaryl ring;

$R^{12}$ is —$OR^d$;

Y is O or S;

q is 1 or 2; and each $R^a$, $R^b$, $R^{b'}$, $R^c$, $R^d$, $R^{d'}$, $R^e$, $R^{e'}$ and $R^f$ is independently hydrogen, $C_1$-$C_8$ alkyl, $C_2$-$C_8$ alkenyl, $C_2$-$C_8$ alkynyl, acyl, cyclyl, heterocyclyl, aryl, heteroaryl, cyclylalkyl, heterocyclylalkyl, arylalkyl, or heteroarylalkyl.

Item 10. The compound according to item 9 represented by general formula (II) or a salt thereof, L is $NR^7$;

n is 0, 1 or 2;

p is 0;

$R^1$ is $C_1$-$C_8$ alkyl, aryl or heteroaryl;

each $R^2$ and $R^3$ is independently hydrogen, $C_1$-$C_8$ alkyl, aryl, halo, heterocyclylalkyl, —$NR^c$C(Y)$R^c$, —$NR^bR^{b'}$ or —$OR^d$, each of which is optionally substituted with 1-3 $R^{11}$;

$R^7$ is hydrogen; and each $R^9$, $R^{10}$ and $R^{11}$ is independently $C_1$-$C_8$ alkyl, heterocyclyl, halo, haloalkyl, haloalkoxy, —CN, —C(O)$OR^a$, —C(Y)$NR^bR^{b'}$, —$OR^d$ or —C(Y)$R^e$;

Y is O;

each $R^a$, $R^b$, $R^{b'}$, $R^c$, $R^{c'}$, $R^d$, $R^{d'}$, $R^e$, $R^{e'}$ and $R^f$ is independently hydrogen, $C_1$-$C_8$ alkyl, cyclyl, heterocyclyl, aryl or heteroaryl.

Item 11. The compound according to item 10 represented by general formula (II) or a salt thereof, wherein:

$R^1$ is $C_1$-$C_8$ alkyl, phenyl or benzodioxolyl;

each $R^2$ and $R^3$ is independently hydrogen, $C_1$-$C_8$ alkyl, phenyl, halo, morholinylalkyl, —$NR^cC(Y)R^c$, —$NR^bR^{b'}$ or —$OR^d$;

$R^9$ is independently $C_1$-$C_8$ alkyl, morpholinyl, tetrahydropyranyl, halo, haloalkyl, haloalkoxy, —CN, —$C(O)OR^a$, —$C(Y)NR^bR^{b'}$, —$OR^d$ or —$C(Y)R^e$; and each $R^a$, $R^b$, $R^{b'}$, $R^c$, $R^{c'}$, $R^d$, $R^{d'}$, $R^e$, $R^{e'}$ and $R^f$ is independently hydrogen, $C_1$-$C_8$ alkyl, $C_3$-$C_8$ cycloalkyl, tetrahydropyranyl, phenyl or pyridyl.

Item 12. The compound according to item 10 represented by general formula (II) or a salt thereof, wherein:

$R^1$ is $C_1$-$C_8$ alkyl, phenyl or benzodioxolyl;

each $R^2$ and $R^3$ is independently hydrogen, $C_1$-$C_8$ alkyl, phenyl, halo, morholinylalkyl, —$NR^cC(Y)R^c$, —$NR^bR^{b'}$ or —$OR^d$, each of which is optionally substituted with 1-3 $R^{11}$;

each $R^9$, $R^{10}$ and $R^{11}$ is independently $C_1$-$C_8$ alkyl, morpholinyl, tetrahydropyranyl, halo, haloalkyl, haloalkoxy, —CN, —$C(O)OR^a$, —$C(Y)NR^bR^{b'}$, —$OR^d$ or —$C(Y)R^e$; and each $R^a$, $R^b$, $R^{b'}$, $R^c$, $R^{c'}$, $R^d$, $R^{d'}$, $R^e$, $R^{e'}$ and $R^f$ is independently hydrogen, $C_1$-$C_8$ alkyl, $C_3$-$C_8$ cycloalkyl, tetrahydropyranyl, phenyl, or pyridyl.

Item 13. The compound according to item 12 represented by general formula (II) or a salt thereof, wherein:

$R^2$ is $C_1$-$C_8$ alkyl, phenyl, halo, morholinylalkyl, —$NR^cC(Y)R^{c'}$, —$NR^bR^{b'}$ or —$OR^d$, each of which is optionally substituted with 1-3 $R^{11}$;

$R^3$ is hydrogen;

$R^9$ is halo, haloalkoxy, —CN, —$C(O)OR^a$ or —$C(Y)NR^bR^{b'}$; and $R^{11}$ is $C_1$-$C_8$ alkyl, morpholinyl, tetrahydropyranyl, halo, —CN, —$OR^d$ or —$C(Y)R^e$;

Item 14. The compound according to item 11 or 13 represented by general formula (II) or a salt thereof, wherein:

$R^2$ is $C_1$-$C_8$ alkyl, phenyl, halo, morholinylalkyl, —$NR^cC(Y)R^{c'}$, —$NR^bR^{b'}$ or —$OR^d$;

$R^3$ is hydrogen; and $R^9$ is halo, haloalkoxy, —CN, —$C(O)OR^a$ or —$C(Y)NR^bR^{b'}$.

In some embodiments, A is CH. In some embodiments, A is N.

In some embodiments, L is $NR^7$. In some embodiments, $R^7$ is H.

In some embodiments, $R^1$ is aryl (e.g., phenyl).

In some embodiments, $R^1$ is phenyl substituted with 1 $R^9$. In some embodiments, $R^1$ is phenyl substituted with 1 $R^9$ in the ortho position. In some embodiments, $R^1$ is phenyl substituted with 1 $R^9$ in the meta position. In some embodiments, $R^9$ is haloalkoxy (e.g., difluoromethoxy or trifluoromethoxy). In some embodiments, $R^9$ is —CN. In some embodiments, $R^9$ is —$C(O)OR^a$. In some embodiments, $R^a$ is hydrogen. In some embodiments, $R^9$ is —$C(Y)NR^bR^{b'}$. In some embodiments, Y is O. In some embodiments, $R^b$ and $R^{b'}$ are both hydrogen. In some embodiments, $R^1$ is:

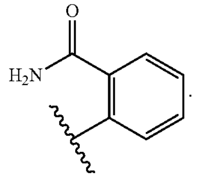

In some embodiments, one of $R^b$ and $R^{b'}$ is hydrogen and the other is $C_1$-$C_8$ alkyl (e.g., methyl).

In some embodiments, $R^1$ is phenyl substituted with 2 $R^9$. In some embodiments, each $R^9$ is independently halo (e.g., each $R^9$ is fluoro or each $R^9$ is chloro). In some embodiments, one $R^9$ is fluoro and the other is chloro. In some embodiments, one $R^9$ is halo (e.g., chloro) and the other is haloalkoxy (e.g., difluoromethoxy or trifluoromethoxy).

In some embodiments, 2 $R^9$ are taken together with the atoms to which they are attached to form a heterocyclyl ring, e.g., a 5-membered heterocyclyl ring (e.g., a dioxole ring). In some embodiments, the dioxole ring is unsubstituted. In some embodiments, the dioxole ring is substituted. In some embodiments, the dioxole ring is substituted with two fluoro substituents. In some embodiments, $R^1$ is selected from:

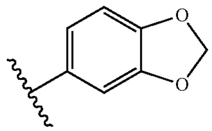
and
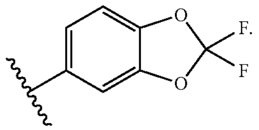

In some embodiments, $R^1$ is aralkyl (e.g., benzyl). In some embodiments, $R^1$ is aralkyl substituted with 2 $R^9$ (e.g., benzyl substituted with 2 $R^9$). In some embodiments, 2 $R^9$ substituents are on the phenyl ring. In some embodiments, each $R^9$ is independently halo (e.g., each $R^9$ is chloro).

In some embodiments, $R^1$ is alkyl (e.g., methyl).

In some embodiments, n is 0.

In some embodiments, n is 1.

In some embodiments, $R^2$ is $C_1$-$C_8$ alkyl (e.g., methyl). In some embodiments, $R^2$ is $C_1$-$C_8$ alkyl substituted with 1 $R^{11}$ (e.g., methyl substituted with 1 $R^{11}$). In some embodiments, $R^{11}$ is heterocyclyl (e.g., morpholino).

In some embodiments, $R^2$ is aryl (e.g., phenyl). In some embodiments, $R^2$ is phenyl substituted with 1 $R^{11}$. In some embodiments, $R^{11}$ is —CN. In some embodiments, $R^{11}$ is —$OR^d$. In some embodiments, $R^d$ is $C_1$-$C_8$ alkyl (e.g., methyl). In some embodiments. $R^{11}$ is halo.

In some embodiments, $R^2$ is halo (e.g., fluoro, chloro, bromo or iodo).

In some embodiments, $R^2$ is —$NR^cC(Y)R^{c'}$. In some embodiments, $R^c$ is hydrogen. In some embodiments, Y is O. In some embodiments, $R^{c'}$ is alkyl (e.g., methyl). In some embodiments, $R^{c'}$ is aryl (e.g., phenyl). In some embodiments, $R^{c'}$ is phenyl substituted with 1 $R^8$. In some embodiments, $R^8$ is —$OR^d$. In some embodiments, $R^d$ is $C_1$-$C_8$ alkyl (e.g., methyl).

In some embodiments, $R^{c'}$ is heteroaryl. In some embodiments, $R^{c'}$ is furanyl. In some embodiments, $R^{c'}$ is pyridyl. In some embodiments, $R^{c'}$ is pyridyl substituted with 1 $R^8$. In some embodiments, $R^8$ is —$OR^d$. In some embodiments, $R^d$ is $C_1$-$C_8$ alkyl (e.g., methyl).

In some embodiments, $R^{c'}$ is cyclyl (e.g., cyclohexyl). In some embodiments, $R^{c'}$ is cyclohexyl substituted with 1 $R^8$. In some embodiments, $R^8$ is —$OR^d$ in some embodiments, $R^d$ is $C_1$-$C_8$ alkyl (e.g., methyl).

In some embodiments, $R^{c'}$ is heterocyclyl (e.g., tetrahydropyranyl).

In some embodiments, $R^2$ is —$NR^bR^{b'}$ in some embodiments, $R^b$ and $R^{b'}$ are both hydrogen. In some embodiments, $R^b$ and $R^{b'}$ are each independently $C_1$-$C_8$ alkyl (e.g., $R^b$ and $R^{b'}$ are both methyl).

In some embodiments, $R^1$ is —$OR^d$. In some embodiments, $R^d$ is $C_1$-$C_8$ alkyl (e.g., methyl or ethyl). In some embodiments, $R^d$ is ethyl substituted with 1 $R^8$. In some embodiments, $R^8$ is —$OR^d$. In some embodiments, $R^d$ is $C_1$-$C_8$ alkyl (e.g., methyl). In some embodiments, $R^1$ is —$OCH_2CH_2OCH_3$. In some embodiments, $R^2$ is —$OCH_2CH_2OCH_2CH_2CH_3$. In some embodiments, $R^2$ is —$OCH_2CH_2OCH_2CH_2CH_2OCH_3$.

In some embodiments, n is 2.

In some embodiments, one $R^1$ is $C_1$-$C_8$ alkyl (e.g., methyl) and the other is halo (e.g., chloro).

In some embodiments, one $R^2$ is —$OR^d$ and the other is halo (e.g., chloro). In some embodiments, $R^d$ is $C_1$-$C_8$ alkyl (e.g., methyl).

In some embodiments, $X^1$ and $X^4$ are N and $X^2$, $X^3$ and $X^5$ are CH.

In some embodiments, $X^1$ and $X^3$ are N and $X^2$, $X^4$ and $X^5$ are CH.

In some embodiments, $X^2$ and $X^3$ are N and $X^1$, $X^4$ and $X^5$ are CH.

In some embodiments, $X^2$ and $X^4$ are N and $X^1$, $X^3$ and $X^5$ are CH.

In some embodiments, the compound is:

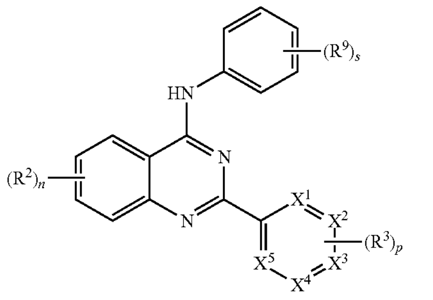

wherein s is 0, 1, 2, 3 or 4.

In some embodiments, $R^9$ is —$C(O)NH_2$, $C_1$-$C_4$ alkoxy, or substituted $C_1$-$C_4$ alkoxy. In some embodiments, $R^9$ is halo, In some embodiments, the compound is:

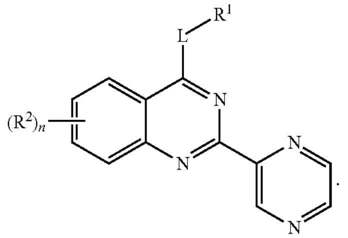

In some embodiments, $R_1$ is selected from methyl, cyclohexyl, t-butyl, and pyridinyl. In some embodiments, $R_1$ is heteroaralkyl (e.g., —$CH_2$-pyridyl). In some embodiments, $LR^1$ is $NH(CH_3)$.

In some embodiments, the compound is:

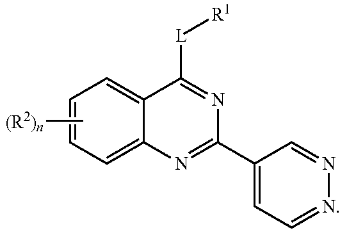

In some embodiments, $R_1$ is selected from methyl, cyclohexyl, t-butyl, and pyridinyl. In some embodiments, $R_1$ is heteroaralkyl (e.g., —$CH_2$-pyridyl). In some embodiments, $LR^1$ is $NH(CH_3)$.

In some embodiments, the compound is:

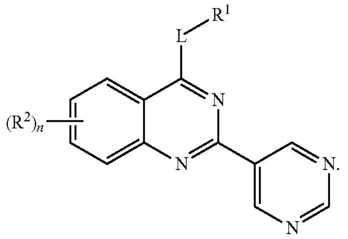

In some embodiments, $R_1$ is selected from methyl, cyclohexyl, t-butyl, and pyridinyl. In some embodiments, $R_1$ is heteroaralkyl (e.g., —$CH_2$-pyridyl). In some embodiments, $LR^1$ is $NH(CH_3)$.

In some embodiments, the compound is:

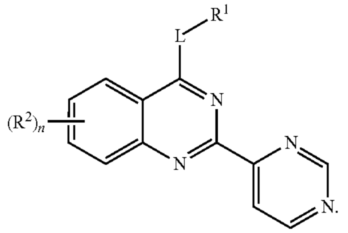

In some embodiments, $R_1$ is selected from methyl, cyclohexyl, t-butyl, and pyridinyl. In some embodiments, $R_1$ is heteroaralkyl (e.g., —$CH_2$-pyridyl). In some embodiments, $LR^1$ is $NH(CH_3)$.

In some embodiments, the compound is:

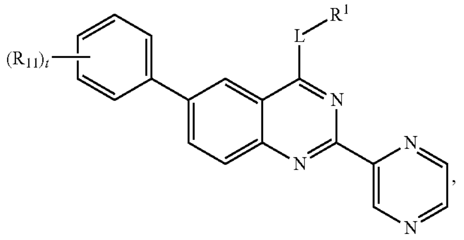

wherein t is 1-3.

In some embodiments, $R_1$ is selected from methyl, cyclohexyl, t-butyl, and pyridinyl. In some embodiments. $R^1$ is heteroaralkyl (e.g., —$CH_2$-pyridyl). In some embodiments, $LR^1$ is $NH(CH_3)$. In some embodiments, $R^1$ is independently halo, nitrile, $C_1$-$C_4$ alkoxy, —$C(O)NH_2$, hydroxy, or $C_1$-$C_4$ hydroxyalkyl. In some embodiments, $R^{11}$ is fluoro. In some embodiments, $R^{11}$ is methoxy, ethoxy, or methoxyethoxy ether. In some embodiments, $R^{11}$ is —$OCH_2CH_2OCH_3$. In some embodiments, $R^{11}$ is —$OCH_2CH_2OCH_2CH_2CH_3$. In some embodiments, $R^{11}$ is —$OCH_2CH_2OCH_2CH_2OCH_3$.

In some embodiments, the compound is:

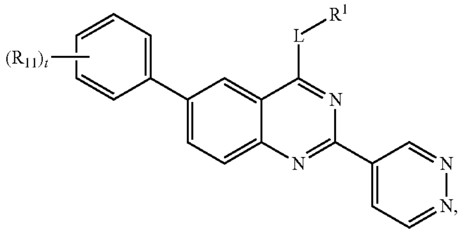

wherein t is 1-3.

In some embodiments, $R_1$ is selected from methyl, cyclohexyl, t-butyl, and pyridinyl. In some embodiments, $LR^1$ is $NH(CH_3)$. In some embodiments, $R^{11}$ is independently halo, nitrile, $C_1$-$C_4$ alkoxy, —$C(O)NH_2$, hydroxy, or $C_1$-$C_4$ hydroxyalkyl. In some embodiments, $R^{11}$ is fluoro. In some embodiments, $R^{11}$ is methoxy, ethoxy, or methoxyethoxy ether. In some embodiments, $R^{11}$ is —$OCH_2CH_2OCH_3$. In some embodiments, $R^{11}$ is —$OCH_2CH_2OCH_2CH_2CH_3$. In some embodiments. $R^{11}$ is —$OCH_2CH_2CH_2OCH_2CH_2OCH_3$.

In some embodiments, the compound is:

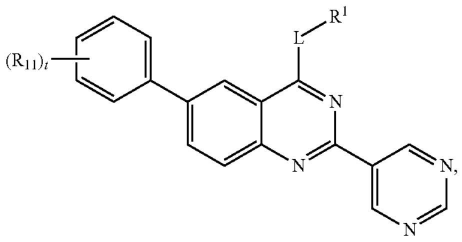

wherein t is 1-3.

In some embodiments, $R_1$ is selected from methyl, cyclohexyl, t-butyl, and pyridinyl. In some embodiments, $LR^1$ is $NH(CH_3)$. In some embodiments, $R^{11}$ is independently halo, nitrile, $C_1$-$C_4$ alkoxy, —$C(O)NH_2$, hydroxy, or $C_1$-$C_4$ hydroxyalkyl. In some embodiments, $R^{11}$ is fluoro. In some embodiments, $R^{11}$ is methoxy, ethoxy, or methoxyethoxy ether. In some embodiments, $R^{11}$ is —$OCH_2CH_2OCH_3$. In some embodiments, $R^{11}$ is —$OCH_2CH_2OCH_2CH_2CH_3$. In some embodiments, $R^{11}$ is —$OCH_2CH_2OCH_2CH_2OCH_3$.

In some embodiments, the compound is:

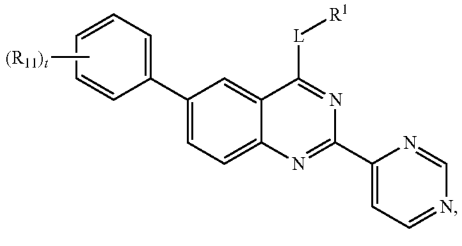

wherein t is 1-3.

In some embodiments, $R_1$ is selected from methyl, cyclohexyl, t-butyl, and pyridinyl. In some embodiments, $LR^1$ is $NH(CH_3)$. In some embodiments, $R^{11}$ is independently halo, nitrile, $C_1$-$C_4$ alkoxy, —$C(O)NH_2$, hydroxy, or $C_1$-$C_4$ hydroxyalkyl. In some embodiments, $R^{11}$ is fluoro. In some embodiments, $R^{11}$ is methoxy, ethoxy, or methoxyethoxy ether. In some embodiments, $R^{11}$ is —$OCH_2CH_2OCH_3$. In some embodiments, $R^{11}$ is —$OCH_2CH_2OCH_2CH_2CH_3$. In some embodiments $R^{11}$ is —$OCH_2CH_2OCH_2CH_2OCH_3$.

Compounds of Formula (III)

The following aspects and embodiments relate to compounds of formula (III).

Item 15. The compound according to item 1 represented by general formula (III) or a salt thereof, wherein:

A is CH or N;

L is O, a direct bond or NH;

one of $X^1$, $X^2$, $X^3$, $X^4$ and $X^5$ is N and the others are CH;

m is 1, 2 or 3;

n is 1, 2, 3 or 4;

$R^1$ is hydrogen, $C_1$-$C_8$ alkyl, $C_2$-$C_8$ alkenyl, $C_2$-$C_5$ alkynyl, alkoxyalkyl, hydroxyalkyl, heteroaryl, heteroarylalkyl, arylalkyl, —$C(Y)R^e$, cyclyl, cyclylalkyl or heterocyclyl, each of which is optionally substituted with 1-3 $R^7$;

$R^2$ is aryl or heteroaryl, each of which is optionally substituted with 1-5 $R^9$;

each $R^3$ or $R^4$ is independently hydrogen, $C_1$-$C_8$ alkyl, $C_2$-$C_8$ alkenyl, $C_2$-$C_8$ alkynyl, aryl, heteroaryl, cyclyl, heterocyclyl, arylalkyl, heteroarylalkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy, silylalkoxyalkyl, —CN, —$NO_2$, —$C(O)OR^a$, —$C(Y)NR^bR^{b'}$, —$NR^cC(Y)R^{c'}$, —$NR^bR^{b'}$, —$OC(O)NR^bR^{b'}$, —$NR^cC(O)OR^{c'}$, —$SO_2NR^bR^{b'}$, —$NR^cSO_2R^{c'}$, —$NR^cC(Y)NR^bR^{b'}$, —$OR^{d'}$, —$SR^{d'}$, —$C(Y)R^e$ or —$S(O)_qR^f$, each of which is optionally substituted with 1-3 $R^{10}$;

each $R^7$, $R^9$ and $R^{10}$ is independently $C_1$-$C_8$ alkyl, $C_2$-$C_8$ alkenyl, $C_2$-$C_8$ alkynyl, aryl, heteroaryl, cyclyl, heterocyclyl, arylalkyl, heteroarylalkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy, silylalkoxyalkyl, oxo, thioxo, —CN, —$NO_2$, —$C(O)OR^a$, —$C(Y)NR^bR^{b'}$, —$NR^cC(Y)R^{c'}$, —$NR^bR^{b'}$, —$OC(O)NR^bR^{b'}$, —$NR^cC(O)OR^{c'}$, —$SO_2NR^bR^{b'}$, —$NR^cSO_2R^{c'}$, —$NR^cC(Y)NR^bR^{b'}$, —$OR^d$, —$SR^{d'}$, —$C(Y)R^e$ or —$S(O)_qR^f$, each of which is optionally substituted with 1-3 $R^{12}$; wherein two $R^7$ or two $R^9$ are optionally be taken together with the atoms to which they are attached to form an optionally substituted cyclyl, heterocyclyl, aryl or heteroaryl ring;

$R^{12}$ is independently $C_1$-$C_8$ alkyl, $C_2$-$C_8$ alkenyl, $C_2$-$C_8$ alkynyl, aryl, heteroaryl, cyclyl, heterocyclyl, arylalkyl, heteroarylalkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy, silylalkoxyalkyl, oxo, thioxo, —CN, —$NO_2$, —$C(O)OR^a$, —$C(Y)NR^bR^{b'}$, —$NR^cC(Y)R^{c'}$, —$NR^bR^{b'}$, —$OC(O)NR^bR^{b'}$, $NR^cC(O)OR^{c'}$, —$SO_2NR^bR^{b'}$, —$NR^cSO_2R^{c'}$, —$NR^cC(Y)NR^bR^{b'}$, —$OR^d$, —$SR^{d'}$, —$C(Y)R^e$ or —$S(O)_qR^f$, each of which is optionally substituted with 1-3 $R^{13}$;

$R^{13}$ is independently $C_1$-$C_8$ alkyl, haloalkyl, halo, heterocyclyl, cyclyl, oxo or —$C(Y)NR^bR^{b'}$;

Y is O or S;

q is 1 or 2; and each $R^a$, $R^b$, $R^{b'}$, $R^c$, $R^{c'}$, $R^d$, $R^{d'}$, $R^e$ and $R^f$ is independently hydrogen, $C_1$-$C_8$ alkyl, $C_2$-$C_8$ alkenyl, $C_2$-$C_8$ alkynyl, acyl, cyclyl, heterocyclyl, aryl, haloalkyl, alkoxyalkyl, alkylaminoalkyl, dialkylaminoalkyl, heteroaryl, cyclylalkyl, heterocyclylalkyl, arylalkyl or heteroarylalkyl.

Item 16. The compound according to item 15 represented by general formula (III) or a salt thereof, wherein:

m is 1;

n is 1;

$R^1$ is hydrogen, $C_1$-$C_8$ alkyl, $C_2$-$C_8$ alkenyl, $C_2$-$C_8$ alkynyl, heteroaryl, heterocyclyl, arylalkyl, cyclylalkyl, heteroarylalkyl, alkoxyalkyl, hydroxyalkyl or —C(O)$R^e$, each of which is optionally substituted with 1-3 $R^7$;

$R^2$ is aryl, heteroaryl or benzofuryl, each of which is optionally substituted with 1-5 $R^9$;

each $R^3$ or $R^4$ is independently hydrogen, $C_1$-$C_8$ alkyl, halo, haloalkyl or —$OR^d$;

$R^6$ is hydrogen or $C_1$-$C_8$ alkyl;

each $R^7$ and $R^9$ is independently $C_1$-$C_8$ alkyl, aryl, heteroaryl, halo, haloalkyl, haloalkoxy, hydroxyalkyl, alkoxyalkyl, oxo, —CN, —$NO_2$, —C(O)$OR^a$, —C(O)$NR^bR^{b'}$, —$NR^bR^{b'}$, —$OR^d$, —C(O)$R^e$ or —$S(O)_qR^f$, each of which is optionally substituted with 1-3 $R^{12}$;

$R^{12}$ is independently $C_1$-$C_8$ alkyl, oxo, halo, haloalkyl, —CN, —C(O)$NR^bR^{b'}$ or —C(O)$R^e$ each of which is optionally substituted with 1-3 $R^{13}$;

$R^{13}$ is independently $C_1$-$C_8$ alkyl, halo or heterocyclyl; and each $R^a$, $R^b$, $R^{b'}$, $R^c$, $R^{c'}$, $R^d$, $R^{d'}$, $R^e$ and $R^f$ is independently hydrogen, $C_1$-$C_3$ alkyl, cyclyl, heterocyclyl, arylalkyl, alkoxyalkyl, heterocyclylalkyl, heteroarylalkyl, alkylaminoalkyl, dialkylaminoalkyl or phenyl.

Item 17. The compound according to Item 16 represented by general formula (III) or a salt thereof, wherein:

$R^1$ is hydrogen, $C_1$-$C_8$ alkyl, $C_2$-$C_4$ alkenyl, $C_2$-$C_8$ alkynyl, alkoxyalkyl, hydroxyalkyl, imidazolyl, pyridylalkyl, phenylalkyl, oxazolylalkyl, thienylalkyl, thiazolidinyl isoindolyl, —C(O)$R^e$, dihydroindenyl, $C_3$-$C_8$ cycloalkyl, $C_3$-$C_8$ cycloalkylalkyl, piperidyl, morpholinyl, pyrrolidinyl, azetidinyl or piperazinyl, each of which is optionally substituted with 1-3 $R^7$;

$R^2$ is phenyl, naphthyl, benzofuryl, indazolyl, benzothienyl, pyridyl, pyrimidinyl, dihydrobenzodioxinyl, benzodioxolyl, benzoimidazolyl, isoxazolyl, pyrazolyl, indolinyl or benzoisoxazolyl, each of which is optionally substituted with 1-5 $R^9$;

each $R^3$ or $R^4$ is independently hydrogen, $C_1$-$C_5$ alkyl, halo, haloalkyl or —$OR^d$;

$R^6$ is hydrogen or $C_1$-$C_8$ alkyl;

each $R^7$ and $R^9$ is independently $C_1$-$C_8$ alkyl, phenyl, halo, haloalkyl, haloalkoxy, hydroxyalkyl, alkoxyalkyl, oxo, —CN, —$NO_2$, —C(O)$OR^a$, —C(O)$NR^bR^{b'}$, —$NR^bR^{b'}$, —$OR^d$, —C(O)$R^e$ or —$S(O)_qR^f$; and each $R^a$, $R^b$, $R^{b'}$, $R^c$, $R^{c'}$, $R^d$, $R^{d'}$, $R^e$ and $R^f$ is independently hydrogen, $C_1$-$C_8$ alkyl, $C_3$-$C_8$ cycloalkyl, pyrrolidinyl, piperidinyl, morpholinyl, piperazinyl, tetrahydropyranyl, phenylalkyl, alkoxyalkyl, morholinylalkyl, oxazolidinylalkyl, imidazolylalkyl, tetrahydropyranylalkyl, pyridylalkyl, pyrazolylalkyl, tetrazolylalkyl, thiazolylalkyl, pyrrolylalkyl, benzoxazolylalkyl, indazolylalkyl, dihydrobenzoxazinylalkyl, tetrahydrofurylalkyl, tetrahydrofuryl, alkylaminoalkyl, dialkylaminoalkyl or phenyl.

Item 18. The compound according to item 16 represented by general formula (III) or a salt thereof, wherein:

$R^1$ is hydrogen, $C_1$-$C_8$ alkyl, $C_2$-$C_8$ alkenyl, $C_2$-$C_8$ alkynyl, alkoxyalkyl, hydroxyalkyl, imidazolyl, furylalkyl, pyridylalkyl, phenylalkyl, oxazolylalkyl, thienylalkyl, thiazolidinyl, isoindolyl, —C(O)$R^e$, dihydroindenyl, $C_3$-$C_8$ cycloalkyl, $C_3$-$C_8$ cycloalkylalkyl, piperidyl, morpholinyl, pyrrolidinyl, azetidinyl or piperazinyl, each of which is optionally substituted with 1-3 $R^7$;

$R^2$ is phenyl, naphthyl, benzofuryl, indazolyl, benzothienyl, pyridyl, pyrimidinyl, dihydrobenzodioxinyl, benzodioxolyl, benzoimidazolyl, isoxazolyl, pyrazolyl, indolinyl or benzisoxazolyl, each of which is optionally substituted with 1-5 $R^9$;

each $R^3$ or $R^4$ is independently hydrogen, $C_1$-$C_8$ alkyl, halo, haloalkyl or —$OR^d$;

$R^6$ is hydrogen or $C_1$-$C_8$ alkyl;

each $R^7$ and $R^9$ is independently $C_1$-$C_8$ alkyl, phenyl, halo, haloalkyl, haloalkoxy, hydroxyalkyl, alkoxyalkyl, oxo, —CN, —$NO_2$, —C(O)$OR^a$, —C(O)$NR^bR^{b'}$, —$NR^bR^{b'}$, —$OR^d$, —C(O)$R^e$ or —$S(O)_qR^f$, each of which is optionally substituted with 1-3 $R^{12}$;

$R^{12}$ is independently $C_1$-$C_8$ alkyl, oxo, halo, haloalkyl, —CN, —C(O)$NR^bR^{b'}$ or —C(O)$R^e$, each of which is optionally substituted with 1-3 $R^{13}$;

$R^{13}$ is independently $C_3$-$C_8$ alkyl, halo or pyrrolidinyl; and each $R^a$, $R^b$, $R^{b'}$, $R^c$, $R^{c'}$, $R^d$, $R^{d'}$, $R^e$ and $R^f$ is independently hydrogen, $C_1$-$C_8$ alkyl, $C_3$-$C_8$ cycloalkyl, pyrrolidinyl, piperidyl, morpholinyl, piperazinyl, tetrahydropyranyl, phenylalkyl, alkoxyalkyl, morpholinylalkyl, oxazolidinylalkyl, imidazolylalkyl, tetrahydropyranylalkyl, pyridylalkyl, pyrazolylalkyl, tetrazolylalkyl, thiazolylalkyl, pyrrolylalkyl, benzoxazolylalkyl, indazolylalkyl, dihydrobenzoxazinylalkyl, tetrahydrofurylalkyl, tetrahydrofuryl, alkylaminoalkyl, dialkylaminoalkyl or phenyl.

Item 19. The compound according to item 18 represented by general formula (III) or a salt thereof, wherein:

A is N;

$R^3$ is hydrogen, $C_1$-$C_8$ alkyl, halo, haloalkyl, or —$OR^d$;

$R^4$ is hydrogen, $C_1$-$C_8$ alkyl, halo, or —$OR^d$;

$R^7$ is $C_1$-$C_8$ alkyl, phenyl, halo, haloalkyl, oxo, —C(O)$OR^a$, —C(O)$NR^bR^{b'}$ or —$OR^d$ each of which is optionally substituted with 1-3 $R^{12}$;

$R^9$ is $C_1$-$C_8$ alkyl, phenyl, halo, haloalkyl, haloalkoxy, hydroxyalkyl, alkoxyalkyl, —CN, —$NO_2$, —C(O)$NR^bR^{b'}$, —C(O)$OR^a$, —$NR^bR^{b'}$, —$OR^d$, —C(O)$R^e$ or —$S(O)_qR^f$, each of which is optionally substituted with 1-3 $R^{12}$; and each $R^a$, $R^b$, $R^{b'}$, $R^c$, $R^{c'}$, $R^d$, $R^{d'}$, $R^e$ and $R^f$ is independently hydrogen, $C_1$-$C_8$ alkyl, $C_3$-$C_8$ cycloalkyl, pyrrolidinyl, piperidyl, morpholinyl, piperazinyl, tetrahydropyranyl, phenylalkyl, alkoxyalkyl, morpholinylalkyl, oxazolidinylalkyl, imidazolylalkyl, tetrahydropyranylalkyl, pyridylalkyl, pyrazolylalkyl, tetrazolylalkyl, thiazolylalkyl, pyrrolylalkyl, benzoxazolylalkyl, indazolylalkyl, tetrahydrofurylalkyl, dihydrobenzoxazinylalkyl, tetrahydrofuryl, alkylaminoalkyl, dialkylaminoalkyl or phenyl.

Item 20. The compound according to item 17 or 19 represented by general formula (III) or a salt thereof, wherein:

A is N;

$R^3$ is hydrogen, $C_1$-$C_8$ alkyl, halo, haloalkyl, or —$OR^d$;

$R^4$ is hydrogen, $C_1$-$C_8$ alkyl, halo, or —$OR^d$;

$R^7$ is $C_1$-$C_8$ alkyl, phenyl, halo, haloalkyl, oxo, —C(O)$OR^a$, —C(O)$NR^bR^{b'}$ or —$OR^d$;

$R^9$ is $C_1$-$C_8$ alkyl, phenyl, halo, haloalkyl, haloalkoxy, hydroxyalkyl, alkoxyalkyl, —CN, —$NO_2$—C(O)$NR^bR^{b'}$, —C(O)$OR^a$, —$NR^bR^{b'}$, —$OR^d$, —C(O)$R^e$ or —$S(O)_qR^f$; and each $R^a$, $R^b$, $R^{b'}$, $R^c$, $R^{c'}$, $R^d$, $R^{d'}$, $R^e$ and $R^f$ is independently hydrogen, $C_1$-$C_8$ alkyl, $C_3$-$C_8$ cycloalkyl, pyrrolidinyl, piperidyl, morpholinyl, piperazinyl, tetrahydropyranyl, phenylalkyl, alkoxyalkyl, morpholinylalkyl, oxazolidinylalkyl, imidazolylalkyl, tetrahydropyranylalkyl, pyridylalkyl, pyrazolylalkyl, tetrazolylalkyl, thiazolylalkyl, pyrrolylalkyl, benzoxazolylalkyl, indazolylalkyl, tetrahydrofurylalkyl, tetrahydrofuryl, dihydrobenzoxazinylalkyl, alkylaminoalkyl, dialkylaminoalkyl or phenyl.

Item 21. The compound according to item 20 represented by general formula (III) or a salt thereof, wherein:

$R^1$ is hydrogen, $C_1$-$C_8$ alkyl, $C_2$-$C_8$ alkenyl, $C_2$-$C_8$ alkynyl, alkoxyalkyl, hydroxyalkyl, imidazolyl, furylalkyl, pyridylalkyl, phenylalkyl, oxazolylalkyl, thienylalkyl, isoindolyl, —C(O)$R^c$, dihydroindenyl, $C_3$-$C_8$ cycloalkyl, $C_3$-$C_8$ cycloalkylalkyl, piperidyl, morpholinyl, pyrrolidinyl, azetidinyl or piperazinyl, each of which is optionally substituted with 1-3 $R^7$;

$R^2$ is phenyl, which is optionally substituted with 1-5 $R^9$; and each $R^a$, $R^b$, $R^{b'}$, $R^c$, $R^{c'}$, $R^d$, $R^{d'}$, $R^e$ and $R^f$ is independently hydrogen, $C_1$-$C_8$ alkyl, pyrrolidinyl, morpholinyl, tetrahydropyranyl, alkoxyalkyl, morpholinylalkyl, tetrahydropyranylalkyl, pyridylalkyl, thiazolylalkyl, pyrrolylalkyl, tetrahydrofuryl, alkylaminoalkyl or phenyl.

In some embodiments, $R^1$ is $C_1$-$C_8$ alkyl, which is optionally substituted with 1-3 $R^7$; or when L is $NR^6$, $R^1$ and $R^6$ may be taken together with the atoms to which they are attached to form a heterocyclyl or heteroaryl ring that is optionally substituted with 1-3 $R^8$.

In some embodiments, A is CH. In some embodiments, A is N.

In some embodiments, L is $NR^6$. In some embodiments, $R^6$ is hydrogen.

In some embodiments, $R^1$ is $C_1$-$C_8$ alkyl, e.g., methyl, ethyl, $C_3$ alkyl (e.g., n-propyl or isopropyl), $C_4$ alkyl (e.g., n-butyl, isobutyl or tert-butyl), or $C_5$ alkyl (e.g., pentan-3-yl).

In some embodiments, $R^1$ is $C_1$-$C_8$ alkyl substituted with 1-3 $R^7$ (e.g., $C_1$-$C_8$ alkyl substituted with 1 $R^7$). In some embodiments, $R^1$ is methyl substituted with 1 $R^7$. In some embodiments, $R^1$ is cyclyl (e.g., cyclopropyl). In some embodiments, $R^7$ is aryl (e.g., phenyl).

In some embodiments, $R^1$ is ethyl substituted with 1 $R^7$. In some embodiments, $R^7$ is aryl (e.g., phenyl). In some embodiments, $R^7$ is —$OR^d$. In some embodiments, $R^d$ is aryl (e.g., phenyl).

In some embodiments, $R^1$ is n-propyl substituted with 1 $R^7$. In some embodiments, $R^1$ is —$OR^d$. In some embodiments, $R^d$ is $C_1$-$C_8$ alkyl (e.g., $C_3$ alkyl, e.g., n-propyl).

In some embodiments, $R^1$ is $C_1$-$C_8$ alkyl substituted with 3 $R^7$. In some embodiments, $R^1$ is ethyl substituted with 3 $R^7$. In some embodiments, each $R^7$ is independently halo (e.g., each $R^7$ is fluoro). In some embodiments, $R^1$ is 2,2,2-trifluoroethyl.

In some embodiments, $R^1$ is $C_2$-$C_8$ alkenyl, e.g., $C_3$ alkenyl (e.g., —$CH_2$—CH═$CH_2$).

In some embodiments, $R^1$ is $C_2$-$C_8$ alkynyl, e.g., $C_3$ alkynyl (e.g. —$CH_2$—C≡CH).

In some embodiments, $R^1$ is cyclyl (e.g., cyclopropyl, cyclobutyl, cyclopentyl or cyclohexyl). In some embodiments, the cyclyl group is a bicyclic group (e.g., indanyl).

In some embodiments, $R^1$ is heterocyclyl (e.g., piperidyl). In some embodiments, $R^1$ is piperidyl substituted with 1 $R^7$. In some embodiments, $R^1$ is —C(Y)$R^e$. In some embodiments, Y is O. In some embodiments, $R^e$ is $C_1$-$C_8$ alkyl (e.g., methyl). In some embodiments, $R^1$ is —$OR^d$.

In some embodiments, $R^6$ is $C_1$-$C_8$ alkyl (e.g., methyl).

In some embodiments, $R^1$ and $R^6$ are taken together with the atoms to which they are attached to form a heterocyclyl ring (e.g. a pyrrolidine ring).

In some embodiments, $R^1$ and $R^6$ are taken together with the atoms to which they are attached to form a heteroaryl ring (e.g., an imidazole ring).

In some embodiments, L is O.

In some embodiments, $R^1$ is $C_1$-$C_8$ alkyl (e.g., methyl).

In some embodiments, $R^2$ is aryl (e.g., phenyl). In some embodiments, $R^2$ is unsubstituted phenyl. In some embodiments, $R^2$ is phenyl substituted with 1-3 $R^9$. In some embodiments, $R^1$ is phenyl substituted with 1 $R^9$.

In some embodiments, $R^2$ is:

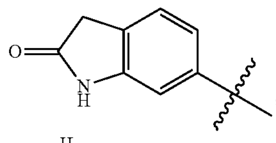

,

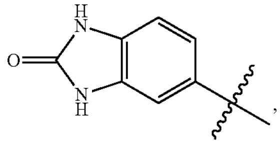

, or

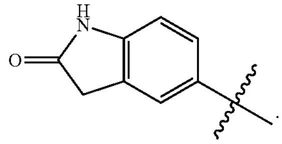

.

In some embodiments, $R^9$ is halo (e.g., fluoro or chloro). In some embodiments, $R^9$ is —CN. In some embodiments, $R^9$ is —$NO_2$. In some embodiments, $R^9$ is haloalkoxy (e.g., trifluoroethoxy). In some embodiments, $R^9$ is —$NR^bR^{b'}$. In some embodiments, $R^b$ and $R^{b'}$ are each independently $C_1$-$C_8$ alkyl (e.g., $R^b$ and $R^{b'}$ are both methyl).

In some embodiments, $R^9$ is —$OR^d$. In some embodiments, $R^9$ is —$OCH_2CH_2OCH_3$. In some embodiments, $R^9$ is —$OCH_2CH_2OCH_2CH_2CH_3$. In some embodiments, $R^9$ is —$OCH_2CH_2OCH_2CH_2OCH_3$. In some embodiments, $R^d$ is hydrogen. In some embodiments, $R^d$ is $C_1$-$C_8$ alkyl (e.g., methyl). In some embodiments, $R^d$ is ethyl.

In some embodiments, $R^9$ is hydroxyalkyl (e.g., —$CH_2OH$). In some embodiments, $R^9$ is alkoxyalkyl (e.g., —CH—O—$CH_3$). In some embodiments, $R^9$ is —C(O)$R^e$. In some embodiments, $R^e$ is heterocyclyl (e.g., morpholino). In some embodiments, $R^9$ is —$S(O)_qR^f$. In some embodiments, q is 1. In some embodiments, $R^f$ is $C_1$-$C_8$ alkyl (e.g., methyl).

In some embodiments, $R^2$ is phenyl substituted with 2 $R^9$. In some embodiments, each $R^9$ is independently halo (e.g., each $R^9$ is fluoro). In some embodiments, each $R^9$ is independently —$OR^d$. In some embodiments, each $R^d$ is independently $C_1$-$C_8$ alkyl (e.g., each $R^d$ is methyl).

In some embodiments, $R^2$ is heteroaryl. In some embodiments, $R^2$ is a 6-membered heteroaryl. In some embodiments, $R^2$ is a 6-membered nitrogen-containing heteroaryl, e.g., pyridyl. In some embodiments, $R^2$ is unsubstituted pyridyl.

In some embodiments, $R^2$ is pyridyl substituted with 1 $R^9$. In some embodiments, $R^9$ is —$OR^d$. In some embodiments, $R^d$ is $C_1$-$C_8$ alkyl (e.g., methyl).

In some embodiments, $R^2$ is a 5-membered heteroaryl. In some embodiments, $R^2$ is a 5-membered nitrogen-containing heteroaryl (e.g., pyrrolyl or oxazolyl).

In some embodiments, m is 0.

In some embodiments, m is 1.

In some embodiments, $R^4$ is $C_1$-$C_8$ alkyl (e.g., methyl). In some embodiments, $R^4$ is —$OR^d$. In some embodiments, $R^d$ is $C_1$-$C_8$ alkyl (e.g., methyl). In some embodiments, $R^4$ is halo. In some embodiments, $R^4$ is methoxy. In some embodiments, $R^d$ is $C_1$-$C_8$ alkyl.

In some embodiments, the compound has the following structure:

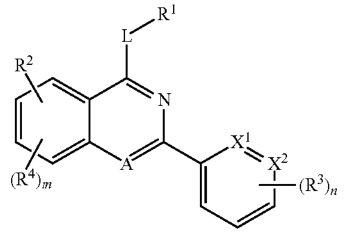

wherein one of $X^1$ and $X^2$ is N and the other is CH.

In some embodiments, $X^1$ is CH and $X^2$ is N. In some embodiments, $X^1$ is N and $X^2$ is CH. In some embodiments, the compound has the following structure:

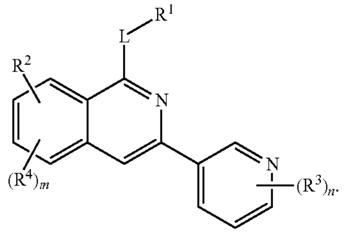

In some embodiments, $R^2$ is aryl. In some embodiments, $R^2$ is heteroaryl. In some embodiments, $R^1$ is $C_1$-$C_8$ alkyl (e.g., methyl).

In some embodiments, the compound has the following structure:

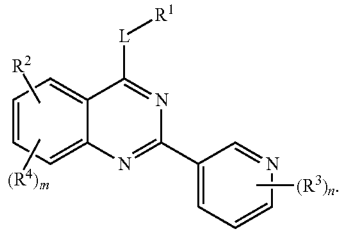

In some embodiments, $R^2$ is aryl. In some embodiments, $R^2$ is heteroaryl. In some embodiments, $R^1$ is $C_1$-$C_8$ alkyl (e.g., methyl).

In some embodiments, the compound has the following structure:

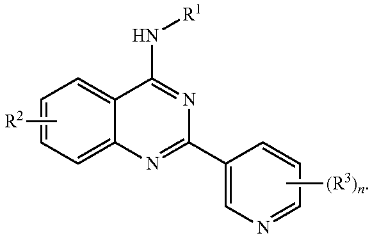

In some embodiments, $R^2$ is aryl. In some embodiments, $R^2$ is heteroaryl. In some embodiments, $R^1$ is $C_1$-$C_8$ alkyl (e.g., methyl).

In some embodiments, the compound has the following structure:

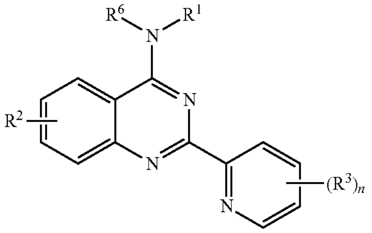

wherein $R^1$ is $C_1$-$C_8$ alkyl, which is optionally substituted with 1-3 $R^7$.

In some embodiments, $R^2$ is aryl. In some embodiments, $R^2$ is heteroaryl. In some embodiments, $R^1$ is $C_1$-$C_8$ alkyl (e.g., methyl).

In some embodiments, the compound has the following structure:

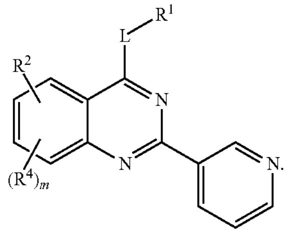

In some embodiments, $R^2$ is aryl. In some embodiments, $R^2$ is heteroaryl. In some embodiments, $R^1$ is $C_1$-$C_8$ alkyl (e.g., methyl).

In some embodiments, $R^2$ is

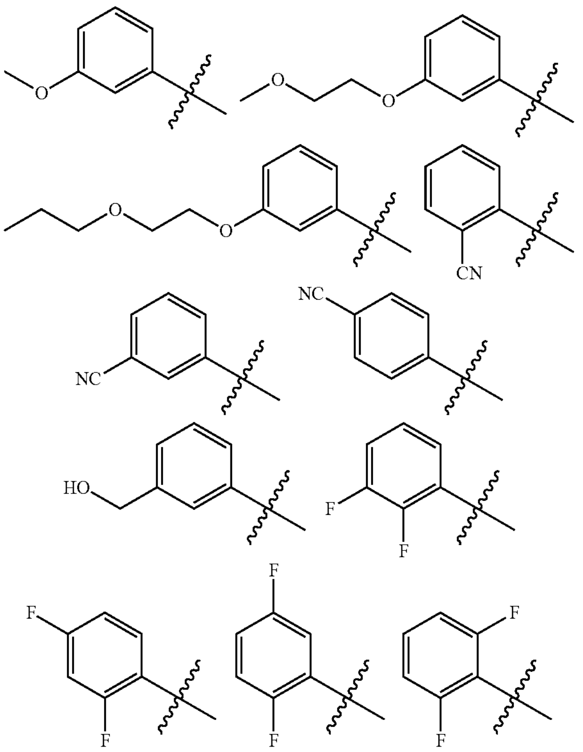

-continued

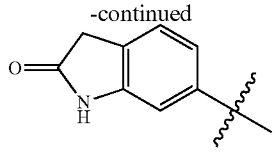

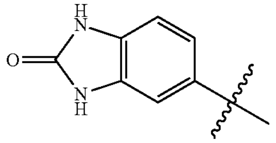

or

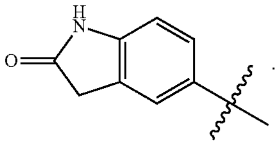

.

In some embodiments, the compound has the following structure:

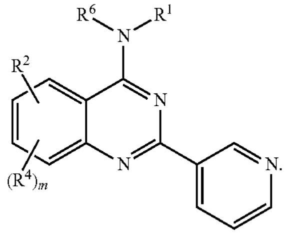

In some embodiments, $R^2$ is aryl. In some embodiments, $R^2$ is heteroaryl. In some embodiments $R^1$ is $C_1$-$C_8$ alkyl (e.g., methyl). In some embodiments, $R^2$ is

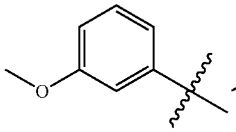

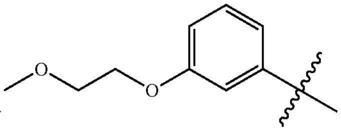

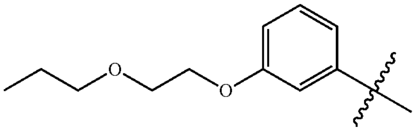

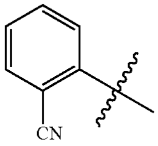

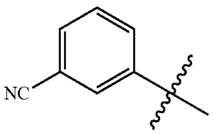

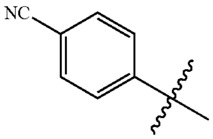

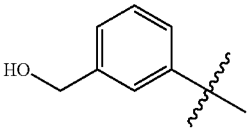

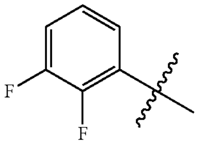

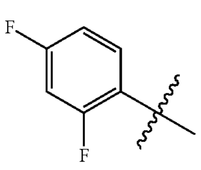

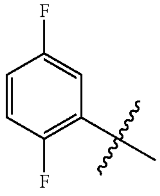

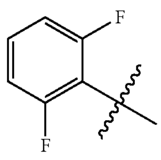

-continued

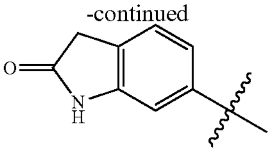

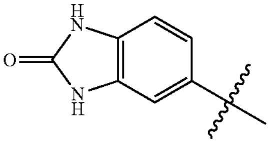

or

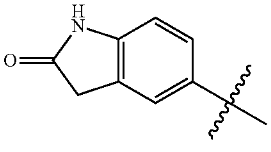

In some embodiments, the compound has the following structure:

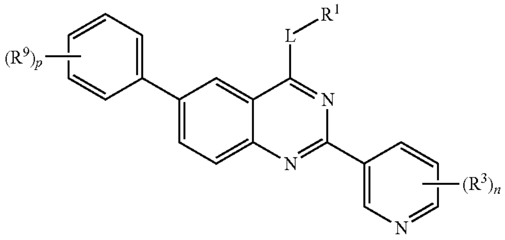

wherein p is 1, 2, 3, 4 or 5.

In some embodiments, L is $NR^6$. In some embodiments, L is O. In some embodiments, $R^1$ is hydrogen or $C_1$-$C_8$ alkyl. In some embodiments, $R^1$ is cyclyl or heterocyclyl. In some embodiments, $R^1$ is aralkyl or heteroaralkyl. In some embodiments, $R^1$ is methyl, cyclohexyl, t-butyl, or

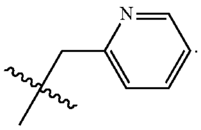 [SMILES: *Cc1ccccn1]

.

In some embodiments, $R^6$ is hydrogen or $C_1$-$C_8$ alkyl.

In some embodiments, $R^9$ is $C_1$-$C_8$ alkyl, halo, —CN, or —$OR^d$. In some embodiments, $R^3$ is hydrogen.

In some embodiments, the compound has the following structure:

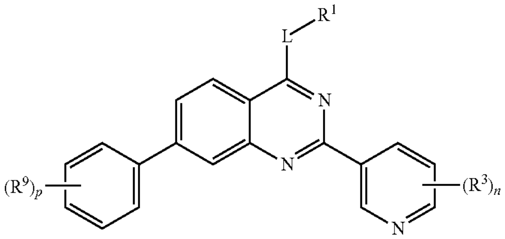

wherein p is 1, 2, 3, 4 or 5.

In some embodiments, L is $NR^6$. In some embodiments, L is O. In some embodiments, $R^1$ is hydrogen or $C_1$-$C_8$ alkyl. In some embodiments, $R^1$ is cyclyl or heterocyclyl. In some embodiments, $R^1$ is aralkyl or heteroaralkyl. In some embodiments, $R^1$ is methyl, cyclohexyl, t-butyl, or

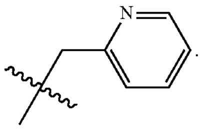

In some embodiments, $R^1$ is hydrogen or $C_1$-$C_8$ alkyl. In some embodiments, $R^9$ is $C_1$-$C_8$ alkyl, halo, —CN, or —$OR^d$. In some embodiments, $R^3$ is hydrogen.

Compounds of Formula (IV)

The following aspects and embodiments relate to compounds of formula (IV), corresponding to formula (I) of U.S. Provisional Patent Application No. 61/291,544, entitled "Therapeutic Compounds and Related Methods of Use" filed on Dec. 31, 2009, and incorporated herein by reference in its entirety.

Item 38. A compound of formula (IV):

(IV)

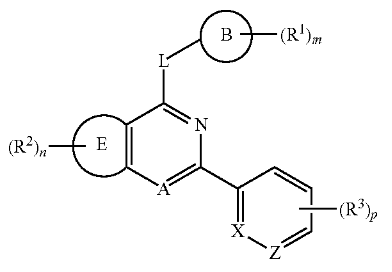

wherein:

A is CH, $CR^4$ or N;

B is aryl or a 5- or 6-membered heteroaryl;

m is 0, 1, 2, 3, 4 or 5;

E is aryl or a 5-membered heteroaryl;

when E is aryl, n is 1, 2, 3 or 4; and when E is a 5-membered heteroaryl, n is 0, 1, 2 or 3:

L is $NR^5$ or O;

one of X and Z is N and the other is CH;

p is 0, 1, 2, 3 or 4;

each $R^1$, $R^2$ and $R^3$ is independently $C_1$-$C_8$ alkyl, $C_2$-$C_8$ alkenyl, $C_2$-$C_8$ alkynyl, aryl, heteroaryl, cyclyl, heterocyclyl, aralkyl, heteroaralkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy, silylalkoxyalkyl, —CN, —$NO_2$, —C(O)$OR^a$, —C(Y)$NR^bR^{b'}$, —$NR^c$C(Y)$R^{c'}$, —$NR^bR^{b'}$, —OC(O)$NR^bR^{b'}$, —$NR^c$C(O)$OR^{c'}$, —$SO_2NR^bR^{b'}$, —$NR^cSO_2R^{c'}$, —$NR^c$(Y)$NR^bR^{b'}$, —$OR^d$, —$SR^{d'}$, —C(Y)$R^e$ or —$S(O)_qR^f$, each of which may be optionally substituted with 1-3 $R^6$; wherein two $R^1$, together with the atoms to which they are attached, may form an optionally substituted cyclyl, heterocyclyl, aryl or heteroaryl ring;

$R^4$ is hydrogen, $C_1$-$C_8$ alkyl, $C_2$-$C_8$ alkenyl, $C_2$-$C_8$ alkynyl, aryl, heteroaryl, cyclyl, heterocyclyl, aralkyl, heteroaralkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy, silylalkoxyalkyl, —CN, —$NO_2$, —C(O)$OR^a$, —C(Y)$NR^bR^{b'}$, —$NR^c$C(Y)$R^{c'}$, —$NR^bR^{b'}$, —OC(O)$NR^bR^{b'}$, —$NR^c$C(O)$OR^{c'}$, —$SO_2NR^bR^{b'}$, —$NR^cSO_2R^{c'}$, —$NR^c$C(Y)$NR^bR^{b'}$, —$OR^d$, —$SR^{d'}$, —C(Y)$R^e$ or —$S(O)_qR^f$, each of which may be optionally substituted with 1-3 $R^6$;

$R^5$ is hydrogen; or when in is not 0, $R^5$ and 1 $R^1$ may be taken together with the atoms to which they are attached to form an optionally substituted heteroaryl or heterocyclyl ring;

each $R^6$ is independently $C_1$-$C_8$ alkyl, $C_2$-$C_8$ alkenyl, $C_2$-$C_8$ alkynyl, aryl, heteroaryl, cyclyl, heterocyclyl, aralkyl, heteroaralkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy, silylalkoxyalkyl, oxo, thiono, —CN, —$NO_2$, —C(O)$OR^a$, —C(Y)$NR^bR^{b'}$, —$NR^c$C(Y)$R^{c'}$, —$NR^bR^{b'}$, OC(O)$NR^bR^{b'}$, —$NR^c$C(O)$OR^{c'}$, —$SO_2NR^bR^{b'}$, —$NR^cSO_2R^{c'}$, —$NR^c$C(Y)$NR^bR^{b'}$, —$OR^d$—$SR^{d'}$, —C(Y)$R^e$ or —$S(O)_qR^f$, each of which may be optionally substituted with 1-3 $R^7$;

each $R^7$ is independently $C_1$-$C_8$ alkyl, $C_2$-$C_8$ alkenyl, $C_1$-$C_8$ alkynyl, aryl, heteroaryl, cyclyl, heterocyclyl, aralkyl, heteroaralkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy, silylalkoxyalkyl, oxo, thiono, —CN, —$NO_2$, —C(O)$OR^a$, —C(Y)$NR^bR^{b'}$, —$NR^c$C(Y)$R^{c'}$, —$NR^bR^{b'}$, —OC(O)$NR^bR^{b'}$, —$NR^c$C(O)$OR^{c'}$, —$SO_2NR^bR^{b'}$, —$NR^cSO_2R^{v'}$, —$NR^c$C(Y)$NR^bR^{b'}$, —$OR^d$, —$SR^{d'}$, —C(Y)$R^e$ or —$S(O)_qR^f$;

each Y is independently O or S;

q is 1 or 2; and each $R^a$, $R^b$, $R^{b'}$, $R^c$, $R^{c'}$, $R^d$, $R^{d'}$, $R^e$, $R^{e'}$ and $R^f$ is independently selected from hydrogen, $C_1$-$C_8$ alkyl, $C_2$-$C_8$ alkenyl, $C_2$-$C_8$ alkynyl, acyl, aryl, heteroaryl, cyclyl, heterocyclyl, aralkyl, heteroaralkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy and silylalkoxyalkyl, each of which may be optionally substituted with 1-3 $R^6$, wherein $R^b$ and $R^{b'}$, together with the atoms to which they are attached, may form an optionally substituted cyclyl or heterocyclyl ring;

or a pharmaceutically acceptable derivative or prodrug thereof, wherein when B is phenyl, two $R^1$ are not taken together to form a pyrazole ring; when B is phenyl, $R^2$ is not

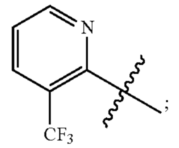

and where in the compound is not:

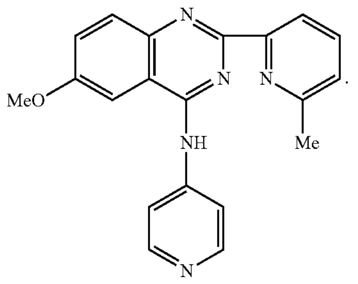 [SMILES: COc1ccc2nc(-c3cccc(C)n3)nc(Nc3ccncc3)c2c1]

In some embodiments, when B is phenyl, $R^2$ is not a substituted pyridyl. In some embodiments, when B is phenyl and n=1, $R^2$ is not a substituted pyridyl.

In some embodiments, when X is N, B is not 4-pyridyl.

In some embodiments, each $R^a$, $R^b$, $R^{b'}$, $R^c$, $R^{c'}$, $R^d$, $R^{d'}$, $R^e$, $R^{e'}$ and $R^f$ is independently selected from hydrogen, $C_1$-$C_8$ alkyl, $C_2$-$C_8$ alkenyl, $C_2$-$C_8$ alkynyl, acyl, aryl, heteroaryl, cyclyl, heterocyclyl, aralkyl, heteroaralkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy and silylalkoxyalkyl, each of which may be optionally substituted with 1-3 $R^6$.

In some embodiments, B is aryl.

Item 39. A compound of formula (IV):

(IV)

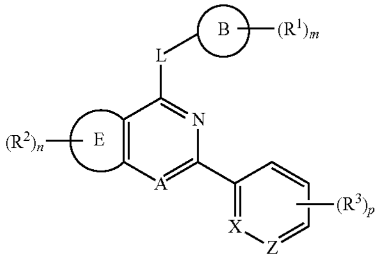

wherein:

A is CH, $CR^4$ or N;

B is aryl or a 5-membered heteroaryl;

m is 0, 1, 2, 3, 4 or 5;

E is aryl or a 5-membered heteroaryl;

when E is aryl, n is 1, 2, 3 or 4; and when E is a 5-membered heteroaryl, n is 0, 1, 2 or 3;

L is $NR^5$ or O;

one of X and Z is N and the other is CH;

p is 0, 1, 2, 3 or 4;

each $R^1$, $R^2$ and $R^3$ is independently $C_1$-$C_8$ alkyl, $C_2$-$C_8$ alkenyl, $C_2$-$C_8$ alkynyl, aryl, heteroaryl, cyclyl, heterocyclyl, aralkyl, heteroaralkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy, silylalkoxyalkyl, —CN, —$NO_2$, —C(O)OR, —C(Y)$NR^bR^{b'}$, —$NR^cC(Y)R^{c'}$, —$NR^bR^{b'}$, —OC(O)$NR^bR^{b'}$, —$NR^cC(O)OR^{c'}$, —$SO_2NR^bR^{b'}$, —$NR^cSO_2R^{c'}$, —$NR^cC(Y)NR^bR^{b'}$, —$OR^d$, —$SR^{d'}$, —C(Y)$R^e$ or —$S(O)_qR^f$, each of which may be optionally substituted with 1-3 $R^6$; wherein two $R^1$, together with the atoms to which they are attached, may form an optionally substituted cyclyl, heterocyclyl, aryl or heteroaryl ring;

$R^4$ is hydrogen, $C_1$-$C_8$ alkyl, $C_2$-$C_8$ alkenyl, $C_2$-$C_8$ alkynyl, aryl, heteroaryl, cyclyl, heterocyclyl, aralkyl, heteroaralkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy, silylalkoxyalkyl, —CN, —$NO_2$, —C(O)$OR^a$, —C(Y)$NR^bR^{b'}$, —$NR^cC(Y)R^{c'}$, —$NR^bR^{b'}$, —OC(O)$NR^bR^{b'}$, —$NR^cC(O)OR^{c'}$, —$SO_2NR^bR^{b'}$, —$NR^cSO_2R^{c'}$, —$NR^cC(Y)NR^bR^{b'}$, —$OR^d$, —$SR^{d'}$, —C(Y)$R^e$ or —$S(O)_qR^f$, each of which may be optionally substituted with 1-3 $R^6$;

$R^5$ is hydrogen; or when m is not 0, $R^5$ and 1 $R^1$ may be taken together with the atoms to which they are attached to form an optionally substituted heteroaryl or heterocyclyl ring:

each $R^6$ is independently $C_1$-$C_8$ alkyl, $C_2$-$C_8$ alkenyl, $C_2$-$C_8$ alkynyl, aryl, heteroaryl, cyclyl, heterocyclyl, aralkyl, heteroaralkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy, silylalkoxyalkyl, oxo, thiono, —CN, —$NO_2$, —C(O)$OR^a$, —C(Y)$NR^bR^{b'}$, —$NR^cC(Y)R^cR^{c'}$, —$NR^bR^{b'}$, —OC(O)$NR^bR^{b'}$, —$NR^cC(O)OR^{c'}$, —$SO_2NR^bR^{b'}$, —$NR^cSO_2R^{c'}$, —$NR^cC(Y)NR^bR^{b'}$, —$OR^d$, —$SR^{d'}$, —C(Y)$R^e$ or —$S(O)_qR^f$, each of which may be optionally substituted with 1-3 $R^7$;

each $R^7$ is independently $C_1$-$C_8$ alkyl, $C_2$-$C_8$ alkenyl, $C_2$-$C_8$ alkynyl, aryl, heteroaryl, cyclyl, heterocyclyl, aralkyl, aralkyl, heteroalkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy, silylalkoxyalkyl, oxo, thiono, —CN, —$NO_2$, —C(O)$OR^a$, —C(Y)$NR^bR^{b'}$, —$NR^cC(Y)R^{c'}$, —$NR^bR^{b'}$, —OC(O)$NR^bR^{b'}$, —$NR^cC(O)OR^{c'}$, —$SO_2NR^bR^{b'}$, —$NR^cSO_2R^{c'}$, —$NR^cC(Y)NR^bR^{b'}$, —$OR^d$ $SR^{d'}$, —C(Y)$R^e$ or —$S(O)_qR^f$;

each Y is independently O or S;

q is 1 or 2; and each $R^a$, $R^b$, $R^{b'}$, $R^c$, $R^{c'}$, $R^d$, $R^{d'}$, $R^e$, $R^{e'}$ and $R^f$ is independently selected from hydrogen, $C_1$-$C_8$ alkyl, $C_2$-$C_8$ alkenyl, $C_2$-$C_8$ alkynyl, acyl, aryl, heteroaryl, cyclyl, heterocyclyl, aralkyl, heteroaralkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy and silylalkoxyalkyl, each of which may be optionally substituted with 1-3 $R^6$ wherein $R^b$ and $R^{b'}$, together with the atoms to which they are attached, may form an optionally substituted cyclyl or heterocyclyl ring;

or a pharmaceutically acceptable derivative or prodrug thereof, wherein when B is phenyl, two $R^1$ are not taken together to form a pyrazole ring; and when B is phenyl, $R^2$ is not

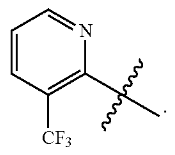

In some embodiments, each $R^a$, $R^b$, $R^{b'}$, $R^c$, $R^{c'}$, $R^d$, $R^{d'}$, $R^e$, $R^{e'}$ and $R^f$ is independently selected from hydrogen, $C_1$-$C_8$ alkyl, $C_2$-$C_8$ alkenyl, $C_2$-$C_8$ alkynyl, acyl, aryl, heteroaryl, cyclyl, heterocyclyl, aralkyl, heteroaralkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy and silylalkoxyalkyl, each of which may be optionally substituted with 1-3 $R^6$.

In some embodiments, when B is phenyl, $R^1$ is not a substituted pyridyl. In some embodiments, when B is phenyl and n=1, $R^2$ is not a substituted pyridyl.

In one aspect, the invention features a compound of formula (IV):

(IV)

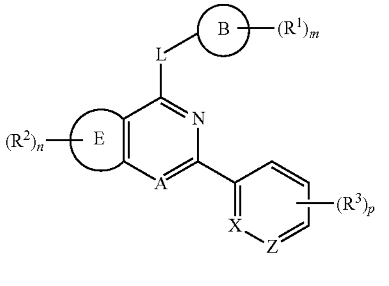

wherein:

A is CH, $CR^4$ or N;

B is aryl or a 5-membered heteroaryl;

E is aryl or a 5-membered heteroaryl;

L is $NR^5$ or O;

one of X and Z is N and the other is CH;

m is 0, 1, 2, 3, 4 or 5;

n is 1, 2, 3 or 4;

p is 0, 1, 2, 3 or 4;

each $R^1$ and $R^3$ is independently $C_1$-$C_8$ alkyl, $C_2$-$C_8$ alkenyl, $C_2$-$C_8$ alkynyl, aryl, heteroaryl, cyclyl, heterocyclyl, aralkyl, heteroaralkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy, silylalkoxyalkyl, —CN, —$NO_2$, —C(O)$OR^a$, —C(Y)$NR^bR^{b'}$, —$NR^cC(Y)R^{c'}$, —$NR^bR^{b'}$, —OC(O)$NR^bR^{b'}$, —$NR^cC(O)OR^{c'}$, —$SO_2NR^bR^{b'}$, —$NR^cSO_2R^{c'}$, —$NR^cC(Y)NR^bR^{b'}$, —$OR^d$, —$SR^{d'}$, —C(Y)$R^e$ or —$S(O)_qR^f$, each of which may be optionally substituted with 1-3 $R^6$; wherein two $R^1$, together with the atoms to which they are attached, may form an optionally substituted cyclyl, heterocyclyl, aryl or heteroaryl ring;

each $R^2$ is independently $C_1$-$C_8$ alkyl, $C_2$-$C_8$ alkenyl, $C_2$-$C_8$ alkynyl, aryl, cyclyl, heterocyclyl, aralkyl, heteroaralkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy, silylalkoxyalkyl, —CN, —$NO_2$, C(O)$OR^a$, —C(Y)$NR^bR^{b'}$, —$NR^cC(Y)R^{c'}$, —$NR^bR^{b'}$, —OC(O)$NR^bR^{b'}$, —$NR^cC(O)OR^{c'}$, $SO_2NR^bR^{b'}$, —$NR^cSO_2R^{c'}$, —$NR^cC(Y)NR^bR^{b'}$, —$OR^d$, —$SR^{d'}$, —C(Y)$R^e$ or —$S(O)_qR^f$, each of which may be optionally substituted with 1-3 $R^6$; wherein two $R^1$, together with the carbons to which they are attached, may form an optionally substituted cyclyl, heterocyclyl, aryl or heteroaryl ring;

$R^4$ is hydrogen, $C_1$-$C_8$ alkyl, $C_2$-$C_8$ alkenyl, $C_2$-$C_8$ alkynyl, aryl, heteroaryl, cyclyl, heterocyclyl, aralkyl, heteroaralkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy, silylalkoxyalkyl, —CN, —$NO_2$, —C(O)$OR^a$, —C(Y)$NR^bR^{b'}$, —$NR^cC(Y)R^{c'}$, —$NR^bR^{b'}$, —OC(O)$NR^bR^{b'}$, —$NR^cC(O)OR^{c'}$, —$SO_2NR^bR^{b'}$, —$NR^cSO_2R^{c'}$, —$NR^cC(Y)NR^bR^{b'}$, —$OR^d$, —$SR^{d'}$, —C(Y)$R^e$ or —$S(O)_qR^f$, each of which may be optionally substituted with 1-3 $R^6$;

$R^5$ is hydrogen; or when m is not 0, $R^5$ and 1 $R^1$ may be taken together with the atoms to which they are attached to form an optionally substituted heteroaryl or heterocyclyl ring;

each $R^6$ is independently $C_1$-$C_8$ alkyl, $C_2$-$C_8$ alkenyl, $C_2$-$C_8$ alkynyl, aryl, heteroaryl, cyclyl, heterocyclyl, aralkyl, heteroaralkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy, silylalkoxyalkyl, oxo, thiono, —CN, —$NO_2$, —C(O)$OR^a$, —C(Y)$NR^bR^{b'}$, —$NR^cC(Y)R^{c'}$, —$NR^bR^{b'}$, —OC(O)$NR^bR^{b'}$, —$NR^cC(O)OR^{c'}$, —$SO_2NR^bR^{b'}$, —$NR^cSO_2R^{c'}$, —$NR^c(Y)NR^bR^{b'}$, —$OR^d$, —$SR^{d'}$, —C(Y)$R^e$ or —$S(O)_qR^f$, each of which may be optionally substituted with 1-3 $R^7$;

each $R^7$ is independently $C_1$-$C_8$ alkyl, $C_2$-$C_8$ alkenyl, $C_2$-$C_8$ alkynyl, aryl, heteroaryl, cyclyl, heterocyclyl, aralkyl, heteroaralkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy, silylalkoxyalkyl, oxo, thiono, —CN, —$NO_2$, —C(O)$OR^a$, —C(Y)$NR^bR^{b'}$, —$NR^cC(Y)R^{c'}$, —$NR^bR^{b'}$, —OC(O)$NR^bR^{b'}$, —$NR^cC(O)OR^{c'}$, —$SO_2NR^bR^{b'}$, —$NR^cSO_2R^{c'}$, —$NR^cC(Y)NR^bR^{b'}$, —$OR^d$, $SR^{d'}$, —C(Y)$R^e$ or —$S(O)_qR^f$;

Y is O or S;

q is 1 or 2; and each $R^a$, $R^b$, $R^{b'}$, $R^c$, $R^{c'}$, $R^d$, $R^{d'}$, $R^e$, $R^{e'}$ and $R^f$ is independently selected from hydrogen, $C_1$-$C_8$ alkyl, $C_2$-$C_8$ alkenyl, $C_2$-$C_8$ alkynyl, acyl, cyclyl, heterocyclyl, aryl, heteroaryl, cyclylalkyl, heterocyclylalkyl, aralkyl and heteroaralkyl, each of which may be optionally further substituted with 1-3 $R^6$ wherein $R^b$ and $R^{b'}$, together with the atoms to which they are attached, may form an optionally substituted cyclyl or heterocyclyl ring;

or a pharmaceutically acceptable derivative or prodrug thereof, wherein when B is phenyl, two $R^1$ are not taken together to form a pyrazole ring.

In some embodiments, each $R^a$, $R^b$, $R^{b'}$, $R^c$, $R^{c'}$, $R^d$, $R^{d'}$, $R^e$, $R^{e'}$ and $R^f$ is independently selected from hydrogen, $C_1$-$C_8$ alkyl, $C_2$-$C_8$ alkenyl, $C_2$-$C_8$ alkynyl, acyl, aryl, heteroaryl, cyclyl, heterocyclyl, aralkyl, heteroaralkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy and silylalkoxyalkyl, each of which may be optionally substituted with 1-3 $R^6$.

In one aspect, the invention features a compound of formula (IV):

(IV)

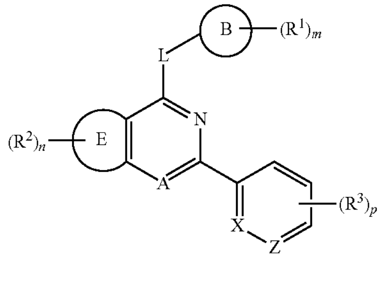

wherein:

A is CH, $CR^4$ or N;

B is aryl or a 5-membered heteroaryl;

E is aryl or a 5-membered heteroaryl;

L is $NR^5$ or O:

one of X and Z is N and the other is CH;

m is 0, 1, 2, 3, 4 or 5;

n is 1, 2, 3 or 4;

p is 0, 1, 2, 3 or 4;

each $R^1$ and $R^3$ is independently $C_1$-$C_8$ alkyl, $C_2$-$C_8$ alkenyl, $C_2$-$C_8$ alkynyl, aryl, heteroaryl, cyclyl, heterocyclyl, aralkyl, heteroaralkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy, silylalkoxyalkyl, —CN, —NO$_2$, —C(O)OR$^a$, —C(Y)NR$^b$R$^{b'}$, —NR$^c$C(Y)R$^{c'}$, —NR$^b$R$^{b'}$, —OC(O)NR$^b$R$^{b'}$, —NR$^c$C(O)OR$^{c'}$, —SO$_2$NR$^b$R$^{b'}$, —NR$^c$SO$_2$R$^{c'}$, —NR$^c$C(Y)NR$^b$R$^{b'}$, —OR$^d$, —SR$^{d'}$, —C(Y)R$^e$ or —S(O)$_q$R$^f$, each of which may be optionally substituted with 1-3 R$^6$; wherein two R$^1$, together with the atoms to which they are attached, may form an optionally substituted cyclyl, heterocyclyl, or aryl ring;

each $R^2$ is independently $C_1$-$C_8$ alkyl, $C_2$-$C_8$ alkenyl, $C_2$-$C_8$ alkynyl, aryl, cyclyl, heterocyclyl, aralkyl, heteroaralkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy, silylalkoxyalkyl, —CN, —NO$_2$, —C(O)OR$^a$, —C(Y)NR$^b$R$^{b'}$, —NR$^c$(Y)R$^{c'}$, —NR$^b$R$^{b'}$, —OC(O)NR$^b$R$^{b'}$, —NR$^c$C(O)OR$^{c'}$, —SO$_2$NR$^b$R$^{b'}$, —NR$^c$SO$_2$R$^{c'}$, —NR$^c$C(Y)NR$^b$R$^{b'}$, —OR$^d$, —SR$^{d'}$, —C(Y)R$^e$ or —S(O)$_q$R$^f$, each of which may be optionally substituted with 1-3 R$^6$; wherein two R$^1$, together with the carbons to which they are attached, may form an optionally substituted cyclyl, heterocyclyl, aryl or heteroaryl ring;

$R^4$ is hydrogen, $C_1$-$C_8$ alkyl, $C_2$-$C_8$ alkenyl, $C_2$-$C_8$ alkynyl, aryl, heteroaryl, cyclyl, heterocyclyl, aralkyl, heteroaralkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy, silylalkoxyalkyl, —CN, —NO$_2$, —C(O)OR$^a$, —C(Y)NR$^b$R$^{b'}$, —NR$^c$C(Y)R$^{c'}$, —NR$^b$R$^{b'}$, —OC(O)NR$^b$R$^{b'}$, —NR$^c$C(O)OR$^{c'}$, —SO$_2$NR$^b$R$^{b'}$, —NR$^c$SO$_2$R$^{c'}$, —NR$^c$C(Y)NR$^b$R$^{b'}$, —OR$^d$, —SR$^{d'}$, —C(Y)R$^e$ or —S(O)$_q$R$^f$, each of which may be optionally substituted with 1-3 R$^6$;

$R^5$ is hydrogen; or when m is not 0, $R^5$ and 1 $R^1$ may be taken together with the atoms to which they are attached to form an optionally substituted heteroaryl or heterocyclyl ring;

each $R^6$ is independently $C_1$-$C_8$ alkyl, $C_2$-$C_8$ alkenyl, $C_2$-$C_8$ alkynyl, aryl, heteroaryl, cyclyl, heterocyclyl, aralkyl, heteroaralkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy, silylalkoxyalkyl, oxo, thiono, —CN, —NO$_2$, —C(O)OR, —C(Y)NR$^b$R$^{b'}$, —NR$^c$C(Y)R$^{c'}$, —NR$^b$R$^{b'}$, —OC(O)NR$^b$R$^{b'}$, —NR$^c$C(O)OR$^{c'}$, —SO$_2$NR$^b$R$^{b'}$, —NR$^c$SO$_2$R$^{c'}$, —NR$^c$C(Y)NR$^b$R$^{b'}$, —OR$^d$, —SR$^{d'}$, —C(Y)R$^e$ or —S(O)$_q$R$^f$, each of which may be optionally substituted with 1-3 R$^7$;

each $R^7$ is independently $C_1$-$C_8$ alkyl, $C_2$-$C_8$ alkenyl, $C_2$-$C_8$ alkynyl, aryl, heteroaryl, cyclyl, heterocyclyl, aralkyl, heteroaralkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy, silylalkoxyalkyl, oxo, thiono, —CN, —NO$_2$—C(O)OR$^a$, —C(Y)NR$^b$R$^{b'}$, —NR$^c$C(Y)R$^{c'}$, —NR$^b$R$^{b'}$, —OC(O)NR$^b$R$^{b'}$, —NR$^3$C(O)OR$^{c'}$, —SO$_2$NR$^b$R$^{b'}$, —NR$^c$SO$_2$R$^{c'}$, —NR$^c$C(Y)NR$^b$R$^{b'}$, —OR$^d$, —SR$^{d'}$, —C(Y)R$^e$ or —S(O)$_q$R$^f$;

Y is O or S;

q is 1 or 2; and each R$^a$, R$^b$, R$^{b'}$, R$^c$, R$^{c'}$, R$^d$, R$^{d'}$, R$^e$, R$^{e'}$ and R$^f$ is independently selected from hydrogen, $C_1$-$C_8$ alkyl, $C_2$-$C_8$ alkenyl, $C_2$-$C_8$ alkynyl, acyl, cyclyl, heterocyclyl, aryl, heteroaryl, cyclylalkyl, heterocyclylalkyl, aralkyl and heteroaralkyl, each of which may be optionally further substituted with 1-3 R$^6$, wherein R$^b$ and R$^{b'}$, together with the atoms to which they are attached, may form an optionally substituted cyclyl or heterocyclyl ring;

In some embodiments, A is N. In some embodiments, A is CH. In some embodiments, A is CR$^4$.

In some embodiments, B is aryl (e.g., phenyl).

In some embodiments, m is 0.

In some embodiments, m is 1. In some embodiments, m is 2. In some embodiments, m is 3.

In some embodiments, $R^1$ is in the ortho position. In some embodiments, $R^1$ is in the meta position. In some embodiments, $R^1$ is in the para position.

In some embodiments, $R^1$ is $C_1$-$C_8$ alkyl (e.g., methyl or tert-butyl). In some embodiments, $R^1$ is heteroaryl (e.g., oxazolyl, oxadiazolyl or quinazolinyl).

In some embodiments, $R^1$ is heteroaryl substituted with 1-3 R$^6$ (e.g., 1 R$^6$).

In some embodiments, $R^1$ is oxadiazolyl substituted with 1 R$^6$. some embodiments, R$^6$ is $C_1$-$C_8$ alkyl (e.g., methyl).

In some embodiments, $R^1$ is heteroaryl substituted with 2 R$^6$. In some embodiments, $R^1$ is quinazolinyl substituted with 2 R$^6$. In some embodiments, one R$^6$ is halo (e.g., bromo) and the other is heteroaryl (e.g., pyridyl).

In some embodiments, m is 1 and $R^1$ is halo (e.g., fluoro, chloro or bromo). In some embodiments, m is 2 and each $R^1$ is halo (e.g., fluoro, chloro or bromo). In some embodiments, m is 3 and each $R^1$ is halo (e.g., fluoro, chloro or bromo). In some embodiments, $R^1$ is haloalkyl (e.g., trifluoromethyl). In some embodiments, $R^1$ is haloalkoxy (e.g., difluoromethoxy or trifluoromethoxy).

In some embodiments, $R^1$ is haloalkoxy substituted with 1 R$^6$. In some embodiments, $R^1$ is —O—CF$_2$—R$^6$. In some embodiments, R$^6$ is —C(Y)NR$^b$R$^{b'}$. In some embodiments, Y is O, R$^b$ is hydrogen and R$^{b'}$ is $C_1$-$C_8$ alkyl (e.g., methyl). In some embodiments, $R^1$ is —O—CF$_2$—CH$_2$—R$^6$. In some embodiments, R$^6$ is —OR$^d$. In some embodiments, R$^d$ is hydrogen. In some embodiments, R$^d$ is $C_1$-$C_8$ alkyl (e.g., methyl). In some embodiments, R$^6$ is —NR$^b$R$^{b'}$. In some embodiments, R$^b$ and R$^{b'}$ are each independently $C_1$-$C_8$ alkyl (e.g., R$^b$ and R$^{b'}$ are both methyl). In some embodiments, R$^6$ is heterocyclyl (e.g., morpholino).

In some embodiments, $R^1$ is aminoalkyl. In some embodiments, $R^1$ is —CH$_2$NH$_2$. In some embodiments, $R^1$ is alkylaminoalkyl. In some embodiments, $R^1$ is —CH$_2$NHCH$_2$CH$_2$CH$_3$. In some embodiments, $R^1$ is dialkylaminoalkyl. In some embodiments, $R^1$ is —CH$_2$N(CH(CH$_3$)$_2$)$_2$.

In some embodiments, $R^1$ is hydroxyalkyl. In some embodiments, $R^1$ is —CH$_2$OH.

In some embodiments, $R^1$ is —CN.

In some embodiments, $R^1$ is —NO.

In some embodiments, $R^1$ is —C(O)OR$^a$. In some embodiments, R$^a$ is hydrogen. In some embodiments, R$^a$ is $C_1$-$C_8$ alkyl (e.g., methyl or ethyl).

In some embodiments, $R^1$ is —NR$^c$C(Y)R$^{c'}$. In some embodiments, one of R$^c$ and R$^{c'}$ is hydrogen and the other is $C_1$-$C_8$ alkyl (e.g., methyl).

In some embodiments, $R^1$ is —OR$^d$. In some embodiments, R$^d$ is hydrogen. In some embodiments, R$^d$ is $C_1$-$C_8$ alkyl (e.g., methyl or ethyl).

In some embodiments, $R^1$ is —SO$_2$NR$^b$R$^{b'}$. In some embodiments, R$^b$ and R$^{b'}$ are both hydrogen.

In some embodiments, $R^1$ is —C(Y)R$^e$. In some embodiments, Y is O. In some embodiments, R$^e$ is $C_1$-$C_8$ alkyl (e.g., methyl). In some embodiments, R$^e$ is heterocyclyl (e.g., pyrrolidinyl, piperidinyl or morpholino).

In some embodiments, $R^1$ is —C(Y)$NR^bR^{b'}$. In some embodiments, Y is S. In some embodiments, Y is O. In some embodiments, $R^b$ and $R^{b'}$ are both hydrogen. In some embodiments, $R^b$ is hydrogen. In some embodiments, $R^b$ is hydrogen and $R^{b'}$ is aralkyl. In some embodiments, $R^b$ is hydrogen and $R^{b'}$ is optionally substituted benzyl. In some embodiments, $R^{b'}$ is $C_1$-$C_8$ alkyl, e.g., methyl, ethyl, $C_3$ alkyl (e.g., n-propyl or isopropyl), $C_4$ alkyl (e.g., n-butyl, sec-butyl or tert-butyl), $C_5$ alkyl (e.g., n-pentyl, isopentyl or pentan-3-yl), $C_6$ alkyl (e.g., n-hexyl or 3,3-dimethylbutan-2-yl), or $C_7$ alkyl (e.g., n-heptyl or 2-heptyl).

In some embodiments, $R^{b'}$ is $C_1$-$C_8$ alkyl substituted with 1 $R^6$. In some embodiments, $R^6$ is —$OR^d$. In some embodiments, $R^d$ is aryl (e.g., phenyl). In some embodiments, $R^{b'}$ is $C_2$-$C_8$ alkenyl, e.g., $C_3$ alkenyl (e.g., —$CH_2$—CH═$CH_2$). In some embodiments, $R^{b'}$ is $C_2$-$C_8$ alkynyl, e.g., $C_3$ alkenyl (e.g., —$CH_2$—C≡CH).

In some embodiments, $R^{b'}$ is aryl (e.g., phenyl). In some embodiments, $R^{b'}$ is aryl substituted with 1 $R^6$ (e.g., phenyl substituted with 1 $R^6$). In some embodiments, $R^6$ is haloalkyl (e.g., trifluoromethyl). In some embodiments, $R^{b'}$ is cyclyl (e.g., cyclopropyl, cyclobutyl, cyclopentyl, cyclohexyl or cycloheptyl). In some embodiments, $R^{b'}$ is cyclyl substituted with 1 $R^6$ (e.g., cyclopropyl substituted with 1 $R^6$ or cyclopentyl substituted with 1 $R^6$). In some embodiments, $R^6$ is $C_1$-$C_8$ alkyl (e.g., methyl). In some embodiments, $R^6$ is —$OR^d$. In some embodiments, $R^d$ is aralkyl (e.g., benzyl).

In some embodiments, $R^{b'}$ is cyclohexyl substituted with 1 $R^6$. In some embodiments, $R^6$ is —C(O)$OR^a$. In some embodiments, $R^a$ is $C_1$-$C_8$ alkyl (e.g., methyl).

In some embodiments, $R^{b'}$ is bicyclyl (e.g., indanyl). In some embodiments, $R^{b'}$ is heterocyclyl, e.g., a 6-membered heterocyclyl. In some embodiments, $R^{b'}$ is a 6-membered oxygen-containing heterocyclyl (e.g., tetrahydropyranyl). In some embodiments, $R^{b'}$ is a 6-membered nitrogen-containing heterocyclyl (e.g., piperidinyl).

In some embodiments, $R^b$ is heterocyclyl substituted with 1 $R^6$ (e.g., piperidinyl substituted with 1 $R^6$). In some embodiments, $R^6$ is —C(O)$OR^a$. In some embodiments, $R^a$ is $C_1$-$C_8$ alkyl (e.g., ethyl). In some embodiments, $R^6$ is —C(Y)$R^e$. In some embodiments, Y is O. In some embodiments, $R^e$ is $C_1$-$C_8$ alkyl (e.g., methyl or ethyl).

In some embodiments, $R^{b'}$ is aralkyl. In some embodiments, the alkyl is a $C_1$-$C_8$ alkyl (e.g., $C_1$, $C_2$, $C_3$ or $C_4$ alkyl). In some embodiments, the alkyl is a straight-chain alkyl. In some embodiments, the alkyl is a branched alkyl. In some embodiments, the aryl is phenyl. In some embodiments, $R^{b'}$ is benzyl. In some embodiments, $R^{b'}$ is phenylethyl. In some embodiments, the aryl is substituted with 1 $R^6$. In some embodiments, $R^6$ is $C_1$-$C_8$ alkyl (e.g., methyl). In some embodiments, $R^6$ is halo (e.g., fluoro or chloro). In some embodiments, $R^6$ is haloalkyl (e.g., trifluoromethyl). In some embodiments, $R^6$ is —$OR^d$. In some embodiments, $R^d$ is $C_1$-$C_8$ alkyl (e.g., methyl). In some embodiments, the aryl is substituted with 2 $R^6$. In some embodiments, each $R^6$ is independently —$OR^d$. In some embodiments, each $R^d$ is independently $C_1$-$C_8$ alkyl (e.g., each $R^d$ is methyl). In some embodiments, each $R^6$ is independently halo (e.g., each $R^6$ is fluoro).

In some embodiments, $R^{b'}$ is heteroaralkyl. In some embodiments, the alkyl is a $C_1$-$C_8$ alkyl (e.g., $C_1$, $C_2$ or $C_3$ alkyl). In some embodiments, the alkyl is a straight-chain alkyl. In some embodiments, the alkyl is a branched alkyl. In some embodiments, the heteroaryl is pyridyl. In some embodiments, the heteroaryl is furanyl. In some embodiments, the heteroaryl is thiazolyl. In some embodiments, the heteroaryl is thienyl. In some embodiments, the heteroaryl is substituted with 1 $R^6$. In some embodiments, $R^6$ is $C_1$-$C_8$ alkyl (e.g., methyl). In some embodiments, $R^6$ is haloalkyl (e.g., trifluoromethyl).

In some embodiments, $R^{b'}$ is cyclylalkyl. In some embodiments, the alkyl is a $C_1$-$C_8$ alkyl (e.g., $C_1$ alkyl). In some embodiments, the cyclyl group is cyclopropyl. In some embodiments, the cyclyl group is cyclopentyl. In some embodiments, the cyclyl group is a bicyclic group. In some embodiments, the bicyclic group is indanyl. In some embodiments, $R^{b'}$ is cyclylalkyl substituted with 1 $R^6$. In some embodiments, $R^6$ is aryl (e.g., phenyl).

In some embodiments, $R^{b'}$ is heterocyclylalkyl. In some embodiments, the alkyl is a $C_1$-$C_8$ alkyl (e.g., $C_1$ alkyl). In some embodiments, the heterocyclyl group is tetrahydropyranyl.

In some embodiments, $R^{b'}$ is haloalkyl (e.g., fluoroethyl, difluoroethyl, trifluoroethyl or trifluoropropyl).

In some embodiments, $R^{b'}$ is alkoxyalkyl. In some embodiments, the alkyl is a $C_1$-$C_8$ alkyl (e.g., $C_1$, $C_2$, $C_3$ or $C_4$ alkyl). In some embodiments, the alkyl is a straight-chain alkyl. In some embodiments, the alkyl is a branched alkyl. In some embodiments, the alkoxy is methoxy.

In some embodiments, $R^b$ and $R^{b'}$ are each independently $C_1$-$C_8$ alkyl (e.g., $R^b$ and $R^{b'}$ are both methyl, both ethyl or both isopropyl).

In some embodiments, $R^1$ and $R^5$, together with the atoms to which they are attached, form a heteroaryl ring (e.g., a substituted heteroaryl ring). In some embodiments, $R^1$ and $R^5$, together with the atoms to which they are attached, form a heterocyclyl ring (e.g., a substituted heterocyclyl ring).

In some embodiments, $R^1$, $R^5$, B and L are taken together to form a bicyclic heteroaryl or heterocyclic ring.

In some embodiments, $R^1$, $R^5$, B and L are taken together to form

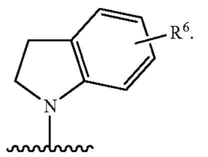

In some embodiments, $R^6$ is halo. In some embodiments, $R^6$ is at the 6, 7, or 8 position.

In some embodiments, $R^1$, $R^5$, B and L are taken together to form a group selected from:

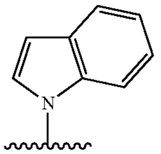
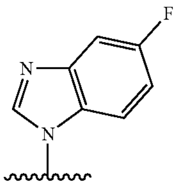
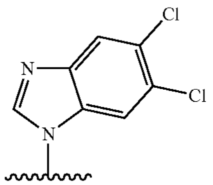
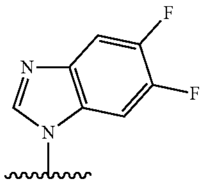
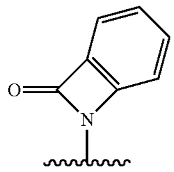

-continued

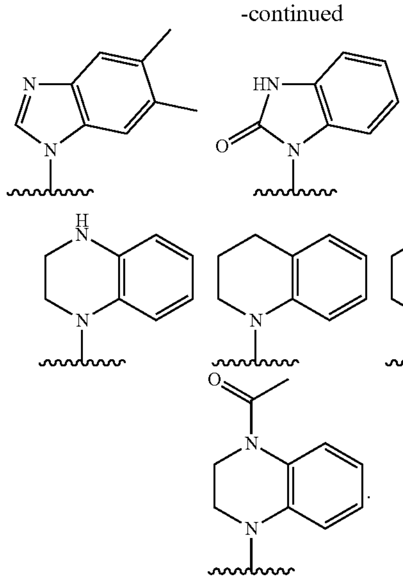

In some embodiments, $R^2$ is aryl.

In some embodiments, each $R^1$ is independently $C_1$-$C_8$ alkyl (e.g., each $R^1$ is methyl). In some embodiments, each $R^1$ is independently halo (e.g., each $R^1$ is fluoro or each $R^1$ is chloro). In some embodiments, one $R^1$ is fluoro and the other is chloro. In some embodiments, one $R^1$ is chloro and the other is bromo.

In some embodiments, each $R^1$ is independently —$OR^d$. In some embodiments, each $R^d$ is independently $C_1$-$C_8$ alkyl (e.g., each $R^d$ is methyl).

In some embodiments, one $R^1$ is halo (e.g., chloro) and the other is $C_3$-$C_8$ alkyl (e.g., methyl). In some embodiments, one $R^1$ is halo (e.g., fluoro) and the other is heterocyclylalkyl (e.g., —$CH_2$-heterocyclyl). In some embodiments, the heterocyclyl is morpholino. In some embodiments, the heterocyclyl is pyrrolidinyl. In some embodiments, the heterocyclyl is piperazinyl. In some embodiments, the piperazinyl is substituted with 1 $R^6$. In some embodiments, $R^6$ is $C_1$-$C_8$ alkyl (e.g., methyl).

In some embodiments, one $R^1$ is halo (e.g., fluoro or chloro) and the other is haloalkyl (e.g., trifluoromethyl).

In some embodiments, one $R^1$ is halo (e.g., chloro) and the other is haloalkoxy (e.g., difluoromethoxy or trifluoromethoxy).

In some embodiments, one $R^1$ is halo (e.g., chloro) and the other is —$C(O)OR^a$. In some embodiments, $R^a$ is hydrogen.

In some embodiments, one $R^1$ is halo (e.g., fluoro or chloro) and the other is —$C(Y)NR^bR^{b'}$. In some embodiments, Y is O. In some embodiments, $R^b$ and $R^{b'}$ are both hydrogen. In some embodiments, one of $R^b$ and $R^{b'}$ is hydrogen and the other is $C_1$-$C_8$ alkyl (e.g., methyl).

In some embodiments, one $R^1$ is halo (e.g., chloro) and the other is —$NR^cC(Y)R^{c'}$. In some embodiments, Y is O. In some embodiments, $R^c$ is hydrogen and $R^{c'}$ is $C_1$-$C_8$ alkyl (e.g., methyl).

In some embodiments, one $R^1$ is halo (e.g., fluoro or chloro) and the other is —$OR^d$. In some embodiments, $R^d$ is hydrogen. In some embodiments, $R^d$ is $C_1$-$C_8$ alkyl (e.g., methyl).

In some embodiments, one $R^1$ is halo (e.g., fluoro or chloro) and the other is —CN.

In some embodiments, one $R^1$ is halo (e.g., chloro) and the other is —$NO_2$.

In some embodiments, one $R^1$ is —$C(O)OR^a$ and the other is —$NO_2$. In some embodiments, $R^a$ is hydrogen.

In some embodiments, one $R^1$ is —C(O)O($R^1$ and the other is —$OR^d$. In some embodiments, each $R^a$ and $R^d$ is hydrogen.

In some embodiments, one $R^1$ is —$C(Y)NR^bR^{b'}$ and the other is haloalkyl (e.g., trifluoromethyl). In some embodiments, $R^b$ and $R^{b'}$ are both hydrogen.

In some embodiments, one $R^1$ is —$C(Y)NR^bR^{b'}$ and the other is haloalkoxy (e.g., trifluoromethoxy). In some embodiments, $R^b$ and $R^{b'}$ are both hydrogen.

In some embodiments, one $R^1$ is —$C(Y)NR^bR^{b'}$ and the other is —$S(O)_qR^f$. In some embodiments, $R^b$ and $R^{b'}$ are both hydrogen. In some embodiments, $R^f$ is $C_1$-$C_8$ alkyl (e.g., methyl).

In some embodiments, one $R^1$ is —$C(Y)NR^bR^{b'}$ and the other is —CN. In some embodiments, $R^b$ and $R^{b'}$ are both hydrogen.

In some embodiments, one $R^1$ is —$OR^d$ and the other is $C_1$-$C_8$ alkyl (e.g., methyl). In some embodiments, $R^d$ is $C_1$-$C_8$ alkyl (e.g., methyl).

In some embodiments, one $R^1$ is —$OR^d$ and the other is haloalkyl (e.g., trifluoromethyl). In some embodiments, $R^d$ is $C_1$-$C_8$ alkyl (e.g., methyl).

In some embodiments, one $R^1$ is —$OR^d$ and the other is —$C(O)OR^a$. In some embodiments, $R^d$ is $C_1$-$C_8$ alkyl (e.g., methyl). In some embodiments, $R^a$ is hydrogen. In some embodiments, $R^a$ is $C_1$-$C_8$ alkyl (e.g., methyl).

In some embodiments, one $R^1$ is —$OR^d$ and the other is —$NR^cC(O)R^{c'}$. In some embodiments, $R^d$ is $C_1$-$C_8$ alkyl (e.g., methyl). In some embodiments, $R^c$ is hydrogen and $R^{c'}$ is $C_1$-$C_8$ alkyl (e.g., methyl).

In some embodiments, one $R^1$ is haloalkyl (e.g., trifluoromethyl) and the other is —CN.

In some embodiments, two $R^1$, together with the atoms to which they are attached, are taken together to form a cyclyl ring (e.g., a substituted cyclyl ring). In some embodiments, two $R^1$, together with the atoms to which they are attached, are taken together to form a heterocyclyl ring (e.g., a substituted heterocyclyl ring). In some embodiments, two $R^1$, together with the atoms to which they are attached, are taken together to form a heteroaryl ring (e.g., a substituted heteroaryl ring).

In some embodiments, two $R^1$ and ring B are taken together to form a group selected from:

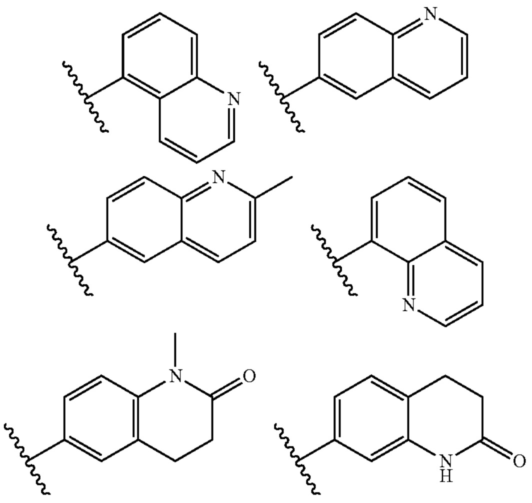

-continued

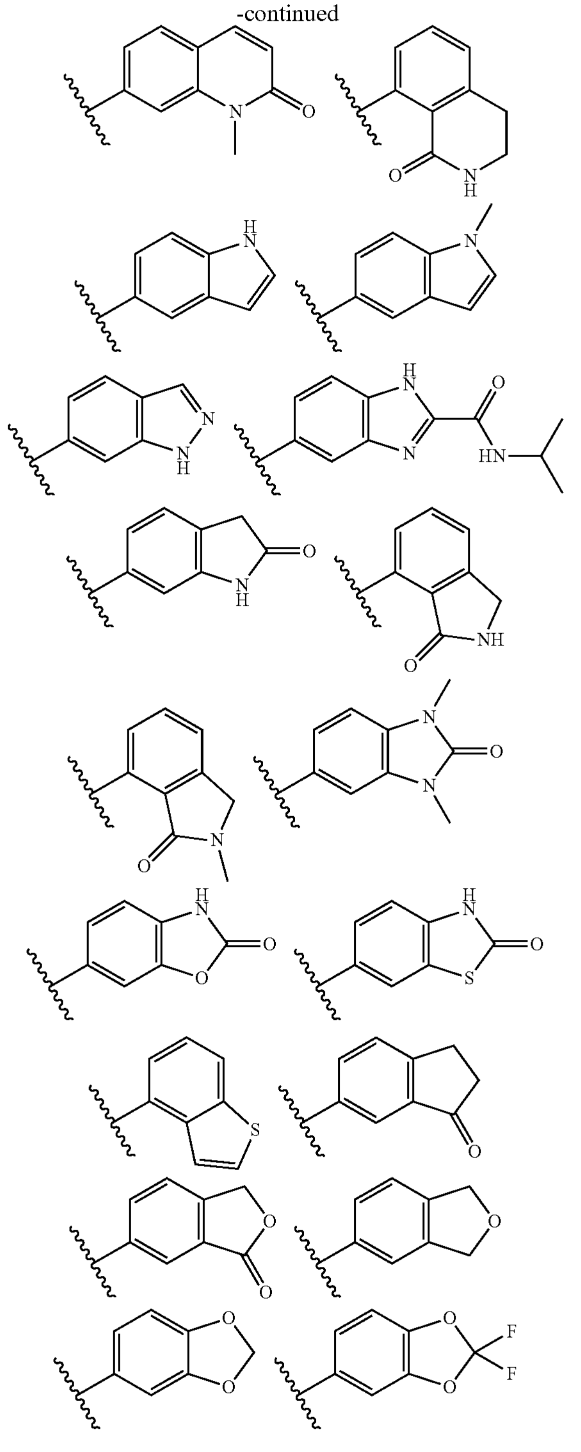

In some embodiments, $R^2$ is aryl.

In some embodiments, each $R^1$ is independently halo (e.g., all three $R^1$ are fluoro or all three $R^1$ are chloro).

In some embodiments, two $R^j$ are independently halo (e.g., both are chloro) and the other is $C_1$-$C_8$ alkyl (e.g., methyl). In some embodiments, two $R^1$ are independently halo (e.g., both are chloro) and the other is heteroaryl (e.g., pyrrolyl). In some embodiments, two $R^1$ are independently halo (e.g., both are fluoro) and the other is —C(Y)$NR^bR^{b'}$ (e.g., —C(O)$NH_2$). In some embodiments, two $R^1$ are independently $C_1$-$C_8$ alkyl (e.g., both are methyl) and the other is halo (e.g., chloro or bromo).

In some embodiments, one $R^1$ is $C_1$-$C_8$ alkyl (e.g., methyl), and two $R^1$, together with the atoms to which they are attached, are taken together to form a heterocyclyl ring.

In some embodiments, one $R^1$ is —$OR^d$, and two $R^1$, together with the atoms to which they are attached, are taken together to form a heterocycyl ring. In some embodiments, $R^d$ is $C_1$-$C_8$ alkyl (e.g., methyl).

In some embodiments, three $R^1$ and ring B are taken together to form a group selected from:

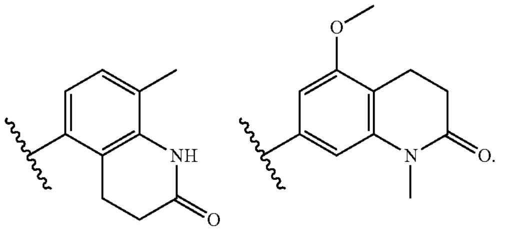 [SMILES: *c1ccc(C)c2c1CCC(=O)N2 ; *c1cc(OC)c2c(c1)N(C)C(=O)CC2]

In some embodiments, B is a 6-membered heteroaryl.

In some embodiments, B is pyridyl. In some embodiments, B is 3-pyridyl. In some embodiments, m is 2. In some embodiments, two $R^1$, together with the atoms to which they are attached, are taken together to form an aryl ring (e.g., a phenyl ring). In some embodiments, in is 3. In some embodiments, one $R^1$ is —$OR^d$, and two $R^1$, together with the atoms to which they are attached, are taken together to form an aryl ring (e.g., a phenyl ring). In some embodiments, $R^d$ is hydrogen.

In some embodiments, B is pyrazolyl. In some embodiments, m is 2. In some embodiments, two $R^1$, together with the atoms to which they are attached, are taken together to form a cyclyl ring (e.g., a cyclohexyl ring), In some embodiments, B is selected from:

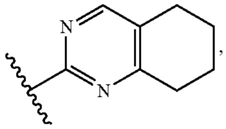

,

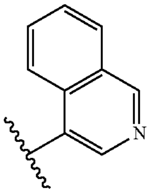

and

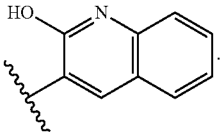

.

In some embodiments, B is a 5-membered heteroaryl (e.g., pyrazolyl).

In some embodiments, m is 1.

In some embodiments, $R^1$ is aryl (e.g., phenyl).

In some embodiments, $R^1$ is phenyl substituted with 1 $R^6$.

In some embodiments, $R^6$ is halo (e.g., chloro). In some embodiments, $R^1$ is selected from:

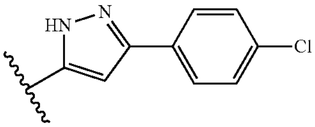

and

-continued

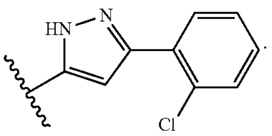

In some embodiments, in is 2.

In some embodiments, one $R^1$ is $C_1$-$C_8$ alkyl (e.g., methyl) and the other is aryl (e.g., phenyl). In some embodiments, the aryl is phenyl substituted with 1 $R^6$. In some embodiments, $R^6$ is halo (e.g., chloro). In some embodiments, $R^1$ is:

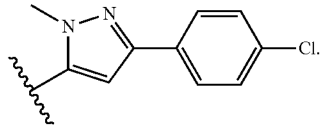 [SMILES: *c1cc(-c2ccc(Cl)cc2)nn1C]

In some embodiments, B is thienyl. In some embodiments, B is selected from:

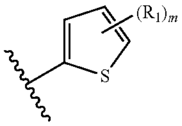
and
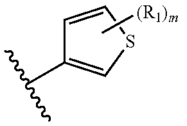

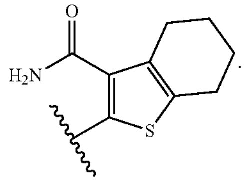

In some embodiments, m is 1. In some embodiments, m is 2. In some embodiments m is 2 and two $R^1$, together with the atoms to which they are attached, form an optionally substituted cyclyl, heterocyclyl, aryl or heteroaryl ring In some embodiments, $R^1$ is —C(O)$OR_a$. In some embodiments, $R^a$ is $C_1$-$C_8$ alkyl (e.g., ethyl).

In some embodiments, $R^1$ is —C(Y)$NR^bR^{b'}$. In some embodiments, Y is O. In some embodiments, $R^b$ and $R^{b'}$ are both hydrogen.

In some embodiments, m is 2.

In some embodiments, one $R^1$ is $C_1$-$C_8$ alkyl (e.g., methyl) and the other is —C(Y)$NR^bR^{b'}$. In some embodiments, Y is O. In some embodiments, $R^b$ and $R^{b'}$ are both hydrogen.

In some embodiments, B is thiazolyl.

In some embodiments, m is 1.

In some embodiments, $R^1$ is aryl (e.g., phenyl).

In some embodiments, in is 2.

In some embodiments, two $R^1$, together with the atoms to which they are attached, form an aryl ring. In some embodiments, the aryl ring is substituted with —C(Y)$R^e$. In some embodiments, Y is O. In some embodiments, $R^e$ is $C_1$-$C_8$ alkyl (e.g., methyl).

In some embodiments, B is:

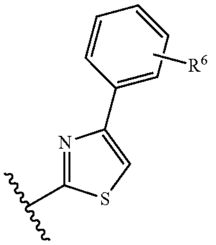

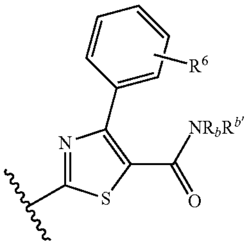

In some embodiments, B is:

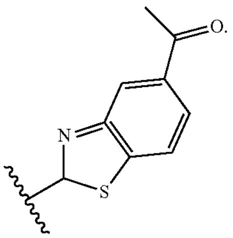

In some embodiments, E is aryl (e.g., phenyl).

In some embodiments, n is 1.

In some embodiments, $R^2$ is $C_1$-$C_8$ alkyl (e.g., methyl).

In some embodiments, $R^2$ is $C_1$-$C_8$ alkyl substituted with 1-3 $R^6$. In some embodiments, $R^2$ is $C_1$ alkyl substituted with 1 $R^6$.

In some embodiments, $R^6$ is —$NR^bR^{b'}$. In some embodiments, $R^b$ and $R^{b'}$ are each independently $C_1$-$C_8$ alkyl (e.g., $R^b$ and $R^{b'}$ are both methyl, or $R^b$ and $R^{b'}$ are both ethyl). In some embodiments, one of $R^b$ and $R^{b'}$ is hydrogen and the other is haloalkyl (e.g., trifluoroethyl).

In some embodiments, $R^6$ is —$OR^d$. In some embodiments, $R^d$ is cyclyl (e.g., cyclopentyl). In some embodiments, $R^d$ is heterocyclylalkyl (e.g., —$CH_2$-tetrahydropyranyl).

In some embodiments, $R^2$ is $C_2$ alkyl substituted with 1 $R^6$.

In some embodiments, $R^6$ is —C(Y)$NR^bR^{b'}$. In some embodiments, Y is O. In some embodiments, $R^b$ and $R^{b'}$ are both hydrogen. In some embodiments, $R^b$ and $R^{b'}$ are each independently $C_1$-$C_8$ alkyl (e.g., $R^b$ and $R^{b'}$ are both methyl). In some embodiments, one of $R^b$ and $R^{b'}$ is hydrogen and the other is $C_1$-$C_8$ alkyl (e.g., methyl).

In some embodiments, $R^6$ is —C(Y)$R^e$. In some embodiments, Y is O. In some embodiments, $R^e$ is heterocyclyl (e.g., morpholino or thiomorpholino). In some embodiments, $R^e$ is thiomorpholino substituted with 2 $R^6$. In some embodiments, each $R^6$ is oxo. In some embodiments, $R^e$ is:

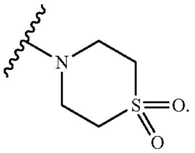 [SMILES: *N1CCS(=O)(=O)CC1]

In some embodiments, $R^2$ is $C_3$ alkyl substituted with 1 $R^6$.

In some embodiments, $R^6$ is —C(Y)$NR^bR^{b'}$. In some embodiments, Y is O. In some embodiments, $R^b$ and $R^{b'}$ are both hydrogen. In some embodiments, $R^b$ and $R^{b'}$ are each independently $C_1$-$C_8$ alkyl (e.g., $R^b$ and $R^{b'}$ are both methyl). In some embodiments, one of $R^b$ and $R^{b'}$ is hydrogen and the other is $C_1$-$C_8$ alkyl (e.g., methyl).

In some embodiments, $R^6$ is —$NR^cC(Y)R^{c'}$. In some embodiments, Y is O. In some embodiments, $R^c$ and $R^{c'}$ are each independently $C_1$-$C_8$ alkyl (e.g., $R^c$ and $R^{c'}$ are both methyl).

In some embodiments, $R^6$ is —$OR^d$. In some embodiments, $R^d$ is hydrogen. In some embodiments, $R^d$ is $C_1$-$C_8$ alkyl (e.g., methyl).

In some embodiments, $R^6$ is silyloxy (e.g., tert-butyldimethylsilyloxy).

In some embodiments, $R^6$ is —$C(Y)R^e$. In some embodiments. Y is O. In some embodiments, $R^e$ is heterocyclyl (e.g., morpholino).

In some embodiments, $R^2$ is ($C_2$-$C_8$ alkynyl. In some embodiments, $R^2$ is $C_2$-$C_8$ alkynyl substituted with 1 $R^6$ (e.g., $C_3$ alkynyl substituted with 1 $R^6$). In some embodiments, $R^2$ is —C≡C—$CH_2$—$R^6$. In some embodiments, $R^6$ is —$NR^b R^{b'}$. In some embodiments, $R^b$ and $R^{b'}$ are each independently $C_1$-$C_8$ alkyl (e.g., $R^b$ and $R^{b'}$ are both methyl). In some embodiments, $R^6$ is —$OR^d$. In some embodiments, $R^d$ is hydrogen. In some embodiments, $R^6$ is silyloxy (e.g., tert-butyldimethylsilyloxy). In some embodiments, $R^6$ is heterocyclyl (e.g., morpholino or thiomorpholino). In some embodiments, $R^6$ is thiomorpholino substituted with 2 $R^7$. In some embodiments, each $R^7$ is oxo. In some embodiments, $R^6$ is:

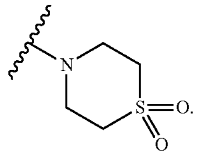 [SMILES: *N1CCS(=O)(=O)CC1]

In some embodiments, $R^2$ is aryl (e.g., phenyl). In some embodiments, $R^2$ is unsubstituted phenyl.

In some embodiments, $R^2$ is phenyl substituted with 1 $R^6$.

In some embodiments, $R^6$ is heterocyclylalkyl (e.g., —$CH_2$-morpholino). In some embodiments, $R^6$ is haloalkyl (e.g., trifluoromethyl). In some embodiments, $R^6$ is —CN. In some embodiments, $R^6$ is —$OR^d$. In some embodiments, $R^d$ is $C_1$-$C_8$ alkyl (e.g., methyl). In some embodiments, $R^6$ is —$C(Y)R^e$. In some embodiments, Y is O. In some embodiments, $R^e$ is heterocyclyl (e.g., morpholino).

In some embodiments, $R^2$ is phenyl substituted with 2 $R^6$.

In some embodiments, each $R^6$ is independently —$OR^d$. In some embodiments, each $R^d$ is $C_1$-$C_8$ alkyl (e.g., methyl). In some embodiments, one $R^6$ is halo (e.g., fluoro) and the other is $C_1$-$C_8$ alkyl (e.g., methyl). In some embodiments, one $R^6$ is —$C(O)OR^a$ and the other is —$OR^d$. In some embodiments, $R^a$ and $R^d$ are each independently $C_1$-$C_8$ alkyl (e.g., $R^a$ and $R^d$ are both methyl).

In some embodiments, $R^2$ is heteroaryl.

In some embodiments, $R^2$ is isoxazolyl. In some embodiments, $R^2$ is isoxazolyl substituted with 2 $R^6$. In some embodiments, each $R^6$ is independently $C_1$-$C_8$ alkyl (e.g., $R^6$ is methyl).

In some embodiments, $R^2$ is pyrazolyl. In some embodiments, $R^2$ is pyrazolyl substituted with 1 $R^6$. In some embodiments, $R^6$ is $C_1$-$C_8$ alkyl (e.g., methyl).

In some embodiments, $R^2$ is pyridyl. In some embodiments, $R^6$ is unsubstituted pyridyl. In some embodiments, $R^2$ is pyridyl substituted with 1 $R^6$. In some embodiments, $R^6$ is halo (e.g., fluoro). In some embodiments, $R^6$ is —$NR^bR^{b'}$. In some embodiments, $R^b$ and $R^{b'}$ are each hydrogen. In some embodiments, $R^6$ is —$OR^d$. In some embodiments, $R^d$ is hydrogen. In some embodiments, $R^d$ is $C_1$-$C_8$ alkyl (e.g., methyl). In some embodiments, $R^6$ is heterocyclyl (e.g., morpholino or piperazinyl). In some embodiments, $R^6$ is piperazinyl substituted with 1 $R^7$. In some embodiments, $R^7$ is $C_1$-$C_8$ alkyl (e.g., methyl).

In some embodiments, $R^2$ is pyrimidinyl.

In some embodiments, $R^2$ is pyridazinyl.

In some embodiments, $R^2$ is cyclyl (e.g., cyclopropyl).

In some embodiments, $R^2$ is heterocyclyl (e.g., morpholino or pyrrolidinyl).

In some embodiments, $R^2$ is aralkyl (e.g., benzyl).

In some embodiments, $R^2$ is heterocyclylalkyl. In some embodiments, the alkyl is $C_1$ alkyl. In some embodiments, the alkyl is $C_2$ alkyl. In some embodiments, the alkyl is $C_3$ alkyl. In some embodiments, the heterocyclyl is piperidinyl. In some embodiments, the heterocyclyl is piperazinyl. In some embodiments, the heterocyclyl is piperazinyl substituted with 1 $R^6$. In some embodiments, $R^6$ is $C_1$-$C_8$ alkyl (e.g., methyl). In some embodiments, the heterocyclyl is pyrrolidinyl. In some embodiments, the heterocyclyl is morpholino. In some embodiments, the heterocyclyl is thiomorpholino. In some embodiments, the heterocyclyl is thiomorpholino substituted with 2 $R^6$. In some embodiments, each $R^6$ is oxo. In some embodiments, the heterocyclyl is:

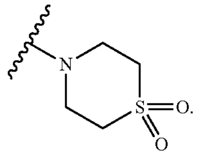 [SMILES: *N1CCS(=O)(=O)CC1]

In some embodiments, $R^2$ is halo (e.g., fluoro, chloro, bromo or iodo).

In some embodiments, $R^2$ is haloalkyl (e.g., trifluoromethyl).

In some embodiments, $R^2$ is haloalkoxy (e.g., trifluoromethoxy).

In some embodiments, $R^2$ is —CN.

In some embodiments, $R^2$ is —$NO_2$.

In some embodiments, $R^2$ is —$C(O)OR^a$. In some embodiments, $R^a$ is hydrogen. In some embodiments, $R^a$ is $C_1$-$C_8$ alkyl (e.g., methyl).

In some embodiments, $R^2$ is —$C(Y)NR^bR^{b'}$. In some embodiments, Y is O. In some embodiments, $R^b$ and $R^{b'}$ are each hydrogen. In some embodiments, $R^b$ and $R^{b'}$ are each independently $C_1$-$C_8$ alkyl (e.g., $R^b$ and $R^{b'}$ are both methyl). In some embodiments, one of $R^b$ and $R^{b'}$ is hydrogen and the other is $C_1$-$C_8$ alkyl (e.g., methyl or ethyl). In some embodiments, the $C_1$-$C_8$ alkyl is ethyl substituted with 2 $R^6$. In some embodiments, each $R^1$ is independently —$OR^d$. In some embodiments, each $R^d$ is $C_1$-$C_8$ alkyl (e.g., each $R^d$ is methyl). In some embodiments, one of $R^b$ and $R^{b'}$ is hydrogen and the other is heterocyclylalkyl (e.g., —$CH_2$—$CH_2$-morpholino). In some embodiments, one of $R^b$ and $R^{b'}$ is hydrogen and the other is haloalkyl (e.g., trifluoroethyl).

In some embodiments, $R^2$ is —$NR^bR^{b'}$. In some embodiments, $R^b$ and $R^{b'}$ are both hydrogen. In some embodiments, $R^b$ and $R^{b'}$ are each independently $C_1$-$C_8$ alkyl (e.g., $R^b$ and $R^{b'}$ are both methyl). In some embodiments, one of $R^b$ and $R^{b'}$ is hydrogen and the other is $C_1$-$C_8$ alkyl (e.g., methyl). In some embodiments, one of $R^b$ and $R^{b'}$ is hydrogen and the other is heterocyclyl (e.g., tetrahydropyranyl). In some embodiments, one of $R^b$ and $R^{b'}$ is hydrogen and the other is heterocyclylalkyl. In some embodiments, the alkyl is $C_1$ alkyl. In some embodiments, the alkyl is $C_2$ alkyl. In some embodiments, the alkyl is $C_3$ alkyl. In some embodiments, the heterocyclyl is morpholino. In some embodiments, the heterocyclyl is pyrrolidinyl. In some embodiments, the heterocyclyl is tetrahydrofuranyl. In some embodiments, the heterocyclyl is tetrahydropyranyl. In some embodiments, one of $R^b$ and $R^{b'}$ is hydrogen and the other is hydroxyalkyl. In some embodiments, the alkyl is $C_2$ alkyl. In some embodiments, one of $R^b$ and $R^{b'}$ is hydrogen and the other is alkoxyalkyl. In some embodiments, the alkyl is $C_2$ alkyl. In some embodiments, the alkyl is $C_3$ alkyl. In some embodiments, the alkoxy is methoxy. In some embodiments, one of $R^b$ and $R^{b'}$ is hydrogen and the other is —C(Y)$R^e$. In some embodiments, Y is O. In some embodiments, $R^e$ is $C_1$-$C_8$ alkyl (e.g., methyl). In some embodiments, $R^e$ is heterocyclyl. In some embodiments, $R^e$ is tetrahydropyranyl.

In some embodiments, $R^2$ is —O$R^d$,

In some embodiments, $R^d$ is hydrogen. In some embodiments, $R^d$ is $C_1$-$C_8$ alkyl (e.g., methyl). In some embodiments, $R^d$ is methyl substituted with 1 $R^6$. In some embodiments, $R^6$ is —C(Y)$R^e$. In some embodiments, Y is O. In some embodiments, $R^e$ is heterocyclyl (e.g., morpholino). In some embodiments, $R^6$ is —C(Y)N$R^bR^{b'}$. In some embodiments, Y is O. In some embodiments, $R^b$ and $R^{b'}$ are each independently $C_1$-$C_8$ alkyl (e.g., $R^b$ and $R^{b'}$ are both methyl or $R^b$ and $R^{b'}$ are both ethyl). In some embodiments, one of $R^b$ and $R^{b'}$ is hydrogen and the other is $C_1$-$C_8$ alkyl (e.g., methyl or ethyl).

In some embodiments, $R^d$ is ethyl. In some embodiments, $R^d$ is $C_3$ alkyl (e.g., isopropyl or n-propyl). In some embodiments, $R^d$ is optionally substituted heteroaralkyl. In some embodiments, $R^d$ is optionally substituted pyrindinalkyl.

In some embodiments, $R^d$ is n-propyl substituted with 1 $R^6$. In some embodiments, $R^6$ is —N$R^c$C(Y)$R^{c'}$. In some embodiments, Y is O. In some embodiments, $R^c$ and $R^{c'}$ are each independently $C_1$-$C_8$ alkyl (e.g., $R^c$ and $R^{c'}$ are both methyl). In some embodiments, $R^d$ is cyclyl (e.g., cyclopentyl).

In some embodiments, $R^d$ is heteroaralkyl (e.g., —$CH_2$-pyridyl). In some embodiments, the pyridyl is substituted with 1 $R^d$. In some embodiments, $R^6$ is alkyl (e.g., methyl) or haloalkyl (e.g., CF). In some embodiments, $R^6$ is —O$R^d$. In some embodiments, $R^d$ is $C_1$-$C_8$ alkyl (e.g., methyl).

In some embodiments, $R^d$ is heterocyclylalkyl. In some embodiments, the alkyl is $C_1$ alkyl. In some embodiments, the alkyl is $C_2$ alkyl. In some embodiments, the alkyl is $C_3$ alkyl. In some embodiments, the alkyl is $C_4$ alkyl. In some embodiments, the heterocyclyl is morpholino. In some embodiments, the heterocyclyl is piperidinyl. In some embodiments, the heterocyclyl is tetrahydrofuranyl. In some embodiments, $R^d$ is cyclylalkyl (e.g., —$CH_2$-cyclobutyl).

In some embodiments, $R^d$ is alkoxyalkyl. In some embodiments, the alkyl is $C_2$ alkyl. In some embodiments, the alkyl is $C_3$ alkyl. In some embodiments, the alkoxy is methoxy.

In some embodiments, $R^d$ is dialkylaminoalkyl. In some embodiments, the alkyl is $C_2$ alkyl. In some embodiments, the alkyl is $C_3$ alkyl. In some embodiments, the dialkylamino is dimethylamino.

In some embodiments, $R^2$ is —C(Y)$R^e$. In some embodiments, Y is O. In some embodiments, $R^e$ is heterocyclyl. In some embodiments, $R^e$ is piperidinyl. In some embodiments, $R^e$ is pyrrolidinyl. In some embodiments, $R^e$ is piperazinyl. In some embodiments, $R^e$ is piperazinyl substituted with 1 $R^6$. In some embodiments, $R^6$ is $C_1$-$C_8$ alkyl (e.g., methyl). In some embodiments, $R^e$ is morpholino. In some embodiments, $R^e$ is thiomorpholino. In some embodiments, $R^e$ is thiomorpholino substituted with 2 $R^6$. In some embodiments, each $R^6$ is oxo. In some embodiments, $R^e$ is:

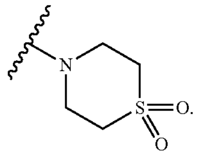 [SMILES: *N1CCS(=O)(=O)CC1]

In some embodiments, n is 2.

In some embodiments, each $R^2$ is independently halo (e.g., each $R^2$ is chloro).

In some embodiments, each $R^2$ is independently —O$R^d$.

In some embodiments, each $R^d$ is $C_1$-$C_8$ alkyl.

In some embodiments, each $R^2$ is methoxy. In some embodiments, one $R^2$ is methoxy and the other is ethoxy. In some embodiments, one $R^2$ is methoxy and the other is propoxy. In some embodiments, one $R^2$ is methoxy and the other is isopropoxy.

In some embodiments, one $R^2$ is methoxy and the other is ethoxy substituted with 1 $R^6$. In some embodiments, $R^6$ is —N$R^bR^{b'}$. In some embodiments, $R^b$ and $R^{b'}$ are each independently $C_1$-$C_8$ alkyl (e.g., $R^b$ and $R^{b'}$ are both methyl). In some embodiments, $R^6$ is —O$R^d$. In some embodiments, $R^d$ is $C_1$-$C_8$ alkyl (e.g., methyl).

In some embodiments, one $R^2$ is methoxy and the other is propoxy substituted with 1 $R^6$. In some embodiments, $R^6$ is —O$R^d$. In some embodiments, $R^d$ is $C_1$-$C_8$ alkyl (e.g., methyl).

In some embodiments, one $R^1$ is —O$R^d$ and the other is $C_1$-$C_8$ alkyl (e.g., methyl). In some embodiments, $R^d$ is $C_1$-$C_8$ alkyl (e.g., methyl or ethyl).

In some embodiments, one $R^2$ is —O$R^d$ and the other is halo (e.g., chloro). In some embodiments, $R^d$ is $C_1$-$C_8$ alkyl (e.g., methyl).

In some embodiments, one $R^2$ is —O$R^d$ and the other is —CN. In some embodiments, $R^d$ is $C_1$-$C_8$ alkyl (e.g., methyl).

In some embodiments, one $R^1$ is —O$R^d$ and the other is —C(O)O$R^a$. In some embodiments, $R^d$ and $R^a$ are both hydrogen.

In some embodiments, one $R^2$ is —O$R^d$ and the other is $C_1$-$C_8$ alkyl (e.g., methyl). In some embodiments, $R^d$ is $C_1$-$C_8$ alkyl (e.g., methyl).

In some embodiments, one $R^1$ is —O$R^d$ and the other is —C(Y)$R^e$. In some embodiments, $R^d$ is $C_1$-$C_8$ alkyl (e.g., methyl). In some embodiments, Y is O. In some embodiments, $R^e$ is heterocyclyl (e.g., morpholino).

In some embodiments, one $R^2$ is halo (e.g., chloro or bromo) and the other is $C_1$-$C_8$ alkyl (e.g., methyl).

In some embodiments, one $R^2$ is $C_1$-$C_8$ alkyl (e.g., methyl) and the other is —CN.

In some embodiments, one $R^2$ is $C_1$-$C_8$ alkyl (e.g., methyl) and the other is heteroaryl (e.g., pyridyl). In some embodiments, the pyridyl is substituted with 1 $R^6$. In some embodiments, $R^6$ is —O$R^d$. In some embodiments, $R^d$ is $C_1$-$C_8$ alkyl (e.g., methyl).

In some embodiments, one $R^2$ is $C_1$-$C_8$ alkyl (e.g., methyl) and the other is heterocyclylalkyl (e.g., —$CH_2$-morpholino).

In some embodiments, p is 0.

In some embodiments, p is 1.

In some embodiments, $R^3$ is $C_1$-$C_8$ alkyl (e.g., methyl). In some embodiments, $R^3$ is halo (e.g., chloro). In some embodiments, $R^3$ is haloalkyl (e.g., trifluoromethyl). In some embodiments. $R^3$ is oxo.

In some embodiments, $R^3$ is —$OR^d$. In some embodiments, $R^d$ is hydrogen. In some embodiments, $R^d$ is $C_1$-$C_8$ alkyl (e.g., methyl).

In some embodiments, $R^3$ is —$NR^bR^{b'}$. In some embodiments, $R^b$ and $R^{b'}$ are both hydrogen. In some embodiments, one of $R^b$ and $R^{b'}$ is hydrogen and the other is $C_1$-$C_8$ alkyl (e.g., methyl).

In some embodiments, $R^3$ is heterocyclyl (e.g., piperazinyl). In some embodiments, $R^3$ is piperazinyl substituted with 1 $R^6$. In some embodiments, $R^6$ is $C_1$-$C_8$ alkyl (e.g., methyl).

In some embodiments, E is a 5-membered heteroaryl ring.

In some embodiments, E is a thiophene ring.

In some embodiments, E is a pyrrole ring.

In some embodiments, n is 1. In some embodiments, $R^2$ is $C_1$-$C_8$ alkyl (e.g., methyl). In some embodiments, E is an N-methylpyrrole ring.

In some embodiments, L is $NR^5$. In some embodiments, $R^5$ is hydrogen.

In some embodiments, L is O.

In some embodiments, the compound is:

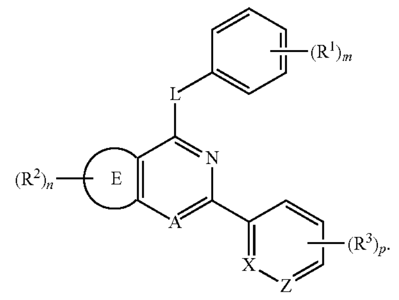

In some embodiments, $R^2$ is $C_1$-$C_4$ alkoxy. In some embodiments, $R^2$ is halo. In some embodiments, $R^1$ is —C(Y)$NR^bR^{b'}$, In some embodiments, the compound is:

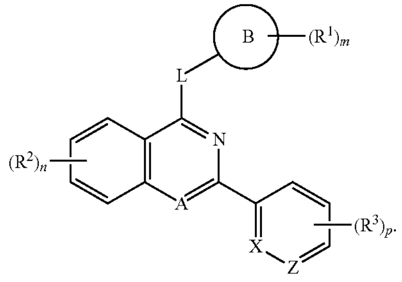

In some embodiments, $R^2$ is $C_1$-$C_4$ alkoxy. In some embodiments, $R^2$ is halo. In some embodiments, $R^1$ is —C(Y)$NR^bR^{b'}$.

In some embodiments, L and

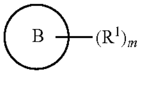

are

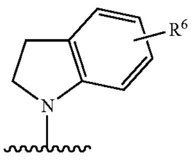

.

In some embodiments, L and

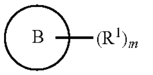

are

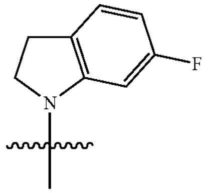

.

In some embodiments, L is NH, and

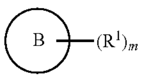

is selected from

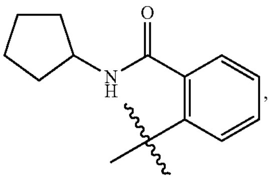

,

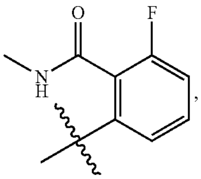

,

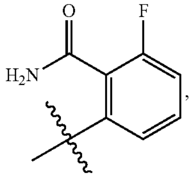

,

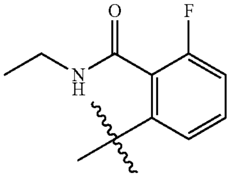

,

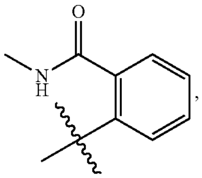

,

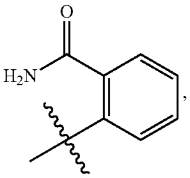

,

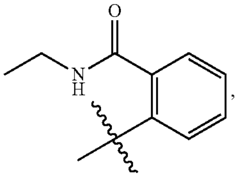

,

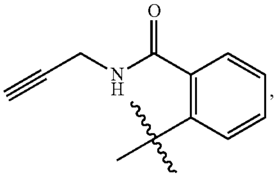

,

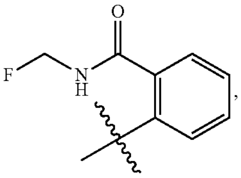

, c,

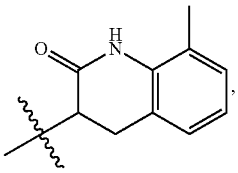

,

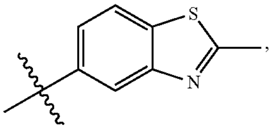

,

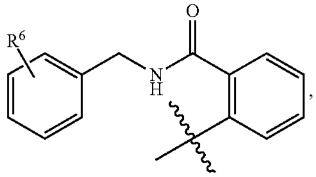

, and

-continued

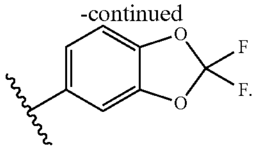

In some embodiments $R^6$ is halo. In some embodiments, $R^b$ or $R^{b'}$ are disubstituted with $R^6$ (e.g., dichloro, 4-fluoro, 3-chloro, or difluoro).

In some embodiments, the compound is:

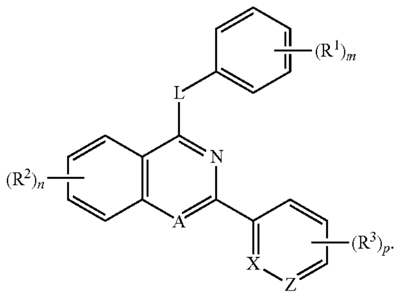

In some embodiments, $R^1$ is —C(Y)NR$^b$R$^{b'}$. In some embodiments, $R^1$ is halo. In some embodiments, $R^2$ is $C_1$-$C_4$ alkoxy. In some embodiments, $R^2$ is halo. In some embodiments, in is 2 and two $R^1$ are 3,4-dichloro; 3,4-difluoro, 3,5-dichloro; 3,5-difluoro; 3-chloro,4-fluoro; or 3-chloro,5-fluoro. In some embodiments, $R^2$ is —C(O)NR$^b$R$^{b'}$ and $R^3$ is H. In some embodiments, $R^b$ and $R^{b'}$ are H. In some embodiments, $R^b$ and $R^{b'}$ are independently $C_1$-$C_4$ alkyl or halo-substituted $C_1$-$C_4$ alkyl. In some embodiments, $R^b$ is methyl and $R^{b'}$ is trifluoroethyl. In some embodiments, $R^1$ is $C_1$-$C_4$ alkoxy or halo-substituted $C_1$-$C_4$ alkoxy. In some embodiments, n and p are zero.

In some embodiments, the compound is:

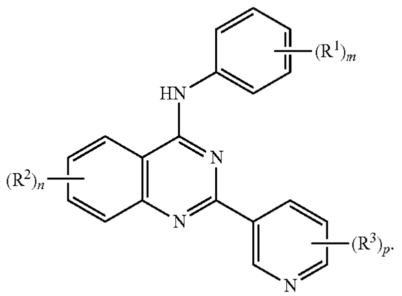

In some embodiments, $R^1$ is —C(Y)NR$^b$R$^{b'}$. In some embodiments, $R^1$ is halo. In some embodiments, $R^2$ is $C_1$-$C_4$ alkoxy. In some embodiments, $R^2$ is halo. In some embodiments, m is 2 and two $R^1$ are 3,4-dichloro; 3,4-difluoro, 3,5-dichloro; 3,5-difluoro; 3-chloro,4-fluoro; or 3-chloro,5-fluoro. In some embodiments, $R^2$ is —C(O)NR$^b$R$^{b'}$ and $R^3$ is H. In some embodiments, $R^b$ and $R^{b'}$ are H. In some embodiments, $R^b$ and $R^{b'}$ are independently $C_1$-$C_4$ alkyl or halo-substituted $C_1$-$C_4$ alkyl. In some embodiments, $R^b$ is methyl and $R^{b'}$ is trifluoroethyl. In some embodiments, $R^1$ is $C_1$-$C_4$ alkoxy or halo-substituted $C_1$-$C_4$ alkoxy. In some embodiments, n and p are zero.

In some embodiments, the compound is:

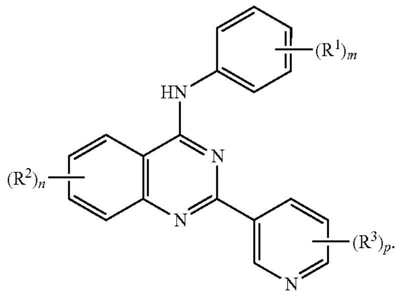

In some embodiments, $R^1$ is —C(Y)NR$^b$R$^{b'}$. In some embodiments, $R^1$ is halo. In some embodiments, $R^2$ is $C_1$-$C_4$ alkoxy. In some embodiments, $R^2$ is halo. In some embodiments, m is 2 and two $R^1$ are 3,4-dichloro; 3,4-difluoro, 3,5-dichloro; 3,5-difluoro; 3-chloro,4-fluoro; or 3-chloro,5-fluoro. In some embodiments, $R^2$ is —C(O)NR$^b$R$^{b'}$ and $R^3$ is H. In some embodiments, $R^b$ and $R^{b'}$ are H. In some embodiments, $R^b$ and $R^{b'}$ are independently $C_1$-$C_4$ alkyl or halo-substituted $C_1$-$C_4$ alkyl. In some embodiments, $R^b$ is methyl and $R^{b'}$ is trifluoroethyl. In some embodiments, $R^1$ is $C_1$-$C_4$ alkoxy or halo-substituted $C_1$-$C_4$ alkoxy. In some embodiments, n and p are zero.

In some embodiments, the compound is:

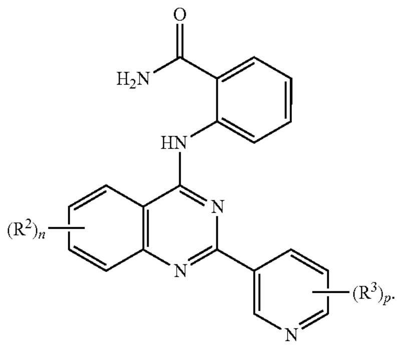

In some embodiments, $R^1$ is —C(Y)NR$^b$R$^{b'}$. In some embodiments, $R^1$ is halo. In some embodiments, $R^2$ is $C_1$-$C_4$ alkoxy. In some embodiments, $R^2$ is halo. In some embodiments, m is 2 and two $R^1$ are 3,4-dichloro; 3,4-difluoro, 3,5-dichloro; 3,5-difluoro; 3-chloro,4-fluoro; or 3-chloro,5-fluoro. In some embodiments, $R^2$ is —C(O)NR$^b$R$^{b'}$ and $R^3$ is H. In some embodiments, $R^b$ and $R^{b'}$ are H. In some embodiments, $R^b$ and $R^{b'}$ are independently $C_1$-$C_4$ alkyl or halo-substituted $C_1$-$C_4$ alkyl. In some embodiments, $R^b$ is methyl and $R^{b'}$ is trifluoroethyl. In some embodiments, $R^1$ is $C_1$-$C_4$ alkoxy or halo-substituted $C_1$-$C_4$ alkoxy. In some embodiments, n and p are zero.

Compounds of Formula (V)

The following aspects and embodiments relate to compounds of formula (V), corresponding to formula (I) of U.S. Provisional Patent Application No. 61/291,550, entitled "Therapeutic Compounds and Related Methods of Use" filed on Dec. 31, 2009, and incorporated herein by reference in its entirety.

Item 40, A compound of formula (V):

(V)

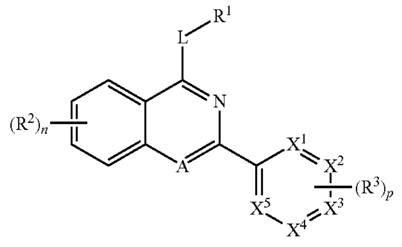

wherein:

L is $CR^4R^5$, O, C(O), $NR^6C(O)$, or $NR^7$;

A is $CR^8$, CH or N;

each $X^1$, $X^2$, $X^3$, $X^4$ and $X^5$ is independently CH or N, provided that at least two of $X^1$, $X^2$, $X^3$, $X^4$ and $X^5$ are N;

n is 0, 1, 2, 3 or 4;

p is 0, 1, 2 or 3;

$R^1$ is $C_1$-$C_8$ alkyl, $C_2$-$C_8$ alkenyl, $C_2$-$C_8$ alkynyl, aryl, heteroaryl, cyclyl, heterocyclyl, aralkyl, heteroaralkyl, cyclylalkyl or heterocyclylalkyl, each of which may be optionally substituted with 1-5 $R^9$; wherein $R^1$ or $R^9$ may optionally be taken together with one of $R^4$, $R^5$, $R^6$ or $R^7$, and the atoms to which they are attached, to form a cyclyl, heterocyclyl, aryl or heteroaryl ring that is optionally substituted with 1-3 $R^{10}$;

each $R^2$ and $R^3$ is independently $C_1$-$C_8$ alkyl, $C_2$-$C_8$ alkenyl, $C_2$-$C_8$ alkynyl, aryl, heteroaryl, cyclyl, heterocyclyl, aralkyl, heteroaralkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy, silylalkoxyalkyl, —CN, —$NO_2$, —C(O)$OR^a$, —C(Y)$NR^bR^{b'}$, —$NR^cC(Y)R^{c'}$, —$NR^bR^{b'}$, —OC(O)$NR^bR^{b'}$, —$NR^cC(O)OR^{c'}$, —$SO_2NR^bR^{b'}$, —$NR^cSO_2R^{c'}$, —$NR^cC(Y)NR^bR^{b'}$, —$OR^d$, —$SR^{d'}$, —C(Y)$R^e$ or —$S(O)_qR^f$; each of which is optionally substituted with 1-3 $R^{11}$;

each $R^4$, $R^5$, $R^6$ and $R^7$ is independently H, $C_1$-$C_8$ alkyl, $C_2$-$C_8$ alkenyl, $C_2$-$C_8$ alkynyl, aryl, heteroaryl, cyclyl, heterocyclyl, aralkyl, heteroaralkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy, silylalkoxyalkyl, —CN, —$NO_2$, —C(O)$OR^a$, —C(Y)$NR^bR^{b'}$, —$NR^cC(Y)R^{c'}$, —$NR^bR^{b'}$, —OC(O)$NR^bR^{b'}$, —$NR^cC(O)OR^{c'}$, —$SO_2NR^bR^{b'}$, —$NR^cSO_2R^{c'}$, —$NR^cC(Y)NR^bR^{b'}$, —$OR^d$, —$SR^{d'}$, —C(Y)$R^e$ or —$S(O)_qR^f$;

each $R^4$, $R^5$, $R^6$ and $R^7$ is independently $C_1$-$C_8$ alkyl, $C_2$-$C_8$ alkenyl, $C_2$-$C_8$ alkynyl, aryl, heteroaryl, cyclyl, heterocyclyl, aralkyl, heteroaralkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy, silylalkoxyalkyl, oxo, thiono, —CN, —$NO_2$, —C(O)$OR^a$, —C(Y)$NR^bR^{b'}$, —$NR^cC(Y)R^{c'}$, $NR^bR^{b'}$, —OC(O)$NR^bR^{b'}$, —$NR^cC(O)OR^{c'}$, —$SO_2NR^bR^{b'}$, —$NR^cSO_2R^{c'}$, —$NR^cC(Y)NR^bR^{b'}$, —$OR^d$, —$SR^{d'}$, —C(Y)$R^e$ or —$S(O)_qR^f$, each of which may be optionally further substituted; wherein two $R^8$, two $R^9$, two $R^{10}$ or two $R^{11}$ may optionally be taken together with the atoms to which they are attached to form an optionally substituted cyclyl, heterocyclyl, aryl or heteroaryl ring;

each Y is independently O or S;

q is 1 or 2; and each $R^a$, $R^b$, $R^{b'}$, $R^c$, $R^{c'}$, $R^d$, $R^{d'}$, $R^e$ and $R^f$ is independently selected from hydrogen, $C_1$-$C_8$ alkyl, $C_2$-$C_8$ alkenyl, $C_2$-$C_8$ alkynyl, acyl, cyclyl, heterocyclyl, aryl, heteroaryl, cyclylalkyl, heterocyclylalkyl, aralkyl and heteroaralkyl, each of which may be optionally substituted with 1-3 $R^8$, or a pharmaceutically acceptable derivative or prodrug thereof.

In some embodiments, A is CH. In some embodiments, A is N.

In some embodiments, L is $NR^7$. In some embodiments, $R^7$ is H.

In some embodiments, $R^1$ is aryl (e.g., phenyl).

In some embodiments, $R^1$ is phenyl substituted with 1 $R^9$. In some embodiments, $R^1$ is phenyl substituted with 1 $R^9$ in the ortho position. In some embodiments, $R^1$ is phenyl substituted with 1 $R^9$ in the meta position. In some embodiments, $R^9$ is haloalkoxy (e.g., difluoromethoxy or trifluoromethoxy). In some embodiments, $R^9$ is —CN. In some embodiments, $R^9$ is —C(O)$OR^a$. In some embodiments, $R^1$ is hydrogen. In some embodiments, $R^9$ is —C(Y)$NR^bR^{b'}$. In some embodiments, Y is O. In some embodiments, $R^b$ and $R^{b'}$ are both hydrogen. In some embodiments, $R^1$ is:

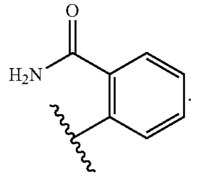 [SMILES: *c1ccccc1C(N)=O]

In some embodiments, one of $R^b$ and $R^{b'}$ is hydrogen and the other is $C_1$-$C_8$ alkyl (e.g., methyl), In some embodiments, $R^1$ is phenyl substituted with 2 $R^9$. In some embodiments, each $R^9$ is independently halo (e.g., each $R^9$ is fluoro or each $R^9$ is chloro). In some embodiments, one $R^9$ is fluoro and the other is chloro. In some embodiments, one $R^9$ is halo (e.g., chloro) and the other is haloalkoxy (e.g., difluoromethoxy or trifluoromethoxy).

In some embodiments, 2 $R^9$ are taken together with the atoms to which they are attached to form a heterocyclyl ring, e.g., a 5-membered heterocyclyl ring (e.g., a dioxole ring). In some embodiments, the dioxole ring is unsubstituted. In some embodiments, the dioxole ring is substituted. In some embodiments, the dioxole ring is substituted with two fluoro substituents. In some embodiments, $R^1$ is selected from:

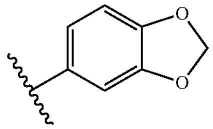

and

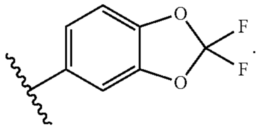

In some embodiments, $R^1$ is aralkyl (e.g., benzyl). In some embodiments, $R^1$ is aralkyl substituted with 2 $R^9$ (e.g., benzyl substituted with 2 $R^9$). In some embodiments, 2 $R^9$ substituents are on the phenyl ring. In some embodiments, each $R^9$ is independently halo (e.g., each $R^9$ is chloro).

In some embodiments, $R^1$ is alkyl (e.g., methyl).

In some embodiments, n is 0.

In some embodiments, n is 1.

In some embodiments, $R^2$ is $C_1$-$C_8$ alkyl (e.g., methyl). In some embodiments, $R^2$ is $C_1$-$C_8$ alkyl substituted with 1 $R^{11}$ (e.g., methyl substituted with 1 $R^{11}$). In some embodiments, $R^{11}$ is heterocyclyl (e.g., morpholino).

In some embodiments, $R^2$ is aryl (e.g., phenyl). In some embodiments, $R^2$ is phenyl substituted with 1 $R^{11}$. In some embodiments, $R^{11}$ is —CN. In some embodiments, $R^{11}$ is —$OR^d$. In some embodiments, $R^d$ is $C_1$-$C_8$ alkyl (e.g., methyl). In some embodiments, $R^{11}$ is halo.

In some embodiments, $R^2$ is halo (e.g., fluoro, chloro, bromo or iodo).

In some embodiments, $R^2$ is —$NR^cC(Y)R^{c'}$. In some embodiments, $R^c$ is hydrogen. In some embodiments, Y is O. In some embodiments, $R^{c'}$ is alkyl (e.g., methyl). In some embodiments, $R^{c'}$ is aryl (e.g., phenyl). In some embodiments, $R^{c'}$ is phenyl substituted with 1 $R^8$. In some embodiments, $R^8$ is —$OR^d$. In some embodiments, $R^d$ is $C_1$-$C_8$ alkyl (e.g., methyl).

In some embodiments, $R^{c'}$ is heteroaryl. In some embodiments, $R^{c'}$ is furanyl. In some embodiments, $R^c$ is pyridyl. In some embodiments, $R^{c'}$ is pyridyl substituted with 1 $R^8$. In some embodiments, $R^8$ is —$OR^d$. In some embodiments, $R^d$ is $C_1$-$C_8$ alkyl (e.g., methyl).

In some embodiments, $R^{c'}$ is cyclyl (e.g., cyclohexyl). In some embodiments, $R^{c'}$ is cyclohexyl substituted with 1 $R^8$. In some embodiments, $R^8$ is —$OR^d$. In some embodiments, $R^d$ is $C_1$-$C_8$ alkyl (e.g., methyl).

In some embodiments, $R^{c'}$ is heterocyclyl (e.g., tetrahydropyranyl).

In some embodiments, $R^1$ is —$NR^bR^{b'}$. In some embodiments, $R^b$ and $R^{b'}$ are both hydrogen. In some embodiments, $R^b$ and $R^{b'}$ are each independently $C_1$-$C_8$ alkyl (e.g., $R^b$ and $R^{b'}$ are both methyl).

In some embodiments, $R^2$ is —$OR^d$. In some embodiments, $R^d$ is $C_1$-$C_8$ alkyl (e.g., methyl or ethyl). In some embodiments, $R^d$ is ethyl substituted with 1 $R^8$. In some embodiments, $R^8$ is —$OR^d$. In some embodiments, $R^d$ is $C_1$-$C_8$ alkyl (e.g., methyl). In some embodiments, $R^2$ is —$OCH_2CH_2OCH_3$. In some embodiments, $R^2$ is —$OCH_2CH_2OCH_2CH_2CH_3$. In some embodiments, $R^2$ is —$OCH_2CH_2OCH_2CH_2OCH_3$.

In some embodiments, n is 2.

In some embodiments, one $R^2$ is $C_1$-$C_8$ alkyl (e.g., methyl) and the other is halo (e.g., chloro).

In some embodiments, one $R^2$ is —$OR^d$ and the other is halo (e.g., chloro). In some embodiments, $R^d$ is $C_1$-$C_8$ alkyl (e.g., methyl).

In some embodiments, $X^1$ and $X^4$ are N and $X^2$, $X^3$ and $X^5$ are CH.

In some embodiments, $X^1$ and $X^3$ are N and $X^2$, $X^4$ and $X^5$ are CH.

In some embodiments, $X^2$ and $X^3$ are N and $X^1$, $X^4$ and $X^5$ are CH.

In some embodiments, $X^2$ and $X^4$ are N and $X^1$, $X^3$ and $X^5$ are CH.

In some embodiments, the compound is:

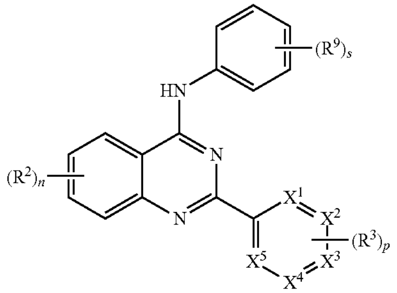

wherein s is 0, 1, 2, 3 or 4.

In some embodiments, $R^9$ is —$C(O)NH_2$, $C_1$-$C_4$ alkoxy, or substituted $C_1$-$C_4$ alkoxy. In some embodiments, $R^9$ is halo, In some embodiments, the compound is:

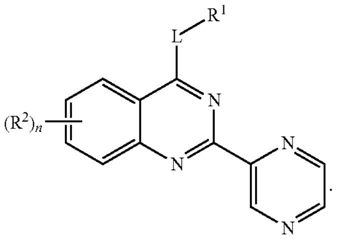

In some embodiments, $R_1$ is selected from methyl, cyclohexyl, t-butyl, and pyridinyl. In some embodiments, $R_1$ is heteroaralkyl (e.g., —$CH_2$-pyridyl). In some embodiments, $LR^1$ is $NH(CH_3)$.

In some embodiments, the compound is:

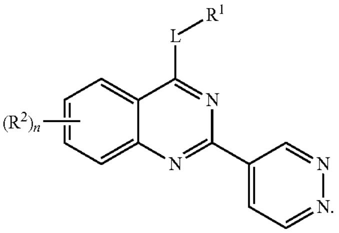

In some embodiments, $R_1$ is selected from methyl, cyclohexyl, t-butyl, and pyridinyl. In some embodiments, $R_1$ is heteroaralkyl (e.g., —$CH_2$-pyridyl). In some embodiments, $LR^1$ is $NH(CH_3)$.

In some embodiments, the compound is:

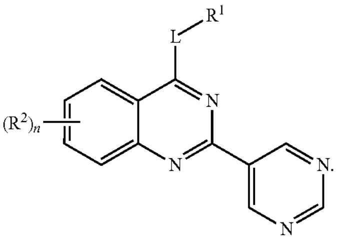

In some embodiments, $R_1$ is selected from methyl, cyclohexyl, t-butyl, and pyridinyl. In some embodiments, $R_1$ is heteroaralkyl (e.g., —$CH_2$-pyridyl). In some embodiments, $LR^1$ is $NH(CH_3)$.

In some embodiments, the compound is:

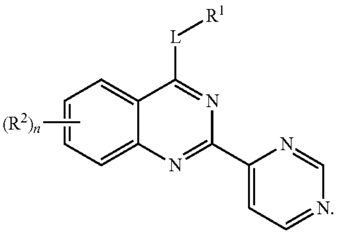

In some embodiments, $R_1$ is selected from methyl, cyclohexyl, t-butyl, and pyridinyl. In some embodiments, $R_1$ is heteroaralkyl (e.g., —$CH_2$-pyridyl). In some embodiments, $LR^1$ is $NH(CH_3)$.

In some embodiments, the compound is:

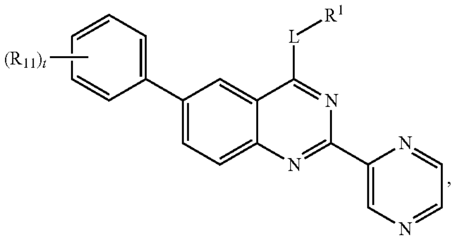

wherein t is 1-3.

In some embodiments, $R_1$ is selected from methyl, cyclohexyl, t-butyl, and pyridinyl. In some embodiments, $R_1$ is heteroaralkyl (e.g., —$CH_2$-pyridyl). In some embodiments, $LR^1$ is $NH(CH_3)$. In some embodiments, $R^{11}$ is independently halo, nitrile, $C_1$-$C_4$ alkoxy, —$C(O)NH_2$, hydroxy, or $C_1$-$C_4$ hydroxyalkyl. In some embodiments, $R^{11}$ is fluoro. In some embodiments, $R^{11}$ is methoxy, ethoxy, or methoxyethoxy ether. In some embodiments, $R^{11}$ is —$OCH_2CH_2OCH_3$. In some embodiments, $R^{11}$ is —$OCH_2CH_2OCH_2CH_3$. In some embodiments, $R^{11}$ is —$OCH_2CH_2OCH_2CH_2OCH_3$.

In some embodiments, the compound is:

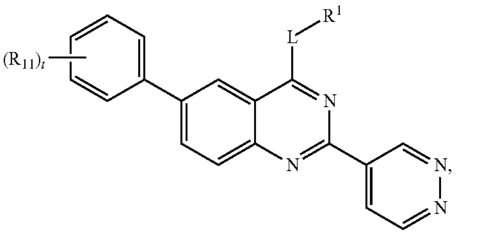

N wherein t is 1-3.

In some embodiments, $R_1$ is selected from methyl, cyclohexyl, t-butyl, and pyridinyl. In some embodiments, $LR^1$ is $NH(CH_3)$. In some embodiments, $R^{11}$ is independently halo, nitrile, $C_1$-$C_4$ alkoxy, —$C(O)NH_2$, hydroxy, or $C_1$-$C_4$ hydroxyalkyl. In some embodiments, $R^{11}$ is fluoro. In some embodiments, $R^{11}$ is methoxy, ethoxy, or methoxyethoxy ether. In some embodiments, $R^{11}$ is —$OCH_2CH_2OCH_3$. In some embodiments, $R^{11}$ is —$OCH_2CH_2OCH_2CH_2CH_3$. In some embodiments, $R^{11}$ is —$OCH_2CH_2OCH_2CH_2OCH_3$.

In some embodiments, the compound is:

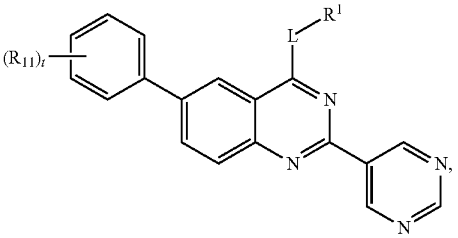

wherein t is 1-3.

In some embodiments, $R_1$ is selected from methyl, cyclohexyl, t-butyl, and pyridinyl. In some embodiments, $LR^1$ is $NH(CH_3)$. In some embodiments, $R^{11}$ is independently halo, nitrile, $C_1$-$C_4$ alkoxy, —$C(O)NH_2$, hydroxy, or $C_1$-$C_4$ hydroxyalkyl. In some embodiments, $R^{11}$ is fluoro. In some embodiments, $R^{11}$ is methoxy, ethoxy, or methoxyethoxy ether. In some embodiments, $R^{11}$ is —$OCH_2CH_2OCH_3$. In some embodiments, $R^{11}$ is —$OCH_2CH_2OCH_2CH_2CH_3$. In some embodiments, $R^{11}$ is —$OCH_2CH_2OCH_2CH_2OCH_3$.

In some embodiments, the compound is:

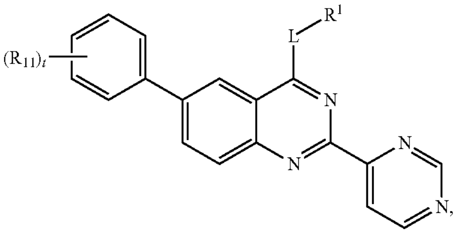

wherein t is 1-3.

In some embodiments, $R_1$ is selected from methyl, cyclohexyl, t-butyl, and pyridinyl. In some embodiments, $LR^1$ is $NH(CH_3)$. In some embodiments, $R^{11}$ is independently halo, nitrile, $C_1$-$C_4$ alkoxy, —$C(O)NH$, hydroxy, or $C_1$-$C_4$ hydroxyalkyl. In some embodiments, $R^{11}$ is fluoro. In some embodiments, $R^{11}$ is methoxy, ethoxy, or methoxyethoxy ether. In some embodiments, $R^{11}$ is —$OCH_2CH_2OCH_3$. In some embodiments, $R^{11}$ is —$OCH_2CH_2OCH_2CH_2CH_3$. In some embodiments, $R^{11}$ is —$OCH_2CH_2OCH_2CH_2OCH_3$.

Compounds of Formula (VI)

The following aspects and embodiments relate to compounds of formula (VI) corresponding to formula (I) of U.S. Provisional Patent Application No. 61/291,554, entitled "Therapeutic Compounds and Related Methods of Use" filed on Dec. 31, 2009, and incorporated herein by reference in its entirety.

Item 41. A compound of formula (VI):

(VI)

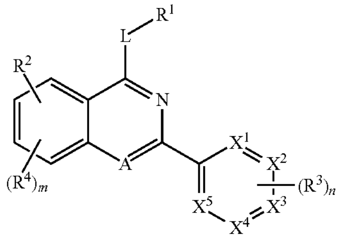

wherein:

A is $CR^5$, CH or N;

L is O or $NR^6$;

1, 2 or 3 of $X^1$, $X^2$, $X^3$, $X^4$ and $X^5$ are N and the others are CH;

m is 0, 1, 2 or 3;

n is 0, 1, 2, 3 or 4;

$R^1$ is hydrogen, $C_1$-$C_8$ alkyl, $C_2$-$C_8$ alkenyl, $C_2$-$C_8$ alkynyl, cyclyl or heterocyclyl, each of which is optionally substituted with 1-3 $R^7$; or when L is $NR^6$, $R^1$ or $R^7$ may be taken together with $R^6$ and the atoms to which they are attached to form a heterocyclyl or heteroaryl ring that is optionally substituted with 1-3 $R^8$;

$R^2$ is aryl or heteroaryl, each of which is optionally substituted with 1-5 $R^9$;

each $R^3$, $R^4$ and $R^5$ is independently $C_1$-$C_8$ alkyl, $C_1$-$C_8$ alkenyl, $C_2$-$C_8$ alkynyl, aryl, heteroaryl, cyclyl, heterocyclyl, aralkyl, heteroaralkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy, silylalkoxyalkyl, —CN, —$NO_2$, —C(O)$OR^a$, —C(Y)$NR^bR^{b'}$, —$NR^cC(Y)R^{c'}$, —$NR^bR^{b'}$, —OC(O)$NR^bR^{b'}$, —$NR^cC(O)OR^{c'}$, —$SO_2NR^bR^{b'}$, —$NR^cSO_2R^{c'}$, —$NR^cC(Y)NR^bR^{b'}$, —$OR^d$, —$SR^{d'}$, —C(Y)$R^e$ or —$S(O)_qR^f$, each of which is optionally substituted with 1-3 $R^{10}$;

$R^6$ is hydrogen, $C_1$-$C_8$ alkyl, $C_2$-$C_8$ alkenyl, $C_2$-$C_8$ alkynyl, cyclyl or heterocyclyl, each of which is optionally substituted with 1-3 $R^{11}$;

each $R^7$, $R^8$, $R^9$ and $R^{10}$ is independently $C_1$-$C_8$ alkyl, $C_2$-$C_8$ alkenyl, $C_2$-$C_8$ alkynyl, aryl, heteroaryl, cyclyl, heterocyclyl, aralkyl, heteroaralkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy, silylalkoxyalkyl, oxo, thiono, —CN, —$NO_2$, —C(O)$OR^a$, —C(Y)$NR^bR^{b'}$, —$NR^cC(Y)R^{c'}$, —$NR^bR^{b'}$, —OC(O)$NR^bR^{b'}$, —$NR^cC(O)OR^{c'}$, —$SO_2NR^bR^{b'}$, —$NR^cSO_2R^{c'}$, —$NR^cC(Y)NR^bR^{b'}$, —$OR^d$, —$SR^{d'}$, —C(Y)$R^e$ or —$S(O)_qR^f$, each of which is optionally substituted with 1-3 $R^{12}$; wherein two $R^7$, two $R^8$, two $R^9$ or two $R^{10}$ may optionally be taken together with the atoms to which they are attached to form an optionally substituted cyclyl, heterocyclyl, aryl or heteroaryl ring;

each $R^{11}$ and $R^{12}$ is independently $C_1$-$C_8$ alkyl, $C_2$-$C_8$ alkenyl, $C_2$-$C_8$ alkynyl, aryl, heteroaryl, cyclyl, heterocyclyl, aralkyl, heteroaralkyl, cyclylalkyl, heterocyclylalkyl, halo, haloalkyl, haloalkoxy, aminoalkyl, alkylaminoalkyl, dialkylaminoalkyl, hydroxyalkyl, alkoxyalkyl, silyloxy, silyloxyalkyl, silylalkoxy, silylalkoxyalkyl, oxo, thiono, —CN, —$NO_2$, —C(O)$OR^a$, —C(Y)$NR^bR^{b'}$, —$NR^cC(Y)R^{c'}$, —$NR^bR^{b'}$, —OC(O)$NR^bR^{b'}$, —$NR^cC(O)OR^{c'}$, —$SO_2NR^bR^{b'}$, —$NR^cSO_2R^{c'}$, —$NR^cC(Y)NR^bR^{b'}$, —$OR^d$, —$SR^{d'}$, —C(Y)$R^e$ or —$S(O)_qR^f$;

each Y is independently O or S;

q is 1 or 2; and each $R^a$, $R^b$, $R^{b'}$, $R^c$, $R^{c'}$, $R^d$, $R^{d'}$, $R^e$ and $R^f$ is independently selected from hydrogen, $C_1$-$C_8$ alkyl, $C_2$-$C_8$ alkenyl, $C_2$-$C_8$ alkynyl, acyl, cyclyl, heterocyclyl, aryl, heteroaryl, cyclylalkyl, heterocyclylalkyl, aralkyl and heteroaralkyl, each of which may be optionally substituted with 1-3 $R^7$;

or a pharmaceutically acceptable derivative or prodrug thereof, wherein when $R^1$ is cyclopropyl, $R^9$ is not

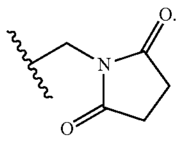 [SMILES: *CN1C(=O)CCC1=O]

In some embodiments, $R^7$ is not:

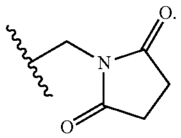 [SMILES: *CN1C(=O)CCC1=O]

In some embodiments, $R^1$ is $C_1$-$C_8$ alkyl, which is optionally substituted with 1-3 $R^7$; or when L is $NR^6$, $R^1$ and $R^6$ may be taken together with the atoms to which they are attached to form a heterocyclyl or heteroaryl ring that is optionally substituted with 1-3 $R^8$.

In some embodiments, A is CH. In some embodiments, A is N.

In some embodiments, L is $NR^6$. In some embodiments, $R^6$ is hydrogen.

In some embodiments, $R^1$ is $C_1$-$C_8$ alkyl, e.g., methyl, ethyl, $C_3$ alkyl (e.g., n-propyl or isopropyl), $C_4$ alkyl (e.g., n-butyl, isobutyl or tert-butyl), or $C_5$ alkyl (e.g., pentan-3-yl).

In some embodiments, $R^1$ is $C_1$-$C_8$ alkyl substituted with 1-3 $R^7$ (e.g., $C_1$-$C_8$ alkyl substituted with 1 $R^7$). In some embodiments, $R^1$ is methyl substituted with 1 $R^7$. In some embodiments, $R^7$ is cyclyl (e.g., cyclopropyl). In some embodiments, $R^7$ is aryl (e.g., phenyl).

In some embodiments, $R^1$ is ethyl substituted with 1 $R^7$. In some embodiments, $R^7$ is aryl (e.g., phenyl). In some embodiments, $R^7$ is —$OR^d$. In some embodiments, $R^d$ is aryl (e.g., phenyl).

In some embodiments, $R^1$ is n-propyl substituted with 1 $R^7$. In some embodiments, $R^1$ is —$OR^d$. In some embodiments, $R^d$ is $C_1$-$C_8$ alkyl (e.g., $C_3$ alkyl, e.g., n-propyl).

In some embodiments, $R^1$ is $C_1$-$C_8$ alkyl substituted with 3 $R^7$. In some embodiments, $R^1$ is ethyl substituted with 3 $R^7$. In some embodiments, each $R^1$ is independently halo (e.g., each $R^1$ is fluoro). In some embodiments, $R^1$ is 2,2,2-trifluoroethyl.

In some embodiments, $R^1$ is $C_2$-$C_8$ alkenyl, e.g., $C_3$ alkenyl (e.g., —$CH_2$—CH═$CH_2$).

In some embodiments, $R^1$ is $C_2$-$C_8$ alkynyl, e.g., $C_3$ alkynyl (e.g. —$CH_2$—C≡CH).

In some embodiments, $R^1$ is cyclyl (e.g., cyclopropyl, cyclobutyl, cyclopentyl or cyclohexyl). In some embodiments, the cyclyl group is a bicyclic group (e.g., indanyl).

In some embodiments, $R^1$ is heterocyclyl (e.g., piperidyl). In some embodiments, $R^1$ is piperidyl substituted with 1 $R^7$. In some embodiments, $R^7$ is —C(Y)$R^e$. In some embodiments, Y is O. In some embodiments, $R^e$ is $C_1$-$C_8$ alkyl (e.g., methyl). In some embodiments, $R^1$ is —$OR^d$.

In some embodiments, $R^6$ is $C_1$-$C_8$ alkyl (e.g., methyl).

In some embodiments, $R^1$ and $R^6$ are taken together with the atoms to which they are attached to form a heterocyclyl ring (e.g., a pyrrolidine ring).

In some embodiments, $R^1$ and $R^6$ are taken together with the atoms to which they are attached to form a heteroaryl ring (e.g., an imidazole ring).

In some embodiments, L is O.

In some embodiments, $R^1$ is $C_1$-$C_8$ alkyl (e.g., methyl).

In some embodiments, $R^2$ is aryl (e.g., phenyl). In some embodiments, $R^2$ is unsubstituted phenyl. In some embodiments, $R^2$ is phenyl substituted with 1-3 $R^9$. In some embodiments, $R^2$ is phenyl substituted with 1 $R^9$.

In some embodiments, $R^2$ is:

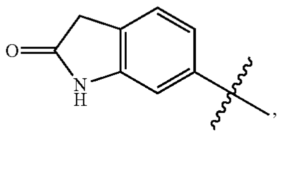

-continued

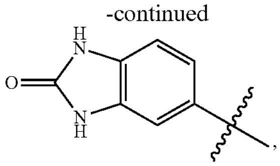

, or

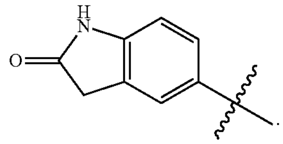

In some embodiments, $R^9$ is halo (e.g., fluoro or chloro). In some embodiments, $R^9$ is —CN. In some embodiments, $R^9$ is —$NO_2$. In some embodiments, $R^9$ is haloalkoxy (e.g., trifluoroethoxy). In some embodiments, $R^9$ is —$NR^bR^{b'}$. In some embodiments, $R^b$ and $R^{b'}$ are each independently $C_1$-$C_8$ alkyl (e.g., $R^b$ and $R^{b'}$ are both methyl).

In some embodiments, $R^9$ is —$OR^d$. In some embodiments, $R^9$ is —$OCH_2CH_2OCH_3$. In some embodiments, $R^9$ is —$OCH_2CH_2OCH_2CH_2CH_3$. In some embodiments, $R^9$ is —$OCH_2CH_2OCH_2CH_2OCH_3$. In some embodiments, $R^d$ is hydrogen. In some embodiments, $R^d$ is $C_1$-$C_5$ alkyl (e.g., methyl). In some embodiments, $R^d$ is methyl substituted with 1 $R^7$. In some embodiments, $R^7$ is —$CYNR^bR^{b'}$. In some embodiments, Y is O and $R^b$ and $R^{b'}$ are each independently $C_1$-$C_8$ alkyl (e.g., $R^b$ and $R^{b'}$ are both methyl). In some embodiments, $R^d$ is ethyl. In some embodiments, $R^d$ is ethyl substituted with 1 $R^7$. In some embodiments, $R^1$ is —$OR^d$. In some embodiments, $R^d$ is $C_1$-$C_8$ alkyl (e.g., methyl). In some embodiments, $R^7$ is heterocyclyl (e.g., morpholino).

In some embodiments, $R^9$ is hydroxyalkyl (e.g., —$CH_2OH$). In some embodiments, $R^9$ is alkoxyalkyl (e.g., —$CH_2$—O—$CH_3$). In some embodiments, $R^9$ is —$C(O)R^e$. In some embodiments, $R^e$ is heterocyclyl (e.g., morpholino). In some embodiments, $R^9$ is —$S(O)_qR^f$. In some embodiments, q is 1. In some embodiments, $R^1$ is $C_1$-$C_8$ alkyl (e.g., methyl).

In some embodiments, $R^2$ is phenyl substituted with 2 $R^9$. In some embodiments, each $R^9$ is independently halo (e.g., each $R^9$ is fluoro). In some embodiments, each $R^9$ is independently —$OR^d$. In some embodiments, each $R^d$ is independently $C_1$-$C_8$ alkyl (e.g., each $R^d$ is methyl).

In some embodiments, $R^2$ is heteroaryl. In some embodiments, $R^2$ is a 6-membered heteroaryl. In some embodiments, $R^2$ is a 6-membered nitrogen-containing heteroaryl, e.g., pyridyl. In some embodiments, $R^2$ is unsubstituted pyridyl.

In some embodiments, $R^2$ is pyridyl substituted with 1 $R^9$. In some embodiments, $R^9$ is —$OR^d$. In some embodiments, $R^d$ is $C_1$-$C_8$ alkyl (e.g., methyl).

In some embodiments, $R^2$ is a 5-membered heteroaryl. In some embodiments, $R^2$ is a 5-membered nitrogen-containing heteroaryl (e.g., pyrrolyl or oxazolyl).

In some embodiments, m is 0.

In some embodiments, in is 1.

In some embodiments, $R^4$ is $C_1$-$C_8$ alkyl (e.g., methyl). In some embodiments, $R^4$ is —$OR^d$. In some embodiments, $R^d$ is $C_1$-$C_8$ alkyl (e.g., methyl). In some embodiments, $R^4$ is halo. In some embodiments, $R^4$ is methoxy. In some embodiments, $R^d$ is $C_1$-$C_8$ alkyl.

In some embodiments, the compound has the following structure:

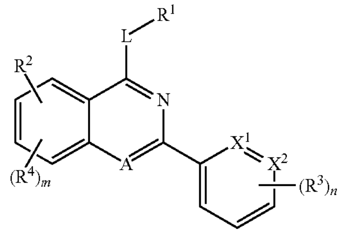

wherein one of $X^1$ and $X^2$ is N and the other is CHI.

In some embodiments, $X^1$ is CH and $X^2$ is N. In some embodiments, $X^1$ is N and $X^2$ is CH. In some embodiments, the compound has the following structure:

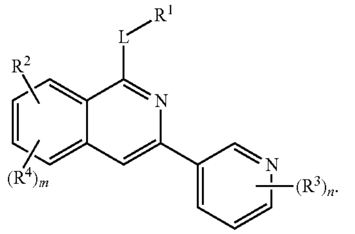

In some embodiments, $R^2$ is aryl. In some embodiments, $R^2$ is heteroaryl. In some embodiments, $R^1$ is $C_1$-$C_8$ alkyl (e.g., methyl).

In some embodiments, the compound has the following structure:

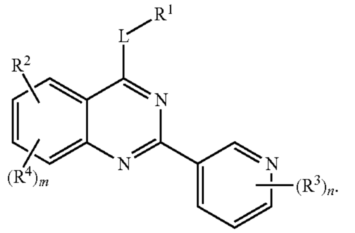

In some embodiments, $R^2$ is aryl. In some embodiments, $R^2$ is heteroaryl. In some embodiments, $R^1$ is $C_1$-$C_8$ alkyl (e.g., methyl).

In some embodiments, the compound has the following structure:

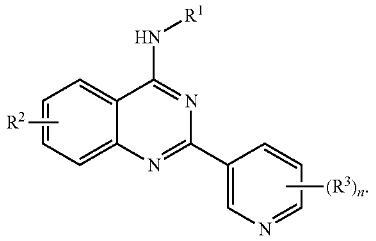

In some embodiments, $R^2$ is aryl. In some embodiments, $R^2$ is heteroaryl. In some embodiments, $R^1$ is $C_1$-$C_8$ alkyl (e.g., methyl).

In some embodiments, the compound has the following structure:

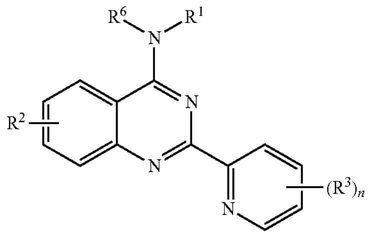

wherein $R^1$ is $C_1$-$C_8$ alkyl, which is optionally substituted with 1-3 $R^7$.

In some embodiments, $R^2$ is aryl. In some embodiments, $R^2$ is heteroaryl. In some embodiments, $R^1$ is $C_1$-$C_8$ alkyl (e.g., methyl).

In some embodiments, the compound has the following structure:

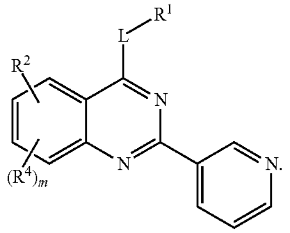

In some embodiments, $R^2$ is aryl. In some embodiments, $R^2$ is heteroaryl. In some embodiments, $R^1$ is $C_1$-$C_8$ alkyl (e.g., methyl).

In some embodiments, $R^2$ is

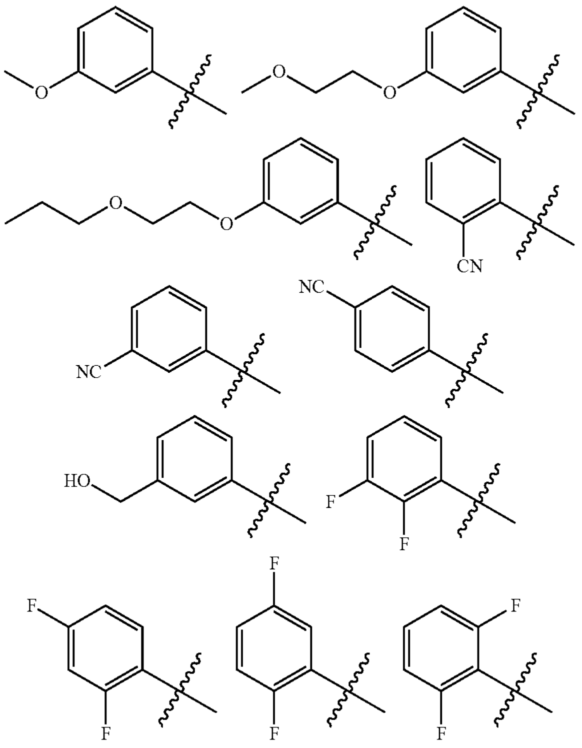

-continued

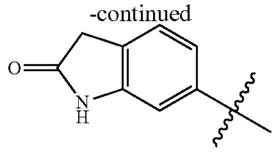

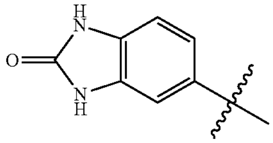

or

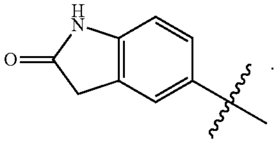

.

In some embodiments, the compound has the following structure:

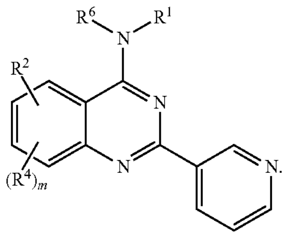

In some embodiments, $R^2$ is aryl. In some embodiments, $R^2$ is heteroaryl. In some embodiments $R^1$ is $C_1$-$C_8$ alkyl (e.g., methyl). In some embodiments, $R^2$ is

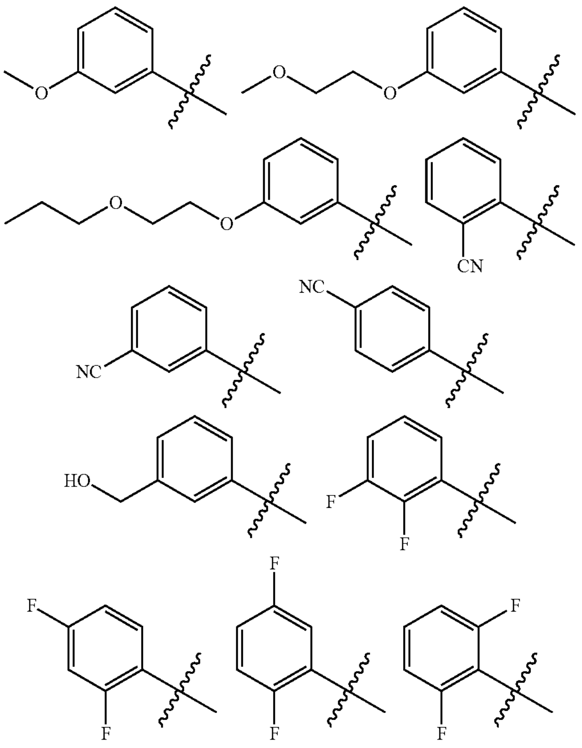

-continued

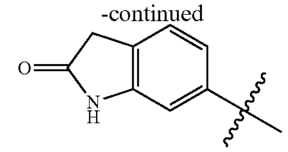

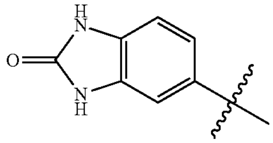

or

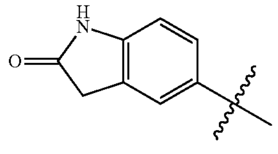

In some embodiments, the compound has the following structure:

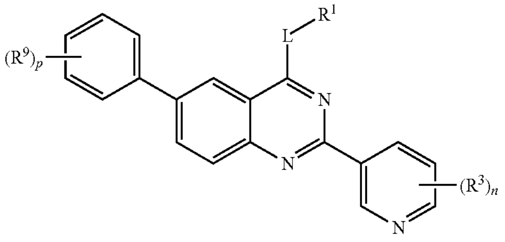

wherein p is 1, 2, 3, 4 or 5,

In some embodiments, L is $NR^6$. In some embodiments, L is O. In some embodiments, $R^1$ is hydrogen or $C_1$-$C_8$ alkyl. In some embodiments, $R^j$ is cyclyl or heterocyclyl. In some embodiments, $R^1$ is aralkyl or heteroaralkyl. In some embodiments, $R^1$ is methyl, cyclohexyl, t-butyl, or

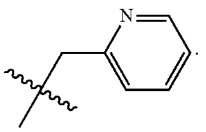 [SMILES: *Cc1ccccn1]

In some embodiments, $R^1$ is hydrogen or $C_1$-$C_8$ alkyl.
In some embodiments, $R^9$ is $C_1$-$C_8$ alkyl, halo, —CN, or —$OR^d$. In some embodiments, $R^3$ is hydrogen.

In some embodiments, the compound has the following structure:

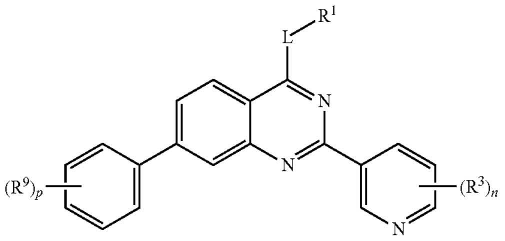

wherein p is 1, 2, 3, 4 or 5.

In some embodiments, L is $NR^6$. In some embodiments, L is O. In some embodiments, $R^1$ is hydrogen or $C_1$-$C_8$ alkyl. In some embodiments, $R^1$ is cyclyl or heterocyclyl. In some embodiments, $R^1$ is aralkyl or heteroaralkyl. In some embodiments, $R^1$ is methyl, cyclohexyl, t-butyl, or

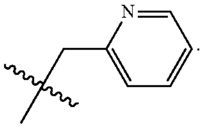 [SMILES: *Cc1ccccn1]

In some embodiments, $R^6$ is hydrogen or $C_1$-$C_8$ alkyl. In some embodiments, $R^9$ is $C_1$-$C_8$ alkyl, halo, —CN, or —$OR^d$. In some embodiments, $R^3$ is hydrogen.

Aspects and Embodiments of Compounds of Formulas (I), (II), (III), (IV), (V), and (VI)

In one aspect, the invention features a composition comprising a compound of formula (I), (II), (III), (IV), (V), or (VI) and an acceptable carrier.

In one aspect, the invention features a pharmaceutical composition comprising a compound of formula (I), (II), (III), (IV), (V), or (VI) and a pharmaceutically acceptable carrier.

In one aspect, the invention features a kit comprising a composition comprising a compound of formula (I), (II), (III), (IV), (V), or (VI) and an acceptable carrier.

In one aspect, the invention features a kit comprising a pharmaceutical composition comprising a compound of formula (I), (II), (III), (IV), (V), or (VI) and a pharmaceutically acceptable carrier.

In one aspect, the invention features a dosage form comprising a composition comprising a compound of formula (I), (II), (III), (IV), (V), or (VI) and an acceptable carrier.

In one aspect, the invention features a dosage form comprising a pharmaceutical composition comprising a compound of formula (I), (II), (III), (IV), (V), or (VI) and a pharmaceutically acceptable carrier.

In one aspect, the invention features a method of treating a disorder that would benefit by the modulation of STEP (e.g., by activation or inhibition of STEP) in a subject, the method comprising administering to a subject in need thereof a compound of formula (I), (II), (III), (IV), (V), or (VI). In one aspect, the invention features a method of treating a disorder that would benefit by the inhibition of STEP, the method comprising administering to a subject in need thereof a compound of formula (I), (II), (III), (IV), (V), or (VI). In some embodiments, the disorder is selected from schizophrenia, schizoaffective disorder, bipolar disorder, manic-depressive disorder, psychosis, mood and anxiety disorders, mania, drug or substance addiction, cognition disorders, learning disabilities, learning and memory disorders, aging and neurologic disorders associated with or linked with cognitive impairments; mild cognitive impairments (MCI), Alzheimer's disease, Alzheimer-related cognition disorders, Huntington's disease, Parkinson's disease, CADASIL syndrome (cerebral autosomal dominant arteriopathy with subcortical infarcts and leukoencephalopathy), amnesia, Wernicke-Korsakoff syndrome, Korsakoff syndrome, mild traumatic head injury (MBTI), traumatic head injury (TBI), fragile X syndrome, stroke, attention-deficit and hyperactivity disorder (ADHD), obsessive compulsive disorder (OCD), post-traumatic stress disorder (PTSD), loss of concentration, autism, cerebral palsy, encephalopathy, and narcolepsy. In some embodiments, the disorder affects learning and memory, neurogenesis, neuronal plasticity, pain perception, mood and anxiety, or neuroendocrine regulation. In some embodiments, the disorder is a cognitive deficit disorder. In some embodiments, the disorder involves pain perception or neuroendocrine regulation. In some embodiments, the disorder affects the central nervous system. In some embodiments the disorder is selected from the group consisting of schizophrenia; refractory, intractable or chronic schizophrenia; emotional disturbance; psychotic disorder; mood disorder; bipolar I type disorder; bipolar II type disorder; depression; endogenous depression; major depression; melancholy and refractory depression; dysthymic disorder; cyclothymic disorder; panic attack; panic disorder; agoraphobia; social phobia; obsessive-compulsive disorder; post-traumatic stress disorder; generalized anxiety disorder; acute stress disorder; hysteria; somatization disorder; conversion disorder; pain disorder; hypochondriasis; factitious disorder; dissociative disorder; sexual dysfunction; sexual desire disorder; sexual arousal disorder; erectile dysfunction; anorexia nervosa; bulimia nervosa; sleep disorder; adjustment disorder; alcohol abuse; alcohol intoxication; drug addiction; stimulant intoxication; narcotism; anhedonia; iatrogenic anhedonia; anhedonia of a psychic or mental cause; anhedonia associated with depression; anhedonia associated with schizophrenia; delirium; cognitive impairment; cognitive impairment associated with Alzheimer's disease, Parkinson's disease and other neurodegenerative diseases; cognitive impairment caused by Alzheimer's disease; Parkinson's disease and associated neurodegenerative diseases; cognitive impairment of schizophrenia; cognitive impairment caused by refractory, intractable or chronic schizophrenia; vomiting; motion sickness; obesity; migraine; pain (ache); mental retardation; autism disorder (autism); Tourette's disorder; tic disorder; attention-deficit/hyperactivity disorder; conduct disorder; and Down's syndrome.

In one aspect, the invention features a method of treating a condition that would benefit by the modulation of STEP (e.g., by activation or inhibition of STEP) in a subject, the method comprising administering to a subject in need thereof a compound of formula (I), (II), (III), (IV), (V), or (VI). In some embodiments, the condition is selected from decreased neurogenesis, cell resilience, or neuronal plasticity due to normal aging, neurodegenerative disorders of the CNS; Alzheimer's disease, Huntington's disease, fragile X syndrome, amyotrophic lateral sclerosis/Lou Gehrig's disease, stroke, Parkinson's disease, parkinsonism, dementia, Pick disease, Corticobasal degeneration, Multiple system atrophy, Progressive supranuclear palsy, traumatic brain injury, head trauma, mild traumatic head injury (MBTI), traumatic head injury (TBI), encephalopathy, intoxication related to ethanol, alcoholism, fetal alcohol syndrome, drug addiction or drug abuse.

In some embodiments, a compound of formula (I), (II), (III), (IV), (V), or (VI) is administered in combination with an additional therapeutic agent. In some embodiments, the additional therapeutic agent is an atypical antipsychotic. In some embodiments, the additional therapeutic agent is selected from the group consisting of aripiprazole, clozapine, ziprasidone, risperidone, quetiapine, olanzapine, amisulpride, asenapine, iloperidone, melperone, paliperidone, perospirone, sertindole and sulpiride. In some embodiments, the additional therapeutic agent is a typical antipsychotic. In some embodiments, the additional therapeutic agent is selected from the group consisting of haloperidol, molindone, loxapine, thioridazine, molindone, thiothixene, pimozide, fluphenazine, trifluoperazine, mesoridazine, chlorprothixene, chlorpromazine, perphenazine, triflupromazine and zuclopenthixol.

DETAILED DESCRIPTION

A compound or composition described herein can be used, e.g., in a method of treating schizophrenia or cognitive deficit. Many of the compounds described herein modulate STEP activity and can be used, e.g., to reduce or inhibit STEP activity, e.g., in a subject.

DEFINITIONS

The term "acyl" refers to an alkylcarbonyl, cycloalkylcarbonyl, arylcarbonyl, heterocyclylcarbonyl, or heteroarylcarbonyl substituent, any of which may be further substituted (e.g., by one or more substituents).

The term "alkenyl" refers to a straight or branched hydrocarbon chain containing 2-12 carbon atoms (unless otherwise noted) and having one or more double bonds. Examples of alkenyl groups include, but are not limited to, allyl, propenyl, 2-butenyl, 3-hexenyl and 3-octenyl groups. One of the double bond carbons may optionally be the point of attachment of the alkenyl substituent.

The term "alkenylene" refers to a divalent alkenyl, e.g. $—CH{=}CH—$, $—CH_2—CH{=}CH—$, and $—CH{=}CH—CH_2—$.

The term "alkynyl" refers to a straight or branched hydrocarbon chain containing 2-12 carbon atoms (unless otherwise noted) and characterized in having one or more triple bonds. Examples of alkynyl groups include, but are not limited to, ethynyl, propargyl, and 3-hexynyl. One of the triple bond carbons may optionally be the point of attachment of the alkynyl substituent.

The term "alkynylene" refers to a divalent alkynyl, e.g. $—CH{\equiv}CH—$, $—CH_2—CH{\equiv}CH—$, and $—CH{\equiv}CH—CH_2—$.

The terms "alkoxyl" or "alkoxy" as used herein refers to an alkyl group, as defined below, having an oxygen radical attached thereto. Representative alkoxy groups include methoxy, ethoxy, propyloxy, tert-butoxy and the like. The term "alkoxyalkyl" refers to an alkyl in which one or more hydrogen atoms are replaced by an alkoxy group.

An "ether" is two hydrocarbons covalently linked by an oxygen.

The term "alkyl" refers to the radical of saturated aliphatic groups, including straight-chain alkyl groups, and branched-chain alkyl groups. In preferred embodiments, a straight chain or branched chain alkyl has 12 or fewer carbon atoms in its backbone (unless otherwise noted) e.g., from 1-12, 1-8, 1-6, or 1-4. Exemplary alkyl moieties include methyl, ethyl, propyl (e.g., n-propyl or isopropyl), butyl (e.g., n-butyl, isobutyl or t-butyl), pentyl (e.g., n-pentyl, isopentyl or pentan-3-yl), hexyl and hepty.

The term "alkylene" refers to a divalent alkyl, e.g., $—CH—$, $—CH_2\ CH_2—$, and $—CH_2CH_2CH_2—$.

The term "alkoxylene" refers to an alkylene wherein a $CH_2$ is substituted with an oxygen. For example, an aryl alkoxylene refers to a group with an alkylene attached to an aryl group through an oxygen, an optionally substituted heteroaryl alkoxylene refers to a group with an alkylene attached to an heteroaryl group through an oxygen.

The term "amino" refers to $—NH_2$.

The term "aminoalkyl" refers to an alkyl in which one or more hydrogen atoms are replaced by an amino group.

The terms "alkylamino" and "dialkylamino" refer to —NH(alkyl) and $—N(alkyl)_2$ radicals respectively.

The term "aralkylamino" or "arylalkylamino" refers to a —NH(aralkyl) radical. The term "alkylaminoalkyl" refers to a (alkyl)NH-alkyl-radical; the term "dialkylaminoalkyl" refers to an $(alkyl)_2N$-alkyl-radical.

The term "amido" refers to a —NHC(O)— or $C(O)NH_2$ substituent.

The term "aryl" refers to a 6-carbon monocyclic, 10-carbon bicyclic, or 14-carbon tricyclic aromatic ring system wherein 0, 1, 2, 3, or 4 atoms of each ring may be substituted by a substituent. Examples of aryl moieties include, but are not limited to, phenyl, naphthyl and the like. The term "arylalkyl" or "aralkyl" refers to alkyl substituted with an aryl. Exemplary aralkyls include but are not limited to benzyl, 1-phenylethyl, 2-phenylethyl, 3-phenylpropyl, 9-fluorenyl, benzhydryl, phenethyl, and trityl groups. The term "arylalkenyl" refers to an alkenyl substituted with an aryl. The term "arylalkynyl" refers to an alkynyl substituted with an aryl. Terms such as "aryl$C_2$-$C_6$ alkyl" are to be read as a further limitation on the size of the alkyl group. The term "arylalkoxy" refers to an alkoxy substituted with aryl. The term "arylenyl" refers to a divalent aryl (i.e., —Ar—).

The terms "cycloalkyl" or "cyclyl" as employed herein include saturated and partially unsaturated cyclic hydrocarbon groups having 3 to 12 carbons, preferably 3 to 8 carbons, and more preferably 3 to 6 carbons, wherein the cycloalkyl group may be optionally substituted. Exemplary cyclyl groups include, without limitation, cyclopropyl, cyclobutyl, cyclopentyl, cyclopentenyl, cyclohexyl, cyclohexenyl, cycloheptyl, and cyclooctyl. Cyclyl moieties also include both bridged and fused ring systems. Cyclyl groups also include those that are fused to additional ring systems, which may be saturated or unsaturated. A cyclyl group may thus be a bicyclic group in which one ring is saturated or partially unsaturated and the other is fully unsaturated (e.g., indanyl).

The term "cyclylalkyl" as used herein, refers to an alkyl group substituted with a cyclyl group. Cyclylalkyl includes groups in which more than one hydrogen atom of an alkyl group has been replaced by a cyclyl group.

The term "cycloalkylalkyl" as used herein, refers to an alkyl group substituted with a cycloalkyl group.

The term "halo" or "halogen" refers to any radical of fluorine, chlorine, bromine or iodine.

The term "haloalkyl" refers to an alkyl group that may have any number of hydrogens available on the group replaced with a halogen atom. Representative haloalkyl groups include but are not limited to: $—CH_2Cl$, $—CH_2ClCF_3$, $—CHBr_2$, $—CF_3$, $—CH_2F$, $—CHF_2$, and $—CH_2CF_3$. The term "fluoroalkyl" refers to an alkyl group that may have any number of hydrogens available on the group replaced with a fluorine atom. Representative fluoroalkyl groups include but are not limited to: $—(CH_2F$, $—CH_2FCF_3$, $—CHF_2$ and $—CF_3$. The term "haloalkoxy" refers to an alkoxy group that may have any number of hydrogen atoms available on the alkyl group replaced with a halogen atom. Representative haloalkoxy groups include but are not limited to: $—OCH_2Cl$, $—OCH_2ClCF_3$, $—OCHBr_2$, $—OCHF_2$ or $—OCF_3$. The term "fluoroalkoxy" refers to an alkoxy group that may have any number of hydrogens available on the group replaced with a fluorine atom, Representative fluoroalkoxy groups include but are not limited to: $—OCH_2F$, $—OCH_2FCF_3$, $—OCHF_2$ or $—OCF_3$.

The term "heteroatom" as used herein means an atom of any element other than carbon or hydrogen. Preferred heteroatoms are nitrogen, oxygen, sulfur, phosphorus and silicon. A heteroatom may be present in any oxidation state (e.g., any oxidized form of nitrogen, sulfur, phosphorus or silicon) and any charged state (e.g., the quaternized form of any basic nitrogen), and includes a substitutable nitrogen of a heterocyclic ring, for example N (as in 3,4-dihydro-2H-pyrrolyl), NH (as in pyrrolidinyl) or $NR^+$ (as in N-substituted pyrrolidinyl).

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent. Examples of heteroaryl groups include pyridyl, furyl or furanyl, imidazolyl, benzimidazolyl, pyrimidinyl, thiophenyl or thienyl, quinolinyl, indolyl, thiazolyl, oxazolyl and the like. The term "heteroarylalkyl" or the term "heteroaralkyl" refers to an alkyl substituted with a heteroaryl. The term "heteroarylalkenyl" refers to an alkenyl substituted with a heteroaryl. The term "heteroarylalkynyl" refers to an alkynyl substituted with a heteroaryl. The term "heteroarylalkoxy" refers to an alkoxy substituted with heteroaryl.

The term "heteroaryl" refers to a group having 5 to 14 ring atoms, preferably 5, 6, 9, or 10 ring atoms; having 6, 10, or 14 π electrons shared in a cyclic array; and having, in addition to carbon atoms, from one to five heteroatoms. A heteroaryl group may be mono-, bi-, tri-, or polycyclic, preferably mono-, bi-, or tricyclic, more preferably mono- or bicyclic. When a heteroaryl is substituted by a hydroxy group, it also includes its corresponding tautomer. The term "heteroaryl," as used herein, also includes groups in which a heteroaromatic ring is fused to one or more aryl rings. Nonlimiting examples of heteroaryl groups include thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, pteridinyl, indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. The term "heteroaryl" may be used interchangeably with the terms "heteroaryl ring", "heteroaryl group," or "heteroaromatic," any of which terms include rings that are optionally substituted. A ring nitrogen atom of a heteroaryl may be oxidized to form the corresponding N-oxide compound, A nonlimiting example of such a heteroaryl having an oxidized ring nitrogen atom is N-oxopyridyl.

The term "heteroarylalkyl" or "heteroaralkyl" refers to an alkyl group substituted by a heteroaryl. Heteroaralkyl includes groups in which more than one hydrogen atom has been replaced by a heteroaryl group.

As used herein, the terms "heterocycle," "heterocyclyl" and "heterocyclic ring" are used interchangeably and refer to a stable 3- to 8-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2/y-pyrrolyl), NH (as in pyrrolidinyl), or $NR^+$ (as in N-substituted pyrrolidinyl). A heterocyclic ring can be attached to its pendant group at any heteroatom or carbon atom that results in a stable structure and any of the ring atoms can be optionally substituted.

Examples of such saturated or partially unsaturated heterocyclic radicals include, without limitation, tetrahydrofuranyl, tetrahydropyranyl, tetrahydrothienyl, piperidinyl, decahydroquinolinyl, oxazolidinyl, piperazinyl, dioxanyl, dioxolanyl, diazepinyl, oxazepinyl, thiazepinyl, morpholinyl, and thiomorpholinyl. A heterocyclyl group may be mono-, bi-, tri-, or polycyclic, preferably mono-, bi-, or tricyclic, more preferably mono- or bicyclic. Additionally, a heterocyclic ring also includes groups in which the heterocyclyl ring is fused to one or more aryl, heteroaryl or cyclyl rings. A ring nitrogen atom of a heterocyclic ring also may be oxidized to form the corresponding N-hydroxy compound.

The term "heterocyclylalkyl" refers to an alkyl group substituted by a heterocyclyl. Heterocyclylalkyl includes groups in which more than one hydrogen atom has been replaced by a heterocyclyl group.

The terms "hetaralkyl" and "heteroaralkyl", as used herein, refers to an alkyl group substituted with a heteroaryl group. Exemplary heteroaralkyl groups include but are not limited to methylpyridyl or methylpyrimidyl.

The term "heterocyclyl" or "heterocyclylalkyl" refers to a nonaromatic 5-8 membered monocyclic, 5-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Examples of heterocyclyl groups include piperazinyl, pyrrolidinyl, dioxanyl, morpholinyl, tetrahydrofuranyl, and include both bridged and fused ring systems. The term "heterocyclylalkyl" refers to an alkyl substituted with a heterocyclyl.

The term "heterocyclylalkyl", as used herein, refers to an alkyl group substituted with a heterocycle group.

The term "heteroalkyl," as used herein, refers to a saturate or unsaturated, straight or branched chain aliphatic group, wherein one or more of the carbon atoms in the chain are independently replaced by a heteroatom. Exemplary hetero atoms include O, S, and N.

In the case of aralkyl, heteroaralkyl, cyclylalkyl, heterocyclylalkyl etc., groups described as optionally substituted, it is intended that either or both aryl, heteroaryl, cyclyl, heterocyclyl and alkyl moieties may be independently optionally substituted or unsubstituted.

The term "hydroxyalkyl" refers to an alkyl in which one or more hydrogen atoms are replaced by a hydroxy group.

The term "oxo" refers to an oxygen atom (=O), which forms a carbonyl when attached to carbon, an N-oxide when attached to nitrogen, and a sulfoxide or sulfone when attached to sulfur.

The term "thioalkyl" as used herein refers to an —S(alkyl) group, where the point of attachment is through the sulfur atom and the alkyl group is as defined above.

The term "thiono" or "thioxo" refers to a sulfur atom (=S), which forms a thioketone when attached to carbon.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms.

The term "substituent" refers to a group "substituted" on a moiety described herein. Any atom on any substituent can be substituted. Substituents can include any substituents described herein. Exemplary substituents include, without limitation, alkyl (e.g., C1, C2, C3, C4, C5, C6, C7, C8, C9, C10, C11, C12 straight or branched chain alkyl), cycloalkyl, haloalkyl (e.g., perfluoroalkyl such as $CF_3$), aryl, heteroaryl, aralkyl, heteroaralkyl, heterocyclyl, alkenyl, alkynyl, cycloalkenyl, heterocycloalkenyl, alkoxy, haloalkoxy (e.g., perfluoroalkoxy such as $OCF_3$), halo, hydroxy, carboxy, carboxylate, cyano, nitro, amino, alkylamino, $SO_3H$, sulfate, phosphate, methylenedioxy (—O—$CH_2$—O— wherein oxygens are attached to vicinal atoms), ethylenedioxy, oxo, thioxo (e.g., C=S), imino (alkyl, aryl, aralkyl), $S(O)_n$ alkyl (where n is 0-2), $S(O)_n$ aryl (where n is 0-2), $S(O)_n$ heteroaryl (where n is 0-2), $S(O)_n$ heterocyclyl (where n is 0-2), amine (mono-, di-, alkyl, cycloalkyl, aralkyl, heteroaralkyl, aryl, heteroaryl, and combinations thereof), ester (alkyl, aralkyl, heteroaralkyl, aryl, heteroaryl), amide (mono-, di-, alkyl, aralkyl, heteroaralkyl, aryl, heteroaryl, and combinations thereof), sulfonamide (mono-, di-, alkyl, aralkyl, heteroaralkyl, and combinations thereof). In one aspect, the substituents on a group are independently any one single, or any subset of the aforementioned substituents. In another aspect, a substituent may itself be substituted with any one of the above substituents.

As used herein, the phrase "optionally substituted" is used interchangeably with the phrase "substituted or unsubstituted." In general, the term "substituted", whether preceded by the term "optionally" or not, means that a hydrogen radical of the designated moiety is replaced with the radical of a specified substituent, provided that the substitution results in a stable or chemically feasible compound. The term "substitutable", when used in reference to a designated atom, means that attached to the atom is a hydrogen radical, which hydrogen atom can be replaced with the radical of a suitable substituent. Unless otherwise indicated, an "optionally substituted" group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

As used herein, the term "optionally substituted" means substituted or unsubstituted.

As used herein, the term "partially unsaturated" refers to a moiety that includes at least one double or triple bond between atoms. The term "partially unsaturated" encompasses rings, e.g., having one or more sites of unsaturation, but that are not completely unsaturated so as to be aryl or heteroaryl.

The term "chiral" refers to molecules which have the property of non-superimposability of the mirror image partner, while the term "achiral" refers to molecules which are superimposable on their mirror image partner. With respect to the nomenclature of a chiral center, terms "R" and "S" configuration are as defined by the IUPAC Recommendations. The term "enantiomers" refers to two stereoisomers of a compound which are non-superimposable mirror images of one another. An equimolar mixture of two enantiomers is called a "racemic mixture" or a "racemate." The term "isomers" or "stereoisomers" refers to compounds which have identical chemical constitution, but differ with regard to the arrangement of the atoms or groups in space. For example, isomers include cis- and trans-isomers, E- and Z-isomers, R- and S-enantiomers, diastereomers, (D)-isomers, (L)-isomers, racemic mixtures thereof, and other mixtures thereof. The term "diastereomers" refers to stereoisomers with two or more centers of dissymmetry and whose molecules are not mirror images of one another.

The term "administration" or "administering" includes routes of introducing the compounds, or a composition thereof, of the invention to a subject to perform their intended function. Examples of routes of administration that may be used include injection (subcutaneous, intravenous, parenterally, intraperitoneally, intrathecal), oral, inhalation, rectal and transdermal. The pharmaceutical compositions may be given by forms suitable for each administration route. For example, these compositions are administered in tablets or capsule form, by injection, inhalation, eye lotion, ointment, suppository, etc. administration by injection, infusion or inhalation; topical by lotion or ointment; and rectal by suppositories. Oral administration is preferred. The injection can be bolus or can be continuous infusion. Depending on the route of administration, a compound described herein can be coated with or disposed in a selected material to protect it from natural conditions which may detrimentally affect its ability to perform its intended function. A compound or composition described herein can be administered alone, or in conjunction with either another agent as described above or with a pharmaceutically-acceptable carrier, or both. A compound or composition described herein can be administered prior to the administration of the other agent, simultaneously with the agent, or after the administration of the agent. Furthermore, a compound described herein can also be administered in a pro-drug form which is converted into its active metabolite, or more active metabolite in vivo.

The language "biological activities" of a compound described herein includes all activities elicited by a compound described herein in a responsive subject or cell. It includes genomic and non-genomic activities elicited by these compounds.

The terms "inhibit" and "inhibitor" as used herein means an agent that measurably slows or stops the production of STriatal-Enriched tyrosine Phosphatase (STEP), or decreases or inactivates STEP, or interferes with STEP-mediated biological pathways. Inhibitors of STEP include compounds of the invention, e.g., compounds of Formulas (I), (II), or (III). A compound can be evaluated to determine if it is an inhibitor by measuring either directly or indirectly the activity of STEP in the presence of the compound suspected to inhibit STEP. Exemplary methods of measure STEP inhibition are described in the EXAMPLES herein.

An "effective amount" or "an amount effective" refers to an amount of the compound or composition which is effective, upon single or multiple dose administrations to a subject and for periods of time necessary, in treating a cell, or curing, alleviating, relieving or improving a symptom of a disorder, e.g., a disorder described herein. An effective amount of a compound described herein may vary according to factors such as the disease state, age, and weight of the subject, and the ability of a compound described herein to elicit a desired response in the subject. Dosage regimens may be adjusted to provide the optimum therapeutic response. An effective amount is also one in which any toxic or detrimental effects (e.g., side effects) of a compound described herein are outweighed by the therapeutically beneficial effects. The term "effective amount" includes an amount effective, at dosages and for periods of time necessary, to achieve the desired result, e.g., modulate or regulate protein tyrosine phosphatases, e.g., STEP, in a subject and/or treat a disorder described herein such as a protein tyrosine phosphatase related disorder. Exemplary disorders include those related to cognition, learning and n memory, neurogenesis. An effective amount may also affect neuronal plasticity, pain perception, mood and anxiety, and neuroendocrine regulation.

An effective amount of a compound described herein may vary according to factors such as the disease state, age, and weight of the subject, and the ability of a compound described herein to elicit a desired response in the subject. Dosage regimens may be adjusted to provide the optimum therapeutic response. An effective amount is also one in which any toxic or detrimental effects (e.g., side effects) of a compound described herein are outweighed by the therapeutically beneficial effects.

A therapeutically effective amount of a compound described herein (i.e., an effective dosage) may range from about 0.001 to 50 mg/kg body weight, preferably about 0.01 to 40 mg/kg body weight, more preferably about 0.1 to 35 mg/kg body weight, still more preferably about 1 to 30 mg/kg, and even more preferably about 10 to 30 mg/kg. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a compound described herein can include a single treatment or, preferably, can include a series of treatments. In one example, a subject is treated with a compound described herein in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of a compound described herein used for treatment may increase or decrease over the course of a particular treatment.

As used herein, an amount of a compound effective to prevent a disorder, or "a prophylactically effective amount" of the compound refers to an amount effective, upon single- or multiple-dose administration to the subject, in preventing or delaying the occurrence of the onset or recurrence of a disorder or a symptom of the disorder.

The language "improved biological properties" refers to any activity inherent in a compound described herein that enhances its effectiveness in vivo. In a preferred embodiment, this term refers to any qualitative or quantitative improved therapeutic property of a compound described herein, such as reduced off-target effects.

The term "modulate" refers to an increase or decrease, e.g., in the activity of an enzyme in response to exposure to a compound or composition described herein, e.g., the activation or inhibition of STEP, in at least a sub-population of cells in a subject such that a desired end result is achieved (e.g., a therapeutic result). In some embodiments, a compound as described herein inhibits a target described herein, e.g., STEP. In some embodiments, a compound as described herein is activates a target described herein, e.g., STEP.

As used herein, the term "subject" is intended to include human and non-human animals. Exemplary human subjects include a human patient having a disorder, e.g., a disorder described herein, or a normal subject. The term "non-human animals" includes all vertebrates, e.g., non-mammals (such as chickens, amphibians, reptiles) and mammals, such as non-human primates, domesticated and/or agriculturally useful animals, e.g., sheep, dog, cat, cow, pig, etc.

As used herein, the term "treat" or "treating" is defined as applying or administering a compound or composition, alone or in combination with a second compound or composition, to a subject, e.g., a patient, or applying or administering the compound or composition to an isolated tissue or cell, e.g., cell line, from a subject, e.g., a patient, who has a disorder (e.g., a disorder as described herein), a symptom of a disorder, or a predisposition toward a disorder, with the purpose to cure, heal, alleviate, relieve, alter, remedy, ameliorate, improve or affect the disorder, one or more symptoms of the disorder or the predisposition toward the disorder (e.g., to prevent at least one symptom of the disorder or to delay onset of at least one symptom of the disorder).

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The term "prodrug" or "pro-drug" includes compounds with moieties that can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", *J. Pharm. Sci.* 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionic acid esters and acyl esters. Prodrugs which are converted to active forms through other mechanisms in vivo are also included.

The language "a prophylactically effective amount" of a compound refers to an amount of a compound described herein any formula herein or otherwise described herein which is effective, upon single or multiple dose administration to the patient, in preventing or treating a disease or condition.

The language "reduced off-target effects" is intended to include a reduction in any undesired side effect elicited by a compound described herein when administered in vivo. In some embodiments, a compound described herein has little to no cardio and/or pulmonary toxicity (e.g., when administered to a subject). In some embodiments, a compound described herein has little to no hallucinogenic activity (e.g., when administered to a subject).

The term "selective" means a greater activity against a first target. In some embodiments a compound has a selectivity of at least 1.25-fold, at least 1.5 fold, at least 2-fold, at least 3-fold, at least 4-fold, at least 5-fold, at least 6-fold, at least 10-fold or at least 100-fold greater towards a first target relative to a second target. In some embodiments, a compound described herein, e.g., a compound of Formulas (I), (II), or (III) is selective toward STEP relative to one or more other protein tyrosine phosphatases.

The term "subject" includes organisms which are capable of suffering from a serotonin-receptor-related disorder or who could otherwise benefit from the administration of a compound described herein of the invention, such as human and non-human animals. Preferred humans include human patients suffering from or prone to suffering from a serotonin-related disorder or associated state, as described herein. The term "non-human animals" of the invention includes all vertebrates, e.g., mammals, e.g., rodents, e.g., mice, and non-mammals, such as non-human primates, e.g., sheep, dog, cow, chickens, amphibians, reptiles, etc.

The phrases "systemic administration," "administered systemically", "peripheral administration" and "administered peripherally" as used herein mean the administration of a compound described herein(s), drug or other material, such that it enters the patient's system and, thus, is subject to metabolism and other like processes, for example, subcutaneous administration.

Compounds

The compounds described herein can be used for a variety of purposes, e.g., therapeutic purposes. Many of the compounds modulate STEP activity and can be used, for example to inhibit STEP, e.g., in a subject.

Exemplary compounds include a compound of formula (I):

(I)

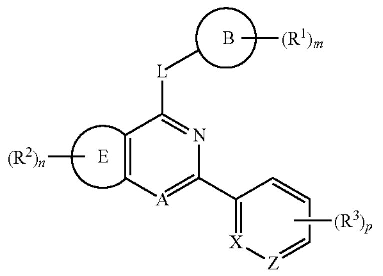

wherein A, B, E, L, X, Z, $R^1$, $R^2$, $R^3$, m, n and p are as defined above in the section relating to compound of Formula (I). In preferred embodiments, L is NH, B is aryl (e.g., phenyl) that may be optionally substituted, E is aryl (e.g., phenyl), A is N, X is CH and Z is N.

Exemplary compounds include a compound of formula (II):

(II)

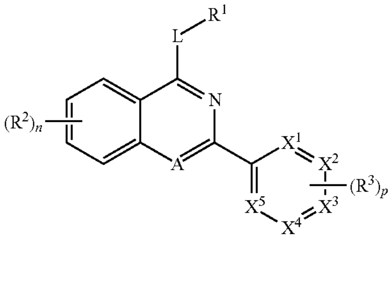

wherein A, L, $X^1$, $X^2$, $X^3$, $X^4$, $X^5$, $R^1$, $R^2$, $R^3$, n and p are as defined above in the section relating to compound of Formula (II).

Exemplary compounds include a compound of formula (III):

(III)

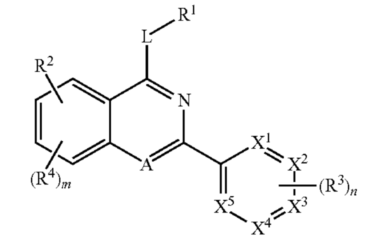

wherein A, L, $X^1$, $X^2$, $X^3$, $X^4$, $X^5$, $R^1$, $R^2$, $R^3$, $R^4$, m and n are as defined above in the section relating to compound of Formula (III).

Exemplary compounds include a compound of formula (IV):

(IV)

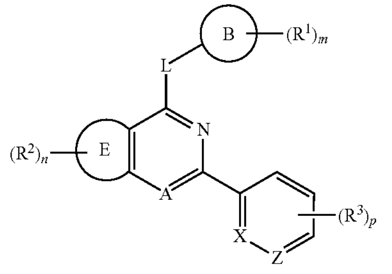

wherein A, B, E, L, X, Z, $R^1$, $R^2$, $R^3$, m, n and p are as defined above in the section relating to compound of Formula (IV). In preferred embodiments, L is NH, B is aryl (e.g., phenyl) that may be optionally substituted, E is aryl (e.g., phenyl), A is N, X is CH and Z is N.

Exemplary compounds include a compound of formula (V):

(V)

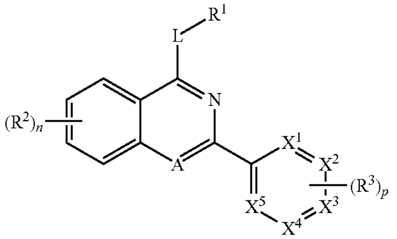

wherein A, L, $X^1$, $X^2$, $X^3$, $X^4$, $X^5$, $R^1$, $R^2$, $R^3$, n and p are as defined above in the section relating to compound of Formula (V).

Exemplary compounds include a compound of formula (VI):

(VI)

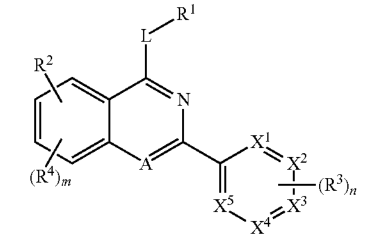

wherein A, L, $X^1$, $X^2$, $X^3$, $X^4$, $R^1$, $R^2$, $R^3$, $R^4$, m, and n are as defined above in the section relating to compound of Formula (VI).

The present invention includes compounds that differ only in the presence of one or more isotopically enriched atoms. For example, compounds having the present structures except for the replacement of hydrogen by deuterium or tritium, the replacement of a carbon by a $^{13}C$- or $^{14}C$-enriched carbon, or the replacement of a fluorine by a $^{19}F$-enriched fluorine are within the scope of this invention. Such compounds are useful, for example, as analytical tools or probes in biological assays, or as bioactive agents.

In the compounds of the present invention, any atom not specifically designated as a particular isotope is meant to represent any stable isotope of that atom unless otherwise stated (e.g., hydrogen, $^2H$ or deuterium and $^3H$ or tritium). The formulas described herein may or may not indicate whether atoms at certain positions are isotopically enriched. When a structural formula is silent with respect to whether a particular position is isotopically enriched, it is to be understood that the isotopes at that particular position are present in natural abundance or, that the particular position is isotopically enriched with one or more naturally occurring stable isotopes. For example, the formula $—CH_2—$ represents the following possible structures: $—CH_2—$, —CHD- or $—CD_2$-.

The variable "D" is defined as deuterium.

The terms "compound" or "compounds," when referring to a compound of this invention or a compound described herein, refers to a collection of molecules having an identical chemical structure, except that there may be isotopic variation among the constituent atoms of the molecules. Thus, it will be clear to those of skill in the art that a compound represented by a particular chemical structure containing indicated hydrogen atoms will contain lesser amounts of isotopologues having deuterium atoms at one or more of the designated hydrogen positions in that structure. Alternatively, a compound represented by a particular chemical structure containing indicated deuterium atoms will contain lesser amounts of isotopologues having hydrogen atoms at one or more of the designated deuterium positions in that structure. The relative amount of such isotopologues in a compound of this invention will depend on a number of factors including isotopic purity of deuterated reagents used to make the compound and the efficiency of incorporation of deuterium in the various synthetic steps used to prepare the compound. The relative amount of such isotopologues in total will be less than 55% of the compound. In other embodiments, the relative amount of such isotopologues in total will be less than 50%, less than 45%, less than 40%, less than 35%, less than 35%, less than 15%, less than 10%, less than 5%, less than 1% or less than 0.5% of the compound.

The term "isotopologue" refers to a species that differs from a specific compound of this invention only in the isotopic composition thereof. Isotopologues can differ in the level of isotopic enrichment at one or more positions and/or in the position(s) of isotopic enrichment.

The compounds of this invention may contain one or more asymmetric centers and thus occur as racemates and racemic mixtures, single enantiomers, individual diastereomers and diastereomeric mixtures. Described herein are enantiomerically enriched compounds (e.g., a compound resolved to an enantiomeric excess of 60%, 70%, 80%, 85%, 90%, 95%, 99% or greater). All such isomeric forms of these compounds are expressly included in the present invention. The compounds of this invention may also contain linkages (e.g., carbon-carbon bonds) or substituents that can restrict bond rotation, e.g. restriction resulting from the presence of a ring or double bond. Accordingly, all cis/trans and E/Z isomers are expressly included in the present invention. The compounds of this invention may also be represented in multiple tautomeric forms, in such instances, the invention expressly includes all tautomeric forms of the compounds described herein, even though only a single tautomeric form may be represented (e.g., alkylation of a ring system may result in alkylation at multiple sites, the invention expressly includes all such reaction products). All such isomeric forms of such compounds are expressly included in the present invention. All crystal forms of the compounds described herein are expressly included in the present invention.

Naturally occurring or synthetic isomers can be separated in several ways known in the art. Methods for separating a racemic mixture of two enantiomers include chromatography using a chiral stationary phase (see, e.g., "Chiral Liquid Chromatography," W. J. Lough, Ed. Chapman and Hall, New York (1989)). Enantiomers can also be separated by classical resolution techniques. For example, formation of diastereomeric salts and fractional crystallization can be used to separate enantiomers. For the separation of enantiomers of carboxylic acids, the diastereomeric salts can be formed by addition of enantiomerically pure chiral bases such as brucine, quinine, ephedrine, strychnine, and the like. Alternatively, diastereomeric esters can be formed with enantiomerically pure chiral alcohols such as menthol, followed by separation of the diastereomeric esters and hydrolysis to yield the free, enantiomerically enriched carboxylic acid. For separation of the optical isomers of amino compounds, addition of chiral carboxylic or sulfonic acids, such as camphorsulfonic acid, tartaric acid, mandelic acid, or lactic acid can result in formation of the diastereomeric salts. For example a compound can be resolved to an enantiomeric excess (e.g., 60%, 70%, 80%, 85%, 90%, 95%, 99% or greater) via formation of diasteromeric salts, e.g. with a chiral base, e.g., (+) or (−) α-methylbenzylamine, or via high performance liquid chromatography using a chiral column. In some embodiments a product is purified directly on a chiral column to provide enantiomerically enriched compound.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic administration to a subject).

Compounds of formulas (I), (II), (Iii), (IV), (V), and (VI) are described herein, for example as provided in the summary above. Exemplary compounds are shown in Tables 1-30 in the Examples section.

Synthetic Methods

A compound described herein may be prepared via a variety of synthetic methods. Representative syntheses are shown in the Examples section.

As can be appreciated by the skilled artisan, further methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis,* 2d Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

Additionally, the compounds disclosed herein can be prepared on a solid support. The term "solid support" refers a material to which a compound is attached to facilitate identification, isolation, purification, or chemical reaction selectivity of the compound. Such materials are known in the art and include, for example, beads, pellets, disks, fibers, gels, or particles such as cellulose beads, pore-glass beads, silica gels, polystyrene beads optionally cross-linked with divinylbenzene and optionally grafted with polyethylene glycol, polyacrylamide beads, latex beads, dimethylacrylamide beads optionally cross-linked with N,N'-bis-acryloyl ethylene diamine, glass particles coated with hydrophobic polymer, and material having a rigid or semi-rigid surface. The solid supports optionally have functional groups such as amino, hydroxy, carboxy, or halo groups, (see, Obrecht, D. and Villalgrodo, J. M., *Solid-Supported Combinatorial and Parallel Synthesis of Small-Molecular-Weight Compound Libraries*, Pergamon-Elsevier Science Limited (1998)), and include those useful in techniques such as the "split and pool" or "parallel" synthesis techniques, solid-phase and solution-phase techniques, and encoding techniques (see, for example, Czarnik, A. W., *Curr. Opin. Chem. Bio*., (1997) 1, 60).

A compound described herein may be modified by appending appropriate functionalities to enhance selective biological properties. Such modifications are known in the art and include those which increase biological penetration into a given biological compartment (e.g., brain, blood, lymphatic system, central nervous system), increase oral availability, increase solubility to allow administration by injection, alter metabolism and alter rate of excretion.

Included herein are pharmaceutically acceptable derivatives or prodrugs of the compounds described herein. A "pharmaceutically acceptable derivative or prodrug" means any pharmaceutically acceptable salt, ester, salt of an ester, or other derivative of a compound of this invention (for example an imidate ester of an amide), which, upon administration to a recipient, is capable of providing (directly or indirectly) a compound described herein. Particularly favored derivatives and prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or lymphatic system) relative to the parent species. In an exemplary embodiment, the prodrug is a derivative including a group that enhances aqueous solubility or active transport through the gut membrane is appended to the structure of formulae described herein. In another exemplary embodiment, the prodrug is suitable for treatment or prevention of those diseases and conditions that require the drug molecule to cross the blood brain barrier. In a preferred embodiment, the prodrug enters the brain, where it is converted into the active form of the drug molecule.

Pharmaceutically acceptable salts of the compounds of this invention include those derived from pharmaceutically acceptable inorganic and organic acids and bases. Examples of suitable acid salts include acetate, adipate, benzoate, benzenesulfonate, butyrate, citrate, digluconate, dodecylsulfate, formate, fumarate, glycolate, hemisulfate, heptanoate, hexanoate, hydrochloride, hydrobromide, hydroiodide, lactate, maleate, malonate, methanesulfonate, 2-naphthalenesulfonate, nicotinate, nitrate, palmoate, phosphate, picrate, pivalate, propionate, salicylate, succinate, sulfate, tartrate, tosylate and undecanoate. Salts derived from appropriate bases include alkali metal (e.g., sodium), alkaline earth metal (e.g., magnesium), ammonium and N-$(alkyl)_4^+$ salts. This invention also envisions the quaternization of any basic nitrogen-containing groups of the compounds disclosed herein. Water or oil-soluble or dispersible products may be obtained by such quaternization.

Evaluating Compounds

A variety of methods can be used to evaluate a compound for ability to modulate STEP activity. Evaluation methods include in vitro assays (e.g., enzyme-based assays), in vitro cell-based signaling assays, and in vivo methods (e.g., testing in animal models). The evaluation methods can evaluate binding activity, phosphatase activity, or an activity downstream of STEP, such as the activity of ERK.

For example, a compound described herein may be evaluated using a fluorescence-based phosphatase assay. A phosphate-containing reagent may be used in the assay which, upon dephosphorylation by a phosphatase, generates a fluorescent product that may be detected using a fluorometer or fluorescence plate reader. Data may be expressed as percentage (%) inhibition of enzyme activity. For compounds showing enzymatic activation, data may be represented as percentage of inhibition but with negative values.

Compositions and Routes of Administration

The invention also provides a pharmaceutical composition, comprising an effective amount of a compound described herein (e.g., a compound capable of treating or preventing a condition as described herein, e.g., a compound of any formula herein or otherwise described herein) and a pharmaceutically acceptable carrier.

The compositions delineated herein include the compounds delineated herein (e.g., a compound described herein), as well as additional therapeutic agents if present, in amounts effective for achieving a modulation of disease or disease symptoms, including those described herein.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compounds of the formulae described herein.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, emulsions and aqueous suspensions, dispersions and solutions. In the case of tablets for oral use, carriers which are commonly used include lactose and corn starch, Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

When the compositions of this invention comprise a combination of a compound of the formulae described herein and one or more additional therapeutic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

The compounds described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.5 to about 100 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

Methods of Treatment

The compounds and compositions described herein can be administered to cells in culture, e.g. in vitro or ex vivo, or to a subject, e.g., in vivo, to treat, prevent, and/or diagnose a variety of disorders, including those described herein below.

The compounds and compositions described herein can be administered to a subject, for example using a method described herein, who is suffering from a disorder described herein, e.g., a disorder that would benefit from the modulation of STEP (e.g., activating or inhibiting STEP). The compounds and compositions described herein can be administered to a subject, for example using a method described herein, who is at risk for a disorder described herein, e.g., a disorder that would benefit from the modulation of STEP (e.g., activating or inhibiting STEP).

Inhibitors of STEP may increase phosphorylation of an NMDA-R. Thus, in some embodiments, a compound described herein, e.g., a compound that inhibits STEP, may be useful for treating a disorder in which increasing phosphorylation of an NMDA-R would be beneficial.

Inhibitors of STEP may activate an ERK1 or ERK2 kinase, for example, in the CNS. Thus, in some embodiments, a compound described herein, e.g., a compound that inhibits STEP, may be useful for treating a disorder in which activate an ERK1 or ERK2 kinase would be beneficial.

Compounds described herein may be useful in treating a variety of disorders, including disorders of the CNS. Exemplary disorders include schizophrenia, schizo-affective disorders, major depression, bipolar disorder, cognitive deficit, mild cognitive impairment (MCI), Alzheimer's disease (AD), attention-deficit/hyperactivity disorder (ADHD), dementia, generalized anxiety disorders, panic disorders, obsessive-compulsive disorders, phobias, post-traumatic stress syndrome, anorexia nervosa, drug addiction, ischemic stroke, head trauma or brain injury, Huntington's disease, Parkinson's disease, spinocerebellar degeneration, motor neuron diseases, epilepsy, neuropathic pain, chronic pain, neuropathies, autism and autistic disorders.

Compounds described herein may be useful for treating or preventing central nervous system disorders selected from the group consisting of schizophrenia; refractory, intractable or chronic schizophrenia; emotional disturbance; psychotic disorder; mood disorder; bipolar I type disorder; bipolar II type disorder; depression; endogenous depression; major depression; melancholy and refractory depression; dysthymic disorder; cyclothymic disorder; panic attack; panic disorder; agoraphobia; social phobia; obsessive-compulsive disorder; post-traumatic stress disorder; generalized anxiety disorder; acute stress disorder; hysteria; somatization disorder; conversion disorder; pain disorder; hypochondriasis; factitious disorder; dissociative disorder; sexual dysfunction; sexual desire disorder; sexual arousal disorder; erectile dysfunction; anorexia nervosa; bulimia nervosa; sleep disorder; adjustment disorder; alcohol abuse; alcohol intoxication; drug addiction; stimulant intoxication; narcotism; anhedonia; iatrogenic anhedonia; anhedonia of a psychic or mental cause; anhedonia associated with depression; anhedonia associated with schizophrenia; delirium; cognitive impairment; cognitive impairment associated with Alzheimer's disease, Parkinson's disease and other neurodegenerative diseases; cognitive impairment caused by Alzheimer's disease; Parkinson's disease and associated neurodegenerative diseases; cognitive impairment of schizophrenia; cognitive impairment caused by refractory, intractable or chronic schizophrenia; vomiting; motion sickness; obesity; migraine; pain (ache); mental retardation; autism disorder (autism); Tourette's disorder; tic disorder; attention-deficit/hyperactivity disorder; conduct disorder; and Down's syndrome.

Compounds described herein may be useful for treating or preventing disorders selected from schizophrenia, schizoaffective disorder, bipolar disorder, manic-depressive disorder, psychosis, mood and anxiety disorders, mania, drug or substance addiction, cognition disorders, learning disabilities, learning and memory disorders, aging and neurologic disorders associated with or linked with cognitive impairments; mild cognitive impairments (MCI), Alzheimer's disease, Alzheimer-related cognition disorders, Huntington's disease, Parkinson's disease, CADASIL syndrome (cerebral autosomal dominant arteriopathy with subcortical infarcts and leukoencephalopathy), amnesia, Wernicke-Korsakoff syndrome, Korsakoff syndrome, mild traumatic head injury (MBTI), traumatic head injury (TBI), fragile X syndrome, stroke, attention-deficit and hyperactivity disorder (ADHD), obsessive compulsive disorder (OCD), post-traumatic stress disorder (PTSD), loss of concentration, autism, cerebral palsy, encephalopathy, and narcolepsy. The disorder may affect learning and memory, neurogenesis, neuronal plasticity, pain perception, mood and anxiety, or neuroendocrine regulation. The disorder may be a cognitive deficit disorder. The disorder may involve pain perception or neuroendocrine regulation.

Schizophrenia

In some embodiments, a compound or composition described herein can be used in the treatment of schizophrenia. Schizophrenia is a psychiatric diagnosis that describes a mental disorder characterized by abnormalities in the perception or expression of reality. Distortions in perception may affect all five senses, including sight, hearing, taste, smell and touch, but most commonly manifests as auditory hallucinations, paranoid or bizarre delusions, or disorganized speech and thinking with significant social or occupational dysfunction. Onset of symptoms typically occurs in young adulthood, with approximately 0.4-0.6% of the population affected. Diagnosis is based on the patient's self-reported experiences and observed behavior.

The disorder is thought to mainly affect cognition, but it also usually contributes to chronic problems with behavior and emotion. People with schizophrenia are likely to have additional (comorbid) conditions, including major depression and anxiety disorders. Social problems, such as long-term unemployment, poverty and homelessness, are common. Furthermore, the average life expectancy of people with the disorder is 10 to 12 years less than those without, due to increased physical health problems and a higher suicide rate.

The Diagnostic and Statistical Manual of Mental Disorders (DSM) contains five sub-classifications of schizophrenia. These include Paranoid type (where delusions and hallucinations are present but thought disorder, disorganized behavior, and affective flattening are absent); Disorganized type (also known as hebephrenic schizophrenia, where thought disorder and flat affect are present together); Catatonic type (the subject may be almost immobile or exhibit agitated, purposeless movement; symptoms can include catatonic stupor and waxy flexibility); Undifferentiated type (psychotic symptoms are present but the criteria for paranoid, disorganized, or catatonic types have not been met); and Residual type (where positive symptoms are present at a low intensity only).

The International Statistical Classification of Diseases and Related Health Problems (10th Revision) defines two additional subtypes. These include Post-schizophrenic depression (a depressive episode arising in the aftermath of a schizophrenic illness where some low-level schizophrenic symptoms may still be present); and Simple schizophrenia (insidious and progressive development of prominent negative symptoms with no history of psychotic episodes.)

An agent for the treatment of schizophrenia may improve so-called positive symptoms in the acute period of schizophrenia such as hallucinations, delusions, excitations and the like. An agent for treating schizophrenia may also improve so-called negative symptoms that are observed in the chronic period of schizophrenia such as apathy, emotional depression, hyposychosis and the like.

Schizoaffective Disorder

Schizoaffective disorder is a psychiatric diagnosis that describes a mental disorder characterized by recurring episodes of elevated or depressed mood, or simultaneously elevated and depressed mood that alternate or occur together with distortions in perception. The perceptual distortion component of the disorder, called psychosis, may affect all five senses, including sight, hearing, taste, smell and touch, but most commonly manifest as auditory hallucinations, paranoid or bizarre delusions, or disorganized speech and thinking with significant social and occupational dysfunction. The elevated, depressed or simultaneously elevated and depressed mood episode components of the disorder, called mood disorder, are broadly recognized as depressive and bipolar types of the illness; the division is based on whether the individual has ever had a manic, hypomanic or mixed episode. Onset of symptoms usually begins in early adulthood and is rarely diagnosed in childhood (prior to age 13). The lifetime prevalence of the disorder is uncertain (due to studies using varying diagnostic criteria), although it is generally agreed to be less than 1 percent, and possibly in the range of 0.5 to 0.8 percent. Diagnosis is based on the patient's self-reported experiences and observed behavior. No laboratory test for schizoaffective disorder currently exists. As a group, people with schizoaffective disorder have a more favorable prognosis than people with schizophrenia, but a worse prognosis than those with mood disorders.

The disorder is thought to mainly affect cognition and emotion, but it also usually contributes to ongoing problems with behavior and motivation. People with schizoaffective disorder are likely to have additional (comorbid) conditions, including anxiety disorders and substance abuse. Social problems, such as long-term unemployment, poverty and homelessness, are common. Furthermore, the average life expectancy of people with the disorder is shorter than those without the disorder, due to increased physical health problems and a higher suicide rate.

Cognitive Deficit

Treatment using a compound or composition described herein may improve a cognitive deficit associated with a cognition-related disorder. Cognitive deficit is an inclusive term to describe any characteristic that acts as a barrier to cognitive performance. The term may describe deficits in global intellectual performance, such as mental retardation, it may describe specific deficits in cognitive abilities (learning disorders, dyslexia), or it may describe drug-induced cognitive/memory impairment, such as that seen with alcohol and the benzodiazepines. Cognitive deficits may be congenital or caused by environmental factors such as brain injuries, neurological disorders, or mental illness.

Exemplary cognition-related disorders (e.g., cognitive dysfunction) include, without limitation, mild cognitive impairment (MCI), dementia, delirium, amnestic disorder, Alzheimer's disease, Parkinson's disease and Huntington's disease; memory disorders including memory deficits associated with depression, senile dementia, dementia of Alzheimer's disease; cognitive deficits or cognitive dysfunction associated with neurological conditions including, for example, Parkinson's disease (PD), Huntington's disease (HD), Alzheimer's disease, depression, schizophrenia and other psychotic disorders such as paranoia and manic-depressive illness; cognitive dysfunction in schizophrenia: disorders of attention and learning such as attention deficit disorders (e.g., attention deficit hyperactivity disorder (ADHD)) and dyslexia; cognitive dysfunction associated with developmental disorders such as Down's syndrome and Fragile X syndrome; loss of executive function: loss of learned information; vascular dementia; schizophrenia; cognitive decline; a neurodegenerative disorder; and other dementias, for example, dementia due to HIV disease, head trauma, Parkinson's disease, Huntington's disease, Pick's disease, Creutzfeldt-Jakob disease, or due to multiple etiologies. Cognition-related disorders also include, without limitation, cognitive dysfunction associated with MCI and dementias such as Lewy Body, vascular, and post stroke dementias. Cognitive dysfunction associated with surgical procedures, traumatic brain injury or stroke may also be treated in accordance with the embodiments described herein.

Major Depression

Major depression (also known as clinical depression, major depressive disorder, unipolar depression, or unipolar disorder) is a mental disorder characterized by a pervasive low mood, low self-esteem, and loss of interest or pleasure in normally enjoyable activities. Types of Major depressive disorder include, e.g., Atypical depression, Melancholic depression, Psychotic depression, Catatonic depression, Postpartum depression, and Seasonal affective disorder.

Bipolar Disorder

Bipolar disorder, also known as manic depressive disorder, manic depressive psychosis, manic depression or bipolar affective disorder, is a psychiatric diagnosis that describes a category of mood disorders defined by the presence of one or more episodes of abnormally elevated mood clinically referred to as mania or, if milder, hypomania. Individuals who experience manic episodes also commonly experience depressive episodes or symptoms, or mixed episodes in which features of both mania and depression are present at the same time. These episodes are usually separated by periods of "normal" mood, but in some individuals, depression and mania may rapidly alternate, known as rapid cycling. Extreme manic episodes can sometimes lead to psychotic symptoms such as delusions and hallucinations. The disorder has been subdivided into bipolar I, bipolar II, cyclothymia, and other types, based on the nature and severity of mood episodes experienced; the range is often described as the bipolar spectrum.

Anxiety Disorders

Anxiety disorder is a blanket term covering several different forms of abnormal and pathological fear and anxiety. Current psychiatric diagnostic criteria recognize a wide variety of anxiety disorders. Recent surveys have found that as many as 18% of Americans may be affected by one or more of them.

Generalized anxiety disorder is a common chronic disorder characterized by long-lasting anxiety that is not focused on any one object or situation. Those suffering from generalized anxiety experience non-specific persistent fear and worry and become overly concerned with everyday matters. Generalized anxiety disorder is the most common anxiety disorder to affect older adults.

In panic disorder, a person suffers from brief attacks of intense terror and apprehension, often marked by trembling, shaking, confusion, dizziness, nausea, difficulty breathing. These panic attacks, defined by the APA as fear or discomfort that abruptly arises and peaks in less than ten minutes, can last for several hours and can be triggered by stress, fear, or even exercise; although the specific cause is not always apparent. In addition to recurrent unexpected panic attacks, a diagnosis of panic disorder also requires that said attacks have chronic consequences: either worry over the attacks' potential implications, persistent fear of future attacks, or significant changes in behavior related to the attacks. Accordingly, those suffering from panic disorder experience symptoms even outside of specific panic episodes. Often, normal changes in heartbeat are noticed by a panic sufferer, leading them to think something is wrong with their heart or they are about to have another panic attack. In some cases, a heightened awareness (hypervigilance) of body functioning occurs during panic attacks, wherein any perceived physiological change is interpreted as a possible life threatening illness (i.e. extreme hypochondriasis).

Obsessive compulsive disorder is a type of anxiety disorder primarily characterized by repetitive obsessions (distressing, persistent, and intrusive thoughts or images) and compulsions (urges to perform specific acts or rituals). The OCD thought pattern may be likened to superstitions insofar as it involves a belief in a causative relationship where, in reality, one does not exist. Often the process is entirely illogical; for example, the compulsion of walking in a certain pattern may be employed to alleviate the obsession of impending harm. And in many cases, the compulsion is entirely inexplicable, simply an urge to complete a ritual triggered by nervousness. In a minority of cases, sufferers of OCD may only experience obsessions, with no overt compulsions; a much smaller number of sufferers experience only compulsions.

The single largest category of anxiety disorders is that of Phobia, which includes all cases in which fear and anxiety is triggered by a specific stimulus or situation. Sufferers typically anticipate terrifying consequences from encountering the object of their fear, which can be anything from an animal to a location to a bodily fluid.

Post-traumatic stress disorder or PTSD is an anxiety disorder which results from a traumatic experience. Post-traumatic stress can result from an extreme situation, such as combat, rape, hostage situations, or even serious accident. It can also result from long term (chronic) exposure to a severe stressor, for example soldiers who endure individual battles but cannot cope with continuous combat. Common symptoms include flashbacks, avoidant behaviors, and depression.

Combination Therapies

In some embodiments, the subject is being treated with an additional therapeutic agent. Such additional agents include atypical antipsychotics such as aripiprazole, clozapine, ziprasidone, risperidone, quetiapine, olanzapine, amisulpride, asenapine, iloperidone, melperone, paliperidone, perospirone, sertindole and sulpiride; and typical antipsychotics such as haloperidol, molindone, loxapine, thioridazine, molindone, thiothixene, pimozide, fluphenazine, trifluoperazine, mesoridazine, chlorprothixene, chlorpromazine, perphenazine, triflupromazine and zuclopenthixol.

Clinical Outcomes

In some embodiments, treatment with a compound or composition described herein, for example, using a method described herein, improves one or more clinical outcomes. For example, in some embodiments, treatment with a compound or composition described herein may improve cognitive function. Elements of cognitive function include memory, orientation, attention, reasoning, language and praxis.

In some embodiments, clinical outcomes may be assessed using known methods. One such method is the Brief Psychiatric Rating Scale (BPRS), a multi-item inventory of general psychopathology traditionally used to evaluate the effects of drug treatment in schizophrenia. The BPRS psychosis cluster (conceptual disorganization, hallucinatory behavior, suspiciousness, and unusual thought content) is considered a particularly useful subset for assessing actively psychotic schizophrenic patients.

In some embodiments, clinical outcomes may be assessed using the 7-point Clinical Global Impression (CGI) rating scale, a commonly used measure of symptom severity, treatment response and the efficacy of treatments. The CGI reflects the impression of a skilled observer, fully familiar with the manifestations of schizophrenia, about the overall clinical state of the patient.

In some embodiments, clinical outcomes may be assessed using the 30-item Positive and Negative Symptoms Scale (PANSS). The name refers to the two types of symptoms in schizophrenia, as defined by the American Psychiatric Association: positive symptoms, which refer to an excess or distortion of normal functions (e.g. hallucinations and delusions), and negative symptoms, which represent a dimunition or loss of normal functions.

In some embodiments, clinical outcomes may be assessed using the Scale for Assessing Negative Symptoms (SANS). SANS assesses five symptom complexes to obtain clinical ratings of negative symptoms in patients with schizophrenia. They are: affective blunting; alogia (impoverished thinking); avolition/apathy; anhedonia/asociality; and disturbance of attention. Assessments are conducted on a six-point scale.

The invention is further illustrated by the following examples which are intended to illustrate but not limit the scope of the invention.

EXAMPLES

Abbreviations

DCM: Dichloromethane
EA, EtOAc or AcOEt: Ethyl acetate
PE: Petroleum ether
DIPEA: Diisopropylethylamine
TEA: Triethyl amine
rt: Room temperature
$SOCl_2$: Thionyl chloride
$POCl_3$: Phosphorous oxychloride
TH: Tetrahydrofuran
NaOAc: Sodium acetate
MeOH: Methanol
i-AmOH: Isoamyl alcohol
NaH: Sodium hydride
$NaBH_3CN$: Sodium cyanoborohydride
n-BuLi: n-Butyl lithium
LHMDS: Lithium bis(trimethylsilyl)amide
LDA: Lithium diisopropylamide
i-PrOH: Isopropyl alcohol
$Na_2SO_4$: Sodium sulfate
$Mg_2SO_4$: Magnesium sulfate
MeCN: Acetonitrile
NaOH: Sodium hydroxide
EtOH: Ethanol
CuI: Copper(I) iodide $Pd(PPh_3)_2Cl_2$: trans-Dichlorobis(triphenylphosphine)palladium(II)
MsCl: Methanesulfonyl chloride
BINAM: [1,1'-Binaphthalene]-2,2'-diamine
Xphos: 2-Dicyclohexylphosphino-2',4',6'-triisopropylbiphenyl
Sphos: 2-Dicyclohexylphosphino-2',6'-dimethoxybiphenyl
DavePhos: 2-(Dicyclohexylphosphino)-2'-(N,N-dimethylamino)biphenyl
$Cs_2CO_3$: Cesium carbonate
$K_2CO_3$: Potassium carbonate
Mwave or μW or mW: Microwave
t-BuOH: tert-Butanol
$K_3PO_4$: Potassium phosphate
$Pd(APhos)_2Cl_2$:Bis(di-tert-butyl(4-dimethylaminophenyl) phosphine)dichloro palladium(II)
$Pd(PPh_3)_4$: Tetrakis(triphenylphosphine)palladium (0)
$Pd(dppf)_2Cl_2$: Dichloro[1,1'-bis(diphenylphosphino)ferrocene]palladium(II)
PdOAc: Palladium(II) acetate
$Pd_2dba_3$: Tris(dibenzylideneacetone)dipalladium (0)
Pd-118: Dichloro[1,1-bis(di-1-butylphosphino)ferrocene] palladium(II)
Xantphos: 9,9-Dimethyl-4,5-bis(diphenylphosphino)xanthene
BINAP: (±)-2,2'-Bis(diphenylphosphino)-1,1'-binaphthalene
EDCI: 1-Ethyl-3-(3-dimethylaminopropyl) carbodiimide
HOBt: Hydroxybenzotriazole
$NH_4OH$: Ammonium hydroxide
$H_2O$: Water
Pd/C: Palladium on carbon
DMF: N,N-Dimethylformamide
KOCN: Potassium cyanate
WSC-HCl or WSCDI: Water Soluble Carbodiimide hydrochloride
HATU: O-(7-Azabenzotriazol-1-yl)-N,N,N',N'-tetramethyluronium hexafluorophosphate
HBTU: O-(Benzotriazol-1-yl)-N,N,N',N'-tetramethyluronium hexafluorophosphate
Py-Brop: Bromotripyrrolidinophosphonium hexafluorophosphate
BOP: Benzotriazole-1-yl-oxy-tris-(dimethylamino)-phosphonium hexafluoro phosphate
DBU: diaza(1,3)bicyclo[5.4.0]undecene
DMSO: Dimethyl sulfoxide
LCMS: Liquid chromatography mass spectrometry
HPLC: High performance liquid chromatography
DMA: N,N-dimethylacetamide
h: hour
TLC: Thin layer chromatography
TFA: Trifluoroacetic acid
$Et_3N$: Triethylamine
DIPEA: N,N-Diisopropylethylamine
O.N: Overnight
TBSO: tert-Butyldimethylsilyloxy
DME: Dimethyl ether
NMP: 1-methyl-2-pyrrolidinone
PS-BEMP: 2-tert-Butylimino-2-diethylamino-1,3-dimethylperhydro-1,3,2-diazaphosphorine supported on Polystyrene
$PBr_3$: Phosphorus tribromide
NaOtBu: Sodium tert-butoxide
KI: Potassium iodide
$PPh_3$: Triphenylphosphine
NMM: N-Methylmorpholine
HCHO: Formaldehyde PG: Protecting group
ISCO: Teledyne ISCO purification systems
BINAM: 1,1'-binaphthyl-2,2'-diamine.

General Experimental

All exemplified target compounds are fully analyzed and characterized (TLC, LCMS, $^{1}$H-NMR) prior to submission for biological evaluation. Thin-layer chromatography was carried out on native silica 254F plates. Visualization was accomplished with ultraviolet or phosphomolybdic acid. $^{1}$H-NMR spectra were recorded on multiple NMR spectrometers, either on 400 MHz on a Avance III 1400 Ultra shield-plus TM digital Spectrometer or on 300 MHz using a Varian Mercury 300Plus Spectrometer, designated by 400 MHz or 300 MHz, respectively. $^{1}$H-NMR spectra were also recorded on a Bruker Spectrospin 300 MHz Spectrometer at 300.13 MHz in DMSO-d6 with TMS as an internal standard and will be designated as Bruker 300 Hz. NMR assignments are based on a combination of the $^{1}$H, $^{13}$C, $^{1}$HCOSY, HMBC and HMQC spectra. Coupling constants are given in hertz (Hz). Anhydrous methylene chloride, tetrahydrofuran, and dimethylformamide were obtained by distillation, and other materials are reagent grade.

LC-MS Methods are listed here:

Method A: Mobile phase: A=0.1% TFA/$H_2O$, B=0.01% TFA/MeCN; Gradient: B=5%-95% in 1.5 min; Flow rate: 2.0 mL/min; Column: sunfire-$C_{18}$, 50×4.6 mm, 3.5 um;

Method B: Mobile phase: A=10 mM $NH_4HCO_3/H_2O$, B=MeCN; Gradient: B=5%-95% in 1.5 min; Flow rate: 2.0 mL/min; Column: Xbridge-$C_{18}$, 50×4.6 mm, 3.5 um;

Method C: Mobile phase: A=10 mM ammonium formate/$H_2O$/4.9% MeCN, B=MeCN; Gradient: B=5%-100% in 2.0 min; Flow rate: 2.5 mL/min; Column: Atlantis T3 3 uM 4.6×30 mm Method D: Mobile phase: A=0.1% formic acid/$H_2O$/4.9% MeCN, B=MeCN; Gradient: B=5%-100% in 2.0 min; Flow rate: 2.5 mL/min; Column: Atlantis T3 3 uM 4.6×30 mm Method E: Mobile phase: A=0.05% TFA/$H_2O$, B=0.05% TFA/MeCN; Gradient: B=5%-100% in 3.0 min; Flow rate: 0.8 mL/min; Column: CAPCELL PAK C18 (Shiseido, UG120, 3 mM, 2.0 mm I.D.×50 mm).

Representative Conditions of PREP-HPLC are listed here:

PREP-HPLC Condition A (Basic Mobile Phase):
Instrument: Gilson 281
Mobile Phase: A=0.01% $NH_4HCO_3/H_2O$, B=MeCN
Flow Rate: 40.0 mL/min
Column: AGT Venusil XBP $C_{18}$, 10.0 um, 30 mm×100 mm PREP-HPLC Condition B (Basic Mobile Phase):
Instrument: Gilson 281
Mobile Phase: A=$NH_3$—$H_2O$, 10 mmol/L, B=MeCN
Flow Rate: 40.0 mL/min
Column: Waters X-Bridge, 5.0 um, 30 mm×150 mm PREP-HPLC Condition C (Basic Mobile Phase):
Instrument: Gilson 281
Mobile Phase: A=0.01% $NH_4HCO_3/H_2O$, B=MeCN
Flow Rate: 30.0 mL/min
Column: Shimadzu PRC-ODS, 10.0 um, 20 mm×250 mm
Gradient: B=xx %-yy % 0.0 to 8.0 min
yy %-95% 8.0 to 8.2 min
95%-95% 8.2 to 11.0 min The following table shows the relationship of representative value (xx %-yy %) of gradient and retention time on LC-MS of corresponding compound.

25%-30% 0.5-1.0 min
30%-50% 1.0-1.5 min
50%-70% 15-1.75 min
70%-90% 1.7-2.0 min

PREP-HPLC Condition D:

Instrument: Waters 600 pump, Waters 2996, Photodiode Array Detector, Waters Micromass ZQ, Gilson 215 Liquid Handler.

Mobile Phase: A=0.05% TFA/$H_2O$, B=MeCN

Flow Rate: 36.0 mL/min

Column: Shiseido CAPCELL PAK C18, UG120, 5 uM, 20 mm I.D.×50 mm

Gradient: B=5%-100% 0.0 to 4.0 min

Scheme 1: General route for the synthesis of compounds with general formula ii

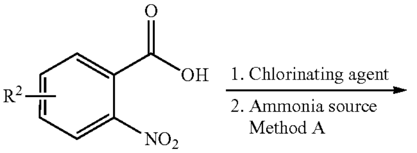

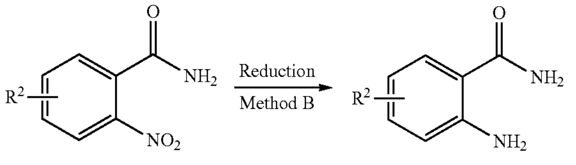

i ii

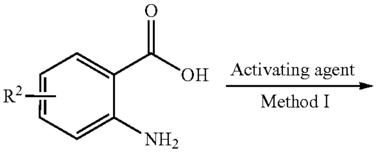

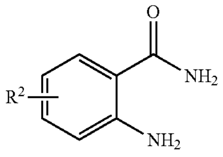

ii

Scheme 2: Representative synthesis of compounds of formula ii (see Scheme 1)

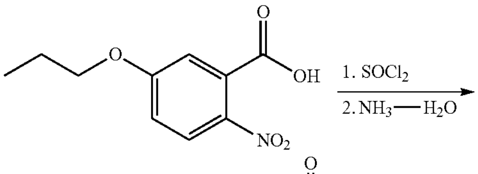

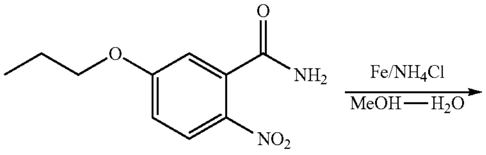

i-a

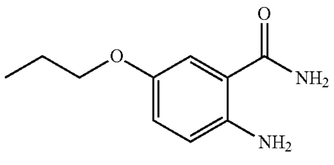

ii-a

Method A: 2-Nitro-5-propoxy-benzamide (i-a)

A mixture of 2-nitro-5-propoxy-benzoic acid (1.97 g, 8.75 mmol) and DMF (0.1 mL) in $SOCl_2$ (20 mL) was stirred at 65° C. for 2 h. After the reaction was completed, the mixture was cooled to room temperature. $SOCl_2$ was removed in vacuo and the residue was dissolved in anhydrous $CH_2Cl_2$ (10 mL), which was added to $NH_3$—$H_2O$ (28%) dropwise. After 1 h, the precipitate was collected and dried in vacuo to give 1.68 g of i-a as a yellow solid (85.2%). LCMS m/z=208.1 (M−16), 225.1 (M+1) (Method B) (retention time=1.88 min).

Method B: 2-Amino-5-propoxy-benzamide (ii-a)

To a mixture of 2-nitro-5-propoxy-benzamide (1.20 g, 5.36 mmol) in MeOH-$H_2O$ (v/v, 3:1, 60 mL) was added $NH_4Cl$ (2.84 g, 53.6 mmol) and Fe (2.99 g, 53.6 mmol). The resulting mixture was stirred at 60° C. for 3 h. After the reaction was completed, the mixture was cooled to room temperature and the iron was filtered off. The filtrate was concentrated to 15 mL and the formed precipitate was collected and dried in vacuo to give 1.02 g of ii-a as a pale yellow solid (98%). LCMS m/z=1781 (M−16), 195.1 (M+1) (Method B) (retention time=1.46 min).

Scheme 3: Representative synthesis of compounds of formula ii by Method I (see Scheme 1)

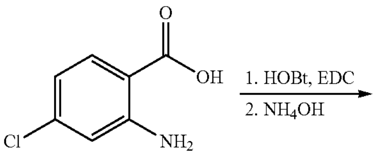

-continued

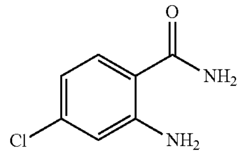

ii-b

Method I: 2-Amino-4-chlorobenzamide (ii-b)

To a mixture of 2-amino-4-chlorobenzoic acid (3.42 g, 20 mmol) in DMF (45 mL) was added HOBt (2.70 g, 20 mmol). After stirring for 10 min, EDC hydrogen chloride (3.82 g, 20 mmol) was added to the mixture. The resulted mixture was stirred at room temperature for 2 h. $NH_4OH$ (28%, 5 mL) was added at 0° C. with vigorous stirring. After addition, the mixture was stirred at room temperature for another 2 h. The reaction mixture was added to water (200 mL) dropwise with stirring, then a precipitate formed. The precipitate was collected and dried in vacuo to give 2.98 g of ii-b as a grey solid (87.6% yield). LCMS m/z=171.0 (M+1), 173.0 (M+3) (Method B) (retention time=1.39 min). $^1H$ NMR (400 MHz, DMSO-$d_6$): δ 7.27 (d, J=9.6 Hz, 1H), 6.68 (d, J=2.4 Hz, 1H), 6.60 (dd, J=8.4, 2.0 Hz, 1H), 5.50-5.82 (m, 4H).

Scheme 4: General route for the synthesis of compounds with general formula vi and vii

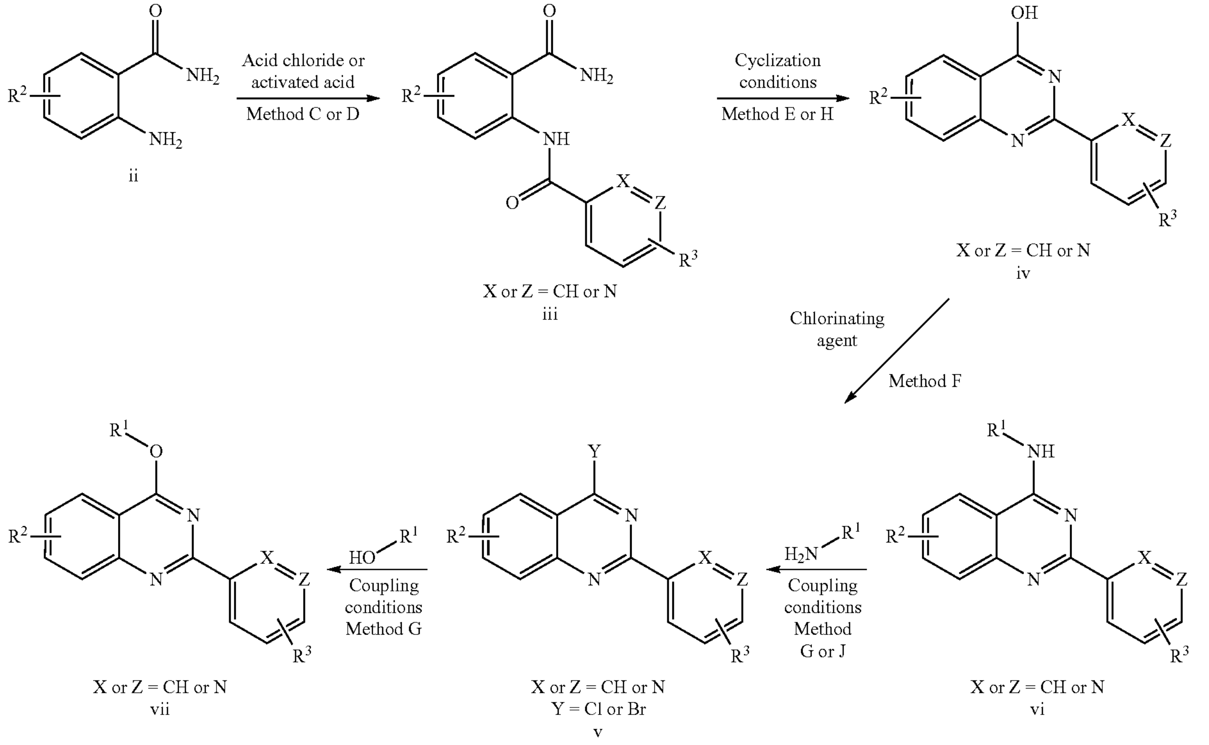

ii

X or Z = CH or N
iii

X or Z = CH or N
iv

X or Z = CH or N
vii

X or Z = CH or N
Y = Cl or Br
v

X or Z = CH or N
vi

Method F for Chlorinating Conditions

F1: $POCl_3$/N,N-dimethylbenzeneamine

F2: $SOCl_2$/DMF/80° C.

F3: $SOCl_2$ (4-8 equiv.)/DMF/DCM/rt-40° C.

F4: Phenylphosphinic dichloride/80-120° C.

F5: $POCl_3$/Δ

F6: $POCl_3$/Toluene/100° C.

F7: $PBr_3$/$CH_2Cl_2$/DMF/60° C.

Method G for Coupling Conditions

G1: i-PrOH/85-100° C.

G2: THF/reflux

G3: i-AmOH/100-130° C.

G4: MeOH/microwave/150° C.

G5: i-AmOH/microwave/150° C.

G6: THF/$Et_3N$/reflux

G7: THF-$H_2O$/NaOAc/rt-60° C.

G8: NaH/THF

G9: n-BuLi/THF

G10: LHMDS/THF

G11: LDA/THF

G12: $KCO_3$/DMF/60° C.

G13: $Cs_2CO_3$/DMA/80° C.

G14: NaOtBu/DMF/Microwave/100° C.

Method J for Coupling Conditions

J1: $Pd(PPh_3)_4$/t-BuOK/Dioxane

J2: $Pd_2(dba)_3$/Xantphos/$Cs_2CO_3$/Dioxane

Scheme 5: Representative synthesis of compounds of formula vi and vii (see Scheme 4)

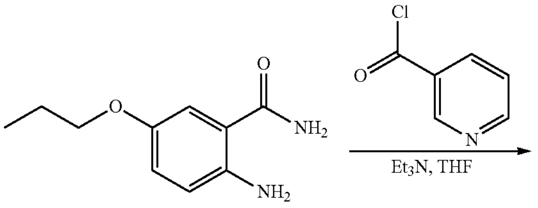

ii-a

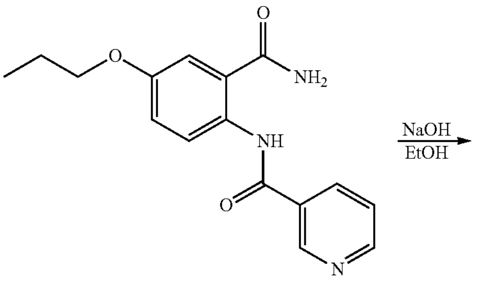

iii-a

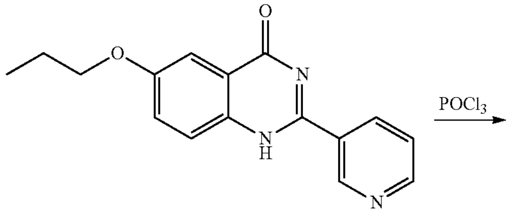

iv-a

-continued

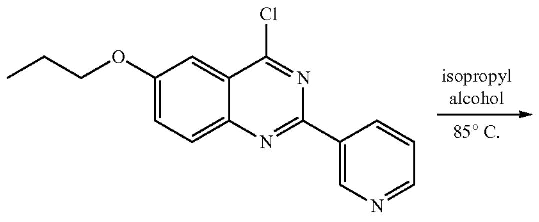

v-a

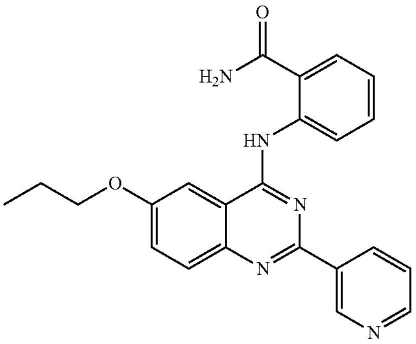

vi-a

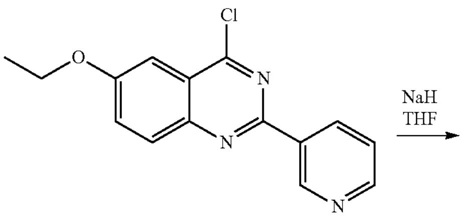

v-b

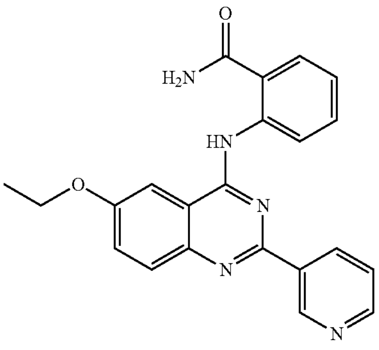

vii-a

Method C: N-(2-Carbamoyl-4-propoxy-phenyl)-nicotinamide (iii-a)

To a solution of 2-amino-5-propoxy-benzamide (760 mg, 3.91 mmol) in THF (15 mL) and $Et_3N$ (1 mL) was added nicotinoyl chloride (607 mg, 4.30 mmol) in anhydrous THF (15 min) dropwise. The resulting mixture was stirred at room temperature for 3 h. After the reaction was completed, the volatiles were removed. The residue was washed with $H_2O$ (10 mL). The pH was adjusted to approximately 5 by adding dilute HCl (2N in water). The resulting solid was collected and dried in vacuo to give 1.00 g of iii-a as a pale yellow solid (89.0%). LCMS m/z=300.1 (M+1) (Method B) (retention time=1.60 min).

Method D: 2-benzamido-5-methoxy-3-methylbenzamide (iii-b)

A 50 mL round-bottom flask was charged with nicotinic acid (41 mg, 0.33 mmol, 1.0 eq.), 2-amino-5-methoxy-3-methylbenzamide (60 mg, 0.33 mmol, 1.0 eq.) and HBTU (190 mg, 0.50 mmol, 1.5 eq), which were suspended in 4 mL, of DMF. DIPEA (86 mg, 0.66 mmol, 2.0 eq.) was added dropwise at room temperature and the reaction mixture was stirred overnight. The reaction mixture was added to water (10 mL) dropwise with stirring. The mixture was extracted with ethyl acetate. The ethyl acetate was evaporated and 55 mg of the orange solid (58.5% yield) was obtained. LCMS m/z=286.1 (M+1) (Method B) (retention time=1.24 min).

Method E: 6-Propoxy-2-pyridin-3-yl-1H-quinazolin-4-one (iv-a)

A mixture of N-(2-carbamoyl-4-propoxy-phenyl)-nicotinamide (980 mg, 3.27 mmol) in EtOH (20 mL) was treated with NaOH (654 mg, 16.37 mmol). The resulting mixture was stirred at room temperature for 18 h. After the reaction was completed, the volatiles were removed in vacuo. The residue was partitioned between $H_2O$ (50 mL) and ethyl acetate (50 mL). The aqueous layer was neutralized to pH 7 by slowly adding aq. citric acid and then a precipitate formed. The precipitate was collected and dried to give 1.00 g of iv-a as a grey solid (quantitative yield). LCMS m/z=282.1 (M+1) (Method B) (retention time=1.60 min).

Method F1: 4-Chloro-6-propoxy-2-pyridin-3-yl-quinazoline (v-a)

(This method is representative of method F1, F2, F3 and F4. These three methods can be implemented in a similar way except for substitution of the appropriate chlorinating reagent, solvent and temperature) To a mixture of 6-propoxy-2-pyridin-3-yl-1H-quinazolin-4-one (1.00 g, 3.56 mmol) in $POCl_3$ (10 mL) was added N,N-dimethylaniline (0.1 mL). The resulting mixture was stirred at 120° C. for 2 h. After the reaction was completed, $POCl_3$ was removed in vacuo, and the residue was added to ice-water slowly. The pH was adjusted to around 7 by slowly adding $NaHCO_3$ (sat.) at 0 (C. The resultant solid was collected and purified by chromatography on silica gel eluted with petroleum ether/ethyl acetate (v/v=4:1 to 1:1) to give 580 mg of v-a as a pale yellow solid (54.7%).

Method F5: 4-chloro-6-methoxy-2-(pyridin-3-yl) quinazoline (v-c)

In a sealed tube, phosphorus oxychloride (11 mL, 120 mmol) was added to 6-methoxy-2-(pyridin-3-yl)quinazolin-4(3H)-one (2.70 g, 10.66 mmol). The mixture was refluxed at 120° C. for 12 h. After cooling, the remaining phosphorus oxychloride was removed in vacuo to leave a tan solid. This residue was added to an ice-water mixture (100 mL) with cooling and allowed to stir. The pH of the suspension was adjusted to about pH 9 via dropwise addition of 28% ammonium hydroxide, and stirring was continued for 30 mins. The resulting solid was filtered to give the desired product as a tan solid (2.55 g, 9.39 mmol, 88%). LC-MS m/z=272.0 (M+1) (retention time=2.05) $^1$H NMR (300 MHz, DMSO) δ 9.55 (s, 1H), 8.81-8.64 (m, 2H), 8.09 (d, J=9.2 Hz, 1H), 7.78 (dd, J=9.2, 2.8 Hz, 1H), 7.61 (dd, J=7.9, 4.8 Hz, 1H), 7.49 (d, J=2.5 Hz, 1H), 4.00 (s, 3H).

Method F6: 6-Bromo-4-chloro-8-fluoro-2-(pyridin-3-yl)quinazoline (v-d)

To a suspension of 6-bromo-8-fluoro-2-(pyridin-3-yl) quinazolin-4-ol (6.16 g, 0.0192 mol) in toluene (60 mL) was added phosphorus oxychloride (5.30 ml, 0.0579 mol) at room temperature. The mixture was refluxed for 3 h. The solvent was evaporated and water was added to the residue under cooling conditions. The suspension was stirred at room temperature for 30 min, the resulting precipitate was filtered and dried to give the title compound (6.5 g, quantitative). $^1$H NMR (400 MHz, DMSO) δ 9.58 (d, J=1.6 Hz, 1H), 8.82 (dd, J=4.7, 1.5 Hz, 1H), 8.80-8.75 (m, 1H), 8.37 (dd, J=9.7, 1.9 Hz, 1H), 8.34-8.29 (m, 1H), 767 (dd, J=7.8, 4.6 Hz, 1H).

Method F7: 4-Bromo-6-methoxy-2-(pyridin-3-yl) quinazoline (v-e)

To a sealed tube containing 6-methoxy-2-(pyridin-3-yl) quinazolin-4(3)-one (1.30 g, 5.13 mmol) in dichloromethane (20 mL) was added 1 M phosphorus tribromide in dichloromethane (10.3 mL, 10.3 mmol) and DMF (2 mL). The reaction mixture was heated at 60° C. for 4 h. After cooling, excess dichloromethane was evaporated leaving a tan residue. This solid was added to an ice-water mixture (100 mL) with cooling and allowed to stir. The pH of the suspension was adjusted to about pH 9 via dropwise addition of 28% ammonium hydroxide, and stirring was continued for 30 mins. The resulting solid was filtered to give the desired product as a tan solid (1.49 g, 4.71 mmol, 92%). LC-MS m/z=318.3 (M+2) (retention time=2.19).

Method G1: 2-(6-Propoxy-2-pyridin-3-yl-quinazolin-4-ylamino)-benzamide (vi-a)

(This method is representative of method G1, G2, and G3. These three methods can be implemented in a similar way except for substitution of the appropriate solvent and temperature) A mixture of 4-chloro-6-propoxy-2-(pyridin-3-yl) quinazoline (90 mg, 0.3 mmol) and 2-aminobenzamide (52 mg, 0.4 mmol) in i-PrOH (5 mL) was stirred at 85° C. for 18 h. The yellow precipitate was collected and washed with i-PrOH (10 mL). The solid was suspended in water (10 mL) and $NH_3$—$H_2O$ (1 mL) was added. After filtration the solid was dried in vacuo to afford 31.0 mg of vi-a as a white solid (30.8%). LCMS m/z=400.1 (M+1) (Method B) (retention time=1.96 min). $^1$H-NMR (400 MHz, DMSO-$d_6$): δ 9.59 (d, J=2.0 Hz, 1H), 9.58 (d, J=7.6 Hz, 1H), 8.69-8.74 (m, 2H), 8.48 (s, 1H), 7.97 (d, J=6.8 Hz, 2H), 7.90 (d, J=8.8 Hz 1H), 7.74 (t, J=7.6 Hz, 1H), 7.56-7.61 (m, 3H), 7.20 (t, J=7.2 Hz, 1H), 4.16 (t, J=6.4 Hz, 2H), 1.86 (dd, J=14.0, 6.8 Hz, 2H), 1.07 (t, J=7.2 Hz, 3H).

Method G8: 2-(6-ethoxy-2-(pyridin-3-yl)quinazolin-4-yloxy)benzamide (vii-a)

(The method G8 is representative of method G6, G7, G9, G10 and G11. These six methods can be implemented in a similar way except for substitution of the appropriate base, solvent and temperature) To a 2.5 dram reaction vial was first added sodium hydride 60% (0.028 g, 0.700 mmol) and salicylamide (0.072 g, 0.525 mmol) in DMF (2 mL). The mixture was allowed to stir at room temperature for 1 h. Then, 4-chloro-6-ethoxy-2-(pyridin-3-yl)quinazoline (0.100 g, 0.350 mmol) was added to the mixture, and the reaction was allowed to proceed at room temperature overnight. LC-MS analysis of the crude mixture showed about 85% of product formed and 10% remaining starting material. Water (30 mL) was added to the mixture, and the product was extracted with chloroform (3×15 mL). The combined organic layers were dried ($Na_2SO_4$), filtered, and concentrated. The crude product was purified via ISCO (silica gel, 97.5:2.5 $CH_2Cl_2$/MeOH; 12 g column) to afford 13.9 mg of the desired product as a white solid (10.3%) LCMS m/z=387 (M+1) (Method C) (retention time=2.05 min). $^1$H NMR (300 MHz, DMSO) δ 11.47 (s, 2H), 9.39 (s, 1H), 8.66 (d, J=2.8 Hz, 1H), 8.56-8.47 (m, 1H), 8.01-7.90 (m, 2H), 7.69-7.55 (m, 2H), 7.55-7.40 (m, 2H), 7.05 (t, J=7.5 Hz, 1H), 6.97 (d, J=8.2 Hz, 1H), 4.23 (q, J=6.9 Hz, 2H), 1.44 (t, J=6.9 Hz, 3H).

Method G13: 4-(4-chlorophenyl)-N-(6-methoxy-2-(pyridin-3-yl)quinazolin-4-yl)thiazol-2-amine (vi-c)

(The method G13 is representative of method G12 also. This method can be implemented in a similar way except for substitution of the appropriate base, solvent and temperature) To a suspension of 4-chloro-6-methoxy-2-(pyridine-3-yl) quinazoline (645.2 mg, 2.375 mmol) and 2-amino-4-(4-chlorophenyl)thiazole (1050 mg, 4.98 mmol) in DMA (40 mL) was added $Cs_2CO_3$ (2430 mg, 7.46 mmol) at room temperature. The mixture was stirred at 80° C. for 9.5 h. Water was added and a precipitate formed which was collected by filtration and washed with $H_2O$. Recrystallization from acetone/DMF/methanol gave 383.6 mg of the product in a 36% yield as yellow solid, >98% purity by $^1$H NMR). $^1$H NMR (400 MHz DMSO-$d_6$) δ 12.52 (s, 1H), 9.78 (d, J=1.56 Hz, 1H), 8.91-8.88 (m, 1H), 8.74 (dd, J=4.74, 1.60 Hz, 1H), 8.33 (brs, 1H), 8.06 (d, J=8.56 Hz, 2H), 7.93 (d, J=9.08 hz, 1H), 7.89 (s, 1H), 7.66-7.59 (m, 2H), 7.55 (d, J=8.56 Hz, 2H), 4.01 (s, 3H).

Method G14: 4-(6-methoxy-2-(pyridin-3-yl)quinazolin-4-ylamino)-1H-pyrazole-5-carboxamide, 2HCl (vi-d)

(The method G14 is representative of method G4 and G5 also. This method can be implemented in a similar way except for substitution of the appropriate solvent and adjustment of the temperature) To a microwave vial containing 4-bromo-6-methoxy-2-(pyridin-3-yl)quinazoline (150.0 mg, 0.47 mmol) in DMF (2 mL) was added 4-amino-1H-pyrazole-5-carboxamide (66.0 mg, 0.52 mmol) and sodium tert-butoxide (50 mg, 0.52 mmol). The reaction mixture was heated at 100° C. for 15 mins by microwave irradiation. Water (50 mL) was added to the reaction mixture, and extracted with ethyl acetate (5×50 mL). The crude material was purified via ISCO (silica, 12 g column, 93% $CH_2Cl_2$-7% MeOH-0.1% $NH_4OH$) giving the product as a yellow solid. The free base was then converted to the HCl salt to yield the final product as an orange solid (59.8 mg, 0.14 mmol, 22%). LC-MS m/z=362.4 (M+1) (retention time=1.57) $^1$H NMR (300 MHz, DMSO) δ 11.28 (s, 1H), 9.62 (d, J=1.7 Hz, 1H), 9.17 (d, J=7.8 Hz, 1H), 8.93 (dd, J=5.2, 1.3 Hz, 1H), 8.60 (s, 1H), 8.05 (s, 1H), 8.03-7.94 (m, 2H), 7.77 (s, 1H), 7.64 (dd, J=9.2, 2.5 Hz 1H), 7.40 (d, J=2.6 Hz, 1H), 3.97 (s, 3H).

Method J1: 1-(6-Methoxy-2-(pyridin-3-yl)quinazolin-4-yl)-1H-benzo[d]imidazol-2(3H)-one (vi-b)

To a 50-mL two-neck round bottom flask equipped with a reflux condenser was added a mixture of 4-chloro-6-methoxy-2-(pyridin-3-yl)quinazoline (50 mg, 0.18 mmol, 1 eq.) and 1H-benzo[d]imidazol-2(3H)-one (27 mg, 0.21 mmol, 1.1 eq.) in 5 mL of dry 1,4-dioxane. $Pd(PPh_3)_4$ (10.6 mg, 0.009 mmol, 0.05 eq) and t-BuOK (41 mg, 0.36 mmol, 2 eq.) were added. The resulting mixture was stirred at 100° C. under $N_2$ atmosphere overnight. After cooling, 20 mL of methanol was added. The mixture was filtered, the filtrate was concentrated in vacuo and then was purified with chromatography on silica gel (ethyl acetate/petroleum ether from 1:4 to 1:2) to give the crude product, which was further purified with reverse phase HPLC to afford 4.8 mg of vi-e as a pale yellow solid (7%). MS m/z=370.1 (M+1) (Method B) (retention time=1.680 min). $^1$H NMR (400 MHz, DMSO-$d_6$): δ 11.51 (s, 1H), 8.78 (d, J=8.0 Hz, 2H), 8.17 (d, J=9.2 Hz, 1H), 7.80 (dd, J=9.2, 2.8 Hz, 1H), 7.70-7.64 (m, 1H), 7.46 (d, J=2.8 Hz, 1H), 7.41 (d, J=8.0 Hz, 1H), 7.20 (d, J=4.0 Hz, 2H), 7.16-7.08 (m, 1H), 3.89 (s, 3H).

Method J2: 6-methoxy-N-(pyridin-2-yl)-2-(pyridin-3-yl)quinazolin-4-amine dihydrochloride (vi-e)

To a suspension of 4-chloro-6-methoxy-2-(pyridine-3-yl) quinazoline (600 mg, 2.208 mmol) in dioxane (40 mL) under $N_2$, was added tris(dibenzylideneacetone)dipalladium(0) (103.1 mg, 0.113 mmol), 4,5-bis(diphenylphosphino)-9,9-dimethylxanthene (132.2 mg, 0.228 mmol) and cesium carbonate (1.1289 g, 3.46 mmol) at room temperature. 2-Aminopyridine (229 mg, 2.43 mmol) was added and the mixture was stirred at 100° C. for 2 h 30 min. Water was added and then a precipitate formed. The solid was collected and washed with water. The solid was dissolved in $CH_2Cl_2$. Purification was carried out using NH-silica gel to give the free base (649.3 mg). The free base was converted to the HC salt by dissolving the compound in $CH_2Cl_2$/MeOH and 1.5 ml of 4N HCl in ethyl acetate was added and then a precipitate formed. The solid was collected and dried in vacuo (at 40 degrees on and 60 degrees for ca. 3 h) and then washed with methanol. The resulting solid was dried in vacuo at 60 degrees to give 682 mg of the desired product as the HCl salt in a 77% yield as a pale yellow solid. $^1$H NMR (DMSO-$d_6$) δ 11.14 (brs, 1H), 9.58 (s, 1H), 9.13 (dd, J=7.96 Hz, 1H), 8.93 (d, J=5.24 Hz, 1H), 8.54 (d, J=4.72 Hz, 1H), 8.48 (d, J=8.32 Hz, 1H), 8.28 (brs, 1H), 8.09 (brt, J=7.16 Hz, 1H), 8.02-7.96 (m, 2H), 7.65 (dd, J=8.80, 2.48 Hz, 1H), 7.34 (brt, J=6.52 Hz, 1H), 4.01 (s, 3H). The 1H of 2HCl was not observed.

Method J3: N-(Biphenyl-4-yl)-6-methoxy-2-(pyridin-3-yl)quinazolin-4-amine hydrochloride (vi-f)

To a suspension of N-(4-bromophenyl)-6-methoxy-2-(pyridin-3-yl)quinazolin-4-amine (548.7 mg, 1.347 mmol) and phenylboronic acid (270 mg, 2.21 mmol) in dioxane/$H_2O$ (2/1) (30 mL) under $N_2$ was added $Na_2CO_3$ (485 mg, 4.58 mmol) and tetrakis(triphenylphosphine) palladium(0) (78 mg, 0.067 mmol) at room temperature. The mixture was stirred at 100° C. for 1 h. Water was added and then a precipitate formed. The solid was dissolved in methanol/acetone at 60° C. The solution was filtrated through Celite to remove any extra palladium. The filtrate was concentrated down to give 493.4 mg of a solid residue in. The solid was added to $CH_2Cl_2$ followed by addition of 4N HCl in ethyl acetate (0.4 mL) at room temperature to form the HCl salt. The mixture was stirred at room temperature and the resulting solid was filtered and dried in vacuo to give 435.2 mg and a yield of 73% as the HCl salt. $^1$H NMR (DMSO-d6) δ 10.24 (br, 1H), 9.54 (s, 1H), 8.92 (d, J=7.52 Hz, 1H), 8.82 (d, J=3.96 Hz, 1H), 8.10 (d, J=2.44 Hz, 1H), 8.03 (d, J=8.68 Hz, 2H), 7.92 (d, J=9.08 Hz, 1H), 7.84 (d, J=8.68 Hz, 2H), 7.81 (m, 1, 7.77-7.75 (m, 2H), 7.62 (dd, J=9.08, 2.44 Hz, 1H), 7.50 (m, 2H), 7.38 (m, 1H), 4.01 (s, 3H). The 1H of HCl was not observed.

The compounds in the following table were prepared in a manner analogous to that described in Scheme 1 and 5 (prepared according to method procedure A-J as designated).

TABLE 1
| Number | Product | Salt type | Molecular Mass | $^1$H-NMR | Solvent | LCMS | LCMS Protocol | Purity percent | Method for Coupling |
|---|---|---|---|---|---|---|---|---|---|
| 1 | 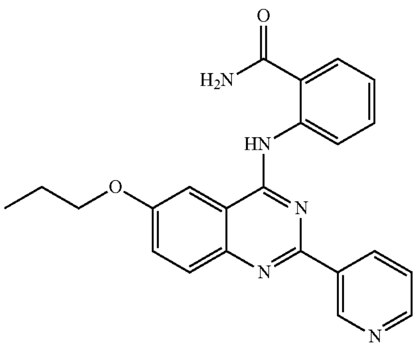 [SMILES: CCCOc1ccc2nc(-c3cccnc3)nc(Nc3ccccc3C(N)=O)c2c1] | | 399.45 | $^1$H-NMR (400 MHz, DMSO-$d_6$): δ 9.59 (d, J = 2.0 Hz, 1H), 9.58 (d, J = 7.6 Hz, 1H), 8.69-8.74 (m, 2H), 8.48 (s, 1H), 7.97 (d, J = 6.8 Hz, 2H), 7.90 (d, J = 8.8 Hz 1H), 7.74 (t, J = 7.6 Hz, 1H), 7.56-7.61 (m, 3H), 7.20 (t, J = 7.2 Hz, 1H), 4.16 (t, J = 6.4 Hz, 2H), 1.86 (dd, J = 7.2, 6.8 Hz, 2H), 1.07 (t, J = 7.2 Hz, 3H). | DMSO | 400.1 (M + 1) | Method B (NH4HCO3) | 95 | Method C, G1 |
| 2 | 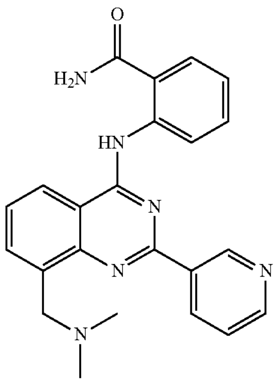 [SMILES: CN(C)Cc1cccc2c(Nc3ccccc3C(N)=O)nc(-c3cccnc3)nc12] | HCl | 398.46 | $^1$H-NMR (400 MHz, DMSO-$d_6$): δ 13.20 (s, 1H), 9.79 (s, 1H), 9.02-9.08 (m, 2H), 8.87 (d, J = 3.2 Hz, 1H), 8.53 (s, 1H), 3.34 (d, J = 8.0 Hz, 1H), 8.19 (d, J = 6.8 Hz, 1H), 7.74-7.99 (m, 5H), 7.28 (t, J = 7.6 Hz, 1H), 4.92 (d, J = 4.0 Hz, 2H), 2.87 (d, J = 3.2 Hz, 6H). | DMSO | 399.1 (M + 1) | Method B (NH4HCO3) | 95 | Method C, G1 |

TABLE 1-continued
| | | | | | | | | | |
|---|---|---|---|---|---|---|---|---|---|
| 3 | 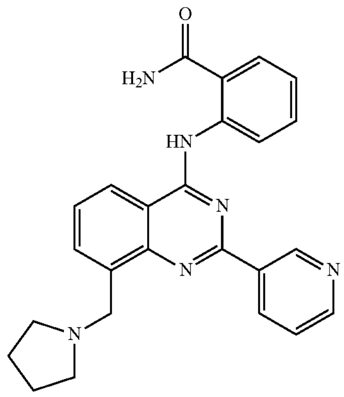 [SMILES: NC(=O)c1ccccc1Nc1nc(-c2cccnc2)nc2c(CN3CCCC3)cccc12] | HCl | 424.50 | $^1$H-NMR (400 MHz, DMSO-$d_6$): δ 13.07 (s, 1H), 9.64 (d, J = 1.6 Hz, 1H), 9.15 (d, J = 8.0 Hz, 1H), 8.78 (ddd, J = 8.0, 4.0, 2.4 Hz, 1H), 8.73 (dd, J = 4.4, 1.2 Hz, 1H), 8.49 (s, 1H), 8.09 (d, J = 8.0 Hz, 1H), 7.92-7.69 (m, 3H), 7.67- 7.74 (m, 2H), 7.62 (dd, J = 8.0, 4.8 Hz, 1H), 7.22 (t, J = 7.6 Hz, 1H), 4.29 (s, 2H), 2.61 (brs, 4H), 1.70 (brs, 4H). | DMSO | 425.2 (M + 1) | Method B (NH4HCO3) | 95 | Meth-od C, G1 |
| 4 | 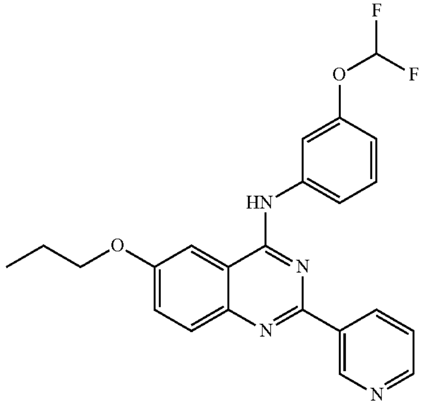 [SMILES: CCCOc1ccc2nc(-c3cccnc3)nc(Nc3cccc(OC(F)F)c3)c2c1] | | 422.43 | $^1$H-NMR (400 MHz, DMSO-$d_6$): δ 9.87 (s, 1H), 9.52 (s, 1H), 8.67 (d, J = 5.6 Hz, 1H). 7.99 (d, J = 2.4 Hz, 1H), 7.94 (s, 1H), 7.86 (d, J = 9.2 Hz, 1H), 7.80 (d, J = 8.0 Hz, 1H), 7.50-7.58 (m, 3H), 7.30 (t, J = 34.0 Hz, 1H), 7.00 (dd, J = 8.4, 2.0 Hz, 1H), 4.16 (t, J = 6.4 Hz, 2H), 1.86 (dd, J = 7.2, 6.4 Hz, 2H), 1.07 (t, J = 7.2 Hz, 3H). | DMSO | 423.1 (M + 1) | Method B (NH4HCO3) | 95 | Meth-od C, G1 |

TABLE 1-continued

| | | | | | | | | | |
|---|---|---|---|---|---|---|---|---|---|
| 5 | 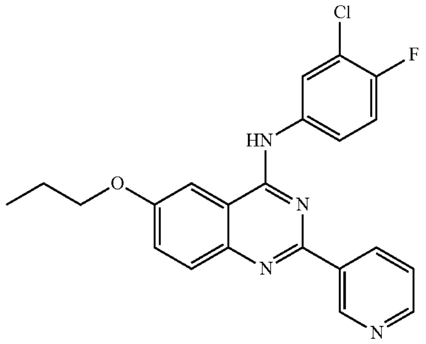 [SMILES: CCCOc1ccc2nc(-c3cccnc3)nc(Nc3ccc(F)c(Cl)c3)c2c1] | HCl | 408.86 | $^1$H-NMR (400 MHz, DMSO-$d_6$): δ 10.28 (s, 1H), 9.48 (s, 1H), 8.93 (d, J = 8.4 Hz, 1H), 8.85 (d, J = 4.4 Hz, 1H), 8.18 (dd, J = 7.6, 2.4 Hz, 1H), 8.06 (d, J = 2.0 Hz, 1H), 7.85-7.93 (m, 3H), 7.62 (dd, J = 8.8, 6.4 Hz, 1H), 7.55 (t, J = 8.8 Hz, 1H), 4.17 (t, J = 6.4 Hz, 3H), 1.86 (dd, J = 7.6, 6.4 Hz, 2H), 1.06 (t, J = 7.6 Hz, 3H). | DMSO | 409.1, 411.1 (M + 1) | Method B (NH4HCO3) | 95 | Meth-od C, G1 |
| 6 | 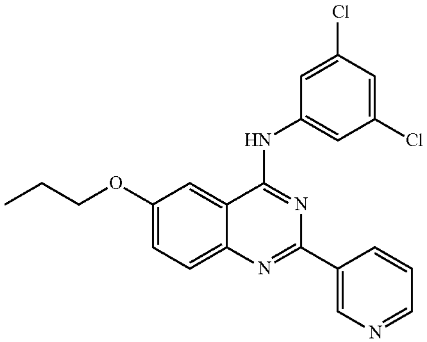 [SMILES: CCCOc1ccc2nc(-c3cccnc3)nc(Nc3cc(Cl)cc(Cl)c3)c2c1] | | 425.31 | $^1$H-NMR (400 MHz, DMSO-$d_6$): δ 9.93 (s, 1H), 9.51 (s, 1H), 8.68-8.71 (m, 2H), 8.16 (d, J = 2.4 Hz, 1H), 7.94 (d, J = 2.0 Hz, 1H), 7.86 (d, J = 8.8 Hz, 1H), 7.56-7.60 (m, 2H), 7.37 (s, 1H), 4.14 (t, J = 6.4 Hz, 2H), 1.84 (dd, J = 10.4 Hz, 7.2 Hz, 2H), 1.07 (t, J = 7.6 Hz, 3H). | DMSO | 425.0, 427.0 (M + 1) | Method B (NH4HCO3) | 95 | Meth-od C, G1 |
| 7 | 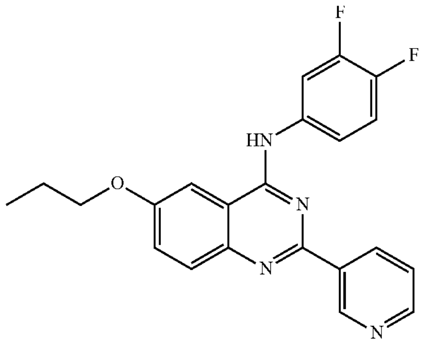 [SMILES: CCCOc1ccc2nc(-c3cccnc3)nc(Nc3ccc(F)c(F)c3)c2c1] | | 392.4 | $^1$H-NMR (400 MHz, DMSO-$d_6$): δ 10.06 (s, 1H), 9.49 (s, 1H), 8.77-8.81 (m, 2H), 8.09 (ddd, J = 10.0, 7.6. 2.4 Hz, 1H), 7.88 (d, J = 9.2 Hz, 1H), 7.69-7.74 (m, 2H), 7.54-7.61 (m, 2H), 4.15 (t, J = 6.4 Hz, 2H), 1.86 (dd, J = 14,0, 7.6 Hz, 2H), 1.06 (t, J = 7.2 Hz, 3H). | DMSO | 393.1 (M + 1) | Method B (NH4HCO3) | 95 | Meth-od C, G1 |

TABLE 1-continued

| | | | | | | | | |
|---|---|---|---|---|---|---|---|---|
| 8 | 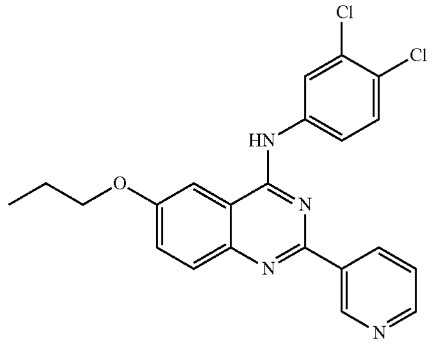 [SMILES: CCCOc1ccc2nc(-c3cccnc3)nc(Nc3ccc(Cl)c(Cl)c3)c2c1] | 425.31 | $^1$H-NMR (400 MHz,. DMSO-$d_6$): δ 10.05 (s, 1H), 9.51 (s, 1H), 8.75-8.80 (m, 2H), 8.34 (d, J = 2.4 Hz, 1H), 7.96-8.00 (m, 2H), 7.88 (d, J = 9.2 Hz, 1H), 7.68-7.75 (m, 2H), 7.59 (dd, J = 9.2, 2.8 Hz, 1H), 4.15 (t, J = 6.4 Hz, 2H), 1.86 (dd, J = 7.2, 6.8 Hz, 2H), 1.06 (t, J = 7.6 Hz, 3H). | DMSO | 425.0, 427.0 (M + 1) | Method B (NH4HCO3) | 95 | Meth-od C, G1 |
| 9 | 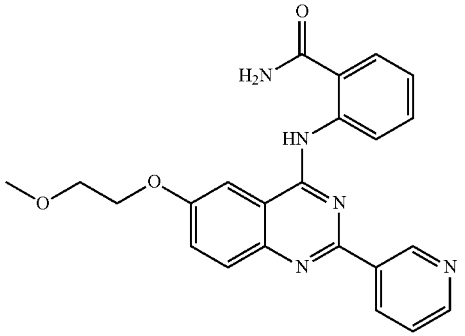 [SMILES: COCCOc1ccc2nc(-c3cccnc3)nc(Nc3ccccc3C(N)=O)c2c1] | 415.44 | $^1$H-NMR (400 MHz, DMSO-$d_6$): δ 13.03 (s, 1H), 9.59 (d, J = 1.2 Hz, 1H), 9.15 (d, J = 8.4 Hz, 1H), 8.69-8.74 (m, 2H), 8.49 (s, 1H), 7.96-8.06 (m, 2H), 7.90 (d, J = 9.2 Hz, 1H), 7.56-7.63 (m, 3H), 7.20 (t, J = 8.0 Hz, 1H), 4.31 (t, J = 4.0 Hz, 2H), 3.79 (t, J = 4.8 Hz, 2H), 3.31 (s, 3H). | DMSO | 416.0 (M + 1) | Method B (NH4HCO3) | 95 | Meth-od C, G1 |
| 10 | 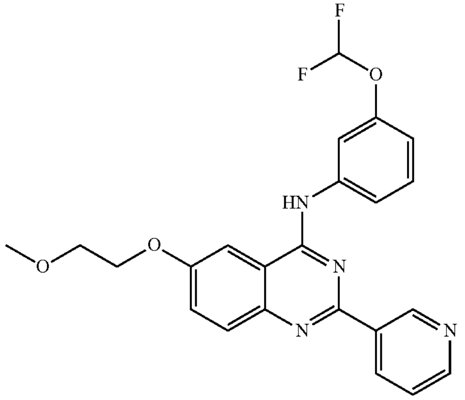 [SMILES: COCCOc1ccc2nc(-c3cccnc3)nc(Nc3cccc(OC(F)F)c3)c2c1] | 438.43 | $^1$H-NMR (400 MHz, DMSO-$d_6$): δ 9.86 (s, 1H), 9.53 (s, 1H), 8.66-8.68 (m, 2H), 8.02 (d, J = 2.8 Hz, 1H), 7.95 (t, J = 2.0 Hz, 1H), 7.86 (d, J = 8.8 Hz, 1H), 7.79 (d, J = 1.2 Hz, 1H), 7.48-7.60 (m, 3H), 7.30 (t, J = 74.4 Hz, 1H), 7.00 (dd, J = 8.0, 2.0 Hz, 1H), 4.33 (t, J = 4.8 Hz, 2H), 3.79 (t, J = 4.4 Hz, 2H), 3.37 (s, 3H). | DMSO | 439.1 (M + 1) | Method B (NH4HCO3) | 95 | Meth-od C, G1 |

TABLE 1-continued

| | | | | | | | | | |
|---|---|---|---|---|---|---|---|---|---|
| 11 | 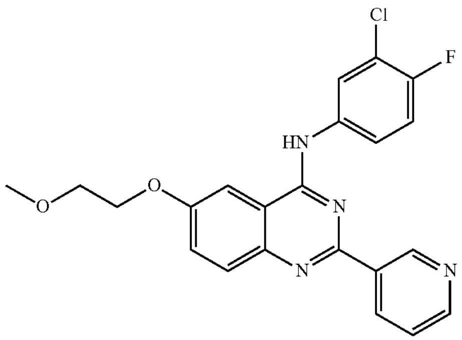 [SMILES: COCCOc1ccc2nc(-c3cccnc3)nc(Nc3ccc(F)c(Cl)c3)c2c1] | HCl | 424.86 | $^1$H-NMR (400 MHz, DMSO-$d_6$): δ 10.27 (s, 1H), 9.48 (s, 1H), 8.93 (d, J = 8.4 Hz, 1H), 8.85 (d, J = 4.8 Hz, 1H), 8.19 (dd, J = 6.8, 2.4 Hz, 1H), 8.10 (d, J = 2.4 Hz, 1H), 7.85-7.93 (m, 3H), 7.64 (dd, J = 9.2, 6.8 Hz, 1H), 7.55 (t, J = 8.8 Hz, 1H), 4.34 (t, J = 4.4 Hz, 2H), 3.78 (t, J = 4.4 Hz, 2H), 3.31 (s, 3H). | DMSO | 425.1, 427.1 (M + 1) | Method B (NH4HCO3) | 95 | Meth-od C, G1 |
| 12 | 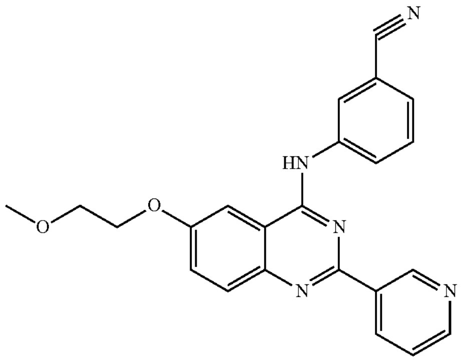 [SMILES: COCCOc1ccc2nc(-c3cccnc3)nc(Nc3cccc(C#N)c3)c2c1] | | 397.43 | $^1$H-NMR (400 MHz, DMSO-$d_6$): δ 10.07 (s, 1H), 9.50 (s, 1H), 8.78 (dd, J = 17.6, 7.6 Hz, 1H), 8.39 (s, 1H), 8.26 (dd, J = 8.0, 2.0 Hz, 1H), 8.02 (d, J = 2.0 Hz, 1H), 7.90 (d, J = 9.2 Hz, 1H), 7.61-7.73 (m, 4H), 4.34 (t, J = 4.8 Hz, 2H), 3.79 (t, J = 4.4 Hz, 2H), 3.35 (s, 3H). | DMSO | 398.1 (M + 1) | Method B (NH4HCO3) | 95 | Meth-od C, G1 |
| 13 | 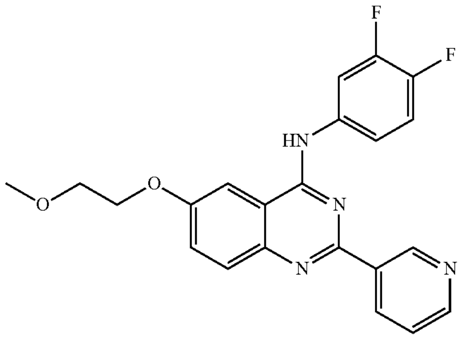 [SMILES: COCCOc1ccc2nc(-c3cccnc3)nc(Nc3ccc(F)c(F)c3)c2c1] | | 408.4 | $^1$H-NMR (400 MHz, DMSO-$d_6$): δ 9.86 (s, 1H), 9.50 (d, J = 1.6 Hz, 1H), 8.67 (dd, J = 4.8, 1.6 Hz, 1H), 8.64 (dt, J = 8.0, 1.6 Hz, 1H), 8.12 (ddd, J = 13.2, 7.2, 2.4 Hz, 1H), 7.98 (d, J = 2.8 Hz, 1H), 7.86 (d, J = 9.2, 1H), 7.69-7.72 (m, 1H), 7.52-7.60 (m, 3H), 4.31 (t, J = 4.0 Hz, 2H), 3.76-3.80 (m, 2H), 3.37 (s, 3H). | DMSO | 409.1 (M + 1) | Method B (NH4HCO3) | 95 | Meth-od C, G1 |

TABLE 1-continued

| | | | | | | | | | |
|---|---|---|---|---|---|---|---|---|---|
| 14 | 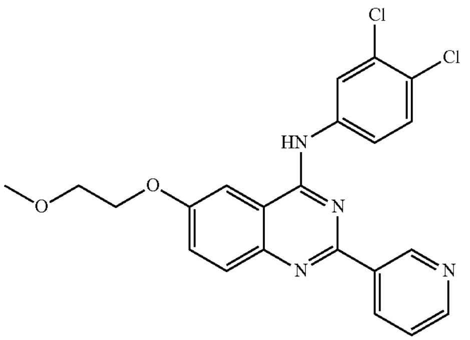 [SMILES: COCCOc1ccc2nc(-c3cccnc3)nc(Nc3ccc(Cl)c(Cl)c3)c2c1] | | 441.31 | $^1$H-NMR (400 MHz, DMSO-$d_6$): δ 9.90 (s, 1H), 9.52 (d, J = 1.2 Hz, 1H), 8.64-8.68 (m, 1H), 8.37 (d, J = 2.8 Hz, 1H), 7.98 (d, J = 2.4 Hz, 1H), 7.96 (dd, J = 10.6, 2.4 Hz, 1H), 7.86 (d, J = 9.2 Hz, 1H), 7.74 (d, J = 9.2 Hz, 1H), 7.59 (dd, J = 8.8, 2.4 Hz, 1H), 7.55 (dd, J = 8.0, 4.8 Hz, 1H), 4.31 (t, J = 4.08 Hz, 2H), 3.78 (t, J = 4.4 Hz, 2H), 3.37 (s, 3H). | DMSO | 441.0, 443.0 (M + 1) 221.9 (M/2 + 1) | Method A (TFA) | 95 | Meth-od C, G1 |
| 15 | 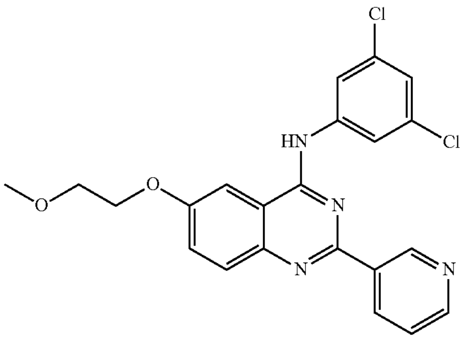 [SMILES: COCCOc1ccc2nc(-c3cccnc3)nc(Nc3cc(Cl)cc(Cl)c3)c2c1] | | 441.31 | $^1$H-NMR (400 MHz, DMSO-$d_6$): δ 9.93 (s, 1H), 9.53 (d, J = 1.6 Hz, 1H), 8.66-8.70 (m, 2H), 8.18 (s, 1H), 8.17 (s, 1H), 7.99 (d, J = 2.4 Hz, 1H), 7.89 (d, J = 8.8 Hz, 1H), 7.61 (dd, J = 8.8, 2.4 Hz, 1H), 7.56 (dd, J = 7.6, 4.8 Hz, 1H), 7.39 (t, J = 2.0 Hz, 1H), 4.33 (t, J = 4.8 Hz, 2H), 3.79 (t, J = 4.4 Hz, 2H), 3.37 (s, 3H). | DMSO | 441.1, 443.1 (M + 1) | Method B (NH4HCO3) | 95 | Meth-od C, G1 |
| 16 | 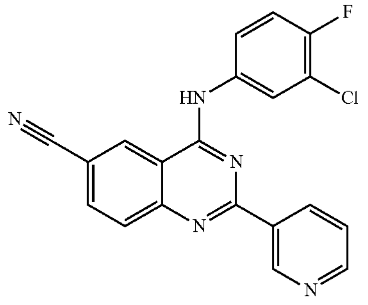 [SMILES: N#Cc1ccc2nc(-c3cccnc3)nc(Nc3ccc(F)c(Cl)c3)c2c1] | HCl | 375.79 | $^1$H-NMR (400 MHz, DMSO-$d_6$): δ 10.34 (s, 1H), 9.53 (d, J = 1.2 Hz, 1H), 9.16 (d, J = 1.2 Hz, 1H), 8.74 (dd, J = 4.0, 1.6 Hz, 1H), 8.68-8.69 (m, 2H), 8.20-8.28 (m, 2H), 8.00 (d, J = 8.4 Hz, 1H), 7.89-7.93 (m, 1H), 7.55-7.61 (m, 2H). | DMSO | 376.0, 378.0 (M + 1) | Method B (NH4HCO3) | 95 | Meth-od C, G1 |

TABLE 1-continued
| | | | | | | | | | |
|---|---|---|---|---|---|---|---|---|---|
| 17 | 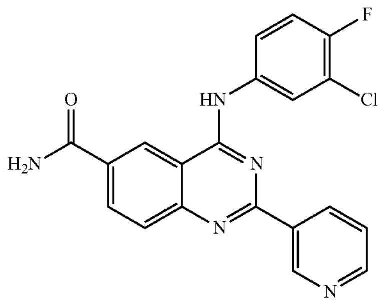 [SMILES: NC(=O)c1ccc2nc(-c3cccnc3)nc(Nc3ccc(F)c(Cl)c3)c2c1] | | 393.8 | $^{1}$H-NMR (400 MHz, DMSO-$d_6$): δ 10.37 (s, 1H), 9.54 (d, J = 1.6 Hz, 1H), 9.09 (s, 1H), 8.69 (d, J = 10.0 Hz, 1H), 8.68 (d, J = 8.0 Hz, 1H), 8.23-8.27 (m, 2H), 8.11 (s, 1H), 8.78 (s, 2H), 7.50-7.58 (m, 3H). | DMSO | 394.1, 396.0 (M + 1) | Method B (NH4HCO3) | 95 | Meth-od C, G1 |
| 18 | 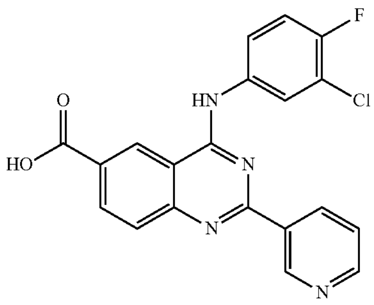 [SMILES: O=C(O)c1ccc2nc(-c3cccnc3)nc(Nc3ccc(F)c(Cl)c3)c2c1] | HCl | 394.79 | $^{1}$H-NMR (400 MHz, DMSO-$d_6$): δ 10.81 (s, 1H), 9.48 (d, J = 0.3 Hz, 1H), 9.23 (d, 0.8 Hz, 1H), 8.69 (d, J = 10.0 Hz, 1H), 8.68 (d, J = 8.0 Hz, 1H), 8.23-8.27 (m, 2H), 8.11 (s, 1H), 8.78 (s, 2H), 7.50-7.58 (m, 3H). | DMSO | 395.0, 397.0 (M + 1) | Method B (NH4HCO3) | 95 | Meth-od C, G1 |
| 19 | 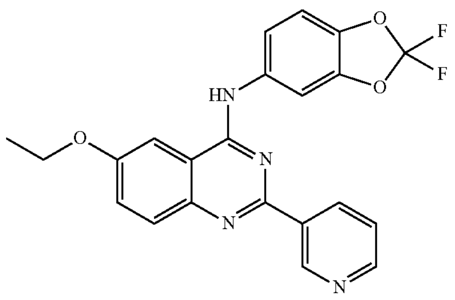 [SMILES: CCOc1ccc2nc(-c3cccnc3)nc(Nc3ccc4c(c3)OC(F)(F)O4)c2c1] | | 422.38 | 1H-NMR (400 MHz, DMSO-$d_6$): δ 10.11 (brs, 1H), 9.48 (s, 1H), 8.79 (d, J = 4.8 Hz, 1H), 8.83 (d, J = 8.0 Hz, 1H), 8.07 (d, J = 2.0 Hz, 1H), 8.02 (d, J = 2.4 Hz, 1H), 7.88-7.90 (m, 1H), 1.77 (d, J = 8.0 Hz, 1H), 7.52-7.62 (m, 3H), 4.27 (q, J = 7.2 Hz, 2H), 1.46 (t, J = 7.2 Hz, 3H). | DMSO | 423.1 (M + 1) | Method B (NH4HCO3) | 95 | Meth-od C, G1 |

TABLE 1-continued

| | | | | | | | | | |
|---|---|---|---|---|---|---|---|---|---|
| 20 | 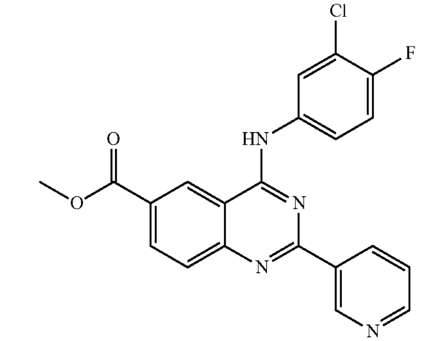 [SMILES: COC(=O)c1ccc2nc(-c3cccnc3)nc(Nc3ccc(F)c(Cl)c3)c2c1] | HCl | 408.81 | $^1$H-NMR (400 MHz, DMSO-$d_6$): δ 10.73 (s, 1H), 9.52 (d, J = 1.6 Hz, 1H), 9.32 (d, J = 1.6 Hz, 1H), 9.01 (d, J = 4.8 Hz, 1H), 8.91 (d, J = 5.2 Hz, 1H), 8.39 (dd, J = 8.4, 1.6 Hz, 1H), 8.17 (dd, J = 8.3, 2.0 Hz, 1H), 8.01 (d, J = 8.8 Hz, 1H), 7.90-7.95 (m, 2H), 7.55 (t, J = 9.2 Hz, 1H), 3.98 (s, 3H). | DMSO | 409.1, 411.1 (M + 1) | Method B (NH4HCO3) | 95 | Meth-od C, G1 |
| 21 | 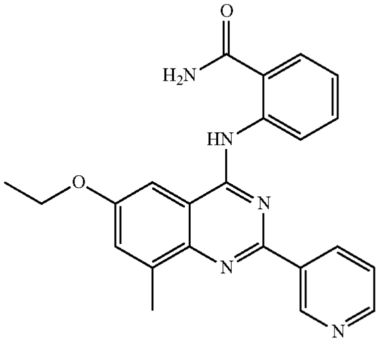 [SMILES: CCOc1cc(C)c2nc(-c3cccnc3)nc(Nc3ccccc3C(N)=O)c2c1] | | 399.45 | $^1$H-NMR (400 MHz, DMSO-$d_6$) δ 12.94 (s, 1H), 9.56 (s, 1H), 9.14 (d, J = 8.0 Hz, 1H), 8.83-8.66 (m, 2H), 8.48 (s, 1H), 8.06-7.91 (m, 2H), 7.76-7.58 (m, 2H), 7.35 (s, 1H), 7.27 (d, J = 2.0 Hz, 1H), 7.18 (t, J = 7.2 Hz, 1H), 4.15 (q, J = 6.8 Hz, 2H), 2.64 (s, 3H), 1.43 (t, J = 6.8 Hz, 1H). | DMSO | 400.1 (M + 1) | Method B (NH4HCO3) | 95 | Meth-od D, G1 |
| 22 | 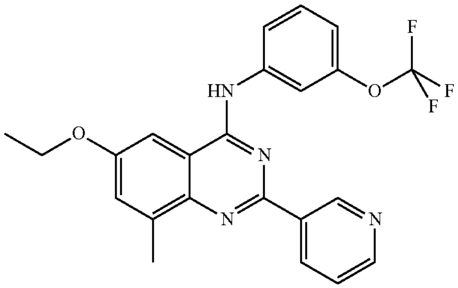 [SMILES: CCOc1cc(C)c2nc(-c3cccnc3)nc(Nc3cccc(OC(F)(F)F)c3)c2c1] | | 440.42 | $^1$H-NMR (400 MHz, DMSO-$d_6$) δ 9.84 (s, 1H), 9.55 (d, J = 1.2 Hz, 1H), 8.73-8.60 (m, 2H), 8.14 (s, 1H), 7.91 (d, J = 8.4 Hz, 1H), 7.80 (d, J = 2.4 Hz, 1H), 7.60 (t, J = 8.0 Hz, 1H), 7.53 (dd, J = 7.6, 4.8 Hz, 1H), 7.45 (d, J = 1.6 Hz, 1H), 7.16 (d, J = 8.4 Hz, 1H), 4.23 (q, J = 6.8 Hz, 2H), 2.70 (s, 3H), 1.44 (t, J = 6.8 Hz, 3H) | DMSO | 440.9 (M + 1) | Method A (TFA) | 95 | Meth-od D, G1 |

TABLE 1-continued
| | | | | | | | | | |
|---|---|---|---|---|---|---|---|---|---|
| 23 | 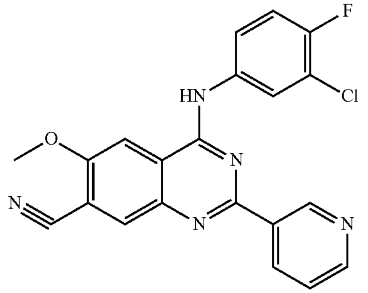 [SMILES: COc1cc2c(Nc3ccc(F)c(Cl)c3)nc(-c3cccnc3)nc2cc1C#N] | | 405.81 | $^1$H-NMR (400 MHz, DMSO-$d_6$) δ 10.08 (s, 1H), 9.42 (s, 1H), 8.68 (d, J = 3.6 Hz, 1H), 8.55 (d, J = 8.4 Hz, 1H), 8.32 (s, 1H), 8.15 (dd, J = 6.8, 2.4 Hz, 1H), 8.04 (s, 1H), 7.93-7.78 (m, 1H), 7.54 (td, J = 8.3, 6.9 Hz, 2H), 4.08 (s, 3H) | DMSO | 406.1, 408.1 (M + 1) | Method B (NH4HCO3) | 95 | Meth-od C, G1 |
| 24 | 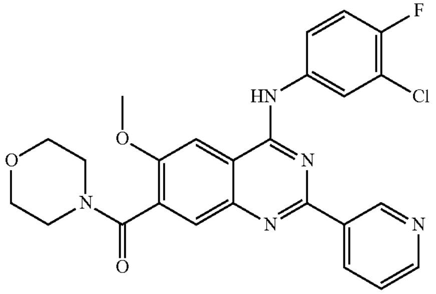 [SMILES: COc1cc2c(Nc3ccc(F)c(Cl)c3)nc(-c3cccnc3)nc2cc1C(=O)N1CCOCC1] | | 493.92 | $^1$H-NMR (400 MHz, DMSO-$d_6$) δ 10.00 (s, 1H), 9.49-9.51 (m, 1H), 8.62-8.70 (m, 2H), 8.21 (dd, J = 6.8, 2.8 Hz, 1H), 8.03 (s, 1H), 7.87-7.91 (m, 1H), 7.75 (s, 1H), 7.53-7.59 (m, 2H), 4.02 (s, 3H), 3.64-3.73 (m, 4H), 3.49-3.58 (m, 2H), 3.14-3.22 (m, 2H). | DMSO | 494.1, 496.1 (M + 1) | Method B (NH4HCO4) | 95 | Meth-od C, G1 |
| 25 | 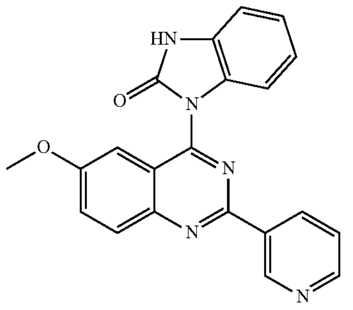 [SMILES: COc1ccc2nc(-c3cccnc3)nc(-n3c(=O)[nH]c4ccccc43)c2c1] | TFA | 369.38 | $^1$H-NMR (400 MHz, DMSO-$d_6$): δ 11.51 (s, 1H), 8.78 (d, J = 8.0 Hz, 2H), 8.17 (d, J = 9.2 Hz, 1H), 7.80 (dd, J = 9.2, 2.8 Hz, 1H), 7.70-7.64 (m, 1H), 7.46 (d, J = 2.8 Hz, 1H), 7.41 (d, J = 8.0 Hz, 1H), 7.20 (d, J = 4.0 Hz, 2H), 7.16-7.08 (m, 1H), 3.89 (s, 3H). | DMSO | 370.1 (M + 1) | Method B (NH4HCO3) | 95 | Meth-od C, J1 |

TABLE 1-continued

| | | | | | | | | |
|---|---|---|---|---|---|---|---|---|
| 26 | 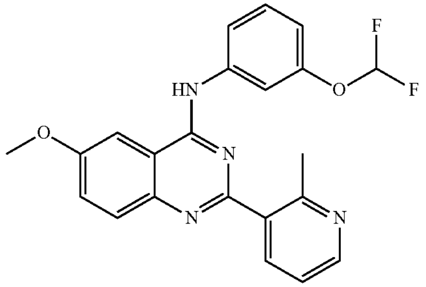 [SMILES: COc1ccc2nc(-c3cccnc3C)nc(Nc3cccc(OC(F)F)c3)c2c1] | 408.4 | $^1$H-NMR (400 MHz, DMSO-$d_6$): δ 9.87 (s, 1H), 8.53 (dd, J = 4.7, 1.5 Hz, 1H), 8.23 (d, J = 6.8 Hz, 1H), 8.00 (d, J = 2.6 Hz, 1H), 7.8 (t, J = 2.1 Hz, 1H), 7.84 (d, J = 9.1 Hz, 1H), 7.73 (dd, J = 8.2, 1.2 Hz, 1H), 7.58 (dd, J = 9.1, 2.6 Hz, 1H), 7.41-7.25 (m, 3H), 7.24 (t, J = 74.0 Hz, 1H), 6.96 (dd, J = 8.0, 2.2 Hz, 1H), 3.99 (s, 3H), 2.75 (s, 3H). | DMSO | 409.1 (M + 1) | Method B (NH4HCO3) | 95 | Meth-od D, G1 |
| 27 | 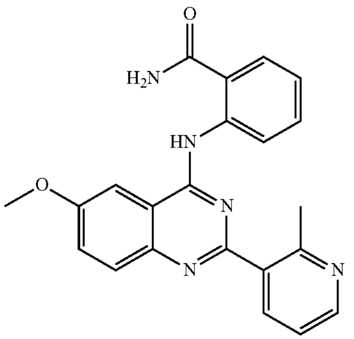 [SMILES: COc1ccc2nc(-c3cccnc3C)nc(Nc3ccccc3C(N)=O)c2c1] | 385.42 | $^1$H-NMR (400 MHz, DMSO-$d_6$): δ 13.09 (s, 1H), 9.08 (d, J = 7.8 Hz, 1H), 8.55 (dd, J = 4.8, 1.6 Hz, 1H), 8.49 (s, 1H), 8.22 (dd, J = 7.8,. 1.7 Hz, 1H), 8.01 (s, 1H), 7.95 (dd, J = 7.9, 1.2 Hz, 1H), 7.87 (d, J = 9.6 Hz, 1H), 7.66-7.58 (m, 3H), 7.40 (dd, J = 7.7, 4.8 Hz, 1H), 7.15 (dd, J = 11.5, 4.4 Hz, 1H), 3.99 (s, 3H), 2.77 (s, 3H). | DMSO | 386.1 (M + 1) | Method B (NH4HCO3) | 95 | Meth-od D, G1 |
| 28 | 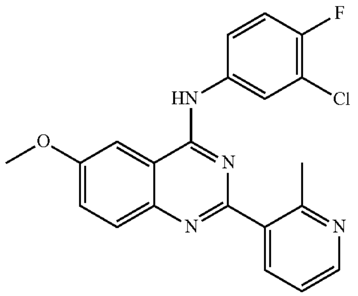 [SMILES: COc1ccc2nc(-c3cccnc3C)nc(Nc3ccc(F)c(Cl)c3)c2c1] | 394.83 | $^1$H-NMR (400 MHz, DMSO-$d_6$): δ 10.10 (s, 1H), 8.63 (d, J = 4.1 Hz, 1H), 8.43 (d, J = 7.6 Hz, 1H), 8.15 (dd, J = 6.8, 2.5 Hz, 1H), 8.03 (d, J = 2.3 Hz, 1H), 7.88-7.78 (m, 2H), 7.58 (ddd, J = 12.5, 8.3, 4.1 Hz, 2H), 7.49 (t, J = 9.1 Hz, 1H), 3.99 (s, 3H), 2.80 (s, 3H). | DMSO | 395.1, 397.1 (M + 1) | Method B (NH4HCO3) | 95 | Meth-od C, G1 |

TABLE 1-continued
| | | | | | | | | | |
|---|---|---|---|---|---|---|---|---|---|
| 29 | 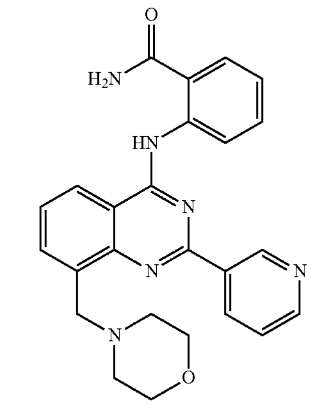 [SMILES: NC(=O)c1ccccc1Nc1nc(-c2cccnc2)nc2c(CN3CCOCC3)cccc12] | HCl | 440.5 | $^1$H-NMR (400 MHz, DMSO-$d_6$): δ 13.19 (s, 1H), 11.12-10.93 (m, 1H), 9.83 (d, J = 1.5 Hz, 1H), 9.21 (d, J = 7.8 Hz, 1H), 9.01 (d, J = 7.8 Hz, 1H), 8.93-8.89 (m, 1H), 8.53 (s, 1H), 8.36 (dd, J = 11.8, 7.9 Hz, 2H), 8.02-7.73 (m, 6H), 7.29 (d, J = 8.02 Hz, 1H), 5.01 (s, 2H), 3.95-3.81 (m, 4H), 3.37 (s, 4H). | DMSO | 441.2 (M + 1) | Method B (NH4HCO3) | 95 | Meth-od C, G1 |
| 30 | 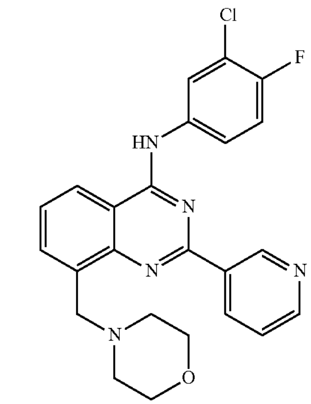 [SMILES: Fc1ccc(Nc2nc(-c3cccnc3)nc3c(CN4CCOCC4)cccc23)cc1Cl] | HCl | 449.91 | $^1$H-NMR (400 MHz, DMSO-$d_6$): δ 10.05 (s, 1H), 9.56 (s, 1H), 8.73-8.66 (m, 2H), 8.47 (d, J = 8.1 Hz, 1H), 8.28 (dd, J = 6.8, 2.5 Hz, 7.99-7.90 (m, 2H), 7.67-7.50 (m, 3H), 4.16 (s, 2H), 3.62 (s, 4H), 2.53 (s, 4H). | DMSO | 450.1, 452.1 (M + 1) | Method B (NH4HCO3) | 95 | Meth-od C, G1 |
| 31 | 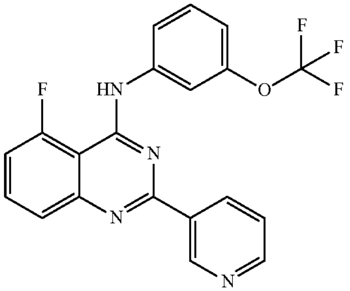 [SMILES: Fc1cccc2nc(-c3cccnc3)nc(Nc3cccc(OC(F)(F)F)c3)c12] | | 400.33 | $^1$H-NMR (400 MHz, DMSO-$d_6$): δ 9.47 (d, J = 2.0 Hz, 2H), 8.70 (dd, J = 4.3, 1.6 Hz, 1H), 8.65-8.59 (m, 1H), 8.06 (s, 1H), 7.91 (dt, J = 8.1, 6.0 Hz, 1H), 7.82 (dd, J = 8.2, 1.2 Hz, 1H), 7.76 (d, J = 8.4 Hz, 1H), 7.59 (t, J = 8.2 Hz, 1H), 7.51 (ddd, J = 20.0, 10.0, 6.4 Hz, 2H), 7.21 (d, J = 8.4 Hz, 1H). | DMSO | 401.1 (M + 1) | Method B (NH4HCO3) | 95 | Meth-od C, G1 |

TABLE 1-continued
| | | | | | | | | | |
|---|---|---|---|---|---|---|---|---|---|
| 32 | 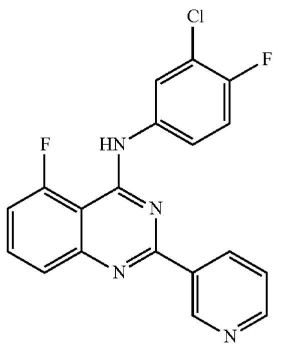 [SMILES: Fc1ccc(Nc2nc(-c3cccnc3)nc3cccc(F)c23)cc1Cl] | HCl | 368.77 | $^1$H-NMR (400 MHz, DMSO-$d_6$): δ 9.53 (d, J = 11.3 Hz, 1H), 9.44 (d, J = 1.2 Hz, 1H), 8.84-8.79 (m, 2H), 8.09 (dd, J = 6.8, 2.6 Hz, 1H), 7.97-7.89 (m, 1H),. 7.85-7.75 (m, 3H), 7.57-7.47 (m, 2H). | DMSO | 369.1, 371.0 (M + 1) | Method B (NH4HCO3) | 95 | Meth-od C, G1 |
| 33 | 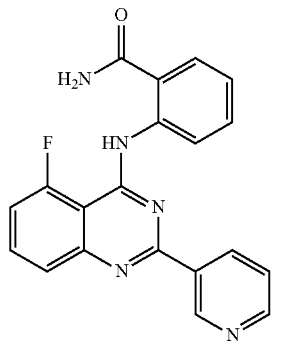 [SMILES: NC(=O)c1ccccc1Nc1nc(-c2cccnc2)nc2cccc(F)c12] | HCl | 359.36 | $^1$H-NMR (400 MHz, DMSO-$d_6$): δ 12.21 (d, J = 12.1 Hz, 1H), 9.53 (d, J = 1.2 Hz, 1H), 8.99 (d, J = 8.1 Hz, 1H), 8.39 (d, J = 4.2 Hz, 1H), 8.71 (d, J = 7.9 Hz, 1H), 8.35 (s, 1H), 7.97-7.76 (m, 5H), 7.72-7.65 (m, 1H), 7.50 (dd, J = 12.1, 7.5 Hz, 1H), 7.29 (t, J = 7.1 Hz, 1H). | DMSO | 360.2 (M + 1) | Method B (NH4HCO3) | 95 | Meth-od C, G1 |
| 34 | 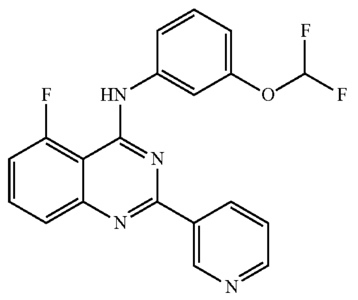 [SMILES: Fc1cccc2nc(-c3cccnc3)nc(Nc3cccc(OC(F)F)c3)c12] | | 382.34 | $^1$H-NMR (400 MHz, DMSO-$d_6$): δ 9.49 (d, J = 1.8 Hz, 1H), 9.42 (s, 1H), 8.71 (dd, J = 4.6, 1.3 Hz, 1H), 8.65 (d, J = 7.8 Hz, 1H), 7.90 (dd, J = 15.8, 9.7 Hz, 2H), 7.73 (dd, J = 19.0, 8.26 Hz, 2H), 7.56-7.12 (m, 4H), 7.04 (dd, J = 8.2, 1.8 Hz, 1H). | DMSO | 383.1 (M + 1) | Method B (NH4HCO3) | 95 | Meth-od C, G1 |

TABLE 1-continued
| | | | | | | | | | |
|---|---|---|---|---|---|---|---|---|---|
| 35 | 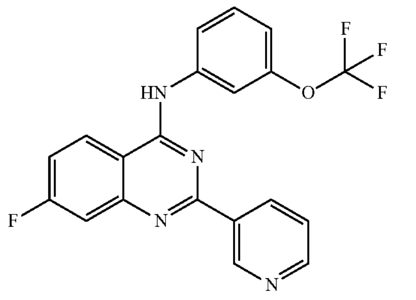 [SMILES: Fc1ccc2c(Nc3cccc(OC(F)(F)F)c3)nc(-c3cccnc3)nc2c1] | HCl | 400.33 | $^1$H-NMR (400 MHz, DMSO-$d_6$): δ 10.43 (s, 1H), 9.52 (s, 1H), 8.89 (d, J = 8.2 Hz, 1H), 8.85 (d, 4.2 Hz, 1H), 8.78 (dd, J = 9.2, 5.9 Hz, 1H), 8.09 (s, 1H), 7.95 (dd, J = 8.2, 1.2 Hz, 1H), 7.80 (dd, J = 7.9, 5.2 Hz, 1H), 7.72-7.58 (m, 3H), 7.21 (d, J = 8.4 Hz, 1H). | DMSO | 401.1 (M + 1) | Method B (NH4HCO3) | 95 | Meth-od C, G1 |
| 36 | 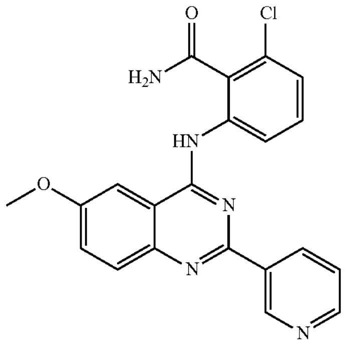 [SMILES: COc1ccc2nc(-c3cccnc3)nc(Nc3cccc(Cl)c3C(N)=O)c2c1] | HCl | 405.84 | $^1$H-NMR (400 MHz,. DMSO-$d_6$): δ 10.74-10.48 (m, 1H), 9.36 (d, J = 1.6 Hz, 1H), 8.95 (d, J = 8.2 Hz, 1H), 8.89-8.85 (m, 1H), 8.05 (d, J = 1.7 Hz, 1H), 8.02 (d, J = 9.15 Hz, 1H), 7.93-7.86 (m, 2H), 7.73-7.63 (m, 3H), 7.60-7.52 (m, 2H), 3.98 (s, 3H). | DMSO | 406.1, 408.1 (M + 1) | Method B (NH4HCO3) | 95 | Meth-od C, G1 |
| 37 | 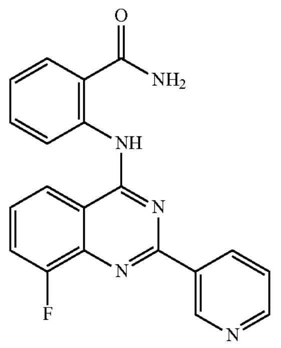 [SMILES: NC(=O)c1ccccc1Nc1nc(-c2cccnc2)nc2c(F)cccc12] | HCl | 359.36 | $^1$H-NMR (400 MHz, DMSO-$d_6$): δ 9.61 (s, 1H), 9.00 (dd, J = 15.4, 8.2 Hz, 2H), 8.36 (d, J = 4.13 Hz, 1H), 8.52 (s, 1H), 8.04-7.94 (m, 3H), 7.86-7.70 (m, 4H), 7.26 (dd, J = 11.2, 4.2 Hz, 1H). | DMSO | 360.1 (M + 1) | Method B (NH4HCO3) | 95 | Meth-od C, G1 |

TABLE 1-continued

| | | | | | | | | | |
|---|---|---|---|---|---|---|---|---|---|
| 38 | 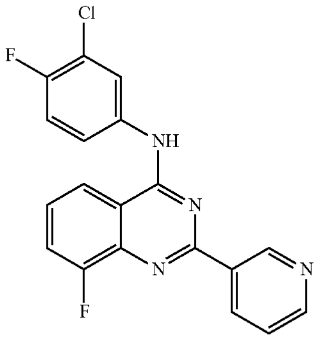 [SMILES: Fc1ccc(Nc2nc(-c3cccnc3)nc3c(F)cccc23)cc1Cl] | HCl | 368.77 | $^{1}$H-NMR (400 MHz, DMSO-$d_6$): δ 10.22 (s, 1H), 9.52 (s, 1H), 8.73 (d, J = 3.6 Hz, 1H), 8.69 (td, J = 8.0, 1.8 Hz, 1H), 8.38 (d, J = 8.4 Hz, 1H), 8.25 (dd, J = 6.8, 2.6 Hz, 1H), 7.91 (ddd, J = 9.0, 4.2, 2.6 Hz, 1H), 7.79 (dd, J = 9.8, 7.9 Hz, 1H), 7.67 (dd, J = 8.2, 5.2 Hz, 1H), 7.61-7.53 (m, 2H). | DMSO | 369.0, 371.0 (M + 1) | Method B (NH4HCO3) | 95 | Meth-od C, G1 |
| 39 | 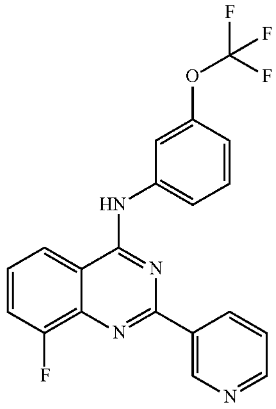 [SMILES: Fc1cccc2c(Nc3cccc(OC(F)(F)F)c3)nc(-c3cccnc3)nc12] | HCl | 400.33 | $^{1}$H-NMR (400 MHz, DMSO-$d_6$): δ 10.47 (s, 1H), 9.52 (d, J = 1.4 Hz, 1H), 9.04 (d, J = 8.0 Hz, 1H), 8.92 (dd, J = 5.2, 1.2 Hz, 1H), 8.52 (d, J = 8.4 Hz, 1H), 8.07 (s, 1H), 7.97 (d, J = 1.2 Hz, 2H), 7.86-7.80 (m, 1H), 7.74-7.68 (m, 1H), 7.62 (t, J = 8.2 Hz, 1H), 7.22 (d, J = 8.4 Hz, 1H). | DMSO | 401.1 (M + 1) | Method B (NH4HCO3) | 95 | Meth-od C, G1 |
| 40 | 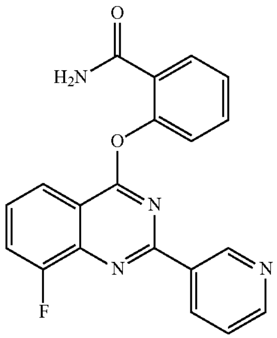 [SMILES: NC(=O)c1ccccc1Oc1nc(-c2cccnc2)nc2c(F)cccc12] | | 360.34 | $^{1}$H-NMR (400 MHz, DMSO-$d_6$): δ 9.68 (d,. J = 1.6 Hz, 1H), 8.82 (t, J = 7.9, 1.8 Hz, 1H), 8.71 (dd, J = 4.6, 1.6 Hz, 1H), 8.22 (d, J = 8.2 Hz, 1H), 7.87 (dd, J = 7.8, 1.9 Hz, 1H), 7.73 (dd, J = 9 2, 7.8 Hz, 1H), 7.59 (dt, J = 8.1, 5.0 Hz, 2H), 7.21-7.15 (m, 1H), 6.66 (d, J = 8.2 Hz, 1H), 6.54 (t, J = 7.4 Hz, 1H). | DMSO | 360.9 (M + 1), 382.9 (M + 23) | Method B (NH4HCO3) | 95 | Meth-od C, G9 |

TABLE 1-continued
| | | | | | | | | |
|---|---|---|---|---|---|---|---|---|
| 41 | 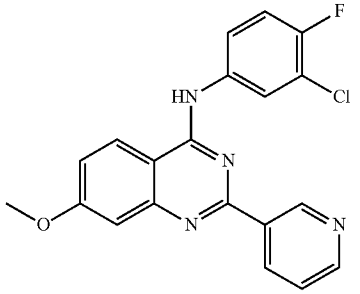 [SMILES: COc1ccc2c(Nc3ccc(F)c(Cl)c3)nc(-c3cccnc3)nc2c1] | 380.08 | $^1$H-NMR (400 MHz, DMSO-$d_6$): δ 10.56 (brs, 1H), 9.62 (d, J = 1.2 Hz, 1H), 9.05 (d, J = 8.4 Hz, 1H), 9.00 (dd, J = 1.6, 4.8 Hz, 1H), 8,71 (d, J = 9.2 Hz, 1H), 8.31 (dd, J = 2.0, 7.2 Hz, 1H), 8.02-7.99 (m, 2H), 7.66 (t, J = 9.2 Hz, 1H), 7.54 (s, 1H), 7.50 (dd, J = 2.4, 9.2 Hz, 1H), 4.11 (s, 3H). | DMSO | 381.1, 383.1 (M + 1) | Method B (NH4HCO3) | 95 | Meth-od C, G1 |
| 42 | 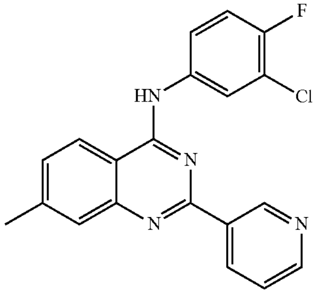 | 476.67 | $^1$H-NMR (400 MHz, DMSO-$d_6$): δ 10.40 (s, 1H), 9.51 (s, 1H), 8.93 (d, J = 8.0 Hz, 1H), 8.88 (d, J = 4.8 Hz, 1H), 8.40 (d, J = 8.8 Hz, 1H), 8.35 (d, J = 1.6 Hz, 1H), 8.20 (dd, J = 4.4, 6.8 Hz, 1H), 8.04 (dd, J = 7.2, 8.8 Hz, 1H), 7.93-7.86 (m, 2H), 7.35 (t, J = 9.2 Hz, 1H). | DMSO | 477.0, 499.0 (M + 1) | Method B (NH4HCO3) | 95 | Meth-od C, G1 |
| 43 | 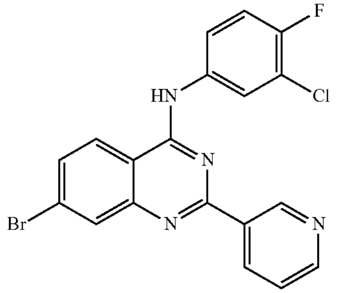 [SMILES: Fc1ccc(Nc2nc(-c3cccnc3)nc3cc(Br)ccc23)cc1Cl] | 429.67 | $^1$H-NMR (400 MHz, DMSO-$d_6$): δ 10.46 (s, 1H), 9.49 (s, 1H), 8.95 (d, J = 8.1 Hz, 1H), 8.89 (d, J = 4.97 Hz, 1H), 8.60 (d, J = 8.9 Hz, 1H), 8.19 (dd, J = 6.8, 2.6 Hz, 1H), 8.14 (d, J = 1.9 Hz, 1H), 7.96-7.83 (m, 3H), 7.53 (t, J = 9.0 Hz, 1H). | DMSO | 429.0, 430.9, 433.0 (M + 1) | Method B (NH4HCO3) | 95 | Meth-od C, G1 |

TABLE 1-continued

| | | | | | | | | | |
|---|---|---|---|---|---|---|---|---|---|
| 44 | 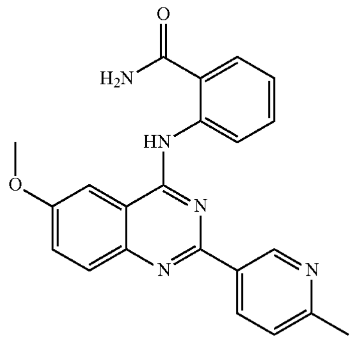 [SMILES: COc1ccc2nc(-c3ccc(C)nc3)nc(Nc3ccccc3C(N)=O)c2c1] | HCl | 385.42 | $^1$H-NMR (400 MHz, DMSO-$d_6$): δ 13.05 (s, 1H), 9.44 (d, J = 1.7 Hz, 1H), 9.16-8.91 (m, 2H), 8.03-7.89 (m, 3H), 7.88-7.82 (m, 1H), 7.75-7.68 (m, 1H), 7.67-7.60 (m, 2H), 7.25 (t, J = 7.6 Hz, 1H), 4.00 (s, 3H), 2.74 (s, 3H). | DMSO | 386.0 (M + 1) 193.4 (M/2 + 1) | Method A (TFA) | 95 | Meth-od C, G1 |
| 45 | 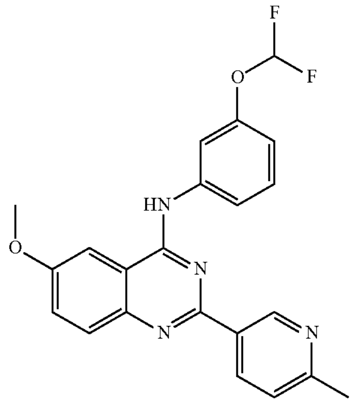 [SMILES: COc1ccc2nc(-c3ccc(C)nc3)nc(Nc3cccc(OC(F)F)c3)c2c1] | HCl | 408.4 | $^1$H-NMR (400 MHz, DMSO-$d_6$): δ 10.37-10.12 (m, 1H), 9.35 (d, J = 1.8 Hz, 1H), 8.95 (dd, J = 4.6, 3.4 Hz, 1H), 8.09 (d, J = 2.3 Hz, 1H), 7.92 (d, J = 9.1 Hz, 1H), 7.87 (s, 1H), 7.84-7.74 (m, 2H), 7.62 (dd, J = 9.1, 2.6 Hz, 1H), 7.54 (t, J = 8.2 Hz, 1H), 7.32 (t, J = 74.0 Hz, 1H), 7.05 (dd, J = 8.3, 1.9 Hz, 1H), 4.00 (s, 3H), 2.72 (s, 3H). | DMSO | 409.0 (M + 1) 205.0 (M/2 + 1) | Method A (TFA) | 95 | Meth-od C, G1 |
| 46 | 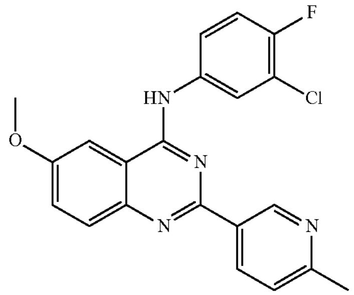 | HCl | 394.83 | $^1$H-NMR (400 MHz, DMSO-$d_6$): δ 10.27 (brs, 1H), 9.32 (d, J = 1.7 Hz, 1H), 8.93 (d, J = 7.5 Hz, 1H), 8.19 (dd, J = 6.8, 2.5 Hz, 1H), 8.07 (d, J = 2.3 Hz, 1H), 7.88-7.92 (m, 2H), 7.84 (d, J = 8.1 Hz, 1H), 7.62 (dd, J = 9.2, 2.5 Hz, 1H), 7.54 (t, J = 9.1 Hz, 1H), 4.00 (s, 3H), 2.72 (s, 3H). | DMSO | 395.0, 397.0 (M + 1) 197.8, 198.8 (M/2 + 1) | Method A (TFA) | 95 | Meth-od C, G1 |

TABLE 1-continued

| | | | | | | | | | |
|---|---|---|---|---|---|---|---|---|---|
| 47 | 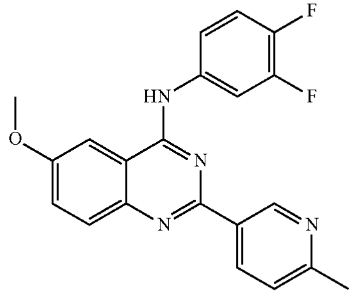 [SMILES: COc1ccc2nc(-c3ccc(C)nc3)nc(Nc3ccc(F)c(F)c3)c2c1] | HCl | 378.37 | $^1$H-NMR (400 MHz, DMSO-$d_6$): δ 10.58-10.30 (m, 1H), 9.32 (d, J = 1.9 Hz, 1H), 9.04 (d, J = 7.9 Hz, 1H), 8.17-8.04 (m, 2H), 7.95 (d, J = 9.0 Hz, 2H), 7.73-7.66 (m, 1H), 7.63 (dd, J = 9.2, 2.6 Hz, 1H), 7.60-7.50 (m, 1H), 4.01 (s, 3H), 2.76 (s, 3H). | DMSO | 379.0 (M + 1) 190.0 (M/2 + 1) | Method A (TFA) | 95 | Meth-od C, G1 |
| 48 | 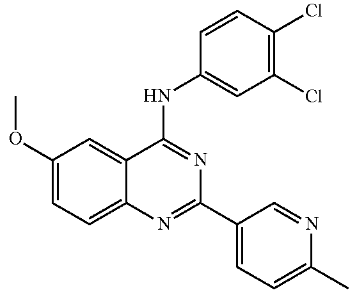 [SMILES: COc1ccc2nc(-c3ccc(C)nc3)nc(Nc3ccc(Cl)c(Cl)c3)c2c1] | HCl | 411.28 | $^1$H-NMR (400 MHz, DMSO-$d_6$): δ 10.29 (s, 1H), 9.33 (d, J = 1.7 Hz, 1H), 9.04-8.89 (m, 1H), 8.31 (d, J = 2.4 Hz, 1H), 8.07 (d, J = 2.4 Hz, 1H), 7.97 (dd, J = 8.8, 2.5 Hz, 1H), 7.91 (d, J = 9.1 Hz, 1H), 7.85 (d, J = 8.6 Hz, 1H), 7.73 (d, J = 8.8 Hz, 1H), 7.62 (dd, J = 9.1, 2.5 Hz, 1H), 4.00 (s, 3H), 2.73 (s, 3H). | DMSO | 411.0, 413.0 (M + 1) 205.0, 206.9 (M/2 + 1) | Method A (TFA) | 95 | Meth-od C, G1 |
| 49 | 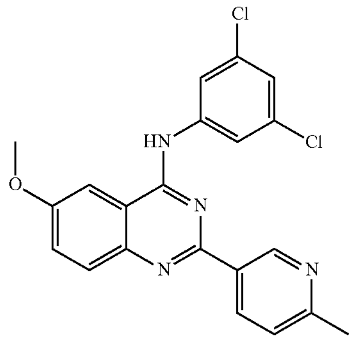 [SMILES: COc1ccc2nc(-c3ccc(C)nc3)nc(Nc3cc(Cl)cc(Cl)c3)c2c1] | | 411.28 | $^1$H-NMR (400 MHz, DMSO-$d_6$): δ 10.30 (s, 1H), 9.31 (d, J = 1.5 Hz, 1H), 8.94 (d, J = 7.3 Hz, 1H), 8.13 (d, J = 1.7 Hz, 2H), 8.07 (d, J = 2.3 Hz, 1H), 7.90 (d, J = 9.2 Hz, 1H), 7.87 (d, J = 8.5 Hz, 1H), 7.61 (dd, J = 9.1, 2.6 Hz, 1H), 7.41 (d, J = 1.7 Hz, 1H), 4.00 (s, 3H), 2.72 (s, 3H). | DMSO | 411.0, 413.0 (M + 1) | Method B (NH4HCO3) | 95 | Meth-od C, G1 |

TABLE 1-continued

| | | | | | | | | | |
|---|---|---|---|---|---|---|---|---|---|
| 50 | 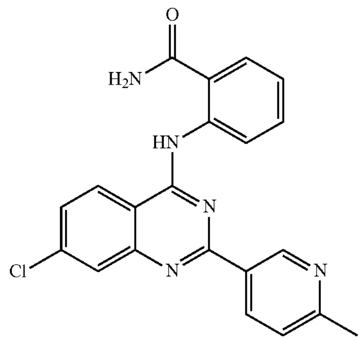 [SMILES: Cc1ccc(-c2nc(Nc3ccccc3C(N)=O)c3ccc(Cl)cc3n2)cn1] | HCl | 389.84 | $^1$H-NMR (400 MHz, DMSO-$d_6$): δ 13.09 (s, 1H), 9.38 (s, 1H), 9.16 (d, J = 8.4 Hz, 1H), 8.83 (d, J = 8.3 Hz, 1H), 8.50 (s, 1H), 8.20 (d, J = 8.8 Hz, 1H), 8.05-7.99 (m, 2H), 7.97 (d, J = 7.9 Hz, 1H), 7.92 (s, 1H), 7.81 (dd, J = 8.8, 2.0 Hz, 1H), 7.68 (t, J = 7.8 Hz, 1H), 7.28 (t, J = 7.6 Hz, 1H), 2.82 (s, 3H). | DMSO | 390.1, 392.1 (M + 1) | Method B (NH4HCO3) | 95 | Meth-od C, G1 |
| 51 | 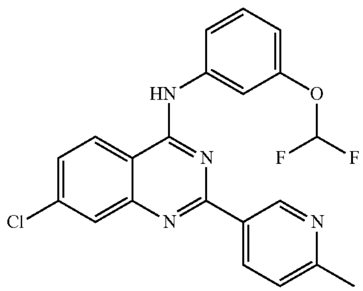 [SMILES: Cc1ccc(-c2nc(Nc3cccc(OC(F)F)c3)c3ccc(Cl)cc3n2)cn1] | HCl | 412.82 | $^1$H-NMR (400 MHz, DMSO-$d_6$): δ 10.49 (s, 1H), 9.35 (d, J = 1.7 Hz, 1H), 9.08 (dd, J = 8.3, 1.5 Hz, 1H), 8.75 (d, J = 9.0 Hz, 1H), 8.02 (d, J = 2.1 Hz, 1H), 7.97 (d, J = 8.3 Hz, 1H), 7.87 (s, 1H), 7.80 (dd, J = 9.0, 2.0 Hz, 2H), 7.53 (t, J = 8.2 Hz, 1H), 7.31 (t, J = 74.0 Hz, 1H), 7.06 (dd, J = 8.1, 2.0 Hz, 1H), 2.79 (s, 3H). | DMSO | 413.0, 415.0 (M + 1) | Method B (NH4HCO3) | 95 | Meth-od C, G1 |
| 52 | 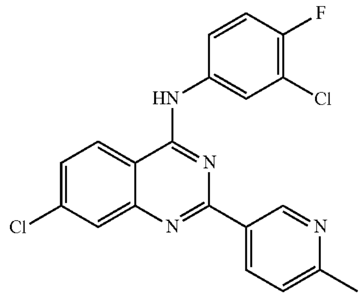 | | 399.25 | $^1$H-NMR (400 MHz, DMSO-$d_6$): δ 10.49 (s, 1H), 9.32 (d, J = 1.7 Hz, 1H), 9.00 (d, J = 8.4 Hz, 1H), 8.69 (d, J = 8.9 Hz, 1H), 8.20 (dd, J = 6.8, 2.6 Hz, 1H), 8.00 (d, J = 2.1 Hz, 1H), 7.96-7.86 (m, 2H), 7.80 (dd, J = 8.9, 2.1 Hz, 1H), 7.53 (t, J = 9.1 Hz, 1H), 2.76 (s, 3H). | DMSO | 399.0, 401.0 (M + 1) | Method B (NH4HCO3) | 95 | Meth-od C, G1 |

TABLE 1-continued

| | | | | | | | | | |
|---|---|---|---|---|---|---|---|---|---|
| 53 | 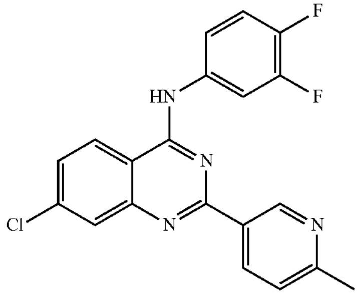 | HCl | 382.79 | $^1$H-NMR (400 MHz, DMSO-$d_6$): δ 10.55 (s, 1H), 9.32 (d, J = 1.7 Hz, 1H), 9.07 (dd, J = 8.2, 1.2 Hz, 1H), 8.73 (d, J = 8.9 Hz, 1H), 8.08 (ddd, J = 13.0, 7.5, 2.6 Hz, 1H), 8.00 (dd, J = 8.9, 5.2 Hz, 2H), 7.80 (dd, J = 8.9, 2.1 Hz, 1H), 7.71 (dd, J = 6.1, 2.9 Hz, 1H), 7.54 (dd, J = 19.7, 9.2 Hz, 1H), 2.78 (s, 3H) | DMSO | 383.0, 385.0 (M + 1) | Method B (NH4HCO3) | 95 | Meth-od C, G1 |
| 54 | 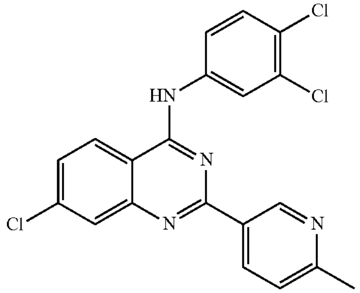 [SMILES: Cc1ccc(-c2nc(Nc3ccc(Cl)c(Cl)c3)c3ccc(Cl)cc3n2)cn1] | HCl | 415.7 | $^1$H-NMR (400 MHz, DMSO-$d_6$): δ 10.63 (s, 1H), 9.30 (d, J = 1.7 Hz, 1H), 9.07 (dd, J = 8.3, 1.8 Hz, 1H), 8.75 (d, J = 9.0 Hz, 1H), 8.29 (d, J = 2.4 Hz, 1H), 8.01 (d, J = 8.4 Hz, 1H), 7.99 (d, J = 2.1 Hz, 1H), 7.96 (dd, J = 8.3, 2.5 Hz, 1H), 7.77 (dd, J = 8.9, 2.1 Hz, 1H), 7.70 (d, J = 8.8 Hz, 1H), 2.81 (s, 3H). | DMSO | 415.0, 417.0, 419.0 (M + 1) | Method B (NH4HCO3) | 95 | Meth-od C, G1 |
| 55 | 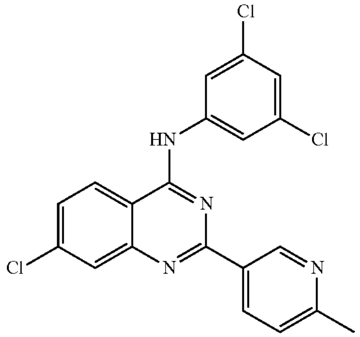 [SMILES: Cc1ccc(-c2nc(Nc3cc(Cl)cc(Cl)c3)c3ccc(Cl)cc3n2)cn1] | HCl | 415.7 | $^1$H-NMR (400 MHz, DMSO-$d_6$): δ 10.54 (s, 1H), 9.32 (s, 1H), 9.01 (dd, J = 8.0, 1.8 Hz, 1H), 8.72 (d, J = 9.0 Hz, 1H), 8.11 (d, J = 1.8 Hz, 2H), 8.01 (d, J = 2.0 Hz, 1H), 7.97 (d, J = 8.5 Hz, 1H), 7.80 (dd, J = 8.9, 2.0 Hz, 1H), 2.78 (s, 3H). | DMSO | 415.0, 417.0, 419.0 (M + 1) | Method B (NH4HCO3) | 95 | Meth-od C, G11 |

TABLE 1-continued
| | | | | | | | | | |
|---|---|---|---|---|---|---|---|---|---|
| 56 | 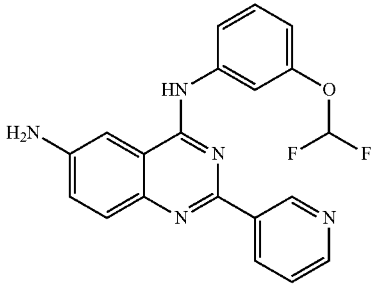 [SMILES: Nc1ccc2nc(-c3cccnc3)nc(Nc3cccc(OC(F)F)c3)c2c1] | | 379.36 | $^1$H-NMR (400 MHz, DMSO-$d_6$): δ 10.16 (s, 1H), 9.47 (s, 1H), 8.79 (dd, J = 8.9, 7.1 Hz, 2H), 7.91 (s, 1H), 7.84-7.77 (m, 2H), 7.76-7.68 (m, 1H), 7.56 (d, J = 2.1 Hz, 1H), 7.51 (t, J = 8.2 Hz, 1H), 7.39 (dd, J = 8.9, 2.2 Hz, 1H), 7.29 (t, J = 74.0 Hz, 1H), 7.00 (dd, J = 8.1, 2.1 Hz, 1H), 4.23 (brs, 2H). | DMSO | 380.1 (M + 1) | Method B (NH4HCO3) | 95 | Meth-od C, G1 |
| 57 | 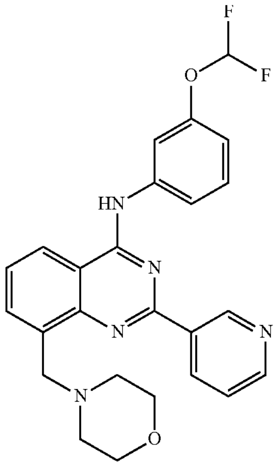 [SMILES: FC(F)Oc1cccc(Nc2nc(-c3cccnc3)nc3c(CN4CCOCC4)cccc23)c1] | HCl | 463.48 | $^1$H-NMR (400 MHz, DMSO-$d_6$): δ 10.43-10.20 (m, 2H), 9.72 (s, 1H), 8.89-8.67 (m, 3H), 8.29-8.21 (m, 1H), 7.97 (s, 1H), 7.87-7.80 (m, 1H), 7.81-7.73 (m, 1H), 7.63-7.46 (m, 2H), 7.30 (t, J = 74.0 Hz, 1H), 7.08-6.98 (m, 1H), 5.00 (s, 2H), 4.05-3.65 (m, 4H), 3.39-3.36 (m, 4H). | DMSO | 464.2 (M + 1) | Method B (NH4HCO3) | 95 | Meth-od C, G1 |
| 58 | 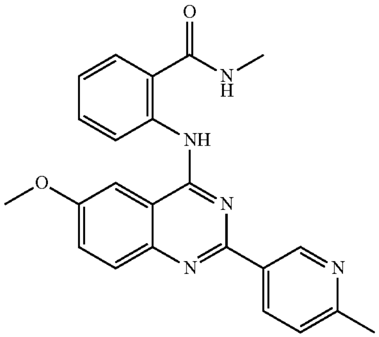 | HCl | 399.45 | $^1$H-NMR (400 MHz, DMSO-$d_6$) δ 12.53 (s, 1H), 9.30 (d, J = 1.6 Hz, 1H), 3.03-8.96 (m, 1H), 8.94-8.88 (m, 1H), 8.71 (d, J = 8.4 Hz, 1H), 7.91-7.83 (m, 3H), 7.67-7.55 (m, 3H), 7.25 (t, J = 7.2 Hz, 1H), 3.98 (s, 3H), 2.80-2.74 (m, 6H). | DMSO | 400.1 (M + 1) | Method B (NH4HCO3) | 95 | Meth-od C, G1 |

TABLE 1-continued
| | | | | | | | | | |
|---|---|---|---|---|---|---|---|---|---|
| 59 | 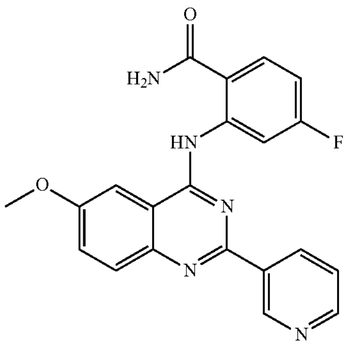 [SMILES: COc1ccc2nc(-c3cccnc3)nc(Nc3cc(F)ccc3C(N)=O)c2c1] | HCl | 389.38 | $^1$H-NMR (400 MHz, DMSO-$d_6$): δ 13.27 (s, 1H), 9.23 (s, 1H), 8.98 (d, J = 5.2 Hz, 1H), 8.91 (d, J = 8.0 Hz, 1H), 8.54 (dd, J = 12.0, 2.6 Hz, 1H), 8.48 (s, 1H), 8.07 (dd, J = 3.0, 5.6 Hz, 1H), 7.97-7.93 (m, 2H), 7.66 (d, J = 9.0 Hz, 1H), 7.37 (dd, J = 9.0, 2.4 Hz, 1H), 7.13 (d, J = 2.0 Hz, 1H), 6.91 (dt, J = 8.4, 2.6 Hz, 1H), 3.80 (s, 3H). | DMSO | 390.1 (M + 1) | Method B (NH4HCO3) | 95 | Meth-od C, G1 |
| 60 | 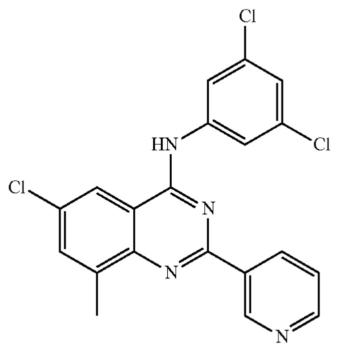 [SMILES: Cc1cc(Cl)cc2c(Nc3cc(Cl)cc(Cl)c3)nc(-c3cccnc3)nc12] | | 415.70 | $^1$H-NMR (400 MHz, DMSO-$d_6$): δ 10.13 (s, 1H), 9.48 (s, 1H), 8.87 (dd, J = 14.0, 6.2 Hz, 2H), 8.54 (d, J = 1.7 Hz, 1H), 8.10 (d, J = 1.8 Hz, 2H), 7.89-7.78 (m, 2H), 7.37 (t, J = 1.8 Hz, 1H), 2.70 (s, 3H). | DMSO | 414.9, 416.9, 419.0 (M + 1) | Method B (NH4HCO3) | 95 | Meth-od C, G1 |
| 61 | 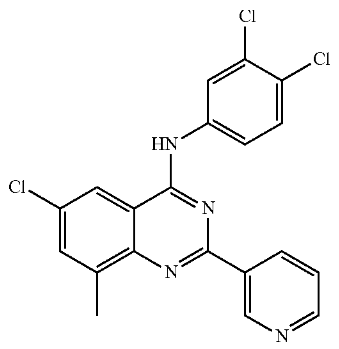 [SMILES: Cc1cc(Cl)cc2c(Nc3ccc(Cl)c(Cl)c3)nc(-c3cccnc3)nc12] | | 415.70 | $^1$H-NMR (400 MHz, DMSO-$d_6$): δ 10.10 (s, 1H), 9.44 (s, 1H), 8.86 (d, J = 7.8 Hz, 1H), 8.79 (d, J = 4.5 Hz, 1H), 8.50 (d, J = 1.7 Hz, 1H), 8.23 (d, J = 2.4 Hz, 1H), 7.89 (dd, J = 8.8, 2.4 Hz, 1H), 7.83-7.71 (m, 2H), 7.62 (d, J = 8.8 Hz, 1H), 2.62 (s, 3H) | DMSO | 414.9, 416.9, 418.9 (M + 1) | Method B (NH4HCO3) | 95 | Meth-od C, G1 |

TABLE 1-continued
| | | | | | | | | |
|---|---|---|---|---|---|---|---|---|
| 62 | 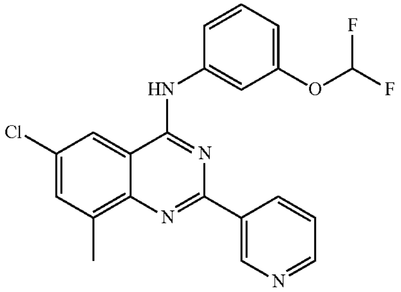 [SMILES: Cc1cc(Cl)cc2c(Nc3cccc(OC(F)F)c3)nc(-c3cccnc3)nc12] | 412.82 | $^1$H-NMR (400 MHz, DMSO-$d_6$): δ: 10.02 (s, 1H), 9.58 (d, J = 1.8 Hz, 1H), 8.76-8.67 (m, 2H), 8.59 (d, J = 1.8 Hz, 1H), 7.96 (s, 1H), 7.82 (d, J = 6.6 Hz, 2H), 7.54 (ddd, J = 16.4, 10.0, 6.4 Hz, 2H), 7.30 (t, J = 74.0 Hz, 1H), 7.01 (dd, J = 8.0, 2.0 Hz, 1H), 2.74 (s. 3H). | DMSO | 413.0, 415.0 (M + 1) | Method B (NH4HCO3) | 95 | Meth-od C, G1 |
| 63 | 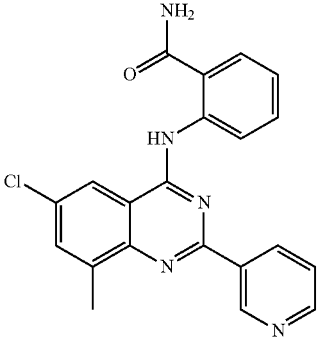 [SMILES: Cc1cc(Cl)cc2c(Nc3ccccc3C(N)=O)nc(-c3cccnc3)nc12] | 389.84 | $^1$H-NMR (400 MHz, DMSO-$d_6$): δ 13.15 (s, 1H), 9.58 (s, 1H), 9.03 (d, J = 0.8 Hz, 1H), 8.78-8.84 (m, 2H), 8.50 (s, 1H), 7.95-8.03 (m, 3H), 7.80 (s, 1H), 7.70-7.74 (m, 2H), 7.23 (d, J = 7.2 Hz, 1H), 2.70 (s, 3H). | DMSO | 391.0, 392.0 (M + 1) | Method B (NH4HCO3) | 95 | Meth-od C, G1 |
| 64 | 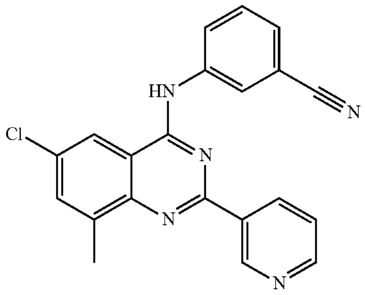 [SMILES: Cc1cc(Cl)cc2c(Nc3cccc(C#N)c3)nc(-c3cccnc3)nc12] | 371.82 | $^1$H-NMR (400 MHz, DMSO-$d_6$): δ 10.31 (s, 1H), 9.48 (d, J = 1.2 Hz, 1H), 9.01 (d, J = 8.4 Hz, 1H), 8.90 (d, J = 4.6 Hz, 1H), 8.61 (d, J = 1.6 Hz, 1H), 8.33 (s, 1H), 8.27 (dd, J = 6.0, 2.0 Hz, 1H), 7.95-7.63 (m, 3H), 2.70 (s, 3H). | DMSO | 372.0 373.1 (M + 1) | Method B (NH4HCO3) | 95 | Meth-od C, G1 |

TABLE 1-continued
| | | | | | | | | |
|---|---|---|---|---|---|---|---|---|
| 65 | 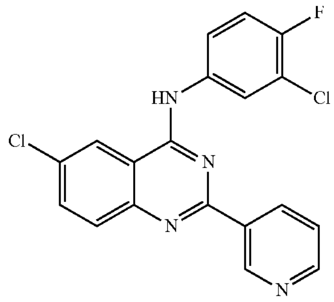 [SMILES: Fc1ccc(Nc2nc(-c3cccnc3)nc3ccc(Cl)cc23)cc1Cl] | 476.67 | $^1$H-NMR (400 MHz, DMSO-$d_6$): δ 10.28 (s, 1H), 9.46 (d, J = 1.2 Hz, 1H), 9.01 (d, J = 1.2 Hz, 1H), 8.83 (dd, J = 8.4, 1.6 Hz, 2H), 8.19-8.14 (m, 2H), 7.89-7.49 (m, 2H). | DMSO | 476.9, 478.9 (M + 1) | Method B (NH4HCO3) | 95 | Meth-od C, G1 |
| 66 | 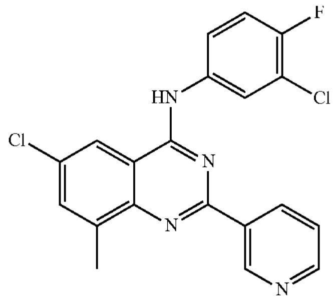 [SMILES: Cc1cc(Cl)cc2c(Nc3ccc(F)c(Cl)c3)nc(-c3cccnc3)nc12] | 399.25 | $^1$H-NMR (400 MHz, DMSO-$d_6$): δ 10.03 (s, 1H), 8.54 (s, 1H), 8.71-8.67 (m, 2H), 8.53 (s, 1H), 8.26 (dd, J = 6.8 Hz, 2.4 Hz, 1H), 7.83 (s, 1H), 7.58-7.52 (m, 2H), 2.72 (s, 3H). | DMSO | 399.0, 401.0 (M + 1) | Method B (NH4HCO3) | 95 | Meth-od C, G1 |
| 67 | 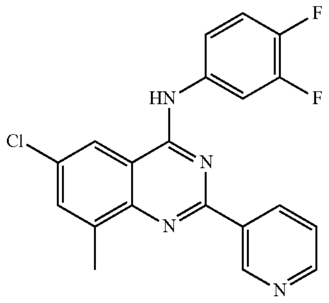 [SMILES: Cc1cc(Cl)cc2c(Nc3ccc(F)c(F)c3)nc(-c3cccnc3)nc12] | 382.79 | $^1$H-NMR (400 MHz, DMSO-$d_6$): δ 10.04 (s, 1H), 9.51 (d, J = 1.2 Hz, 1H), 8.72-8.69 (m, 2H), 8.53 (d, J = 2.0 Hz, 1H), 8.08 (ddd, J = 9.2, 7.6, 2.4 Hz, 1H), 7.79-7.48 (m, 4H), 2.69 (s, 3H). | DMSO | 383.0, 385.0 (M + 1) | Method B (NH4HCO3) | 95 | Meth-od C, G1 |

TABLE 1-continued
| | | | | | | | | | |
|---|---|---|---|---|---|---|---|---|---|
| 68 | 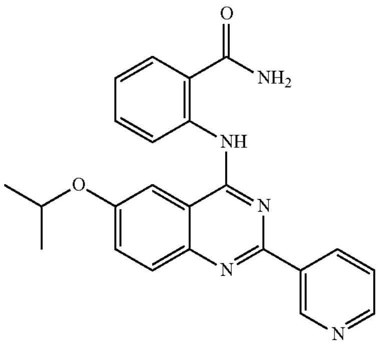 [SMILES: CC(C)Oc1ccc2nc(-c3cccnc3)nc(Nc3ccccc3C(N)=O)c2c1] | HCl | 399.45 | $^1$H-NMR (400 MHz, DMSO-d6): δ 13.02 (s, 1H), 9.59 (s, 1H) , 9.09 (d, J = 8.0 Hz, 1H), 8.96 (d, J = 8.4 Hz, 1H) , 8.91 (d, J = 4.61 Hz, 1H), 8.48 (s, 1H), 7.97 (dd, J = 8.0, 2.8 Hz, 4H), 7.72 (t, J = 7.6 Hz, 1H), 7.64-7.61 (m, 2H), 7.26 (t, J = 7.6 Hz, 1H), 4.88-4.82 (m, 1H), 1.43 (d, J = 6.0 Hz, 6H). | DMSO | 400.1 (M + 1) | Method B (NH4HCO3) | 95 | Meth-od C, G1 |
| 69 | 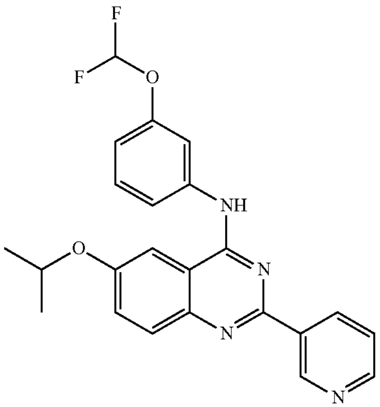 [SMILES: CC(C)Oc1ccc2nc(-c3cccnc3)nc(Nc3cccc(OC(F)F)c3)c2c1] | HCl | 422.43 | $^1$H-NMR (400 MHz, DMSO-$d_6$): δ 10.63 (s, 1H), 9.51 (s, 1H), 9.09 (d, J = 7.6 Hz, 1H), 8.91 (d, J = 7.6 Hz, 1H), 8.23 (s, 1H), 8.03-7.97 (m, 1H), 7.83-7.80 (m, 2H), 7.64 (dd, J = 9.2, 2.4 Hz, 1H), 7.55 (t, J = 8.1 Hz, 1H), 7.32 (t, J = 74.0 Hz, 1H), 7.08 (d, J = 7.4 Hz, 1H), 5.02-4.97 (m, 1H), 1.39 (d, J = 6.0 Hz, 6H). | DMSO | 423.0 (M + 1) | Method B (NH4HCO3) | 95 | Meth-od C, G1 |
| 70 | 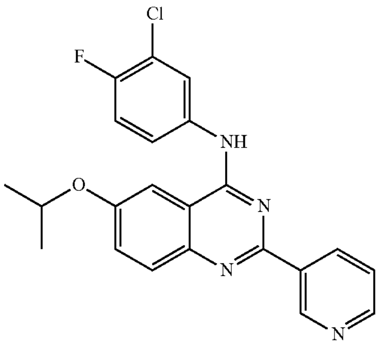 [SMILES: CC(C)Oc1ccc2nc(-c3cccnc3)nc(Nc3ccc(F)c(Cl)c3)c2c1] | HCl | 408.86 | $^1$H-NMR (400 MHz, DMSO-$d_6$): δ 10.61 (s, 1H), 9.48 (s, 1H), 9.05 (d, J = 7.2 Hz, 1H), 8.93 (d, J = 5.2 Hz, 1H), 8.19-8.15 (m, 2H), 8.01-7.92 (m, 3H), 7.63-7.53 (m, 2H), 5.01-4.94 (m, 1H), 1.39 (d, J = 6.0 Hz, 6H). | DMSO | 409.1, 411.1 (M + 1) | Method B (NH4HCO3) | 95 | Meth-od C, G1 |

TABLE 1-continued
| | | | | | | | | | |
|---|---|---|---|---|---|---|---|---|---|
| 71 | 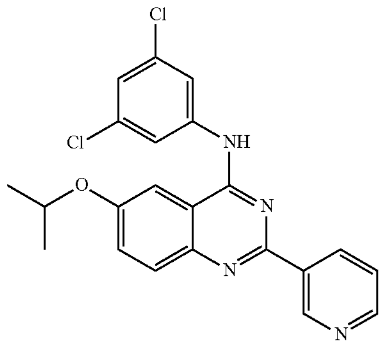 [SMILES: CC(C)Oc1ccc2nc(-c3cccnc3)nc(Nc3cc(Cl)cc(Cl)c3)c2c1] | HCl | 425.31 | $^1$H NMR (400 MHz, DMSO-$d_6$): δ 9.92 (s, 1H), 9.52 (d, J = 1.2 Hz, 1H), 8.70-8.66 (m, 2H), 8.17 (d, J = 1.6 Hz, 2H), 7.98 (d, J = 2.4 Hz, 1H), 7.88 (d, J = 8.8 Hz, 1H), 7.60-7.56 (m, 2H), 7.39 (t, J = 1.8 Hz, 1H), 4.94-4.88 (m, 1H), 1.39 (d, J = 6.0 Hz, 6H). | DMSO | 424.9, 426.9 (M + 1) | Method B (NH4HCO3) | 95 | Meth-od C, G1 |
| 72 | 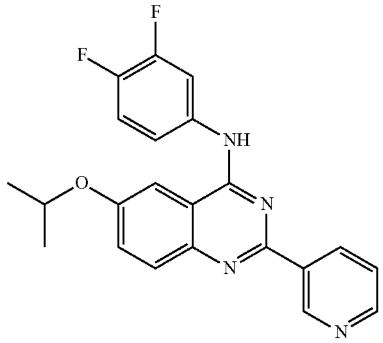 | HCl | 392.4 | $^1$H-NMR (400 MHz, DMSO-$d_6$): δ 10.28 (s, 1H), 9.49 (d, J = 1.2 Hz, 1H), 8.93 (d, J = 8.0 Hz, 1H), 8.86-8.84 (m, 1H), 8.10-8.05 (m, 2H), 7.93-7.85 (m, 2H), 7.71-7.69 (m, 2H), 7.61-7.52 (m, 1H), 4.97-4.91 (m, 1H), 1.39 (d, J = 6.0 Hz, 6H). | DMSO | 393.0 (M + 1) | Method B (NH4HCO3) | 95 | Meth-od C, G1 |
| 73 | 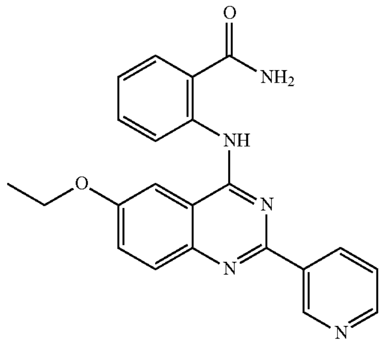 [SMILES: CCOc1ccc2nc(-c3cccnc3)nc(Nc3ccccc3C(N)=O)c2c1] | HCl | 385.42 | $^1$H-NMR (400 MHz, DMSO-$d_6$): δ 13.03 (s, 1H), 9.53 (d, J = 1.2 Hz, 1H), 9.10 (d, J = 3.4 Hz, 1H), 8.93-8.90 (m, 2H), 8.49 (s, 1H), 8.01-7.91 (m, 4H), 7.69 (t, J = 7.6 Hz, 1H), 7.59-7.54 (m, 2H), 7.24 (t, J = 7.6 Hz, 1H), 4.21 (q, J = 6.8 Hz, 2H), 1.46 (t, J = 6.9 Hz, 3H). | DMSO | 386.1 (M + 1) | Method B (NH4HCO3) | 95 | Meth-od C, G1 |

TABLE 1-continued
| | | | | | | | | | |
|---|---|---|---|---|---|---|---|---|---|
| 74 | 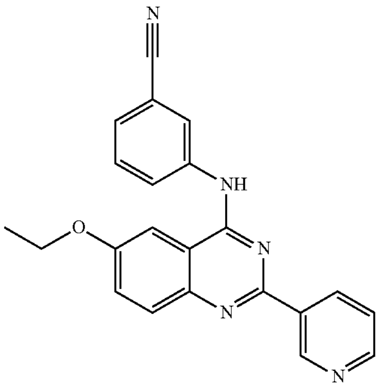 [SMILES: CCOc1ccc2nc(-c3cccnc3)nc(Nc3cccc(C#N)c3)c2c1] | HCl | 367.4 | $^1$H-NMR (400 MHz, DMSO-$d_6$): δ 10.35 (s, 1H), 9.49 (s, 1H), 8.95 (d, J = 7.6 Hz, 1H), 8.85 (d, J = 4.8 Hz, 1H), 8.37 (s, 1H), 8.28 (d, J = 7.6 Hz, 1H), 8.08 (s, 1H), 7.94-7.85 (m, 2H), 7.73-7.60 (m, 3H), 4.28 (q, J = 6.8 Hz, 2H), 1.46 (t, J = 6.8 Hz, 3H). | DMSO | 368.1 (M + 1) | Method B (NH4HCO3) | 95 | Meth-od C, G1 |
| 75 | 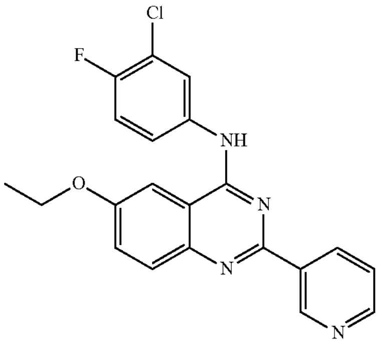 [SMILES: CCOc1ccc2nc(-c3cccnc3)nc(Nc3ccc(F)c(Cl)c3)c2c1] | HCl | 394.83 | $^1$H-NMR (400 MHz, DMSO-$d_6$): δ 10.64 (s, 1H), 9.44 (s, 1H), 8.99 (d, J = 8.4 Hz, 1H), 8.91 (d, J = 4.4 Hz, 1H), 8.17 (d, J = 3.2 Hz, 2H), 7.59-7.50 (m, 2H), 4.26 (q, J = 8.8 Hz, 2H), 1.44 (t, J =- 6.8 Hz, 3H). | DMSO | 395.1 397.1 (M + 1) | Method B (NH4HCO3) | 95 | Meth-od C, G1 |
| 76 | 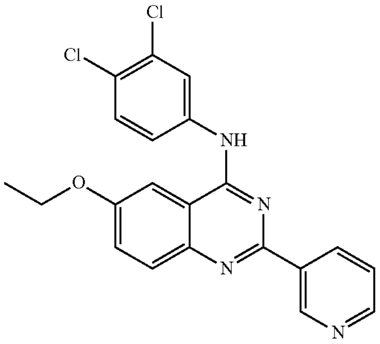 [SMILES: CCOc1ccc2nc(-c3cccnc3)nc(Nc3ccc(Cl)c(Cl)c3)c2c1] | HCl | 411.28 | $^1$H-NMR (400 MHz, DMSO-$d_6$): δ 10.48 (s, 1H), 9.47 (s, 1H), 9.02 (d, J = 7.6 Hz, 1H), 8.91 (d, J = 4.4 Hz, 1H), 8.28 (d, J = 1.6 Hz, 1H), 8.13 (s, 1H), 8.01-7.91 (m, 3H), 7.72 (d, J = 8.8 Hz, 1H), 7.59-7.57 (m, 1H), 4.26 (q, J = 6.8 Hz, 2H), 1.44 (t, J = 6.8 Hz, 3H). | DMSO | 411.0 413.0 415.0 (M + 1) | Method B (NH4HCO3) | 95 | Meth-od C, G1 |

TABLE 1-continued
| | | | | | | | | | |
|---|---|---|---|---|---|---|---|---|---|
| 77 | 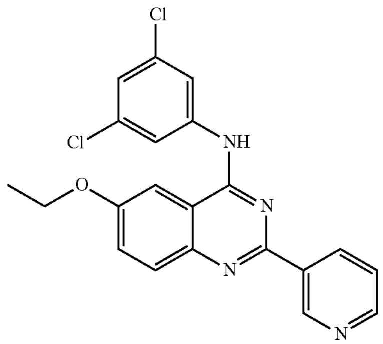 [SMILES: CCOc1ccc2nc(-c3cccnc3)nc(Nc3cc(Cl)cc(Cl)c3)c2c1] | HCl | 411.28 | $^1$H-NMR (400 MHz, DMSO-$d_6$): δ 10.23 (s, 1H), 9.48 (s, 1H), 8.93 (d, J = 8.0 Hz, 1H), 8.85 (d, J = 4.8 Hz, 1H), 8.14 (s, 2H), 8.05 (d, J = 1.6 Hz, 1H), 7.92-7.85 (m, 2H), 7.61 (dd, J = 9.1, 1.8 Hz, 1H), 7.41 (s, 1H), 4.26 (q, J = 6.8 Hz, 2H), 1.45 (t, J = 6.8 Hz, 3H). | DMSO | 411.0 413.1 415.0 (M + 1) | Method B (NH4HCO3) | 95 | Meth-od C, G1 |
| 78 | 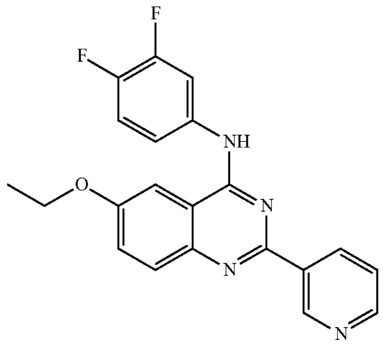 [SMILES: CCOc1ccc2nc(-c3cccnc3)nc(Nc3ccc(F)c(F)c3)c2c1] | HCl | 378.37 | $^1$H-NMR (400 MHz, DMSO-$d_6$): δ 10.39 (s, 1H), 9.49 (s, 1H), 8.98 (d, J = 8.0 Hz, 1H), 8.88 (d, J = 4.8 Hz, 1H), 8.11-8.05 (m, 2H), 7.95-7.91 (m, 2H), 7.72-7.52 (m, 3H), 4.28 (q, J = 6.8 Hz, 2H), 1.45 (t, J = 6.8 Hz, 3H). | DMSO | 379.1 (M + 1) | Method B (NH4HCO3) | 95 | Meth-od C, G1 |
| 79 | 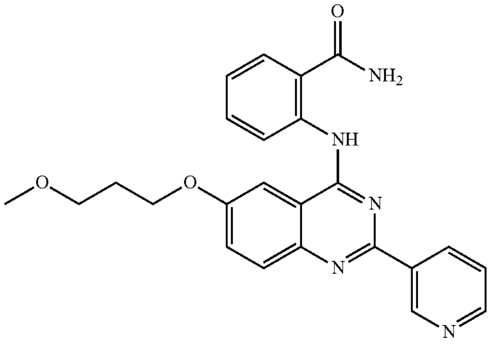 [SMILES: COCCCOc1ccc2nc(-c3cccnc3)nc(Nc3ccccc3C(N)=O)c2c1] | HCl | 429.47 | $^1$H-NMR (400 MHz, DMSO-$d_6$): δ 12.99 (s, 1H), 9.59 (d, J = 1.6 Hz, 1H), 9.14 (d, J = 7.6 Hz, 1H), 8.75-8.69 (m, 2H), 8.48 (s, 1H), 7.99-7.96 (m, 2H), 7.90 (d, J = 8.8 Hz, 1H), 7.76-7.72 (m, 1H), 7.61-7.56 (m, 3H), 7.22-7.19 (m, 1H), 4.24 (t, J = 6.0 Hz, 2H), 3.56 (t, J = 6.0 Hz, 2H), 3.28 (s, 3H), 2.11-2.04 (m, 2H). | DMSO | 430.1 (M + 1) | Method B (NH4HCO3) | 95 | Meth-od C, G1 |

TABLE 1-continued
| | | | | | | | | | |
|---|---|---|---|---|---|---|---|---|---|
| 80 | 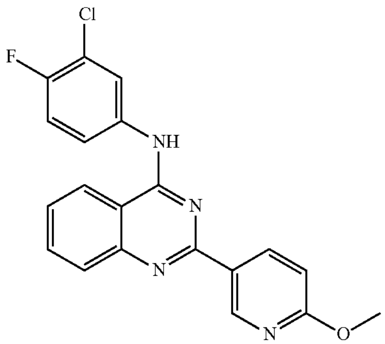 [SMILES: COc1ccc(-c2nc(Nc3ccc(F)c(Cl)c3)c3ccccc3n2)cn1] | HCl | 380.80 | $^1$H-NMR (400 MHz, DMSO-$d_6$): δ 11.67 (s, 1H), 9.18 (d, J = 2.0 Hz, 1H), 8.90 (d, J = 8.4 Hz, 1H), 8.66 (dd, J = 8.8, 2.4 Hz, 1H), 8.35 (d, J = 8.4 Hz, 1H), 8.14-8.08 (m, 2H), 7.90-7.81 (m, 2H), 7.62 (t, J = 9.2 Hz, 1H), 7.09 (d, J = 8.8 Hz, 1H), 3.98 (s, 3H). | DMSO | 380.9, 382.9 (M + 1) | Method A (TFA) | 95 | Meth-od C, G1 |
| 81 | 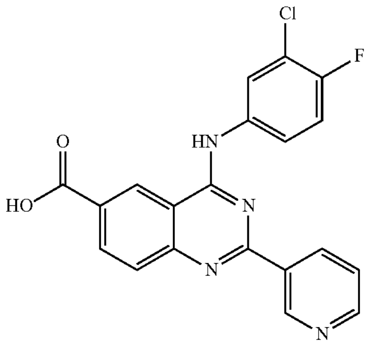 [SMILES: O=C(O)c1ccc2nc(-c3cccnc3)nc(Nc3ccc(F)c(Cl)c3)c2c1] | HCl | 394.79 | $^1$H-NMR (400 MHz, DMSO-$d_6$): δ 10.81 (s, 1H), 9.49 (d, J = 1.2 Hz, 1H), 9.28 (d, J = 0.8 Hz, 1H), 9.15 (d, J = 8.0 Hz, 1H), 9.02 (d, J = 5.2 Hz, 1H), 8.37- 8.34 (m, 1H), 8.12-8.09 (m, 2H), 8.01 (d, J = 8.4 Hz, 1H), 7.95-7.91 (m, 1H), 7.53 (t, J = 9.0 Hz, 1H). | DMSO | 395.0, 397.0 (M + 1) | Method B ($NH_4HCO_3$) | 95 | Meth-od C, G1 |
| 82 | 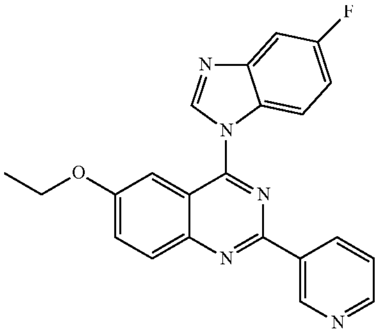 [SMILES: CCOc1ccc2nc(-c3cccnc3)nc(-n3cnc4cc(F)ccc43)c2c1] | | 385.39 | $^1$H-NMR (400 MHz, DMSO-$d_6$): δ 9.63 (d, J = 1.6 Hz, 1H), 9.13 (s, 1H), 8.80-8.75 (m, 2H), 8.21 (d, J = 9.2 Hz, 1H), 7.97-7.94 (m, 1H), 7.82 (dd, J = 9.2, 2.8 Hz, 1H), 7.73 (dd, J = 9.2, 2.4 Hz, 1H), 7.64-7.61 (m, 1H), 7.38-7.32 (m, 2H), 4.18 (q, J = 6.8 Hz, 2H), 3.19 (t, J = 7.0 Hz, 3H). | DMSO | 386.1 (M + 1) | Method B ($NH_4HCO_3$) | 95 | Meth-od C, G10 |

TABLE 1-continued
| | | | | | | | | | |
|---|---|---|---|---|---|---|---|---|---|
| 83 | 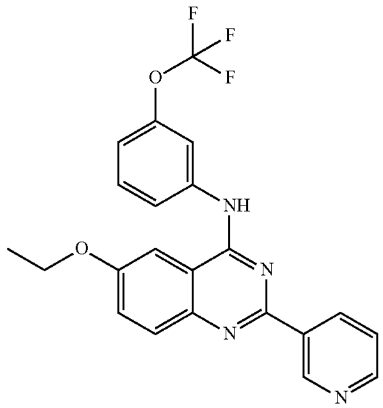 [SMILES: CCOc1ccc2nc(-c3cccnc3)nc(Nc3cccc(OC(F)(F)F)c3)c2c1] | HCl | 426.39 | $^1$H-NMR (400 MHz, DMSO-$d_6$): δ 10.43 (s, 1H), 9.49 (d, J = 1.6 Hz, 1H), 8.99 (d, J = 8.0 Hz, 1H), 8.89 (dd, J = 9.2, 1.6 Hz, 1H), 8.13 (d, J = 2.4 Hz, 1H), 8.05 (s, 1H), 7.97-7.89 (m, 3H), 7.65-7.61 (m, 2H), 7.23 (d, J = 8.4 Hz, 1H), 4.29 (q, J = 6.8 Hz, 2H), 1.46 (t, J = 7.2 Hz, 3H). | DMSO | 427.1 (M + 1) | Method B ($NH_4HCO_3$) | 95 | Meth-od C, G1 |
| 84 | 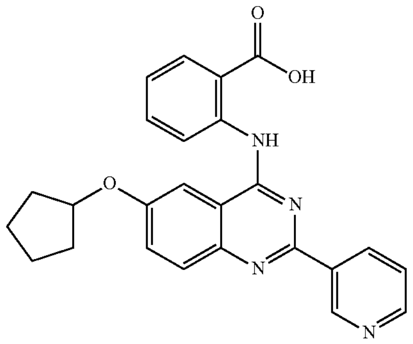 [SMILES: O=C(O)c1ccccc1Nc1nc(-c2cccnc2)nc2ccc(OC3CCCC3)cc12] | | 426.47 | $^1$H-NMR (400 MHz, DMSO-$d_6$): δ 12.00 (s, 1H), 9.55 (s, 1H), 9.12 (d, J = 8.0 Hz, 1H), 8.94 (d, J = 4.8 Hz, 1H), 8.84 (d, J = 8.4 Hz, 1H), 8.11-8.09 (m, 1H), 8.02-7.99 (m, 1H), 7.96 (d, J = 9.2 Hz, 1H), 7.82-7.11 (m, 1H), 7.65 (s, 1H); 7.62-7.59 (m, 1H), 7.30 (t, J = 7.2, Hz, 1H), 5.06-5.03 (m, 1H), 2.15-2.09 (m, 2H), 1.86-1.74 (m, 4H), 1.68-1.65 (m, 2H) | DMSO | 427.0 (M + 1) | Method B ($NH_4HCO_3$) | 95 | Meth-od C, G1 |
| 85 | 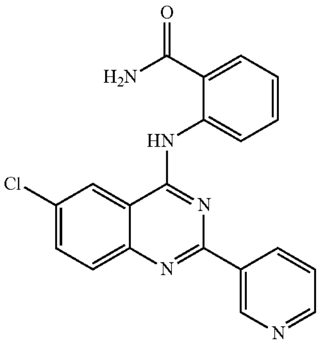 [SMILES: NC(=O)c1ccccc1Nc1nc(-c2cccnc2)nc2ccc(Cl)cc12] | | 375.81 | 1H-NMR (400 MHz, DMSO-d6): δ 13.09 (s, 1H), 9.58 (s, 1H), 9.12 (d, J = 8.4 Hz, 1H), 8.94 (d, J = 4.4 Hz, 1H), 8.88 (d, J = 8.4 Hz, 1H), 8.50 (s, 1H), 8.25 (s, 1H), 8.01-7.96 (m, 5H), 7.71 (t, J = 8.0 Hz, 1H), 7.27 (t, J = 8.0 Hz, 1H). | DMSO | 376.0, 378.0 (M + 1) 397.9 (M + 23) 188.4 (M/2 + 1) | Method A (TFA) | 95 | Meth-od C, G1 |

TABLE 1-continued
| | | | | | | | | |
|---|---|---|---|---|---|---|---|---|
| 86 | 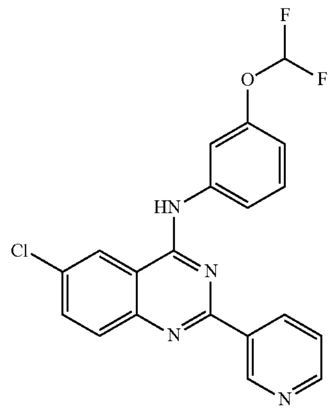 [SMILES: FC(F)Oc1cccc(Nc2nc(-c3cccnc3)nc3ccc(Cl)cc23)c1] | 398.79 | $^1$H-NMR (400 MHz, DMSO-$d_6$): δ 10.10 (s, 1H), 9.54 (s, 1H), 8.78 (s, 1H), 8.71-8.67 (m, 2H), 7.96 (s, 1H), 7.91 (d, J = 8.0 Hz, 2H), 7.82 (d, J = 8.0 Hz, 1H), 7.56-7.51 (m, 2H), 7.30 (t, J = 74.0 Hz, 1H), 7.01 (dd, J = 2.0, 8.0 Hz, 1H). | DMSO | 399.0, 401.0 (M + 1) 199.9, 200.8 (M/2 + 1) | Method A (TFA) | 95 | Meth-od C, G1 |
| 87 | 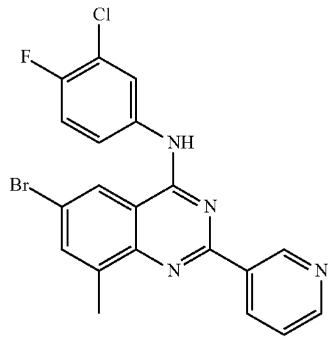 [SMILES: Cc1cc(Br)cc2c(Nc3ccc(F)c(Cl)c3)nc(-c3cccnc3)nc12] | 443.7 | $^1$H-NMR (400 MHz, DMSO-$d_6$): δ 10.09 (s, 1H), 9.39 (s, 1H), 8.93 (d, J = 8.4 Hz, 1H), 8.90 (d, J = 5.6 Hz, 1H), 8.62 (d, J = 1.6 Hz, 1H), 8.11 (dd, J = 6.8, 2.4 Hz, 1H), 7.95-7.91 (m, 1H), 7.89-7.85 (m, 1H), 7.80 (s, 1H), 7.45 (t, J = 8.8 Hz, 1H), 2.66 (s, 3H). | DMSO | 443.0, 445.0, 447.0 (M + 1) | Method B ($NH_4HCO_3$) | 98 | Meth-od C, G1 |
| 88 | 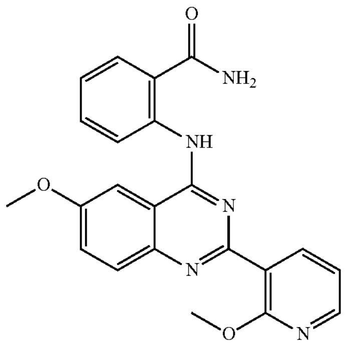 [SMILES: COc1ccc2nc(-c3cccnc3OC)nc(Nc3ccccc3C(N)=O)c2c1] | 401.42 | $^1$H-NMR (400 MHz, DMSO-$d_6$): δ 13.19 (s, 1H), 9.43 (d, J = 8.0 Hz, 1H), 8.53 (s, 1H), 8.31 (dd, J = 4.8, 1.6 Hz, 1H), 8.26 (dd, J = 1.6, 7.2 Hz, 1H), 8.03 (s, 1H), 7.96-7.89 (m, 1H), 7.86 (d, J = 9.2 Hz, 1H), 7,65-7.54 (m, 3H), 7.18-7.12 (m, 2H), 4.02 (s, 3H), 3.98 (s, 3H). | DMSO | 402.1 (M + 1) | Method B ($NH_4HCO_3$) | 95 | Meth-od C, G1 |

TABLE 1-continued

| | | | | | | | | | |
|---|---|---|---|---|---|---|---|---|---|
| 89 | 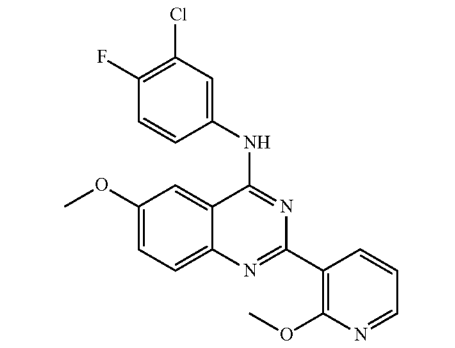 [SMILES: COc1ccc2nc(-c3cccnc3OC)nc(Nc3ccc(F)c(Cl)c3)c2c1] | | 410.83 | $^1$H-NMR (400 MHz, DMSO-$d_6$): δ 9.79 (s, 1H), 8.52 (dd, J = 2.4, 7.2 Hz, 1H), 8.28 (dd, J = 5.6, 2.4 Hz, 1H), 8.12 (dd, J = 2.4, 5.2 Hz, 1H), 7.98-7.94 (m, 2H), 7.82 (d, J = 9.2 Hz, 1H), 7.56 (dd, J = 9.2, 2.8 Hz, 1H), 7.47 (t, J = 9.2 Hz, 1H), 7.14-7.11 (m, 1H), 4.00 (s, 3H), 3.9 (s, 3H). | DMSO | 411.1, 413.1 (M + 1) | Method B ($NH_4HCO_3$) | 95 | Meth-od C, G1 |
| 90 | 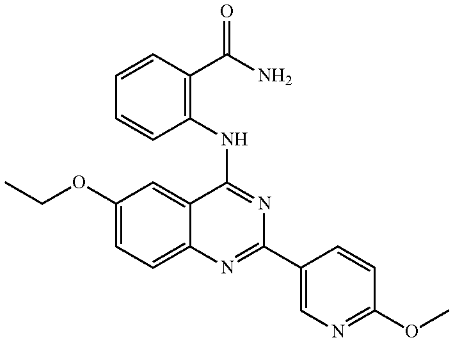 [SMILES: CCOc1ccc2nc(-c3ccc(OC)nc3)nc(Nc3ccccc3C(N)=O)c2c1] | | 415.44 | $^1$H-NMR (400 MHz, DMSO-$d_6$): δ 13.03 (s, 1H), 9.21 (d, J = 2.2 Hz, 1H), 9.16 (d, J = 7.9 Hz, 1H), 8.67 (dd, J = 8.7, 2.4 Hz, 1H), 8.50 (s, 1H), 8.02 (s, 1H), 7.99-7.93 (m, 1H), 7.84 (d, J = 8.9 Hz, 1H), 7.78-7.72 (m, 1H), 7.56 (dd, J = 11.2, 2.1 Hz, 2H), 7.19 (t, J = 7.2 Hz, 1H), 6.99 (d, J = 8.8 Hz, 1H), 4.24 (q, J = 6.9 Hz, 2H), 3.96 (s, 3H), 1.46 (t, J = 6.9 Hz, 3H). | DMSO | 416.1 (M + 1) | Method B ($NH_4HCO_3$) | 95 | Meth-od D, G1 |
| 91 | 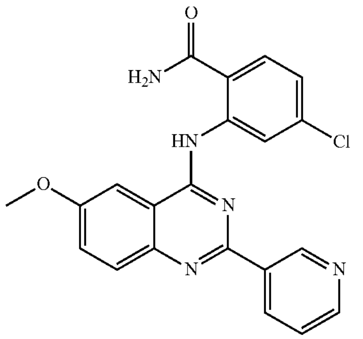 [SMILES: COc1ccc2nc(-c3cccnc3)nc(Nc3cc(Cl)ccc3C(N)=O)c2c1] | HCl | 405.84 | $^1$H-NMR (400 MHz, DMSO-$d_6$): δ 13.28 (s, 1H), 9.55 (d, J = 1.7 Hz, 1H), 9.31 (d, J = 2.1 Hz, 1H), 8.90 (d, J = 8.3 Hz, 1H), 8.83 (dd, J = 5.0, 1.4 Hz, 1H), 8.58 (s, 1H), 8.12 (s, 1H), 8.01 (d, J = 8.6 Hz, 1H), 7.93 (d, J = 9.1 Hz, 1H), 7.82 (dd, J = 7.9, 5.0 Hz, 1H), 7.63 (dd, J = 9.1, 2.6 Hz, 1H), 7.54 (d, J = 2.5 Hz, 1H), 7.30 (dd, J = 8.5, 2.2 Hz, 1H), 3.98 (s, 3H). | DMSO | 406.0, 408.0 (M + 1) | Method A (TFA) | 95 | Meth-od C, G1 |

TABLE 1-continued

| | | | | | | | | | |
|---|---|---|---|---|---|---|---|---|---|
| 92 | 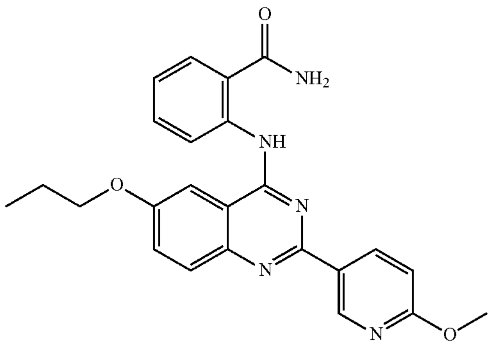 [SMILES: CCCOc1ccc2nc(-c3ccc(OC)nc3)nc(Nc3ccccc3C(N)=O)c2c1] | | 429.47 | $^1$H-NMR (400 MHz, DMSO-$d_6$): δ 12.99 (s, 1H), 9.21 (d, J = 2.0 Hz, 1H), 9.14 (d, J = 8.4 Hz, 1H), 8.67 (dd, J = 8.7, 2.3 Hz, 1H), 8.49 (s, 1H), 8.05-7.90 (m, 2H), 7.85 (d, J = 9.0 Hz, 1H), 7.75 (t, J = 7.2 Hz, 1H), 7.67-7.47 (m, 2H), 7.20 (t, J = 7.5 Hz, 1H), 6.99 (d, J = 8.8 Hz, 1H), 4.15 (t, J = 6.3 Hz, 2H), 3.96 (s, 3H), 1.07 (t, J = 7.4 Hz, 3H), 1.86 (dd, J = 14.0, 6.7 Hz, 2H). | DMSO | 430.1 (M + 1) | Method B ($NH_4HCO_3$) | 95 | Meth-od C, G1 |
| 93 | 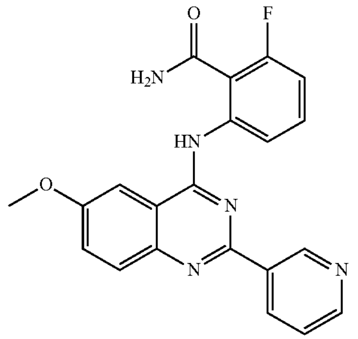 [SMILES: COc1ccc2nc(-c3cccnc3)nc(Nc3cccc(F)c3C(N)=O)c2c1] | HCl | 389.38 | $^1$H-NMR (400 MHz, DMSO-$d_6$): δ 11.34 (s, 1H), 9.52 (d, J = 1.7 Hz, 1H), 8.99 (d, J = 7.8 Hz, 1H), 8.85 (dd, J = 5.2, 1.3 Hz, 1H), 8.22 (d, J = 8.1 Hz, 1H), 8.11-8.00 (m, 2H), 7.95 (d, J = 9.1 Hz, 1H), 7.87 (dd, J = 7.9, 5.3 Hz, 1H), 7.77-7.59 (m, 3H), 7.27-7.16 (m, 1H), 3.99 (s, 3H). | DMSO | 390.1 (M + 1) | Method B ($NH_4HCO_3$) | 95 | Meth-od C, G1 |
| 94 | 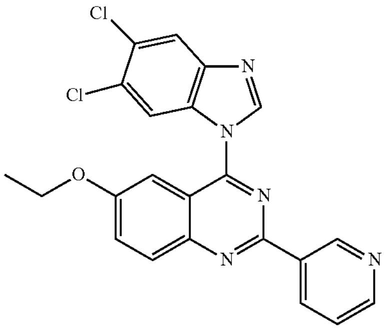 [SMILES: CCOc1ccc2nc(-c3cccnc3)nc(-n3cnc4cc(Cl)c(Cl)cc43)c2c1] | | 436.29 | $^1$H-NMR (400 MHz, DMSO-$d_6$): δ 9.62 (s, 1H), 9.17 (s, 1H), 8.77 (d, J = 8.0 Hz, 1H), 8.76 (d, J = 4.0 Hz, 1H), 8.26-8.07 (m, 3H), 7.83 (dd, J = 9.1, 2.5 Hz, 1H), 7.63 (dd, J = 7.5, 5.0 Hz, 1H), 7.36 (d, J = 2.4 Hz, 1H), 4.18 (q, J = 6.8 Hz, 2H), 1.39 (t, J = 6.9 Hz, 3H). | DMSO | 436.1, 438.0 (M + 1) | Method B ($NH_4HCO_3$) | 95 | Meth-od C, G1 |

TABLE 1-continued
| | | | | | | | | |
|---|---|---|---|---|---|---|---|---|
| 95 | 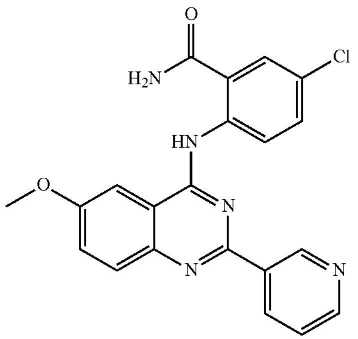 [SMILES: COc1ccc2nc(-c3cccnc3)nc(Nc3ccc(Cl)cc3C(N)=O)c2c1] | 405.84 | $^1$H-NMR (400 MHz, DMSO-$d_6$): δ 12.93 (s, 1H), 9.58 (s, 1H), 9.16 (d, J = 9.0 Hz, 1H), 8.70-8.74 (m, 2H), 8.59 (s, 1H), 8.13 (s, 1H), 8.05 (d, J = 2.3 Hz, 1H), 7.92 (d, J = 9.1 Hz, 1H), 7.82 (dd, J = 8.9, 2.1 Hz, 1H), 7.65-7.49 (m, 3H), 3.98 (s, 3H). | DMSO | 406.1, 408.0 (M + 1) | Method B ($NH_4HCO_3$) | 95 | Meth-od C, G1 |
| 96 | 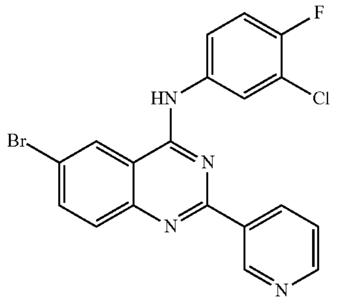 [SMILES: Fc1ccc(Nc2nc(-c3cccnc3)nc3ccc(Br)cc23)cc1Cl] | 429.67 | $^1$H-NMR (400 MHz, DMSO-$d_6$): δ 10.45 (s, 1H), 9.47 (s, 1H), 9.02-8.92 (m, 3H), 8.18-8.16 (m, 1H), 8.06-8.04 (m, 1H), 7.96-7.84 (m, 3H), 7.54-7.50 (m, 1H). | DMSO | 429.9, 431.0, 433.0 (M + 1) | Method B ($NH_4HCO_3$) | 95 | Meth-od C, G1 |
| 97 | 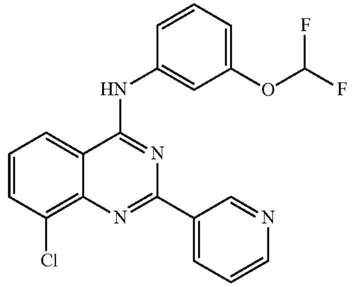 [SMILES: FC(F)Oc1cccc(Nc2nc(-c3cccnc3)nc3c(Cl)cccc23)c1] | 398.79 | $^1$H-NMR (400 MHz, DMSO-$d_6$): δ 10.25 (s, 1H), 9.58 (s, 1H), 8.85-8.76 (m, 2H), 8.60 (d, J = 7.2 Hz, 1H), 8.12-8.10 (m, 1H), 7.92 (s, 1H), 7.83-7.80 (m, 1H), 7.71-7.64 (m, 2H), 7.56-7.52 (m, 1H), 7.30 (t, J = 74.0 Hz, 1H), 7.05-7.03 (m, 1H). | DMSO | 399.0, 401.0 (M + 1) | Method B ($NH_4HCO_3$) | 95 | Meth-od C, G1 |

TABLE 1-continued
| | | | | | | | | |
|---|---|---|---|---|---|---|---|---|
| 98 | 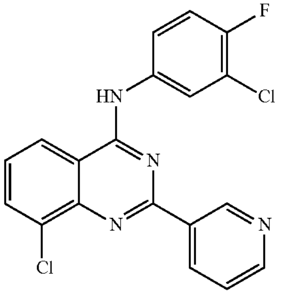 [SMILES: Fc1ccc(Nc2nc(-c3cccnc3)nc3c(Cl)cccc23)cc1Cl] | 385.22 | $^1$H-NMR (400 MHz, DMSO-$d_6$): δ 10.47 (s, 1H), 9.50 (s, 1H), 9.04 (d, J = 8.0 Hz, 1H), 8.93 (d, J = 5.2 Hz, 2H), 8.64 (d, J = 8.8 Hz, 1H), 8.20-8.18 (m, 1H), 8.11 (d, J = 8.4 Hz, 1H), 7.97-7.92 (m, 2H), 7.68-7.64 (m, 1H), 7.53 (t, J = 9.2 Hz, 1H). | DMSO | 385.0, 386.9 (M + 1) | Method B ($NH_4HCO_3$) | 95 | Meth-od C, G1 |
| 99 | 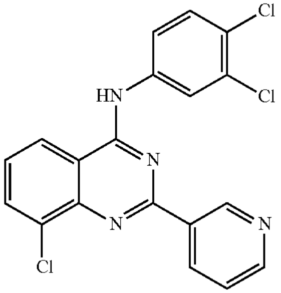 [SMILES: Clc1ccc(Nc2nc(-c3cccnc3)nc3c(Cl)cccc23)cc1Cl] | 401.66 | $^1$H-NMR (400 MHz, DMSO-$d_6$): δ 10.42 (s, 1H), 9.55 (d, J = 1.6 Hz, 1H), 8.96 (d, J = 4.0 Hz, 1H), 8.88-8.87 (m, 1H), 8.61 (d, J = 7.6 Hz, 1H), 8.32 (d, J = 2.4 Hz, 1H), 8.14-8.12 (m, 1H), 7.99-7.95 (m, 1H), 7.88 (dd, J = 8.0, 5.2 Hz, 1H), 7.74 (d, J = 8.8 Hz, 1H), 7.70-7.67 (m, 1H). | DMSO | 400.9, 402.9, 404.9 (M + 1) | Method B ($NH_4HCO_3$) | 95 | Meth-od C, G1 |
| 100 | 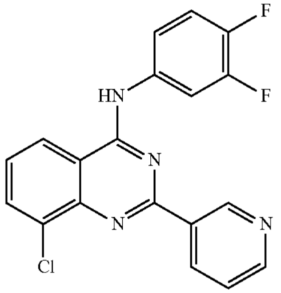 [SMILES: Fc1ccc(Nc2nc(-c3cccnc3)nc3c(Cl)cccc23)cc1F] | 368.77 | $^1$H-NMR (400 MHz, DMSO-$d_6$): δ 10.47 (s, 1H), 9.51 (d, J = 1.2 Hz, 1H), 9.04 (d, J = 3.0 Hz, 1H), 8.92 (d, J = 5.6 Hz, 1H), 8.65 (d, J = 8.0 Hz, 1H), 8.11-8.05 (m, 2H), 7.97 (dd, J = 8.0, 4.0 Hz, 1H), 7.75-7.73 (m, 1H), 7.66 (t, J = 8.0 Hz, 1H), 7.58-7.51 (m, 1H). | DMSO | 369.0, 371.0 (M + 1) | Method B ($NH_4HCO_3$) | 95 | Meth-od C, G1 |

TABLE 1-continued
| | | | | | | | | |
|---|---|---|---|---|---|---|---|---|
| 101 | 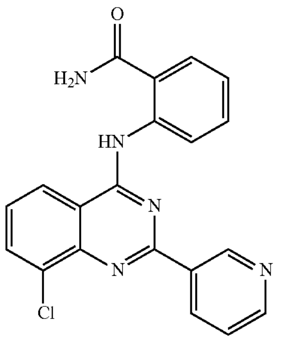 [SMILES: NC(=O)c1ccccc1Nc1nc(-c2cccnc2)nc2c(Cl)cccc12] | 375.09 | $^{1}$H-NMR (400 MHz, DMSO-$d_6$): δ 13.18 (s, 1H), 9.61 (s, 1H), 9.02 (d, J = 8.4 Hz, 1H), 8.93 (d, J = 8.4 Hz, 1H), 8.83 (d, J = 4.0 Hz, 1H), 8.52 (s, 1H), 8.16-8.08 (m, 2H), 7.98-7.94 (m, 2H), 7.80-7.67 (m, 3H), 7.26 (t, J = 7.6 Hz, 1H). | DMSO | 376.0, 378.0 (M + 1) | Method B ($NH_4HCO_3$) | 95 | Meth-od C, G1 |
| 102 | 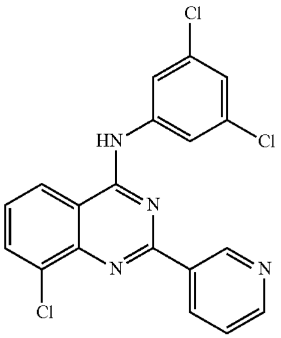 [SMILES: Clc1cc(Cl)cc(Nc2nc(-c3cccnc3)nc3c(Cl)cccc23)c1] | 401.68 | $^{1}$H-NMR (400 MHz, DMSO-$d_6$): δ 10.47 (s, 1H), 9.49 (d, J = 2.0 Hz, 1H), 9.00-8.98 (m, 1H), 8.91 (dd, J = 5.2, 1.6 Hz, 1H), 8.64-8.62 (m, 1H), 8.12-8.09 (m, 3H), 7.94 (dd, J = 8.0, 5.2 Hz, 1H), 7.67 (t, J = 8.0 Hz, 1H), 7.41 (t, J = 2.0 Hz, 1H). | DMSO | 400.9, 402.9, 404.9 (M + 1) | Method B ($NH_4HCO_3$) | 95 | Meth-od C, G1 |
| 103 | 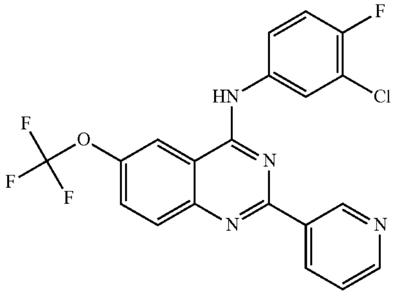 [SMILES: Fc1ccc(Nc2nc(-c3cccnc3)nc3ccc(OC(F)(F)F)cc23)cc1Cl] | 434.77 | $^{1}$H-NMR (400 MHz, DMSO-$d_6$): δ 10.17 (d, J = 1.2 Hz, 1H), 9.51 (s, 1H), 8.71-8.62 (m, 3H), 8.25-8.22 (m, 1H), 8.04-8.00 (m, 1H), 7.92-7.87 (m, 2H), 7.58-7.53 (m, 2H). | DMSO | 435.1, 437.1 (M + 1) | Method B ($NH_4HCO_3$) | 95 | Meth-od C, G1 |

TABLE 1-continued
| | | | | | | | | |
|---|---|---|---|---|---|---|---|---|
| 104 | 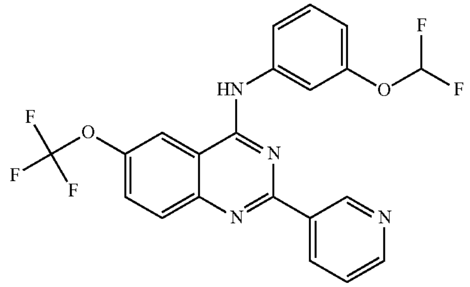 [SMILES: FC(F)Oc1cccc(Nc2nc(-c3cccnc3)nc3ccc(OC(F)(F)F)cc23)c1] | 448.35 | $^1$H-NMR (400 MHz, DMSO-$d_6$): δ 10.16 (s, 1H), 9.55 (d, J = 1.2 Hz, 1H), 8.72-8.68 (m, 3H), 8.05 (d, J = 9.2 Hz, 1H), 7.92-7.95 (m, 2H), 7.80 (dd, J = 8.0, 1.2 Hz, 1H), 7.57-7.53 (m, 2H), 7.31 (t, J = 74.4 Hz, 1H), 7.03 (dd, J = 8.0, 1.2 Hz, 1H). | DMSO | 449.1 (M + 1) | Method B ($NH_4HCO_3$) | 95 | Meth-od C, G1 |
| 105 | 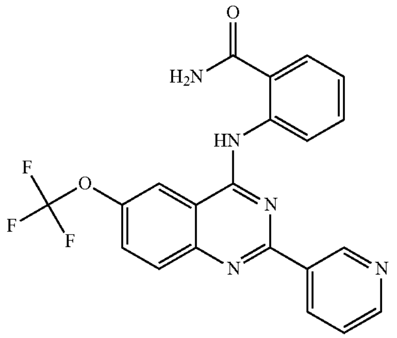 [SMILES: NC(=O)c1ccccc1Nc1nc(-c2cccnc2)nc2ccc(OC(F)(F)F)cc12] | 425.36 | $^1$H-NMR (400 MHz, DMSO-$d_6$): δ 13.24 (s, 1H), 9.59 (s, 1H), 9.05 (d, J = 8.0 Hz, 1H), 8.74-8.73 (m, 2H), 8.54 (s, 1H), 8.10-7.91 (m, 5H), 7.77-7.73 (m, 1H), 7.61-7.58 (m, 1H), 7.26 (t, J = 7.6 Hz, 1H | DMSO | 426.1 (M + 1) | Method B (NH4HCO3) | 95 | Meth-od C, G1 |
| 106 | 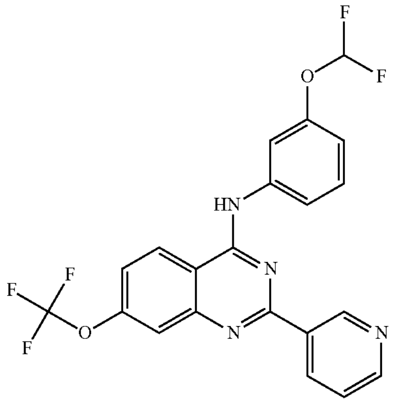 [SMILES: FC(F)Oc1cccc(Nc2nc(-c3cccnc3)nc3cc(OC(F)(F)F)ccc23)c1] | 448.35 | $^1$H-NMR (400 MHz, DMSO-$d_6$): δ 10.23 (s, 1H), 9.55 (d, J = 1.6 Hz, 1H), 8.76 (d, J = 9.1 Hz, 1H), 8.74-8.67 (m, 2H), 7.94 (t, J = 2.0 Hz, 1H), 7.82-7.78 (m, J = 10.3 Hz, 2H), 7.68 (dd, J = 9.0, 1.8 Hz, 1H), 7.59-7.50 (m, 2H), 7.30 (t, J = 74.0 Hz, 1H), 7.03 (dd, J = 8.2, 2.2 Hz, 1H). | DMSO | 449.0 (M + 1) 225.0 (M/2 + 1) | Method A (TFA) | 95 | Meth-od C, G1 |

TABLE 1-continued
| | | | | | | | | |
|---|---|---|---|---|---|---|---|---|
| 107 | 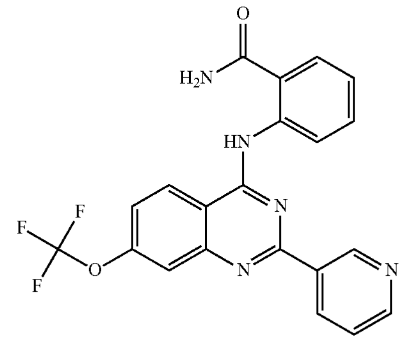 [SMILES: NC(=O)c1ccccc1Nc1nc(-c2cccnc2)nc2cc(OC(F)(F)F)ccc12] | 425.36 | $^1$H-NMR (400 MHz, DMSO-$d_6$): δ 13.17 (s, 1H), 9.59 (s, 1H), 9.04 (d, J = 8.0 Hz, 1H), 8.74-8.70 (m, 2H), 8.51 (s, 1H), 8.30 (d, J = 9.0 Hz, 1H), 8.02-7.90 (m, 2H), 7.86-7.69 (m, 3H), 7.65-7.56 (m, 1H), 7.25 (t, J = 9.8 Hz, 1H). | DMSO | 426.0 (M + 1) | Method B (NH4HCO3) | 95 | Meth-od C, G1 |
| 108 | 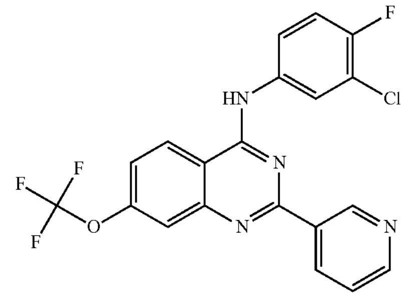 [SMILES: Fc1ccc(Nc2nc(-c3cccnc3)nc3cc(OC(F)(F)F)ccc23)cc1Cl] | 434.77 | $^1$H-NMR (400 MHz, DMSO-$d_6$): δ 10.26 (s, 1H), 9.52 (s, 1H), 8.81-8.59 (m, 3H), 8.24 (dd, J = 6.9, 2.5 Hz, 1H), 7.89-7.52 (m, 1H), 7.79 (s, 1H), 7.70 (d, J = 9.1 Hz, 1H), 7.65-7.50 (m, 2H). | DMSO | 435.0, 437.0 (M + 1) 218.1 (M/2 + 1) | Method A (TFA) | 95 | Meth-od C, G1 |
| 109 | 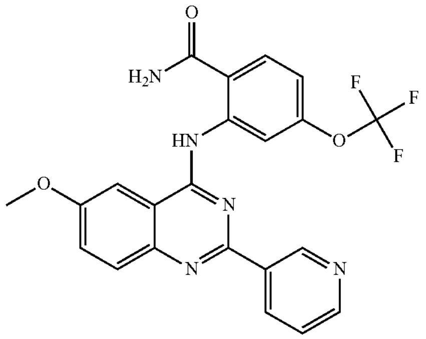 [SMILES: COc1ccc2nc(-c3cccnc3)nc(Nc3cc(OC(F)(F)F)ccc3C(N)=O)c2c1] | 455.39 | $^1$H-NMR (400 MHz, DMSO-$d_6$): δ 13.35 (s, 1H), 9.58 (s, 1H), 9.27 (s, 1H), 8.83-8.70 (m, 2H), 8.62 (s, 1H), 8.18 (s, 1H), 8.11 (d, J = 8.8 Hz, 1H), 7.92 (d, J = 9.1 Hz, 1H), 7.68-7.58 (m, 2H), 7.54 (d, J = 2.5 Hz, 1H), 7.19 (dd, J = 8.4, 2.17 Hz, 1H), 3.98 (s, 3H). | DMSO | 456.0 (M + 1) 228.5 (M/2 + 1) | Method A (TFA) | 95 | Meth-od C, J1 |

TABLE 1-continued
| | | | | | | | | |
|---|---|---|---|---|---|---|---|---|
| 110 | 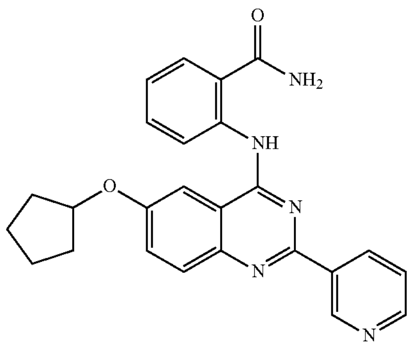 | 425.48 | $^1$H-NMR (400 MHz, DMSO-$d_6$): δ 13.08 (s, 1H), 9.59 (s, 1H), 9.07 (d, J = 7.6 Hz, 1H), 9.02 (d, J = 8.0 Hz, 1H), 8.89 (d, J = 4.0 Hz, 1H), 8.50 (s, 1H), 7.92-7.99 (m, 4H), 7.73 (t, J = 7.6 Hz, 1H), 7.59-7.60 (m, 2H), 7.25 (t, J = 7.6 Hz, 1H), 2.12-2.15 (m, 2H), 5.02-5.03 (m, 1H), 1.67-1.86 (m, 6H). | DMSO | 426.1 (M + 1) | Method B (NH4HCO3) | 95 | Meth-od C, G1 |
| 111 | 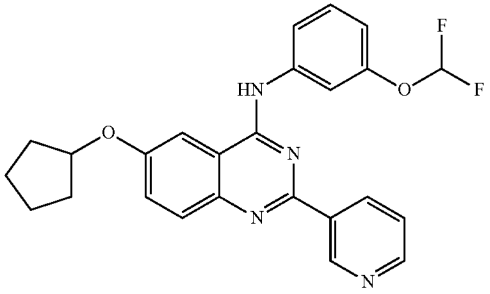 [SMILES: FC(F)Oc1cccc(Nc2nc(-c3cccnc3)nc3ccc(OC4CCCC4)cc23)c1] | 448.46 | $^1$H-NMR (400 MHz, DMSO-$d_6$): δ 10.26 (s, 1H), 9.50 (d, J = 1.6 Hz, 1H), 8.95 (d, J = 7.2 Hz, 1H), 8.55 (d, J = 4.4 Hz, 1H), 8.08 (s, 1H), 7.94 (d, J = 8.8 Hz, 1H), 7.85 (d, J = 9.6 Hz, 2H), 7.79 (d, J = 8.8 Hz, 1H), 7.60-7.63 (m, 1H), 7.55 (t, J = 8.0 Hz, 1H), 7.31 (t, J = 74.0 Hz, 1H), 7.05 (d, J = 8.4 Hz, 1H), 5.14 (s, 1H), 2.03-2.09 (m, 2H), 1.61-1.81 (m, 6H). | DMSO | 449.0 (M + 1) | Method B (NH4HCO3) | 95 | Meth-od C, G1 |
| 112 | 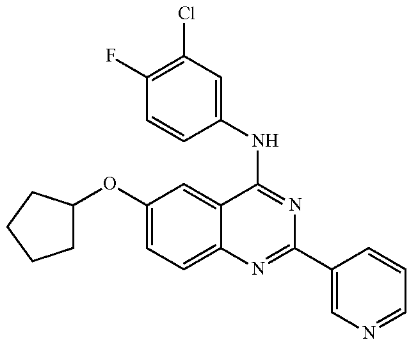 [SMILES: Fc1ccc(Nc2nc(-c3cccnc3)nc3ccc(OC4CCCC4)cc23)cc1Cl] | 434.89 | $^1$H-NMR (400 MHz, DMSO-$d_6$): δ 10.47 (s, 1H), 9.47 (s, 1H), 8.97 (d, J = 7.6 Hz, 1H), 8.89 (d, J = 4.4 Hz, 1H), 8.16-8.19 (m, 1H), 7.53-7.61 (m, 2H), 8.10 (s, 1H), 7.90-7.96 (m, 3H), 5.15 (s, 1H), 2.09-2.10 (m, 2H), 1.67-1.78 (m, 6H). | DMSO | 435.0, 437.0 (M + 1) | Method B (NH4HCO3) | 95 | Meth-od C, G1 |

TABLE 1-continued
| | | | | | | | | |
|---|---|---|---|---|---|---|---|---|
| 113 | 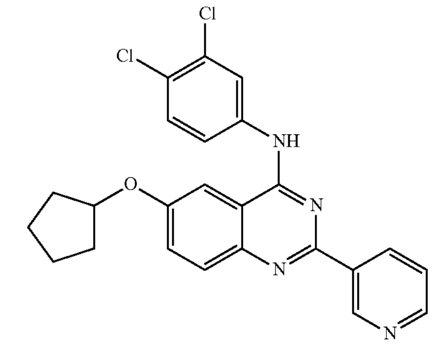 [SMILES: Clc1ccc(Nc2nc(-c3cccnc3)nc3ccc(OC4CCCC4)cc23)cc1Cl] | 451.35 | $^1$H-NMR (400 MHz, DMSO-$d_6$): δ 10.23 (s, 1H), 9.49 (s, 1H), 8.85 (d, J = 7.6 Hz, 1H), 8.80 (d, J = 4.0 Hz, 1H), 8.32 (s, 1H), 8.03 (s, 1H), 7.97-7.99 (m, 1H), 7.88 (d, J = 8.8 Hz, 1H), 7.77-7.79 (m, 1H), 7.75 (d, J = 8.3 Hz, 1H), 7.55-7.58 (m, 1H), 5.13 (s, 1H), 2.08 (d, J = 8.4 Hz, 2H), 1.79 (d, J = 9.6 Hz, 4H). | DMSO | 451.0, 453.0 (M + 1) | Method B (NH4HCO3) | 95 | Meth-od C, G1 |
| 114 | 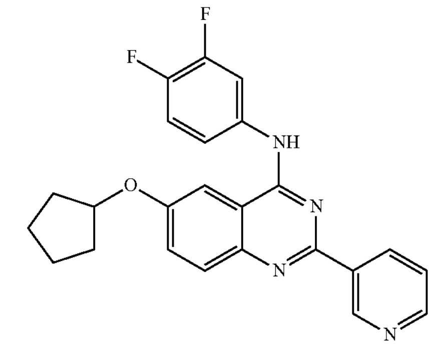 | 418.44 | $^1$H-NMR (400 MHz, DMSO-$d_6$): δ 10.24 (s, 1H), 9.49 (s, 1H), 8.92 (d, J = 8.0 Hz, 1H), 8.40 (d, J = 6.4 Hz, 1H), 8.04-8.11 (m, 2H), 7.92 (d, J = 9.2 Hz, 1H), 7.84-7.91 (m, 1H), 7.69-7.71 (m, 1H), 7.52-7.61 (m, 2H), 5.13 (s, 1H), 2.06-2.11 (m, 2H), 1.65-1.81 (m, 6H). | DMSO | 419.0 (M + 1) | Method B (NH4HCO3) | 95 | Meth-od C, G1 |
| 115 | 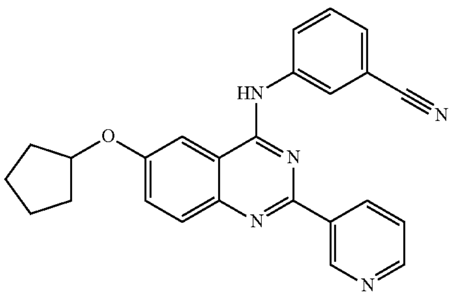 [SMILES: N#Cc1cccc(Nc2nc(-c3cccnc3)nc3ccc(OC4CCCC4)cc23)c1] | 407.47 | $^1$H-NMR (400 MHz, DMSO-$d_6$): δ 10.70 (s, 1H), 9.45 (s, 1H), 8.98 (d, J = 6.8 Hz, 1H), 8.89 (d, J = 6.0 Hz, 1H), 8.37 (s, 1H), 8.32 (d, J = 6.8 Hz, 1H), 8.18 (s, 1H), 7.93 (t, J = 9.2 Hz, 2H), 7.70 (t, J = 7.2 Hz, 2H), 7.56 (d, J = 8.8 Hz, 1H), 5.18 (s, 1H), 2.09 (s, 2H), 1.77 (m, 4H), 1.66 (m, 2H). | DMSO | 408.0 (M + 1) | Method B (NH4HCO3) | 95 | Meth-od C, G1 |

TABLE 1-continued
| | | | | | | | | |
|---|---|---|---|---|---|---|---|---|
| 116 | 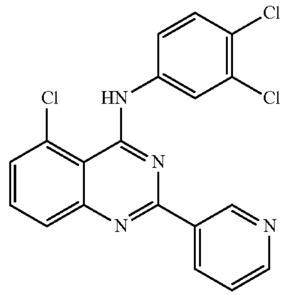 [SMILES: Clc1ccc(Nc2nc(-c3cccnc3)nc3cccc(Cl)c23)cc1Cl] | 401.68 | $^1$H-NMR (400 MHz, DMSO-$d_6$): δ 9.81 (s, 1H), 9.47 (s, 1H), 8.71 (d, J = 6.4 Hz, 1H), 8.62 (d, J = 7.6 Hz, 1H), 8.26 (s, 1H), 7.88 (t, J = 7.2 Hz, 3H), 7.75-7.73 (m, 2H), 7.57-7.56 (m, 1H). | DMSO | 401.0, 403.0 405.0 (M + 1) | Method B (NH4HCO3) | 95 | Meth-od C, G1 |
| 117 | 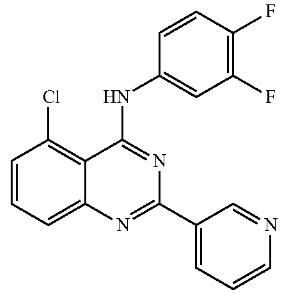 [SMILES: Fc1ccc(Nc2nc(-c3cccnc3)nc3cccc(Cl)c23)cc1F] | 368.77 | $^1$H-NMR (400 MHz, DMSO-$d_6$): δ 9.74 (s, 1H), 9.45 (d, J = 1.2 Hz, 1H), 8.70 (dd, J = 4.4, 1.6 Hz, 1H), 8.60 (d, J = 8.0 Hz, 1H), 8.04-8.00 (m, 1H), 7.88-7.85 (m, 2H), 7.74 (dd, J = 8.4, 1.6 Hz, 1H), 7.85-7.63 (m, 1H), 7.57-7.56 (m, 2H). | DMSO | 369.1, 371.1 (M + 1) | Method B (NH4HCO3) | 95 | Meth-od C, G1 |
| 118 | 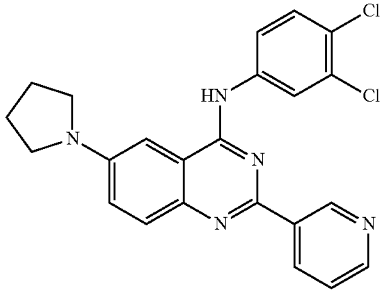 [SMILES: Clc1ccc(Nc2nc(-c3cccnc3)nc3ccc(N4CCCC4)cc23)cc1Cl] | 436.34 | $^1$H-NMR (400 MHz, DMSO-$d_6$): δ 10.33 (s, 1H), 8.87-8.20 (m, 2H), 8.27 (d, J = 1.6 Hz, 1H), 7.99 (d, J = 8.4 Hz, 1H), 7.90-7.72 (m, 3H), 7.39-7.36 (m, 2H), 3.44 (brs, 4H), 2.05 (brs, 4H). | DMSO | 435.9, 437.9, 439.8 (M + 1) | Method B (NH4HCO3) | 95 | Meth-od C, G1 |

TABLE 1-continued
| | | | | | | | | |
|---|---|---|---|---|---|---|---|---|
| 119 | 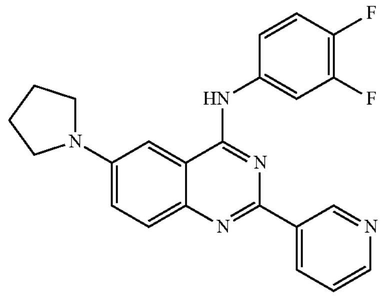 [SMILES: Fc1ccc(Nc2nc(-c3cccnc3)nc3ccc(N4CCCC4)cc23)cc1F] | 403.43 | $^1$H-NMR (400 MHz, DMSO-$d_6$): δ 10.38 (s, 1H), 9.43 (d, J = 1.2 Hz, 1H), 8.85-8.80 (m, 2H), 8.07-8.05 (m, 1H), 7.90 (d, J = 8.0 Hz, 1H), 7.81 (t, J = 6.8 Hz, 1H), 7.69-7.67 (m, 1H), 7.58-7.83 (m, 1H), 7.43-7.41 (m, 2H), 3.45 (brs, 4H), 2.06 (brs, 4H). | DMSO | 403.9 (M + 1) | Method B (NH4HCO3) | 95 | Meth-od C, G1 |
| 120 | 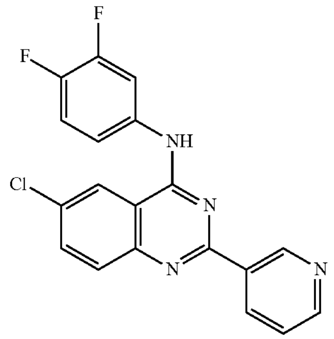 [SMILES: Fc1ccc(Nc2nc(-c3cccnc3)nc3ccc(Cl)cc23)cc1F] | 368.77 | $^1$H-NMR (400 MHz, DMSO-$d_6$): δ 10.28 (s, 1H), 9.49 (s, 1H), 8.77-8.87 (m, 3H), 8.06-8.12 (m, 1H), 7.90-7.95 (m, 2H), 7.78-7.81 (m, 1H), 7.57-7.73 (m, 1H), 7.53 (dd, J = 19.6 Hz, 9.2 Hz, 1H). | DMSO | 369.0, 371.1 (M + 1) | Method A (TFA) | 95 | Meth-od C, G1 |
| 121 | 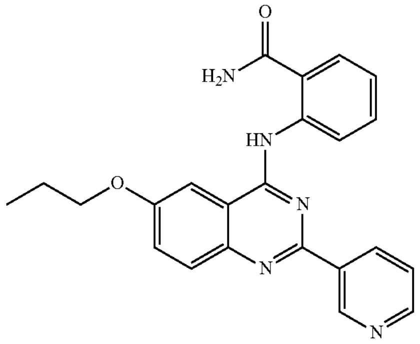 [SMILES: CCCOc1ccc2nc(-c3cccnc3)nc(Nc3ccccc3C(N)=O)c2c1] | 401.68 | 1H-NMR (400 MHz, DMSO-d6): δ 10.37 (s, 1H), 9.52 (s, 1H), 8.95 (d, J = 3.2 Hz, 1H), 8.87 (m, 1H), 8.81 (s, 1H), 8.32 (d, J = 2.0 Hz, 1H), 7.95-7.99 (m, 3H), 7.87-7.89 (m, 1H), 7.72 (d, J = 8.8 Hz, 1H). | DMSO | 401.0, 403.0, 405.0 (M + 1) | Method B (NH4HCO3) | 95 | Meth-od C, G1 |

TABLE 1-continued
| | | | | | | | | |
|---|---|---|---|---|---|---|---|---|
| 122 | 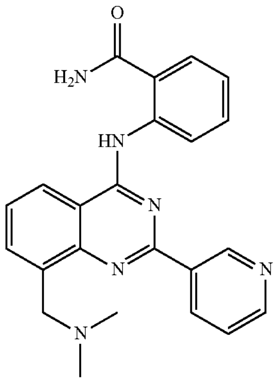 | 385.22 | 1H-NMR (400 MHz, DMSO-d6): δ 10.09 (s, 1H), 9.50 (s, 1H), 8.69 (s, 2H), 8.64 (d, J = 8.0 Hz, 1H), 8.26 (dd, J = 10.6 Hz, 1.8 Hz, 1H), 7.89-7.90 (m, 3H), 7.51-7.57 (m, 2H). | DMSO | 385.0, 387.0 (M + 1) | Method B (NH4HCO3) | 95 | Meth-od C, G1 |
| 123 | 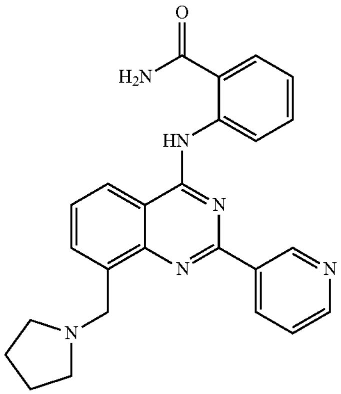 [SMILES: NC(=O)c1ccccc1Nc1nc(-c2cccnc2)nc2c(CN3CCCC3)cccc12] | 357.8 | 1H-NMR (400 MHz, DMSO-d6): δ 10.25 (s, 1H), 9.52 (s, 1H), 8.67-8.76 (m, 3H), 8.44 (s, 1H), 8.27 (m, 1H), 7.96 (s, 2H), 7.66-7.69 (m, 2H), 7.57-7.59 (m, 1H). | DMSO | 358.0 (M + 1) | Method A (TFA) | 95 | Meth-od C, G1 |

TABLE 1-continued
| | | | | | | | | |
|---|---|---|---|---|---|---|---|---|
| 124 | 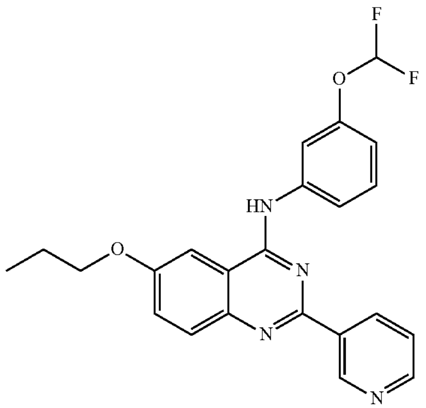 | 411.86 | 1H-NMR (400 MHz, DMSO-d6): δ 10.53 (s, 1H), 9.54 (s, 1H), 9.08 (d, J = 8.4 Hz, 1H), 8.94-8.90 (m, 2H), 8.15 (d, J = 8.4 Hz, 2H), 8.00-7.93 (m, 5H), 7.39 (s, 2H). | DMSO | 412.0, 414.0 (M + 1) | Method A (TFA) | 95 | Meth-od C, G1 |
| 125 | 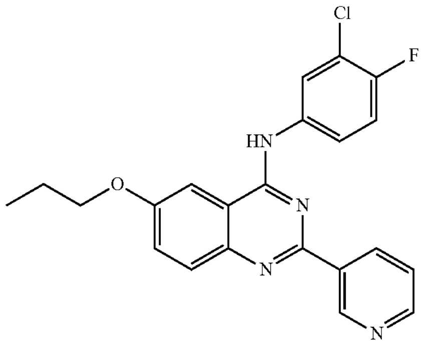 | 411.86 | 1H-NMR (400 MHz, DMSO-d6): δ 10.64 (s, 1H), 9.54 (s, 1H), 9.22 (s, 1H), 8.92-8.98 (m, 2H), 8.70 (s, 1H), 8.10 (s, 1H), 8.03-8.05 (m, 1H), 7.95 (s, 2H), 7.69 (s, 2H), 7.53 (s, 2H). | DMSO | 412.0, 414.0 (M + 1) | Method A (TFA) | 95 | Meth-od C, G1 |
| 126 | 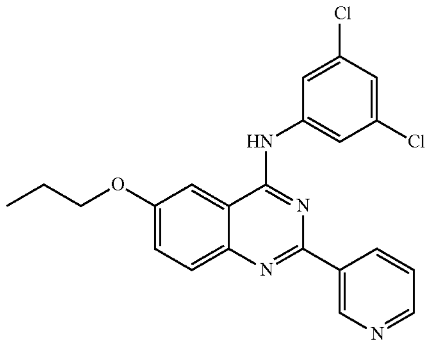 | 364.35 | 1H-NMR (400 MHz, DMSO-d6): δ 10.65 (s, 1H), 9.47 (s, 1H), 9.02 (d, J = 7.6 Hz, 1H), 8.92 (s, 1H), 8.21 (s, 1H), 8.08-8.10 (m, 1H), 7.95-7.97 (m, 2H), 7.74-7.75 (m, 1H), 7.54-7.62 (m, 2H), 4.00 (s, 3H). | DMSO | 365.1 (M + 1), 183.1 (M/2 + 1) | Method A (TFA) | 95 | Meth-od C, G1 |

TABLE 1-continued
| | | | | | | | | |
|---|---|---|---|---|---|---|---|---|
| 127 | 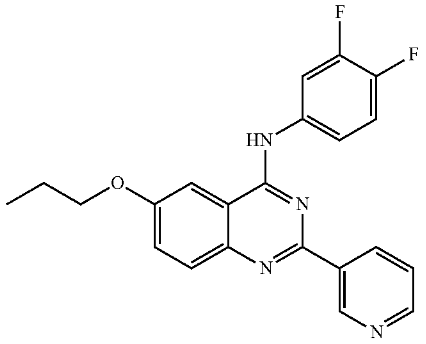 | 397.26 | 1H-NMR (400 MHz, DMSO-d6): δ 10.56 (s, 1H), 9.48 (s, 1H), 9.02 (d, J = 8.0 Hz, 1H), 8.91-8.92 (m, 1H), 8.28 (d, J = 2.4 Hz, 1H), 8.16-8.17 (m, 1H), 7.92-8.03 (m, 3H), 7.72 (d, J = 8.8 Hz, 1H), 7.58-7.61 (m, 1H), 4.00 (s, 3H). | DMSO | 397.0, 399.0 (M + 1), 200.1 (M/2 + 1) | Method A (TFA) | 95 | Meth-od C, G1 |
| 128 | 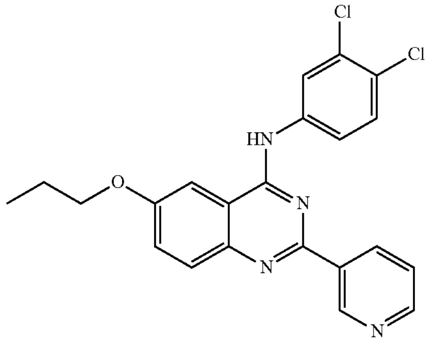 [SMILES: CCCOc1ccc2nc(-c3cccnc3)nc(Nc3ccc(Cl)c(Cl)c3)c2c1] | 407.45 | 1H-NMR (400 MHz, DMSO-d6): δ 10.32 (s, 1H), 9.55 (s, 1H), 8.92-8.84 (m, 2H), 8.16-8.09 (m, 3H), 7.95-7.89 (m, 3H), 7.83-7.79 (m, 1H), 7.62-7.58 (m, 1H), 7.36 (s, 2H), 3.40 (s, 3H). | DMSO | 408.1 (M + 1) | Method A (TFA) | 95 | Meth-od C, G1 |
| 129 | 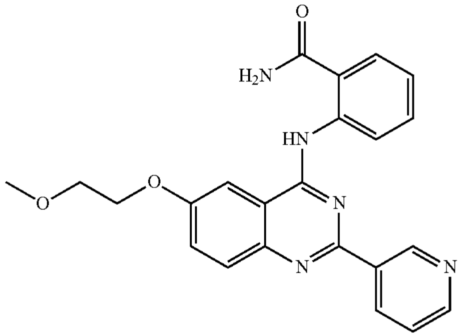 | 362.81 | 1H-NMR (400 MHz, DMSO-d6): δ 10.06 (s, 1H), 9.51 (s, 1H), 8.82-8.85 (m, 2H), 8.10- 8.11 (m, 1H), 8.05 (d, J = 2.0 Hz, 1H), 7.98-7.93 (m, 2H), 7.75-7.77 (m, 1H), 7.59-7.61 (m, 1H), 7.52 (t, J = 8.0 Hz, 1H), 7.27-7.28 (m, 1H), 3.99 (s, 3H). | DMSO | 363.0, 365.0 (M + 1), 182.1 (M/2 + 1) | Method A (TFA) | 95 | Meth-od C, G1 |

TABLE 1-continued
| | | | | | | | | |
|---|---|---|---|---|---|---|---|---|
| 130 | 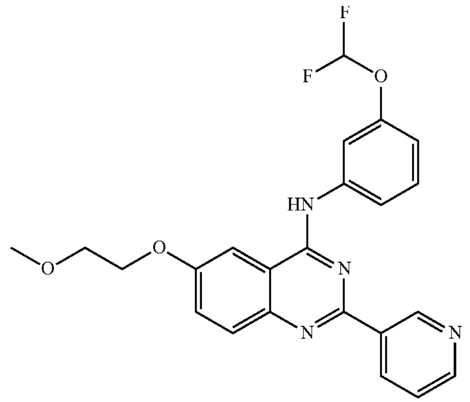 [SMILES: COCCOc1ccc2nc(-c3cccnc3)nc(Nc3cccc(OC(F)F)c3)c2c1] | 380.8 | 1H-NMR (300 MHz, DMSO-d6): δ 10.02 (s, 1H), 9.50 (s, 1H), 7.7 -8.79 (m, 2H), 8.19-8.24 (m, 1H), 7.86-8.00 (m, 3H), 7.52-7.70 (m, 3H), 3.98 (s, 3H). | DMSO | 381.1, 383.1 (M + 1), 191.1 (M/2 + 1) | Method A (TFA) | 95 | Meth-od C, G1 |
| 131 | 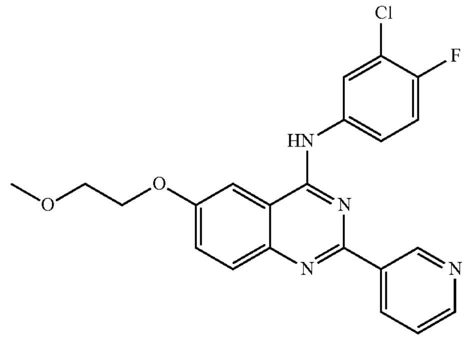 | 371.39 | 1H-NMR (300 MHz, DMSO-d6): δ 13.08 (s, 1H), 9.59 (s, 1H), 9.07 (d, J = 8.1 Hz, 1H), 8.96 (d, J = 8.1 Hz, 1H), 8.83 (d, J = 3.9 Hz, 1H), 8.49 (s, 1H), 7.89-7.99 (m, 3H), 7.80-7.84 (m, 1H), 7.72 (t, J = 7.8 Hz, 1H), 7.60-7.63 (m, 2H), 7.23 (t, J = 7.5 Hz, 1H), 3.98 (s, 3H). | DMSO | 371.9 (M + 1) | Method A (TFA3) | 95 | Meth-od C, G1 |
| 132 | 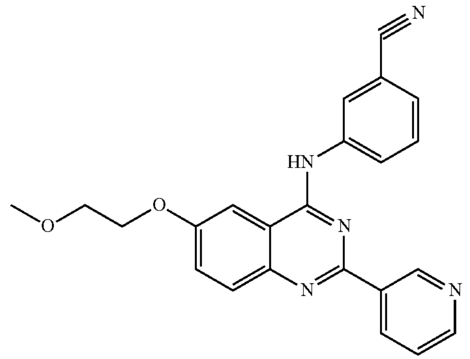 | 362.81 | 1H-NMR (400 MHz, DMSO-d6): δ 10.12 (s, 1H), 9.28 (s, 1H), 8.69 (d, J = 4.0 Hz, 1H), 8.59 (d, J = 8.4 Hz, 1H), 8.00 (d, J = 2.8 Hz, 1H), 7.87 (d, J = 9.2 Hz, 1H), 7.68-7.70 (m, 2H), 7.57-7.63 (m, 2H), 7.48-7.53 (m, 1H), 7.40-7.44 (m, 1H), 3.86 (s, 3H). | DMSO | 363.0, 365.1 (M + 1), 182.1 (M/2 + 1) | Method A (TFA) | 95 | Meth-od C, G1 |

TABLE 1-continued
| | | | | | | | | |
|---|---|---|---|---|---|---|---|---|
| 133 | 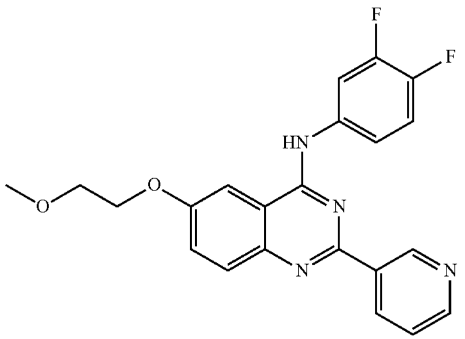 | 348.35 | 1H-NMR (400 MHz, DMSO-d6): δ 9.46 (s, 1H), 9.11 (s, 1H), 8.79-8.76 (m, 2H), 8.00-7.94 (m, 1H), 7.83-7.73 (m, 3H), 7.62-7.48 (m, 3H), 3.00 (s, 3H). | DMSO | 349.1 (M + 1), 175.1 (M/2 + 1) | Method A (TFA) | 95 | Meth-od C, G1 |
| 134 | 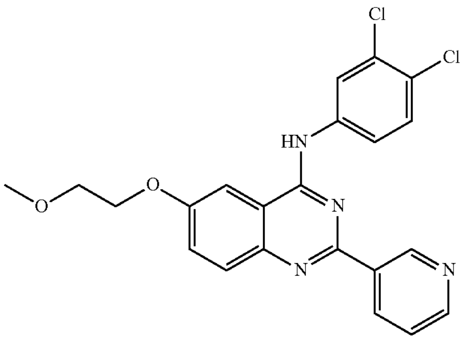 [SMILES: COCCOc1ccc2nc(-c3cccnc3)nc(Nc3ccc(Cl)c(Cl)c3)c2c1] | 381.26 | 1H-NMR (400 MHz, DMSO-d6): δ 9.48 (s, 1H), 9.13 (s, 1H), 8.75-8.77 (m, 2H), 8.18 (s, 1H), 7.72-7.85 (m, 5H), 7.49-7.50 (m, 1H), 3.00 (s, 3H). | DMSO | 381.0, 383.0, 385.0 (M + 1) | Method A (TFA) | 95 | Meth-od C, G1 |
| 135 | 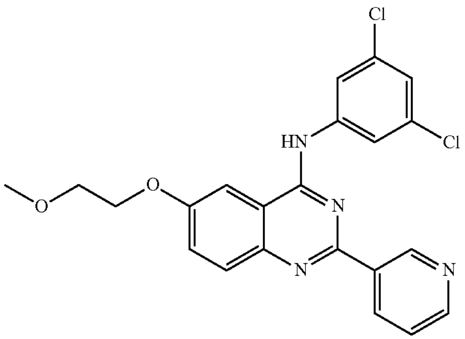 | 364.8 | 1H-NMR (400 MHz, DMSO-d6): δ 9.43 (m, 2H), 8.94-8.89 (m, 2H), 8.08- 8.06 (m, 1H), 7.92-7.81 (m, 4H), 7.57-7.53 (m, 2H), 3.03 (s, 3H). | DMSO | 365.0, 367.0 (M + 1), 183.1 (M/2 + 1) | Method A (TFA) | 95 | Meth-od C, G1 |

TABLE 1-continued
| | | | | | | | | |
|---|---|---|---|---|---|---|---|---|
| 136 | 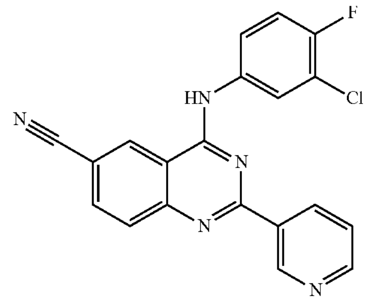 [SMILES: N#Cc1ccc2nc(-c3cccnc3)nc(Nc3ccc(F)c(Cl)c3)c2c1] | 337.38 | 1H-NMR (400 MHz, DMSO-d6): δ 9.52-9.44 (m, 2H), 8.98 (d, J = 8.0 Hz, 1H), 8.92 (d, J = 4.4 Hz, 1H), 8.36-8.19 (m, 2H), 8.02-7.84 (m, 3H), 7.73-7.69 (m, 2H), 7.55 (d, J = 6.8 Hz, 1H), 3.04 (s, 3H). | DMSO | 338.1 (M + 1), 169.6 (M/2 + 1) | Method A (TFA) | 95 | Meth-od C, G1 |
| 137 | 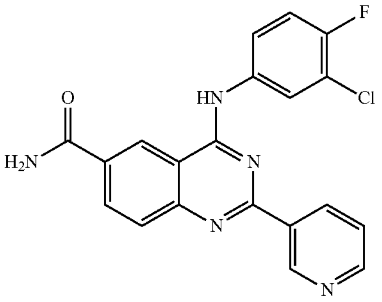 [SMILES: NC(=O)c1ccc2nc(-c3cccnc3)nc(Nc3ccc(F)c(Cl)c3)c2c1] | 364.35 | 1H-NMR (400 MHz, DMSO-d6): δ 9.97 (s, 1H), 9.51 (s, 1H), 8.69-8.66 (m, 2H), 8.16-8.08 (m, 2H), 7.75-7.73 (m, 1H), 7.61-7.53 (m, 3H), 7.40 (d. J = 7.6 Hz, 1H), 4.01 (s, 3H). | DMSO | 183.1 (M/2 + 1) 365.1 (M + 1) | Method A (TFA) | 95 | Meth-od C, G1 |
| 138 | 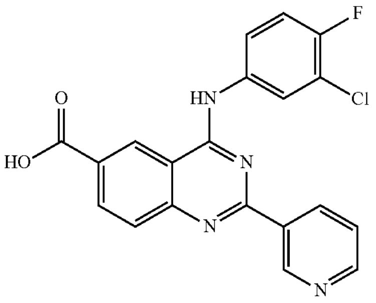 [SMILES: O=C(O)c1ccc2nc(-c3cccnc3)nc(Nc3ccc(F)c(Cl)c3)c2c1] | 397.26 | 1H-NMR (400 MHz, DMSO-d6): δ 10.01 (s, 1H), 9.53 (s, 1H), 8.67-8.70 (m, 2H), 8.41 (d, J = 2.4 Hz, 1H), 8.10 (d, J = 8.4 Hz, 1H), 7.95-7.99 (m, 1H), 7.73 (d, J = 8.8 Hz, 1H), 7.56-7.63 (m, 2H), 7.42 (d, J = 8.4 Hz, 1H), 4.02 (s, 3H). | DMSO | 397.0, 399.0 (M + 1) | Method A (TFA) | 95 | Meth-od C, G1 |

TABLE 1-continued
| | | | | | | | | |
|---|---|---|---|---|---|---|---|---|
| 139 | 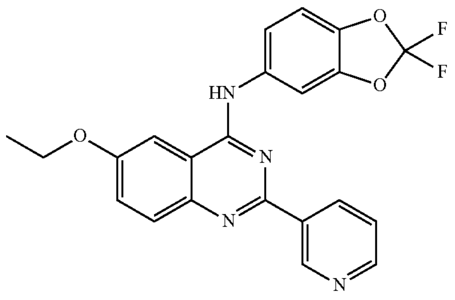 | 380.8 | 1H-NMR (400 MHz, DMSO-d6): δ 10.21 (s, 1H), 9.48 (s, 1H), 8.99 (d, J = 8.0 Hz, 1H), 8.89 (d, J =4.8 Hz, 1H), 8.15-8.22 (m, 2H), 7.92-7.95 (m, 2H), 7.62 (t, J = 8.0 Hz, 1H), 7.52 (t, J = 8.8 Hz, 1H), 7.43 (d, J = 8.0 Hz, 1H), 4.02 (s, 3H). | DMSO | 191.1 (M/2 + 1) 381.1, 383.1 (M + 1) | Method A (TFA) | 95 | Meth-od C, G1 |
| 140 | 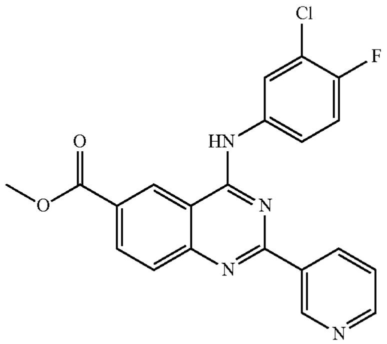 | 401.68 | 1H-NMR (400 MHz, DMSO-d6): δ 10.11 (s, 1H), 8.50 (m, 1H), 8.63-8.70 (m, 3H), 8.14 (d, J = 2.0 Hz, 2H), 7.92 (m, 2H), 7.57 (m, 1H), 7.38 (t, J = 1.6 Hz, 1H). | DMSO | 401.0, 403.0 (M + 1) | Method B (NH4HCO3) | 95 | Meth-od C, G1 |
| 141 | 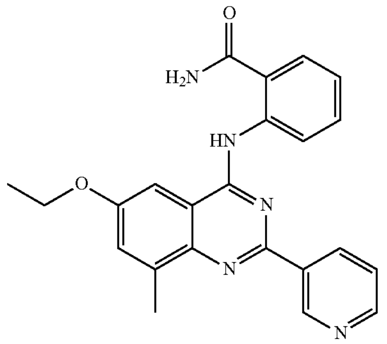 | 348.35 | 1H-NMR (400 MHz, DMSO-d6): δ 9.46 (s, 1H), 9.11 (s, 1H), 8.76-8.70 (m, 2H), 7.95-7.99 (m, 1H), 7.78-7.60 (m, 3H), 7.54-7.44 (m, 3H), 3.00 (s, 3H). | DMSO | 175.1 (M/2 + 1) 349.1 (M + 1) | Method A (TFA) | 95 | Meth-od C, G1 |

TABLE 1-continued
| | | | | | | | | |
|---|---|---|---|---|---|---|---|---|
| 142 | 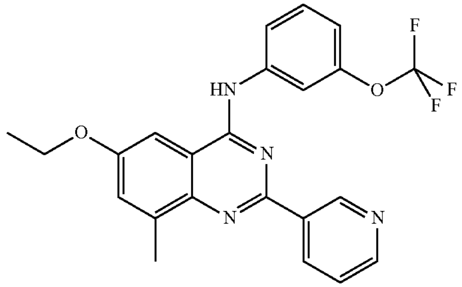 | 397.26 | 1H-NMR (400 MHz, DMSO-d6): δ 10.30 (s, 1H), 8.39 (s, 1H), 8.83 (s, 2H), 8.03-8.12 (m, 3H), 7.79-7.81 (m, 2H), 7.50-7.51 (m, 1H), 7.32 (s, 1H), 3.96 (s, 3H). | DMSO | 397.0, 399.0, 401.0 (M + 1) | Method B (NH4HCO3) | 95 | Meth-od C, G1 |
| 143 | 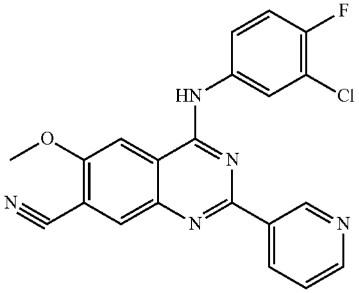 | 452.34 | 1H-NMR (400 MHz, DMSO-d6): δ 9.86 (s, 1H), 9.51 (s, 1H), 8.65-8.66 (m, 2H), 8.34 -8.35 (m, 1H), 7.95-7.96 (m, 1H), 7.72- 7.80 (m, 4H), 7.54 (m, 1H), 3.84 (m, 4H), 3.56 (m, 4H). | DMSO | 452.1, 454.0 (M + 1) | Method B (NH4HCO3) | 95 | Meth-od C, G1 |
| 144 | 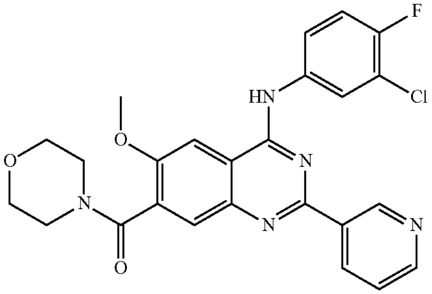 [SMILES: COc1cc2c(Nc3ccc(F)c(Cl)c3)nc(-c3cccnc3)nc2cc1C(=O)N1CCOCC1] | 435.88 | 1H-NMR (400 MHz, DMSO-d6): δ 9.83 (s, 1H), 9.49 (s, 1H), 8.62-8.65 (m, 2H), 8.21-8.23 (m, 1H), 7.89-7.91 (m, 1H), 7.78-7.81 (m, 1H), 7.72-7.73 (m, 2H), 7.51-7.54 (m, 2H), 3.84 (t, J = 4.0 Hz, 4H), 3.36 (m, 4H). | DMSO | 436.1, 438.1 (M + 1) | Method B (NH4HCO3) | 95 | Meth-od C, G1 |

TABLE 1-continued
| | | | | | | | | |
|---|---|---|---|---|---|---|---|---|
| 145 | 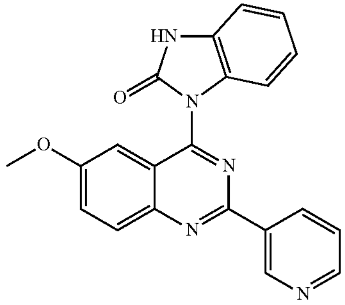 | 419.43 | 1H-NMR (400 MHz, DMSO-d6): δ 10.50 (s, 1H), 9.45 (s, 1H), 8.83-8.90 (m, 2H), 8.06-8.08 (m, 1H), 7.70-7.93 (m, 5H), 7.56 (dd, J = 19.6, 9.6 Hz, 1H), 3.82-3.83 (m, 4H), 3.39-3.41 (m, 4H). | DMSO | 420.1 (M + 1) | Method B (NH4HCO3) | 95 | Meth-od C, G1 |
| 146 | 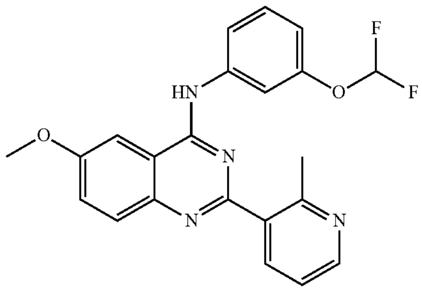 [SMILES: COc1ccc2nc(-c3cccnc3C)nc(Nc3cccc(OC(F)F)c3)c2c1] | 408.46 | 1H-NMR (400 MHz, DMSO-d6): δ 10.54 (s, 1H), 9.44 (s, 1H), 8.90 (d, J = 8.0 Hz, 1H), 8.84 (d, J = 4.4 Hz, 1H), 8.34 (s, 1H), 8.27 (d, J = 7.2 Hz, 1H), 7.67- 7.92 (m, 6H), 3.82-3.83 (m, 4H), 3.39-3.40 (m, 4H). | DMSO | 409.2 (M + 1) | Method B (NH4HCO3) | 95 | Meth-od C, G1 |
| 147 | 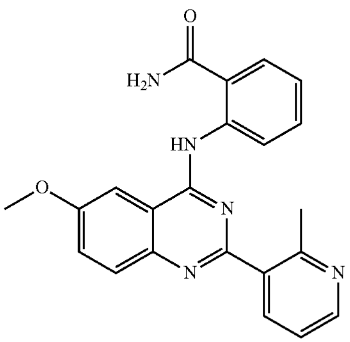 | 452.34 | 1H-NMR (400 MHz, DMSO-d6): δ 10.42 (s, 1H), 9.42 (s, 1H), 8.85-8.87 (m, 2H), 8.11 (s, 2H), 7.73-7.88 (m, 4H), 7.38 (s, 1H), 3.82-3.83 (m, 4H), 3.39-3.40 (m, 4H). | DMSO | 452.1, 454.1, 456.1 (M + 1) | Method B (NH4HCO3) | 95 | Meth-od C, G1 |

TABLE 1-continued
| | | | | | | | | |
|---|---|---|---|---|---|---|---|---|
| 148 | 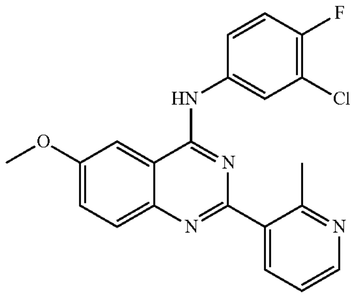 | 426.47 | 1H-NMR (400 MHz, DMSO-d6): δ 12.93 (s, 1H), 9.57 (m, 1H), 9.12 (d, J = 8.4 Hz, 1H), 8.68-8.72 (m, 2H), 8.56 (s, 1H), 8.02 (d, J = 6.8 Hz, 1H), 7.96 (s, 1H), 7.72-7.84 (m, 3H), 7.56-7.57 (m, 1H), 7.40 (m, 1H), 7.19 (t, J = 8.0 Hz, 1H), 3.84 (t, J = 4.4 Hz, 4H), 3.35 (t, J = 4.4 Hz, 4H). | DMSO | 427.2 (M + 1) | Method B (NH4HCO3) | 95 | Meth-od C, G1 |
| 149 | 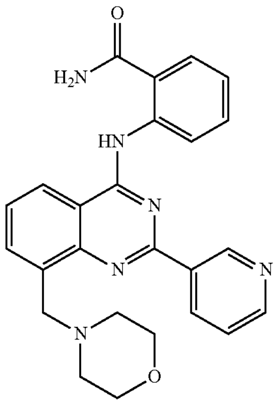 [SMILES: NC(=O)c1ccccc1Nc1nc(-c2cccnc2)nc2c(CN3CCOCC3)cccc12] | 393.84 | 1H-NMR (400 MHz, DMSO-d6): δ 9.71 (s, 1H), 9.48 (s, 1H), 8.62-8.63 (m, 2H), 8.23 (m, 1H), 7.92 (m, 1H), 7.77 (d, J = 9.6 Hz, 1H), 7.51-7.56 (m, 3H), 7.42 (m, 1H), 3.12 (s, 6H). | DMSO | 394.1, 396.1 (M + 1) | Method B (NH4HCO3) | 95 | Meth-od C, G1 |
| 150 | 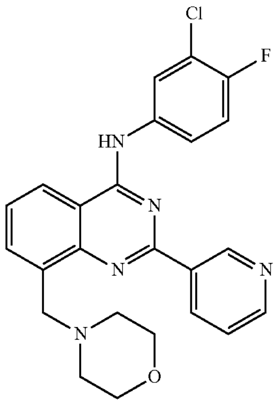 [SMILES: Fc1ccc(Nc2nc(-c3cccnc3)nc3c(CN4CCOCC4)cccc23)cc1Cl] | 377.39 | 1H-NMR (400 MHz, DMSO-d6): δ 9.72 (s, 1H), 9.48 (m, 1H), 8.60-8.63 (m, 2H), 8.08- 8.14 (m, 1H), 7.77 (d, J = 9.2 Hz, 1H), 7.69-7.71 (m, 1H), 7.50-7.57 (m, 3H), 7.42-7.43 (m, 1H), 3.12 (s, 6H). | DMSO | 378.2 (M + 1) | Method B (NH4HCO3) | 95 | Meth-od C, G1 |

TABLE 1-continued
| | | | | | | | | |
|---|---|---|---|---|---|---|---|---|
| 151 | 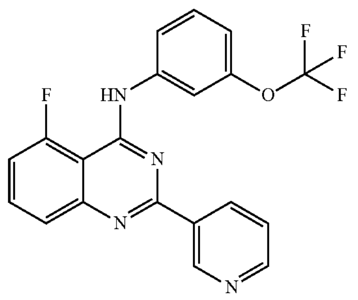 [SMILES: Fc1cccc2nc(-c3cccnc3)nc(Nc3cccc(OC(F)(F)F)c3)c12] | 410.3 | 1H-NMR (400 MHz, DMSO-d6): δ 9.72 (s, 1H), 9.49 (s, 1H), 8.60-8.64 (m, 2H), 8.17 (s, 2H), 7.76 (d, J = 8.8 Hz, 1H), 7.51-7.53 (m, 2H), 7.37 (s, 1H), 7.32 (s, 1H), 3.11 (s, 6H). | DMSO | 410.1, 412.0, 414.1 (M + 1) | Method B (NH4HCO3) | 95 | Meth-od C, G1 |
| 152 | 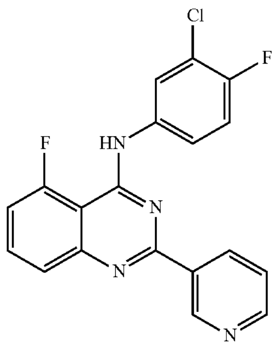 [SMILES: Fc1ccc(Nc2nc(-c3cccnc3)nc3cccc(F)c23)cc1Cl] | 410.3 | 1H-NMR (400 MHz, DMSO-d6): δ 10.44 (s, 1H), 9.45 (s, 1H), 8.83-8.91 (m, 2H), 8.26-8.27 (m, 1H), 7.72-7.99 (m, 4H), 7.57-7.61 (m, 2H), 3.14 (s, 6H). | DMSO | 410.1, 412.1, 414.0 (M + 1) | Method B (NH4HCO3) | 95 | Meth-od C, G1 |
| 153 | 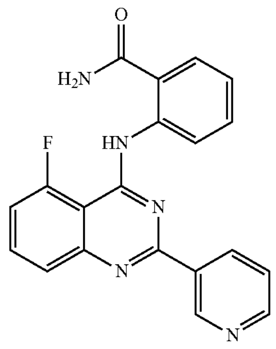 [SMILES: NC(=O)c1ccccc1Nc1nc(-c2cccnc2)nc2cccc(F)c12] | 366.42 | 1H-NMR (400 MHz, DMSO-d6): δ 9.82 (s, 1H), 9.48 (s, 1H), 8.55-8.64 (m, 2H), 8.41 (s, 1H), 8.28 (d, J = 8.0 Hz, 1H), 7.79 (d, J = 9.6 Hz, 1H), 7.69 (t, J = 8.0 Hz, 1H), 7.50-7.61 (m, 3H), 7.43 (m, 1H), 3.12 (s, 6H). | DMSO | 367.1 (M + 1) | Method B (NH4HCO3) | 95 | Meth-od C, G1 |

TABLE 1-continued
| | | | | | | | | |
|---|---|---|---|---|---|---|---|---|
| 154 | 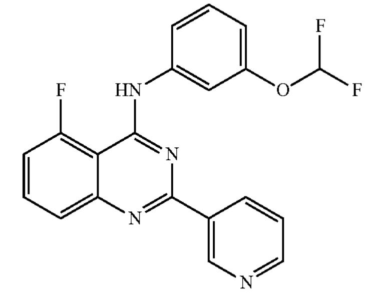 [SMILES: Fc1cccc2nc(-c3cccnc3)nc(Nc3cccc(OC(F)F)c3)c12] | 435.23 | 1H-NMR (400 MHz, DMSO-d6): δ 10.57 (s, 1H), 9.53 (s, 1H), 8.86-8.94 (m, 3H), 8.32-8.33 (m, 1H), 8.21 (s, 1H), 7.97-8.01 (m, 2H), 7.84-7.88 (m, 1H), 7.73 (d, J = 8.8 Hz, 1H). | DMSO | 435.1, 437.1, 439.1 (M + 1) | Method B (NH4HCO3) | 95 | Meth-od C, G1 |
| 155 | 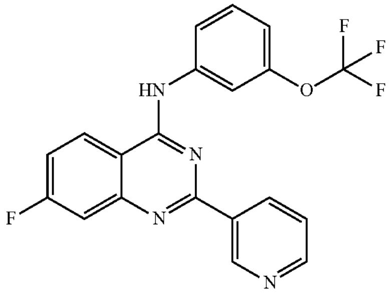 [SMILES: Fc1ccc2c(Nc3cccc(OC(F)(F)F)c3)nc(-c3cccnc3)nc2c1] | 402.32 | 1H-NMR (400 MHz, DMSO-d6): δ 10.32 (s, 1H), 9.51-9.52 (m, 1H), 8.65-8.78 (m, 3H), 8.19 (s, 1H), 8.11 (m, 1H), 7.97 (d, J = 8.0 Hz, 1H), 7.71 (m, 1H), 7.55-7.59 (m, 2H). | DMSO | 403.1 (M + 1) | Method B (NH4HCO3) | 95 | Meth-od C, G1 |
| 156 | 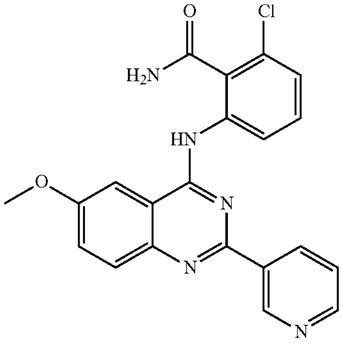 | 435.23 | 1H-NMR (400 MHz, DMSO-d6): δ 10.65 (s, 1H), 9.46 (s, 1H), 8.88- 8.97 (m, 3H), 8.17 (s, 1H), 8.10-8.11 (m, 2H), 7.97 (s, 1H), 7.95 (s, 1H), 7.39 (s, 1H). | DMSO | 435.1, 437.0, 439.1 (M + 1) | Method B (NH4HCO3) | 95 | Meth-od C, G1 |

TABLE 1-continued
| | | | | | | | | |
|---|---|---|---|---|---|---|---|---|
| 157 | 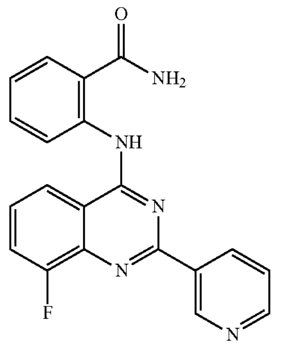 [SMILES: NC(=O)c1ccccc1Nc1nc(-c2cccnc2)nc2c(F)cccc12] | 418.77 | 1H-NMR (400 MHz, DMSO-d6): δ 10.62 (s, 1H), 9.52 (s, 1H), 8.99 (d, J = 8.0 Hz, 1H), 8.88-8.90 (m, 2H), 8.20-8.23 (m, 2H), 8.01 (d, J = 8.0 Hz, 1H), 7.92-7.95 (m, 2H), 7.54 (t, J = 9.2 Hz, 1H). | DMSO | 419.1, 421.1 (M + 1) | Method B (NH4HCO3) | 95 | Meth-od C, G1 |
| 158 | 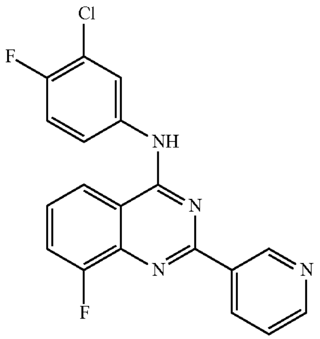 [SMILES: Fc1ccc(Nc2nc(-c3cccnc3)nc3c(F)cccc23)cc1Cl] | 409.36 | 1H-NMR (400 MHz, DMSO-d6): δ 13.24 (s, 1H), 9.56 (s, 1H), 9.10 (d, J = 8.4 Hz, 1H), 8.96 (s, 1H), 8.87 (d, J = 8.0 Hz, 1H), 8.54 (s, 1H), 8.33 (d, J = 8.8 Hz, 1H), 8.18 (s, 1H), 7.95-8.01 (m, 4H), 7.70 (t, J = 7.6 Hz, 1H), 7.27 (t, J = 7.2 Hz, 1H). | DMSO | 410.1 (M + 1) | Method B (NH4HCO3) | 95 | Meth-od C, G1 |
| 159 | 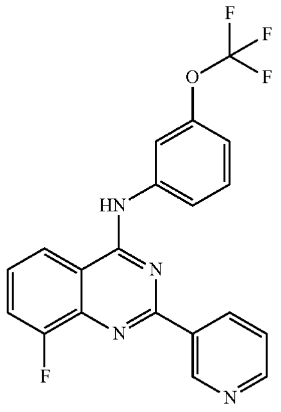 [SMILES: Fc1cccc2c(Nc3cccc(OC(F)(F)F)c3)nc(-c3cccnc3)nc12] | 391.35 | 1H-NMR (400 MHz, DMSO-d6): δ 10.82 (s, 1H), 8.50 (s, 1H), 9.04 (d, J = 8.0 Hz, 1H), 8.96 (d, J = 8.8 Hz, 2H), 8.37 (s, 1H), 8.30-8.28 (m, 1H), 8.21 (s, 1H), 7.98 (d, J = 7.6 Hz, 2H), 7.68-7.69 (m, 2H). | DMSO | 392.2 (M + 1) | Method B (NH4HCO3) | 95 | Meth-od C, G1 |

TABLE 1-continued
| | | | | | | | | |
|---|---|---|---|---|---|---|---|---|
| 160 | 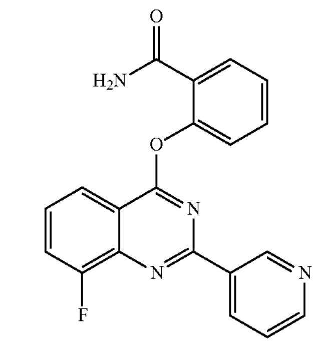 [SMILES: NC(=O)c1ccccc1Oc1nc(-c2cccnc2)nc2c(F)cccc12] | 450.34 | 1H-NMR (400 MHz, DMSO-d6): δ 10.40 (s, 1H), 9.54-9.55 (m, 1H), 8.82-8.84 (m, 1H), 8.67-8.73 (m, 2H), 8.16-8.21 (m, 2H), 7.93-8.00 (m, 2H), 7.54-7.64 (m, 2H), 7.21 (d, J = 8.0 Hz, 1H). | DMSO | 451.1 (M + 1) | Method B (NH4HCO3) | 95 | Meth-od C, G1 |
| 161 | 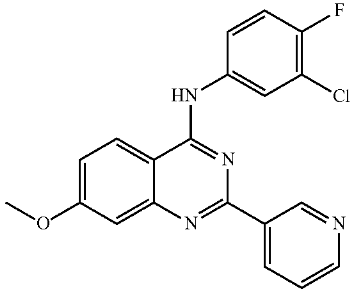 | 416.78 | 1H-NMR (400 MHz. DMSO-d6): δ 10.10 (s, 1H), 9.49 (s, 1H), 8.62-8.72 (m, 3H), 8.13 (s, 1H), 7.88-7.92 (m, 3H), 7.51-7.60 (m, 2H), 7.14-7.16 (m, 1H). | DMSO | 417.1, 419.1 (M + 1) | Method B (NH4HCO3) | 95 | Meth-od C, G1 |
| 162 | 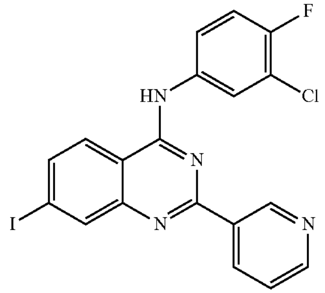 [SMILES: Fc1ccc(Nc2nc(-c3cccnc3)nc3cc(I)ccc23)cc1Cl] | 375.81 | 1H-NMR (400 MHz, DMSO-d6): δ 13.13 (s, 1H), 9.53 (s, 1H), 9.01 (d, J = 8.0 Hz, 1H), 8.68-8.72 (m, 2H), 8.50 (s, 1H), 8.10 (d, J = 8.8, 1H), 7.88-7.97 (m, 3H), 7.70-7.72 (m, 2H), 7.57-7.59 (m, 1H), 7.22 (t, J = 7.6, 1H). | DMSO | 376.0, 378.0 (M + 1) | Method B (NH4HCO3) | 95 | Meth-od C, G1 |

TABLE 1-continued
| | | | | | | | | | |
|---|---|---|---|---|---|---|---|---|---|
| 163 | 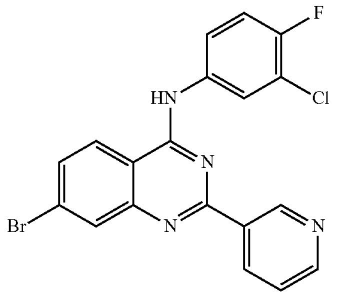 [SMILES: Fc1ccc(Nc2nc(-c3cccnc3)nc3cc(Br)ccc23)cc1Cl] | | 376.8 | 1H-NMR (400 MHz, DMSO-d6): δ 12.07 (s, 1H), 9.56 (s, 1H), 8.84 (d, J = 8.4 Hz, 1H), 8.71-8.73 (m, 2H), 8.34 (s, 1H), 7.96-8.09 (m, 3H), 7.59-7.80 (m, 2H), 7.29 (t, J = 7.2 Hz, 1H). | DMSO | 377.0, 379.0 (M + 1) | Method B (NH4HCO3) | 95 | Meth-od C, G1 |
| 164 | 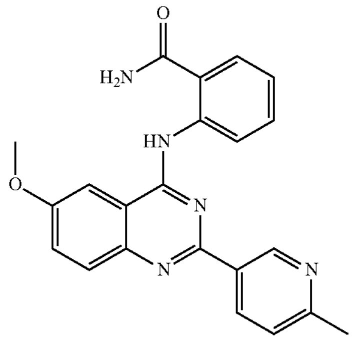 | | 394.37 | 1H-NMR (400 MHz, DMSO-d6): δ 9.90 (s, 1H), 9.53 (s, 1H), 8.67 (d, J = 5.2 Hz, 2H), 7.99 (d, J = 2.4 Hz, 1H), 7.94 (m, 1H), 7.87 (d, J = 9.2 Hz, 1H), 7.80 (d, J = 8.4 Hz, 7.49-7.59 (m, 3H), 7.31 (t, J = 74.0 Hz, 1H), 7.00 (d, J = 8.0 Hz, 1H), 3.99 (s, 3H). | DMSO | 395.1 (M + 1) | Method B (NH4HCO3) | 95 | Meth-od C, G1 |
| 165 | 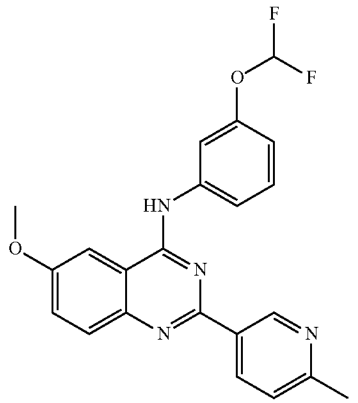 | HCl | 458.51 | 1H-NMR (400 MHz, DMSO-d6): δ 9.42 (s, 1H), 8.98 (d, J = 8.4 Hz, 1H), 8.68-8.71 (m, 2H), 7.94 (d, J = 7.6 Hz, 1H), 7.70 (t, J = 8.0 Hz, 1H), 7.57 (t, J = 5.6 Hz, 1H), 7.53 (s, 1H), 7.38 (s, 1H), 7.19 (t, J = 7.2 Hz, 1H), 4.52 (s, 2H), 4.00 (s, 3H), 3.63 (s, 2H), 2.89 (s, 6H). | DMSO | 459.1 (M + 1) 230.2 (M/2 + 1) | Method A (TFA) | 95 | Meth-od C, G1 |

TABLE 1-continued
| | | | | | | | | | |
|---|---|---|---|---|---|---|---|---|---|
| 166 | 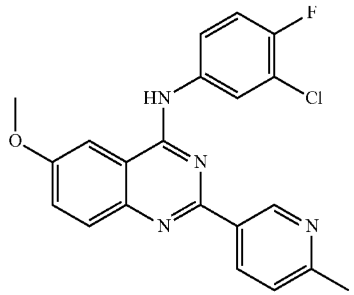 | | 467.92 | 1H-NMR (400 MHz, DMSO-d6): δ 9.71 (s, 1H), 9.50 (d, J = 1.6 Hz, 1H), 8.62-8.67 (m, 2H), 8.20 (dd, J = 6.8, 2.4 Hz, 1H), 7.86-7.89 (m, 2H), 7.51-7.55 (m, 2H), 7.31 (s, 1H), 4.24 (t, J = 6.0 Hz, 2H), 3.98 (s, 3H), 2.77 (t, J = 5.6 Hz, 2H), 2.29 (s, 6H). | DMSO | 468.1 (M + 1) 234.6 (M/2 + 1) | Method B (NH4HCO3) | 95 | Meth-od C, G1 |
| 167 | 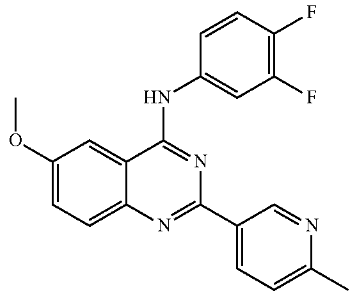 | HCl | 428.82 | 1H-NMR (400 MHz, DMSO-d6): δ 10.41 (s, 1H), 9.50 (d, J = 1.6 Hz, 1H), 8.98 (d, J = 8.4 Hz, 1H), 8.88 (dd, J = 5.2, 1.6 Hz, 1H), 8.13 (d, J = 2.8 Hz, 1H), 8.00 (t, J = 2.0 Hz, 1H), 7.89-7.95 (m, 3H), 7.62 (dd, J = 9.2, 3.2 Hz, 1H), 7.36 (t, J = 73.6 Hz, 1H), 7.16 (d, J = 2.0 Hz, 1H), 4.01 (s, 3H). | DMSO | 429.1, 431.1 (M + 1) | Method B (NH4HCO3) | 95 | Meth-od C, G1 |
| 168 | 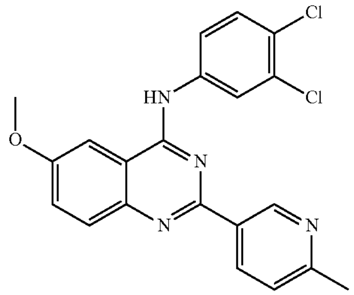 | | 385.42 | 1H-NMR (400 MHz, DMSO-d6): δ 13.03 (s, 1H), 9.62 (d, J = 1.6 Hz, 1H), 9.20 (d, J = 8.4 Hz, 1H), 8.74-8.77 (m, 1H), 8.70 (dd, J = 4.4, 1.6 Hz, 1H), 8.48 (s, 1H), 7.96-7.99 (m, 2H), 7.72-7.76 (m, 1H), 7.57- 7.60 (m, 1H), 7.47 (m, 1H), 7.41 (m, 1H), 7.17-7.21 (m, 1H), 3.95 (s, 3H), 2.72 (s, 3H). | DMSO | 386.1 (M + 1) | Method B (NH4HCO3) | 95 | Meth-od C, G1 |

TABLE 1-continued
| | | | | | | | | | |
|---|---|---|---|---|---|---|---|---|---|
| 169 | 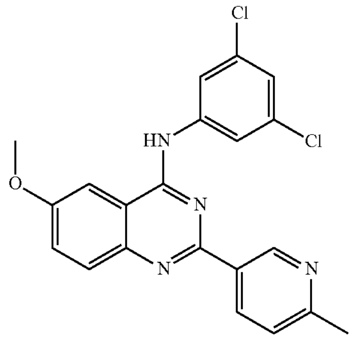 | HCl | 368.77 | 1H-NMR (400 MHz, DMSO-d6): δ 10.31 (s, 1H), 9.47 (s, 1H), 8.86-8.93 (m, 2H), 8.54 (dd, J = 10.0, 2.8 Hz, 1H), 8.21 (dd, J = 6.8, 2.4 Hz, 1H), 7.82-8.00 (m, 4H), 7.52 (t, J = 9.2 Hz, 1H). | DMSO | 369.0, 371.0 (M + 1) | Method B (NH4HCO3) | 95 | Meth-od C, G1 |
| 170 | 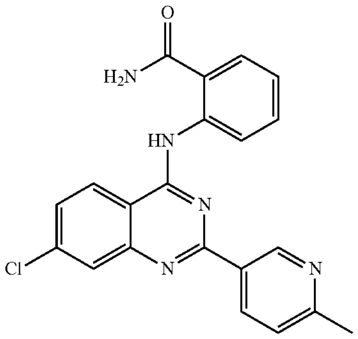 | HCl | 400.33 | 1H-NMR (400 MHz, DMSO-d6): δ 10.35 (s, 1H), 9.53 (s, 1H), 8.99 (d, J = 8.0 Hz, 1H), 8.89 (d, J = 4.0 Hz, 1H), 8.60 (dd, J = 10.4, 3.2 Hz, 1H), 7.97-8.09 (m, 3H), 7.88-7.92 (m, 2H), 7.62 (t, J = 8.0 Hz, 1H), 7.21 (d, J = 8.0 Hz, 1H). | DMSO | 401.1 (M + 1) | Method B (NH4HCO3) | 95 | Meth-od C, G1 |
| 171 | 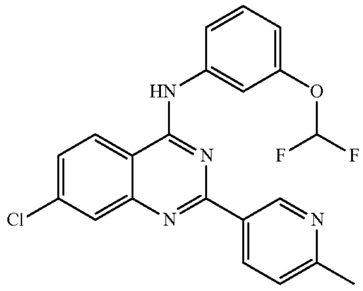 | | 359.36 | 1H-NMR (400 MHz, DMSO-d6): δ 13.06 (s, 1H), 9.58 (s, 1H), 9.07 (d, J = 8.4 Hz, 1H), 8.72 (d, J = 5.6 Hz, 2H), 8.52 (s, 1H), 7.96-8.02 (m, 3H), 7.83-7.87 (m, 2H), 7.74 (t, J = 8.0 Hz, 1H), 7.59 (t, J = 6.0 Hz, 1H), 7.23 (t, J = 7.6 Hz, 1H). | DMSO | 360.1 (M + 1) | Method B (NH4HCO3) | 95 | Meth-od C, G1 |

TABLE 1-continued
| | | | | | | | | | |
|---|---|---|---|---|---|---|---|---|---|
| 172 | 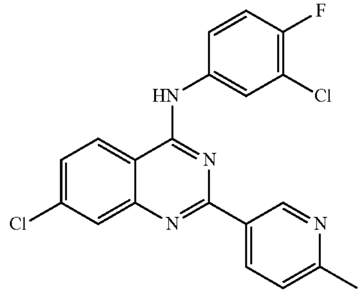 | HCl | 382.34 | 1H-NMR (400 MHz, DMSO-d6): δ 10.30 (s, 1H), 9.53 (d, J = 1.2 Hz, 1H), 8.98 (d, J = 8.0 Hz, 1H), 8.88 (d, J = 4.4 Hz, 1H), 8.62 (dd, J = 10.0, 2.8 Hz, 1H), 8.01-8.05 (m, 1H), 7.84-7.92 (m, 4H), 7.50-7.56 (m, 1H), 7.32 (t, J = 74.0 Hz, 1H), 7.03 (dd, J = 8.0, 2.0 Hz, 1H). | DMSO | 383.1 (M + 1) | Method B (NH4HCO3) | 95 | Meth-od C, G1 |
| 173 | 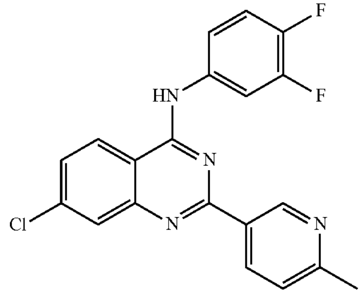 | | 348.35 | 1H-NMR (400 MHz, DMSO-d6): δ 10.09 (s, 1H), 9.51 (s, 1H), 8.79- 8.76 (m, 2H), 8.38 (s, 1H), 8.16-8.11 (m, 1H), 7.36-7.66 (m, 4H), 7.59-7.50 (m, 1H), 2.57 (s, 3H). | DMSO | 349.1 (M + 1), 175.1 (M/2 + 1) | Method A (TFA) | 95 | Meth-od C, G1 |
| 174 | 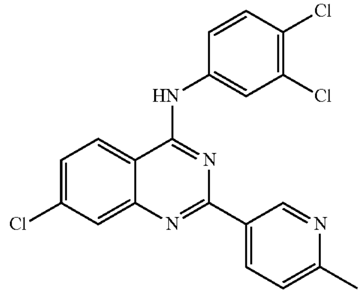 | | 364.8 | 1H-NMR (300 Hz, CD3OD): δ 9.50 (d, J = 1.2 Hz, 1H), 9.14 (d, J = 8.4 Hz, 1H), 8.94 (d, J = 4.8 Hz, 1H), 8.35 (s, 1H), 8.09-7.99 (m, 2H), 7.93 (s, 2H), 7.78-7.73 (m, 1H), 7.39 (t, J = 9.0 Hz, 1H), 2.64 (s, 3H). | CD3OD | 365.1, 367.1 (M + 1) | Method A (TFA) | 95 | Meth-od C, G1 |

TABLE 1-continued
| | | | | | | | | |
|---|---|---|---|---|---|---|---|---|
| 175 | 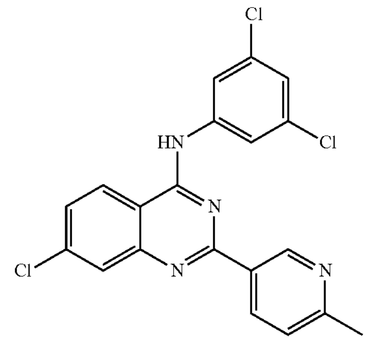 | 381.26 | 1H-NMR (400 MHz, DMSO-d6): δ 10.13 (s, 1H), 9.51 (s, 1H), 8.84-8.79 (m, 2H), 8.36-8.34 (m, 2H), 7.96 (dd, J = 8.8, 2.5 Hz, 1H), 7.85-7.70 (m, 4H), 2.55 (s, 3H). | DMSO | 381.0, 383.0 (M + 1) | Method B (NH4HCO3) | 95 | Meth-od C, G1 |
| 176 | 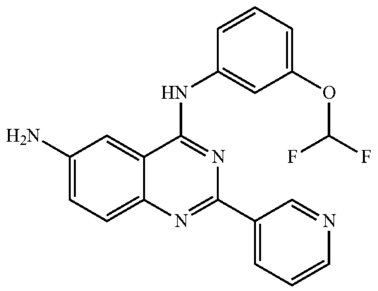 [SMILES: Nc1ccc2nc(-c3cccnc3)nc(Nc3cccc(OC(F)F)c3)c2c1] | 346.81 | 1H-NMR (300 Hz, CD3OD): δ 9.48 (d, J = 1.2 Hz, 1H), 8.99-8.95 (m, 1H), 8.82-8.80 (m, 1H), 8.30-8.29 (m, 1H), 7.90-7.81 (m, 5H), 7.52-7.46 (m, 2H), 2.62 (s, 3H). | DMSO | 347.0, 349.1 (M + 1) | Method A (TFA) | 95 | Meth-od C, G1 |
| 177 | 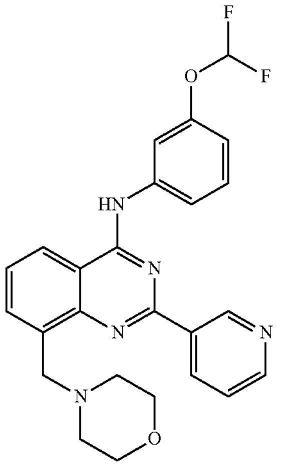 [SMILES: FC(F)Oc1cccc(Nc2nc(-c3cccnc3)nc3c(CN4CCOCC4)cccc23)c1] | 346.81 | 1H-NMR (400 MHz, DMSO-d6): δ 10.12 (s, 1H), 9.52 (s, 1H), 8.84-8.78 (m, 2H), 8.42 (s, 1H), 8.16-8.15 (m, 1H), 7.94-7.91 (m, 1H), 7.85 (d, J = 8.4 Hz, 1H), 7.79 (d, J = 8.1 Hz, 1H), 7.75-7.71 (m, 1H), 7.50 (t, J = 8.1 Hz, 1H), 7.27-7.23 (m, 1H), 2.56 (s, 3H). | DMSO | 347.1, 349.1 (M + 1) | Method A (TFA) | 95 | Meth-od C, G1 |

TABLE 1-continued
| | | | | | | | | |
|---|---|---|---|---|---|---|---|---|
| 178 | 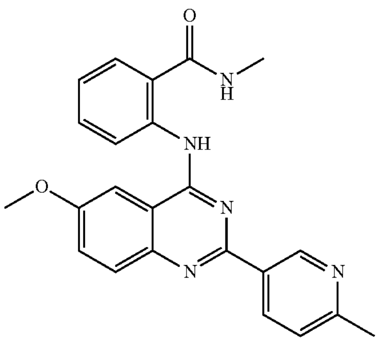 | 380.37 | 1H-NMR (400 MHz, DMSO-d6): δ 10.60 (s, 1H), 9.50 (d, J = 2.1 Hz, 1H), 9.00 (d, J = 8.1 Hz, 1H), 8.90 (dd, J = 5.1, 1.2 Hz, 1H), 8.55 (s, 1H), 8.43 (s, 1H), 8.25 (d, J = 7.8 Hz, 1H), 7.96-7.90 (m, 2H), 7.84 (d, J = 8.1 Hz, 1H), 7.27 (t, J = 8.2 Hz, 1H), 7.57 (d, J = 7.8 Hz, 1H), 2.62 (s, 3H). | DMSO | 381.1 (M + 1) | Method B (NH4HCO3) | 95 | Meth-od C, G1 |
| 179 | 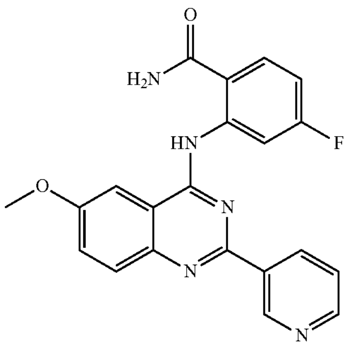 | 414.81 | 1H-NMR (400 MHz, DMSO-d6): δ 10.59 (s, 1H), 9.50 (s, 1H), 9.02 (d, J = 8.4 Hz, 1H), 8.92 (d, J = 5.2 Hz, 1H), 8.59 (d, J = 2.8 Hz, 1H), 8.54 (s, 1H), 8.34 (dd, J = 8.6, 2.6 Hz, 1H), 7.96-7.90 (m, 2H), 7.81 (d, J = 8.8 Hz, 2H), 2.56 (s, 3H). | DMSO | 415.1, 417.1 (M + 1) | Method B (NH4HCO3) | 95 | Meth-od C, G1 |
| 180 | 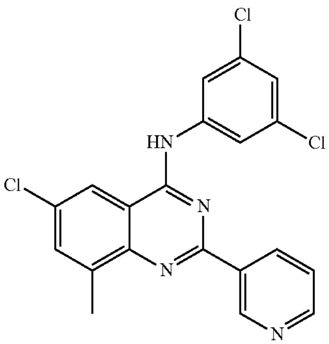 | 401.37 | 1H-NMR (400 MHz, DMSO-d6): δ 13.91 (s, 1H), 10.38 (s, 1H), 9.59 (s, 1H), 8.79-8.76 (m, 1H), 8.73 (d, J = 4.8 Hz, 1H), 8.61 (d, J = 2.4 Hz, 1H), 8.44 (s, 1H), 8.33 (dd, J = 9.0, 2.6 Hz, 1H), 8.20 (d, J = 8.8 Hz, 1H), 7.88 (d, J = 8.4 Hz, 1H), 7.81 (dd, J = 8.4, 1.2 Hz, 1H), 7.60-7.57 (m, 1H), 2.58 (s, 3H). | DMSO | 402.0 (M + 1) | Method A (TFA) | 95 | Meth-od C, G1 |

TABLE 1-continued
| | | | | | | | | |
|---|---|---|---|---|---|---|---|---|
| 181 | 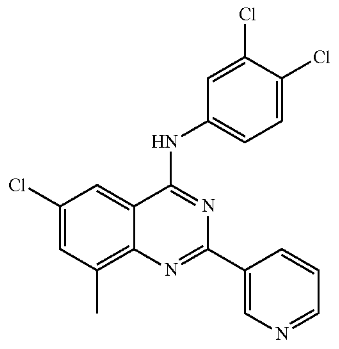 | 381.26 | 1H-NMR (400 MHz, DMSO-d6): δ 10.40 (s, 1H), 9.47 (s, 1H), 8.98 (d, J = 7.5 Hz, 1H), 8.91 (d, J = 4.5 Hz, 1H), 8.48 (s, 1H), 8.12 (d, J = 2.1 Hz, 2H), 7.97-7.93 (m, 1H), 7.88 (d, J = 8.4 Hz, 1H), 7.80 (d, J = 7.8 Hz, 1H), 7.40 (s, 1H), 2.55 (s, 3H). | DMSO | 381.0, 383.0 (M + 1) | Method B (NH4HCO3) | 95 | Meth-od C, G1 |
| 182 | 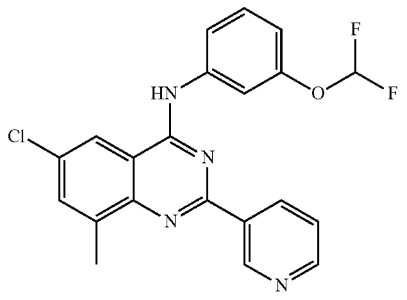 | 390.82 | 1H-NMR (400 MHz, DMSO-d6): δ 12.25 (s, 1H), 9.54 (s, 1H), 9.25 (s, 1H), 8.84-8.80 (m, 2H), 8.09 (d, J = 8.0 Hz, 1H), 7.96 (s, 1H), 7.88 (d, J = 8.0 Hz, 1H), 7.81 (d, J = 9.2 Hz, 1H), 7.77-7.75 (m, 1H), 7.29 (d, J = 8.4 Hz, 1H), 2.56 (s, 3H). | DMSO | 391.1, 393.0 (M + 1) | Method B (NH4HCO3) | 95 | Meth-od C, G1 |
| 183 | 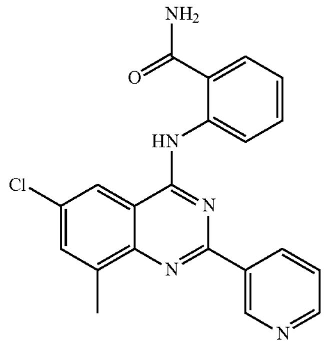 | 366.34 | 1H-NMR (400 MHz, DMSO-d6): δ 9.98 (s, 1H), 9.50 (d, J = 1.6 Hz, 1H), 8.69 (dd, J = 4.8, 1.6 Hz, 1H), 8.66-8.63 (m, 1H), 8.30 (s, 1H), 7.99-7.95 (m, 2H), 7.82 (d, J = 8.4 Hz, 1H), 7.76 (dd, J = 8.6, 1.4 Hz, 1H), 7.58-7.55 (m, 1H), 2.55 (s, 3H). | DMSO | 367.1 (M + 1), 184.1 (M/2 + 1) | Method A (TFA) | 95 | Meth-od C, G1 |

TABLE 1-continued
| | | | | | | | | |
|---|---|---|---|---|---|---|---|---|
| 184 | 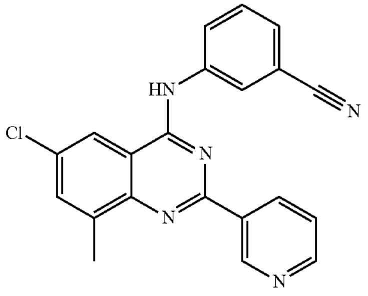 | 415.7 | 1H-NMR (400 MHz, DMSO-d6): δ 10.09 (s, 1H), 9.51 (s, 1H), 8.75-8.72 (m, 2H), 8.38 (s, 2H), 8.32 (s, 1H), 7.83 (d, J = 8.8 Hz, 1H), 7.77 (d, J = 8.0 Hz, 1H), 7.66-7.64 (m, 1H), 2.55 (s, 3H). | DMSO | 414.8, 416.8 (M + 1) | Method B (NH4HCO3) | 95 | Meth-od C, G1 |
| 185 | 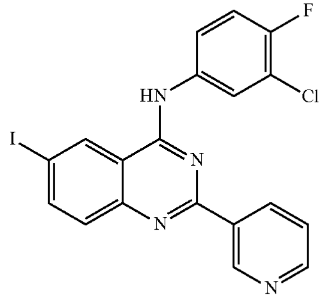 [SMILES: Fc1ccc(Nc2nc(-c3cccnc3)nc3ccc(I)cc23)cc1Cl] | 354.4 | 1H-NMR (400 MHz, DMSO-d6): δ 10.26 (s, 1H), 9.56 (s, 1H), 8.93 (d, J = 8.0 Hz, 1H), 8.81 (d, J = 4.0 Hz, 1H), 8.65 (s, 1H), 8.48 (s, 1H), 8.21 (d, J = 8.0 Hz, 1H), 7.86 (d, J = 8.4 Hz, 1H), 7.88-7.88 (m, 3H), 7.65 (t, J = 7.6 Hz, 1H), 2.65 (s, 3H), 2.58 (s, 3H). | DMSO | 355.1 (M + 1), 178.1 (M/2 + 1) | Method A (TFA) | 95 | Meth-od C, G1 |
| 186 | 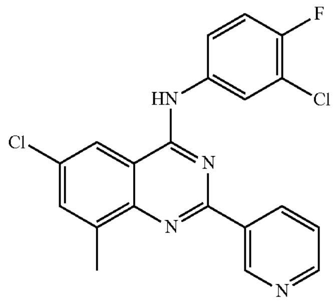 | 356.38 | 1H-NMR (400 MHz, DMSO-d6): δ 12.18 (s, 1H), 9.57 (s, 1H), 9.07 (d, J = 8.4 Hz, 1H), 8.71 (d, J = 5.6 Hz, 2H), 8.10 (d, J = 8.0 Hz, 1H), 7.99 (s, 1H), 7.86-7.76 (m, 3H), 7.58 (t, J = 6.2 Hz, 1H), 7.23 (t, J = 7.4 Hz, 1H), 2.55 (s, 3H). | DMSO | 357.1 (M + 1) | Method A (TFA) | 95 | Meth-od C, G1 |

TABLE 1-continued
| | | | | | | | | |
|---|---|---|---|---|---|---|---|---|
| 187 | 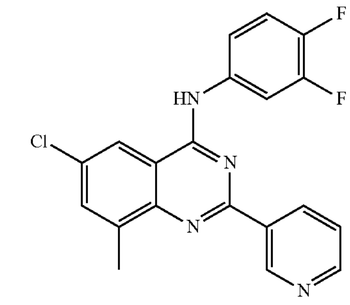 | 337.38 | 1H-NMR (400 MHz, DMSO-d6): δ 10.10 (s, 1H), 9.51 (s, 1H), 8.65-8.70 (m, 2H), 3.45 (s, 1H), 8.38 (s, 1H), 8.28 (d, J = 8.0 Hz, 1H), 7.83 (d, J = 8.8 Hz, 1H), 7.76 (d, J = 8.0 Hz, 1H), 7.69 (t, J = 7.8 Hz, 1H), 7.62 (d, J = 7.2 Hz, 1H), 7.54-7.57 (m, 1H), 2.56 (s, 3H). | DMSO | 338.1 (M + 1) | Method B (NH4HCO3) | 95 | Meth-od C, G1 |
| 188 | 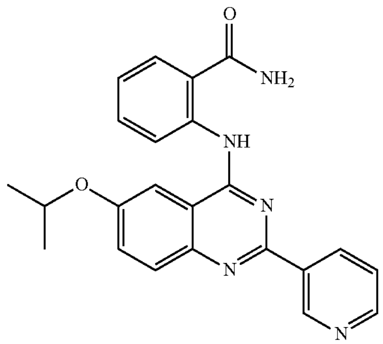 | 355.39 | 1H-NMR (400 MHz, DMSO-d6): δ 13.11 (s, 1H), 9.61 (s, 1H), 9.09 (d, J = 8.8 Hz, 1H), 8.89 (d, J = 8.0 Hz, 1H), 8.81 (s, 1H), 8.50 (s, 1H), 8.01-7.98 (m, 2H), 7.96 (dd, J = 7.8, 1.0 Hz, 1H), 7.86 (d, J = 8.8 Hz, 1H), 7.78-7.72 (m, 3H), 7.23 (t, J = 7.4 Hz, 1H), 2.56 (s, 3H). | DMSO | 356.2 (M + 1) | Method B (NH4HCO3) | 95 | Meth-od C, G1 |
| 189 | 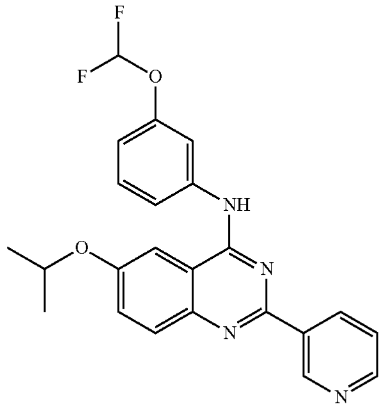 | 385.42 | 1H-NMR (400 MHz, DMSO-d6): δ 12.62 (s, 1H), 9.58 (s, 1H), 9.03 (d, J = 8.4 Hz, 1H), 8.92 (d, J = 4.0 Hz, 1H), 8.74-8.69 (m, 2H), 7.92-7.87 (m, 2H), 7.72 (t, J = 7.6 Hz, 1H), 7.66-7.56 (m, 3H), 7.23 (t, J = 7.6 Hz, 1H), 4.00 (s, 3H), 2.84 (d, J = 4.4 Hz, 3H). | DMSO | 386.2 (M + 1) | Method B (NH4HCO3) | 95 | Meth-od C, G1 |

TABLE 1-continued
| | | | | | | | | |
|---|---|---|---|---|---|---|---|---|
| 190 | 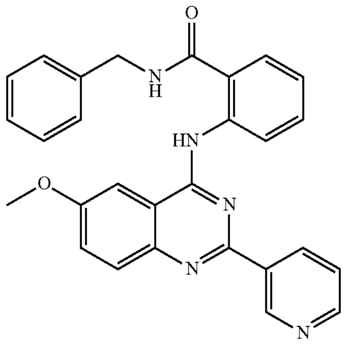 [SMILES: COc1ccc2nc(-c3cccnc3)nc(Nc3ccccc3C(=O)NCc3ccccc3)c2c1] | 461.51 | 1H-NMR (400 MHz, DMSO-d6): δ 12.40 (s, 1H), 9.57 (d, J = 1.2 Hz, 1H), 9.48 (t, J = 6.0 Hz, 1H), 8.89 (d, J = 8.8 Hz, 1H), 8.73-8.68 (m, 2H), 7.96 (dd, J = 8.0, 1.2 Hz, 1H), 7.89 (d, J = 8.8 Hz, 1H), 7.76-7.72 (m, 1H), 7.61-7.55 (m, 3H), 7.34-7.20 (m, 6H), 4.52 (d, J = 5.6 Hz, 2H), 3.93 (s, 3H). | DMSO | 462.2 (M + 1) | Method B (NH4HCO3) | 95 | Meth-od C, G1 |
| 191 | 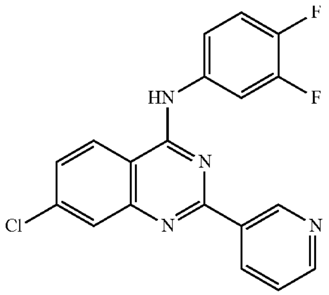 [SMILES: Fc1ccc(Nc2nc(-c3cccnc3)nc3cc(Cl)ccc23)cc1F] | 368.77 | 1H NMR (300 MHz, DMSO-d6): δ 10.32 (s, 1H), 9.55-9.45 (m, 1H), 8.93-8.76 (m, 2H), 8.63 (d, J = 8.9 Hz, 1H), 8.10 (ddd, J = 13.2, 7.5, 2.6 Hz, 1H), 7.97 (d, J = 2.1 Hz, 1H), 7.80-7.67 (m, 3H), 7.62-7.49 (m, 1H). | DMSO | 369.0, 371.0 (M + 1) | Method B (NH4HCO3) | 97 | Meth-od C, G1 |
| 192 | 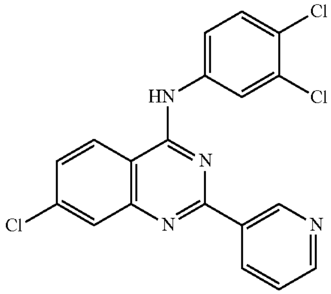 [SMILES: Clc1ccc2c(Nc3ccc(Cl)c(Cl)c3)nc(-c3cccnc3)nc2c1] | 401.68 | 1H NMR (300 MHz, DMSO-d6): δ 10.38 (s, 1H), 9.58-9.43 (m, 1H), 8.90-8.79 (m, 2H), 8.65 (d, J = 9.0 Hz, 1H), 8.33 (d, J = 2.4 Hz, 1H), 8.01-7.90 (m, 2H), 7.82-7.68 (m, 3H). | DMSO | 401.0, 403.0, 405.0 (M + 1) | Method B (NH4HCO3) | 97 | Meth-od C, G1 |

TABLE 1-continued
| | | | | | | | | |
|---|---|---|---|---|---|---|---|---|
| 193 | 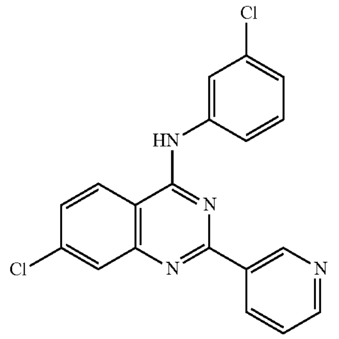 [SMILES: Clc1cccc(Nc2nc(-c3cccnc3)nc3cc(Cl)ccc23)c1] | 367.23 | 1H NMR (300 MHz, DMSO-d6): δ 10.19 (s, 1H), 9.53 (d, J = 2.1 Hz, 1H), 8.78-8.56 (m, 3H), 8.17 (t, J = 2.0 Hz, 1H), 7.96 (d, J = 2.1 Hz, 1H), 7.93-7.85 (m, 1H), 7.75 (dd, J = 8.9, 2.2 Hz, 1H), 7.58 (ddd, J = 8.0, 4.8, 0.7 Hz, 1H), 7.51 (t, J = 8.1 Hz, 1H), 7.26 (ddd, J = 8.0, 2.0, 0.8 Hz, 1H). | DMSO | 367.0, 369.0 (M + 1) | Method B (NH4HCO3) | 98 | Meth-od C, G1 |
| 194 | 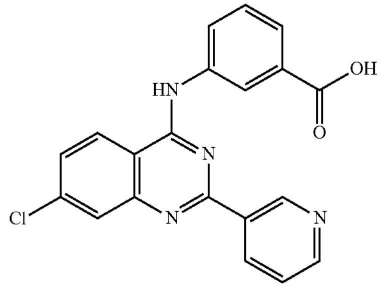 [SMILES: O=C(O)c1cccc(Nc2nc(-c3cccnc3)nc3cc(Cl)ccc23)c1] | 376.80 | 1H NMR (300 MHz, DMSO-d6): δ 13.11 (s, 1H), 10.27 (s, 1H), 9.58 (d, J = 2.1 Hz, 1H), 8.87-8.62 (m, 4H), 8.21-8.10 (m, 1H), 7.96 (d, J = 2.1 Hz, 1H), 7.82-7.68 (m, 2H), 7.64-7.53 (m, 2H). | DMSO | 377.0, 379.0 (M + 1) | Method A (TFA) | 95 | Meth-od C, G1 |
| 195 | 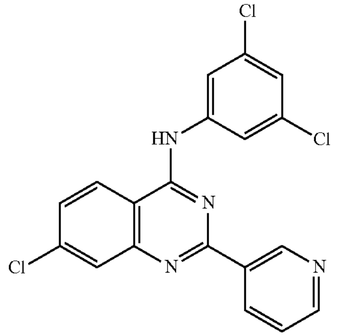 [SMILES: Clc1cc(Cl)cc(Nc2nc(-c3cccnc3)nc3cc(Cl)ccc23)c1] | 401.68 | 1H NMR (300 MHz, DMSO-d6): δ 10.32 (s, 1H), 9.52-9.49 (m, 1H), 8.85-8.73 (m, 2H), 8.61 (d, J = 9.0 Hz, 1H), 8.18-8.08 (m, 2H), 7.99-7.95 (m, 1H), 7.77 (dd, J = 8.9, 2.2 Hz, 1H), 7.71 (dd, J = 7.8, 5.0 Hz, 1H), 7.42-7.39 (m, 1H). | DMSO | 401.0, 403.0, 405.0 (M + 1) | Method B (NH4HCO3) | 97 | Meth-od C, G1 |

TABLE 1-continued
| | | | | | | | | |
|---|---|---|---|---|---|---|---|---|
| 196 | 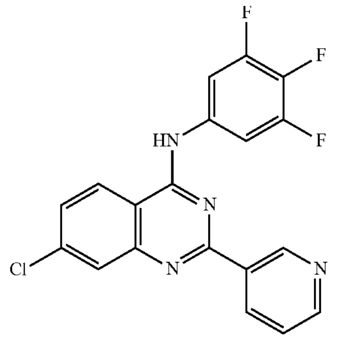 [SMILES: Fc1cc(Nc2nc(-c3cccnc3)nc3cc(Cl)ccc23)cc(F)c1F] | 386.76 | 1H-NMR (300 MHz, DMSO-d6): δ 10.43 (s, 1H), 9.49 (d, J = 1.9 Hz, 1H), 8.95-8.82 (m, 2H), 8.64 (d, J = 9.0 Hz, 1H), 8.01-7.82 (m, 4H), 7.78 (dd, J = 8.9, 2.2 Hz, 1H). | DMSO | 387.0, 389.1 (M + 1) | Method B (NH4HCO3) | 97 | Meth-od C, G1 |
| 197 | 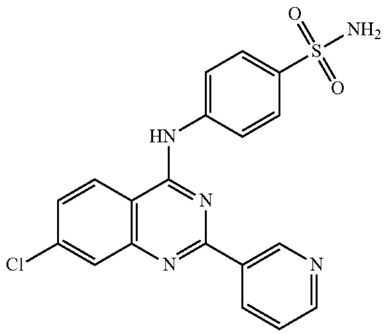 [SMILES: NS(=O)(=O)c1ccc(Nc2nc(-c3cccnc3)nc3cc(Cl)ccc23)cc1] | 411.86 | 1H NMR (400 MHz, DMSO-d6): δ 10.50 (brs, 1H), 9.56 (s, 1H), 9.08-8.93 (m, 1H), 8.92-8.82 (m, 1H), 8.73 (d, J = 8.9 Hz, 1H), 8.21-8.11 (m, 2H), 8.02 (d, J = 1.9 Hz, 1H), 7.98-7.77 (m, 4H), 7.38 (s, 2H). | DMSO | 412.1, 414.1 (M + 1) | Method B (NH4HCO3) | 97 | Meth-od C, G1 |
| 198 | 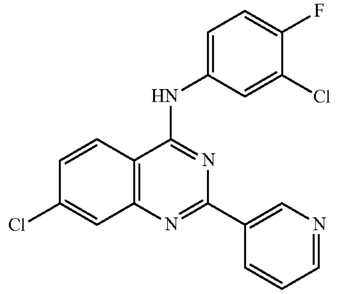 [SMILES: Fc1ccc(Nc2nc(-c3cccnc3)nc3cc(Cl)ccc23)cc1Cl] | 385.22 | 1H NMR (400 MHz, DMSO-d6): δ 10.25 (s, 1H), 9.51 (d, J = 1.4 Hz, 1H), 8.77-8.69 (m, 2H), 8.60 (d, J = 9.0 Hz, 1H), 8.27-8.20 (m, 1H), 7.97 (d, J = 2.1 Hz, 1H), 7.90 (ddd, J = 9.0, 4.3, 2.6 Hz, 1H), 7.76 (dd, J = 8.9, 2.1 Hz, 1H), 7.64 (dd, J = 8.0, 4.9 Hz, 1H), 7.55 (t, J = 9.1 Hz, 1H). | DMSO | 385.0, 387.0 (M + 1) | Method B (NH4HCO3) | 100 | Meth-od C, G1 |

TABLE 1-continued
| | | | | | | | | |
|---|---|---|---|---|---|---|---|---|
| 199 | 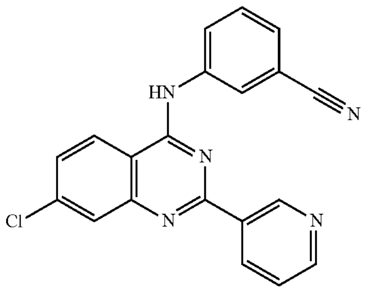 [SMILES: N#Cc1cccc(Nc2nc(-c3cccnc3)nc3cc(Cl)ccc23)c1] | 357.80 | 1H NMR (400 MHz, DMSO-d6): δ 10.36 (s, 1H), 9.53-9.49 (m, 1H), 8.81-8.70 (m, 2H), 8.64 (d, J = 8.9 Hz, 1H), 8.45-8.36 (m, 1H), 8.29-8.21 (m, 1H), 7.98 (d, J = 2.1 Hz, 1H), 7.77 (dd, J = 8.9, 2.1 Hz, 1H), 7.74-7.61 (m, 3H). | DMSO | 357.9, 359.9 (M + 1) | Method B (NH4HCO3) | 99 | Meth-od C, G1 |
| 200 | 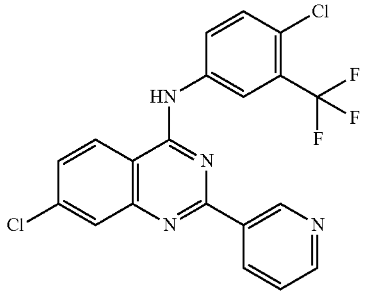 [SMILES: FC(F)(F)c1cc(Nc2nc(-c3cccnc3)nc3cc(Cl)ccc23)ccc1Cl] | 435.23 | 1H-NMR (400 MHz, DMSO-d6): δ 10.44 (s, 1H), 9.53 (s, 1H), 8.84-8.74 (m, 2H), 8.69-8.61 (m, 2H), 8.26 (dd, J = 8.8, 2.6 Hz, 1H), 7.99 (d, J = 2.1 Hz, 1H), 7.83 (d, J = 8.8 Hz, 1H), 7.78 (dd, J = 8.9, 2.1 Hz, 1H), 7.70 (dd, J = 7.7, 5.3 Hz, 1H). | DMSO | 435.0, 437.0 (M + 1) | Method B (NH4HCO3) | 99 | Meth-od C, G1 |
| 201 | 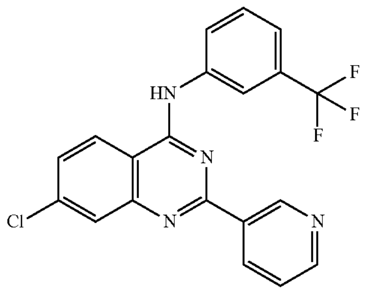 [SMILES: FC(F)(F)c1cccc(Nc2nc(-c3cccnc3)nc3cc(Cl)ccc23)c1] | 400.78 | 1H-NMR (400 MHz, DMSO-d6): δ 10.45 (s, 1H), 9.53 (d, J = 1.5 Hz, 1H), 3.85 (d, J = 8.1 Hz, 1H), 8.82 (dd, J = 5.0, 1.4 Hz, 1H), 8.69 (d, J = 9.0 Hz, 1H), 8.49 (s, 1H), 8.21 (d, J = 8.0 Hz, 1H), 7.99 (d, J = 2.1 Hz, 1H), 7.83-7.67 (m, 3H), 7.56 (d, J = 7.8 Hz, 1H). | DMSO | 401.1, 403.0 (M + 1) | Method B (NH4HCO3) | 99 | Meth-od C, G1 |

TABLE 1-continued
| | | | | | | | | |
|---|---|---|---|---|---|---|---|---|
| 202 | 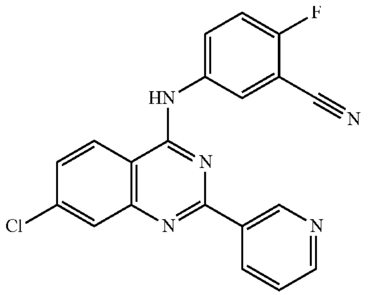 [SMILES: N#Cc1cc(Nc2nc(-c3cccnc3)nc3cc(Cl)ccc23)ccc1F] | 375.79 | 1H-NMR (400 MHz, DMSO-d6): δ 10.47 (s, 1H), 9.49 (s, 1H), 8.87-8.77 (m, 2H), 8.63 (d, J = 8.9 Hz, 1H), 8.42 (dd, J = 5.8, 2.7 Hz, 1H), 8.26 (ddd, J = 9.1, 4.9, 2.8 Hz, 1H), 7.98 (d, J = 2.1 Hz, 1H), 7.83-7.72 (m, 2H), 7.66 (t, J = 9.1 Hz, 1H). | DMSO | 375.9, 377.9 (M + 1) | Method B (NH4HCO3) | 99 | Meth-od C, G1 |
| 203 | 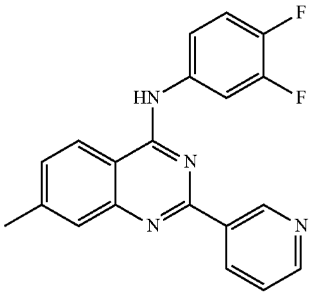 [SMILES: Cc1ccc2c(Nc3ccc(F)c(F)c3)nc(-c3cccnc3)nc2c1] | 348.35 | 1H-NMR (400 MHz, DMSO-d6): δ 10.42 (s, 1H), 9.51 (s, 1H), 8.91 (d, J = 6.8 Hz, 1H), 8.86 (d, J = 4.4 Hz, 1H), 8.57 (d, J = 8.3 Hz, 1H), 8.11 (ddd, J = 13.0, 7.5, 2.5 Hz, 1H), 7.90-7.68 (m, 3H), 7.65-7.46 (m, 2H), 2.56 (s, 3H). | DMSO | 349.1 (M + 1) | Method B (NH4HCO3) | 100 | Meth-od C, G1 |
| 204 | 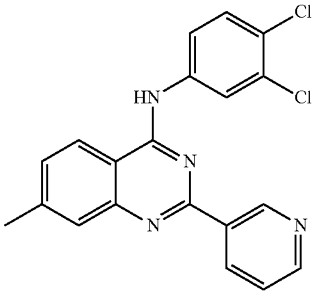 [SMILES: Cc1ccc2c(Nc3ccc(Cl)c(Cl)c3)nc(-c3cccnc3)nc2c1] | 381.26 | 1H-NMR (400 MHz, DMSO-d6): δ 10.05 (s, 1H), 9.54 (s, 1H), 8.75-8.65 (m, 2H), 8.46 (d, J = 8.5 Hz, 1H), 8.42 (d, J = 2.4 Hz, 1H), 7.98 (dd, J = 8.8, 2.4 Hz, 1H), 7.72 (d, J = 9.1 Hz, 2H), 7.57 (dd, J = 7.9, 4.9 Hz, 1H), 7.53 (d, J = 8.5 Hz, 1H), 2.55 (s, 3H). | DMSO | 381.0, 383.0 (M + 1) | Method B (NH4HCO3) | 100 | Meth-od C, G1 |

TABLE 1-continued
| | | | | | | | | |
|---|---|---|---|---|---|---|---|---|
| 205 | 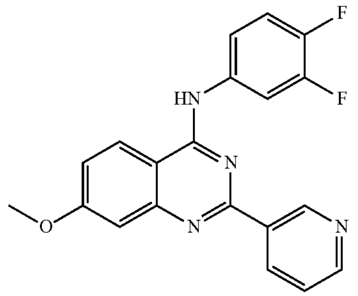 [SMILES: COc1ccc2c(Nc3ccc(F)c(F)c3)nc(-c3cccnc3)nc2c1] | 364.35 | 1H-NMR (400 MHz, DMSO-d6): δ 9.98 (s, 1H), 9.53 (s, 1H), 8.79-8.58 (m, 2H), 8.49 (d, J = 9.0 Hz, 1H), 8.13 (ddd, J = 9.2, 7.1, 1.7 Hz, 1H), 7.84-7.65 (m, 1H), 7.67-7.46 (m, 2H), 7.41-7.23 (m, 2H), 3.97 (s, 3H). | DMSO | 365.1 (M + 1) | Method B (NH4HCO3) | 95 | Meth-od C, G1 |
| 206 | 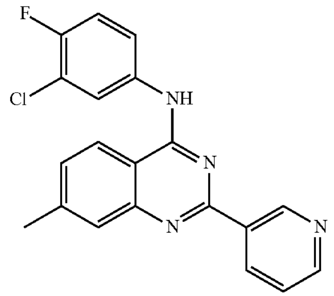 [SMILES: Cc1ccc2c(Nc3ccc(F)c(Cl)c3)nc(-c3cccnc3)nc2c1] | 364.80 | 1H-NMR (400 MHz, DMSO-d6): δ 10.32 (s, 1H), 9.50 (d, J = 1.4 Hz, 1H), 8.92-8.77 (m, 2H), 8.53 (d, J = 8.5 Hz, 1H), 8.24 (dd, J = 6.8, 2.5 Hz, 1H), 7.98-7.87 (m, 1H), 7.83-7.70 (m, 2H), 7.60-7.50 (m, 2H), 2.56 (s, 3H). | DMSO | 365.1, 367.1 (M + 1) | Method B (NH4HCO3) | 100 | Meth-od C, G1 |
| 207 | 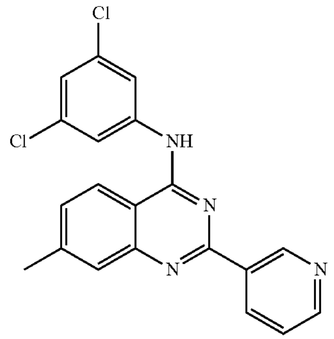 [SMILES: Cc1ccc2c(Nc3cc(Cl)cc(Cl)c3)nc(-c3cccnc3)nc2c1] | 381.26 | 1H-NMR (400 MHz, DMSO-d6): δ 10.21 (s, 1H), 9.53 (s, 1H), 8.87-8.73 (m, 2H), 8.50 (d, J = 8.5 Hz, 1H), 8.17 (d, J = 1.7 Hz, 2H), 7.77 (s, 1H), 7.72 (dd, J = 7.8, 5.1 Hz, 1H), 7.57 (dd, J = 8.4, 0.9 Hz, 1H), 7.39 (t, J = 1.6 Hz, 1H), 2.56 (s, 3H). | DMSO | 381.1, 383.0 (M + 1) | Method B (NH4HCO3) | 99 | Meth-od C, G1 |

TABLE 1-continued
| | | | | | | | | |
|---|---|---|---|---|---|---|---|---|
| 208 | 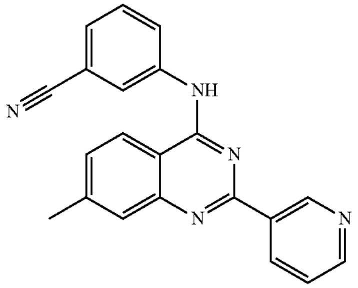 | 337.38 | 1H-NMR (400 MHz, DMSO-d6): δ 10.12 (s, 1H), 9.53 (d, J = 1.6 Hz, 1H), 8.77-8.63 (m, 2H), 8.53-8.42 (m, 2H), 8.28 (d, J = 8.3 Hz, 1H), 7.75 (s, 1H), 7.69 (t, J = 7.9 Hz, 1H), 7.62 (d, J = 7.7 Hz, 1H), 7.60-7.51 (m, 2H), 2.55 (s, 3H). | DMSO | 338.2 (M + 1) | Method B (NH4HCO3) | 100 | Meth-od C, G1 |
| 209 | 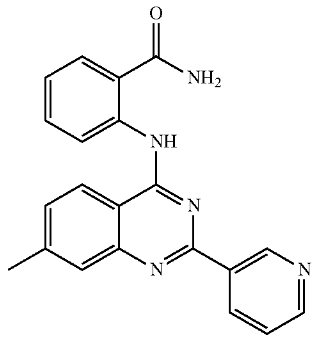 [SMILES: Cc1ccc2c(Nc3ccccc3C(N)=O)nc(-c3cccnc3)nc2c1] | 355.39 | 1H-NMR (400 MHz, DMSO-d6): δ 13.09 (s, 1H), 9.60 (s, 1H), 9.02 (d, J = 8.4 Hz, 1H), 8.96 (d, J = 8.4 Hz, 1H), 8.85 (d, J = 4.0 Hz, 1H), 8.49 (s, 1H), 8.13 (d, J = 8.4 Hz, 1H), 7.97 (d, J = 7.8 Hz, 1H), 7.92 (s, 1H), 7.83 (dd, J = 8.0, 5.2 Hz, 1H), 7.80 (s, 1H), 7.73 (t, J = 7.4 Hz, 1H), 7.61 (d, J = 8.0 Hz, 1H), 7.25 (t, J = 7.6 Hz, 1H), 2.56 (s, 3H). | DMSO | 356.1 (M + 1) | Method B (NH4HCO3) | 99 | Meth-od C, G1 |
| 210 | 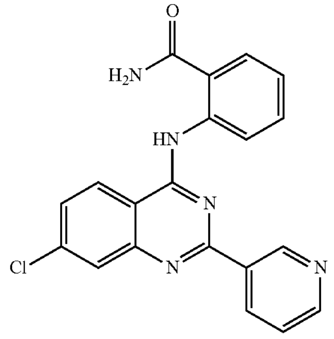 [SMILES: NC(=O)c1ccccc1Nc1nc(-c2cccnc2)nc2cc(Cl)ccc12] | 375.81 | 1H-NMR (400 MHz, DMSO-d6): 13.13 (s, 1H), 9.59 (s, 1H), 9.03-8.89 (m, 3H), 3.50 (s, 1H), 8.21-8.19 (d, J = 8.6 Hz, 1H), 7.99-7.87 (m, 4H), 7.82-7.79 (dd, J = 8.8, 2.3 Hz, 1H), 7.74-7.70 (m, 1H), 7.28-7.24 (m, 1H). | DMSO | 376.1, 378.1 (M + 1) | Method B (NH4HCO3) | 98 | Meth-od C, G1 |

TABLE 1-continued
| | | | | | | | | | |
|---|---|---|---|---|---|---|---|---|---|
| 211 | 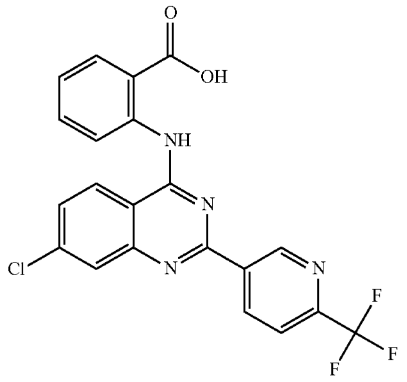 [SMILES: O=C(O)c1ccccc1Nc1nc(-c2ccc(C(F)(F)F)nc2)nc2cc(Cl)ccc12] | | 444.79 | 1H-NMR (400 MHz, DMSO-d6): δ 13.68 (brs, 1H), 11.98 (s, 1H), 9.49 (s, 1H), 8.83-8.64 (m, 2H), 8.11-7.90 (m, 3H), 7.81 (d, J = 2.0 Hz, 1H), 7.75-7.62 (m, 2H), 7.22 (t, J = 7.6 Hz, 1H). | DMSO | 444.9, 446.9 (M + 1) | Method B (NH4HCO3) | 100 | Meth-od C, G1 |
| 212 | 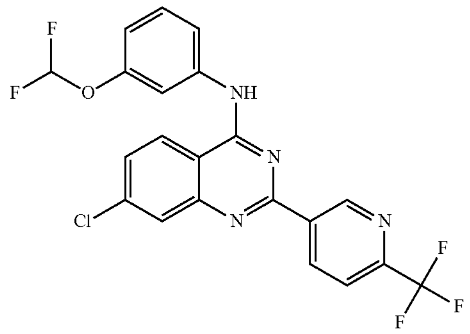 [SMILES: FC(F)Oc1cccc(Nc2nc(-c3ccc(C(F)(F)F)nc3)nc3cc(Cl)ccc23)c1] | HCl | 466.79 | 1H-NMR (400 MHz, DMSO-d6): δ 10.36 (s, 1H), 9.62 (s, 1H), 8.90 (dd, J = 8.2, 1.3 Hz, 1H), 8.69 (d, J = 9.0 Hz, 1H), 8.05 (d, J = 8.2 Hz, 1H), 7.99 (d, J = 2.1 Hz, 1H), 7.92-7.86 (m, 1H), 7.86-7.79 (m, 1H), 7.77 (dd, J = 8.9, 2.1 Hz, 1H), 7.53 (t, J = 8.2 Hz, 1H), 7.30 (t, J = 73.3 Hz, 1H), 7.04 (dd, J = 8.1, 2.1 Hz, 1H). | DMSO | 466.9, 468.9 (M + 1) | Method B (NH4HCO3) | 100 | Meth-od C, G1 |
| 213 | 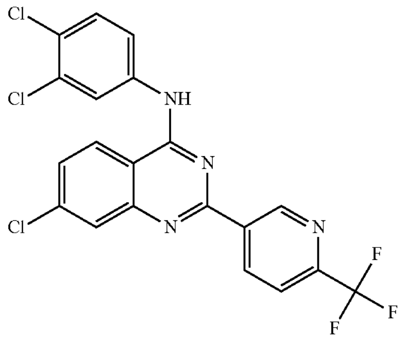 [SMILES: FC(F)(F)c1ccc(-c2nc(Nc3ccc(Cl)c(Cl)c3)c3ccc(Cl)cc3n2)cn1] | | 469.67 | 1H-NMR (400 MHz, DMSO-d6): δ 10.31 (s, 1H), 9.57 (s, 1H), 8.85 (dd, J = 8.1, 1.3 Hz, 1H), 8.60 (d,. J = 9.0 Hz, 1H), 8.35-8.23 (m, 1H), 8.06 (d, J = 8.2 Hz, 1H), 8.00-7.90 (m, 2H), 7.80-7.65 (m, 2H). | DMSO | 468.9, 470.8 (M + 1) | Method B (NH4HCO3) | 100 | Meth-od C, G1 |

TABLE 1-continued
| | | | | | | | | |
|---|---|---|---|---|---|---|---|---|
| 214 | 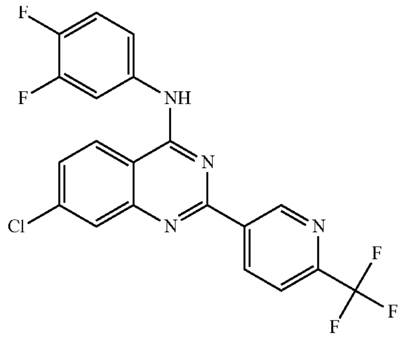 | 436.77 | 1H-NMR (400 MHz, DMSO-d6): δ 10.35 (s, 1H), 9.56 (s, 1H), 8.84 (d, J = 8.3 Hz, 1H), 8.64 (d, J = 9.0 Hz, 1H), 8.14-7.99 (m, 2H), 7.95 (d, J = 2.1 Hz, 1H), 7.81-7.65 (m, 2H), 7.59-7.48 (m, 1H). | DMSO | 436.9, 438.9 (M + 1) | Method B (NH4HCO3) | 100 | Meth-od C, G1 |
| 215 | 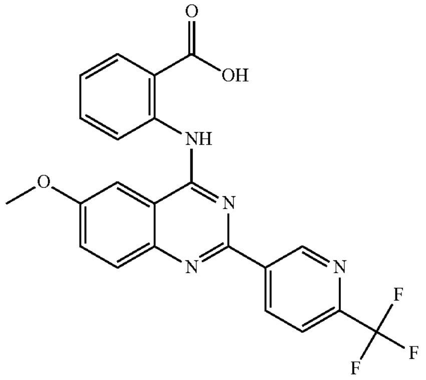 [SMILES: COc1ccc2nc(-c3ccc(C(F)(F)F)nc3)nc(Nc3ccccc3C(=O)O)c2c1] | 440.37 | 1H-NMR (400 MHz, DMSO-d6): δ 13.81 (brs, 1H), 11.97 (s, 1H), 9.57 (s, 1H), 9.01-8.91 (m, 1H), 8.84 (d, J = 8.3 Hz, 1H), 8.06 (dd, J = 7.9, 1.4 Hz, 1H), 8.01 (d, J = 8.2 Hz, 1H), 7.82 (d, J = 9.1 Hz, 1H), 7.79-7.70 (m, 1H), 7.52 (dd, J = 9.1, 2.6 Hz, 1H), 7.49-7.44 (m, 1H), 7.20 (t, J = 7.6 Hz, 1H), 3.94 (s, 3H). | DMSO | 441.1 (M + 1) | Method B (NH4HCO3) | 100 | Meth-od C, G1 |
| 216 | 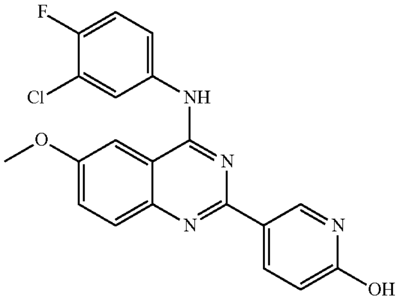 [SMILES: COc1ccc2nc(-c3ccc(O)nc3)nc(Nc3ccc(F)c(Cl)c3)c2c1] | 396.80 | 1H-NMR (400 MHz, DMSO-d6): δ 11.89 (s, 1H), 9.80 (s, 1H), 8.34 (dd, J = 9.6, 2.6 Hz, 1H), 8.22 (s, 1H), 8.11 (dd, J = 6.9, 2.6 Hz, 1H), 7.88 (d, J = 2.7 Hz, 1H), 7.84-7.77 (m, 1H), 7.74 (d, J = 9.1 Hz, 1H), 7.56-7.43 (m, 2H), 6.44 (d, J = 9.6 Hz, 1H), 3.95 (s, 3H). | DMSO | 397.1, 399.1 (M + 1) | Method B (NH4HCO3) | 100 | Meth-od C, G1 |

TABLE 1-continued
| | | | | | | | | |
|---|---|---|---|---|---|---|---|---|
| 217 | 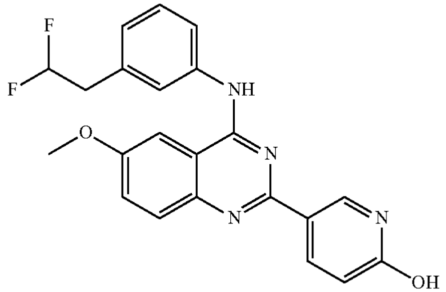 [SMILES: COc1ccc2nc(-c3ccc(O)nc3)nc(Nc3cccc(CC(F)F)c3)c2c1] | 410.37 | 1H-NMR (400 MHz, DMSO-d6): δ 11.89 (s, 1H), 9.80 (s, 1H), 8.36 (dd, J = 9.6, 2.6 Hz, 1H), 8.25 (d, J = 2.2 Hz, 1H), 7.92 (d, J = 2.6 Hz, 1H), 7.80-7.67 (m, 3H), 7.53-7.46 (m, 2H), 7.27 (t, J = 74.0 Hz, 1H), 6.98 (dd, J = 8.2, 2.0 Hz, 1H), 6.43 (d, J = 9.5 Hz, 1H), 3.96 (s, 3H). | DMSO | 411.1 (M + 1) | Method B (NH4HCO3) | 100 | Meth-od C, G1 |
| 218 | 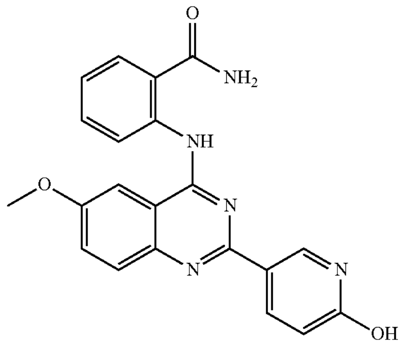 [SMILES: COc1ccc2nc(-c3ccc(O)nc3)nc(Nc3ccccc3C(N)=O)c2c1] | 387.39 | 1H-NMR (400 MHz, DMSO-d6): δ 12.98 (s, 1H), 12.58-12.05 (m, 1H), 8.55 (s, 2H), 8.41 (s, 1H), 8.33 (dd, J = 9.7, 2.5 Hz, 1H), 8.11-7.98 (m, 1H), 7.97- 7.86 (m, 2H), 7.79-7.64 (m, 3H), 7.44-7.29 (m, 1H), 6.52 (d, J = 9.7 Hz, 1H), 3.98 (s, 3H). | DMSO | 388.2 (M + 1) | Method B (NH4HCO3) | 100 | Meth-od C, G1 |
| 219 | 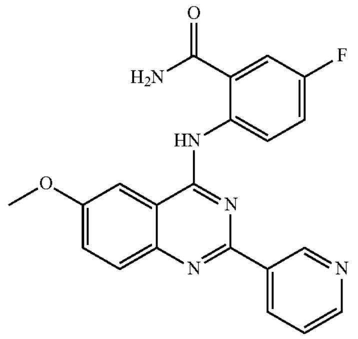 [SMILES: COc1ccc2nc(-c3cccnc3)nc(Nc3ccc(F)cc3C(N)=O)c2c1] | 389.38 | 1H-NMR (400 MHz, DMSO-d6): δ 12.73 (s, 1H), 9.56 (s, 1H), 9.10 (dd, J = 8.9, 5.4 Hz, 1H), 8.79-8.63 (m, 2H), 8.50 (s, 1H), 8.08 (s, 1H), 7.95-7.76 (m, 2H), 7.68-7.45 (m, 4H), 3.97 (s, 3H). | DMSO | 390.1 (M + 1) | Method B (NH4HCO3) | 98 | Meth-od C, G1 |

TABLE 1-continued
| | | | | | | | | |
|---|---|---|---|---|---|---|---|---|
| 220 | 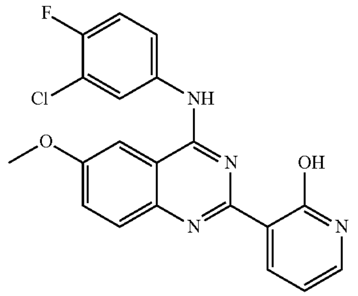 [SMILES: COc1ccc2nc(-c3cccnc3O)nc(Nc3ccc(F)c(Cl)c3)c2c1] | 369.80 | 1H-NMR (400 MHz, DMSO-d6): δ 14.87 (brs, 1H), 10.08 (brs, 1H), 8.85-7.66 (m, 6H), 7.69-6.63 (m, 3H), 3.96 (s, 3H). | DMSO | 397.1, 399.1 (M + 1) | Method B (NH4HCO3) | 100 | Meth-od C, G1 |
| 221 | 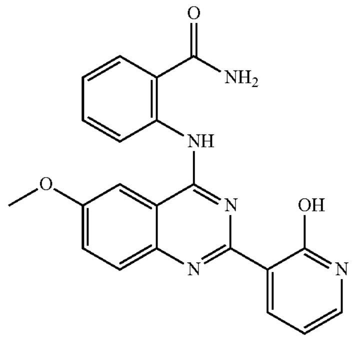 [SMILES: COc1ccc2nc(-c3cccnc3O)nc(Nc3ccccc3C(N)=O)c2c1] | 387.39 | 1H-NMR (400 MHz, DMSO-d6): δ 14.80 (brs, 1H), 13.19 (s, 1H), 8.68 (d, J = 7.3 Hz, 1H), 8.44 (s, 1H), 8.38 (d, J = 8.0 Hz, 1H), 8.13 (d, J = 9.1 Hz, 1H), 8.10-8.03 (m, 1H), 7.95 (d, J = 7.8 Hz, 1H), 7.90 (s, 1H), 7.86 (s, 1H), 7.78-7.65 (m, 2H), 7.43 (t, J = 7.5 Hz, 1H), 6.78 (t, J = 6.8 Hz, 1H), 3.99 (s, 3H). | DMSO | 388.1 (M + 1) | Method B (NH4HCO3) | 100 | Meth-od C, G1 |
| 222 | 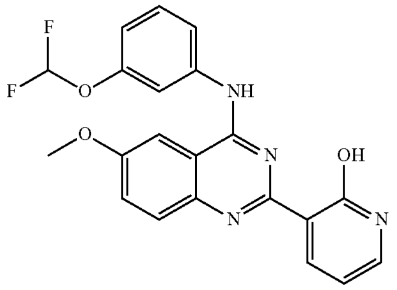 [SMILES: COc1ccc2nc(-c3cccnc3O)nc(Nc3cccc(OC(F)F)c3)c2c1] | 410.37 | 1H-NMR (400 MHz, DMSO-d6): δ 15.33 (brs, 1H), 13.47 (brs, 1H), 11.69 (s, 1H), 8.62 (dd, J = 7.5, 2.1 Hz, 1H), 8.45 (d, J = 2.3 Hz, 1H), 8.17 (d, J = 9.2 Hz, 1H), 8.07 (dd, J = 6.2, 2.1 Hz, 1H), 7.81-7.68 (m, 3H), 7.61 (t, J = 8.1 Hz, 1H), 7.32 (t, J = 74.0 Hz, 1H), 7.26-7.18 (m, 1H), 6.80-6.69 (m, 1H), 4.03 (s, 3H). | DMSO | 411.1 (M + 1) | Method B (NH4HCO3) | 100 | Meth-od C, G1 |

TABLE 1-continued
| | | | | | | | | |
|---|---|---|---|---|---|---|---|---|
| 223 | 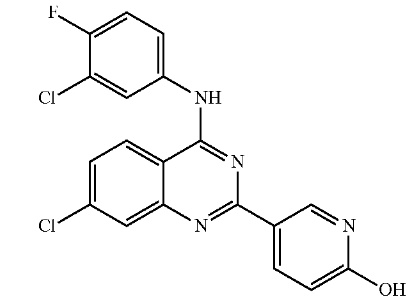 [SMILES: Oc1ccc(-c2nc(Nc3ccc(F)c(Cl)c3)c3ccc(Cl)cc3n2)cn1] | 401.22 | 1H-NMR (400 MHz, DMSO-d6): δ 11.22 (brs, 1H), 8.47 (d, J = 8.8 Hz, 1H), 8.30 (dd, J = 9.6, 2.3 Hz, 1H), 8.27- 8.18 (m, 1H). 8.11 (dd, J =- 6.8, 2.4 Hz, 1H), 7.90-7.73 (m, 2H), 7.60 (dd, J = 8.8, 1.8 Hz, 1H), 7.47 (t, J = 9.1 Hz, 1H), 6.44 (d, J = 9.6 Hz, 1H). | DMSO | 401.0, 403.0 (M + 1) | Method B (NH4HCO3) | 100 | Meth-od C, G1 |
| 224 | 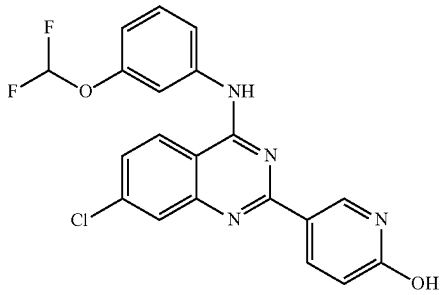 [SMILES: Oc1ccc(-c2nc(Nc3cccc(OC(F)F)c3)c3ccc(Cl)cc3n2)cn1] | 414.79 | 1H-NMR (400 MHz, DMSO-d6): δ 12.00 (s, 1H), 10.07 (s, 1H), 8.54 (d, J = 8.9 Hz, 1H), 8.34 (dd, J = 9.6, 2.6 Hz, 1H), 8.30 (d, J = 2.3 Hz, 1H), 7.87-7.69 (m, 3H), 7.62 (dd, J = 8.9, 2.1 Hz, 1H), 7.48 (t, J = 8.2 Hz, 1H), 7.26 (t, J = 74.0 Hz, 1H), 7.00 (dd, J = 8.1, 2.0 Hz, 1H), 6.44 (d, J = 9.6 Hz, 1H). | DMSO | 415.1, 417.1 (M + 1) | Method B (NH4HCO3) | 100 | Meth-od C, G1 |
| 225 | 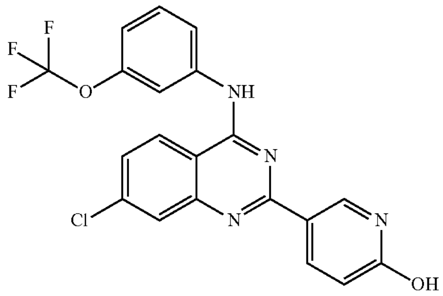 [SMILES: Oc1ccc(-c2nc(Nc3cccc(OC(F)(F)F)c3)c3ccc(Cl)cc3n2)cn1] | 432.78 | 1H-NMR (400 MHz, DMSO-d6): δ 12.06 (s, 1H), 10.15 (s, 1H), 8.55 (d, J = 9.0 Hz, 1H), 8.34 (dd, J = 9.6, 2.5 Hz, 1H), 8.29 (s, 1H), 7.97 (s, 1H), 7.88 (d, J = 8.0 Hz, 1H), 7.84 (d, J = 2.1 Hz, 1H), 7.65 (dd, J = 8.8, 2.1 Hz, 1H), 7.57 (t, J = 8.2 Hz, 1H), 7.17 (d, J = 7.8 Hz, 1H), 6.44 (d, J = 9.6 Hz, 1H). | DMSO | 433.0, 435.0 (M + 1) | Method B (NH4HCO3) | 100 | Meth-od C, G1 |

TABLE 1-continued
| | | | | | | | | |
|---|---|---|---|---|---|---|---|---|
| 226 | 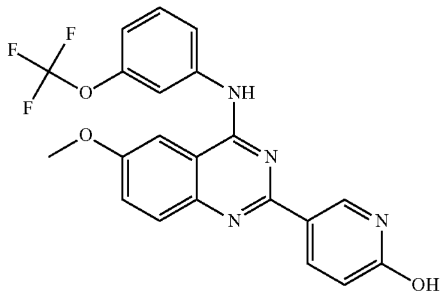 [SMILES: COc1ccc2nc(-c3ccc(O)nc3)nc(Nc3cccc(OC(F)(F)F)c3)c2c1] | 428.36 | 1H-NMR (400 MHz, DMSO-d6): δ 12.28 (brs, 1H), 8.47-8.06 (m, 3H), 8.06-7.76 (m, 3H), 7.67-7.59 (m, 2H), 7.28 (s, 1H), 6.47 (d, J = 9.7 Hz, 1H), 3.98 (s, 3H). | DMSO | 429.1 (M + 1) | Method B (NH4HCO3) | 94 | Meth-od C, G1 |
| 227 | 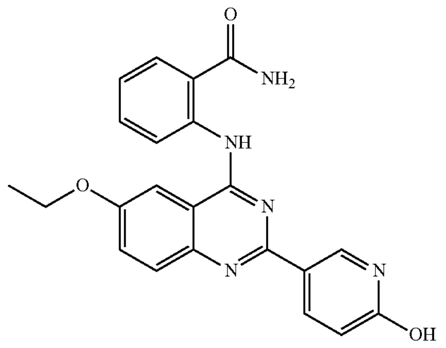 [SMILES: CCOc1ccc2nc(-c3ccc(O)nc3)nc(Nc3ccccc3C(N)=O)c2c1] | 401.42 | 1H-NMR (400 MHz, DMSO-d6): δ 12.97 (s, 1H), 12.27 (s, 1H), 8.73-8.56 (m, 1H), 8.53 (s, 1H), 8.42 (s, 1H), 8.33 (dd, J = 9.7, 2.6 Hz, 1H), 8.04-7.86 (m, 3H), 7.74-7.59 (m, 3H), 7.34 (t, J = 8.7 Hz, 1H), 6.52 (d, J = 9.7 Hz, 1H), 4.23 (q, J = 6.9 Hz, 2H), 1.45 (t, J = 6.9 Hz, 3H). | DMSO | 402.2 (M + 1) | Method B (NH4HCO3) | 100 | Meth-od C, G1 |
| 228 | 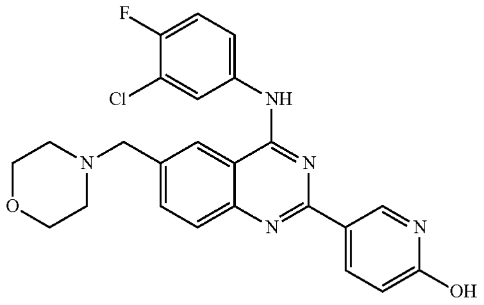 [SMILES: Oc1ccc(-c2nc(Nc3ccc(F)c(Cl)c3)c3cc(CN4CCOCC4)ccc3n2)cn1] | 465.91 | 1H-NMR (400 MHz, DMSO-d6): δ 8.43-8.31 (m, 2H), 8.27 (s, 1H), 8.14 (dd, J = 6.7, 2.3 Hz, 1H), 7.89-7.70 (m, 3H), 7.47 (t, J = 9.1 Hz, 1H), 6.44 (d, J = 9.6 Hz, 1H), 3.62 (d, J = 9.3 Hz, 6H), 2.42 (s, 4H). | DMSO | 466.1, 468.1 (M + 1) | Method B (NH4HCO3) | 97 | Meth-od C, G1 |

TABLE 1-continued
| | | | | | | | | |
|---|---|---|---|---|---|---|---|---|
| 229 | 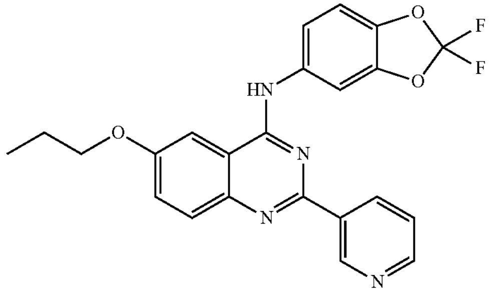 [SMILES: CCCOc1ccc2nc(-c3cccnc3)nc(Nc3ccc4c(c3)OC(F)(F)O4)c2c1] | 436.41 | 1H-NMR (400 MHz, DMSO-d6): δ 10.28 (brs, 1H), 9.47 (s, 1H), 8.91 (d, J = 7.2 Hz, 1H), 8.84 (d, J = 5.2 Hz, 1H), 8.08-8.06 (m, 2H), 7.91 (d, J = 7.6 Hz, 1H), 7.85 (t, J = 8 Hz, 1H), 7.65-7.60 (m, 2H), 7.54-7.52 (m, 1H), 4.17 (t, J = 7.6 Hz, 2H), 1.86 (q, J = 6.8 Hz, 2H), 1.08-1.03 (m, 3H). | DMSO | 423.1 (M + 1) | Method B (NH4HCO3) | 95 | Meth-od C, G1 |
| 230 | 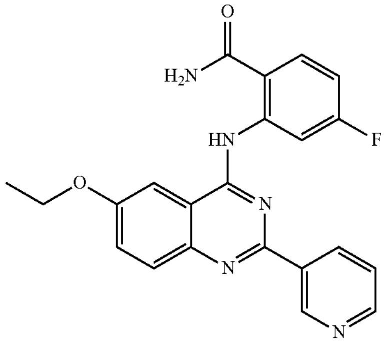 [SMILES: CCOc1ccc2nc(-c3cccnc3)nc(Nc3cc(F)ccc3C(N)=O)c2c1] | 403.41 | 1H-NMR (400 MHz, DMSO-d6): δ 13.42 (s, 1H), 9.53 (s, 1H), 9.10 (d, J = 12.8 Hz, 1H), 8.70-8.65 (m, 2H), 8.50 (s, 1H), 8.07-8.04 (m, 2H), 7.86 (d, J = 8.8 Hz, 1H), 7.60-7.55 (m, 2H), 7.48 (s, 1H), 7.06-7.01 (m, 1H), 4.21 (q, J = 6.8 Hz, 2H), 1.45 (t, J = 7.2 Hz, 3H). | DMSO | 403.9 (M + 1) | Method A (TFA) | 95 | Meth-od C, G1 |
| 231 | 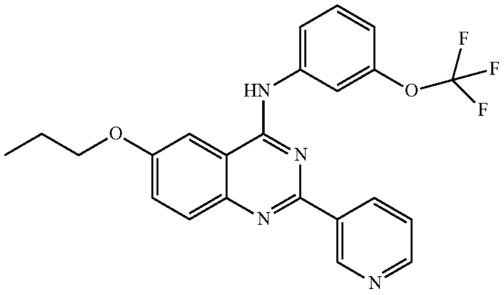 [SMILES: CCCOc1ccc2nc(-c3cccnc3)nc(Nc3cccc(OC(F)(F)F)c3)c2c1] | 440.42 | 1H-NMR (400 MHz, DMSO-d6): δ 10.57 (s, 1H), 9.48 (s, 1H), 9.01 (d, J = 7.6 Hz, 1H), 8.90 (d, J = 5.2 Hz, 1H), 8.19 (s, 1H), 8.04 (s, 1H), 7.98 (d, J = 8.8 Hz, 2H), 7.93 (t, J = 5.8 Hz, 1H), 7.64-7.60 (m, 2H), 7.22 (d, J = 8.4 Hz, 1H), 4.19 (t, J = 6.4 Hz, 1H), 1.87-1.81 (m, 2H), 1.06 (t, J = 7.2 Hz, 3H). | DMSO | 440.9 (M + 1) | Method A (TFA) | 95 | Meth-od C, G1 |

TABLE 1-continued
| | | | | | | | | | |
|---|---|---|---|---|---|---|---|---|---|
| 232 | 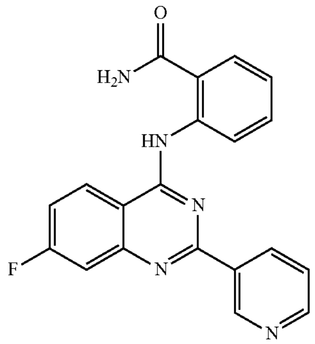 [SMILES: NC(=O)c1ccccc1Nc1nc(-c2cccnc2)nc2cc(F)ccc12] | | 359.12 | 1H-NMR (400 MHz, DMSO-d6): δ 13.10 (s, 1H), 9.54 (s, 1H), 8.96 (d, J = 8.4 Hz, 8.22-8.17 (m, 1H), 7.97-7.93 (m, 2H), 7.70-7.59 (m, 4H), 7.21 (t, J = 8.0 Hz, 1H). | DMSO | 360.1 (M + 1) | Method B (NH4HCO3) | 95 | Meth-od C, G1 |
| 233 | 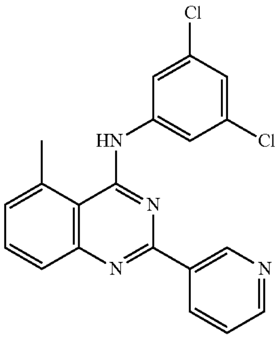 [SMILES: Cc1cccc2nc(-c3cccnc3)nc(Nc3cc(Cl)cc(Cl)c3)c12] | | 381.26 | 1H-NMR (400 MHz, DMSO-d6): δ 9.48 (s, 1H), 9.08 (s, 1H), 8.67-8.70 (m, 1H), 3.64 (d, J = 8.0 Hz, 1H), 7.98 (s, 2H), 7.76-7.73 (m, 2H), 7.55-7.57 (m, 1H), 7.43-7.46 (m, 1H), 7.36 (s, 1H), 2.99 (s, 3H). | DMSO | 381.0, 383.0, 385.0 (M + 1) | Method B (NH4HCO3) | 95 | Meth-od C, G1 |
| 234 | 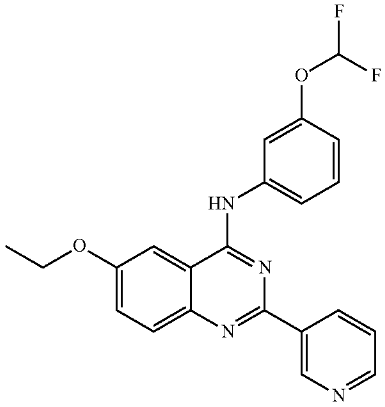 [SMILES: CCOc1ccc2nc(-c3cccnc3)nc(Nc3cccc(OC(F)F)c3)c2c1] | HCl | 408.4 | 1H-NMR (400 MHz, DMSO-d6): δ 10.38 (s, 1H), 9.51 (s, 1H), 9.00 (d, J = 7.2 Hz, 1H), 8.88 (d, J = 4.8 Hz, 1H), 8.13 (s, 1H), 7.96 (d, J = 7.2 Hz, 1H), 7.88-7.91 (m, 2H), 7.86 (s, 1H), 7.80 (d, J = 8.4 Hz, 1H), 7.63 (d, J = 2.4 Hz, 1H), 7.62 (dd, J = 9.2, 2.0 Hz,. 1H), 7.55 (t, J = 8.4 Hz, 1H), 7.31 (t, J = 74.0 Hz, 1H), 7.05 (d, J = 8.0 Hz, 1H), 4.28 (q, J = 6.8 Hz, 2H), 1.46 (t, J = 6.8 Hz, 3H). | DMSO | 409.2 (M + 1) | Method B (NH4HCO3) | 95 | Meth-od C, G1 |

TABLE 1-continued
| | | | | | | | | |
|---|---|---|---|---|---|---|---|---|
| 235 | 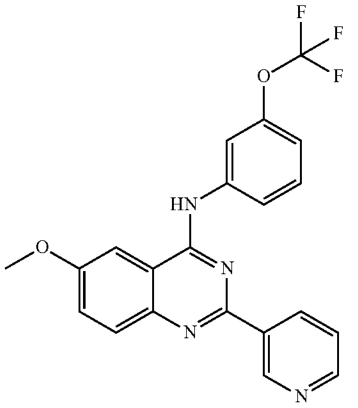 [SMILES: COc1ccc2nc(-c3cccnc3)nc(Nc3cccc(OC(F)(F)F)c3)c2c1] | 412.36 | 1H-NMR (400 MHz, DMSO-d6): δ 10.81 (s, 1H), 9.49 (s, 1H), 9.02 (d, J = 8.4 Hz, 1H), 8.91 (dd, J = 5.2, 1.2 Hz, 1H), 8.31 (d, J = 2.0 Hz, 1H), 8.06 (s, 1H), 8.01 (d, J = 8.8 Hz, 2H), 7.94-7.91 (m, 1H), 7.64-7.60 (m, 2H), 7.22 (d, J = 8.4 Hz, 1H), 4.02 (s, 3H). | DMSO | 412.9 (M + 1) | Method A (TFA) | 95 | Meth-od C, G1 |
| 236 | 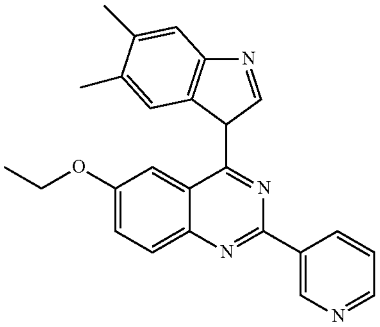 [SMILES: CCOc1ccc2nc(-c3cccnc3)nc(C3C=Nc4cc(C)c(C)cc43)c2c1] | 395.46 | 1H-NMR (400 MHz, DMSO-d6): δ 9.64 (s, 1H), 8.90 (s, 1H), 8.77 (dd, J = 13.5, 6.2 Hz, 2H), 8.19 (d, J = 9.2 Hz, 1H), 7.81 (dd, J = 9.2, 2.4 Hz, 1H), 7.72=7.56 (m, 3H), 7.33 (d, J = 2.0 Hz, 1H), 4.15 (q, J = 6.8 Hz, 2H), 2.39 (s, 3H), 2.35 (s, 3H), 1.38 (t, J = 6.8 Hz, 3H). | DMSO | 396.2 (M + 1) | Method B (NH4HCO3) | 98 | Meth-od C, G1 |
| 237 | 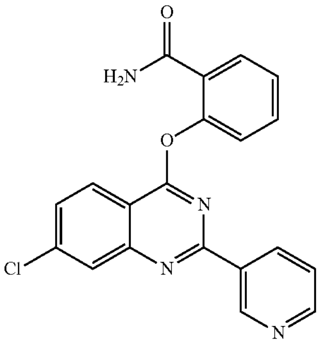 [SMILES: NC(=O)c1ccccc1Oc1nc(-c2cccnc2)nc2cc(Cl)ccc12] | 376.8 | 1H-NMR (400 MHz, DMSO-d6): δ 11.64 (brs, 1H), 11.31 (brs, 1H), 9.45 (s, 1H), 8.82-8.69 (m, 1H), 8.61 (s, 1H), 8.15 (d, J = 2.0 Hz, 1H), 8.04-7.91 (m, 1H), 7.81 (dd, J = 8.9, 2.1 Hz, 1H), 7.70-7.55 (m, 1H), 7.47 (s, 1H), 7.06 (s, 1H), 5.98 (d, J = 8.2 Hz, 1H). | DMSO | 376.9, 378.9 (M + 1) | Method B (NH4HCO3) | 95 | Meth-od C, G1 |

TABLE 1-continued
| | | | | | | | | |
|---|---|---|---|---|---|---|---|---|
| 238 | 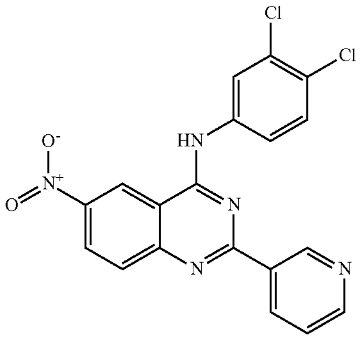 [SMILES: O=[N+]([O-])c1ccc2nc(-c3cccnc3)nc(Nc3ccc(Cl)c(Cl)c3)c2c1] | 412.23 | 1H-NMR (400 MHz, DMSO-d6): δ 10.70 (s, 1H), 9.62 (d, J = 2.4 Hz, 1H), 9.51 (d, J = 1.6 Hz, 1H), 8.76-8.79 (m, 2H), 8.57 (dd, J = 6.8, 2.0 Hz, 1H), 8.29 (d, J = 2.4 Hz, 1H), 8.01 (d, J = 8.8 Hz, 1H), 7.94 (dd, J = 6.8, 2.0 Hz, 1H), 7.71 (m, 2H). | DMSO | 412.0, 414.0, 416.0 (M + 1) | Method B (NH4HCO3) | 95 | Meth-od C, G1 |
| 239 | 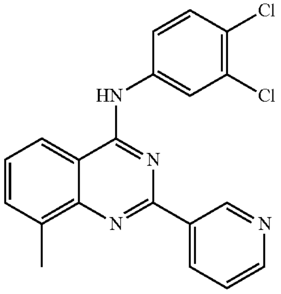 [SMILES: Cc1cccc2c(Nc3ccc(Cl)c(Cl)c3)nc(-c3cccnc3)nc12] | 381.26 | 1H-NMR (400 MHz, DMSO-d6): 10.04 (s, 1H), 9.59 (d, J = 1.2 Hz, 1H), 8.74-8.70 (m, 2H), 8.42-8.39 (m, 2H), 7.98 (dd, J = 2.4 Hz, 1H), 7.79 (d, J = 7.2 Hz, 1H), 7.72 (d, J = 8.8 Hz, 1H), 7.59-7.55 (m, 2H), 2.75 (s, 3H). | DMSO | 381, 383 (M + 1) | Method B (NH4HCO3) | 95 | Meth-od C, G1 |
| 240 | 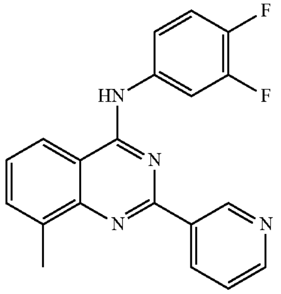 [SMILES: Cc1cccc2c(Nc3ccc(F)c(F)c3)nc(-c3cccnc3)nc12] | 348.35 | 1H-NMR (400 MHz, DMSO-d6): 10.00 (s, 1H), 9.57 (d, J = 1.2 Hz, 1H), 8.72-8.70 (m, 2H), 8.38 (d, J = 8.4 Hz, 1H), 8.17-8.12 (m, 1H), 7.79-7.74 (m, 2H), 7.59-7.50 (m, 3H), 2.74 (s, 3H). | DMSO | 349.2 (M + 1) | Method B (NH4HCO3) | 95 | Meth-od C, G1 |

TABLE 1-continued
| | | | | | | | | |
|---|---|---|---|---|---|---|---|---|
| 241 | 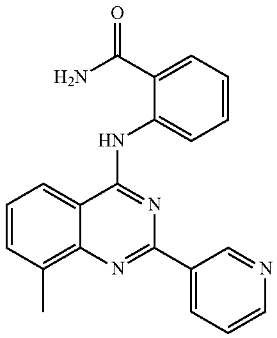 [SMILES: Cc1cccc2c(Nc3ccccc3C(N)=O)nc(-c3cccnc3)nc12] | 355.39 | 1H-NMR (400 MHz, DMSO-d6): 11.10 (s, 1H), 9.60 (d, J = 1.6 Hz, 1H), 9.16 (d, J = 8.4 Hz, 1H), 8.82-8.72 (m, 2H), 8.50 (s, 1H), 8.04 (d, J = 8.4 Hz, 1H), 7.97-7.92 (m, 2H), 7.77-7.72 (m, 2H), 7.63-7.60 (m, 2H), 7.24-7.19 (m, 1H), 2.76 (s, 3H). | DMSO | 356.2 (M + 1) | Method B (NH4HCO3) | 95 | Meth-od C, G1 |
| 242 | 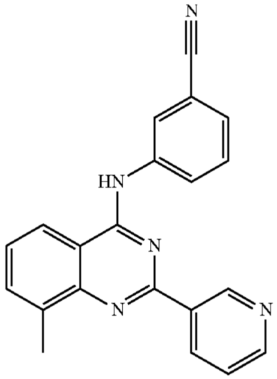 [SMILES: Cc1cccc2c(Nc3cccc(C#N)c3)nc(-c3cccnc3)nc12] | 337.4 | 1H-NMR (400 MHz, DMSO-d6): 10.12 (s, 1H), 9.57 (s, 1H), 8.73-8.70 (m, 2H), 8.46 (s, 1H), 8.41 (d, J = 8.4 Hz, 1H), 8.28 (d, J = 8.0 Hz, 1H), 7.80 (d, J = 7.6 Hz, 1H), 7.72-7.56 (m, 4H), 2.76 (s, 3H). | DMSO | 338.2 (M + 1) | Method B (NH4HCO3) | 95 | Meth-od C, G1 |

TABLE 1-continued
| | | | | | | | | |
|---|---|---|---|---|---|---|---|---|
| 243 | 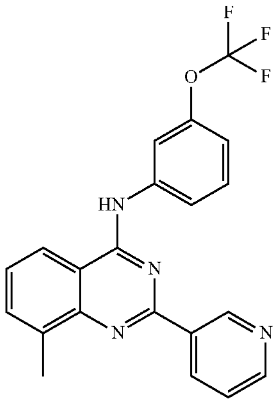 [SMILES: Cc1cccc2c(Nc3cccc(OC(F)(F)F)c3)nc(-c3cccnc3)nc12] | 396.37 | 1H-NMR (400 MHz, DMSO-d6): 10.07 (s, 1H), 9.59 (s, 1H), 8.75-8.69 (m, 2H), 8.44 (d, J = 8.0 Hz, 1H), 8.20 (s, 1H), 7.97-7.94 (m, 1H), 7.89 (d, J = 7.2 Hz, 1H), 7.62-7.54 (m, 3H), 7.16 (d, J = 8.4 Hz, 1H), 2.76 (s, 3H). | DMSO | 397.1 (M + 1) | Method B (NH4HCO3) | 95 | Meth-od C, G1 |
| 244 | 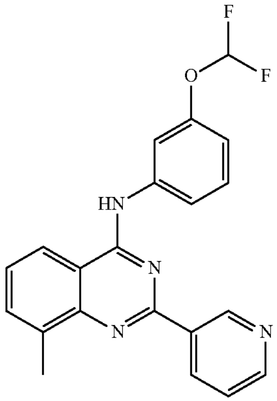 [SMILES: Cc1cccc2c(Nc3cccc(OC(F)F)c3)nc(-c3cccnc3)nc12] | 378.37 | 1H-NMR (400 MHz, DMSO-d6): 9.98 (s, 1H), 9.60 (s, 1H), 8.75-8.69 (m, 2H), 8.44 (d, J = 8.0 Hz, 1H), 7.98 (s, 1H), 7.84 (d, J = 7.6 Hz, 1H), 7.79 (d, J = 6.8 Hz, 1H), 7.58-7.00 (m, 4H), 6.98 (d, J = 2.0 Hz, 1H), 2.76 (s, 3H). | DMSO | 379.2 (M + 1) | Method B (NH4HCO3) | 95 | Meth-od C, G1 |

TABLE 1-continued
| | | | | | | | | |
|---|---|---|---|---|---|---|---|---|
| 245 | 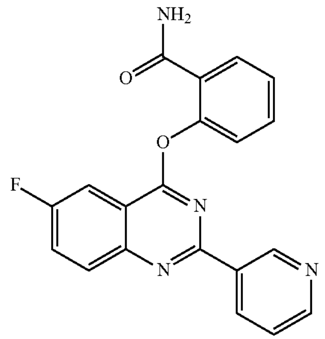 [SMILES: NC(=O)c1ccccc1Oc1nc(-c2cccnc2)nc2ccc(F)cc12] | 360.34 | 1H-NMR (400 MHz, DMSO-d6): δ 11.95-11.11 (m, 2H), 9.43 (d, J = 1.6 Hz, 1H), 8.71 (dd, J = 4.7, 1.5 Hz, 1H), 8.56 (td, J = 8.0, 1.9 Hz, 1H), 8.15 (dd, J = 9.2, 5.3 Hz, 1H), 8.08 (dd, J = 9.4, 2.7 Hz, 1H), 8.02-7.88 (m, 2H), 7.54 (dd, J = 7.90, 4.81 Hz, 1H), 7.50-7.40 (m, 1H), 7.04 (t, J = 7.1 Hz, 1H), 6.96 (d, J = 8.1 Hz, 1H). | DMSO | 360.8 (M + 1) | Method B (NH4HCO3) | 95 | Meth-od C, G1 |
| 246 | 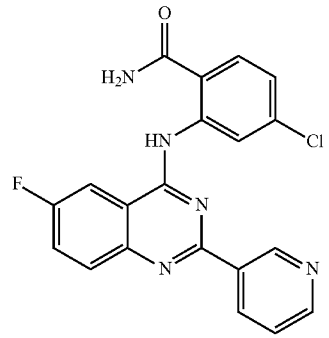 [SMILES: NC(=O)c1ccc(Cl)cc1Nc1nc(-c2cccnc2)nc2ccc(F)cc12] | 393.8 | 1H-NMR (400 MHz, DMSO-d6): δ 13.29 (s, 1H), 9.54 (s, 1H), 9.29 (s, 1H), 8.06 (d, J = 0.9 Hz, 1H), 7.99 (d, J = 8.5 Hz, 2H), 7.82 (dd, J = 26.4, 8.4 Hz, 2H), 7.58 (dd, J = 7.9, 4.8 Hz, 1H), 7.28 (d, J = 8.0 Hz, 1H), 8.72 (d, J = 3.6 Hz, 1H), 8.67 (d, J = 7.8 Hz, 1H), 8.64-8.53 (m, 1H). | DMSO | 394.0, 396.0 (M + 1) | Method B (NH4HCO3) | 95 | Meth-od C, G1 |
| 247 | 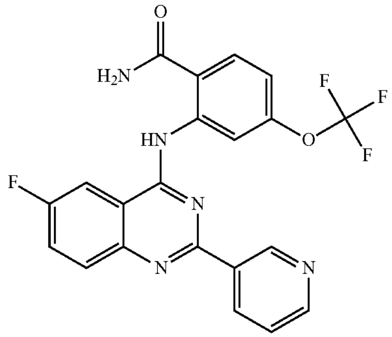 [SMILES: NC(=O)c1ccc(OC(F)(F)F)cc1Nc1nc(-c2cccnc2)nc2ccc(F)cc12] | | 1H-NMR (400 MHz, DMSO-d6): δ 13.36 (brs, 1H), 9.54 (s, 1H), 9.36-9.08 (m, 1H), 8.12 (d, J = 8.8 Hz, 2H), 8.08-7.96 (m, 1H), 7.94-7.78 (m, 2H), 7.57 (dd, J = 7.8, 4.8 Hz, 1H), 7.29- 7.16 (m, 1H), 8.94-8.49 (m, 3H). | DMSO | 444.1 (M + 1) | Method B (NH4HCO3) | 95 | Meth-od C, G1 |

TABLE 1-continued
| | | | | | | | | |
|---|---|---|---|---|---|---|---|---|
| 248 | 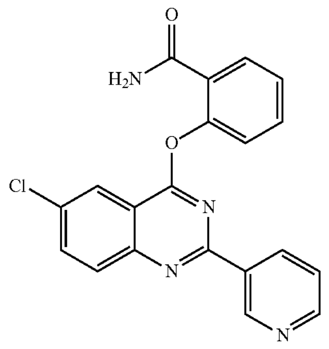 [SMILES: NC(=O)c1ccccc1Oc1nc(-c2cccnc2)nc2ccc(Cl)cc12] | 376.8 | 1H-NMR (400 MHz, DMSO-d6): δ 9.57 (s, 1H), 8.71 (d, J = 5.6 Hz, 2H), 8.40 (d, J = 1.8 Hz, 1H), 8.01-7.97 (m, 2H), 7.89 (dd, J = 7.8, 1.5 Hz, 1H), 7.63-7.51 (m, 1H), 7.29 (t, J = 7.4 Hz, 1H), 6.79 (d, J = 8.4 Hz, 1H), 6.76-6.74 (m, 1H). | DMSO | 377.0, 379.0 (M + 1) | Method B (NH4HCO3) | 95 | Meth-od C, G1 |
| 249 | 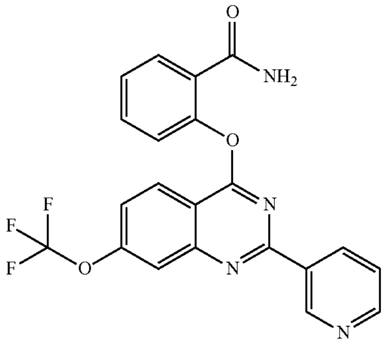 [SMILES: NC(=O)c1ccccc1Oc1nc(-c2cccnc2)nc2cc(OC(F)(F)F)ccc12] | 426.35 | 1H-NMR (400 MHz, DMSO-d6): δ 9.70 (d, J = 1.5 Hz, 1H), 8,74 (td, J = 8.0, 1.9 Hz, 1H), 8.71 (dd, J = 4.7, 1.7 Hz, 1H), 8.50 (d, J = 9.0 Hz, 1H), 7.88 (dd, J = 7.8, 1.9 Hz, 1H), 7.76 (d, J = 1.1 Hz, 1H), 7.20-7.11 (m, 1H), 7.64-7.56 (m, 2H)., 6.70-6.60 (m, 1H), 6.52 (dd, J = 10.8, 3.9 Hz, 1H). | DMSO | 427.1 (M + 1) | Method B (NH4HCO3) | 95 | Meth-od C, G1 |
| 250 | 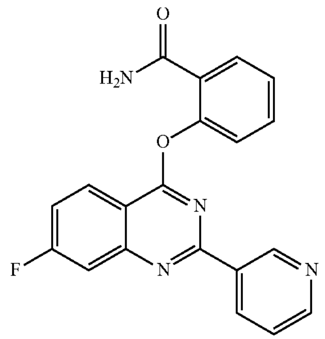 [SMILES: NC(=O)c1ccccc1Oc1nc(-c2cccnc2)nc2cc(F)ccc12] | 360.34 | 1H-NMR (400 MHz, DMSO-d6): δ 9.69 (s, 1H), 8.83 (d, J = 7.4 Hz, 1H), 8.71 (d, J = 3.9 Hz, 1H), 8.49 (t, J = 7.2 Hz, 1H), 7.85 (d, J = 7.8 Hz, 1H), 7.63-7.51 (m, 3H), 7.14 (t, J = 7.0 Hz, 1H), 6.61 (d, J = 8.0 Hz, 1H), 6.46 (t, J = 7.2 Hz, 1H). | DMSO | 360.8 (M + 1) | Method B (NH4HCO3) | 95 | Meth-od C, G1 |

TABLE 1-continued
| | | | | | | | | |
|---|---|---|---|---|---|---|---|---|
| 251 | 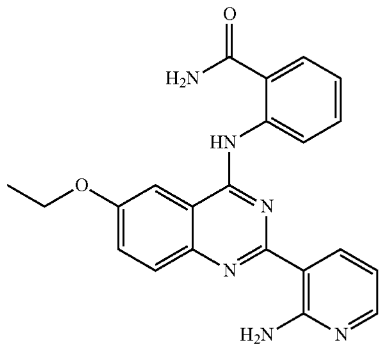 [SMILES: CCOc1ccc2nc(-c3cccnc3N)nc(Nc3ccccc3C(N)=O)c2c1] | 400.43 | 1H-NMR (400 MHz, DMSO-d6): δ 12.92 (s, 1H), 9.04 (d, J = 8.3 Hz, 1H), 8.66 (dd, J = 7.7, 1.7 Hz, 1H), 8.48 (s, 1H), 8.10 (dd, J = 4.6, 1.7 Hz, 1H), 8.01-7.94 (m, 2H), 7.89 (d, J = 8.9 Hz, 1H), 7.72 (t, J = 7.7 Hz, 1H), 7.55 (m, 2H), 7.20 (t, J = 7.5 Hz, 1H), 6.74 (dd, J = 7.7, 4.7 Hz, 1H), 4.24 (q, J = 6.9 Hz, 2H), 1.46 (t, J = 6.9 Hz, 3H). | DMSO | 401.0 (M + 1) | Method B (NH4HCO3) | 95 | Meth-od C, G1 |
| 252 | 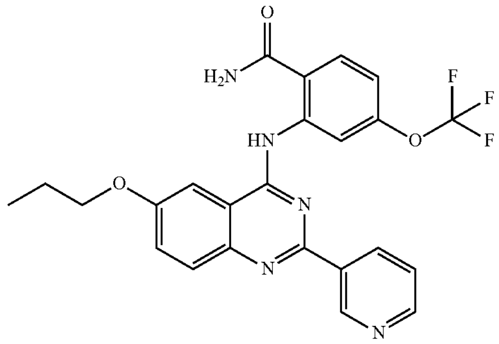 [SMILES: CCCOc1ccc2nc(-c3cccnc3)nc(Nc3cc(OC(F)(F)F)ccc3C(N)=O)c2c1] | 483.44 | 1H-NMR (400 MHz, DMSO-d6): δ 13.28 (s, 1H), 9.54 (s, 1H), 9.28 (s, 1H), 8.70-8.66 (m, 2H), 8.59 (s, 1H), 8.11 (d, J = 8.8 Hz, 2H), 7.90 (d, J = 8.9 Hz, 1H), 7.64-7.49 (m, 3H), 7.18 (d, J = 8.2 Hz, 1H), 4.14 (t, J = 6.2 Hz, 2H), 1.86 (q, J = 6.8 Hz, 2H), 1.07 (t, J = 7.2 Hz, 3H). | DMSO | 484.0 (M + 1) | Method B (NH4HCO3) | 95 | Meth-od C, G1 |
| 253 | 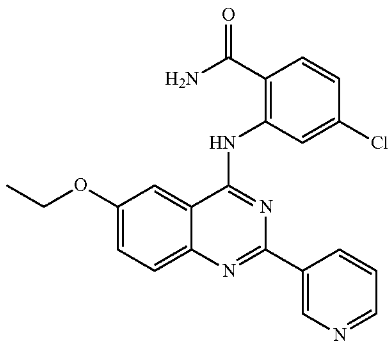 [SMILES: CCOc1ccc2nc(-c3cccnc3)nc(Nc3cc(Cl)ccc3C(N)=O)c2c1] | | 1H-NMR (400 MHz, DMSO-d6): δ 13.24 (s, 1H), 9.56 (s, 1H), 9.39 (d, J = 2.1 Hz, 1H), 8.77-8.73 (m, 2H), 8.55 (s, 1H), 8.09 (s, 1H), 8.00 (d, J = 8.6 Hz, 1H), 7.90 (d, J = 9.1 Hz, 1H), 7.65 (dd, J = 7.9, 4.9 Hz, 1H), 7.59 (dd, J = 9.1, 2.5 Hz, 1H), 4.24 (q, J = 6.9 Hz, 2H), 1.46 (t, J = 6.9 Hz, 3H). | DMSO | 420.0, 422.0 (M + 1) | Method B (NH4HCO3) | 95 | Meth-od C, G1 |

TABLE 1-continued
| | | | | | | | | |
|---|---|---|---|---|---|---|---|---|
| 254 | 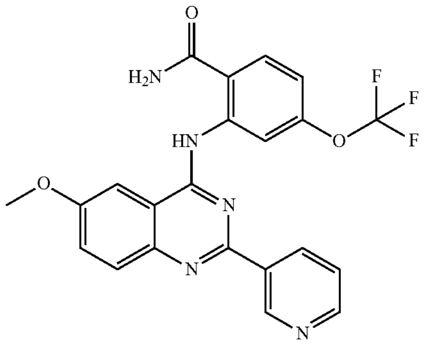 | 469.42 | 1H-NMR (400 MHz, DMSO-d6): δ 13.34 (s, 1H), 9.60 (s, 1H), 9.35 (s, 1H), 8.77 (d, J = 3.5 Hz, 1H), 8.72 (d, J = 7.9 Hz, 1H), 8.67 (s, 1H), 8.22 (s, 1H), 8.17 (d, J = 8.8 Hz, 1H), 7.94 (d, J = 9.1 Hz, 1H), 7.69-7.58 (m, 2H), 7.55 (s, 1H), 7.24 (d, J = 8.5 Hz, 1H), 4.29 (q, J = 7.0 Hz, 2H), 1.53 (t, J = 6.9 Hz, 3H). | DMSO | 470.2 (M + 1) | Method B (NH4HCO3) | 95 | Method C, G1 |
| 255 | 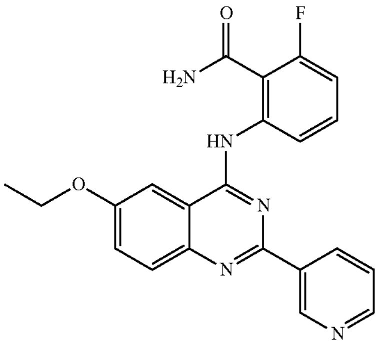 [SMILES: CCOc1ccc2nc(-c3cccnc3)nc(Nc3cccc(F)c3C(N)=O)c2c1] | 403.41 | 1H-NMR (400 MHz, DMSO-d6): δ 11.43 (s, 1H), 9.53 (s, 1H), 8.68-8.66 (m, 2H), 8.56 (d, J = 8.3 Hz, 1H), 8.23 (s, 1H), 8.12 (s, 1H), 7.88 (d, J = 9.1 Hz, 1H), 7.72-7.64 (m, 1H), 7.61-7.47 (m, 3H), 7.17-7.08 (m, 1H), 4.23 (q, J = 6.9 Hz, 2H), 1.46 (t, J = 6.9 Hz, 3H). | DMSO | 404.2 (M + 1) | Method B (NH4HCO3) | 95 | Method C, G1 |

TABLE 1-continued

| Number | Product | Salt Type | Molecular Mass | $^1$H NMR | $^1$H NMR Solvent | LCMS | Retention Time (min) | LCMS Protocol | Purity percent | Method of Coupling |
|---|---|---|---|---|---|---|---|---|---|---|
| 256 | 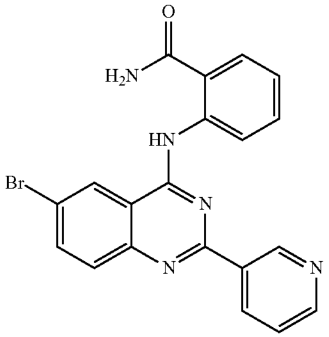 [SMILES: NC(=O)c1ccccc1Nc1nc(-c2cccnc2)nc2ccc(Br)cc12] | HCl | 456.723 | 1H NMR (300 MHz, DMSO) δ 9.55 (s, 1H), 9.09 (d, J = 8.0 Hz, 1H), 9.01-8.76 (m, 2H), 8.50 (s, 1H), 8.37 (s, 1H), 8.13-7.91 (m, 4H), 7.85 (d, J = 8.9 Hz, 1H), 7.69 (t, J = 7.7 Hz, 1H), 7.25 (t, J = 7.6 Hz, 1H). | DMSO | 420 (M + 1) | 1.89 | Method D | 100 | Meth-od G1 |
| 257 | 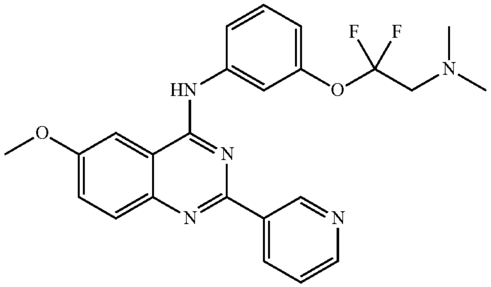 | HCl | 524.39 | 1H NMR (300 MHz, DMSO) δ 10.68 (s, 1H), 9.50 (s, 1H), 9.08 (d, J = 8.1 Hz, 1H), 8.92 (d, J = 5.2 Hz, 1H), 8.28 (s, 1H), 8.11 (s, 1H), 8.06-7.93 (m, 2H), 7.87 (d, J = 7.6 Hz, 1H), 7.70-7.51 (m, 2H), 7.19 (d, J =7.6 Hz, 1H), 4.28 (t, J = 9.1 Hz, 2H), 4 | DMSO | 452 (M + 1) | 1.34 | Method D | 100 | Meth-od G1 |
| 258 | 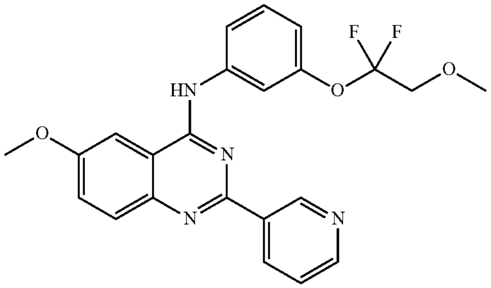 | HCl | 474.89 | 1H NMR (300 MHz, DMSO) δ 10.36 (s, 1H), 9.52 (s, 1H), 9.00 (d, J = 8.2 Hz, 1 H), 8.89 (d, J = 4.4 Hz, 1H), 8.12 (s, 1H), 8.02-7.78 (m, 4H), 7.64 (d, J = 9.2 Hz, 1H), 7.54 (t, J = 8.2 Hz, 1H), 7.07 (d, J = 7.7 Hz, 1H), 4.08-3.87 (m, 5H), 3.46 (s, 3H). | DMSO | 439 (M + 1) | 2.21 | Method C | 98 | Meth-od G1 |

TABLE 1-continued
| | | | | | | | | | | |
|---|---|---|---|---|---|---|---|---|---|---|
| 259 | 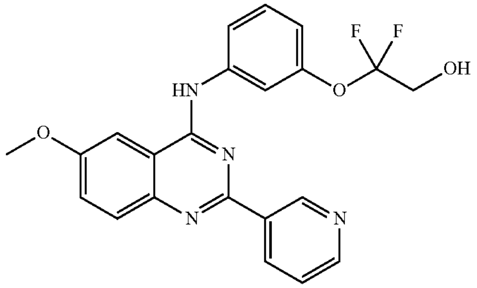 [SMILES: COc1ccc2nc(-c3cccnc3)nc(Nc3cccc(OC(F)(F)CO)c3)c2c1] | HCl | 460.86 | 1H NMR (300 MHz, DMSO) δ 10.61 (s, 1H), 9.51 (s, 1H), 9.10 (d, J = 8.2 Hz, 1H), 8.94 (d, J = 4.9 Hz, 1H), 8.22 (s, 1H), 8.08-7.94 (m, 2H), 7.93-7.78 (m, 2H), 7.65 (d, J = 9.1 Hz, 1H), 7.53 (t, J = 8.2 Hz, 1H), 7.08 (d, J = 7.3 Hz, 1H), 4.01 (s, 3H), 3 | DMSO | 425 (M + 1) | 1.64 | Method C | 98 | Meth-od G11 |
| 260 | 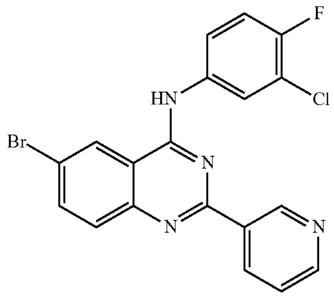 [SMILES: Fc1ccc(Nc2nc(-c3cccnc3)nc3ccc(Br)cc23)cc1Cl] | HCl | 429.67 | No Data | | 428.9 (M + 1) | 2.35 | Method C | 100 | Meth-od G1 |
| 261 | 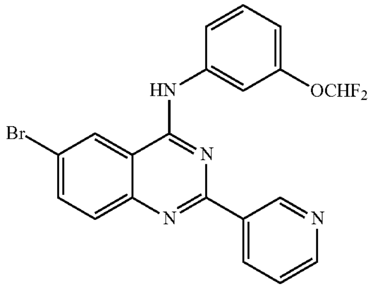 [SMILES: FC(F)Oc1cccc(Nc2nc(-c3cccnc3)nc3ccc(Br)cc23)c1] | HCl | 443.24 | 1H NMR (300 MHz, DMSO) δ 10.35 (s, 1H), 9.52 (d, J = 1.5 Hz, 1H), 8.97 (dd, J = 6.6, 1.8 Hz, 2H), 8.91-8.83 (m, 1H), 8.07 (dd, J = 8.9, 2.0 Hz, 1H), 7.85 (dd, J = 14 6, 8.2 Hz, 4H), 7.54 (dd, J = 11.7, 4.6 Hz, 1H), 7.31 (s, 1H), 7.10-6.99 (m, 1H). | DMSO | 442.96 (M + 1) | 2.36 | Method C | 100 | Meth-od G1 |

TABLE 1-continued
| | | | | | | | | | | |
|---|---|---|---|---|---|---|---|---|---|---|
| 262 | 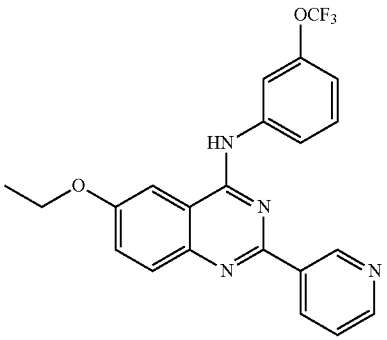 [SMILES: CCOc1ccc2nc(-c3cccnc3)nc(Nc3cccc(OC(F)(F)F)c3)c2c1] | HCl | 426.39 | 1H NMR (300 MHz, DMSO) δ 10.71 (s, 1H), 9.47 (s, 1H), 9.01 (d, J = 8.2 Hz, 1H), 8.90 (d, J = 4.0 Hz, 1H), 8.23 (s, 1H), 8.08-7.86 (m, 4H), 7.61 (t, J = 8.2 Hz, 2H), 7.22 (d, J = 7.6 Hz, 1H), 4.28 (d, J = 7.0 Hz, 2H), 1.44 (t, J = 6.9 Hz, 3H). | DMSO | 427.1 (M + 1) | 2.47 | Method C | 93 | Method G1 |
| 263 | 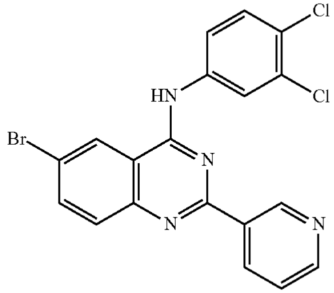 [SMILES: Clc1ccc(Nc2nc(-c3cccnc3)nc3ccc(Br)cc23)cc1Cl] | HCl | 446.13 | 1H NMR (300 MHz, DMSO) δ 10.35 (s, 1H), 9.47 (s, 1H), 8.90 (s, 3H), 8.27 (s, 1H), 8.02 (d, J = 8.9 Hz, 1H), 7.94 (d, J = 8.8 Hz, 1 H), 7.81 (d, J = 9.0 Hz, 2H), 7.68 (d, J = 8.8 Hz, 1H). | DMSO | 494.0 (M + 1) | 2.29 | Method C | 91 | Method G1 |
| 264 | 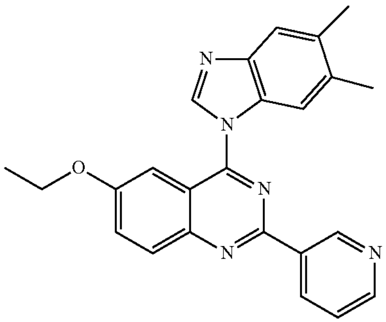 [SMILES: CCOc1ccc2nc(-c3cccnc3)nc(-n3cnc4cc(C)c(C)cc43)c2c1] | | 395.46 | 1H NMR (300 MHz, DMSO) δ 9.63 (s, 1H), 8.88 (s, 1H), 8.83-8.71 (m, 2H), 8.18 (d, J = 9.2 Hz, 1H), 7.30 (dd, J = 9.2, 2.3 Hz, 1H), 7.69-7.57 (m, 3H), 7.32 (d, J = 2.1 Hz, 1H), 4.14 (q, J = 6.6 Hz, 2H), 2.39 (s, 3H), 2.35 (s, 3H), 1.37 (t, J = 6.9 Hz, 3 | DMSO | 396.10 (M + 1) | 2.3 | Method C | 100 | Method G1 |

TABLE 1-continued
| | | | | | | | | | | |
|---|---|---|---|---|---|---|---|---|---|---|
| 265 | 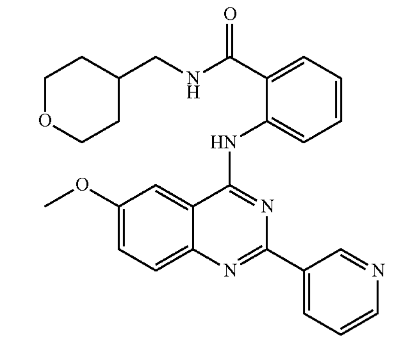 [SMILES: COc1ccc2nc(-c3cccnc3)nc(Nc3ccccc3C(=O)NCC3CCOCC3)c2c1] | HCl | 469.53 | 1H NMR (300 MHz, DMSO) δ 12.13 (s, 1H), 9.54 (s, 1H), 8.99 (d, J = 7.4 Hz, 1H), 8.85 (s, 2H), 8.61 (d, J = 8.2 Hz, 1H), 7.95 (d, J = 9.1 Hz, 1H), 7.86 (d, J = 7.3 Hz, 2H), 7.68 (dd, J = 15.1, 7.8 Hz, 3H), 7.32 (d, J = 6.8 Hz, 1H), 4.00 (s, 3H), 3.71 (d, J | DMSO | 470.1 (M + 1) | 2.15 | Method C | 100 | Meth-od G1 |
| 266 | 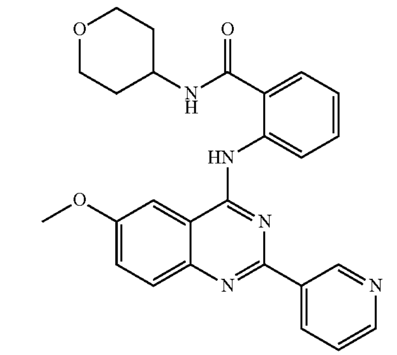 [SMILES: COc1ccc2nc(-c3cccnc3)nc(Nc3ccccc3C(=O)NC3CCOCC3)c2c1] | HCl | 455.51 | 1H NMR (300 MHz, DMSO) δ 12.07 (s, 1H), 9.52 (s, 1H), 8.82-8.65 (m, 4H), 7.88 (dd, J = 8.1, 5.0 Hz, 2H), 7.73-7.55 (m, 4H), 7.27 (t, J = 7.2 Hz, 1H), 3.98 (m, 1H), 3.82 (d, J = 10.4 Hz, 2H), 3.35 (t, J = 11.7 Hz, 2H), 1.68 (d, J = 10.3 Hz, 2H), 1.55- | DMSO | 456.1 (M + 1) | 2.09 | Method C | 100 | Meth-od G1 |
| 267 | 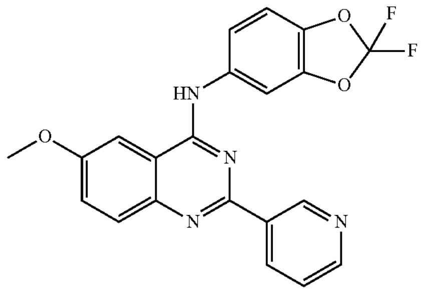 [SMILES: COc1ccc2nc(-c3cccnc3)nc(Nc3ccc4c(c3)OC(F)(F)O4)c2c1] | HCl | 408.36 | 1H NMR (300 MHz, DMSO) δ 10.57 (s, 1H), 9.45 (d, J = 1.5 Hz, 1H), 8.99 (d, J = 8.0 Hz, 1H), 8.89 (d, J = 3.9 Hz, 1H), 8.16 (d, J = 2.3 Hz, 1H), 8.05 (d, J = 2.0 Hz, 1H), 7.94 (t, J = 7.4 Hz, 2H), 7.63 (ddd, J = 9.3, 6.9, 2.3 Hz, 2H), 7.52 (d, J = 8.7 Hz, | DMSO | 409.1 (M + 1) | 2.3 | Method C | 100 | Meth-od G1 |

TABLE 1-continued
| | | | | | | | | | | |
|---|---|---|---|---|---|---|---|---|---|---|
| 268 | 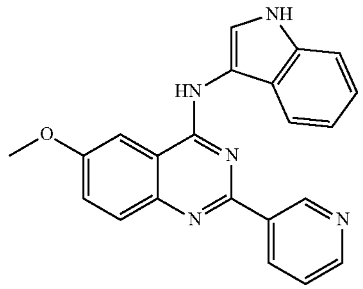 [SMILES: COc1ccc2nc(-c3cccnc3)nc(Nc3c[nH]c4ccccc34)c2c1] | HCl | 367.4 | 1H NMR (300 MHz, DMSO) δ 11.12 (s, 1H), 9.81 (s, 1H), 9.43-9.37 (m, 1H), 8.58 (ddd, J = 8.0, 4.8, 1.4 Hz, 2H), 8.09 (d, J = 2.5 Hz, 1H), 7.89 (d, J = 2.2 Hz, 1H), 7.80 (s, 1H), 7.72 (d, J = 7.9 Hz, 1H), 7.53-7.41 (m, 3H), 7.17 (t, J = 7.5 Hz, 1H), 7.0 | DMSO | 368.1 (M + 1) | 1.98 | Method C | 100 | Meth-od G1 |
| 269 | 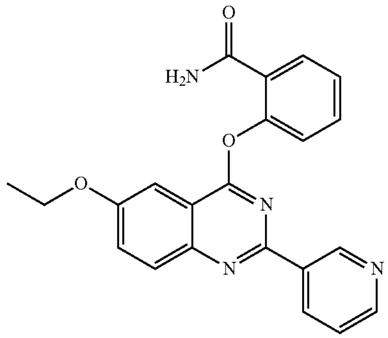 [SMILES: CCOc1ccc2nc(-c3cccnc3)nc(Oc3ccccc3C(N)=O)c2c1] | | 386.4 | 1H NMR (300 MHz, DMSO) δ 11.47 (s, 2H), 9.39 (s, 1H), 8.66 (d, J = 2.8 Hz, 1H), 8.56-8.47 (m, 1H), 8.01-7.90 (m, 2H), 7.69-7.55 (m, 2H), 7.55-7.40 (m, 2H), 7.05 (t, J = 7.5 Hz, 1H), 6.97 (d, J = 8.2 Hz, 1H), 4.23 (q, J = 6.9 Hz, 2H), 1.44 (t, J = | DMSO | 387.0 (M + 1) | 2.05 | Method C | 100 | Meth-od G8 |
| 270 | 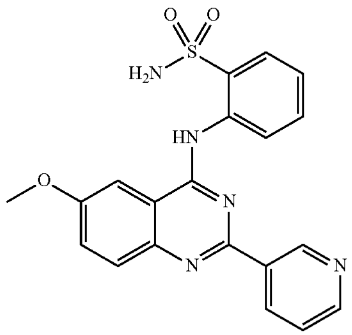 [SMILES: COc1ccc2nc(-c3cccnc3)nc(Nc3ccccc3S(N)(=O)=O)c2c1] | | 407.45 | 1H NMR (300 MHz, DMSO) δ 10.52 (s, 1H), 9.44 (s, 1H), 8.92 (d, J = 7.4 Hz, 1H), 8.86 (d, J = 5.1 Hz, 1H), 8.46 (d, J = 6.4 Hz, 1H), 8.01 (d, J = 8.7 Hz, 2H), 7.92-7.74 (m, 6H), 7.68 (dd, J = 9.2, 2.4 Hz, 1H), 7.48 (t, J = 7.8 Hz, 1H), 3.98 (s, 4H). | DMSO | 408.0 (M + 1) | 1.92 | Method C | 100 | Meth-od G1, with two drops of conc. HCl |

TABLE 1-continued
| | | | | | | | | | | |
|---|---|---|---|---|---|---|---|---|---|---|
| 271 | 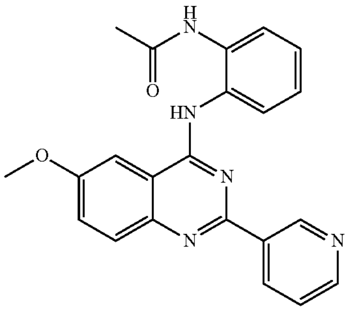 [SMILES: COc1ccc2nc(-c3cccnc3)nc(Nc3ccccc3NC(C)=O)c2c1] | HCl | 385.42 | 1H NMR (300 MHz, DMSO) δ 9.75 (s, 1H), 9.66 (s, 1H), 9.39 (s, 1H), 8.61 (d, J = 3.1 Hz, 1H), 8.54 (d, J = 8.2 Hz, 1H), 7.85 (s, 1H), 7.82 (s, 2H), 7.71 (d, J = 7.4 Hz, 1H), 7.54 (d, J = 9.1 Hz, 1H), 7.46 (dd, J = 7.5, 5.2 Hz, 1H), 7.35-7.23 (m, 2H), 3.9 | DMSO | 386.1 (M + 1) | 1.79 | Method C | 96 | Meth-od G2 |
| 272 | 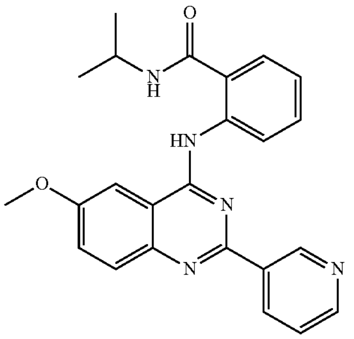 [SMILES: COc1ccc2nc(-c3cccnc3)nc(Nc3ccccc3C(=O)NC(C)C)c2c1] | HCl | 413.47 | 1H NMR (300 MHz, DMSO) δ 12.30 (s, 1H), 9.57 (d, J = 2.1 Hz, 1H), 8.89 (d, J = 8.0 Hz, 1H), 8.77-8.67 (m, 2H), 8.63 (d, J = 7.7 Hz, 1H), 7.94-7.83 (m, 2H), 7.71 (t, J = 7.1 Hz, 1H), 7.66-7.52 (m, 3H), 7.25 (t, J = 7.4 Hz, 1H), 4.24-4.06 (m, 1H), 3 | DMSO | 414.2 (M + 1) | 2.36 | Method C | 100 | Meth-od G1 |
| 273 | 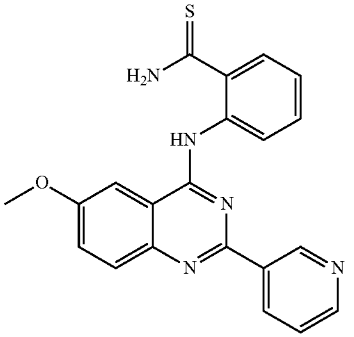 | HCl | 387.46 | 1H NMR (300 MHz, DMSO) δ 10.96 (s, 1H), 10.29 (s, 1H), 9.85 (s, 1H), 9.51 (d, J = 2.0 Hz, 1H), 8.71-8.62 (m, 2H), 8.47 (dd, J = 8.2, 0.9 Hz, 1H), 7.89 (d, J = 9.1 Hz, 1H), 7.67-7.62 (m, 2H), 7.60 (d, J = 2.5 Hz, 1H), 7.57 (d, J = 2.6 Hz, 1H), 7.55-7 | DMSO | 388.1 (M + 1) | 2.01 | Method C | 95 | Meth-od G1 |

TABLE 1-continued
| | | | | | | | | | | |
|---|---|---|---|---|---|---|---|---|---|---|
| 274 | 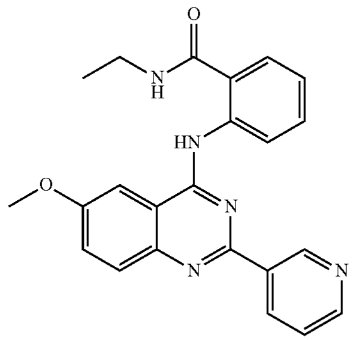 [SMILES: CCNC(=O)c1ccccc1Nc1nc(-c2cccnc2)nc2ccc(OC)cc12] | HCl | 399.45 | 1H NMR (300 MHz, DMSO) δ 12.45 (s, 1H), 9.57 (d, J = 1.3 Hz, 1H), 8.96 (dd, J = 8.4, 0.9 Hz, 1H), 8.89 (t, J = 5.2 Hz, 1H) 8.75-8.66 (m, 2H), 7.94-7.84 (m, 2H), 7.72 (t, J = 7.9 Hz, 1H), 7.65-7.52 (m, 3H), 7.24 (t, J = 7.8 Hz, 1H), 4.00 (s, 3H), 3. | DMSO | 400.3 (M + 1) | 2.21 | Method C | 100 | Meth-od G1 |
| 275 | 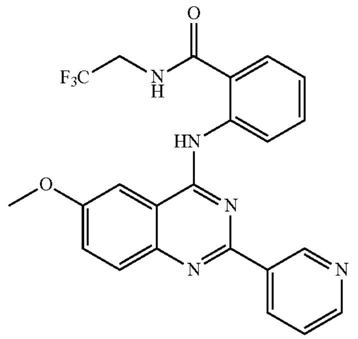 [SMILES: COc1ccc2nc(-c3cccnc3)nc(Nc3ccccc3C(=O)NCC(F)(F)F)c2c1] | HCl | 453.42 | 1H NMR (300 MHz, DMSO) δ 11.70 (s, 1H), 9.54 (d, J = 2.0 Hz, 1H), 9.40 (t, J = 6.1 Hz, 1H), 8.79 (d, J = 7.7 Hz, 1H), 8.73-8.63 (m, 2H), 7.89 (d, J = 9.8 Hz, 2H), 7.76 (t, J = 7.1 Hz, 1H), 7.64-7.50 (m, 3H), 7.30 (t, J = 7.1 Hz, 1H), 4.16-4.01 (m, 2 | DMSO | 454.0 (M + 1) | 2.28 | Method C | 100 | Meth-od G1 |
| 276 | 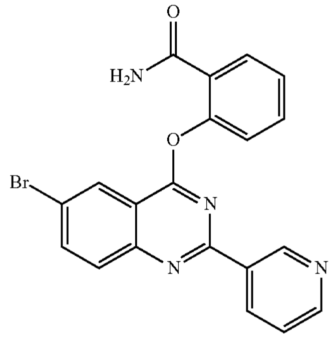 [SMILES: NC(=O)c1ccccc1Oc1nc(-c2cccnc2)nc2ccc(Br)cc12] | | 421.25 | 1H NMR (300 MHz, DMSO) δ 9.26 (d, J = 2.2 Hz, 1H), 8.71-8.62 (m, 2H), 8.46 (dt, J = 8.0, 1.9 Hz, 1H), 8.21 (dd, J = 8.9, 2.3 Hz, 1H), 8.03 (d, J = 8.9 Hz, 1H), 7.89 (s, 1H), 7.78 (dd, J = 7.6, 1.6 Hz, 1H), 7.72-7.62 (m, 1H), 7.56-7.45 (m, 3H), 7.32 | DMSO | 423.0 (M + 1) | 1.85 | Method C | 94 | Meth-od G1 |

TABLE 1-continued
| | | | | | | | | | | |
|---|---|---|---|---|---|---|---|---|---|---|
| 277 | 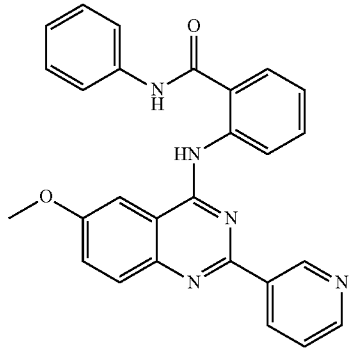 [SMILES: COc1ccc2nc(-c3cccnc3)nc(Nc3ccccc3C(=O)Nc3ccccc3)c2c1] | HCl | 447.49 | 1H NMR (300 MHz, DMSO) δ 11.25 (s, 1H), 10.46 (s, 1H), 9.45 (s, 1H), 8.93 (d, J = 7.9 Hz, 1H), 8.82 (d, J = 3.9 Hz, 1H), 8.22 (d, J = 8.1 Hz, 1H), 7.97-7.79 (m, 4H), 7.73 (t, J = 7.1 Hz, 1H), 7.62 (dd, J = 9.1, 2.5 Hz, 1H), 7.53-7.39 (m, 3H), 7.19 (t, | DMSO | 448.1 (M + 1) | 2.67 | Method C | 100 | Meth-od G1 |
| 278 | 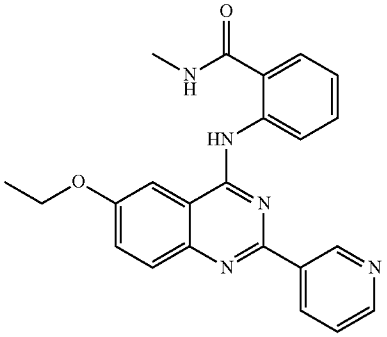 [SMILES: CCOc1ccc2nc(-c3cccnc3)nc(Nc3ccccc3C(=O)NC)c2c1] | HCl | 399.45 | 1H NMR (300 MHz, DMSO) δ 12.59 (s, 1H), 9.57 (d, J = 1.4 Hz, 1H), 9.03 (dd, J = 8.4, 0.9 Hz, 1H), 8.91 (d, J = 4.6 Hz, 1H), 8.76-8.64 (m, 2H), 7.88 (t, J = 7.8 Hz, 2H), 7.72 (t, J = 7.9 Hz, 1H), 7.63-7.53 (m, 3H), 7.22 (td, J = 7.9, 1.1 Hz, 1H), 4.28 | DMSO | 400.1 (M + 1) | 2.5 | Method C | 100 | Meth-od G1 |
| 279 | 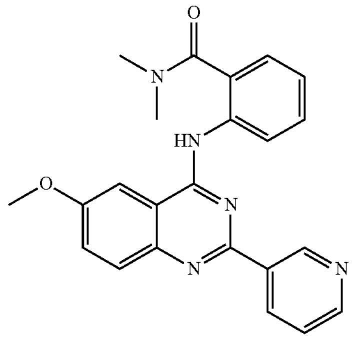 [SMILES: COc1ccc2nc(-c3cccnc3)nc(Nc3ccccc3C(=O)N(C)C)c2c1] | HCl | 399.45 | 1H NMR (300 MHz, DMSO) δ 9.99 (s, 1H), 9.37 (d, J = 1.4 Hz, 1H), 8.61 (dd, J = 4.7, 1.7 Hz, 1H), 8.58-8.51 (m, 1H), 7.84 (dd, J = 9.0, 5.3 Hz, 3H), 7.65-7.42 (m, 4H), 7.38 (t, J = 7.5 Hz, 1H), 3.95 (s, 3H), 2.74 (s, 6H). | DMSO | 400.1 (M + 1) | 2.2 | Method C | 100 | Meth-od G1 |

TABLE 1-continued
| | | | | | | | | | | |
|---|---|---|---|---|---|---|---|---|---|---|
| 280 | 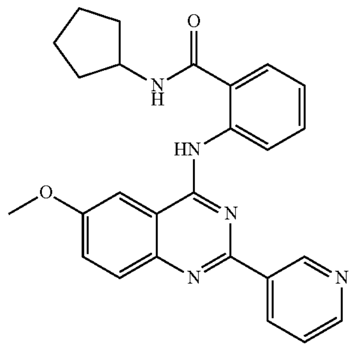 [SMILES: COc1ccc2nc(-c3cccnc3)nc(Nc3ccccc3C(=O)NC3CCCC3)c2c1] | HCl | 439.51 | 1H NMR (300 MHz, DMSO) δ 12.05 (s, 1H), 9.51 (d, J = 1.6 Hz, 1H), 9.04 (d, J = 8.1 Hz, 1H), 8.88 (dd, J = 5.2, 1.3 Hz, 1H), 8.60 (d, J = 7.0 Hz, 1H), 8.44 (d, J = 8.0 Hz, 1H), 8.00-7.87 (m, 2H), 7.83 (dd, J = 7.8, 1.4 Hz, 1H), 7.77 (d, J = 1.9 Hz, 1H), | DMSO | 440.1 (M + 1) | 2.52 | Method C | 100 | Meth-od G1 |
| 281 | 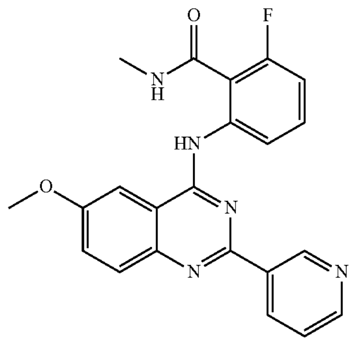 [SMILES: CNC(=O)c1c(F)cccc1Nc1nc(-c2cccnc2)nc2ccc(OC)cc12] | HCl | 403.41 | 1H NMR (300 MHz, DMSO) δ 10.98 (s, 1H), 9.50 (s, 1H), 8.72-8.55 (m, 3H), 8.38 (d, J = 8.2 Hz, 1H), 7.87 (d, J = 8.9 Hz, 1H), 7.72-7.45 (m, 4H), 7.19-7.07 (m, 1H), 3.96 (s, J = 5.2 Hz, 3H), 2.73 (d, J = 4.5 Hz, 3H). | DMSO | 404.1 (M + 1) | 2.18 | Method C | 100 | Meth-od G1 |
| 282 | 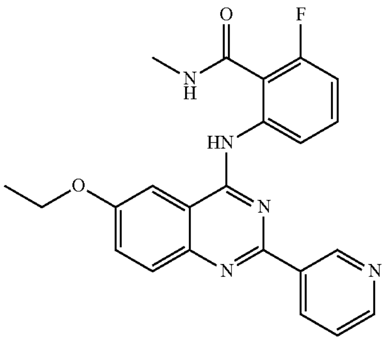 [SMILES: CCOc1ccc2nc(-c3cccnc3)nc(Nc3cccc(F)c3C(=O)NC)c2c1] | HCl | 417.44 | 1H NMR (300 MHz, DMSO) δ 10.96 (s, 1H), 9.50 (d, J = 1.9 Hz, 1H), 8.71-8.55 (m, 3H), 8.33 (d, J = 8.2 Hz, 1H), 7.86 (d, J = 9.0 Hz, 1H), 7.66 (dd, J = 14.8, 8.3 Hz, 1H), 7.60-7.47 (m, 3H), 7.21-7.05 (m, 1H), 4.24 (q, J = 6.9 Hz, 2H), 2.73 (d, J = 4. | DMSO | 419.1 (M + 1) | 2.38 | Method C | 100 | Meth-od G1 |

TABLE 1-continued
| | | | | | | | | | | |
|---|---|---|---|---|---|---|---|---|---|---|
| 283 | 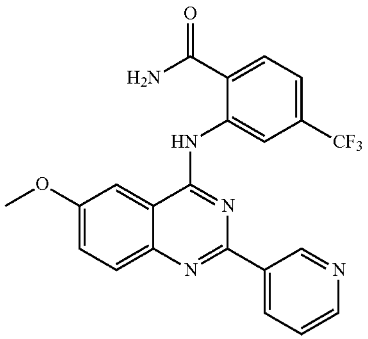 [SMILES: COc1ccc2nc(-c3cccnc3)nc(Nc3cc(C(F)(F)F)ccc3C(N)=O)c2c1] | HCl | 439.39 | 1H NMR (300 MHz, DMSO) δ 13.10 (s, 1H), 9.68 (d, J = 1.1 Hz, 1H), 9.52 (d, J = 1.4 Hz, 1H), 8.75-8.58 (m, 3H), 8.26 (s, 1H), 8.15 (d, J = 8.2 Hz, 1H), 7.85 (d, J = 9.1 Hz, 1H), 7.59-7.47 (m, 3H), 7.45 (d, J = 2.5 Hz, 1H), 3.95 (s, 3H). | DMSO | 440.1 (M + 1) | 2.25 | Method C | 100 | Meth-od G1 |
| 284 | 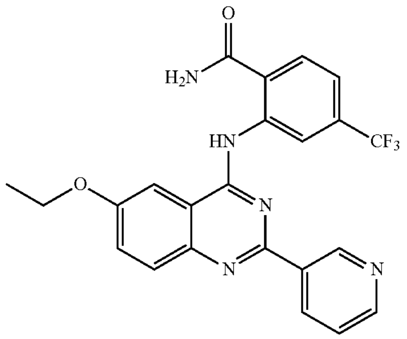 [SMILES: CCOc1ccc2nc(-c3cccnc3)nc(Nc3cc(C(F)(F)F)ccc3C(N)=O)c2c1] | HCl | 453.42 | 1H NMR (300 MHz, DMSO) δ 13.08 (s, 1H), 9.70 (s, 1H), 9.55 (d, J = 1.3 Hz, 1H), 8.77-8.60 (m, 3H), 8.26 (s, 1H), 8.15 (d, J = 8.5 Hz, 1H), 7.88 (d, J = 9.1 Hz, 1H), 7.62-7.39 (m, 4H), 4.21 (q, J = 7.1 Hz, 2H), 1.45 (t, J = 6.9 Hz, 3H). | DMSO | 454.1 (M + 1) | 2.43 | Metho C | 95 | Meth-od G1 |
| 285 | 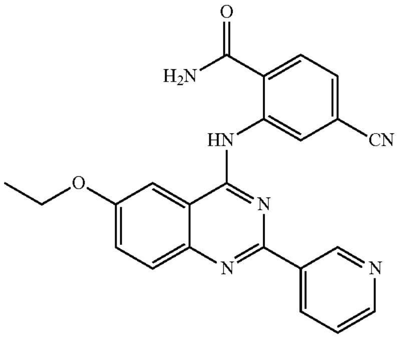 [SMILES: CCOc1ccc2nc(-c3cccnc3)nc(Nc3cc(C#N)ccc3C(N)=O)c2c1] | HCl | 410.43 | 1H NMR (300 MHz, DMSO) δ 12.87 (s, 1H), 9.50 (d, J = 1.5 Hz, 2H), 8.73- 8.59 (m, 3H), 8.26 (s, 1H), 8.07 (d, J = 8.2 Hz, 1H), 7.85 (d, J = 9.1 Hz, 1H), 7.64 (dd, J = 8.1, 1.5 Hz, 1H), 7.59-7.49 (m, 2H), 7.42 (d, J = 2.4 Hz, 1H), 4.19 (q, J = 6.9 Hz, 2H | DMSO | 411.1 (M + 1) | 2.16 | Method C | 95 | Meth-od G1 |

TABLE 1-continued
| | | | | | | | | | | |
|---|---|---|---|---|---|---|---|---|---|---|
| 286 | 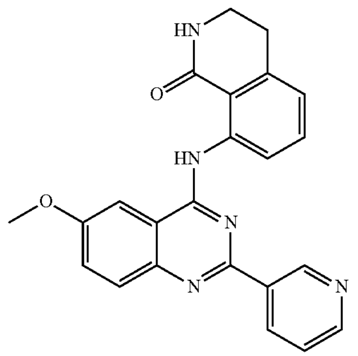 [SMILES: COc1ccc2nc(-c3cccnc3)nc(Nc3cccc4c3C(=O)NCC4)c2c1] | HCl | 397.43 | 1H NMR (300 MHz, DMSO) δ 13.63 (s, 1H), 9.55 (s, 1H), 9.13 (d, J = 8.3 Hz, 1H), 8.75-8.58 (m, 3H), 7.84 (d, J = 9.8 Hz, 1H), 7.69-7.48 (m, 4H), 7.01 (d, J = 7.4 Hz, 1H), 3.94 (s, 3H), 3.46-3.36 (m, 2H), 2.96 (t, J =- 5.7 Hz, 2H). | DMSO | 398.3 (M + 1) | 2.12 | Method C | 100 | Meth-od G1 |
| 287 | 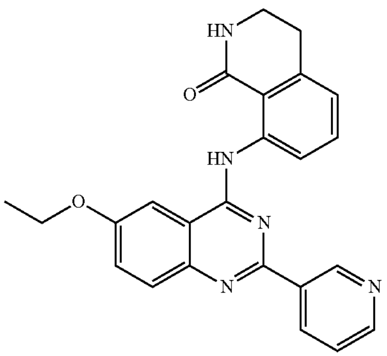 [SMILES: CCOc1ccc2nc(-c3cccnc3)nc(Nc3cccc4c3C(=O)NCC4)c2c1] | HCl | 411.46 | 1H NMR (300 MHz, DMSO) δ 13.61 (s, 1H), 9.56 (s, 1H), 9.14 (d, J = 8.1 Hz, 1H), 8.75- 8.60 (m, 3H), 7.84 (d, J = 9.8 Hz, 1H), 7.70-7.46 (m, 4H), 7.02 (d, J = 7.2 Hz, 1H), 4.19 (q, J = 6.9 Hz, 3H), 3.48-3.3 (m, 2H),7 2.96 (t, J = 6.1 Hz, 2H), 1.44 (t, | DMSO | 412.4 (M + 1) | 2.4 | Method C | 100 | Meth-od G1 |
| 288 | 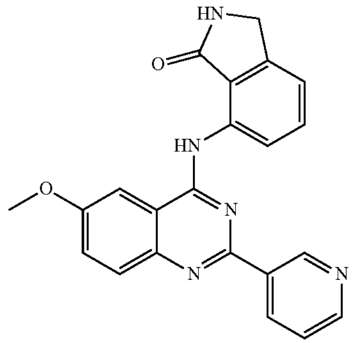 [SMILES: COc1ccc2nc(-c3cccnc3)nc(Nc3cccc4c3C(=O)NC4)c2c1] | HCl | 383.4 | 1H NMR (300 MHz, DMSO) δ 11.62 (s, 1H), 9.60 (d, J = 1.5 Hz, 1H), 9.02 (s, 1H), 8.88 (d, J = 8.0 Hz, 1H), 8.80-8.65 (m, 2H), 7.90 (d, J = 9.0 Hz, 1H), 7.75 (t, J = 7.9 Hz, 1H), 7.66-7.51 (m, 3H), 7.27 (d, J = 7.6 Hz, 1H), 4.47 (s, 2H), 3.97 (s, 3H). | DMSO | 384.1 (M + 1) | 2.01 | Method C | 95 | Meth-od G1 |

TABLE 1-continued
| | | | | | | | | | | |
|---|---|---|---|---|---|---|---|---|---|---|
| 289 | 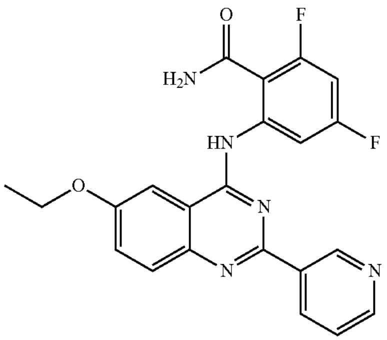 [SMILES: CCOc1ccc2nc(-c3cccnc3)nc(Nc3cc(F)cc(F)c3C(N)=O)c2c1] | HCl | 421.4 | 1H NMR (300 MHz, DMSO) δ 12.07 (s, 1H), 9.48 (d, J = 1.6 Hz, 1H), 8.76-8.55 (m, 3H), 8.34 (s, 1H), 8.14 (s, 1H), 7.87 (d, J = 9.1 Hz, 1H), 7.62-7.49 (m, 2H), 7.38 (d, J = 2.5 Hz, 1H), 7.14 (ddd, J = 11.5, 9.0, 2.6 Hz, 1H), 4.19 (q, J = 6.9 Hz, 2H), 1. | DMSO | 422.2 (M + 1) | 2.35 | Method C | 100 | Meth-od G1 |
| 290 | 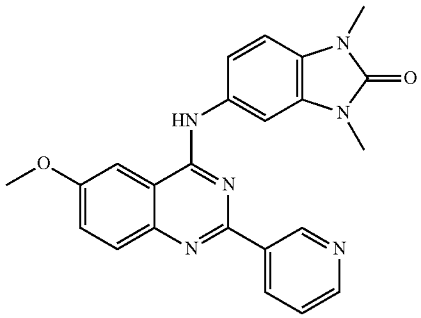 [SMILES: COc1ccc2nc(-c3cccnc3)nc(Nc3ccc4c(c3)n(C)c(=O)n4C)c2c1] | HCl | 412.44 | 1H NMR (300 MHz, DMSO) δ 9.82 (s, 1H), 9.50 (d, J = 2.0 Hz, 1H), 8.68-8.58 (m, 2H), 7.98 (d, J = 2.5 Hz, 1H), 7.85 (d, J = 1.8 Hz, 1H), 7.80 (d, J = 9.1 Hz, 1H), 7.55-7.43 (m, 3H), 7.23 (d, J = 8.4 Hz, 1H), 3.96 (s, 3H), 3.37 (d, J = 4.2 Hz, 6H). | DMSO | 413.0 (M + 1) | 1.79 | Method C | | Meth-od G1 |
| 291 | 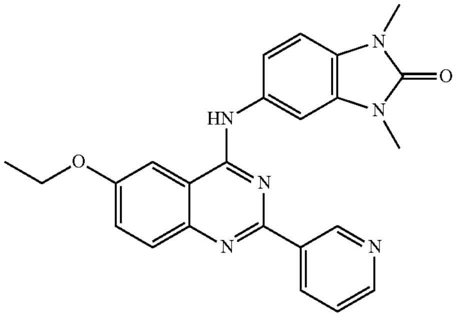 [SMILES: CCOc1ccc2nc(-c3cccnc3)nc(Nc3ccc4c(c3)n(C)c(=O)n4C)c2c1] | HCl | 426.47 | 1H NMR (300 MHz, DMSO) δ 9.78 (s, 1H), 9.50 (d, J = 2.0 Hz, 1H), 8.68-8.57 (m, 2H), 7.97 (d, J = 2.5 Hz, 1H), 7.85 (d, J = 1.3 Hz, 1H), 7.79 (d, J = 9.1 Hz, 1H), 7.55-7.43 (m, 3H), 7.22 (d, J = 8.4 Hz, 1H), 4.22 (q, J = 6.9 Hz, 2H), 3.37 (d, J = 4.3 H | DMSO | 427.1 (M + 1) | 1.92 | Method C | | Meth-od G1 |

TABLE 1-continued
| | | | | | | | | | | |
|---|---|---|---|---|---|---|---|---|---|---|
| 292 | 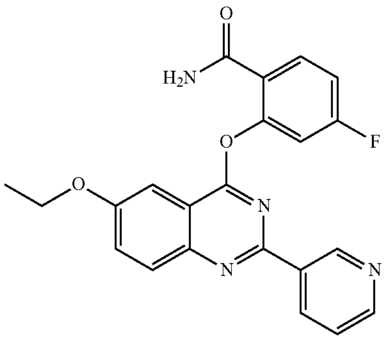 [SMILES: CCOc1ccc2nc(-c3cccnc3)nc(Oc3cc(F)ccc3C(N)=O)c2c1] | | 404.39 | 1H NMR (300 MHz, DMSO) δ 9.36 (d, J = 1.4 Hz, 1H), 8.66 (d, J = 2.7 Hz, 1H), 8.52 (d, J = 7.8 Hz, 1H), 7.97 (d, J = 8.9 Hz, 2H), 7.64 (d, J = 13.5 Hz, 2H), 7.50 (dd, J = 7.7, 4.2 Hz, 1H), 6.86 (t, J = 6.8 Hz, 1H), 6.70 (dd, J = 11.8, 1.7 Hz, 1H), 4.22 (q, | DMSO | 405.1 (M + 1) | 1.98 | Method C | 95 | Meth-od G8 |
| 293 | 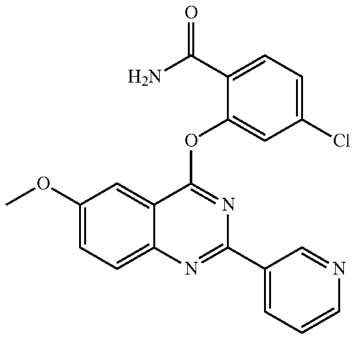 [SMILES: COc1ccc2nc(-c3cccnc3)nc(Oc3cc(Cl)ccc3C(N)=O)c2c1] | | 406.82 | 1H NMR (300 MHz, DMSO) δ 9.23 (d, J = 1.4 Hz, 1H), 8.63 (d, J = 3.6 Hz, 1H), 8.43 (d, J = 8.0 Hz, 1H), 8.00 (d, J = 9.1 Hz, 1H), 7.92 (s, 1H), 7.81-7.65 (m, 4H), 7.55 (dd, J = 8.4, 2.1 Hz, 1H), 7.48 (dd, J = 6.7, 3.8 Hz, 1H), 7.37 (s, 1H), 3.97 (s, 3H). | DMSO | 407.1 (M + 1) | 1.88 | Method C | 100 | Meth-od G8 |
| 294 | 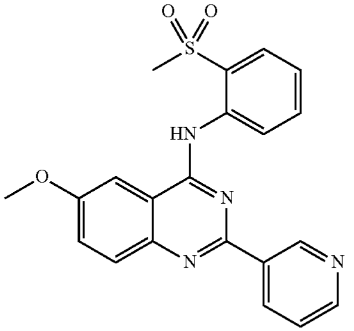 [SMILES: COc1ccc2nc(-c3cccnc3)nc(Nc3ccccc3S(C)(=O)=O)c2c1] | HCl | 406.46 | 1H NMR (300 MHz, DMSO) δ 10.11 (s, 1H), 9.39 (d, J = 1.4 Hz, 1H), 8.63 (dd, J = 4.7, 1.7 Hz, 1H), 8.59-8.53 (m, 1H), 8.50 (dd, J = 8.2, 0.8 Hz, 1H), 8.03 (dd, J = 8.0, 1.4 Hz, 1H), 7.96-7.84 (m, 2H), 7.65-7.46 (m, 4H), 3.94 (s, 3H), 3.25 (s, 3H). | DMSO | 407.1 (M + 1) | 2.13 | Method C | 95 | Meth-od G1 |

TABLE 1-continued
| Number | Starting Material 1 | Starting Material 2 | Product | Salt Type |
|---|---|---|---|---|
| 295 | 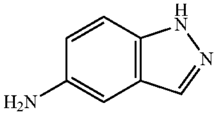 | 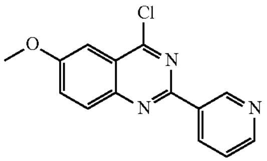 [SMILES: COc1ccc2nc(-c3cccnc3)nc(Cl)c2c1] | 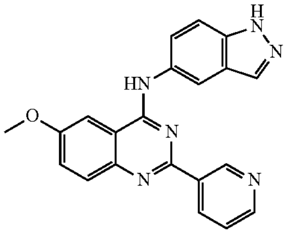 | |
| 296 | 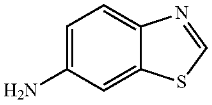 | 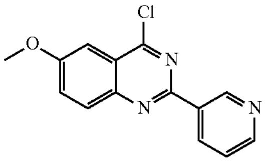 [SMILES: COc1ccc2nc(-c3cccnc3)nc(Cl)c2c1] | 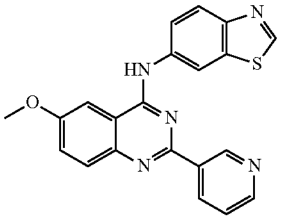 | |
| 297 | 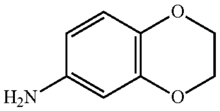 | 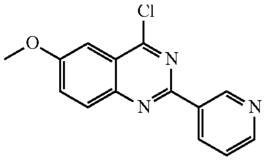 [SMILES: COc1ccc2nc(-c3cccnc3)nc(Cl)c2c1] | 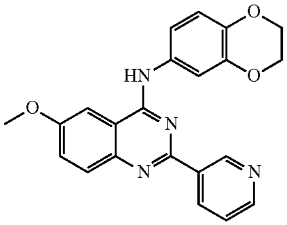 [SMILES: COc1ccc2nc(-c3cccnc3)nc(Nc3ccc4c(c3)OCCO4)c2c1] | |
| 298 | 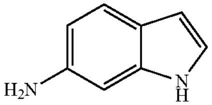 | 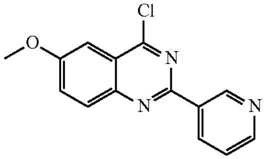 [SMILES: COc1ccc2nc(-c3cccnc3)nc(Cl)c2c1] | 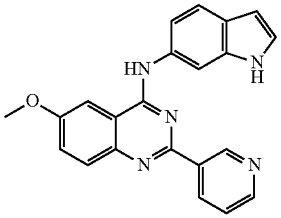 [SMILES: COc1ccc2nc(-c3cccnc3)nc(Nc3ccc4cc[nH]c4c3)c2c1] | |

TABLE 1-continued
| | | | |
|---|---|---|---|
| 299 | 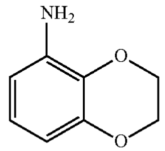 [SMILES: Nc1cccc2c1OCCO2] | 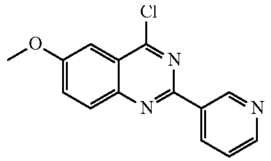 [SMILES: COc1ccc2nc(-c3cccnc3)nc(Cl)c2c1] | 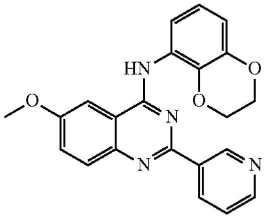 [SMILES: COc1ccc2nc(-c3cccnc3)nc(Nc3cccc4c3OCCO4)c2c1] |
| 300 | 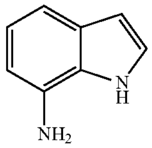 | 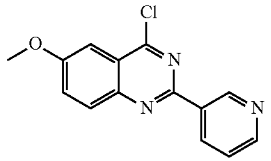 [SMILES: COc1ccc2nc(-c3cccnc3)nc(Cl)c2c1] | 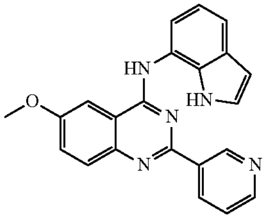 [SMILES: COc1ccc2nc(-c3cccnc3)nc(Nc3cccc4cc[nH]c34)c2c1] |
| 301 | 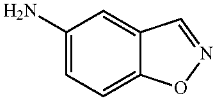 | 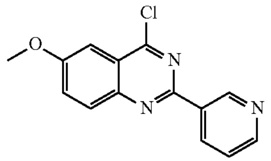 [SMILES: COc1ccc2nc(-c3cccnc3)nc(Cl)c2c1] | 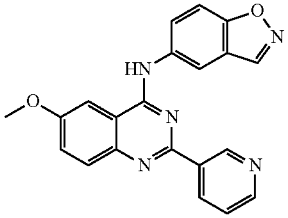 [SMILES: COc1ccc2nc(-c3cccnc3)nc(Nc3ccc4oncc4c3)c2c1] |
| 302 | 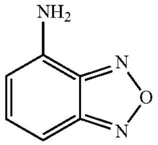 | 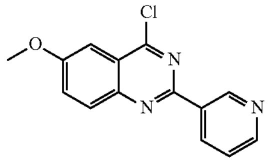 [SMILES: COc1ccc2nc(-c3cccnc3)nc(Cl)c2c1] | 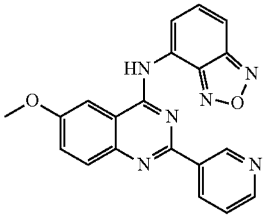 [SMILES: COc1ccc2nc(-c3cccnc3)nc(Nc3cccc4nonc34)c2c1] |

TABLE 1-continued
| | | | |
|---|---|---|---|
| 303 | 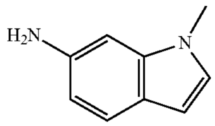 | 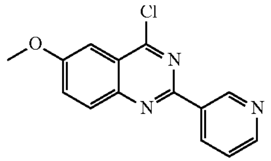 [SMILES: COc1ccc2nc(-c3cccnc3)nc(Cl)c2c1] | 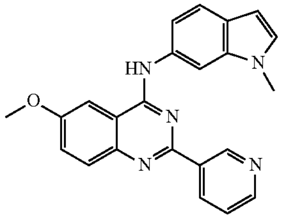 [SMILES: COc1ccc2nc(-c3cccnc3)nc(Nc3ccc4ccn(C)c4c3)c2c1] |
| 304 | 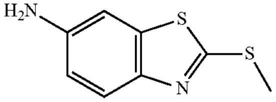 | 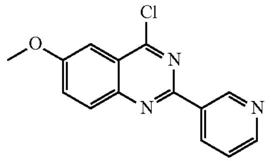 [SMILES: COc1ccc2nc(-c3cccnc3)nc(Cl)c2c1] | 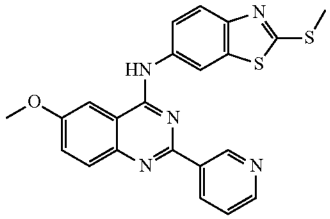 |
| 305 | 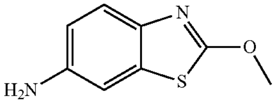 | 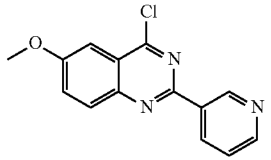 [SMILES: COc1ccc2nc(-c3cccnc3)nc(Cl)c2c1] | 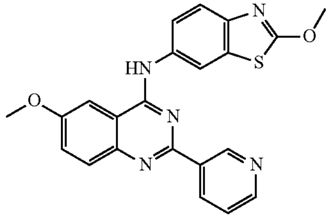 |
| 306 | 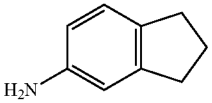 | 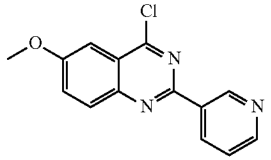 [SMILES: COc1ccc2nc(-c3cccnc3)nc(Cl)c2c1] | 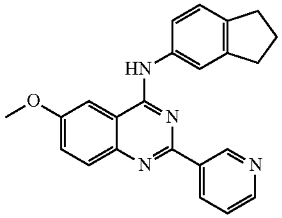 [SMILES: COc1ccc2nc(-c3cccnc3)nc(Nc3ccc4c(c3)CCC4)c2c1] |

TABLE 1-continued
| | | | | |
|---|---|---|---|---|
| 307 | 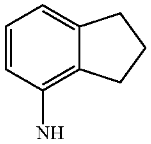 | 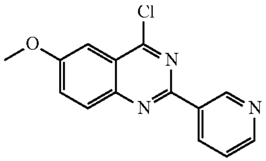 [SMILES: COc1ccc2nc(-c3cccnc3)nc(Cl)c2c1] | 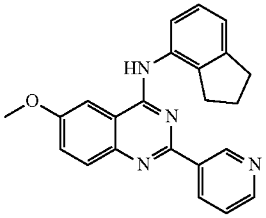 [SMILES: COc1ccc2nc(-c3cccnc3)nc(Nc3cccc4c3CCC4)c2c1] | |
| 308 | 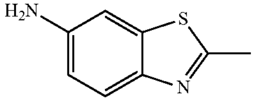 | 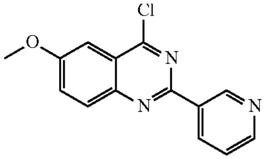 [SMILES: COc1ccc2nc(-c3cccnc3)nc(Cl)c2c1] | 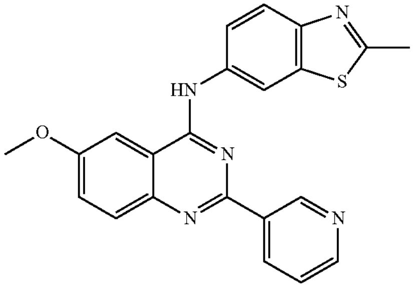 | HCl |
| 309 | 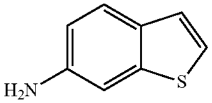 | 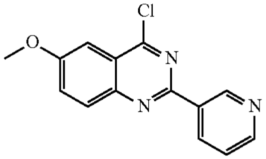 [SMILES: COc1ccc2nc(-c3cccnc3)nc(Cl)c2c1] | 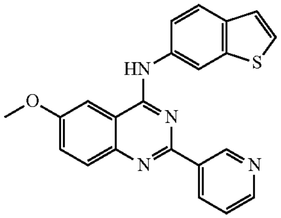 [SMILES: COc1ccc2nc(-c3cccnc3)nc(Nc3ccc4ccsc4c3)c2c1] | HCl |
| 310 | 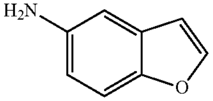 HCl | 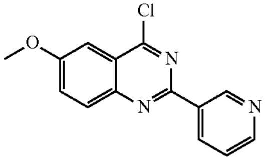 [SMILES: COc1ccc2nc(-c3cccnc3)nc(Cl)c2c1] | 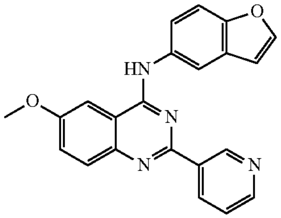 [SMILES: COc1ccc2nc(-c3cccnc3)nc(Nc3ccc4occc4c3)c2c1] | HCl |

TABLE 1-continued
| | | | | |
|---|---|---|---|---|
| 311 | 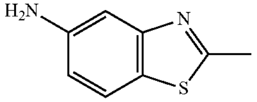 | 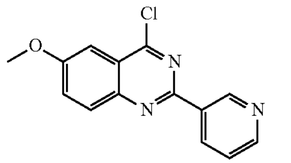 [SMILES: COc1ccc2nc(-c3cccnc3)nc(Cl)c2c1] | 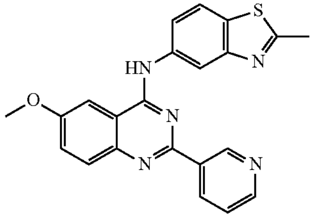 | HCl |
| 312 | 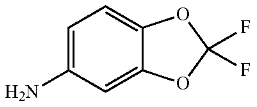 | 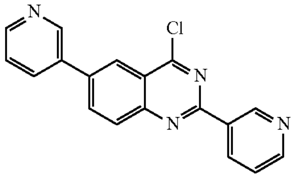 [SMILES: Clc1nc(-c2cccnc2)nc2ccc(-c3cccnc3)cc12] | 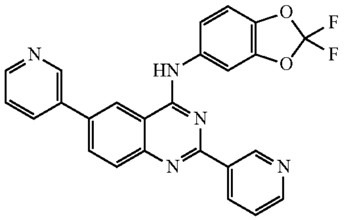 [SMILES: FC1(F)Oc2ccc(Nc3nc(-c4cccnc4)nc4ccc(-c5cccnc5)cc34)cc2O1] | 3 HCl |
| 313 | 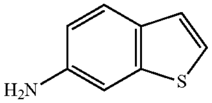 | 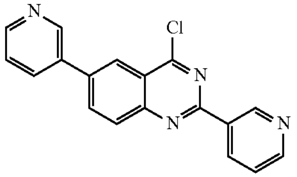 [SMILES: Clc1nc(-c2cccnc2)nc2ccc(-c3cccnc3)cc12] | 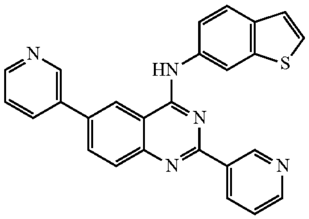 [SMILES: c1cncc(-c2ccc3nc(-c4cccnc4)nc(Nc4ccc5ccsc5c4)c3c2)c1] | 2 HCl |
| 314 | 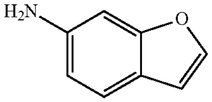 HCl | 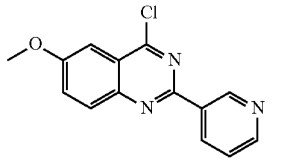 [SMILES: COc1ccc2nc(-c3cccnc3)nc(Cl)c2c1] | 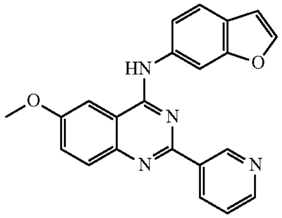 [SMILES: COc1ccc2nc(-c3cccnc3)nc(Nc3ccc4ccoc4c3)c2c1] | HCl |

TABLE 1-continued
| | | | | |
|---|---|---|---|---|
| 315 | 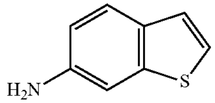 | 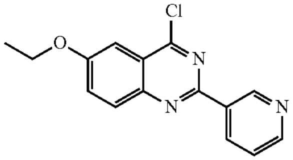 [SMILES: CCOc1ccc2nc(-c3cccnc3)nc(Cl)c2c1] | 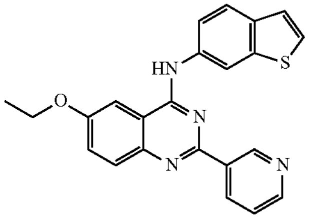 [SMILES: CCOc1ccc2nc(-c3cccnc3)nc(Nc3ccc4ccsc4c3)c2c1] | HCl |
| 316 | 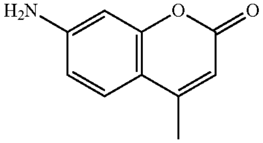 | 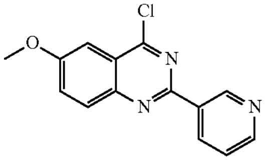 [SMILES: COc1ccc2nc(-c3cccnc3)nc(Cl)c2c1] | 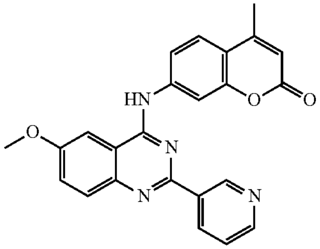 [SMILES: COc1ccc2nc(-c3cccnc3)nc(Nc3ccc4c(C)cc(=O)oc4c3)c2c1] | |
| 317 | 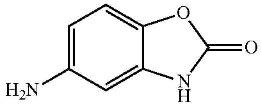 [SMILES: Nc1ccc2oc(=O)[nH]c2c1] | 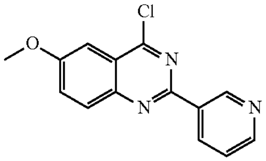 [SMILES: COc1ccc2nc(-c3cccnc3)nc(Cl)c2c1] | 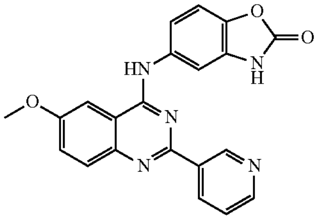 | |
| 318 | 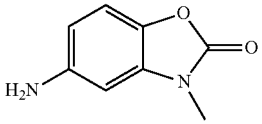 | 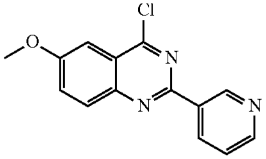 [SMILES: COc1ccc2nc(-c3cccnc3)nc(Cl)c2c1] | 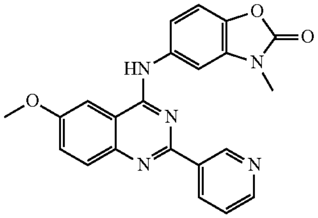 | |

TABLE 1-continued
| | | | |
|---|---|---|---|
| 319 | 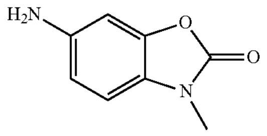 | 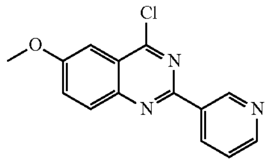 [SMILES: COc1ccc2nc(-c3cccnc3)nc(Cl)c2c1] | 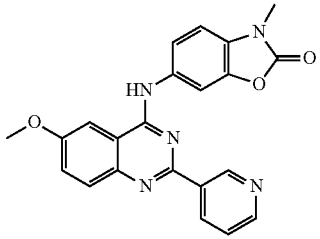 |
| 320 | 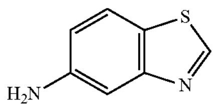 | 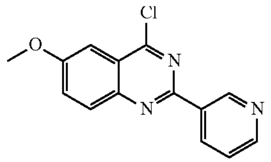 [SMILES: COc1ccc2nc(-c3cccnc3)nc(Cl)c2c1] | 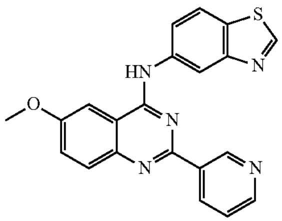 [SMILES: COc1ccc2nc(-c3cccnc3)nc(Nc3ccc4scnc4c3)c2c1] |
| 321 | 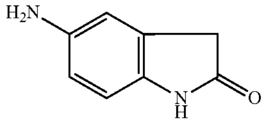 | 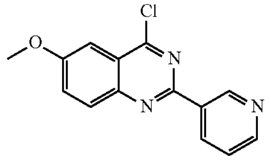 [SMILES: COc1ccc2nc(-c3cccnc3)nc(Cl)c2c1] | 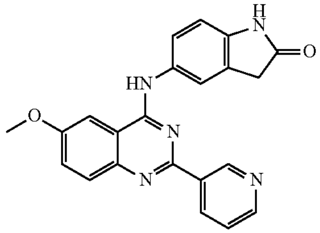 [SMILES: COc1ccc2nc(-c3cccnc3)nc(Nc3ccc4c(c3)CC(=O)N4)c2c1] |
| 322 | 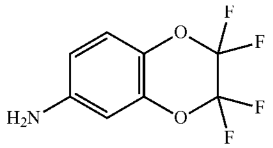 [SMILES: Nc1ccc2c(c1)OC(F)(F)C(F)(F)O2] | 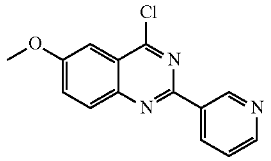 [SMILES: COc1ccc2nc(-c3cccnc3)nc(Cl)c2c1] | 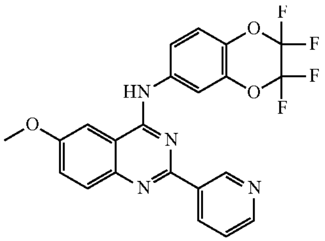 [SMILES: COc1ccc2nc(-c3cccnc3)nc(Nc3ccc4c(c3)OC(F)(F)C(F)(F)O4)c2c1] |

TABLE 1-continued
| | | | | |
|---|---|---|---|---|
| 323 | 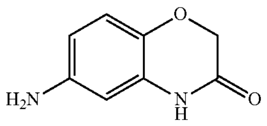 [SMILES: Nc1ccc2c(c1)NC(=O)CO2] | 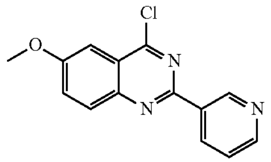 [SMILES: COc1ccc2nc(-c3cccnc3)nc(Cl)c2c1] | 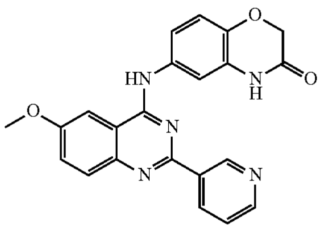 [SMILES: COc1ccc2nc(-c3cccnc3)nc(Nc3ccc4c(c3)NC(=O)CO4)c2c1] | |
| 324 | 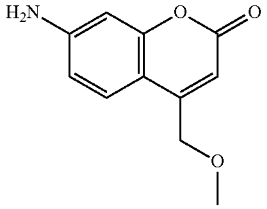 | 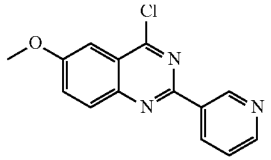 [SMILES: COc1ccc2nc(-c3cccnc3)nc(Cl)c2c1] | 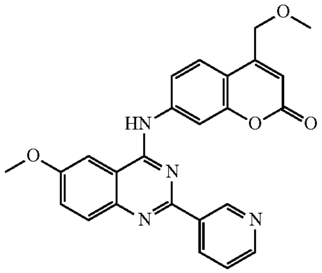 | HCl |
| 325 | 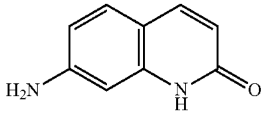 [SMILES: Nc1ccc2ccc(=O)[nH]c2c1] | 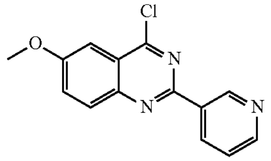 [SMILES: COc1ccc2nc(-c3cccnc3)nc(Cl)c2c1] | 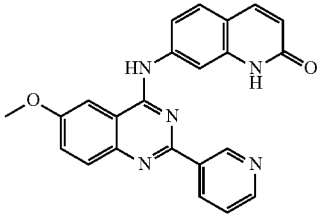 | HCl |
| 326 | 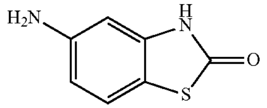 [SMILES: Nc1ccc2sc(=O)[nH]c2c1] | 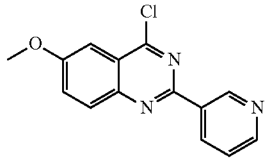 [SMILES: COc1ccc2nc(-c3cccnc3)nc(Cl)c2c1] | 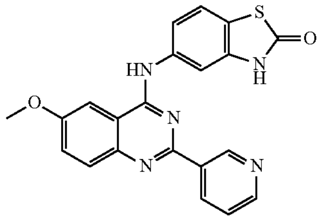 [SMILES: COc1ccc2nc(-c3cccnc3)nc(Nc3ccc4sc(=O)[nH]c4c3)c2c1] | HCl |

TABLE 1-continued
| | | | | |
|---|---|---|---|---|
| 327 | 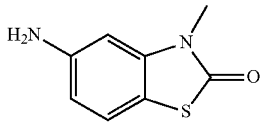 | 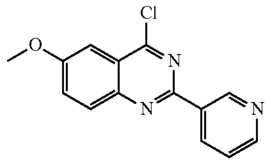 [SMILES: COc1ccc2nc(-c3cccnc3)nc(Cl)c2c1] | 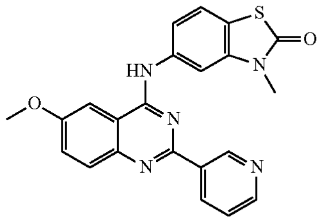 [SMILES: COc1ccc2nc(-c3cccnc3)nc(Nc3ccc4sc(=O)n(C)c4c3)c2c1] | HCl |
| 328 | 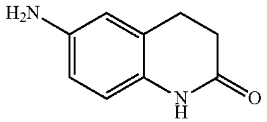 [SMILES: Nc1ccc2c(c1)CCC(=O)N2] | 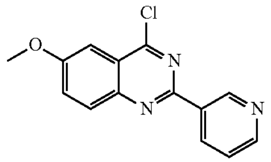 [SMILES: COc1ccc2nc(-c3cccnc3)nc(Cl)c2c1] | 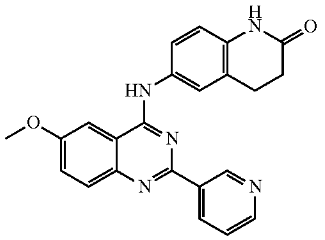 [SMILES: COc1ccc2nc(-c3cccnc3)nc(Nc3ccc4c(c3)CCC(=O)N4)c2c1] | HCl |
| 329 | 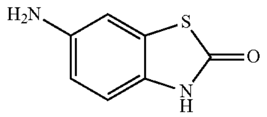 | 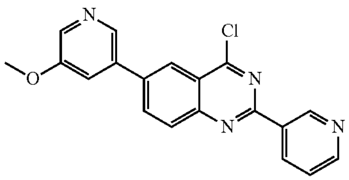 [SMILES: COc1cncc(-c2ccc3nc(-c4cccnc4)nc(Cl)c3c2)c1] | 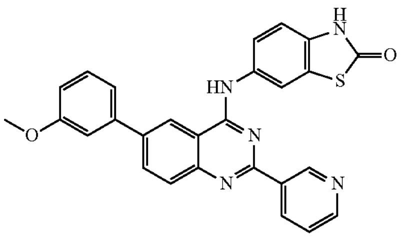 [SMILES: COc1cccc(-c2ccc3nc(-c4cccnc4)nc(Nc4ccc5[nH]c(=O)sc5c4)c3c2)c1] | 2 HCl |
| 330 | 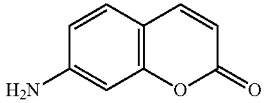 | 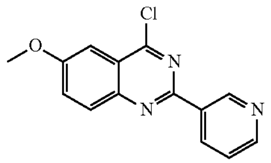 [SMILES: COc1ccc2nc(-c3cccnc3)nc(Cl)c2c1] | 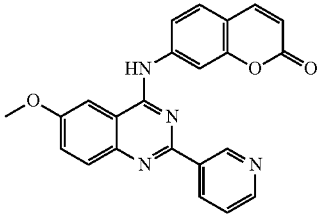 [SMILES: COc1ccc2nc(-c3cccnc3)nc(Nc3ccc4ccc(=O)oc4c3)c2c1] | HCl |

TABLE 1-continued
| | | | | |
|---|---|---|---|---|
| 331 | 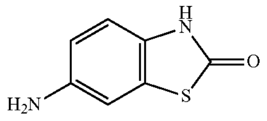 | 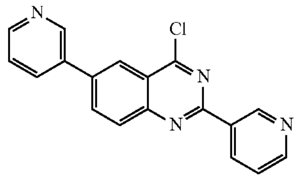 [SMILES: Clc1nc(-c2cccnc2)nc2ccc(-c3cccnc3)cc12] | 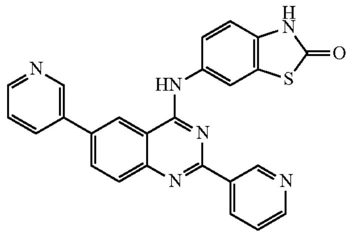 [SMILES: O=c1[nH]c2ccc(Nc3nc(-c4cccnc4)nc4ccc(-c5cccnc5)cc34)cc2s1] | 2 HCl |
| 332 | 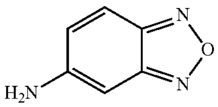 | 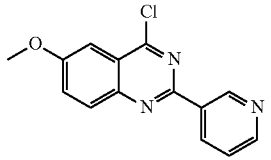 [SMILES: COc1ccc2nc(-c3cccnc3)nc(Cl)c2c1] | 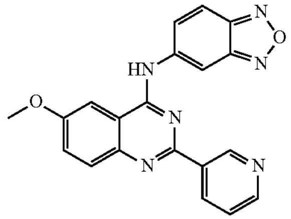 [SMILES: COc1ccc2nc(-c3cccnc3)nc(Nc3ccc4nonc4c3)c2c1] | HCl |
| 333 | 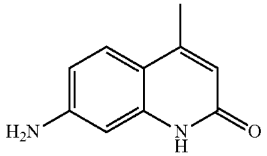 | 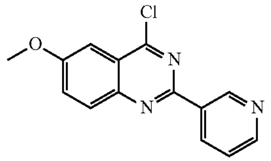 [SMILES: COc1ccc2nc(-c3cccnc3)nc(Cl)c2c1] | 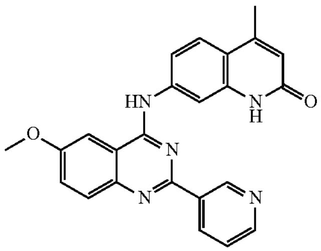 [SMILES: COc1ccc2nc(-c3cccnc3)nc(Nc3ccc4c(C)cc(=O)[nH]c4c3)c2c1] | HCl |
| 334 | 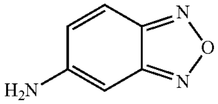 | 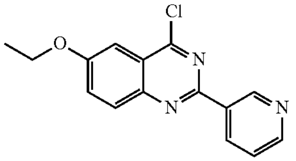 [SMILES: CCOc1ccc2nc(-c3cccnc3)nc(Cl)c2c1] | 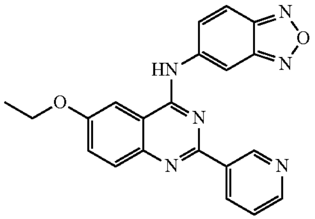 [SMILES: CCOc1ccc2nc(-c3cccnc3)nc(Nc3ccc4nonc4c3)c2c1] | HCl |

TABLE 1-continued
| | | | | |
|---|---|---|---|---|
| 335 | 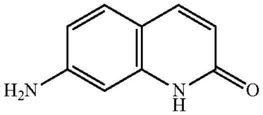 | 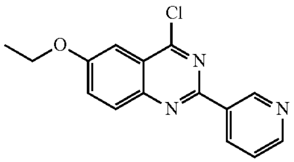 [SMILES: CCOc1ccc2nc(-c3cccnc3)nc(Cl)c2c1] | 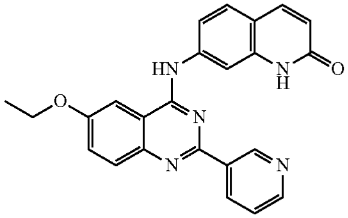 [SMILES: CCOc1ccc2nc(-c3cccnc3)nc(Nc3ccc4ccc(=O)[nH]c4c3)c2c1] | HCl |
| 336 | 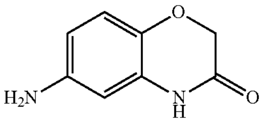 [SMILES: Nc1ccc2c(c1)NC(=O)CO2] | 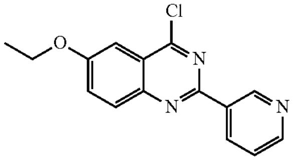 [SMILES: CCOc1ccc2nc(-c3cccnc3)nc(Cl)c2c1] | 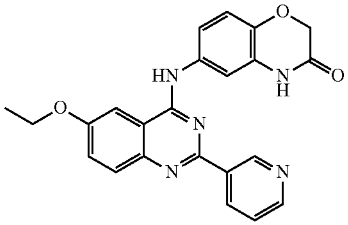 [SMILES: CCOc1ccc2nc(-c3cccnc3)nc(Nc3ccc4c(c3)NC(=O)CO4)c2c1] | HCl |
| 337 | 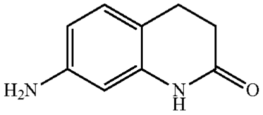 [SMILES: Nc1ccc2c(c1)NC(=O)CC2] | 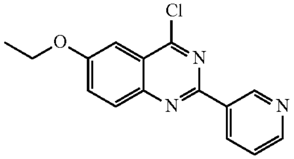 [SMILES: CCOc1ccc2nc(-c3cccnc3)nc(Cl)c2c1] | 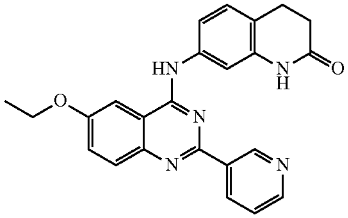 [SMILES: CCOc1ccc2nc(-c3cccnc3)nc(Nc3ccc4c(c3)NC(=O)CC4)c2c1] | HCl |
| 338 | 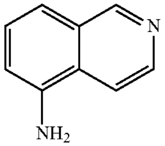 | 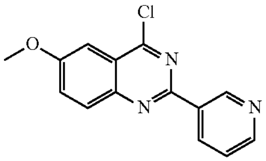 [SMILES: COc1ccc2nc(-c3cccnc3)nc(Cl)c2c1] | 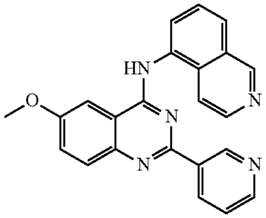 [SMILES: COc1ccc2nc(-c3cccnc3)nc(Nc3cccc4cnccc34)c2c1] | |

TABLE 1-continued
| | | | |
|---|---|---|---|
| 339 | 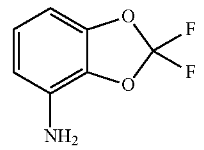 | 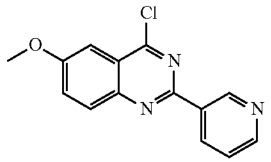 [SMILES: COc1ccc2nc(-c3cccnc3)nc(Cl)c2c1] | 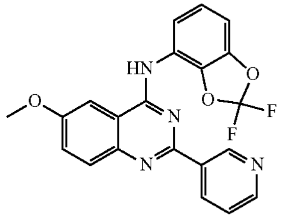 [SMILES: COc1ccc2nc(-c3cccnc3)nc(Nc3cccc4c3OC(F)(F)O4)c2c1] |
| 340 | 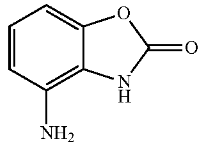 | 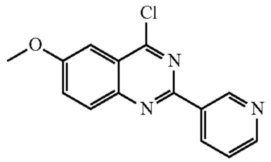 [SMILES: COc1ccc2nc(-c3cccnc3)nc(Cl)c2c1] | 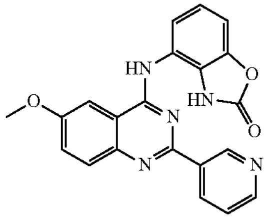 [SMILES: COc1ccc2nc(-c3cccnc3)nc(Nc3cccc4oc(=O)[nH]c34)c2c1] |
| 341 | 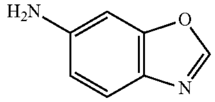 | 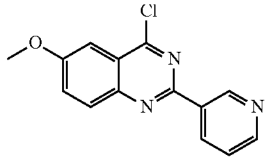 [SMILES: COc1ccc2nc(-c3cccnc3)nc(Cl)c2c1] | 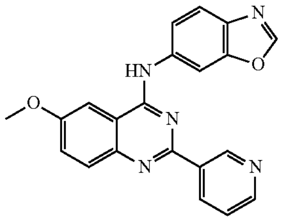 [SMILES: COc1ccc2nc(-c3cccnc3)nc(Nc3ccc4ncoc4c3)c2c1] |
| 342 | 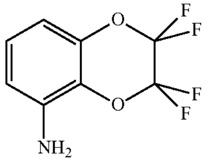 | 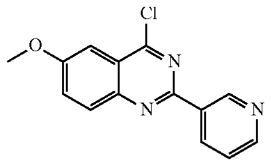 [SMILES: COc1ccc2nc(-c3cccnc3)nc(Cl)c2c1] | 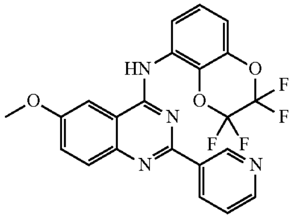 [SMILES: COc1ccc2nc(-c3cccnc3)nc(Nc3cccc4c3OC(F)(F)C(F)(F)O4)c2c1] |

TABLE 1-continued
| | | | | |
|---|---|---|---|---|
| 343 | 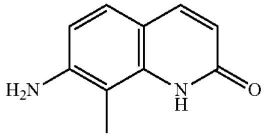 | 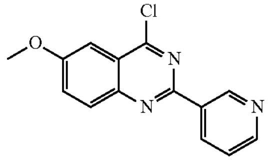 [SMILES: COc1ccc2nc(-c3cccnc3)nc(Cl)c2c1] | 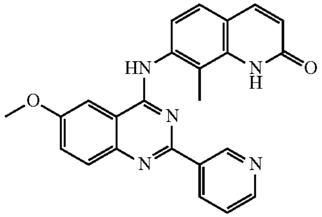 [SMILES: COc1ccc2nc(-c3cccnc3)nc(Nc3ccc4ccc(=O)[nH]c4c3C)c2c1] | |
| 344 | 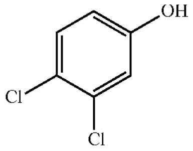 | 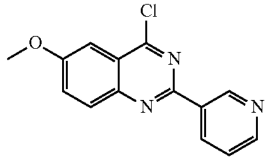 [SMILES: COc1ccc2nc(-c3cccnc3)nc(Cl)c2c1] | 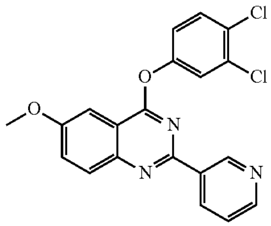 [SMILES: COc1ccc2nc(-c3cccnc3)nc(Oc3ccc(Cl)c(Cl)c3)c2c1] | HCl |
| 345 | 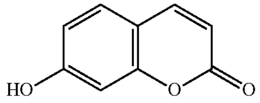 [SMILES: O=c1ccc2ccc(O)cc2o1] | 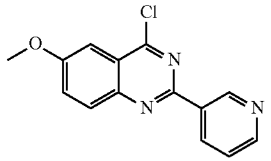 [SMILES: COc1ccc2nc(-c3cccnc3)nc(Cl)c2c1] | 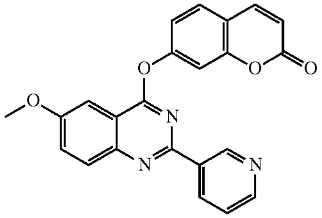 [SMILES: COc1ccc2nc(-c3cccnc3)nc(Oc3ccc4ccc(=O)oc4c3)c2c1] | HCl |
| 346 | 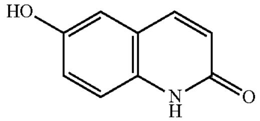 [SMILES: O=c1ccc2cc(O)ccc2[nH]1] | 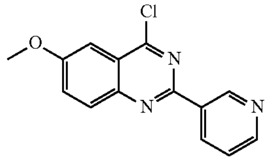 [SMILES: COc1ccc2nc(-c3cccnc3)nc(Cl)c2c1] | 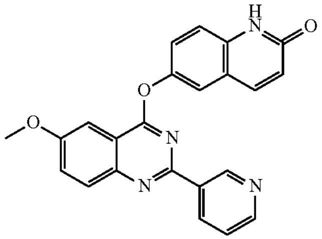 | HCl |

TABLE 1-continued
| | | | | |
|---|---|---|---|---|
| 347 | 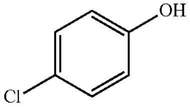 | 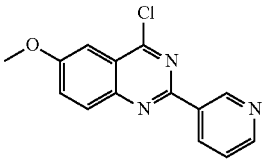 [SMILES: COc1ccc2nc(-c3cccnc3)nc(Cl)c2c1] | 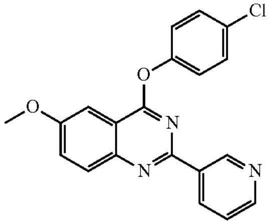 [SMILES: COc1ccc2nc(-c3cccnc3)nc(Oc3ccc(Cl)cc3)c2c1] | HCl |
| 348 | 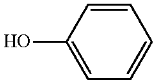 | 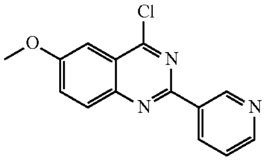 [SMILES: COc1ccc2nc(-c3cccnc3)nc(Cl)c2c1] | 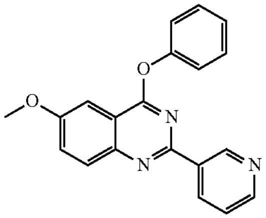 [SMILES: COc1ccc2nc(-c3cccnc3)nc(Oc3ccccc3)c2c1] | HCl |
| 349 | 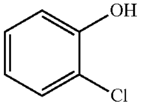 | 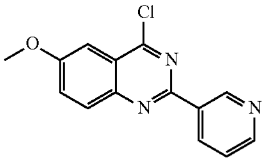 [SMILES: COc1ccc2nc(-c3cccnc3)nc(Cl)c2c1] | 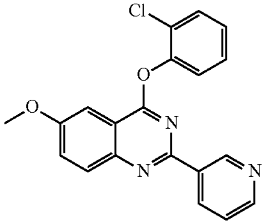 [SMILES: COc1ccc2nc(-c3cccnc3)nc(Oc3ccccc3Cl)c2c1] | HCl |
| 350 | 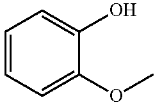 | 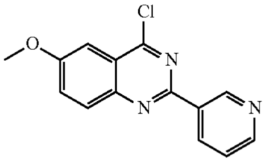 [SMILES: COc1ccc2nc(-c3cccnc3)nc(Cl)c2c1] | 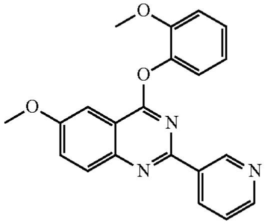 [SMILES: COc1ccc2nc(-c3cccnc3)nc(Oc3ccccc3OC)c2c1] | HCl |

TABLE 1-continued
| | | | | |
|---|---|---|---|---|
| 351 | 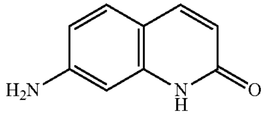 [SMILES: Nc1ccc2ccc(=O)[nH]c2c1] | 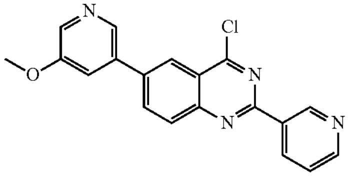 [SMILES: COc1cncc(-c2ccc3nc(-c4cccnc4)nc(Cl)c3c2)c1] | 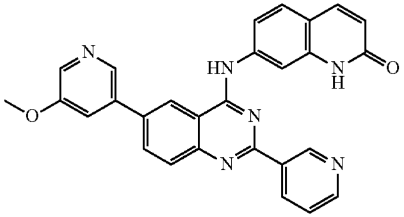 [SMILES: COc1cncc(-c2ccc3nc(-c4cccnc4)nc(Nc4ccc5ccc(=O)[nH]c5c4)c3c2)c1] | 2 HCl |
| 352 | 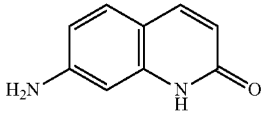 [SMILES: Nc1ccc2ccc(=O)[nH]c2c1] | 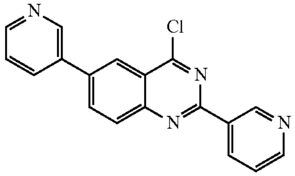 [SMILES: Clc1nc(-c2cccnc2)nc2ccc(-c3cccnc3)cc12] | 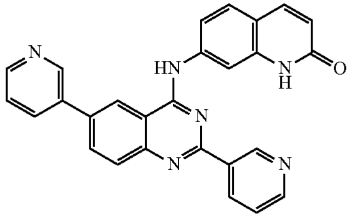 [SMILES: O=c1ccc2ccc(Nc3nc(-c4cccnc4)nc4ccc(-c5cccnc5)cc34)cc2[nH]1] | 2 HCl |
| 353 | 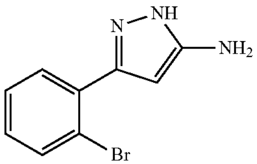 [SMILES: Nc1cc(-c2ccccc2Br)n[nH]1] | 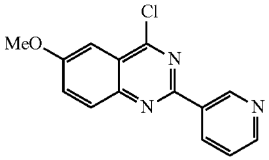 [SMILES: COc1ccc2nc(-c3cccnc3)nc(Cl)c2c1] | 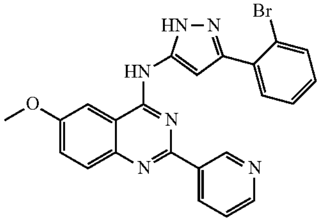 [SMILES: COc1ccc2nc(-c3cccnc3)nc(Nc3cc(-c4ccccc4Br)n[nH]3)c2c1] | HCl |
| 354 | 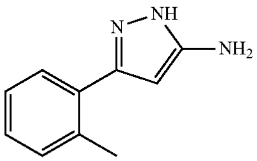 | 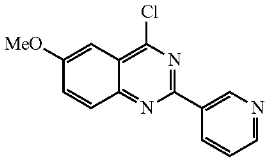 [SMILES: COc1ccc2nc(-c3cccnc3)nc(Cl)c2c1] | 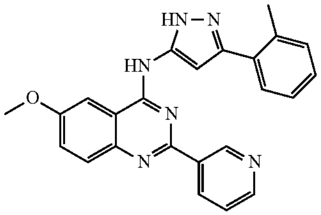 [SMILES: COc1ccc2nc(-c3cccnc3)nc(Nc3cc(-c4ccccc4C)n[nH]3)c2c1] | HCl |

TABLE 1-continued
| | | | | |
|---|---|---|---|---|
| 355 | 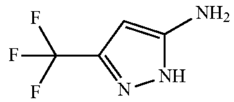 | 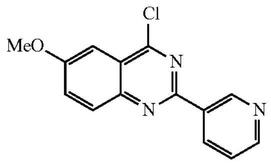 [SMILES: COc1ccc2nc(-c3cccnc3)nc(Cl)c2c1] | 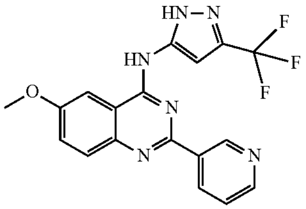 [SMILES: COc1ccc2nc(-c3cccnc3)nc(Nc3cc(C(F)(F)F)n[nH]3)c2c1] | HCl |
| 356 | 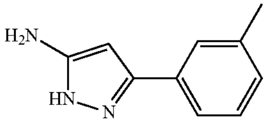 | 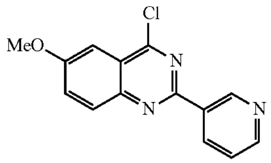 [SMILES: COc1ccc2nc(-c3cccnc3)nc(Cl)c2c1] | 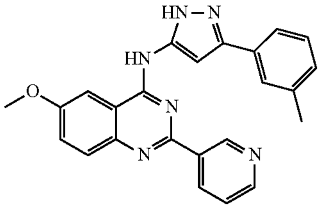 [SMILES: COc1ccc2nc(-c3cccnc3)nc(Nc3cc(-c4cccc(C)c4)n[nH]3)c2c1] | HCl |
| 357 | 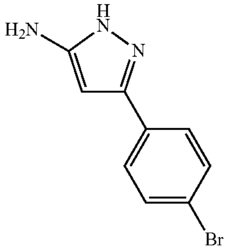 [SMILES: Nc1cc(-c2ccc(Br)cc2)n[nH]1] | 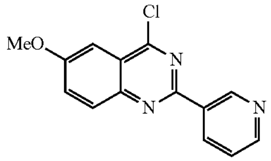 [SMILES: COc1ccc2nc(-c3cccnc3)nc(Cl)c2c1] | 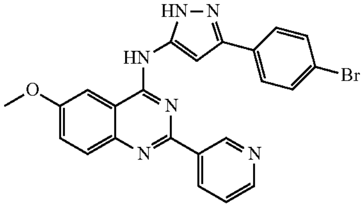 [SMILES: COc1ccc2nc(-c3cccnc3)nc(Nc3cc(-c4ccc(Br)cc4)n[nH]3)c2c1] | HCl |
| 358 | 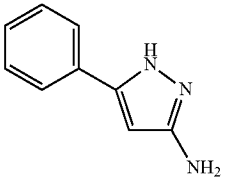 [SMILES: Nc1cc(-c2ccccc2)[nH]n1] | 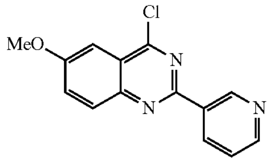 [SMILES: COc1ccc2nc(-c3cccnc3)nc(Cl)c2c1] | 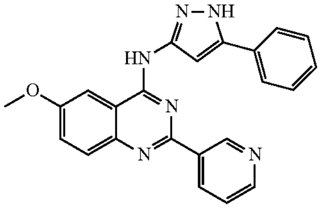 [SMILES: COc1ccc2nc(-c3cccnc3)nc(Nc3cc(-c4ccccc4)[nH]n3)c2c1] | HCl |

TABLE 1-continued
| | | | | |
|---|---|---|---|---|
| 359 | 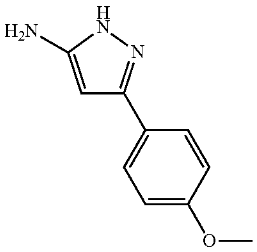 | 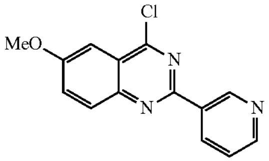 [SMILES: COc1ccc2nc(-c3cccnc3)nc(Cl)c2c1] | 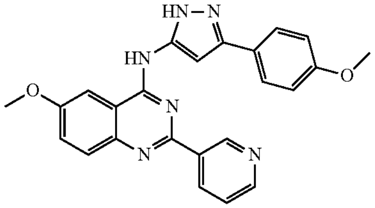 | HCl |
| 360 | 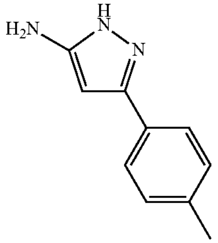 | 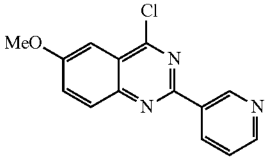 [SMILES: COc1ccc2nc(-c3cccnc3)nc(Cl)c2c1] | 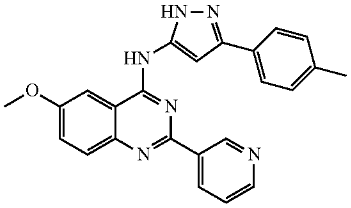 | HCl |
| 361 | 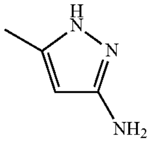 | 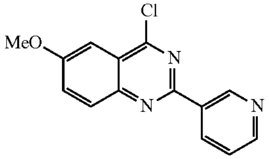 [SMILES: COc1ccc2nc(-c3cccnc3)nc(Cl)c2c1] | 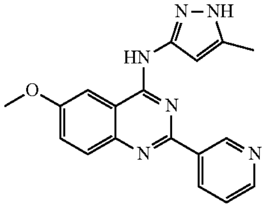 [SMILES: COc1ccc2nc(-c3cccnc3)nc(Nc3cc(C)[nH]n3)c2c1] | HCl |
| 362 | 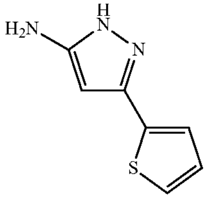 [SMILES: Nc1cc(-c2cccs2)n[nH]1] | 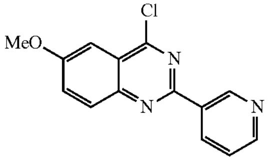 [SMILES: COc1ccc2nc(-c3cccnc3)nc(Cl)c2c1] | 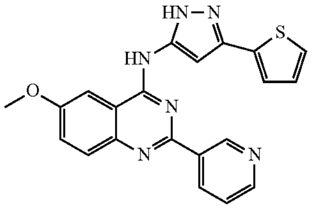 [SMILES: COc1ccc2nc(-c3cccnc3)nc(Nc3cc(-c4cccs4)n[nH]3)c2c1] | HCl |

TABLE 1-continued
| | | | | |
|---|---|---|---|---|
| 363 | 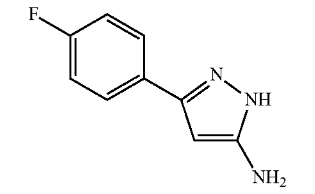 | 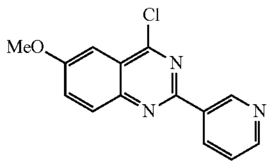 [SMILES: COc1ccc2nc(-c3cccnc3)nc(Cl)c2c1] | 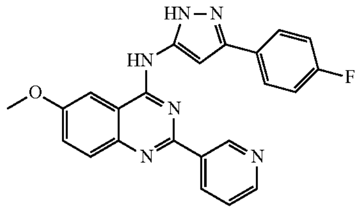 [SMILES: COc1ccc2nc(-c3cccnc3)nc(Nc3cc(-c4ccc(F)cc4)n[nH]3)c2c1] | HCl |
| 364 | 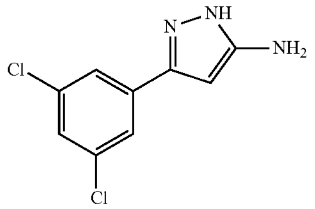 [SMILES: Nc1cc(-c2cc(Cl)cc(Cl)c2)n[nH]1] | 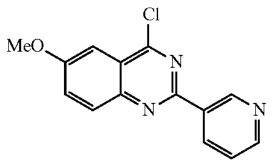 [SMILES: COc1ccc2nc(-c3cccnc3)nc(Cl)c2c1] | 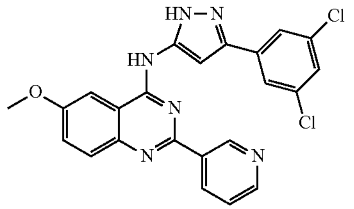 [SMILES: COc1ccc2nc(-c3cccnc3)nc(Nc3cc(-c4cc(Cl)cc(Cl)c4)n[nH]3)c2c1] | 2 HCl |
| 365 | 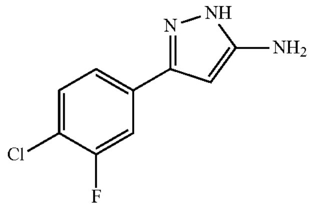 [SMILES: Nc1cc(-c2ccc(Cl)c(F)c2)n[nH]1] | 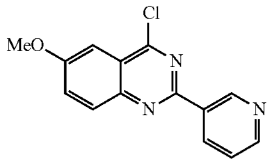 [SMILES: COc1ccc2nc(-c3cccnc3)nc(Cl)c2c1] | 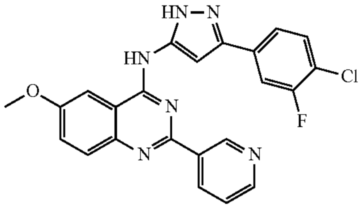 [SMILES: COc1ccc2nc(-c3cccnc3)nc(Nc3cc(-c4ccc(Cl)c(F)c4)n[nH]3)c2c1] | 2 HCl |
| 366 | 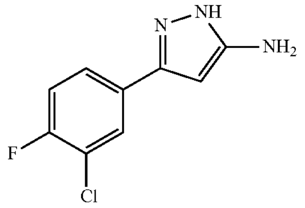 [SMILES: Nc1cc(-c2ccc(F)c(Cl)c2)n[nH]1] | 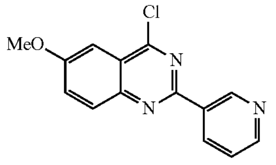 [SMILES: COc1ccc2nc(-c3cccnc3)nc(Cl)c2c1] | 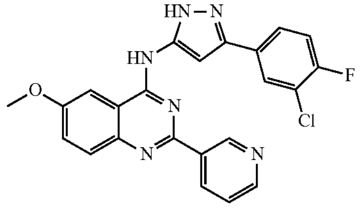 [SMILES: COc1ccc2nc(-c3cccnc3)nc(Nc3cc(-c4ccc(F)c(Cl)c4)n[nH]3)c2c1] | 2 HCl |
| 367 | 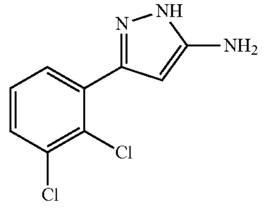 [SMILES: Nc1cc(-c2cccc(Cl)c2Cl)n[nH]1] | 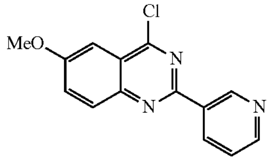 [SMILES: COc1ccc2nc(-c3cccnc3)nc(Cl)c2c1] | 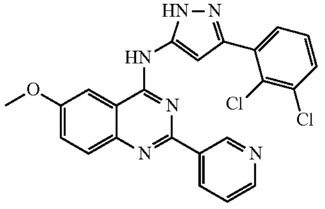 [SMILES: COc1ccc2nc(-c3cccnc3)nc(Nc3cc(-c4cccc(Cl)c4Cl)n[nH]3)c2c1] | 2 HCl |

TABLE 1-continued
| | | | | |
|---|---|---|---|---|
| 368 | 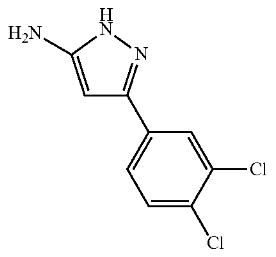 [SMILES: Nc1cc(-c2ccc(Cl)c(Cl)c2)n[nH]1] | 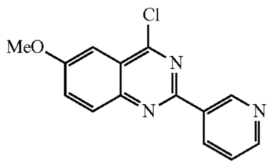 [SMILES: COc1ccc2nc(-c3cccnc3)nc(Cl)c2c1] | 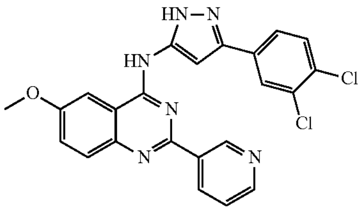 [SMILES: COc1ccc2nc(-c3cccnc3)nc(Nc3cc(-c4ccc(Cl)c(Cl)c4)n[nH]3)c2c1] | 2 HCl |
| 369 | 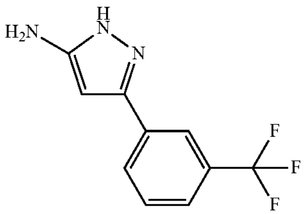 [SMILES: Nc1cc(-c2cccc(C(F)(F)F)c2)n[nH]1] | 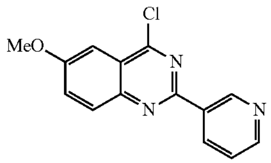 [SMILES: COc1ccc2nc(-c3cccnc3)nc(Cl)c2c1] | 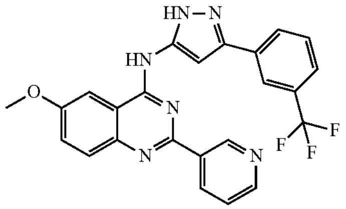 [SMILES: COc1ccc2nc(-c3cccnc3)nc(Nc3cc(-c4cccc(C(F)(F)F)c4)n[nH]3)c2c1] | HCl |
| 370 | 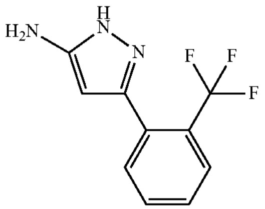 [SMILES: Nc1cc(-c2ccccc2C(F)(F)F)n[nH]1] | 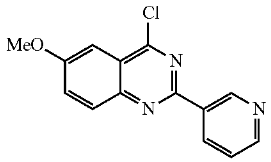 [SMILES: COc1ccc2nc(-c3cccnc3)nc(Cl)c2c1] | 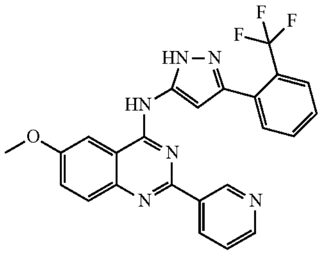 [SMILES: COc1ccc2nc(-c3cccnc3)nc(Nc3cc(-c4ccccc4C(F)(F)F)n[nH]3)c2c1] | HCl |
| 371 | 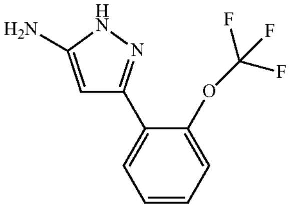 [SMILES: Nc1cc(-c2ccccc2OC(F)(F)F)n[nH]1] | 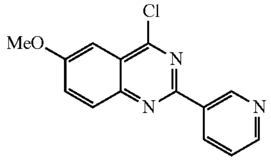 [SMILES: COc1ccc2nc(-c3cccnc3)nc(Cl)c2c1] | 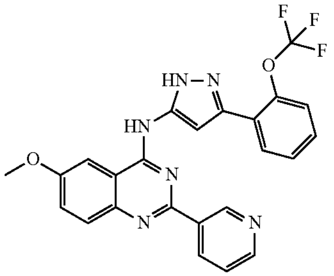 [SMILES: COc1ccc2nc(-c3cccnc3)nc(Nc3cc(-c4ccccc4OC(F)(F)F)n[nH]3)c2c1] | 2 HCl |

TABLE 1-continued
| | | | | |
|---|---|---|---|---|
| 372 | 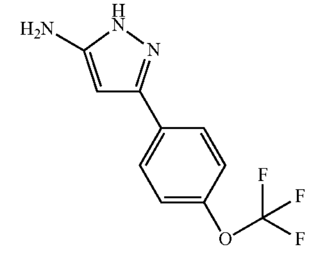 [SMILES: Nc1cc(-c2ccc(OC(F)(F)F)cc2)n[nH]1] | 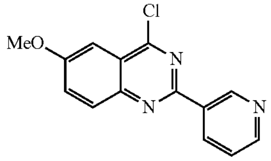 [SMILES: COc1ccc2nc(-c3cccnc3)nc(Cl)c2c1] | 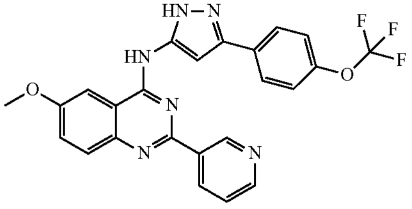 [SMILES: COc1ccc2nc(-c3cccnc3)nc(Nc3cc(-c4ccc(OC(F)(F)F)cc4)n[nH]3)c2c1] | 2 HCl |
| 373 | 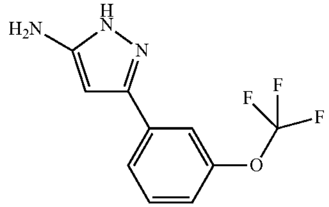 [SMILES: Nc1cc(-c2cccc(OC(F)(F)F)c2)n[nH]1] | 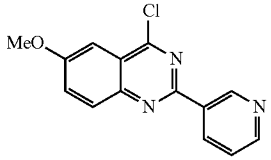 [SMILES: COc1ccc2nc(-c3cccnc3)nc(Cl)c2c1] | 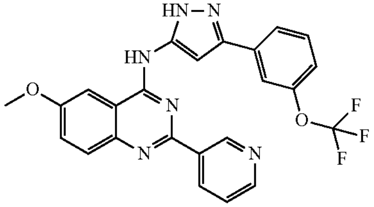 [SMILES: COc1ccc2nc(-c3cccnc3)nc(Nc3cc(-c4cccc(OC(F)(F)F)c4)n[nH]3)c2c1] | 2 HCl |
| 374 | 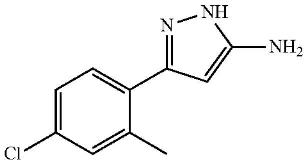 | 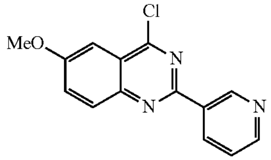 [SMILES: COc1ccc2nc(-c3cccnc3)nc(Cl)c2c1] | 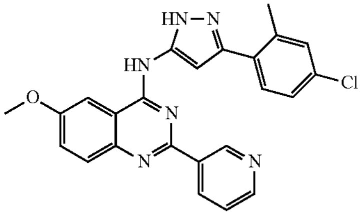 [SMILES: COc1ccc2nc(-c3cccnc3)nc(Nc3cc(-c4ccc(Cl)cc4C)n[nH]3)c2c1] | 2 HCl |
| 375 | 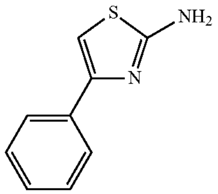 [SMILES: Nc1nc(-c2ccccc2)cs1] | 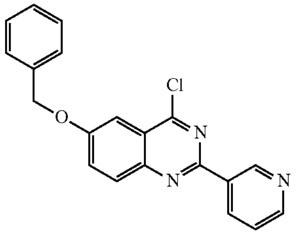 [SMILES: Clc1nc(-c2cccnc2)nc2ccc(OCc3ccccc3)cc12] | 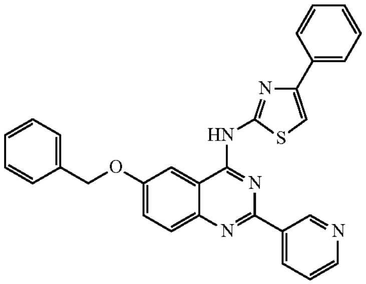 [SMILES: c1ccc(COc2ccc3nc(-c4cccnc4)nc(Nc4nc(-c5ccccc5)cs4)c3c2)cc1] | 2 HCl |

TABLE 1-continued
| | | | | |
|---|---|---|---|---|
| 376 | 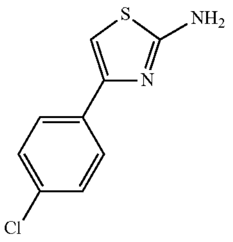 [SMILES: Nc1nc(-c2ccc(Cl)cc2)cs1] | 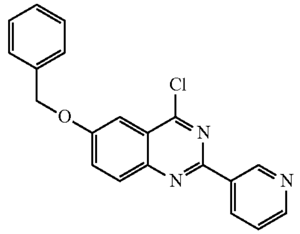 [SMILES: Clc1nc(-c2cccnc2)nc2ccc(OCc3ccccc3)cc12] | 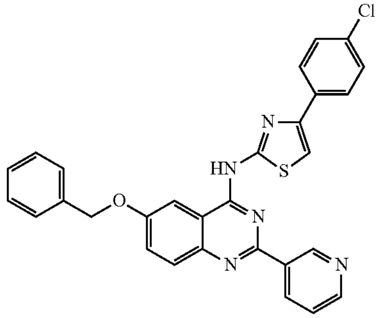 [SMILES: Clc1ccc(-c2csc(Nc3nc(-c4cccnc4)nc4ccc(OCc5ccccc5)cc34)n2)cc1] | 2 HCl |
| 377 | 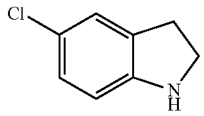 | 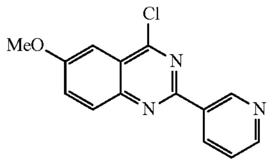 [SMILES: COc1ccc2nc(-c3cccnc3)nc(Cl)c2c1] | 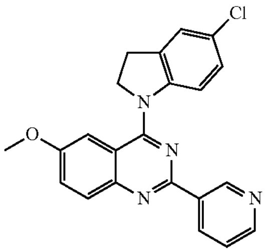 [SMILES: COc1ccc2nc(-c3cccnc3)nc(N3CCc4cc(Cl)ccc43)c2c1] | 2 HCl |
| 378 | 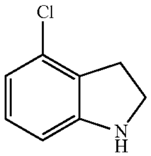 | 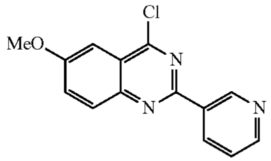 [SMILES: COc1ccc2nc(-c3cccnc3)nc(Cl)c2c1] | 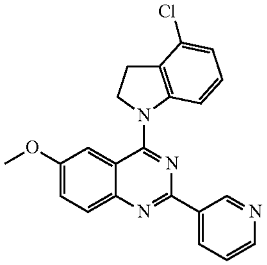 [SMILES: COc1ccc2nc(-c3cccnc3)nc(N3CCc4c(Cl)cccc43)c2c1] | 2 HCl |
| 379 | 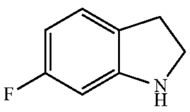 | 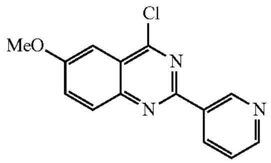 [SMILES: COc1ccc2nc(-c3cccnc3)nc(Cl)c2c1] | 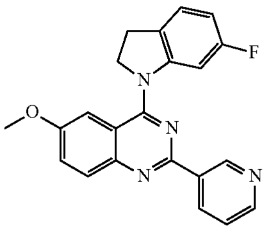 [SMILES: COc1ccc2nc(-c3cccnc3)nc(N3CCc4ccc(F)cc43)c2c1] | 2 HCl |

TABLE 1-continued
| | | | | |
|---|---|---|---|---|
| 380 | 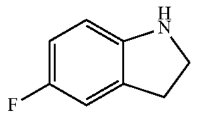 | 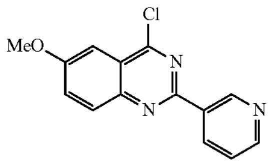 [SMILES: COc1ccc2nc(-c3cccnc3)nc(Cl)c2c1] | 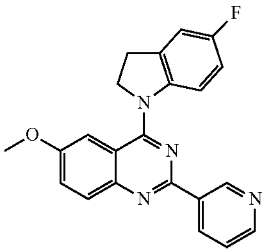 [SMILES: COc1ccc2nc(-c3cccnc3)nc(N3CCc4cc(F)ccc43)c2c1] | 2 HCl |
| 381 | 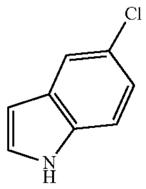 | 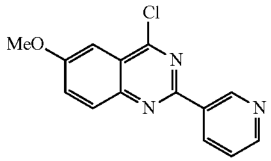 [SMILES: COc1ccc2nc(-c3cccnc3)nc(Cl)c2c1] | 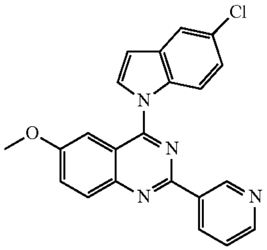 [SMILES: COc1ccc2nc(-c3cccnc3)nc(-n3ccc4cc(Cl)ccc43)c2c1] | HCl |
| 382 | 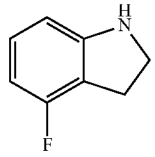 | 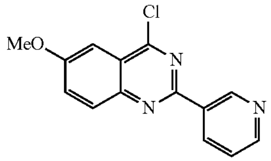 [SMILES: COc1ccc2nc(-c3cccnc3)nc(Cl)c2c1] | 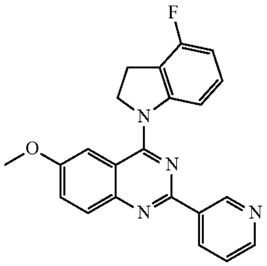 [SMILES: COc1ccc2nc(-c3cccnc3)nc(N3CCc4c(F)cccc43)c2c1] | HCl |
| 383 | 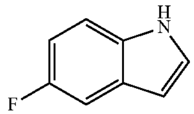 | 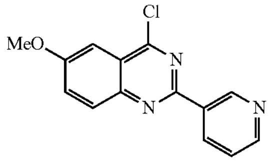 [SMILES: COc1ccc2nc(-c3cccnc3)nc(Cl)c2c1] | 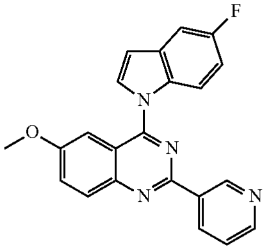 [SMILES: COc1ccc2nc(-c3cccnc3)nc(-n3ccc4cc(F)ccc43)c2c1] | 2 HCl |

TABLE 1-continued
| | | | | |
|---|---|---|---|---|
| 384 | 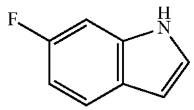 | 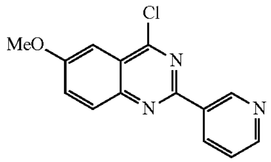 [SMILES: COc1ccc2nc(-c3cccnc3)nc(Cl)c2c1] | 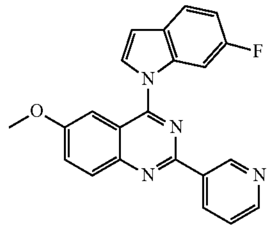 [SMILES: COc1ccc2nc(-c3cccnc3)nc(-n3ccc4ccc(F)cc43)c2c1] | 2 HCl |
| 385 | 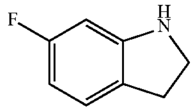 | 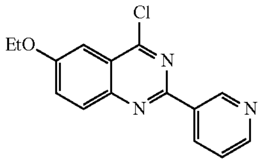 [SMILES: CCOc1ccc2nc(-c3cccnc3)nc(Cl)c2c1] | 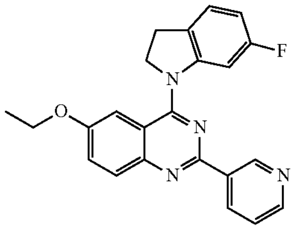 [SMILES: CCOc1ccc2nc(-c3cccnc3)nc(N3CCc4ccc(F)cc43)c2c1] | 2 HCl |
| 386 | 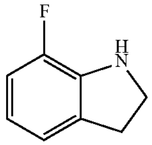 | 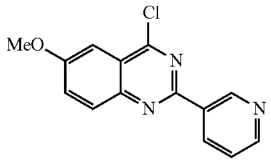 [SMILES: COc1ccc2nc(-c3cccnc3)nc(Cl)c2c1] | 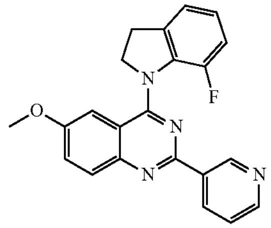 [SMILES: COc1ccc2nc(-c3cccnc3)nc(N3CCc4cccc(F)c43)c2c1] | 2 HCl |
| 387 | 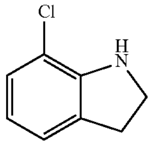 | 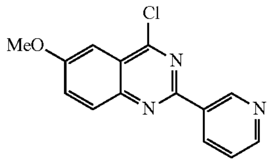 [SMILES: COc1ccc2nc(-c3cccnc3)nc(Cl)c2c1] | 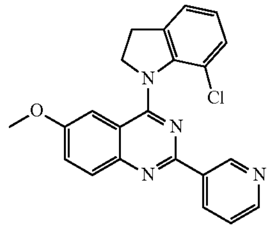 [SMILES: COc1ccc2nc(-c3cccnc3)nc(N3CCc4cccc(Cl)c43)c2c1] | 2 HCl |

TABLE 1-continued
| | | | | |
|---|---|---|---|---|
| 388 | 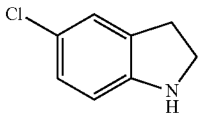 | 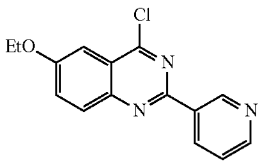 [SMILES: CCOc1ccc2nc(-c3cccnc3)nc(Cl)c2c1] | 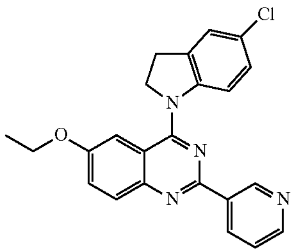 [SMILES: CCOc1ccc2nc(-c3cccnc3)nc(N3CCc4cc(Cl)ccc43)c2c1] | 2 HCl |
| 389 | 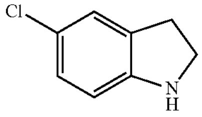 | 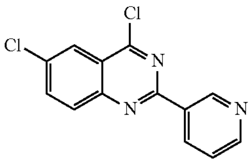 [SMILES: Clc1ccc2nc(-c3cccnc3)nc(Cl)c2c1] | 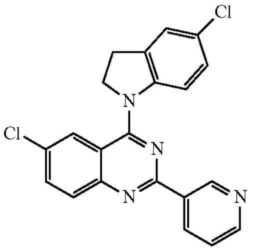 [SMILES: Clc1ccc2c(c1)CCN2c1nc(-c2cccnc2)nc2ccc(Cl)cc12] | 2 HCl |
| 390 | 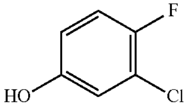 | 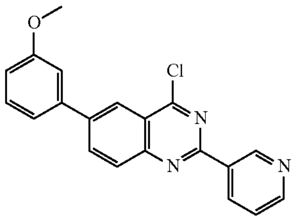 [SMILES: COc1cccc(-c2ccc3nc(-c4cccnc4)nc(Cl)c3c2)c1] | 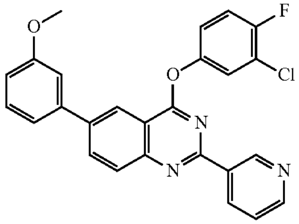 | HCl |
| 391 | 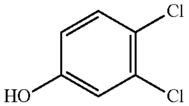 | 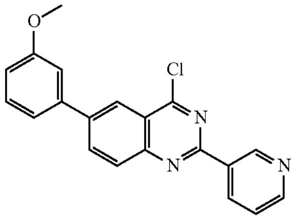 [SMILES: COc1cccc(-c2ccc3nc(-c4cccnc4)nc(Cl)c3c2)c1] | 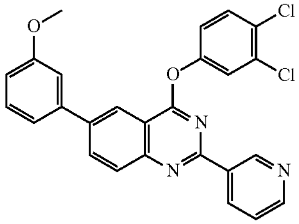 [SMILES: COc1cccc(-c2ccc3nc(-c4cccnc4)nc(Oc4ccc(Cl)c(Cl)c4)c3c2)c1] | HCl |

TABLE 1-continued
| | | | | |
|---|---|---|---|---|
| 392 | 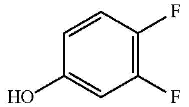 | 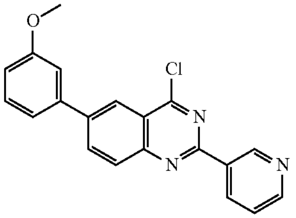 [SMILES: COc1cccc(-c2ccc3nc(-c4cccnc4)nc(Cl)c3c2)c1] | 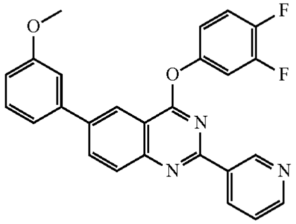 [SMILES: COc1cccc(-c2ccc3nc(-c4cccnc4)nc(Oc4ccc(F)c(F)c4)c3c2)c1] | HCl |
| 393 | 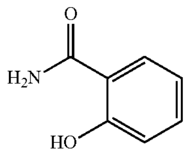 | 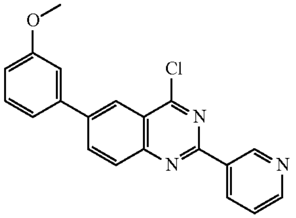 [SMILES: COc1cccc(-c2ccc3nc(-c4cccnc4)nc(Cl)c3c2)c1] | 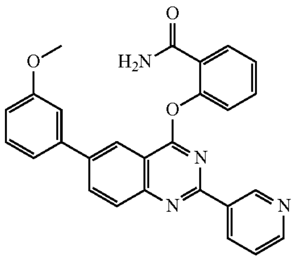 [SMILES: COc1cccc(-c2ccc3nc(-c4cccnc4)nc(Oc4ccccc4C(N)=O)c3c2)c1] | HCl |
| 394 | 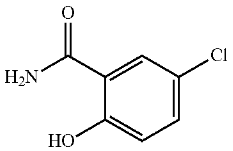 [SMILES: NC(=O)c1cc(Cl)ccc1O] | 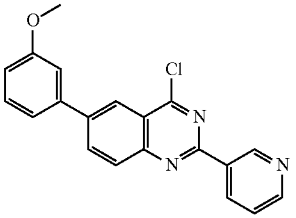 [SMILES: COc1cccc(-c2ccc3nc(-c4cccnc4)nc(Cl)c3c2)c1] | 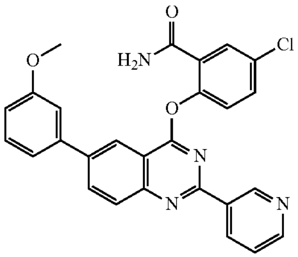 [SMILES: COc1cccc(-c2ccc3nc(-c4cccnc4)nc(Oc4ccc(Cl)cc4C(N)=O)c3c2)c1] | HCl |
| 395 | 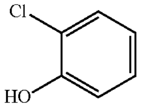 | 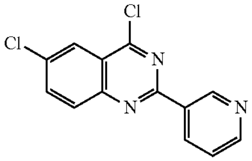 [SMILES: Clc1ccc2nc(-c3cccnc3)nc(Cl)c2c1] | 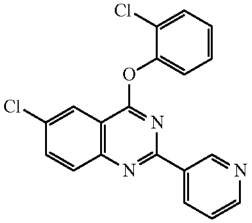 [SMILES: Clc1ccc2nc(-c3cccnc3)nc(Oc3ccccc3Cl)c2c1] | HCl |

TABLE 1-continued
| | | | | |
|---|---|---|---|---|
| 396 | 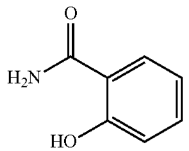 | 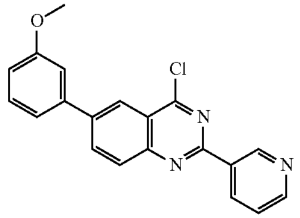 [SMILES: COc1cccc(-c2ccc3nc(-c4cccnc4)nc(Cl)c3c2)c1] | 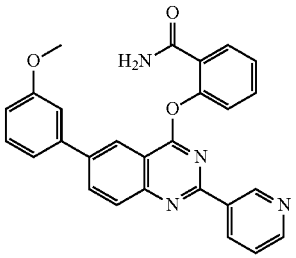 [SMILES: COc1cccc(-c2ccc3nc(-c4cccnc4)nc(Oc4ccccc4C(N)=O)c3c2)c1] | HCl |
| 397 | 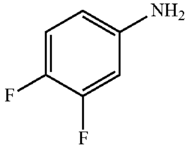 | 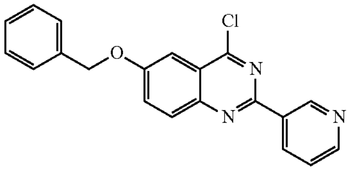 [SMILES: Clc1nc(-c2cccnc2)nc2ccc(OCc3ccccc3)cc12] | 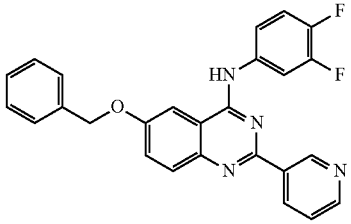 [SMILES: Fc1ccc(Nc2nc(-c3cccnc3)nc3ccc(OCc4ccccc4)cc23)cc1F] | HCl |
| 398 | 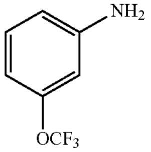 | 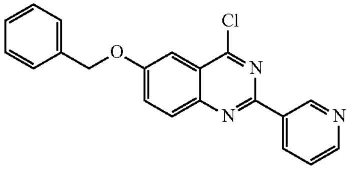 [SMILES: Clc1nc(-c2cccnc2)nc2ccc(OCc3ccccc3)cc12] | 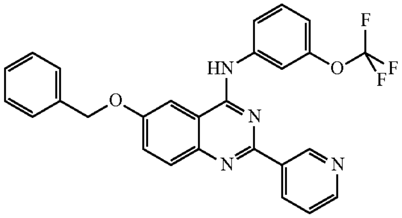 [SMILES: FC(F)(F)Oc1cccc(Nc2nc(-c3cccnc3)nc3ccc(OCc4ccccc4)cc23)c1] | |
| 399 | 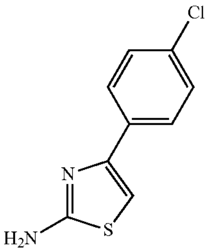 [SMILES: Nc1nc(-c2ccc(Cl)cc2)cs1] | 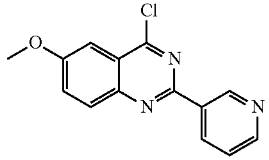 [SMILES: COc1ccc2nc(-c3cccnc3)nc(Cl)c2c1] | 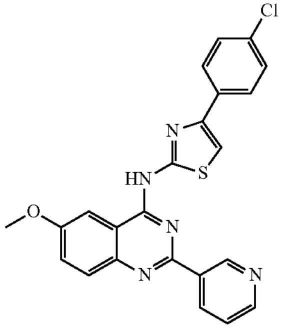 [SMILES: COc1ccc2nc(-c3cccnc3)nc(Nc3nc(-c4ccc(Cl)cc4)cs3)c2c1] | |

TABLE 1-continued
| | | | | |
|---|---|---|---|---|
| 400 | 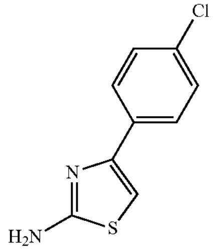 [SMILES: Nc1nc(-c2ccc(Cl)cc2)cs1] | 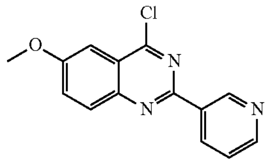 [SMILES: COc1ccc2nc(-c3cccnc3)nc(Cl)c2c1] | 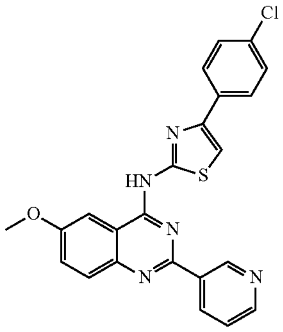 [SMILES: COc1ccc2nc(-c3cccnc3)nc(Nc3nc(-c4ccc(Cl)cc4)cs3)c2c1] | 2 HCl |
| 401 | 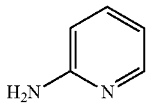 | 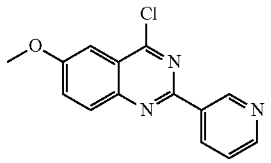 [SMILES: COc1ccc2nc(-c3cccnc3)nc(Cl)c2c1] | 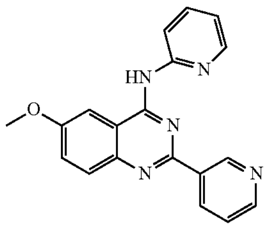 [SMILES: COc1ccc2nc(-c3cccnc3)nc(Nc3ccccn3)c2c1] | 2 HCl |
| 402 | 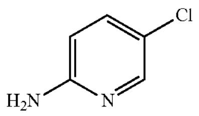 | 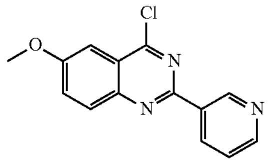 [SMILES: COc1ccc2nc(-c3cccnc3)nc(Cl)c2c1] | 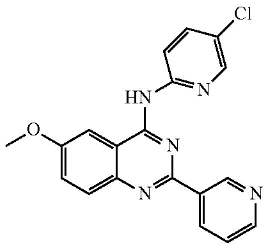 [SMILES: COc1ccc2nc(-c3cccnc3)nc(Nc3ccc(Cl)cn3)c2c1] | 2 HCl |

TABLE 1-continued
| | | | | |
|---|---|---|---|---|
| 403 | 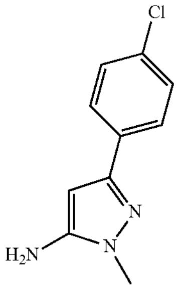 | 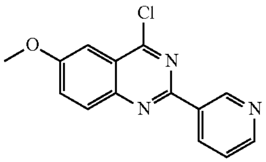 [SMILES: COc1ccc2nc(-c3cccnc3)nc(Cl)c2c1] | 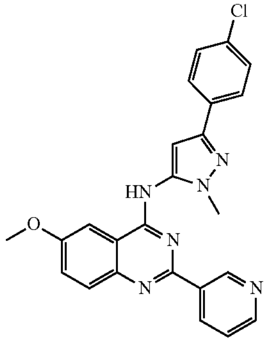 [SMILES: COc1ccc2nc(-c3cccnc3)nc(Nc3cc(-c4ccc(Cl)cc4)nn3C)c2c1] | 2 HCl |
| 404 | 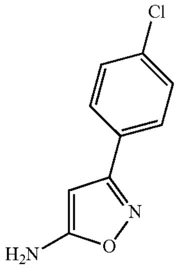 [SMILES: Nc1cc(-c2ccc(Cl)cc2)no1] | 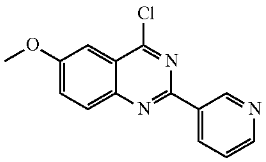 [SMILES: COc1ccc2nc(-c3cccnc3)nc(Cl)c2c1] | 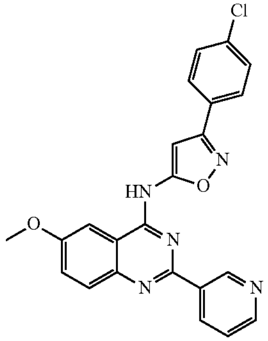 [SMILES: COc1ccc2nc(-c3cccnc3)nc(Nc3cc(-c4ccc(Cl)cc4)no3)c2c1] | HCl |
| 405 | 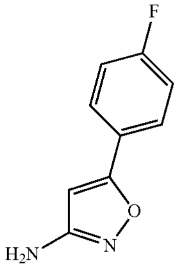 [SMILES: Nc1cc(-c2ccc(F)cc2)on1] | 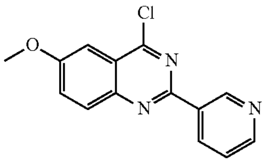 [SMILES: COc1ccc2nc(-c3cccnc3)nc(Cl)c2c1] | 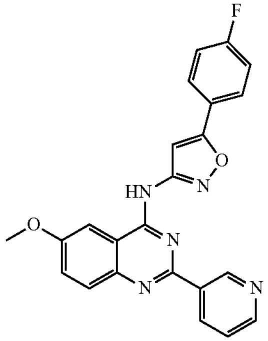 [SMILES: COc1ccc2nc(-c3cccnc3)nc(Nc3cc(-c4ccc(F)cc4)on3)c2c1] | HCl |

TABLE 1-continued
| | | | | |
|---|---|---|---|---|
| 406 | 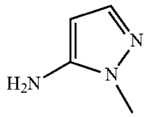 | 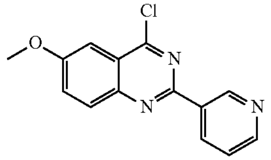 [SMILES: COc1ccc2nc(-c3cccnc3)nc(Cl)c2c1] | 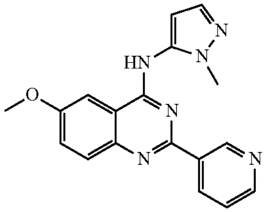 [SMILES: COc1ccc2nc(-c3cccnc3)nc(Nc3ccnn3C)c2c1] | HCl |
| 407 | 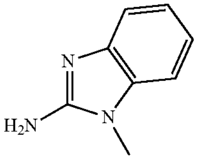 | 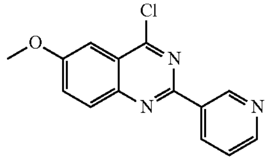 [SMILES: COc1ccc2nc(-c3cccnc3)nc(Cl)c2c1] | 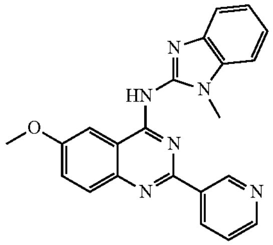 [SMILES: COc1ccc2nc(-c3cccnc3)nc(Nc3nc4ccccc4n3C)c2c1] | 2 HCl |
| 408 | 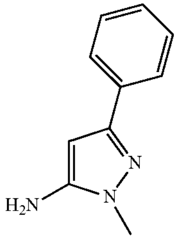 | 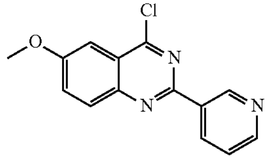 [SMILES: COc1ccc2nc(-c3cccnc3)nc(Cl)c2c1] | 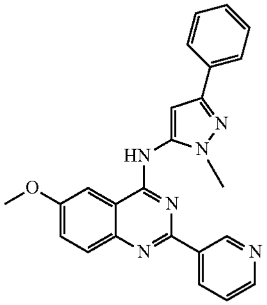 [SMILES: COc1ccc2nc(-c3cccnc3)nc(Nc3cc(-c4ccccc4)nn3C)c2c1] | HCl |
| 409 | 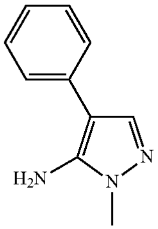 | 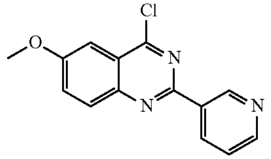 [SMILES: COc1ccc2nc(-c3cccnc3)nc(Cl)c2c1] | 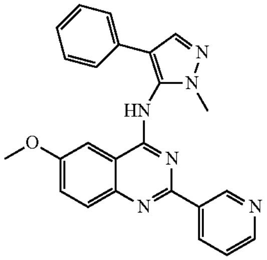 [SMILES: COc1ccc2nc(-c3cccnc3)nc(Nc3c(-c4ccccc4)cnn3C)c2c1] | HCl |

TABLE 1-continued
| | | | | |
|---|---|---|---|---|
| 410 | 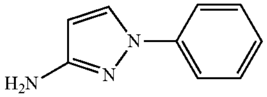 [SMILES: Nc1ccn(-c2ccccc2)n1] | 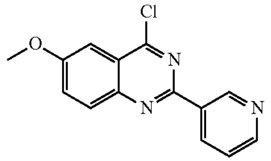 [SMILES: COc1ccc2nc(-c3cccnc3)nc(Cl)c2c1] | 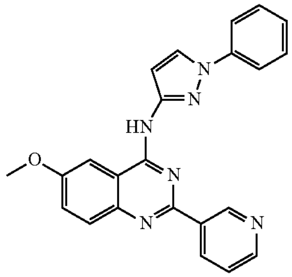 [SMILES: COc1ccc2nc(-c3cccnc3)nc(Nc3ccn(-c4ccccc4)n3)c2c1] | HCl |
| 411 | 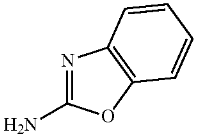 | 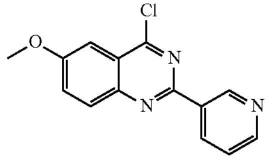 [SMILES: COc1ccc2nc(-c3cccnc3)nc(Cl)c2c1] | 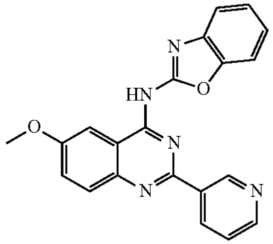 [SMILES: COc1ccc2nc(-c3cccnc3)nc(Nc3nc4ccccc4o3)c2c1] | |
| 412 | 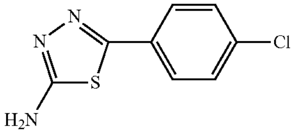 | 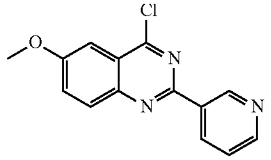 [SMILES: COc1ccc2nc(-c3cccnc3)nc(Cl)c2c1] | 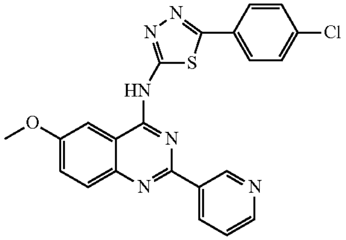 [SMILES: COc1ccc2nc(-c3cccnc3)nc(Nc3nnc(-c4ccc(Cl)cc4)s3)c2c1] | HCl |

TABLE 1-continued

| | | | |
|---|---|---|---|
| 413 | 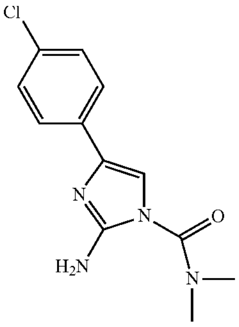 [SMILES: CN(C)C(=O)n1cc(-c2ccc(Cl)cc2)nc1N] | 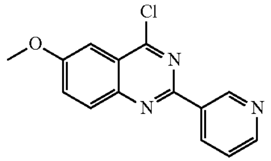 [SMILES: COc1ccc2nc(-c3cccnc3)nc(Cl)c2c1] | 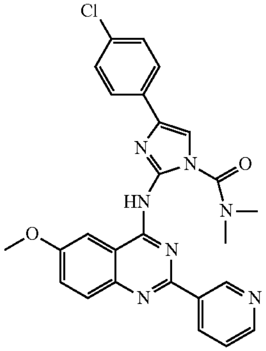 |

| Number | $^1$H NMR | $^1$H NMR Solvent | Purity percent | Method of Coupling |
|---|---|---|---|---|
| 295 | $^1$H NMR (400 MHz, DMSO) δ 13.12 (s, 1H), 9.90 (s, 1H), 9.47 (d, J = 1.4 Hz, 1H), 8.70-8.54 (m, 2H), 8.20-8.15 (m, 1H), 8.14 (s, 1H), 8.01 (d, J = 2.6 Hz, 1H), 7.88-7.75 (m, 2H), 7.65 (d, J = 8.9 Hz, 1H), 7.59-7.44 (m, 2H), 3.98 (s, 3H). | DMSO | >98 | G1 |
| 296 | $^1$H NMR (400 MHz, DMSO) δ 10.04 (s, 1H), 9.54-9.47 (m, 1H), 9.36 (s, 1H), 8.72 (d, J = 2.0 Hz, 1H), 8.69-8.59 (m, 2H), 8.19 (d, J = 8.8 Hz, 1H), 8.08-7.97 (m, 2H), 7.86 (d, J = 9.1 Hz, 1H), 7.61-7.47 (m, 2H), 3.99 (s, 3H). | DMSO | >98 | G1 |
| 297 | $^1$H NMR (400 MHz, DMSO) δ 9.64 (s, 1H), 9.55-9.45 (m, 1H), 8.72 - 8.60 (m, 2H), 7.95 (d, J = 2.7 Hz, 1H), 7.82 (d, J= 9.1 Hz, 1H), 7.58-7.48 (m, 3H), 7.34 (dd, J = 8.7, 2.5 Hz, 1H), 6.96 (d, J = 8.7 Hz, 1H), 4.39-4.23 (m, 4H), 3.97 (s, 3H). | DMSO | >98 | G1 |
| 298 | $^1$H NMR (400 MHz, DMSO) δ 11.21 (s, 1H), 9.79 (s, 1H), 9.53 (d, J = 1.4 Hz, 1H), 8.75-8.58 (m, 2H), 8.07 (s, 1H), 8.03 (d, J = 2.7 Hz, 1H), 7.82 (d, J = 9.1 Hz, 1H), 7.61 (d, J = 8.5 Hz, 1H), 7.56-7.47 (m, 2H), 7.43 (dd, J = 8.5, 1.8 Hz, 1H), 7.39-7.34 (m, 1H), 6.50-6.41 (m, 1H), 3.99 (s, 3H). | DMSO | >98 | G1 |
| 299 | $^1$H NMR (400 MHz, DMSO) δ 9.54 (s, 1H), 9.42-9.34 (m, 1H), 8.61 (dd, J = 4.7, 1.7 Hz, 1H), 8.57-8.47 (m, 1H), 7.93 (d, J = 2.7 Hz, 1H), 7.81 (d, J = 9.1 Hz, 1H), 7.56-7.44 (m, 2H), 7.19 (dd, J = 7.9, 1.5 Hz, 1H), 7.00-6.91 (m, 1H), 6.88 (dd, J = 8.2, 1.6 Hz, 1H), 4.34-4.17 (m, 4H), 3.95 (s, 3H). | DMSO | >98 | G1 |
| 300 | $^1$H NMR (400 MHz, DMSO) δ 10.76 (s, 1H), 10.01 (s, 1H), 9.17-9.06 (m, 1H), 8.53 (dd, J = 4.7, 1.7 Hz, 1H), 8.36-8.27 (m, 1H), 8.05 (d, J = 2.7 Hz, 1H), 7.84 (d, J = 9.1 Hz, 1H), 7.60-7.48 (m, 2H), 7.36 (ddd, J = 8.0, 4.8, 0.8 Hz, 1H), 7.32-7.28 (m, 1H), 7.25 (d, J = 6.8 Hz, 1H), 7.16-7.04 (m, 1H), 6.54 (dd, J = 3.0, 1.9 Hz, 1H), 3.98 (s, 3H). | DMSO | >98 | G1 |
| 301 | $^1$H NMR (400 MHz, DMSO) δ 10.02 (s, 1H), 9.48 (d, J = 1.5 Hz, 1H), 9.33 (d, J = 1.0 Hz, 1H), 8.69-8.59 (m, 2H), 8.37 (d, J = 1.7 Hz, 1H), 8.10 (dd, J = 9.0, 2.1 Hz, 1H), 8.00 (d, J = 2.7 Hz, 1H), 7.90 (d, J = 9.0 Hz, 1H), 7.86 (d, J = 9.1 Hz, 1H), 7.57 (dd, J = 9.1, 2.7 Hz, 1H), 7.54-7.47 (m, 1H), 3.99 (s, 3H). | DMSO | >98 | G1 |

TABLE 1-continued

| | | | | |
|---|---|---|---|---|
| 302 | $^1$H NMR (400 MHz, DMSO) δ 10.52 (s, 1H), 9.18 (dd, J = 2.2. 0.8 Hz, 1H), 8.60 (dd, J = 4.7, 1.7 Hz, 1H), 8.45-8.36 (m, 1H), 8.03 (d, J = 2.7 Hz, 1H), 7.97-7.90 (m, 2H), 7.88 (d, J = 7.0 Hz, 1H), 7.77 (dd, J = 9.0, 7.1 Hz, 1H), 7.61 (dd, J = 9.1, 2.7 Hz, 1H), 7.44 (ddd, J = 8.0, 4.8, 0.8 Hz, 1H), 4.01 (s, 3H). | DMSO | >98 | G1 |
| 303 | $^1$H NMR (400 MHz, DMSO) δ 9.86 (s, 1H), 9.60-9.56 (rn, 1H), 8.72-8.67 (m, 1H), 8.65 (dd, J = 4.8, 1.7 Hz, 1H), 8.26-8.21 (m, 1H), 8.05 (d, J = 2.7 Hz, 1H), 7.83 (d, J = 9.1 Hz, 1H), 7.62 (d, J = 8.4 Hz, 1H), 7.56-7.50 (m, 2H), 7.46 (dd, J = 8.5, 1.8 Hz, 1H), 7.35 (d, J = 3.1 Hz, 1H), 6.46 (dd, J = 3.1, 0.8 Hz, 1H), 3.99 (s, 3H), 3.86 (s, 3H). | DMSO | >98 | G1 |
| 304 | $^1$H NMR (400 MHz, DMSO) δ.96 (s, 1H), 9.51-9.45 (m, 1H), 8.68-8.59 (m, 2H), 8.57-8.52 (m, 1H), 8.02-7.88 (m, 3H), 7.87-7.80 (m, 1H), 7.58-7.46 (m, 2H), 3.98 (s, 3H), 2.83 (s, 3H). | DMSO | >98 | G1 |
| 305 | $^1$H NMR (400 MHz, DMSO) δ 9.94 (s, 1H), 9.51-9.43 (rn, 1H), 8.68-8.58 (m, 2H), 8.39 (d, J = 2.0 Hz, 1H), 7.99 (d, J = 2.7 Hz, 1H), 7.87-7.80 (m, 2H), 7.78 (d, J = 8.6 Hz, 1H), 7.54 (dd, J = 9.1, 2.7 Hz, 1H), 7.51 (ddd, J = 8.0, 4.8, 0.8 Hz, 1H), 4.19 (s, 3H), 3.98 (s, 3H). | DMSO | >98 | G1 |
| 306 | $^1$H NMR (400 MHz, DMSO) δ 9.72 (s, 1H), 9.52-9.47 (m, 1H), 8.67-8.60 (m, 2H), 7.98 (d, J = 2.7 Hz, 1H), 7.82 (d, J = 9.1 Hz, 1H), 7.78-7.74 (rn, 1H), 7.68-7.62 (m, 1H), 7.55-7.48 (m, 2H), 7.32 (d, J = 8.1 Hz, 1H), 3.97 (s, 3H), 2.99-2.88 (m, 4H), 2.15-2.04 (m, 2H). | DMSO | >98 | G1 |
| 307 | $^1$H NMR (400 MHz, $CDCl_3$) δ 9.74 (s, 1H), 9.37-9.31 (m, 1H), 8.60 (dd, J = 4.7, 1.7 Hz, 1H), 8.53-8.46 (m, 1H), 7.95 (d, J = 2.7 Hz, 1H), 7.82 (d, J = 9.1 Hz, 1H), 7.52 (dd, J = 9.1, 2.7 Hz, 1H), 7.47 (ddd, J = 8.0, 4.8, 0.8 Hz, 1H), 7.34 (d, J = 7.0 Hz, 1H), 7.31-7.24 (m, 1H), 7.22 (d, J = 7.1 Hz, 1H), 3.96 (s, 3H), 2.99 (t, J = 7.3 Hz, 2H), 2.82 (t, J = 7.4 Hz, 2H), 2.06-1.96 (m, 2H). | DMSO | >98 | G1 |
| 308 | $^1$H NMR (400 MHz, DMSO) δ 10.45 (s, 1H), 9.50-9.44 (m, 1H), 8.94-8.87 (m, 1H), 8.83 (dd, J = 5.1, 1.5 Hz, 1H), 8.54 (d, J = 2.0 Hz, 1H), 8.13 (d, J = 2.4 Hz, 1H), 8.02 (d, J = 8.7 Hz, 1H), 7.97-7.89 (m, 2H), 7.83 (dd, J = 8.0, 5.2 Hz, 1H), 7.63 (dd, J = 9.1, 2.7 Hz, 1H), 4.01 (s, 3H), 2.83 (s, 3H). | DMSO | >98 | G1 |
| 309 | $^1$H NMR (400 MHz, DMSO) δ 10.64 (s, 1H), 9.47 (d, J = 1.5 Hz, 1H), 8.94 (d, J = 8.1 Hz, 1H), 8.86 (dd, J = 5.2, 1.5 Hz, 1H), 8.54-8.48 (m, 1H), 8.23-8.16 (m, 1H), 8.04-7.94 (m, 2H), 7.92-7.83 (m, 2H), 7.78 (d, J = 5.4 Hz, 1H), 7.65 (dd, J = 9.1, 2.6 Hz, 1H), 7.51 (dd, J = 5.4, 0.7 Hz, 1H), 4.02 (s, 3H). | DMSO | >98 | G1 |
| 310 | $^1$H NMR (400 MHz, DMSO) δ 10.86 (s, 1H), 9.43 (d, J = 1.6 Hz, 1H), 8.94 (d, J = 7.5 Hz, 1H), 8.89 (dd, J = 5.2, 1.5 Hz, 1H), 8.30-8.20 (m, 1H), 8.13-7.99 (m, 3H), 7.94-7.84 (m, 1H), 7.74 (d, J = 1.3 Hz, 2H), 7.67 (dd, J = 9.1, 2.5 Hz, 1H), 7.08 (d, J = 2.2 Hz, 1H), 4.02 (s, 3H). | DMSO | >98 | G1 |
| 311 | $^1$H NMR (400 MHz, DMSO) δ 10.53 (s, 1H), 9.48 (d, J = 1.5 Hz, 1H), 8.93 (d, J = 7.7 Hz, 1H), 8.85 (dd, J = 5.2, 1.5 Hz, 1H), 8.44 (d, J = 1.9 Hz, 1H), 8.20-8.15 (m, 1H), 8.13 (d, J = 8.7 Hz, 1H), 7.97 (d, J = 8.1 Hz, 1H), 7.92 (dd, J = 8.7, 2.0 Hz, 1H), 7.86 (dd, J = 7.8, 5.1 Hz, 1H), 7.64 (dd, J = 9.1, 2.6 Hz, 1H), 4.02 (s, 3H), 2.85 (s, 3H). | DMSO | >98 | G1 |
| 312 | $^1$H NMR (400 MHz, DMSO) δ 10.85 (s, 1H), 9.54 (d, J = 1.5 Hz, 1H), 9.47 (s, 1H), 9.32 (s, 1H), 9.03 (d, J = 8.0 Hz, 1H), 8.93-8.87 (m, 1H), 8.86-8.78 (m, 2H), 8.44 (dd, J = 8.8, 1.9 Hz, 1H), 8.14 (d, J = 2.1 Hz, 1H), 8.10 (d, J = 8.7 Hz, 1H), 7.99-7.89 (rn, 2H), 7.78-7.71 (m, 1H), 7.55 (d, J = 8.7 Hz, 1H). | DMSO | >98 | G1 |
| 313 | $^1$H NMR (400 MHz, DMSO) δ 11.07 (s, 1H), 9.54 (d, J = 1.6 Hz, 1H), 9.51 (d, J = 2.0 Hz, 1H), 9.46-9.39 (rn, 1H), 9.10-9.01 (m, 1H), 8.97-8.88 (m, 2H), 8.86 (dd, J = 5.3, 1.3 Hz, 1H), 8.63-8.55 (m, 1H), 8.48 (dd, J = 8.8, 1.9 Hz, 1H), 8.15 (d, J = 8.7 Hz, 1H), 8.04-7.90 (m, 4H), 7.79 (d, J = 5.4 Hz, 1H), 7.52 (dd, J = 5.4, 0.7 Hz, 1H). | DMSO | >98 | G1 |

TABLE 1-continued

| | | | | |
|---|---|---|---|---|
| 314 | $^1$H NMR (400 MHz, DMSO) δ 10.49 (s, 1H), 9.48 (d, J = 1.5 Hz, 1H), 8.93 (d, J = 7.9 Hz, 1H), 8.85 (dd, J = 5.2, 1.5 Hz, 1H), 8.24 (s, 1H), 8.16 (d, J = 2.5 Hz, 1H), 8.05 (d, J = 2.2 Hz, 1H), 7.96 (d, J = 9.1 Hz, 1H), 7.87 (dd, J = 8.1, 5.3 Hz, 1H), 7.77 (d, J = 8.4 Hz, 1H), 7.72 (dd, J = 8.4, 1.8 Hz, 1H), 7.64 (dd, J = 9.1, 2.6 Hz, 1H), 7.03 (dd, J = 2.2, 1.0 Hz, 1H), 4.02 (s, 3H). | DMSO | >98 | G1 |
| 315 | $^1$H NMR (400 MHz, DMSO) δ 10.72 (s, 1H), 9.46 (d, J = 1.5 Hz, 1H), 8.96 (d, J = 8.2 Hz, 1H), 8.87 (dd, J = 5.2, 1.5 Hz, 1H), 8.50 (d, J = 1.8 Hz, 1H), 8.21 (d, J = 2.4 Hz, 1H), 8.06-7.96 (rn, 2H), 7.93-7.84 (m, 2H), 7.78 (d, J = 5.4 Hz, 1H), 7.63 (dd, J = 9.1, 2.6 Hz, 1H), 7.51 (dd, J = 5.4, 0.7 Hz, 1H), 4.29 (q, J = 7.0 Hz, 2H), 1.46 (t, J = 7.0 Hz, 3H). | DMSO | >98 | G1 |
| 316 | $^1$H NMR (400 MHz, DMSO) δ 10.04 (s, 1H), 9.60-9.52 (rn, 1H), 8.75-8.63 (m, 2H), 8.16 (d, J = 2.0 Hz, 1H), 8.04-7.95 (m, 2H), 7.93-7.83 (m, 2H), 7.63-7.53 (m, 2H), 6.32 (d, J = 1.2 Hz, 1H), 4.01 (s, 3H), 2.47 (s, 3H). | DMSO | >98 | G1 (0.1 N HCl added) |
| 317 | $^1$H NMR (400 MHz, DMSO) δ 11.82 (s, 1H), 10.06 (s, 1H), 9.53-9.46 (m, 1H), 8.81-8.70 (m, 2H), 8.04 (d, J = 2.6 Hz, 1H), 7.88 (d, J = 9.1 Hz, 1H), 7.81 (d, J = 2.1 Hz, 1H), 7.67 (dd, J = 7.9, 5.0 Hz, 1H), 7.57 (dd, J = 9.1, 2.7 Hz, 1H), 7.53 (dd, J = 8.7, 2.1 Hz, 1H), 7,39 (d, J = 8.6 Hz, 1H), 4.00 (s, 3H). | DMSO | >98 | G1 (0.1 N HCl added) |
| 318 | $^1$H NMR (400 MHz, DMSO) δ 9.89 (s, 1H), 9.57-9.48 (m, 1H), 8.72-8.58 (m, 2H), 8.01 (d, J = 2.1 Hz, 1H), 7.99 (d, J = 2.7 Hz, 1H), 7.85 (d, J = 9.1 Hz, 1H), 7.59-7.49 (m, 3H), 7.43 (d, J = 8.6 Hz, 1H), 3.98 (s, 3H), 3.41 (s, 3H). | DMSO | >98 | G1 (0.1 N HCl added) |
| 319 | $^1$H NMR (400 MHz, DMSO) δ 9.88 (s 1H), 9.52-9.44 (m, 1H), 8.71-8.59 (m, 2H), 8.02-7.91 (m, 2H), 7.83 (d, J = 9.1 Hz, 1H), 7.66 (dd, J = 8.4, 2.0 Hz, 1H), 7.58-7.48 (m, 2H), 7.36 (d, J = 8.4 Hz, 1H), 3.98 (s, 3H), 3.40 (s, 3H). | DMSO | >98 | G1 (0.1 N HCl added) |
| 320 | $^1$H NMR (400 MHz, DMSO) δ 10.01 (s, 1H), 9.58-9.51 (m, 1H), 9.45 (s, 1H), 8.75 (d, J = 1.9 Hz, 1H), 8.71-8.63 (m, 2H), 8.25 (d, J = 8.7 Hz, 1H), 8.08-8.00 (m, 2H), 7.86 (d, J = 9.1 Hz, 1H), 7.61-7.50 (m, 2H), 4.00 (s, 3H). | DMSO | >98 | G1 (0.1 N HCl added) |
| 321 | $^1$H NMR (400 MHz, DMSO) δ 10.43 (s, 1H), 9.72 (s, 1H), 9.51-9.45 (m, 1H), 8.67-8.57 (m, 2H), 7.96 (d, J = 2.7 Hz, 1H), 7.81 (d, J = 9.1 Hz, 1H), 7.73-7.68 (m, 1H), 7.64 (dd, J = 8.3, 2.1 Hz, 1H), 7.56-7.48 (m, 2H), 6.93 (d, J = 8.3 Hz, 1H), 3.97 (s, 3H), 3.58 (s, 2H). | DMSO | >98 | G1 (0.1 N HCl added) |
| 322 | $^1$H NMR (400 MHz, DMSO) δ 9.95 (s, 1H), 9.54-9.45 (m, 1H), 8.67 (dd, J = 4.7, 1.7 Hz, 1H), 8.66-8.60 (m, 1H), 8.15 (d, J = 2.4 Hz, 1H), 7.94 (d, J = 2.6 Hz, 1H), 7.89-7.83 (m, 2H), 7.63-7.52 (rn, 3H), 3.98 (s, 3H). | DMSO | >98 | G1 (0.1 N HCl added) |
| 323 | $^1$H NMR (400 MHz, DMSO) δ 10.99 (s, 1H), 9.75 (s, 1H), 9.55-9.49 (m, 1H), 8.69- 8.62 (m, 2H), 7.96 (d, J = 2.7 Hz, 1H), 7.83 (d, J = 9.1 Hz, 1H), 7.58-7.49 (m, 3H), 7.35 (dd, J = 8.7, 2.5 Hz, 1H), 7.06 (d, J = 8.6 Hz, 1H), 4.62 (s, 2H), 3.97 (s, 3H). | DMSO | >98 | G1 (0.1 N HCl added) |
| 324 | $^1$H NMR (400 MHz, DMSO) δ 10.24 (s, 1H), 9.58-9.51 (m, 1H), 8.92-8.84 (m, 1H), 8.80 (dd, J = 5.0, 1.5 Hz, 1H), 8.16 (d, J = 2.0 Hz, 1H), 8.07 (d, J = 2.6 Hz, 1H), 7.98 (dd, J = 8.8, 2.1 Hz, 1H), 7.91 (d, J = 9.1 Hz, 1H), 7.83-7.72 (m, 2H), 7.61 (dd, J = 9.1, 2.6 Hz, 1H), 6.37 (s, 1H), 4.75 (d, J = 1.2 Hz, 2H), 4.01 (s, 3H), 3.47 (s, 3H). | DMSO | >98 | G1 (0.1 N HCl added) |
| 325 | $^1$H NMR (400 MHz, DMSO) δ 12.01 (s, 1H), 10.15 (s, 1H), 9.58 (d, J = 1.5 Hz, 1H), 8.94-8.86 (m, 1H), 8.78 (dd, J = 5.0, 1.5 Hz, 1H), 8.07 (d, J = 2.6 Hz, 1H), 8.04-7.98 (m, 1H), 7.91 (dd, J = 9.3, 2.2 Hz, 2H), 7.78-7.69 (m, 2H), 7.66 (dd, J = 8.5, 2.0 Hz, 1H), 7.61 (dd, J = 9.1, 2.7 Hz, 1H), 6.44 (d, J = 9.5 Hz, 1H), 4.01 (s, 3H). | DMSO | >98 | G1 (0.1 N HCl added) |
| 326 | $^1$H NMR (400 MHz, DMSO) δ 12.19 (s, 1H), 10.21 (s, 1H), 9.58-9.51 (rn, 1H), 8.94-8.86 (m, 1H), 8.81 (dd, J = 5.1, 1.6 Hz, 1H), 8.10 (d, J = 2.6 Hz, 1H), 7.96-7.88 (m, 2H), 7.79 (dd, J = 7.9, 5.1 Hz, 1H), 7.68-7.56 (rn, 3H). 4.00 (s, 3H). | DMSO | >98 | G1 (0.1 N HCl added) |

TABLE 1-continued

| | | | | |
|---|---|---|---|---|
| 327 | $^1$H NMR (400 MHz, DMSO) δ 10.43 (s, 1H), 9.57-9.50 (m, 1H), 9.07-8.98 (m, 1H), 8.88 (dd, J = 5.2, 1.4 Hz, 1H), 8.16 (d, J = 2.5 Hz, 1H), 8.06 (d, J = 1.9 Hz, 1H), 8.00-7.89 (m, 2H), 7.75 (d, J = 8.5 Hz, 1H), 7.67 (dd, J = 8.5, 2.0 Hz, 1H), 7.63 (dd, J = 9.1, 2.6 Hz, 1H), 4.02 (s, 3H), 3.47 (s, 3H). | DMSO | >98 | G1 (0.1 N HCl added) |
| 328 | $^1$H NMR (400 MHz, DMSO) δ 10.68 (s, 1H), 10.24 (s, 1H), 9.45 (d, J = 1.6 Hz, 1H), 9.05-8.95 (m, 1H), 8.92 (dd, J = 5.2, 1.5 Hz, 1H), 8.25-8.16 (rn, 1H), 8.09-7.99 (m, 1H), 7.98-7.89 (m, 1H), 7.71-7.60 (m, 3H), 6.98 (d, J = 8.3 Hz, 1H), 4.00 (s, 3H), 2.99 (t, J = 7.5 Hz, 2H), 2.57-2.52 (m, 2H). | DMSO | >98 | G1 (0.1 N HCl added) |
| 329 | $^1$H NMR (400 MHz, DMSO) δ 12.05 (s, 1H), 10.98 (s, 1H), 9.50 (d, J = 1.6 Hz, 1H), 9.32 (s, 1H), 9.03 (d, J = 8.2 Hz, 1H), 8.98 (d, J = 1.7 Hz, 1H), 8.92 (dd, J = 5.3, 1.4 Hz, 1H), 8.53 (d, J = 2.6 Hz, 1H), 8.46 (dd, J = 8.8, 1.8 Hz, 1H), 8.30 (s, 1H), 8.13 (d, J = 2.1 Hz, 1H), 8.09 (d, J = 8.7 Hz, 1H), 7.95 (dd, J = 7.7, 5.3 Hz, 1H), 7.82 (dd, J = 8.6, 2.1 Hz, 1H), 7.26 (d, J = 8.6 Hz, 1H), 4.06 (s, 3H). | DMSO | >98 | G1 (0.1 N HCl added) |
| 330 | $^1$H NMR (400 MHz, DMSO) δ 10.40 (s, 1H), 9.54 (d, J = 1.5 Hz, 1H), 9.05-8.97 (m, 1H), 8.87 (dd, J = 5.2, 1.5 Hz, 1H), 8.15-8.06 (m, 3H), 8.00-7.87 (m, 3H), 7.81 (d, J = 8.5 Hz, 1H), 7.64 (dd, J = 9.1, 2.7 Hz, 1H), 6.43 (d, J = 9.4 Hz, 1H), 4.02 (s, 3H). | DMSO | >98 | G1 (0.1 N HCl added) |
| 331 | $^1$H NMR (400 MHz, DMSO) δ 12.05 (s, 1H), 10.77 (s, 1H), 9.51 (d, J = 1.5 Hz, 1H), 9.43- 9.35 (m, 1H), 9.31-9.21 (m, 1H), 9.04- 8.93 (m, 1H), 8.88 (dd, J = 5.2, 1.5 Hz, 1H), 8.81 (dd, J = 5.1, 1.4 Hz, 1H), 8.73 (d, J = 8.4 Hz, 1H), 8.42 (dd, J = 8.8, 1.8 Hz, 1H), 8.13 (d, J = 2.1 Hz, 1H), 8.09 (d, J = 8.7 Hz, 1H), 7.94-7.83 (m, 2H), 7.80 (dd, J = 8.6, 2.2 Hz, 1H), 7.27 (d, J = 8.6 Hz, 1H). | DMSO | >98 | G1 (0.1 N HCl added) |
| 332 | $^1$H NMR (400 MHz, DMSO) δ 10.57 (s, 1H), 9.55 (d, J = 1.6 Hz, 1H), 9.09-9.01 (rn, 1H), 8.90 (dd, J = 5.3, 1.5 Hz, 1H), 8.65-8.59 (m, 1H), 8.24-8.16 (m, 2H), 8.14 (dd, J = 9.6, 0.8 Hz, 1H), 8.03-7.92 (m, 2H), 7.65 (dd, J = 9.1, 2.7 Hz, 1H), 4.03 (s, 3H). | DMSO | >98 | G1 (0.1 N HCl added) |
| 333 | $^1$H NMR (400 MHz, DMSO) δ 11.81 (s, 1H), 10.31 (s, 1H), 9.58 (d, J = 1.5 Hz, 1H), 9.08 (d, J = 7.9 Hz, 1H), 8.87 (dd, J = 5.2, 1.5 Hz, 1H), 8.13 (d, J = 2.6 Hz, 1H), 8.04 (d, J = 2.0 Hz, 1H), 7.98-7.88 (m, 2H), 7.81 (d, J = 8.8 Hz, 1H), 7.69 (dd, J = 8.8, 2.1 Hz, 1H), 7.63 (dd, J = 9.1, 2.7 Hz, 1H), 6.36 (s, 1H), 4.02 (s, 3H), 2.46 (d, J = 1.1 Hz, 3H). | DMSO | >98 | G1 (0.1 N HCl added) |
| 334 | $^1$H NMR (400 MHz, DMSO) δ 10.51 (s, 1H), 9.53 (d, J = 1.6 Hz, 1H), 9.08-9.02 (m, 1H), 8.90 (dd, J = 5.3, 1.5 Hz, 1H), 8.63-8.59 (m, 1H), 8.22-8.10 (m, 3H), 8.00-7.92 (m, 2H), 7.63 (dd, J = 9.1, 2.6 Hz, 1H), 4.30 (q, J = 7.0 Hz, 2H), 1.46 (t, J = 7.0 Hz, 3H). | DMSO | >98 | G1 (0.1 N HCl added) |
| 335 | $^1$H NMR (400 MHz, DMSO) δ 11.99 (s, 1H), 10.34 (s, 1H), 9.62-9.52 (m, 1H), 9.11 (d, J = 8.2 Hz, 1H), 8.90 (d, J = 4.4 Hz, 1H), 8.13 (d, J = 2.6 Hz, 1H), 8.06 (d, J = 1.8 Hz, 1H), 8.00-7.88 (m, 3H), 7.75 (d, J = 8.6 Hz, 1H), 7.68-7.60 (m, 2H), 6.46 (d, J = 9.5 Hz, 1H), 4.29 (q, J = 7.0 Hz, 2H), 1.46 (t, J = 7.0 Hz, 3H). | DMSO | >98 | G1 (0.1 N HCl added) |
| 336 | $^1$H NMR (400 MHz, DMSO) δ 11.02 (s, 1H), 10.49 (s, 1H), 9.50 (d, J = 1.6 Hz, 1H), 9.02 (d, J = 8.1 Hz, 1H), 8.90 (dd, J = 5.2, 1.5 Hz, 1H), 8.15 (d, J = 2.3 Hz, 1H), 8.00 (d, J = 9.1 Hz, 1H), 7.93 (dd, J = 7.8, 5.4 Hz, 1H), 7.63 (dd, J = 9.1, 2.6 Hz, 1H), 7.54 (d, J = 2.4 Hz, 1H), 7.35 (dd, J = 8.7, 2.5 Hz, 1H), 7.08 (d, J = 8.6 Hz, 1H), 4.64 (s, 2H), 4.28 (q, J = 6.9 Hz, 2H), 1.45 (t, J = 7.0 Hz, 3H). | DMSO | >98 | G1 (0.1 N HCl added) |

TABLE 1-continued

| | | | | |
|---|---|---|---|---|
| 337 | $^1$H NMR (400 MHz, DMSO) δ 10.36 (s, 1H), 10.25 (s, 1H), 9.50 (d, J = 1.6 Hz, 1H), 8.98 (d, J = 8.1 Hz, 1H), 8.86 (dd, J = 5.2, 1.5 Hz, 1H), 8.10 (d, J = 2.4 Hz, 1H), 7.94 (d, J = 9.1 Hz, 1H), 7.87 (dd, J = 7.7, 5.2 Hz, 1H), 7.61 (dd, J = 9.1, 2.6 Hz, 1H), 7.47 (d, J = 1.9 Hz, 1H), 7.36 (dd, J = 8.1, 2.1 Hz, 1H), 7.28 (d, J = 8.1 Hz, 1H), 4.27 (q, J = 7.0 Hz, 2H), 2.93 (t, J = 7.5 Hz, 2H), 2.56-2.52 (m, 2H), 1.45 (t, J = 7.0 Hz, 3H). | DMSO | >98 | G1 (0.1 N HCl added) |
| 338 | $^1$H NMR (400 MHz, DMSO) δ 10.25 (s, 1H), 9.50-9.39 (m, 1H), 9.03 (dd, J = 2.1, 0.7 Hz, 1H), 8.52 (dd, J = 4.7, 1.7 Hz, 1H), 8.48 (d, J = 6.0 Hz, 1H), 8.31-8.24 (m, 1H), 8.16 (d, J = 8.2 Hz, 1H), 8.12 (d, J = 2.7 Hz, 1H), 8.04 (d, J = 7.3 Hz, 1H), 7.91-7.78 (rn, 3H), 7.58 (dd, J = 9.1, 2.7 Hz, 1H), 7.35 (ddd, J = 8.0, 4.8, 0.7 Hz, 1H), 4.01 (s, 3H). | DMSO | >98 | J2 |
| 339 | $^1$H NMR (400 MHz, DMSO) δ 10.23 (s, 1H), 9.37 (dd, J = 2.1, 0.7 Hz, 1H), 8.62 (dd, J = 4.7, 1.7 Hz, 1H), 8.57-8.49 (m, 1H), 7.93 (d, J = 2.7 Hz, 1H), 7.89 (d, J = 9.1 Hz, 1H), 7.58 (dd, J = 9.1, 2.7 Hz, 1H), 7.47 (ddd, J = 8.0, 4.8, 0.8 Hz, 1H), 7.40-7.30 (m, 3H), 3.98 (s, 3H). | DMSO | >98 | J2 |
| 340 | $^1$H NMR (400 MHz, DMSO) δ 11.31 (s, 1H), 9,56 (s, 1H), 9.54 (dd, J = 2.1, 0.7 Hz, 1H), 8.80-8.66 (rn, 2H), 8.14 (d, J = 9.2 Hz, 1H), 7.77 (dd, J = 9.2, 2.8 Hz, 1H), 7.58 (ddd, J = 8.0, 4.8, 0.8 Hz, 1H), 7.36 (d, J = 2.8 Hz, 1H), 7.03-6.94 (m, 1H), 6.68 (dd, J = 7.3, 0.8 Hz, 1H), 6.56 (dd, J = 8.2, 0.8 Hz, 1H), 3.86 (s, 3H). | DMSO | >98 | J2 |
| 341 | $^1$H NMR (400 MHz, DMSO) δ 10.00 (s, 1H), 9.54-9.49 (m, 1H), 8.75 (s, 1H), 8.69-8.62 (m, 2H), 8.50 (d, J = 1.7 Hz, 1H), 8.02 (d, J = 2.7 Hz, 1H), 7.91-7.85 (m, 2H), 7.83 (dd, J = 8.6, 1.9 Hz, 1H), 7.60-7.51 (m, 2H), 4.00 (s, 3H). | DMSO | >98 | J2 |
| 342 | $^1$H NMR (400 MHz, DMSO) δ 10.08 (s, 1H), 9.34-9.27 (m, 1H), 8.60 (dd, J = 4.7, 1.7 Hz, 1H), 8.51-8.44 (rn, 1H), 7.94 (d, J = 2.7 Hz, 1H), 7.88 (d, J = 9.1 Hz, 1H), 7.58 (dd, J = 9.1, 2.7 Hz, 1H), 7.56=7.51 (m, 1H), 7.51-7.47 (m, 2H), 7.45 (ddd, J = 8.0, 4.8, 0.8 Hz, 1H), 3.98 (s, 3H). | DMSO | >98 | J2 |
| 343 | $^1$H NMR (400 MHz, DMSO) δ 10.99 (s, 1H), 9.93 (s, 1H), 9.26 (d, J = 1.4 Hz, 1H), 8.59 (dd, J = 4.8, 1.7 Hz, 1H), 8.50-8.43 (m, 1H), 8.01 (d, J = 2.7 Hz, 1H), 7.98 (d, J = 9.5 Hz, 1H), 7.85 (d, J = 9.1 Hz, 1H), 7.65 (d, J = 8.4 Hz, 1H), 7.55 (dd, J = 9.1, 2.7 Hz, 1H), 7.49-7.42 (m, 1H), 7.36 (d, J = 8.3 Hz, 1H), 6.55 (dd, J = 9.5, 1.7 Hz, 1H), 3.98 (s, 3H), 2.33 (s, 3H). | DMSO | >98 | J2 |
| 344 | $^1$H NMR (400 MHz, DMSO) δ 9.34-9.28 (m, 1H), 8.81-8.75 (m, 1H), 8.74-8.65 (m, 1H), 8.06 (d, J = 9.2 Hz, 1H), 7.93 (d, J = 2.7 Hz, 1H), 7.85 (d, J = 8.8 Hz, 1H), 7.80-7.72 (m, 2H), 7.69 (d, J = 2.8 Hz, 1H), 7.59 (dd, J = 8.8, 2.7 Hz, 1H), 4.00 (s, 3H). | DMSO | >98 | G8 using DMF instead of THF |
| 345 | $^1$H NMR (400 MHz, DMSO) δ 9.35-9.29 (m, 1H), 8.87-8.78 (m, 2H), 8.19 (d, J = 9.4 Hz, 1H), 8.09 (d, J = 9.2 Hz, 1H), 7.94 (d, J = 8.5 Hz, 1H), 7.86 (dd, J = 8.0, 5.3 Hz, 1H), 7.77 (dd, J = 9.1, 2.9 Hz, 1H), 7.72 (d, J = 2.8 Hz, 1H), 7.67 (d, J = 2.3 Hz, 1H), 7.54 (dd, J = 8.5, 2.3 Hz, 1H), 6.56 (d, J = 9.6 Hz, 1H), 4.02 (s, 3H). | DMSO | >98 | G12 at room tempera-ture |
| 346 | $^1$H NMR (400 MHz, DMSO) δ 11.98 (s, 1H), 9.29 (d, J = 1.7 Hz, 1H), 8.88-8.87 (m, 2H), 8.08 (d, J = 9.2 Hz, 1H), 7.97 (d, J = 9.6 Hz, 1H), 7.88 (dd, J = 8.1, 5.4 Hz, 1H), 7.81 (d, J = 2.6 Hz, 1H), 7.78-7.72 (m, 2H), 7.67 (dd, J = 8.9, 2.6 Hz, 1H), 7.48 (d, J = 8.9 Hz, 1H), 6.60 (d, J = 9.5 Hz, 1H), 4.02 (s, 3H). | DMSO | >98 | G12 at room tempera-ture |
| 347 | $^1$H NMR (400 MHz, DMSO) δ 9.33-9.28 (m, 1H), 8.87-8.67 (m, 2H), 8.06 (d, J = 9.1 Hz, 1H), 7.91-7.79 (m, 1H), 7.75 (dd, J = 9.1, 2.9 Hz, 1H), 7.71 (d, J = 2.8 Hz, 1H), 7.67-7.61 (m, 2H), 7.58-7.51 (m, 2H), 4.01 (s, 3H). | DMSO | >98 | G12 at room tempera-ture |
| 348 | $^1$H NMR (400 MHz, DMSO) δ 9.28 (d, J = 2.0 Hz, 1H), 8.85-8.67 (m, 2H), 8.06 (d, J = 9.0 Hz, 1H), 7.88-7.77 (m, 1H), 7.77-7.69 (m, 2H), 7.62-7.54 (m, 2H), 7.51-7.45 (m, 2H), 7.44-7.37 (m, 1H), 4.02 (d, J = 3.9 Hz, 3H). | DMSO | >98 | G12 at room tempera-ture |

TABLE 1-continued

| | | | | |
|---|---|---|---|---|
| 349 | $^1$H NMR (400 MHz, DMSO) δ 9.23 (dd, J = 2.1, 0.7 Hz, 1H), 8.80 (dd, J = 5.2, 1.6 Hz, 1H), 8.72-8.64 (m, 1H), 8.09 (d, J = 9.1 Hz, 1H), 7.84-7.71 (m, 4H), 7.66 (dd, J = 8.1, 1.6 Hz, 1H), 7.61-7.54 (m, 1H), 7.52-7.45 (m, 1H), 4.02 (s, 3H). | DMSO | >98 | G12 at room tempera-ture |
| 350 | $^1$H NMR (400 MHz, DMSO) δ 9.22 (d, J = 1.7 Hz, 1H), 8.87-8.79 (m, 1H), 8.77-8.67 (m, 1H), 8.06 (d, J = 9.2 Hz, 1H), 7.92-7.79 (m, 1H), 7.74 (dd, J = 9.1, 2.9 Hz, 1H), 7.70 (d, J = 2.8 Hz, 1H), 7.45-7.37 (m, 2H), 7.33-7.27 (m, 1H), 7.17-7.09 (m, 1H), 4.01 (s, 3H), 3.71 (s, 3H). | DMSO | >98 | G12 at room tempera-ture |
| 351 | $^1$H NMR (400 MHz, DMSO) δ 12.03 (s, 1H), 10.69 (s, 1H), 9.65 (d, J = 1.8 Hz, 1H), 9.26-9.21 (m, 1H), 9.20-9.12 (m, 1H), 8.99-8.88 (m, 2H), 8.52 (d, J = 2.6 Hz, 1H), 8.49-8.42 (m, 1H), 8.25-8.17 (m, 1H), 8.15-8.08 (m, 2H), 8.02-7.96 (m, 1H), 7.93 (d, J = 9.4 Hz, 1H), 7.77 (d, J = 8.5 Hz, 1H), 7.72 (dd, J = 8.5, 1.9 Hz, 1H), 6.47 (d, J = 9.6 Hz, 1H), 4.04 (s, 3H). | DMSO | >98 | G1 |
| 352 | $^1$H NMR (400 MHz, DMSO) δ 12.04 (s, 1H), 10.92 (s, 1H), 9.65 (d, J = 1.7 Hz, 1H), 9.58-9.50 (m, 1H), 9.46-9.39 (m, 1H), 9.27-9.18 (m, 1H), 9.01-8.92 (m, 2H), 8.88 (dd, J = 5.3, 1.2 Hz, 1H), 8.48 (dd, J = 8.8, 1.9 Hz, 1H), 8.20-8.10 (m, 2H), 8.09-8.01 (m, 2H), 7.93 (d, J = 9.5 Hz, 1H), 7.81-7.72 (m, 2H), 6.47 (d, J = 9.5 Hz, 1H). | DMSO | >98 | G1 |
| 353 | 1H NMR (300 MHz, DMSO) δ 10.90 (s, 1H), 9.63 (s, 1H),. 8.89 (d, J = 8.0 Hz, 1H), 8.76 (d, J = 4.0 Hz, 1H), 8.19 (d, J = 2.1 Hz, 1H), 7.89 (d, J = 9.1 Hz, 1H), 7.83 (d, J = 7.9 Hz, 1H) 7.78-7.65 (m, 2H), 7.63-7.49 (m, 2H), 7.47-7.33 (m, 2H), 3.98 (s, 3H). | DMSO | >98 | G1 |
| 354 | 1H NMR (300 MHz, DMSO) δ 11.44 (s, 1H), 9.58 (d, J = 1.8 Hz, 1H), 9.16 (d, J = 8.2 Hz, 1H), 8.96 (dd, J = 5.3, 1.3 Hz, 1H), 8.29 (d, J = 2.5 Hz, 1H), 8.13 (d, J = 9.2 Hz, 1H), 7.99 (dd, J = 8.0, 5.4 Hz, 1H), 7.72-7.49 (m, 2H), 7.44-7.27 (m, 3H), 7.12 (s, 1H), 3.99 (s, 3H), 2.52 (s, 3H). | DMSO | >98 | G1 |
| 355 | 1H NMR (300 MHz, DMSO) δ 11.38 (s, 1H), 9.53 (s, 1H), 9.18 (d, J = 8.1 Hz, 1H), 8.97 (d, J = 5.3 Hz, 1H), 8.21 (s, 1H), 8.14-8.02 (m, 1H), 7.92 (d, J = 9.1 Hz, 1H), 7.60 (d, J = 9.1 Hz, 1H), 6.90 (s, 1H), 3.99 (s, 3H). | DMSO | >98 | G1 |
| 356 | 1H NMR (300 MHz, DMSO) δ 11.30 (s, 1H), 9.59 (d, J = 1.8 Hz, 1H), 9.19 (d, J = 8.2 Hz, 1H), 8.97 (dd, J = 5.3, 1.2 Hz, 1H), 8.24 (d, J = 2.5 Hz, 1H), 8.11-7.93 (m, 2H), 7.76-7.54 (m, 4H), 7.40 (t, J = 7.6 Hz, 1H), 7.26 (s, 1H), 7.21 (d, J = 7.4 Hz, 1H), 3.98 (s, 3H), 2.41 (s, 3H). | DMSO | >98 | G1 |
| 357 | 1H NMR (300 MHz, DMSO) δ 11.21 (s, 1H), 9.59 (d, J = 1.7 Hz, 1H), 9.22 (d, J = 8.1 Hz, 1H), 9.02-8.95 (m, 1H), 8.23 (d, J = 2.5 Hz, 1H), 8 13-7.96 (m, 3H), 7.85 (d, J = 8.7 Hz, 2H), 7.72 (d, J = 8.7 Hz, 2H), 7.60 (dd, J = 9.1, 2.6 Hz, 1H), 7.31 (s, 1H), 3.98 (s, 3H). | DMSO | >98 | G1 |
| 358 | 1H NMR (300 MHz, DMSO) δ 10.87 (s, 1H), 9.65-9.55 (m, 1H), 8.93 (dt, J = 8.0, 1.8 Hz, 1H), 8.81 (dd, J = 5.0, 1.6 Hz, 1H), 8.18 (d, J = 2.6 Hz, 1H), 7.94-7.,82 (m, 4H), 7.78 (dd, J = 8.0, 5.0 Hz, 1H), 7.60-7.46 (m, 4H), .44-7.35 (m, 1H), 7.32 (s, 1H), 3.98 (s, 3H). | DMSO | >98 | G1 |
| 359 | H NMR (300 MHz, DMSO) δ 11.29 (s, 1H), 9.59 (s, 1H), 9.20 (d, J = 8.1 Hz, 1H), 9.01-8.94 (m, 1H), 8.25 (s, 1H), 8.12- 7.98 (m, 2H), 7.90-7.75 (m, 2H), 7.62 (d, J = 9.1 Hz, 1H), 7.21 (s, 1H), 7.08 (d, J = 8.6 Hz, 2H), 3.99 (s, 3H), 3.84 (s, 3H). | DMSO | >98 | G1 |
| 360 | 1H NMR (300 MHz, DMSO) δ 11.29 (s, 1H), 9.60 (s, 1H), 9.21 (d, J = 8.0 Hz, 1H), 8.99 (d, J = 5.3 Hz, 1H), 8.26 (d, J = 2.2 Hz, 1H), 8.11-7.99 (m, 2H), 7.77 (d, J = 8.0 Hz, 2H), 7.62 (dd, J = 9.1, 2.4 Hz, 1H), 7.32 (d, J = 8.1 Hz, 2H), 7.26 (s, 1H), 3.99 (s, 3H), 2.37 (s, 3H). | DMSO | >98 | G1 |
| 361 | 1H NMR (300 MHz, DMSO) δ 11.00 (s, 1H), 9.55 (d, J = 1.7 Hz, 1H), 8.96 (dt, J = 8.1, 1.7 Hz, 1H), 8.86 (dd, J = 5.1, 1.5 Hz, 1H), 8.19 (d, J = 2.6 Hz, 1H), 7.97 (d, J = 9.2 Hz, 1H), 7.83 (dt, J = 9.5, 4.8 Hz, 1H), 7.55 (dd, J = 9.1, 2.6 Hz, 1H), 6.72 (s, 1H), 3.95 (d, J = 7.0 Hz, 3H), 2.35 (d, J = 3.5 Hz, 3H). | DMSO | >98 | G1 |

TABLE 1-continued

| | | | | |
|---|---|---|---|---|
| 362 | H NMR (300 MHz, DMSO) δ 11.21 (s, 1H), 9.58 (d, J = 1.5 Hz, 1H), 9.21-9.06 (m, 1H), 8.95 (d, J = 4.3 Hz, 1H), 8.22 (d, J = 2.3 Hz, 1H), 8.09-7.92 (m, 2H), 7.70-7.51 (m, 3H), 7.24-7.17 (m, 1H), 7.13 (s, 1H), 3.99 (s, 3H). | DMSO | >98 | G1 |
| 363 | 1H NMR (300 MHz, DMSO) δ 11.07 (s, 1H), 9.60 (s, 1H), 9.13 (d, J = 6.5 Hz, 1H), 8.93 (d, J = 5.1 Hz, 1H), 8.23 (s, 1H), 8.05-7.85 (m, 4H), 7.67-7.54 (m, 1H), 7.43-7.23 (m, 3H), 3.99 (s, 3H). | DMSO | >98 | G1 |
| 364 | 1H NMR (300 MHz, DMSO) δ 11.16 (s, 1H), 9.57 (d, J = 1.5 Hz, 1H), 9.14 (d, J = 8.1 Hz, 1H), 8.93 (d, J = 5.2 Hz, 1H), 8.18 (d, J = 2.4 Hz, 1H), 8.03-7.89 (m, 4H), 7.61-7.54 (m, 2H), 7.32 (s, 1H), 3.97 (s, 3H). | DMSO | >98 | G1 |
| 365 | 1H NMR (300 MHz, DMSO) δ 11.29 (s, 1H), 9.58 (d, J = 1.6 Hz,. 1H), 9.27 (d, J = 8.2 Hz, 1H), 9.06- 8.99 (m, 1H), 8.18 (d, J = 2.5 Hz, 1H), 8.10 (dd, J = 8.1, 5.5 Hz, 1H), 8.02 (d, J = 9.1 Hz, 1H), 7.91 (dd, J = 10.7, 1.8 Hz, 1H), 7.80-7.65 (m, 2H), 7.57 (dd, J = 9.1, 2.6 Hz, 1H), 7.29 (s, 1H), 3.96 (s, 3H). | DMSO | >98 | G1 |
| 366 | 1H NMR (300 MHz, DMSO) δ 11.17 (s, 1H), 9.60 (s, 1H), 9.24 (d, J = 8.2 Hz, 1H), 8.98 (d, J = 5.1 Hz, 1H), 8.22 (d, J = 2.5 Hz, 1H), 8.11-8.04 (m, 1H), 8.02-7.91 (m, 2H), 7.82-7.68 (m, 2H), 7.62 (dd, J = 9.1, 2.5 Hz, 1H), 7.36 (s, 1H), 4.01 (d, J = 11.0 Hz, 3H). | DMSO | >98 | G1 |
| 367 | 1H NMR (300 MHz, DMSO) δ 11.53 (s, 1H), 9.58 (d, J = 1.8 Hz, 1H), 9.20 (d, J = 8.2 Hz, 1H), 8.98 (dd, J = 5.3, 1.3 Hz, 1H), 8.25 (d, J = 2.5 Hz, 1H), 8.12 (d, J = 9.1 Hz, 1H), 8.04-7.95 (rn, 1H), 7.80-7.68 (m, 2H), 7.63-7.57 (m, 1H), 7.56-7.48 (rn, 1H), 7.31 (s, 1H), 3.99 (d, J = 6.7 Hz, 3H). | DMSO | >98 | G1 |
| 368 | 1H NMR (300 MHz, DMSO) δ 11.24 (s, 1H), 9.59 (d, J = 1.7 Hz, 1H), 9.26 (d, J = 8.3 Hz, 1H), 9.00 (d, J = 4.2 Hz, 1H), 8.23 (d, J = 2.6 Hz, 1H), 8.16 (d, J = 2.0 Hz, 1H), 8.09 (dd, J = 8.1, 5.4 Hz, 1H), 8.01 (d, J = 9.2 Hz, 1H), 7.91 (dd, J = 8.4, 2.1 Hz, 1H), 7.77 (d, J = 8.4 Hz, 1H), 7.62 (dd, J = 9.1, 2.5 Hz, 1H), 7.37 (s, 1H), 3.98 (s, 3H). | DMSO | >98 | G1 |
| 369 | 1H NMR (300 MHz, DMSO) δ 11.33 (s, 1H), 9.62 (s, 1H), 9.27 (d, J = 8.4 Hz, 1H), 9.01 (d, J = 5.2 Hz, 1H), 8.29-8.19 (m, 3H), 8.13-8.01 (m, 2H), 7.79-7.73 (m, 2H), 7.63 (dd, J = 9.1, 2.6 Hz, 1H), 7.42 (s, 1H), 3.99 (s, 3H). | DMSO | >98 | G1 |
| 370 | 1H NMR (300 MHz, DMSO) δ 11.31 (s, 1H), 9.55 (d, J = 1.7 Hz, 1H), 9.07 (d, J = 7.9 Hz, 1H), 8.92 (d, J = 4.0 Hz, 1H), 8.26 (d, J = 2.5 Hz, 1H), 8.04 (d, J = 9.1 Hz, 1H), 7.98-7.68 (m, 5H), 7.63 (dd, J = 9.2, 2.5 Hz, 1H), 7.13 (s, 1H), 4.00 (s, 3H). | DMSO | >98 | G1 |
| 371 | 1H NMR (300 MHz, CDCl3) δ 11.29 (s, 1H), 9.57 (d, J = 1.8 Hz, 1H), 9.07 (d, J = 8.1 Hz, 1H), 8.93 (dd, J = 5.2, 1.3 Hz, 1H), 8.25 (d, J = 2.5 Hz, 1H), 8.07-7.97 (m, 2H), 7.92 (dd, J = 8.0, 5.3 Hz, 1H), 7.67-7.51 (m, 4H), 7.28 (s, 1H), 3.99 (s, 3H). | DMSO | >98 | G1 |
| 372 | 1H NMR (300 MHz, DMSO) δ 11.32 (s, 1H), 9.60 (d, J = 1.7 Hz, 1H), 9.27 (d, J = 8.1 Hz, 1H), 9.03 (d, J = 5.4 Hz, 1H), 8.22 (d, J = 2.5 Hz, 1H), 8.12 (dd, J = 8.1, 5.7 Hz, 1H), 8.03 (d, J = 8.8 Hz, 3H), 7.59 (dd, J = 9.1, 2.5 Hz, 1H), 7.52 (d, J = 8.1 Hz, 2H), 7.32 (s, 1H), 3.98 (d, J = 6.7 Hz, 3H). | DMSO | >98 | G1 |
| 373 | 1H NMR (300 MHz, DMSO) δ 11.38 (s, 1H), 9.61 (d, J = 1.6 Hz, 1H), 9.26 (d, J = 8.2 Hz, 1H), 9.02 (d, J = 5.3 Hz, 1H), 8.23 (d, J = 2.4 Hz, 1H), 8.12-8.01 (m, 2H), 7.95 (d, J = 8.0 Hz, 1H), 7.89 (s, 1H), 7.71-7.56 (m, 2H), 7.45-7.33 (m, 2H), 4.10-3.90 (m, 3H). | DMSO | >98 | G1 |
| 374 | 1H NMR (300 MHz, DMSO) δ 11.29 (s, 1H), 9.56 (s, 1H), 9.12 (d, J = 7.7 Hz, 1H), 8.94 (d, J = 4.9 Hz, 1H), 8.26 (d, J = 2.3 Hz, 1H), 8.07-7.90 (m, 2H), 7.71-7.57 (m, 2H), 7.51 (s, 1H), 7.47-7.37 (m, 1H), 7.17 (s, 1H), 3.99 (s, 3H), 2.53 (s, 3H). | DMSO | >98 | G1 |

TABLE 1-continued

| | | | | |
|---|---|---|---|---|
| 375 | 1H NMR (300 MHz, DMSO) δ 13.13-11.88 (m, 1H), 9.66 (d, J = 1.4 Hz, 1H), 9.36 (d, J = 8.2 Hz, 1H), 9.00 (d, J = 5.4 Hz, 1H), 8.38 (d, J = 2.2 Hz, 1H), 8.14 (dd, J = 8.1, 5.6 Hz, 1H), 8.01 (d, J = 7.5 Hz, 2H), 7.89 (d, J = 9.1 Hz, 1H), 7.78 (s, 1H), 7.64-7.35 (m, 9H), 5.23 (s, 2H). | DMSO | >98 | J NaOtBu, Pd(OAc)2, Tri-t-butyl-phos-phonium tetrafluoro-borate, Toluene |
| 376 | 1H NMR (300 MHz, DMSO) δ 12.49 (s, 1H), 9.63 (s, 1H), 9.27 (d, J = 8.1 Hz, 1H), 8.96 (d, J = 5.4 Hz, 1H), 8.34 (s, 1H), 8.07 (dd, J = 8.1, 5.6 Hz, 1H), 7.99 (d, J = 3.3 Hz, 2H), 7.85 (d, J = 9.1 Hz, 1H), 7.80 (s, 1H), 7.64-7.35 (m, 9H), 5.21 (s, 2H). | DMSO | >98 | J NaOtBu, Pd(OAc)2, Tri-t-butyl-phos-phonium tetrafluoro-borate, Toluene |
| 377 | 1H NMR (300 MHz, DMSO) δ 9.56 (d, J = 1.8 Hz, 1H), 9.30-9.21 (m, 1H), 9.01 (dd, J = 5.5, 1.2 Hz, 1H), 8.18-8.03 (m, 2H), 7.76-7.64 (m, 2H), 7.55-7.45 (m, 2H), 7.33 (dd, J = 8.6, 2.3 Hz, 1H), 4.69 (t, J = 7.9 Hz, 2H), 3.92 (s, 3H), 3.26 (t, J = 7.8 Hz, 2H). | DMSO | >98 | G8 |
| 378 | 1H NMR (300 MHz, DMSO) δ 9.54 (d, J = 1.9 Hz, 1H), 8.70-8.65 (m, 2H), 7.95 (d, J = 9.2 Hz, 1H), 7.66-7.50 (m, 2H), 7.45-7.36 (m, 2H), 7.27 (t, J = 8.0 Hz, 1H), 7.07 (d, J = 7.9 Hz, 1H), 4.61 (t, J = 8.1 Hz, 2H), 3.87 (s, 3H), 3.38-3.17 (m, 5H). | DMSO | >98 | G8 at 50° C. |
| 379 | 1H NMR (400 MHz, DMSO) δ 9.54 (d, J = 1.9 Hz, 1H), 9.28-9.18 (m, 1H), 8.99 (dd, J = 5.5, 1.3 Hz, 1H), 8.18-8.02 (m, 2H), 7.69 (dd, J = 9.2, 2.7 Hz, 1H), 7.58-7.46 (m, 2H), 7.39 (dd, J = 8.2, 5.9 Hz, 1H), 6.96-6.85 (m, 1H), 4.71 (t, J = 8.0 Hz, 2H), 3.92 (s, 3H), 3.22 (t, J = 7.8 Hz, 2H). | DMSO | >98 | G8 at 50° C. |
| 380 | 1H NMR (300 MHz, DMSO) δ 9.55 (d, J = 1.8 Hz, 1H), 9.11 (d, J = 8.1 Hz, 1H), 8.93 (dd, J = 5.3, 1.4 Hz, 1H), 8.10-7.93 (m, 2H), 7.76 (dd, J = 8.7, 4.7 Hz, 1H), 7.67 (dd, J = 9.2, 2.6 Hz, 1H), 7.52 (d, J = 2.6 Hz, 1H), 7.28 (dd, J = 8.4, 2.6 Hz, 1H), 7.12 (td, J = 9.0, 2.7 Hz, 1H), 4.70 (t, J = 7.9 Hz, 2H), 3.92 (s, 3H), 3.26 (t, J = 7.5 Hz, 2H). | DMSO | >98 | G8 at 50° C. |
| 381 | 1H NMR (300 MHz, DMSO) δ 9.66 (d, J = 2.0 Hz, 1H), 9.15-9.06 (m, 1H), 8.91 (dd, J = 5.2. 1.5 Hz, 1H), 8.27-8.17 (m, 2H), 8.01 (d, J = 8.9 Hz, 1H), 7.94 (dd, J = 8.2, 5.2 Hz, 1H), 7.88-7.78 (m, 2H), 7.42 (d, J = 2.7 Hz, 1H), 7.35 (dd, J = 8.8, 2.2 Hz, 1H), 6.96 (d, J = 3.5 Hz, 1H), 3.91 (s, 3H). | DMSO | >98 | G8 at 50° C. |
| 382 | 1H NMR (300 MHz, DMSO) δ 9.56 (d, J = 1.6 Hz, 1H), 9.26 (d, J = 8.2 Hz, 1H), 9.05-8.98 (m, 1H), 8.20-8.02 (m, 2H), 7.69 (dd, J = 9.2, 2.7 Hz, 1H), 7.53-7.40 (m, 2H), 7.32 (dd, J = 14.0, 8.0 Hz, 1H), 6.92 (t, J = 8.5 Hz, 1H), 4.71 (t, J = 7.9 Hz, 2H), 3.91 (s, 3H), 3.28 (t, J = 7.8 Hz, 2H). | DMSO | >98 | G8 at 50° C. |
| 383 | 1H NMR (300 MHz, DMSO) δ 9.66 (d, J = 1.5 Hz, 1H), 9.23-9.09 (m, 1H), 8.93 (dd, J = 5.3, 1.5 Hz, 1H), 8.31-8.16 (m, 2H), 8.08-7.93 (m, 2H), 7.82 (dd, J = 9.2, 2.8 Hz, 1H), 7.56 (dd, J = 9.4, 2.5 Hz, 1H), 7.43 (d, J = 2.7 Hz, 1H), 7.19 (td, J = 9.2, 2.7 Hz, 1H), 7.02-6.89 (m, 1H), 3.91 (s, 3H). | DMSO | >98 | G8 at 50° C. |
| 384 | 1H NMR (300 MHz, DMSO) δ 9.66 (d, J = 1.6 Hz, 1H), 9.23- 9.09 (m, 1H), 8.94 (dd, J = 5.3, 1.5 Hz, 1H), 8.26-8.14 (m, 2H), 8.00 (dd, J = 8.1, 5.3 Hz, 1H), 7.90-7.73 (m, 3H), 7.45 (d, J = 2.7 Hz, 1H), 7.25-7.10 (m, 1H), 6.98 (d, J = 3.5 Hz, 1H), 3.92 (s, 3H). | DMSO | >98 | G8 at 50° C. |

TABLE 1-continued

| | | | | |
|---|---|---|---|---|
| 385 | 1H NMR (300 MHz, DMSO) δ 9.54 (d, J = 1.8 Hz, 1H), 9.21 (dt, J = 8.2, 1.6 Hz, 1H), 8.98 (dd, J = 5.5, 1.3 Hz, 1H), 8.20-8.00 (m, 2H), 7.68 (dd, J = 9.2, 2.7 Hz, 1H), 7.55-7.31 (m, 3H), 7.00-6.78 (m, 1H), 4.69 (t, J = 7.9 Hz, 2H), 4.19 (q, J = 7.0 Hz, 2H), 3.22 (t, J = 7.9 Hz, 2H), 1.41 (t, J = 6.9 Hz, 3H). | DMSO | >98 | G8 at 50° C. |
| 386 | 1H NMR (300 MHz, DMSO) δ 9.42 (d, J = 1.5 Hz, 1H), 9.06 (d, J = 8.1 Hz, 1H), 8.93 (d, J = 5.4 Hz, 1H), 8.09-7.99 (m, 2H), 7.68 (dd, J = 9.1, 2.7 Hz, 1H), 7.53 (d, J = 2.6 Hz, 1H), 7.30-7.16 (m, 3H), 4.66 (t, J = 7.9 Hz, 2H), 3.98 (s, 3H), 3.29 (t, J = 7.7 Hz, 2H). | DMSO | >98 | G8 at 50° C. |
| 387 | 1H NMR (300 MHz, DMSO) δ 9.37 (d, J = 1.4 Hz, 1H), 9.11 (d, J = 8.2 Hz, 1H), 8.99 (d, J = 4.9 Hz, 1H), 8.14 (dd, J = 8.2, 5.6 Hz, 1H), 8.06 (d, J = 9.2 Hz, 1H), 7.70 (dd, J = 9.2, 2.6 Hz, 1H), 7.51 (d, J = 2.7 Hz, 1H), 7.45-7.36 (m, 2H), 7.26-7.15 (m, 1H), 4.83 (d, J = 9.5 Hz, 1H), 4.49- 4.38 (m, 2H), 4.00 (s, 3H), 3.48-3.28 (m, 1H), 3.27-3.05 (m, 1H). | DMSO | >98 | G8 at 50° C. |
| 388 | 1H NMR (400 MHz, DMSO) δ 9.56 (d, J = 1.9 Hz, 1H), 9.31-9.19 (m, 1H), 9.00 (dd, J = 5.5, 1.3 Hz, 1H), 8.21-8.02 (rn, 2H), 7.73-7.64 (m, 2H), 7.47 (dd, J = 5.4, 2.4 Hz, 2H), 7.32 (dd, J = 8.6, 2.3 Hz, 1H), 4.67 (t, J = 8.0 Hz, 2H), 4.18 (q, J = 7.0 Hz, 2H), 3.26 (t, J = 7.8 Hz, 2H), 1.41 (t, J = 6.9 Hz, 3H). | DMSO | >98 | G8 at 50° C. |
| 389 | 1H NMR (400 MHz, DMSO) δ 9.54 (d, J = 1.8 Hz, 1H), 9.25 (dt, J = 8.2, 1.6 Hz, 1H), 9.04 (dd, J = 5.5, 1.1 Hz, 1H), 8.26 (d, J = 2.1 Hz, 1H), 8.16 (dd, J = 8.0, 5.6 Hz, 1H), 8.11-7.96 (m, 2H), 7.91 (d, J = 8.6 Hz, 1H), 7.47 (d, J = 2.1 Hz, 1H), 7.34 (dd, J = 8.6, 2.3 Hz, 1H), 4.68 (t, J = 7.9 Hz, 2H), 3.25 (t, J = 7.8 Hz, 2H). | DMSO | >98 | G8 at 50° C. |
| 390 | $^1$H NMR (400 MHz, DMSO) δ 9.37 (d, J = 1.4 Hz, 1H), 8.82 (dd, J = 5.1, 1.5 Hz, 1H), 8.76 {dd, J = 8.1 Hz, 1H), 8.62 (d, J = 1.9 Hz, 1H), 8.46 (dd, J = 8.8, 2.1 Hz, 1H), 8.20 (d, J = 8.7 Hz, 1H), 7.91 (dd, J = 6.3, 2.6 Hz, 1H), 7.80 (dd, J = 8.0, 5.1 Hz, 1H), 7.71-7.59 (m, 2H), 7.52-7.38 (m, 3H), 7.10-7.01 (m, 1H), 3.89 (s, 3H). | DMSO | >98 | G8 with DMF instead of THF |
| 391 | 1H NMR (400 MHz, DMSO) δ 9.383 (d, J = 1.4 Hz, 1H), 8.82 (d, J = 5.1 Hz, 1H), 8.76 (d, J = 7.9 Hz, 1H), 8.63 (d, J = 1.8 Hz, 1H), 8.46 (dd, J = 8.8, 2.2 Hz, 1H), 8.20 (d, J = 8.7 Hz, 1H), 7.97 (d, J = 2.7 Hz, 1H), 7.87 (d, J = 8.8 Hz, 1H), 7.84-7.76 (m, 1H), 7.64 (dd, J = 8.8, 2.7 Hz, 1H), 7.52-7.39 (m, 3H), 7.10- 7.02 (m, 1H), 3.88 (s, 3H). | DMSO | >98 | G8 with DMF instead of THF |
| 392 | $^1$H NMR (400 MHz, DMSO) δ 9.39 (t, J = 3.2 Hz, 1H), 8.93-8.82 (m, 2H), 8.62 (d, J = 1.8 Hz, 1H), 8.47 (dd, J = 8.8, 2.2 Hz, 1H), 8.21 (d, J = 9.0 Hz, 1H), 7.91 (dd, J = 8.1, 5.3 Hz, 1H), 7.84- 7.77 (m, 1H), 7.73-7.63 (m, 1H), 7.53-7.40 (m, 4H), 7.09-7.03 (m, 1H), 3.87 (d, J = 6.5 Hz, 3H). | DMSO | >98 | G8 with DMF instead of THF |
| 393 | $^1$H NMR (400 MHz, DMSO) δ 11.71 (s, 1H), 11.10 (s, 1H), 9.42 (d, J = 1.9 Hz, 1H), 8.90-8.69 (m, 2H), 8.62 (d, J = 1.7 Hz, 1H), 8.40 (dd, J = 8.8, 1.9 Hz, 1H), 8.14 (d, J = 8.7 Hz, 1H), 7.92 (d, J = 7.7 Hz, 1H), 7.84-7.69 (m, 1H), 7.57-7.40 (m, 3H), 7.11- 7.02 (m, 2H), 6.96 (d, J = 8.3 Hz, 1H), 3.89 (s, 3H). | DMSO | >98 | G8 with DMF instead of THF |
| 394 | $^1$H NMR (400 MHz, DMSO) δ 9.43-9.29 (m, 1H), 8.75-8.64 (m, 2H), 8.60-8.48 (m, 1H), 8.47-8.32 (m, 1H), 8.21-8.01 (m, 2H), 7.86-7.74 (m, 2H), 7.64 (d, J = 8.6 Hz, 1H), 7.59-7.34 (m, 4H), 7.13-7.01 (m, 1H), 6.87 (d, J = 8.7 Hz, 1H), 3.90 (t, J = 5.3 Hz, 3H). | DMSO | >98 | G8 with DMF instead of THF |
| 395 | $^1$H NMR (400 MHz, DMSO) δ 9.24 (dd, J = 2.2, 0.8 Hz, 1H), 8.76 (dd, J = 5.0, 1.7 Hz, 1H), 8.61-8.54 (m, 1H), 8.49 (dd, J = 1.8, 1.1 Hz, 1H), 8.21-8.12 (m, 2H), 7.75 (dd, J = 8.0, 1.5 Hz, 1H), 7.70-7.62 (m, 2H), 7.62-7.53 (m, 1H), 7.53-7.44 (m, 1H). | DMSO | >98 | G8 with DMF instead of THF |

TABLE 1-continued

| | | | | |
|---|---|---|---|---|
| 396 | $^1$H NMR (400 MHz, DMSO) δ 11.71 (s, 1H), 11.10 (s, 1H), 9.42 (d, J = 1.9 Hz, 1H), 8.90-8.69 (m, 2H), 8.62 (d, J = 1.7 Hz, 1H), 8.40 (dd, J = 8.8, 1.9 Hz, 1H), 8.14 (d, J = 8.7 Hz, 1H), 7.92 (d, J = 7.7 Hz, 1H), 7.84-7.69 (m, 1H), 7.57-7.40 (m, 3H), 7.11-7.02 (m, 2H), 6.96 (d, J = 8.3 Hz, 1H), 3.89 (s, 3H). | DMSO | >98 | G12 |
| 397 | $^1$H NMR (400 MHz, DMSO) δ 10.40 (s, 1H), 9.50 (d, J = 1.6 Hz, 1H), 8.99 (d, J = 8.2 Hz, 1H), 8.88 (dd, J = 5.3, 1.5 Hz, 1H), 8.30 (d, J = 2.5 Hz, 1H), 8.14-8.06 (m, 1H), 7.99-7.88 (m, 2H), 7.78 -7.66 (m, 2H), 7.61-7.51 (m, 3H), 7.50-7.34 (m, 3H), 5.34 (s, 2H). | DMSO | >98 | Method G1 |
| 398 | $^1$H NMR (400 MHz, DMSO) δ 9.96 (s, 1H), 9.52 (d, J = 1.4 Hz, 1H), 8.68 (dd, J = 9.9 Hz, 1H), 8.65 (d, J = 9.9 Hz, 1H), 8.16 (dd, J = 2.5, 5.4 Hz, 2H), 7.68-7.41 (m, 2H), 7.78-7.66 (m, 8H), 7.39-7.19 (m, 1H), 5.30 (s, 2H). | DMSO | >98 | Method G1 |
| 399 | 1H NMR (DMSO-d6) ppm 12.52 (s, 1H), 9.78 (d, J = 1.56 Hz, 1H), 8.91-8.88 (m, 1H), 8.74 (dd, J = 4.74, 1.60 Hz, 1H), 8.33 (brs, 1H), 8.06 (d, J = 8.56 Hz, 2H), 7.93 (d, J = 9.08 hz, 1H), 7.89 (s, 1H), 7.66-7.59 (m, 2H), 7.55 (d, J = 8.56 Hz, 2H), 4.01 (s, 3H). | DMSO | >98 | G13 |
| 400 | 1H NMR (DMSO-d6) ppm 12.80-12.40 (br, 1H), 9.77 (d, J = 1.84 Hz, 1H), 9.32 (d, J = 8.04 Hz, 1H), 8.97 (dd, J = 5.36, 1.40 Hz, 1H), 8.34 (d, J = 2.68 Hz, 1H), 8.09-8.06 (m, 3H), 7.97 (d, J = 9.12 Hz, 1H), 7.91 (s, 1H), 7.64 (dd, J = 9.12, 2.68 Hz, 1H), 7.55 (d, J = 8.60 Hz, 2H), 4.01 (s, 3H). The 1H of 2HCl was not observed. | DMSO | >98 | G13 |
| 401 | 1H NMR (DMSO-d6) ppm 11.14 (brs, 1H), 9.58 (s, 1H), 9.13 (dd, J = 7.96 Hz, 1H), 8.93 (d, J = 5.24 Hz, 1H), 8.54 (d, J = 4.72 Hz, 1H), 8.48 (d, J = 8.32 Hz, 1H), 8.28 (brs, 1H), 8.09 (brt, J = 7.16 Hz, 1H), 8.02-7.96 (m, 2H), 7.65 (dd, J = 8.80, 2.48 Hz, 1H), 7.34 (brt, J = 6.52 Hz, 1H), 4.01 (s, 3H). The 1H of 2HCl was not observed. | DMSO | >98 | J2 |
| 402 | 1H NMR (DMSO-d6) ppm 10.89 (s, 1H), 9.57 (d, J = 1.60 Hz, 1H), 9.04 (d, J = 8.04 Hz, 1H), 8.88 (dd, J = 5.16, 1.40 Hz, 1H), 8.55 (dd, J = 2.64, 0.52 Hz, 1H), 8.50 (d, J = 8.92 Hz, 1H), 8.22 (d, J = 2.68 Hz, 1H), 8.08 (d, J = 8.92, 2.68 Hz, 1H), 7.94-7.90 (m, 2H), 7.61 (dd, J = 9.08, 2.68 Hz, 1H), 3.99 (s, 3H). The 1H of 2HCl was not observed. | DMSO | DMSO | J2 |
| 403 | 1H NMR (DMSO-d6) ppm 10.53 (s, 1H), 9.38 (s, 1H), 8.99 (d, J = 8.08 Hz, 1H), 8.88 (d, J = 4.60 Hz, 1H), 8.11 (brs, 1H), 8.01-7.95 (m, 2H), 7.90 (d, J = 8.60 Hz, 2H), 7.66 (dd, J = 9.12, 2.68 Hz, 1H), 7.50 (d, J = 8.60 Hz, 2H), 6.93 (s, 1H), 4.00 (s, 3H), 3.80 (s, 3H). The 1H of 2HCl was not observed. | DMSO | >98 | J2 |
| 404 | 1H NMR (DMSO-d6) ppm 11.81 (brs, 1H), 9.64 (s, 1H), 9.00 (d, J = 7.48 Hz, 1H), 8.85 (brs, 1H), 8.14 (d, J = 2.56 Hz, 1H), 8.00 (d, J = 8.60 Hz, 2H), 7.96 (d, J = 9.08 Hz, 1H), 7.86 (br, 1H), 7.66-7.63 (m, 3H), 7.25 (s, 1H), 4.00 (s, 3H). The 1H of HCl was not observed. | DMSO | >98 | J2 |
| 405 | 1H NMR (DMSO-d6) ppm 11.80 (brs, 1H), 9.55 (brs, 1H), 9.04 (d, J = 7.92 Hz, 1H), 8.88 (brs, 1H), 8.14 (d, J = 2.60 Hz, 1H), 8.05-8.02 (m, 2H), 7.96 (d, J = 9.12 Hz, 1H), 7.89 (m, 1H), 7.64 (dd, J = 9.12, 2.60 Hz, 1H), 7.42 (t, J = 8.84 Hz, 2H), 7.23 (s, 1H), 3.99 (s, 3H). The 1H of HCl was not observed. | DMSO | >98 | J2 |
| 406 | 1H NMR (DMSO-d6) ppm 10.31 (s, 1H), 9.37 (s, 1H), 8.88 (m, 2H), 8.04 (d, J = 2.60 Hz, 1H), 7.94 (d, J = 9.12 Hz, 1H), 7.91 (m, 1H), 7.64 (dd, J = 9.12, 2.68 Hz, 1H), 7.56 (d, J = 1.83 Hz, 1H), 6.40 (d, J = 1.88 Hz, 1H), 3.98 (s, 3H), 3.74 (s, 3H) . The 1H of HCl was not observed. | DMSO | >98 | J2 |
| 407 | 1H NMR (DMSO-d6) ppm 12.89 (brs, 1H), 9.56 (s, 1H), 8.92 (d, J = 4.92 Hz, 2H), 8.04 (d, J = 8.84 Hz, 1H), 7.98 (d, J = 2.88 Hz, 1H), 7.84 (br, 1H), 7.71-7.66 (m, 3H), 7.45-7.39 (m, 2H), 4.00 (s, 3H), 3.94 (s, 3H). The 1H of 2HCl was not observed. | DMSO | >98 | J2 |

TABLE 1-continued

| | | | | |
|---|---|---|---|---|
| 408 | 1H NMR (DMSO-d6) ppm 10.39 (s, 1H), 9.38 (s, 1H), 8.90 (d, J = 8.00 Hz, 1H), 8.84 (d, J = 4.76 hz, 1H), 8.06 (d, J = 2.68 Hz, 1H), 7.95 (d, J = 9.16 Hz, 1H), 7.90-7.88 (m, 3H), 7.65 (dd, J = 9.16, 2.68 Hz, 1H), 7.44 (brt, J = 7.40 Hz, 2H), 7.35-7.31 (m, 1H), 6.88 (s, 1H), 3.99 (s, 3H), 3.80 (s, 3H). The 1H of HCl was not observed. | DMSO | >98 | J2 Tempera-ture at 100° C. |
| 409 | 1H NMR (DMSO-d6) ppm 10.44 (brs, 1H), 9.01 (s, 1H), 8.68 (brs, 1H), 8.39 (brs, 1H), 8.23 (s, 1H), 8.07 (brs, 1H), 7.84 (d, J = 9.04 Hz, 1H), 7.70-7.54 (m, 2H), 7.44 (brd, J = 7.32 Hz, 2H), 7.15 (brt, J = 7.56 Hz, 2H), 7.00 (brt, 7.40 Hz, 1H), 3.97 (s, 3H), 3.93 (s, 3H). The 1H of HCl was not observed. | DMSO | >98 | J2 Tempera-ture at 100° C. |
| 410 | 1H NMR (DMSO-d6) ppm 11.13 (s, 1H), 9.59 (d, J = 1.64 Hz, 1H), 9.03 (brs, 1H), 8.88 (brs, 1H), 8.63 (d, J = 2.52 Hz, 1H), 8.23 (d, J = 2.32 Hz, 1H), 7.93-7.82 (brm, 4H), 7.61-7.53 (m, 3H), 7.35-7.31 (brm, 2H), 4.00 (s, 3H). The 1H of HCl was not observed. | DMSO | >98 | J2 Tempera-ture at 100° C. |
| 411 | 1H NMR (DMSO-d6) ppm 9.54 (s, 1H), 8.79 (s, 1H), 8.69 (d, J = 7.60 Hz, 1H), 7.89 (brd, J = 8.96 Hz, 2H), 7.68-7.58 (m, 4H), 7.38-7.30 (m, 2H), 3.98 (s, 3H). The 1H of NH— was not observed. | DMSO | >98 | J2 Tempera-ture at 100° C. |
| 412 | 1H NMR (DMSO-d6) ppm 9.70 (s, 1H), 9.05 (d, J = 7.88 Hz, 1H), 8.85 (brd, J = 4.44 Hz, 1H), 8.24 (brs, 1H), 8.04 (d, J = 8.44 Hz, 2H), 7.94 (d, J = 9.00 Hz, 1H), 7.84 (m, 1H), 7.66 (d, J = 8.44 Hz, 2H), 7.62 (dd, J = 9.00, 2.64 Hz, 1H), 3.99 (s, 3H). The 1H of HCl and NH— were not observed. | DMSO | >98 | G12 Tempera-ture at 100° C. |
| 413 | 1H NMR (CDCl3) ppm 15.18 (brs, 1H), 9.57 (d, J = 2.32 Hz, 1H), 8.86 (dd, J = 4.80, 1.56 Hz, 1H), 8.59-8.56 (m, 1H), 7.78-7.73 (m, 4H), 7.55-7.52 (m, 1H), 7.43 (d, J = 8.56 Hz, 2H), 7.38 (dd, J = 8.88, 2.96 Hz, 1H), 7.34 (s, 1H), 3.97 (s, 3H), 3.30 (s, 3H), 3.11 (s, 3H). | CDCl3 | >98 | J2 Tempera-ture at 100° C. |

| Number | Starting Material 1 | Starting Material 2 | Product | Salt type |
|---|---|---|---|---|
| 414 | 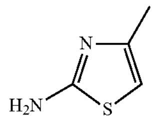 | 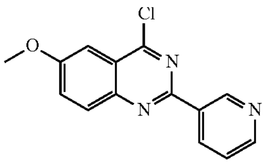 [SMILES: COc1ccc2nc(-c3cccnc3)nc(Cl)c2c1] | 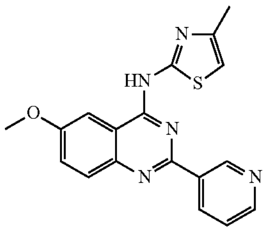 [SMILES: COc1ccc2nc(-c3cccnc3)nc(Nc3nc(C)cs3)c2c1] | 2 HCl |

TABLE 1-continued
| | | | | |
|---|---|---|---|---|
| 415 | 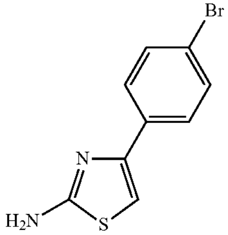 | 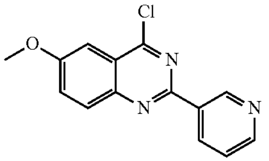 [SMILES: COc1ccc2nc(-c3cccnc3)nc(Cl)c2c1] | 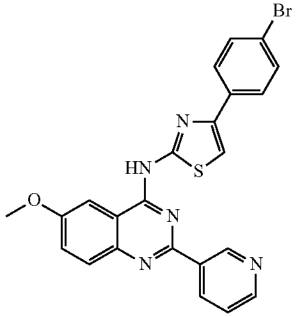 [SMILES: COc1ccc2nc(-c3cccnc3)nc(Nc3nc(-c4ccc(Br)cc4)cs3)c2c1] | 2 HCl |
| 416 | 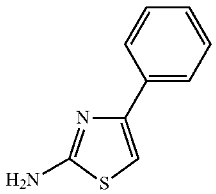 [SMILES: Nc1nc(-c2ccccc2)cs1] | 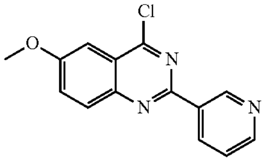 [SMILES: COc1ccc2nc(-c3cccnc3)nc(Cl)c2c1] | 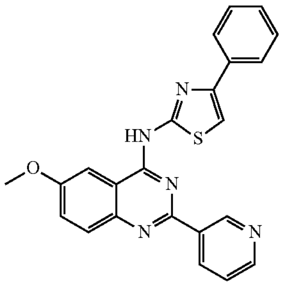 [SMILES: COc1ccc2nc(-c3cccnc3)nc(Nc3nc(-c4ccccc4)cs3)c2c1] | HCl |
| 417 | 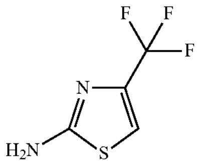 | 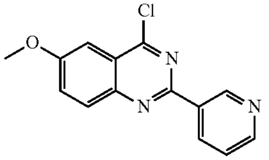 [SMILES: COc1ccc2nc(-c3cccnc3)nc(Cl)c2c1] | 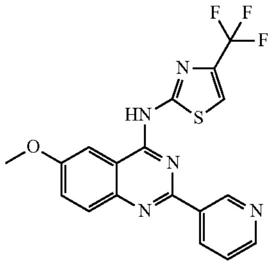 [SMILES: COc1ccc2nc(-c3cccnc3)nc(Nc3nc(C(F)(F)F)cs3)c2c1] | HCl |
| 418 | 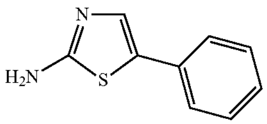 [SMILES: Nc1ncc(-c2ccccc2)s1] | 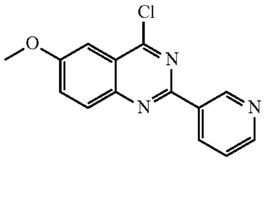 [SMILES: COc1ccc2nc(-c3cccnc3)nc(Cl)c2c1] | 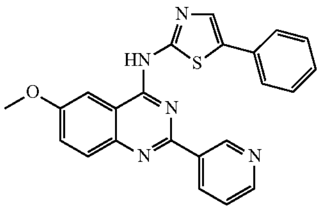 [SMILES: COc1ccc2nc(-c3cccnc3)nc(Nc3ncc(-c4ccccc4)s3)c2c1] | HCl |

TABLE 1-continued
| | | | | |
|---|---|---|---|---|
| 419 | 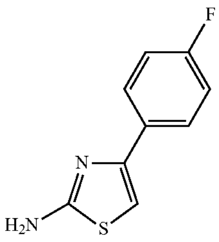 [SMILES: Nc1nc(-c2ccc(F)cc2)cs1] | 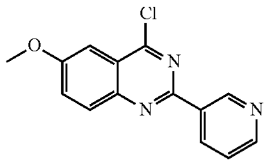 [SMILES: COc1ccc2nc(-c3cccnc3)nc(Cl)c2c1] | 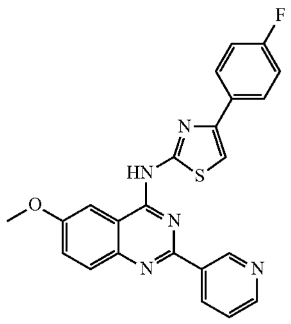 [SMILES: COc1ccc2nc(-c3cccnc3)nc(Nc3nc(-c4ccc(F)cc4)cs3)c2c1] | HCl |
| 420 | 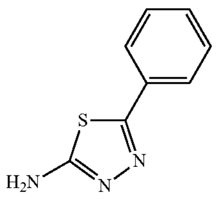 [SMILES: Nc1nnc(-c2ccccc2)s1] | 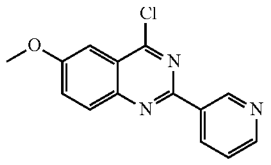 [SMILES: COc1ccc2nc(-c3cccnc3)nc(Cl)c2c1] | 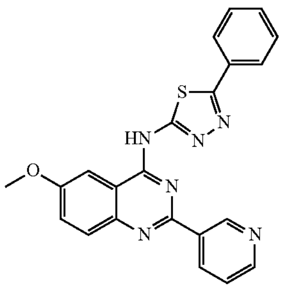 [SMILES: COc1ccc2nc(-c3cccnc3)nc(Nc3nnc(-c4ccccc4)s3)c2c1] | HCl |
| 421 | 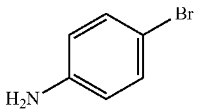 | 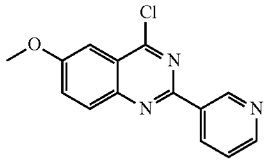 [SMILES: COc1ccc2nc(-c3cccnc3)nc(Cl)c2c1] | 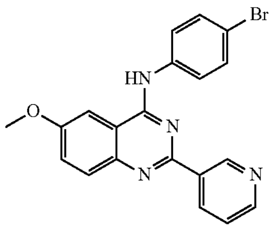 | |

TABLE 1-continued
| | | | | |
|---|---|---|---|---|
| 422 | 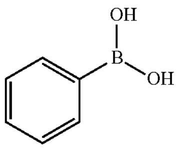 | 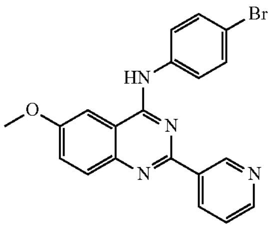 [SMILES: COc1ccc2nc(-c3cccnc3)nc(Nc3ccc(Br)cc3)c2c1] | 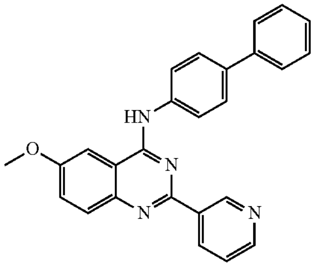 [SMILES: COc1ccc2nc(-c3cccnc3)nc(Nc3ccc(-c4ccccc4)cc3)c2c1] | HCl |
| 423 | 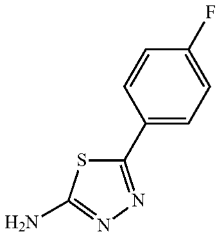 [SMILES: Nc1nnc(-c2ccc(F)cc2)s1] | 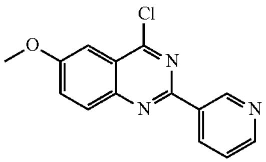 [SMILES: COc1ccc2nc(-c3cccnc3)nc(Cl)c2c1] | 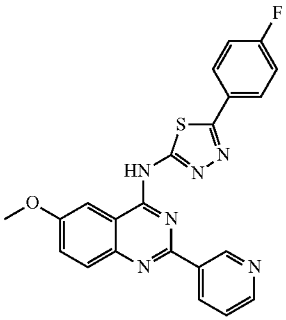 [SMILES: COc1ccc2nc(-c3cccnc3)nc(Nc3nnc(-c4ccc(F)cc4)s3)c2c1] | HCl |
| 424 | 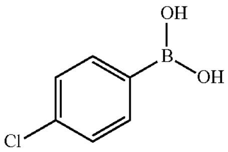 | 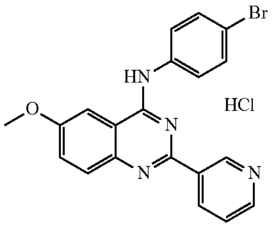 [SMILES: COc1ccc2nc(-c3cccnc3)nc(Nc3ccc(Br)cc3)c2c1 ; Cl] | 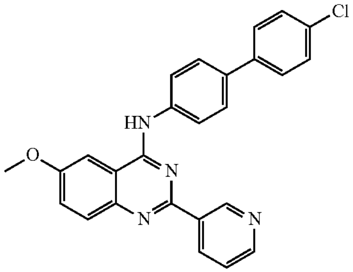 [SMILES: COc1ccc2nc(-c3cccnc3)nc(Nc3ccc(-c4ccc(Cl)cc4)cc3)c2c1] | HCl |

TABLE 1-continued
| | | | | |
|---|---|---|---|---|
| 425 | 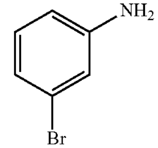 | 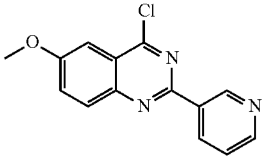 [SMILES: COc1ccc2nc(-c3cccnc3)nc(Cl)c2c1] | 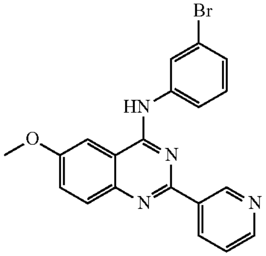 [SMILES: COc1ccc2nc(-c3cccnc3)nc(Nc3cccc(Br)c3)c2c1] | HCl |
| 426 | 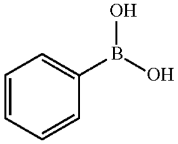 | 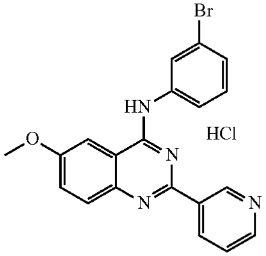 [SMILES: COc1ccc2nc(-c3cccnc3)nc(Nc3cccc(Br)c3)c2c1 ; Cl] HCl | 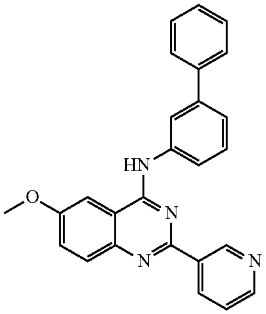 [SMILES: COc1ccc2nc(-c3cccnc3)nc(Nc3cccc(-c4ccccc4)c3)c2c1] | HCl |
| 427 | 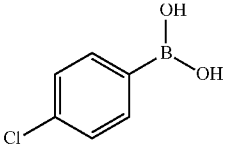 | 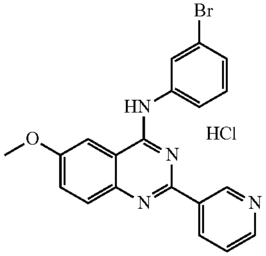 [SMILES: COc1ccc2nc(-c3cccnc3)nc(Nc3cccc(Br)c3)c2c1 ; Cl] HCl | 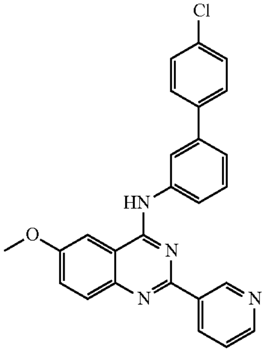 [SMILES: COc1ccc2nc(-c3cccnc3)nc(Nc3cccc(-c4ccc(Cl)cc4)c3)c2c1] | HCl |

TABLE 1-continued
| | | | | |
|---|---|---|---|---|
| 428 | 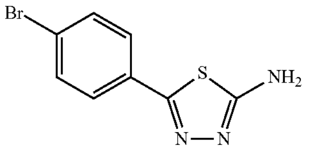 [SMILES: Nc1nnc(-c2ccc(Br)cc2)s1] | 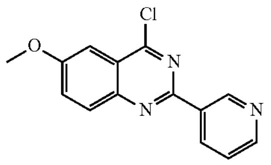 [SMILES: COc1ccc2nc(-c3cccnc3)nc(Cl)c2c1] | 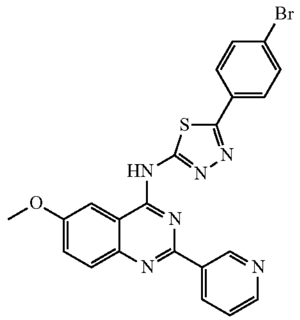 [SMILES: COc1ccc2nc(-c3cccnc3)nc(Nc3nnc(-c4ccc(Br)cc4)s3)c2c1] | 4 HCl |
| 429 | 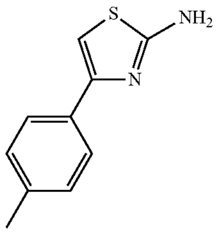 | 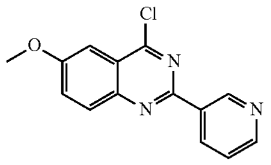 [SMILES: COc1ccc2nc(-c3cccnc3)nc(Cl)c2c1] | 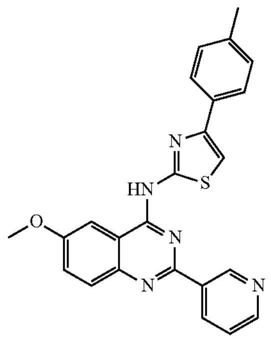 [SMILES: COc1ccc2nc(-c3cccnc3)nc(Nc3nc(-c4ccc(C)cc4)cs3)c2c1] | HCl |
| 430 | 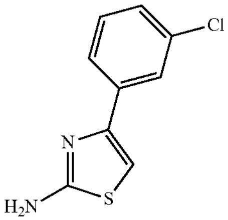 | 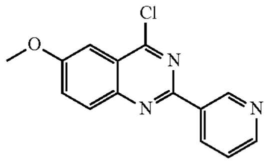 [SMILES: COc1ccc2nc(-c3cccnc3)nc(Cl)c2c1] | 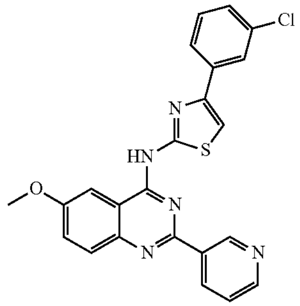 [SMILES: COc1ccc2nc(-c3cccnc3)nc(Nc3nc(-c4cccc(Cl)c4)cs3)c2c1] | 2 HCl |

TABLE 1-continued
| | | | | |
|---|---|---|---|---|
| 431 | 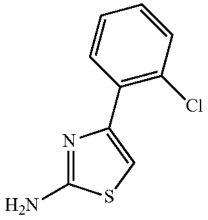 | 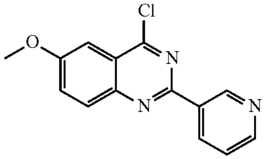 [SMILES: COc1ccc2nc(-c3cccnc3)nc(Cl)c2c1] | 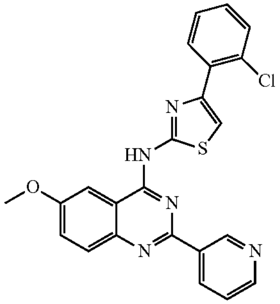 [SMILES: COc1ccc2nc(-c3cccnc3)nc(Nc3nc(-c4ccccc4Cl)cs3)c2c1] | HCl |
| 432 | 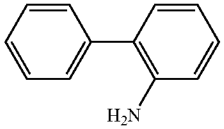 | 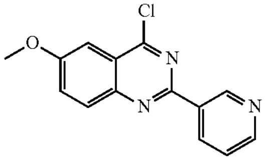 [SMILES: COc1ccc2nc(-c3cccnc3)nc(Cl)c2c1] | 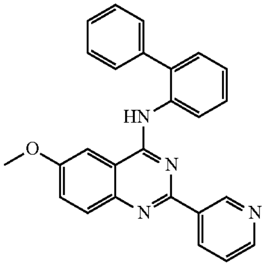 [SMILES: COc1ccc2nc(-c3cccnc3)nc(Nc3ccccc3-c3ccccc3)c2c1] | HCl |
| 433 | 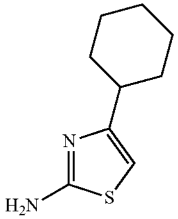 | 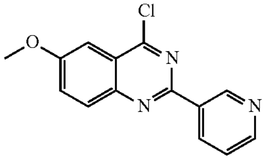 [SMILES: COc1ccc2nc(-c3cccnc3)nc(Cl)c2c1] | 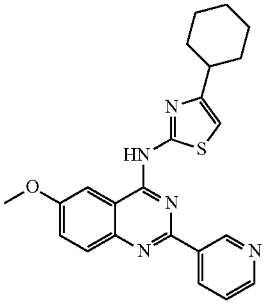 [SMILES: COc1ccc2nc(-c3cccnc3)nc(Nc3nc(C4CCCCC4)cs3)c2c1] | HCl |

TABLE 1-continued
| | | | | |
|---|---|---|---|---|
| 434 | 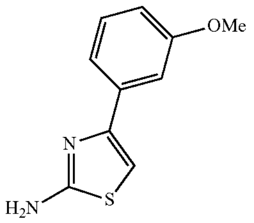 [SMILES: COc1cccc(-c2csc(N)n2)c1] | 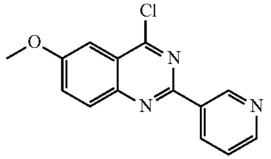 [SMILES: COc1ccc2nc(-c3cccnc3)nc(Cl)c2c1] | 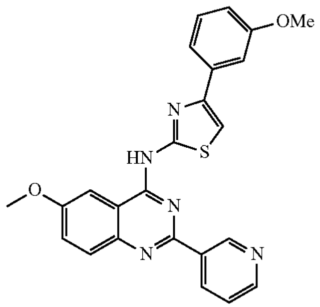 [SMILES: COc1cccc(-c2csc(Nc3nc(-c4cccnc4)nc4ccc(OC)cc34)n2)c1] | 2 HCl |
| 435 | 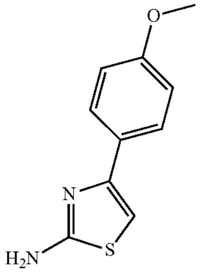 | 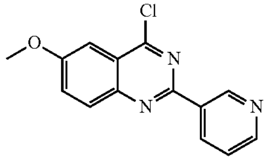 [SMILES: COc1ccc2nc(-c3cccnc3)nc(Cl)c2c1] | 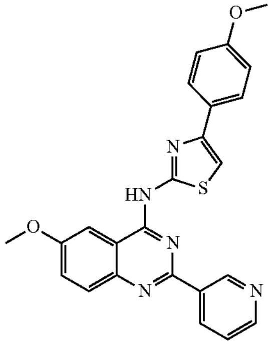 | 2 HCl |
| 436 | 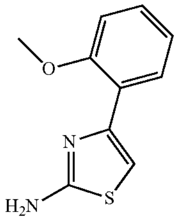 | 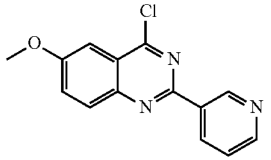 [SMILES: COc1ccc2nc(-c3cccnc3)nc(Cl)c2c1] | 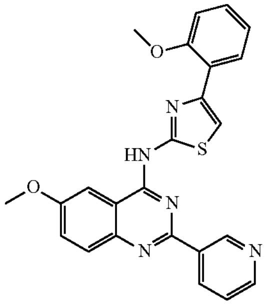 [SMILES: COc1ccc2nc(-c3cccnc3)nc(Nc3nc(-c4ccccc4OC)cs3)c2c1] | HCl |

TABLE 1-continued
| | | | | |
|---|---|---|---|---|
| 437 | 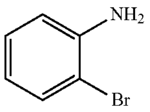 | 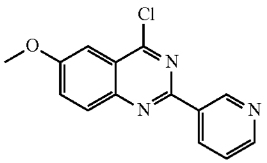 [SMILES: COc1ccc2nc(-c3cccnc3)nc(Cl)c2c1] | 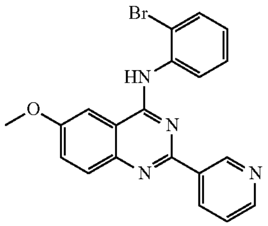 [SMILES: COc1ccc2nc(-c3cccnc3)nc(Nc3ccccc3Br)c2c1] | |
| 438 | 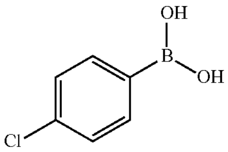 | 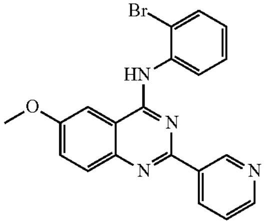 [SMILES: COc1ccc2nc(-c3cccnc3)nc(Nc3ccccc3Br)c2c1] | 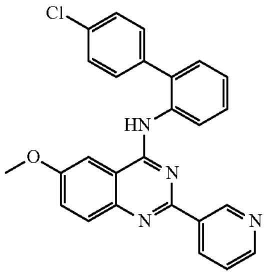 [SMILES: COc1ccc2nc(-c3cccnc3)nc(Nc3ccccc3-c3ccc(Cl)cc3)c2c1] | HCl |
| 439 | 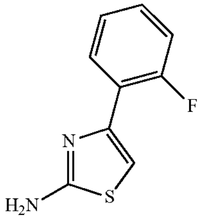 [SMILES: Nc1nc(-c2ccccc2F)cs1] | 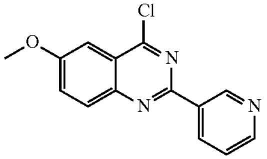 [SMILES: COc1ccc2nc(-c3cccnc3)nc(Cl)c2c1] | 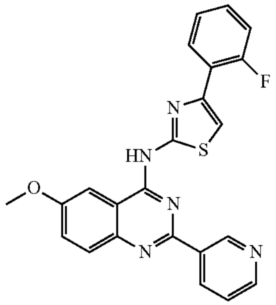 [SMILES: COc1ccc2nc(-c3cccnc3)nc(Nc3nc(-c4ccccc4F)cs3)c2c1] | HCl |

TABLE 1-continued
| | | | | |
|---|---|---|---|---|
| 440 | 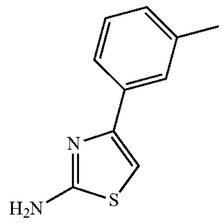 | 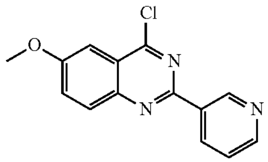 [SMILES: COc1ccc2nc(-c3cccnc3)nc(Cl)c2c1] | 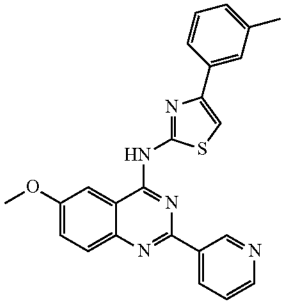 | HCl |
| 441 | 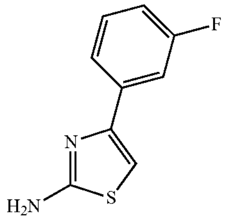 [SMILES: Nc1nc(-c2cccc(F)c2)cs1] | 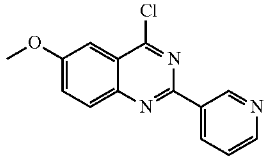 [SMILES: COc1ccc2nc(-c3cccnc3)nc(Cl)c2c1] | 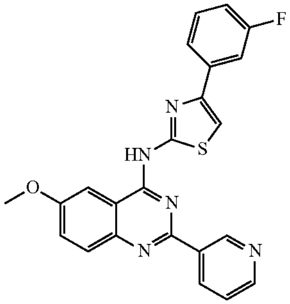 [SMILES: COc1ccc2nc(-c3cccnc3)nc(Nc3nc(-c4cccc(F)c4)cs3)c2c1] | HCl |
| 442 | 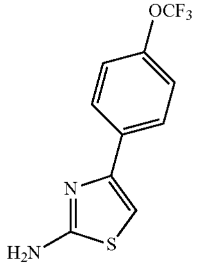 [SMILES: Nc1nc(-c2ccc(OC(F)(F)F)cc2)cs1] | 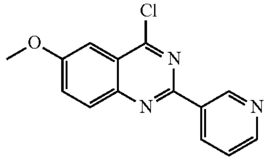 [SMILES: COc1ccc2nc(-c3cccnc3)nc(Cl)c2c1] | 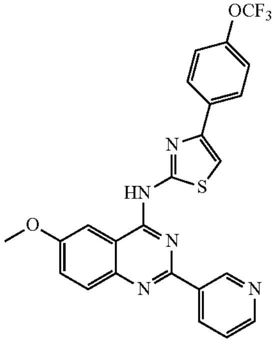 [SMILES: COc1ccc2nc(-c3cccnc3)nc(Nc3nc(-c4ccc(OC(F)(F)F)cc4)cs3)c2c1] | 2 HCl |

TABLE 1-continued
| | | | | |
|---|---|---|---|---|
| 443 | 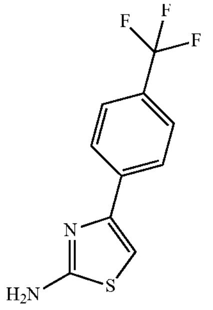 [SMILES: Nc1nc(-c2ccc(C(F)(F)F)cc2)cs1] | 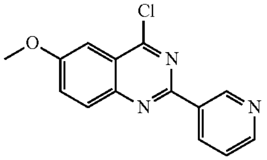 [SMILES: COc1ccc2nc(-c3cccnc3)nc(Cl)c2c1] | 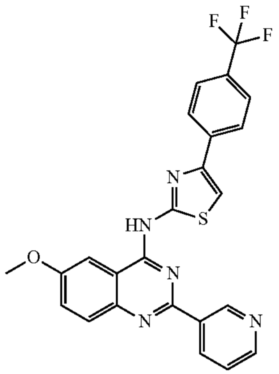 [SMILES: COc1ccc2nc(-c3cccnc3)nc(Nc3nc(-c4ccc(C(F)(F)F)cc4)cs3)c2c1] | 2 HCl |
| 444 | 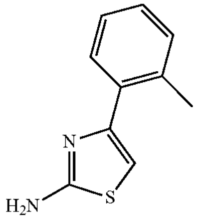 | 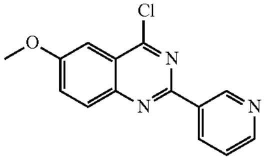 [SMILES: COc1ccc2nc(-c3cccnc3)nc(Cl)c2c1] | 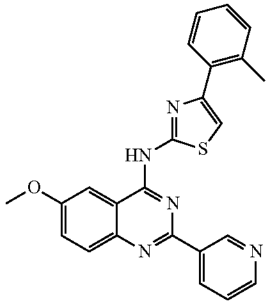 | 2 HCl |
| 445 | 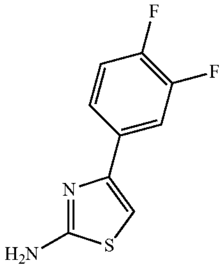 [SMILES: Nc1nc(-c2ccc(F)c(F)c2)cs1] | 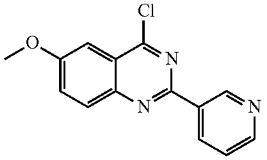 [SMILES: COc1ccc2nc(-c3cccnc3)nc(Cl)c2c1] | 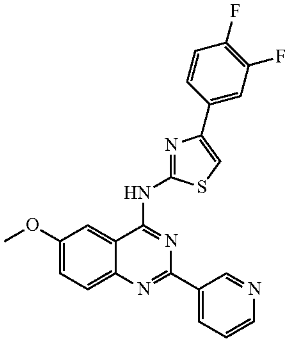 [SMILES: COc1ccc2nc(-c3cccnc3)nc(Nc3nc(-c4ccc(F)c(F)c4)cs3)c2c1] | 2 HCl |

TABLE 1-continued
| | | | | |
|---|---|---|---|---|
| 446 | 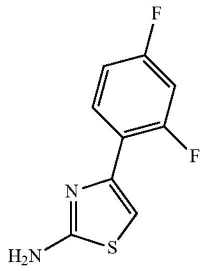 [SMILES: Nc1nc(-c2ccc(F)cc2F)cs1] | 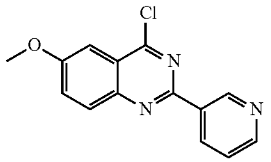 [SMILES: COc1ccc2nc(-c3cccnc3)nc(Cl)c2c1] | 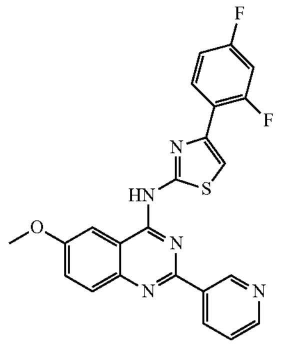 [SMILES: COc1ccc2nc(-c3cccnc3)nc(Nc3nc(-c4ccc(F)cc4F)cs3)c2c1] | HCl |
| 447 | 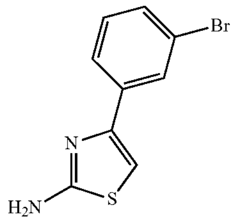 | 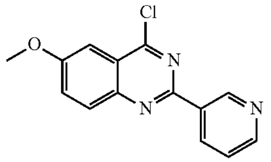 [SMILES: COc1ccc2nc(-c3cccnc3)nc(Cl)c2c1] | 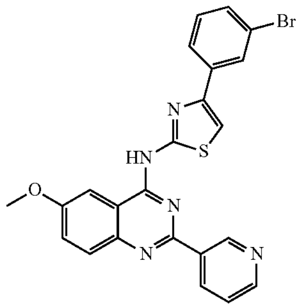 | 2 HCl |
| 448 | 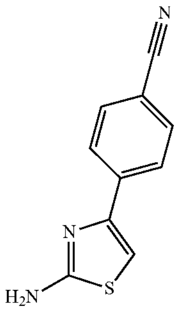 [SMILES: N#Cc1ccc(-c2csc(N)n2)cc1] | 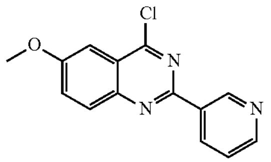 [SMILES: COc1ccc2nc(-c3cccnc3)nc(Cl)c2c1] | 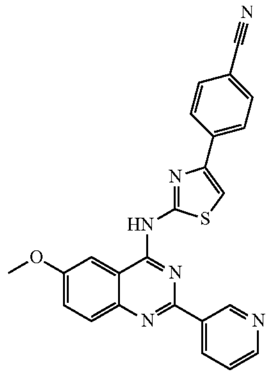 [SMILES: COc1ccc2nc(-c3cccnc3)nc(Nc3nc(-c4ccc(C#N)cc4)cs3)c2c1] | HCl |

TABLE 1-continued
| | | | | |
|---|---|---|---|---|
| 449 | 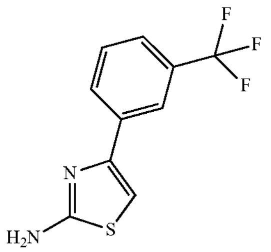 [SMILES: Nc1nc(-c2cccc(C(F)(F)F)c2)cs1] | 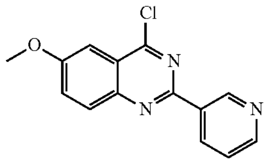 [SMILES: COc1ccc2nc(-c3cccnc3)nc(Cl)c2c1] | 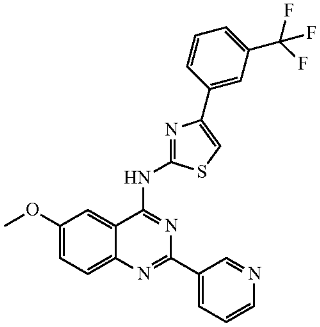 [SMILES: COc1ccc2nc(-c3cccnc3)nc(Nc3nc(-c4cccc(C(F)(F)F)c4)cs3)c2c1] | 2 HCl |
| 450 | 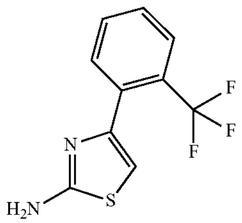 [SMILES: Nc1nc(-c2ccccc2C(F)(F)F)cs1] | 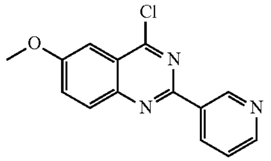 [SMILES: COc1ccc2nc(-c3cccnc3)nc(Cl)c2c1] | 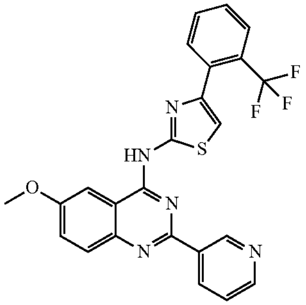 [SMILES: COc1ccc2nc(-c3cccnc3)nc(Nc3nc(-c4ccccc4C(F)(F)F)cs3)c2c1] | 2 HCl |
| 451 | 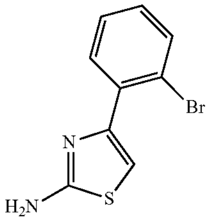 | 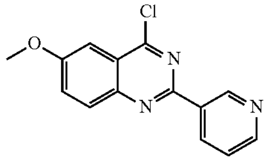 [SMILES: COc1ccc2nc(-c3cccnc3)nc(Cl)c2c1] | 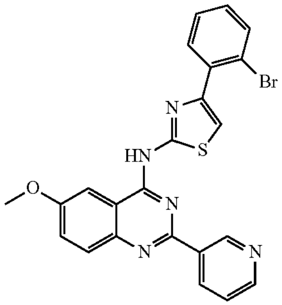 [SMILES: COc1ccc2nc(-c3cccnc3)nc(Nc3nc(-c4ccccc4Br)cs3)c2c1] | HCl |

TABLE 1-continued
| | | | | |
|---|---|---|---|---|
| 452 | 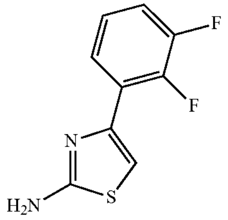 [SMILES: Nc1nc(-c2cccc(F)c2F)cs1] | 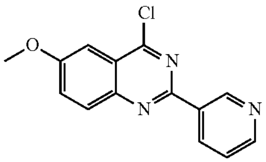 [SMILES: COc1ccc2nc(-c3cccnc3)nc(Cl)c2c1] | 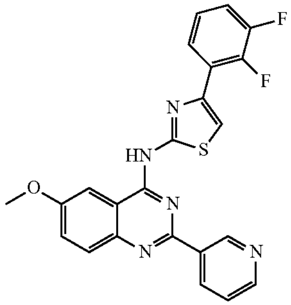 [SMILES: COc1ccc2nc(-c3cccnc3)nc(Nc3nc(-c4cccc(F)c4F)cs3)c2c1] | HCl |
| 453 | 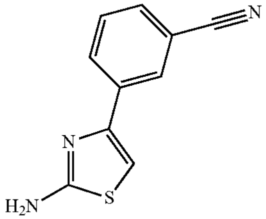 [SMILES: N#Cc1cccc(-c2csc(N)n2)c1] | 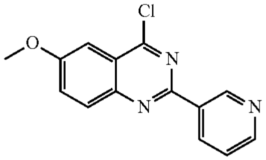 [SMILES: COc1ccc2nc(-c3cccnc3)nc(Cl)c2c1] | 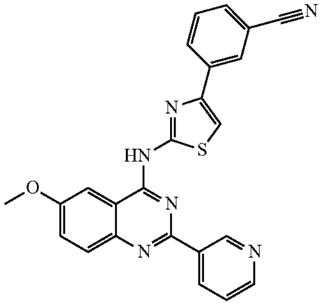 [SMILES: COc1ccc2nc(-c3cccnc3)nc(Nc3nc(-c4cccc(C#N)c4)cs3)c2c1] | 2 HCl |
| 454 | 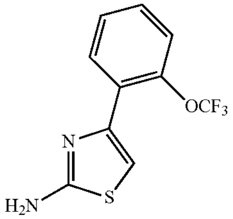 | 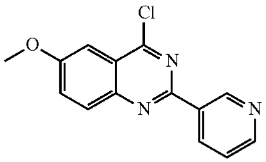 [SMILES: COc1ccc2nc(-c3cccnc3)nc(Cl)c2c1] | 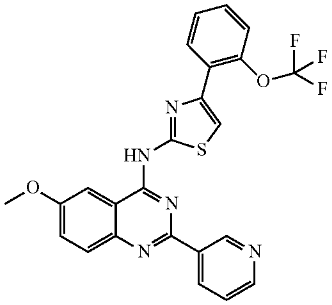 [SMILES: COc1ccc2nc(-c3cccnc3)nc(Nc3nc(-c4ccccc4OC(F)(F)F)cs3)c2c1] | 2 HCl |

TABLE 1-continued
| | | | | |
|---|---|---|---|---|
| 455 | 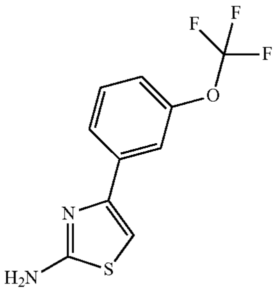 [SMILES: Nc1nc(-c2cccc(OC(F)(F)F)c2)cs1] | 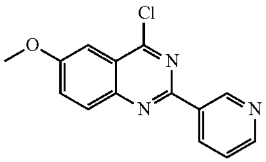 [SMILES: COc1ccc2nc(-c3cccnc3)nc(Cl)c2c1] | 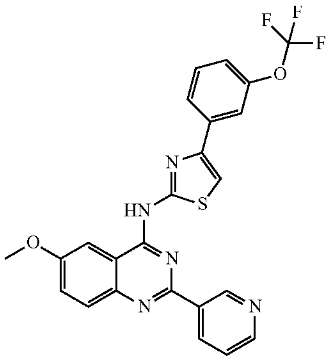 [SMILES: COc1ccc2nc(-c3cccnc3)nc(Nc3nc(-c4cccc(OC(F)(F)F)c4)cs3)c2c1] | HCl |
| 456 | 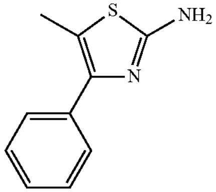 | 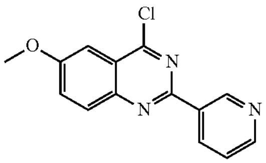 [SMILES: COc1ccc2nc(-c3cccnc3)nc(Cl)c2c1] | 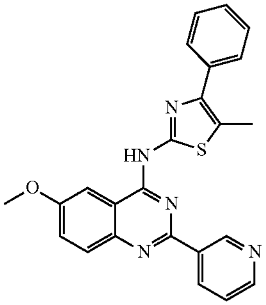 [SMILES: COc1ccc2nc(-c3cccnc3)nc(Nc3nc(-c4ccccc4)c(C)s3)c2c1] | 2 HCl |
| 457 | 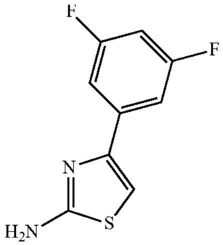 [SMILES: Nc1nc(-c2cc(F)cc(F)c2)cs1] | 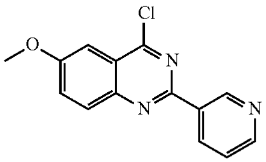 [SMILES: COc1ccc2nc(-c3cccnc3)nc(Cl)c2c1] | 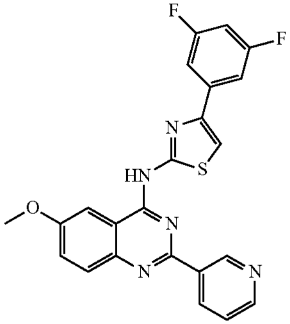 [SMILES: COc1ccc2nc(-c3cccnc3)nc(Nc3nc(-c4cc(F)cc(F)c4)cs3)c2c1] | HCl |

TABLE 1-continued
| | | | | |
|---|---|---|---|---|
| 458 | 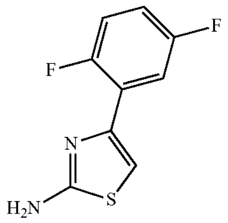 [SMILES: Nc1nc(-c2cc(F)ccc2F)cs1] | 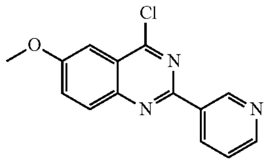 [SMILES: COc1ccc2nc(-c3cccnc3)nc(Cl)c2c1] | 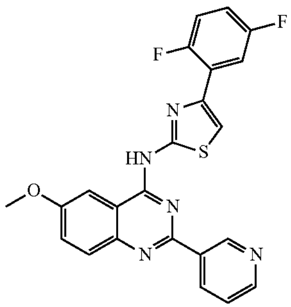 [SMILES: COc1ccc2nc(-c3cccnc3)nc(Nc3nc(-c4cc(F)ccc4F)cs3)c2c1] | HCl |
| 459 | 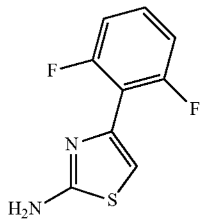 [SMILES: Nc1nc(-c2c(F)cccc2F)cs1] | 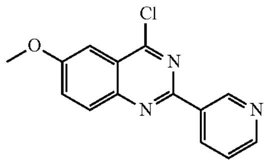 [SMILES: COc1ccc2nc(-c3cccnc3)nc(Cl)c2c1] | 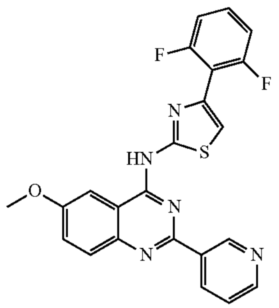 [SMILES: COc1ccc2nc(-c3cccnc3)nc(Nc3nc(-c4c(F)cccc4F)cs3)c2c1] | HCl |
| 460 | 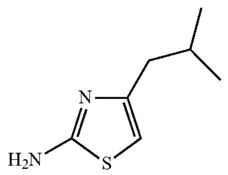 | 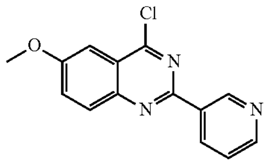 [SMILES: COc1ccc2nc(-c3cccnc3)nc(Cl)c2c1] | 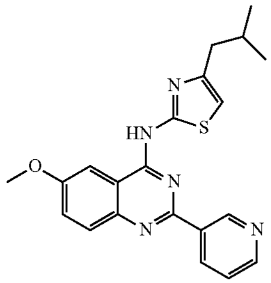 [SMILES: COc1ccc2nc(-c3cccnc3)nc(Nc3nc(CC(C)C)cs3)c2c1] | 2 HCl |

TABLE 1-continued
| | | | | |
|---|---|---|---|---|
| 461 | 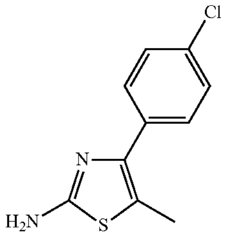 | 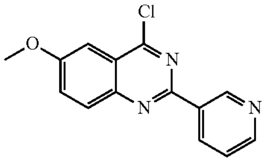 [SMILES: COc1ccc2nc(-c3cccnc3)nc(Cl)c2c1] | 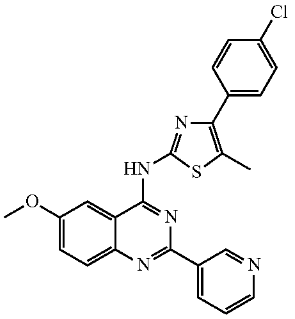 [SMILES: COc1ccc2nc(-c3cccnc3)nc(Nc3nc(-c4ccc(Cl)cc4)c(C)s3)c2c1] | 2 HCl |
| 462 | 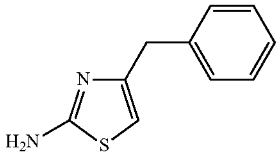 [SMILES: Nc1nc(Cc2ccccc2)cs1] | 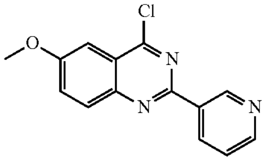 [SMILES: COc1ccc2nc(-c3cccnc3)nc(Cl)c2c1] | 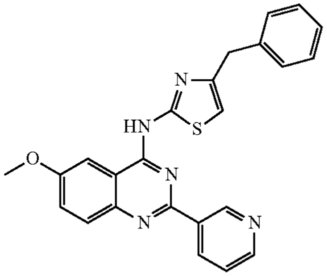 [SMILES: COc1ccc2nc(-c3cccnc3)nc(Nc3nc(Cc4ccccc4)cs3)c2c1] | 2 HCl |
| 463 | 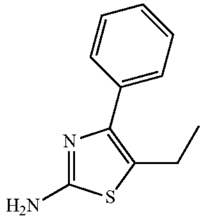 | 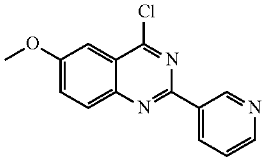 [SMILES: COc1ccc2nc(-c3cccnc3)nc(Cl)c2c1] | 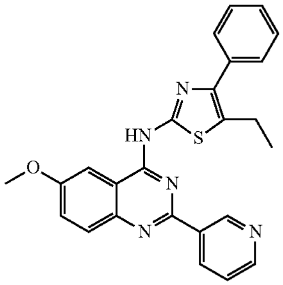 [SMILES: CCc1sc(Nc2nc(-c3cccnc3)nc3ccc(OC)cc23)nc1-c1ccccc1] | 2 HCl |

TABLE 1-continued
| | | | | |
|---|---|---|---|---|
| 464 | 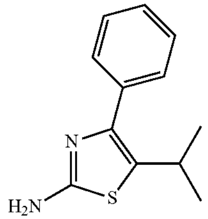 | 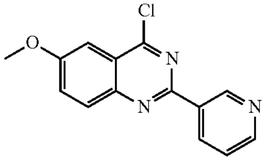 [SMILES: COc1ccc2nc(-c3cccnc3)nc(Cl)c2c1] | 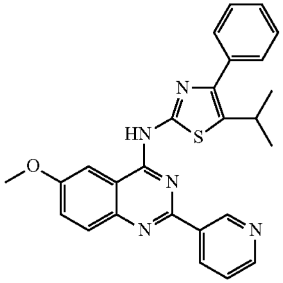 [SMILES: COc1ccc2nc(-c3cccnc3)nc(Nc3nc(-c4ccccc4)c(C(C)C)s3)c2c1] | 2 HCl |
| 465 | 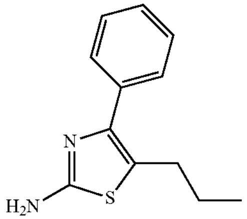 | 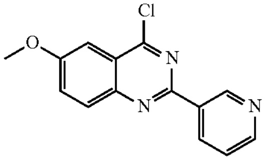 [SMILES: COc1ccc2nc(-c3cccnc3)nc(Cl)c2c1] | 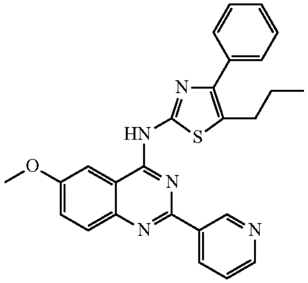 [SMILES: CCCc1sc(Nc2nc(-c3cccnc3)nc3ccc(OC)cc23)nc1-c1ccccc1] | 2 HCl |
| 466 | 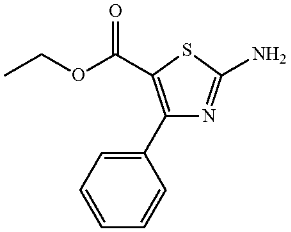 [SMILES: CCOC(=O)c1sc(N)nc1-c1ccccc1] | 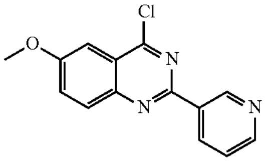 [SMILES: COc1ccc2nc(-c3cccnc3)nc(Cl)c2c1] | 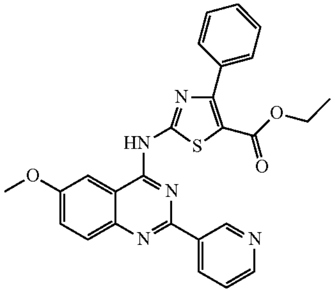 [SMILES: CCOC(=O)c1sc(Nc2nc(-c3cccnc3)nc3ccc(OC)cc23)nc1-c1ccccc1] | 2 HCl |

TABLE 1-continued
| | | | | |
|---|---|---|---|---|
| 467 | 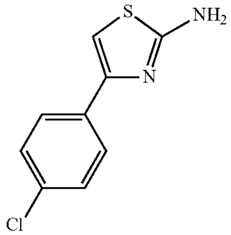 [SMILES: Nc1nc(-c2ccc(Cl)cc2)cs1] | 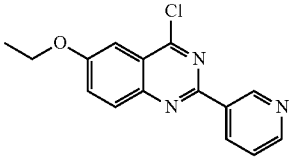 [SMILES: CCOc1ccc2nc(-c3cccnc3)nc(Cl)c2c1] | 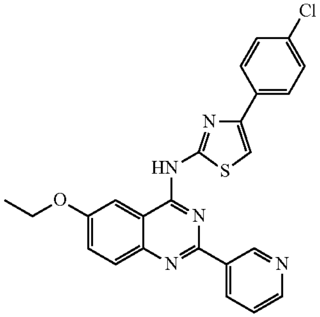 [SMILES: CCOc1ccc2nc(-c3cccnc3)nc(Nc3nc(-c4ccc(Cl)cc4)cs3)c2c1] | HCl |
| 468 | 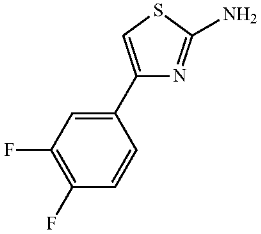 [SMILES: Nc1nc(-c2ccc(F)c(F)c2)cs1] | 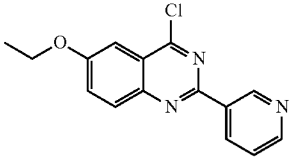 [SMILES: CCOc1ccc2nc(-c3cccnc3)nc(Cl)c2c1] | 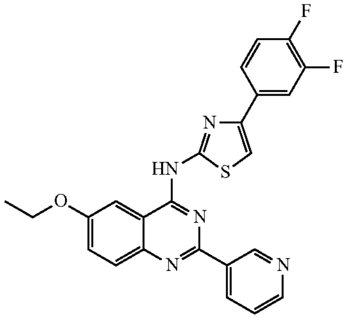 [SMILES: CCOc1ccc2nc(-c3cccnc3)nc(Nc3nc(-c4ccc(F)c(F)c4)cs3)c2c1] | 2 HCl |
| 469 | 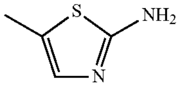 | 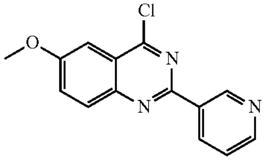 [SMILES: COc1ccc2nc(-c3cccnc3)nc(Cl)c2c1] | 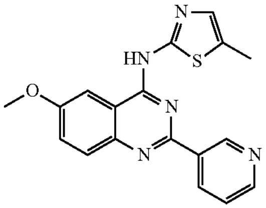 [SMILES: COc1ccc2nc(-c3cccnc3)nc(Nc3ncc(C)s3)c2c1] | 2 HCl |

TABLE 1-continued
| | | | | |
|---|---|---|---|---|
| 470 | 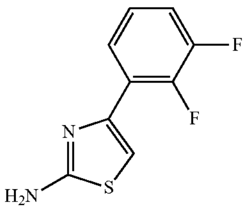 [SMILES: Nc1nc(-c2cccc(F)c2F)cs1] | 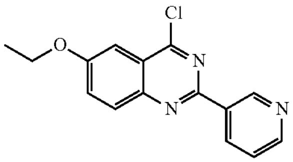 [SMILES: CCOc1ccc2nc(-c3cccnc3)nc(Cl)c2c1] | 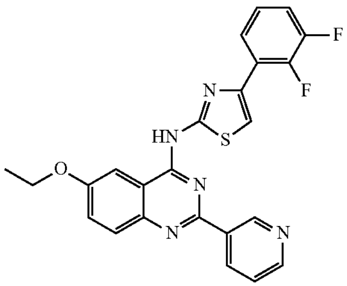 [SMILES: CCOc1ccc2nc(-c3cccnc3)nc(Nc3nc(-c4cccc(F)c4F)cs3)c2c1] | HCl |
| 471 | 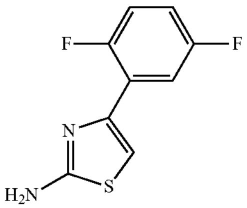 [SMILES: Nc1nc(-c2cc(F)ccc2F)cs1] | 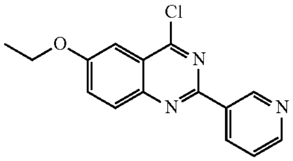 [SMILES: CCOc1ccc2nc(-c3cccnc3)nc(Cl)c2c1] | 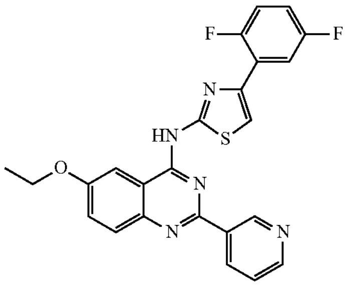 [SMILES: CCOc1ccc2nc(-c3cccnc3)nc(Nc3nc(-c4cc(F)ccc4F)cs3)c2c1] | 2 HCl |
| 472 | 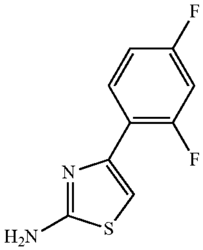 [SMILES: Nc1nc(-c2ccc(F)cc2F)cs1] | 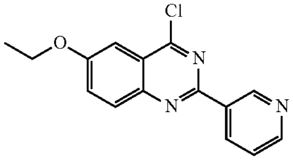 [SMILES: CCOc1ccc2nc(-c3cccnc3)nc(Cl)c2c1] | 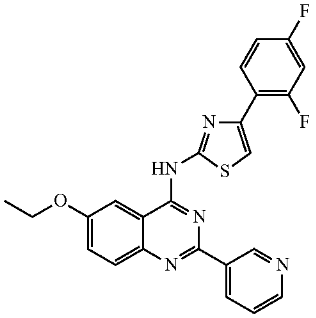 [SMILES: CCOc1ccc2nc(-c3cccnc3)nc(Nc3nc(-c4ccc(F)cc4F)cs3)c2c1] | 3 HCl |

TABLE 1-continued
| | | | | |
|---|---|---|---|---|
| 473 | 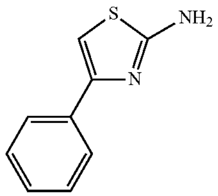 [SMILES: Nc1nc(-c2ccccc2)cs1] | 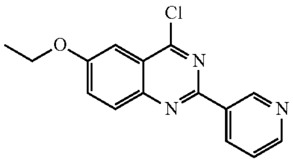 [SMILES: CCOc1ccc2nc(-c3cccnc3)nc(Cl)c2c1] | 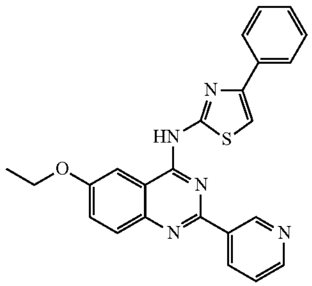 [SMILES: CCOc1ccc2nc(-c3cccnc3)nc(Nc3nc(-c4ccccc4)cs3)c2c1] | 2 HCl |
| 474 | 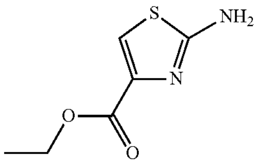 | 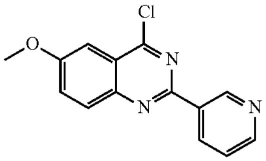 [SMILES: COc1ccc2nc(-c3cccnc3)nc(Cl)c2c1] | 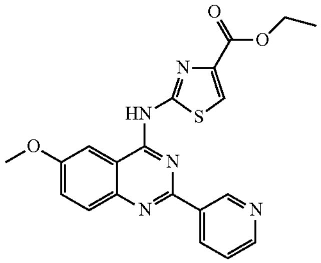 [SMILES: CCOC(=O)c1csc(Nc2nc(-c3cccnc3)nc3ccc(OC)cc23)n1] | |
| 475 | 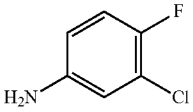 | 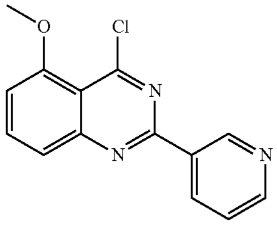 [SMILES: COc1cccc2nc(-c3cccnc3)nc(Cl)c12] | 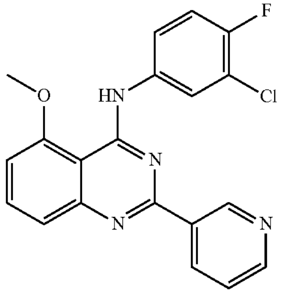 [SMILES: COc1cccc2nc(-c3cccnc3)nc(Nc3ccc(F)c(Cl)c3)c12] | HCl |

TABLE 1-continued
| | | | |
|---|---|---|---|
| 476 | 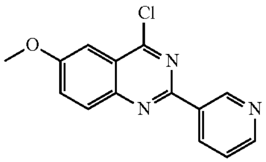 [SMILES: COc1ccc2nc(-c3cccnc3)nc(Cl)c2c1] | 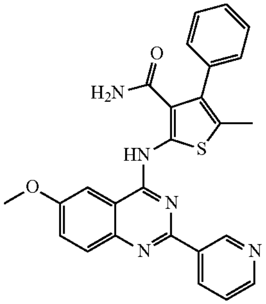 [SMILES: COc1ccc2nc(-c3cccnc3)nc(Nc3sc(C)c(-c4ccccc4)c3C(N)=O)c2c1] | HCl |
| 477 | 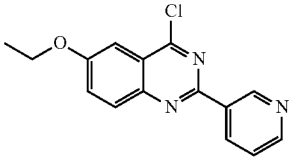 [SMILES: CCOc1ccc2nc(-c3cccnc3)nc(Cl)c2c1] | 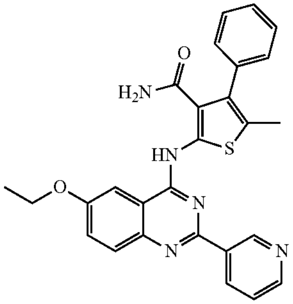 [SMILES: CCOc1ccc2nc(-c3cccnc3)nc(Nc3sc(C)c(-c4ccccc4)c3C(N)=O)c2c1] | HCl |
| 478 | 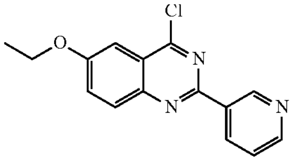 [SMILES: CCOc1ccc2nc(-c3cccnc3)nc(Cl)c2c1] | 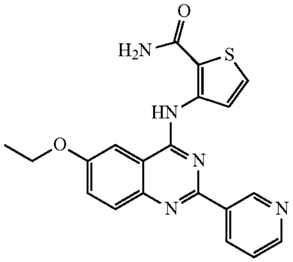 [SMILES: CCOc1ccc2nc(-c3cccnc3)nc(Nc3ccsc3C(N)=O)c2c1] | HCl |

TABLE 1-continued
| | | | |
|---|---|---|---|
| 479 | 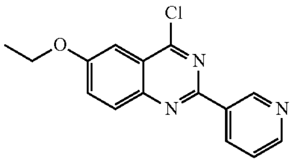 [SMILES: CCOc1ccc2nc(-c3cccnc3)nc(Cl)c2c1] | 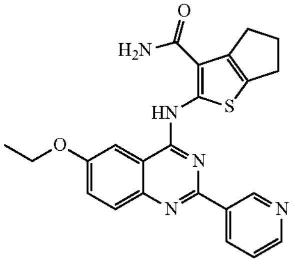 [SMILES: CCOc1ccc2nc(-c3cccnc3)nc(Nc3sc4c(c3C(N)=O)CCC4)c2c1] | HCl |
| 480 | 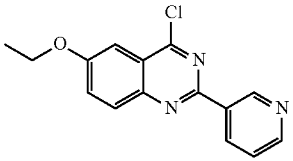 [SMILES: CCOc1ccc2nc(-c3cccnc3)nc(Cl)c2c1] | 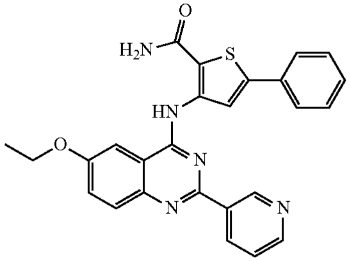 [SMILES: CCOc1ccc2nc(-c3cccnc3)nc(Nc3cc(-c4ccccc4)sc3C(N)=O)c2c1] | HCl |
| 481 | 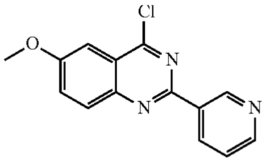 [SMILES: COc1ccc2nc(-c3cccnc3)nc(Cl)c2c1] | 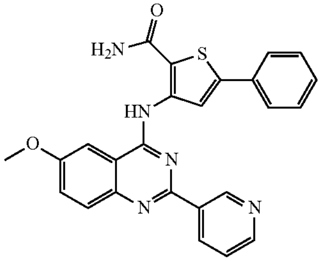 [SMILES: COc1ccc2nc(-c3cccnc3)nc(Nc3cc(-c4ccccc4)sc3C(N)=O)c2c1] | HCl |
| 482 | 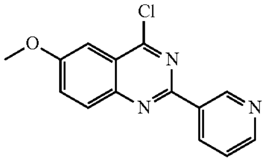 [SMILES: COc1ccc2nc(-c3cccnc3)nc(Cl)c2c1] | 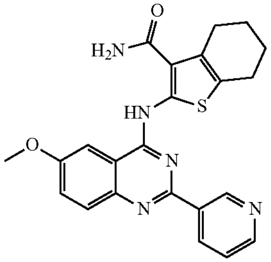 [SMILES: COc1ccc2nc(-c3cccnc3)nc(Nc3sc4c(c3C(N)=O)CCCC4)c2c1] | HCl |

TABLE 1-continued
| | | | |
|---|---|---|---|
| 483 | 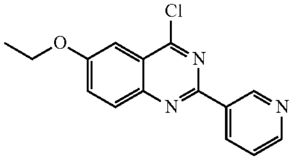 [SMILES: CCOc1ccc2nc(-c3cccnc3)nc(Cl)c2c1] | 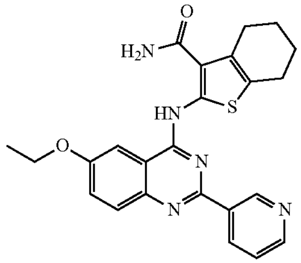 [SMILES: CCOc1ccc2nc(-c3cccnc3)nc(Nc3sc4c(c3C(N)=O)CCCC4)c2c1] | HCl |
| 484 | 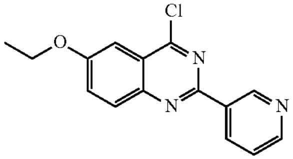 [SMILES: CCOc1ccc2nc(-c3cccnc3)nc(Cl)c2c1] | 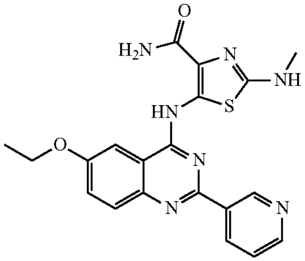 [SMILES: CCOc1ccc2nc(-c3cccnc3)nc(Nc3sc(NC)nc3C(N)=O)c2c1] | HCl |
| 485 | 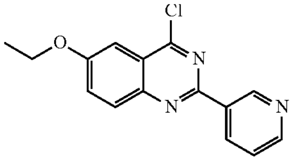 [SMILES: CCOc1ccc2nc(-c3cccnc3)nc(Cl)c2c1] | 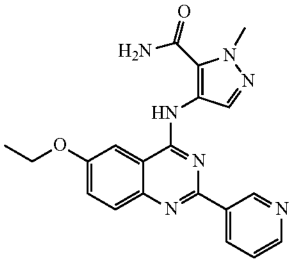 [SMILES: CCOc1ccc2nc(-c3cccnc3)nc(Nc3cnn(C)c3C(N)=O)c2c1] | HCl |
| 486 | 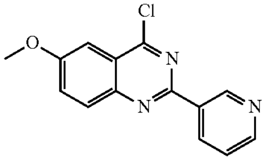 [SMILES: COc1ccc2nc(-c3cccnc3)nc(Cl)c2c1] | 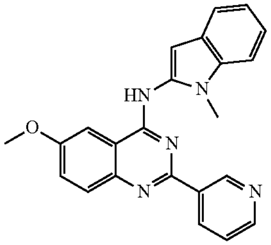 [SMILES: COc1ccc2nc(-c3cccnc3)nc(Nc3cc4ccccc4n3C)c2c1] | 2 HCl |

TABLE 1-continued
| | | | |
|---|---|---|---|
| 487 | 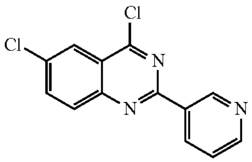 [SMILES: Clc1ccc2nc(-c3cccnc3)nc(Cl)c2c1] | 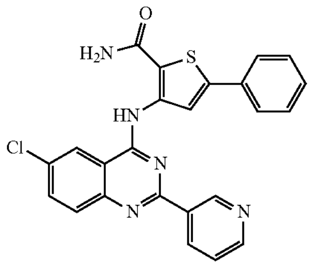 [SMILES: NC(=O)c1sc(-c2ccccc2)cc1Nc1nc(-c2cccnc2)nc2ccc(Cl)cc12] | 2 HCl |
| 488 | 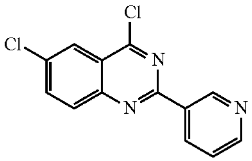 [SMILES: Clc1ccc2nc(-c3cccnc3)nc(Cl)c2c1] | 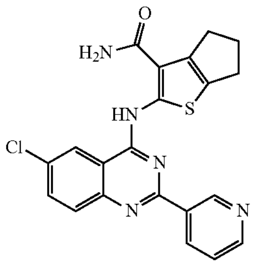 [SMILES: NC(=O)c1c(Nc2nc(-c3cccnc3)nc3ccc(Cl)cc23)sc2c1CCC2] | 2 HCl |
| 489 | 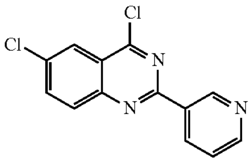 [SMILES: Clc1ccc2nc(-c3cccnc3)nc(Cl)c2c1] | 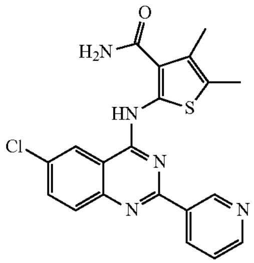 [SMILES: Cc1sc(Nc2nc(-c3cccnc3)nc3ccc(Cl)cc23)c(C(N)=O)c1C] | 2 HCl |
| 490 | 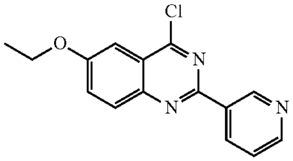 [SMILES: CCOc1ccc2nc(-c3cccnc3)nc(Cl)c2c1] | 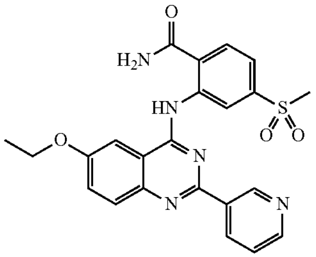 [SMILES: CCOc1ccc2nc(-c3cccnc3)nc(Nc3cc(S(C)(=O)=O)ccc3C(N)=O)c2c1] | |

TABLE 1-continued
| | | | |
|---|---|---|---|
| 491 | 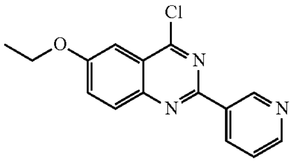 [SMILES: CCOc1ccc2nc(-c3cccnc3)nc(Cl)c2c1] | 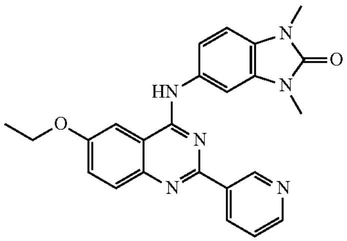 [SMILES: CCOc1ccc2nc(-c3cccnc3)nc(Nc3ccc4c(c3)n(C)c(=O)n4C)c2c1] | |
| 492 | | 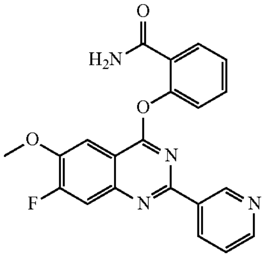 [SMILES: COc1cc2c(Oc3ccccc3C(N)=O)nc(-c3cccnc3)nc2cc1F] | |
| 493 | | 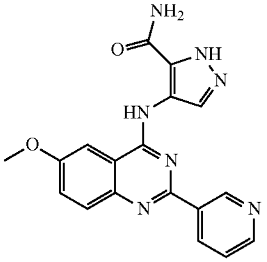 [SMILES: COc1ccc2nc(-c3cccnc3)nc(Nc3cn[nH]c3C(N)=O)c2c1] | 2 HCl |
| 494 | | 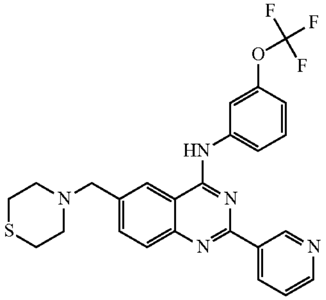 [SMILES: FC(F)(F)Oc1cccc(Nc2nc(-c3cccnc3)nc3ccc(CN4CCSCC4)cc23)c1] | |

TABLE 1-continued
| | | |
|---|---|---|
| 495 | 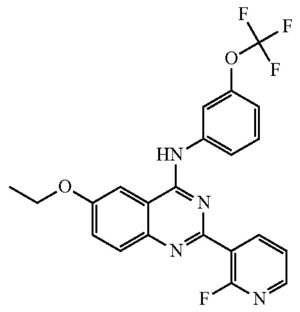 [SMILES: CCOc1ccc2nc(-c3cccnc3F)nc(Nc3cccc(OC(F)(F)F)c3)c2c1] | |
| 496 | 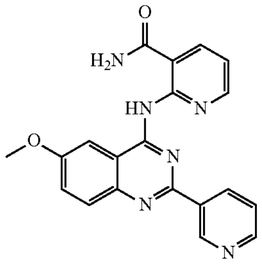 [SMILES: COc1ccc2nc(-c3cccnc3)nc(Nc3ncccc3C(N)=O)c2c1] | |
| 497 | 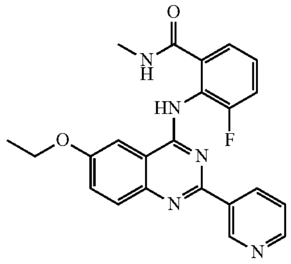 [SMILES: CCOc1ccc2nc(-c3cccnc3)nc(Nc3c(F)cccc3C(=O)NC)c2c1] | 2 HCl |

TABLE 1-continued
| | | |
|---|---|---|
| 498 | 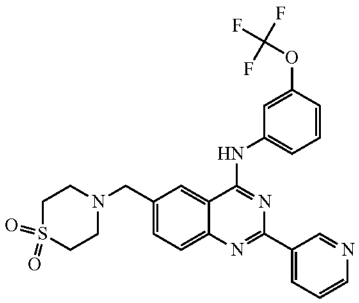 [SMILES: O=S1(=O)CCN(Cc2ccc3nc(-c4cccnc4)nc(Nc4cccc(OC(F)(F)F)c4)c3c2)CC1] | |
| 499 | 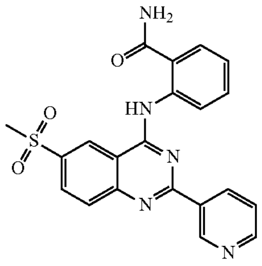 [SMILES: CS(=O)(=O)c1ccc2nc(-c3cccnc3)nc(Nc3ccccc3C(N)=O)c2c1] | 2 HCl |
| 501 | 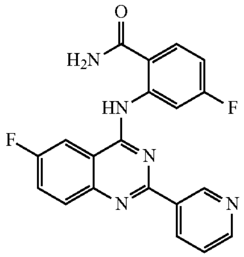 [SMILES: NC(=O)c1ccc(F)cc1Nc1nc(-c2cccnc2)nc2ccc(F)cc12] | HCl |
| 502 | 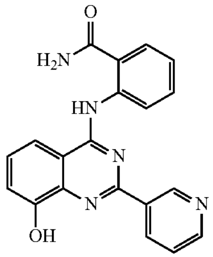 [SMILES: NC(=O)c1ccccc1Nc1nc(-c2cccnc2)nc2c(O)cccc12] | |

TABLE 1-continued
| | | | | |
|---|---|---|---|---|
| 503 | | | 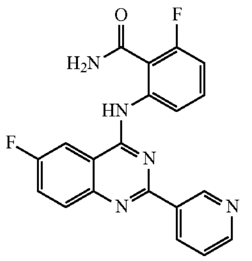 [SMILES: NC(=O)c1c(F)cccc1Nc1nc(-c2cccnc2)nc2ccc(F)cc12] | |
| 504 | | | 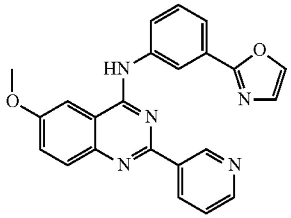 [SMILES: COc1ccc2nc(-c3cccnc3)nc(Nc3cccc(-c4ncco4)c3)c2c1] | HCl |
| 505 | 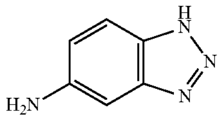 | 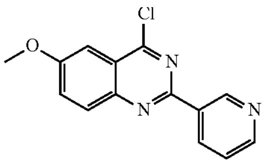 [SMILES: COc1ccc2nc(-c3cccnc3)nc(Cl)c2c1] | 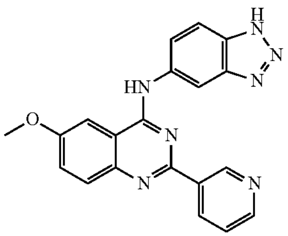 [SMILES: COc1ccc2nc(-c3cccnc3)nc(Nc3ccc4[nH]nnc4c3)c2c1] | |
| 506 | 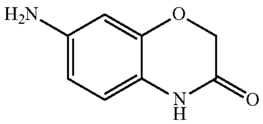 | 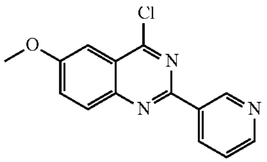 [SMILES: COc1ccc2nc(-c3cccnc3)nc(Cl)c2c1] | 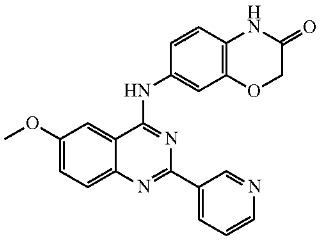 | |

TABLE 1-continued
| | | | |
|---|---|---|---|
| 507 | 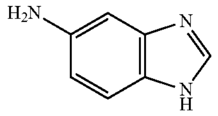 | 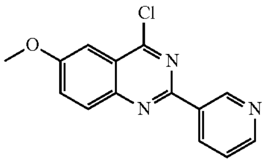 [SMILES: COc1ccc2nc(-c3cccnc3)nc(Cl)c2c1] | 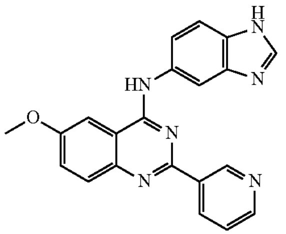 [SMILES: COc1ccc2nc(-c3cccnc3)nc(Nc3ccc4[nH]cnc4c3)c2c1] |
| 508 | 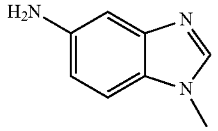 | 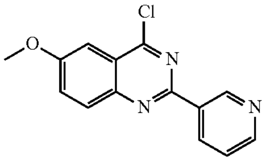 [SMILES: COc1ccc2nc(-c3cccnc3)nc(Cl)c2c1] | 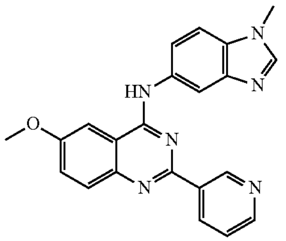 [SMILES: COc1ccc2nc(-c3cccnc3)nc(Nc3ccc4c(c3)ncn4C)c2c1] |
| 509 | 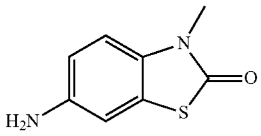 | 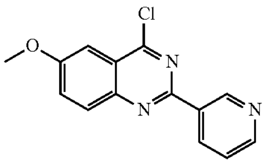 [SMILES: COc1ccc2nc(-c3cccnc3)nc(Cl)c2c1] | 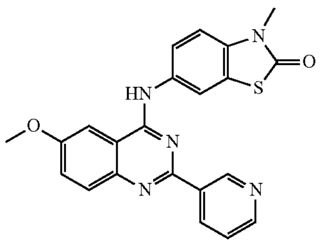 [SMILES: COc1ccc2nc(-c3cccnc3)nc(Nc3ccc4c(c3)sc(=O)n4C)c2c1] |
| 510 | 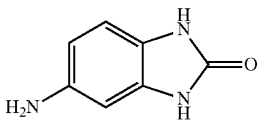 [SMILES: Nc1ccc2[nH]c(=O)[nH]c2c1] | 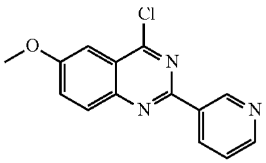 [SMILES: COc1ccc2nc(-c3cccnc3)nc(Cl)c2c1] | 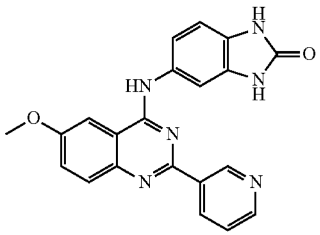 [SMILES: COc1ccc2nc(-c3cccnc3)nc(Nc3ccc4[nH]c(=O)[nH]c4c3)c2c1] |

TABLE 1-continued
| | | | | |
|---|---|---|---|---|
| 511 | 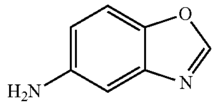 | 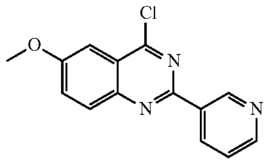 [SMILES: COc1ccc2nc(-c3cccnc3)nc(Cl)c2c1] | 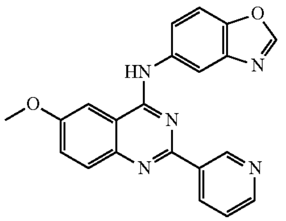 [SMILES: COc1ccc2nc(-c3cccnc3)nc(Nc3ccc4ocnc4c3)c2c1] | |
| 512 | 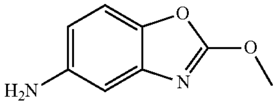 | 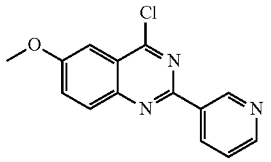 [SMILES: COc1ccc2nc(-c3cccnc3)nc(Cl)c2c1] | 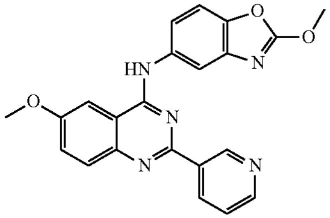 | |
| 513 | 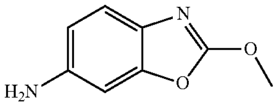 | 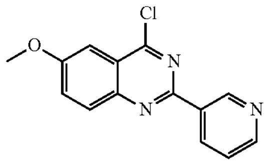 [SMILES: COc1ccc2nc(-c3cccnc3)nc(Cl)c2c1] | 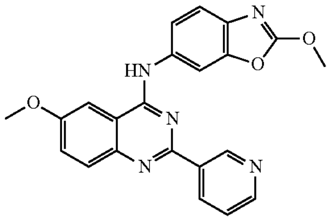 | |
| 514 | 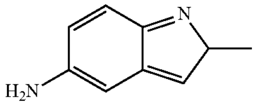 | 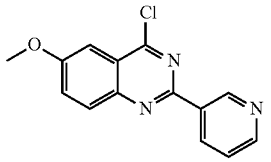 [SMILES: COc1ccc2nc(-c3cccnc3)nc(Cl)c2c1] | 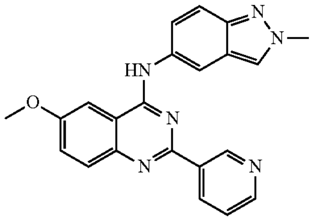 | 2 HCl |

TABLE 1-continued
| | | | | |
|---|---|---|---|---|
| 515 | 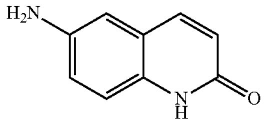 | 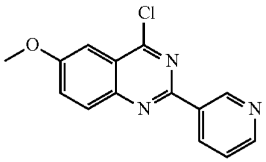 [SMILES: COc1ccc2nc(-c3cccnc3)nc(Cl)c2c1] | 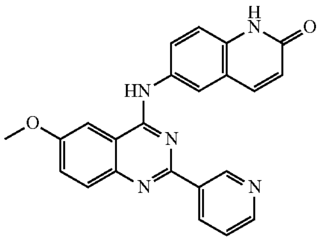 [SMILES: COc1ccc2nc(-c3cccnc3)nc(Nc3ccc4[nH]c(=O)ccc4c3)c2c1] | HCl |
| 516 | 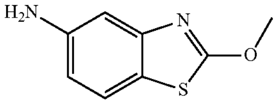 | 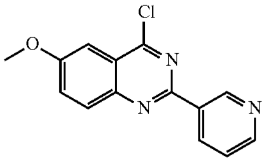 [SMILES: COc1ccc2nc(-c3cccnc3)nc(Cl)c2c1] | 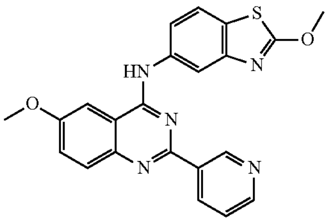 | |
| 517 | 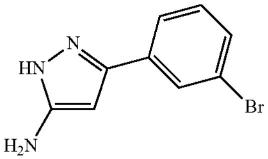 [SMILES: Nc1cc(-c2cccc(Br)c2)n[nH]1] | 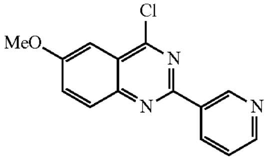 [SMILES: COc1ccc2nc(-c3cccnc3)nc(Cl)c2c1] | 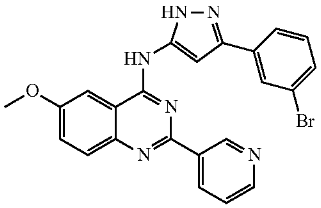 [SMILES: COc1ccc2nc(-c3cccnc3)nc(Nc3cc(-c4cccc(Br)c4)n[nH]3)c2c1] | HCl |
| 518 | 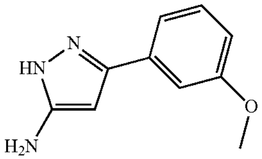 | 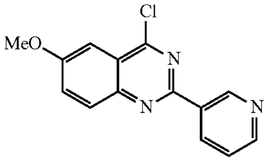 [SMILES: COc1ccc2nc(-c3cccnc3)nc(Cl)c2c1] | 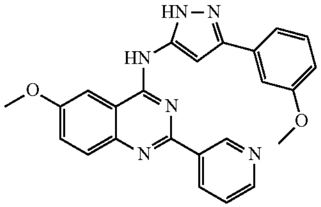 [SMILES: COc1cccc(-c2cc(Nc3nc(-c4cccnc4)nc4ccc(OC)cc34)[nH]n2)c1] | 2 HCl |

TABLE 1-continued
| | | | | |
|---|---|---|---|---|
| 519 | 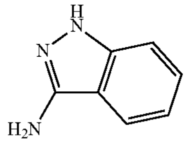 | 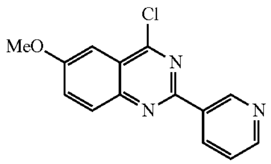 [SMILES: COc1ccc2nc(-c3cccnc3)nc(Cl)c2c1] | 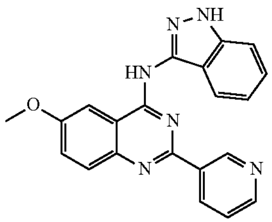 [SMILES: COc1ccc2nc(-c3cccnc3)nc(Nc3n[nH]c4ccccc34)c2c1] | 2 HCl |
| 520 | 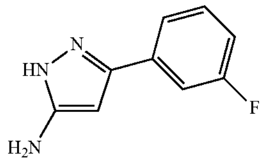 | 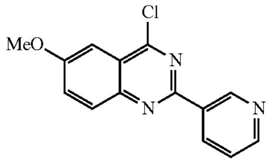 [SMILES: COc1ccc2nc(-c3cccnc3)nc(Cl)c2c1] | 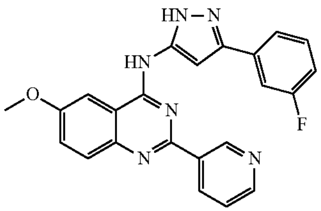 [SMILES: COc1ccc2nc(-c3cccnc3)nc(Nc3cc(-c4cccc(F)c4)n[nH]3)c2c1] | HCl |
| 521 | 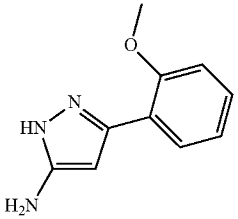 | 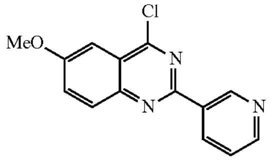 [SMILES: COc1ccc2nc(-c3cccnc3)nc(Cl)c2c1] | 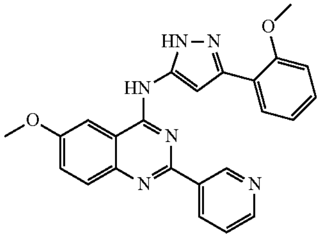 [SMILES: COc1ccc2nc(-c3cccnc3)nc(Nc3cc(-c4ccccc4OC)n[nH]3)c2c1] | HCl |
| 1758 | 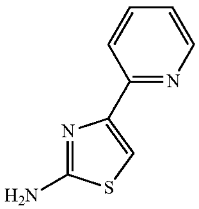 [SMILES: Nc1nc(-c2ccccn2)cs1] | 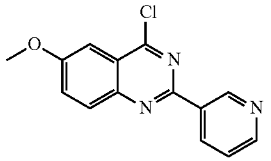 [SMILES: COc1ccc2nc(-c3cccnc3)nc(Cl)c2c1] | 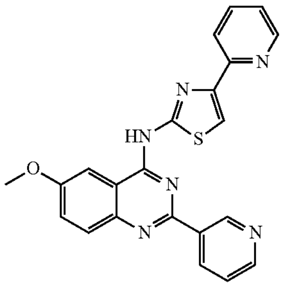 [SMILES: COc1ccc2nc(-c3cccnc3)nc(Nc3nc(-c4ccccn4)cs3)c2c1] | 3 HCl |

TABLE 1-continued

| | | | | |
|---|---|---|---|---|
| 1759 | 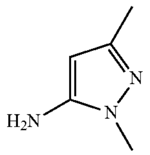 | 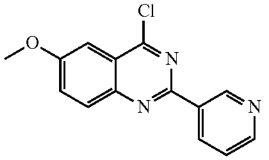 [SMILES: COc1ccc2nc(-c3cccnc3)nc(Cl)c2c1] | 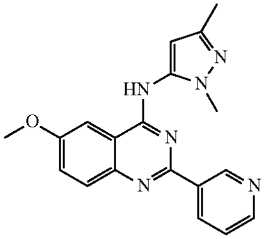 [SMILES: COc1ccc2nc(-c3cccnc3)nc(Nc3cc(C)nn3C)c2c1] | 3 HCl |

| Number | $^1$H NMR | $^1$H NMR Solvent | Purity percent | Method of Coupling | LCMS | Retention Time | LCMS Method |
|---|---|---|---|---|---|---|---|
| 414 | 1H NMR (DMSO-d6) ppm 9.72 (s, 1H), 9.16 (brs, 1H), 8.93 (d, J = 4.36 Hz, 1H), 8.14 (br, 1H), 7.96 (brm, 2H), 7.63 (dd, J = 9.08, 2.56 Hz, 1H), 7.00 (s, 1H), 3.98 (s, 3H), 2.37 (s, 3H). The 1H of 2HCl and NH— were not observed. | DMSO | >98 | G12 Temperature at 100° C. | | | |
| 415 | 1H NMR (DMSO-d6) ppm 12.60 (brs, 1H), 9.78 (s, 1H), 9.12 (d, J = 8.00 Hz, 1H), 8.86 (brs, 1H), 8.35 (brd, J = 2.60 Hz, 1H), 8.01 (d, J = 8.56 Hz, 2H), 7.96 (d, J = 9.08 Hz, 1H), 7.92 (s, 1H), 7.86 (m, 1H), 7.69 (d, J = 8.56 Hz, 2H), 7.63 (dd, J = 9.08, 2.60 Hz, 1H), 4.02 (s, 3H). The 1H of HCl was not observed. | DMSO | >98 | G12 Temperature at 100° C. | | | |
| 416 | 1H NMR (DMSO-d6) ppm 12.80-12.40 (br, 1H), 9.79 (d, J = 1.64 Hz, 1H), 9.16 (d, J = 7.88 Hz, 1H), 8.88 (d, J = 3.88 Hz, 1H), 8.36 (brd, J = 2.64 Hz, 1H), 8.06-8.04 (m, 2H), 7.96 (d, J = 9.08 Hz, 1H), 7.90 (m, 1H), 7.85 (s, 1H), 7.63 (dd, J = 9.08, 2.64 Hz, 1H), 7.49 (m, 2H), 7.38 (m, 1H), 4.02 (s, 3H). The 1H of HCl was not observed. | DMSO | >98 | G12 Temperature at 100° C. | | | |
| 417 | 1H NMR (DMSO-d6) ppm 12.80 (s, 1H), 9.74 (d, J = 1.60 Hz, 1H), 9.01 (brs, 1H), 8.83 (brs, 1H), 8.31 (d, J = 2.64 Hz, 1H), 8.15 (d, J = 1.00 Hz, 1H), 7.96 (d, J = 9.12 Hz, 1H), 7.78 (br, 1H), 7.64 (dd, J = 9.12, 2.64 Hz, 1H), 3.99 (s, 3H). The 1H of HCl was not observed. | DMSO | >98 | G12 Temperature at 100° C. | | | |

TABLE 1-continued

| | | | | |
|---|---|---|---|---|
| 418 | 1H NMR (DMSO-d6) ppm 12.60 (br, 1H), 9.79 (d, J = 1.72 Hz, 1H), 9.19 (d, J = 8.00 Hz, 1H), 8.93 (dd, J = 5.16, 1.44 Hz, 1H), 8.23 (brs, 1H), 8.10 (s, 1H), 7.99 (m, 1H), 7.95 (d, J = 9.08 Hz, 1H), 7.77-7.75 (br, 2H), 7.62 (dd, J = 9.08, 2.72 Hz, 1H), 7.50 (m, 2H), 7.37 (m, 1H), 3.99 (s, 3H). The 1H of HCl was not observed. | DMSO | >98 | G12 Temperature at 100° C. |
| 419 | 1H NMR (DMSO-d6) ppm 12.56 (s, 1H), 9.78 (s, 1H), 9.09 (d, J = 8.20 Hz, 1H), 8.84 (d, J = 3.96 Hz, 1H), 8.35 (d, J = 2.60 Hz, 1H), 8.10-8.07 (m, 2H), 7.95 (d, J = 9.12 Hz, 1H), 7.83 (brt, J = 6.60 Hz, 2H), 7.63 (dd, J = 9.12, 2.60 Hz, 1H), 7.32 (m, 2H), 4.02 (s, 3H). The 1H of HCl was not observed. | DMSO | >98 | G12 Temperature at 100° C. |
| 420 | 1H NMR (DMSO-d6) ppm 9.74 (s, 1H), 9.04 (d, J = 6.68 Hz, 1H), 8.86 (brs, 1H), 8.29 (brs, 1H), 8.05 (brs, J = 7.44 Hz, 2H), 7.97 (d, J = 9.08 Hz, 1H), 7.89 (br, 1H), 7.67-7.58 (m, 4H), 4.00 (s, 3H). The 1H of HCl and NH— were not observed. | DMSO | >98 | G12 Temperature at 100° C. |
| 421 | 1H NMR (DMSO-d6) ppm 9.88 (s, 1H), 9.51 (dd, J = 2.16, 0.8 Hz, 1H), 8.68-8.64 (m, 2H), 7.98 (d, J = 2.40 Hz, 1H), 7.91 (d, J = 8.84 Hz, 2H), 7.86 (d, J = 9.12 Hz, 1H), 7.68 (d, J = 8.34 Hz, 2H), 7.58-7.53 (m, 2H), 3.98 (s, 3H). | DMSO | >98 | G1 |
| 422 | 1H NMR (DMSO-d6) ppm 10.24 (br, 1H), 9.54 (s, 1H), 8.92 (d, J = 7.52 Hz, 1H), 8.82 (d, J = 3.96 Hz, 1H), 8.10 (d, J = 2.44 Hz, 1H), 8.03 (d, J = 8.68 Hz, 2H), 7.92 (d, J = 9.08 Hz, 1H), 7.84 (d, J = 8.68 Hz, 2H), 7.81 (m, 1H), 7.77-7.75 (m, 2H), 7.62 (dd, J = 9.08, 2.44 Hz, 1H), 7.50 (m, 2H), 7.38 (m, 1H), 4.01 (s, 3H). The 1H of HCl was not observed. | DMSO | >98 | J3 using $Na_2CO_3$ instead of $K_2CO_3$ |

TABLE 1-continued

| | | | | |
|---|---|---|---|---|
| 423 | 1H NMR (DMSO-d6) ppm 9.72 (s, 1H), 9.09 (d, J = 8.00 Hz, 1H), 8.89 (d, J = 4.24 Hz, 1H), 8.26 (brs, 1H), 8.12-8.09 (m, 2H), 7.96 (d, J = 9.12 Hz, 1H), 7.91 (m, 1H), 7.64 (dd, J = 9.12, 2.64 Hz, 1H), 7.45 (t, J = 8.80 Hz, 2H), 3.99 (s, 3H). The 1H of HCl and NH— were not observed. | DMSO | >98 | G13 using $K_2CO_3$ instead of $Cs_2CO_3$ |
| 424 | 1H NMR (DMSO-d6) ppm 10.30-10.15 (br, 1H), 9.54 (s, 1H), 8.91 (brs, 1H), 8.82 (brs, 1H), 8.10 (brs, 1H), 8.04 (d, J = 8.56 Hz, 2H), 7.92 (d, J = 9.6 Hz, 1H), 7.85 (d, J = 8.56 Hz, 2H), 7.80 (m, 1H), 7.79 (d, J = 8.56 Hz, 2H), 7.65-7.59 (brm, 1H), 7.55 (d, J = 8.56 Hz, 2H), 4.01 (s, 3H). The 1H of HCl was not observed. | DMSO | >98 | J3 |
| 425 | 1H NMR (DMSO-d6) ppm 9.91 (s, 1H), 9.53 (d, J = 1.84 Hz, 1H), 8.69 (d, J = 5.56 Hz, 2H), 8.31 (t, J = 1.88 Hz, 1H), 7.99 (d, J = 2.68 Hz, 1H), 7.98-7.94 (m, 1H), 7.87 (d, J = 9.08 Hz, 1H), 7.60-7.54 (m, 2H), 7.46 (t, J = 8.04 Hz, 1H), 7.39-7.35 (m, 1H), 3.99 (s, 3H). The 1H of HCl was not observed. | DMSO | >98 | G1 |
| 426 | 1H NMR (DMSO-d6) ppm 10.25 (br, 1H), 9.52 (s, 1H), 8.89 (brs, 1H), 8.88 (brs, 1H), 8.22 (brs, 1H), 8.11 (brs, 1H), 7.98-7.92 (brm, 2H), 7.80-7.70 (brm, 3H), 7.63-7.69 (brm, 2H), 7.55-7.50 (brm, 3H), 7.41 (m, 1H), 4.00 (s, 3H). The 1H of HCl was not observed. | DMSO | >98 | G13 using $K_2CO_3$ instead of $Cs_2CO_3$ at 120° C. |
| 427 | 1H NMR (DMSO-d6) ppm 10.31 (br, 1H), 9.51 (brs, 1H), 8.92 (brd, J = 7.44 Hz, 1H), 8.84 (brs, 1H), 8.22 (brs, 1H), 8.12 (brd, J = 2.28 Hz, 1H), 8.00-7.93 (brm, 2H), 7.83-7.77 (brm, 3H), 7.64-7.54 (brm, 5H), 4.01 (s, 3H). The 1H of HCl was not observed. | DMSO | >98 | J3 using $Na_2CO_3$ instead of $K_2CO_3$ |
| 428 | 1H NMR (DMSO-d6) ppm 9.73 (d, J = 1.72 Hz, 1H), 9.06 (d, J = 8.08 Hz, 1H), 8.88 (d, J = 3.72 Hz, 1H), 8.28 (brs, 1H), 8.01-7.96 (m, 3H), 7.88 (m, 1H), 7.81 (d, J = 8.60 Hz, 2H), 7.65 (dd, J = 9.08, 2.64 Hz, 1H), 4.00 (s, 3H). The 1H of 4HCl and NH— were not observed. | DMSO | >98 | G13 using $K_2CO_3$ instead of $Cs_2CO_3$ |

TABLE 1-continued

| | | | | |
|---|---|---|---|---|
| 429 | 1H NMR (DMSO-d6) ppm 12.60 (br, 1H), 9.78 (d, J = 1.76 Hz, 1H), 9.28 (d, J = 8.04 Hz, 1H), 8.95 (dd, J = 5.20, 1.20 Hz, 1H), 8.36 (d, J = 2.28 Hz, 1H), 8.04-7.93 (m, 4H), 7.77 (s, 1H), 7.64 (dd, J = 9.12, 2.68 Hz, 1H), 7.30 (d, J = 8.04 Hz, 2H), 4.02 (s, 3H), 2.36 (s, 3H). The 1H of HCl was not observed. | DMSO | >98 | G13 using $K_2CO_3$ instead of $Cs_2CO_3$ |
| 430 | 1H NMR (DMSO-d6) ppm 12.70-12.40 (br, 1H), 9.71 (s, 1H), 9.27 (d, J = 8.20 Hz, 1H), 8.94 (d, J = 4.24 Hz, 1H), 8.34 (d, J = 2.64 Hz, 1H), 8.13 (t, J = 1.80 Hz, 1H), 8.04-7.95 (m, 4H), 7.63 (dd, J = 9.08, 2.68 Hz, 1H), 7.52 (t, J = 7.88 Hz, 1H), 7.44-7.42 (m, 1H), 4.02 (s, 3H). The 1H of 2HCl was not observed. | DMSO | >98 | G13 using $K_2CO_3$ instead of $Cs_2CO_3$ |
| 431 | 1H NMR (DMSO-d6) ppm 12.57 (br, 1H), 9.80 (brs, 1H), 9.04 (d, J = 7.36 Hz, 1H), 8.82 (brs, 1H), 8.34 (brs, 1H), 7.99 (brd, J = 7.28 Hz, 1H), 7.95 (d, J = 9.08 Hz, 1H), 7.82 (brs, 1H), 7.76 (brm, 1H), 7.62 (m, 2H), 7.50-7.41 (m, 2H), 4.00 (s, 3H). The 1H of HCl was not observed. | DMSO | >98 | G13 using $K_2CO_3$ instead of $Cs_2CO_3$ |
| 432 | 1H NMR (DMSO-d6) ppm 10.40 (br, 1H), 9.23 (s, 1H), 8.80 (d, J = 4.68 Hz, 1H), 8.66 (brd, J = 8.20 Hz, 1H), 7.92 (brs, 1H), 7.87 (brd, J = 9.28 Hz, 1H), 7.78 (brm, 1H), 7.63-7.52 (m, 5H), 7.47-7.44 (m, 2H), 7.21-7.12 (m, 3H), 3.91 (s, 3H). The 1H of HCl was not observed. | DMSO | >98 | G13 using $K_2CO_3$ instead of $Cs_2CO_3$ |
| 433 | 1H NMR (DMSO-d6) ppm 12.34 (br, 1H), 9.75 (s, 1H), 9.01 (d, J = 7.52 Hz, 1H), 8.81 (brs, 1H), 8.40-8.20 (br, 1H), 7.92 (d, J = 9.08 Hz, 1H), 7.77 (m, 1H), 7.60 (dd, J = 9.08, 2.72 Hz, 1H), 6.95 (br, 1H), 3.98 (s, 3H), 2.67 (m, 1H), 2.05 (m, 2H), 1.83-1.70 (m, 3H), 1.54-1.23 (m, 5H). The 1H of HCl was not observed. | DMSO | >98 | G13 using $K_2CO_3$ instead of $Cs_2CO_3$ |
| 434 | 1H NMR (DMSO-d6) ppm 12.58 (br, 1H), 9.79 (s, 1H), 9.19 (d, J = 7.32 Hz, 1H), 8.90 (d, J = 5.6 Hz, 1H), 8.36 (s, 1H), 7.96 (d, J = 9.08 Hz, 1H), 7.94 (m, 1H), 7.88 (s, 1H), 7.65-7.62 (m, 3H), 7.40 (t, J = 8.16 Hz, 1H), 6.96-6.93 (m, 1H), 4.02 (s, 3H), 3,84 (s, 3H). The 1H of 2HCl was not observed. | DMSO | >98 | G13 using $K_2CO_3$ instead of $Cs_2CO_3$ |

TABLE 1-continued

| | | | | |
|---|---|---|---|---|
| 435 | 1H NMR (DMSO-d6) ppm 12.80-12.40 (br, 1H), 9.79 (d, J = 1.44 Hz, 1H), 9.26 (d, J = 8.24 Hz, 1H), 8.93 (d, J = 4.08 Hz, 1H), 8.36 (d, J = 2.28 Hz, 1H), 8.02-7.96 (m, 4H), 7.68 (s, 1H), 7.64 (dd, J = 9.12, 2.68 Hz, 1H), 7.05 (d, J = 8.92 Hz, 2H), 4.02 (s, 3H), 3.82 (s, 3H). The 1H of 2HCl was not observed. | DMSO | >98 | G13 using $K_2CO_3$ instead of $Cs_2CO_3$ |
| 436 | 1H NMR (DMSO-d6) ppm 12.52 (br, 1H), 9.79 (s, 1H), 9.23 (d, J = 8.00 Hz, 1H), 8.91 (d, J = 4.12 Hz, 1H), 8.35 (brs, 1H), 8.25 (d, J = 7.6 Hz, 1H), 7.96 (d, J = 9.08 Hz, 1H), 7.93 (m, 1H), 7.85 (s, 1H), 7.64 (dd, J = 9.08, 2.68 Hz, 1H), 7.39-7.35 (m, 1H), 7.18 (d, J = 7.72 Hz, 1H), 7.11-7.07 (m, 1H), 4.02 (s, 3H), 3.96 (s, 3H). The 1H of HCl was not observed. | DMSO | >98 | G13 using $K_2CO_3$ instead of $Cs_2CO_3$ |
| 437 | 1H NMR (DMSO-d6) ppm 9.94 (s, 1H), 9.27 (d, J = 1.92 Hz, 1H), 8.59 (dd, J = 4.72, 1.68 Hz, 1H), 8.45 (dt, J = 8.04, 1.8 Hz, 1H), 7.96 (d, J = 2.72 Hz, 1H), 7.84 (d, J = 8.28 Hz, 2H), 7.67 (d, J = 8.00 Hz, 1H), 7.55 (m, 2H), 7.46-7.43 (m, 1H), 7.33 (m, 1H), 3.96 (s, 3H). | DMSO | >98 | G13 using $K_2CO_3$ instead of $Cs_2CO_3$ at 120° C. |
| 438 | 1H NMR (DMSO-d6) ppm 10.48 (br, 1H), 9.23 (s, 1H), 8.83 (brd, J = 3.68 Hz, 1H), 8.70 (brd, J = 7.36 Hz, 1H), 7.95 (brs, 1H), 7.91 (d, J = 9.12 Hz, 1H), 7.82 (m, 1H), 7.63-7.51 (m, 5H), 7.48 (d, J = 8.52 Hz, 2H), 7.26 (d, J = 8.52 Hz, 2H), 3.93 (s, 3H). The 1H of HCl was not observed. | DMSO | >98 | J3 using $Na_2CO_3$ instead of $K_2CO_3$ |
| 439 | 1H NMR (DMSO-d6) ppm 12.60 (br, 1H), 9.78 (s, 1H), 9.17 (d, J = 7.96 Hz, 1H), 8.88 (d, J = 4.20 Hz, 1H), 8.35 (d, J = 2.60 Hz, 1H), 8.24-8.21 (m, 1H), 7.96 (d, J = 9.08 Hz, 1H), 7.91-7.88 (brm, 1H), 7.74 (d, J = 2.48 Hz, 1H), 7.63 (dd, J = 9.08, 2.60 Hz, 1H), 7.47-7.41 (m, 1H), 7.36 8m, 2H), 4.02 (s, 3H). The 1H of HCl was not observed. | DMSO | >98 | G13 at 100° C. |

TABLE 1-continued

| | | | | |
|---|---|---|---|---|
| 440 | 1H NMR (DMSO-d6) ppm 12.60-12.45 (br, 1H), 9.79 (d, J = 1.52 Hz, 1H), 9.15 (d, J = 8.36 Hz, 1H), 8.88 (d, J = 5.04 Hz, 1H), 8.35 (d, J = 2.44 Hz, 1H), 7.96 (d, J = 9.12 Hz, 1H), 7.89 (brt, J = 7.08 Hz, 2H), 7.82 (brm, 1H), 7.81 (s, 1H), 7.63 (dd, J = 9.12, 2.44 Hz, 1H), 7.37 (t, J = 7.64 Hz, 1H), 7.19 (d, J = 7.48 Hz, 1H), 4.02 (s, 3H), 2.40 (s, 3H). The 1H of HCl was not observed. | DMSO | >98 | G13 at 100° C. |
| 441 | 1H NMR (DMSO-d6) ppm 12.60 (br, 1H), 9.77 (s, 1H), 9.25 (d, J = 8.08 Hz, 1H), 8.93 (d, J = 4.28 Hz, 1H), 8.34 (d, J = 2.60 Hz, 1H), 8.01-7.84 (m, 5H), 7.63 (dd, J = 9.12, 2.60 Hz, 1H), 7.56-7.51 (m, 1H), 7.21 (m, 1H). The 1H of HCl was not observed. | DMSO | >98 | G13 at 100° C. |
| 442 | 1H NMR (DMSO-d6) ppm 12.66 (brs, 1H), 9.78 (d, J = 1.68 Hz, 1H), 9.27 (d, J = 8.08 Hz, 1H), 8.94 (dd, J = 5.20, 1.40 Hz, 1H), 8.36 (d, J = 2.56 Hz, 1H), 8.17 (d, J = 8.84 Hz, 2H), 8.01 (m, 1H), 7.97 (d, J = 9.08 Hz, 1H), 7.93 (s, 1H), 7.64 (dd, J = 9.08, 2.56 Hz, 1H), 7.49 (brd, J = 8.84 Hz, 2H), 4.02 (s, 3H). The 1H of 2HCl was not observed. | DMSO | >98 | G13 at 100° C. |
| 443 | 1H NMR (DMSO-d6) ppm 12.64 (br, 1H), 9.79 (s, 1H), 9.13 (d, J = 7.56 Hz, 1H), 8.87 (d, J = 5.08 Hz, 1H), 8.36 (d, J = 2.60 Hz, 1H), 8.27 (d, J = 8.00 Hz, 2H), 8.08 (s, 1H), 7.96 (d, J = 9.12 Hz, 1H), 7.87 (m, 1H), 7.86 (d, J = 8.00 Hz, 2H), 7.64 (dd, J = 9.12, 2.60 Hz, 1H), 4.02 (s, 3H). The 1H of 2HCl was not observed. | DMSO | >98 | G13 at 100° C. |
| 444 | 1H NMR (MeOD-d4) ppm 9.79 (s, 1H), 9.37 (br, 1H), 8.49 (dd, J = 5.28, 1.32 Hz, 1H), 8.12 (m, 1H), 8.09 (d, J = 2.72 Hz, 1H), 7,98 (d, J = 9.16 Hz, 1H), 7.68 (dd, J = 9.16, 2.72 Hz, 1H), 7.58 (d, J = 7.12 Hz, 1H), 7.42-7.30 (m, 3H), 7.30 (s, 1H), 4.05 (s, 3H), 2.50 (s, 3H). The 1H of 2HCl was not observed. | MeOD | >98 | G13 |

TABLE 1-continued

| | | | | |
|---|---|---|---|---|
| 445 | 1H NMR (DMSO-d6) ppm 12.59 (br, 1H), 9.78 (d, J = 1.48 Hz, 1H), 9,19 (d, J = 8.00 Hz, 1H), 8.90 (dd, J = 5.16, 1.48 Hz, 1H), 8.34 (d, J = 2.60 Hz, 1H), 8.10-8.04 (m, 1H), 7.97-7.88 (m, 4H), 7.64 (dd, J = 2.60 Hz, 1H), 7.59-7.52 (m, 1H), 4.02 (s, 3H). The 1H of 2HCl was not observed. | DMSO | >98 | G13 |
| 446 | 1H NMR (DMSO-d6) ppm 12.61 (br, 1H), 9.78 (d, J = 1.72 Hz, 1H), 9.20 (d, J = 7.92 Hz, 1H), 8.90 (d, J = 4.00 Hz, 1H), 8.35 (d, J = 2.60 Hz, 1H), 8.27-8.21 (m, 1H), 7.96 (d, J = 9.12 Hz, 1H), 7.93 (m, 1H), 7.71 (d, J = 2.56 Hz, 1H), 7.64 (dd, J = 9.12, 2.60 Hz, 1H), 7.43 (m, 1H), 7.27 (m, 1H), 4.02 (s, 1H). The 1H of HCl was not observed. | DMSO | >98 | G13 |
| 447 | 1H NMR (DMSO-d6) ppm 12.57 (br, 1H), 9.77 (d, J = 1.76 Hz, 1H), 9.25 (d, J = 8.08 Hz, 1H), 8.93 (dd, J = 5.16, 1.2 Hz, 1H), 8.34 (d, J = 2.60 Hz, 1H), 8.29 (t, J = 1.76 Hz, 1H), 8.05 (dd, J = 7.84, 1.12 Hz, 1H), 8.02-7.98 (m, 1H), 7.99 (s, 1H), 7.96 (d, J = 9.08 Hz, 1H), 7.64 (dd, J = 9.08, 2.60 Hz, 1H), 7.58-7.56 (m, 1H), 7.45 (t, J = 7.84 Hz, 1H), 4.02 (s, 3H). The 1H of 2HCl was not observed. | DMSO | >98 | G13 |
| 448 | 1H NMR (DMSO-d6) ppm 12.62 (br, 1H), 9.77 (d, J = 1.52 Hz, 1H), 9.10 (d, J = 8.16 Hz, 1H), 8.85 (dd, J = 5.00, 1.56 Hz, 1H), 8.34 (d, J = 2.60 Hz, 1H), 8.24 (d, J = 8.60 Hz, 2H), 8.13 (s, 1H), 7.96 (d, J = 8.60 Hz, 2H), 7.96 (d, J = 9.08 Hz, 1H), 7.86-7.83 (brm, 1H), 7.63 (dd, J = 9.08, 2.60 Hz, 1H), 4.02 (s, 3H). The 1H of HCl was not observed. | DMSO | >98 | G13 |
| 449 | 1H NMR (DMSO-d6) ppm 12.56 (brs, 1H), 9.79 (brs, 1H), 9.11 (d, J = 8.04 Hz, 1H), 8.87 (brs, 1H), 8.43 (brs, 1H), 8.34 (brs, 2H), 8.09 (s, 1H), 7.96 (d, J = 9.08 Hz, 1H), 7.87 (brs, 1H), 7.74 (brd, J = 5.00 Hz, 2H), 7.64 (dd, J = 9.08, 2.48 Hz, 1H), 4.03 (s, 3H). The 1H of 2HCl was not observed. | DMSO | >98 | G13 at 100° C. |

TABLE 1-continued

| | | | | |
|---|---|---|---|---|
| 450 | 1H NMR (DMSO-d6) ppm 12.63 (br, 1H), 9.80 (d, J = 1.72 Hz, 1H), 9.27 (d, J = 8.16 Hz, 1H), 8.93 (dd, J = 5.20, 1.36 Hz, 1H), 8.33 (d, J = 2.24 Hz, 1H), 7.99 (m, 1H), 7.98 (d, J = 9.08 Hz, 1H), 7.88 (brd, J = 7.72 Hz, 1H), 7.71-7.75 (m, 2H), 7.70-7.63 (m, 2H), 7.45 (s, 1H), 3.98 (s, 3H). The 1H of 2HCl was not observed. | DMSO | >98 | G13 at 100° C. |
| 451 | 1H NMR (DMSO-d6) ppm 12.70 (br, 1H), 9.79 (d, J = 1.60 Hz, 1H), 9.30 (d, J = 7.56 Hz, 1H), 8.95 (d, J = 4.96 Hz, 1H), 8.34 (d, J = 2.20 Hz, 1H), 8.02 (m, 1H), 7.98 (d, J = 9.12 Hz, 1H), 7.85-7.77 (m, 2H), 7.73 (s, 1H), 7.64 (dd, J = 9.12, 2.68 Hz, 1H), 7.52 (m, 1H), 7.36 (m, 1H), 4.00 (s, 3H). The 1H of HCl was not observed. | DMSO | >98 | G13 |
| 452 | 1H NMR (DMSO-d6) ppm 12.64 (br, 1H), 9.78 (d, J = 1.72 Hz, 1H), 9.19 (d, J = 7.92 Hz, 1H), 8.90 (d, J = 3.88 Hz, 1H), 8.36 (d, J = 2.64 Hz, 1H), 8.02-7.91 (m, 3H), 7.83 (d, J = 2.40 hz, 1H), 7.64 (dd, J = 9.08, 2.64 Hz, 1H), 7.46 (m, 1H), 7.36 (m, 1H), 4.02 (s, 3H). The 1H of HCl was not observed. | DMSO | >98 | G13 |
| 453 | 1H NMR (DMSO-d6) ppm 12.62 (br, 1H), 9.77 (d, J = 1.84 Hz, 1H), 9.30 (d, J = 8.00 Hz, 1H), 8.46 (dd, J = 5.36, 1.48 Hz, 1H), 8.48 (br, 1H), 8.39-8.33 (m, 2H), 8.08 (s, 1H), 8.05 (m, 1H), 7.97 (d, J = 9.12 Hz, 1H), 7.85-7.83 (m, 1H), 7.71 (t, J = 7.84 Hz, 1H), 7.64 (dd, J = 9.12, 2.60 Hz, 1H), 4.02 (s, 3H). The 1H of 2HCl was not observed. | DMSO | >98 | G13 |
| 454 | 1H NMR (DMSO-d6) ppm 12.65 (br, 1H), 9.79 (d, J = 1.72 Hz, 1H), 9.25 (d, J = 8.04 Hz, 1H), 8.92 (d, J = 5.36 Hz, 1H), 8.36 (d, J = 2.60 Hz, 1H), 8.24-8.22 (,m, 1H), 7.97 (d, J = 9.08 Hz, 1H), 7.96 (m, 1H), 7.69 (s, 1H), 7.65 (dd, J = 9.08, 2.60 Hz, 1H), 7.55 (m, 3H), 4.02 (s, 3H). The 1H of 2HCl was not observed. | DMSO | >98 | G13 |

TABLE 1-continued

| | | | | |
|---|---|---|---|---|
| 455 | 1H NMR (DMSO-d6) ppm 12.52 (br, 1H), 9.78 (d, J = 1.48 Hz, 1H), 9.03 (d, J = 6.6 Hz, 1H), 8.81 (d, J = 4.72 Hz, 1H), 8.34 (d, J = 2.56 Hz, 1H), 8.09 (d, J = 7.88 Hz, 1H), 8.03 (brs, 2H), 7.96 (d, J = 9.12 Hz, 1H), 7.78 (br, 1H), 7.65 (m, 2H), 7.38 (m, 1H), 4.02 (s, 3H). The 1H of HCl was not observed. | DMSO | >98 | G13 |
| 456 | 1H NMR (DMSO-d6) ppm 12.45 (br, 1H), 9.78 (d, J = 1.64 Hz, 1H), 9.15 (br, 1H), 8.89 (d, J = 4.52 Hz, 1H), 8.30 (brs, 1H), 7.94 (d, J = 9.08 Hz, 1H), 7.90 (brm, 1H), 7.76 (m, 2H), 7.62 (dd, J = 9.08, 2.64 Hz, 1H), 7.51 (m, 2H), 7.40 (m, 1H), 3.99 (s, 3H), 2.61 (s, 3H). The 1H of 2HCl was not observed. | DMSO | >98 | G13 |
| 457 | 1H NMR (DMSO-d6) ppm 12.55 (br, 1H), 9.78 (d, J = 1.48 Hz, 1H), 9.08 (d, J = 8.48 Hz, 1H), 8.84 (dd, J = 5.04, 1.56 Hz, 1H), 8.34 (d, J = 2.72 Hz, 1H), 8.09 (s, 1H), 7.96 (d, J = 9.12 Hz, 1H), 7.84 (m, 1H), 7.77 (m, 2H), 7.64 (dd, J = 9.12, 2.72 Hz, 1H), 7.25 (m, 1H), 4.02 (s, 3H). The 1H of HCl was not observed. | DMSO | >98 | G13 |
| 458 | 1H NMR (DMSO-d6) ppm 12.55 (br, 1H), 9.77 (d, J = 1.56 Hz, 1H), 9.14 (d, J = 8.00 Hz, 1H), 8.87 (dd, J = 5.08, 1.48 Hz, 1H), 8.34 (d, J = 2.60 Hz, 1H), 7.98 (m, 1H), 7.96 (d, J = 9.08 Hz, 1H), 7.89-7.86 (brm, 1H), 7.83 (d, J = 2.44 Hz, 1H), 7.64 (dd, J = 9.08, 2.60 Hz, 1H), 7.47-7.41 (m, 1H), 7.29 (m, 1H), 4.02 (s, 3H). The 1H of HCl was not observed. | DMSO | >98 | G13 |
| 459 | 1H NMR (DMSO-d6) ppm 12.66 (br, 1H), 9.79 (d, J = 1.60 Hz, 1H), 9.25 (d, J = 7.16 Hz, 1H), 8.92 (d, J = 5.20 Hz, 1H), 8.35 (d, J = 2.56 Hz, 1H), 7.98 (d, J = 9.12 Hz, 1H), 7.97 (m, 1H), 7.68 (s, 1H), 7.64 (dd, J = 9.12, 2.56 Hz, 1H), 7.55 (m, 1H), 7.27 (m, 2H), 3.99 (s, 3H). The 1H of HCl was not observed. | DMSO | >98 | G13 |

TABLE 1-continued

| | | | | |
|---|---|---|---|---|
| 460 | 1H NMR (DMSO-d6) ppm 9.73 (s, 1H), 9.17 (brs, 1H), 8.92 (dd, J = 5.16, 1.4 Hz, 1H), 8.30-8.10 (br, 1H), 7.97 (d, J = 9.04 Hz, 1H), 7.96 (m, 1H), 7.63 (dd, J = 9.04, 2.72 Hz, 1H), 7.02 (s, 1H), 3.98 (s, 3H), 2.57 (d, J = 7.16 Hz, 2H), 2.08 (m, 1H), 0.94 (d, J = 6.60 Hz, 6H). The 1H of HCl and NH— were not observed. | DMSO | >98 | G13 |
| 461 | 1H NMR (DMSO-d6) ppm 12.80-12.20 (br, 1H), 9.78 (d, J = 1.76 Hz, 1H), 9.28 (d, J = 8.04 Hz, 1H), 8.96 (dd, J = 5.28, 1.32 Hz, 1H), 8.29 (brs, 1H), 8.07-8.03 (brm, 1H), 7.95 (d, J = 9.12 Hz, 1H), 7.79 (d, J = 8.60 Hz, 2H), 7.62 (dd, J = 9.12, 2.64 Hz, 1H), 7.57 (d, J = 8.60 Hz, 2H), 3.99 (s, 3H), 2.61 (brs, 3H). The 1H of 2HCl was not observed. | DMSO | >98 | G13 |
| 462 | 1H NMR (DMSO-d6) ppm 12.80-12.20 (br, 1H), 9.74 (s, 1H), 9.19 (d, J = 4.96 Hz, 1H), 8.91 (dd, J = 5.2, 1.4 Hz, 1H), 8.22 (brs, 1H), 7.96 (br, 1H), 7.95 (d, J = 9.08 Hz, 1H), 7.61 (dd, J = 9.08, 2.68 Hz, 1H), 7.35-7.31 (m, 4H), 7.23 (m, 1H), 7.09 (brs, 1H), 4.07 (brs, 2H), 3.96 (brs, 3H). The 1H of 2HCl was not observed. | DMSO | >98 | G13 |
| 463 | 1H NMR (DMSO-d6) ppm 12.50 (br, 1H), 9.78 (d, J = 1.76 Hz, 1H), 9.25 (brs, 1H), 8.96 (brd, J = 4.68 Hz, 1H), 8.29 (brs, 1H), 8.04 (brs, 1H), 7.96 (d, J = 9.20 Hz, 1H), 7.70 (brm, 2H), 7.63 (dd, J = 9.20, 2.68 Hz, 1H), 7.51 (brm, 2H), 7.41 (brm, 1H), 3.99 (s, 3H), 3.02 (q, J = 7.40 Hz, 2H), 1.49 (t, J = 7.40 Hz, 3H). The 1H of 2HCl was not observed. | DMSO | >98 | G13 |
| 464 | 1H NMR (DMSO-d6) ppm 12.53 (br, 1H), 9.78 (d, J = 1.76 Hz, 1H), 9.20 (d, J = 8.36 Hz, 1H), 8.94 (dd, J = 5.2, 1.4 Hz., 1H), 8.29 (brs, 1H), 8.00 (brm, 1H), 7.96 (d, J = 9.12 Hz, 1H), 7.66-7.61 (m, 3H), 7.52 (brm, 2H), 7.43 (t, J = 7.40 Hz, 1H), 3.98 (s, 3H), 1.43 (d, J = 6.8 Hz, 6H). The 1H of 2HCl was not observed. The CH proton of iPr group was not observed because of overlapping the H2O peak. | DMSO | >98 | G13 |

TABLE 1-continued

| | | | | |
|---|---|---|---|---|
| 465 | 1H NMR (DMSO-d6) ppm 12.59 (brs, 1H), 9.77 (d, J = 1.72 Hz, 1H), 9.25 (d, J = 7.76 Hz, 1H), 8.96 (d, J = 4.04 Hz, 1H), 8.29 (br, 1H), 8.04 (m, 1H), 7.96 (d, J = 9.12 Hz, 1H), 7.69 (brd, J = 7.12 Hz, 2H), 7.63 (dd, J = 9.12, 2.68 Hz, 1H), 7.51 (t, J = 7.36 Hz, 2H), 7.42 (t, J = 7.36 Hz, 1H), 3.99 (s, 3H), 2.96 (t, J = 7.52 Hz, 2H), 1.78 (m, 2H), 1.01 (t, J = 7.24 Hz, 3H). The 1H of 2HCl was not observed. | DMSO | >98 | G13 |
| 466 | 1H NMR (DMSO-d6) ppm 12.96 (brs, 1H), 9.74 (d, J = 2.04 Hz, 1H), 9.11 (d, J = 7.96 Hz, 1H), 8.90 (d, J = 4.96 Hz, 1H), 8.31 (brd, J = 2.64 Hz, 1H), 7.97 (d, J = 9.12 Hz, 1H), 7.87 (brm, 1H), 7.83-7.80 (m, 2H), 7.64 (dd, J = 9.12, 2.62 Hz, 1H), 7.48 (m, 3H), 4.25 (q, J = 7.04 Ha, 2H), 3.98 (s, 3H), 1.29 (t, J = 7.04 Hz, 3H). The 1H of 2HCl was not observed. | DMSO | >98 | G13 |
| 467 | 1H NMR (DMSO-d6) ppm 12.63 (br, 1H), 9.76 (d, J = 1.76 Hz, 1H), 9.29 (d, J = 8.16 Hz, 1H), 8.95 (dd, J = 5.28, 1.36 Hz, 1H), 8.32 (brd, J = 2.60 Hz, 1H), 8.07 (d, J = 8.52 Hz, 2H), 8.08-8.00 (m, 1H), 7.95 (d, J = 9.12 Hz, 1H), 7.90 (s, 1H), 7.61 (dd, J = 9.12, 2.60 Hz, 1H), 7.55 (d, J = 8.52 Hz, 2H), 4.24 (q, J = 6.88 Hz, 2H), 1.47 (t, J = 6.88 Hz, 3H). The 1H of HCl was not observed. | DMSO | >98 | G13 |
| 468 | 1H NMR (DMSO-d6) ppm 12.58 (brs, 1H), 9.76 (d, J = 1.80 Hz, 1H), 9.27 (d, J = 8.16 Hz, 1H), 8.94 (dd, J = 5.20, 1.32 Hz, 1H), 8.32 (d, J = 2.48 Hz, 1H), 8.09-8.01 (m, 2H), 7.96-7.89 (m, 3H), 7.62-7.52 (m, 2H), 4.29 (q, J = 6.88 Hz, 2H), 1.47 (t, J = 6.88 Hz, 3H). The 1H of 2HCl was not observed. | DMSO | >98 | G13 |
| 469 | 1H NMR (DMSO-d6) ppm 9.72 (s, 1H), 9.13 (brd, J = 5.52 Hz, 1H), 8.92 (d, J = 3.52 Hz, 1H), 8.16 (brs, 1H), 7.95 (brd, J = 9.08 Hz, 2H), 7.62 (dd, J = 2.4 Hz, 1H), 7.39 (brs, 1H), 3.97 (s, 3H), 2.47 (s, 3H). The 1H of 2HCl and NH— were not observed. | DMSO | >98 | G13 |

TABLE 1-continued

| | | | | |
|---|---|---|---|---|
| 470 | 1H NMR (DMSO-d6) ppm 12.58 (brs, 1H), 9.76 (d, J = 1.68 Hz, 1H), 9.17 (d, J = 8.12 Hz, 1H), 8.89 (dd, J = 5.12, 1.48 Hz, 1H), 8.32 (d, J = 2.56 Hz, 1H), 8.01-8.00 (m, 1H), 7.94 (d, J = 9.08 Hz, 1H), 7.930-7.90 (m, 1H), 7.81 (d, J = 2.4 Hz, 1H), 7.60 (dd, J = 9.08, 2.40 Hz, 1H), 7.50-7.43 (m, 1H), 7.38-7.33 (m, 1H), 4.28 (q, J = 7.00 Hz, 2H), 1.47 (t, J = 7.00 Hz, 3H). The 1H of HCl was not observed. | DMSO | >98 | G13 |
| 471 | 1H NMR (DMSO-d6) ppm 12.53 (brs, 1H), 9.73 (d, J = 1.76 Hz, 1H), 9.29 (d, J = 8.16 Hz, 1H), 8.95 (dd, J = 5.32, 1.36 Hz, 1H), 8.29 (d, J = 2.56 Hz, 1H), 8.05-8.02 (brm, 1H), 7.97-7.92 (m, 1H), 7.93 (d, J = 9.08 Hz, 1H), 7.78 (d, J = 2.36 Hz, 1H), 7.60 (dd, J = 9.08, 2.6 Hz, 1H), 7.46-7.40 (m, 1H), 7.31-7.25 (m, 1H), 4.27 (q, J = 6.92 Hz, 2H), 1.47 (t, J = 6.92 Hz, 3H). The 1H of 2HCl was not observed. | DMSO | >98 | G13 |
| 472 | 1H NMR (DMSO-d6) ppm 12.61 (brs, 1H), 9.76 (d, J = 1.8 Hz, 1H), 9.29 (d, J = 8.16 Hz, 1H), 8.95 (dd, J = 5.24, 1.2 Hz, 1H), 8.32 (d, J = 2.52 Hz, 1H), 8.24-8.20 (m, 1H), 8.05-8.01 (brm, 1H), 7.95 (d, J = 9.08 Hz, 1H), 7.68 (d, J = 2.52 HZ, 1H), 7.61 (dd, J = 9.08, 2.52 Hz, 1H), 7.46-7.40 (m, 1H), 7.28-7.24 (m, 1H), 4.28 (q, J = 6.92 Hz, 2H), 1.47 (t, J = 6.92 Hz, 3H). The 1H of 3HCl was not observed. | DMSO | >98 | G13 |
| 473 | 1H NMR (DMSO-d6) ppm 12.63 (brs, 1H), 9.78 (d, J = 1.68 Hz, 1H), 9.32 (d, J = 8.12 Hz, 1H), 8.97 (d, J = 5.24 Hz, 1H), 8.35 (d, J = 2.16 Hz, 1H), 8.08-8.04 (m, 3H), 7.96 (d, J = 9.08 Hz, 1H), 7.85 (s, 1H), 7.62 (dd, J = 9.08, 2.52 Hz, 1H), 7.49 (t, J = 7.44 Hz, 2H), 7.38 (t, J = 7.28 Hz, 1H), 4.30 (q, J = 6.96 Hz, 2H), 1.47 (t, J = J = 6.96 Hz, 3H). The 1H of 2HCl was not observed. | DMSO | >98 | G13 |

TABLE 1-continued

| | | | | | | | |
|---|---|---|---|---|---|---|---|
| 474 | 1H NMR (DMSO-d6) ppm 12.68 (s, 1H), 9.73 (d, J = 1.64 Hz, 1H), 8.87-8.84 (m, 1H), 8.75-8.73 (m, 1H), 8.33 (brs, 1H), 8.24 (brs, 1H). 7.93 (d, J = 9.16 Hz, 1H), 7.64-7.59 (m, 2H), 4.34 (q, J = 7.08 Hz, 2H), 3.98 (s, 3H), 1.34 (t, J = 7.08 Hz, 3H). | DMSO | >98 | G13 | | | |
| 475 | 1H NMR (300 MHz, DMSO) δ 10.35 (s, 1H), 9.42 (s, 1H), 8.99-8.76 (m, 2H), 8.11 (d, J = 6.7 Hz, 1H), 7.99-7.75 (m, 3H), 7.67-7.43 (m, 2H), 7.23 (d, J = 8.2 Hz, 1H), 4.14 (s, 3H). | DMSO | 98 | G1 | 381 (M + 1) | 2.07 | Method A (Formic acid) |
| 476 | 1H NMR (300 MHz, DMSO) δ 13.78 (s, 1H), 9.62 (d, J = 1.7 Hz, 1H), 9.21 (d, J = 8.1 Hz, 1H), 8.98 (d, J = 4.2 Hz, 1H), 8.07 (dd, J = 7.9, 5.3 Hz, 1H), 7.83 (d, J = 9.1 Hz, 2H), 7.63-7.50 (m, 4H), 7.41 (d, J = 6.5 Hz, 2H), 7.14 (d, J = 2.5 Hz, 1H), 5.30 (s, 1H), 3.91 (s, 3H), 2.15 (s, 3H). | DMSO | 95 | Method G1 | 468.1 (M + 1) | | Method C |
| 477 | 1H NMR (300 MHz, DMSO) δ 13.78 (s, 1H), 9.64 (d, J = 1.5 Hz, 1H), 9.11 (d, J = 8.2 Hz, 1H), 8.90 (d, J = 3.8 Hz, 1H), 7.95 (dd, J = 10.6, 2.6 Hz, 1H), 7.84 (d, J = 9.1 Hz, 2H), 7.60-7.48 (m, 4H), 7.38 (d, J = 6.5 Hz, 2H), 7.17 (d, J = 2.4 Hz, 1H), 5.28 (s, 1H), 4.14 (q, J = 6.9 Hz, 2H), 2.15 (s, 3H), 1.42 (t, J = 6.9 Hz, 3H). | DMSO | 95 | Method G1 | 482.1 (M + 1) | | Method C |
| 478 | 1H NMR (300 MHz, DMSO) δ 12.59 (s, 1H), 9.56 (s, 1H), 8.70 (d, J = 5.8 Hz, 2H), 8.58 (d, J = 5.2 Hz, 1H), 7.95 (d, J = 5.2 Hz, 2H), 7.87 (d, J = 9.1 Hz, 2H), 7.64-7.49 (m, 2H), 7.40 (d, J = 2.4 Hz, 1H), 4.21 (q, J = 6.8 Hz, 2H), 1.44 (t, J = 6.9 Hz, 3H). | DMSO | 99 | Method G1 | 392.1 (M + 1) | | Method C |
| 479 | 1H NMR (300 MHz, DMSO) δ 13.75 (s, 1H), 9.60 (s, 1H), 8.98 (s, 1H), 8.82 (d, J = 3.6 Hz, 1H), 7.82 (d, J = 9.0 Hz, 3H), 7.52 (d, J = 9.3 Hz, 1H), 7.15 (s, 1H), 6.94-6.62 (s, 1H), 4.13 (d, J = 6.9 Hz, 2H), 2.90 (d, J = 21.9 Hz, 4H), 2.41 (s, 2H), 1.43 (t, J = 6.9 Hz, 3H). | DMSO | 95 | Method G1 | 432.1 (M + 1) | | Method C |

TABLE 1-continued

| | | | | | | |
|---|---|---|---|---|---|---|
| 480 | 1H NMR (300 MHz, DMSO) δ 12.50 (s, 1H), 9.56 (s, 1H), 8.89 (s, 1H), 8.68 (d, J = 5.3 Hz, 2H), 8.00-7.79 (m, 3H), 7.73 (d, J = 7.2 Hz, 4H), 7.62-7.38 (m, 9H), 7.34 (d, J = 2.2 Hz, 2H), 4.18 (dd, J = 13.5, 6.5 Hz, 2H), 1.43 (t, J = 6.9 Hz, 3H). | DMSO | 99 | Method G1 | 468.1 (M + 1) | Method C |
| 481 | 1H NMR (300 MHz, DMSO) δ 12.51 (s, 1H), 9.54 (s, 1H), 8.86 (s, 1H), 8.74-8.61 (m, 2H), 7.90 (s, J = 15.7 Hz, 2H), 7.83 (d, J = 9.1 Hz, 1H), 7.72 (d, J = 7.1 Hz, 2H), 7.63-7.40 (m, 6H), 7.33 (d, J = 2.3 Hz, 1H), 3.92 (s, 3H). | DMSO | 99 | Method G1 | 454.1 (M + 1) | Method C |
| 482 | 1H NMR (300 MHz, DMSO) δ 13.70 (s, 1H), 9.70 (d, J = 2.1 Hz, 1H), 8.81 (d, J = 8.0 Hz, 1H), 8.70 (dd, J = 4.8, 1.7 Hz, 1H), 7.90 (d, J = 9.1 Hz, 1H), 7.66-7.53 (m, 2H), 7.29 (d, J = 2.2 Hz, 1H), 3.95 (s, 3H), 2.78 (d, J = 12.9 Hz, 4H), 1.78 (s, 4H). | DMSO | 99 | Method G1 | 432.1 (M + 1) | Method C |
| 483 | 1H NMR (300 MHz, DMSO) δ 13.64 (s, 1H), 9.68 (s, 1H), 8.79 (d, J = 7.9 Hz, 1H), 8.69 (d, J = 4.7 Hz, 1H), 7.86 (d, J = 9.0 Hz, 1H), 7.63-7.50 (m, 2H), 7.24 (s, 1H), 4.18 (q, J = 6.7 Hz, 2H), 2.76 (d, J = 10.4 Hz, 4H), 1.78 (s, 4H), 1.43 (t, J = 6.9 Hz, 3H). | DMSO | 99 | Method G1 | 446.1 (M + 1) | Method C |
| 484 | 1H NMR (300 MHz, DMSO) δ 12.82 (s, 1H), 9.67 (d, J = 2.1 Hz, 1H), 8.77 (dt, J = 8.1, 2.0 Hz, 1H), 8.71 (dd, J = 4.8, 1.7 Hz, 1H), 7.87 (d, J = 9.1 Hz, 1H), 7.83 (s, 1H), 7.60-7.53 (m, 3H), 7.48 (s, 1H), 7.20 (d, J = 2.6 Hz, 1H), 4.20 (q, J = 6.9 Hz, 2H), 2.90 (d, J = 4.7 Hz, 3H), 1.44 (t, J = 6.9 Hz, 3H). | DMSO | 95 | Method G1 | 422.1 (M + 1) | Method C |
| 485 | 1H NMR (300 MHz, DMSO) δ 9.66 (s, 1H), 9.44 (d, J = 1.4 Hz, 1H), 8.64-8.55 (m, 2H), 7.90 (s, 1H), 7.81 (d, J = 9.1 Hz, 1H), 7.76 (d, J = 2.5 Hz, 1H), 7.69 (s, 2H), 7.54-7.45 (m, 2H), 4.19 (q, J = 7.0 Hz, 2H), 4.04 (s, 3H), 1.42 (t, J = 6.9 Hz, 3H). | DMSO | 99 | Method G1 | 390.1 (M + 1) | Method C |

TABLE 1-continued

| | | | | | | |
|---|---|---|---|---|---|---|
| 486 | 1H NMR (300 MHz, DMSO) δ 9.57 (d, J = 1.5 Hz, 1H), 9.07 (d, J = 4.6 Hz, 1H), 8.94 (dd, J = 5.2, 1.4 Hz, 1H), 8.04 (d, J = 9.1 Hz, 1H), 7.97 (dd, J = 6.7, 5.0 Hz, 1H), 7.67 (dd, J = 9.1, 2.8 Hz, 1H), 7.55 (d, J = 2.7 Hz, 1H), 7.36 (dd, J = 6.4, 2.3 Hz, 2H), 7.14-7.03 (m, 2H), 3.74 (s, 3H), 3.69 (s, 3H). | DMSO | 99 | Method G1 | 382.5 (M + 1) | Method C |
| 487 | 1H NMR (300 MHz, DMSO) δ 12.59 (s, 1H), 9.58 (d, J = 2.0 Hz, 1H), 8.94 (d, J = 8.2 Hz, 1H), 8.84 (d, J = 5.2 Hz, 1H), 8.73 (s, 1H), 8.09 (s, 1H), 7.95 (s, 3H), 7.82 (dd, J = 8.4, 5.4 Hz, 2H), 7.75 (d, J = 7.4 Hz, 2H), 7.59-7.42 (m, 3H). | DMSO | 99 | Method G1 | 458.4 (M + 1) | Method C |
| 488 | 1H NMR (300 MHz, DMSO) δ 13.79 (s, 1H), 9.49 (d, J = 1.5 Hz, 1H), 8.96 (d, J = 8.0 Hz, 1H), 8.86 (d, J = 3.7 Hz, 1H), 7.95-7.71 (m, 4H), 7.65 (d, J = 1.6 Hz, 1H), 6.76 (s, 1H), 2.85 (d, J = 22.5 Hz, 4H), 2.44-2.29 (m, 2H). | DMSO | 93 | Method G1 | 422.4 (M + 1) | Method C |
| 489 | 1H NMR (300 MHz, DMSO) δ 9.53 (d, J = 1.8 Hz, 1H), 9.04 (d, J = 7.9 Hz, 1H), 8.93 (d, J = 3.9 Hz, 1H), 7.95 (dd, J = 8.0, 5.2 Hz, 1H), 7.90-7.78 (m, 2H), 7.70 (d, J = 1.7 Hz, 1H), 2.29 (s, 3H), 2.24 (s, 3H). | DMSO | 94 | Method G1 | 410.3 (M + 1) | Method C |
| 490 | 1H NMR (300 MHz, DMSO) δ 13.07 (s, 1H), 9.93 (d, J = 1.8 Hz, 1H), 9.64 (d, J = 1.6 Hz, 1H), 8.90-8.78 (m, 1H), 8.76-8.62 (m, 2H), 8.29 (s, 1H), 8.18 (d, J = 8.3 Hz, 1H), 7.89 (d, J = 9.1 Hz, 1H), 7.71 (dd, J = 8.3, 1.9 Hz, 1H), 7.65 (s, 1H), 7.57 (dd, J = 9.1, 2.5 Hz, 1H), 7.53-7.44 (m, 2H), 7.01 (s, 1H), 4.21 (q, J = 6.9 Hz, 2H), 3.34 (s, 3H), 1.44 (t, J = 6.9 Hz, 3H). | DMSO | 99 | Method G1 | 464.2 (M + 1) | Method C |
| 491 | 1H NMR (300 MHz, DMSO) δ 9.78 (s, 1H), 9.50 (d, J = 2.0 Hz, 1H), 8.68-8.57 (m, 2H), 7.97 (d, J = 2.5 Hz, 1H), 7.85 (d, J = 1.8 Hz, 1H), 7.79 (d, J = 9.1 Hz, 1H), 7.55-7.43 (m, 3H), 7.22 (d, J = 8.4 Hz, 1H), 4.22 (q, J = 6.9 Hz, 2H), 3.37 (d, J = 4.3 Hz, 6H), 1.43 (t, J = 6.9 Hz, 3H). | DMSO | 99 | Method G1 | 427.5 (M + 1) | Method C |

TABLE 1-continued

| | | | | | | | |
|---|---|---|---|---|---|---|---|
| 492 | 1H NMR (300 MHz, DMSO) δ 11.48 (s, 1H), 10.97 (s, 1H), 9.28 (d, J = 1.5 Hz, 1H), 8.64 (dd, J = 4.6, 1.7 Hz, 1H), 8.40 (d, J = 8.1 Hz, 1H), 7.94-7.80 (m, 3H), 7.53-7.35 (m, 2H), 7.02 (t, J = 7.5 Hz, 1H), 6.90 (d, J = 8.2 Hz, 1H), 4.04 (s, H). | DMSO | 99 | Method F5, G13 | 391.1 (M + 1) | | Method C |
| 493 | 1H NMR (300 MHz, DMSO) δ 11.28 (s, 1H), 9.62 (d, J = 1.7 Hz, 1 H), 9.17 (d, J = 7.8 Hz, 1H), 8.93 (dd, J = 5.2, 1.3 Hz, 1H), 8.60 (s, 1H), 8.05 (s, 1H), 8.03-7.94 (m, 2H), 7.77 (s, 1H), 7.64 (dd, J = 9.2, 2.5 Hz 1H), 7.40 (d, J = 2.6 Hz, 1H), 3.97 (s, 3H). | DMSO | 99 | Method G14 | 362.4 (M + 1) | | Method C |
| 494 | $^1$H-NMR (400 MHz, DMSO-$d_6$): δ 10.14 (s, 1H), 9.54 (s, 1H), 8.70-8.67 (m, 2H), 8.48 (s, 1H), 8.16 (s, 1H), 7.96-7.89 (m, 3H), 7.60 (t, J = 8.0 Hz, 1H), 7.55-7.52 (m, 1H), 7.17 (d, J = 8.8 Hz, 1H), 3.71 (s, 2H), 2.72-2.65 (m, 8H). | DMSO | 95 | Method G1 | 498.1 (M + 1) | t = 2.128 min | Method B (NH4HCO3) |
| 495 | $^1$H-NMR (400 MHz, DMSO-$d_6$): δ 10.71 (s, 1H), 9.37 (s, 1H), 8.93 (s, 1H), 8.67 (d, J = 3.2 Hz, 1H), 8.48 (d, J = 8.0 Hz, IH), 7.93 (s, 1H), 7.39 (d, J = 8.0 Hz, 1H), 7.65 (m, 2H), 7.04 (d, J = 8.0 Hz, 1H), 2.95 (t, J = 8.0 Hz, 2H), 2.64 (t, J = 8.0 Hz, 2H). | DMSO | 95 | Method G1 | 402.0 (M + 1) | t = 1.746 min | Method B (NH4HCO3) |
| 496 | $^1$H-NMR (400 MHz, DMSO-$d_6$): δ 11.38 (s, 1H), 9.51 (s, 1H), 8.67-8.60 (m, 3H), 8.24-8.10 (m, 2H), 7.88-7.83 (m, 2H), 7.58-7.55 (m, 3H), 7.33 (dd, J = 7.2, 4.8 Hz, 1H), 3.97 (s, 3H). | DMSO | 95 | Method J1 | 373.0 (M + 1) | t = 1.523 min | Method B (NH4HCO3) |
| 497 | $^1$H-NMR (400 MHz, DMSO-$d_6$): δ 9.92 (s, 1H), 9.30 (s, 1H), 8.60 (d, J = 3.4 Hz, 1H), 8.48 (d, J = 8.0 Hz, 1H), 8.40 (d, J = 4.4 Hz, 1H), 7.87 (d, J = 2.2 Hz, 1H), 7.84 (d, J = 9.1 Hz, 1H), 7.59-7.40 (m, 5H), 4.24 (q, J = 6.9 Hz, 2H), 2.55 (d, J = 4.5 Hz, 3H), 1.45 (t, J = 6.9 Hz, 3H). | DMSO | 95 | Method G1 | 418.2 (M + 1) | t = 1.782 min | Method B ($NH_4HCO_3$) |
| 498 | $^1$H-NMR (400 MHz, DMSO-$d_6$): δ 10.14 (s, 1H), 9.54 (d, J = 2.0 Hz, 1H), 8.70-8.67 (m, 2H), 8.50 (s, 1H), 8.15 (s, 1H), 7.94- 7.92 (m, 3H), 7.61 (t, J = 8.0 Hz, 1H), 7.55 (dd, J = 8.0, 4.8 Hz, 1H), 7.18 (d, J = 8.0 Hz, 1H), 3.90 (s, 2H), 3.17 (s, 4H), 2.98 (s, 4H). | DMSO | 95 | Method G1 | 530.0 (M + 1) | t = 1.856 min | Method B ($NH_4HCO_3$) |

TABLE 1-continued

| | | | | | | | |
|---|---|---|---|---|---|---|---|
| 499 | $^1$H-NMR (400 MHz, DMSO-$d_6$): δ 13.19 (s, 1H), 9.65 (s, 1H), 9.17 (d, J = 8.2 Hz, 1H), 8.97 (d, J = 4.5 Hz, 1H), 8.93 (s, 1H), 8.81 (d, J = 8.2 Hz, 1H), 8.45 (s, 1H), 8.40 (dd, J = 8.7, 1.7 Hz, 1H), 8.16 (d, J = 8.7 Hz, 1H), 7.99 (dd, J = 16.0, 10.4 Hz, 3H), 7.74 (t, J = 7.4 Hz, 1H), 7.32 (t, J = 7.6 Hz, 1H), 3.38 (s, 3H). | DMSO | 95 | Method G1 | 420.1 (M + 1) | t = 1.478 min | Method B ($NH_4HCO_3$) |
| 501 | $^1$H-NMR (400 MHz, DMSO-$d_6$): δ 13.46 (s, 1H), 9.46 (s, 1H), 8.97 (d, J = 7.9 Hz, 1H), 8.93 (d, J = 4.4 Hz, 1H), 8.77 (d, J = 12.1 Hz, 1H), 8.55 (s, 1H), 8.16-7.91 (m, 4H), 7.83 (t, J = 7.5 Hz, 1H), 7.73 (d, J = 9.3 Hz, 1H), 7.05 (t, J = 6.9 Hz, 1H). | DMSO | 95 | Method G1 | 378.1 (M + 1) | t = 1.873 min | Method B ($NH_4HCO_3$) |
| 502 | $^1$H-NMR (400 MHz, DMSO-$d_6$): δ 13.00 (s, 1H), 9.83 (s, 1H), 9.17 (d, J = 8.0 Hz, 1H), 9.00 (d, J = 8.0 Hz, 1H), 8.73-8.72 (m, 1H), 8.49 (s, 1H), 7.96 (d, J = 8.4 Hz, 1H), 7.92 (s, 1H), 7.76 (t, J = 7.2 Hz, 1H), 7.63-7.53 (m, 3H), 7.28 (d, J = 7.6 Hz, 1H), 7.22 (t, J = 7.6 Hz, 1H). | DMSO | 95 | Method G1 | 358.0 (M + 1) | t = 1.644 min | Method B ($NH_4HCO_3$) |
| 503 | $^1$H-NMR (400 MHz, DMSO-$d_6$): δ 11.34 (s, 1H), 9.50 (s, 1H), 8.69 (d, J = 3.6 Hz, 1H), 8.65 (d, J = 7.6 Hz, 1H), 8.40 (d, J = 8.4 Hz, 1H), 8.15 (s, 1H), 8.10 (s, 1H), 8.00-7.97 (m, 1H), 7.91-7.84 (m, 2H), 7.69-7.66 (m, 1H), 7.55-7.52 (m, 1H), 7.16 (t, J = 9.2 Hz, 1H). | DMSO | 95 | Method G1 | 378.0 (M + 1) | t = 1.780 min | Method B ($NH_4HCO_3$) |
| 504 | 1H-NMR (300 MHz, DMSO): δ 10.48 (s, 1H), 9.57 (s, 1H), 9.13 (d, J = 7.6 Hz, 1H), 8.97-8.80 (m, 2H), 8.31 (s, 1H), 8.19 (s, 1H), 8.10 (d, J = 6.5 Hz, 1H), 7.97 (d, J = 9.1 Hz, 2H), 7.83 (d, J = 7.7 Hz, 1H), 7.66 (t, J = 7.9 Hz, 2H), 7.47 (d, J = 5.4 Hz, 1H), 4.02 (s, 3H). | DMSO | 95 | Method G1 | 396.1 (M + 1) | | Method C |
| 505 | $^1$H NMR (400 MHz, DMSO) δ 15.71 (s, 1H), 10.01 (s, 1H), 9.59-9.51 (m, 1H), 8.73-8.62 (m, 2H), 8.60-8.54 (m, 1H), 8.13-7.96 (m, 2H), 7.93-7.82 (m, 2H), 7.62-7.49 (m, 2H), 4.01 (s, 3H). | DMSO | >98 | G1 | | | |

TABLE 1-continued

| | | | | |
|---|---|---|---|---|
| 506 | $^1H$ NMR (400 MHz, DMSO) δ 10.77 (s, 1H), 9.75 (s, 1H), 9.55-9.46 (m, 1H), 8.73-8.60 (m, 2H), 7.96 (d, J = 2.7 Hz, 1H), 7.83 (d, J = 9.1 Hz, 1H), 7.63 (m, J = 2.1 Hz, 1H), 7.58-7.47 (m, 3H), 6.99 (d, J = 8.5 Hz, 1H), 4.64 (s, 2H), 3.97 (s, 3H). | DMSO | >98 | G1 (0.1 N HCl added) |
| 507 | $^1H$ NMR (400 MHz, DMSO) δ 12.54 (s, 1H), 9.85 (s, 1H), 9.51 (s, 1H), 8.70-8.60 (m, 2H), 8.27- 8.16 (m, 2H), 8.03 (d, J = 2.5 Hz, 1H), 7.83 (d, J = 9.1 Hz, 1H), 7.72-7.59 (m, 2H), 7.56-7.47 (m, 2H), 3.99 (s, 3H). | DMSO | >98 | G1 |
| 508 | $^1H$ NMR (400 MHz, DMSO) δ 9.87 (s, 1H), 9.50-9.47 (m, 1H), 8.66-8.61 (m, 2H), 8.21 (s, 1H), 8.16 (d, J = 1.6 Hz, 1H), 8.02 (d, J = 2.7 Hz, 1H), 7.83 (d, J = 9.1 Hz, 1H), 7.74 (dd, J = 8.7, 1.9 Hz, 1H), 7.67 (d, J = 8.6 Hz, 1H), 7.56-7.47 (m, 2H), 3,99 (s, 3H), 3.90 (s, 3H). | DMSO | >98 | G1 |
| 509 | $^1H$ NMR (400 MHz, DMSO) δ 9.90 (s, 1H), 9.47 (dd, J = 2.1, 0.8 Hz, 1H), 8.67-8.60 (m, 2H), 8.15 (d, J = 2.1 Hz, 1H), 7.97 (d, J = 2.7 Hz, 1H), 7.88-7.81 (m, 2H), 7.57-7.49 (m, 2H), 7.44 (d, J = 8.7 Hz, 1H), 3.98 (s, 3H), 3.47 (s, 3H). | DMSO | >98 | G1 (0.1 N HCl added) |
| 510 | $^1H$ NMR (400 MHz, DMSO) δ 10.76 (s, 1H), 10.62 (s, 1H), 9.71 (s, 1H), 9.53-9.48 (m, 1H), 8.68-8.62 (m, 2H), 7.98 (d, J = 2.6 Hz, 1H), 7.81 (d, J = 9.1 Hz, 1H), 7.63 (d, J = 1.8 Hz, 1H), 7.55-7.49 (m, 2H), 7.37 (dd, J = 8.4, 2.0 Hz, 1H), 7.01 (d, J = 8.3 Hz, 1H), 3.97 (s, 3H). | DMSO | >98 | G1 (0.1 N HCl added) |
| 511 | $^1H$ NMR (400 MHz, DMSO) δ 9.96 (s, 1H), 9.49 (dd, J = 2.1, 0.8 Hz, 1H), 8.79 (s, 1H), 8.67-8.61 (m, 2H), 8.39-8.36 (m, 1H), 8.02 (d, J = 2.7 Hz, 1H), 7.90- 7.84 (m, 3H), 7.56 (dd, J = 9.1, 2.7 Hz, 1H), 7.54-7.50 (m, 1H), 3.99 (s, 3H). | DMSO | >98 | J2 |
| 512 | $^1H$ NMR (400 MHz, DMSO) δ 9.87 (s, 1H), 9.48 (dd, J = 2.1, 0.8 Hz, 1H), 8.67-8.61 (m, 2H), 8.10-8.08 (m, 1H), 8.00 (d, J = 2.7 Hz, 1H), 7.84 (d, J = 9.1 Hz, 1H), 7.65-7.63 (m, 2H), 7.57- 7.49 (m, 2H), 4.22 (s, 3H), 3.99 (s, 3H). | DMSO | >98 | G1 |

TABLE 1-continued

| | | | | |
|---|---|---|---|---|
| 513 | $^{1}$H NMR (400 MHz, DMSO) δ 9.92 (s, 1H), 9.49 (dd, J = 2.1, 0.8 Hz, 1H), 8.67-8.60 (m, 2H), 8.22 (d, J = 1.8 Hz, 1H), 8.00 (d, J = 2.7 Hz, 1H), 7.85 (d, J = 9.1 Hz, 1H), 7.70-7.64 (m, 1H), 7.60 (d, J = 8.5 Hz, 1H), 7.57-7.49 (m, 2H), 4.21 (s, 3H), 3.98 (s, 3H). | DMSO | >98 | J2 |
| 514 | $^{1}$H NMR (400 MHz, DMSO) δ 10.97 (s, 1H), 9.43 (d, J = 1.6 Hz, 1H), 8.98-8.91 (m, 1H), 8.89 (dd, J = 5.2, 1.3 Hz, 1H), 8.43 (s, 1H), 8.27 (s, 1H), 8.13-8.04 (m, 2H), 7.92-7.85 (m, 1H), 7.73 (d, J = 9.2 Hz, 1H), 7.70-7.63 (m, 2H), 4.21 (s, 3H), 4.02 (s, 3H). | DMSO | >98 | G1 |
| 515 | $^{1}$H NMR (400 MHz, DMSO) δ 11.90 (s, 1H), 10.45 (s, 1H), 9.46 (d, J = 1.7 Hz, 1H), 8.97-8.89 (m, 1H), 8.85 (dd, J = 5.2, 1.5 Hz, 1H), 8.16-8.10 (m, 2H), 8.03-7.97 (m, 2H), 7.94 (d, J = 9.1 Hz, 1H), 7.90-7.82 (m, 1H), 7.63 (dd, J = 9.1, 2.6 Hz, 1H), 7.44 (d, J = 8.8 Hz, 1H), 6.58 (d, J = 9.4 Hz, 1H), 4.00 (s, 3H). | DMSO | >98 | G1 (0.1 N HCl added) |
| 516 | $^{1}$H NMR (400 MHz, DMSO) δ 9.90 (s, 1H), 9.53-9.50 (m, 1H), 8.68-8.63 (m, 2H), 8.27 (d, J = 2.0 Hz, 1H), 8.01 (d, J = 2.7 Hz, 1H), 7.96 (d, J = 8.6 Hz, 1H), 7.85 (d, J = 9.1 Hz, 1H), 7.81 (dd, J = 8.7, 2.1 Hz, 1H), 7.58-7.50 (m, 2H), 4.20 (s, 3H), 3.99 (s, 3H). | DMSO | >98 | G1 |
| 517 | $^{1}$H NMR (300 MHz, DMSO) δ 11.35 (s, 1H), 9.58 (d, J = 1.6 Hz, 1H), 9.24 (d, J = 8.2 Hz, 1H), 9.05-8.97 (m, 1H), 9.05-8.95 (m, 1H), 8.21 (d, J = 2.4 Hz, 1H), 8.11-8.02 (m, 3H), 7.90 (d, J = 7.8 Hz, 1H), 7.58 (dd, J = 8.8, 2.0 Hz, 2H), 7.52-7.46 (m, 1H), 7.28 (s, 1H), 3.98 (d, J = 9.2 Hz, 3H). | DMSO | >98 | G1 |
| 518 | $^{1}$H NMR (300 MHz, DMSO) δ 11.32 (s, 1H), 9.60 (s, 1H), 9.23 (d, J = 8.0 Hz, 1H), 8.98 (d, J = 5.4 Hz, 1H), 8.26 (s, 1H), 8.06 (dd, J = 13.2, 7.3 Hz, 2H), 7.63 (d, J = 9.1 Hz, 1H), 7.50-7.36 (m, 4H), 7.32 (s, 1H), 7.06-6.90 (m, 1H), 3.99 (s, 3H), 3.86 (s, 3H). | DMSO | >98 | G1 |

TABLE 1-continued

| | | | | | |
|---|---|---|---|---|---|
| | 519 | 1H NMR (300 MHz, DMSO) δ 13.17 (s, 1H), 11.46 (s, 1H), 9.19 (d, J = 1.7 Hz, 1H), 8.95-8.78 (m, 2H), 8.31 (d, J = 2.6 Hz, 1H), 8.18 (d, J = 9.2 Hz, 1H), 7.86 (dd, J = 7.9, 5.4 Hz, 1H), 7.77-7.54 (m, 3H), 7.44 (dd, J = 11.4, 3.9 Hz, 1H), 7.20-7.02 (m, 1H), 4.01 (s, 3H). | DMSO | >98 | G1 |
| | 520 | $^{1}$H NMR (300 MHz, DMSO) δ 11.10 (s, 1H), 9.59 (d, J = 1.8 Hz, 1H), 9.15 (d, J = 8.0 Hz, 1H), 8.93 (d, J = 3.9 Hz, 1H), 8.22 (d, J = 2.6 Hz, 1H), 7.99 (t, J = 7.4 Hz, 2H), 7.72 (dd, J = 8.4, 4.7 Hz, 2H), 7.63-7.50 (m, 2H), 7.35 (s, 1H), 7.27-7.18 (m, 1H), 3.99 (s, 3H). | DMSO | >98 | G1 |
| | 521 | $^{1}$H NMR (300 MHz, DMSO) δ 11.51 (s, 1H), 9.63 (d, J = 1.9 Hz, 1H), 9.18 (d, J = 8.1 Hz, 1H), 8.98 (dd, J = 5.2, 1.2 Hz, 1H), 8.31 (d, J = 2.5 Hz, 1H), 8.17 (d, J = 9.1 Hz, 1H), 8.01 (dd, J = 8.0, 5.3 Hz, 1H), 7.84 (dd, J = 7.7, 1.5 Hz, 1H), 7.66 (dd, J = 9.1, 2.5 Hz, 1H), 7.48-7.35 (m, 2H), 7.21 (d, J = 8.2 Hz, 1H), 7.10 (t, J = 7.5 Hz, 1H), 3.99 (d, J = 6.3 Hz, 6H). | DMSO | >98 | G1 |
| | 1758 | 1H NMR (DMSO-d6) ppm 13.00-12.40 (br, 1H), 9.79 (d, J = 1.68 Hz, 1H), 9.30 (d, J = 8.20 Hz, 1H), 8.95 (dd, J = 5.32, 1.44 Hz, 1H), 8.71 (d, J = 4.24 Hz, 1H), 8.37 (brd, J = 2.56 Hz, 1H), 8.25-8.21 (m, 2H), 8.11-8.02 (m, 2H), 7.98 (d, J = 9.12 Hz, 1H), 7.66 (dd, J = 9.12, 2.68 Hz, 1H), 7.53-7.50 (m, 1H), 4.03 (s, 3H). The 1H of 3HCl was not observed. | DMSO | >98 | G13 |
| | 1759 | IH NMR (DMSO-d6) pprn 10.35 (br, 1H), 9.37 (d, J = 1.6 Hz, 1H), 8.96 (d, J = 7.28 Hz, 1H), 8.90 (d, J = 4.2 Hz, 1H), 8.04 (s, 1H), 7.98 (m, 1H), 7.95 (d, J = 9.16 Hz, 1H), 7.64 (dd, J = 9.16, 2.56 Hz, 1H), 6.18 (s, 1H), 3.98 (s, 3H), 3.66 (s, 3H), 2.24 (s, 3H). The 1H of 3HCl was not observed. | DMSO | >98 | J2 |

Scheme 6: General route for the synthesis of compounds with general formula xiv
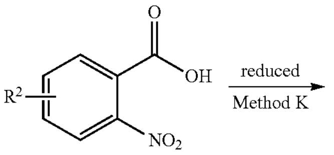
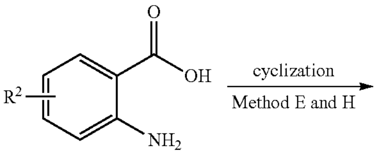
viii
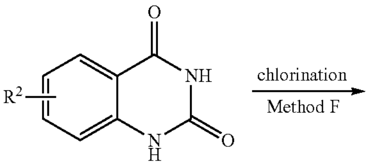
ix
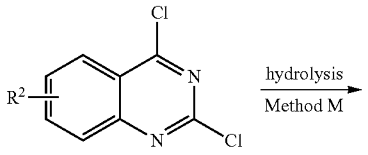
x
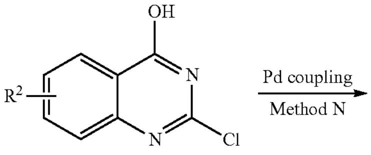
xi
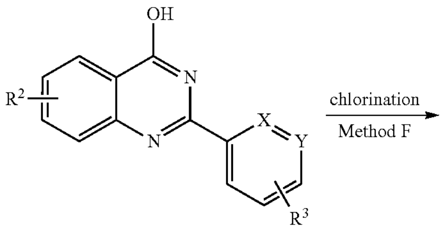
X or Z = CH or N
xii
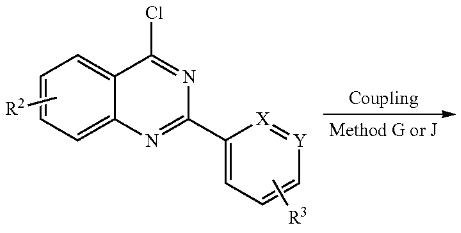
X or Z = CH or N
xiii
-continued
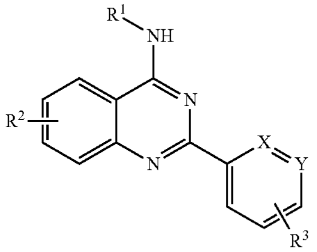
X or Z = CH or N
xiv
Scheme 7: Representative synthesis of pyridine of formula xiv-a (see Scheme 6)
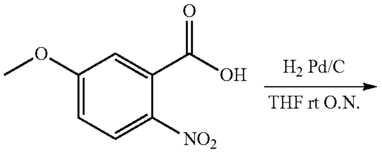
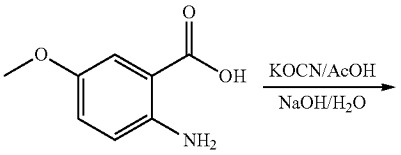
viii-a
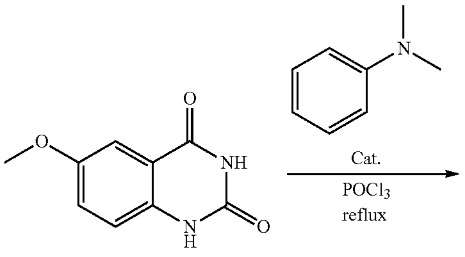
ix-a
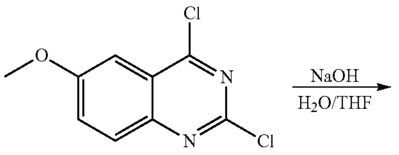
x-a
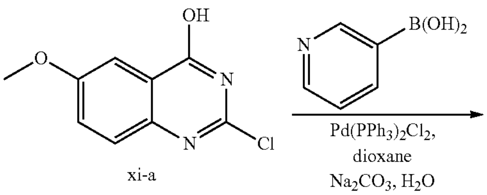
xi-a
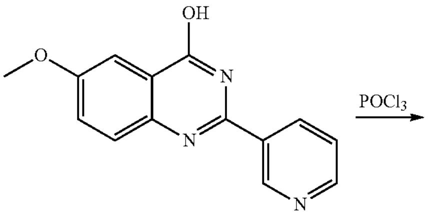
xii-a -continued

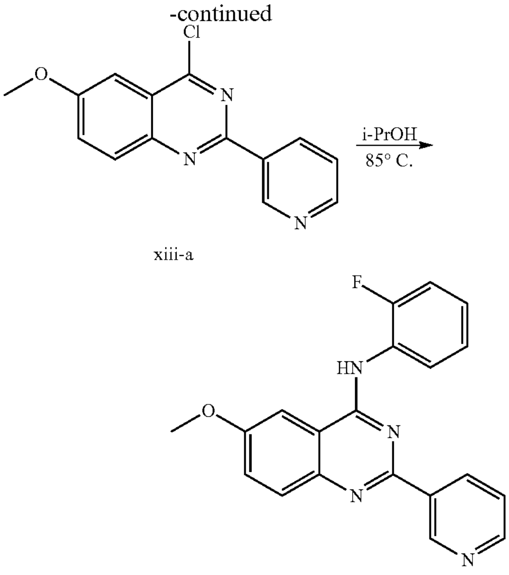

xiii-a xiv-a

Method K: 2-Amino-5-methoxybenzoic acid (viii-a)

5-Methoxy-2-nitrobenzoic acid (30.0 g, 152.2 mmol) was hydrogenated over Pd/C (10% c, 300 mg) in THF (250 mL) at room temperature under $H_2$ balloon. The mixture was stirred for 18 h. After the reaction was completed, the catalyst was removed by filtration over Celite and the filtrate was concentrated to afford 25.0 g of 2-amino-5-methoxybenzoic acid as a brown solid (98%). LCMS m/z=168.1 (M+1), 150.1 (M−17) (Method B) (retention time=0.53 min) $^1$H NMR (400 MHz, DMSO-$d_6$): δ 7.31 (d, J=2.8 Hz, 1H), 6.61 (dd, J=8.8, 3.2 Hz, 1H), 6.44 (d, J=8.8 Hz, 1H), 3.60 (s, 3H).

Method H: 6-Methoxyquinazoline-2,4(1H, 3H)-dione (ix-a)

2-Amino-5-methoxybenzoic acid (13.0 g, 77.8 mmol, 1.0 eq.) was suspended in water (200 mL) and glacial acetic acid (5.2 mL) at 35° C. A freshly prepared solution of potassium cyanate (8.21 g, 101.4 mmol, 1.3 eq.) in water (86 mL) was added dropwise to the stirred mixture. After 4 h, NaOH (104.0 g, 2600 mL, 33.4 eq.) was added in portions, keeping the reaction temperature below 40° C. A clear solution was obtained momentarily before a precipitate formed. After cooling, the precipitate was filtered off and dissolved in hot water which was acidified to pH 5. The precipitate was collected and washed with water, dried by lyophilization to afford 9.63 g of 6-methoxyquinazoline-2,4(1H, 3H)-dione as a white solid (65%). LCMS m/z=193.1 (M+1) (Method B) (retention time=1.22 min). $^1$H NMR (400 MHz, DMSO-$d_6$): δ 11.26 (s, 1H), 11.01 (s, 1H), 7.31-7.25 (m, 2H), 7.10 (d, 1H, J=8.8 Hz), 3.77 (s, 3H).

Method F1: 2,4-Dichloro-6-methoxyquinazoline (x-a)

To a mixture of 6-methoxyquinazoline-2,4(1H, 3H)-dione (9.63 g, 50.2 mmol) in $POCl_3$ (150 mL) was added N,N-dimethylaniline (0.5 mL). The resulting mixture was stirred at 120° C. for 2 h. After the reaction was completed, $POCl_3$ was removed in vacuo, and the residue was added to ice-water slowly. The pH was adjusted to ~7 by slowly adding $NaHCO_3$ (sat.) at 0° C., then a precipitate formed. The solid was collected and dried in vacuo to give 11.2 g of 2,4-dichloro-6-methoxyquinazoline in a 98% yield as a brown solid. LCMS m/z=229.1, 231.0 (M+1) (Method B) (retention time=1.87 min). $^1$H-NMR (400 MHz, DMSO-$d_6$): δ 7.89 (d, J=9.2 Hz, 1H), 7.71 (dd, J=8.8, 2.4 Hz, 1H), 7.38 (d, J=1.6 Hz, 1H), 3.91 (s, 3H).

Method M: 2-Chloro-6-methoxyquinazolin-4-ol (xi-a)

A mixture of 2,4-dichloro-6-methoxyquinazoline (4.20 g, 18.5 mmol, 1.0 eq.) in THF (60 mL) and 1120 (60 mL) was treated with NaOH (4.00 g, 100 mmol, 5.4 eq.). The resulting mixture was stirred at 40° C. for 2 h. The reaction color turned to dark green and then a precipitate formed. After the reaction was completed, the mixture was cooled to room temperature. The precipitate was filtered off and the filtrate was concentrated down to 60 mL. The pH was then adjusted to 6 by adding 2N HCl in water. The precipitate which formed was collected and dried in vacuo to give 4.00 g of 2-chloro-6-methoxyquinazolin-4-ol as a grey solid (98%). LCMS m/z=211.1, 213.0 (M+1) (Method B) (retention time=1.11 min).

Method N: 6-Methoxy-2-(pyridin-3-yl) quinazolin-4-ol (xii-a)

To a mixture of 2-chloro-6-methoxyquinazolin-4-ol (1.20 g, 5.7 mmol, 1.0 eq.), pyridin-3-ylboronic acid (1.27 g, 8.6 mmol, 1.5 eq.), $K_2CO_3$ (2.37 g, 17.1 mmol, 3.0 eq.) in dioxane (100 mL) and $1H_2O$ (10 ml) was added $Pd(PPh_3)_2Cl_2$ (230 mg, 0.29 mmol, 0.05 eq.) under $N_2$ atmosphere. The resulting mixture was stirred at 105° C. under $N_2$ atmosphere overnight. After reaction was completed, the mixture was cooled to room temperature, and the resultant precipitate was removed by filtration. The filtrate was concentrated in vacuo and the residue was partitioned between $H_2O$ (30 mL) and ethyl acetate (100 mL×3). The combined organic layers were washed with brine, dried over $MgSO_4$. After filtration and evaporation, the crude product was obtained, which was combined with the filter cake and dried in vacuo to give 1.35 g of 6-methoxy-2-(pyridin-3-yl) quinazolin-4-ol as a gray solid. LCMS m/z=254.1 (M+1) (Method B) (retention time=1.39 min). The crude product was used for the next step without further purification.

Method F1: 4-Chloro-6-methoxy-2-(pyridin-3-yl) quinazoline (xiii-a)

To a mixture of 6-methoxy-2-(pyridin-3-yl) quinazolin-4-ol (600 mg, 2.37 mmol) in $POCl_3$ (5 mL) was added N,N-dimethyl aniline (1 drop). The resulting mixture was stirred at 120° C. for 30 min. After the reaction was completed, $POCl_3$ was removed in vacuo, and the residue was added to ice-water slowly. The pH was adjusted to ~7 by slowly adding $NaHCO_3$ (sat.) at 0° C. and then a precipitate formed. The solid was collected and was purified by chromatography on silica gel eluted with petroleum ether/ethyl acetate (v/v=4:1 to 1:1) to give 260 mg of 4-chloro-6-methoxy-2-(pyridin-3-yl) quinazoline as a pale yellow solid (40.4%). LCMS m/z=272.1, 274.0 (M+1) (Method B) (retention time=1.90 min).

Method G1: N-(2-Fluorophenyl)-6-methoxy-2-(pyridin-3-yl)quinazolin-4-amine (xiv-a)

A mixture of 4-chloro-6-methoxy-2-(pyridin-3-yl) quinazoline (80 mg, 0.293 mmol, 1.0 eq.) and 2-fluoroaniline (65 mg, 0.58 mmol, 2 eq.) in i-PrOH (5 mL) was stirred at 85° C. for 18 h. After the reaction was completed, the mixture was filtered, and the filter cake was washed with $H_2O$ (10 ml) and diethyl ether (10 mL). After drying, the crude product was purified by PREP-HPLC (Condition C: Gradient: B=5%-50%, Target Peak: at 7.2 min) to give 16.5 mg of N-(2-fluorophenyl)-6-methoxy-2-(pyridin-3-yl)quinazolin-4-amine as a yellow solid, yield 16.4%. LCMS m/z=347.0 (M+1) (Method A) (retention time=1.31 min). $^1$H-NMR (400 MHz, DMSO-$d_6$): δ 10.08 (s, 1H), 9.33 (s, 1H), 8.72 (d, J=4.4 Hz, 1H), 8.66 (d, J=8.0 Hz, 1H), 8.80 (d, J=1.2 Hz, 1H), 7.88 (d, J=9.2 Hz, 1H), 7.70-7.65 (m, 2H), 7.58 (dd, J=8.8, 1.2 Hz, 1H), 7.44-7.35 (m, 3H), 3.97 (s, 3H).

The compounds in the following table were prepared in a manner analogous to that described in Scheme 6 substituting with appropriate nitro benzoic acid, boronic acid and aniline

TABLE 2

| Number | Product | Salt type | Molecular Mass | $^1$H-NMR |
|---|---|---|---|---|
| 522 | 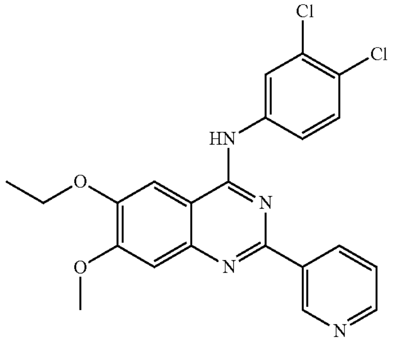 [SMILES: CCOc1cc2c(Nc3ccc(Cl)c(Cl)c3)nc(-c3cccnc3)nc2cc1OC] | | 455.34 | 1H-NMR (400 MHz, DMSO-d6): δ 9.76 (s, 1H), 9.52-9.51 (m, 1H), 8.63-8.66 (m, 2H), 8.32 (d, J = 2.4 Hz, 1H), 7.94-7.91 (m, 2H), 7.72 (d, J = 8.3 Hz, 1H), 7.54 (q, J = 3.2 Hz, 1H), 7.32 (s, 1H), 4.87-4.90 (m, 1H), 3.96 (s, 3H), 1.38 (d, J = 6.0 Hz, 6H). |
| 523 | 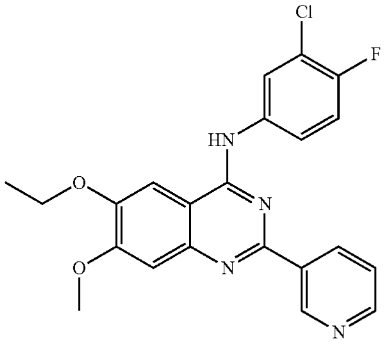 | | 438.88 | 1H-NMR (400 MHz, DMSO-d6): δ 9.58 (s, 1H), 9.49 (d, J = 2.0 Hz, 1H), 8.60-8.66 (m, 2H), 8.18 (dd, J = 6.4, 2.4 Hz, 1H), 7.84-7.88 (m, 2H), 7.50-7.54 (m, 2H), 7.31 (s, 1H), 4.85-4.88 (m, 1H), 3.96 (s, 3H), 1.38 (d, J = 6.4 Hz, 6H). |
| 524 | 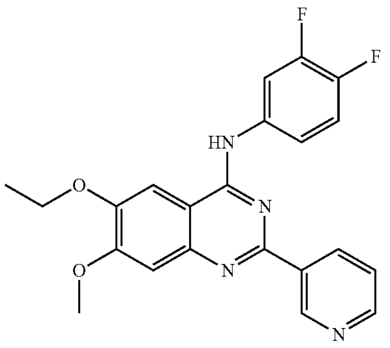 [SMILES: CCOc1cc2c(Nc3ccc(F)c(F)c3)nc(-c3cccnc3)nc2cc1OC] | | 422.43 | 1H-NMR (400 MHz, DMSO-d6): δ 9.76 (s, 1H), 9.48 (s, 1H), 8.60-8.65 (m, 2H), 8.04-8.10 (m, 1H), 7.92 (s, 1H), 7.49-7.66 (m, 3H), 7.30 (s, 1H), 4.86-4.92 (m, 1H), 3.96 (s, 3H), 1.37 (d, J = 6.0 Hz, 6H) |

TABLE 2-continued
| | | | | |
|---|---|---|---|---|
| 525 | 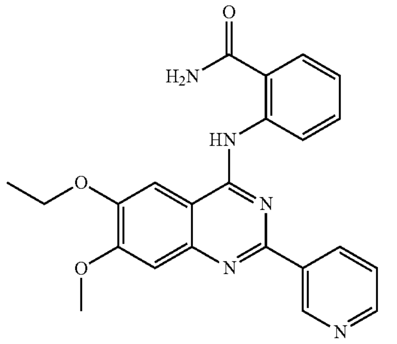 [SMILES: CCOc1cc2c(Nc3ccccc3C(N)=O)nc(-c3cccnc3)nc2cc1OC] | HCl | 429.47 | 1H-NMR (400 MHz, DMSO-d6): δ 12.96 (s, 1H), 9.60 (d, J = 8.0 Hz, 1H), 9.14 (d, J = 8.0 Hz, 1H), 8.68-8.74 (m, 2H), 8.46 (s, 1H), 7.95-7.96 (m, 2H), 7.74-7.70 (m, 1H), 7.59-7.54 (m, 2H), 7.36 (s, 1H), 7.19-7.15 (m, 1H), 4.76-4.82 (m, 1H), 3.99 (s, 3H), 1.44 (d, J = 6.0 Hz, 6H). |
| 526 | 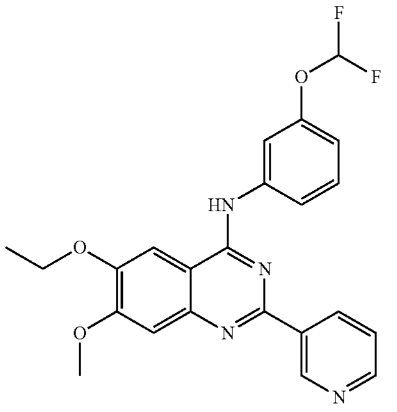 [SMILES: CCOc1cc2c(Nc3cccc(OC(F)F)c3)nc(-c3cccnc3)nc2cc1OC] | | 452.45 | 1H-NMR (400 MHz, DMSO-d6): δ 9.70 (s, 1H), 9.52-9.53 (m, 1H), 8.64-8.67 (m, 2H), 7.89-7.94 (m, 2H), 7.73-7.74 (m, 1H), 7.48-7.53 (m, 3H), 7.32 (t, J = 83.6 Hz, 1H), 6.96-6.99 (m, 1H), 4.89-4.92 (m, 1H), 3.98 (s, 3H), 1.38 (d, J = 6.0 Hz, 6H). |
| 527 | 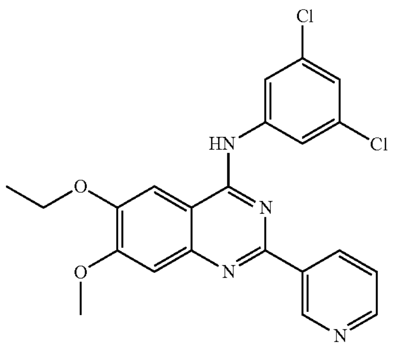 [SMILES: CCOc1cc2c(Nc3cc(Cl)cc(Cl)c3)nc(-c3cccnc3)nc2cc1OC] | | 455.34 | 1H-NMR (400 MHz, DMSO-d6): δ 9.53 (s, 1H), 9.52 (d, J = 1.6 Hz, 1H), 8.64-8.68 (m, 2H), 8.12-8.13 (m, 2H), 7.90 (s, 1H), 7.54-7.58 (m, 1H), 7.34-7.36 (m, 2H), 4.86-4.92 (m, 1H), 3.98 (s, 3H), 1.40 (d, J = 6.0 Hz, 6H). |
| 528 | 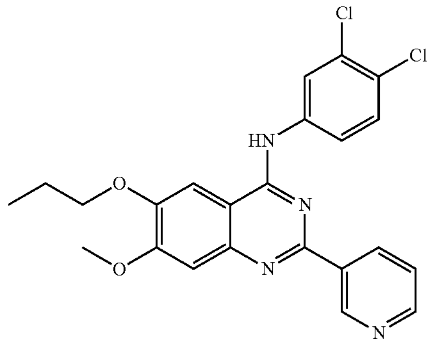 [SMILES: CCCOc1cc2c(Nc3ccc(Cl)c(Cl)c3)nc(-c3cccnc3)nc2cc1OC] | | 455.34 | 1H-NMR (400 MHz, DMSO-d6): δ 9.76 (s, 1H), 9.52 (d, J = 1.2 Hz, 1H), 8.64-8.67 (m, 2H), 8.32 (d, J = 2.8 Hz, 1H), 7.94 (dd, J = 6.8, 2.4 Hz, 1H), 7.86 (s, 1H), 7.72 (d, J = 8.3 Hz, 1H), 7.53-7.56 (m, 1H), 7.32 (s, 1H), 4.14 (t, J = 6.4 Hz, 2H), 3.99 (s, 3H), 1.85-1.92 (m, 2H), 1.06 (t, J = 7.2 Hz, 3H). |

TABLE 2-continued
| | | | | |
|---|---|---|---|---|
| 529 | 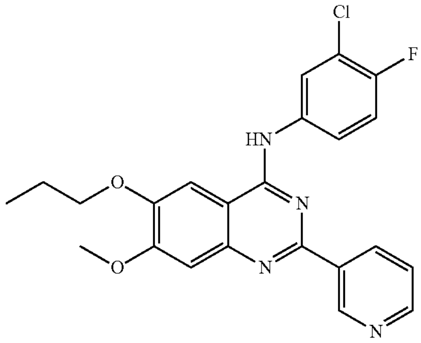 [SMILES: CCCOc1cc2c(Nc3ccc(F)c(Cl)c3)nc(-c3cccnc3)nc2cc1OC] | | 438.88 | 1H-NMR (400 MHz, DMSO-d6): δ 9.72 (s, 1H), 9.50 (d, J = 1.6 Hz, 1H), 8.62-8.66 (m, 2H), 8.20 (dd, J = 6.4, 2.4 Hz, 1H), 7.85-7.89 (m, 2H), 7.50-7.55 (m, 2H), 7.31 (s, 1H), 4.13 (t, J = 6.4 Hz, 2H), 3.98 (s, 3H), 1.82-1.90 (m, 2H), 1.06 (t, J = 7.6 Hz, 3H). |
| 530 | 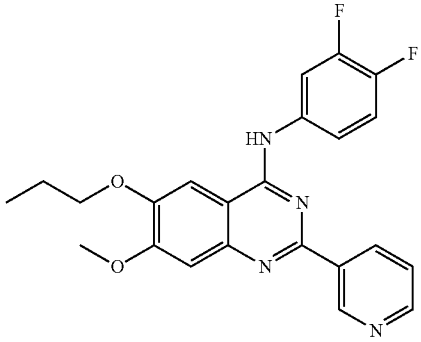 | | 422.43 | 1H-NMR (400 MHz, DMSO-d6): δ 9.74-9.76 (m, 1H), 9.52 (d, J = 1.6 Hz, 1H), 8.64-8.69 (m, 2H), 8.08-8.14 (m, 1H), 7.90 (s, 1H), 7.68-7.70 (m, 1H), 7.52-7.60 (m, 2H), 7.34 (s, 1H), 4.16 (t, J = 6.4 Hz, 2H), 4.01 (s, 3H), 1.85-1.94 (m, 2H), 1.09 (t, J = 7.2 Hz, 3H). |
| 531 | 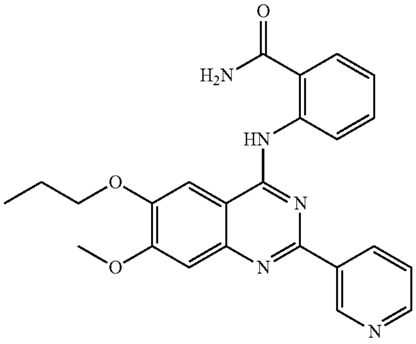 [SMILES: CCCOc1cc2c(Nc3ccccc3C(N)=O)nc(-c3cccnc3)nc2cc1OC] | HCl | 429.47 | 1H-NMR (400 MHz, DMSO-d6): δ 12.86 (s, 1H), 9.59 (d, J = 1.6 Hz, 1H), 9.05 (d, J = 8.4 Hz, 1H), 8.85 (d, J = 8.0 Hz, 1H), 8.76-8.78 (m, 1H), 8.44 (s, 1H), 7.96 (dd, J = 8.0, 1.6 Hz, 2H), 7.70-7.73 (m, 2H), 7.53 (s, 1H), 7.37 (s, 1H), 6.96-7.22 (m, 1H), 4.16 (t, J = 6.4 Hz, 2H), 4.01 (s, 3H), 1.86-1.90 (m, 2H), 1.07 (t, J = 7.2 Hz, 3H). |
| 532 | 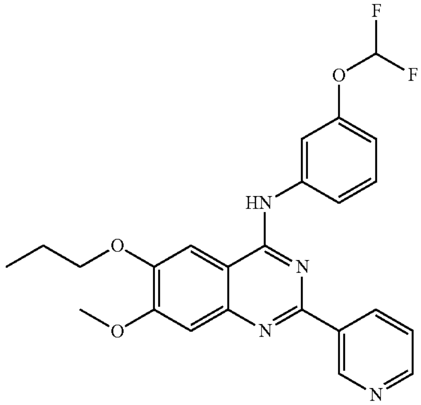 [SMILES: CCCOc1cc2c(Nc3cccc(OC(F)F)c3)nc(-c3cccnc3)nc2cc1OC] | | 452.45 | 1H-NMR (400 MHz, DMSO-d6): δ 9.67 (s, 1H), 9.50 (d, J = 4.0 Hz, 1H), 8.62-8.65 (m, 2H), 7.89-7.92 (m, 3H), 7.44-7.54 (m, 1H), 7.29-7.31 (m, 3H), 7.26 (t, J = 74.0 Hz, 1H), 4.14 (t, J = 6.8 Hz, 2H), 3.98 (s, 3H), 1.84-1.90 (m, 2H), 1.06 (t, J = 7.2 Hz, 3H). |

TABLE 2-continued
| | | | | |
|---|---|---|---|---|
| 533 | 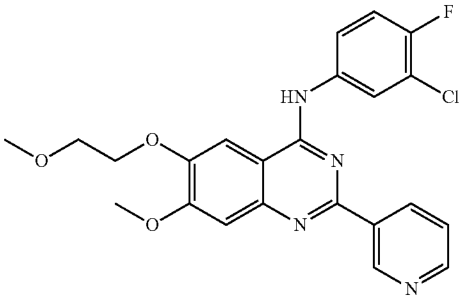 [SMILES: COCCOc1cc2c(Nc3ccc(F)c(Cl)c3)nc(-c3cccnc3)nc2cc1OC] | HCl | 454.88 | 1H-NMR (400 MHz, DMSO-d6): δ 9.73 (s, 1H), 9.50 (d, J = 2.4 Hz, 1H), 8.62-8.67 (m, 2H), 8.20 (dd, J = 7.2 Hz, 2.8 Hz, 1H), 7.85-7.89 (m, 2H), 7.51-7.57 (m, 2H), 7.33 (s, 1H), 4.31 (t, J = 4.0 Hz, 2H), 3.99 (s, 3H) 3.80 (t, J = 4.8 Hz, 2H), 3.37 (s, 3H). |
| 534 | 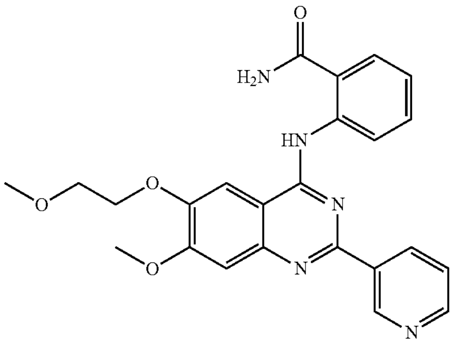 [SMILES: COCCOc1cc2c(Nc3ccccc3C(N)=O)nc(-c3cccnc3)nc2cc1OC] | | 445.47 | 1H-NMR (400 MHz, CD3OD): δ 9.34 (s, 1H), 8.92 (d, J = 6.0 Hz, 1H), 8.73 (m, 2H), 7.84 (s, 1H), 7.76 (d, J = 8.0 Hz, 1H), 7.54 (t, J = 8.0 Hz, 1H), 7.32 (s, 1H), 7.15 (s, 2H), 4.21 (s, 2H), 3.92 (s, 3H), 3.78 (t, J = 4.4 Hz, 2H), 3.40 (s, 3H). |
| 535 | 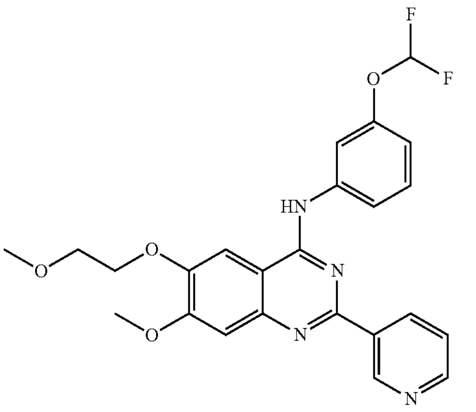 [SMILES: COCCOc1cc2c(Nc3cccc(OC(F)F)c3)nc(-c3cccnc3)nc2cc1OC] | HCl | 468.45 | 1H-NMR (400 MHz, DMSO-d6): δ 9.72 (s, 1H), 9.53 (s, 1H), 8.66 (d, J = 5.6 Hz, 2H), 7.91 (d, J = 6.4 Hz, 2H), 7.75 (d, J = 7.2 Hz, 1H), 7.51 (dd, J = 7.6 Hz, 2H), 7.34 (s, 1H), 7.30 (t, J = 74.0 Hz, 1H), 6.97 (dd, J = 8.0, 2.0 Hz, 1H), 4.32 (t, J = 4.4 Hz, 2H), 3.99 (s, 3H), 3.80 (t, J = 4.4 Hz, 2H), 3.37 (s, 3H). |
| 536 | 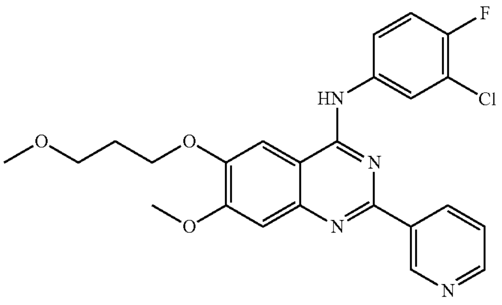 [SMILES: COCCCOc1cc2c(Nc3ccc(F)c(Cl)c3)nc(-c3cccnc3)nc2cc1OC] | | 468.91 | 1H-NMR (400 MHz, DMSO-d6): δ 10.42 (s, 1H), 9.47 (s, 1H), 8.96 (d, J = 6.4 Hz, 1H), 8.90 (d, J = 5.2 Hz, 1H), 8.11 (dd, J = 6.8 Hz, 2.4 Hz, 1H), 8.05 (s, 2H), 7.85-7.94 (m, 2H), 7.55 (t, J = 9.2 Hz, 1H), 7.47 (s, 1H) 4.26 (t, J = 6.4 Hz, 2H), 4.01 (s, 3H), 3.55 (t, J = 6.0 Hz, 2H), 3.29 (s, 3H), 2.06-2.13 (m, 2H). |

TABLE 2-continued
| | | | |
|---|---|---|---|
| 537 | 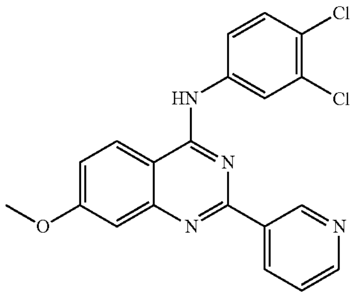 | 397.26 | 1H-NMR (400 MHz, DMSO-d6): δ 10.08 (s, 1H), 9.54 (s, 1H), 8.76 (s, 2H), 8.49 (d, J = 7.0 Hz, 1H), 8.36 (s, 1H), 7.95 (d, J = 7.5 Hz, 1H), 7.66-7.23 (m, 2H), 7.33 (s, 2H), 3.98 (s, 3H). |
| 538 | 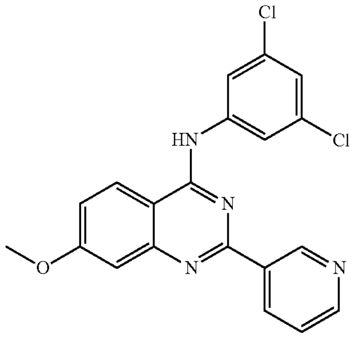 [SMILES: COc1ccc2c(Nc3cc(Cl)cc(Cl)c3)nc(-c3cccnc3)nc2c1] | 397.26 | 1H-NMR (400 MHz, DMSO-d6): 10.00 (s, 1H), 8.54 (d, J = 1.3 Hz, 1H), 8.71-8.56 (m, 2H), 8.47 (d, J = 9.2 Hz, 1H), 8.17 (s, 1H), 8.16 (s, 1H), 7.59-7.56 (m, 1H), 7.35-7.30 (m, 3H), 3.98 (s, 3H). |
| 539 | 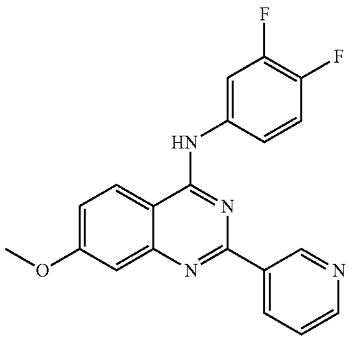 [SMILES: COc1ccc2c(Nc3ccc(F)c(F)c3)nc(-c3cccnc3)nc2c1] | 364.35 | 1H-NMR (400 MHz, DMSO-d6): δ 9.94 (s, 1H), 9.53 (d, J = 1.6 Hz, 1H), 8.70-8.65 (m, 2H), 8.47 (d, J = 8.4 Hz, 1H), 8.12 (ddd, J = 13.2, 7.6, 2.8 Hz, 1H), 7.72-7.70 (m, 1H), 7.58-7.49 (m, 2H), 7.32-7.27 (m, 2H), 3.97 (s, 3H). |
| 540 | 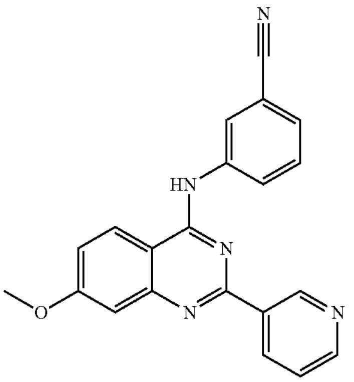 [SMILES: COc1ccc2c(Nc3cccc(C#N)c3)nc(-c3cccnc3)nc2c1] | 353.38 | 1H-NMR (400 MHz, DMSO-d6): δ 10.06 (s, 1H), 9.53 (d, J = 1.6 Hz, 1H), 8.71-8.66 (m, 2H), 8.50-8.43 (m, 2H), 8.26-8.24 (m, 1M), 7.70-7.54 (m, 3H), 7.34-7.30 (m, 2H), 3.98 (s, 3H), |

TABLE 2-continued
| | | | |
|---|---|---|---|
| 541 | 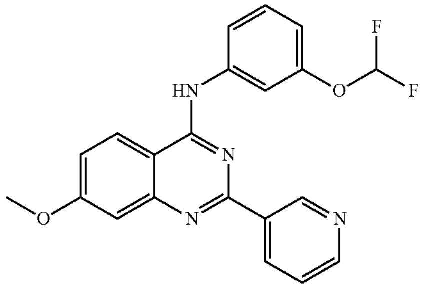 [SMILES: COc1ccc2c(Nc3cccc(OC(F)F)c3)nc(-c3cccnc3)nc2c1] | 394.37 | 1H-NMR (400 MHz, DMSO-d6): δ 9.93 (s, 1H), 9.54 (s, 1H), 8.68 (d, J = 5.2 Hz, 2H), 8.51 (d, J = 9.2 Hz, 1H), 7.96 (s, 1H), 7.79 (d, J = 7.6 Hz, 1H), 7.55-7.10 (m, 5H), 6.96 (dd, J = 8.0, 2.0 Hz, 1H), 3.96 (s, 3H). |
| 542 | 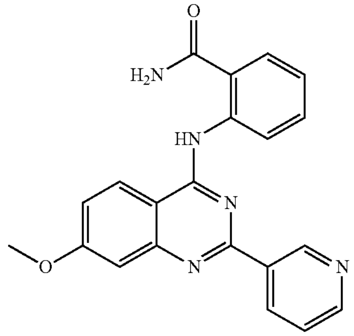 [SMILES: COc1ccc2c(Nc3ccccc3C(N)=O)nc(-c3cccnc3)nc2c1] | 371.39 | 1H-NMR (400 MHz, DMSO-d6): δ 12.97 (s, 1H), 9.60 (s, 1H), 9.10 (d, J = 8.4 Hz, 1H), 8.75-8.71 (m, 2H), 8.48 (s, 1H), 8.07 (d, J = 9.6 Hz, 1H), 7.95-7.90 (m, 2H), 7.74-7.70 (m, 1H), 7.58 (dd, J = 8.0, 4.8 Hz, 1H), 7.35-7.33 (m, 2H), 7.19 (t, J = 7.2 Hz, 1H), 3.97 (s, 3H). |
| 543 | 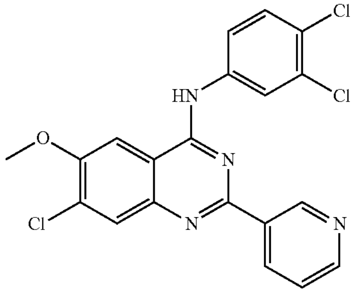 [SMILES: COc1cc2c(Nc3ccc(Cl)c(Cl)c3)nc(-c3cccnc3)nc2cc1Cl] | 431.7 | 1H-NMR (400 MHz, DMSO-d6): δ 10.03 (s, 1H), 9.49-9.48 (m, 1H), 8.69-8.67 (m, 1H), 8.63-8.59 9m, 1H), 8.31 (d, J = 2.4 Hz, 1H), 8.04 (s, 1H), 8.00 (s, 1H), 7.93-7.90 (m, 1H), 7.74 (d, J = 8.8 Hz, 1H), 7.56-7.53 (m, 1H), 4.07 (s, 3H). |
| 544 | 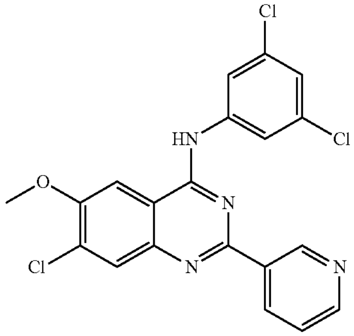 [SMILES: COc1cc2c(Nc3cc(Cl)cc(Cl)c3)nc(-c3cccnc3)nc2cc1Cl] | 431.7 | 1H-NMR (400 MHz, DMSO-d6): δ 9.94 (s, 1H), 9.46 (d, J = 3.2 Hz, 1H), 8.68 (dd, J = 4.8, 2.0 Hz, 1H), 8.60-8.57 (m, 1H), 8.09 (s, 1H), 8.08 (s, 1H), 7.97 (s, 2H), 7.54 (dd, J = 8.8, 4.8 Hz, 1H), 7.38 (t, J = 2.0 Hz, 1H), 4.05 (s, 3H). |
| 545 | 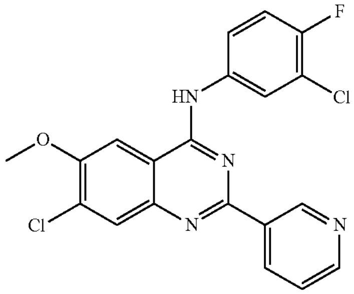 [SMILES: COc1cc2c(Nc3ccc(F)c(Cl)c3)nc(-c3cccnc3)nc2cc1Cl] | 415.25 | 1H-NMR (400 MHz, DMSO-d6): δ 10.02 (s, 1H), 9.47 (s, 1H), 8.70-8.62 (m, 2H), 8.19-8.17 (m, 1H), 8.04 (s, 1H), 8 00 (s, 1H), 7.84-7.88 (m, 1H), 7.59-7.53 (m, 2H), 4.07 (s, 3H). |

TABLE 2-continued
| | | | |
|---|---|---|---|
| 546 | 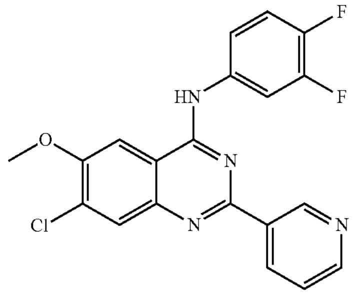 [SMILES: COc1cc2c(Nc3ccc(F)c(F)c3)nc(-c3cccnc3)nc2cc1Cl] | 398.79 | 1H-NMR (400 MHz, DMSO-d6): δ 10.01 (s, 1H), 9.47 (d, J = 1.6 Hz, 1H), 8.69-8.67 (m, 1H), 8.62-8.59 (m, 1H), 8.08-8.04 (m, 2H), 8.00 (s, 1H), 7.65-7.53 (m, 3H), 4.07 (s, 3H). |
| 547 | 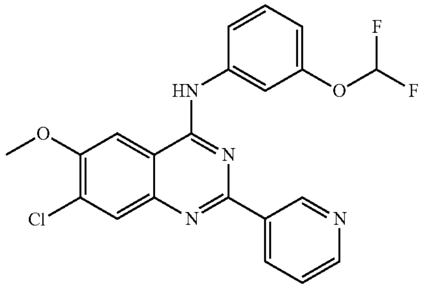 [SMILES: COc1cc2c(Nc3cccc(OC(F)F)c3)nc(-c3cccnc3)nc2cc1Cl] | 428.82 | 1H-NMR (400 MHz, DMSO-d6): δ 10.32 (s, 1H), 9.45 (d, J = 1.2 Hz, 1H), 8.89 (d, J = 8.0 Hz, 1H), 8.83 (d, J = 4.0 Hz, 1H), 8.21 (s, 1H), 8.00 (s, 1H), 7.85-7.78 (m, 3H), 7.55-7.51 (m, 1H), 7.31 (t, J = 72.8 Hz, 1H), 7.05-7.03 (m, 1H), 4.07 (s, 3H). |
| 548 | 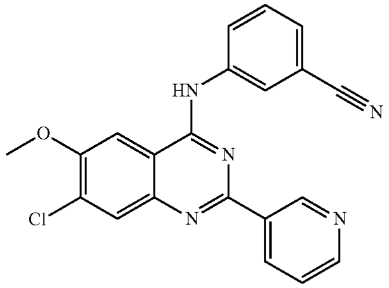 [SMILES: COc1cc2c(Nc3cccc(C#N)c3)nc(-c3cccnc3)nc2cc1Cl] | 387.82 | 1H-NMR (400 MHz, DMSO-d6): δ 10.62 (s, 1H), 9.38 (s, 1H), 8.97-8.90 (m, 2H), 8.32-8.26 (m, 3H), 7.97-7.94 (m, 2H), 7.69-7.65 (m, 2H), 4.08 (s, 3H). |
| 549 | 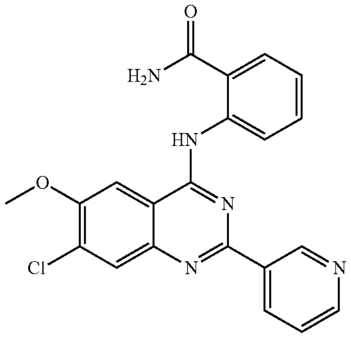 [SMILES: COc1cc2c(Nc3ccccc3C(N)=O)nc(-c3cccnc3)nc2cc1Cl] | 405.84 | 1H-NMR (400 MHz, DMSO-d6): δ 12.98 (s, 1H), 9.36 (s, 1H), 8.94-8.77 (m, 3H), 8.48 (s, 1H), 7.98-7.83 (m, 4H), 7.59-7.14 (m, 2H), 7.17 (s, 1H), 3.96 (s, 3H). |
| 550 | 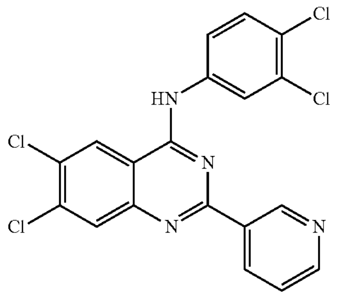 [SMILES: Clc1ccc(Nc2nc(-c3cccnc3)nc3cc(Cl)c(Cl)cc23)cc1Cl] | 436.12 | 1H-NMR (400 MHz, DMSO-d6): δ 10.24 (s, 1H), 9.39 (s, 1H), 8.87 (s, 1H), 8.81 (d, J = 4.4 Hz, 1H), 8.73 (d, J = 8.0 Hz, 1H), 8.24 (s, 1H), 8.01 (s, 1H), 7.88 (d, J = 8.8 Hz, 1H), 7.76-7.73 (m, 1H), 7.66 (d, J = 8.8 Hz, 1H). |

TABLE 2-continued
| | | | |
|---|---|---|---|
| 551 | 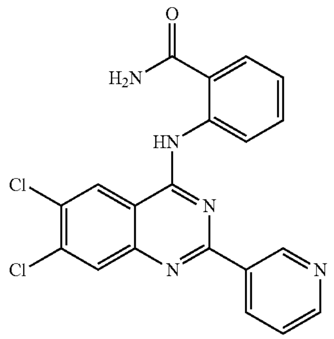 [SMILES: NC(=O)c1ccccc1Nc1nc(-c2cccnc2)nc2cc(Cl)c(Cl)cc12] | 410.26 | 1H-NMR (400 MHz, DMSO-d6): δ 13.15 (s, 1H), 9.46 (s, 1H), 8.87 (d, J = 8.4 Hz, 1H), 8.74 (d, J = 3.6 Hz, 1H), 8.68 (d, J = 7.2 Hz, 1H), 8.49 (s, 1H), 8.23 (s, 1H), 8.02 (s, 2H), 7.94 (d, J = 8.0 Hz, 1H), 7.69-7.61 (m, 2H), 7.23-7.20 (m, 1H). |
| 552 | 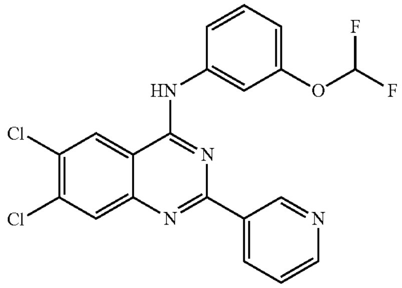 [SMILES: FC(F)Oc1cccc(Nc2nc(-c3cccnc3)nc3cc(Cl)c(Cl)cc23)c1] | 433.24 | 1H-NMR (400 MHz, DMSO-d6): δ 10.30 (s, 1H), 9.53 (s, 1H), 9.02 (s, 1H), 8.83-8.80 (m, 2H), 8.20 (s, 1H), 7.91 (s, 1H), 7.81-7.79 (m, 1H), 7.74-7.71 (m, 1H), 7.56-7.52 (m, 1H), 7.30 (t, J = 73.6 Hz, 1H), 7.05 (d, J = 8.8 Hz, 1H). |
| 553 | 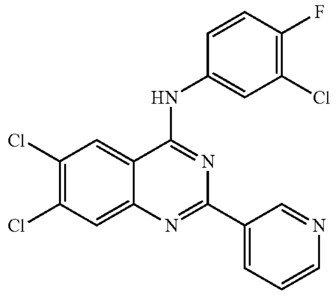 [SMILES: Fc1ccc(Nc2nc(-c3cccnc3)nc3cc(Cl)c(Cl)cc23)cc1Cl] | 419.67 | 1H-NMR (400 MHz, DMSO-d6): δ 10.43 (s, 1H), 9.40 (s, 1H), 8.97 (s, 1H), 8.89-8.85 (m, 2H), 8.15-8.14 (m, 1H), 8.05 (s, 1H), 7.89-7.87 (m, 2H), 7.51-7.47 (m, 1H). |
| 554 | 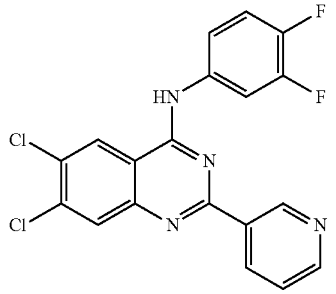 [SMILES: Fc1ccc(Nc2nc(-c3cccnc3)nc3cc(Cl)c(Cl)cc23)cc1F] | 403.21 | 1H-NMR (400 MHz, DMSO-d6): δ 10.39 (s, 1H), 9.40 (s, 1H), 8.96 (s, 1H), 8.84-8.89 (m, 2H), 8.04-8.00 (m, 2H), 7.88 (s, 1H), 7.69-7.67 (m, 1H), 7.54-7.47 (m, 1H). |
| 555 | 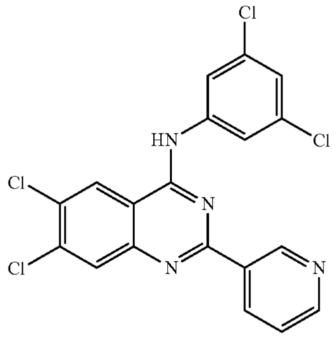 [SMILES: Clc1cc(Cl)cc(Nc2nc(-c3cccnc3)nc3cc(Cl)c(Cl)cc23)c1] | 436.12 | 1H-NMR (400 MHz, DMSO-d6): δ 10.26 (s, 1H), 8.28 (s, 1H), 8.88 (d, J = 4.8 Hz, 1H), 8.85 (s, 1H), 8.76 (d, J = 8.0 Hz, 1H), 7.97 (s, 1H), 7.96 (s, 1H), 7.90-7.86 (m, 2H), 7.29 (s, 1H). |

TABLE 2-continued
| | | | |
|---|---|---|---|
| 556 | 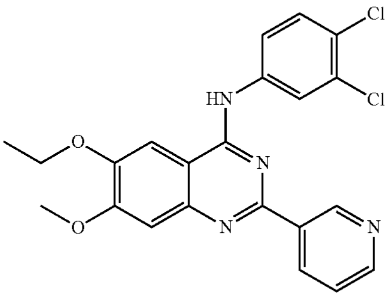 [SMILES: CCOc1cc2c(Nc3ccc(Cl)c(Cl)c3)nc(-c3cccnc3)nc2cc1OC] | 441.31 | 1H-NMR (400 MHz, DMSO-d6): δ 9.74 (s, 1H), 9.50 (s, 1H), 8.66-8.64 (m, 2H), 8.31 (s, 1H), 7.90 (d, J = 8.8 Hz, 1H), 7.84 (s, 1H), 7.68 (d, J = 8.8 Hz, 1H), 7.52 (dd, J = 7.4, 5.0 Hz, 1H), 7.29 (s, 1H), 4.22 (q, J = 6.8 Hz, 2H), 3.97 (s, 3H), 1.45 (t, J = 6.8 Hz, 3H). |
| 557 | 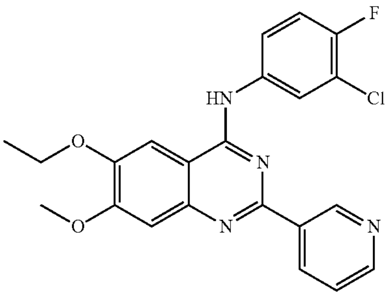 [SMILES: CCOc1cc2c(Nc3ccc(F)c(Cl)c3)nc(-c3cccnc3)nc2cc1OC] | 424.86 | 1H-NMR (400 MHz, DMSO-d6) δ 9.93 (s, 1H), 9.48 (s, 1H), 8.74-8.73 (m, 2H), 8.18-8.16 (m, 1H), 7.90-7.85 (m, 2H), 7.67-7.65 (m, 1H), 7.53 (t, J = 9 Hz, 1H), 7.33 (s, 1H), 4.24 (q, J = 7.2 Hz, 2H), 3.98 (s, 3H), 1.46 (t, J = 7.2 Hz, 3H). |
| 558 | 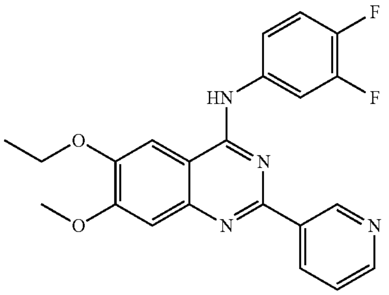 [SMILES: CCOc1cc2c(Nc3ccc(F)c(F)c3)nc(-c3cccnc3)nc2cc1OC] | 408.4 | 1H-NMR (400 MHz, DMSO-d6): δ 9.68 (s, 1H), 9.49 (s, 1H), 8.66-8.61 (m, 2H), 8.10-8.04 (m, 1H), 7.84 (s, 1H), 7.66-7.64 (m, 1H), 7.56-7.49 (m, 2H), 7.30 (s, 1H), 4.23 (q, J = 6.8 Hz, 2H), 3.98 (s, 3H), 1.46 (t, J = 6.8 Hz, 3H). |
| 559 | 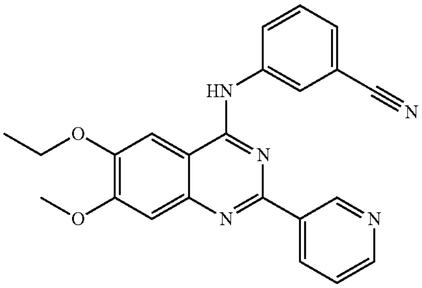 [SMILES: CCOc1cc2c(Nc3cccc(C#N)c3)nc(-c3cccnc3)nc2cc1OC] | 397.43 | 1H-NMR (400 MHz, DMSO-d6): δ 10.27 (s, 1H), 9.43 (s, 1H), 8.82-8.78 (m, 2H), 8.32 (s, 1H), 8.23 (d, J = 7.6 Hz, 1H), 7.98 (s, 1H), 7.77-7.73 (m, 1H), 7.68-7.60 (m, 2H), 7.35 (s, 1H), 4.23 (q, J = 6.8 Hz, 2H), 3.96 (s, 3H), 1.44 (t, J = 6.8 Hz, 3H). |
| 560 | 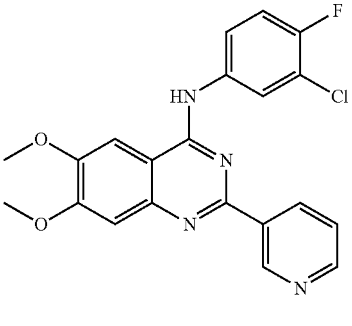 [SMILES: COc1cc2nc(-c3cccnc3)nc(Nc3ccc(F)c(Cl)c3)c2cc1OC] | 410.83 | 1H-NMR (400 MHz, DMSO-d6): δ 9.89 (s, 1H), 9.48 (s, 1H), 8.74 (d, J = 6.0 Hz, 2H), 8.16 (dd, J = 6.8, 2.4 Hz, 1H), 7.85-7.88 (m, 2H), 7.67 (t, J = 6.4 Hz, 1H), 7.53 (t, J = 8.7 Hz, 1H), 7.32 (s, 1H), 3.93 (s, 6H). |

TABLE 2-continued
| | | | | |
|---|---|---|---|---|
| 561 | 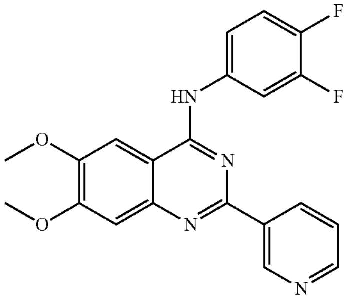 [SMILES: COc1cc2nc(-c3cccnc3)nc(Nc3ccc(F)c(F)c3)c2cc1OC] | | 394.37 | 1H-NMR (400 MHz, DMSO-d6): δ 9.92 (s, 1H), 9.49 (s, 1H), 8.77 (d, J = 6.4 Hz, 2H), 8.02-8.08 (m, 1H), 7.90 (s, 1H), 7.70-7.74 (m, 1H), 7.64-7.66 (m, 1H), 7.52-7.59 (m, 1H), 7.33 (s, 1H), 3.99 (s, 3H), 3.98 (s, 3H). |
| 562 | 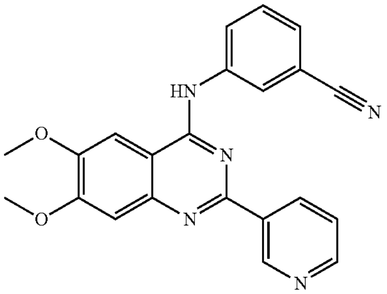 [SMILES: COc1cc2nc(-c3cccnc3)nc(Nc3cccc(C#N)c3)c2cc1OC] | | 383.4 | 1H-NMR (400 MHz, DMSO-d6): δ 9.87 (s, 1H), 9.50 (d, J = 1.6 Hz, 1H), 8.63-8.68 (m, 2H), 8.38 (s, 1H), 8.23 (d, J = 8.4 Hz, 1H), 7.89 (s, 1H), 7.69 (t, J = 7.8 Hz, 1H), 7.61 (d, J = 7.6 Hz, 1H), 7.52-7.56 (m, 1H), 7.33 (s, 1H), 4.00 (s, 3H), 3.98 (s, 3H). |
| 563 | 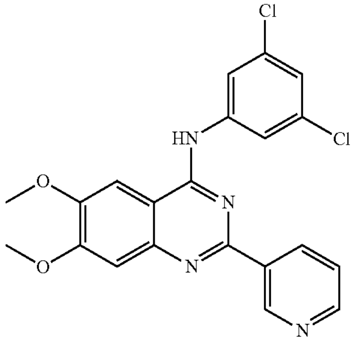 [SMILES: COc1cc2nc(-c3cccnc3)nc(Nc3cc(Cl)cc(Cl)c3)c2cc1OC] | | 427.28 | 1H-NMR (400 MHz, DMSO-d6): δ 9.70 (s, 1H), 9.50 (d, J = 1.6 Hz, 1H), 8.66 (d, J = 4.8 Hz, 1H), 8.62 (d, J = 8.0 Hz, 1H), 8.11 (d, J = 1.2 Hz, 2H), 7.73 (s, 1H), 7.53 (dd, J = 7.6, 4.8 Hz, 1H), 7.31 (s, 1H), 7.28 (s, 1H), 3.97 (s, 6H). |
| 564 | 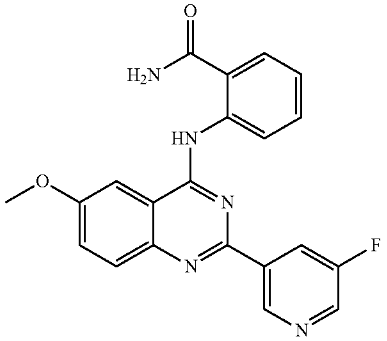 [SMILES: COc1ccc2nc(-c3cncc(F)c3)nc(Nc3ccccc3C(N)=O)c2c1] | 2 HCl | 389.3824 | 1H-NMR (400 MHz, DMSO-d6): δ 13.08 (s, 1H), 9.40 (s, 1H), 8.86 (d, J = 8.1 Hz, 1H), 8.78 (s, 1H), 8.53 (d, J = 10.0 Hz, 1H), 8.46 (s, 1H), 8.03 (d, J = 8.7 Hz, 1H), 8.00-7.88 (m, 2H), 7.73 (t, J = 7.8 Hz, 1H), 7.66 (d, J = 10.3 Hz, 2H), 7.28 (t, J = 7.6 Hz, 1H), 3.99 (s, 3H). |
| 565 | 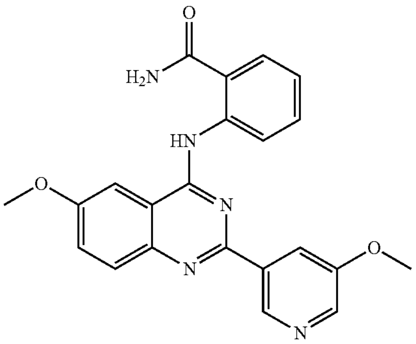 | 2 HCl | 401.4180 | 1H-NMR (400 MHz, CD3OD): δ 9.20 (s, 1H), 8.85 (s, 1H), 8.78 (s, 1H), 8.72 (d, J = 8.2 Hz, 1H), 8.02 (d, J = 9.1 Hz, 1H), 7.95 (d, J = 7.7 Hz, 1H), 7.77-7.67 (m, 3H), 7.39 (t, J = 7.6 Hz, 1H), 4.18 (s, 3H), 4.08 (s, 3H). |

TABLE 2-continued

| Number | $^1$H-NMR Solvent | LCMS | LCMS Protocol | Purity Percent | Method for Coupling |
|---|---|---|---|---|---|
| 522 | DMSO | 454.9, 457.0 (M + 1), 228.8 (M/2 + 1) | Method A (TFA) | 95 | Method N, G1 |
| 523 | DMSO | 439.1, 441.1 (M + 1), 220.1, 220.8 (M/2 + 1) | Method A (TFA) | 95 | Method N, G1 |
| 524 | DMSO | 423.2 (M + 1), 212.2 (M/2 + 1) | Method A (TFA) | 95 | Method N, G1 |
| 525 | DMSO | 430.2 (M + 1) 215.7 (M/2 + 1) | Method A (TFA) | 95 | Method N, G1 |
| 526 | DMSO | 453.1 (M + 1) | Method B (NH4HCO3) | 95 | Method N, G1 |
| 527 | DMSO | 455.0, 457.0 (M + 1) | Method B (NH4HCO3) | 95 | Method N, G1 |
| 528 | DMSO | 455.1, 457.1 (M + 1) 229.1 (M/2 + 1) | Method A (TFA) | 95 | Method N, G1 |
| 529 | DMSO | 439.1, 441.1 (M + 1) 220.1, 220.8 (M/2 + 1) | Method A (TFA) | 95 | Method N, G1 |
| 530 | DMSO | 423.0 (M + 1) 445.0 (M + 23) 212.1 (M/2 + 1) | Method A (TFA) | 95 | Method N, G1 |
| 531 | DMSO | 430.1 (M + 1) | Method B (NH4HCO3) | 95 | Method N, G1 |
| 532 | DMSO | 453.1 (M + 1) 227.2 (M/2 + 1) | Method A (TFA) | 95 | Method N, G1 |
| 533 | DMSO | 455.1, 457.1 (M + 1) | Method B (NH4HCO3) | 95 | Method N, G1 |
| 534 | CD3OD | 446.2, 447.2 (M + 1) | Method B (NH4HCO3) | 95 | Method N, G1 |
| 535 | DMSO | 469.1 (M + 1) | Method B (NH4HCO3) | 95 | Method N, G1 |
| 536 | DMSO | 469.0, 471.0 (M + 1) 234.9, 235.6 (M/2 + 1) | Method A (TFA) | 95 | Method N, G1 |
| 537 | DMSO | 397.1, 399.0 (M + 1) | Method B (NH4HCO3) | 95 | Method N, G1 |
| 538 | DMSO | 397.0, 399.0 (M + 1) | Method B (NH4HCO3) | 95 | Method N, G1 |
| 539 | DMSO | 365.2 (M + 1) | Method B (NH4HCO3) | 95 | Method N, G1 |
| 540 | DMSO | 354.2 (M + 1) | Method B (NH4HCO3) | 95 | Method N, G1 |
| 541 | DMSO | 395.1 (M + 1) | Method B (NH4HCO3) | 95 | Method N, G1 |
| 542 | DMSO | 372.1 (M + 1) | Method B (NH4HCO3) | 95 | Method N, G1 |
| 543 | DMSO | 430.9, 432.9, 434.9 (M + 1) | Method B (NH4HCO3) | 95 | Method N, G1 |
| 544 | DMSO | 430.9, 432.9, 434.9 (M + 1) | Method B (NH4HCO3) | 95 | Method N, G1 |
| 545 | DMSO | 415.1, 417.0, 419.0 (M + 1) | Method B (NH4HCO3) | 95 | Method N, G1 |
| 546 | DMSO | 399.1, 401.1 (M + 1) | Method B (NH4HCO3) | 95 | Method N, G1 |
| 547 | DMSO | 429.1, 431.1 (M + 1) | Method B (NH4HCO3) | 95 | Method N, G1 |
| 548 | DMSO | 387.9, 390.0 (M + 1) | Method B (NH4HCO3) | 95 | Method N, G1 |
| 549 | DMSO | 405.9, 408.0 (M + 1) | Method B (NH4HCO3) | 95 | Method N, G1 |
| 550 | DMSO | 434.9, 436.9, 438.8 (M + 1) | Method B (NH4HCO3) | 95 | Method N, G1 |

TABLE 2-continued

| | | | | | |
|---|---|---|---|---|---|
| 551 | DMSO | 410.0, 412.0, 413.9 (M + 1) 432.0 (M + 22) | Method A (TFA) | 95 | Method N, G1 |
| 552 | DMSO | 432.9, 434.9 (M + 1) | Method B (NH4HCO3) | 95 | Method N, G1 |
| 553 | DMSO | 419.0, 421.0, 423.0 (M + 1) | Method B (NH4HCO3) | 95 | Method N, G1 |
| 554 | DMSO | 402.9, 404.9 (M + 1) | Method B (NH4HCO3) | 95 | Method N, G1 |
| 555 | DMSO | 434.9, 436.9, 438.9 (M + 1) | Method A (TFA) | 95 | Method N, G1 |
| 556 | DMSO | 441.0, 443.0 (M + 1) | Method B (NH4HCO3) | 95 | Method N, G1 |
| 557 | DMSO | 425.0, 427.0 (M + 1) | Method B (NH4HCO3) | 95 | Method N, G1 |
| 558 | DMSO | 409.0 (M + 1) | Method B (NH4HCO3) | 95 | Method N, G1 |
| 559 | DMSO | 398.1 (M + 1) | Method B (NH4HCO3) | 95 | Method N, G1 |
| 560 | DMSO | 411.1, 413.1 (M + 1) | Method A (TFA) | 95 | Method N, G1 |
| 561 | DMSO | 395.0 (M + 1) 198.1 (M/2 + 1) | Method A (TFA) | 95 | Method N, G1 |
| 562 | DMSO | 384.2 (M + 1) | Method B (NH4HCO3) | 95 | Method N, G1 |
| 563 | DMSO | 427.1, 429.1, 431.0 (M + 1) | Method B (NH4HCO3) | 95 | Method N, G1 |
| 564 | DMSO | 390.0 (M + 1) | Method B (NH4HCO3) | 95 | Method N, G1 |
| 565 | MeOD | 402.1 (M + 1) | Method B (NH4HCO3) | 95 | Method N, G1 |

Scheme 8: General route for the synthesis of compounds with general formula xix

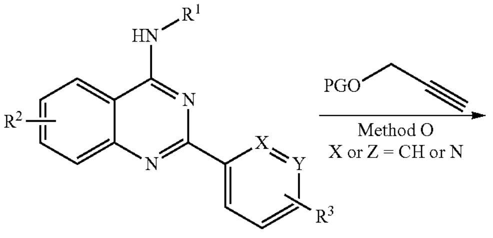

vi

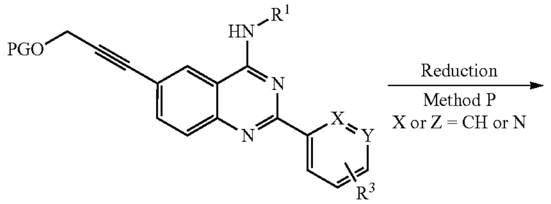

xv

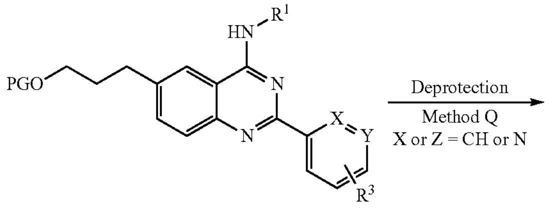

xvi

-continued

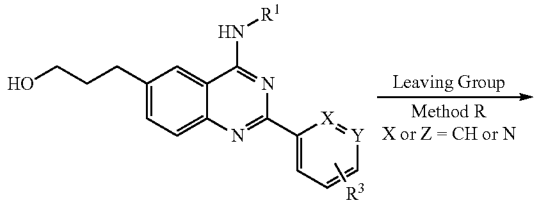

xvii

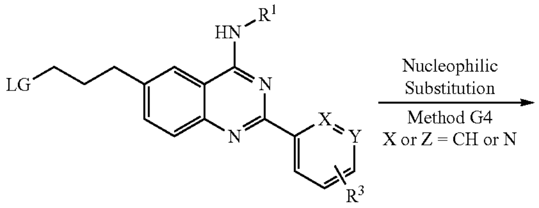

xviii

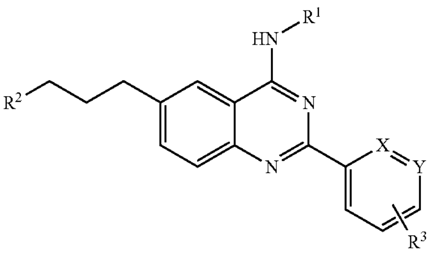

xix

Scheme 9: Representative synthesis of compounds of formula xix (see Scheme 8)

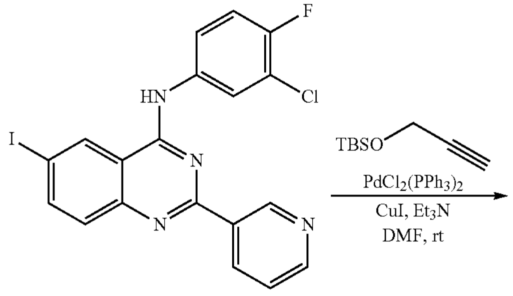

vi-c

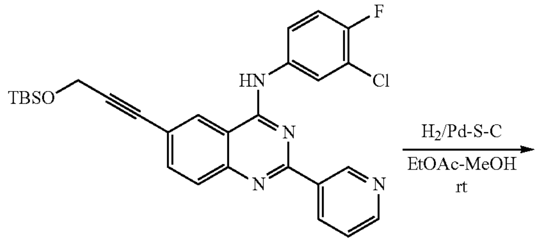

xv-a

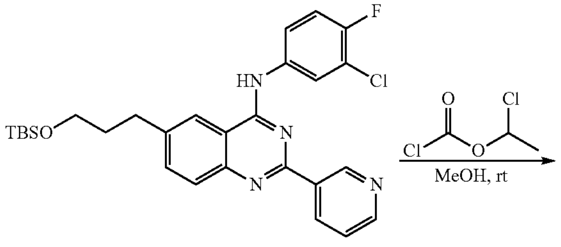

xvi-a

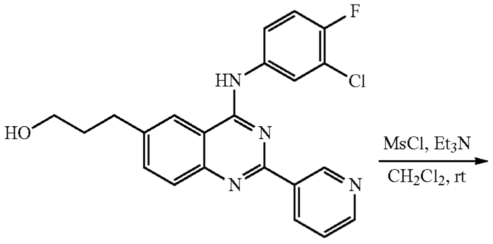

xvii-a

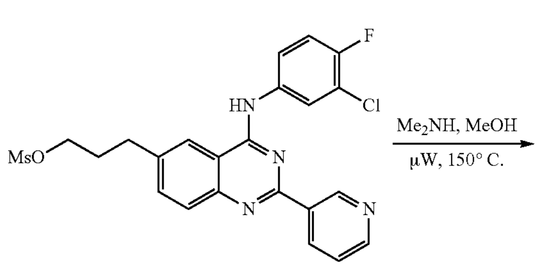

xviii-a

-continued

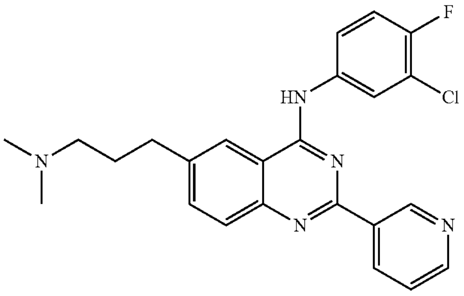

xix-a

Method O1: $CuI/Pd(PPh_3)_2Cl_2/Et_3N$/DMF/rt
O2: Propargyl bromide/$CuI/Pd(PPh_3)_2C_2$/Nucleophile/DMF/rt
O3: $Pd(OAc)_2/PPh_3$/TBAB/piperidine/THF-$H_2O$/rt Method O1: 6-(3-(tert-butyldimethylsilyloxy)prop-1-ynyl)-N-(3-chloro-4-fluorophenyl)-2-(pyridin-3-yl) quinazolin-4-amine (xv-a)

A suspension of N-(3-chloro-4-fluorophenyl)-6-iodo-2-(pyridin-3-yl)quinazolin-4-amine (synthesized as described in Scheme 1 and 4, substituting 5-iodo-2-nitrobenzoic acid for 2-nitro-5-propoxy-benzoic acid and 3-chloro-4-fluoroaniline for 2-aminobenzamide) (1.00 g, 2.10 mmol), tert-butyldimethyl(2-propynyloxy)silane (0.85 ml, 4.20 mmol), copper(I) iodide (4.0 mg, 0.021 mmol), dichlorobis(triphenylphosphine) palladium (II) ($Pd(PPh_3)_2Cl_2$) (29 mg, 0.042 mmol), and triethylamine (1.17 ml, 8.39 mmol) in DMF (15 mL) was stirred overnight at room temperature under argon atmosphere. Water (30 mL) and ethyl acetate (30 mL) were added to the mixture. The resultant precipitate was removed by filtration. The filtrate was extracted with EtOAc (2×50 mL). The combined organic layer was washed with water (1×100 mL) and brine (1×100 mL) and was dried over $Na_2SO_4$. After filtration and evaporation, the crude product was obtained, which was purified by column chromatography on silica gel (eluted with hexane/ethyl acetate 6:1 to 1:3) to give 0.73 g of 6-(3-(tert-butyldimethylsilyloxy)prop-1-ynyl)-N-(3-chloro-4-fluorophenyl)-2-(pyridin-3-yl)quinazolin-4-amine as light brown solid (67%). LCMS m/z=519 (M+1) (Method D) (retention time=3.22 min). $^1H$ NMR (300 MHz, DMSO) δ 9.99 (s, 1H), 9.35 (s, 1H), 8.62-8.44 (m, 3H), 8.11 (dd, J=6.8, 2.6 Hz, 1H), 7.76-7.66 (m, 3H), 7.45-7.30 (m, 2H), 4.48 (s, 2H), 0.75 (s, 9H), 0.16 (s, 6H).

Method P: 6-(3-(tert-butyldimethylsilyloxy)propyl)-N-(3-chloro-4-fluorophenyl)-2-(pyridin-3-yl) quinazolin-4-amine (xvi-a)

A suspension of 6-(3-(tert-butyldimethyl silyloxy)prop-1-ynyl)-N-(3-chloro-4-fluorophenyl)-2-(pyridin-3-yl) quinazolin-4-amine (0.20 g, 0.39 mmol) and 5% Pd—S—C (40 mg) in EtOAc (5 mL) and MeOH (5 mL) was stirred overnight at room temperature under hydrogen atmosphere. The reaction mixture was filtered through Celite. The filtrate was concentrated in vacuo. The residue was purified by column chromatography on silica gel (eluted with hexane/ethyl acetate 6:1 to 2:3) to give 0.15 g of 6-(3-(tert-butyldimethylsilyloxy)propyl)-N-(3-chloro-4-fluorophenyl)-2-(pyridin-3-yl)quinazolin-4-amine as yellow solid (74%). LCMS m/z=523 (M+1) (Method D) (retention time=3.35 min). $^1H$ NMR (300 MHz, $CDCl_3$) δ 9.69 (dd, J=2.2, 0.8 Hz, 1H), 8.79-8.65 (m, 2H), 8.07 (dd, J=6.5, 2.7 Hz, 1H), 7.94 (d, J=8.5 Hz, 1H), 7.76-7.61 (m, 3H), 7.47-7.37 (m, 2H), 7.31-7.18 (m, 1H), 3.68 (t, J=6.1 Hz, 2H), 3.01-2.83 (m, 2H), 2.03-1.86 (m, 2H), 0.94 (s, 9H), 0.08 (s, 6H).

Method Q: 3-(4-(3-chloro-4-fluorophenylamino)-2-(pyridin-3-yl)quinazolin-6-yl)propan-1-ol (xvii-a)

To a suspension of 6-(3-(tert-butyldimethylsilyloxy)propyl)-N-(3-chloro-4-fluorophenyl)-2-(pyridin-3-yl)quinazolin-4-amine (0.35 g, 0.67 mmol) in MeOH (10 mL) was added 1-chloroethyl chloroformate (7.2 μl, 0.067 mmol). The mixture was stirred overnight at room temperature. Methanol was removed in vacuo. Sat. $NaHCO_3$ aqueous (10 mL) and $CH_2Cl_2$ (10 mL) were added to the residue and stirred for a while. The resultant solid was collected by filtration and dried to give 0.25 g of 3-(4-(3-chloro-4-fluorophenylamino)-2-(pyridin-3-yl)quinazolin-6-yl)propan-1-ol as light yellow solid (91%). MS i/z=409 (M+1) (Method D) (retention time=1.71 min), $^1H$ NMR (300 MHz, DMSO) δ 10.01 (s, 1H), 9.51 (s, 1H), 8.66 (m, 2H), 8.37 (s, 1H), 8.29-8.20 (m, 1H), 7.94-7.67 (m, 3H), 7.63-7.43 (m, 2H), 4.60 (t, J=5.0 Hz, 1H), 3.56-3.35 (m, 2H), 2.94-2.69 (m, 2H), 2.15-1.56 (m, 2H).

Method R: 3-(4-(3-chloro-4-fluorophenylamino)-2-(pyridin-3-yl)quinazolin-6-yl)propyl methanesulfonate (xviii-a)

To a suspension of 3-(4-(3-chloro-4-fluorophenylamino)-2-(pyridin-3-yl)quinazolin-6-yl)propan-1-ol (0.25 g, 0.61 mmol) and triethylamine (0.17 ml, 1.22 mmol) in $CH_2Cl_2$ (10 mL) was added methanesulfonyl chloride (0.057 ml, 0.73 mmol). The mixture was stirred at room temperature for 1 h. Water (10 mL.) was added to the mixture and stirred for a while. The resultant precipitate was collected by filtration and washed with $CH_2Cl_2$ and dried to give 0.27 g of 3-(4-(3-chloro-4-fluorophenylamino)-2-(pyridin-3-yl)quinazolin-6-yl)propyl methanesulfonate as pale yellow solid (91%), which was used without further purification.

Method G4: N-(3-chloro-4-fluorophenyl)-6-(3-(dimethylamino)propyl)-2-(pyridin-3-yl)quinazolin-4-amine dihydrochloride (xviv-a)

(This method is representative of method G4 and G5. These two methods can be implemented in a similar way except for substitution of the appropriate solvent and temperature) A solution of 3.-(4-(3-chloro-4-fluorophenylamino)-2-(pyridin-3-yl)quinazolin-6-yl)propyl methanesulfonate (40 mg, 82 mmol) and 40% $Me_2NH$ aqueous (1 mL) in methanol (2 mL) was placed in a microwave reaction vial. The mixture was heated under microwave irradiation conditions at 150° C. for 30 minutes after which the solvent was removed in vacuo. The crude product was obtained, which was purified by column chromatography on basic silica gel (eluted with ethyl acetate/methanol 1:0→5:1). The HCl salt generated by 4 M HCl in dioxane was crystallized from 2-propanol to give 10 mg of N-(3-chloro-4-fluorophenyl)-6-(3-(dimethylamino)propyl)-2-(pyridin-3-yl)quinazolin-4-amine dihydrochloride as pale brown powder (24%). LCMS m/z=436 (M+1) (Method C) (retention time=1.68 min). $^1H$ NMR (300 MHz, DMSO) δ 10.59 (s, 1H), 10.18 (s, 1H), 9.51 (s, 1H), 8.98-8.76 (m, 2H), 8.65 (s, 1H), 8.26 (dd, J=6.8, 2.6 Hz, 1H), 8.05-7.74 (m, 4H), 7.54 (t, J=9.1 Hz, 1H), 3.19-3.03 (m, 2H), 2.97-2.83 (m, 2H), 2.78 (s, 3H), 2.77 (s, 3H), 2.16 (s, 2H).

Scheme 10: Method O2: Representative synthesis of compounds of formula xx

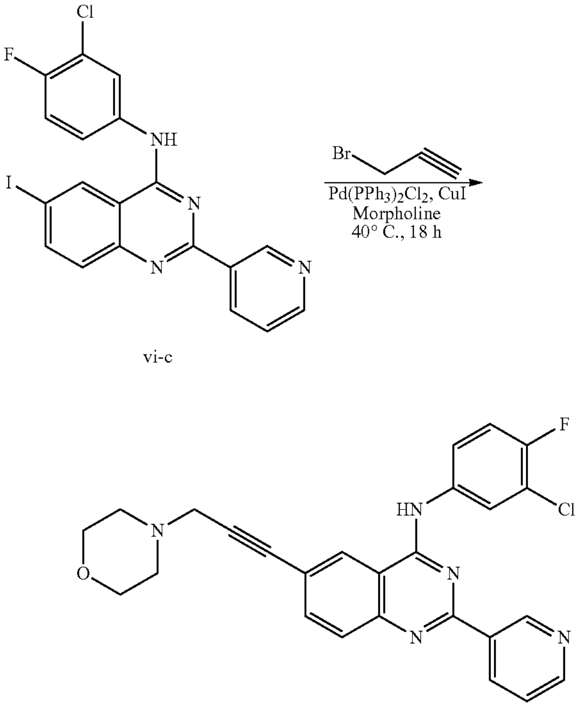

vi-c xx-a

N-(3-chloro-4-fluorophenyl)-6-(3-morpholinoprop-1-ynyl)-2-(pyridin-3-yl) quinazolin-4-amine (xx-a)

To a solution of N-(3-chloro-4-fluorophenyl)-6-iodo-2-(pyridin-3-yl)quinazolin-4-amine (synthesized as described in Scheme 1 and 4, substituting 5-iodo-2-nitrobenzoic acid for 2-nitro-5-propoxy-benzoic acid and 3-chloro-4-fluoroaniline for 2-aminobenzamide) (2.19 g, 4.6 mmol, 1 eq.), $Pd(PPh_3)_2Cl_2$ (161 mg, 0.23 mmol, 0.05 eq.), CuI (87 mg, 0.46 mmol, 0.1 eq.) in morpholine (15 mL) was added 3-bromoprop-1-yne (814 mg, 6.9 mmol, 1.5 eq.) at 0° C. under Ar atmosphere, following a procedure from *Tetrahedron,* 2007, 63, 10671-10683. The mixture was stirred at 40° C. overnight. After cooling, the mixture was filtered and methanol (60 mL) was added to the filtrate to form a precipitate. The precipitate was collected and re-crystallized from ethyl acetate twice to afford 1.60 g of xx-a as yellow solid (yield 74%). LCMS m/z=474.1 (M+1), 476.1 (M+3) (Method C) (retention time=1.97 min).

The compounds in the following table were prepared in a manner analogous to that described in Scheme 8 substituting with appropriate nucleophile.

TABLE 3
| Number | Product | Salt type | Molecular Mass | $^1$H-NMR |
|---|---|---|---|---|
| 566 | 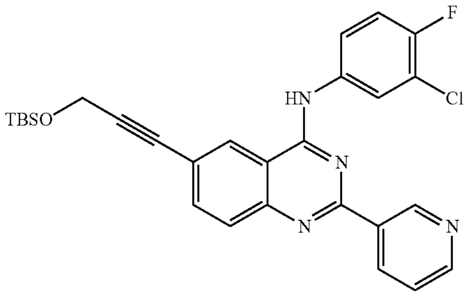 [SMILES: CC(C)(C)[Si](C)(C)OCC#Cc1ccc2nc(-c3cccnc3)nc(Nc3ccc(F)c(Cl)c3)c2c1] | | 519.085 | 1H NMR (300 MHz, DMSO) δ 9.99 (s, 1H), 9.35 (s, 1H), 8.62-8.44 (m, 3H), 8.11 (dd, J = 6.8, 2.6 Hz, 1H), 7.76-7.66 (m, 3H), 7.45-7.30 (m, 2H), 4.48 (s, 2H), 0.75 (s, 9H), 0.00 (s, 6H). |
| 567 | 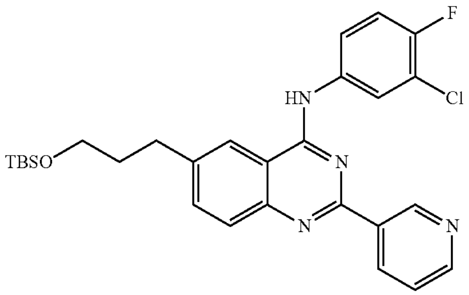 [SMILES: CC(C)(C)[Si](C)(C)OCCCc1ccc2nc(-c3cccnc3)nc(Nc3ccc(F)c(Cl)c3)c2c1] | | 523.117 | 1H NMR (300 MHz, CDCl3) δ 9.69 (dd, J = 2.2, 0.8 Hz, 1H), 8.79-8.65 (m, 2H), 8.07 (dd, J = 6.5, 2.7 Hz, 1H), 7.94 (d, J = 8.5 Hz, 1H), 7.76-7.61 (m, 3H), 7.47-7.37 (m, 2H), 7.31-7.18 (m, 1H), 3.68 (t, J = 6.1 Hz, 2H), 3.01-2.83 (m, 2H), 2.03-1. |
| 568 | 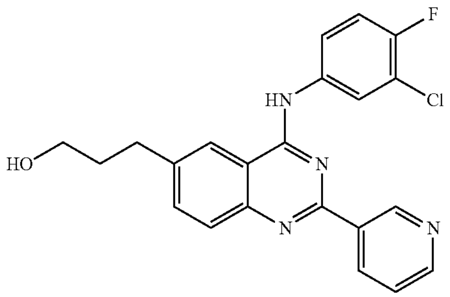 [SMILES: OCCCc1ccc2nc(-c3cccnc3)nc(Nc3ccc(F)c(Cl)c3)c2c1] | | 408.856 | 1H NMR (300 MHz, DMSO) δ 10.01 (s, 1H), 9.51 (s, 1H), 8.66 (m, 2H), 8.37 (s, 1H), 8.29-8.20 (m, 1H), 7.94-7.67 (m, 3H), 7.63-7.43 (m, 2H), 4.60 (t, J = 5.0 Hz, 1H), 3.56-3.35 (m, 2H), 2.94-2.69 (m, 2H), 2.15-1.56 (m, 2H). |
| 569 | 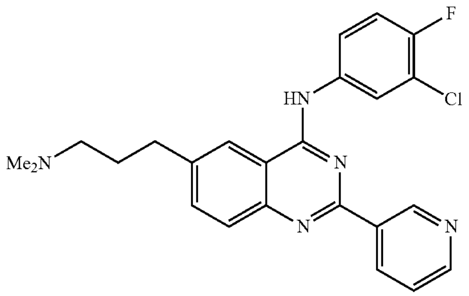 [SMILES: CN(C)CCCc1ccc2nc(-c3cccnc3)nc(Nc3ccc(F)c(Cl)c3)c2c1] | 2 HCl | 508.846 | 1H NMR (300 MHz, DMSO) δ 10.59 (s, 1H), 10.18 (s, 1H), 9.51 (s, 1H), 8.98-8.76 (m, 2H), 8.65 (s, 1H), 8.26 (dd, J = 6.8, 2.6 Hz, 1H), 8.05-7.74 (m, 4H), 7.54 (t, J = 9.1 Hz, 1H), 3.19-3.03 (m, 2H), 2.97-2.83 (m, 2H), 2.78 (s, 3H), 2.77 (s, 3H), 2. |
| 570 | 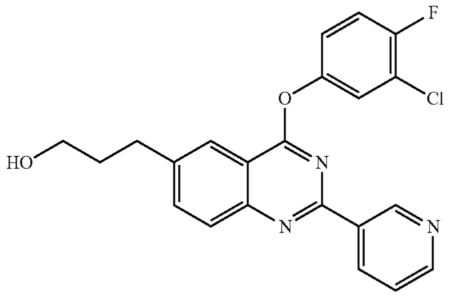 [SMILES: OCCCc1ccc2nc(-c3cccnc3)nc(Oc3ccc(F)c(Cl)c3)c2c1] | | 409.841 | 1H NMR (300 MHz, CDCl3) δ 9.49 (d, J = 1.4 Hz, 1H), 8.73-8.51 (m, 2H), 8.14 (s, 1H), 8.01 (d, J = 8.6 Hz, 1H), 7.81 (dd, J = 8.6, 1.9 Hz, 1H), 7.51-7.13 (m, 4H), 3.77 (dd, J = 11.5, 6.2 Hz, 2H), 3.11-2.85 (m, 2H), 2.16-1.93 (m, 2H), 1.44 (t, J = 5 |

TABLE 3-continued
| | | | | |
|---|---|---|---|---|
| 571 | 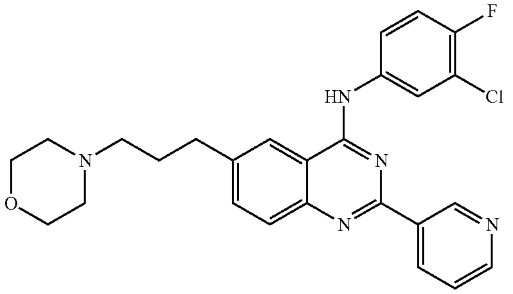 [SMILES: Fc1ccc(Nc2nc(-c3cccnc3)nc3ccc(CCCN4CCOCC4)cc23)cc1Cl] | 2 HCl | 550.882 | 1H NMR (300 MHz, DMSO) δ 10.83-10.37 (m, 2H), 9.51 (s, 1H), 8.97-8.74 (m, 2H), 8.62 (s, 1H), 8.27 (d, J = 4.2 Hz, 1H), 8.05-7.72 (m, 4H), 7.54 (t, J = 9.0 Hz, 1H), 3.96 (d, J = 12.7 Hz, 2H), 3.76 (t, J = 12.1 Hz, 2H), 3.47 (d, J = 12.0 Hz, 2H), 3.24 |
| 572 | 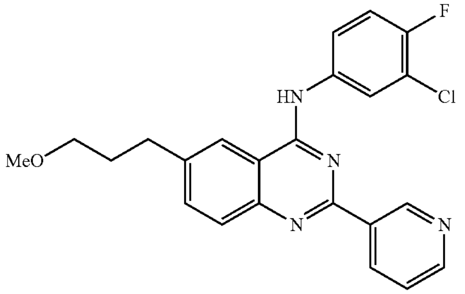 [SMILES: COCCCc1ccc2nc(-c3cccnc3)nc(Nc3ccc(F)c(Cl)c3)c2c1] | | 422.882 | 1H NMR (300 MHz, DMSO) δ 9.99 (s, 1H), 9.51 (s, 1H), 8.75-8.60 (m, 2H), 8.37 (s, 1H), 8.26 (dd, J = 6.9, 2.6 Hz, 1H), 7.99-7.88 (m, 1H), 7.88-7.73 (m, 2H), 7.60-7.46 (m, 2H), 3.39 (dd, J = 8.4, 4.1 Hz, 2H), 3.27 (s, 3H), 2.92-2.78 (m, 2H), 2.05 |
| 573 | 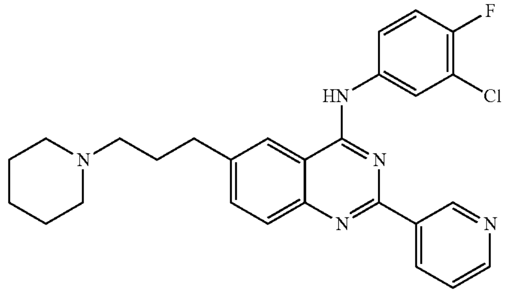 [SMILES: Fc1ccc(Nc2nc(-c3cccnc3)nc3ccc(CCCN4CCCCC4)cc23)cc1Cl] | HCl | 548.909 | 1H NMR (300 MHz, DMSO) δ 10.69 (s, 1H), 10.12 (s, 1H), 9.51 (s, 1H), 9.02-8.30 (m, 2H), 8.69 (s, 1H), 8.27 (dd, J = 6.9, 2.7 Hz, 1H), 8.08-7.78 (m, 4H), 7.54 (t, J = 9.1 Hz, 1H), 3.46 (d, J = 10.2 Hz, 2H), 3.17-3.00 (m, 2H), 2.99-2.75 (m, 4H), 2.3 |
| 574 | 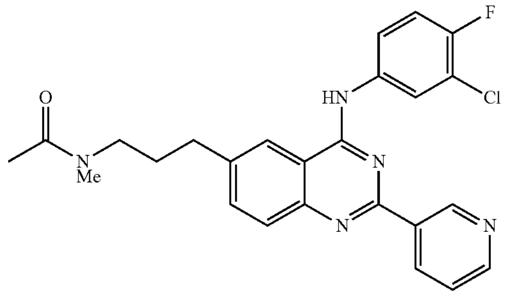 [SMILES: CC(=O)N(C)CCCc1ccc2nc(-c3cccnc3)nc(Nc3ccc(F)c(Cl)c3)c2c1] | HCl | 500.395 | 1H NMR (300 MHz, DMSO) δ 10.68 (s, 1H), 9.49 (s, 1H), 9.12-8.99 (m, 1H), 8.94 (d, J = 3.9 Hz, 1H), 8.58 (d, J = 11.5 Hz, 1H), 8.17 (dd, J = 6.7, 2.6 Hz, 1H), 8.07-7.82 (m, 5H), 7.55 (t, J = 9.1 Hz, 1H), 3.43-3.29 (m, 2H), 3.08-2.65 (m, 5H), 2.09- |
| 575 | 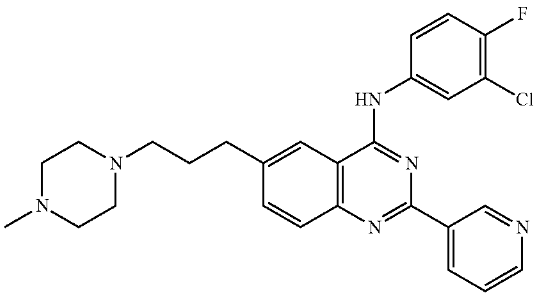 [SMILES: CN1CCN(CCCc2ccc3nc(-c4cccnc4)nc(Nc4ccc(F)c(Cl)c4)c3c2)CC1] | HCl | 600.39 | 1H NMR (300 MHz, DMSO) δ 11.79 (s, 1H), 10.81 (s, 1H), 9.50 (s, 1H), 8.98 (d, J = 8.2 Hz, 1H) 8.89 (d, J = 5.0 Hz, 1H), 8.75 (s, 1H), 8.27 (d, J = 4.8 Hz, 1H), 8.10-7.79 (m, 4H), 7.53 (t, J = 9.1 Hz, 1H), 5.18-3.09 (m, 10H), 3.01-2.69 (m, 5H), 2.37 |

TABLE 3-continued
| | | | |
|---|---|---|---|
| 576 | 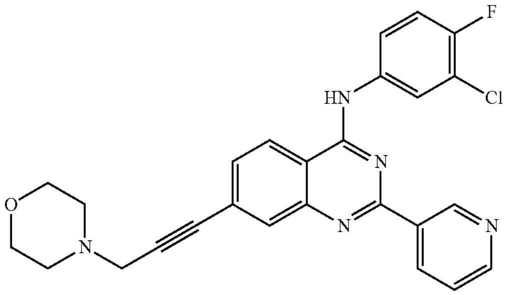 [SMILES: Fc1ccc(Nc2nc(-c3cccnc3)nc3cc(C#CCN4CCOCC4)ccc23)cc1Cl] | 473.93 | 1H NMR (300 MHz, DMSO) δ 10.17 (s, 1H), 9.52 (s, 1H), 8.70 (s, 1H), 8.66 (d, J = 8.1 Hz, 1H), 8.55 (d, J = 8.4 Hz, 1H), 8.27 (dd, J = 6.9, 2.6 Hz, 1H), 7.93 (s, 2H), 7.70 (d, J = 8.4 Hz, 1H), 7.61-7.51 (m, 2H), 3.67-3.61 (m, 6H), 2.61-2.55 (m, 4H). |
| 577 | 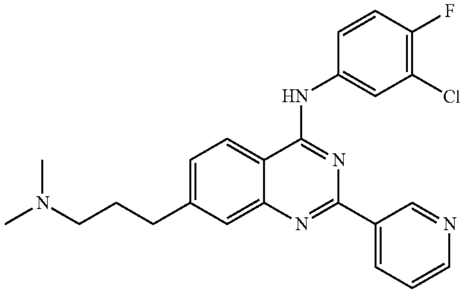 [SMILES: CN(C)CCCc1ccc2c(Nc3ccc(F)c(Cl)c3)nc(-c3cccnc3)nc2c1] | 435.92 | 1H NMR (300 MHz, DMSO) δ 10.08 (s, 1H), 9.54 (s, 1H), 8.77-8.63 (m, 2H), 8.52 (d, J = 8.4 Hz, 1H), 8.29 (d, J = 6.8 Hz, 1H), 7.93 (s, 1H), 7.79 (s, 1H), 7.64-7.51 (m, 3H), 3.00 (t, J = 8.2 Hz, 2H), 2.87 (t, J = 7.6 Hz, 2H), 2.72 (s, 6H), 2.14-1.99 ( |
| 578 | 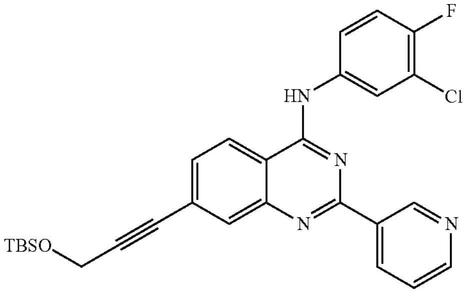 [SMILES: CC(C)(C)[Si](C)(C)OCC#Cc1ccc2c(Nc3ccc(F)c(Cl)c3)nc(-c3cccnc3)nc2c1] | 519.09 | 1H NMR (300 MHz, DMSO) δ 10.17 (s, 1H), 9.67-9.43 (m, 1H), 8.68 (s, 2H), 8.55 (d, J = 8.4 Hz, 1H), 8.28 (s, 1H), 7.89 (s, 2H), 7.68 (s, 1H), 7.56 (d, J = 9.1 Hz, 2H), 4.64 (s, 2H), 0.92 (s, 9H), 0.18 (s, 6H). |
| 579 | 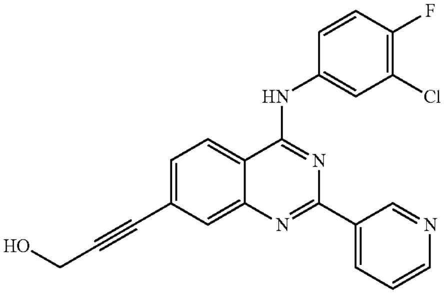 [SMILES: OCC#Cc1ccc2c(Nc3ccc(F)c(Cl)c3)nc(-c3cccnc3)nc2c1] | 404.82 | 1H NMR (300 MHz, DMSO) δ 10.19 (s, 1H), 9.51 (s, 1H), 8.65 (d, J = 8.1 Hz, 2H), 8.64 (d, J = 8.4 Hz, 1H), 8.26 (s, 1H), 7.85 (s, 2H), 7.67-7.60 (m, 1H), 7.52 (d, J = 7.0 Hz, 2H), 5.48 (s, 1H), 4.39 (d, J = 5.8 Hz, 2H). |
| 580 | 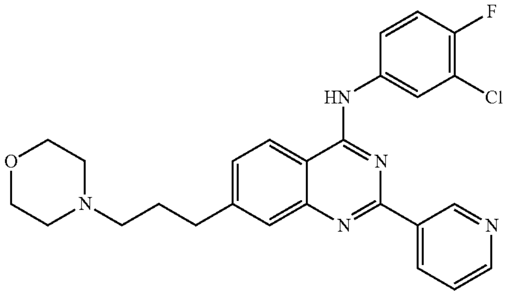 [SMILES: Fc1ccc(Nc2nc(-c3cccnc3)nc3cc(CCCN4CCOCC4)ccc23)cc1Cl] | 477.96 | 1H NMR (300 MHz, DMSO) δ 9.99 (s, 1H), 9.51 (s, 1H), 8.73-8.61 (m, 2H), 8.45 (d, J = 8.6 Hz, 1H), 8.28 (dd, J = 6.8, 2.5 Hz, 1H), 7.97-7.86 (m, 1H), 7.71 (s, 1H), 7.60-7.47 (m, 3H), 3.63-3.51 (m, 4H), 2.82 (t, J = 7.5 Hz, 2H), 2.42-2.25 (m, 6H), |

TABLE 3-continued
| | | | |
|---|---|---|---|
| 581 | 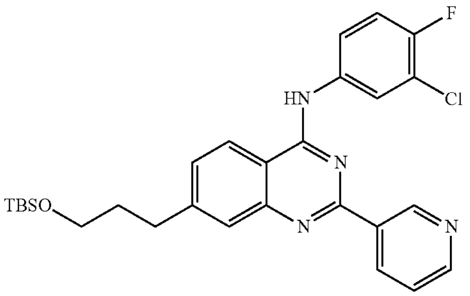 [SMILES: CC(C)(C)[Si](C)(C)OCCCc1ccc2c(Nc3ccc(F)c(Cl)c3)nc(-c3cccnc3)nc2c1] | 523.12 | 1H NMR (300 MHz, CDCl3) δ 9.67 (d, J = 1.3 Hz, 1H), 8.76-8.66 (m, 2H), 8.03 (dd, J = 6.5, 5.7 Hz, 1H), 7.82-7.74 (m, 2H), 7.64 (ddd, J = 8.9, 4.0, 2.7 Hz, 1H), 7.46 (s, 1H), 7.44-7.37 (m, 2H), 7.20 (t, J = 3.7 Hz, 1H), 3.67 (t, J = 6.1 Hz, 2H), 2.95 |
| 582 | 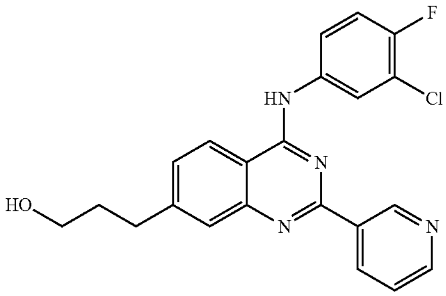 [SMILES: OCCCc1ccc2c(Nc3ccc(F)c(Cl)c3)nc(-c3cccnc3)nc2c1] | 408.86 | 1H NMR (300 MHz, CD3OD) δ 9.50 (d, J = 1.3 Hz, 1H), 8.77 (d, J = 8.0 Hz. 1H), 8.62 (dd, J = 4.9, 1.6 Hz, 1H), 8.26 (d, J = 8.5 Hz, 1H), 8.18 (dd, J = 6.7, 2.6 Hz, 1H), 7.83-7.71 (m, 2H), 7.61-7.47 (m, 2H), 7.30 (t, J = 9.0 Hz, 1H), 3.65 (t, J = 6.4 Hz |
| 583 | 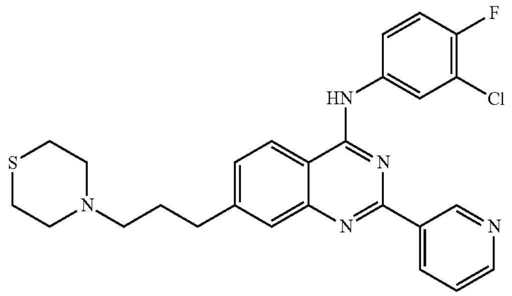 [SMILES: Fc1ccc(Nc2nc(-c3cccnc3)nc3cc(CCCN4CCSCC4)ccc23)cc1Cl] | 494.03 | 1H NMR (300 MHz, CD3OD) δ 9.50-9.46 (m, 1H), 8.77-8.70 (m, 1H), 8.61 (dd, J = 4.9, 1.6 Hz, 1H), 8.22 (d, J = 8.5 Hz, 1H), 8.17 (dd, J = 6.8, 2.6 Hz, 1H), 7.75 (ddd, J = 9.0, 4.2, 2.7 Hz, 1H), 7.70 (s, 1H), 7.54 (ddd, J = 8.0, 4.9, 0.8 Hz, 1H), 7.46 (d |
| 584 | 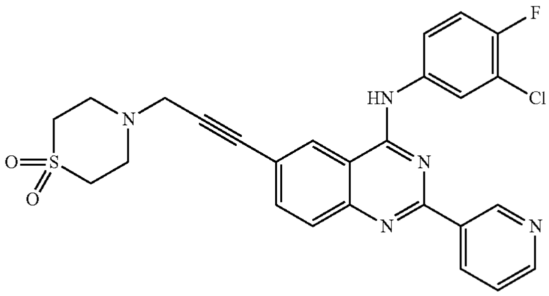 [SMILES: O=S1(=O)CCN(CC#Cc2ccc3nc(-c4cccnc4)nc(Nc4ccc(F)c(Cl)c4)c3c2)CC1] | 522 | 1H NMR (300 MHz, DMSO) δ 10.15 (s, 1H), 8.74-8.61 (m, 2H), 8.25 (d, J = 3.5 Hz, 1H), 7.96-7.80 (m, 4H), 7.59-7.46 (m, 2H), 3.79 (s, 2H), 3.18 (s, 4H), 3.06 (s, 4H). |
| 585 | 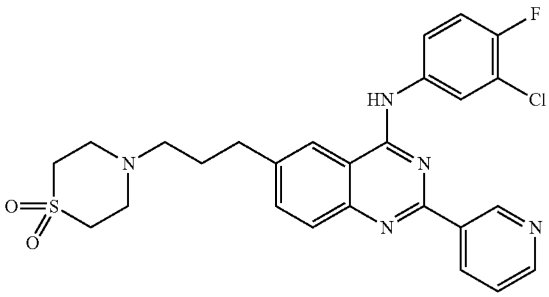 [SMILES: O=S1(=O)CCN(CCCc2ccc3nc(-c4cccnc4)nc(Nc4ccc(F)c(Cl)c4)c3c2)CC1] | 526.06 | 1H NMR (300 MHz, DMSO) δ 9.99 (s, 1H), 9.52 (d, J = 2.0 Hz, 1H), 8.72-8.62 (m, 2H), 8.37 (s, 1H), 8.27 (dd, J = 6.9, 2.6 Hz, 1H), 7.96-7.88 (m, 1H), 7.83 (d, J = 2.6 Hz, 2H), 7.61-7.50 (m, 2H), 3.10 (s, J = 17.4 Hz, 6H), 2.95-2.80 (m, 8H), 2.58- |

TABLE 3-continued
| | | | | |
|---|---|---|---|---|
| 586 | 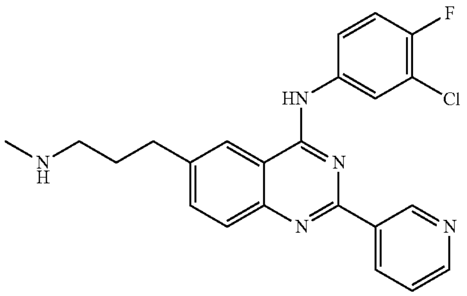 [SMILES: CNCCCc1ccc2nc(-c3cccnc3)nc(Nc3ccc(F)c(Cl)c3)c2c1] | HCl | 494.82 | 1H NMR (300 MHz, DMSO) δ 10.49 (s, 1H), 9.50 (s, 1H), 8.96-8.53 (m, 5H), 8.25 (dd, J = 6.9, 2.5 Hz, 1H), 8.05-7.73 (m, 4H), 7.54 (t, J = 9.1 Hz, 1H), 3.02-2.78 (m, 4H), 2.64-2.37 (m, 3H), 2.15-1.99 (m, 2H). |
| 587 | 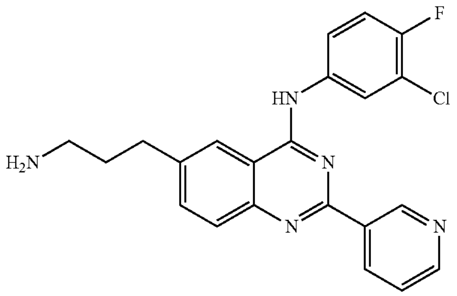 [SMILES: NCCCc1ccc2nc(-c3cccnc3)nc(Nc3ccc(F)c(Cl)c3)c2c1] | HCl | 480.79 | 1H NMR (300 MHz, DMSO) δ 10.61 (s, 1H), 9.50 (s, 1H), 9.00-8.78 (m, 2H), 8.66 (s, 1H), 8.25 (dd, J = 6.8, 2.6 Hz, 1H), 8.13-7.75 (m, 7H), 7.54 (t, J = 9.1 Hz, 1H), 3.02-2.73 (m, 4H), 2.14-1.94 (m, 2H). |
| 588 | 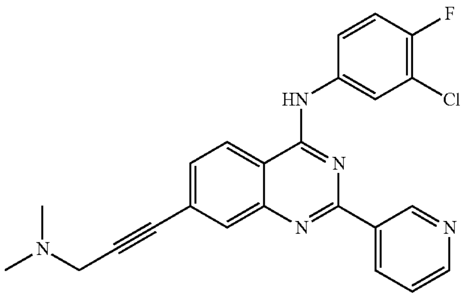 [SMILES: CN(C)CC#Cc1ccc2c(Nc3ccc(F)c(Cl)c3)nc(-c3cccnc3)nc2c1] | | 431.89 | 1H NMR (300 MHz, DMSO) δ 10.18 (s, 1H), 8.65 (d, J = 6.6 Hz, 1H), 8.56 (d, J = 8.7 Hz, 1H), 8.28 (dd, J = 6.9, 2.5 Hz, 1H), 8.01 (s, 1H), 7.91 (dd, J = 7.0, 3.5 Hz, 1H), 7.73 (d, J = 8.5 Hz, 1H), 7.68-7.39 (m, 3H), 4.07 (s, 2H), 2.67 (s, 6H). |
| 589 | 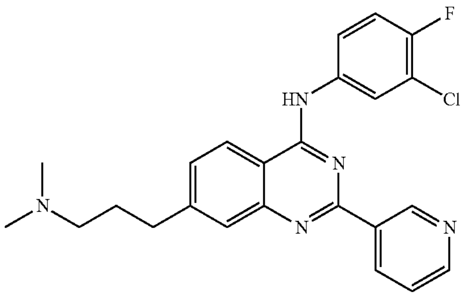 [SMILES: CN(C)CCCc1ccc2c(Nc3ccc(F)c(Cl)c3)nc(-c3cccnc3)nc2c1] | | 435.92 | 1H NMR (300 MHz, DMSO) δ 10.06 (s, 1H), 9.53 (s, 1H), 8.76-8.62 (m, 2H), 8.51 (d, J = 8.4 Hz, 1H), 8.28 (dd, J = 6.9, 2.5 Hz, 1H), 7.92 (dd, J = 4.5, 1.8 Hz, 1H), 7.79 (s, 1H), 7.65-7.49 (m, 3H), 3.08-2.95 (m, 2H), 2.86 (t, J = 7.6 Hz, 2H), 2.71 (s, J = 7.2 Hz, 6H), 2.05 (dt, J = 13.8, 7.1 Hz, 2H). |
| 590 | 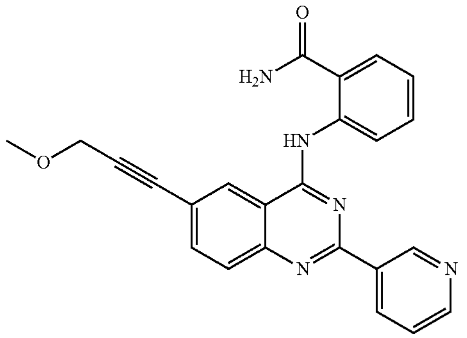 [SMILES: COCC#Cc1ccc2nc(-c3cccnc3)nc(Nc3ccccc3C(N)=O)c2c1] | | 409.44 | 1H NMR (300 MHz, DMSO): δ 13.19 (s, 1H), 9.11 (s, 1H), 8.88 (s, 1H), 8.53 (s, 1H), 8.29 (s, 1H), 8.06 (s, 1H), 7.94 (d, J = 10.6 Hz, 4H), 7.78 (s, 1H), 7.25 (s, 1H), 4.44 (s, 2H), 3.37 (s, 3H). |

TABLE 3-continued

| | | |
|---|---|---|
| 591 | 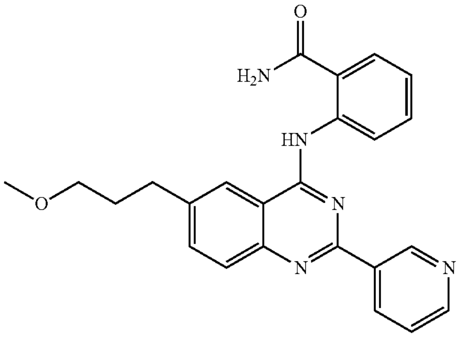 [SMILES: COCCCc1ccc2nc(-c3cccnc3)nc(Nc3ccccc3C(N)=O)c2c1] | 413.47 |

| Number | $^1$H-NMR Solvent | LCMS | Retention Time (Min) | LCMS Protocol | Purity Percent | Method for Coupling |
|---|---|---|---|---|---|---|
| 566 | DMSO | 519 (M + 1) | 3.22 | Method D | 96 | Method O1 |
| 567 | DMSO | 523 (M + 1) | 3.35 | Method D | 100 | Methods O1, P |
| 568 | DMSO | 409 (M + 1) | 1.71 | Method D | 100 | Methods O1, P, Q |
| 569 | DMSO | 436 (M + 1) | 1.68 | Method C | 100 | Method G4 |
| 570 | CDCl3 | 410 (M + 1) | 1.95 | Method D | 100 | Methods O1, P, Q |
| 571 | DMSO | 478 (M + 1) | 2.01 | Method C | 100 | Method G4 |
| 572 | DMSO | 423 (M + 1) | 2.09 | Method D | 100 | Method G4 |
| 573 | DMSO | 476 (M + 1) | 1.79 | Method C | 100 | Method G4 |
| 574 | DMSO | 464 (M + 1) | 1.78 | Method D | 95 | Method G4 followed by acylation with acetyl chloride/TE A/DCM, rt |
| 575 | DMSO | 491 (M + 1) | 1.76 | Method C | 100 | Method G4 |
| 576 | DMSO | 473.9 (M + 1) | 2.2 | Method C | 100 | Method O1 |
| 577 | DMSO | 436.0 (M + 1) | 1.68 | Method C | 100 | Methods O1, P |
| 578 | DMSO | 518.8 (M + 1) | 3.18 | Method C | 100 | Method O1 |
| 579 | DMSO | 404.9 (M + 1) | 2.05 | Method C | 100 | Methods O1, Q |
| 580 | DMSO | 477.9 (M + 1) | 1.99 | Method C | 100 | Methods O1, P |
| 581 | CDCl3 | 523.1 (M + 1) | 3.35 | Method C | 100 | Methods O1, P |
| 582 | CD3OD | 409.0 (M + 1) | 1.99 | Method C | 100 | Methods O1, P, Q |
| 583 | CD3OD | 494.0 (M + 1) | 2.29 | Method C | 91 | Method G4 |
| 584 | DMSO | 522.0 (M + 1) | 2.18 | Method C | 100 | Method O2 |
| 585 | DMSO | 526.1 (M + 1) | 2.11 | Method C | 91 | Methods O2, P |
| 586 | DMSO | 422 (M + 1) | 1.64 | Method B (Ammonium formate) | 100 | Method O2 |
| 587 | DMSO | 408 (M + 1) | 1.60 | Method B (Ammonium formate) | 100 | Method O2 |
| 588 | DMSO | 431.9 (M + 1) | | Method C | 99 | Method O1 |
| 589 | DMSO | 436.0 (M + 1) | | Method C | 99 | Method O1, P |
| 590 | DMSO | 410.5 (M + 1) | | Method C | 95 | Method O1 |
| 591 | DMSO | 414.5 (M + 1) | | Method C | 95 | Method O1, P |

Scheme 11: General route for the synthesis of compounds with general formula xxi:

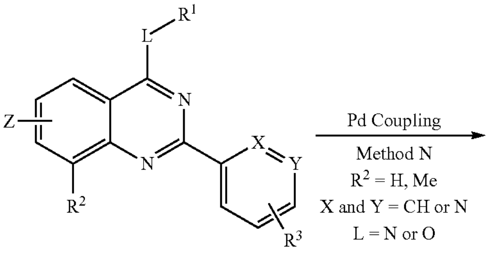

vi

Z = Br, Cl

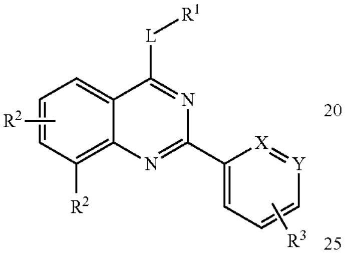

xxi

Method N1: $Pd(APhos)_2Cl_2/K_3PO_4$ or $Cs_2CO_3$/Boronic acid or ester/Dioxane-$H_2O$, heat Method N2: $Pd(PPh_3)_2Cl_2/K_2CO_3$/Boronic acid or ester/DME-EtOH-$H_2O$/microwave, 120° C.

Method N3: $Pd(OAc)_2$/Xphos/$Cs_2CO_3$/THF-$H_2O$, 80° C.

Method N4: $Pd(OAc)_2$/Sphos/$K_2CO_3$/MeCN-$H_2O$, microwave, 120° C.

Method N5: $Pd(PPh_3)_4/K_3PO_4$/Dioxane-$H_2O$, heat

Method N6: $Pd(dppf)Cl_2$—$CH_2Cl_2/K_3PO_4$/Dioxane-$H_2O$, heat

Scheme 12: Method N1: Representative synthesis of compounds of formula xxi (see Scheme 11).

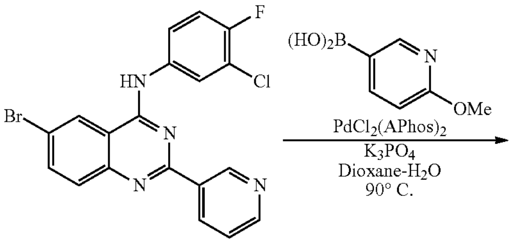

vi-g

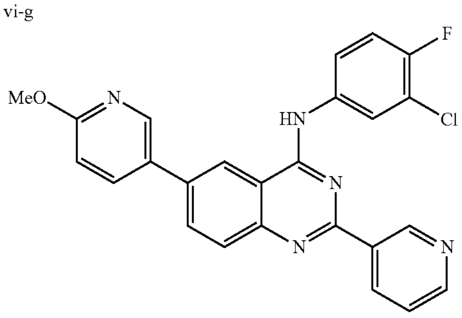

xxi-a

N-(3-chloro-4-fluorophenyl)-6-(6-methoxypyridin-3-yl)-2-(pyridin-3-yl)quinazolin-4-amine (xxi-a)

A 2.0 dram reaction vial was charged with 6-bromo-N-(3-chloro-4-fluorophenyl)-2-(pyridin-3-yl)quinazolin-4-amine (synthesized as described in Scheme 1 and 4, substituting 5-bromo-2-nitrobenzoic acid for 2-nitro-5-propoxy-benzoic acid and 3-chloro-4-fluoroaniline for 2-aminobenzamide) (100 mg, 0.233 mmol, 1.0 equiv), 6-methoxypyridin-3-ylboronic acid (44.5 mg, 0.291 mmol, 1.25 equiv), $Pd(APhos)_2Cl_2$ (6.6 mg, 0.0093 mmol, 4 mol %) and potassium phosphate monohydrate (69 mg, 0.70 mmol, 3.0 equiv). The mixture was suspended in dioxane/water (9:1, 4 mL), and the reaction was heated at 90° C. for 14 h. The reaction mixture was cooled to room temperature, diluted with water (15 mL) and the resultant precipitate was collected by filtration. The crude product was purified by stirring in methanol for 30 min at 60° C. to give the desired product as a pale yellow solid (58 mg, 54%) LCMS m/z=458.1 (M+1) (Method C) (retention time=2.56 min). $^1H$ NMR (300 MHz, DMSO) δ 10.12 (s, 1H), 9.53 (s, 1H), 8.82 (s, 1H), 8.70 (dd, J=16.9, 5.4 Hz, 3H), 8.25 (d, J=8.6 Hz, 3H), 8.01-7.87 (m, 2H), 7.57 (dd, J=11.2, 6.0 Hz, 2H), 7.03 (d, J=8.6 Hz, 1H), 3.94 (s, 3H).

Scheme 13: Method N2: Representative synthesis of compounds of formula xxi (see Scheme 11)

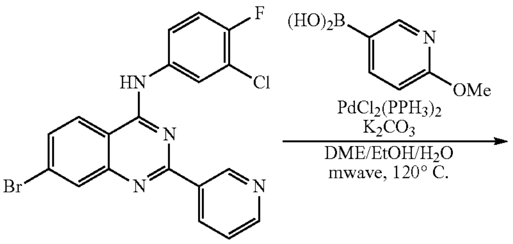

vi-h

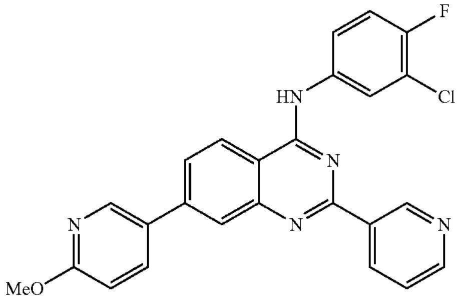

xxi-b

N-(3-chloro-4-fluorophenyl)-7-(6-methoxypyridin-3-yl)-2-(pyridin-3-yl)quinazolin-4-amine (xxi-b)

A microwave vial was charged with 7-bromo-N-(3-chloro-4-fluorophenyl)-2-(pyridin-3-yl)quinazolin-4-amine (synthesized as described in Scheme 1 and 4, substituting 4-bromo-2-nitrobenzoic acid for 2-nitro-5-propoxy-benzoic acid and 3-chloro-4-fluoroaniline for 2-aminobenzamide) (100 mg, 0.233 mmol), 6-methoxypyridin-3-ylboronic acid (44.5 mg, 0.291 mmol, 1.25 equiv), $Pd(PPh_3)_2Cl_2$ (8.1 mg, 5 mol %) and potassium carbonate (160.1 mg, 1.16 mmol, 5.0 equiv). The mixture was suspended in DME/water/ethanol (7:3:2, 4 mL), and the reaction was heated under microwave irradiation conditions at 120° C. for 10 minutes. The crude reaction mixture was diluted with water (10 mL) and then filtered. The solid residue was dissolved in methanol/THF (1:1, 5 mL) with heating and then filtered through Celite to remove the catalyst. The resulting filtrate was concentrated to afford the desired product as a tan solid (7.0 mg, 6.5%). LCMS m/z=458.1 (M+1) (Method C) (retention time=2.51 min). $^{1}$H NMR (300 MHz, DMSO) δ 10.12 (s, 1H), 9.55 (s, 1H), 8.76 (d, J=2.5 Hz, 1H), 8.72-8.65 (m, 2H), 8.62 (d, J=8.6 Hz, 1H), 8.34-8.26 (m, 2H), 8.15 (d, J=1.6 Hz, 1H), 8.02 (d, J=8.7 Hz, 1H), 7.97-7.88 (m, 1H), 7.61-7.49 (m, 2H), 6.99 (d, J=8.7 Hz, 1H), 3.94 (s, 3H).

Scheme 14: Method N3: Representative synthesis of compounds of formula xxi (see Scheme 11). (This method is representative of method N4 except for substitution of the appropriate ligand, solvent and the use of microwave instead of heating)

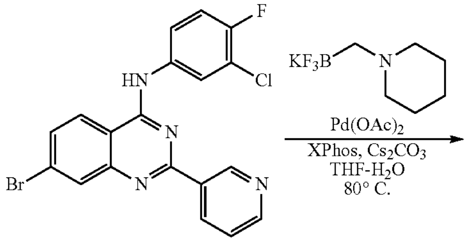

vi-h

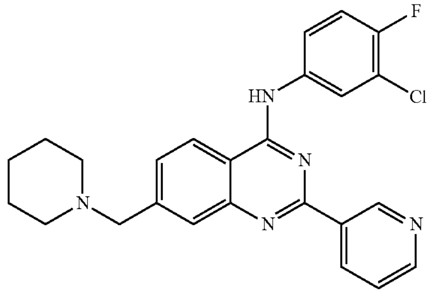

xxi-c

N-(3-chloro-4-fluorophenyl)-7-(piperidin-1-ylmethyl)-2-(pyridin-3-yl)quinazolin-4-amine (xxi-c)

A dry 15 mL sealed tube was charged with 7-bromo-N-(3-chloro-4-fluorophenyl)-2-(pyridin-3-yl)quinazolin-4-amine (synthesized as described in Scheme 1 and 4, substituting 4-bromo-2-nitrobenzoic acid for 2-nitro-5-propoxy-benzoic acid and 3-chloro-4-fluoroaniline for 2-aminobenzamide) (100 mg, 0.233 mmol), potassium 1-trifluoroboratomethylpiperidine (52.5 mg, 0.256 mmol), cesium carbonate (227.5 mg, 0.698 mmol), $Pd(OAc)_2$ (1.6 mg, 3 mol %) and XPhos (6.7 mmol, 6 mol %) in THF/water (10:1, 3.3 mL). The reaction mixture was stirred at 80° C. for 16 hours. The reaction mixture was filtered through a pad of Celite and solvent was removed in vacuo. The crude product was purified by ISCO (silica, 12 g column, 97% dichloromethane-3% methanol-0.1% $NH_4OH$) to yield the desired compound as a yellow solid (23.3 mg, 22%). LCMS m/z=448.0 (M+1) (Method C) (retention time=1.95 min). $^{1}$H NMR (300 MHz, $CD_3OD$) δ 9.40 (d, J=1.4 Hz, 1H), 8.70-8.62 (m, 1H), 8.56 (dd, J=4.9, 1.6 Hz, 1H), 8.18-8.09 (m, 2H), 7.69 (ddd, J=6.8, 4.1, 2.1 Hz, 2H), 7.54-7.45 (m, 2H), 7.23 (t, J=9.0 Hz, 1H), 3.61 (s, 2H), 2.47 (s, 4H), 1.64 (dd, J=13.9, 8.9 Hz, 5H), 1.49 (d, J=4.1 Hz, 2H).

Scheme 15: Method N5: Representative synthesis of compounds of formula xxi (see Scheme 11)

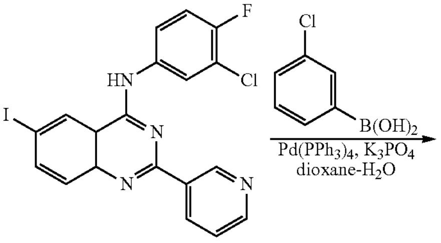

vi-i

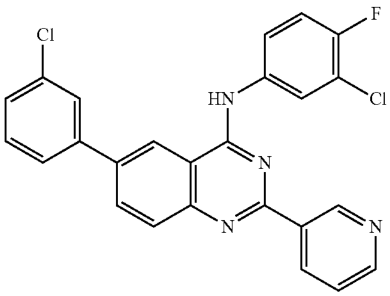

xxi-d

N-(3-chloro-4-fluorophenyl)-6-(3-chlorophenyl)-2-(pyridin-3-yl)quinazolin-4-amine (xxi-d)

A mixture of N-(3-chloro-4-fluorophenyl)-6-iodo-2-(pyridin-3-yl)quinazolin-4-amine (1.0 g, 2.10 mmol), 3-chlorophenylboronic acid (0.49 g, 3.13 mmol), $Pd(PPh_3)_4$ (0.24 g, 0.210 mmol), $K_3PO_4$ (1.34 g, 6.31 mmol) in dioxane (20 mL) and water (2.0 mL) was stirred under reflux for 2 h. Ethyl acetate (20 mL) was added to the cooled mixture and filtered. The filtered solid was recrystallized from DMF and water to give the title compound (0.50 g, 51.6%). $^{1}$H NMR (400 MHz, DMSO) δ 10.20 (s, 1H), 9.54 (s, 1H), 8.87 (s, 1H), 8.74-8.65 (m, 2H), 8.31-8.23 (m, 2H), 8.04-7.85 (m, 4H), 7.64-7.49 (m, 4H).

Scheme 16: Method N6: Representative synthesis of compounds of formula xxi (see Scheme 11)

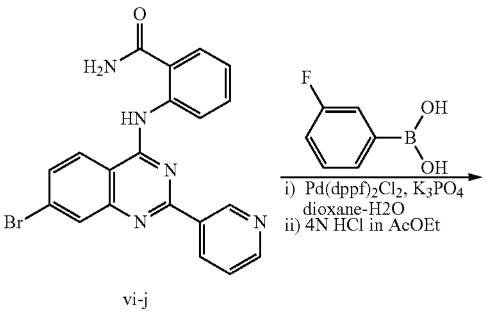

vi-j

-continued

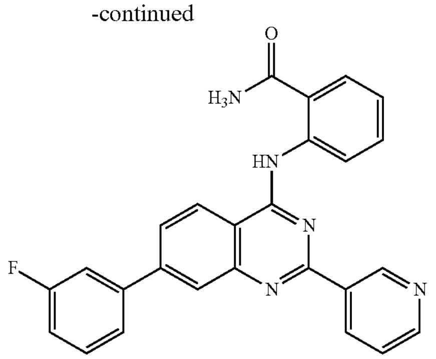

xxi-e 2-(7-(3-fluorophenyl)-2-(pyridin-3-yl)quinazolin-4-ylamino)benzamide dihydrochloride (xxi-e)

A mixture of 2-(7-bromo-2-(pyridin-3-yl)quinazolin-4-ylamino)benzamide (0.40 g, 0.952 mmol), 3-fluorophenylboronic acid (0.20 g 1.43 mmol), $Pd(dppf)_2Cl_2$ (77 mg, 0.094 mmol), $K_3PO_4$ (606 mg, 2.85 mmol) in dioxane (8 mL) and water (2 mL) was refluxed under argon atmosphere for 4 h and cooled. Ethyl acetate (10 ml) was added to the mixture and a precipitate formed and was filtered. The filtered solid was recrystallized from DMF and water to give the title compound as free form. The solid as free form was suspended in ethyl acetate (10 mL) and 4N HCl in ethyl acetate (0.71 mL) was added to the suspension. A precipitate formed and was subjected to sonication for 20 min, filtered and dried to give the title compound (0.24 g, 49.6%). $^1$H NMR (400 MHz, DMSO) δ 13.19 (s, 1H), 9.64 (s, 1H), 9.21-9.08 (m, 1H), 9.07-8.89 (m, 2H), 8.51 (s, 1H), 8.38-8.26 (m, 2H), 8.16 (d, J=8.5 Hz, 1H), 8.07-7.87 (m, 3H), 7.83-7.70 (m, 3H), 7.62 (dd, J=14.2, 7.7 Hz, 1H), 7.40-7.22 (m, 2H).

The compounds in the following table were prepared in a manner analogous to that described in Scheme 11 substituting with appropriate boronic acid/ester or boronate salt, catalyst and solvent TABLE 4
| Number | PRODUCT | Salt type | Molecular Mass | $^1$H-NMR |
|---|---|---|---|---|
| 592 | 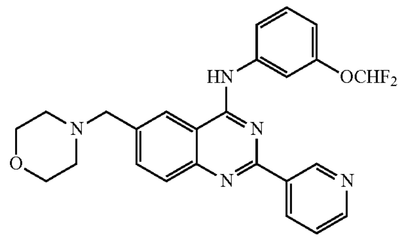 [SMILES: FC(F)Oc1cccc(Nc2nc(-c3cccnc3)nc3ccc(CN4CCOCC4)cc23)c1] | 2 HCl | 536.401 | $^1$H NMR (300 MHz, DMSO) δ 11.34 (s, 1H), 10.53 (s, 1H), 9.56 (s, 1H), 9.17-8.95 (m, 2H), 8.89 (d, J = 4.5 Hz, 1H), 8.19 (d, J = 8.8 Hz, 1H), 8.08-7.81 (m, 4H), 7.62-6.98 (m, 3H), 4.53 (s, 2H), 4.05-3.74 (m, 4H), 3.48-3.07 (m, 4H). |
| 593 | 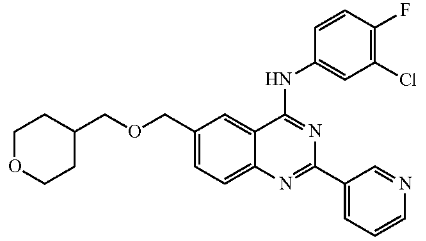 [SMILES: Fc1ccc(Nc2nc(-c3cccnc3)nc3ccc(COCC4CCOCC4)cc23)cc1Cl] | HCl | 515.406 | $^1$H NMR (300 MHz, DMSO) δ 10.40 (s, 1H), 9.51 (s, 1H), 9.00-8.78 (m, 2H), 8.55 (s, 1H), 8.20 (d, J = 4.4 Hz, 1H), 8.03-7.75 (m, 4H), 7.54 (t, J = 9.1 Hz, 1H), 4.68 (s, 2H), 3.83 (d, J = 11.2 Hz, 2H), 3.44-3.18 (m, 4H), 1.98-1.78 (m, 1H), 1.62 (d, J |
| 594 | 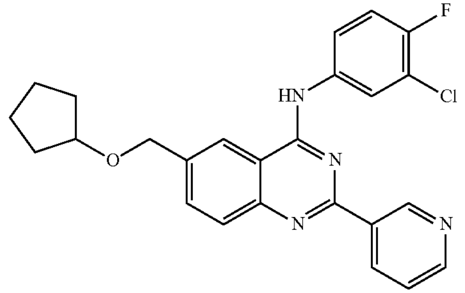 [SMILES: Fc1ccc(Nc2nc(-c3cccnc3)nc3ccc(COC4CCCC4)cc23)cc1Cl] | | 448.920 | 1H NMR (300 MHz, DMSO) δ 10.10 (s, 1H), 9.51 (s, 1H), 8.75-8.60 (m, 2H), 8.47 (s, 1H), 8.32-8.19 (m, 1H), 7.97-7.77 (m, 3H), 7.63-7.44 (m, 2H), 4.62 (s, 2H), 4.16-3.97 (m, 1H), 1.88-1.42 (m, 8H). |

TABLE 4-continued
| | | | |
|---|---|---|---|
| 595 | 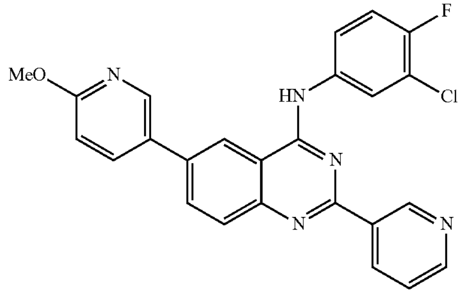 | 457.89 | $^1$H NMR (300 MHz, DMSO) δ 10.12 (s, 1H), 9.53 (s, 1H), 8.82 (s, 1H), 8.70 (dd, J = 16.9, 5.4 Hz, 3H), 8.25 (d, J = 8.6 Hz, 3H), 8.01-7.87 (m, 2H), 7.57 (dd, J = 11.2, 6.0 Hz, 2H), 7.03 (d, J = 8.6 Hz, 1H), 3.94 (s, 3H). |
| 596 | 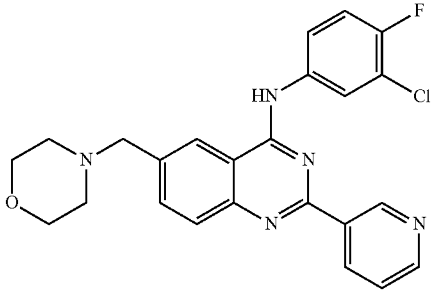 [SMILES: Fc1ccc(Nc2nc(-c3cccnc3)nc3ccc(CN4CCOCC4)cc23)cc1Cl] | 449.91 | $^1$H NMR (300 MHz, DMSO) δ 10.13 (s, 1H), 9.52 (s, 1H), 8.67 (d, J = 9.8 Hz, 2H), 8.47 (s, 1H), 8.34-8.20 (m, 1H), 8.02-7.84 (m, 3H), 7.54 (t, J = 9.2 Hz, 2H), 3.64 (d, J = 17.6 Hz, 6H), 2.43 (s, 4H). |
| 597 | 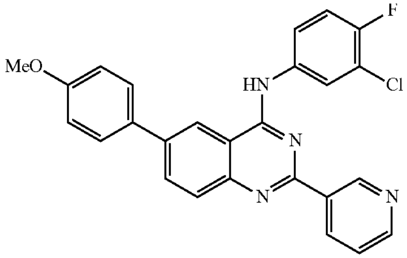 [SMILES: COc1ccc(-c2ccc3nc(-c4cccnc4)nc(Nc4ccc(F)c(Cl)c4)c3c2)cc1] | 456.9 | |

TABLE 4-continued
| | | | |
|---|---|---|---|
| 598 | 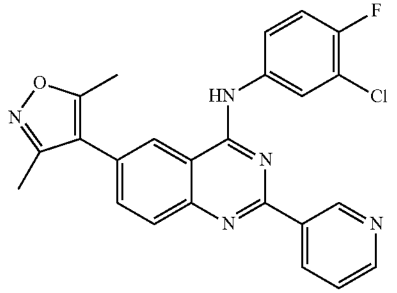 [SMILES: Cc1noc(C)c1-c1ccc2nc(-c3cccnc3)nc(Nc3ccc(F)c(Cl)c3)c2c1] | 445.88 | $^1$H NMR (300 MHz, DMSO) δ 10.04 (s, 1H), 9.52 (s, 1H), 8.68 (t, J = 6.5 Hz, 2H), 8.51 (s, 1H), 8.22 (dd, J = 6.7, 2.4 Hz, 1H), 8.03-7.83 (m, 3H), 7.54 (dd, J = 11.9, 6.6 Hz, 2H), 2.50 (s, 3H), 2.33 (s, 3H). |
| 599 | 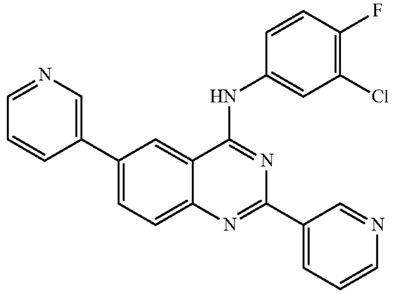 [SMILES: Fc1ccc(Nc2nc(-c3cccnc3)nc3ccc(-c4cccnc4)cc23)cc1Cl] | 427.86 | $^1$H NMR (300 MHz, DMSO) δ 10.10 (s, 1H), 9.51 (s, 1H), 9.13 (s, 1H), 8.86 (s, 1H), 8.66 (s, 3H), 8.24 (s, 3H), 7.94 (d, J = 8.7 Hz, 2H), 7.55 (dd, J = 16.7, 9.9 Hz, 3H). |
| 600 | 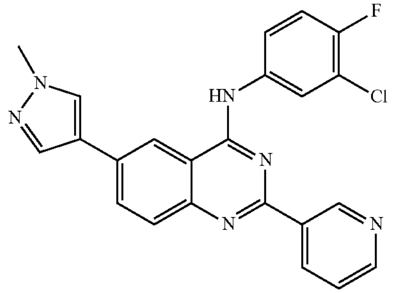 [SMILES: Cn1cc(-c2ccc3nc(-c4cccnc4)nc(Nc4ccc(F)c(Cl)c4)c3c2)cn1] | 430.86 | $^1$H NMR (300 MHz, DMSO) δ 9.98 (s, 1H), 9.51 (d, J = 1.6 Hz, 1H), 8.66 (dd, J = 11.7, 2.2 Hz, 3H), 8.38-8.20 (m, 2H), 8.20-8.02 (m, 2H), 8.02-7.80 (m, 2H), 7.71-7.42 (m, 2H), 3.93 (s, 3H). |

TABLE 4-continued
| | | | |
|---|---|---|---|
| 601 | 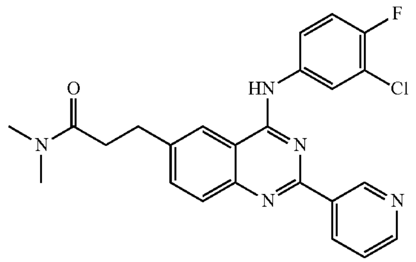 [SMILES: CN(C)C(=O)CCc1ccc2nc(-c3cccnc3)nc(Nc3ccc(F)c(Cl)c3)c2c1] | 449.91 | $^1$H NMR (300 MHz, DMSO) δ 9.99 (s, 1H), 9.52 (d, J = 1.3 Hz, 1H), 8.77-8.55 (m, 2H), 8.41 (s, 1H), 8.28 (dd, J = 6.9, 2.6 Hz, 1H), 8.08-7.77 (m, 3H), 7.65-7.44 (m, 2H), 3.34 (s, 8H), 3.15-2.90 (m, 5H), 2.90-2.64 (m, 5H). |
| 602 | 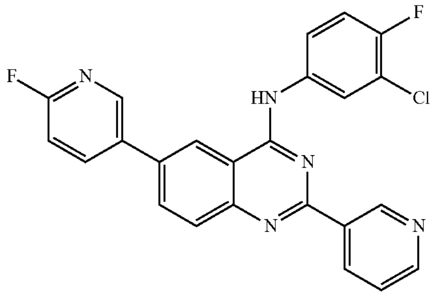 [SMILES: Fc1ccc(-c2ccc3nc(-c4cccnc4)nc(Nc4ccc(F)c(Cl)c4)c3c2)cn1] | 445.85 | $^1$H NMR (300 MHz, DMSO) δ 10.09 (s, 1H), 9.50 (s, 1H), 8.88-8.74 (m, 2H), 8.66 (dd, J = 14.1, 5.5 Hz, 2H), 8.56-8.42 (m, 1H), 8.23 (dd, J = 10.0, 5.7 Hz, 2H), 7.98-7.85 (m, 2H), 7.62-7.46 (m, 2H), 7.45-7.36 (m, 1H). |
| 603 | 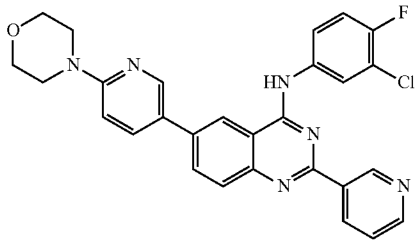 [SMILES: Fc1ccc(Nc2nc(-c3cccnc3)nc3ccc(-c4ccc(N5CCOCC5)nc4)cc23)cc1Cl] | 512.97 | $^1$H NMR (300 MHz, DMSO) δ 10.05 (s, 1H), 9.51 (s, 1H), 8.70 (dd, J = 24.1, 7.0 Hz, 4H), 8.22 (dd, J = 14.3, 7.3 Hz, 2H), 8.10 (d, J = 7.9 Hz, 1H), 7.89 (d, J = 8.4 Hz, 2H), 7.53 (d, J = 7.4 Hz, 2H), 7.00 (d, J = 8.8 Hz, 1H), 3.74 (s, 4H), 3.55 (d, J = 4.7 |

TABLE 4-continued
| | | | |
|---|---|---|---|
| 604 | 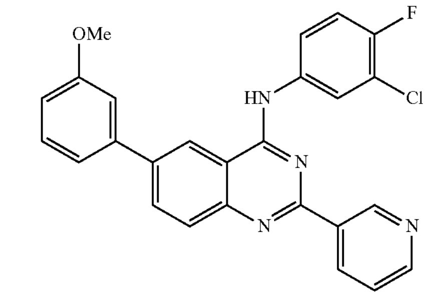 [SMILES: COc1cccc(-c2ccc3nc(-c4cccnc4)nc(Nc4ccc(F)c(Cl)c4)c3c2)c1] | 456.9 | $^1$H NMR (300 MHz, DMSO) δ 10.16 (s, 1H), 9.53 (s, 1H), 8.81 (s, 1H), 8.73-8.60 (m, 2H), 8.30-8.20 (m, 2H), 7.99-7.89 (m, 2H), 7.55 (dd, J = 8.2, 4.7 Hz, 2H), 7.46 (t, J = 7.6 Hz, 3H), 7.10-6.96 (m, 1H), 3.88 (s, 3H). |
| 605 | 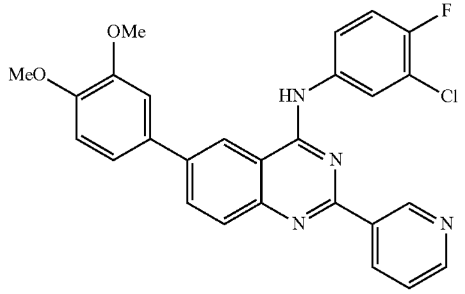 [SMILES: COc1ccc(-c2ccc3nc(-c4cccnc4)nc(Nc4ccc(F)c(Cl)c4)c3c2)cc1OC] | 486.92 | $^1$H NMR (300 MHz, DMSO) δ 10.16 (s, 1H), 9.54 (s, 1H), 8.79 (d, J = 9.7 Hz, 1H), 8.71 (s, 2H), 8.26 (d, J = 8.7 Hz, 1H), 7.95 (dd, J = 8.7, 3.7 Hz, 2H), 7.56 (dd, J = 11.7,6.4 Hz, 1H), 7.43 (d, J = 15.2 Hz, 2H), 7.22-7.06 (m, 2H), 3.92 (s, 3H), 3.84 (s, |
| 606 | 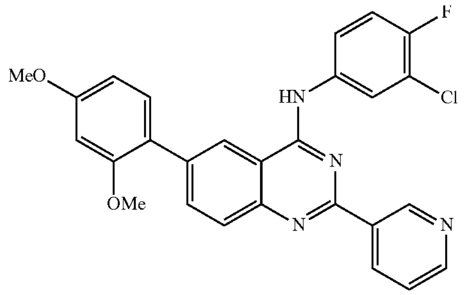 [SMILES: COc1ccc(-c2ccc3nc(-c4cccnc4)nc(Nc4ccc(F)c(Cl)c4)c3c2)c(OC)c1] | 486.92 | |

TABLE 4-continued
| | | | |
|---|---|---|---|
| 607 | 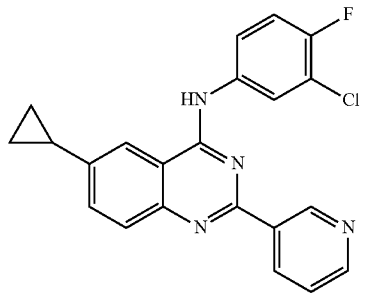 [SMILES: Fc1ccc(Nc2nc(-c3cccnc3)nc3ccc(C4CC4)cc23)cc1Cl] | 390.84 | |
| 608 | 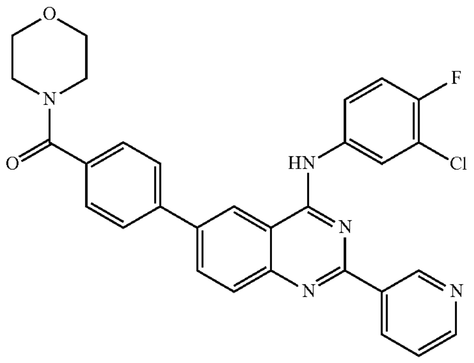 [SMILES: O=C(c1ccc(-c2ccc3nc(-c4cccnc4)nc(Nc4ccc(F)c(Cl)c4)c3c2)cc1)N1CCOCC1] | 539.99 | $^1$H NMR (300 MHz, DMSO) δ 10.15 (s, 1H), 9.51 (s, 1H), 8.84 (s, 1H), 8.66 (dd, J = 9.7, 6.5 Hz, 2H), 8.29-8.19 (m, 2H), 7.92 (ddd, J = 8.9, 7.5, 4.6 Hz, 4H), 7.65-7.48 (m, 4H), 3.64 (s, 6H), 3.35 (s, 2H). |
| 609 | 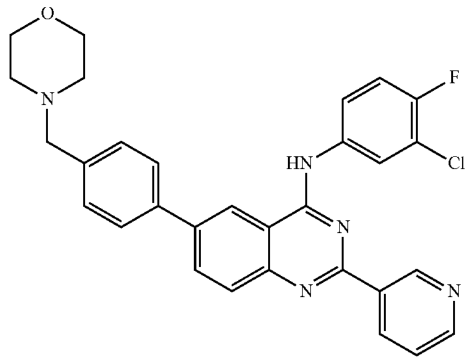 [SMILES: Fc1ccc(Nc2nc(-c3cccnc3)nc3ccc(-c4ccc(CN5CCOCC5)cc4)cc23)cc1Cl] | 526 | |

TABLE 4-continued
| | | | |
|---|---|---|---|
| 610 | 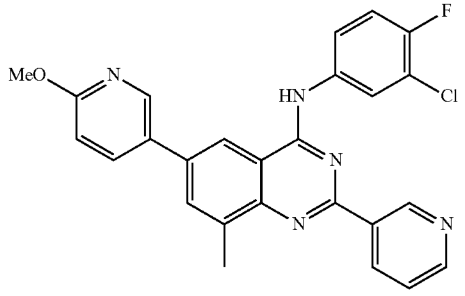 [SMILES: COc1ccc(-c2cc(C)c3nc(-c4cccnc4)nc(Nc4ccc(F)c(Cl)c4)c3c2)cn1] | 471.91 | $^1H$ NMR (300 MHz, DMSO) δ 10.03 (s, 1H), 9.56 (d, J = 2.1 Hz, 1H), 8.77-8.66 (m, 3H), 8.64 (s, 1H), 8.24 (ddd, J = 8.7, 6.6, 2.6 Hz, 2H), 8.13 (s, 1H), 7.96-7.90 (m, 1H), 7.62-7.52 (m, 2H), 7.01 (d, J = 8.7 Hz, 1H), 3.94 (s, 3H), 2.78 (s, 3H). |
| 611 | 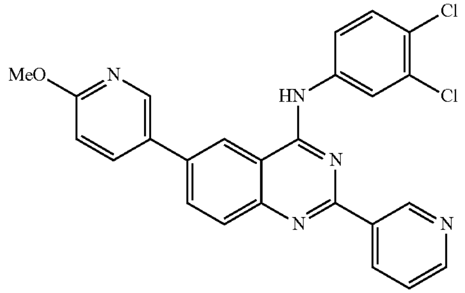 [SMILES: COc1ccc(-c2ccc3nc(-c4cccnc4)nc(Nc4ccc(Cl)c(Cl)c4)c3c2)cn1] | 474.34 | $^1H$ NMR (300 MHz, DMSO) δ 10.09 (s, 1H), 9.53 (s, 1H), 8.77 (s, 1H), 8.67 (dd, J = 12.3, 4.1 Hz, 3H), 8.35 (d, J = 2.3 Hz, 1H), 8.27-8.13 (m, 2H), 8.02-7.88 (m, 2H), 7.72 (d, J = 8.8 Hz, 1H), 7.55 (dd, J = 7.7, 4.6 Hz, 1H), 7.00 (d, J = 8.6 Hz, 1H), 3. |
| 612 | 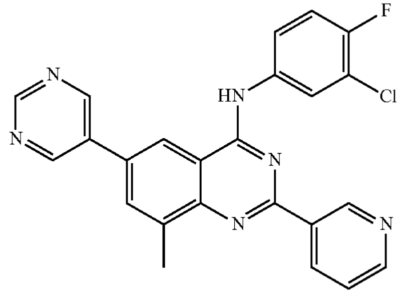 [SMILES: Cc1cc(-c2cncnc2)cc2c(Nc3ccc(F)c(Cl)c3)nc(-c3cccnc3)nc12] | 442.88 | |

TABLE 4-continued
| | | | |
|---|---|---|---|
| 613 | 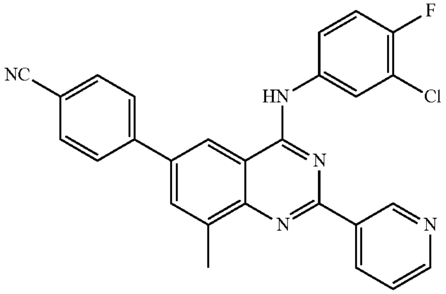 [SMILES: Cc1cc(-c2ccc(C#N)cc2)cc2c(Nc3ccc(F)c(Cl)c3)nc(-c3cccnc3)nc12] | 465.91 | $^1$H NMR (300 MHz, DMSO) δ 10.12 (s, 1H), 9.54 (s, 1H), 8.75-8.63 (m, 3H), 8.20 (dd, J = 8.2, 5.6 Hz, 2H), 8.09 (d, J = 8.5 Hz, 2H), 8.01 (d, J = 8.5 Hz, 2H), 7.88 (s, 1H), 7.55 (d, J = 9.1 Hz, 2H), 2.76 (s, 3H). |
| 614 | 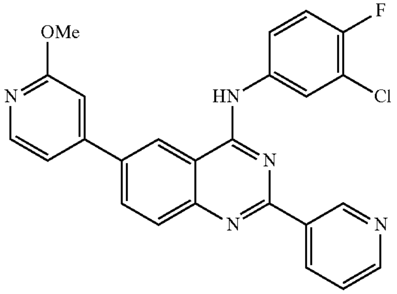 [SMILES: COc1cc(-c2ccc3nc(-c4cccnc4)nc(Nc4ccc(F)c(Cl)c4)c3c2)ccn1] | 457.89 | $^1$H NMR (300 MHz, DMSO) δ 10.18 (s, 1H), 9.51 (s, 1H), 8.92 (s, 1H), 8.67 (dd, J = 12.7, 5.8 Hz, 2H), 8.39-8.16 (m, 3H), 7.91(dd, J = 14.8, 5.7 Hz, 2H), 7.65-7.45 (m, 3H), 7.35 (s, 1H), 3.94 (s, 3H). |
| 615 | 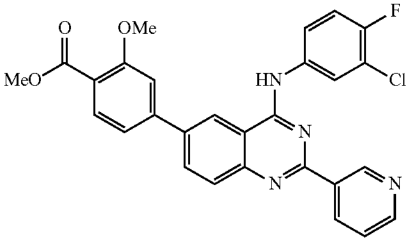 [SMILES: COC(=O)c1ccc(-c2ccc3nc(-c4cccnc4)nc(Nc4ccc(F)c(Cl)c4)c3c2)cc1OC] | 514.93 | $^1$H NMR (300 MHz, DMSO) δ 10.19 (s, 1H), 9.52 (s, 1H), 8.86 (s, 1H), 8.67 (dd, J = 10.1, 3.4 Hz, 2H), 8.28 (ddd, J = 9.4, 7.7, 2.1 Hz, 2H), 8.06-7.75 (m, 2H), 7.54 (dd, J = 9.0, 4.1 Hz, 4H), 3.99 (s, 3H), 3.82 (s, 3H) |

TABLE 4-continued
| | | | |
|---|---|---|---|
| 616 | 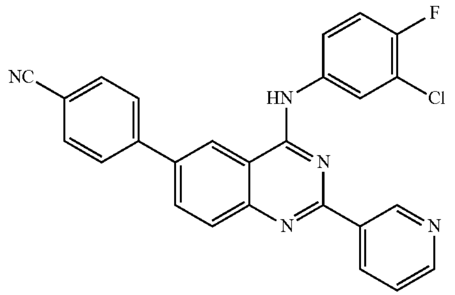 [SMILES: N#Cc1ccc(-c2ccc3nc(-c4cccnc4)nc(Nc4ccc(F)c(Cl)c4)c3c2)cc1] | 451.88 | $^1H$ NMR (300 MHz, DMSO) δ 10.16 (s, 1H), 9.50 (s, 1H), 8.86 (s, 1H), 8.66 (dd, J = 15.2, 6.9 Hz, 2H), 8.35-8.16 (m, 2H), 8.15-7.82 (m, 6H), 7.55 (dd, J = 11.1, 6.0 Hz, 2H). |
| 617 | 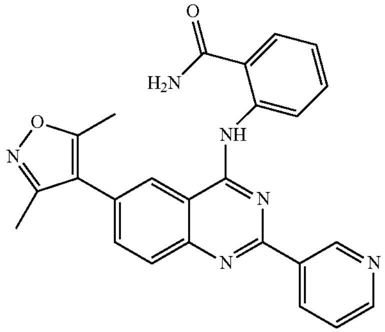 [SMILES: Cc1noc(C)c1-c1ccc2nc(-c3cccnc3)nc(Nc3ccccc3C(N)=O)c2c1] | 436.47 | |
| 618 | 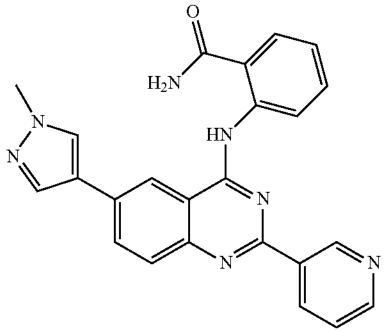 [SMILES: Cn1cc(-c2ccc3nc(-c4cccnc4)nc(Nc4ccccc4C(N)=O)c3c2)cn1] | 421.45 | |

TABLE 4-continued
| | | | |
|---|---|---|---|
| 619 | 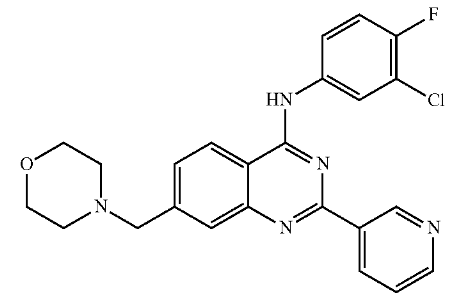 [SMILES: Fc1ccc(Nc2nc(-c3cccnc3)nc3cc(CN4CCOCC4)ccc23)cc1Cl] | 449.91 | $^1$H NMR (300 MHz, DMSO) δ 10.06 (s, 1H), 9.52 (d, J = 1.3 Hz, 1H), 8.73-8.64 (m, 2H), 8.51 (d, J = 8.5 Hz, 1H), 8.27 (dd, J = 6.9, 2.6 Hz, 1H), 7.96-7.86 (m, 1H), 7.82 (s, 1H), 7.64 (d, J = 8.4 Hz, 1H), 7.57 (t, J = 3.9 Hz, 1H), 7.52 (t, J = 9.1 Hz, 1H), 3.69 (s, 2H), 3.62 (s, 4H), 2.44 (s, 4H). |
| 620 | 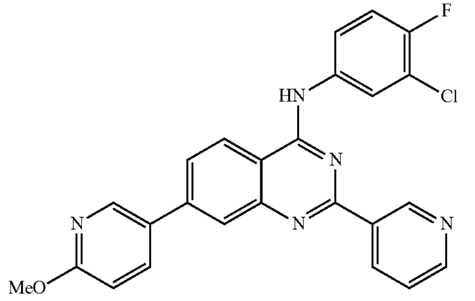 [SMILES: COc1ccc(-c2ccc3c(Nc4ccc(F)c(Cl)c4)nc(-c4cccnc4)nc3c2)cn1] | 457.89 | $^1$H NMR (300 MHz, DMSO) δ 10.12 (s, 1H), 9.55 (s, 1H), 8.76 (d, J = 2.5 Hz, 1H), 8.72-8.65 (m, 2H), 8.62 (d, J = 8.6 Hz, 1H), 8.34-8.26 (m, 2H), 8.15 (d, J = 1.6 Hz, 1H), 8.02 (d, J = 8.7 Hz, 1H), 7.97-7.88 (m, 1H), 7.61-7.49 (m, 2H), 6.99 (d, J = 8.7 Hz, 1H), 3.94 (s, 3H). |
| 621 | 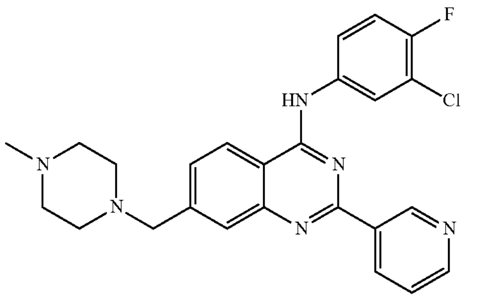 [SMILES: CN1CCN(Cc2ccc3c(Nc4ccc(F)c(Cl)c4)nc(-c4cccnc4)nc3c2)CC1] | 462.95 | $^1$H NMR (300 MHz, $CD_3OD$) δ 9.40 (s, 1H), 8.66 (d, J = 8.0 Hz, 1H), 8.56 (s, 1H), 8.19-8.09 (m, 2H), 7.74 (s, 1H), 7.72-7.65 (m, 1H), 7.54-7.45 (m, 2H), 7.24 (t, J = 9.0 Hz, 1H), 3.68 (d, J = 8.0 Hz, 2H), 2.75-2.41 (m, 8H), 2.30 (s, 3H). |

TABLE 4-continued
| | | | |
|---|---|---|---|
| 622 | 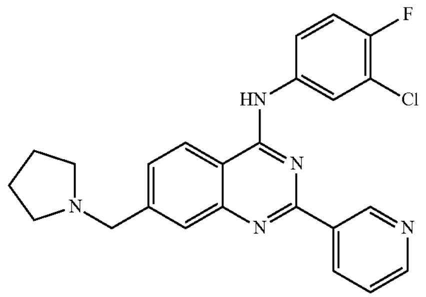 [SMILES: Fc1ccc(Nc2nc(-c3cccnc3)nc3cc(CN4CCCC4)ccc23)cc1Cl] | 433.91 | |
| 623 | 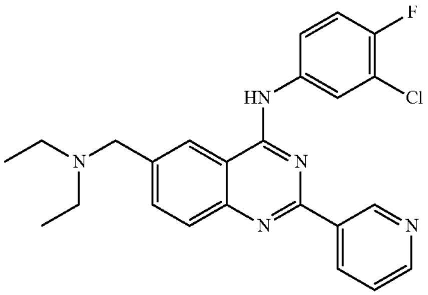 [SMILES: CCN(CC)Cc1ccc2nc(-c3cccnc3)nc(Nc3ccc(F)c(Cl)c3)c2c1] | 435.92 | |
| 624 | 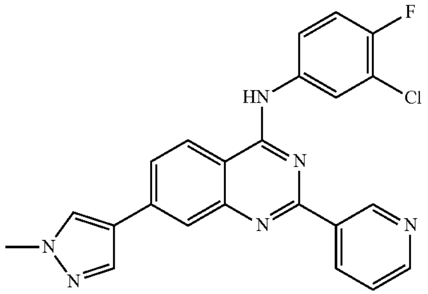 [SMILES: Cn1cc(-c2ccc3c(Nc4ccc(F)c(Cl)c4)nc(-c4cccnc4)nc3c2)cn1] | 430.865 | $^{1}H$ NMR (300 MHz, DMSO) δ 10.01 (s, 1H), 9.52 (d, J = 1.3 Hz, 1H), 8.72-8.60 (m, 2H), 8.49 (d, J = 8.6 Hz, 1H), 8.44 (s, 1H), 8.28 (dd, J = 6.9, 2.6 Hz, 1H), 8.15 (s, 1H), 8.03 (d, J = 1.5 Hz, 1H), 7.95-7.83 (m, 2H), 7.60-7.45 (m, 2H), 3.91 (s, 3H). |

TABLE 4-continued
| | | | |
|---|---|---|---|
| 625 | 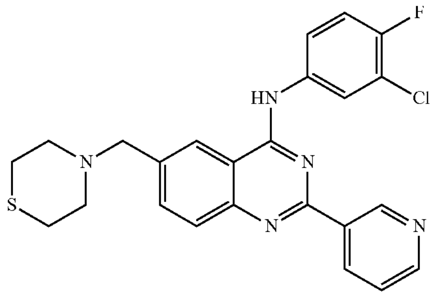 [SMILES: Fc1ccc(Nc2nc(-c3cccnc3)nc3ccc(CN4CCSCC4)cc23)cc1Cl] | 465.97 | $^1$H NMR (300 MHz, $CD_3OD$) δ 9.56-9.50 (m, 1H), 8.79 (dt, J = 8.1, 1.6 Hz, 1H), 8.63 (dd, J = 4.9, 1.7 Hz, 1H), 8.30 (s, 1H), 8.19 (dd, J = 6.7, 2.6 Hz, 1H), 7.91 (d, J = 1.1 Hz, 2H), 7.80 (ddd, J = 9.0, 4.2, 2.7 Hz, 1H), 7.58 (dd, J = 8.0, 4.9 Hz, 1H), 7.33 (t, J = 9.0 Hz, 1H), 3.75 (s, 2H), 2.84-2.66 (m, 8H). |
| 626 | 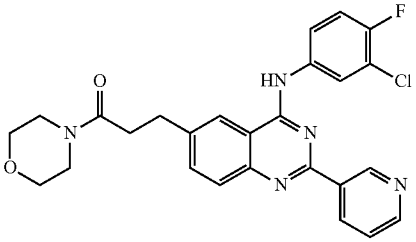 [SMILES: O=C(CCc1ccc2nc(-c3cccnc3)nc(Nc3ccc(F)c(Cl)c3)c2c1)N1CCOCC1] | 491.94 | $^1$H NMR (300 MHz, DMSO) δ 10.00 (s, 1H), 9.52 (s, 1H), 8.73-8.63 (m, 2H), 8.42 (s, 1H), 8.28 (dd, J = 6.8, 2.6 Hz, 1H), 7.92 (ddd, J = 6.8, 4.2, 2.0 Hz, 1H), 7.85 (s, 2H), 7.60-7.50 (m, 2H), 3.56-3.43 (m, 9H), 3.07 (t, J = 7.6 Hz, 2H), 2.79 (t, J = 7.7 Hz, 2H). |
| 627 | 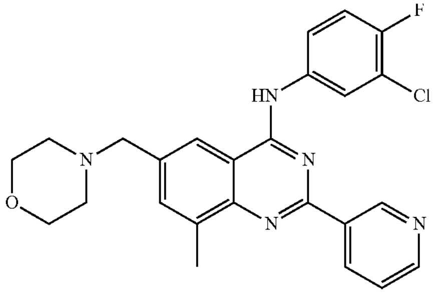 [SMILES: Cc1cc(CN2CCOCC2)cc2c(Nc3ccc(F)c(Cl)c3)nc(-c3cccnc3)nc12] | 463.93 | $^1$H NMR (300 MHz, DMSO) δ 9.99 (s, 1H), 9.54 (s, 1H), 8.67 (d, J = 5.3 Hz, 2H), 8.30-8.22 (m, 2H), 7.96-7.87 (m, 1H), 7.73 (s, 1H), 7.60-7.46 (m, 2H), 3.60 (s, 6H), 2.71 (s, 3H), 2.41 (s, 4H). |

TABLE 4-continued

| | | | |
|---|---|---|---|
| 628 | 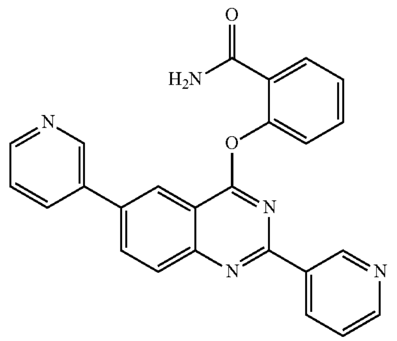 [SMILES: NC(=O)c1ccccc1Oc1nc(-c2cccnc2)nc2ccc(-c3cccnc3)cc12] | 419.43 | $^1$H NMR (300 MHz, DMSO) δ 9.41 (d, J = 1.4 Hz, 1H), 9.15 (d, J = 1.7 Hz, 1H), 8.74-8.64 (m, 3H), 8.55 (dt, J = 7.9, 1.8 Hz, 1H), 8.42 (dd, J = 8.7, 2.0 Hz, 1H), 8.36-8.29 (m, 1H), 8.15 (d, J = 8.7 Hz, 1H), 7.90 (dd, J = 7.8, 1.7 Hz, 1H), 7.61 (dd, J = 8.0, 4.8 Hz, 1H), 7.53 (dd, J = 7.9, 4.8 Hz, 1H), 7.43 (t, J = 7.6 Hz, 1H), 7.03 (t, J = 7.5 Hz, 1H), 6.93 (d, J = 7.7 Hz, 1H). |

| $^1$H-NMR Solvent | LCMS | Retention Time (min) | LCMS Protocol | Purity Percent | Method for Coupling |
|---|---|---|---|---|---|
| DMSO | 464 (M + 1) | 2.01 | Method C | 100 | Method N3 |
| DMSO | 479 (M + 1) | 2.08 | Method D | 97 | Method N3 |
| DMSO | 449 (M + 1) | 2.62 | Method D | 92 | Method N3 |
| DMSO | 458.2 (M + 1) | 2.56 | Method C | 100 | Method N1 |
| DMSO | 449.9 (M + 1) | 2.13 | Method C | 100 | Method N3 |
| DMSO | 456.0 (M + 1) | 2.64 | Method C | 100 | Method N1 |
| DMSO | 446 (M + 1) | 2.35 | Method C | 100 | Method N1 |
| DMSO | 427.95 (M + 1) | 2.25 | Method C | 100 | Method N1 |
| DMSO | 430.9 (M + 1) | 2.17 | Method C | 100 | Method N1 |
| DMSO | 449.9 (M + 1) | 2.04 | Method C | 100 | Method N1 |
| DMSO | 445.9 (M + 1) | 2.43 | Method C | 99 | Method N1 |
| DMSO | 512.9 (M + 1) | 2.5 | Method C | 100 | Method N1 |
| DMSO | 458.9 (M + 1) | 2.65 | Method C | 100 | Method N1 |
| DMSO | 486.9 (M + 1) | 2.48 | Method C | 100 | Method N1 |
| DMSO | 487.1 (M + 1) | 2.58 | Method C | 100 | Method N1 |
| DMSO | 390.9 (M + 1) | 2.48 | Method C | 100 | Method N1 |
| DMSO | 539.9 (M + 1) | 2.23 | Method C | 100 | Method N1 |
| | 526.16 (M + 1) | 2.55 | Method C | 94 | Method N1 |

TABLE 4-continued

| | | | | | |
|---|---|---|---|---|---|
| $CDCl_3$ | 471.9 (M + 1) | 2.93 | Method C | 100 | Method N1 |
| DMSO | 474.02 (M + 1) | 2.72 | Method C | 100 | Method N1 |
| DMSO | 443.1 (M + 1) | 2.37 | Method C | 100 | Method N1 |
| DMSO | 466.1 (M + 1) | 2.78 | Method C | 100 | Method N1 |
| DMSO | 458.1 (M + 1) | 2.62 | Method C | 100 | Method N1 |
| DMSO | 515.1 (M + 1) | 2.54 | Method C | 100 | Method N1 |
| DMSO | 452.0 (M + 1) | 2.61 | Method C | 96 | Method N1 |
| | 437.2 (M + 1) | 2.08 | Method C | 95 | Method N1 |
| | 422.2 (M + 1) | 1.8 | Method C | 100 | Method N1 |
| DMSO | 449.9 (M + 1) | 2.13 | Method C | 100 | Method N3 |
| DMSO | 458.1 (M + 1) | 2.51 | Method C | 100 | Method N2 |
| $CD_3OD$ | 463.0 (M + 1) | 1.71 | Method C | 100 | Method N3 |
| | 434.0 (M + 1) | 1.73 | Method C | 100 | Method N3 |
| | 436.0 (M + 1) | 1.84 | Method C | 100 | Method N3 |
| DMSO | 431.0 (M + 1) | 2.12 | Method C | 100 | Method N2 |
| $CD_3OD$ | 466.0 (M + 1) | 2.46 | Method C | 94 | Method N3 |
| DMSO | 491.9 (M + 1) | 2 | Method C | 93 | Method N1 |
| DMSO | 464.0 (M + 1) | 2.52 | Method C | 100 | Method N3 |
| DMSO | 420.1 (M + 1) | 2.12 | Method C | 99 | Method N4 |

| Number | Starting Material 1 | Starting Material 2 |
|---|---|---|
| 629 | 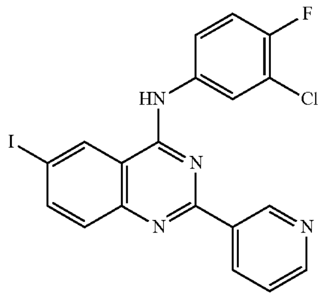 [SMILES: Fc1ccc(Nc2nc(-c3cccnc3)nc3ccc(I)cc23)cc1Cl] | 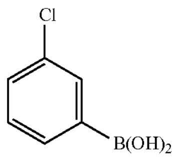 |

TABLE 4-continued
| | | |
|---|---|---|
| 630 | 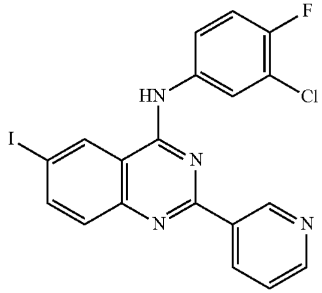 [SMILES: Fc1ccc(Nc2nc(-c3cccnc3)nc3ccc(I)cc23)cc1Cl] | 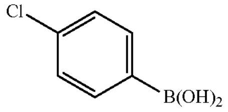 |
| 631 | 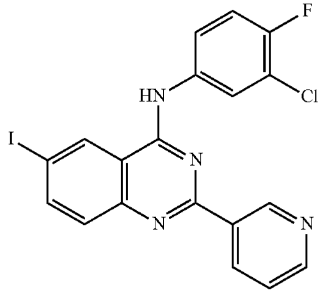 [SMILES: Fc1ccc(Nc2nc(-c3cccnc3)nc3ccc(I)cc23)cc1Cl] | 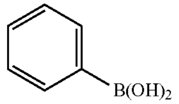 |
| 632 | 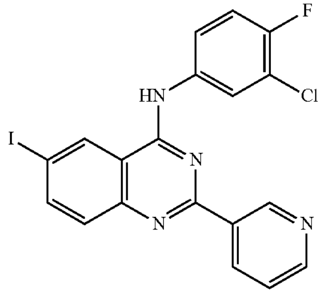 [SMILES: Fc1ccc(Nc2nc(-c3cccnc3)nc3ccc(I)cc23)cc1Cl] | 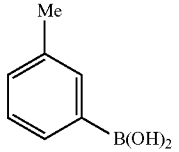 |

TABLE 4-continued
| | | |
|---|---|---|
| 633 | 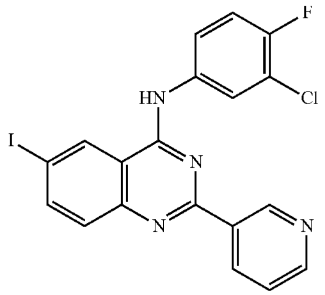 [SMILES: Fc1ccc(Nc2nc(-c3cccnc3)nc3ccc(I)cc23)cc1Cl] | 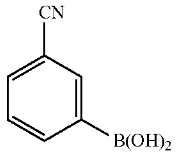 |
| 634 | 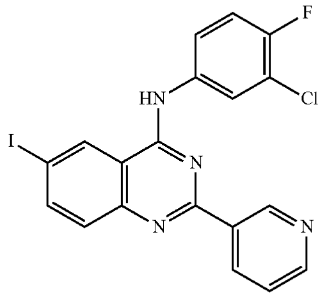 [SMILES: Fc1ccc(Nc2nc(-c3cccnc3)nc3ccc(I)cc23)cc1Cl] | 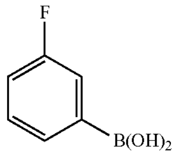 |
| 635 | 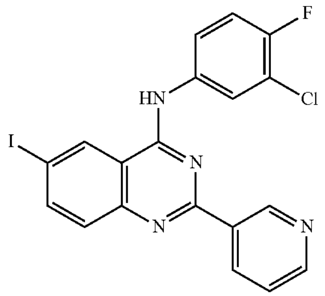 [SMILES: Fc1ccc(Nc2nc(-c3cccnc3)nc3ccc(I)cc23)cc1Cl] | 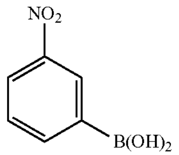 |

TABLE 4-continued
| | | |
|---|---|---|
| 636 | 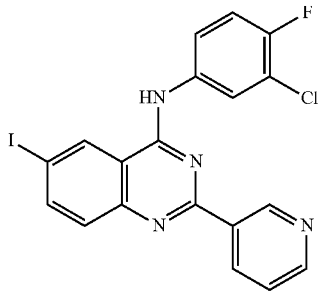 [SMILES: Fc1ccc(Nc2nc(-c3cccnc3)nc3ccc(I)cc23)cc1Cl] | 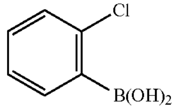 |
| 637 | 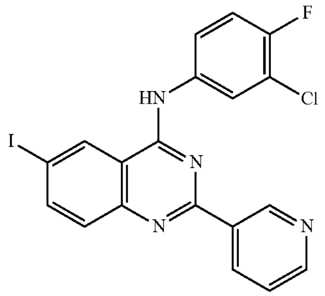 [SMILES: Fc1ccc(Nc2nc(-c3cccnc3)nc3ccc(I)cc23)cc1Cl] | 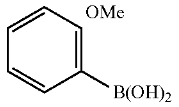 |
| 638 | 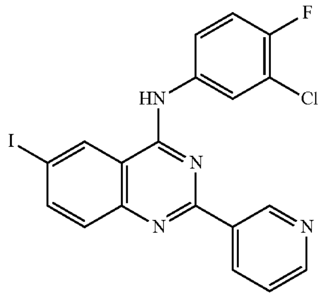 [SMILES: Fc1ccc(Nc2nc(-c3cccnc3)nc3ccc(I)cc23)cc1Cl] | 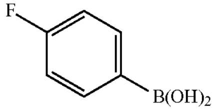 |

TABLE 4-continued
| | | |
|---|---|---|
| 639 | 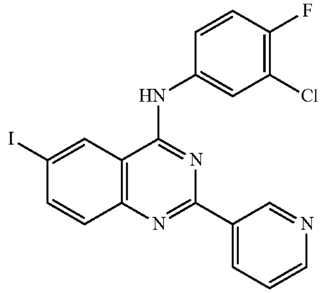 [SMILES: Fc1ccc(Nc2nc(-c3cccnc3)nc3ccc(I)cc23)cc1Cl] | 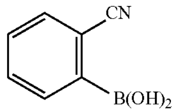 |
| 640 | 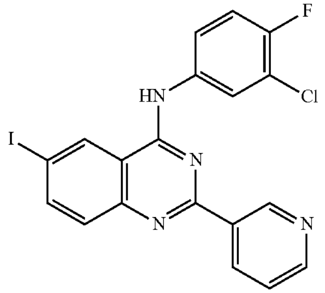 [SMILES: Fc1ccc(Nc2nc(-c3cccnc3)nc3ccc(I)cc23)cc1Cl] | 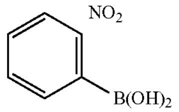 |
| 641 | 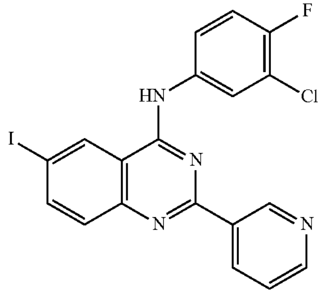 [SMILES: Fc1ccc(Nc2nc(-c3cccnc3)nc3ccc(I)cc23)cc1Cl] | 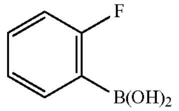 |

TABLE 4-continued
| | | |
|---|---|---|
| 642 | 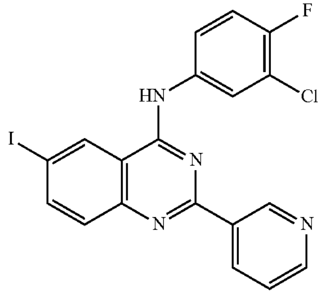 [SMILES: Fc1ccc(Nc2nc(-c3cccnc3)nc3ccc(I)cc23)cc1Cl] | 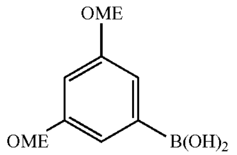 |
| 643 | 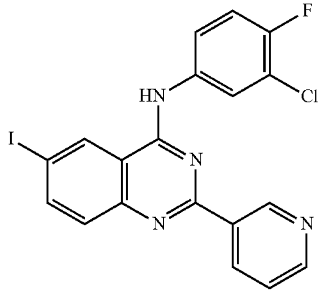 [SMILES: Fc1ccc(Nc2nc(-c3cccnc3)nc3ccc(I)cc23)cc1Cl] | 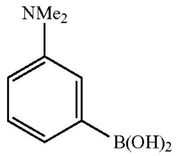 |
| 644 | 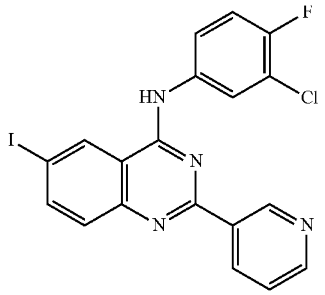 [SMILES: Fc1ccc(Nc2nc(-c3cccnc3)nc3ccc(I)cc23)cc1Cl] | 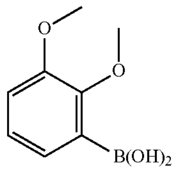 |

TABLE 4-continued
| | | |
|---|---|---|
| 645 | 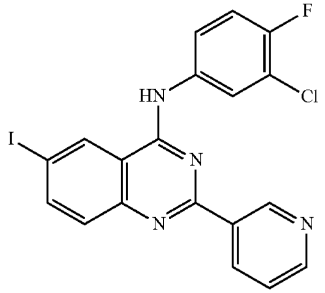 [SMILES: Fc1ccc(Nc2nc(-c3cccnc3)nc3ccc(I)cc23)cc1Cl] | 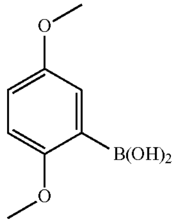 |
| 646 | 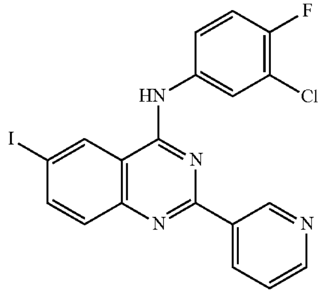 [SMILES: Fc1ccc(Nc2nc(-c3cccnc3)nc3ccc(I)cc23)cc1Cl] | 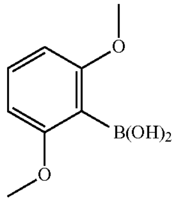 |
| 647 | 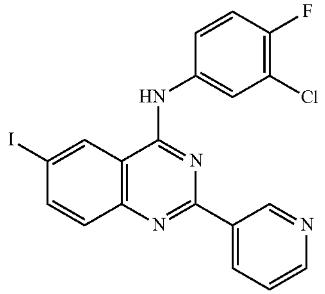 [SMILES: Fc1ccc(Nc2nc(-c3cccnc3)nc3ccc(I)cc23)cc1Cl] | 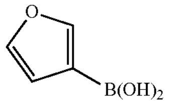 |

TABLE 4-continued
| | | |
|---|---|---|
| 648 | 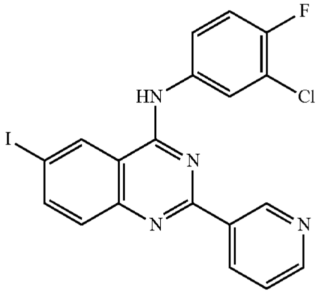 [SMILES: Fc1ccc(Nc2nc(-c3cccnc3)nc3ccc(I)cc23)cc1Cl] | 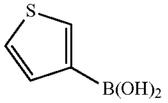 |
| 649 | 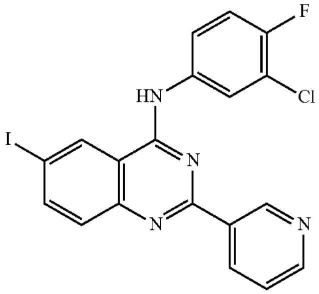 [SMILES: Fc1ccc(Nc2nc(-c3cccnc3)nc3ccc(I)cc23)cc1Cl] | 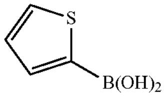 |
| 650 | 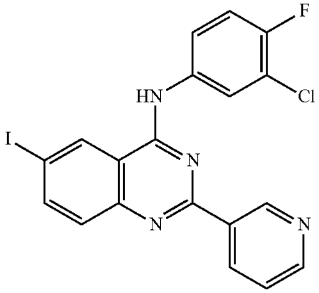 [SMILES: Fc1ccc(Nc2nc(-c3cccnc3)nc3ccc(I)cc23)cc1Cl] | 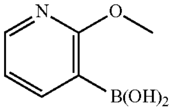 |

TABLE 4-continued
| | | |
|---|---|---|
| 651 | 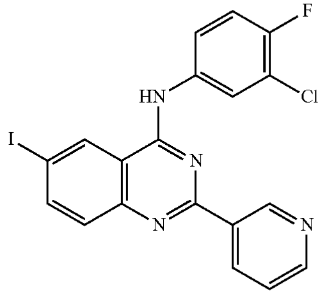 [SMILES: Fc1ccc(Nc2nc(-c3cccnc3)nc3ccc(I)cc23)cc1Cl] | 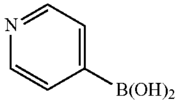 |
| 652 | 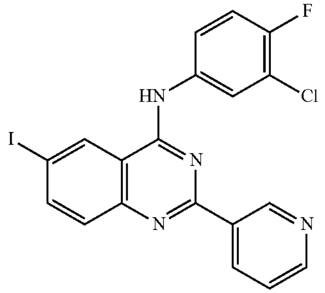 [SMILES: Fc1ccc(Nc2nc(-c3cccnc3)nc3ccc(I)cc23)cc1Cl] | 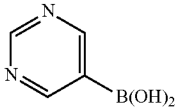 |
| 653 | 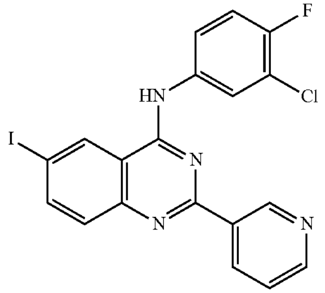 [SMILES: Fc1ccc(Nc2nc(-c3cccnc3)nc3ccc(I)cc23)cc1Cl] | 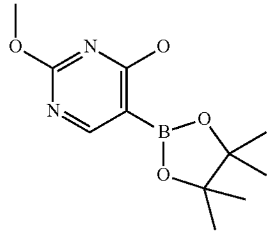 [SMILES: COc1ncc(B2OC(C)(C)C(C)(C)O2)c(O)n1] |

TABLE 4-continued
| | | |
|---|---|---|
| 654 | 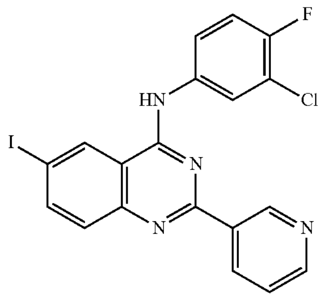 [SMILES: Fc1ccc(Nc2nc(-c3cccnc3)nc3ccc(I)cc23)cc1Cl] | 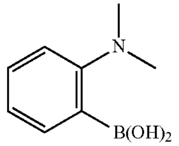 |
| 655 | 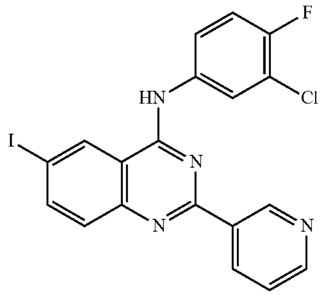 [SMILES: Fc1ccc(Nc2nc(-c3cccnc3)nc3ccc(I)cc23)cc1Cl] | 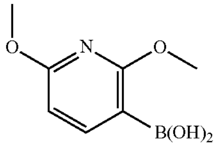 |
| 656 | 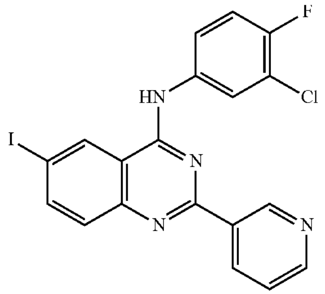 [SMILES: Fc1ccc(Nc2nc(-c3cccnc3)nc3ccc(I)cc23)cc1Cl] | 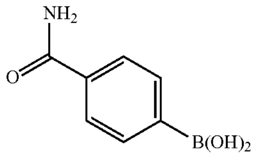 |

TABLE 4-continued
| | | |
|---|---|---|
| 657 | 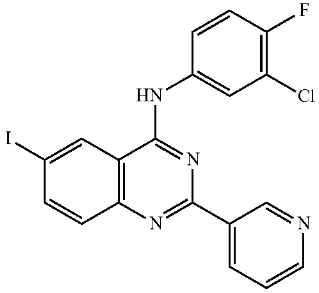 [SMILES: Fc1ccc(Nc2nc(-c3cccnc3)nc3ccc(I)cc23)cc1Cl] | 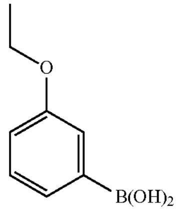 |
| 658 | 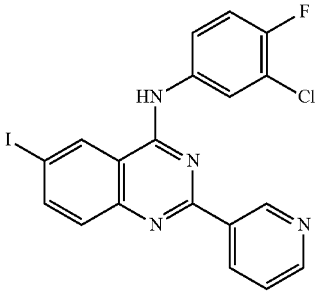 [SMILES: Fc1ccc(Nc2nc(-c3cccnc3)nc3ccc(I)cc23)cc1Cl] | 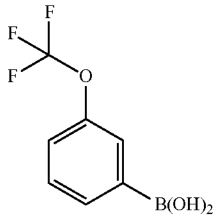 |
| 659 | 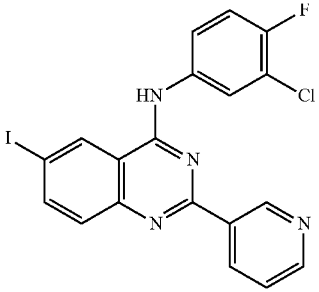 [SMILES: Fc1ccc(Nc2nc(-c3cccnc3)nc3ccc(I)cc23)cc1Cl] | 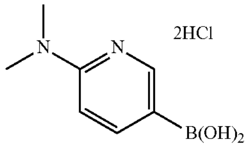 |

TABLE 4-continued
| | | |
|---|---|---|
| 660 | 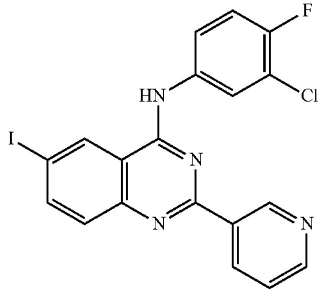 [SMILES: Fc1ccc(Nc2nc(-c3cccnc3)nc3ccc(I)cc23)cc1Cl] | 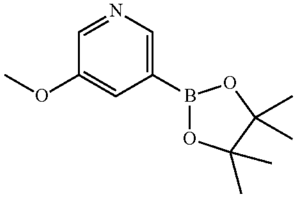 |
| 661 | 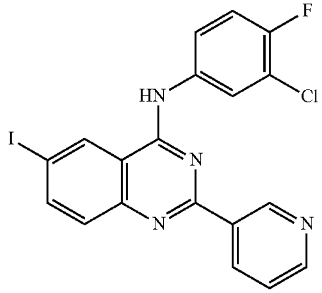 [SMILES: Fc1ccc(Nc2nc(-c3cccnc3)nc3ccc(I)cc23)cc1Cl] | 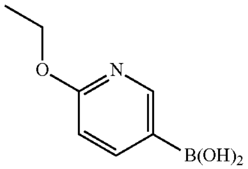 |
| 662 | 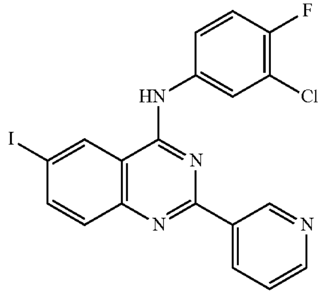 [SMILES: Fc1ccc(Nc2nc(-c3cccnc3)nc3ccc(I)cc23)cc1Cl] | 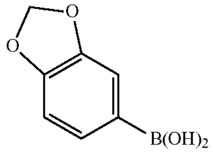 |

TABLE 4-continued
| | | |
|---|---|---|
| 663 | 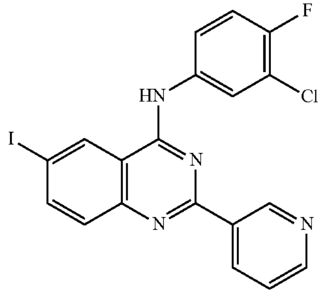 [SMILES: Fc1ccc(Nc2nc(-c3cccnc3)nc3ccc(I)cc23)cc1Cl] | 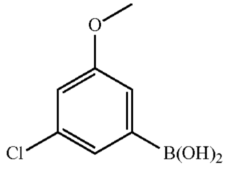 |
| 664 | 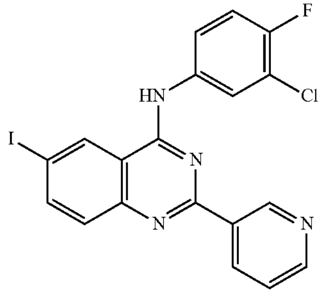 [SMILES: Fc1ccc(Nc2nc(-c3cccnc3)nc3ccc(I)cc23)cc1Cl] | 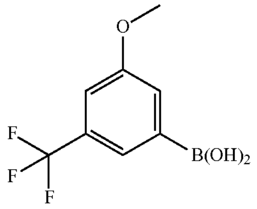 |
| 665 | 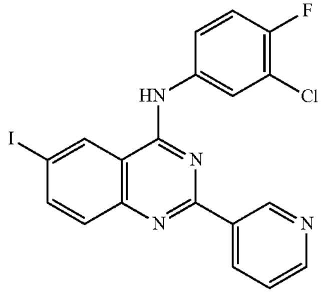 [SMILES: Fc1ccc(Nc2nc(-c3cccnc3)nc3ccc(I)cc23)cc1Cl] | 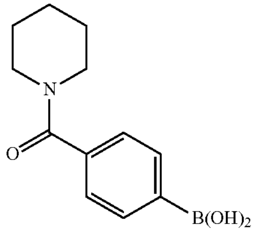 [SMILES: O=C(c1ccc(B(O)O)cc1)N1CCCCC1] |

TABLE 4-continued
| | | |
|---|---|---|
| 666 | 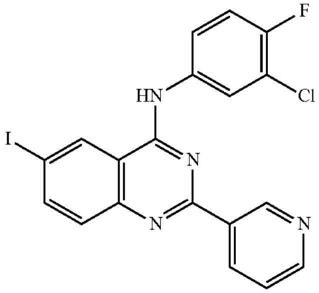 [SMILES: Fc1ccc(Nc2nc(-c3cccnc3)nc3ccc(I)cc23)cc1Cl] | 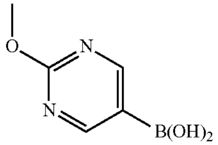 |
| 667 | 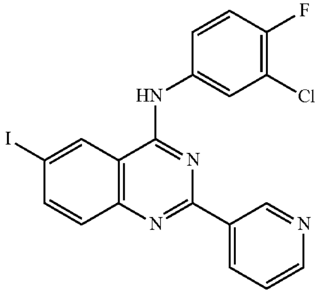 [SMILES: Fc1ccc(Nc2nc(-c3cccnc3)nc3ccc(I)cc23)cc1Cl] | 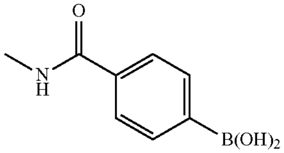 |
| 668 | 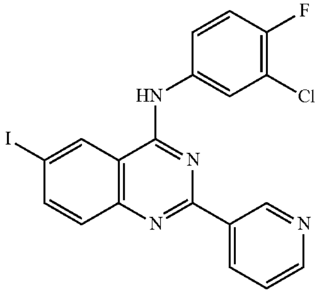 [SMILES: Fc1ccc(Nc2nc(-c3cccnc3)nc3ccc(I)cc23)cc1Cl] | 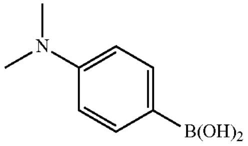 |

TABLE 4-continued
| | | |
|---|---|---|
| 669 | 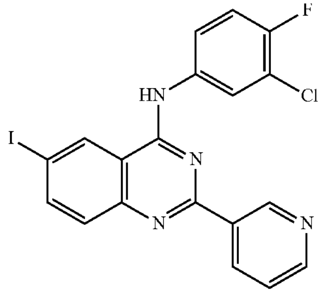 [SMILES: Fc1ccc(Nc2nc(-c3cccnc3)nc3ccc(I)cc23)cc1Cl] | 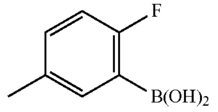 |
| 670 | 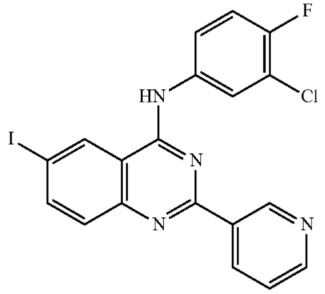 [SMILES: Fc1ccc(Nc2nc(-c3cccnc3)nc3ccc(I)cc23)cc1Cl] | 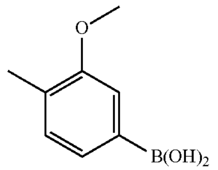 |
| 671 | 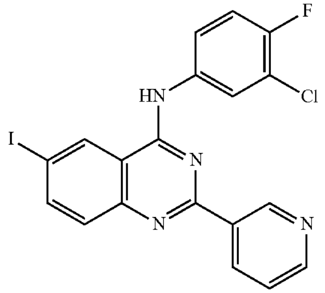 [SMILES: Fc1ccc(Nc2nc(-c3cccnc3)nc3ccc(I)cc23)cc1Cl] | 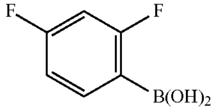 |

TABLE 4-continued
| | | |
|---|---|---|
| 672 | 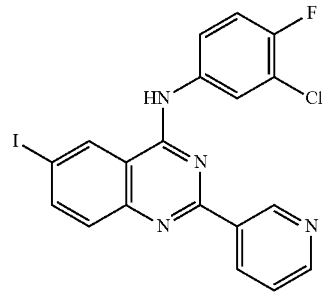 [SMILES: Fc1ccc(Nc2nc(-c3cccnc3)nc3ccc(I)cc23)cc1Cl] | 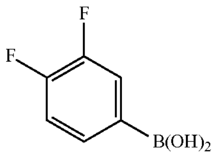 |
| 673 | 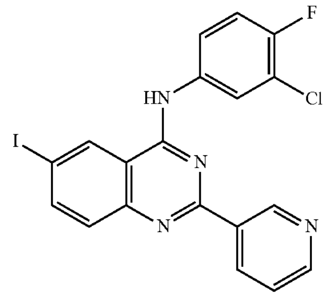 [SMILES: Fc1ccc(Nc2nc(-c3cccnc3)nc3ccc(I)cc23)cc1Cl] | 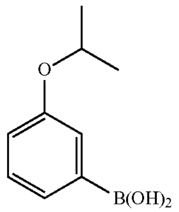 |
| 674 | 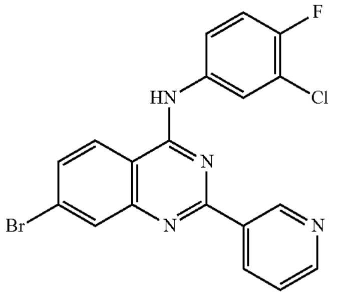 [SMILES: Fc1ccc(Nc2nc(-c3cccnc3)nc3cc(Br)ccc23)cc1Cl] | 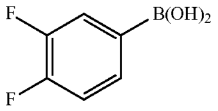 |

TABLE 4-continued
| | | |
|---|---|---|
| 675 | 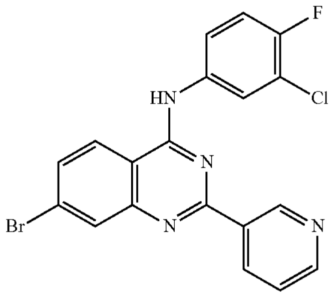 [SMILES: Fc1ccc(Nc2nc(-c3cccnc3)nc3cc(Br)ccc23)cc1Cl] | 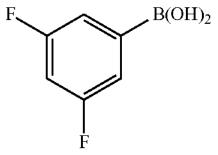 [SMILES: OB(O)c1cc(F)cc(F)c1] |
| 676 | 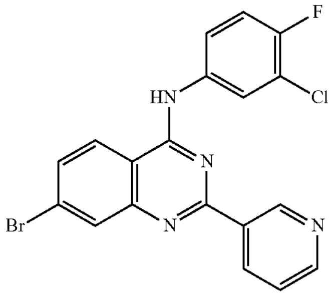 [SMILES: Fc1ccc(Nc2nc(-c3cccnc3)nc3cc(Br)ccc23)cc1Cl] | 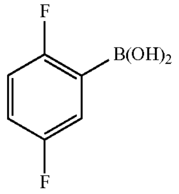 [SMILES: OB(O)c1cc(F)ccc1F] |
| 677 | 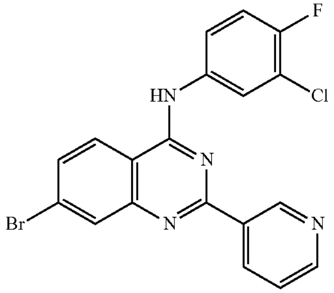 [SMILES: Fc1ccc(Nc2nc(-c3cccnc3)nc3cc(Br)ccc23)cc1Cl] | 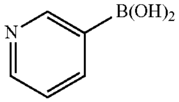 |

TABLE 4-continued
| | | |
|---|---|---|
| 678 | 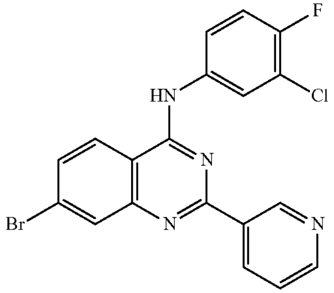 [SMILES: Fc1ccc(Nc2nc(-c3cccnc3)nc3cc(Br)ccc23)cc1Cl] | 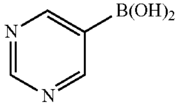 |
| 679 | 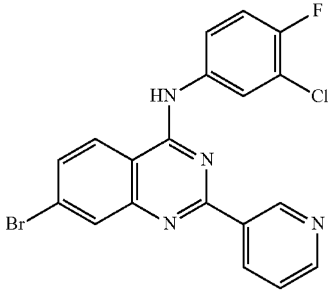 [SMILES: Fc1ccc(Nc2nc(-c3cccnc3)nc3cc(Br)ccc23)cc1Cl] | 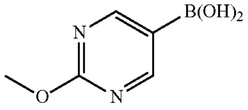 |
| 680 | 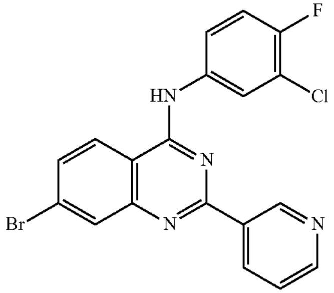 [SMILES: Fc1ccc(Nc2nc(-c3cccnc3)nc3cc(Br)ccc23)cc1Cl] | 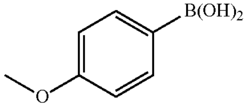 |

TABLE 4-continued
| | | |
|---|---|---|
| 681 | 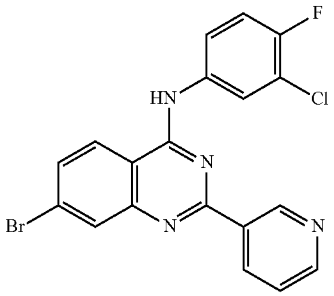 [SMILES: Fc1ccc(Nc2nc(-c3cccnc3)nc3cc(Br)ccc23)cc1Cl] | 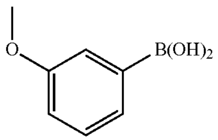 |
| 682 | 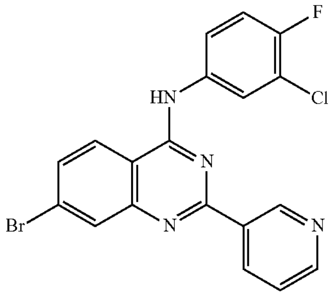 [SMILES: Fc1ccc(Nc2nc(-c3cccnc3)nc3cc(Br)ccc23)cc1Cl] | 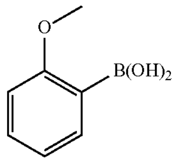 |
| 683 | 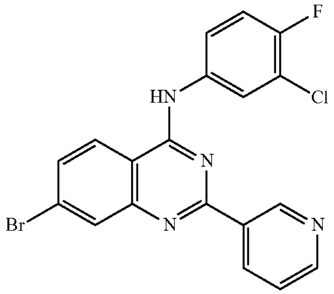 [SMILES: Fc1ccc(Nc2nc(-c3cccnc3)nc3cc(Br)ccc23)cc1Cl] | 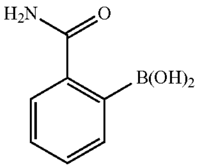 |

TABLE 4-continued
| | | |
|---|---|---|
| 684 | 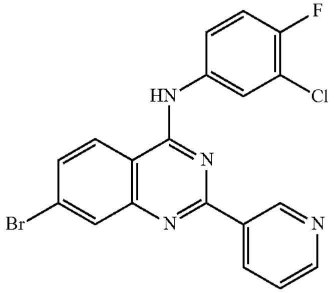 [SMILES: Fc1ccc(Nc2nc(-c3cccnc3)nc3cc(Br)ccc23)cc1Cl] | 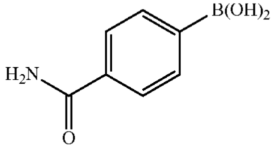 [SMILES: NC(=O)c1ccc(B(O)O)cc1] |
| 685 | 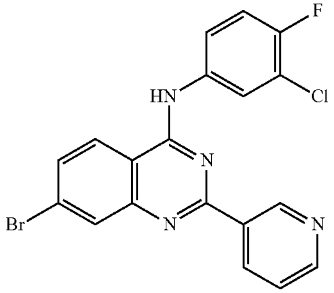 [SMILES: Fc1ccc(Nc2nc(-c3cccnc3)nc3cc(Br)ccc23)cc1Cl] | 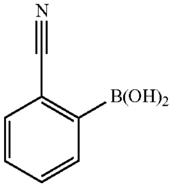 [SMILES: N#Cc1ccccc1B(O)O] |
| 686 | 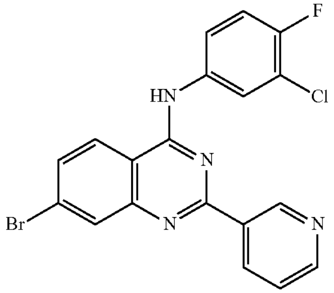 [SMILES: Fc1ccc(Nc2nc(-c3cccnc3)nc3cc(Br)ccc23)cc1Cl] | 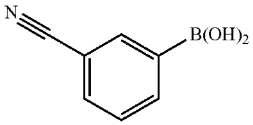 [SMILES: N#Cc1cccc(B(O)O)c1] |

TABLE 4-continued
| | | |
|---|---|---|
| 687 | 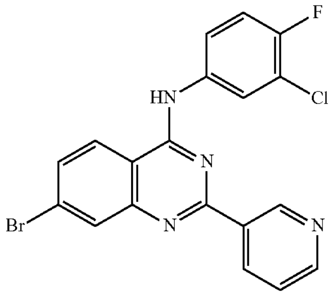 [SMILES: Fc1ccc(Nc2nc(-c3cccnc3)nc3cc(Br)ccc23)cc1Cl] | 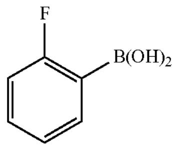 |
| 688 | 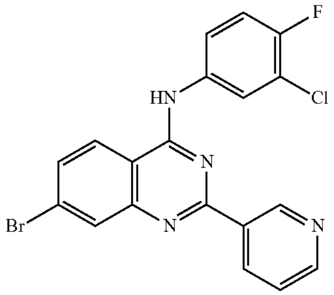 [SMILES: Fc1ccc(Nc2nc(-c3cccnc3)nc3cc(Br)ccc23)cc1Cl] | 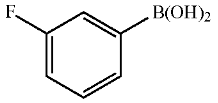 |
| 689 | 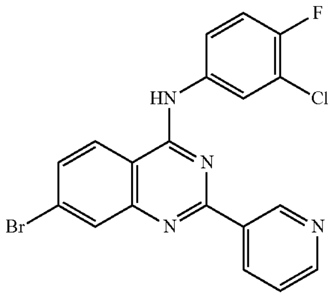 [SMILES: Fc1ccc(Nc2nc(-c3cccnc3)nc3cc(Br)ccc23)cc1Cl] | 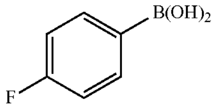 |

TABLE 4-continued
| | | |
|---|---|---|
| 690 | 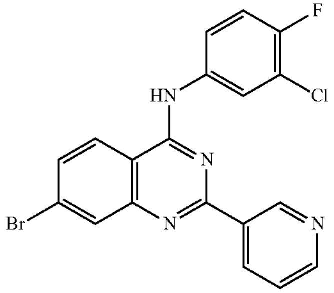 [SMILES: Fc1ccc(Nc2nc(-c3cccnc3)nc3cc(Br)ccc23)cc1Cl] | 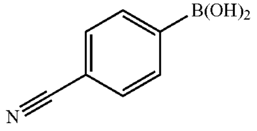 [SMILES: N#Cc1ccc(B(O)O)cc1] |
| 691 | 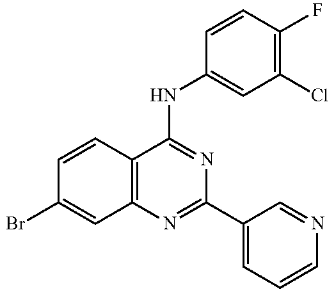 [SMILES: Fc1ccc(Nc2nc(-c3cccnc3)nc3cc(Br)ccc23)cc1Cl] | 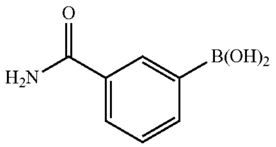 [SMILES: NC(=O)c1cccc(B(O)O)c1] |
| 692 | 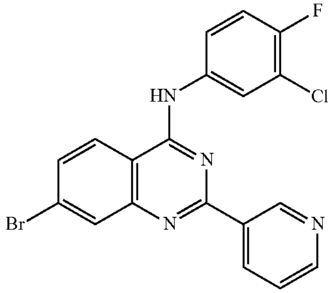 [SMILES: Fc1ccc(Nc2nc(-c3cccnc3)nc3cc(Br)ccc23)cc1Cl] | 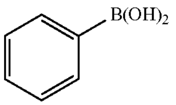 |

TABLE 4-continued
| | | |
|---|---|---|
| 693 | 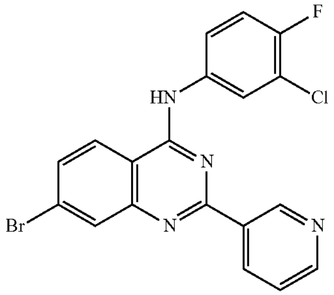 [SMILES: Fc1ccc(Nc2nc(-c3cccnc3)nc3cc(Br)ccc23)cc1Cl] | 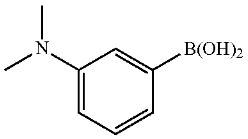 |
| 694 | 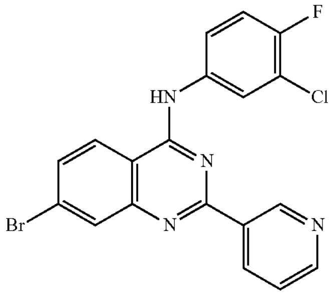 [SMILES: Fc1ccc(Nc2nc(-c3cccnc3)nc3cc(Br)ccc23)cc1Cl] | 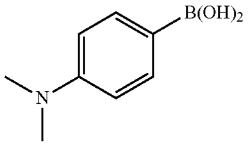 |
| 695 | 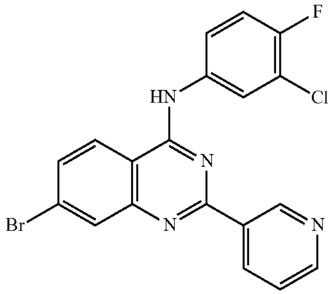 [SMILES: Fc1ccc(Nc2nc(-c3cccnc3)nc3cc(Br)ccc23)cc1Cl] | 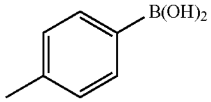 |

TABLE 4-continued
| | | |
|---|---|---|
| 696 | 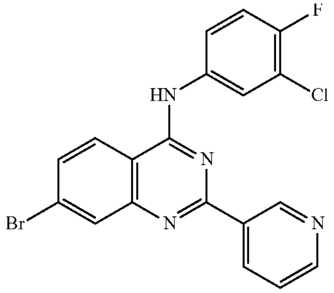 [SMILES: Fc1ccc(Nc2nc(-c3cccnc3)nc3cc(Br)ccc23)cc1Cl] | 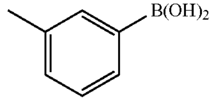 |
| 697 | 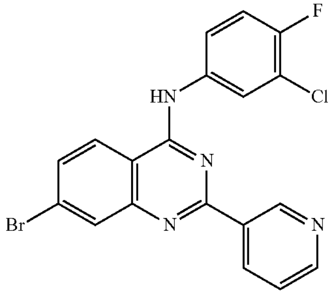 [SMILES: Fc1ccc(Nc2nc(-c3cccnc3)nc3cc(Br)ccc23)cc1Cl] | 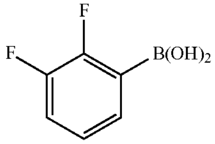 [SMILES: OB(O)c1cccc(F)c1F] |
| 698 | 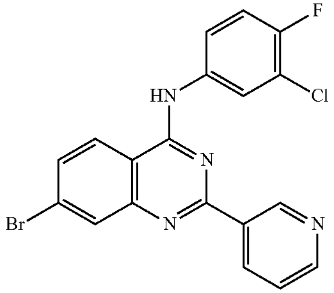 [SMILES: Fc1ccc(Nc2nc(-c3cccnc3)nc3cc(Br)ccc23)cc1Cl] | 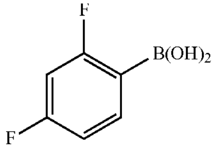 [SMILES: OB(O)c1ccc(F)cc1F] |

TABLE 4-continued
| | | |
|---|---|---|
| 699 | 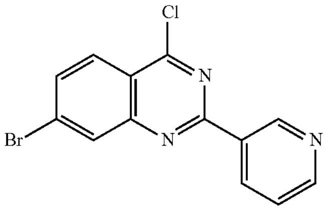 [SMILES: Clc1nc(-c2cccnc2)nc2cc(Br)ccc12] | 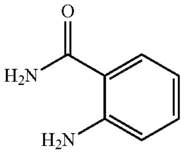 |
| 700 | 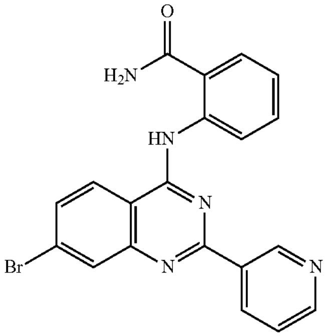 [SMILES: NC(=O)c1ccccc1Nc1nc(-c2cccnc2)nc2cc(Br)ccc12] | 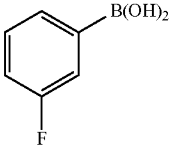 |
| 701 | 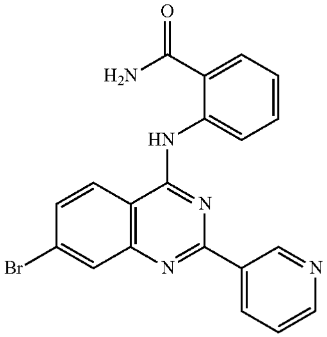 [SMILES: NC(=O)c1ccccc1Nc1nc(-c2cccnc2)nc2cc(Br)ccc12] | 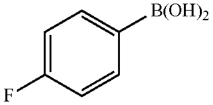 |

TABLE 4-continued
| | | |
|---|---|---|
| 702 | 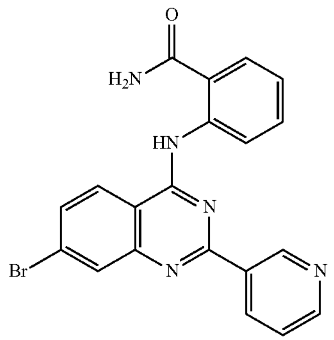 [SMILES: NC(=O)c1ccccc1Nc1nc(-c2cccnc2)nc2cc(Br)ccc12] | 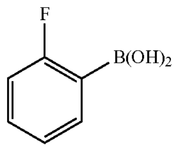 |
| 703 | 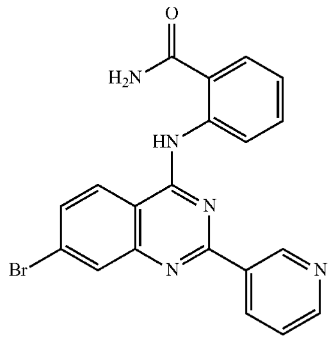 [SMILES: NC(=O)c1ccccc1Nc1nc(-c2cccnc2)nc2cc(Br)ccc12] | 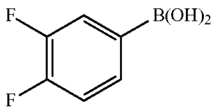 [SMILES: OB(O)c1ccc(F)c(F)c1] |
| 704 | 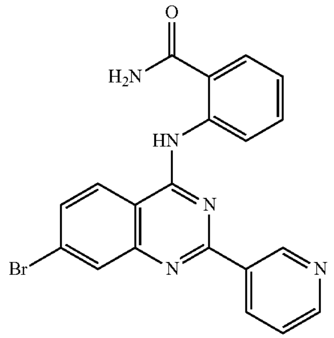 [SMILES: NC(=O)c1ccccc1Nc1nc(-c2cccnc2)nc2cc(Br)ccc12] | 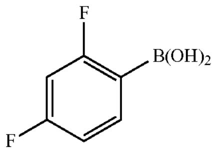 [SMILES: OB(O)c1ccc(F)cc1F] |

TABLE 4-continued
| | | |
|---|---|---|
| 705 | 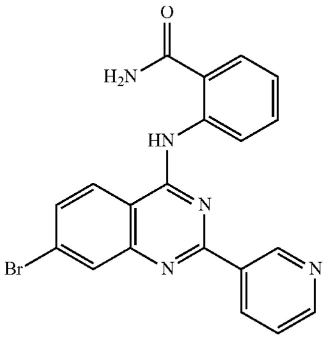 [SMILES: NC(=O)c1ccccc1Nc1nc(-c2cccnc2)nc2cc(Br)ccc12] | 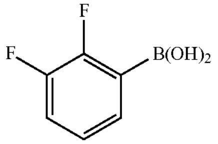 [SMILES: OB(O)c1cccc(F)c1F] |
| 706 | 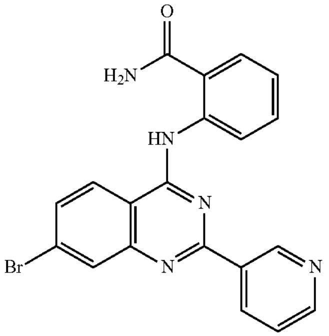 [SMILES: NC(=O)c1ccccc1Nc1nc(-c2cccnc2)nc2cc(Br)ccc12] | 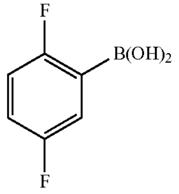 [SMILES: OB(O)c1cc(F)ccc1F] |
| 707 | 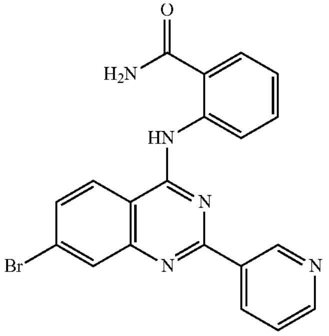 [SMILES: NC(=O)c1ccccc1Nc1nc(-c2cccnc2)nc2cc(Br)ccc12] | 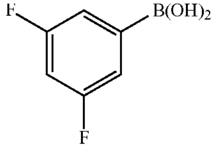 [SMILES: OB(O)c1cc(F)cc(F)c1] |

TABLE 4-continued
| | | |
|---|---|---|
| 708 | 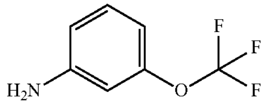 | 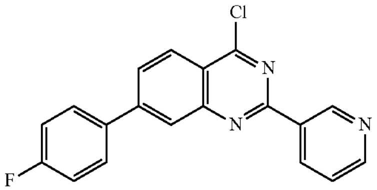 [SMILES: Fc1ccc(-c2ccc3c(Cl)nc(-c4cccnc4)nc3c2)cc1] |
| 709 | 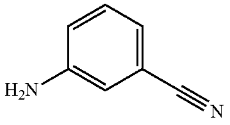 | 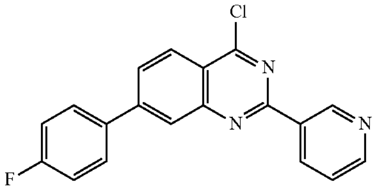 [SMILES: Fc1ccc(-c2ccc3c(Cl)nc(-c4cccnc4)nc3c2)cc1] |
| 710 | 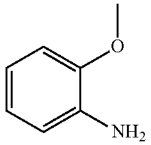 | 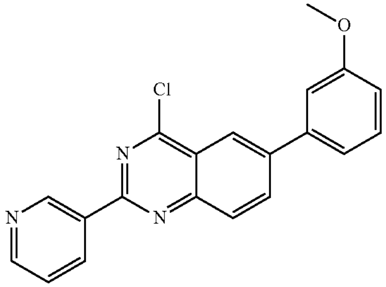 [SMILES: COc1cccc(-c2ccc3nc(-c4cccnc4)nc(Cl)c3c2)c1] |
| 711 | 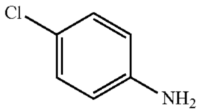 | 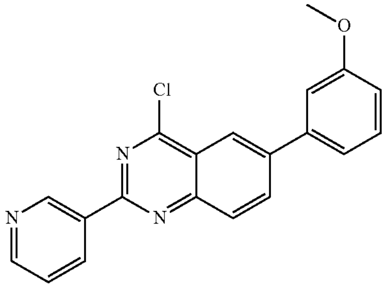 [SMILES: COc1cccc(-c2ccc3nc(-c4cccnc4)nc(Cl)c3c2)c1] |

TABLE 4-continued
| | | |
|---|---|---|
| 712 | 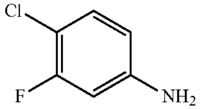 | 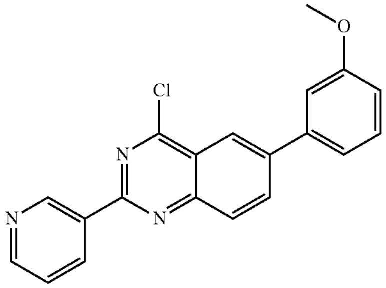 [SMILES: COc1cccc(-c2ccc3nc(-c4cccnc4)nc(Cl)c3c2)c1] |
| 713 | 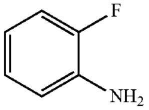 | 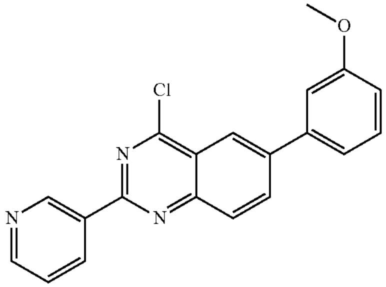 [SMILES: COc1cccc(-c2ccc3nc(-c4cccnc4)nc(Cl)c3c2)c1] |
| 714 | 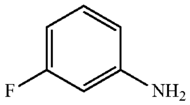 | 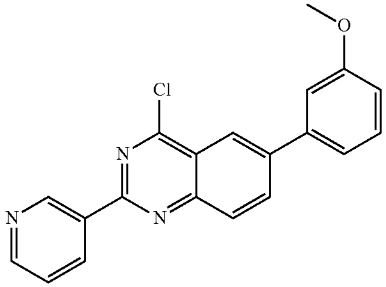 [SMILES: COc1cccc(-c2ccc3nc(-c4cccnc4)nc(Cl)c3c2)c1] |

TABLE 4-continued
| | | |
|---|---|---|
| 715 | 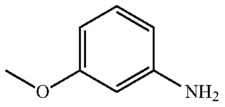 | 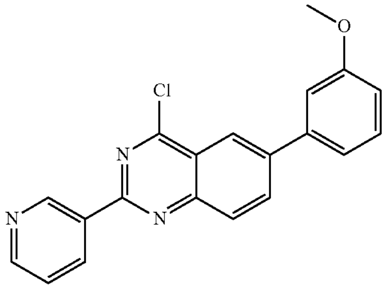 [SMILES: COc1cccc(-c2ccc3nc(-c4cccnc4)nc(Cl)c3c2)c1] |
| 716 | 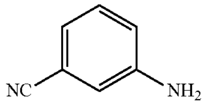 | 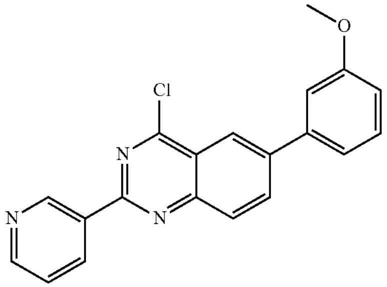 [SMILES: COc1cccc(-c2ccc3nc(-c4cccnc4)nc(Cl)c3c2)c1] |
| 717 | 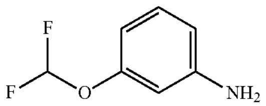 | 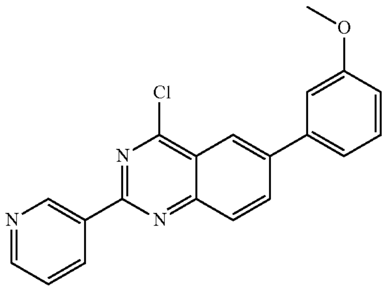 [SMILES: COc1cccc(-c2ccc3nc(-c4cccnc4)nc(Cl)c3c2)c1] |

TABLE 4-continued
| | | |
|---|---|---|
| 718 | 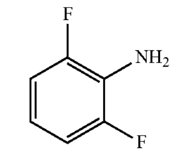 | 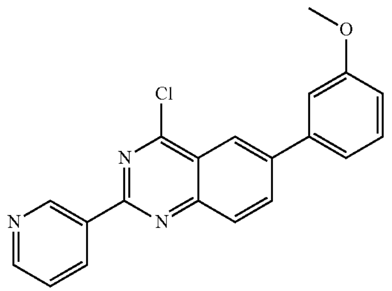 [SMILES: COc1cccc(-c2ccc3nc(-c4cccnc4)nc(Cl)c3c2)c1] |
| 719 | 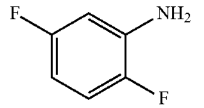 | 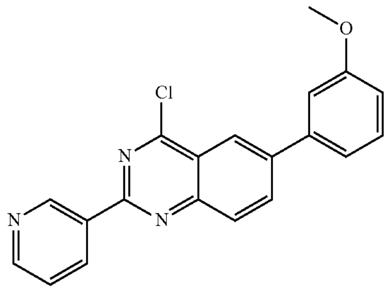 [SMILES: COc1cccc(-c2ccc3nc(-c4cccnc4)nc(Cl)c3c2)c1] |
| 720 | 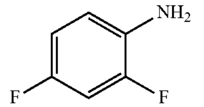 | 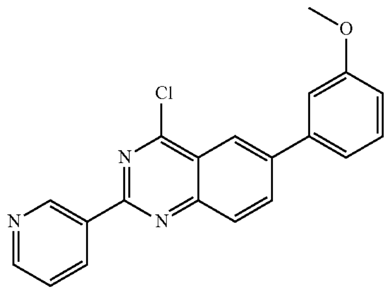 [SMILES: COc1cccc(-c2ccc3nc(-c4cccnc4)nc(Cl)c3c2)c1] |

TABLE 4-continued
| | | |
|---|---|---|
| 721 | 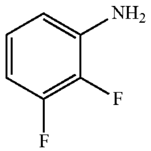 | 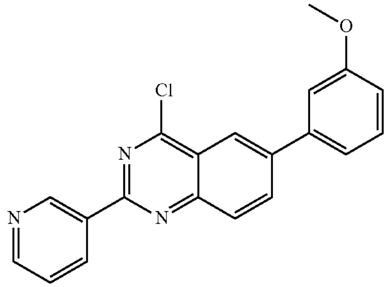 [SMILES: COc1cccc(-c2ccc3nc(-c4cccnc4)nc(Cl)c3c2)c1] |
| 722 | 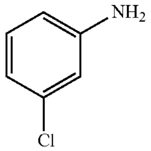 | 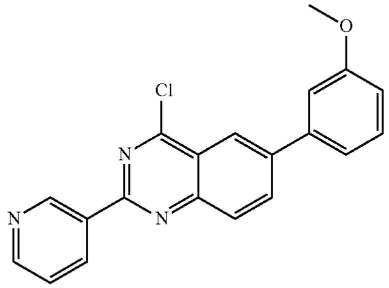 [SMILES: COc1cccc(-c2ccc3nc(-c4cccnc4)nc(Cl)c3c2)c1] |
| 723 | 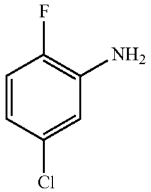 | 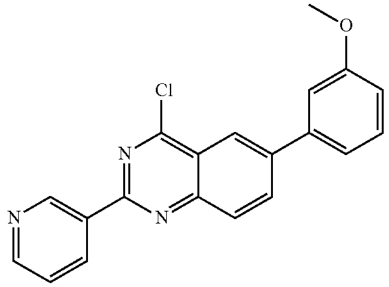 [SMILES: COc1cccc(-c2ccc3nc(-c4cccnc4)nc(Cl)c3c2)c1] |

TABLE 4-continued
| | | |
|---|---|---|
| 724 | 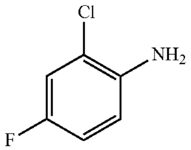 | 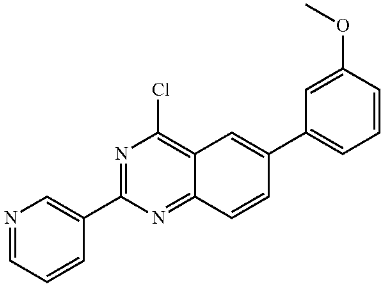 [SMILES: COc1cccc(-c2ccc3nc(-c4cccnc4)nc(Cl)c3c2)c1] |
| 725 | 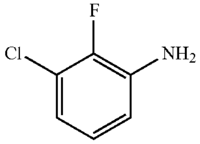 | 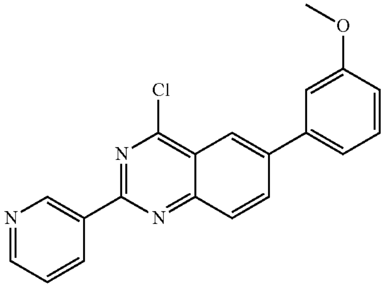 [SMILES: COc1cccc(-c2ccc3nc(-c4cccnc4)nc(Cl)c3c2)c1] |
| 726 | 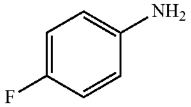 | 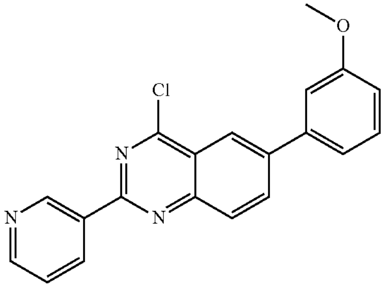 [SMILES: COc1cccc(-c2ccc3nc(-c4cccnc4)nc(Cl)c3c2)c1] |

TABLE 4-continued
| | | |
|---|---|---|
| 727 | 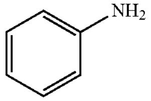 | 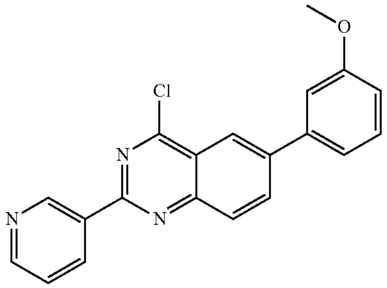 [SMILES: COc1cccc(-c2ccc3nc(-c4cccnc4)nc(Cl)c3c2)c1] |
| 728 | 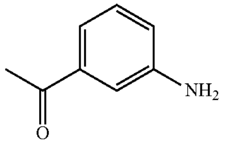 | 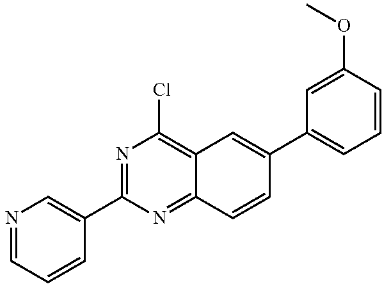 [SMILES: COc1cccc(-c2ccc3nc(-c4cccnc4)nc(Cl)c3c2)c1] |
| 729 | 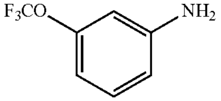 | 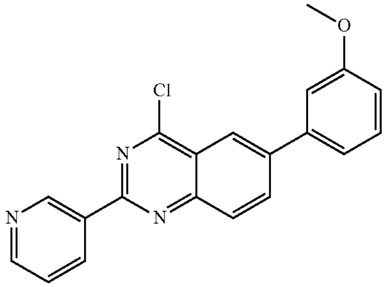 [SMILES: COc1cccc(-c2ccc3nc(-c4cccnc4)nc(Cl)c3c2)c1] |

TABLE 4-continued
| | | |
|---|---|---|
| 730 | 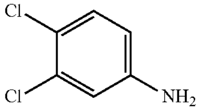 | 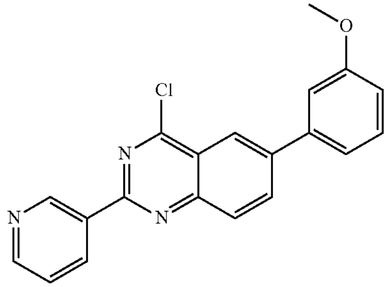 [SMILES: COc1cccc(-c2ccc3nc(-c4cccnc4)nc(Cl)c3c2)c1] |
| 731 | 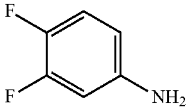 | 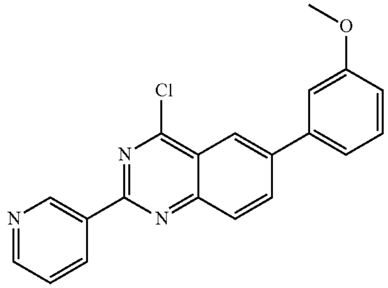 [SMILES: COc1cccc(-c2ccc3nc(-c4cccnc4)nc(Cl)c3c2)c1] |
| 732 | 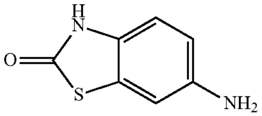 | 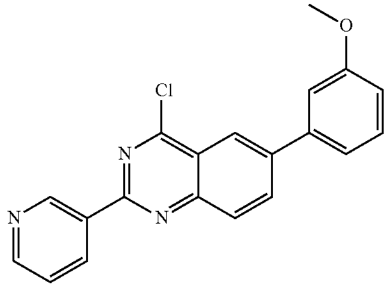 [SMILES: COc1cccc(-c2ccc3nc(-c4cccnc4)nc(Cl)c3c2)c1] |

TABLE 4-continued
| | | |
|---|---|---|
| 733 | 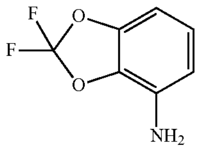 | 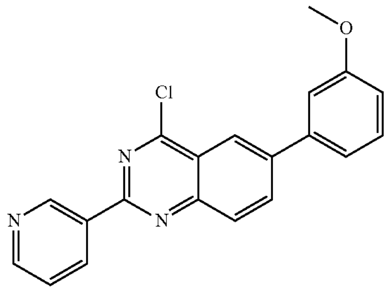 [SMILES: COc1cccc(-c2ccc3nc(-c4cccnc4)nc(Cl)c3c2)c1] |
| 734 | 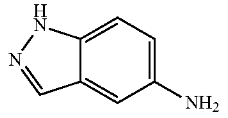 | 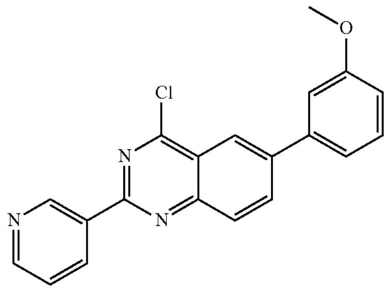 [SMILES: COc1cccc(-c2ccc3nc(-c4cccnc4)nc(Cl)c3c2)c1] |
| 735 | 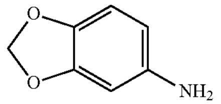 | 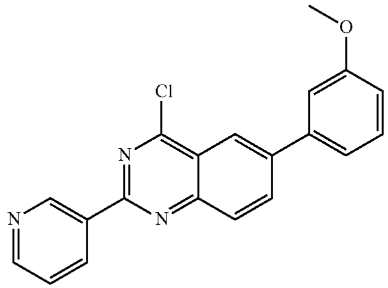 [SMILES: COc1cccc(-c2ccc3nc(-c4cccnc4)nc(Cl)c3c2)c1] |

TABLE 4-continued
| | | |
|---|---|---|
| 736 | 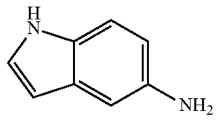 | 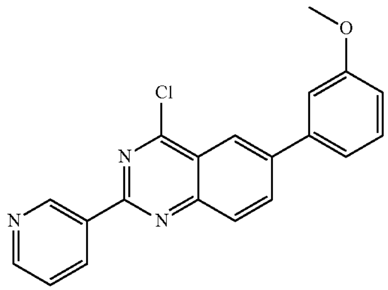 [SMILES: COc1cccc(-c2ccc3nc(-c4cccnc4)nc(Cl)c3c2)c1] |
| 737 | 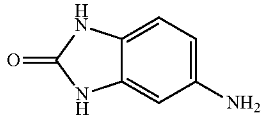 | 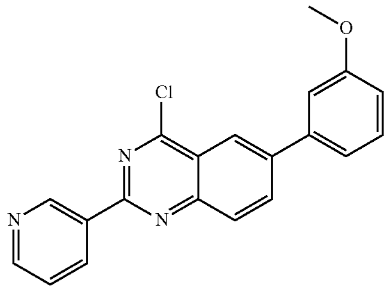 [SMILES: COc1cccc(-c2ccc3nc(-c4cccnc4)nc(Cl)c3c2)c1] |
| 738 | 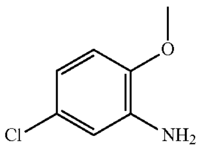 | 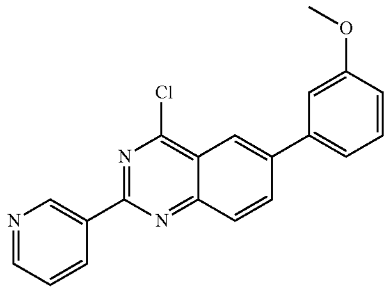 [SMILES: COc1cccc(-c2ccc3nc(-c4cccnc4)nc(Cl)c3c2)c1] |

TABLE 4-continued
| | | |
|---|---|---|
| 739 | 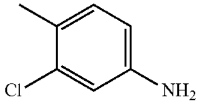 | 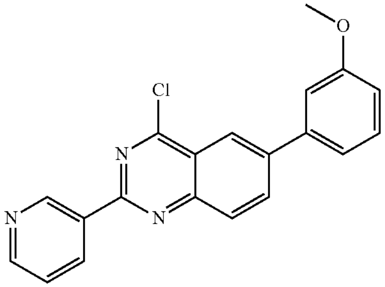 [SMILES: COc1cccc(-c2ccc3nc(-c4cccnc4)nc(Cl)c3c2)c1] |
| 740 | 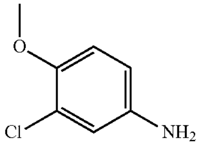 | 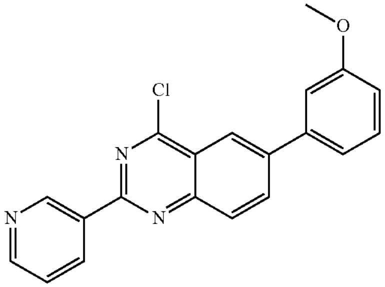 [SMILES: COc1cccc(-c2ccc3nc(-c4cccnc4)nc(Cl)c3c2)c1] |
| 741 | 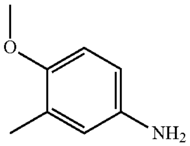 | 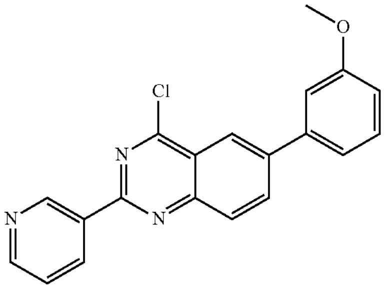 [SMILES: COc1cccc(-c2ccc3nc(-c4cccnc4)nc(Cl)c3c2)c1] |

TABLE 4-continued
| | | |
|---|---|---|
| 742 | 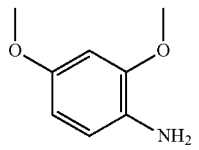 | 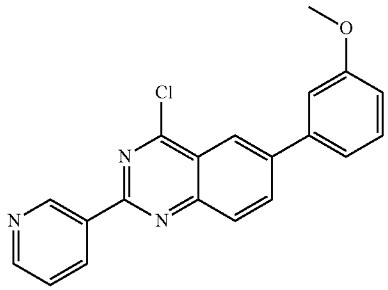 [SMILES: COc1cccc(-c2ccc3nc(-c4cccnc4)nc(Cl)c3c2)c1] |
| 743 | 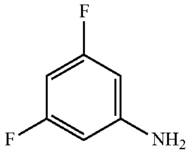 | 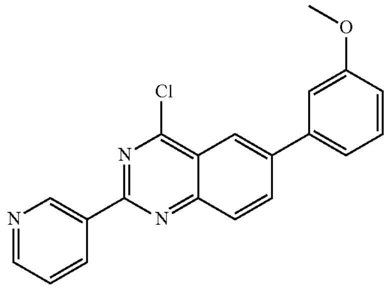 [SMILES: COc1cccc(-c2ccc3nc(-c4cccnc4)nc(Cl)c3c2)c1] |
| 744 | 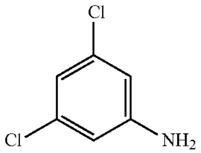 | 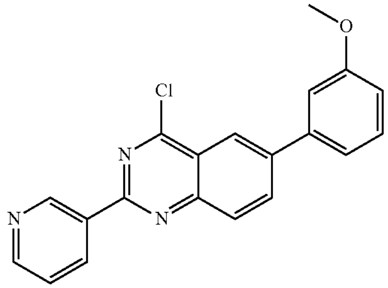 [SMILES: COc1cccc(-c2ccc3nc(-c4cccnc4)nc(Cl)c3c2)c1] |

TABLE 4-continued
| | | |
|---|---|---|
| 745 | 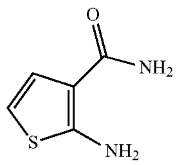 | 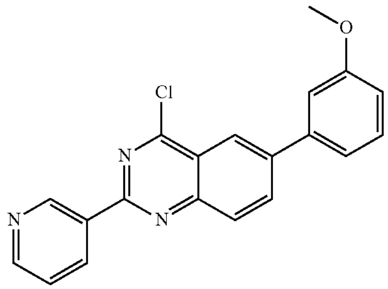 [SMILES: COc1cccc(-c2ccc3nc(-c4cccnc4)nc(Cl)c3c2)c1] |
| 746 | 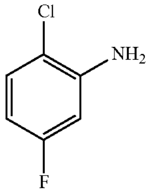 | 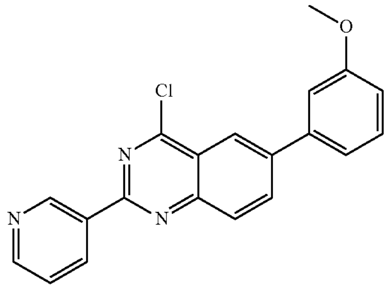 [SMILES: COc1cccc(-c2ccc3nc(-c4cccnc4)nc(Cl)c3c2)c1] |
| 747 | 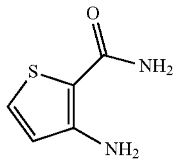 | 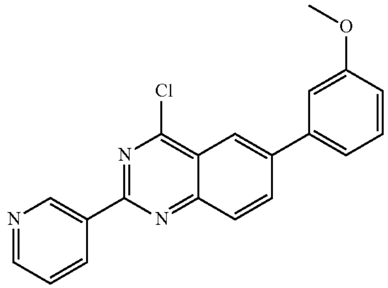 [SMILES: COc1cccc(-c2ccc3nc(-c4cccnc4)nc(Cl)c3c2)c1] |

TABLE 4-continued
| Number | Product | Salt type |
|---|---|---|
| 629 | 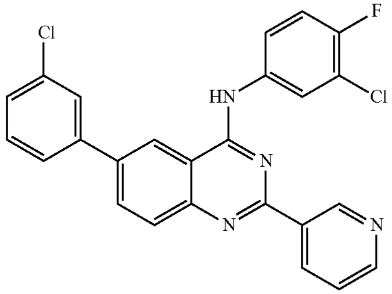 [SMILES: Fc1ccc(Nc2nc(-c3cccnc3)nc3ccc(-c4cccc(Cl)c4)cc23)cc1Cl] | |
| 630 | 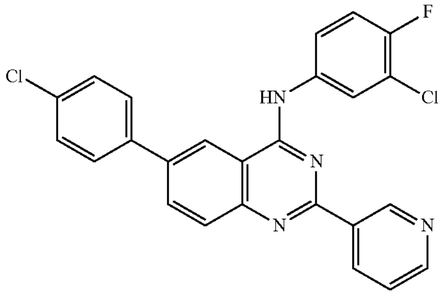 [SMILES: Fc1ccc(Nc2nc(-c3cccnc3)nc3ccc(-c4ccc(Cl)cc4)cc23)cc1Cl] | |
| 631 | 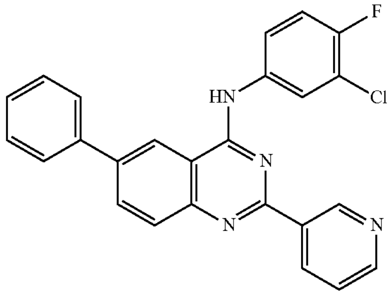 [SMILES: Fc1ccc(Nc2nc(-c3cccnc3)nc3ccc(-c4ccccc4)cc23)cc1Cl] | |

TABLE 4-continued
632 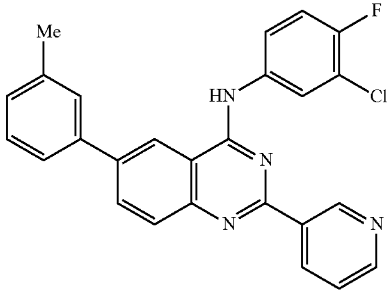 [SMILES: Fc1cccc(-c2ccc3nc(-c4cccnc4)nc(Nc4ccc(F)c(Cl)c4)c3c2)c1]
633 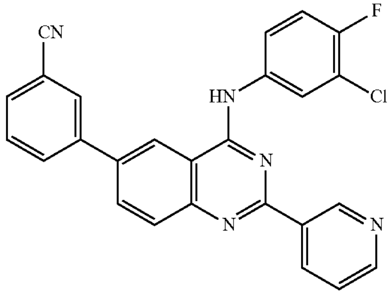
634 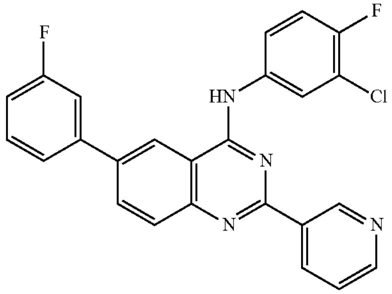

TABLE 4-continued
| | |
|---|---|
| 635 | 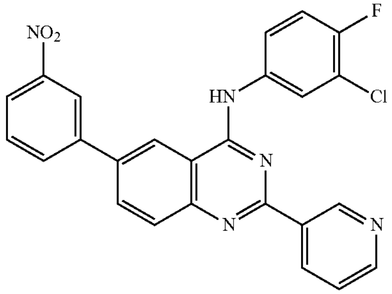 [SMILES: O=[N+]([O-])c1cccc(-c2ccc3nc(-c4cccnc4)nc(Nc4ccc(F)c(Cl)c4)c3c2)c1] |
| 636 | 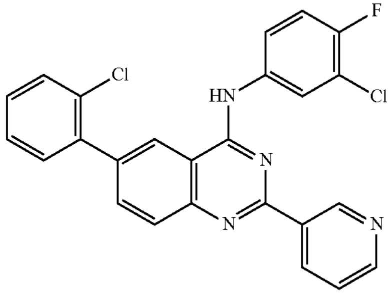 |
| 637 | 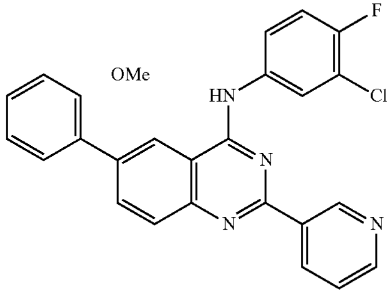 [SMILES: Fc1ccc(Nc2nc(-c3cccnc3)nc3ccc(-c4ccccc4)cc23)cc1Cl ; "OMe"] |

TABLE 4-continued
| | |
|---|---|
| 638 | 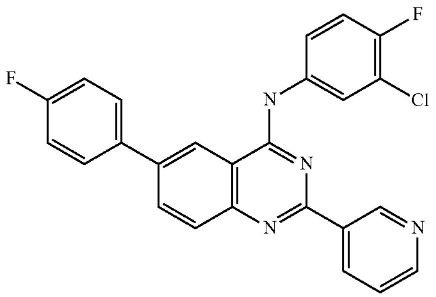 [SMILES: Fc1ccc(-c2ccc3nc(-c4cccnc4)nc(Nc4ccc(F)c(Cl)c4)c3c2)cc1] |
| 639 | 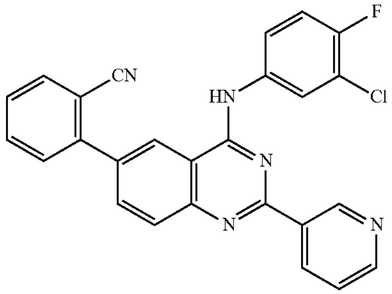 [SMILES: N#Cc1ccccc1-c1ccc2nc(-c3cccnc3)nc(Nc3ccc(F)c(Cl)c3)c2c1] |
| 640 | 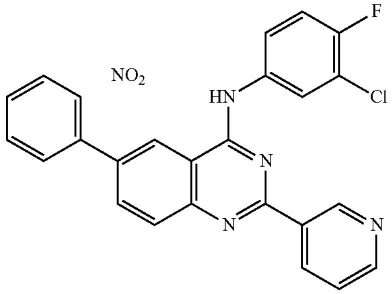 |

TABLE 4-continued
| | |
|---|---|
| 641 | 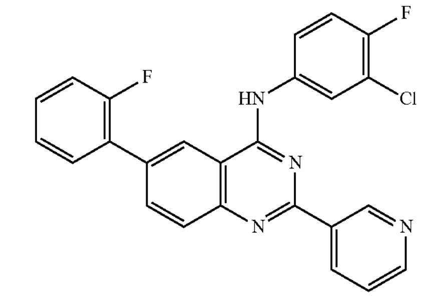 [SMILES: Fc1ccc(Nc2nc(-c3cccnc3)nc3ccc(-c4ccccc4F)cc23)cc1Cl] |
| 642 | 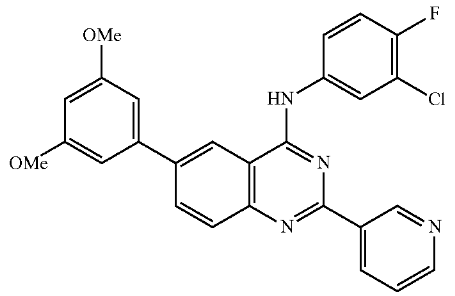 [SMILES: COc1cc(OC)cc(-c2ccc3nc(-c4cccnc4)nc(Nc4ccc(F)c(Cl)c4)c3c2)c1] |
| 643 | 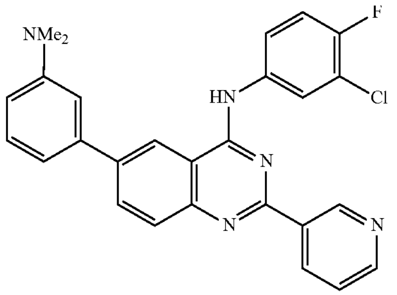 [SMILES: CN(C)c1cccc(-c2ccc3nc(-c4cccnc4)nc(Nc4ccc(F)c(Cl)c4)c3c2)c1] |

TABLE 4-continued
| | |
|---|---|
| 644 | 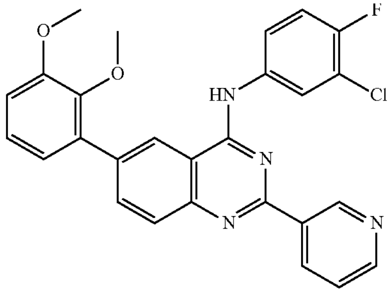 [SMILES: COc1cccc(-c2ccc3nc(-c4cccnc4)nc(Nc4ccc(F)c(Cl)c4)c3c2)c1OC] |
| 645 | 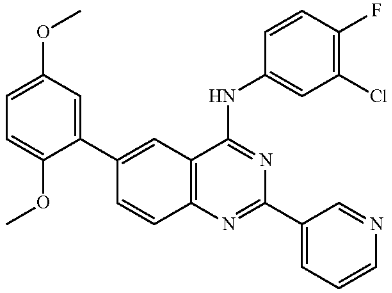 [SMILES: COc1ccc(OC)c(-c2ccc3nc(-c4cccnc4)nc(Nc4ccc(F)c(Cl)c4)c3c2)c1] |
| 646 | 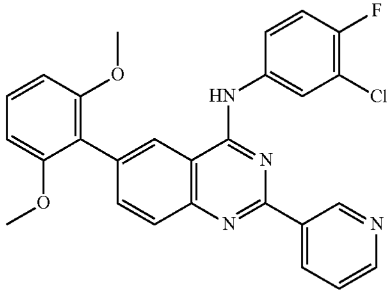 [SMILES: COc1cccc(OC)c1-c1ccc2nc(-c3cccnc3)nc(Nc3ccc(F)c(Cl)c3)c2c1] |

TABLE 4-continued
| | |
|---|---|
| 647 | 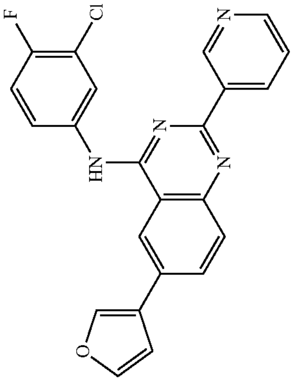 |
| 648 | 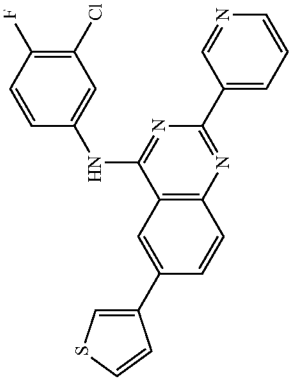 |
| 649 | 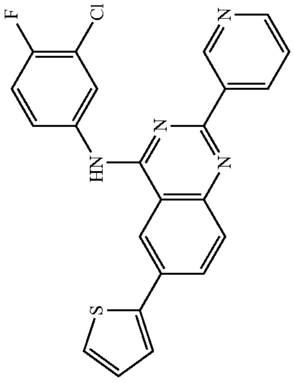 |

TABLE 4-continued
| | |
|---|---|
| 650 | 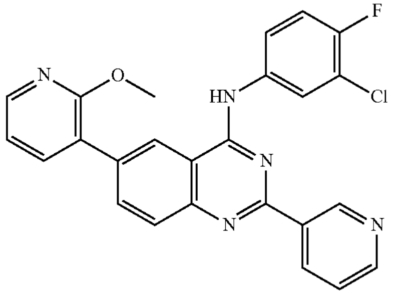 [SMILES: COc1ncccc1-c1ccc2nc(-c3cccnc3)nc(Nc3ccc(F)c(Cl)c3)c2c1] |
| 651 | 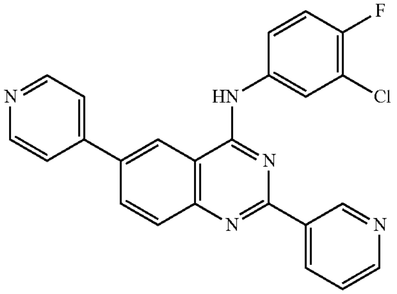 [SMILES: Fc1ccc(Nc2nc(-c3cccnc3)nc3ccc(-c4ccncc4)cc23)cc1Cl] |
| 652 | 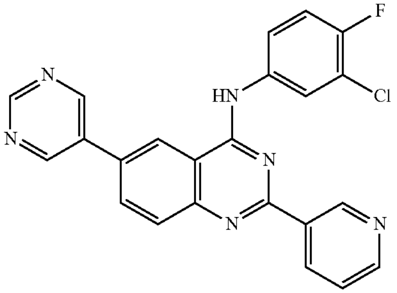 [SMILES: Fc1ccc(Nc2nc(-c3cccnc3)nc3ccc(-c4cncnc4)cc23)cc1Cl]

TABLE 4-continued
| | |
|---|---|
| 653 | 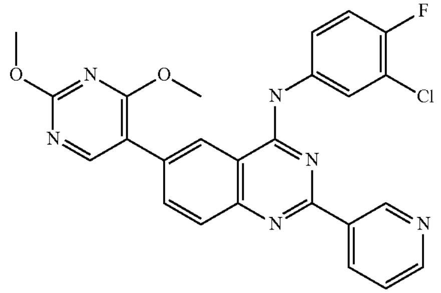 [SMILES: COc1ncc(-c2ccc3nc(-c4cccnc4)nc(Nc4ccc(F)c(Cl)c4)c3c2)c(OC)n1] |
| 654 | 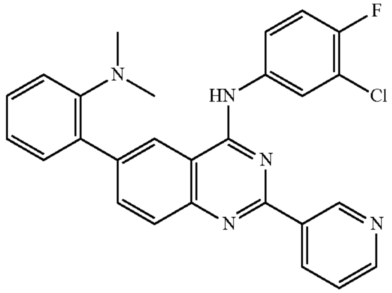 [SMILES: CN(C)c1ccccc1-c1ccc2nc(-c3cccnc3)nc(Nc3ccc(F)c(Cl)c3)c2c1] |
| 655 | 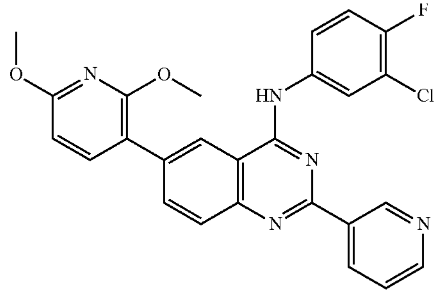 [SMILES: COc1ccc(-c2ccc3nc(-c4cccnc4)nc(Nc4ccc(F)c(Cl)c4)c3c2)c(OC)n1] |

TABLE 4-continued
| | |
|---|---|
| 656 | 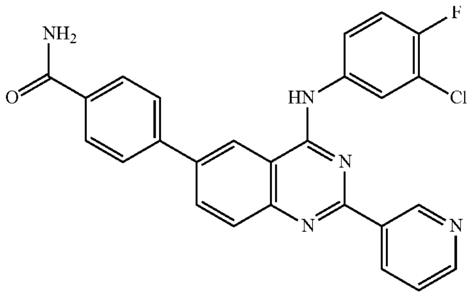 [SMILES: NC(=O)c1ccc(-c2ccc3nc(-c4cccnc4)nc(Nc4ccc(F)c(Cl)c4)c3c2)cc1] |
| 657 | 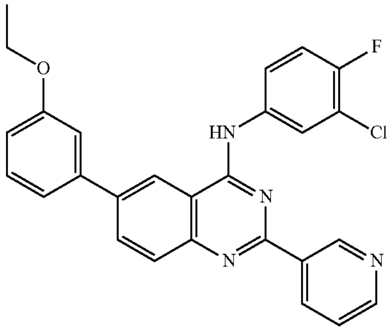 [SMILES: CCOc1cccc(-c2ccc3nc(-c4cccnc4)nc(Nc4ccc(F)c(Cl)c4)c3c2)c1] |
| 658 | 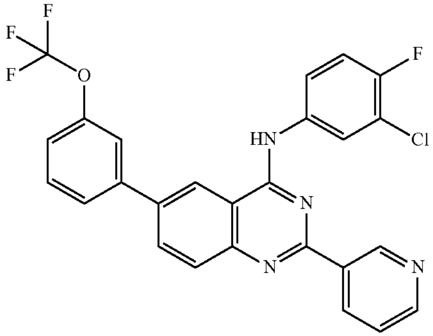 [SMILES: Fc1ccc(Nc2nc(-c3cccnc3)nc3ccc(-c4cccc(OC(F)(F)F)c4)cc23)cc1Cl] |

TABLE 4-continued
| | |
|---|---|
| 659 | 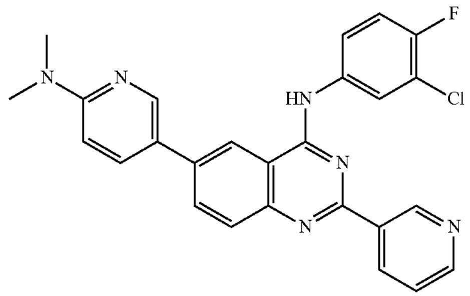 |
| 660 | 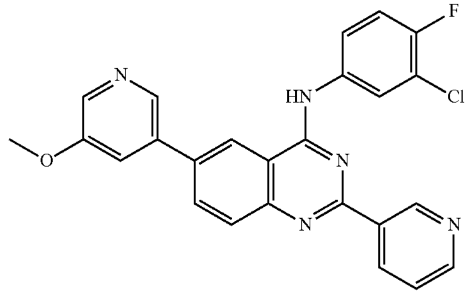 [SMILES: COc1cncc(-c2ccc3nc(-c4cccnc4)nc(Nc4ccc(F)c(Cl)c4)c3c2)c1] |
| 661 | 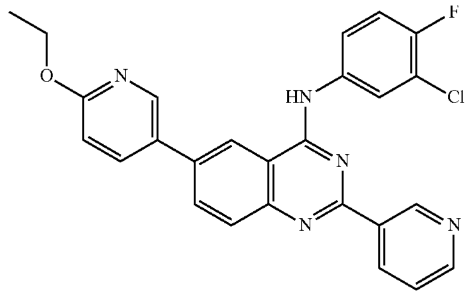 [SMILES: CCOc1ccc(-c2ccc3nc(-c4cccnc4)nc(Nc4ccc(F)c(Cl)c4)c3c2)cn1] |

TABLE 4-continued
| | |
|---|---|
| 662 | 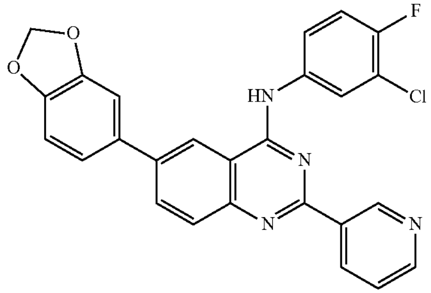 [SMILES: Fc1ccc(Nc2nc(-c3cccnc3)nc3ccc(-c4ccc5c(c4)OCO5)cc23)cc1Cl] |
| 663 | 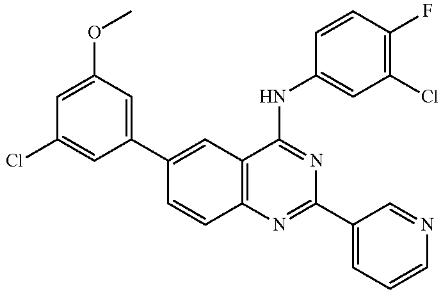 [SMILES: COc1cc(Cl)cc(-c2ccc3nc(-c4cccnc4)nc(Nc4ccc(F)c(Cl)c4)c3c2)c1] |
| 664 | 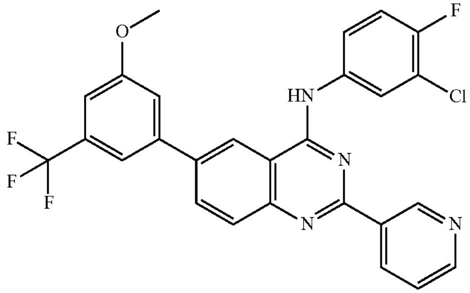 [SMILES: COc1cc(-c2ccc3nc(-c4cccnc4)nc(Nc4ccc(F)c(Cl)c4)c3c2)cc(C(F)(F)F)c1] |

TABLE 4-continued
| | | |
|---|---|---|
| 665 | 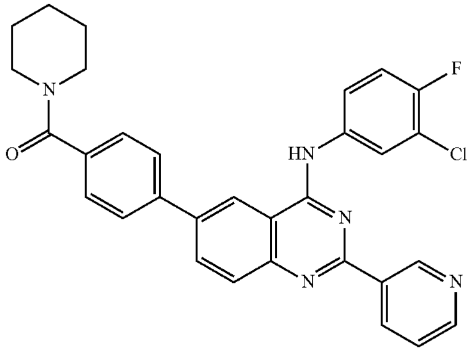 [SMILES: O=C(c1ccc(-c2ccc3nc(-c4cccnc4)nc(Nc4ccc(F)c(Cl)c4)c3c2)cc1)N1CCCCC1] | |
| 666 | 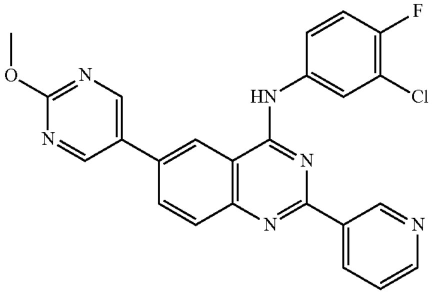 [SMILES: COc1ncc(-c2ccc3nc(-c4cccnc4)nc(Nc4ccc(F)c(Cl)c4)c3c2)cn1] | 2 HCl |
| 667 | 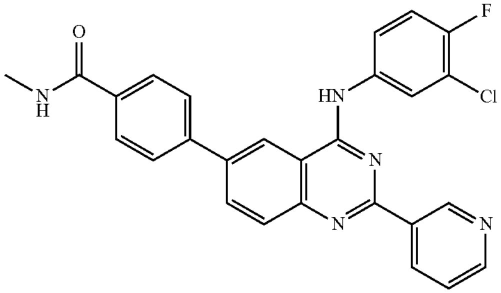 [SMILES: CNC(=O)c1ccc(-c2ccc3nc(-c4cccnc4)nc(Nc4ccc(F)c(Cl)c4)c3c2)cc1] | HCl |

TABLE 4-continued
| | | |
|---|---|---|
| 668 | 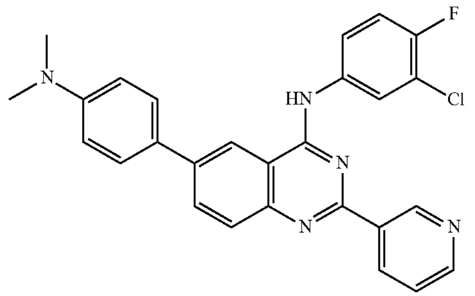 [SMILES: CN(C)c1ccc(-c2ccc3nc(-c4cccnc4)nc(Nc4ccc(F)c(Cl)c4)c3c2)cc1] | 2 HCl |
| 669 | 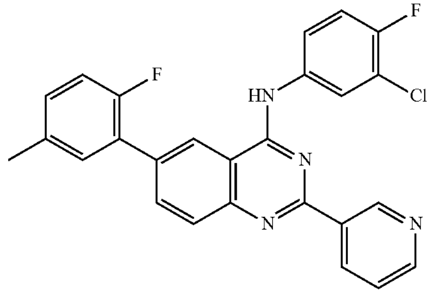 [SMILES: Cc1ccc(F)c(-c2ccc3nc(-c4cccnc4)nc(Nc4ccc(F)c(Cl)c4)c3c2)c1] | HCl |
| 670 | 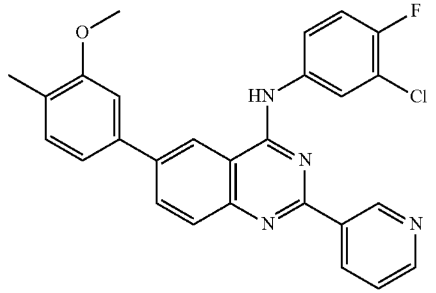 [SMILES: COc1cc(-c2ccc3nc(-c4cccnc4)nc(Nc4ccc(F)c(Cl)c4)c3c2)ccc1C] | HCl |

TABLE 4-continued
| | | |
|---|---|---|
| 671 | 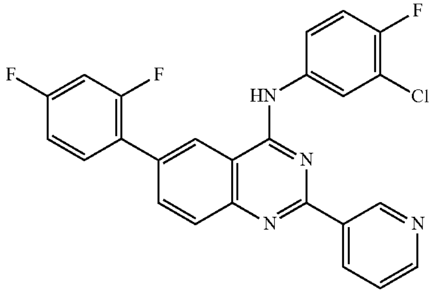 [SMILES: Fc1ccc(-c2ccc3nc(-c4cccnc4)nc(Nc4ccc(F)c(Cl)c4)c3c2)c(F)c1] | HCl |
| 672 | 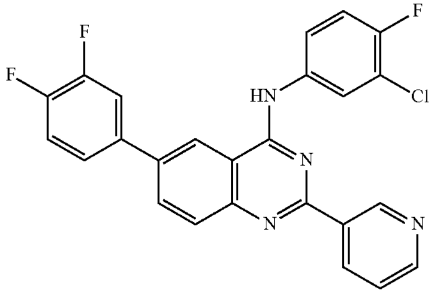 [SMILES: Fc1ccc(-c2ccc3nc(-c4cccnc4)nc(Nc4ccc(F)c(Cl)c4)c3c2)cc1F] | HCl |
| 673 | 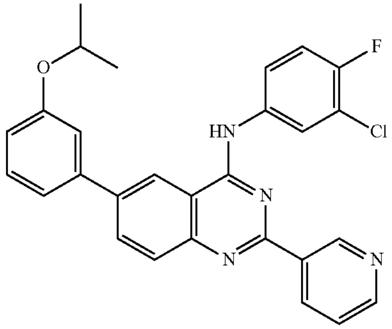 [SMILES: CC(C)Oc1cccc(-c2ccc3nc(-c4cccnc4)nc(Nc4ccc(F)c(Cl)c4)c3c2)c1] | HCl |

TABLE 4-continued
| | | |
|---|---|---|
| 674 | 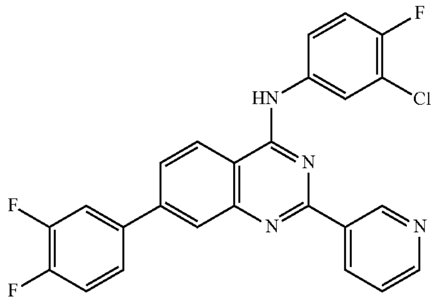 [SMILES: Fc1ccc(-c2ccc3c(Nc4ccc(F)c(Cl)c4)nc(-c4cccnc4)nc3c2)cc1F] | HCl |
| 675 | 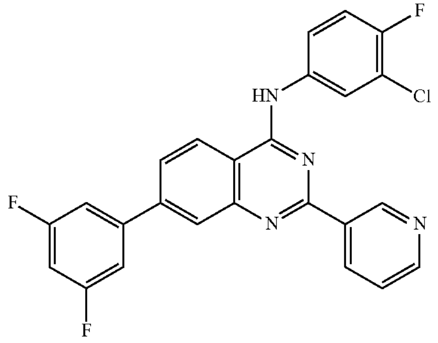 [SMILES: Fc1cc(F)cc(-c2ccc3c(Nc4ccc(F)c(Cl)c4)nc(-c4cccnc4)nc3c2)c1] | HCl |
| 676 | 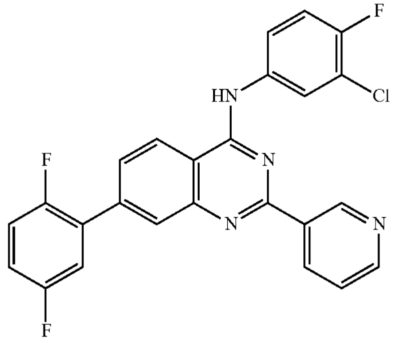 [SMILES: Fc1ccc(F)c(-c2ccc3c(Nc4ccc(F)c(Cl)c4)nc(-c4cccnc4)nc3c2)c1] | HCl |

TABLE 4-continued
| | | |
|---|---|---|
| 677 | 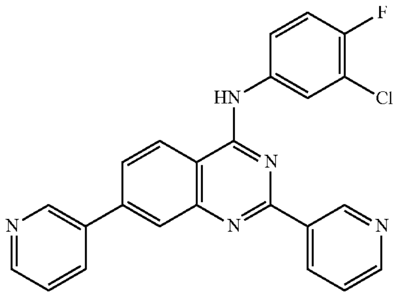 [SMILES: Fc1ccc(Nc2nc(-c3cccnc3)nc3cc(-c4cccnc4)ccc23)cc1Cl] | 2 HCl |
| 678 | 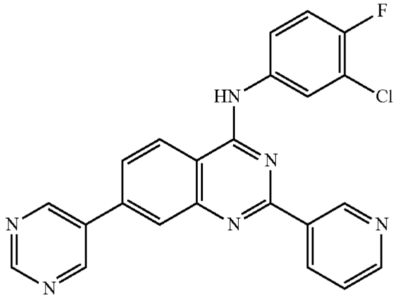 [SMILES: Fc1ccc(Nc2nc(-c3cccnc3)nc3cc(-c4cncnc4)ccc23)cc1Cl] | HCl |
| 679 | 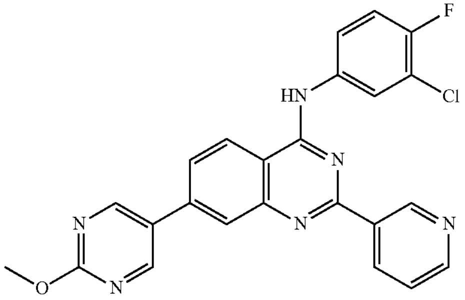 [SMILES: COc1ncc(-c2ccc3c(Nc4ccc(F)c(Cl)c4)nc(-c4cccnc4)nc3c2)cn1] | 2 HCl |

TABLE 4-continued
| | |
|---|---|
| 680 | 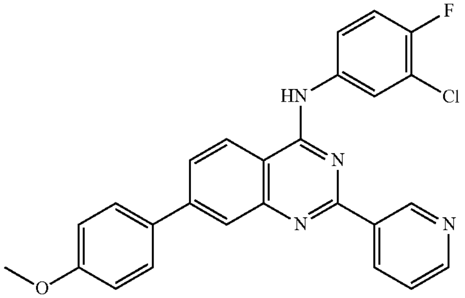 |
| 681 | 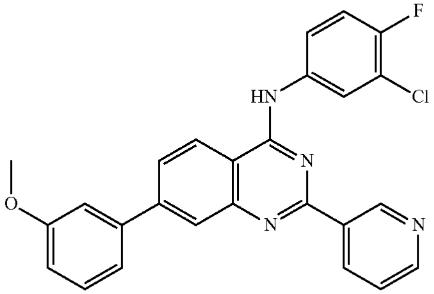 [SMILES: COc1cccc(-c2ccc3c(Nc4ccc(F)c(Cl)c4)nc(-c4cccnc4)nc3c2)c1] |
| 682 | 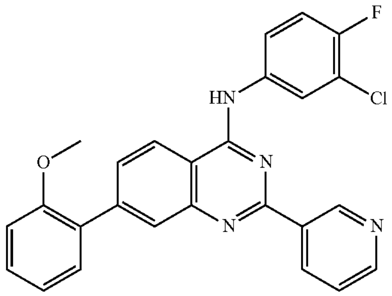 [SMILES: COc1ccccc1-c1ccc2c(Nc3ccc(F)c(Cl)c3)nc(-c3cccnc3)nc2c1] |

TABLE 4-continued
| | |
|---|---|
| 683 | 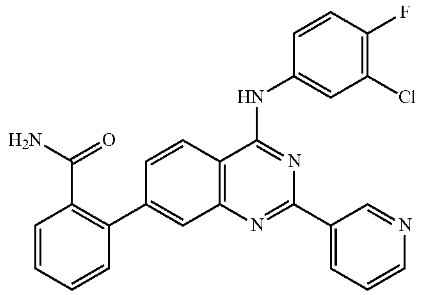 [SMILES: NC(=O)c1ccccc1-c1ccc2c(Nc3ccc(F)c(Cl)c3)nc(-c3cccnc3)nc2c1] |
| 684 | 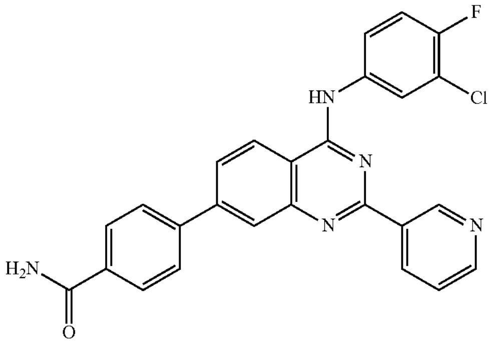 [SMILES: NC(=O)c1ccc(-c2ccc3c(Nc4ccc(F)c(Cl)c4)nc(-c4cccnc4)nc3c2)cc1] |
| 685 | 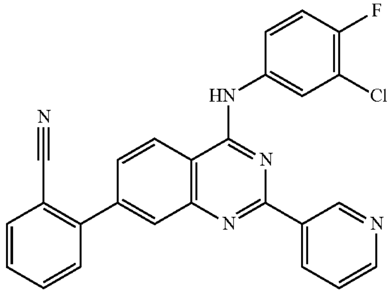 [SMILES: N#Cc1ccccc1-c1ccc2c(Nc3ccc(F)c(Cl)c3)nc(-c3cccnc3)nc2c1] |

TABLE 4-continued
| | |
|---|---|
| 686 | 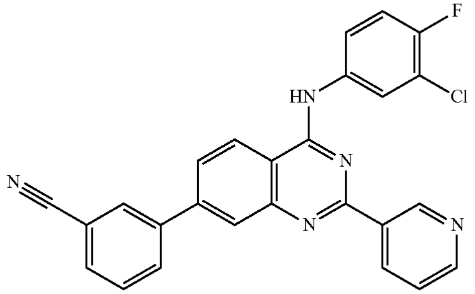 [SMILES: N#Cc1cccc(-c2ccc3c(Nc4ccc(F)c(Cl)c4)nc(-c4cccnc4)nc3c2)c1] |
| 687 | 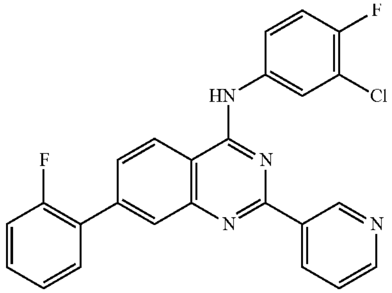 [SMILES: Fc1ccc(Nc2nc(-c3cccnc3)nc3cc(-c4ccccc4F)ccc23)cc1Cl] |
| 688 | 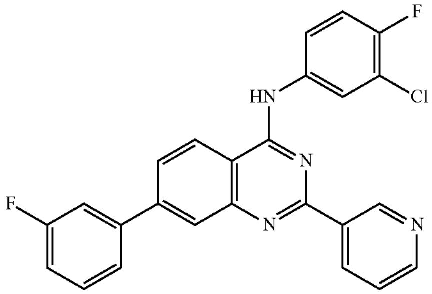 [SMILES: Fc1cccc(-c2ccc3c(Nc4ccc(F)c(Cl)c4)nc(-c4cccnc4)nc3c2)c1] |

TABLE 4-continued
| | | |
|---|---|---|
| 689 | 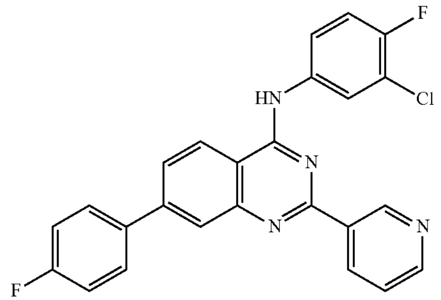 [SMILES: Fc1ccc(-c2ccc3c(Nc4ccc(F)c(Cl)c4)nc(-c4cccnc4)nc3c2)cc1] | |
| 690 | 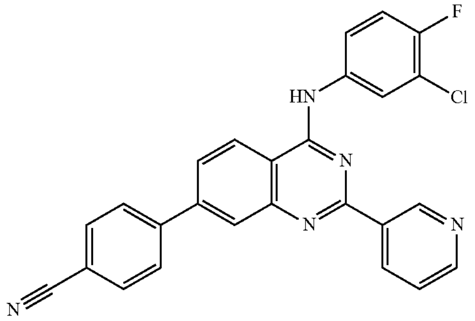 [SMILES: N#Cc1ccc(-c2ccc3c(Nc4ccc(F)c(Cl)c4)nc(-c4cccnc4)nc3c2)cc1] | |
| 691 | 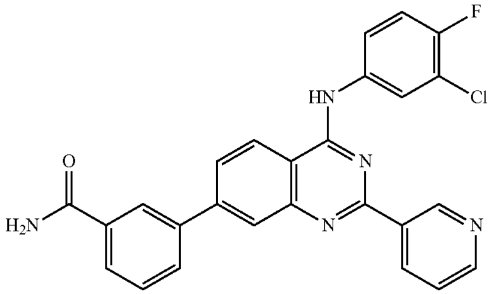 [SMILES: NC(=O)c1cccc(-c2ccc3c(Nc4ccc(F)c(Cl)c4)nc(-c4cccnc4)nc3c2)c1] | HCl |

TABLE 4-continued
| | | |
|---|---|---|
| 692 | 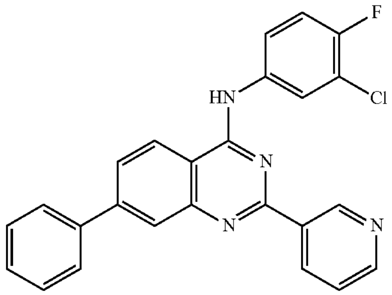 [SMILES: Fc1ccc(Nc2nc(-c3cccnc3)nc3cc(-c4ccccc4)ccc23)cc1Cl] | HCl |
| 693 | 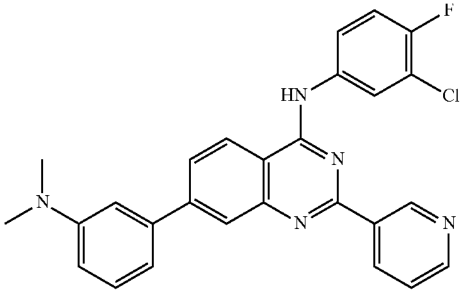 [SMILES: CN(C)c1cccc(-c2ccc3c(Nc4ccc(F)c(Cl)c4)nc(-c4cccnc4)nc3c2)c1] | 3 HCl |
| 694 | 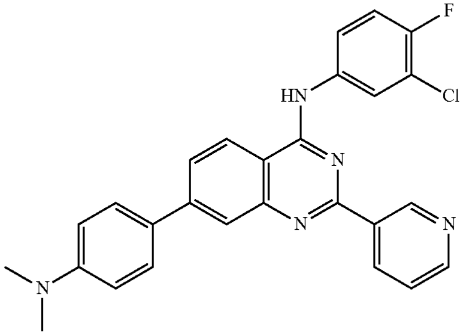 [SMILES: CN(C)c1ccc(-c2ccc3c(Nc4ccc(F)c(Cl)c4)nc(-c4cccnc4)nc3c2)cc1] | 3 HCl |

TABLE 4-continued
| | | |
|---|---|---|
| 695 | 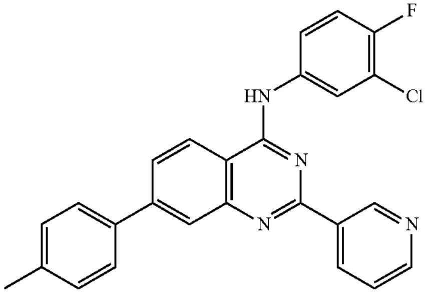 [SMILES: Cc1ccc(-c2ccc3c(Nc4ccc(F)c(Cl)c4)nc(-c4cccnc4)nc3c2)cc1] | HCl |
| 696 | 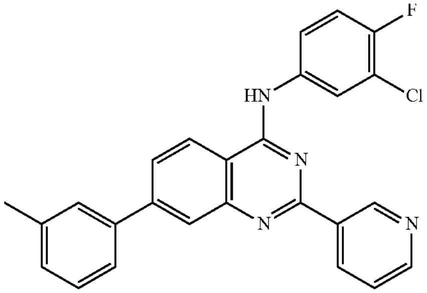 [SMILES: Cc1cccc(-c2ccc3c(Nc4ccc(F)c(Cl)c4)nc(-c4cccnc4)nc3c2)c1] | HCl |
| 697 | 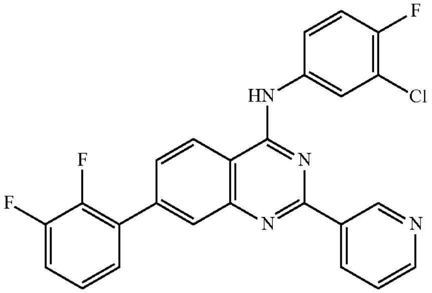 [SMILES: Fc1ccc(Nc2nc(-c3cccnc3)nc3cc(-c4cccc(F)c4F)ccc23)cc1Cl] | HCl |

TABLE 4-continued
| | | |
|---|---|---|
| 698 | 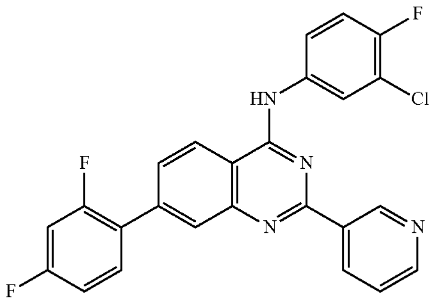 [SMILES: Fc1ccc(-c2ccc3c(Nc4ccc(F)c(Cl)c4)nc(-c4cccnc4)nc3c2)c(F)c1] | HCl |
| 699 | 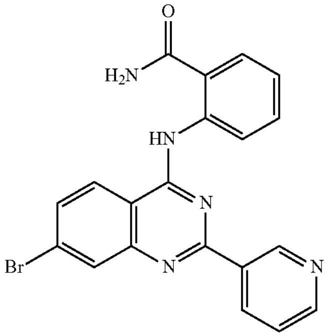 [SMILES: NC(=O)c1ccccc1Nc1nc(-c2cccnc2)nc2cc(Br)ccc12] | 2 HCl |
| 700 | 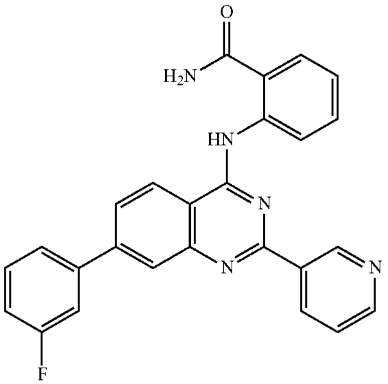 [SMILES: NC(=O)c1ccccc1Nc1nc(-c2cccnc2)nc2cc(-c3cccc(F)c3)ccc12] | 2 HCl |

TABLE 4-continued
| | | |
|---|---|---|
| 701 | 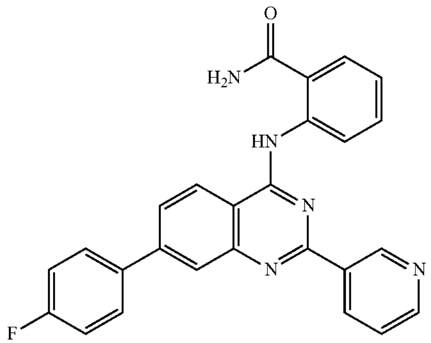 [SMILES: NC(=O)c1ccccc1Nc1nc(-c2cccnc2)nc2cc(-c3ccc(F)cc3)ccc12] | 2 HCl |
| 702 | 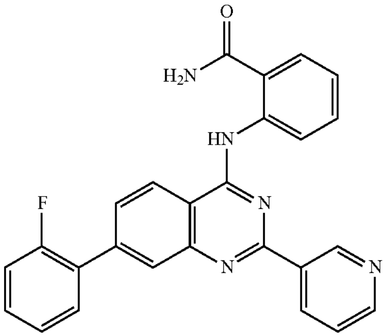 [SMILES: NC(=O)c1ccccc1Nc1nc(-c2cccnc2)nc2cc(-c3ccccc3F)ccc12] | 2 HCl |
| 703 | 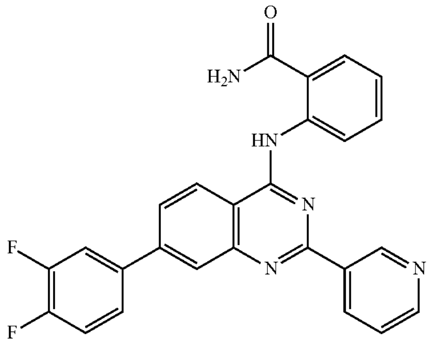 [SMILES: NC(=O)c1ccccc1Nc1nc(-c2cccnc2)nc2cc(-c3ccc(F)c(F)c3)ccc12] | 2 HCl |

TABLE 4-continued
| | | |
|---|---|---|
| 704 | 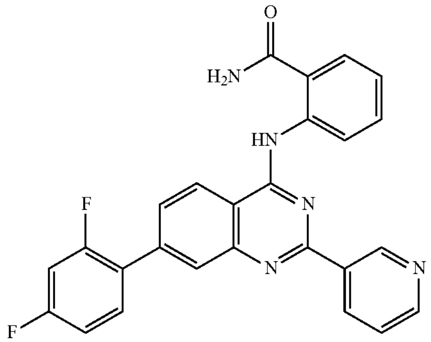 [SMILES: NC(=O)c1ccccc1Nc1nc(-c2cccnc2)nc2cc(-c3ccc(F)cc3F)ccc12] | 2 HCl |
| 705 | 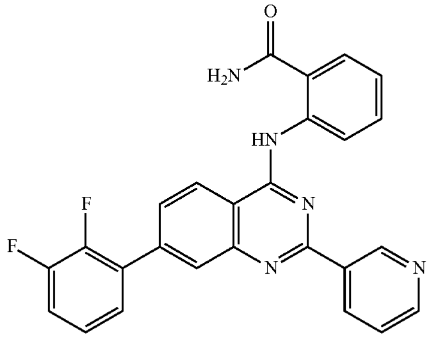 [SMILES: NC(=O)c1ccccc1Nc1nc(-c2cccnc2)nc2cc(-c3cccc(F)c3F)ccc12] | 2 HCl |
| 706 | 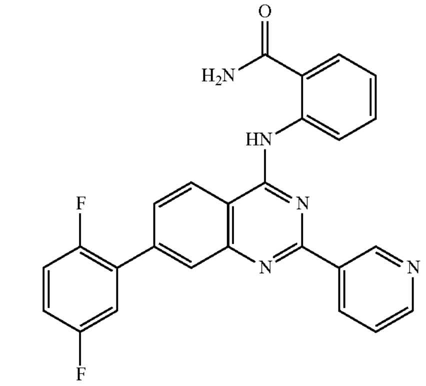 [SMILES: NC(=O)c1ccccc1Nc1nc(-c2cccnc2)nc2cc(-c3cc(F)ccc3F)ccc12] | 2 HCl |

TABLE 4-continued
| | | |
|---|---|---|
| 707 | 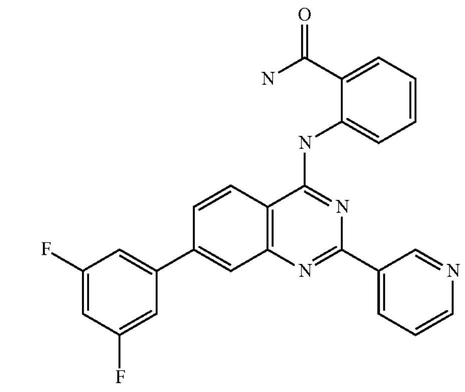 [SMILES: NC(=O)c1ccccc1Nc1nc(-c2cccnc2)nc2cc(-c3cc(F)cc(F)c3)ccc12] | 2 HCl |
| 708 | 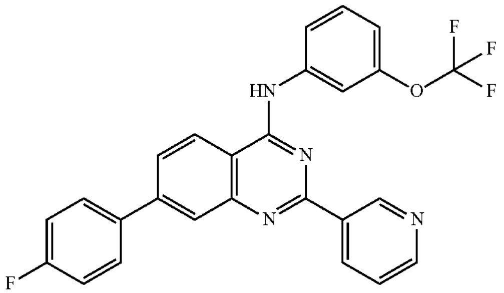 [SMILES: Fc1ccc(-c2ccc3c(Nc4cccc(OC(F)(F)F)c4)nc(-c4cccnc4)nc3c2)cc1] | HCl |
| 709 | 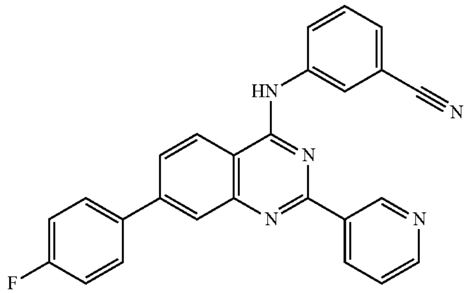 [SMILES: N#Cc1cccc(Nc2nc(-c3cccnc3)nc3cc(-c4ccc(F)cc4)ccc23)c1] | HCl |

TABLE 4-continued
| | |
|---|---|
| 710 | 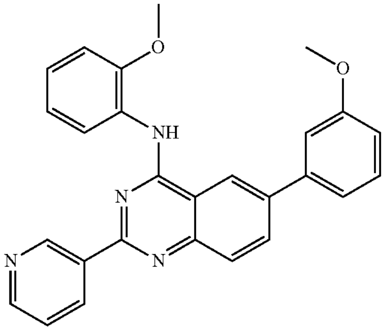 [SMILES: COc1cccc(-c2ccc3nc(-c4cccnc4)nc(Nc4ccccc4OC)c3c2)c1] |
| 711 | 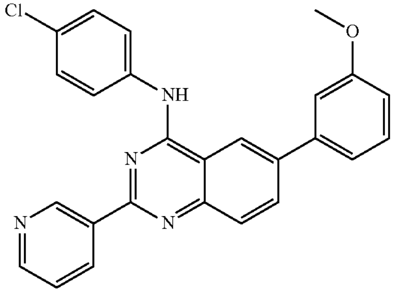 [SMILES: COc1cccc(-c2ccc3nc(-c4cccnc4)nc(Nc4ccc(Cl)cc4)c3c2)c1] |
| 712 | 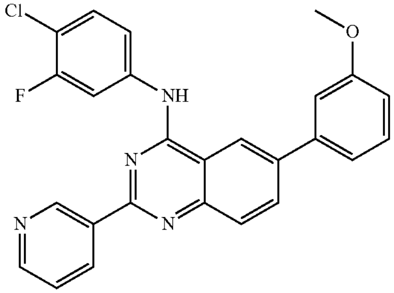 [SMILES: COc1cccc(-c2ccc3nc(-c4cccnc4)nc(Nc4ccc(Cl)c(F)c4)c3c2)c1] |

TABLE 4-continued
| | |
|---|---|
| 713 | 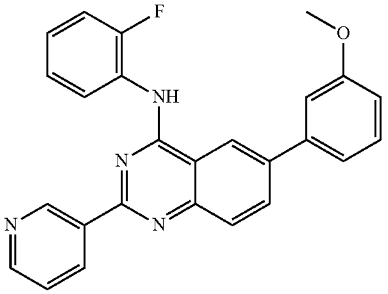 [SMILES: COc1cccc(-c2ccc3nc(-c4cccnc4)nc(Nc4ccccc4F)c3c2)c1] |
| 714 | 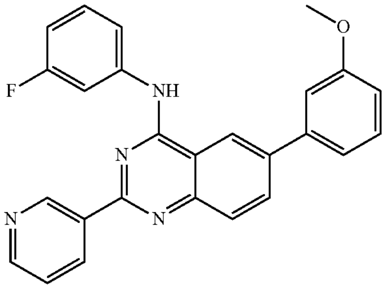 [SMILES: COc1cccc(-c2ccc3nc(-c4cccnc4)nc(Nc4cccc(F)c4)c3c2)c1] |
| 715 | 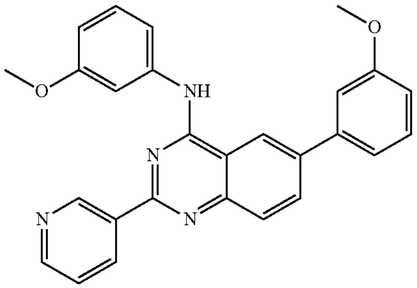 [SMILES: COc1cccc(Nc2nc(-c3cccnc3)nc3ccc(-c4cccc(OC)c4)cc23)c1] |

TABLE 4-continued
| | |
|---|---|
| 716 | 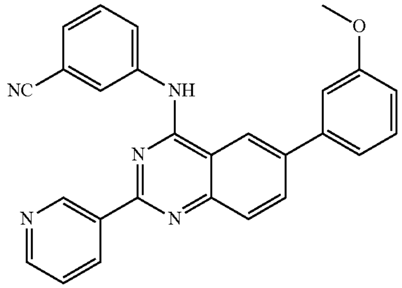 [SMILES: COc1cccc(-c2ccc3nc(-c4cccnc4)nc(Nc4cccc(C#N)c4)c3c2)c1] |
| 717 | 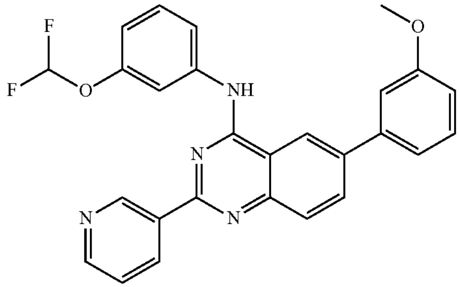 [SMILES: COc1cccc(-c2ccc3nc(-c4cccnc4)nc(Nc4cccc(OC(F)F)c4)c3c2)c1] |
| 718 | 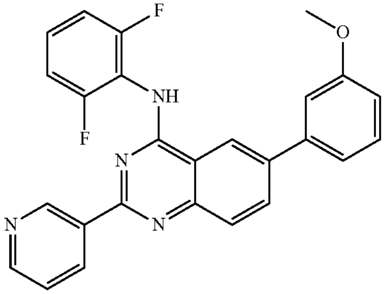 |

TABLE 4-continued
| | |
|---|---|
| 719 | 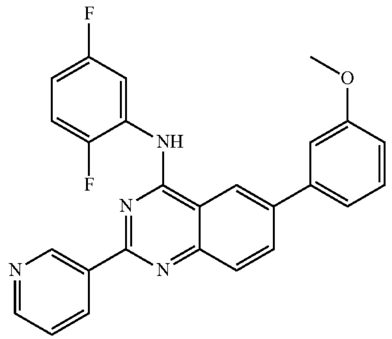 [SMILES: COc1cccc(-c2ccc3nc(-c4cccnc4)nc(Nc4cc(F)ccc4F)c3c2)c1] |
| 720 | 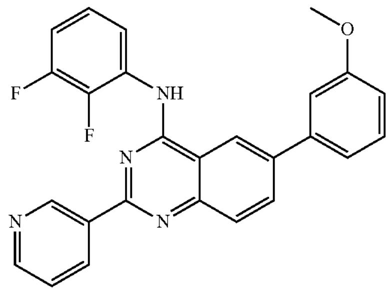 [SMILES: COc1cccc(-c2ccc3nc(-c4cccnc4)nc(Nc4cccc(F)c4F)c3c2)c1] |
| 721 | 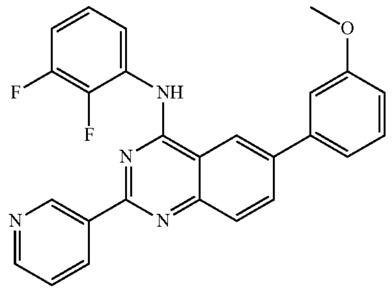 [SMILES: COc1cccc(-c2ccc3nc(-c4cccnc4)nc(Nc4cccc(F)c4F)c3c2)c1] |

TABLE 4-continued
| | |
|---|---|
| 722 | 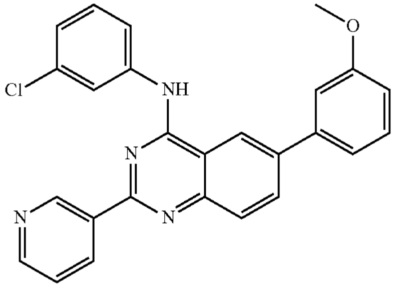 [SMILES: COc1cccc(-c2ccc3nc(-c4cccnc4)nc(Nc4cccc(Cl)c4)c3c2)c1] |
| 723 | 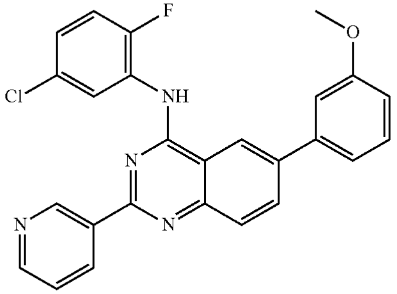 [SMILES: COc1cccc(-c2ccc3nc(-c4cccnc4)nc(Nc4cc(Cl)ccc4F)c3c2)c1] |
| 724 | 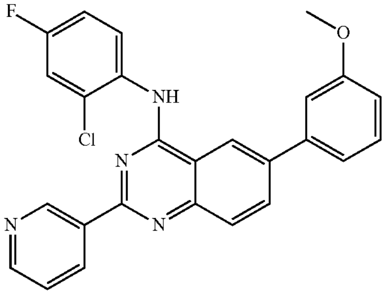 [SMILES: COc1cccc(-c2ccc3nc(-c4cccnc4)nc(Nc4ccc(F)cc4Cl)c3c2)c1] |

TABLE 4-continued
| | |
|---|---|
| 725 | 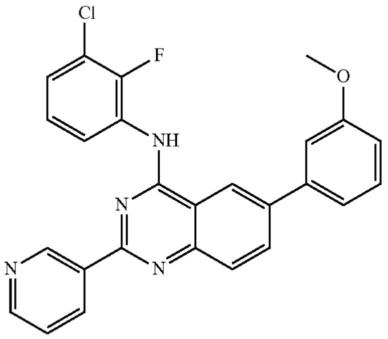 [SMILES: COc1cccc(-c2ccc3nc(-c4cccnc4)nc(Nc4cccc(Cl)c4F)c3c2)c1] |
| 726 | 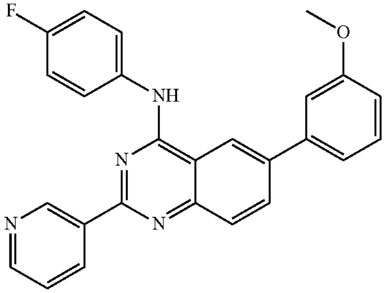 [SMILES: COc1cccc(-c2ccc3nc(-c4cccnc4)nc(Nc4ccc(F)cc4)c3c2)c1] |
| 727 | 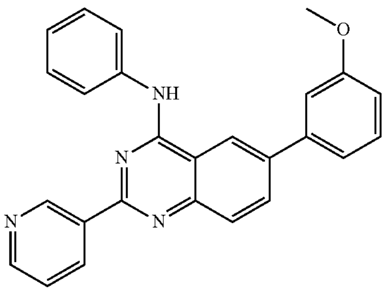 [SMILES: COc1cccc(-c2ccc3nc(-c4cccnc4)nc(Nc4ccccc4)c3c2)c1] |

TABLE 4-continued
| | |
|---|---|
| 728 | 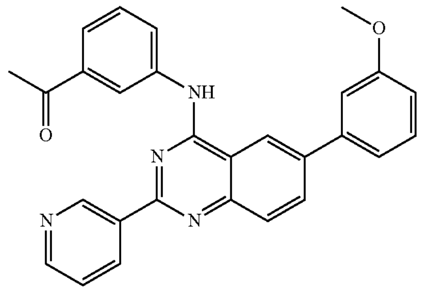 [SMILES: COc1cccc(-c2ccc3nc(-c4cccnc4)nc(Nc4cccc(C(C)=O)c4)c3c2)c1] |
| 729 | 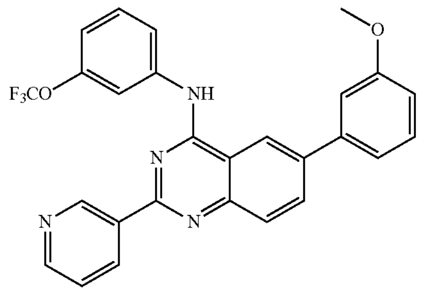 [SMILES: COc1cccc(-c2ccc3nc(-c4cccnc4)nc(Nc4cccc(OC(F)(F)F)c4)c3c2)c1] |
| 730 | 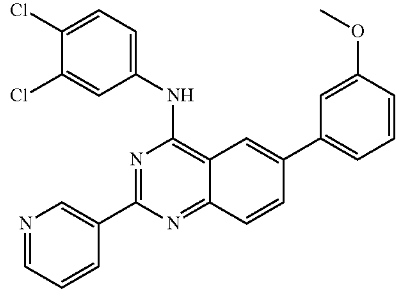 |

TABLE 4-continued
| | |
|---|---|
| 731 | 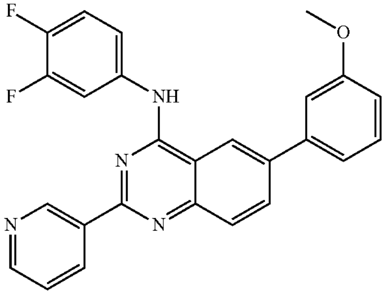 [SMILES: COc1cccc(-c2ccc3nc(-c4cccnc4)nc(Nc4ccc(F)c(F)c4)c3c2)c1] |
| 732 | 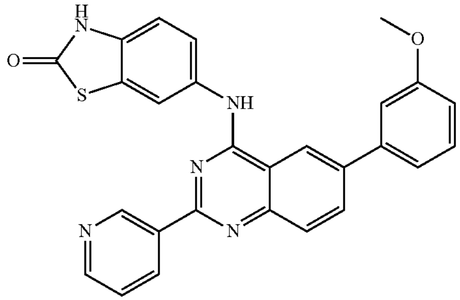 [SMILES: COc1cccc(-c2ccc3nc(-c4cccnc4)nc(Nc4ccc5[nH]c(=O)sc5c4)c3c2)c1] |
| 733 | 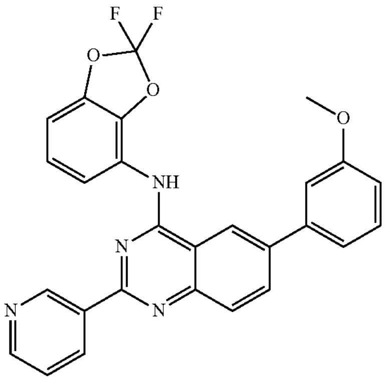 [SMILES: COc1cccc(-c2ccc3nc(-c4cccnc4)nc(Nc4cccc5c4OC(F)(F)O5)c3c2)c1] |

TABLE 4-continued
| | |
|---|---|
| 734 | 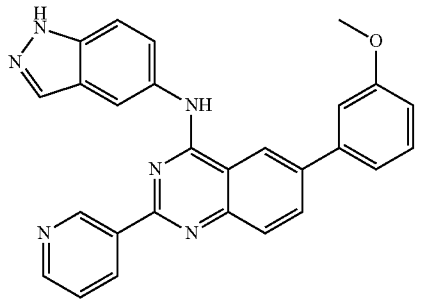 [SMILES: COc1cccc(-c2ccc3nc(-c4cccnc4)nc(Nc4ccc5[nH]ncc5c4)c3c2)c1] |
| 735 | 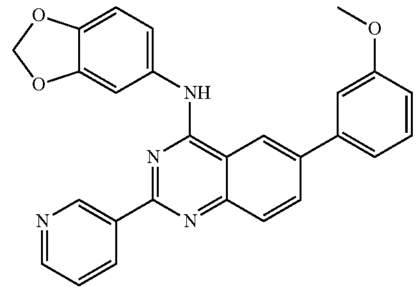 [SMILES: COc1cccc(-c2ccc3nc(-c4cccnc4)nc(Nc4ccc5c(c4)OCO5)c3c2)c1] |
| 736 | 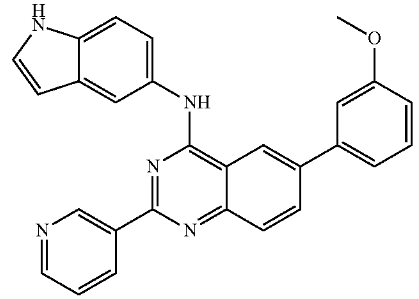 [SMILES: COc1cccc(-c2ccc3nc(-c4cccnc4)nc(Nc4ccc5[nH]ccc5c4)c3c2)c1] |

TABLE 4-continued
| | | |
|---|---|---|
| 737 | 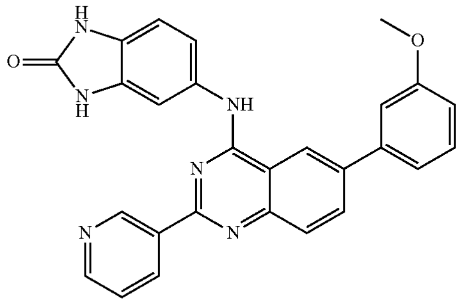 [SMILES: COc1cccc(-c2ccc3nc(-c4cccnc4)nc(Nc4ccc5[nH]c(=O)[nH]c5c4)c3c2)c1] | HCl |
| 738 | 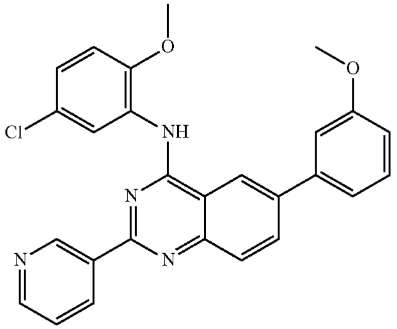 [SMILES: COc1cccc(-c2ccc3nc(-c4cccnc4)nc(Nc4cc(Cl)ccc4OC)c3c2)c1] | |
| 739 | 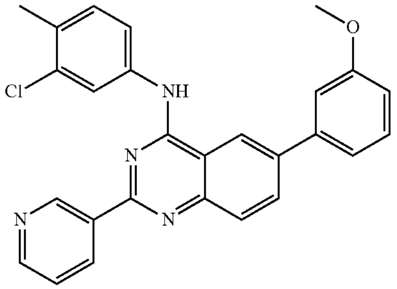 [SMILES: COc1cccc(-c2ccc3nc(-c4cccnc4)nc(Nc4ccc(C)c(Cl)c4)c3c2)c1] | |

TABLE 4-continued
| | |
|---|---|
| 740 | 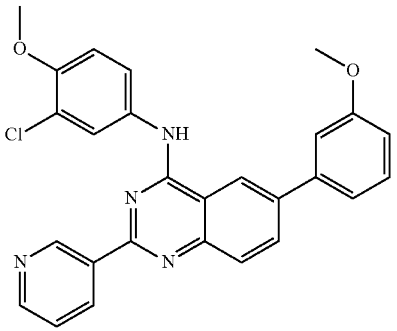 [SMILES: COc1cccc(-c2ccc3nc(-c4cccnc4)nc(Nc4ccc(OC)c(Cl)c4)c3c2)c1] |
| 741 | 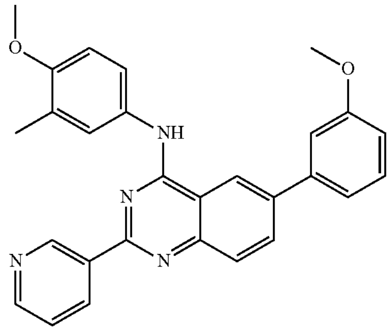 [SMILES: COc1cccc(-c2ccc3nc(-c4cccnc4)nc(Nc4ccc(OC)c(C)c4)c3c2)c1] |
| 742 | 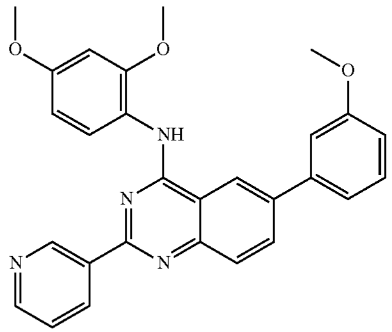 [SMILES: COc1cccc(-c2ccc3nc(-c4cccnc4)nc(Nc4ccc(OC)cc4OC)c3c2)c1] |

TABLE 4-continued
| | |
|---|---|
| 743 | 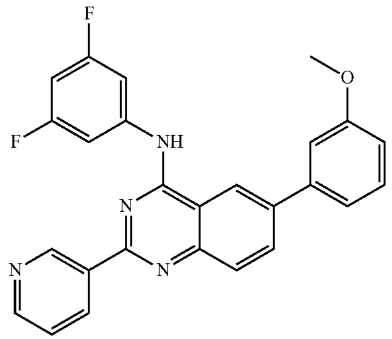 [SMILES: COc1cccc(-c2ccc3nc(-c4cccnc4)nc(Nc4cc(F)cc(F)c4)c3c2)c1] |
| 744 | 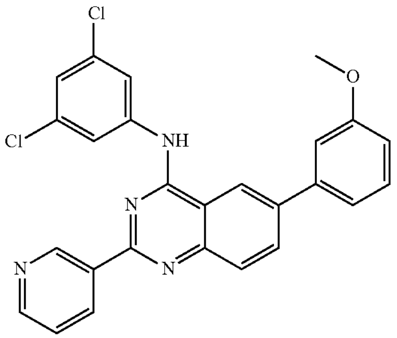 [SMILES: COc1cccc(-c2ccc3nc(-c4cccnc4)nc(Nc4cc(Cl)cc(Cl)c4)c3c2)c1] |
| 745 | 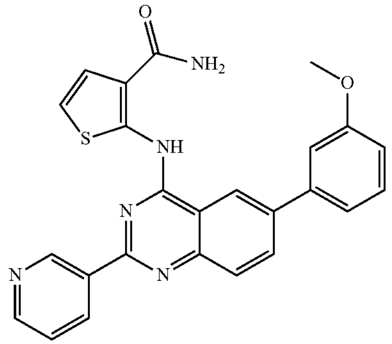 [SMILES: COc1cccc(-c2ccc3nc(-c4cccnc4)nc(Nc4sccc4C(N)=O)c3c2)c1] |

TABLE 4-continued
| | | |
|---|---|---|
| 746 | 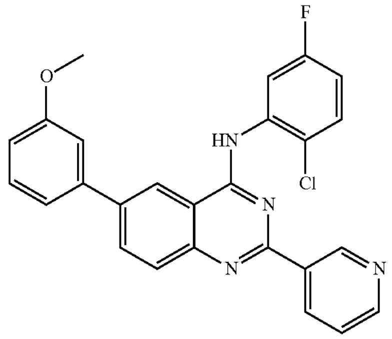 [SMILES: COc1cccc(-c2ccc3nc(-c4cccnc4)nc(Nc4cc(F)ccc4Cl)c3c2)c1] | 2 HCl |
| 747 | 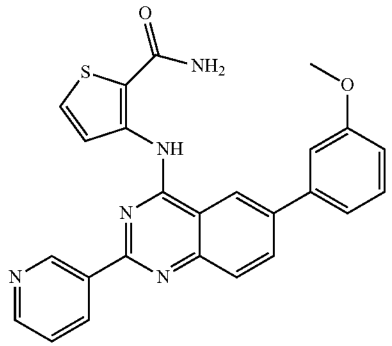 [SMILES: COc1cccc(-c2ccc3nc(-c4cccnc4)nc(Nc4ccsc4C(N)=O)c3c2)c1] | |
| Number | $^1$H NMR | $^1$H NMR Solvent | Purity Percent | Method of Coupling |
|---|---|---|---|---|
| 629 | $^1$H NMR (400 MHz, DMSO) δ 10.20 (s, 1H), 9.54 (s, 1H), 8.87 (s, 1H), 8.74-8.65 (m, 2H), 8.31-8.23 (m, 2H), 8.04-7.85 (m, 4H), 7.64-7.49 (m, 4H). | DMSO | >98 | N5 |
| 630 | $^1$H NMR (400 MHz, DMSO) δ 10.20 (s, 1H), 9.54 (d, J = 1.4 Hz, 1H), 8.86 (s, 1H), 8.76-8.64 (m, 2H), 8.26 (dd, J = 6.8, 2.3 Hz, 2H), 8.03-7.89 (m, 4H), 7.70-7.52 (m, 4H). | DMSO | >98 | N5 |
| 631 | $^1$H NMR (400 MHz, DMSO) δ 10.20 (s, 1H), 9.54 (d, J = 1.4 Hz, 1H), 8.86 (s, 1H), 8.76-8.64 (m, 2H), 8.26 (dd, J = 6.8, 2.3 Hz, 2H), 8.03-7.89 (m, 4H), 7.70-7.52 (m, 4H). | DMSO | >98 | N5 |

TABLE 4-continued

| | | | | |
|---|---|---|---|---|
| 632 | $^1$H NMR (400 MHz, DMSO) δ 10.22-10.11 (m, 1H), 9.54 (s, 1H), 8.86-8.77 (m, 1H), 8.74-8.65 (m, 2H), 8.30-8.17 (m, 2H), 8.01-7.90 (m, 2H), 7.74-7.66 (m, 2H), 7.60-7.51 (m, 2H), 7.51-7.42 (m, 1H), 7.28 (d, J = 7.5 Hz, 1H), 2.45 (s, 3H). | DMSO | >98 | N5 |
| 633 | $^1$H NMR (400 MHz, DMSO) δ 10.20 (s, 1H), 9.61-9.53 (m, 1H), 8.92 (s, 1H), 8.73-8.67 (m, 2H), 8.43-8.24 (m, 3H), 8.14-7.89 (m, 3H), 7.84-7.76 (m, 1H), 7.66-7.53 (m, 2H). | DMSO | >98 | N5 |
| 634 | $^1$H NMR (400 MHz, DMSO) δ 10.20 (s, 1H), 9.55 (d, J = 1.2 Hz, 1H), 8.89 (s, 1H), 8.75-8.67 (m, 2H), 8.35-8.22 (m, 2H), 8.00 (d, J = 8.7 Hz, 1H), 7.96-7.90 (m, 1H), 7.84-7.75 (m, 2H), 7.66-7.52 (m, 3H), 7.34-7.27 (m, 1H). | DMSO | >98 | N5 |
| 635 | $^1$H NMR (400 MHz, DMSO) δ 10.27 (s, 1H), 9.54 (d, J = 1.2 Hz, 1H), 8.94 (s, 1H), 8.77-8.66 (m, 3H), 8.40-8.21 (m, 4H), 7.99 (d, J = 8.9 Hz, 1H), 7.88 (t, J = 8.0 Hz, 2H), 7.61-7.50 (m, 2H). | DMSO | >98 | N5 |
| 636 | $^1$H NMR (400 MHz, DMSO) δ 10.13 (s, 1H), 9.56 (s, 1H), 8.77-8.68 (m, 2H), 8.65 (s, 1H), 8.27 (dd, J = 6.9, 2.6 Hz, 1H), 8.04-7.97 (m, 2H), 7.96-7.88 (m, 1H), 7.70-7.43 (m, 6H). | DMSO | >98 | N5 |
| 637 | $^1$H NMR (400 MHz, DMSO) δ 10.10 (s, 1H), 9.56 (s, 1H), 8.76-8.68 (m, 2H), 8.63 (s, 1H), 8.28 (dd, J = 6.7, 2.7 Hz, 1H), 8.05 (dd, J = 8.7, 1.8 Hz, 1H), 8.00-7.90 (m, 2H), 7.70-7.43 (m, 4H), 7.21 (d, J = 8.1 Hz, 1H), 7.14 (t, J = 7.4 Hz, 1H), 3.82 (s, 3H). | DMSO | >98 | N5 |
| 638 | $^1$H NMR (400 MHz, DMSO) δ 10.16 (s, 1H), 9.54 (s, 1H), 8.81 (s, 1H), 8.74-8.64 (m, 2H), 8.30-8.17 (m, 2H), 8.01-7.87 (m, 4H), 7.61-7.51 (m, 2H), 7.42 (t, J = 8.8 Hz, 2H). | DMSO | >98 | N5 |

TABLE 4-continued

| | | | | |
|---|---|---|---|---|
| 639 | 1H NMR (400 MHz, DMSO) δ 10.21 (s, 1H), 9.57 (s, 1H), 8.80 (d, J = 1.8 Hz, 1H), 8.76-8.69 (m, 2H), 8.27 (dd, J = 6.9, 2.6 Hz, 1H), 8.14 (dd, J = 8.6, 1.8 Hz, 1H), 8.10-8.02 (m, 2H), 7.97-7.88 (m, 2H), 7.83 (d, J = 6.8 Hz, 1H), 7.70 (td, J = 7.6, 1.2 Hz, 1H), 7.63-7.52 (m, 2H). | DMSO | >98 | N5 |
| 640 | $^1$H NMR (400 MHz, DMSO) δ 10.12 (s, 1H), 9.55 (s, 1H), 8.77-8.66 (m, 2H), 8.62 (s, 1H), 8.25 (dd, J = 6.8, 2.3 Hz, 1H), 8.16 (d, J = 8.3 Hz, 1H), 7.99-7.80 (m, 4H), 7.80-7.71 (m, 2H), 7.61-7.49 (m, 2H). | DMSO | >98 | N5 |
| 641 | 1H NMR (400 MHz, DMSO) δ 9.57 (s, 1H), 8.85-8.55 (m, 3H), 8.20-7.95 (m, 3H), 7.85-7.20 (m, 7H) | DMSO | >98 | N5 |
| 642 | $^1$H NMR (400 MHz, DMSO) δ 10.19 (s, 1H), 9.55 (d, J = 1.2 Hz, 1H), 8.83 (s, 1H), 8.74-8.66 (m, 2H), 8.32-8.23 (m, 2H), 8.02-7.89 (m, 2H), 7.61-7.53 (m, 2H), 7.05 (d, J = 2.2 Hz, 2H), 6.62 (t, J = 2.1 Hz, 1H), 3.88 (s, 6H). | DMSO | >98 | N5 |
| 643 | $^1$H NMR (400 MHz, DMSO) δ 10.18 (s, 1H), 9.55 (d, J = 2.0 Hz, 1H), 8.81 (d, J = 1.7 Hz, 1H), 8.74-8.65 (m, 2H), 8.31-8.20 (m, 2H), 8.04-7.88 (m, 2H), 7.65-7.53 (m, 2H), 7.42-7.34 (m, 1H), 7.23-7.09 (m, 2H), 6.83 (dd, J = 8.3, 1.9 Hz, 1H), 3.02 (s, 6H). | DMSO | >98 | N5 |
| 644 | 1H NMR (400 MHz, DMSO) δ 10.14 (s, 1H), 9.55 (s, 1H), 8.77-8.68 (m, 2H), 8.65 (d, J = 1.5 Hz, 1H), 8.28 (dd, J = 6.9, 2.6 Hz, 1H), 8.05 (dd, J = 8.6, 1.7 Hz, 1H), 8.01-7.90 (m, 2H), 7.60-7.51 (m, 2H), 7.29-7.21 (m, 1H), 7.18 (dd, J = 8.3, 1.6 Hz, 1H), 7.12 (dd, J = 7.6, 1.6 Hz, 1H), 3.89 (s, 3H), 3.58 (s, 3H). | DMSO | >98 | N5 |

TABLE 4-continued

| | | | | |
|---|---|---|---|---|
| 645 | 1H NMR (400 MHz, DMSO) δ 10.09 (s, 1H), 9.56 (s, 1H), 8.74-8.67 (m, 2H), 8.64 (s, 1H), 8.28 (dd, J = 6.9, 2.6 Hz, 1H), 8.06 (dd, J = 8.6, 1.7 Hz, 1H), 7.98-7.89 (m, 2H), 7.62-7.51 (m, 2H), 7.14 (d, J = 9.0 Hz, 1H), 7.09 (d, J = 3.1 Hz, 1H), 7.02 (dd, J = 8.9, 3.1 Hz, 1H), 3.81 (s, 3H), 3.76 (s, 3H). | DMSO | >98 | N5 |
| 646 | 1H NMR (400 MHz, DMSO) δ 9.99 (s, 1H), 9.56 (d, J = 0.9 Hz, 1H), 8.71 (dd, J = 7.1, 1.6 Hz, 2H), 8.46 (d, J = 1.5 Hz, 1H), 8.29 (dd, J = 6.9, 2.6 Hz, 1H), 8.00-7.87 (m, 2H), 7.73 (dd, J = 8.5, 1.7 Hz, 1H), 7.63-7.47 (m, 2H), 7.41 (t, J = 8.4 Hz, 1H), 6.84 (d, J = 8.5 Hz, 2H), 3.77-3.66 (m, 6H). | DMSO | >98 | N5 |
| 647 | $^{1}$H NMR (400 MHz, DMSO) δ 10.06-9.96 (m, 1H), 9.52 (s, 1H), 8.75-8.62 (m, 3H), 8.40-8.33 (m, 1H), 8.28-8.22 (m, 1H), 8.22-8.14 (m, 1H), 7.97-7.85 (m, 3H), 7.64-7.49 (m, 2H), 7.16 (s, 1H). | DMSO | >98 | N5 |
| 648 | $^{1}$H NMR (400 MHz, DMSO) δ 10.10 (s, 1H), 9.54 (s, 1H), 8.85 (s, 1H), 8.77-8.65 (m, 2H), 8.32 (d, J = 3.7 Hz, 1H), 8.26 (dd, J = 6.8, 2.6 Hz, 1H), 8.12 (s, 1H), 7.94 (d, J = 8.7 Hz, 2H), 7.86-7.76 (m, 2H), 7.64-7.54 (m, 2H). | DMSO | >98 | N5 |
| 649 | 1H NMR (400 MHz, DMSO) δ 10.20 (s, 1H), 9.53 (s, 1H), 8.78 (s, 1H), 8.71-8.64 (m, 2H), 8.26-8.19 (m, 2H), 7.95-7.90 (m, 2H), 7.77-7.69 (m, 2H), 7.60-7.53 (m, 2H), 7.26 (t, J = 3.7 Hz, 1H). | DMSO | >98 | N5 |
| 650 | $^{1}$H NMR (400 MHz, DMSO) δ 10.12 (s, 1H), 9.55 (d, J = 2.2 Hz, 1H), 8.75-8.67 (m, 3H), 8.33-8.23 (m, 2H), 8.13 (dd, J = 8.7, 1.8 Hz, 1H), 8.00-7.90 (m, 3H), 7.63-7.51 (m, 2H), 7.22 (dd, J = 7.3, 5.0 Hz, 1H), 3.95 (s, 3H). | DMSO | >98 | N5 |

TABLE 4-continued

| | | | | |
|---|---|---|---|---|
| 651 | $^1$H NMR (400 MHz, DMSO) δ 10.22 (s, 1H), 9.53 (s, 1H), 8.97 (s, 1H), 8.75 (d, J = 5.5 Hz, 2H), 8.73-8.64 (m, 2H), 8.38-8.30 (m, 1H), 8.24 (d, J = 6.8 Hz, 1H), 8.05-7.97 (m, 1H), 7.97-7.88 (m, 3H), 7.63-7.51 (m, 2H). | DMSO | >98 | N5 |
| 652 | 1H NMR (400 MHz, DMSO) δ 10.05 (s, 1H), 9.50 (s, 1H), 9.33 (s, 2H), 9.26 (s, 1H), 8.90 (s, 1H), 8.69 (d, J = 3.6 Hz, 1H), 8.64 (d, J = 8.0 Hz, 1H), 8.33 (d, J = 8.6 Hz, 1H), 8.22 (dd, J = 6.7, 2.0 Hz, 1H), 7.96 (d, J = 8.7 Hz, 1H), 7.93-7.86 (m, 1H), 7.61-7.48 (m, 2H). | DMSO | >98 | N5 |
| 653 | $^1$H NMR (400 MHz, DMSO) δ 10.10 (s, 1H), 9.55 (d, J = 1.2 Hz, 1H), 8.77-8.67 (m, 2H), 8.61 (s, 1H), 8.26 (dd, J = 6.9, 2.6 Hz, 1H), 8.12 (dd, J = 8.7, 1.8 Hz, 1H), 8.01-7.89 (m, 3H), 7.62-7.51 (m, 2H), 4.02 (s, 3H), 4.00 (s, 3H). | DMSO | >98 | N5 |
| 654 | $^1$H NMR (400 MHz, DMSO) δ 10.09 (s, 1H), 9.56 (s, 1H), 8.77-8.68 (m, 2H), 8.65 (d, J = 1.6 Hz, 1H), 8.30 (dd, J = 6.9, 2.6 Hz, 1H), 8.17 (dd, J = 8.7, 1.7 Hz, 1H), 7.99-7.88 (m, 2H), 7.61-7.50 (m, 2H), 7.42-7.33 (m, 2H), 7.21-7.08 (m, 2H), 2.53 (s, 6H). | DMSO | >98 | N5 |
| 655 | $^1$H NMR (400 MHz, DMSO) δ 10.08 (s, 1H), 9.55 (s, 1H), 8.74-8.66 (m, 2H), 8.63 (s, 1H), 8.26 (dd, J = 6.8, 2.5 Hz, 1H), 8.12 (d, J = 8.7 Hz, 1H), 7.97-7.88 (m, 3H), 7.62-7.51 (m, 2H), 6.61 (d, J = 3.1 Hz, 1H), 3.97 (s, 3H), 3.96 (s, 3H). | DMSO | >98 | N5 |
| 656 | $^1$H NMR (400 MHz, DMSO) δ 10.21 (s, 1H), 9.54 (d, J = 2.0 Hz, 1H), 8.91 (s, 1H), 8.76-8.65 (m, 2H), 8.31 (d, J = 8.8 Hz, 1H), 8.26 (dd, J = 6.8, 2.6 Hz, 1H), 8.15-7.89 (m, 7H), 7.61-7.52 (m, 2H), 7.46 (s, 1H). | DMSO | >98 | N5 |

TABLE 4-continued

| | | | | |
|---|---|---|---|---|
| 657 | $^1$H NMR (400 MHz, DMSO) δ 10.21 (s, 1H), 9.54 (d, J = 2.0 Hz, 1H), 8.91 (s, 1H), 8.76-8.65 (m, 2H), 8.31. (d, J = 8.8 Hz, 1H), 8.26 (dd, J = 6.8, 2.6 Hz, 1H), 8.15-7.89 (m, 7H), 7.61-7.52 (m, 2H), 7.46 (s, 1H). | DMSO | >98 | N5 |
| 658 | $^1$H NMR (400 MHz, DMSO) δ 10.20 (s, 1H), 9.54 (s, 1H), 8.88 (s, 1H), 8.79-8.61 (m, 2H), 8.34-8.22 (m, 2H), 8.05-7.84 (m, 4H), 7.72 (t, J = 8.0 Hz, 1H), 7.65-7.53 (m, 2H), 7.47 (d, J = 8.4 Hz, 1H). | DMSO | >98 | N5 |
| 659 | 1H NMR (400 MHz, DMSO) δ 10.06 (s, 1H), 9.53 (s, 1H), 8.75 (s, 1H), 8.75-8.66 (m, 3H), 8.28-8.21 (m, 1H), 8.20 (dd, J = 7.7, 1.8 Hz, 1H), 8.06 (dd, J = 8.9, 2.5 Hz, 1H), 7.96-7.90 (m, 2H), 7.58-7.54 (m, 2H), 6.81 (d, J = 8.9 Hz, 1H), 3.11 (s, 6H). | DMSO | >98 | N5 |
| 660 | $^1$H NMR (400 MHz, DMSO) δ 10.15 (s, 1H), 9.54 (s, 1H), 8.51 (s, 1H), 8.76 (s, 1H), 8.74-8.66 (m, 2H), 8.39 (d, J = 2.7 Hz, 1H), 8.37-8.30 (m, 1H), 8.26 (dd, J = 6.8, 2.6 Hz, 1H), 8.03-7.97 (m, 1H), 7.97-7.90 (m, 1H), 7.85 (d, J = 1.9 Hz, 1H), 7.62-7.52 (m, 2H), 3.98 (s, 3H). | DMSO | >98 | N5 |
| 661 | $^1$H NMR (400 MHz, DMSO) δ 10.06 (s, 1H), 9.52 (d, J = 1.3 Hz, 1H), 8.76 (d, J = 19.6 Hz, 1H), 8.73-8.61 (m, 3H), 8.29-8.16 (m, 3H), 7.99-7.87 (m, 2H), 7.61-7.51 (m, 2H), 6.98 (d, J = 8.6 Hz, 1H), 4.39 (q, J = 7.0 Hz, 2H), 1.37 (t, J = 7.0 Hz, 3H). | DMSO | >98 | N5 |
| 662 | $^1$H NMR (400 MHz, DMSO) δ 10.11 (s, 1H), 9.53 (dd, J = 2.1, 0.7 Hz, 1H), 8.75 (d, J = 1.9 Hz, 1H), 8.73-8.64 (m, 2H), 8.25 (dd, J = 6.9, 2.6 Hz, 1H), 8.19 (dd, J = 8.7, 1.9 Hz, 1H), 7.97-7.89 (m, 2H), 7.61-7.50 (m, 3H), 7.41 (dd, J = 8.1, 1.9 Hz, 1H), 7.11 (d, J = 8.1 Hz, 1H), 6.13 (s, 2H). | DMSO | >98 | N5 |
| 663 | $^1$H NMR (400 MHz, DMSO) δ 10.19 (s, 1H), 9.54 (s, 1H), 8.85 (s, 1H), 8.76-8.66 (m, 2H), 8.33-8.22 (m, 2H), 8.00-7.89 (m, 2H), 7.62-7.52 (m, 3H), 7.43 (s, 1H), 7.14 (s, 1H), 3.91 (s, 3H). | DMSO | >98 | N5 |

TABLE 4-continued

| | | | | |
|---|---|---|---|---|
| 664 | $^1$H NMR (400 MHz, DMSO) δ 10.16 (s, 1H), 9.52 (d, J = 1.3 Hz, 1H), 8.89-8.81 (m, 1H), 8.73-8.64 (m, 2H), 8.37-8.28 (m, 1H), 8.28-8.21 (m, 1H), 8.01-7.86 (m, 2H), 7.81-7.69 (m, 2H), 7.60-7.51 (m, 2H), 7.33 (s, 1H), 3.97 (s, 3H). | DMSO | >98 | N5 |
| 665 | 1H NMR (400 MHz, DMSO) δ 10.1.9 (s, 1H), 9.53 (d, J = 1.9 Hz, 1H), 8.89 (s, 1H), 8.73-8.61 (m, 2H), 8.57 (d, J = 4.5 Hz, 1H), 8.34-8.18 (m, 2H), 8.09-7.86 (m, 5H), 7.62-7.49 (m, 2H), 2.88-2.80 (m, 4H). | DMSO | >98 | N5 |
| 666 | $^1$H NMR (400 MHz, DMSO) δ 10.57 (s, 1H), 9.52 (d, J = 1.6 Hz, 1H), 9.21 (s, 2H), 9.08-9.02 (m, 1H), 9.02-8.96 (m, 1H), 8.89 (dd, J = 5.2, 1.5 Hz, 1H), 8.39-8.30 (m, 1H), 8.25-8.18 (m, 1H), 8.07-7.87 (m, 3H), 7.56 (t, J = 9.1 Hz, 1H). | DMSO | >98 | N5 |
| 667 | $^1$H NMR (400 MHz, DMSO) δ 10.78 (s, 1H), 9.53 (s, 1H), 9.16-9.02 (m, 2H), 8.99-8.88 (m, 1H), 8.66-8.55 (m, 1H), 8.38 (d, J = 8.2 Hz, 1H), 8.20 (d, J = 5.0 Hz, 1H), 8.04 (dt, J = 27.3, 13.6 Hz, 7H), 7.57 (t, J = 8.8 Hz, 1H), 2.84 (d, J = 3.8 Hz, 3H). | DMSO | >98 | N5 |
| 668 | $^1$H NMR (400 MHz, DMSO) δ 10.49 (s, 1H), 9.53 (d, J = 1.5 Hz, 1H), 8.99-8.83 (m, 3H), 8.34-8.25 (m, 1H), 8.21 (dd, J = 6.8, 2.6 Hz, 1H), 8.03 (d, J = 8.7 Hz, 1H), 7.98-7.91 (m, 1H), 7.86 (dd, J = 7.8, 5.2 Hz, 1H), 7.78-7.70 (m, 2H), 7.57 (t, J = 9.1 Hz, 1H), 7.47 (t, J = 7.6 Hz, 1H), 7.29 (d, J = 7.5 Hz, 1H), 2.45 (s, 6H). | DMSO | >98 | N5 |
| 669 | $^1$H NMR (400 MHz, DMSO) δ 10.22 (s, 1H), 9.55 (d, J = 1.4 Hz, 1H), 8.81-8.70 (m, 3H), 8.25 (dd, J = 6.8, 2.6 Hz, 1H), 8.13-8.05 (m, 1H), 7.99 (d, J = 8.7 Hz, 1H), 7.97-7.89 (m, 1H), 7.64 (dd, J = 7.9, 4.9 Hz, 1H), 7.61-7.49 (m, 2H), 7.37-7.26 (m, 2H), 2.41 (s, 3H). | DMSO | >98 | N5 |

TABLE 4-continued

| | | | | |
|---|---|---|---|---|
| 670 | $^1$H NMR (400 MHz, DMSO) δ 10.77 (s, 1H), 9.52 (d, J = 1.6 Hz, 1H), 9.09-8.95 (m, 2H), 8.90 (dd, J = 5.2, 1.5 Hz, 1H), 8.41-8.29 (m, 1H), 8.23 (dd, J = 6.8, 2.6 Hz, 1H), 8.05 (d, J = 8.7 Hz, 1H), 8.01-7.88 (m, 2H), 7.56 (t, J = 9.1 Hz, 1H), 7.50-7.38 (m, 2H), 7.32 (d, J = 8.2 Hz, 1H), 3.97 (s, 3H), 2.23 (s, 3H). | DMSO | >98 | N5 |
| 671 | $^1$H NMR (400 MHz, DMSO) δ 10.77 (s, 1H), 9.52 (d, J = 1.6 Hz, 1H), 9.09-8.95 (m, 2H), 8.90 (dd, J = 5.2, 1.5 Hz, 1H), 8.41-8.29 (m, 1H), 8.23 (dd, J = 6.8, 2.6 Hz, 1H), 8.05 (d, J = 8.7 Hz, 1H), 8.01-7.88 (m, 2H), 7.56 (t, J = 9.1 Hz, 1H), 7.50-7.38 (m, 2H), 7.32 (d, J = 8.2 Hz, 1H), 3.97 (s, 3H), 2.23 (s, 3H). | DMSO | >98 | N5 |
| 672 | $^1$H NMR (400 MHz, DMSO) δ 10.67 (s, 1H), 9.47 (d, J = 1.6 Hz, 1H), 9.04-8.94 (m, 2H), 8.89 (dd, J = 5.3, 1.5 Hz, 1H), 8.26 (dd, J = 8.8, 1.9 Hz, 1H), 8.18 (dd, J = 6.8, 2.6 Hz, 1H), 8.09-8.00 (m, 1H), 8.00-7.87 (m, 3H), 7.86-7.77 (m, 1H), 7.68-7.57 (m, 1H), 7.53 (t, J = 9.1 Hz, 1H). | DMSO | >98 | N5 |
| 673 | $^1$H NMR (400 MHz, DMSO) δ 10.82 (s, 1H), 9.53 (s, 1H), 9.17-9.04 (m, 1H), 9.04-8.93 (m, 2H), 8.34 (dd, J = 8.7, 1.7 Hz, 1H), 8.18 (dd, J = 6.8, 2.6 Hz, 1H), 8.08 (d, J = 8.6 Hz, 1H), 8.05-7.89 (m, 2H), 7.57 (t, J = 9.0 Hz, 1H), 7.53-7.44 (m, 3H), 7.09-6.98 (m, 1H), 4.82 (dt, J = 11.7, 5.9 Hz, 1H), 1.33 (d, J = 6.0 Hz, 6H). | DMSO | >98 | N5 |
| 674 | $^1$H NMR (400 MHz, DMSO) δ 10.60 (s, 1H), 9.50 (d, J = 1.7 Hz, 1H), 9.11-9.02 (m, 1H), 8.99-8.91 (m, 1H), 8.76 (d, J = 8.8 Hz, 1H), 8.25 (d, J = 1.4 Hz, 1H), 8.19 (dd, J = 6.8, 2.6 Hz, 1H), 8.10-7.92 (m, 4H), 7.82-7.72 (m, 1H), 7.65-7.56 (m, 1H), 7.52 (t, J = 9.1 Hz, 1H). | DMSO | >98 | N5 |

TABLE 4-continued

| | | | | |
|---|---|---|---|---|
| 675 | $^1H$ NMR (400 MHz, DMSO) δ 10.51 (s, 1H), 9.51 (d, J = 1.7 Hz, 1H), 9.07-9.00 (m, 1H), 8.93 (dd, J = 5.3, 1.4 Hz, 1H), 8.75 (d, J = 8.8 Hz, 1H), 8.28 (d, J = 1.7 Hz, 1H), 8.21 (dd, J = 6.8, 2.6 Hz, 1H), 8.10 (dd, J = 8.7, 1.9 Hz, 1H), 8.02-7.93 (m, 2H), 7.74-7.65 (m, 2H), 7.52 (t, J = 9.1 Hz, 1H), 7.40-7.31 (m, 1H). | DMSO | >98 | N5 |
| 676 | $^1H$ NMR (400 MHz, DMSO) δ 10.63 (s, 1H), 9.54 (d, J = 1.7 Hz, 1H), 9.10 (d, J = 8.1 Hz, 1H), 8.95 (dd, J = 5.3, 1.4 Hz, 1H), 8.81 (d, J = 8.7 Hz, 1H), 8.26-8.14 (m, 2H), 8.08-7.91 (m, 3H), 7.75-7.64 (m, 1H), 7.51 (ddd, J = 14.7, 14.2, 6.9 Hz, 2H), 7.44-7.34 (m, 1H). | DMSO | >98 | N5 |
| 677 | $^1H$ NMR (400 MHz, DMSO) δ 10.52 (s, 1H), 9.60-9.49 (m, 1H), 9.37-9.31 (m, 1H), 8.99 (d, J = 8.3 Hz, 1H), 8.95-8.81 (m, 3H), 8.75 (d, J = 8.3 Hz, 1H), 8.40 (d, J = 1.7 Hz, 1H), 8.30-8.18 (m, 2H), 8.04-7.87 (m, 3H), 7.56 (t, J = 9.1 Hz, 1H). | DMSO | >98 | N5 |
| 678 | $^1H$ NMR (400 MHz, DMSO) δ 10.42 (s, 1H), 9.50 (d, J = 1.6 Hz, 1H), 9.38 (s, 2H), 9.30 (s, 1H), 9.00-8.92 (m, 1H), 8.92-8.86 (m, 1H), 8.76 (d, J = 8.7 Hz, 1H), 8.34 (d, J = 1.7 Hz, 1H), 8.23 (dd, J = 6.8, 2.6 Hz, 1H), 8.15 (dd, J = 8.6, 1.8 Hz, 1H), 7.99-7.85 (m, 2H), 7.52 (t, J = 9.1 Hz, 1H). | DMSO | >98 | N5 |
| 679 | $^1H$ NMR (400 MHz, DMSO) δ 10.47 (s, 1H), 9.58-9.49 (m, 1H), 9.21 (s, 2H), 9.09-8.98 (m, 1H), 8.92 (d, J = 3.8 Hz, 1H), 8.77 (d, J = 8.8 Hz, 1H), 8.32 (d, J = 1.8 Hz, 1H), 8.27-8.20 (m, 1H), 8.15 (dd, J = 8.7, 1.8 Hz, 1H), 8.03-7.89 (m, 2H), 7.55 (t, J = 9.1 Hz, 1H), 4.02 (s, 3H). | DMSO | >98 | N5 |

TABLE 4-continued

| | | | | |
|---|---|---|---|---|
| 680 | $^1$H NMR (400 MHz, DMSO) δ 10.09 (s, 1H), 9.56 (d, J = 1.3 Hz, 1H), 8.75-8.67 (m, 2H), 8.60 (d, J = 8.7 Hz, 1H), 8.32 (dd, J = 6.9, 2.6 Hz, 1H), 8.10 (d, J = 1.6 Hz, 1H), 8.03-7.87 (m, 4H), 7.60-7.50 (m, 2H), 7.12 (d, J = 8.8 Hz, 2H), 3.85 (s, 3H). | DMSO | >98 | N5 |
| 681 | $^1$H NMR (400 MHz, DMSO) δ 10.05 (s, 1H), 9.55-9.46 (m, 1H), 8.69-8.60 (m, 2H), 8.56 (d, J = 8.7 Hz, 1H), 8.25 (dd, J = 6.9, 2.6 Hz, 1H), 8.10 (d, J = 1.8 Hz, 1H), 7.96 (dd, J = 8.7, 1.9 Hz, 1H), 7.91-7.85 (m, 1H), 7.55-7.35 (m, 5H), 7.03-6.95 (m, 1H), 3.83 (s, 3H). | DMSO | >98 | N5 |
| 682 | $^1$H NMR (400 MHz, DMSO) δ 10.09 (s, 1H), 9.55 (d, J = 1.9 Hz, 1H), 8.74-8.67 (m, 2H), 8.57 (d, J = 8.7 Hz, 1H), 8.32 (dd, J = 6.9, 2.6 Hz, 1H), 8.00-7.91 (m, 2H), 7.80 (dd, J = 8.6, 1.7 Hz, 1H), 7.60-7.41 (m, 4H), 7.21 (d, J = 7.8 Hz, 1H), 7.12 (td, J = 7.4, 0.9 Hz, 1H), 3.84 (s, 3H). | DMSO | >98 | N5 |
| 683 | $^1$H NMR (400 MHz, DMSO) δ 10.10 (s, 1H), 9.55 (s, 1H), 8.74-8.65 (m, 2H), 8.56 (d, J = 8.6 Hz, 1H), 8.35-8.26 (m, 1H), 7.99-7.89 (m, 2H), 7.81 (s, 1H), 7.70 (dd, J = 8.6, 1.6 Hz, 1H), 7.63-7.47 (m, 6H), 7.40 (s, 1H). | DMSO | >98 | N5 |
| 684 | $^1$H NMR (400 MHz, DMSO) δ 10.16 (s, 1H), 9.61-9.53 (m, 1H), 8.76-8.62 (m, 3H), 8.35-8.28 (m, 1H), 8.24 (d, J = 1.8 Hz, 1H), 8.16-7.99 (m, 6H), 7.99-7.92 (m, 1H), 7.63-7.51 (m, 2H), 7.45 (s, 1H). | DMSO | >98 | N5 |
| 685 | $^1$H NMR (400 MHz, DMSO) δ 10.21 (s, 1H), 9.55 (d, J = 1.5 Hz, 1H), 8.78-8.62 (m, 3H), 8.31 (dd, J = 6.9, 2.6 Hz, 1H), 8.15-8.00 (m, 2H), 8.00-7.80 (m, 5H), 7.74-7.65 (m, 1H), 7.64-7.51 (m, 2H). | DMSO | >98 | N5 |

TABLE 4-continued

| | | | | |
|---|---|---|---|---|
| 686 | $^1H$ NMR (400 MHz, DMSO) δ 10.18 (s, 1H), 9.60-9.55 (m, 1H), 8.77-8.65 (m, 2H), 8.46 (s, 1H), 8.37-8.28 (m, 2H), 8.17-8.10 (m, 1H), 7.99-7.93 (m, 2H), 7.81-7.72 (m, 2H), 7.62-7.50 (m, 3H). | DMSO | >98 | N5 |
| 687 | $^1H$ NMR (400 MHz, DMSO) δ 10.18 (s, 1H), 9.56 (d, J = 2.2 Hz, 1H), 8.75-8.61 (m, 3H), 8.32 (dd, J = 6.8, 2.6 Hz, 1H), 8.07 (s, 1H), 7.99-7.91 (m, 1H), 7.91-7.85 (m, 1H), 7.82-7.75 (m, 1H), 7.61-7.50 (m, 3H), 7.47-7.36 (m, 2H). | DMSO | >98 | N5 |
| 688 | $^1H$ NMR (400 MHz, DMSO) δ 10.14 (s, 1H), 9.60-9.53 (m, 1H), 8.74-8.61 (m, 3H), 8.31 (dd, J = 6.9, 2.6 Hz, 1H), 8.20 (d, J = 1.8 Hz, 1H), 8.06 (dd, J = 8.7, 1.9 Hz, 1H), 7.99-7.90 (m, 1H), 7.86-7.77 (m, 2H), 7.65-7.48 (m, 3H), 7.37-7.26 (m, 1H). | DMSO | >98 | N5 |
| 689 | $^1H$ NMR (400 MHz, DMSO) δ 10.13 (s, 1H), 9.56 (d, J = 1.5 Hz, 1H), 8.75-8.60 (m, 3H), 8.31 (dd, J = 6.9, 2.6 Hz, 1H), 8.15 (d, J = 1.7 Hz, 1H), 8.07-7.88 (m, 4H), 7.65-7.49 (m, 2H), 7.39 (t, J = 8.8 Hz, 2H). | DMSO | >98 | N5 |
| 690 | $^1H$ NMR (400 MHz, DMSO) δ 10.14 (s, 1H), 9.54 (d, J = 1.6 Hz, 1H), 8.76-8.60 (m, 3H), 8.34-8.25 (m, 1H), 8.21 (d, J = 1.7 Hz, 1H), 8.13 (d, J = 8.4 Hz, 2H), 8.10-7.97 (m, 3H), 7.97-7.87 (m, 1H), 7.62-7.45 (m, 2H). | DMSO | >98 | N5 |
| 691 | $^1H$ NMR (400 MHz, DMSO) δ 10.45 (s, 1H), 9.54 (d, J = 1.6 Hz, 1H), 8.99-8.91 (m, 1H), 8.91-8.83 (m, 1H), 8.75 (d, J = 8.8 Hz, 1H), 8.42 (s, 1H), 8.31 (t, J = 3.2 Hz, 1H), 8.29-8.22 (m, 2H), 8.13 (dd, J = 8.7, 1.8 Hz, 1H), 8.08 (d, J = 7.8 Hz, 1H), 8.03-7.92 (m, 2H), 7.86 (dd, J = 8.0, 5.2 Hz, 1H), 7.65 (t, J = 7.7 Hz, 1H), 7.59-7.46 (m, 2H). | DMSO | >98 | N5 |

TABLE 4-continued

| | | | | |
|---|---|---|---|---|
| 692 | $^1H$ NMR (400 MHz, DMSO) δ 10.38 (s, 1H), 9.56 (d, J = 1.5 Hz, 1H), 8.93 (d, J = 8.2 Hz, 1H), 8.85 (dd, J = 5.1, 1.5 Hz, 1H), 8.71 (d, J = 8.8 Hz, 1H), 8.27 (dd, J = 6.8, 2.6 Hz, 1H), 8.21 (d, J = 1.7 Hz, 1H), 8.10 (dd, J = 8.7, 1.8 Hz, 1H), 8.01-7.90 (m, 3H), 7.83 (dd, J = 7.8, 5.0 Hz, 1H), 7.64-7.46 (m, 4H). | DMSO | >98 | N5 |
| 693 | $^1H$ NMR (400 MHz, DMSO) δ 10.91 (s, 1H), 9.52 (d, J = 1.5 Hz, 1H), 9.14 (d, J = 8.1 Hz, 1H), 9.00 (dd, J = 5.4, 1.2 Hz, 1H), 8.91 (d, J = 8.8 Hz, 1H), 8.34 (d, J = 5.1 Hz, 1H), 8.20 (dd, J = 6.8, 2.6 Hz, 1H), 8.14-8.04 (m, 2H), 8.04-7.89 (m, 2H), 7.75-7.48 (m, 4H), 3.18 (s, 6H). | DMSO | >98 | N5 |
| 694 | $^1H$ NMR (400 MHz, DMSO) δ 10.99 (s, 1H), 9.52 (d, J = 1.7 Hz, 1H), 9.08 (d, J = 8.0 Hz, 1H), 8.97 (dd, J = 5.3, 1.4 Hz, 1H), 8.30 (d, J = 8.3 Hz, 1H), 8.33 (d, J = 2.3 Hz, 1H), 8.18 (dd, J = 6.8, 2.6 Hz, 1H), 8.10 (dd, J = 8.8, 1.8 Hz, 1H), 8.04-7.91 (m, 2H), 7.85 (d, J = 8.7 Hz, 2H), 7.56 (t, J = 9.1 Hz, 1H), 7.09 (s, 2H), 3.05 (s, 6H). | DMSO | >98 | N5 |
| 695 | $^1H$ NMR (400 MHz, DMSO) δ 10.67 (s, 1H), 9.53 (d, J = 1.7 Hz, 1H), 9.07 (d, J = 8.2 Hz, 1H), 8.95 (dd, J = 5.3, 1.4 Hz, 1H), 8.78 (d, J = 8.7 Hz, 1H), 8.26 (s, 1H), 8.21 (dd, J = 6.8, 2.6 Hz, 1H), 8.09 (dd, J = 8.7, 1.8 Hz, 1H), 8.04-7.92 (m, 2H), 7.79-7.67 (m, 2H), 7.55 (t, J = 9.1 Hz, 1H), 7.46 (t, J = 7.6 Hz, 1H), 7.32 (d, J = 7.5 Hz, 1H), 2.45 (s, 3H). | DMSO | >98 | N5 |
| 696 | $^1H$ NMR (400 MHz, DMSO) δ 10.48 (s, 1H), 9.54 (d, J = 1.5 Hz, 1H), 8.97 (d, J = 8.1 Hz, 1H), 8.93-8.84 (m, 1H), 8.71 (d, J = 8.8 Hz, 1H), 8.30-8.16 (m, 2H), 8.08 (dd, J = 8.7, 1.8 Hz, 1H), 8.01-7.78 (m, 4H), 7.55 (t, J = 9.1 Hz, 1H), 7.39 (d, J = 7.9 Hz, 2H), 2.40 (s, 3H). | DMSO | >98 | N5 |

TABLE 4-continued

| | | | | |
|---|---|---|---|---|
| 697 | $^1$H NMR (400 MHz, DMSO) δ 10.68 (s, 1H), 9.52 (s, 1H), 9.08 (d, J = 8.1 Hz, 1H), 8.95 (d, J = 4.7 Hz, 1H), 8.82 (d, J = 8.7 Hz, 1H), 8.25-8.12 (m, 2H), 8.06-7.88 (m, 3H), 7.63-7.48 (m, 3H), 7.47-7.35 (m, 1H). | DMSO | >98 | N5 |
| 698 | $^1$H NMR (400 MHz, DMSO) δ 10.47 (s, 1H), 9.53 (d, J = 1.6 Hz, 1H), 9.01-8.92 (m, 1H), 8.87 (dd, J = 5.1, 1.4 Hz, 1H), 8.73 (d, J = 8.7 Hz, 1H), 8.24 (dd, J = 6.8, 2.6 Hz, 1H), 8.09 (s, 1H), 7.99-7.78 (m, 4H), 7.59-7.42 (m, 2H), 7.37-7.25 (m, 1H). | DMSO | >98 | N5 |
| 699 | $^1$H NMR (400 MHz, DMSO) δ 13.12 (s, 1H), 9.59 (s, 1H), 9.10 (d, J = 8.1 Hz, 1H), 9.00-8.86 (m, 2H), 8.50 (s, 1H), 8.22-8.07 (m, 2H), 8.03-7.86 (m, 4H), 7.72 (t, J = 7.9 Hz, 1H), 7.28 (t, J = 7.1 Hz, 1H). | DMSO | >98 | Scheme 4 synthesis using method N6 coupling |
| 700 | $^1$H NMR (400 MHz, DMSO) δ 13.19 (s, 1H), 9.64 (s, 1H), 9.21-9.08 (m, 1H), 9.07-8.89 (m, 2H), 3.51 (s, 1H), 8.38-8.26 (m, 2H), 8.16 (d, J = 8.5 Hz, 1H), 8.07-7.87 (m, 3H), 7.83-7.70 (m, 3H), 7.62 (dd, J = 14.2, 7.7 Hz, 1H), 7.40-7.22 (m, 2H). | DMSO | >98 | N6 |
| 701 | $^1$H NMR (400 MHz, DMSO) δ 13.17 (s, 1H), 9.65 (s, 1H), 9.13-8.99 (m, 2H), 8.89 (d, J = 5.1 Hz, 1H), 8.50 (s, 1H), 8.31 (d, J = 8.7 Hz, 1H), 8.21 (d, J = 1.8 Hz 1H), 8.11 (dd, J = 3.6, 1.9 Hz, 1H), 8.05-7.84 (m, 5H), 7.81-7.67 (m, 1H), 7.46-7.34 (m, 2H), 7.27 (dd, J = 11.8, 4.5 Hz, 1H). | DMSO | >98 | N6 |
| 702 | $^1$H NMR (400 MHz, DMSO) δ 13.19 (s, 1H), 9.66 (d, J = 1.8 Hz, 1H), 9.20 (d, J = 7.5 Hz, 1H), 9.04-8.89 (m, 2H), 8.50 (s, 1H), 8.35 (d, J = 8.7 Hz, 1H), 8.17 (s, 1H), 8.11-7.86 (m, 4H), 7.86-7.68 (m, 2H), 7.65-7.52 (m, 1H), 7.52-7.39 (m, 2H), 7.39-7.23 (m, 1H). | DMSO | >98 | N6 |

TABLE 4-continued

| | | | | |
|---|---|---|---|---|
| 703 | $^{1}H$ NMR (400 MHz, DMSO) δ 13.17 (s, 1H), 9.62 (d, J = 1.6 Hz, 1H), 9.18 (d, J = 8.2 Hz, 1H), 9.03-8.91 (m, 2H), 8.51 (s, 1H), 8.34-8.20 (m, 2H), 8.16-7.86 (m, 5H), 7.84-7.68 (m, 2H), 7.68-7.54 (m, 1H), 7.35-7.19 (m, 1H). | DMSO | >98 | N6 |
| 704 | $^{1}H$ NMR (400 MHz, DMSO) δ 13.19 (s, 1H), 9.61 (d, J = 1.8 Hz, 1H), 9.32-9.22 (m, 1H), 9.02 (dd, J = 5.5, 1.2 Hz, 1H), 8.88 (d, J = 7.8 Hz, 1H), 8.75 (s, 1H), 8.53 (s, 1H), 8.28 (d, J = 8.7 Hz, 1H), 8.16-8.07 (m, 2H), 8.01-7.88 (m, 3H), 7.85-7.76 (m, 1H), 7.76-7.65 (m, 1H), 7.54-7.42 (m, 1H), 7.37-7.19 (m, 2H). | DMSO | >98 | N6 |
| 705 | $^{1}H$ NMR (400 MHz, DMSO) δ 13.20 (s, 1H), 9.63 (s, 1H), 9.26 (d, J = 8.1 Hz, 1H), 9.01 (d, J = 5.0 Hz, 1H), 8.91 (d, J = 3.3 Hz, 1H), 8.52 (s, 1H), 8.33 (d, J = 8.7 Hz, 1H), 8.21-8.06 (m, 2H), 8.06-7.87 (m, 3H), 7.72 (t, J = 7.7 Hz, 1H), 7.66-7.52 (m, 2H), 7.49-7.35 (m, 1H), 7.29 (t, J = 7.5 Hz, 1H). | DMSO | >98 | N6 |
| 706 | $^{1}H$ NMR (400 MHz, DMSO) δ 9.64 (d, J = 1.7 Hz, 1H), 9.25 (d, J = 3.2 Hz, 1H), 9.05-8.89 (m, 2H), 8.67-8.45 (m, 1H), 8.34 (d, J = 8.7 Hz, 1H), 8.19 (s, 1H), 8.09 (dd, J = 8.0, 5.5 Hz, 1H), 8.04-7.88 (m, 3H), 7.79-7.62 (m, 2H), 7.56-7.35 (m, 2H), 7.35-7.23 (m, 1H). | DMSO | >98 | N6 |
| 707 | $^{1}H$ NMR (400 MHz, DMSO) δ 13.18 (s, 1H), 9.62 (d, J = 1.6 Hz, 1H), 9.16 (d, J = 8.1 Hz, 1H), 9.08-8.88 (m, 2H), 8.51 (s, 1H), 8.37-8.23 (m, 2H), 8.19-8.09 (m, 1H), 8.09-7.88 (m, 3H), 7.83-7.63 (m, 3H), 7.43-7.32 (m, 1H), 7.32-7.21 (m, 1H). | DMSO | >98 | N6 |

TABLE 4-continued

| | | | | |
|---|---|---|---|---|
| 708 | $^1$H NMR (400 MHz, DMSO) δ 10.52 (s, 1H), 9.56 (d, J = 1.6 Hz, 1H), 9.04 (d, J = 7.8 Hz, 1H), 8.92 (d, J = 4.8 Hz, 1H), 8.78 (d, J = 8.8 Hz, 1H), 8.24 (d, J = 1.7 Hz, 1H), 8.13-8.08 (m, 2H), 8.08-7.98 (m, 3H), 7.98-7.88 (m, 1H), 7.63 (t, J = 8.2 Hz, 1H), 7.42 (t, J = 8.8 Hz, 2H), 7.28-7.15 (m, 1H). | DMSO | >98 | N6/F5 followed by G1 |
| 709 | $^1$H NMR (400 MHz, DMSO) δ 10.60 (s, 1H), 9.56 (s, 1H), 9.07 (d, J = 7.9 Hz, 1H), 8.93 (d, J = 4.3 Hz, 1H), 8.77 (d, J = 8.7 Hz, 1H), 8.41 (s, 1H), 8.37-8.27 (m, 1H), 8.24 (d, J = 1.7 Hz, 1H), 8.11 (dd, J = 8.7, 1.8 Hz, 1H), 8.08-7.94 (m, 3H), 7.79-7.65 (m, 2H), 7.41 (t, J = 8.8 Hz, 2H). | DMSO | >98 | N6/F5 followed by G1 |
| 710 | 1H NMR (DMSO-d6) ppm 3.81 (s, 3H), 3.88 (s, 3H), 7.11-7.71 (m, 9H), 7.91 (d, 1H, J = 8.7 Hz), 8.23 (d, 1H, J = 8.7 Hz), 8.53-8.64 (m, 2H), 8.87 (d, 1H, J = 1.5 Hz), 9.37 (d, 1H, J = 1.5 Hz), 9.83 (s, 1H) | DMSO | >98 | N6/F5 followed by G1 |
| 711 | 1H NMR (DMSO-d6) ppm 3.89 (s, 3H), 7.04 (d, 1H, J = 4.1 Hz), 7.48-7.57 (m, 5H), 7.98 (dd, 1H, J = 7.1, 1.7 Hz), 8.26-8.29 (m, 3H), 8.27 (dd, 1H, J = 7.1, 8.7 Hz), 8.78-9.53 (m, 3H), 9.54 (s, 1H), 10.37 (s, 1H) | DMSO | >98 | N6/F5 followed by G1 |
| 712 | 1H NMR (DMSO-d6) ppm 3.89 (s, 3H), 7.05 (d, 1H, J = 4.1 Hz), 7.48-7.57 (m, 4H), 7.88 (dd, 1H, J = 7.1, 1.7 Hz), 8.25-8.29 (m, 3H), 8.37 (dd, 1H, J = 7.1, 8.7 Hz), 8.78-9.53 (m, 3H), 9.54 (s, 1H), 10.37 (s, 1H) | DMSO | >98 | N6/F5 followed by G1 |
| 713 | 1H NMR (DMSO-d6) ppm 3.88 (s, 3H), 7.05-7.51 (m, 9H), 7.95 (d, 1H, J = 8.7 Hz), 8.26 (d, 1H, J = 8.7 Hz), 8.54-8.88 (m, 3H), 9.38 (s, 1H), 10.19 (s, 1H) | DMSO | >98 | N6/F5 followed by G1 |
| 714 | 1H NMR (DMSO-d6) ppm 3.89 (s, 3H), 7.04-7.06 (m, 2H), 7.46-7.76 (m, 8H), 7.95 (d, 2H, J = 8.6 Hz), 8.24 (d, 1H, J = 1.7 Hz), 8.69-8.87 (m, 3H), 9.56 (s, 1H), 10.18 (s, 1H) | DMSO | >98 | N6/F5 followed by G1 |

TABLE 4-continued

| | | | | |
|---|---|---|---|---|
| 715 | 1H NMR (DMSO-d6) ppm 3.84 (s, 3H), 3.89 (s, 3H), 6.81-7.56 (m, 2H), 7.40-7.70 (m, 7H), 7.95 (d, 1H, J = 8.5 Hz), 8.23 (d, 1H, J = 1.5 Hz), 8.69-8.89 (m, 3H), 9.58 (s, 1H), 10.06 (s, 1H) | DMSO | >98 | N6/F5 followed by G1 |
| 716 | 1H NMR (DMSO-d6) ppm 3.88 (s, 3H), 7.03-7.06 (m, 1H), 7.50-8.39 (m, 10H), 8.86-8.98 (m, 3H), 9.58 (s, 1H), 10.06 (s, 1H) | DMSO | >98 | N6/F5 followed by G1 |
| 717 | 1H NMR (DMSO-d6) ppm 3.89 (s, 3H), 7.02-7.07 (m, 2H), 7.31 (s, 1H), 7.47-7.56 (m, 5H), 7.81-8.26 (m, 4H), 8.26-8.90 (m, 3H), 9.57 (s, 1H), 10.27 (s, 1H) | DMSO | >98 | N6/F5 followed by G1 |
| 718 | 1H NMR (DMSO-d6) ppm 3.87 (s, 3H), 7.03-7.50 (m, 8H), 7.98 (d, 1H, J = 8.7 Hz), 8.30 (d, 1H, J = 8.7 Hz), 8.48-8.91 (m, 3H), 9.30 (s, 1H), 10.19 (s, 1H) | DMSO | >98 | N6/F5 followed by G1 |
| 719 | 1H NMR (DMSO-d6) ppm 3.88 (s, 3H), 7.03-7.54 (m, 8H), 7.97 (d, 1H, J = 8.7 Hz), 8.28 (d, 1H, J = 8.7 Hz), 8.56-8.86 (m, 3H), 9.40 (s, 1H), 10.23 (s, 1H) | DMSO | >98 | N6/F5 followed by G1 |
| 720 | 1H NMR (DMSO-d6) ppm 3.88 (s, 3H), 7.03-7.52 (m, 8H), 7.95 (d, 1H, J = 8.7 Hz), 8.26 (d, 1H, J = 8.7 Hz), 8.52-8.85 (m, 3H), 9.38 (s, 1H), 10.17 (s, 1H) | DMSO | >98 | N6/F5 followed by G1 |
| 721 | 1H NMR (DMSO-d6) ppm 3.87 (s, 3H), 7.05-7.54 (m, 8H), 8.00 (d, 1H, J = 8.7 Hz), 8.27 (d, 1H, J = 8.7 Hz), 8.55-8.87 (m, 3H), 9.38 (s, 1H), 10.34 (s, 1H) | DMSO | >98 | N6/F5 followed by G1 |
| 722 | 1H NMR (DMSO-d6) ppm 3.89 (s, 3H), 7.05-7.53 (m, 7H), 7.93 (s, 1H), 7.96 (d, 1H, J = 8.7 Hz), 8.16 (s, 1H), 8.26 (d, 1H, J = 8.7 Hz), 8.74-8.89 (m, 3H), 9.55 (s, 1H), 10.27 (s, 1H) | DMSO | >98 | N6/F5 followed by G1 |
| 723 | 1H NMR (DMSO-d6) ppm 3.88 (s, 3H), 7.03-7.54 (m, 7H), 7.92 (s, 1H), 7.97 (d, 1H, J = 8.7 Hz), 8.28 (d, 1H, J = 8.7 Hz), 8.56-8.85 (m, 3H), 9.40 (s, 1H), 10.25 (s, 1H) | DMSO | >98 | N6/F5 followed by G1 |
| 724 | 1H NMR (DMSO-d6) ppm 3.88 (s, 3H), 7.03-7.74 (m, 8H), 7.98 (d, 1H, J = 8.7 Hz), 8.27 (d, 1H, J = 8.7 Hz), 8.52-8.87 (m, 3H), 9.32 (s, 1H), 10.22 (s, 1H) | DMSO | >98 | N6/F5 followed by G1 |

TABLE 4-continued

| | | | | |
|---|---|---|---|---|
| 725 | 1H NMR (DMSO-d6) ppm 3.89 (s, 3H), 7.05-7.71 (m, 8H), 7.99 (d, 1H, J = 8.6 Hz), 8.30 (d, 1H, J = 8.7 Hz), 8.67-8.92 (m, 3H), 9.37 (s, 1H), 10.52 (s, 1H) | DMSO | >98 | N6/F5 followed by G1 |
| 726 | 1H NMR (DMSO-d6) ppm 3.89 (s, 3H), 7.03-7.71 (m, 9H), 7.99 (d, 1H, J = 8.7 Hz), 8.29 (d, 1H, J = 8.7 Hz), 8.67-8.92 (m, 3H), 9.37 (s, 1H), 10.52 (s, 1H) | DMSO | >98 | N6/F5 followed by G1 |
| 727 | 1H NMR (DMSO-d6 at 70° C.) ppm 3.89 (s, 3H), 7.02-7.52 (m, 8H), 7.90 (d, 1H, J = 8.5 Hz), 7.93 (s, 1H), 7.99 (d, 1H, J = 8.6 Hz), 8.22 (s, 1H), 8.74-8.91 (m, 3H), 9.52 (s, 1H), 10.23 (s, 1H) | DMSO | >98 | N6/F5 followed by G1 |
| 728 | $^1$H NMR (DMSO-$d_6$) ppm 2.50 (s, 3H), 3.89 (s, 3H), 7.06 (s, 1H), 7.49-7.85 (m, 9H), 8.01-8.96 (m, 4H), 9.58 (s, 1H), 10.50 (s, 1H) | DMSO | >98 | N6/F5 followed by G1 |
| 729 | $^1$H NMR (DMSO-$d_6$) ppm 3.89 (s, 3H), 7.04 (br s, 1H), 7.22 (s, 1H), 7.49-8.30 (m, 9H), 8.77-8.91 (m, 3H), 9.55 (s, 1H), 10.37 (s, 1H) | DMSO | >98 | N6/F5 followed by G1 |
| 730 | $^1$H NMR (DMSO-$d_6$) ppm 3.89 (s, 3H), 7.04 (s, 1H), 7.49-8.32 (m, 9H), 8.91-9.04 (m, 3H), 9.54 (s, 1H), 10.63 (s, 1H) | DMSO | >98 | N6/F5 followed by G1 |
| 731 | $^1$H NMR (DMSO-$d_6$) ppm 3.87 (s, 3H), 7.03 (s, 1H), 7.44-8.25 (m, 9H), 8.71-8.84 (m, 3H), 9.52 (s, 1H), 10.23 (s, 1H) | DMSO | >98 | N6/F5 followed by G1 |
| 732 | $^1$H NMR (400 MHz, DMSO) δ 12.02 (s, 1H), 10.53 (s, 1H), 9.49 (s, 1H), 9.02-8.72 (m, 3H), 8.30 (dd, J = 8.7, 1.6 Hz, 1H), 8.05 (dd, J = 32.2, 5.3 Hz, 2H), 7.81-7.72 (m, 2H), 7.49 (dd, J = 8.0, 5.4 Hz, 3H), 7.25 (t, J = 9.2 Hz, 1H), 7.11-6.98 (m, 1H), 3.89 (s, 3H). | DMSO | >98 | N6/F5 followed by G1 |
| 733 | $^1$H NMR (400 MHz, DMSO) δ 10.54 (s, 1H), 9.43 (s, 1H), 8.86 (d, J = 1.8 Hz, 1H), 8.64 (dd, J = 21.1, 5.9 Hz, 2H), 8.31 (dd, J = 8.7, 1.9 Hz, 1H), 8.01 (d, J = 8.7 Hz, 1H), 7.59-7.45 (m, 4H), 7.42-7.30 (m, 3H), 7.09-6.98 (m, 1H), 3.89 (s, 3H). | DMSO | >98 | N6/F5 followed by G1 |

TABLE 4-continued

| | | | | |
|---|---|---|---|---|
| 734 | $^1H$ NMR (400 MHz, DMSO) δ 13.18 (s, 1H), 10.57 (s, 1H), 9.48 (s, 1H), 8.98 (d, J = 1.3 Hz, 1H), 8.78 (t, J = 7.1 Hz, 2H), 8.30 (dd, J = 8.7, 1.7 Hz, 1H), 8.18 (d, J = 8.4 Hz, 2H), 8.01 (d, J = 8.7 Hz, 1H), 7.83 (dd, J = 8.9, 1.8 Hz, 1H), 7.74-7.62 (m, 2H), 7.56-7.43 (m, 2H), 7.09-7.01 (m, 1H), 3.90 (s, 3H). | DMSO | >98 | N6/F5 followed by G1 |
| 735 | $^1H$ NMR (400 MHz, DMSO) δ 11.16 (s, 1H), 10.11 (s, 1H), 9.51 (d, J = 1.2 Hz, 1H), 8.91 (d, J = 1.7 Hz, 1H), 8.71-8.58 (m, 2H), 8.23 (dd, J = 8.7, 1.9 Hz, 1H), 7.95 (dd, J = 23.9, 5.2 Hz, 2H), 7.60-7.34 (m, 5H), 7.06-6.98 (m, 1H), 6.06 (s, 2H), 3.89 (s, 3H). | DMSO | >98 | N6/F5 followed by G1 |
| 736 | $^1H$ NMR (400 MHz, DMSO) δ 10.78 (s, 1H), 10.65 (s, 1H), 10.08 (s, 1H), 9.55 (d, J = 2.0 Hz, 1H), 8.88 (d, J = 1.8 Hz, 1H), 8.76-8.66 (m, 2H), 8.24 (dd, J = 8.7, 1.9 Hz, 1H), 7.94 (d, J78.7 Hz, 1H), 7.65 (d, J = 1.9 Hz, 1H), 7.58 (dd, J = 7.7, 5.1 Hz, 1H), 7.49 (dt, J = 4.7, 3.1 Hz, 3H), 7.41 (dd, J = 8.4, 2.0 Hz, 1H), 7.08-6.99 (m, 3H), 3.88 (s, 3H). | DMSO | >98 | N6/F5 followed by G1 |
| 737 | $^1H$ NMR (400 MHz, DMSO) δ 9.93 (s, 1H), 9.40 (s, 1H), 8.86 (d, J = 1.7 Hz, 1H), 8.64 (dd, J = 28.9, 5.8 Hz, 2H), 8.27 (dd, J = 8.7, 1.9 Hz, 1H), 7.96 (d, J = 8.7 Hz, 1H), 7.87 (d, J = 2.6 Hz, 1H), 7.61-7.45 (m, 5H), 7.38 (dd, J = 8.8, 2.6 Hz, 1H), 7.24 (d, J = 8.9 Hz, 1H), 7.09-6.98 (m, 1H), 3.89 (d, J = 2.9 Hz, 1H), 3.83 (s, 3H). | DMSO | >98 | N6/F5 followed by G1 |
| 738 | $^1H$ NMR (400 MHz, DMSO) δ 10.19 (s, 1H), 9.56 (s, 1H), 8.88 (d, J = 1.7 Hz, 1H), 8.75 (t, J = 7.2 Hz, 2H), 8.27 (dd, J = 8.6, 1.4 Hz, 1H), 8.14 (d, J = 1.6 Hz, 1H), 7.97 (d, J = 8.7 Hz, 1H), 7.84 (dd, J = 8.2, 2.0 Hz, 1H), 7.63 (dd, J = 7.7, 4.9 Hz, 1H), 7.48 (dd, J = 11.4, 4.0 Hz, 4H), 7.10-6.98 (m, 1H), 3.89 (s, 3H), 3.83 (s, 3H). | DMSO | >98 | N6/F5 followed by G1 |

TABLE 4-continued

| | | | | |
|---|---|---|---|---|
| 739 | $^{1}$H NMR (400 MHz, DMSO) δ 10.07 (s, 1H), 9.55 (s, 1H), 8.85 (s, 1H), 8.70 (d, J = 5.5 Hz, 2H), 8.24 (dd, J = 8.7, 1.5 Hz, 1H), 8.10 (d, J = 2.4 Hz, 1H), 7.99-7.83 (m, 2H), 7.60-7.40 (m, 4H), 7.30 (d, J = 9.0 Hz, 1H), 7.04 (dd, J = 7.1, 4.4 Hz, 1H), 3.90 (s, 3H), 2.29 (s, 3H). | DMSO | >98 | N6/F5 followed by G1 |
| 740 | $^{1}$H NMR (400 MHz, DMSO) δ 10.05 (s, 1H), 9.60 (s, 1H), 8.89 (d, J = 1.8 Hz, 1H), 8.71 (dd, J = 12.8, 6.3 Hz, 2H), 8.24 (dd, J = 8.7, 1.9 Hz, 1H), 7.95 (d, J = 8.7 Hz, 1H), 7.68 (d, J = 1.7 Hz, 1H), 7.61-7.45 (m, 5H), 7.44-7.37 (m, 1H), 7.24 (d, J = 8.0 Hz, 1H), 3.89 (s, 3H), 3.65 (s, 3H). | DMSO | >98 | N6/F5 followed by G1 |
| 741 | $^{1}$H NMR (400 MHz, DMSO) δ 10.04 (s, 1H), 9.60 (s, 1H), 8.89 (d, J = 1.7 Hz, 1H), 8.71 (dd, J = 12.7, 6.3 Hz, 2H), 8.24 (dd, J = 8.7, 1.9 Hz, 1H), 7.95 (d, J = 8.7 Hz, 1H), 7.68 (d, J = 1.7 Hz, 1H), 7.59-7.45 (m, 4H), 7.44-7.37 (m, 1H), 7.25 (t, J = 6.7 Hz, 1H), 7.07-6.98 (m, 1H), 3.89 (s, 6H), 2.19 (s, 3H). | DMSO | >98 | N6/F5 followed by G1 |
| 742 | $^{1}$H NMR (400 MHz, DMSO) δ 9.73 (s, 1H), 9.37 (s, 1H), 8.86 (d, J = 1.6 Hz, 1H), 8.63 (d, J = 3.4 Hz, 1H), 8.54 (d, J = 8.0 Hz, 1H), 8.23 (dd, J = 8.7, 1.8 Hz, 1H), 7.91 (d, J = 8.7 Hz, 1H), 7.55-7.42 (m, 5H), 7.05-6.98 (m, 1H), 6.77 (d, J = 2.6 Hz, 1H), 6.68 (dd, J = 8.6, 2.6 Hz, 1H), 3.89 (s, 3H), 3.85 (s, 3H), 3.79 (s, 3H). | DMSO | >98 | N6/F5 followed by G1 |
| 743 | $^{1}$H NMR (400 MHz, DMSO) δ 10.25 (s, 1H), 9.56 (s, 1H), 8.84 (d, J = 1.7 Hz, 1H), 8.71 (d, J = 9.1 Hz, 1H), 8.27 (dd, J = 8.7, 1.8 Hz, 1H), 7.99 (d, J = 8.7 Hz, 1H), 7.86-7.77 (m, 2H), 7.65-7.56 (m, 1H), 7.52-7.44 (m, 4H), 7.09-6.99 (m, 2H), 3.89 (s, 3H). | DMSO | >98 | N6/F5 followed by G1 |

TABLE 4-continued

| | | | | |
|---|---|---|---|---|
| 744 | $^1$H NMR (400 MHz, DMSO) δ 10.42 (s, 1H), 9.55 (s, 1H), 8.87 (d, J = 26.7 Hz, 3H), 8.31 (dd, J = 8.7, 1.7 Hz, 2H), 8.17 (d, J = 1.7 Hz, 2H), 8.02 (d, J = 8.7 Hz, 1H), 7.81 (s, 1H), 7.54-7.39 (m, 3H), 7.11-6.98 (m, 1H), 3.89 (s, 3H). | DMSO | >98 | N6/F5 followed by G1 |
| 745 | $^1$H NMR (400 MHz, DMSO) δ 14.27 (s, 1H), 9.79 (s, 1H), 9.32 (d, J = 8.4 Hz, 1H), 8.98 (d, J = 5.2 Hz, 1H), 8.34 (dd, J = 8.7, 1.8 Hz, 1H), 8.29-8.19 (m, 2H), 8.07 (dd, J = 14.6, 8.3 Hz, 2H), 7.93 (s, 1H), 7.64 (d, J = 5.9 Hz, 1H), 7.52 (t, J = 7.9 Hz, 1H), 7.39 (dd, J = 8.9, 4.9 Hz, 2H), 7.23 (d, J = 5.8 Hz, 1H), 7.08 (dd, J = 8.2, 1.8 Hz, 1H), 3.86 (s, 3H). | DMSO | >98 | N6/F5 followed by G1 |
| 746 | $^1$H NMR (400 MHz, DMSO) δ 11.10 (s, 1H), 9.36 (s, 1H), 9.11 (s, 1H), 9.00 (dd, J = 23.2, 6.7 Hz, 2H), 8.41 (d, J = 9.1 Hz, 1H), 8.16 (d, J = 8.7 Hz, 1H), 8.05 (dd, J = 7.9, 5.5 Hz, 1H), 7.80-7.65 (m, 2H), 7.59-7.44 (m, 3H), 7.41-7.32 (m, 1H), 7.06 (d, J = 8.0 Hz, 1H), 3.90 (s, 3H). | DMSO | | N6/F5 followed by G1 |
| 747 | $^1$H NMR (400 MHz, DMSO) δ 12.92 (d, J = 17.9 Hz, 1H), 9.64 (s, 1H), 9.09 (d, J = 7.9 Hz, 1H), 8.92 (d, J = 4.9 Hz, 1H), 8.52 (d, J = 5.4 Hz, 1H), 8.38 (s, 1H), 8.30 (dd, J = 8.7, 1.7 Hz, 1H), 8.04 (d, J = 8.7 Hz, 1H), 7.98-7.84 (m, 3H), 7.50 (t, J = 7.9 Hz, 1H), 7.39 (dd, J = 8.1, 5.0 Hz, 2H), 7.06 (dd, J = 8.2, 1.8 Hz, 2H), 3.89 (s, 3H). | DMSO | >98 | N6/F5 followed by G1 |

TABLE 4-continued
| Number | Starting Material 1 | Starting Material 2 |
| --- | --- | --- |
| 748 | 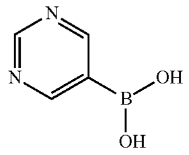 | 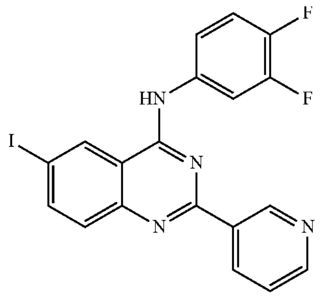 [SMILES: Fc1ccc(Nc2nc(-c3cccnc3)nc3ccc(I)cc23)cc1F] |
| 749 | 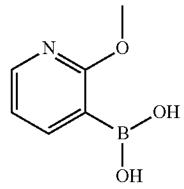 | 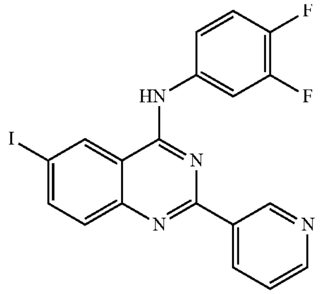 [SMILES: Fc1ccc(Nc2nc(-c3cccnc3)nc3ccc(I)cc23)cc1F] |
| 750 | 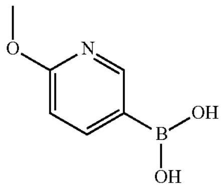 | 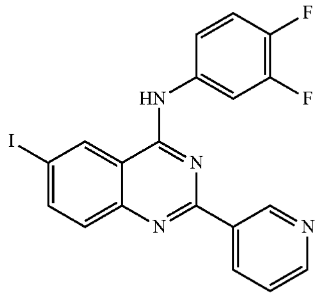 [SMILES: Fc1ccc(Nc2nc(-c3cccnc3)nc3ccc(I)cc23)cc1F] |

TABLE 4-continued
| | | |
|---|---|---|
| 751 | 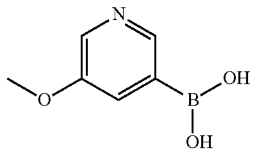 | 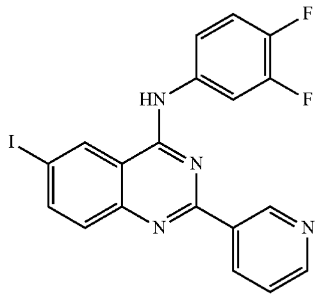 [SMILES: Fc1ccc(Nc2nc(-c3cccnc3)nc3ccc(I)cc23)cc1F] |
| 752 | 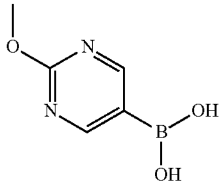 | 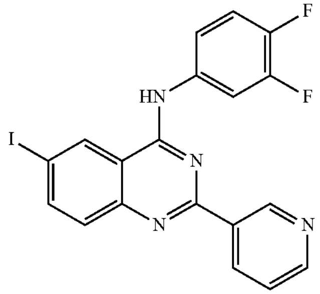 [SMILES: Fc1ccc(Nc2nc(-c3cccnc3)nc3ccc(I)cc23)cc1F] |
| 753 | 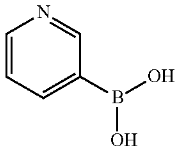 | 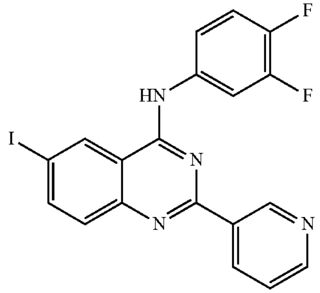 [SMILES: Fc1ccc(Nc2nc(-c3cccnc3)nc3ccc(I)cc23)cc1F] |

TABLE 4-continued
| | | |
|---|---|---|
| 754 | 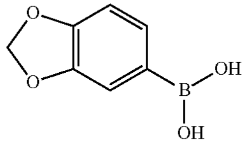 [SMILES: OB(O)c1ccc2c(c1)OCO2] | 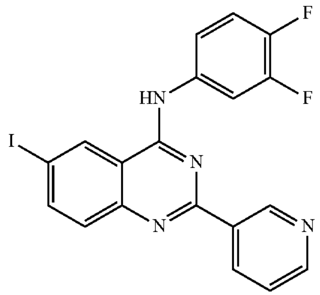 [SMILES: Fc1ccc(Nc2nc(-c3cccnc3)nc3ccc(I)cc23)cc1F] |
| 755 | 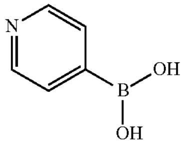 | 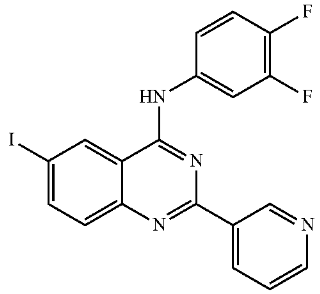 [SMILES: Fc1ccc(Nc2nc(-c3cccnc3)nc3ccc(I)cc23)cc1F] |
| 756 | 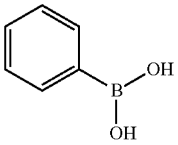 | 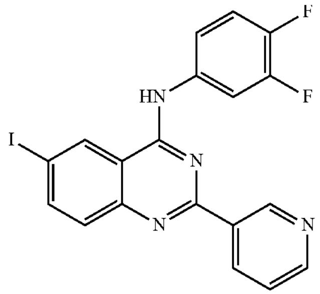 [SMILES: Fc1ccc(Nc2nc(-c3cccnc3)nc3ccc(I)cc23)cc1F] |

TABLE 4-continued
| | | |
|---|---|---|
| 757 | 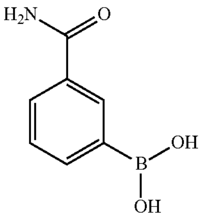 [SMILES: NC(=O)c1cccc(B(O)O)c1] | 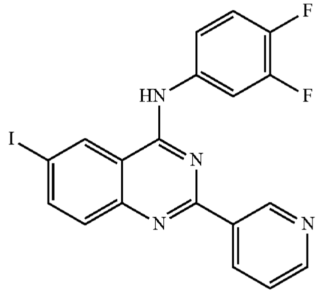 [SMILES: Fc1ccc(Nc2nc(-c3cccnc3)nc3ccc(I)cc23)cc1F] |
| 758 | 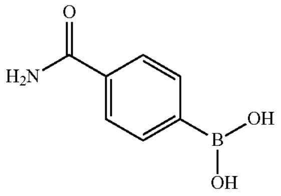 [SMILES: NC(=O)c1ccc(B(O)O)cc1] | 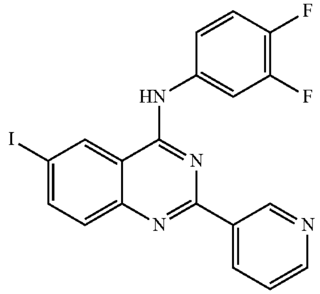 [SMILES: Fc1ccc(Nc2nc(-c3cccnc3)nc3ccc(I)cc23)cc1F] |
| 759 | 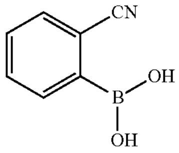 [SMILES: N#Cc1ccccc1B(O)O] | 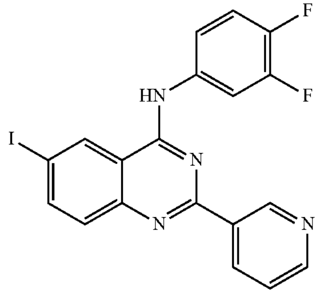 [SMILES: Fc1ccc(Nc2nc(-c3cccnc3)nc3ccc(I)cc23)cc1F] |

TABLE 4-continued
| | | |
|---|---|---|
| 760 | 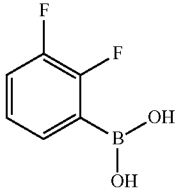 [SMILES: OB(O)c1cccc(F)c1F] | 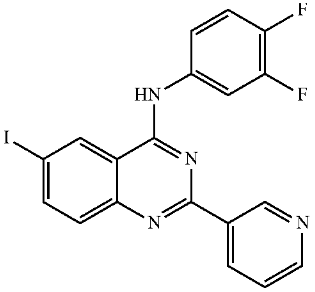 [SMILES: Fc1ccc(Nc2nc(-c3cccnc3)nc3ccc(I)cc23)cc1F] |
| 761 | 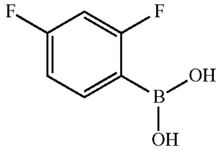 [SMILES: OB(O)c1ccc(F)cc1F] | 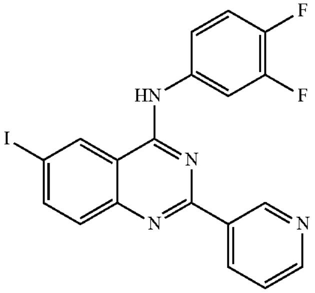 [SMILES: Fc1ccc(Nc2nc(-c3cccnc3)nc3ccc(I)cc23)cc1F] |
| 762 | 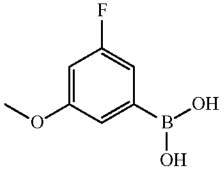 | 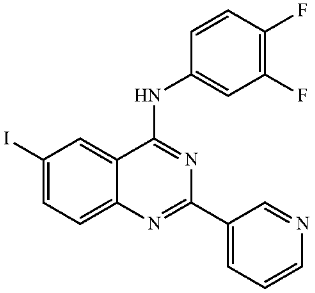 [SMILES: Fc1ccc(Nc2nc(-c3cccnc3)nc3ccc(I)cc23)cc1F] |

TABLE 4-continued
| | | |
|---|---|---|
| 763 | 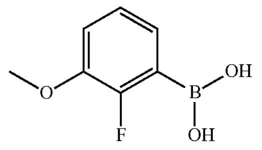 | 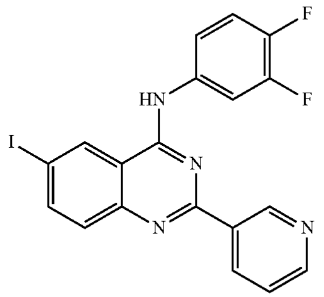 [SMILES: Fc1ccc(Nc2nc(-c3cccnc3)nc3ccc(I)cc23)cc1F] |
| 764 | 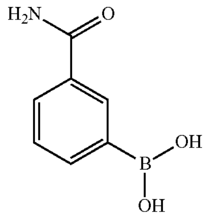 [SMILES: NC(=O)c1cccc(B(O)O)c1] | 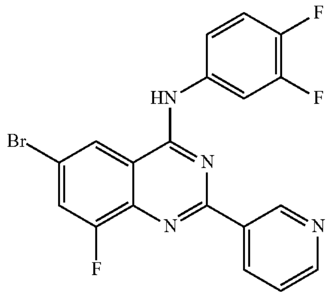 [SMILES: Fc1ccc(Nc2nc(-c3cccnc3)nc3c(F)cc(Br)cc23)cc1F] |
| 765 | 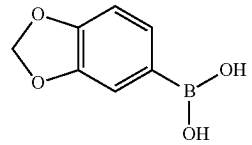 [SMILES: OB(O)c1ccc2c(c1)OCO2] | 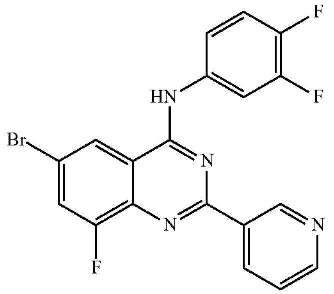 [SMILES: Fc1ccc(Nc2nc(-c3cccnc3)nc3c(F)cc(Br)cc23)cc1F] |

TABLE 4-continued
| | | |
|---|---|---|
| 766 | 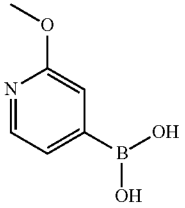 | 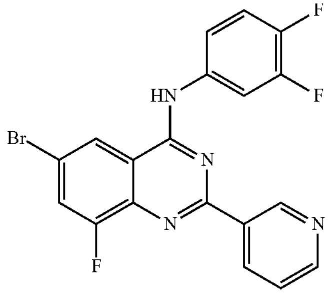 [SMILES: Fc1ccc(Nc2nc(-c3cccnc3)nc3c(F)cc(Br)cc23)cc1F] |
| 767 | 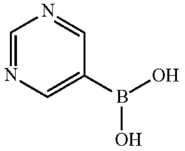 | 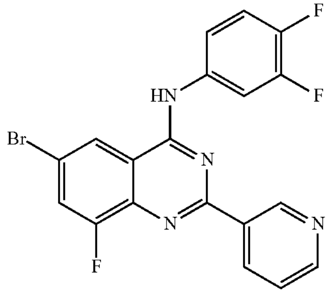 [SMILES: Fc1ccc(Nc2nc(-c3cccnc3)nc3c(F)cc(Br)cc23)cc1F] |
| 768 | 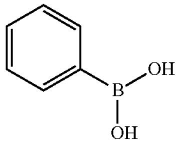 | 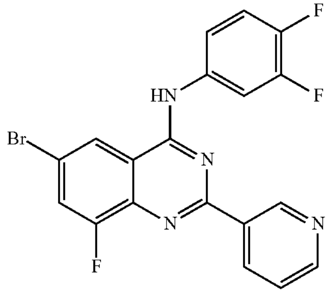 [SMILES: Fc1ccc(Nc2nc(-c3cccnc3)nc3c(F)cc(Br)cc23)cc1F] |

TABLE 4-continued
| | | |
|---|---|---|
| 769 | 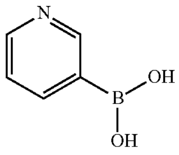 | 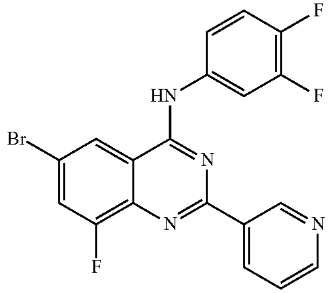 [SMILES: Fc1ccc(Nc2nc(-c3cccnc3)nc3c(F)cc(Br)cc23)cc1F] |
| 770 | 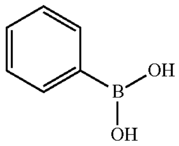 | 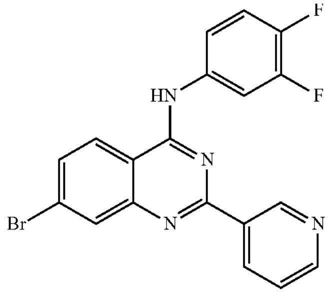 [SMILES: Fc1ccc(Nc2nc(-c3cccnc3)nc3cc(Br)ccc23)cc1F] |
| 771 | 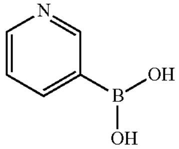 | 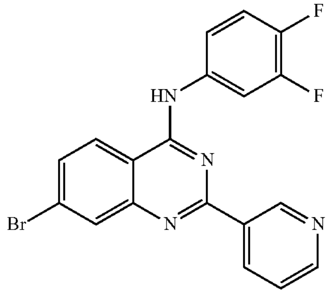 [SMILES: Fc1ccc(Nc2nc(-c3cccnc3)nc3cc(Br)ccc23)cc1F] |

TABLE 4-continued
| | | |
|---|---|---|
| 772 | 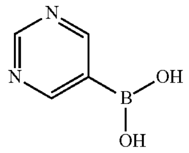 | 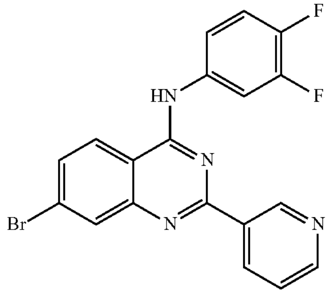 [SMILES: Fc1ccc(Nc2nc(-c3cccnc3)nc3cc(Br)ccc23)cc1F] |
| 773 | 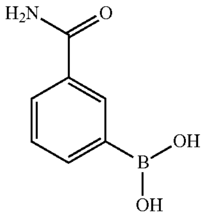 [SMILES: NC(=O)c1cccc(B(O)O)c1] | 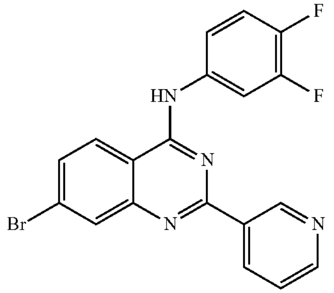 [SMILES: Fc1ccc(Nc2nc(-c3cccnc3)nc3cc(Br)ccc23)cc1F] |
| 774 | 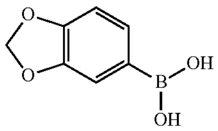 [SMILES: OB(O)c1ccc2c(c1)OCO2] | 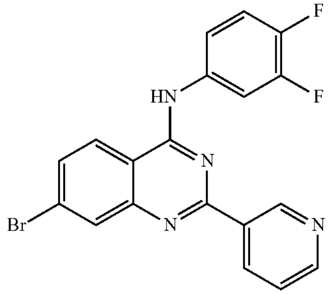 [SMILES: Fc1ccc(Nc2nc(-c3cccnc3)nc3cc(Br)ccc23)cc1F] |

TABLE 4-continued
| | | |
|---|---|---|
| 775 | 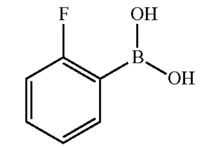 | 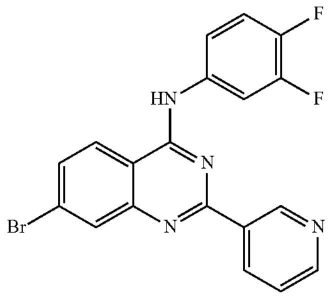 [SMILES: Fc1ccc(Nc2nc(-c3cccnc3)nc3cc(Br)ccc23)cc1F] |
| 776 | 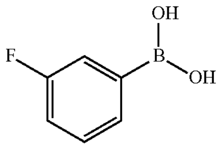 | 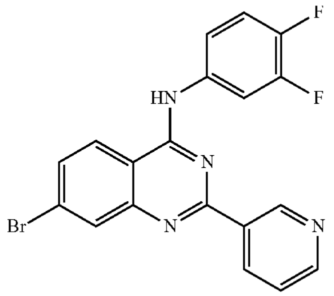 |
| 777 | 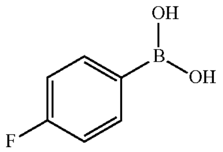 | 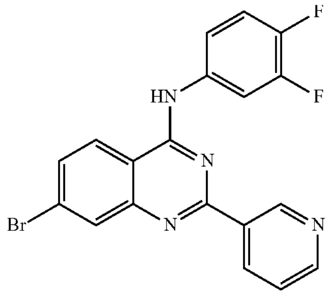 |

TABLE 4-continued
| | | |
|---|---|---|
| 778 | 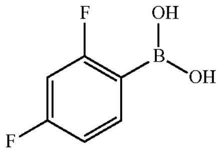 | 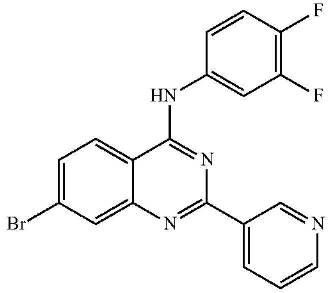 [SMILES: Fc1ccc(Nc2nc(-c3cccnc3)nc3cc(Br)ccc23)cc1F] |
| 779 | 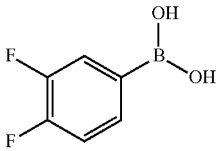 [SMILES: OB(O)c1ccc(F)c(F)c1] | 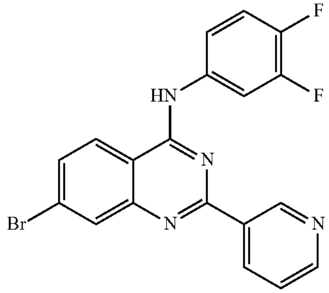 [SMILES: Fc1ccc(Nc2nc(-c3cccnc3)nc3cc(Br)ccc23)cc1F] |
| 780 | 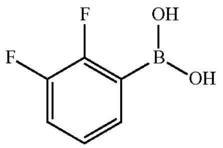 | 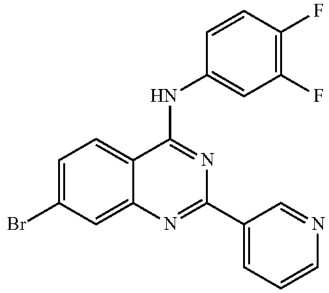 [SMILES: Fc1ccc(Nc2nc(-c3cccnc3)nc3cc(Br)ccc23)cc1F] |

TABLE 4-continued
| | | |
|---|---|---|
| 781 | 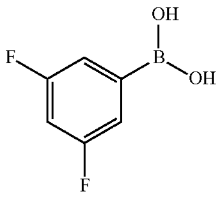 | 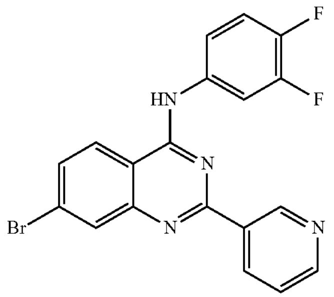 [SMILES: Fc1ccc(Nc2nc(-c3cccnc3)nc3cc(Br)ccc23)cc1F] |
| 782 | 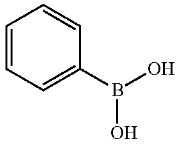 | 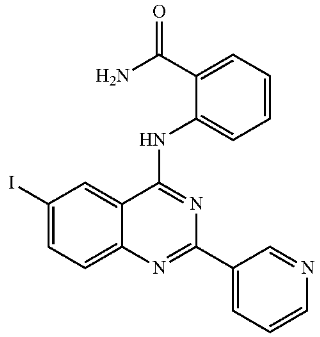 [SMILES: NC(=O)c1ccccc1Nc1nc(-c2cccnc2)nc2ccc(I)cc12] |
| 783 | 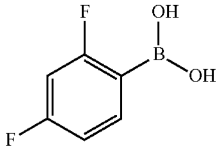 [SMILES: OB(O)c1ccc(F)cc1F] | 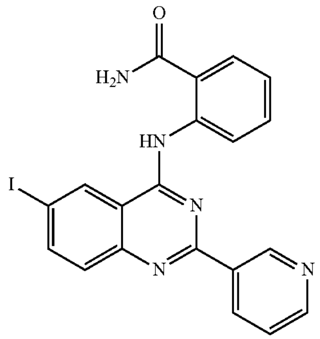 [SMILES: NC(=O)c1ccccc1Nc1nc(-c2cccnc2)nc2ccc(I)cc12] |

TABLE 4-continued
| | | |
|---|---|---|
| 784 | 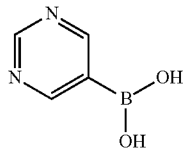 | 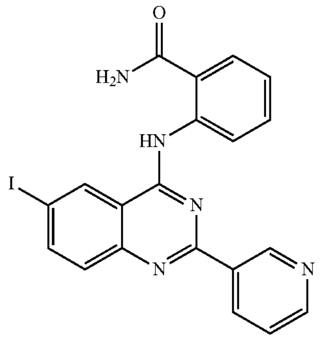 [SMILES: NC(=O)c1ccccc1Nc1nc(-c2cccnc2)nc2ccc(I)cc12] |
| 785 | 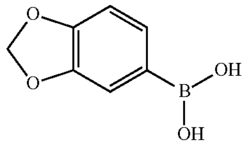 [SMILES: OB(O)c1ccc2c(c1)OCO2] | 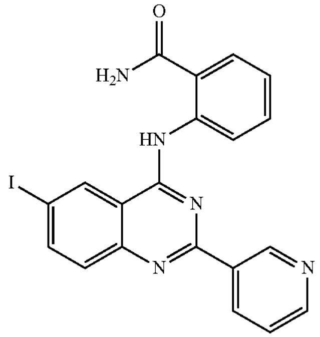 [SMILES: NC(=O)c1ccccc1Nc1nc(-c2cccnc2)nc2ccc(I)cc12] |
| 786 | 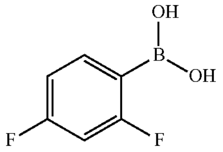 [SMILES: OB(O)c1ccc(F)cc1F] | 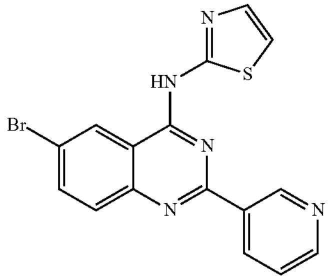 [SMILES: Brc1ccc2nc(-c3cccnc3)nc(Nc3nccs3)c2c1] |

TABLE 4-continued
| | | |
|---|---|---|
| 787 | 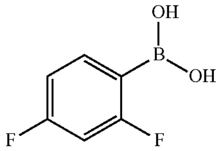 | 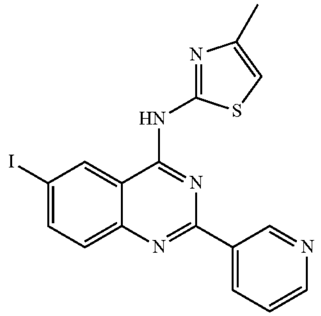 [SMILES: Cc1csc(Nc2nc(-c3cccnc3)nc3ccc(I)cc23)n1] |
| 788 | | |
| 789 | | |
| 790 | | |
| 791 | | |
| 792 | | |
| 793 | | |
| 794 | | |
| 795 | | |
| 796 | | |
| 797 | | |
| 798 | | |
| 799 | | |
| 800 | | |
| 801 | | |
| Number | Product | Salt type | $^1$H NMR |
|---|---|---|---|
| 748 | 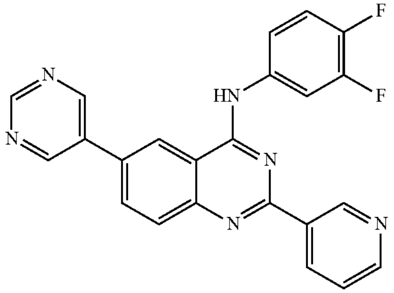 [SMILES: Fc1ccc(Nc2nc(-c3cccnc3)nc3ccc(-c4cncnc4)cc23)cc1F] | 2 HCl | $^1$H NMR (400 MHz, DMSO) δ 10.71 (s, 1H), 9.56 (s, 1H), 9.45 (s, 2H), 9.29 (s, 1H), 9.22 (s, 1H), 9.13 (d, J = 7.8 Hz, 1H), 8.96 (d, J = 4.3 Hz, 1H), 8.47 (d, J = 8.4 Hz, 1H), 8.16-8.08 (m, 2H), 8.07-7.99 (m, 1H), 7.75 (s, 1H), 7.59 (dd, J = 19.3, 9.0 Hz, 1H). |

TABLE 4-continued
| | | | |
|---|---|---|---|
| 749 | 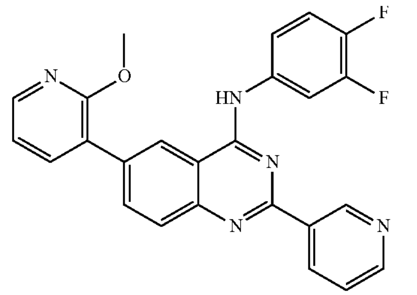 [SMILES: COc1ncccc1-c1ccc2nc(-c3cccnc3)nc(Nc3ccc(F)c(F)c3)c2c1] | | $^1$H NMR (400 MHz, DMSO) δ 10.12 (s, 1H), 9.55 (d, J = 1.4 Hz, 1H), 8.74-8.66 (m, 3H), 8.28 (d, J = 4.9 Hz, 1H), 8.17-8.08 (m, 2H), 7.98-7.91 (m, 2H), 7.73 (d, J = 9.1 Hz, 1H), 7.61-7.51 (m, 2H), 7.22 (dd, J = 7.3, 5.0 Hz, 1H), 3.95 (s, 3H). |
| 750 | 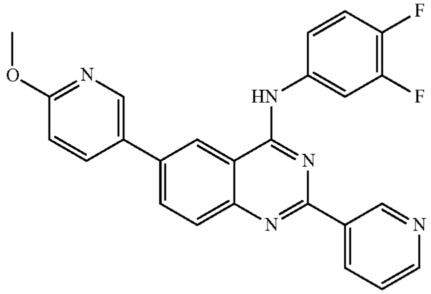 [SMILES: COc1ccc(-c2ccc3nc(-c4cccnc4)nc(Nc4ccc(F)c(F)c4)c3c2)cn1] | 2 HCl | $^1$H NMR (400 MHz, DMSO) δ 10.92 (s, 1H), 9.55 (d, J = 1.5 Hz, 1H), 9.33 (s, 1H), 9.10-8.99 (m, 2H), 8.93 (d, J = 5.2 Hz, 1H), 8.54 (d, J =2.5 Hz, 1H), 8.46 (dd, J = 8.8, 1.8 Hz, 1H), 8.33 (s, 1H), 8.18 (ddd, J = 13.0, 7.4, 2.4 Hz, 1H), 8.08 (d, J = 8.7 Hz, 1H), 8.01-7.93 (m, 1H), 7.84 (d, J = 9.0 Hz, 1H), 7.57 (dd, J = 19.7, 9.1 Hz, 1H), 4.03 (s, 3H). |
| 751 | 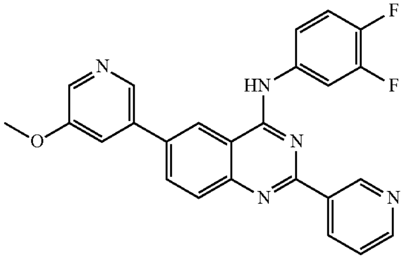 [SMILES: COc1cncc(-c2ccc3nc(-c4cccnc4)nc(Nc4ccc(F)c(F)c4)c3c2)c1] | HCl | $^1$H NMR (400 MHz, DMSO) δ 10.57 (s, 1H), 9.53 (d, J = 1.7 Hz, 1H), 9.00 (dd, J = 14.9, 4.8 Hz, 2H), 8.90 (dd, J = 5.1, 1.4 Hz, 1H), 8.78 (d, J = 2.1 Hz, 1H), 8.31 (dt, J = 8.7, 2.2 Hz, 2H), 8.11 (ddd, J = 12.9, 7.5, 2.5 Hz, 1H), 8.03 (d, J = 8.7 Hz, 1H), 7.93 (dd, J = 8.0, 5.1 Hz, 1H), 7.75 (dd, J = 6.0, 2.9 Hz, 1H), 7.63-7.51 (m, 1H), 7.03 (d, J = 8.6 Hz, 1H), 3.94 (d, J = 8.4 Hz, 3H). |

TABLE 4-continued
| | | |
|---|---|---|
| 752 | 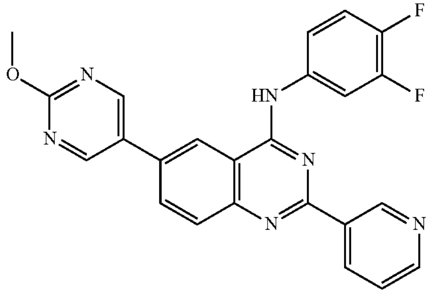 [SMILES: COc1ncc(-c2ccc3nc(-c4cccnc4)nc(Nc4ccc(F)c(F)c4)c3c2)cn1] | $^{1}$H NMR (400 MHz, DMSO) δ 10.05 (s, 1H), 9.52 (s, 1H), 9.14 (d, J = 5.6 Hz, 2H), 8.84 (s, 1H), 8.68 (dd, J = 14.0, 6.4 Hz, 2H), 8.28 (dd, J = 8.7, 1.7 Hz, 1H), 8.17-8.06 (m, 1H), 7.96 (d, J = 8.7 Hz, 1H), 7.70(d, J = 9.0 Hz, 1H), 7.62-7.50 (m, 2H), 4.02 (s, 3H). |
| 753 | 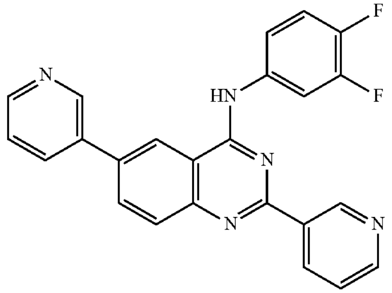 [SMILES: Fc1ccc(Nc2nc(-c3cccnc3)nc3ccc(-c4cccnc4)cc23)cc1F] | $^{1}$H NMR (400 MHz, DMSO) δ 10.17 (s, 1H), 9.54 (d, J = 1.5 Hz, 1H), 9.16 (d, J = 1.9 Hz, 1H), 8.93 (d, J = 1.7 Hz, 1H), 8.74-8.60 (m, 3H), 8.35-8.26 (m, 2H), 8.19-8.07 (m, 1H), 8.01 (d, J = 8.7 Hz, 1H), 7.77-7.69 (m, 1H), 7.64-7.51 (m, 3H). |
| 754 | 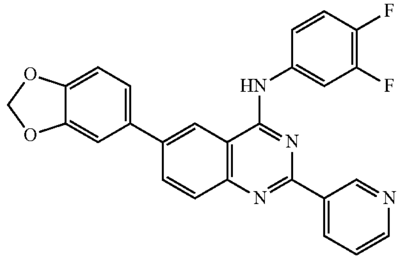 [SMILES: Fc1ccc(Nc2nc(-c3cccnc3)nc3ccc(-c4ccc5c(c4)OCO5)cc23)cc1F] | $^{1}$H NMR (400 MHz, DMSO) δ 10.12 (s, 1H), 9.53 (d, J = 1.4 Hz, 1H), 8.79-8.62 (m, 3H), 8.24-8.06 (m, 2H), 7.94 (t, J = 7.7 Hz, 1H), 7.73 (dd, J = 6.2, 2.9 Hz, 1H), 7.56 (ddd, J = 15.3, 10.1, 4.8 Hz, 3H), 7.41 (dd, J = 8.1, 1.8 Hz, 1H), 7.11 (d, J = 8.1 Hz, 1H), 6.13 (s, 2H). |

TABLE 4-continued
| | | | |
|---|---|---|---|
| 755 | 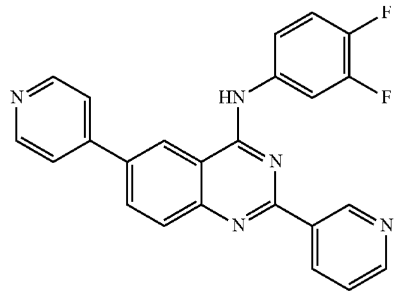 [SMILES: Fc1ccc(Nc2nc(-c3cccnc3)nc3ccc(-c4ccncc4)cc23)cc1F] | 2 HCl | $^1$H NMR (400 MHz, DMSO) δ 11.36 (s, 1H), 9.73 (d, J = 1.7 Hz, 1H), 9.52 (d, J = 1.8 Hz, 1H), 9.13-9.02 (m, 3H), 8.96 (dd, J = 5.4, 1.4 Hz, 1H), 8.79 (d, J = 6.9 Hz, 2H), 8,56 (dd, J = 8.9, 1.9 Hz, 1H), 8.19 (ddd, J = 13.0, 7.5, 2.5 Hz, 1H), 8.09 (d, J = 8.8 Hz, 1H), 8.02 (dd, J = 8.0, 5.4 Hz, 1H), 7.90 (dt, J = 9.0, 2.8 Hz,1H), 7.62-7.50 (m, 1H). |
| 756 | 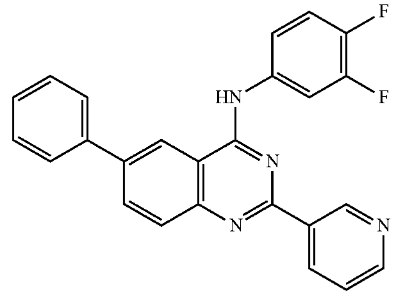 [SMILES: Fc1ccc(Nc2nc(-c3cccnc3)nc3ccc(-c4ccccc4)cc23)cc1F] | | $^1$H NMR (400 MHz, DMSO) δ 10.19 (s, 1H), 9.55 (d, J = 1.4 Hz, 1H), 8.86 (d, J = 1.7 Hz, 1H), 8.69 (dd, J = 8.8, 2.9 Hz, 2H), 8.25 (dd, J = 8.7, 1.8 Hz, 1H), 8.18-8.07 (m, 1H), 7.99 (d, J = 8.7 Hz, 1H), 7.92 (d, J = 7.2 Hz, 2H), 7.78-7.68 (m, 1H), 7.62-7.53 (m, 4H), 7.47 (t, J = 7.4 Hz, 1H). |
| 757 | 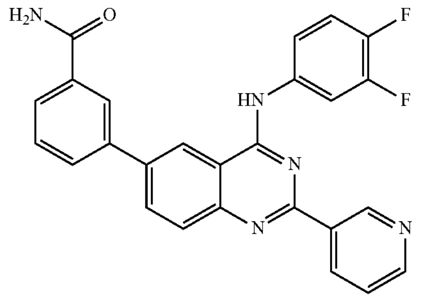 [SMILES: NC(=O)c1cccc(-c2ccc3nc(-c4cccnc4)nc(Nc4ccc(F)c(F)c4)c3c2)c1] | 2 HCl | $^1$H NMR (400 MHz, DMSO) δ 10.84 (s, 1H), 9.55 (s, 1H), 9.19-9.05 (m, 2H), 8.95 (d, J = 4.1 Hz, 1H), 8.53 (s, 1H), 8.41 (dd, J = 8.7, 1.7 Hz, 1H), 8.28 (s, 1H), 8.16-8.07 (m, 3H), 8.05-7.92 (m, 2H), 7.79(d, J = 9.1 Hz, 1H), 7.70-7.46 (m, 3H). |

TABLE 4-continued
| | | | |
|---|---|---|---|
| 758 | 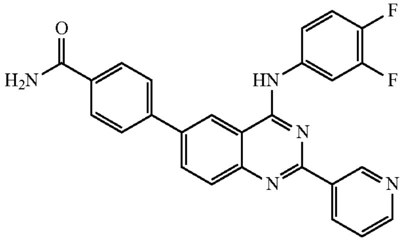 [SMILES: NC(=O)c1ccc(-c2ccc3nc(-c4cccnc4)nc(Nc4ccc(F)c(F)c4)c3c2)cc1] | 2 HCl | $^{1}H$ NMR (400 MHz, DMSO) δ 10.78 (s, 1H), 9.55 (d, J = 1.8 Hz, 1H), 9.12 (d, J = 8.6 Hz, 2H), 8.96 (dd, J = 5.4, 1.4 Hz, 1H), 8.40 (dd, J = 8.8, 1.8 Hz, 1H), 8.16-7.96 (m, 8H), 7.79-7.71 (m, 1H), 7.64-7.53 (m, 1H), 7.47 (s, 1H). |
| 759 | 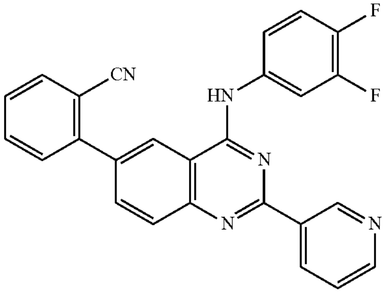 [SMILES: N#Cc1ccccc1-c1ccc2nc(-c3cccnc3)nc(Nc3ccc(F)c(F)c3)c2c1] | HCl | $^{1}H$ NMR (400 MHz, DMSO) δ 10.41 (s, 1H), 9.56 (s, 1H), 8.98-8.77 (m, 3H), 8.23-8.02 (m, 4H), 7.99-7.65 (m, 5H), 7.56 (dd, J = 19.1, 9.4 Hz, 1H). |
| 760 | 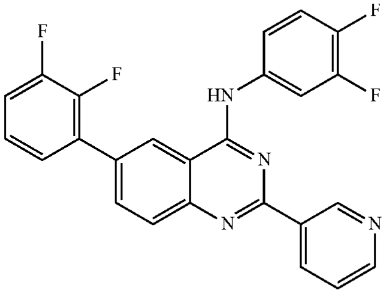 [SMILES: Fc1ccc(Nc2nc(-c3cccnc3)nc3ccc(-c4cccc(F)c4F)cc23)cc1F] | 2 HCl | $^{1}H$ NMR (400 MHz, DMSO) δ 10.51 (s, 1H), 9.55 (d, J = 1.6 Hz, 1H), 9.04 (d, J = 8.1 Hz, 1H), 8.95-8.84 (m, 2H), 8.21-8.02 (m, 3H), 7.93 (dt, J = 10.6, 5.3 Hz, 1H), 7.77-7.68 (m, 1H), 7.63-7.51 (m, 3H), 7.49-7.38 (m, 1H). |
| 761 | 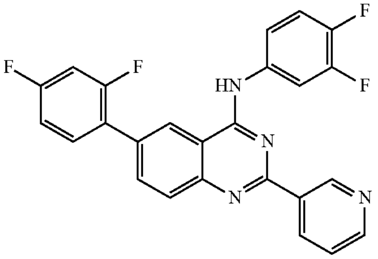 [SMILES: Fc1ccc(-c2ccc3nc(-c4cccnc4)nc(Nc4ccc(F)c(F)c4)c3c2)c(F)c1] | 2 HCl | $^{1}H$ NMR (400 MHz, DMSO) δ 10.51 (s, 1H), 9.55 (d, J = 1.5 Hz, 1H), 9.03 (d, J = 8.2 Hz, 1H), 8.91 (dd, J = 5.3, 1.5 Hz, 1H), 8.82 (s, 1H), 8.16-8.00 (m, 3H), 7.94 (dd, J = 8.0, 5.2 Hz, 1H), 7.87-7.78 (m, 1H), 7.75-7.66 (m, 1H), 7.61-7.44 (m, 2H), 7.39-7.28 (m, 1H). |

TABLE 4-continued
| | | | |
|---|---|---|---|
| 762 | 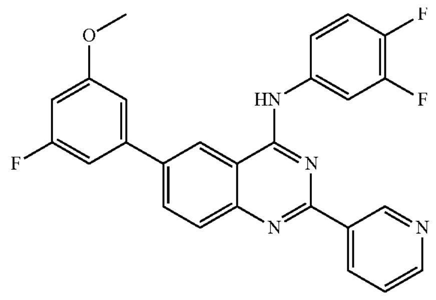 [SMILES: COc1cc(F)cc(-c2ccc3nc(-c4cccnc4)nc(Nc4ccc(F)c(F)c4)c3c2)c1] | HCl | $^1$H NMR (400 MHz, DMSO) δ 10.75 (s, 1H), 9.53 (d, J = 1.7 Hz, 1H), 9.07 (dd, J = 23.2, 4.9 Hz, 2H), 8.95 (dd, J = 5.3, 1.4 Hz, 1H), 8.36 (dd, J = 8.8, 1.9 Hz, 1H), 8.15-7.96 (m, 3H), 7.76 (dd, J = 9.0, 4.1 Hz, 1H), 7.64-7.50 (m, 1H), 7.41 (dt, J = 12.9, 1.6 Hz, 2H), 6.99-6.90 (m, 1H), 3.90 (s, 3H). |
| 763 | 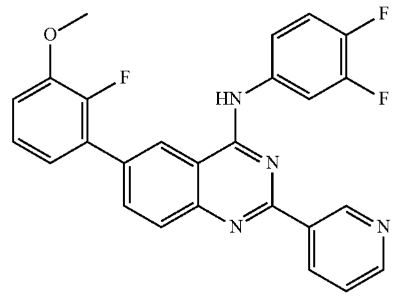 [SMILES: COc1cccc(-c2ccc3nc(-c4cccnc4)nc(Nc4ccc(F)c(F)c4)c3c2)c1F] | HCl | $^1$H NMR (400 MHz, DMSO) δ 10.54 (s, 1H), 9.55 (s, 1H), 9.05 (d, J = 8.2 Hz, 1H), 8.92 (d, J = 4.6 Hz, 1H), 8.84 (s, 1H), 8.17-8.02 (m, 3H), 7.96 (dd, J = 7.9, 5.4 Hz, 1H), 7.72 (d, J = 9.0 Hz, 1H), 7.56 (dd, J = 19.6, 9.1 Hz, 1H), 7.39-7.21 (m, 3H), 3.89 (s, 3H). |
| 764 | 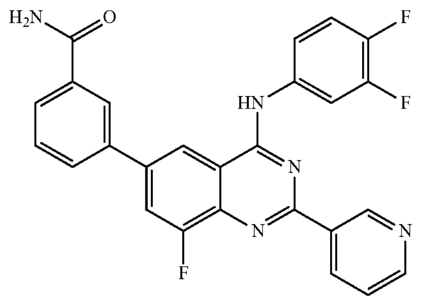 [SMILES: NC(=O)c1cccc(-c2cc(F)c3nc(-c4cccnc4)nc(Nc4ccc(F)c(F)c4)c3c2)c1] | HCl | $^1$H NMR (400 MHz, DMSO) δ 10.68 (s, 1H), 9.51 (d, J = 1.3 Hz, 1H), 9.04 (d, J = 3.1 Hz, 1H), 8.97-8.87 (m, 2H), 8.51 (s, 1H), 8.32-8.22 (m, 2H), 8.16-8.05 (m, 2H), 8.00-7.90 (m, 2H), 7.80-7.73 (m, 1H), 7.65 (t, J = 7.8 Hz, 1H), 7.60-7.47 (m, 2H). |

TABLE 4-continued
| | | | |
|---|---|---|---|
| 765 | 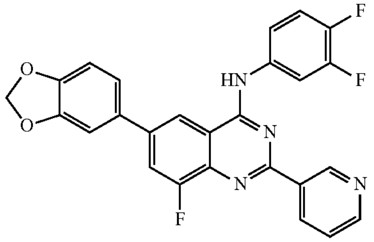 [SMILES: Fc1ccc(Nc2nc(-c3cccnc3)nc3c(F)cc(-c4ccc5c(c4)OCO5)cc23)cc1F] | HCl | $^1$H NMR (400 MHz, DMSO) δ 10.43 (s, 1H), 9.46 (d, J = 1.3 Hz, 1H), 9.01 (d, J = 8.1 Hz, 1H), 8.91 (d, 1H), 8.63 (s, 1H), 8.13-7.91 (m, 3H), 7.73-7.66 (m, 1H), 7.59-7.49 (m, 2H), 7.44 (dd, J = 8.2, 1.8Hz, 1H), 7.07 (d, J = 8.1 Hz, 1H), 6.12 (s, 2H). |
| 766 | 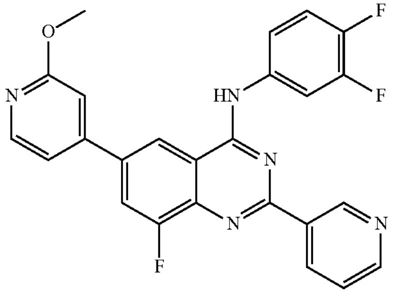 [SMILES: COc1cc(-c2cc(F)c3nc(-c4cccnc4)nc(Nc4ccc(F)c(F)c4)c3c2)ccn1] | | $^1$H NMR (400 MHz, DMSO) δ 10.33 (s, 1H), 9.52 (s, 1H), 8.83 (s, 1H), 8.70 (d, J = 6.3 Hz, 2H), 8.32 (d, J = 8.6 Hz, 2H), 8.13-8.03 (m, 1H), 7.70 (d, J = 7.3 Hz, 1H), 7.58 (dd, J = 7.3, 5.7 Hz, 3H), 7.42 (s, 1H), 3.95 (s, 3H). |
| 767 | 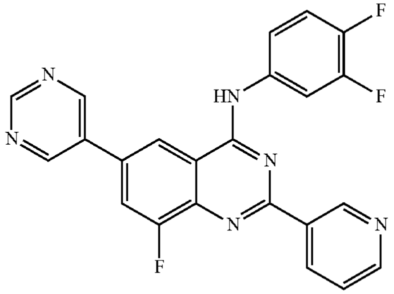 [SMILES: Fc1ccc(Nc2nc(-c3cccnc3)nc3c(F)cc(-c4cncnc4)cc23)cc1F] | 2 HCl | $^1$H NMR (400 MHz, DMSO) δ 10.71 (s, 1H), 9.52-9.41 (m, 3H), 9.26 (s, 1H), 9.11-9.02 (m, 2H), 8.96 (d, J = 5.4 Hz, 1H), 8.37 (d, J = 11.6 Hz, 1H), 8.14-7.99 (m, 2H), 7.80-7.71 (m, 1H), 7.55 (d, J = 9.1 Hz, 1H). |

TABLE 4-continued
| | | | |
|---|---|---|---|
| 768 | 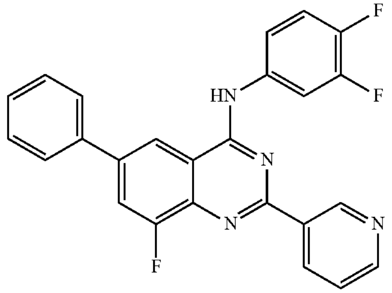 | HCl | $^1$H NMR (400 MHz, DMSO) δ 10.53 (s, 1H), 9.51 (d, J = 1.6 Hz, 1H), 9.07-9.00 (m, 1H), 8.91 (dd, J = 5.3, 1.5 Hz, 1H), 8.79 (s, 1H), 8.20 (dd, J = 11.9, 1.6 Hz, 1H), 8.13-8.03 (m, 1H), 8.00-7.91 (m, 3H), 7.76-7.68 (m, 1H), 7.62-7.44 (m, 4H). |
| 769 | 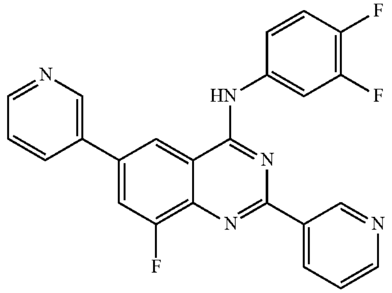 [SMILES: Fc1ccc(Nc2nc(-c3cccnc3)nc3c(F)cc(-c4cccnc4)cc23)cc1F] | 3 HCl | $^1$H NMR (400 MHz, DMSO) δ 11.13 (s, 1H), 9.64 (d, J = 1.7 Hz, 1H), 9.47 (d, J = 1.5 Hz, 1H), 9.38 (s, 1H), 9.09 (t, J = 7.3 Hz, 2H), 9.01-8.94 (m, 1H), 8.91-8.83 (m, 1H), 8.39 (dd, J = 11.6, 1.3 Hz, 1H), 8.22-8.13 (m, 1H), 8.11-7.98 (m, 2H), 7.93-7.84 (m, 1H), 7.53 (dd, J = 19.7, 9.2 Hz, 1H). |
| 770 | 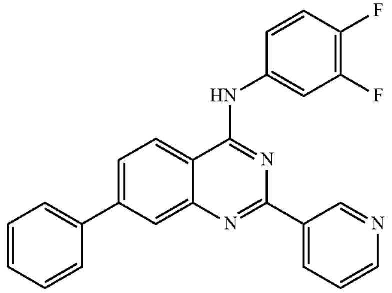 [SMILES: Fc1ccc(Nc2nc(-c3cccnc3)nc3cc(-c4ccccc4)ccc23)cc1F] | 2 HCl | $^1$H NMR (400 MHz, DMSO) δ 10.69 (s, 1H), 9.55 (d, J = 1.7 Hz, 1H), 9.12 (d, J = 8.2 Hz, 1H), 8.97 (dd, J = 5.4, 1.4 Hz, 1H), 8.81 (d, J = 8.7 Hz, 1H), 8.30 (d, J = 1.3 Hz, 1H), 8.15-7.99 (m, 3H), 7.96-7.88 (m, 2H), 7.81-7.72 (m, 1H), 7.63-7.47 (m, 4H). |

TABLE 4-continued
| | | | |
|---|---|---|---|
| 771 | 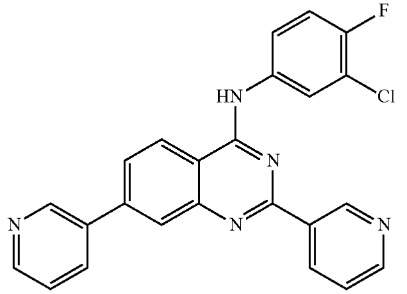 [SMILES: Fc1ccc(Nc2nc(-c3cccnc3)nc3cc(-c4cccnc4)ccc23)cc1Cl] | 3 HCl | $^1$H NMR (400 MHz, DMSO) δ 10.89 (s, 1H), 9.54-9.45 (m, 2H), 9.17 (t, J = 8.6 Hz, 1H), 9.10-8.93 (m, 4H), 8.48 (d, J = 1.6 Hz, 1H), 8.25-8.06 (m, 4H), 7.89-7.79 (m, 1H), 7.53 (dd, J = 19.6, 9.2 Hz, 1H). |
| 772 | 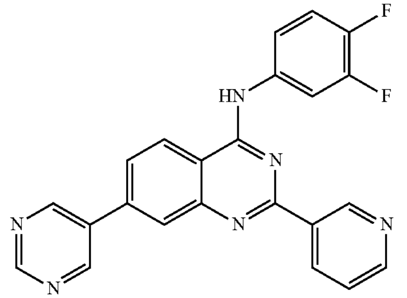 [SMILES: Fc1ccc(Nc2nc(-c3cccnc3)nc3cc(-c4cncnc4)ccc23)cc1F] | 3 HCl | $^1$H NMR (400 MHz, DMSO) δ 10.67 (s, 1H), 9.54 (d, J = 1.7 Hz, 1H), 9.40 (s, 2H), 9.31 (s, 1H), 9.20 (d, J = 8.2 Hz, 1H), 9.02 (d, J = 4.3 Hz, 1H), 8.89 (d, J = 8.7 Hz, 1H), 8.43 (s, 1H), 8.22 (dd, J = 8.7, 1.9 Hz, 1H), 8.17-8.06 (m, 2H), 7.82-7.74 (m, 1H), 7.56 (dd, J = 19.7, 9.2 Hz, 1H). |
| 773 | 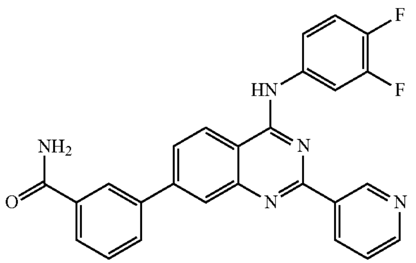 [SMILES: NC(=O)c1cccc(-c2ccc3c(Nc4ccc(F)c(F)c4)nc(-c4cccnc4)nc3c2)c1] | 2 HCl | $^1$H NMR (400 MHz, DMSO) δ 10.81 (s, 1H), 9.56 (s, 1H), 9.11 (d, J = 8.2 Hz, 1H), 8.94 (dd, J = 17.5, 6.7 Hz, 2H), 8.42 (d, J = 11.9 Hz, 2H), 8.28 (s, 1H), 8.22-7.94 (m, 5H), 7.81 (d, J = 8.8 Hz, 1H), 7.71-7.45 (m, 3H). |

TABLE 4-continued
| | | | |
|---|---|---|---|
| 774 | 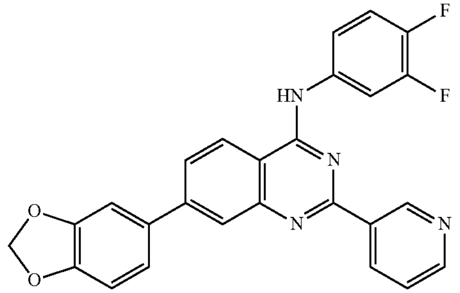 [SMILES: Fc1ccc(Nc2nc(-c3cccnc3)nc3cc(-c4ccc5c(c4)OCO5)ccc23)cc1F] | HCl | $^1$H NMR (400 MHz, DMSO) δ 10.32 (s, 1H), 9.54 (s, 1H), 8.95-8.78 (m, 2H), 8.65 (d, J = 8.8 Hz, 1H), 8.19-8.09 (m, 2H), 8.02 (d, J = 8.7, 1H), 7.85-7.69 (m, 2H), 7.62-7.37 (m, 3H), 7.09 (d, J = 7.0 Hz, 1H), 6.13 (s, 2H). |
| 775 | 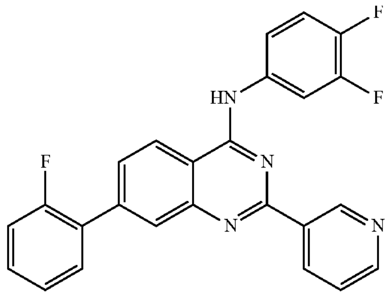 [SMILES: Fc1ccc(Nc2nc(-c3cccnc3)nc3cc(-c4ccccc4F)ccc23)cc1F] | 2 HCl | $^1$H NMR (400 MHz, DMSO) δ 10.59 (s, 1H), 9.56 (d, J = 1.7 Hz, 1H), 9.11 (d, J = 8.1 Hz, 1H), 9.01-8.88 (m, 1H), 8.79 (d, J = 8.7 Hz, 1H), 8.18-8.06 (m, 2H), 8.05-7.91 (m, 2H), 7.82-7.72 (m, 2H), 7.61-7.52 (m, 2H), 7.48-7.37 (m, 2H). |
| 776 | 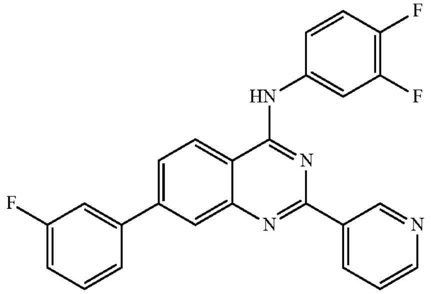 [SMILES: Fc1cccc(-c2ccc3c(Nc4ccc(F)c(F)c4)nc(-c4cccnc4)nc3c2)c1] | 2 HCl | $^1$H NMR (400 MHz, DMSO) δ 10.46 (s, 1H), 9.53 (d, J = 1.6 Hz, 1H), 9.04 (dt, J = 8.1, 1.6 Hz, 1H), 8.91 (dd, J = 5.2, 1.4 Hz, 1H), 8.73 (d, J = 8.7 Hz, 1H), 8.24 (d, J = 1.8 Hz, 1H), 8.15-8.04 (m, 2H), 7.96 (dd, J = 8.0, 5.3 Hz, 1H), 7.84-7.70 (m, 2H), 7.65-7.48 (m, 2H), 7.39-7.25 (m, 1H). |

TABLE 4-continued
| | | | |
|---|---|---|---|
| 777 | 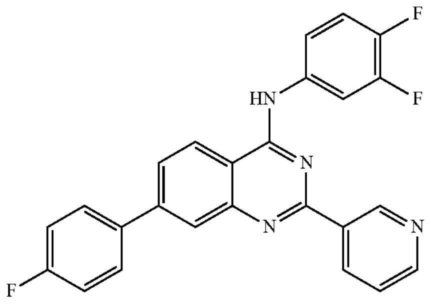 [SMILES: Fc1ccc(-c2ccc3c(Nc4ccc(F)c(F)c4)nc(-c4cccnc4)nc3c2)cc1] | 2 HCl | $^1$H NMR (400 MHz, DMSO) δ 10.62 (s, 1H), 9.55 (d, J = 1.7 Hz, 1H), 9.12 (d, J = 8.1 Hz, 1H), 8.96 (dd, J = 5.3, 1.3 Hz, 1H), 8.78 (d, J = 8.7 Hz, 1H), 8.25 (d, J = 1.7 Hz, 1H), 8.16-7.91 (m, 6H), 7.81-7.69 (m, 1H), 7.56 (dd, J = 19.7, 9.1 Hz, 1H), 7.41 (t, J = 8.8 Hz, 1H). |
| 778 | 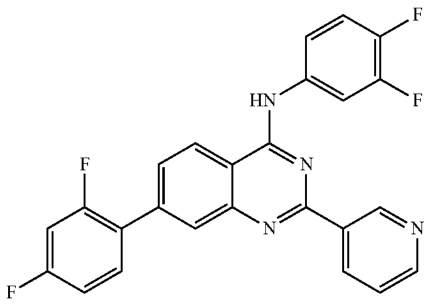 [SMILES: Fc1ccc(-c2ccc3c(Nc4ccc(F)c(F)c4)nc(-c4cccnc4)nc3c2)c(F)c1] | 2 HCl | $^1$H NMR (400 MHz, DMSO) δ 10.65 (s, 1H), 9.55 (d, J = 1.7 Hz, 1H), 9.14 (d, J = 8.1 Hz, 1H), 8.97 (dd, J = 5.4, 1.3 Hz, 1H), 8.81 (d, J = 8.7 Hz, 1H), 8.20-8.00 (m, 3H), 7.96-7.71 (m, 3H), 7.63-7.42 (m, 2H), 7.38-7.25 (m, 1H). |
| 779 | 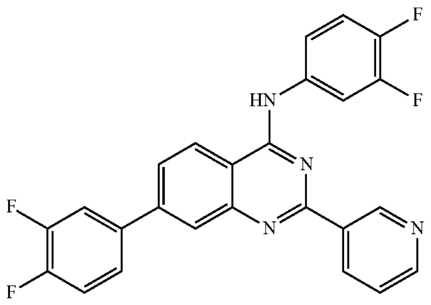 [SMILES: Fc1ccc(Nc2nc(-c3cccnc3)nc3cc(-c4ccc(F)c(F)c4)ccc23)cc1F] | HCl | $^1$H NMR (400 MHz, DMSO) δ 10.40 (s, 1H), 9.54 (d, J = 1.6 Hz, 1H), 9.00 (d, J = 8.1 Hz, 1H), 8.90 (dd, J = 5.2, 1.4 Hz, 1H), 8.71 (d, J = 8.7 Hz, 1H), 8.23 (d, J = 1.8 Hz, 1H), 8.17-8.01 (m, 3H), 7.93 (dd, J = 8.0, 5.2 Hz, 1H), 7.84-7.71 (m, 2H), 7.69-7.49 (m, 2H). |

TABLE 4-continued
| | | | |
|---|---|---|---|
| 780 | 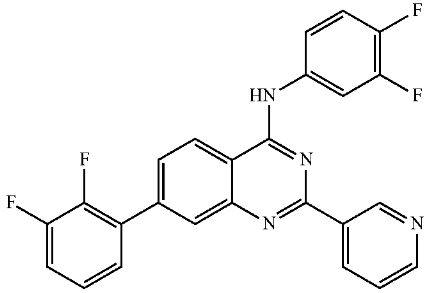 [SMILES: Fc1ccc(Nc2nc(-c3cccnc3)nc3cc(-c4cccc(F)c4F)ccc23)cc1F] | 2 HCl | 1H NMR (400 MHz, DMSO) δ 10.78 (s, 1H), 9.54 (d, J = 1.6 Hz, 1H), 9.19 (d, J = 8.1 Hz, 1H), 9.06-8.96 (m, 1H), 8.87 (d, J = 8.7 Hz, 1H), 8.22-8.04 (m, 3H), 7.93 (t, J = 10.1 Hz, 1H), 7.78 (dd, J = 6.1, 2.9 Hz, 1H), 7.64-7.49 (m, 3H), 7.47-7.35 (m, 1H). |
| 781 | 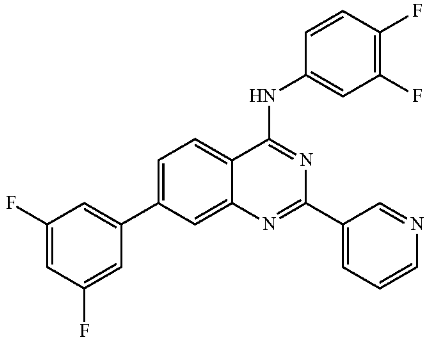 [SMILES: Fc1cc(F)cc(-c2ccc3c(Nc4ccc(F)c(F)c4)nc(-c4cccnc4)nc3c2)c1] | 2 HCl | $^{1}$H NMR (400 MHz, DMSO) δ 10.47 (s, 1H), 9.53 (d, J = 1.7 Hz, 1H), 9.08 (d, J = 8.1 Hz, 1H), 8.94 (dd, J = 5.3, 1.3 Hz, 1H), 8.74 (d, J = 8.8 Hz, 1H), 8.29 (d, J = 1.8 Hz, 1H), 8.17-7.95 (m, 3H), 7.80-7.55 (m, 3H), 7.61-7.48 (m, 1H), 7.42-7.30 (m, 1H). |
| 782 | 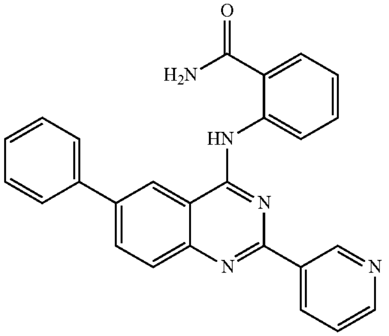 [SMILES: NC(=O)c1ccccc1Nc1nc(-c2cccnc2)nc2ccc(-c3ccccc3)cc12] | 2 HCl | $^{1}$H NMR (400 MHz, DMSO) δ 13.20 (s, 1H), 9.63 (s, 1H), 9.20 (d, J = 8.1 Hz, 1H), 8.97 (dd, J = 5.3, 1.3 Hz, 1H), 8.89 (d, J = 8.3 Hz, 1H), 8.56 (d, J = 1.6 Hz, 1H), 8.46 (s, 1H), 8.31 (dd, J = 8.7, 1.8 Hz, 1H), 8.13-7.92 (m, 4H), 7.90-7.83 (m, 2H), 7.77-7.70 (m, 1H), 7.59 (dd, J = 10.4, 4.8 Hz, 2H), 7.53-7.46 (m, 2H), 7.34-7.25 (m, 1H). |

TABLE 4-continued
| | | | |
|---|---|---|---|
| 783 | 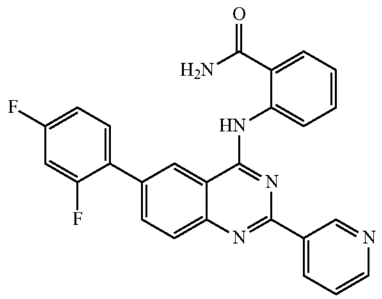 [SMILES: NC(=O)c1ccccc1Nc1nc(-c2cccnc2)nc2ccc(-c3ccc(F)cc3F)cc12] | 2 HCl | $^1$H NMR (400 MHz, DMSO) δ 13.22 (s, 1H), 9.65 (s, 1H), 9.19 (d, J = 8.1 Hz, 1H), 9.00-8.91 (m, 2H), 8.44 (d, J = 12.8 Hz, 2H), 8.18-7.89 (m, 5H), 7.84-7.70 (m, 2H), 7.56-7.45 (m, 1H), 7.38-7.23 (m, 2H). |
| 784 | 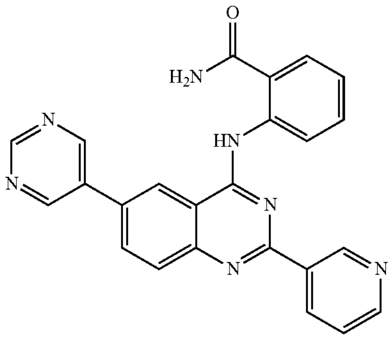 [SMILES: NC(=O)c1ccccc1Nc1nc(-c2cccnc2)nc2ccc(-c3cncnc3)cc12] | 2 HCl | $^1$H NMR (400 MHz, DMSO) δ 13.15 (s, 1H), 9.65 (s, 1H), 9.38-9.27 (m, 3H), 9.17 (d, J = 9.2 Hz, 1H), 8.92 (dd, J = 25.3, 6.7 Hz, 2H), 8.68 (s, 1H), 8.45 (d, J = 8.9 Hz, 2H), 8.12 (d, J = 9.8 Hz, 1H), 8.04-7.92 (m, 3H), 7.74 (t, J = 7.6 Hz, 1H), 7.30 (t, J = 8.1 Hz, 1H). |
| 785 | 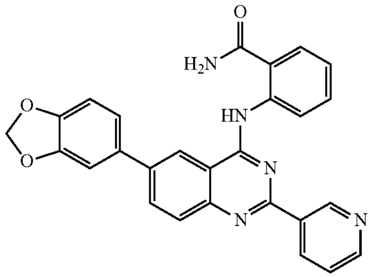 [SMILES: NC(=O)c1ccccc1Nc1nc(-c2cccnc2)nc2ccc(-c3ccc4c(c3)OCO4)cc12] | 2 HCl | $^1$H NMR (400 MHz, DMSO) δ 13.10 (s, 1H), 9.63 (s, 1H), 9.18 (d, J = 8.0 Hz, 1H), 8.96 (dd, J = 5.3, 1.3 Hz, 1H), 8.87 (d, J = 8.1 Hz, 1H), 8.46 (d, J = 21.1 Hz, 2H), 8.27 (dd, J = 8.7, 1.3 Hz, 1H), 8.09-7.89 (m, 4H), 7.74 (t, J = 7.1 Hz, 1H), 7.46 (d, J = 1.8 Hz, 1H), 7.38 (dd, J = 8.1, 1.9 Hz, 1H), 7.30 (t, J = 7.2 Hz, 1H), 7.12 (d, J = 8.1 Hz, 1H), 6.12 (s, 2H). |

TABLE 4-continued
| | | | |
|---|---|---|---|
| 786 | 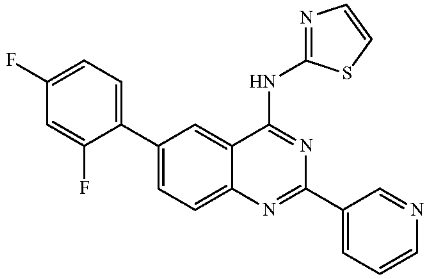 [SMILES: Fc1ccc(-c2ccc3nc(-c4cccnc4)nc(Nc4nccs4)c3c2)c(F)c1] | 2 HCl | 1H NMR (DMSO-d6) ppm 9.79 (d, J = 1.56 Hz, 1H), 9.26 (brd, J = 7.2 Hz, 1H), 9.00-8.90 (brm, 2H), 8.18 (d, J = 8.64 Hz, 1H), 8.11 (d, J = 8.64 Hz, 1H), 8.01 (brt, J = 6.28 Hz, 1H), 7.86-7.80 (brm, 1H), 7.72 (d, J = 3.96 Hz, 1H), 7.53-7.46 (m, 2H), 7.37-7.32 (brm, 1H). The 1H of 2HCl and NH— were not observed. |
| 787 | 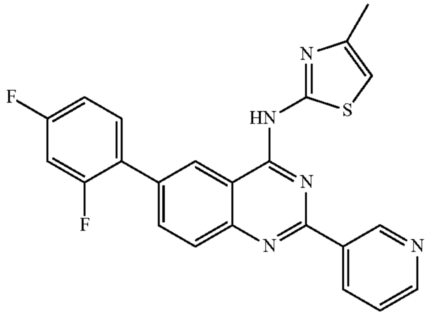 [SMILES: Cc1csc(Nc2nc(-c3cccnc3)nc3ccc(-c4ccc(F)cc4F)cc23)n1] | | 1H NMR (DMSO-d6) ppm 12.63 (brs, 1H), 9.80 (d, J = 1.64 Hz, 1H), 9.05-8.91 (brm, 2H), 8.76 (brd, J = 4.6 Hz, 1H), 8.10 (brd, J = 8.64 Hz, 1H), 8.02 (d, J = 8.64 Hz, 1H), 7.86-7.80 (brm, 1H), 7.66-7.62 (brm, 1H), 7.51-7.45 (brm, 1H), 7.34-7.30 (brm, 1H), 6.94 (brs, 1H), 2.35 (brs, 3H). |
| 788 | 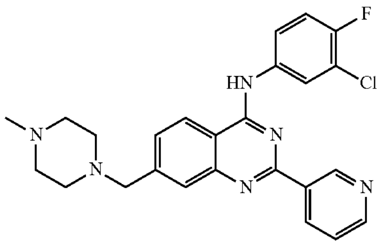 [SMILES: CN1CCN(Cc2ccc3c(Nc4ccc(F)c(Cl)c4)nc(-c4cccnc4)nc3c2)CC1] | | 1H NMR (300 MHz, CD3OD) δ 9.40 (s, 1H), 8.65 (s, J = 8.0 Hz, 1H), 8.56 (d, J = 3.2 Hz, 1H), 8.18-8.08 (m, 2H), 7.76-7.65 (m, 2H), 7.54-7.44 (m, 2H), 7.23 (t, J = 9.0 Hz, 1H), 3.66 (s, J = 8.0 Hz, 2H), 2.55 (s, J = 20.6 Hz, 8H), 2.30 (s, 3H). |

TABLE 4-continued
| | | |
|---|---|---|
| 789 | 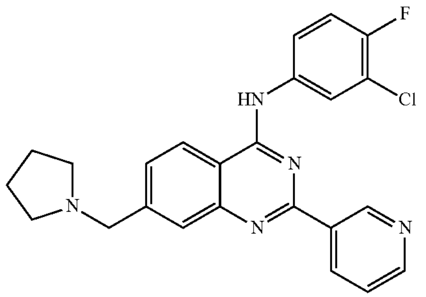 [SMILES: Fc1ccc(Nc2nc(-c3cccnc3)nc3cc(CN4CCCC4)ccc23)cc1Cl] | |
| 790 | 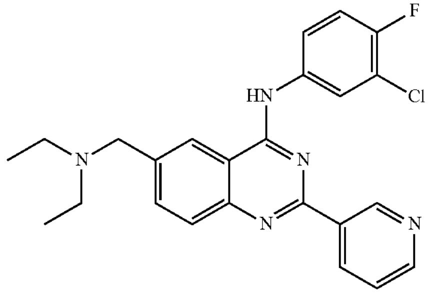 [SMILES: CCN(CC)Cc1ccc2nc(-c3cccnc3)nc(Nc3ccc(F)c(Cl)c3)c2c1] | |
| 791 | 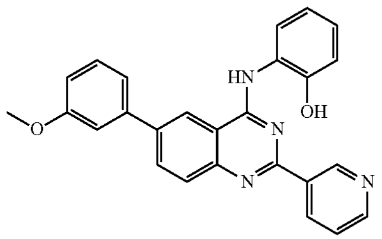 [SMILES: COc1cccc(-c2ccc3nc(-c4cccnc4)nc(Nc4ccccc4O)c3c2)c1] | $^{1}$H-NMR (400 MHz, DMSO-$d_6$): δ 12.20 (s, 1H), 9.64 (s, 1H), 9.58 (s, 1H), 8.73 (d, J = 5.5 Hz, 2H), 8.60 (s, 1H), 8.53 (dd, J = 7.2, 1.5 Hz, 1H), 8.28-8.25 (m, 1H), 7.99 (d, J = 8.7 Hz, 1H), 7.61-7.58 (m, 1H), 7.50 (t, J = 4.5 Hz, 3H), 7.30 (d, J = 5.8 Hz, 1H), 7.06 (dd, J = 7.4, 4.1 Hz, 1H), 6.49 (t, J = 6.9 Hz, 1H), 3.91 (s, 3H). |

TABLE 4-continued
| | | | |
|---|---|---|---|
| 792 | 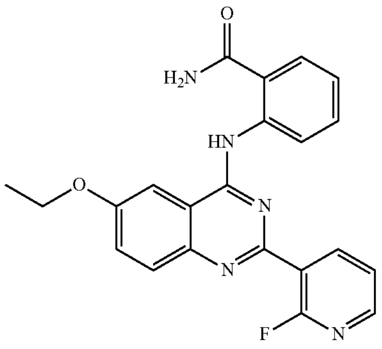 [SMILES: CCOc1ccc2nc(-c3cccnc3F)nc(Nc3ccccc3C(N)=O)c2c1] | HCl | $^1$H-NMR (400 MHz, DMSO-$d_6$): δ 13.42 (s, 1H), 8.99 (d, J = 8.0 Hz, 1H), 8.64 (td, J = 7.6, 2.0 Hz, 1H), 8.51 (s, 1H), 8.44 (d, J = 4.4 Hz, 1H), 8.01-7.95 (m, 3H), 7.68-7.58 (m, 4H), 7.24 (t, J = 7.8 Hz, 1H), 4.26 (q, J = 2.8 Hz, 2H), 1.47 (t, J = 2.8 Hz, 3H). |
| 793 | 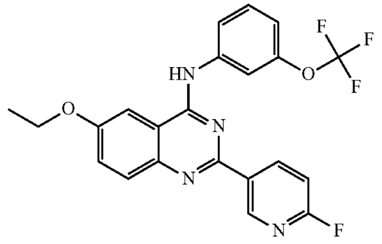 [SMILES: CCOc1ccc2nc(-c3ccc(F)nc3)nc(Nc3cccc(OC(F)(F)F)c3)c2c1] | HCl | $^1$H-NMR (400 MHz, DMSO-$d_6$): δ 10.31 (s, 1H), 9.13 (d, J = 2.0 Hz, 1H), 8.83 (td, J = 8.4, 2.4 Hz, 1H), 8.09 (d, J = 1.2 Hz, 2H), 7.93 (d, J = 8.4 Hz, 2H), 7.66-7.60 (m, 2H), 7.36 (dd, J = 8.8, 2.4 Hz, 1H), 7.22 (d, J = 8.0 Hz, 1H), 4.28 (q, J = 6.8 Hz, 2H), 1.47 (t, J = 6.8 Hz, 3H). |
| 794 | 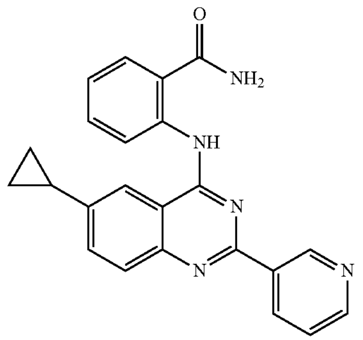 [SMILES: NC(=O)c1ccccc1Nc1nc(-c2cccnc2)nc2ccc(C3CC3)cc12] | 2HCl | |

TABLE 4-continued
| | | | |
|---|---|---|---|
| 795 | 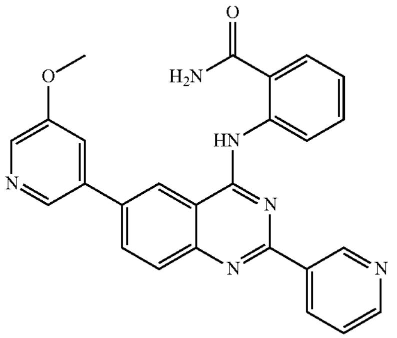 [SMILES: COc1cncc(-c2ccc3nc(-c4cccnc4)nc(Nc4ccccc4C(N)=O)c3c2)c1] | 3HCl | 1H-NMR (300 MHz, DMSO): δ 13.10 (s, 1H), 9.61 (s, 1H), 9.12 (d, J = 9.8 Hz, 1H), 8.93 (s, 1H), 8.83 (d, J = 15.2 Hz, 2H), 8.66 (s, 1H), 8.58-8.36 (m, 3H), 8.08 (d, J = 11.6 Hz, 2H),7.96 (d, J = 9.2 Hz, 3H), 7.73 (s, 1H), 7.29 (t, J = 8.7 Hz, 1H), 4.02 (s, 3H). |
| 796 | 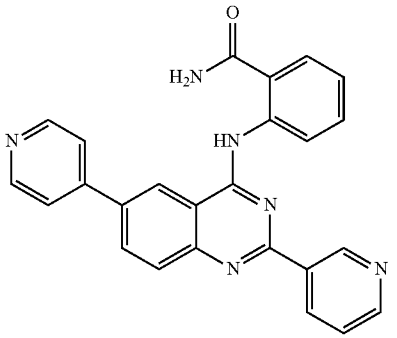 [SMILES: NC(=O)c1ccccc1Nc1nc(-c2cccnc2)nc2ccc(-c3ccncc3)cc12] | 3HCl | 1H-NMR (300 MHz, DMSO): δ 12.79 (s, 1H), 9.54 (d, J = 1.6 Hz, 1H), 9.18 (d, J = 8.2 Hz, 1H), 9.08 (d, J = 6.7 Hz, 2H), 9.05-8.96 (m, 2H), 8.63-8.46 (m, 4H), 8.39 (s, 1H), 8.08 (dd, J = 11.6, 8.5 Hz, 2H), 7.92 (d, J = 6.7 Hz, 1H), 7.77 (s, 1H), 7.68 (t, J = 7.1 Hz, 1H), 7.32 (t, J = 7.2 Hz, 1H). |
| 797 | 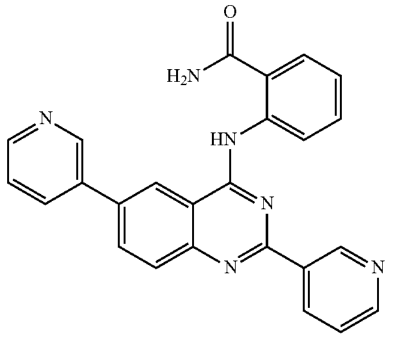 [SMILES: NC(=O)c1ccccc1Nc1nc(-c2cccnc2)nc2ccc(-c3cccnc3)cc12] | 3HCl | 1H-NMR (300 MHz, DMSO): δ 12.81 (s, 1H), 9.54 (s, 1H), 9.45 (s, 1H), 9.23 (d, J = 8.2 Hz, 1H), 9.08-8.93 (m, 3H), 8.83 (s, 1H), 8.52 (d, J = 8.2 Hz, 1H), 8.47-8.34 (m, 2H), 8.14 (ddd, J = 12.9, 8.1, 4.9 Hz, 3H), 7.92 (d, J = 6.6 Hz, 1H), 7.79 (s, 1H), 7.68 (t, J = 7.2 Hz, 1H), 7.32 (t, J = 7.2 Hz, 1H). |

TABLE 4-continued
| | | | |
|---|---|---|---|
| 798 | 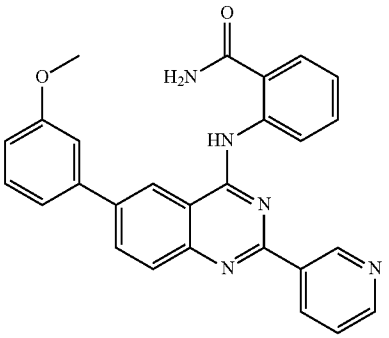 [SMILES: COc1cccc(-c2ccc3nc(-c4cccnc4)nc(Nc4ccccc4C(N)=O)c3c2)c1] | 2HCl | 1H-NMR (300 MHz, DMSO): δ 13.20 (s, 1H), 9.62 (s, 1H), 9.13 (d, J = 8.1 Hz, 1H), 8.94 (d, J = 3.5 Hz, 2H), 8.55 (s, 1H), 8.48 (s, 1H), 8.31 (d, J = 8.7 Hz, 1H), 8.06 (d, J = 8.7 Hz, 1H), 7.96 (s, 3H), 7.74 (s, 1H), 7.55-7.40 (m, 3H), 7.29 (s, 1H), 7.06 (d, J = 7.4 Hz, 1H), 3.90 (s, 3H). |
| 799 | 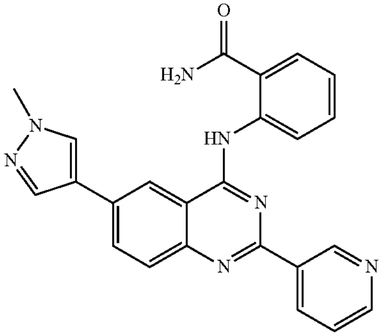 [SMILES: Cn1cc(-c2ccc3nc(-c4cccnc4)nc(Nc4ccccc4C(N)=O)c3c2)cn1] | | 1H-NMR (300 MHz, DMSO): δ 13.13 (s, 1H), 9.60 (d, J = 1.4 Hz, 1H), 9.12 (d, J = 7.8 Hz, 1H), 8.73 (dd, J = 9.7, 6.4 Hz, 2H), 8.52 (s, 1H), 8.35 (s, 1H), 8.28 (s, 1H), 8.14 (d, J = 8.7 Hz, 1H), 8.08-7.88 (m, 4H), 7.76 (d, J = 7.2 Hz, 1H), 7.59 (dd, J = 7.4, 4.8 Hz, 1H), 7.23 (t, J = 7.1 Hz, 1H), 3.94 (s, 3H). |
| 800 | 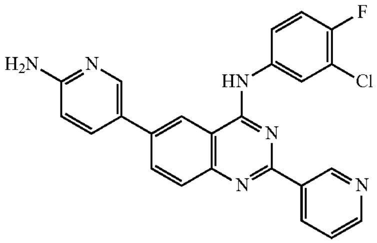 [SMILES: Nc1ccc(-c2ccc3nc(-c4cccnc4)nc(Nc4ccc(F)c(Cl)c4)c3c2)cn1] | | $^{1}$H NMR (400 MHz, DMSO) δ 10.08 (s, 1H), 9.59-9.49 (m, 1H), 8.79-8.63 (m, 3H), 8.55 (d, J = 2.1 Hz, 1H), 8.27 (dd, J = 6.9, 2.6 Hz, 1H), 8.18 (dd, J = 8.7, 1.9 Hz, 1H), 8.02-7.90 (m, 3H), 7.63-7.51 (m, 2H), 6.62 (d, J = 8.6 Hz, 1H), 6.24 (s, 2H). |

TABLE 4-continued

| | | |
|---|---|---|
| 801 | 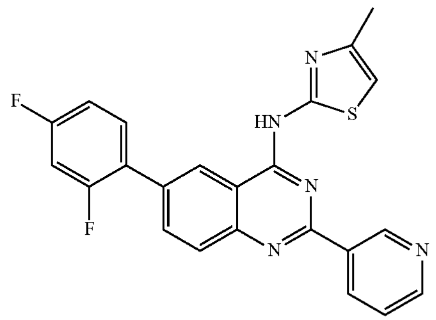 [SMILES: Cc1csc(Nc2nc(-c3cccnc3)nc3ccc(-c4ccc(F)cc4F)cc23)n1] | 1H NMR (DMSO-d6) ppm 9.78 (brs, 1H), 9.20-8.80 (br, 3H), 8.14 (brd, J = 8.64 Hz, 1H), 8.04 (d, J = 8.64 Hz, 1H), 7.83 brm, 2H), 7.52-7.47 (m, 1H), 7.35-7.31 (m, 1H), 7.00 (brs, 1H), 2.36 (brs, 3H), 2.30 (brs, 3H). The 1H of MsOH and NH were not observed. |

| Number | $^1$H NMR Solvent | Purity percent | Method of Coupling | LCMS | LCMS Method |
|---|---|---|---|---|---|
| 748 | DMSO | >98 | Method N6 | | |
| 749 | DMSO | >98 | Method N6 | | |
| 750 | DMSO | >98 | Method N6 | | |
| 751 | DMSO | >98 | Method N6 | | |
| 752 | DMSO | >98 | Method N6 | | |
| 753 | DMSO | >98 | Method N6 | | |
| 754 | DMSO | >98 | Method N6 | | |
| 755 | DMSO | >98 | Method N6 | | |
| 756 | DMSO | >98 | Method N6 | | |
| 757 | DMSO | >98 | Method N6 | | |
| 758 | DMSO | >98 | Method N6 | | |
| 759 | DMSO | >98 | Method N6 | | |
| 760 | DMSO | >98 | Method N6 | | |
| 761 | DMSO | >98 | Method N6 | | |
| 762 | DMSO | >98 | Method N6 | | |
| 763 | DMSO | >98 | Method N6 | | |
| 764 | DMSO | >98 | Method N6 | | |
| 765 | DMSO | >98 | Method N6 | | |
| 766 | DMSO | >98 | Method N6 | | |
| 767 | DMSO | >98 | Method N6 | | |
| 768 | DMSO | >98 | Method N6 | | |
| 769 | DMSO | >98 | Method N6 | | |
| 770 | DMSO | >98 | Method N6 | | |
| 771 | DMSO | >98 | Method N6 | | |
| 772 | DMSO | >98 | Method N6 | | |
| 773 | DMSO | >98 | Method N6 | | |
| 774 | DMSO | >98 | Method N6 | | |
| 775 | DMSO | >98 | Method N6 | | |
| 776 | DMSO | >98 | Method N6 | | |
| 777 | DMSO | >98 | Method N6 | | |
| 778 | DMSO | >98 | Method N6 | | |
| 779 | DMSO | >98 | Method N6 | | |
| 780 | DMSO | >98 | Method N6 | | |
| 781 | DMSO | >98 | Method N6 | | |

TABLE 4-continued

| | | | | | |
|---|---|---|---|---|---|
| 782 | DMSO | >98 | Method N6 | | |
| 783 | DMSO | >98 | Method N6 | | |
| 784 | DMSO | >98 | Method N6 | | |
| 785 | DMSO | >98 | Method N6 | | |
| 786 | DMSO | >98 | N6 using $Na_2CO_3$ instead of $K_3PO_4$ | | |
| 787 | DMSO | >98 | N6 using $Na_2CO_3$ instead of $K_3PO_4$ | | |
| 788 | CD3OD | 99 | Method N3 | 463.0 (M + 1) | Method C |
| 789 | | 99 | Method N3 | 434.0 (M + 1) | Method C |
| 790 | | 99 | Method N3 | 436.0 (M + 1) | Method C |
| 791 | DMSO | 95 | Method N1 | 422.2 (M + 1) | Method B (NH4HCO3) |
| 792 | DMSO | 95 | Method N1 | 404.0 (M + 1) | Method B (NH4HCO3) |
| 793 | DMSO | 95 | Method N1 | 445.0 (M + 1) | Method B (NH4HCO3) |
| 794 | DMSO | 95 | Method N1 | 382.5 (M + 1) | Method C |
| 795 | DMSO | 95 | Method N1 | 449.4 (M + 1) | Method C |
| 796 | DMSO | 95 | Method N1 | 419.1 (M + 1) | Method C |
| 797 | DMSO | 95 | Method N1 | 419.1 (M + 1) | Method C |
| 798 | DMSO | 95 | Method N1 | 448.1 (M + 1) | Method C |
| 799 | DMSO | 95 | Method N1 | 422.2 (M + 1) | Method C |
| 800 | DMSO | >98 | N5 | | |
| 801 | DMSO | >98 | N6 using $Na_2CO_3$ instead of $K_3PO_4$ | | |

TABLE 4-continued
| Number | PRODUCT | Salt type | Molecular Mass |
| --- | --- | --- | --- |
| 802 | 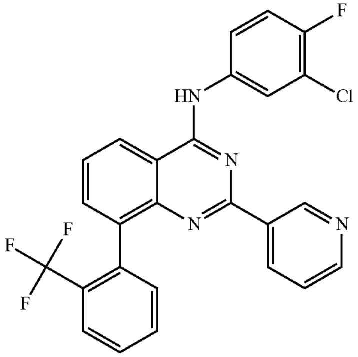 [SMILES: Fc1ccc(Nc2nc(-c3cccnc3)nc3c(-c4ccccc4C(F)(F)F)cccc23)cc1Cl] | | 494.87 |
| 803 | 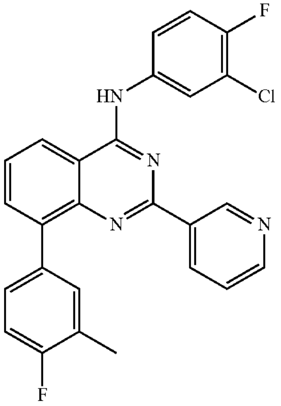 [SMILES: Cc1cc(-c2cccc3c(Nc4ccc(F)c(Cl)c4)nc(-c4cccnc4)nc23)ccc1F] | | 458.89 |

TABLE 4-continued
| | | |
|---|---|---|
| 804 | 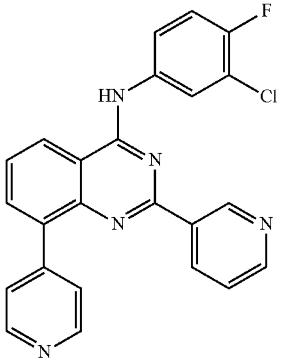 [SMILES: Fc1ccc(Nc2nc(-c3cccnc3)nc3c(-c4ccncc4)cccc23)cc1Cl] | 427.86 |
| 805 | 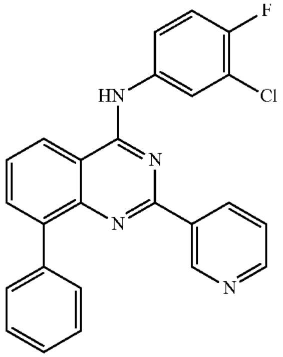 [SMILES: Fc1ccc(Nc2nc(-c3cccnc3)nc3c(-c4ccccc4)cccc23)cc1Cl] | 426.87 |
| 806 | 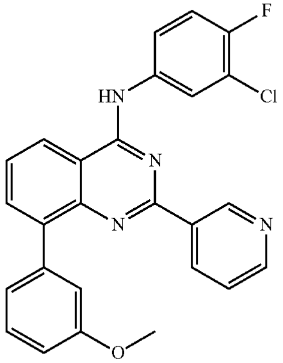 [SMILES: COc1cccc(-c2cccc3c(Nc4ccc(F)c(Cl)c4)nc(-c4cccnc4)nc23)c1] | 456.9 |

TABLE 4-continued

| | | |
|---|---|---|
| 807 | 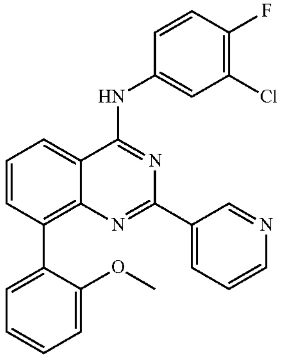 [SMILES: COc1ccccc1-c1cccc2c(Nc3ccc(F)c(Cl)c3)nc(-c3cccnc3)nc12] | 456.9 |

| Number | $^1$H-NMR | $^1$H-NMR Solvent | LCMS | LCMS Protocol | Purity percent | Method for Coupling |
|---|---|---|---|---|---|---|
| 802 | $^1$H-NMR (400 MHz, DMSO-$d_6$): δ10.18 (s, 1H), 9.21 (d, J = 1.8 Hz, 1H), 8.65-8.60 (m, 2H), 8.34-8.24 (m, 2H), 7.96-7.90 (m, 2H), 7.85-7.68 (m, 4H), 7.56 (t, J = 9.0 Hz, 1H), 7.51-7.44 (m, 2H). | DMSO | 495.0, 497.0 (M + 1) | Method B (NH4HCO3) | 95 | Method N1 |
| 803 | $^1$H-NMR (400 MHz, DMSO-$d_6$): δ10.14 (s, 1H), 9.44 (s, 1H), 8.73-8.63 (m, 1H), 8.55 (t, J = 6.5 Hz, 2H), 8.27 (d, J = 4.6 Hz, 1H), 7.96 (d, J = 6.8 Hz, 2H), 7.76-7.64 (m, 3H), 7.58-7.52 (m, 2H), 7.31 (t, J = 9.2 Hz, 1H), 2.37 (s, 3H). | DMSO | 459.0, 461.0 (M + 1) | Method B (NH4HCO3) | 95 | Method N1 |
| 804 | $^1$H-NMR (400 MHz, DMSO-$d_6$): δ 10.19 (s, 1H), 9.42 (d, J = 1.5 Hz, 1H), 8.74 (d, J = 5.6 Hz, 2H), 8.69-8.63 (m, 2H), 8.52 (d, J = 8.0 Hz, 1H), 8.28 (dd, J = 6.8, 2.6 Hz, 1H), 8.05 (d, J = 7.2 Hz, 1H), 7.96-7.91 (m, 1H), 7.80 (dd, J = 14.6, 6.8 Hz, 3H), 7.59-7.52 (m, 2H). | DMSO | 428.0, 430.0 (M + 1) 214.6 (M/2 + 1) | Method A (TFA) | 95 | Method N1 |
| 805 | $^1$H-NMR (400 MHz, DMSO-$d_6$): δ 10.13 (s, 1H), 9.43 (d, J = 1.6 Hz, 1H), 8.66 (dd, J = 4.7, 1.6 Hz, 1H), 8.59-8.56 (m, 1H), 8.52 (td, J = 7.9, 1.8 Hz, 1H), 8.30 (dd, J = 6.84, 2.60 Hz, 1H), 7.99-7.92 (m, 2H), 7.82-7.73 (m, 3H), 7.58-7.51 (m, 4H), 7.46 (t, J = 7.4 Hz, 1H). | DMSO | 427.1, 429.1 (M + 1) | Method A (TFA) | 95 | Method N1 |

TABLE 4-continued

| | | | | | | |
|---|---|---|---|---|---|---|
| 806 | $^{1}$H-NMR (400 MHz, DMSO-$d_6$): δ 10.13 (s, 1H), 9.45 (s, 1H), 8.67 (dd, J = 4.7, 1.7 Hz, 1H), 8.62-8.49 (m, 2H), 8.29 (dd, J = 6.8, 2.6 Hz, 1H), 8.03-7.88 (m, 2H), 7.81-7.68 (m, 1H), 7.62-7.49 (m, 2H), 7.48-7.30 (m, 3H), 7.04 (dd, J = 7.8, 2.1 Hz, 1H), 3.87-3.81 (m, 3H). | DMSO | 457.1, 459.1 (M + 1) | Method A (TFA) | 95 | Method N1 |
| 807 | $^{1}$H-NMR (400 MHz, DMSO-d6): δ10.10 (s, 1H), 9.31 (d, J = 1.6 Hz, 1H), 8.63 (dd, J = 4.8, 1.7 Hz, 1H), 8.61-8.52 (m, 1H), 8.41 (td, J = 8.0, 1.9 Hz, 1H), 8.30 (dd, J = 6.9, 2.6 Hz, 1H), 7.97-7.92 (m, 1H), 7.83 (dd, J = 7.2, 1.2 Hz, 1H), 7.73- 7.66 (m, 1H), 7.62-7.40 (m, 3H), 7.36 (dd, J = 7.4, 1.7 Hz, 1H), 7.19 (d, J = 8.1 Hz, 1H), 7.10 (t, J = 7.4 Hz, 1H), 3.66 (s, 3H). | DMSO | 457.1, 459.1 (M + 2) | Method B (NH4HCO3) | 95 | Method N1 |

Scheme 20: General route for the synthesis of compounds with general formula xxii

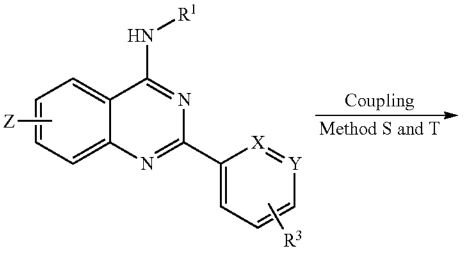

vi

Z = Br

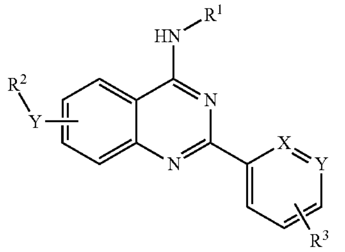

xxii

Y = O, NH

X or Z = CH or N

Scheme 21: Representative synthesis of compounds of formula xxii (see Scheme 20)

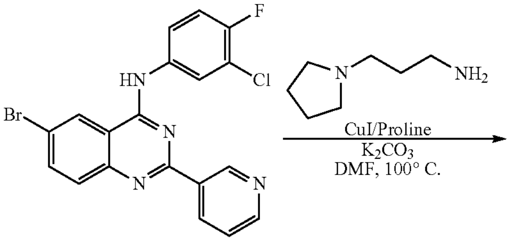

vi-g

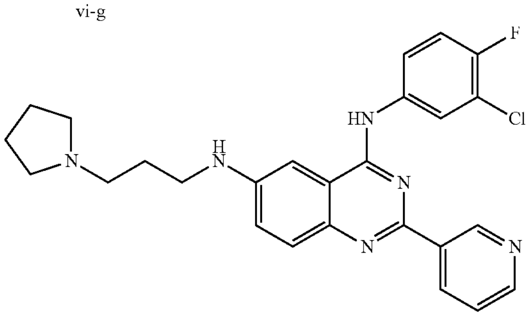

xxii-a

Method S: $N^4$-(3-chloro-4-fluorophenyl)-2-(pyridin-3-yl)-$N^6$-(3(pyrrolidin-1-yl)propyl)quinazoline-4,6-diamine (xxii-a)

A 2.0 dram reaction vial was charged with 6-bromo-N-(3-chloro-4-fluorophenyl)-2-(pyridin-3-yl)quinazolin-4-amine (synthesized as described in Scheme 1 and 4, substituting 5-bromo-2-nitrobenzoic acid for 2-nitro-5-propoxy-benzoic acid and 3-chloro-4-fluoroaniline for 2-aminobenzamide) (100 mg, 0.233 mmol, 1.0 equiv), 3-(pyrrolidin-1-yl)propan-1-amine (40 mg, 0.345 mmol, 1.5 equiv), copper(I) iodide (4.4 mg, 0.023 mmol, 0.1 equiv), L-proline (5.3 mg, 0.046 nm tool, 0.2 equiv), and potassium carbonate (96 mg, 0.69 mmol, 3.0 equiv) in 1DMF (3 mL). The reaction mixture was heated at 100° C. overnight. After cooling, water was added to the reaction mixture, and the resultant precipitate was collected by filtration. The crude product was purified via prep-TLC (silica, 2000 micron plate, 95% dichloromethane-5% methanol-0.1% $NH_4OH$) to yield the desired compound as a brown solid (17.2 mg, 15%). LCMS m/z=477.4 (M+1) (Method C) (retention time=1.68 min). $^1H$ NMR (300 MHz, DMSO) δ 9.68 (s, 1H), 9.46 (s, 1H), 8.59 (d, J=9.4 Hz, 2H), 8.25 (dd, J=6.8, 2.6 Hz, 1H), 7.93 (dd, J=8.3, 3.5 Hz, 1H), 7.69-7.59 (m, 1H), 7.52 (dd, J=11.0, 7.1 Hz, 2H), 7.36-7.19 (m, 2H), 6.41 (s, 1H), 3.34 (m, 2H) 2.69 (m, 6H), 2.02-1.82 (m, 2H), 1.75 (bs, 4H).

Scheme 22: Representative synthesis of compounds of formula xxii (see Scheme 20)

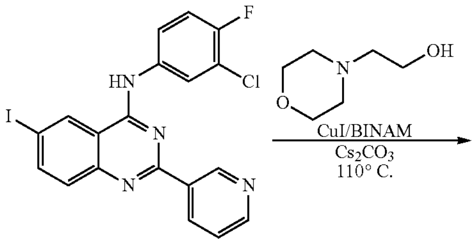

vi-i

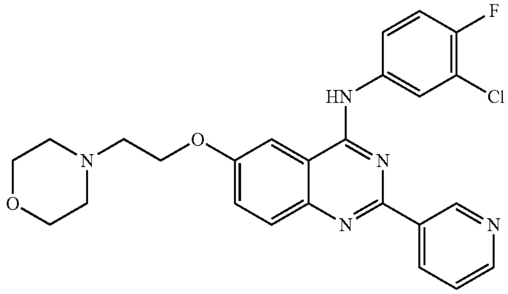

xxii-b

Method T: N-(3-chloro-4-fluorophenyl)-6-(2-morpholinoethoxy)-2-(pyridin-3-yl)quinazolin-4-amine (xxii-b)

A 2.5 dram reaction vial was charged with N-(3-chloro-4-fluorophenyl)-6-iodo-2-(pyridin-3-yl)quinazolin-4-amine (0.250 g, 0.524 mmol), 2-morpholinoethanol (1 ml, 8.17 mmol) as solvent, copper(I) iodide (0.020 g, 0.105 mmol), racemic-2,2'-diamino-1,1'-binaphthyl (0.030 g, 0.105 mmol), and cesium carbonate (0.513 g, 1.573 mmol). The reaction mixture was heated at 110° C. overnight. After cooling, water was added to the reaction mixture, and the resultant precipitate was collected by filtration. The solid residue was purified via ISCO (silica, 12 g column, 95% dichloromethane-5% methanol-0.1% $NH_4OH$) to yield the desired compound as a brown solid. The solid was further washed with a mixture of water and saturated $NaHCO_3$ solution and dried. The product off the column was further purified by prep TLC (silica gel, 1000 micron, 95% dichloromethane-5% methanol-0.1% $NH_4OH$) to afford the desired product as a light brown solid (21.2 mg, 8%), LCMS m/z=480.0 (M+1) (Method C) (retention time=2.09 min). $^1H$ NMR (300 MHz, DMSO) δ 9.81 (s, 1H), 9.47 (d, J=1.8 Hz, 1H), 8.66-8.57 (m, 2H), 8.21 (dd, J=6.8, 2.6 Hz, 1H), 7.92 (d, J=2.5 Hz, 1H), 7.87 (ddd, J=8.9, 4.3, 2.7 Hz, 1H), 7.81 (d, J=9.1 Hz, 1H), 7.57-7.47 (m, 3H), 4.25 (t, J=5.8 Hz, 2H), 3.64-3.55 (m, 4H), 2.78 (t, J=5.7 Hz, 2H), 2.55-2.49 (m, 4H).

The compounds in the following table were prepared in a manner analogous to that described in Scheme 20 substituting with appropriate amine or alcohol

TABLE 5

| Number | Product | Salt type | Molecular Mass | ¹H-NMR | ¹H-NMR Solvent | LCMS | Retention Time (min.) | LCMS Protocol | Purity Percent | Method for Coupling |
|---|---|---|---|---|---|---|---|---|---|---|
| 808 | 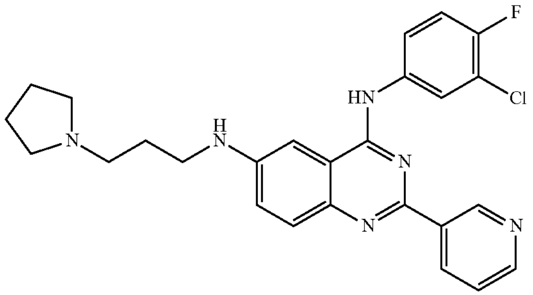 [SMILES: Fc1ccc(Nc2nc(-c3cccnc3)nc3ccc(NCCCN4CCCC4)cc23)cc1Cl] | | 476.98 | 1H NMR (300 MHz, DMSO) δ 9.68 (s, 1H), 9.46 (s, 1H), 8.59 (d, J = 9.4 Hz, 2H), 8.25 (dd, J = 6.8, 2.6 Hz, 1H), 7.93 (dd, J = 8.3, 3.5 Hz, 1H), 7.69-7.59 (m, 1H), 7.52 (dd, J =11.0, 7.1 Hz, 2H), 7.36-7.19 (m, 2H), 6.41 (s, 1H), 3.34 (m, 2H), 2.69 (m, | DMSO | 477.4 (M + 1) | 1.68 | Method C | 95 | Method S |
| 809 | 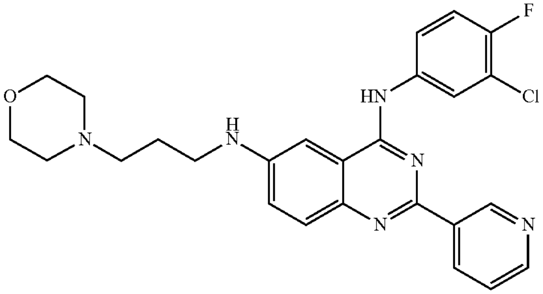 [SMILES: Fc1ccc(Nc2nc(-c3cccnc3)nc3ccc(NCCCN4CCOCC4)cc23)cc1Cl] | | 492.98 | 1H NMR (300 MHz, DMSO) δ 9.63 (s, 1H), 9.46 (s, 1H), 8.60 (td, J = 4.2, 2.4 Hz, 2H), 8.23 (dd, J = 6.8, 2.6 Hz, 1H), 7.90 (ddd, J = 8.9, 4.2, 2.6 Hz, 1H), 7.65 (d, J = 9.0 Hz, 1H), 7.57-7.45 (m, 2H), 7.32 (dd, J = 9.1, 2.2 Hz, 1H), 7.20 (s, 1H), 6.38 (s | DMSO | 493 (M + 1) | 1.97 | Method C | 100 | Method S |
| 810 | 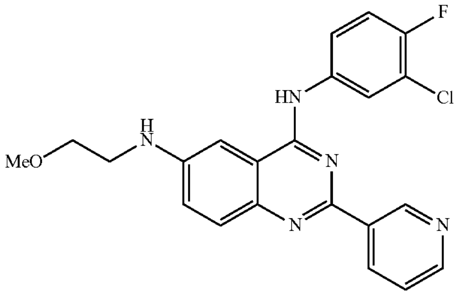 [SMILES: COCCNc1ccc2nc(-c3cccnc3)nc(Nc3ccc(F)c(Cl)c3)c2c1] | | 423.87 | 1H NMR (300 MHz, DMSO) δ 9.60 (s, 1H), 9.46 (s, 1H), 8.60 (dd, J = 9.1, 3.1 Hz, 2H), 8.22 (dd, J = 6.9, 25 Hz, 1H), 7.89 (ddd, J = 9.0, 4.3, 2.7 Hz, 1H), 7.64 (d, J = 9.0 Hz, 1H), 7 58-7.46 (m, 2H), 7.37 (dd, J = 9.1, 2.2 Hz, 1H), 7.25 (s, 1H), 6.40 (t | DMSO | 423.9 (M + 1) | 2.16 | Method C | 100 | Method S |

TABLE 5-continued

| Number | Product | Salt type | Molecular Mass | $^1$H-NMR | $^1$H-NMR Solvent | LCMS | Retention Time (min.) | LCMS Protocol | Purity Percent | Method for Coupling |
|---|---|---|---|---|---|---|---|---|---|---|
| 811 | 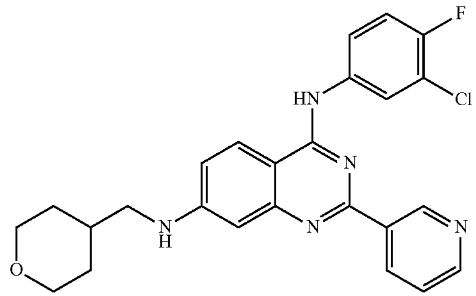 [SMILES: Fc1ccc(Nc2nc(-c3cccnc3)nc3cc(NCC4CCOCC4)ccc23)cc1Cl] | | 463.93 | 1H NMR (300 MHz, DMSO) δ 9.62 (s, 1H), 9.49 (d, J = 1.7 Hz, 1H), 8.70-8.59 (m, 2H), 8.27 (dd, J = 6.9, 2.5 Hz, 1H), 8.19 (dd, J = 9.0, 5.0 Hz, 1H), 7.91-7.82 (m, 1H), 7.57-7.43 (m, 2H), 7.01 (dd, J = 9.0, 2.1 Hz, 1H), 6.77 (t, J = 5.3 Hz, 1H), 6.72 | DMSO | 464.0 (M + 1) | 2.19 | Method C | 100 | Method S |
| 812 | 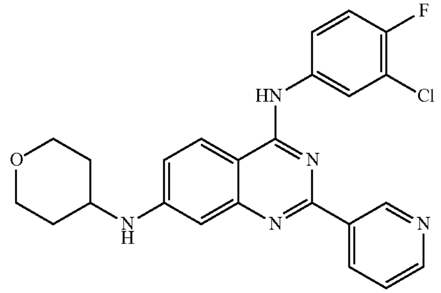 [SMILES: Fc1ccc(Nc2nc(-c3cccnc3)nc3cc(NC4CCOCC4)ccc23)cc1Cl] | | 449.91 | 1H NMR (300 MHz, DMSO) δ 9.65 (s, 1H), 9.49 (d, J = 2.1 Hz, 1H), 8.69-8.59 (m, 2H), 8.27 (dd, J = 6.9, 2.6 Hz, 1H), 8.20 (d, J = 9.0 Hz, 1H), 7.87 (ddd, J = 9.0, 4.3, 2.7 Hz, 1H), 7.56-7.43 (m, 2H), 7.00 (dd, J = 9.1, 2.2 Hz, 1H), 6.79 (d, J = 2.1 Hz, | DMSO | 449.9 (M + 1) | 2.12 | Method C | 100 | Method S |
| 813 | 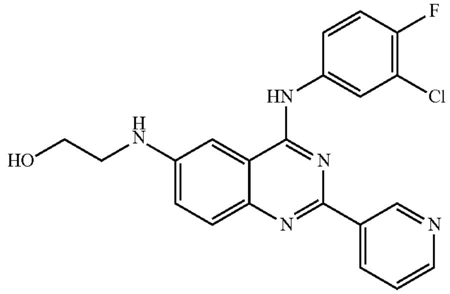 [SMILES: OCCNc1ccc2nc(-c3cccnc3)nc(Nc3ccc(F)c(Cl)c3)c2c1] | | 409.84 | 1H NMR (300 MHz, DMSO) δ 9.71 (s, 1H), 9.46 (s, 1H), 8.66-8.55 (m, 2H), 8.24 (d, J = 4.3 Hz, 1H), 796-7.87 (m, 1H), 7.64 (d, J = 9.1 Hz, 1H), 7.58-7.46 (m, 3H), 7.36 (d, J = 9.0 Hz, 1H), 7.28 (s, 1 H), 6.38 (s, 1H), 4.96 (s, 1H), 3.69 (s, 2H), 3.42 | DMSO | 409.9 (M + 1) | 1.86 | Method C | 100 | Method S |

TABLE 5-continued

| Number | Product | Salt type | Molecular Mass | $^1$H-NMR | $^1$H-NMR Solvent | LCMS | Retention Time (min.) | LCMS Protocol | Purity Percent | Method for Coupling |
|---|---|---|---|---|---|---|---|---|---|---|
| 814 | 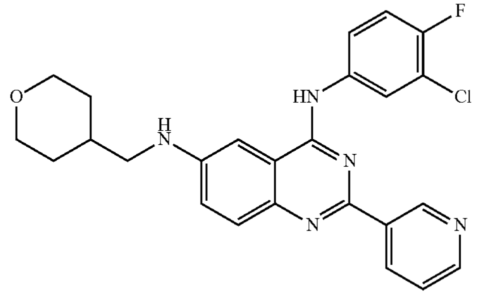 [SMILES: Fc1ccc(Nc2nc(-c3cccnc3)nc3ccc(NCC4CCOCC4)cc23)cc1Cl] | | 463.93 | 1H NMR (300 MHz, DMSO) δ 9.59 (s, 1H), 9 45 (d, J = 1.2 Hz, 1H), 8.60 (dd, J = 7.4, 5.7 Hz, 2H), 6.23 (dd, J = 6.8, 2.5 Hz, 1H), 7.90 (dd, J = 9.0, 2.7 Hz, 1H), 7.64 (d, J = 9.0 Hz, 1H), 7.57-7.46 (m, 2H, 7.36 (d, J = 9.1 Hz, 1H), 7.19 (s, 1H), 6.38 (s | DMSO | 464.0 (M + 1) | 2.19 | Method C | 95 | Method S |
| 815 | 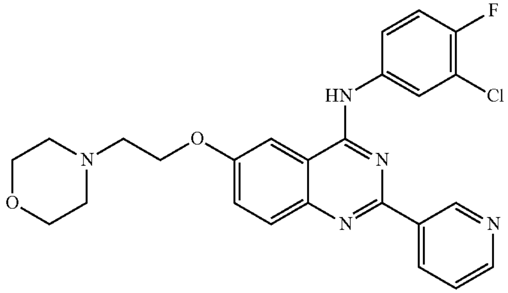 [SMILES: Fc1ccc(Nc2nc(-c3cccnc3)nc3ccc(OCCN4CCOCC4)cc23)cc1Cl] | | 479.93 | 1H NMR (300 MHz, DMSO) δ 9.81 (s, 1H), 9.47 (d, J = 1.8 Hz, 1H), 8.66-8.57 (m, 2H), 8.21 (dd, J = 6.8, 2.6 Hz, 1H), 7.92 (d, J = 2.5 Hz, 1H), 7.87 (ddd, J = 8.9, 4.3, 2.7 Hz, 1H), 7.81 (d, J = 9.1 Hz, 1H), 7.57-7.47 (m, 3H), 4.25 (t, J = 5.8 Hz, 2H), | DMSO | 480.0 (M + 1) | 2.09 | Method C | 91 | Method T |
| 816 | 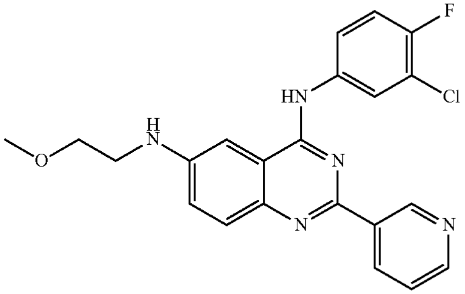 [SMILES: COCCNc1ccc2nc(-c3cccnc3)nc(Nc3ccc(F)c(Cl)c3)c2c1] | | 423.87 | 1H NMR (300 MHz, DMS0) δ 9.60 (s, 1H), 9.47 (s, 1 H), 8.67-8.55 (m, 2H), 8.23 (dd, J = 6.9, 2.5 Hz, 1H), 7.90 (ddd, J = 9.0, 4.3, 2.7 Hz, 1H), 7.65 (d, J = 9.0 Hz, 1H), 7.58-7.47 (m, 2H), 7.37 (dd, J = 9.1, 2.2 Hz, 1H), 7.25 (d, J = 1.3 Hz, 1H), 6.41 (t, J = 5.6 Hz, 1H), 3.63 (t, J = 5.7 Hz, 2H), 3.48-3.35 (m, 5H). | DMSO | 423.9 (M + 1) | | Method C | 99 | Method S |

TABLE 5-continued

| Number | Product | Salt type | Molecular Mass | $^1$H-NMR | $^1$H-NMR Solvent | LCMS | Retention Time (min.) | LCMS Protocol | Purity Percent | Method for Coupling |
|---|---|---|---|---|---|---|---|---|---|---|
| 817 | 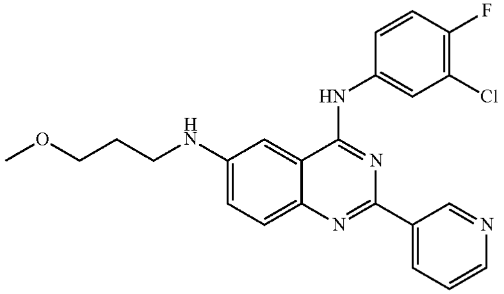 [SMILES: COCCCNc1ccc2nc(-c3cccnc3)nc(Nc3ccc(F)c(Cl)c3)c2c1] | | 437.9 | 1H NMR (300 MHz, DMSO) δ 9.63 (s, 1H), 9.47 (s, 1H), 8.66-8.55 (m, 2H), 8.23 (dd, J = 6.9, 2.5 Hz, 1H), 7.90 (ddd, J = 8.8, 4.3, 2.5 Hz, 1H), 7.65 (d, J = 9.0 Hz, 1H), 7.58-7.45 (m, 2H), 7.32 (dd, J = 9.0, 1.8 Hz, 1H), 7.21 (s, 1H), 6.34 (t, J = 5.0 Hz, 1H), 3.50 (t, J = 6.1 Hz, 2H), 3.31-3.20 (m, 5H), 1.92 (p, J = 6.5 Hz, 2H). | DMSO | 438.1 (M + 1) | | Method C | 99 | Method S |
| 818 | 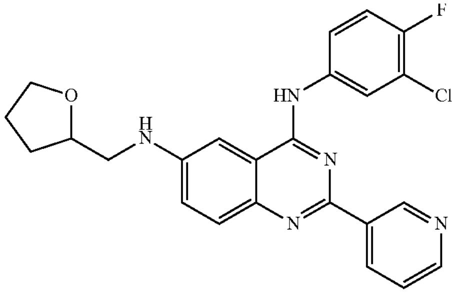 [SMILES: Fc1ccc(Nc2nc(-c3cccnc3)nc3ccc(NCC4CCCO4)cc23)cc1Cl] | | 449.91 | 1H NMR (300 MHz, DMSO) δ 9.61 (s, 1H), 9.46 (d, J = 2.1 Hz, 1H), 8.65-8.56 (m, 2H), 8.23 (dd, J = 6.9, 2.6 Hz, 1H), 7.90 (ddd, J = 8.9, 4.2, 2.6 Hz, 1H), 7.64 (d, J = 9.0 Hz, 1H), 7.58-7.47 (m, 2H), 7.40 (dd, J = 8.9, 2.2 Hz, 1H), 7.26 (d, J = 1.7 Hz, 1H), 6.39 (t, J = 5.7 Hz, 1H), 4.12 (t, J = 6.2 Hz, 1H), 3.85 (dd, J = 14.2, 7.2 Hz, 1H), 3.70 (dd, J = 14.2, 7.7 Hz, 1H), 3.34-3.25 (m, 5H), 2.15-1.99 (m, 1H), 1.97-1.80 (m, 3H), 1.74-158 (m, 2H). | DMSO | 449.9 (M + 1) | | Method C | 94 | Method S |
| 819 | 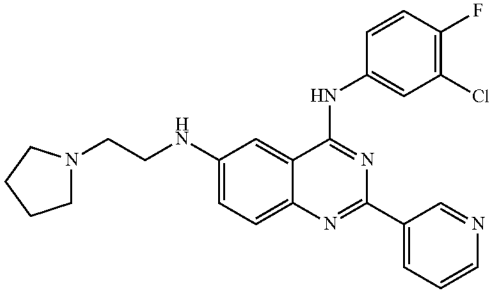 [SMILES: Fc1ccc(Nc2nc(-c3cccnc3)nc3ccc(NCCN4CCCC4)cc23)cc1Cl] | | | 1H-NMR (300 MHz, DMSO): δ 10.04 (s, 1H), 9.48 (s, 1H), 8.67 (s, 2H), 8.43-8.31 (m, 1H), 8.14-8.01 (m, 1H), 7.72 (d, J = 9.0 Hz, 1H), 7.65 (s, 1H), 7.54 (dd, J = 9.7 Hz, 2H), 7.35 (d, J = 9.0 Hz, 1H), 6.77 (s, 1H), 3.67 (broad doublet, 4H), 3.41 (bs, 2H). 3.08 (d, J = 4.7 Hz, 2H), 2.03 (bs, 2H). 1.91 (bs, 2H). | DMSO | 463.9 (M + 1) | | Method C | 95 | Method S |

Scheme 23: General route for the synthesis of compounds with general formula xxv
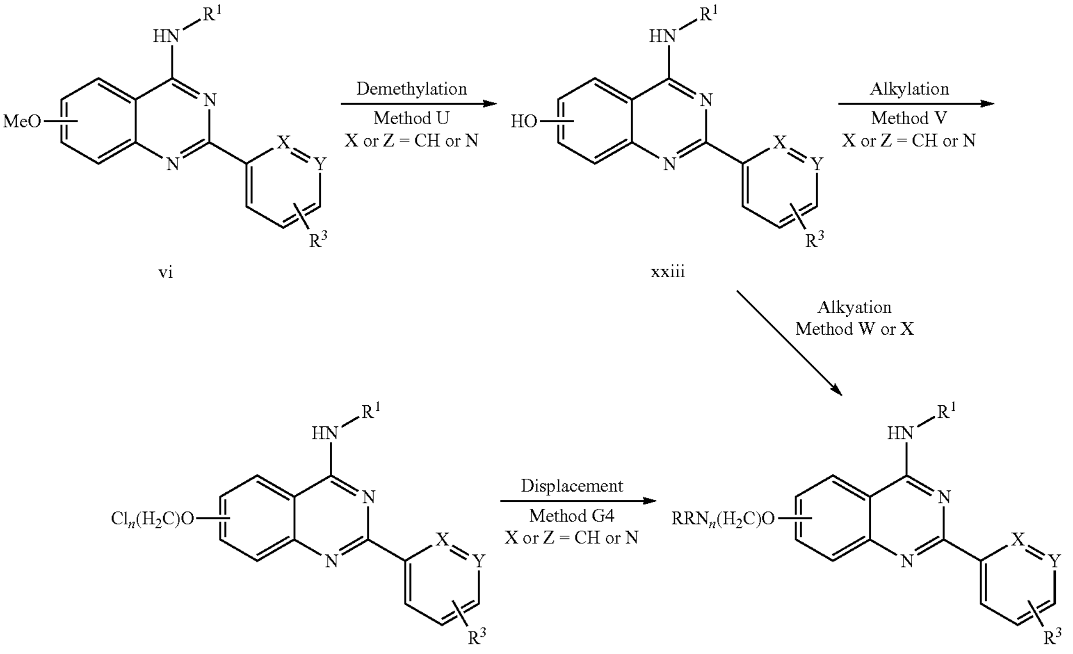
vi xxiii xxiv xxv
X or Z = CH or N
Scheme 24: Representative synthesis of compounds of formula xxv (see Scheme 23)
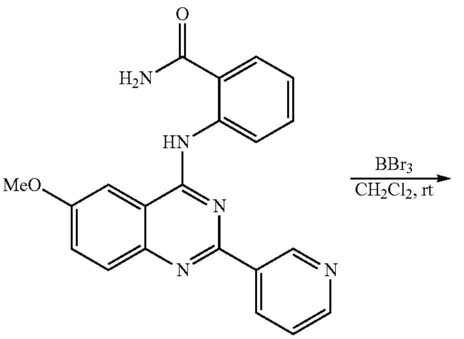
vi-f
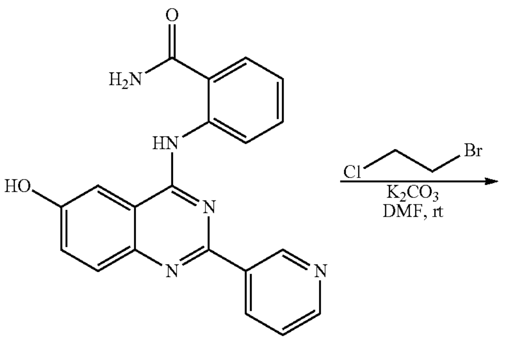
xxiii-a
-continued
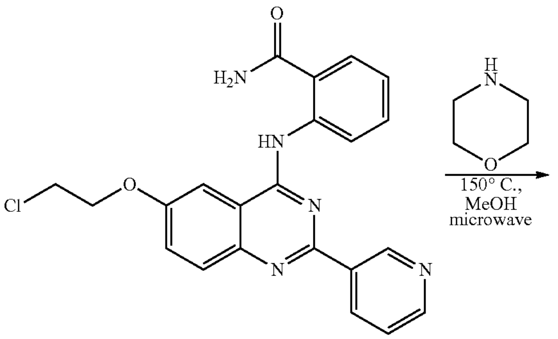
xxiv-a
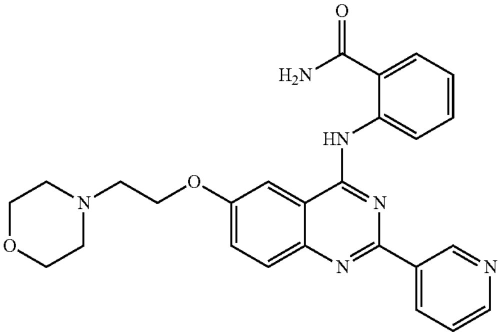
xxv-a Method U: 2-(6-hydroxy-2-(pyridin-3-yl)quinazolin-4-ylamino)benzamide (xxiii-a)

To a suspension of 2-(6-methoxy-2-(pyridin-3-yl)quinazolin-4-ylamino)benzamide (synthesized as described in Scheme 1 and 4, substituting 5-methoxy-2-nitrobenzoic acid for 2-nitro-5-propoxy-benzoic acid) (371 mg, 1.0 mmol) in $CH_2Cl_2$ (4.5 mL) was slowly added boron tribromide, 1M solution in dichloromethane (4.5 ml, 4.5 mmol) at 0° C. The reaction mixture was stirred overnight at room temperature after which it was carefully poured into a vigorously stirring mixture of ice and saturated solution of aqueous $NaHCO_3$. The resultant solid was collected by filtration, dried and then stirred in a saturated solution of aqueous $NH_4Cl$ for 1 h after which the suspension was filtered to give the desired product as a yellowish tan solid (262 mg, 73%). LCMS m/z=357.9 (M+1) (Method C) (retention time=1.68 min), $^1$H NMR (300 MHz, DMSO) δ 12.80 (s, 1H), 10.50 (s, 1H), 9.57 (s, 1H), 9.15 (d, J=8.5 Hz, 1H), 8.70 (t, J=7.3 Hz, 2H), 8.50 (s, 1H), 8.08-7.79 (m, 3H), 7.73 (t, J=7.5 Hz, 1H), 7.57 (dd, J=7.6, 4.8 Hz, 1H), 7.46 (d, J=8.5 Hz, 2H), 7.19 (t, J=7.6 Hz, 1H).

Method V: 2-(6-(2-chloroethoxy)-2-(pyridin-3-yl)quinazolin-4-ylamino)benzamide (xxiv-a)

The suspension of 2-(6-hydroxy-2-(pyridin-3-yl)quinazolin-4-ylamino)benzamide (50 mg, 0.14 mmol), 1-bromo-2-chloroethane (0.015 ml, 0.15 mmol), and potassium carbonate (23 mg, 0.17 mmol) in DMF (5 mL) was stirred for 3 days at room temperature. Water (10 mL) was added to the mixture and extracted with ethyl acetate (2×10 mL). The combined organic layer was washed with water (1×20 mL) and brine (1×20 mL) and was dried over $MgSO_4$. After filtration and evaporation, the crude product was obtained, which was washed with hexane and dried to give 48 mg of 2-(6-(2-chloroethoxy)-2-(pyridin-3-yl)quinazolin-4-ylamino)benzamide as light brown solid (79%).

Method G4: 2-(6-(2-morpholinoethoxy)-2-(pyridin-3-yl)quinazolin-4-ylamino)benzamide (xxv-a)

2-(6-(2-morpholinoethoxy)-2-(pyridin-3-yl)quinazolin-4-ylamino)benzamide was prepared from 2-(6-(3-chloroethoxy)-2-(pyridin-3-yl)quinazolin-4-ylamino)benzamide and morpholine in a manner analogous to that described for N-(3-chloro-4-fluorophenyl)-6-(3-(dimethylamino)propyl)-2-(pyridin-3-yl)quinazolin-4-amine dihydrochloride in Scheme 9 using Method G4 to give 50 mg of 2-(6-(2-morpholinoethoxy)-2-(pyridin-3-yl)quinazolin-4-ylamino)benzamide as light yellow solid. LCMS m/z=485 (M+1) (Method C) (retention time=1.71 min). $^1$H NMR (300 MHz, DMSO) δ 9.57 (s, 1H), 9.12 (d, J=8.5 Hz, 1H), 8.78-8.63 (m, 2H), 8.48 (s, 1H), 8.02-7.93 (m, 2H), 7.88 (d, J=9.0 Hz, 1H), 7.73 (t, J=8.0 Hz, 1H), 7.63-7.49 (m, 3H), 7.20 (t, J=7.6 Hz, 1H), 4.29-4.16 (m, 2H), 3.65-3.51 (m, 4H), 3.44-3.21 (m, 2H), 2.45-2.31 (m, 4H), 2.06-1.91 (m, 2H).

Scheme 25: Representative synthesis of compounds of formula xxv-b (see Scheme 23)

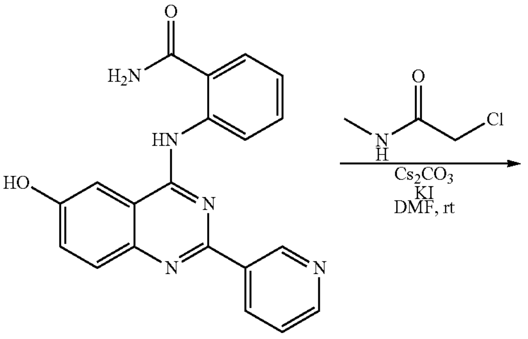

xxiii-a

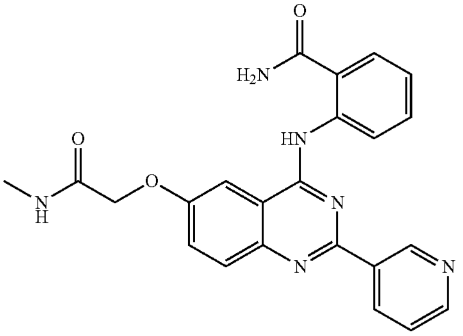

xxv-b

Method W: 2-(6-(2-(2-methylamino)-2-oxoethoxy)-2-(pyridin-3-yl)quinazolin-4-ylamino)benzamide The suspension of 2-(6-hydroxy-2-(pyridin-3-yl)quinazolin-4-ylamino)benzamide (synthesized as described in Scheme 24) (0.20 g, 0.56 mmol), 2-chloro-N-methylacetamide (90 mg, 0.80 mmol), cesium carbonate (0.37 g, 112 mmol) and potassium iodide (0.19 g, 1.12 mmol) in DMF (10 mL) was stirred for 4 days at room temperature. Water (20 mL) was added to the mixture. The resultant solid was collected by filtration. The obtained solid was washed with $CH_2Cl_2$-THF (1:1) solution and dried to give 0.11 g of 2-(6-(2-(methylamino)-2-oxoethoxy)-2-(pyridin-3-yl)quinazolin-4-ylamino)benzamide as pale brown solid (46%), LCMS m/z=429 (M+1) (Method C) (retention time=1.65 min). $^1$H NMR (300 MHz, DMSO) δ 9.58 (s, 1H), 9.12 (d, J=8.4 Hz, 1H), 8.82-8.64 (m, 2H), 8.48 (s, 1H), 8.32-8.17 (m, 1H), 8.10-7.87 (m, 3H), 7.81-7.49 (m, 4H), 7.21 (t, J=7.5 Hz, 1H), 4.66 (s, 2H), 2.71 (d, J=4.5 Hz, 3H).

Scheme 26: Representative synthesis of compounds of formula xxv-c (see Scheme 23)

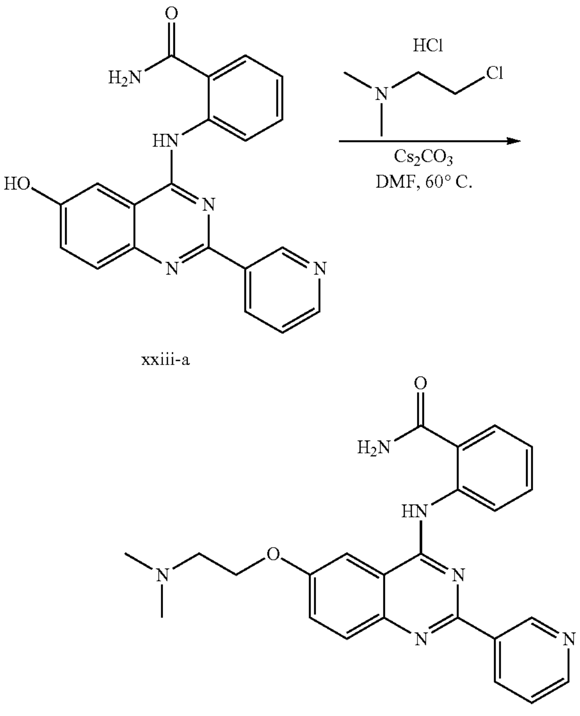

xxiii-a xxv-c

Method X: 2-(6-(2-(dimethylamino)ethoxy-2-(pyridin-3-yl)quinazolin-4-ylamino)benzamide A suspension of 2-(6-hydroxy-2-(pyridin-3-yl)quinazolin-4-ylamino)benzamide (synthesized as described in Scheme 24) (25 mg, 0.07 mmol), 2-chloro-N,N-dimethylethylamine hydrochloride (20 mg, 0.14 mmol) and cesium carbonate (68.4 mg, 0.21 mmol) in DMF (1 mL) was stirred at 60° C. overnight. The reaction mixture was cooled to room temperature, diluted with water (5 mL) and extracted with dichloromethane (3×5 mL). The combined organic extracts were dried over $Na_2SO_4$ and concentrated in vacuo. The crude product was purified by prep-TLC (silica, 2000 micron plate, 95% dichloromethane-5% methanol-0.1% $NH_4OH$) to yield the desired compound as a brown solid (12.6 mg, 40%). LCMS m/z=428.9 (M+1) (Method C) (retention time=1.41 min). $^1H$ NMR (300 MHz, DMSO) δ 12.99 (s, 1H), 9.59 (d, J=1.3 Hz, 1H), 9.12 (d, J=8.4 Hz, 1H), 8.81-8.66 (m, 2H), 8.52 (s, 1H), 8.06-7.88 (m, 3H), 7.80-7.53 (m, 4H), 7.22 (t, J=7.6 Hz, 1H), 4.46 (s, 2H), 3.35 (s, 2H), 2.69 (s, 6H).

The compounds in the following table were prepared in a manner analogous to that described in Scheme 23 substituting with appropriate nucleophile.

TABLE 6
| Number | Product | Salt type | Molecular Mass |
|---|---|---|---|
| 820 | 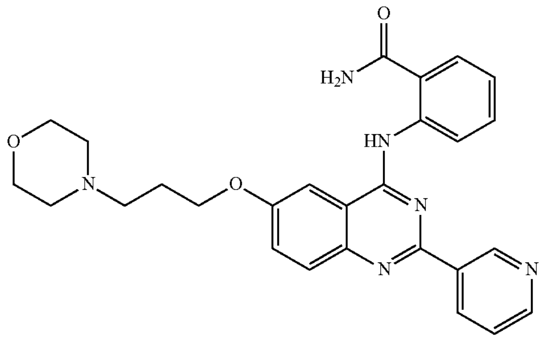 [SMILES: NC(=O)c1ccccc1Nc1nc(-c2cccnc2)nc2ccc(OCCCN3CCOCC3)cc12] | | 484.550 |
| 821 | 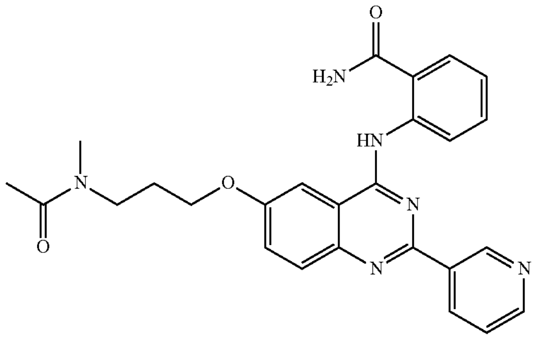 [SMILES: CC(=O)N(C)CCCOc1ccc2nc(-c3cccnc3)nc(Nc3ccccc3C(N)=O)c2c1] | | 470.523 |

TABLE 6-continued
| | | | |
|---|---|---|---|
| 822 | 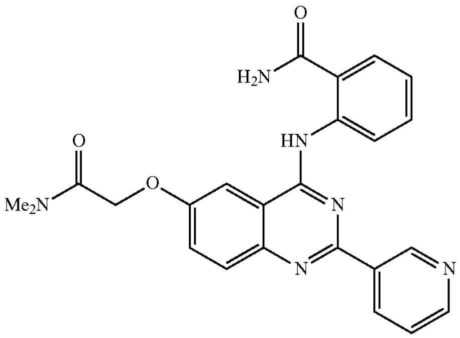 [SMILES: CN(C)C(=O)COc1ccc2nc(-c3cccnc3)nc(Nc3ccccc3C(N)=O)c2c1] | | 442.470 |
| 823 | 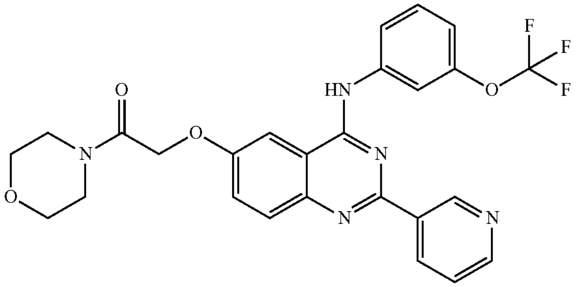 [SMILES: O=C(COc1ccc2nc(-c3cccnc3)nc(Nc3cccc(OC(F)(F)F)c3)c2c1)N1CCOCC1] | HCl | 561.94 |
| 824 | 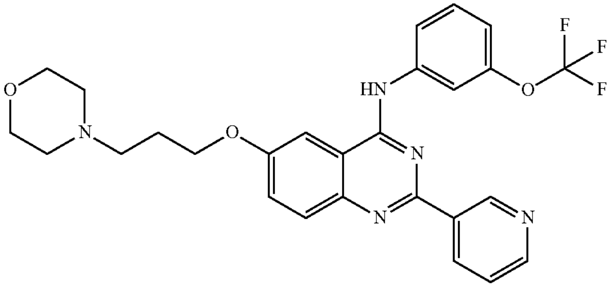 [SMILES: FC(F)(F)Oc1cccc(Nc2nc(-c3cccnc3)nc3ccc(OCCCN4CCOCC4)cc23)c1] | HCl | 598.44 |

TABLE 6-continued
| | | | |
|---|---|---|---|
| 825 | 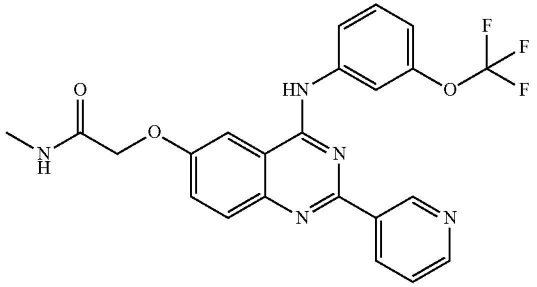 [SMILES: CNC(=O)COc1ccc2nc(-c3cccnc3)nc(Nc3cccc(OC(F)(F)F)c3)c2c1] | | 469.42 |
| 826 | 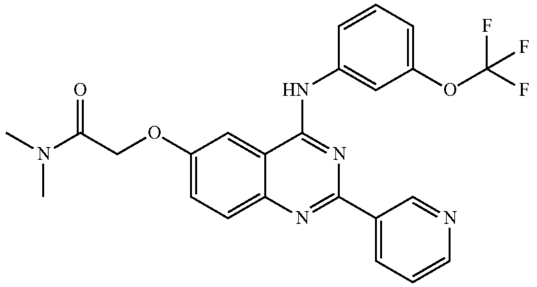 [SMILES: CN(C)C(=O)COc1ccc2nc(-c3cccnc3)nc(Nc3cccc(OC(F)(F)F)c3)c2c1] | | 483.44 |
| 827 | 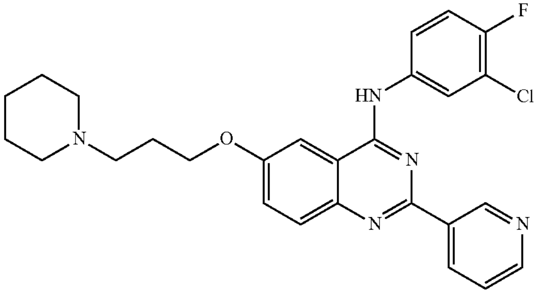 [SMILES: Fc1ccc(Nc2nc(-c3cccnc3)nc3ccc(OCCCN4CCCCC4)cc23)cc1Cl] | HCl | 564.91 |

TABLE 6-continued
| | | |
|---|---|---|
| 828 | 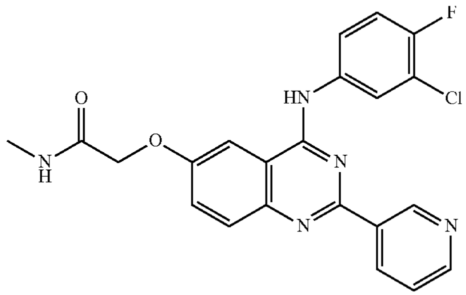 [SMILES: CNC(=O)COc1ccc2nc(-c3cccnc3)nc(Nc3ccc(F)c(Cl)c3)c2c1] | 437.85 |
| 829 | 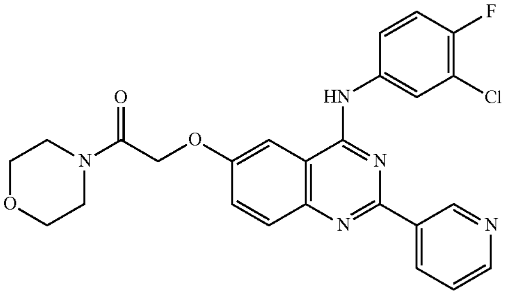 [SMILES: O=C(COc1ccc2nc(-c3cccnc3)nc(Nc3ccc(F)c(Cl)c3)c2c1)N1CCOCC1] | 493.92 |
| 830 | 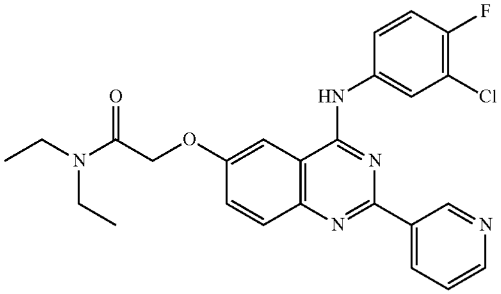 [SMILES: CCN(CC)C(=O)COc1ccc2nc(-c3cccnc3)nc(Nc3ccc(F)c(Cl)c3)c2c1] | 479.93 |

TABLE 6-continued
| | | | |
|---|---|---|---|
| 831 | 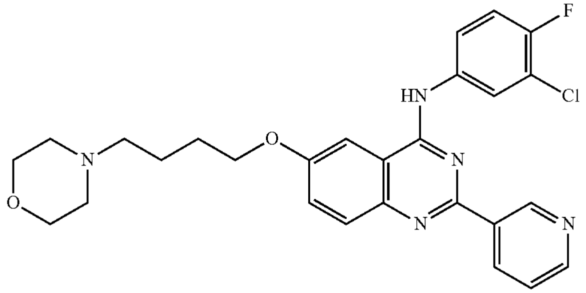 [SMILES: Fc1ccc(Nc2nc(-c3cccnc3)nc3ccc(OCCCCN4CCOCC4)cc23)cc1Cl] | HCl | 580.91 |
| 832 | 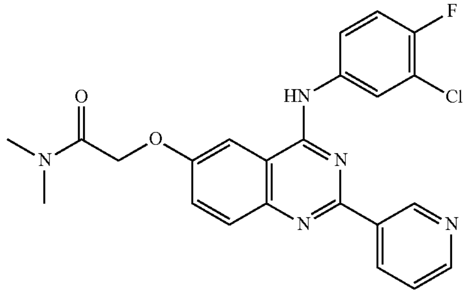 [SMILES: CN(C)C(=O)COc1ccc2nc(-c3cccnc3)nc(Nc3ccc(F)c(Cl)c3)c2c1] | | 451.88 |
| 833 | 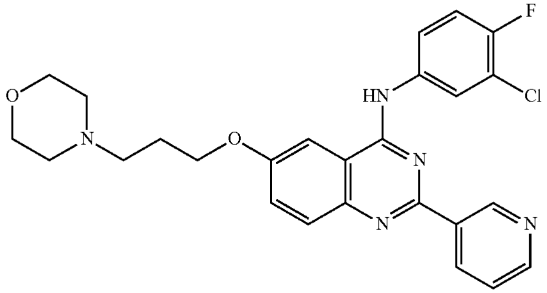 [SMILES: Fc1ccc(Nc2nc(-c3cccnc3)nc3ccc(OCCCN4CCOCC4)cc23)cc1Cl] | HCl | 566.88 |

TABLE 6-continued
| | | |
|---|---|---|
| 834 | 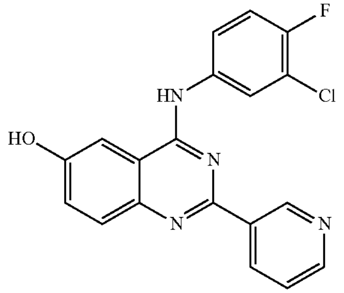 [SMILES: Oc1ccc2nc(-c3cccnc3)nc(Nc3ccc(F)c(Cl)c3)c2c1] | 366.78 |
| 835 | 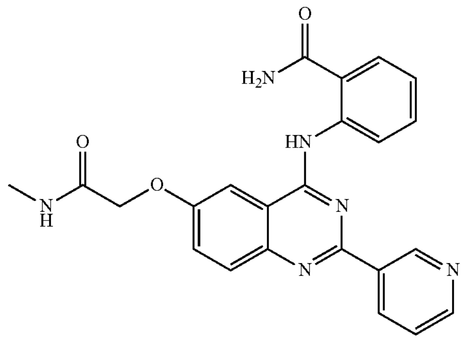 [SMILES: CNC(=O)COc1ccc2nc(-c3cccnc3)nc(Nc3ccccc3C(N)=O)c2c1] | 428.44 |
| 836 | 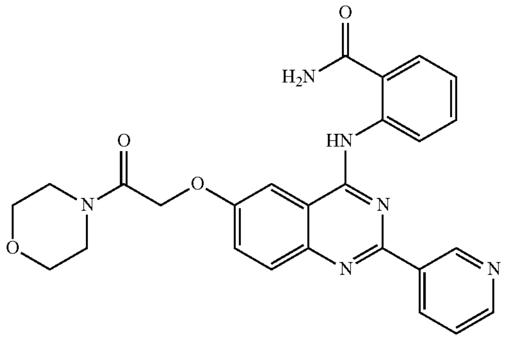 [SMILES: NC(=O)c1ccccc1Nc1nc(-c2cccnc2)nc2ccc(OCC(=O)N3CCOCC3)cc12] | 484.51 |

TABLE 6-continued
| | | | |
|---|---|---|---|
| 837 | 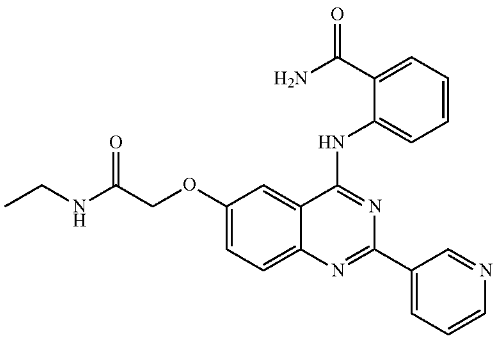 [SMILES: CCNC(=O)COc1ccc2nc(-c3cccnc3)nc(Nc3ccccc3C(N)=O)c2c1] | | 442.47 |
| 838 | 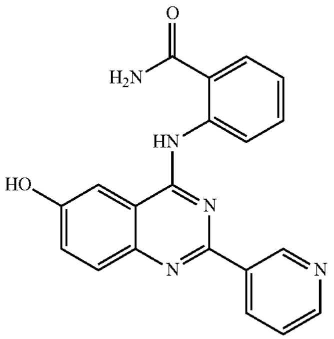 | | 357.37 |
| 839 | 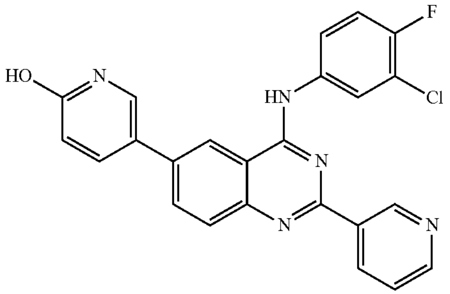 [SMILES: Oc1ccc(-c2ccc3nc(-c4cccnc4)nc(Nc4ccc(F)c(Cl)c4)c3c2)cn1] | 2HCl | 443.86 |

TABLE 6-continued
| | | | |
|---|---|---|---|
| 840 | 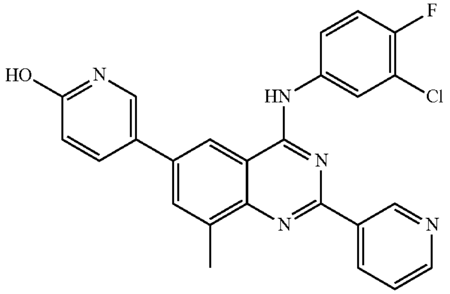 | 2HCl | 457.89 |
| 841 | 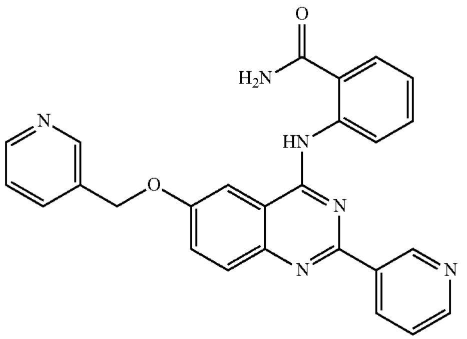 [SMILES: NC(=O)c1ccccc1Nc1nc(-c2cccnc2)nc2ccc(OCc3cccnc3)cc12] | | 448.48 |
| 842 | 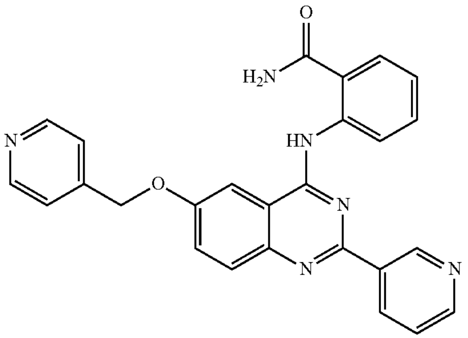 [SMILES: NC(=O)c1ccccc1Nc1nc(-c2cccnc2)nc2ccc(OCc3ccncc3)cc12] | | 448.48 |

TABLE 6-continued
| | | |
|---|---|---|
| 843 | 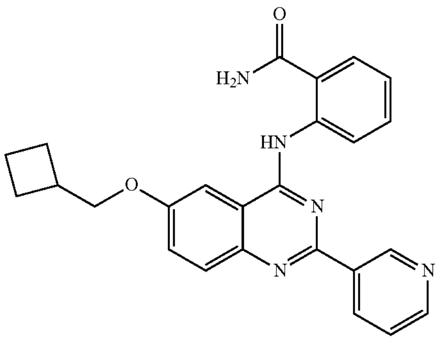 [SMILES: NC(=O)c1ccccc1Nc1nc(-c2cccnc2)nc2ccc(OCC3CCC3)cc12] | 425.48 |
| 844 | 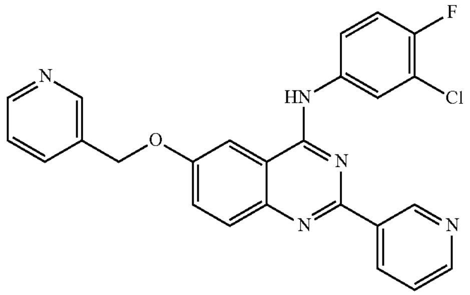 [SMILES: Fc1ccc(Nc2nc(-c3cccnc3)nc3ccc(OCc4cccnc4)cc23)cc1Cl] | 457.89 |
| 845 | 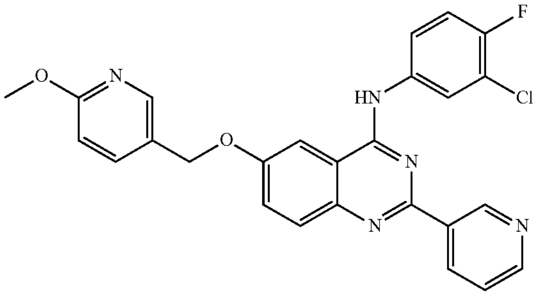 [SMILES: COc1ccc(COc2ccc3nc(-c4cccnc4)nc(Nc4ccc(F)c(Cl)c4)c3c2)cn1] | 487.91 |

TABLE 6-continued
| Number | Starting Material $R^1$ | Starting Material $R^3$ | Product | Salt Type |
|---|---|---|---|---|
| 846 | 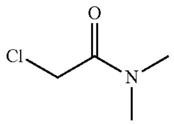 | 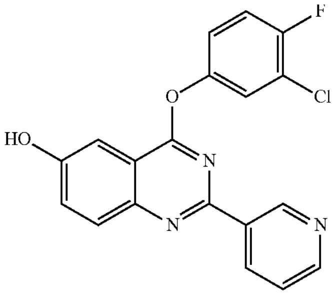 [SMILES: Oc1ccc2nc(-c3cccnc3)nc(Oc3ccc(F)c(Cl)c3)c2c1] | 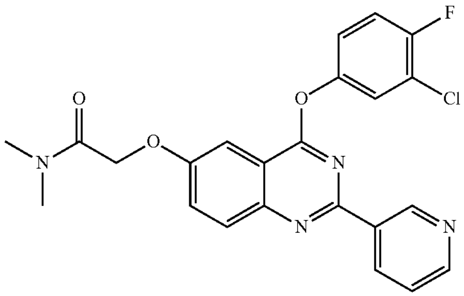 [SMILES: CN(C)C(=O)COc1ccc2nc(-c3cccnc3)nc(Oc3ccc(F)c(Cl)c3)c2c1] | HCl |
| 847 | 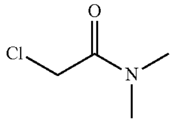 | 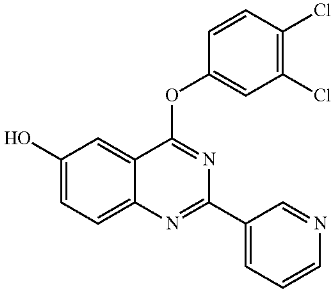 [SMILES: Oc1ccc2nc(-c3cccnc3)nc(Oc3ccc(Cl)c(Cl)c3)c2c1] | 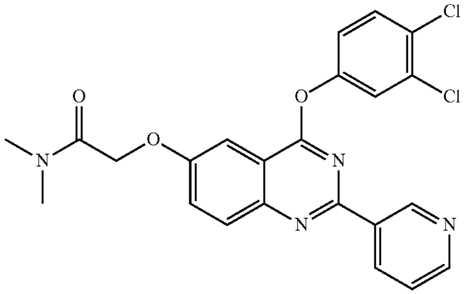 [SMILES: CN(C)C(=O)COc1ccc2nc(-c3cccnc3)nc(Oc3ccc(Cl)c(Cl)c3)c2c1] | |
| 848 | 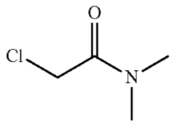 | 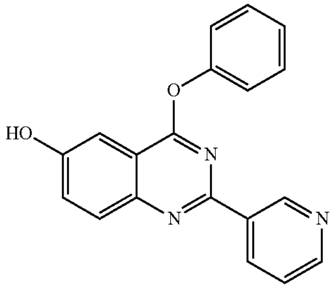 [SMILES: Oc1ccc2nc(-c3cccnc3)nc(Oc3ccccc3)c2c1] | 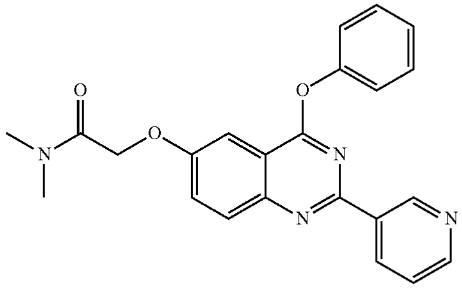 [SMILES: CN(C)C(=O)COc1ccc2nc(-c3cccnc3)nc(Oc3ccccc3)c2c1] | |

TABLE 6-continued
| | | | | |
|---|---|---|---|---|
| 849 | 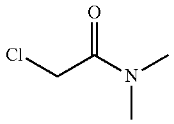 | 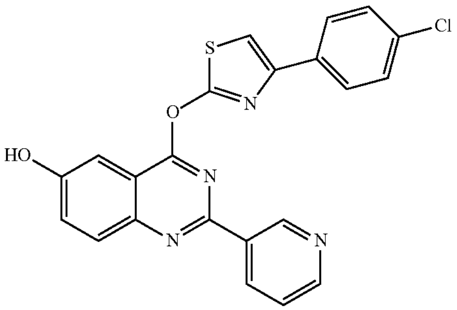 [SMILES: Oc1ccc2nc(-c3cccnc3)nc(Oc3nc(-c4ccc(Cl)cc4)cs3)c2c1] | 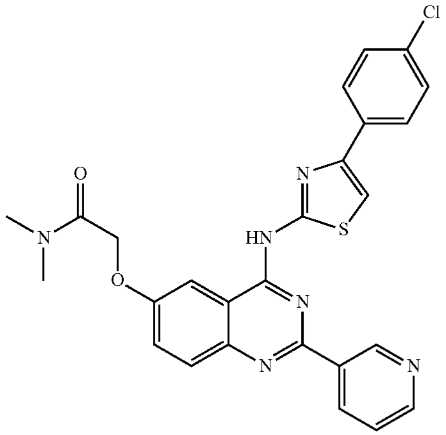 [SMILES: CN(C)C(=O)COc1ccc2nc(-c3cccnc3)nc(Nc3nc(-c4ccc(Cl)cc4)cs3)c2c1] | 2HCl |
| 850 | 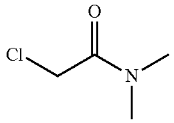 | 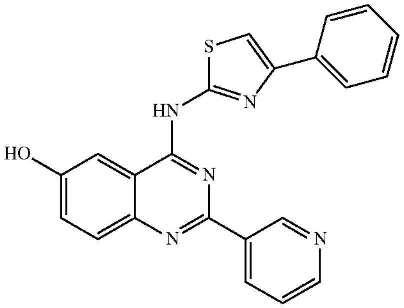 [SMILES: Oc1ccc2nc(-c3cccnc3)nc(Nc3nc(-c4ccccc4)cs3)c2c1] | 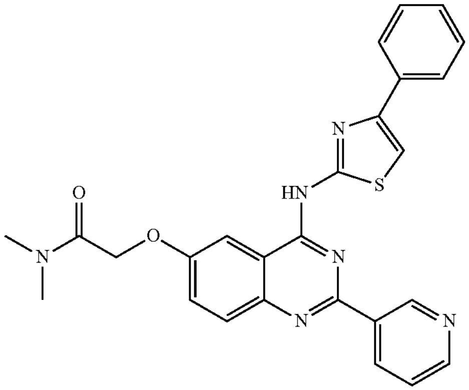 [SMILES: CN(C)C(=O)COc1ccc2nc(-c3cccnc3)nc(Nc3nc(-c4ccccc4)cs3)c2c1] | 2HCl |

TABLE 6-continued
| | | | | |
|---|---|---|---|---|
| 851 | 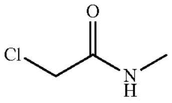 | 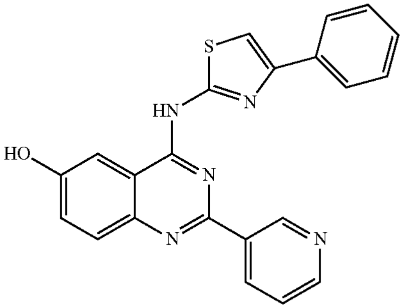 [SMILES: Oc1ccc2nc(-c3cccnc3)nc(Nc3nc(-c4ccccc4)cs3)c2c1] | 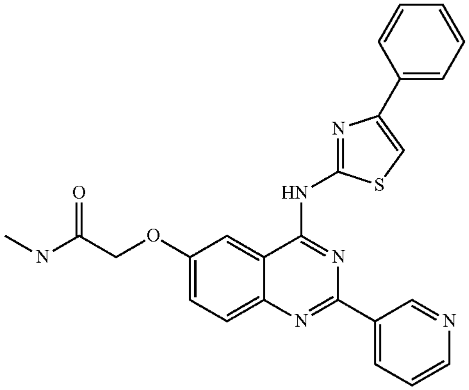 [SMILES: CNC(=O)COc1ccc2nc(-c3cccnc3)nc(Nc3nc(-c4ccccc4)cs3)c2c1] | 2HCl |
| 852 | 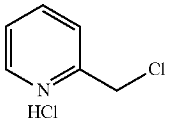 | 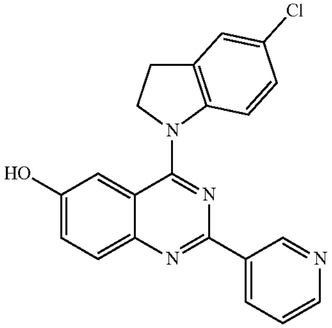 [SMILES: Oc1ccc2nc(-c3cccnc3)nc(N3CCc4cc(Cl)ccc43)c2c1] | 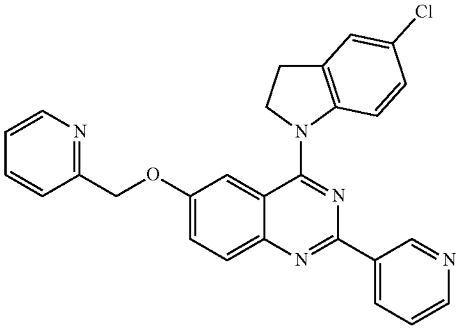 [SMILES: Clc1ccc2c(c1)CCN2c1nc(-c2cccnc2)nc2ccc(OCc3ccccn3)cc12] | 3HCl |
| 853 | 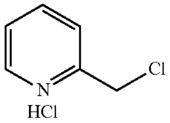 | 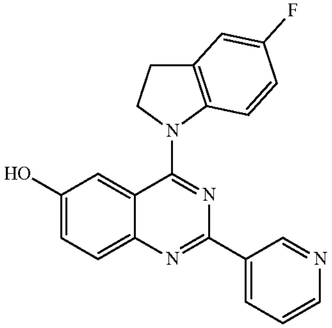 [SMILES: Oc1ccc2nc(-c3cccnc3)nc(N3CCc4cc(F)ccc43)c2c1] | 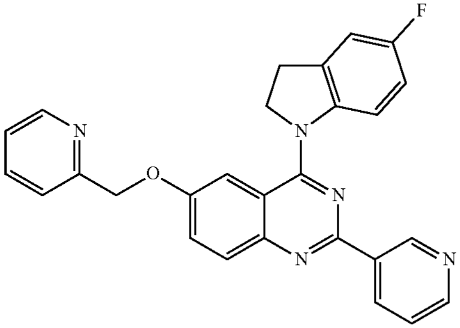 [SMILES: Fc1ccc2c(c1)CCN2c1nc(-c2cccnc2)nc2ccc(OCc3ccccn3)cc12] | 3HCl |

TABLE 6-continued
| | | | | |
|---|---|---|---|---|
| 854 | 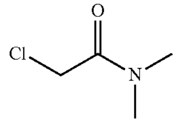 | 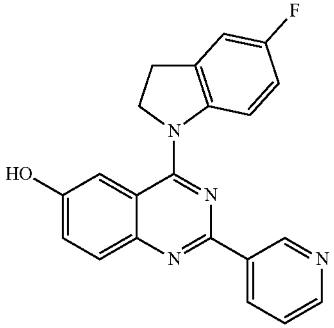 [SMILES: Oc1ccc2nc(-c3cccnc3)nc(N3CCc4cc(F)ccc43)c2c1] | 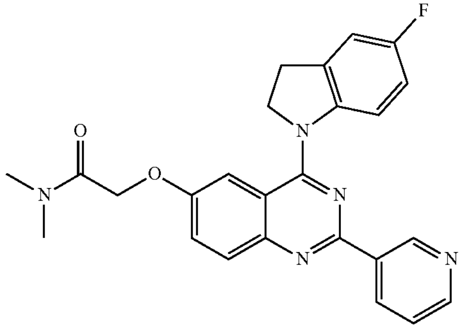 [SMILES: CN(C)C(=O)COc1ccc2nc(-c3cccnc3)nc(N3CCc4cc(F)ccc43)c2c1] | 2HCl |
| 855 | 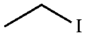 | 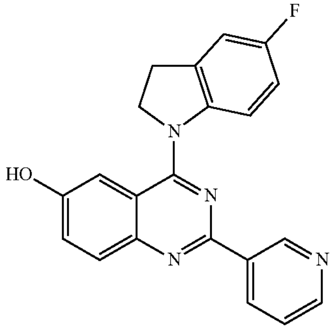 | 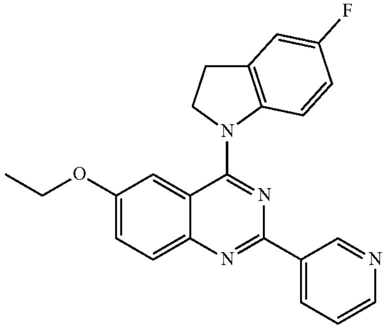 [SMILES: CCOc1ccc2nc(-c3cccnc3)nc(N3CCc4cc(F)ccc43)c2c1] | 2HCl |
| 856 | 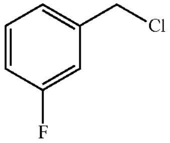 | 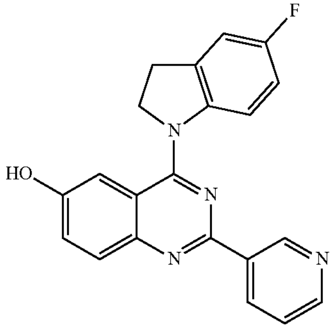 [SMILES: Oc1ccc2nc(-c3cccnc3)nc(N3CCc4cc(F)ccc43)c2c1] | 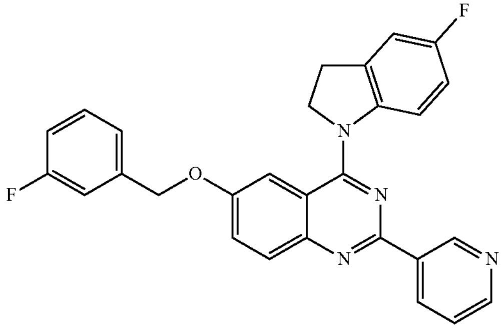 [SMILES: Fc1cccc(COc2ccc3nc(-c4cccnc4)nc(N4CCc5cc(F)ccc54)c3c2)c1] | 2HCl |

TABLE 6-continued
| | | | | |
|---|---|---|---|---|
| 857 | 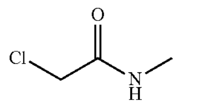 | 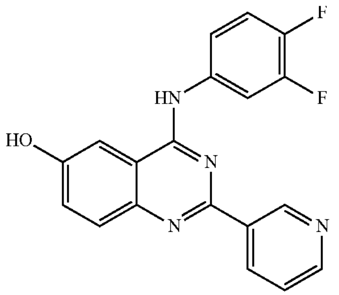 [SMILES: Oc1ccc2nc(-c3cccnc3)nc(Nc3ccc(F)c(F)c3)c2c1] | 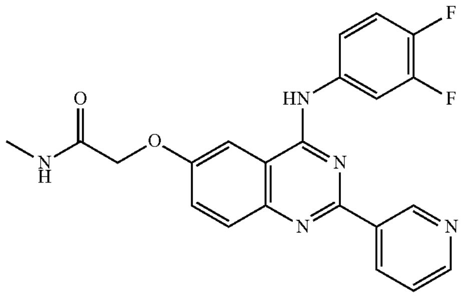 [SMILES: CNC(=O)COc1ccc2nc(-c3cccnc3)nc(Nc3ccc(F)c(F)c3)c2c1] | HCl |
| 858 | 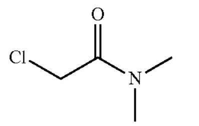 | 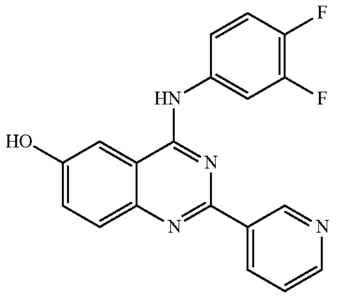 [SMILES: Oc1ccc2nc(-c3cccnc3)nc(Nc3ccc(F)c(F)c3)c2c1] | 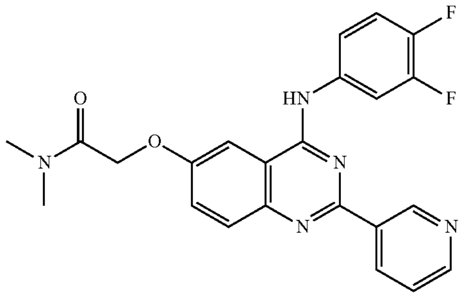 [SMILES: CN(C)C(=O)COc1ccc2nc(-c3cccnc3)nc(Nc3ccc(F)c(F)c3)c2c1] | |
| 859 | 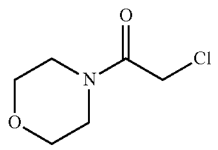 | 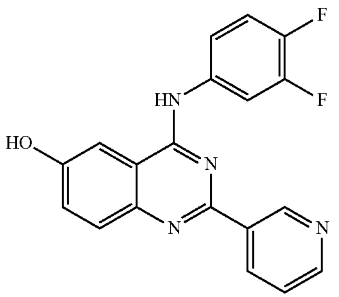 [SMILES: Oc1ccc2nc(-c3cccnc3)nc(Nc3ccc(F)c(F)c3)c2c1] | 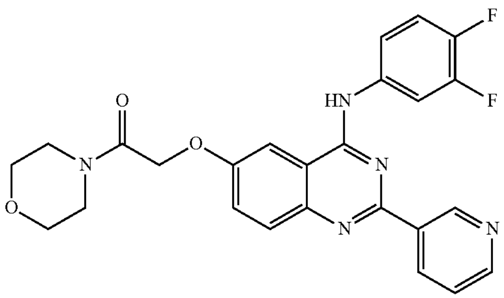 [SMILES: O=C(COc1ccc2nc(-c3cccnc3)nc(Nc3ccc(F)c(F)c3)c2c1)N1CCOCC1] | HCl |

TABLE 6-continued
| | | | | |
|---|---|---|---|---|
| 860 | 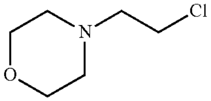 | 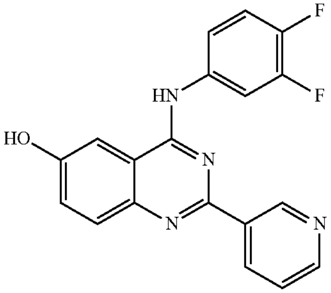 [SMILES: Oc1ccc2nc(-c3cccnc3)nc(Nc3ccc(F)c(F)c3)c2c1] | 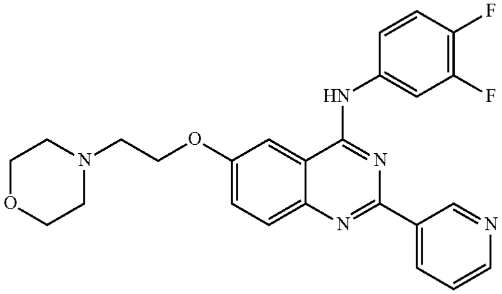 [SMILES: Fc1ccc(Nc2nc(-c3cccnc3)nc3ccc(OCCN4CCOCC4)cc23)cc1F] | 2HCl |
| 861 | 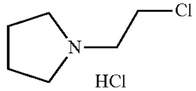 HCl | 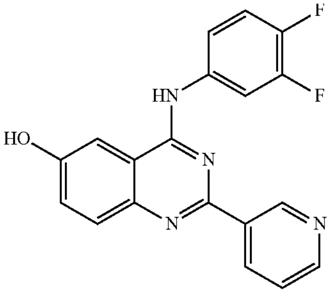 [SMILES: Oc1ccc2nc(-c3cccnc3)nc(Nc3ccc(F)c(F)c3)c2c1] | 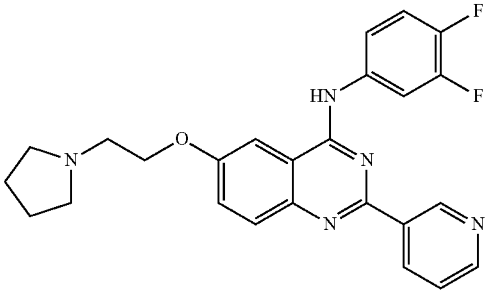 [SMILES: Fc1ccc(Nc2nc(-c3cccnc3)nc3ccc(OCCN4CCCC4)cc23)cc1F] | 3HCl |
| 862 | 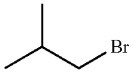 | 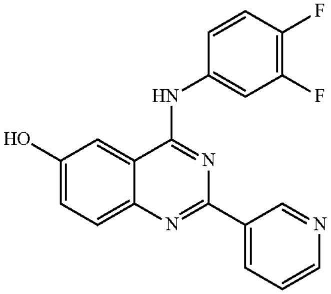 [SMILES: Oc1ccc2nc(-c3cccnc3)nc(Nc3ccc(F)c(F)c3)c2c1] | 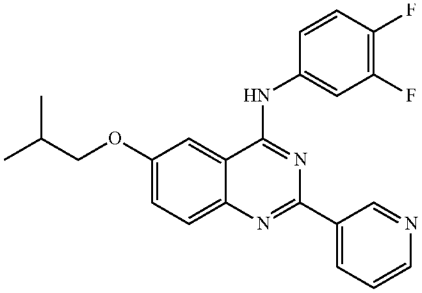 [SMILES: CC(C)COc1ccc2nc(-c3cccnc3)nc(Nc3ccc(F)c(F)c3)c2c1] | 2HCl |

TABLE 6-continued
| | | | | |
|---|---|---|---|---|
| 863 | 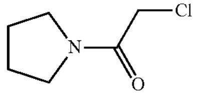 | 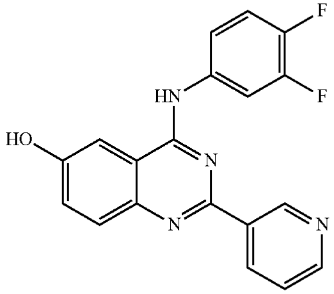 [SMILES: Oc1ccc2nc(-c3cccnc3)nc(Nc3ccc(F)c(F)c3)c2c1] | 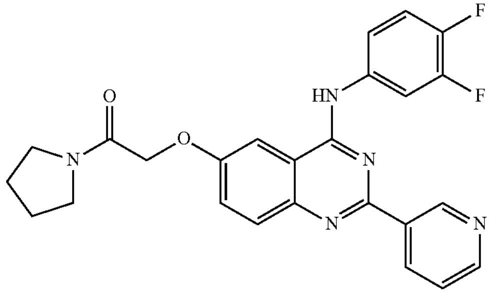 [SMILES: O=C(COc1ccc2nc(-c3cccnc3)nc(Nc3ccc(F)c(F)c3)c2c1)N1CCCC1] | 2HCl |
| 864 | 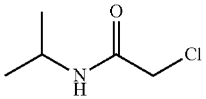 | 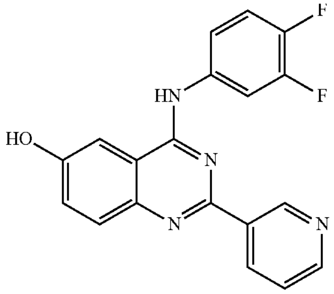 [SMILES: Oc1ccc2nc(-c3cccnc3)nc(Nc3ccc(F)c(F)c3)c2c1] | 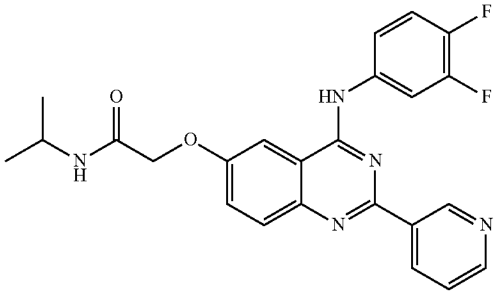 [SMILES: CC(C)NC(=O)COc1ccc2nc(-c3cccnc3)nc(Nc3ccc(F)c(F)c3)c2c1] | 2HCl |
| 865 | 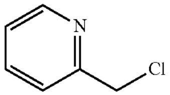 HCl | 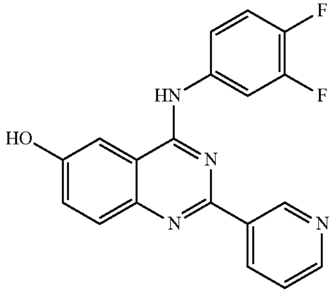 [SMILES: Oc1ccc2nc(-c3cccnc3)nc(Nc3ccc(F)c(F)c3)c2c1] | 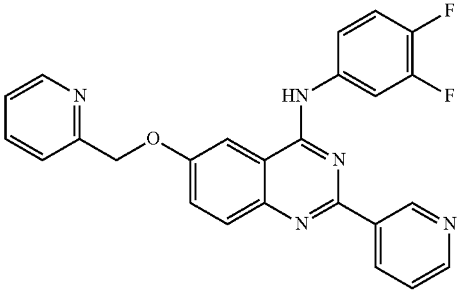 [SMILES: Fc1ccc(Nc2nc(-c3cccnc3)nc3ccc(OCc4ccccn4)cc23)cc1F] | 3HCl |

TABLE 6-continued
| | | | | |
|---|---|---|---|---|
| 866 | 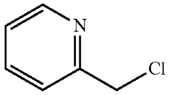 HCl | 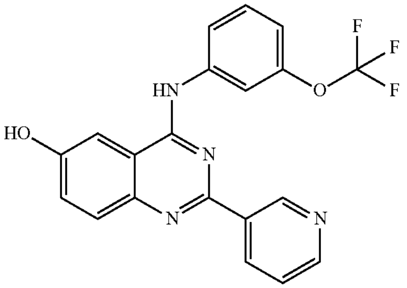 [SMILES: Oc1ccc2nc(-c3cccnc3)nc(Nc3cccc(OC(F)(F)F)c3)c2c1] | 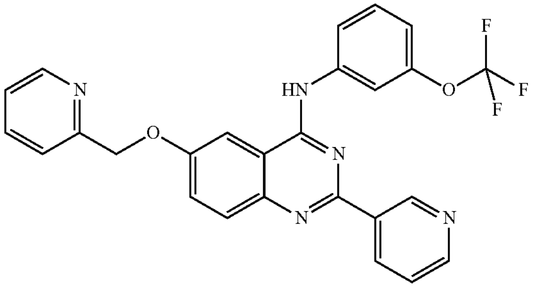 [SMILES: FC(F)(F)Oc1cccc(Nc2nc(-c3cccnc3)nc3ccc(OCc4ccccn4)cc23)c1] | 4HCl |
| 867 | 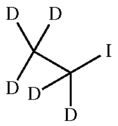 | 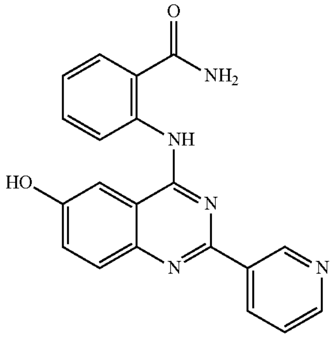 [SMILES: NC(=O)c1ccccc1Nc1nc(-c2cccnc2)nc2ccc(O)cc12] | 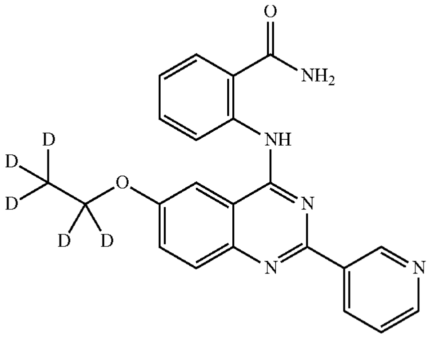 [SMILES: [2H]C([2H])([2H])C([2H])([2H])Oc1ccc2nc(-c3cccnc3)nc(Nc3ccccc3C(N)=O)c2c1] | HCl |
| 868 | | | 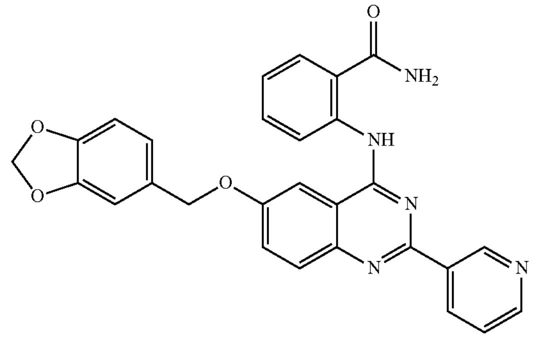 [SMILES: NC(=O)c1ccccc1Nc1nc(-c2cccnc2)nc2ccc(OCc3ccc4c(c3)OCO4)cc12] | 2HCl |

TABLE 6-continued
| | | |
|---|---|---|
| 869 | 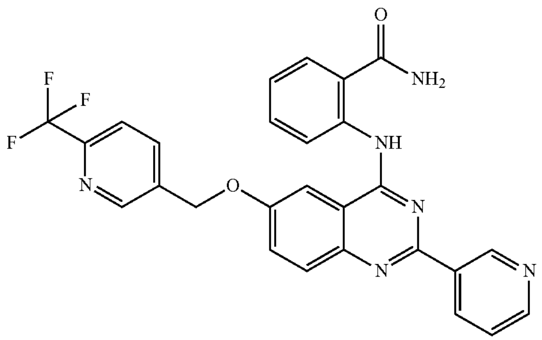 [SMILES: NC(=O)c1ccccc1Nc1nc(-c2cccnc2)nc2ccc(OCc3ccc(C(F)(F)F)nc3)cc12] | 3HCl |
| 870 | 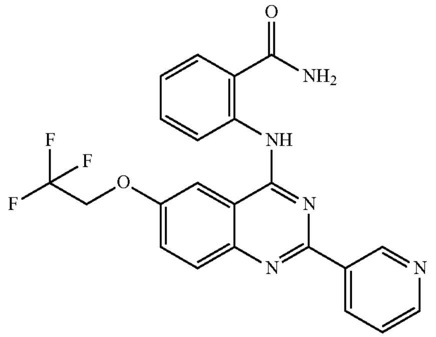 [SMILES: NC(=O)c1ccccc1Nc1nc(-c2cccnc2)nc2ccc(OCC(F)(F)F)cc12] | 2HCl |
| 871 | 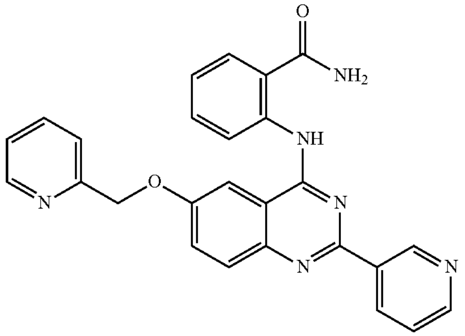 [SMILES: NC(=O)c1ccccc1Nc1nc(-c2cccnc2)nc2ccc(OCc3ccccn3)cc12] | 4HCl |

TABLE 6-continued
| | | |
|---|---|---|
| 872 | 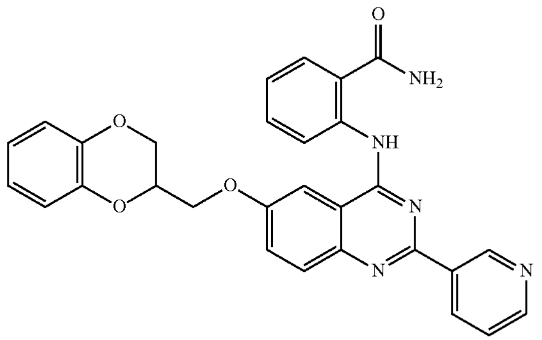 [SMILES: NC(=O)c1ccccc1Nc1nc(-c2cccnc2)nc2ccc(OCC3COc4ccccc4O3)cc12] | 2HCl |
| 873 | 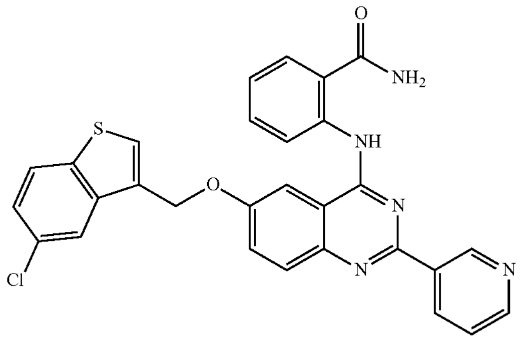 [SMILES: NC(=O)c1ccccc1Nc1nc(-c2cccnc2)nc2ccc(OCc3csc4ccc(Cl)cc34)cc12] | 3HCl |
| 874 | 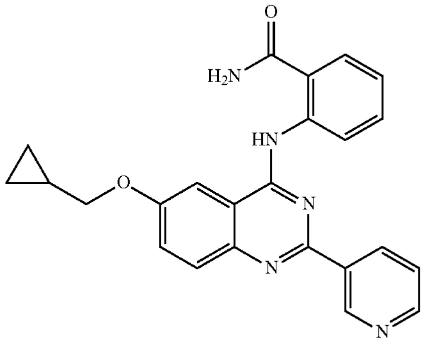 [SMILES: NC(=O)c1ccccc1Nc1nc(-c2cccnc2)nc2ccc(OCC3CC3)cc12] | 2HCl |

TABLE 6-continued
| | | | | |
|---|---|---|---|---|
| 875 | | | 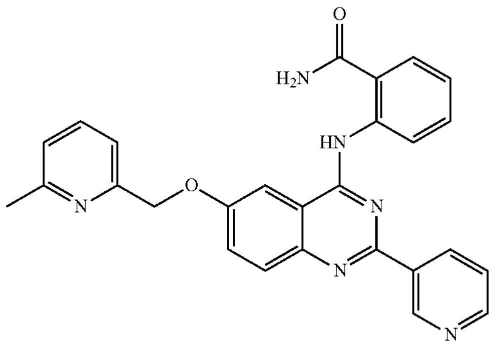 [SMILES: Cc1cccc(COc2ccc3nc(-c4cccnc4)nc(Nc4ccccc4C(N)=O)c3c2)n1] | 3HCl |
| 876 | | | 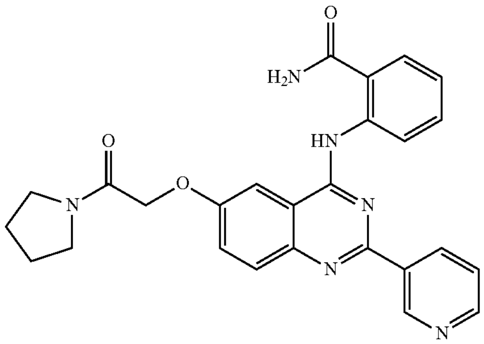 [SMILES: NC(=O)c1ccccc1Nc1nc(-c2cccnc2)nc2ccc(OCC(=O)N3CCCC3)cc12] | CF3COOH |
| 1757 | 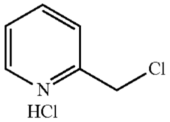 | 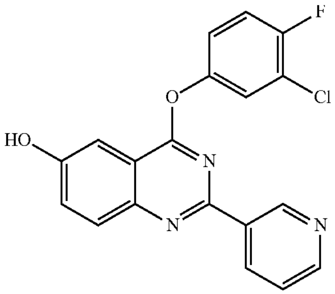 | 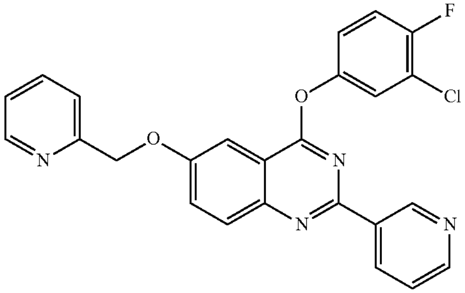 [SMILES: Fc1ccc(Oc2nc(-c3cccnc3)nc3ccc(OCc4ccccn4)cc23)cc1Cl] | |

TABLE 6-continued

| Number | $^1$H-NMR | $^1$H-NMR Solvent | LCMS | Retention Time (min.) | LCMS Protocol | Purity Percent | Method for Coupling |
|---|---|---|---|---|---|---|---|
| 820 | 1H NMR (300 MHz, DMSO) δ 9.57 (s, 1H), 9.12 (d, J = 8.5 Hz, 1H), 8.78-8.63 (m, 2H), 8.48 (s, 1H), 8.02-7.93 (m, 2H), 7.88 (d, J = 9.0 Hz, 1H), 7.73 (t, J = 8.0 Hz, 1H), 7.63-7.49 (m, 3H), 7.20 (t, J = 7.6 Hz, 1H), 4.29-4.16 (m, 2H), 3.65-3.51 (m | DMSO | 485 (M + 1) | 1.71 | Method C | 100 | Methods V, G4 |
| 821 | 1H NMR (300 MHz, DMSO) δ 9.58 (s, 1H), 9.24-9.08 (m, 1H), 8.82-8.61 (m, 2H), 8.49 (s, 1H), 8.09-7.84 (m, 3H), 7.73 (t, J = 7.8 Hz, 1H), 7.67-7.47 (m, 3H), 7.19 (t, J = 7.5 Hz, 1H), 4.29-4.09 (m, 2H), 3.63-3.42 (m, 2H), 3.07-2.77 (m, 3H), 2.2 | DMSO | 471 (M + 1) | 1.75 | Method C | 100 | Methods V, G4 followed by acylation with acetyl chloride/TEA in DCM at rt. |
| 822 | 1H NMR (300 MHz, DMSO) δ 9.58 (s, 1H), 9.16 (d, J = 8.4 Hz, 1H), 8.82-8.60 (m, 2H), 8.49 (s, 1H), 8.05-7.80 (m, 3H), 7.79-7.68 (m, 1H), 7.67-7.51 (m, 2H), 7.43 (s, 1H), 7.29-7.12 (m, 1H), 5.03 (s, 2H), 3.10 (s, 3H), 2.89 (s, 3H). | DMSO | 443 (M + 1) | 1.63 | Method C | 100 | Method W |
| 823 | 1H NMR (300 MHz, DMSO) δ 10.51 (s, 1H), 9.49 (s, 1H), 8.95 (d, J = 6.6 Hz, 1H), 8.85 (d, J = 5.0 Hz, 1H), 8.26 (s, 1H), 8.10 (s, 1H), 8.03-7.80 (m, 3H), 7.73-7.51 (m, 2H), 7.19 (d, J = 7.4 Hz, 1H), 5.12 (s, 2H), 3.75-3.36 (m, 8H). | DMSO | 526 (M + 1) | 2.02 | Method C | 100 | Method W |
| 824 | 1H NMR (300 MHz, DMSO) δ 10.98 (s, 1H), 10.59 (s, 1H), 9.50 (s, 1H), 8.96 (d, J = 8.1 Hz, 1H), 8.86 (d, J = 5.1 Hz, 1H), 8.31 (s, 1H), 8.10 (s, 1H), 8.07-7.93 (m, 2H), 7.92-7.80 (m, 1H), 7.71-7.54 (m, 2H), 7.21 (d, J = 8.0 Hz, 1H), 4.47-4.23 (m, 2 | DMSO | 526 (M + 1) | 2.25 | Method C | 100 | Methods V, G4 |
| 825 | 1H NMR (300 MHz, DMSO) δ 9.95 (s, 1H), 9.51 (s, 1H), 8.76-8.56 (m, 2H), 8.26-8.08 (m, 2H), 8.01 (s, 1H), 7.95-7.81 (m, 2H), 7.70-7.56 (m, 2H), 7.52 (dd, J = 7.9, 4.9 Hz, 1H), 7.17 (d, J = 8.3 Hz, 1H), 4.69 (s, 2H), 2.71 (d, J = 4.5 Hz, 3H). | DMSO | 470 (M + 1) | 2.04 | Method C | 100 | Method W |
| 826 | 1H NMR (300 MHz, DMSO) δ 9.92 (s, 1H), 9.51 (s, 1H), 8.74- | DMSO | 484 (M + 1) | 1.71 | Method D | 100 | Method W |

TABLE 6-continued

| | | | | | | | |
|---|---|---|---|---|---|---|---|
| | 8.57 (m, 2H), 8.17 (s, 1H), 8.01 (d, J = 2.5 Hz, 1H), 7.96-7.83 (m, 2H), 7.70-7.46 (m, 3H), 7.16 (d, J = 7.0 Hz, 1H), 5.03 (s, 2H), 3.06 (s, 3H), 2.88 (s, 3H). | | | | | | |
| 827 | 1H NMR (300 MHz, DMSO) δ 10.59 (s, 1H), 9.99 (s, 1H), 9.49 (s, 1H), 8.97 (d, J = 7.7 Hz, 1H), 8.87 (d, J = 5.3 Hz, 1H), 8.33-8.18 (m, 2H), 8.04-7.83 (m, 3H), 7.68-7.47 (m, 2H), 4.41-4.27 (m, 2H), 3.55-3.43 (m, 2H), 3.34-3.20 (m, 2H), 3.03-2. | DMSO | 492 (M + 1) | 1.81 | Method C | 100 | Methods V, G4 |
| 828 | 1H NMR (300 MHz, DMSO) δ 9.87 (s, 1H), 9.49 (s, 1H), 8.76-8.53 (m, 2H), 8.32-8.08 (m, 2H), 8.01-7.77 (m, 3H), 7.69-7.43 (m, 3H), 4.67 (s, 2H), 2.71 (d, J = 4.6 Hz, 3H). | DMSO | 438 (M + 1) | 1.65 | Method D | 100 | Method W |
| 829 | 1H NMR (300 MHz, DMSO) δ 9.86 (s, 1H), 9.50 (s, 1H), 8.76-8.57 (m, 2H), 8.27 (d, J = 7.0 Hz, 1H), 8.05-7.80 (m, 3H), 7.69-7.45 (m, 3H), 5.04 (s, 2H), 3.78-3.41 (m, 8H). | DMSO | 494 (M + 1) | 1.98 | Method C | 98 | Method W |
| 830 | 1H NMR (300 MHz, DMSO) δ 9.85 (s, 1H), 9.50 (s, 1H), 8.76-8.53 (m, 2H), 8.26 (dd, J = 6.9, 2.5 Hz, 1H), 8.08-7.76 (m, 3H), 7.71-7.41 (m, 3H), 4.98 (s, 2H), 3.52-3.09 (m, 4H), 1.37-0.88 (m, 6H). | DMSO | 480 (M + 1) | 2.20 | Method C | 100 | Method W |
| 831 | 1H NMR (300 MHz, DMSO) δ 10.71 (s, 2H), 9.48 (s, 1H), 9.10-8.95 (m, 1H), 8.94-8.79 (m, 1H), 8.36-8.27 (m, 1H), 8.26-8.16 (m, 1H), 8.07-7.83 (m, 3H), 7.68-7.46 (m, 2H), 4.39-4.18 (m, 2H), 4.05-3.89 (m, 2H), 3.79 (t, J = 11.9 Hz, 2H), 3.53- | DMSO | 508 (M + 1) | 2.14 | Method C | 100 | Methods V, G4 |
| 832 | 1H NMR (300 MHz, DMSO) δ 9.85 (s, 1H), 9.50 (s, 1H), 8.71-8.58 (m, 2H), 8.25 (dd, J = 6.8, 2.5 Hz, 1H), 8.01-7.80 (m, 3H), 7.66-7.45 (m, 3H), 5.02 (s, 2H), 3.06 (s, 3H), 2.88 (s, 3H). | DMSO | 452 (M + 1) | 1.99 | Method C | 100 | Method W |
| 833 | 1H NMR (300 MHz, DMSO) δ 11.18 (s, 1H), 10.93 (s, 1H), 9.48 (s, 1H), 9.08 (d, J = 8.4 Hz, 1H), 8.94 (d, J = 5.0 Hz, 1H), 8.42 (s, 1H), 8.23 (dd, J = 6.8, 2.5 Hz, 1H), 8.12-7.89 (m, 3H), 7.63 (d, | DMSO | 494 (M + 1) | 2.10 | Method C | 100 | Methods V, G4 |

TABLE 6-continued

| | | | | | | | |
|---|---|---|---|---|---|---|---|
| | J = 9.1 Hz, 1H), 7.54 (t, J = 9.1 Hz, 1H), 4.45-4.26 (m, | | | | | | |
| 834 | 1H NMR (300 MHz, DMSO) δ 9.98-9.59 (m, 1H), 9.53-9.41 (m, 1H), 8.71-8.48 (m, 2H), 8.31 (dd, J = 6.9, 2.5 Hz, 1H), 8.01-7.85 (m, 1H), 7.83-7.66 (m, 2H), 7.59-7.35 (m, 3H). | DMSO | 367 (M + 1) | 1.69 | Method D | 100 | Method U |
| 835 | 1H NMR (300 MHz, DMSO) δ 9.58 (s, 1H), 9.12 (d, J = 8.4 Hz, 1H), 8.82-8.64 (m, 2H), 8.48 (s, 1H), 8.32-8.17 (m, 1H), 8.10-7.87 (m, 3H), 7.81-7.49 (m, 4H), 7.21 (1, J = 7.5 Hz, 1H), 4.66 (s, 2H), 2.71 (d, J = 4.5 Hz, 3H). | DMSO | 429 (M + 1) | 1.65 | Method C | 100 | Method W |
| 836 | 1H NMR (300 MHz, DMSO) δ 9.58 (s, 1H), 9.13 (d, J = 8.3 Hz, 1H), 8.78-8.64 (m, 2H), 8.50 (s, 1H), 8.02-7.80 (m, 3H), 7.73 (t, J = 7.9 Hz, 1H), 7.68-7.53 (m, 2H), 7.49 (s, 1H), 7.20 (t, J = 7.5 Hz, 1H), 5.07 (s, 2H), 3.79-3.40 (m, 8H). | DMSO | 485 (M + 1) | 1.72 | Method C | 91 | Method W |
| 837 | 1H NMR (300 MHz, DMSO) δ 9.59 (s, 1H), 9.12 (d, J = 8.4 Hz, 1H), 8.78-8.63 (m, 1H), 8.49 (s, 1H), 8.29 (s, 1H), 8.11-7.88 (m, 2H), 7.79-7.47 (m, 4H), 7.26-7.14 (m, 1H), 4.58 (s, 2H), 3.27-3.08 (m, 2H), 1.18-0.93 (m, 3H). | DMSO | 443 (M + 1) | 1 .69 | Method C | 100 | Method W |
| 838 | 1H NMR (300 MHz, DMSO) δ 12.80 (s, 1H), 10.50 (s, 1H), 9.57 (s, 1H), 9.15 (d, J = 8.5 Hz, 1H), 8.70 (t, J = 7.3 Hz, 2H), 8.50 (s, 1H), 8.08-7.79 (m, 3H), 7.73 (t, J = 7.5 Hz, 1H), 7.57 (dd, J = 7.6, 4.8 Hz, 1H), 7.46 (d, J = 8.5 Hz, 2H), 7.19 (t, J = 7.6 Hz, 1H). | DMSO | 357.9 (M + 1) | 1.68 | Method C | 100 | Method U |
| 839 | 1H NMR (300 MHz, DMSO) δ 10.57 (s, 1H), 9.49 (s, 1H), 8.97 (d, J = 8.2 Hz, 1H), 8.89 (s, 1H), 8.81 (s, 1H), 8.16 (ddd, J = 12.2, 10.9, 5.2 Hz, 3H), 8.05 (d, J = 2.3 Hz, 1H), 8.00-7.86 (m, 3H), 7.55 (1, J = 9.1 Hz, 1H), 6.55 (d, J = 9.5 Hz, 1H). | DMSO | 443.9 (M + 1) | 1.87 | Method C | 100 | Method U |
| 840 | 1H NMR (300 MHz, DMSO) δ 10.27 (s, 1H), 9.47 (s, 1H), 9.09 (d, J = 8.1 Hz, 1H), 8.91 (d, J = 4.4 Hz, 1H), 8.56 (s, 1H), 8.18-8.08 (m, 2H), 8.01 (d, J = 6.3 Hz, 3H), 7.96-7.89 (m, 1H), 7.49 (t, | DMSO | 458.0 (M + 1) | 2.12 | Method D | 100 | Method U |

TABLE 6-continued

| Number | ¹H NMR | ¹H NMR Solvent | m/z | Retention time | LC/MS Method | Purity percent | Method of Coupling |
|---|---|---|---|---|---|---|---|
| | J = 9.1 Hz, 1H), 6.52 (d, J = 9.6 Hz, 1H), 2.71 (s, 3H). | | | | | | |
| 841 | 1H NMR (300 MHz, DMSO) δ 13.08 (s, 1H), 9.59 (s, 1H), 9.16 (d, J = 8.4 Hz, 1H), 8.88-8.44 (m, 5H), 8.12-7.85 (m, 4H), 7.73 (q, J = 8.7 Hz, 3H), 7.58 (dd, J = 7.9, 4.8 Hz, 1H), 7.49 (dd, J = 7.8, 4.8 Hz, 1H), 7.21 (t, J = 7.6 Hz, 1H), 5.36 (s, 2H). | DMSO | 449.2 (M + 1) | 1.93 | Method C | 96 | Method X |
| 842 | 1H NMR (300 MHz, DMSO) δ 13.00 (s, 1H), 9.57 (s, 1H), 9.12 (d, J = 8.4 Hz, 1H), 8.76-8.60 (m, 4H), 8.50 (s, 1H), 8.03-7.89 (m, 3H), 7.68 (dd, J = 15.6, 5.2 Hz, 3H), 7.57 (t, J = 4.6 Hz, 3H), 7.19 (t, J = 7.6 Hz, 1H), 5.37 (s, 2H). | DMSO | 449.1 (M + 1) | 1.89 | Method C | 100 | Method X |
| 843 | 1H NMR (300 MHz, DMSO) δ 12.95 (s, 1H), 9.56 (s, 1H), 9.10 (d, J = 8.4 Hz, 1H), 8.75-8.64 (m, 2H), 8.46 (s, 1H), 7.98-7.91 (m, 2H), 7.85 (dd, J = 9.0, 0.8 Hz, 1H), 7.71 (t, J = 7.9 Hz, 1H), 7.61-7.48 (m, 3H), 7.18 (t, J = 7.6 Hz, 1H), 4.12 (d, J = 6.6 Hz, 2H), 2.84 (dd, J = 14.3, 7.4 Hz, 1H), 2.18-2.05 (m, 2H), 1.97-1.84 (m, 5H). | DMSO | 426.2 (M + 1) | 2.46 | Method C | 100 | Method X |
| 844 | 1H-NMR (400 MHz, DMSO-d6): δ 9.95 (s, 1H), 9.54 (d, J = 1.6 Hz, 1H), 8.82 (d, J = 1.7 Hz, 1H), 8.78-8.59 (m, 3H), 8.29 (dd, J = 6.8, 2.6 Hz, 1H), 8.16 (d, J = 2.5 Hz, 1H), 8.06-7.86 (m, 3H), 7.69 (dd, J = 9.1, 2.5 Hz, 1H), 7.64-7.47 (m, 3H), 5.37 (s, 2H). | DMSO | 458.1, 460.1 (M + 1) 229.6, 230.3 (M/2 + 1) | | Method A | 95 | Method X |
| 845 | 1H-NMR (400 MHz, DMSO-d6): δ 9.74 (s, 1H), 9.34 (s, 1H), 8.57-8.41 (m, 2H), 8.22 (d, J = 2.2 Hz, 1H), 8.10 (dd, J = 6.8, 2.6 Hz, 1H), 7.95 (d, J = 2.5 Hz, 1H), 7.80-7.63 (m, 3H), 7.53-7.30 (m, 3H), 6.82-6.68 (m, 1H), 5.07 (s, 2H), 3.71 (s, 3H). | DMSO | 488.1, 490.1 (M + 1) 244.6, 245.4 (M/2 + 1) | | Method A | 95 | Method X |

| Number | ¹H NMR | ¹H NMR Solvent | Purity percent | Method of Coupling |
|---|---|---|---|---|
| 846 | 1H NMR (400 MHz, DMSO) δ 9.31 (d, J = 1.7 Hz, 1H), 8.83-8.76 (m, 1H), 8.76-8.67 (m, 1H), 8.07 (d, J = 9.2 Hz, 1H), 7.86 (dd, J = 6.3, 2.8 Hz 1H), 7.83-7.73 (m, 2H), 7.70 (d, J = 2.8 Hz, 1H), | DMSO | >98 | Method X using $K_2CO_3$ instead of $Cs_2CO_3$ |

TABLE 6-continued

| | | | | |
|---|---|---|---|---|
| | 7.68-7.61 (m, 1H), 7.60-7.52 (m, 1H), 5.12 (s, 2H), 3.05 (s, 3H), 2.88 (s, 3H). | | | |
| 847 | 1H NMR (400 MHz, DMSO) δ 9.28 (dd, J = 2.2, 0.8 Hz, 1H), 8.65 (dd, J = 4.8, 1.7 Hz, 1H), 8.50-8.44 (m, 1H), 8.04 (d, J = 9.2 Hz, 1H), 7.92 (d, J = 2.7 Hz, 1H), 7.85 (d, J = 8.8 Hz, 1H), 7.75 (dd, J = 9.2, 2.9 Hz, 1H), 7.67 (d, J = 2.8 Hz, 1H), 7.56 (dd, J = 8.8, 2.7 Hz, 1H), 7.52 (ddd, J = 8.0, 4.8, 0.8 Hz, 1H), 5.10 (s, 2H), 3.05 (s, 3H), 2.88 (s, 3H). | DMSO | >98 | Method X using $K_2CO_3$ instead of $Cs_2CO_3$ |
| 848 | $^1$H NMR (400 MHz, $CDCl_3$) δ 9.45 (dd, J = 2,1, 0.8 Hz, 1H), 8.61 (dd, J = 4.8, 1.7 Hz, 1H), 8.59-8.53 (m, 1H), 8.01 (dd, J = 8.7, 0.8 1H), 7.72-7.62 (m, 2H), 7.56-7.47 (m, 2H), 7.39-7.29 (m, 4H), 4.90 (s, 2H), 3.15 (s, 3H), 3.04 (s, 3H). | CDCl3 | >98 | Method X using $K_2CO_3$ instead of $Cs_2CO_3$ |
| 849 | 1H NMR (300 MHz, DMSO) δ 13.01-11.72 (m, 1H), 9.70 (s, 1H), 9.40-9.30 (m, 1H), 8.99 (d, J = 4.5 Hz, 1H), 8.23 (d, J = 2.6 Hz, 1H), 8.12 (dd, J = 8.1, 5.5 Hz, 1H), 8.06-7.98 (m, 2H), 7.92 (d, J = 9.1 Hz, 1H), 7.84 (d, J = 4.9 Hz, 1H), 7.63 (dd, J = 9.1, 2.6 Hz, 1H), 7.56-7.49 (m, 2H), 5.05 (s, 3H), 3.11 (s, 3H), 2.92 (s, 3H). | DMSO | >98 | W |
| 850 | 1H NMR (300 MHz, DMSO) δ 9.74 (d, J = 1.8 Hz, 1H), 9.47-9.36 (m, 1H), 9.01 (dd, J = 5.5, 1.2 Hz, 1H), 8.28 (d, J = 2.6 Hz, 1H), 8.16 (dd, J = 8.2, 5.5 Hz, 1H), 8.06-7.93 (m, 3H), 7.81 (s, 1H), 7.66 (dd, J = 9.1, 2.6 Hz, 1H), 7.54-7.44 (m, 2H), 7.42-7.33 (m, 1H), 5.07 (s, 2H), 3.11 (s, 3H), 2.91 (s, 3H). | DMSO | >98 | W |
| 851 | 1H NMR (300 MHz, DMSO) δ 12.67 (s, 1H), 9.31-9.25 (m, 1H), 8.73 (dd, J = 4.8, 1.6 Hz, 1H), 8.52-8.42 (m, 1H), 7.74 (d, J = 3.9 Hz, 1H), 7.66 (d, J = 2.9 Hz, 1H), 7.61-7.47 (m, 4H), 7.45-7.31 (m, 3H), 5.27 (s, 2H), 3.30 (s, 3H). | DMSO | >98 | W |
| 852 | 1H NMR (300 MHz, DMSO) δ 9.56 (d, J = 1.8 Hz, 1H), 9.25 (d, J = 8.2 Hz, 1H), 9.08-8.98 (m, 1H), 8.81 (d, J = 4.5 Hz, 1H), 8.31 (td, J = 7.8, 1.6 Hz, 1H), 8.20-8.08 (m, 1H), 7.95 (d, J = 7.9 Hz, 1H), 7.88-7.63 (m, 4H), 7.47 (d, J = 2.1 Hz, 1H), 7.30 (dd, J = 8.6, 2.2 Hz, 1H), 5.60 (s, 2H), 4.63 (t, J = 7.8 Hz, 2H), 3.25 (t, J = 7.7 Hz, 2H). | DMSO | >98 | W |
| 853 | 1H NMR (300 MHz, DMSO) δ 9.56 (d, J = 1.8 Hz, 1H), 9.22 (d, J = 8.3 Hz, 1H), 9.00 (dd, J = 5.5, 1.3 Hz, 1H), 8.80 (d, J = 4.4 Hz, 1H), 8.29 (td, J = 7.8, 1.6 Hz, 1H), 8.21-8.05 (m, 2H), 8.00-7.66 (m, 5H), 7.29 (dd, J = 8.4, 2.6 Hz, 1H), 7.12 (td, J = 9.0, 2.8 Hz, 1H), 5.59 (s, 2H), 4.66 (t, J = 7.8 Hz, 2H), 3.25 (t, J = 7.6 Hz, 2H). | DMSO | >98 | W |
| 854 | 1H NMR (300 MHz, DMSO) δ 9.55 (d, J = 1.8 Hz, 1H), 9.30-9.18 (m, 1H), 9.00 (dd, J = 5.5, 1.3 Hz, 1H), 8.18-3.02 (m, 2H), 7.87 (dd, J = 8.8, 4.8 Hz, 1H), 7.71 (dd, J = 9.2, 2.7 Hz, 1H), 7.49 (d, J = 2.7 Hz, 1H), 7.29 (dd, J = 8.4, 2.6 Hz, 1H), 7.13 (td, J = 9.1, 2.8 Hz, 1H), 5.05 (s, 2H), 4.63 | DMSO | >98 | W |

TABLE 6-continued

| | | | | |
|---|---|---|---|---|
| | (d, J = 7.7 Hz, 2H), 3.25 (t, J = 7.5 Hz, 2H), 3.02 (s, 3H), 2.86 (s, 3H). | | | |
| 855 | 1H NMR (300 MHz, DMSO) δ 9.55 (d, J = 1.7 Hz, 1H), 9.15 (d, J = 8.2 Hz, 1H), 8.99-8.90 (m, 1H), 8.10-7.98 (m, 2H), 7.77 (dd, J = 8.9, 4.7 Hz, 1H), 7.67 (dd, J = 9.1, 2.7 Hz, 1H), 7.51 (d, J = 2.6 Hz, 1H), 7.28 (dd, J = 8.4, 2.7 Hz, 1H), 7.12 (dd, J = 10.3, 7.7 Hz, 1H), 4.70 (t, J = 7.8 Hz, 2H), 4.23-4.14 (m, 2H), 3.26 (t, J = 7.9 Hz, 2H), 1.41 (t, J = 6.9 Hz, 3H). | DMSO | >98 | W |
| 856 | 1H NMR (300 MHz, DMSO) δ 9.54 (d, J = 1.7 Hz, 1H), 9.19 (d, J = 8.1 Hz, 1H), 8.98 (d, J = 4.3 Hz, 1H), 8.15-8.02 (m, 2H), 7.90-7.72 (m, 2H), 7.60 (d, J = 2.6 Hz, 1H), 7.53-7.41 (m, 1H), 7.40-7.05 (m, SH), 5.34 (s, 2H), 4.59 (t, J = 7.8 Hz, 2H), 3.22 (t, J = 7.5 Hz, 2H). | DMSO | >98 | W |
| 857 | $^1$H NMR (400 MHz, DMSO) δ 10.56 (s, 1H), 9.49 (d, J = 1.8 Hz, 1H), 9.11 (d, J = 8.0 Hz, 1H), 8.95 (dd, J = 5.4, 1.3 Hz, 1H), 8.26 (dd, J = 24.6, 3.5 Hz, 2H), 8.12-7.95 (m, 3H), 7.71 (dt, J = 9.1, 4.5 Hz, 2H), 7.56 (dd, J = 19.7, 9.1 Hz, 1H), 4.75 (s, 2H), 2.72 (d, J = 5.0 Hz, 3H). | DMSO | >98 | Method W |
| 858 | $^1$H NMR (400 MHz, DMSO) δ 9.77 (br s, J = 81.7 Hz, 1H), 9.50 (d, J = 1.5 Hz, 1H), 8.71-8.57 (m, 2H), 8.22-8.07 (m, 1H), 7.97 (t, J = 5.1 Hz, 1H), 7.87 (d, J = 9.1 Hz, 1H), 7.81-7.39 (m, 4H), 5.01 (s, 2H), 3.07 (s, 3H), 2.90 (s, 3H). | DMSO | >98 | Method W |
| 859 | $^1$H NMR (400 MHz, DMSO) δ 10.62 (s, 1H), 9.50 (d, J = 1.7 Hz, 1H), 9.01 (d, J = 3.1 Hz, 1H), 8.90 (dd, J = 5.3, 1,5 Hz, 1H), 8.32 (d, J = 2.3 Hz, 1H), 8.20-8.09 (m, 1H), 7.95 (dd, J = 8.5, 4.7 Hz, 2H), 7.83-7.74 (m, 1H), 7.67 (dd, J = 9.1, 2.6 Hz, 1H), 7.55 (dd, J = 19.7, 9.1 Hz, 1H), 5.15 (s, 2H), 4.29-3.00 (m, 8H). | DMSO | >98 | Method W |
| 860 | $^1$H NMR (400 MHz, DMSO) δ 10.39 (s, 1H), 9.51 (d, J = 1.6 Hz, 1H), 8,81 (dd, J = 19.3, 6.0 Hz, 2H), 8.29 (s, 1H), 8.16 (dd, J = 10.6, 7.5 Hz, 1H), 7.94 (d, J = 9.0 Hz, 1H), 7.77 (s, 2H), 7.69-7.51 (m, 2H), 4.67 (s, 2H), 3.99 (s, 2H), 3.81 (br s, 4H), 3.70 (br s, 4H). | DMSO | >98 | Method W |
| 861 | $^1$H NMR (400 MHz, DMSO) δ 10.82 (s, 1H), 9.50 (d, J = 1.3 Hz, 1H), 9.02 (d, J = 8.0 Hz, 1H), 8.90 (d, J = 4.4 Hz, 1H), 8.46 (s, 1H), 8.21-8.10 (m, 1H), 8.03-7.90 (m, 2H), 7.84 (d, J = 8.7 Hz, 1H), 7.68 (dd, J = 9.1, 2.3 Hz, 1H), 7.55 (dd, J = 19.6, 9.3 Hz, 1H), 4,67 (s, 2H), 3,23-3.05 (m, 6H), 2.10-1.78 (m, 4H). | DMSO | >98 | Method W |
| 862 | $^1$H NMR (400 MHz, DMSO) δ 10.77 (s, 1H), 9.49 (d, J = 1.6 Hz, 1H), 9.12 (d, J = 8.1 Hz, 1H), 8.99-8.91 (m, 1H), 8.23 (d, J = 2.1 Hz, 1H), 8.12-7.99 (m, 3H), 7.78-7.71 (m, 1H), 7.66-7.54 (m, 2H), 4.02 (d, J = 6.5 Hz, 2H), 2.24-2.00 (m, 1H), 1.07 (d, J = 6.7 Hz, 6H). | DMSO | >98 | Method W |

TABLE 6-continued

| | | | | |
|---|---|---|---|---|
| 863 | $^1$H NMR (400 MHz, $CDCl_3$) δ 10.71 (s, 1H), 9.80 (s, 1H), 9.40 (d, J = 8.2 Hz, 1H), 3.95 (d, J = 5.2 Hz, 1H), 8.54 (d, J = 2.4 Hz, 1H), 8.24 (d, J = 9.2 Hz, 1H), 8.08 (dd, J = 8.0, 5.6 Hz, 1H), 7.86-7.76 (m, 1H), 7.69 (d, J = 8.7 Hz, 1H), 7.56 (d, J = 8.8, 2.2 Hz, 1H), 7.31 (s, 1H), 5.08 (s, 2H), 3.69 (t, J = 6.8 Hz, 2H), 3.55 (t, J = 6.9 Hz, 2H), 2.13-2.01 (m, 2H), 1.98-1.35 (m, 2H). | DMSO | >98 | Method W |
| 864 | 1H NMR (400 MHz, DMSO) δ 10.62 (s, 1H), 9.50 (d, J = 1.9 Hz, 1H), 9.12 (d, J = 8.2 Hz, 1H), 8.96 (dd, J = 5.5, 1.4 Hz, 1H), 8.27 (d, J = 2.6 Hz, 1H), 8.20 (d, J = 8.0 Hz, 1H), 8.15-7.97 (m, 3H), 7.75 (ddd, J = 11.9, 7.4, 3.3 Hz, 2H), 7.56 (dt, J = 10.6, 9.1 Hz, 1H), 4.74 (s, 2H), 4.07-3.93 (m, 1H), 1.13 (d, J = 6.6 Hz, 6H).. | DMSO | >98 | Method W |
| 865 | $^1$H NMR (400 MHz, DMSO) δ 10.8 (s, 1H), 9.51 (d, J = 1.8 Hz, 1H), 9.15 (d, J = 8.2 Hz, 1H), 8.97 (dd, J = 5.4, 1.3 Hz, 1H), 8.82-8.74 (m, 1H), 8.55 (d, J = 2.6 Hz, 1H), 8.23-8.19 (m, 1H), 8.16-8.01 (m, 3H), 7.94 (d, J = 7.9 Hz, 1H), 7.85-7.75 (m, 2H), 7.70 (dd, J = 7.0, 5.8 Hz, 1H), 7.61-7.49 (m, 1H), 5,63 (s, 2H). | DMSO | >98 | Method W |
| 866 | $^1$H NMR (400 MHz, DMSO) δ 10.62 (s, 1H), 9.50 (d, J = 1.8 Hz, 1H), 9.11 (d, J = 8.1 Hz, 1H), 8.95 (d, J = 5.4 Hz, 1H), 8.76 (d, J = 5.0 Hz, 1H), 8.42 (s, 1H), 8.18 (t, J = 7.8 Hz, 1H), 8.08-7.96 (m, 4H), 7.89 (d, J = 7.8 Hz, 1H), 7.80 (dd, J = 9.1, 2.6 Hz, 1H), 7.64 (t, J = 8.2 Hz, 2H), 7.24 (d, J = 8.3 Hz, 1H), 5.57 (s, 2H). | DMSO | >98 | Method W |
| 867 | 1H NMR (300 MHz, DMSO) d 9.58 (s, 1H), 9.05 (d, J = 8.2 Hz, 1H), 8.98 (d, J = 8.1 Hz, 1H), 8.88 (d, J = 5.1 Hz, 1H), 8.47 (s, 1H), 8.05-7.85 (m, 4H), 7.71 (m, 1H), 7.61 (d, J = 8.1 Hz, 2H), 7.24 (dd, J = 7.6 Hz, 1H). | DMSO | 94 | Method X (K2CO3, DMF-THF (1:1), rt) |
| 868 | 1H NMR (300 MHz, DMSO) δ 13.07 (s, 1H), 9.59 (d, J = 1.4 Hz, 1H), 9.13 (d, J = 8.1 Hz, 1H), 8.97 (d, J = 7.8 Hz, 1H), 8.92 (d, J = 4.1 Hz, 1H), 8.49 (s, 1H), 8.08-7.92 (m, 4H), 7.80-7.64 (m, 3H), 7.26 (td, J = 7.8, 1.1 Hz, 1H), 7.14 (d, J = 1.5 Hz, 1H), 7.09 (dd, J = 7.9, 1.6 Hz, 1H), 6.95 (d, J = 7.9 Hz, 1H), 6.03 (s, 2H), 5.19 (s, 2H). | DMSO | 99 | Method X |
| 869 | $^1$H-NMR (400 MHz, DMSO-$d_6$): δ 9.67 (s, 1H), 9.40 (d, J = 7.6 Hz, 1H), 9.01 (d, J = 8.4 Hz, 2H), 8.93 (d, J = 8.4 Hz, 1H), 8.31 (d, J = 7.6 Hz, 1H), 8.22 (t, J = 7.2 Hz, 1H), 8.01 (d, J = 9.2 Hz, 1H), 7.97-7.92 (m, 2H), 7.79-7.71 (m, 3H), 7.33 (t, J = 8.0 Hz, 1H), 5.54 (s, 2H). | DMSO | 98 | Method X |
| 870 | $^1$H-NMR (400 MHz, CD3OD): δ 9.62 (d, J = 6.9 Hz, 1H), 9.40 (d, J = 8.2 Hz, 1H), 8.99 (d, J = 5.3 Hz, 1H), 8.82 (t, J = 8.2 Hz, 1H), 8.22 (dd, J = 8.1, 5.7 Hz, 1H), 8.02-7.88 (m, 2H), 7.76-7.60 (m, 3H), 7.31 (t, J = 7.6 Hz, 1H), 4.81 (q, J = 8.1 Hz, 2H). | MeOD | 95 | Method W |

TABLE 6-continued

| | | | | |
|---|---|---|---|---|
| 871 | $^1$H-NMR (400 MHz, DMSO-$d_6$): δ 12.96 (s, 1H), 9.59 (s, 1H), 9.24 (d, J = 8.1 Hz, 1H), 9.00 (s, 1H), 8.80 (d, J = 5.7 Hz, 2H), 8.50 (s, 1H), 8.22 (t, J = 7.2 Hz, 1H), 8.09 (d, J = 9.2 Hz, 2H), 7.99-7.79 (m, 5H), 7.74-7.54 (m, 6H), 7.30 (t, J = 7.5 Hz, 1H), 5.55 (s, 2H). | DMSO-$d_6$ | 95 | Method X |
| 872 | $^1$H-NMR (400 MHz, DMSO-$d_6$): δ 12.82 (s, 1H), 9.58 (s, 1H), 9.13 (d, J = 6.9 Hz, 1H), 8.93 (s, 1H), 8.82 (d, J = 8.0 Hz, 1H), 8.43 (s, 1H), 8.04-7.88 (m, 4H), 7.74-7.69 (m, 3H), 7.28 (t, J = 7.6 Hz, 1H), 7.01-6.91 (m, 2H), 6.87-6.85 (m, 2H), 4.74-4.70 (m, 1H), 4.55-4.53 (m, 1H), 4.50-4.47 (m, 1H), 4.29-4.24 (m, 1H). | DMSO | 95 | Method X |
| 873 | $^1$H-NMR (400 MHz, DMSO-$d_6$): δ 13.07 (s, 1H), 9.61 (s, 1H), 9.05-9.00 (m, 2H), 8.88 (d, J = 4 Hz, 1H), 8.51 (s, 1H), 8.25 (s, 1H), 8.11-8.08 (m, 2H), 7.99-7.97 (m, 3H), 7.91-7.88 (m, 2H), 7.76-7.72 (m, 2H), 7.47 (dd, J = 2.0, 8.8 Hz, 1H), 7.27 (t, J = 8.8 Hz, 1H), 5.61 (s, 2H). | DMSO | 95 | Method X |
| 874 | $^1$H-NMR (400 MHz, DMSO-$d_6$): δ 12.89 (s, 1H), 10.72 (s, 1H), 9.83 (s, 1H), 9.38 (d, J = 8.2 Hz, 1H), 9.22 (d, J = 5.6 Hz, 1H), 9.03 (d, J = 8.3 Hz, 1H), 8.51 (s, 1H), 8.37-8.27 (m, 1H), 8.02-7.86 (m, 3H), 7.71 (t, J = 7.6 Hz, 1H), 7.55 (d, J = 9.0 Hz, 1H), 7.51 (s, 1H), 7.25 (t, J = 7.5 Hz, 1H), 4.71 (d, J = 7.3 Hz, 2H), 1.56 (s, 1H), 0.81-0.64 (m, 4H). | DMSO | 95 | Method X |
| 875 | $^1$H-NMR (400 MHz, DMSO-$d_6$): δ 12.88 (s, 1H), 9.57 (s, 1H), 9.24 (d, J = 8.1 Hz, 1H), 9.01 (d, J = 5.3 Hz, 1H), 8.73 (d, J = 8.2 Hz, 1H), 8.49 (s, 1H), 8.37 (t, J = 7.8 Hz, 1H), 8.10 (dd, J = 11.3, 7.0 Hz, 2H), 7.97 (d, J = 7.8 Hz, 2H), 7.86 (s, 2H), 7.80 (d, J = 7.1 Hz, 2H), 7.71 (t, J = 7.8 Hz, 1H), 7.30 (t, J = 7.5 Hz, 1H), 5.65 (s, 2H); 2.78 (s, 3H). | DMSO | 95 | Method X |
| 876 | $^1$H-NMR (400 MHz, DMSO-$d_6$): δ 12.93 (s, 1H), 10.74 (s, 1H), 9.75 (s, 1H), 9.40 (s, 1H), 9.05 (d, J = 8.0 Hz, 2H), 8.99 (d, J = 6.0 Hz, 1H), 7.99 (s, 1H), 7.98-7.96 (m, 1H), 7.89-7.86 (m, 2H), 7.72-7.51 (m, 2H), 7.24 (t, J = 6.0 Hz, 1H), 5.84 (s, 2H), 3.60-3.56 (m, 2H), 3.43-3.39 (m, 2H), 2.06-2.01 (m, 2H), 1.99-1.84 (m, 2H). | DMSO | 95 | Method W |
| 1757 | $^1$H NMR (400 MHz, DMSO) δ 9.32-9.27 (m, 1H), 8.66 (dd, J = 4.8, 1.7 Hz, 1H), 8.64-8.60 (m, 1H), 8.50-8.43 (m, 1H), 8.10-8.03 (m, 1H), 7.93-7.80 (m, 4H), 7.68-7.60 (m, 2H), 7.59-7.49 (m, 2H), 7.39 (ddd, J = 7.5, 4.8, 1.1 Hz, 1H), 5.43 (s, 2H). | DMSO | >98 | Method W using $K_2CO_3$ instead of $Cs_2CO_3$ |

Scheme 27: General route for the synthesis of compounds with general formula xiv

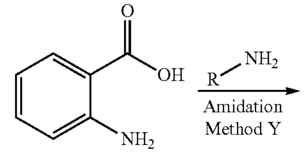

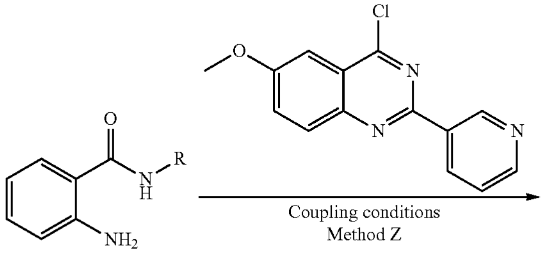

ii

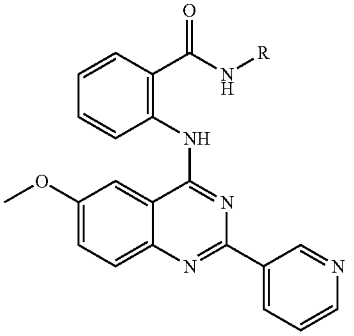

xiv

Scheme 28: Representative synthesis of compounds of formula xiv (see Scheme 27)

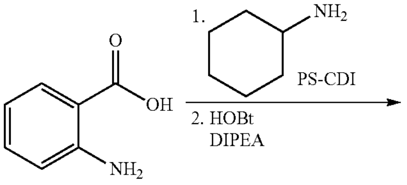

-continued

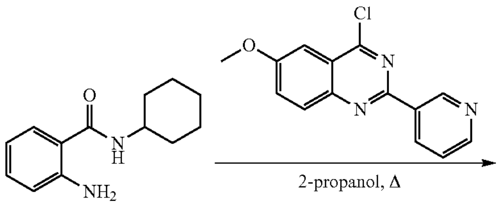

ii-b

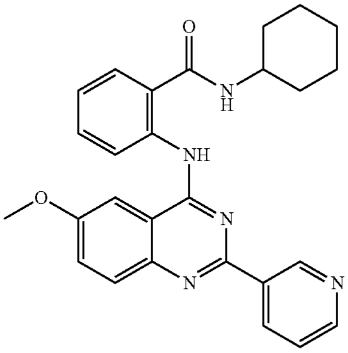

xiv-f

Method Y: 2-Amino-N-cyclohexyl-benzamide (ii-b)

To a dry reaction vial was added cyclohexylamine (40 uμmol, 1.0 eq) and PS-carbodiimide resin (72 μmol, 1.8 eq). The solution of 2-amino-benzoic acid (44 μmol, 1.1 eq), diisopropyl ethyl amine (10 μLl) and HOBt (44 μmol, 1.1 eq) in THF (500 μL) was added to the above vial. The reaction mixture was heated at 40° C. for 6 h on a shaker. The resin was removed by filtration and washed with 10% MeOH/$CH_2Cl_2$. The solvent was removed in vacuo and the residue was applied to solid phase extraction cartridge (basic silica, 200 mg) and eluted with 50% EtOAc/$CH_2Cl_2$. After removal of the solvents, the crude 2-amino-N-cyclohexyl-benzamide was obtained and used for the following reaction.

Method Z: N-Cyclohexyl-2-(6-methoxy-2-pyridin-3-yl-quinazolin-4-ylamino)-benzamide (xiv-f)

To the crude amide was added the solution of 4-chloro-6-methoxy-2-pyridin-3-yl-quinazoline (20 μmol) in 2-propanol (200 μL). The mixture was refluxed for 8 h. After evaporation, the residue was dissolved in 5% TFA/MeOH-DMF (1:1) and purified by PREP-HPLC Condition D. The target fraction was lyophilized to afford the titled compound whose structure was finally confirmed by LCMS using LCMS Method E.

The compounds in the following table were prepared in a manner analogous to that described in Scheme 27, replacing cyclohexylamine with the appropriate amine.

TABLE 7
| Number | Product | Exact Mass | LCMS (M + 1) | Method of Coupling |
|---|---|---|---|---|
| 877 | 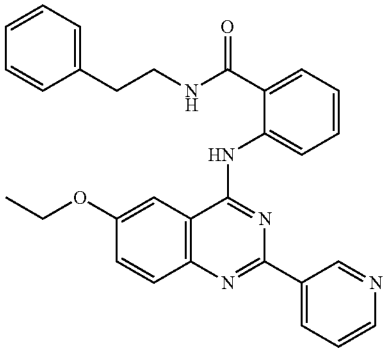 [SMILES: CCOc1ccc2nc(-c3cccnc3)nc(Nc3ccccc3C(=O)NCCc3ccccc3)c2c1] | 489 | 490 | Methods Y, Z |
| 878 | 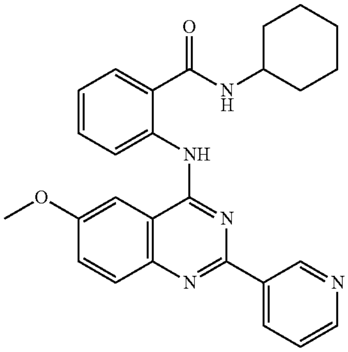 [SMILES: COc1ccc2nc(-c3cccnc3)nc(Nc3ccccc3C(=O)NC3CCCCC3)c2c1] | 453 | 454 | Methods Y, Z |
| 879 | 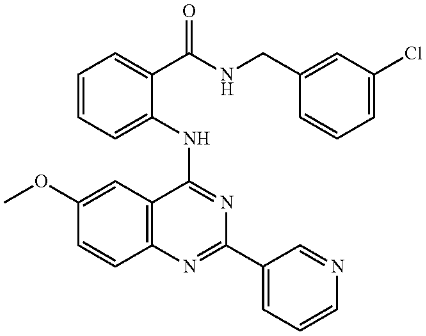 [SMILES: COc1ccc2nc(-c3cccnc3)nc(Nc3ccccc3C(=O)NCc3cccc(Cl)c3)c2c1] | 495 | 496 | Methods Y, Z |
| 880 | 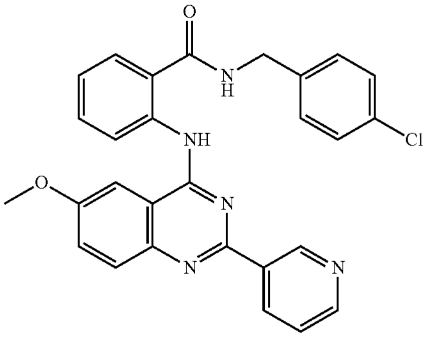 [SMILES: COc1ccc2nc(-c3cccnc3)nc(Nc3ccccc3C(=O)NCc3ccc(Cl)cc3)c2c1] | 495 | 496 | Methods Y, Z |

TABLE 7-continued
| Number | Product | Exact Mass | LCMS (M + 1) | Method of Coupling |
|---|---|---|---|---|
| 881 | 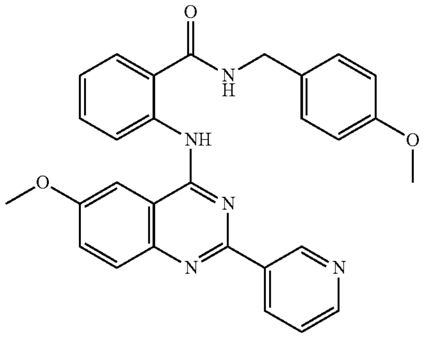 | 491 | 492 | Methods Y, Z |
| 882 | 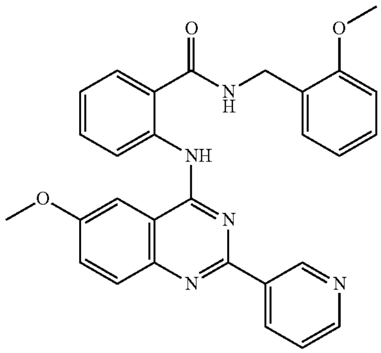 | 491 | 492 | Methods Y, Z |
| 883 | 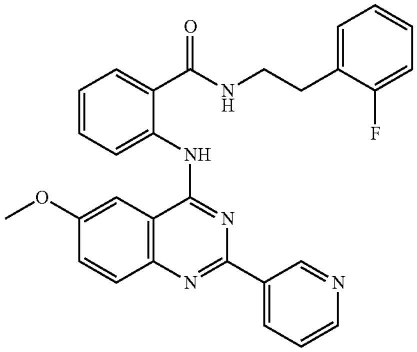 [SMILES: COc1ccc2nc(-c3cccnc3)nc(Nc3ccccc3C(=O)NCCc3ccccc3F)c2c1] | 493 | 494 | Methods Y, Z |
| 884 | 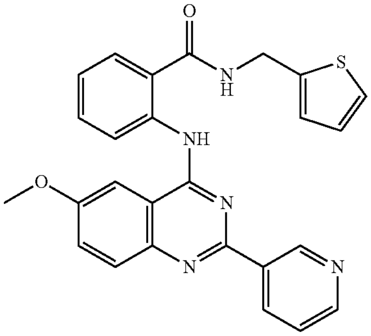 [SMILES: COc1ccc2nc(-c3cccnc3)nc(Nc3ccccc3C(=O)NCc3cccs3)c2c1] | 467 | 468 | Methods Y, Z |

TABLE 7-continued
| Number | Product | Exact Mass | LCMS (M + 1) | Method of Coupling |
|---|---|---|---|---|
| 885 | 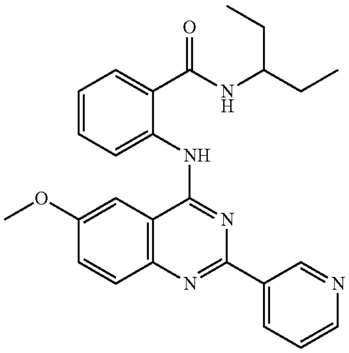 [SMILES: CCC(CC)NC(=O)c1ccccc1Nc1nc(-c2cccnc2)nc2ccc(OC)cc12] | 441 | 442 | Methods Y, Z |
| 886 | 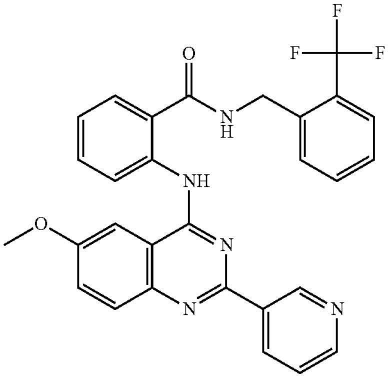 [SMILES: COc1ccc2nc(-c3cccnc3)nc(Nc3ccccc3C(=O)NCc3ccccc3C(F)(F)F)c2c1] | 529 | 530 | Methods Y, Z |
| 887 | 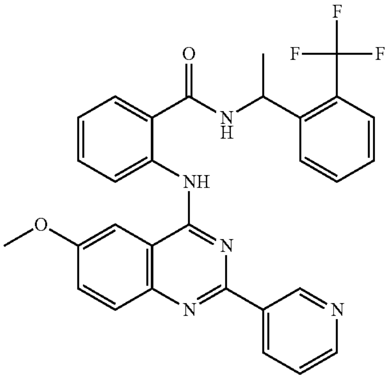 [SMILES: COc1ccc2nc(-c3cccnc3)nc(Nc3ccccc3C(=O)NC(C)c3ccccc3C(F)(F)F)c2c1] | 543 | 544 | Methods Y, Z |
| 888 | 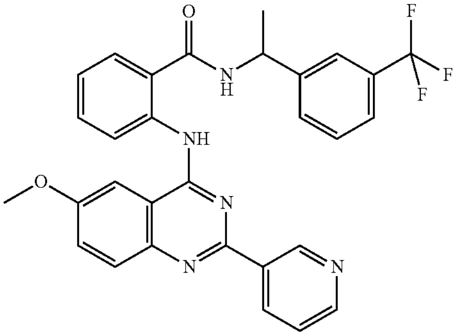 [SMILES: COc1ccc2nc(-c3cccnc3)nc(Nc3ccccc3C(=O)NC(C)c3cccc(C(F)(F)F)c3)c2c1] | 543 | 544 | Methods Y, Z |

TABLE 7-continued
| Number | Product | Exact Mass | LCMS (M + 1) | Method of Coupling |
|---|---|---|---|---|
| 889 | 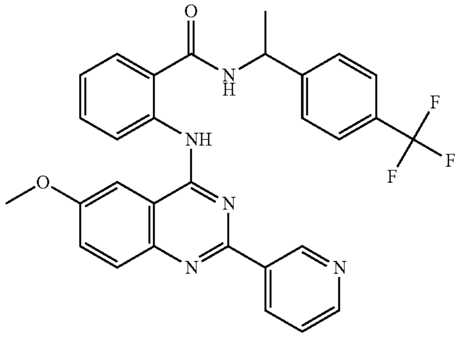 [SMILES: COc1ccc2nc(-c3cccnc3)nc(Nc3ccccc3C(=O)NC(C)c3ccc(C(F)(F)F)cc3)c2c1] | 543 | 544 | Methods Y, Z |
| 890 | 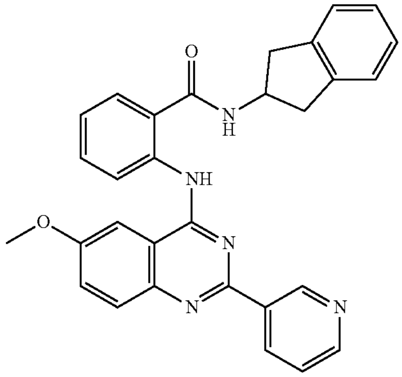 [SMILES: COc1ccc2nc(-c3cccnc3)nc(Nc3ccccc3C(=O)NC3Cc4ccccc4C3)c2c1] | 487 | 488 | Methods Y, Z |
| 891 | 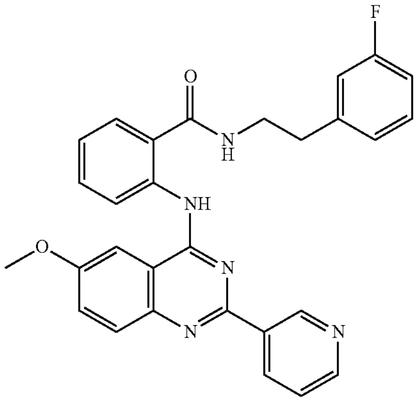 [SMILES: COc1ccc2nc(-c3cccnc3)nc(Nc3ccccc3C(=O)NCCc3cccc(F)c3)c2c1] | 493 | 494 | Methods Y, Z |
| 892 | 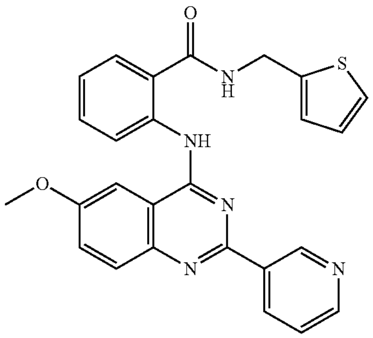 [SMILES: COc1ccc2nc(-c3cccnc3)nc(Nc3ccccc3C(=O)NCc3cccs3)c2c1] | 467 | 468 | Methods Y, Z |

TABLE 7-continued
| Number | Product | Exact Mass | LCMS (M + 1) | Method of Coupling |
|---|---|---|---|---|
| 893 | 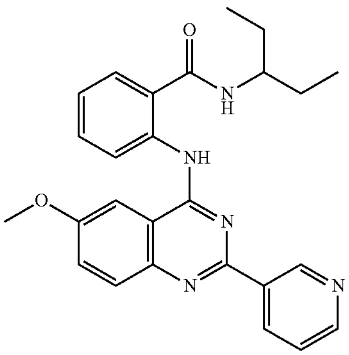 [SMILES: CCC(CC)NC(=O)c1ccccc1Nc1nc(-c2cccnc2)nc2ccc(OC)cc12] | 441 | 442 | Methods Y, Z |
| 894 | 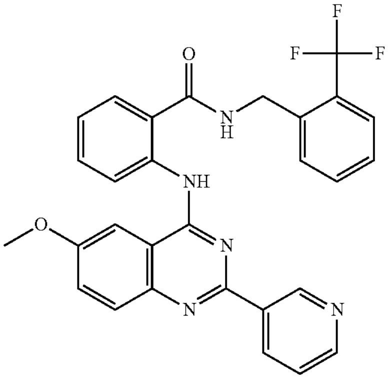 [SMILES: COc1ccc2nc(-c3cccnc3)nc(Nc3ccccc3C(=O)NCc3ccccc3C(F)(F)F)c2c1] | 529 | 530 | Methods Y, Z |
| 895 | 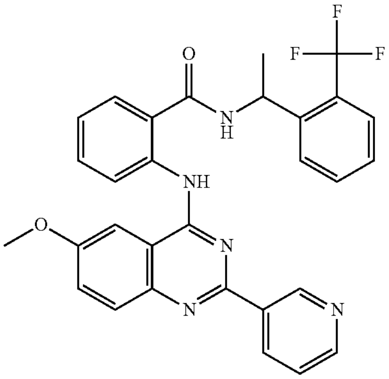 [SMILES: COc1ccc2nc(-c3cccnc3)nc(Nc3ccccc3C(=O)NC(C)c3ccccc3C(F)(F)F)c2c1] | 543 | 544 | Methods Y, Z |
| 896 | 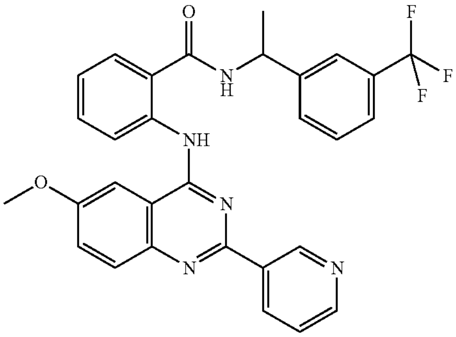 [SMILES: COc1ccc2nc(-c3cccnc3)nc(Nc3ccccc3C(=O)NC(C)c3cccc(C(F)(F)F)c3)c2c1] | 543 | 544 | Methods Y, Z |

TABLE 7-continued
| Number | Product | Exact Mass | LCMS (M + 1) | Method of Coupling |
|---|---|---|---|---|
| 897 | 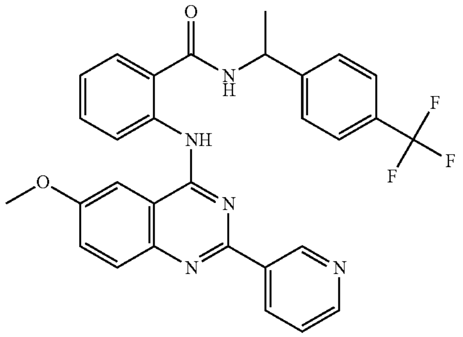 [SMILES: COc1ccc2nc(-c3cccnc3)nc(Nc3ccccc3C(=O)NC(C)c3ccc(C(F)(F)F)cc3)c2c1] | 543 | 544 | Methods Y, Z |
| 898 | 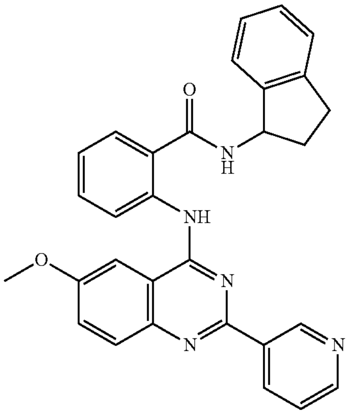 [SMILES: COc1ccc2nc(-c3cccnc3)nc(Nc3ccccc3C(=O)NC3CCc4ccccc43)c2c1] | 487 | 488 | Methods Y, Z |
| 899 | 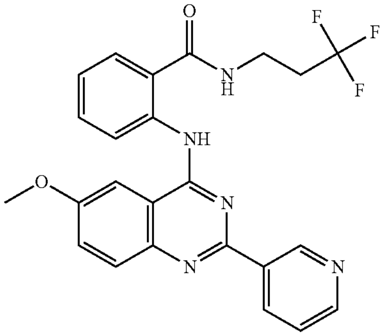 [SMILES: COc1ccc2nc(-c3cccnc3)nc(Nc3ccccc3C(=O)NCCC(F)(F)F)c2c1] | 467 | 468 | Methods Y, Z |
| 900 | 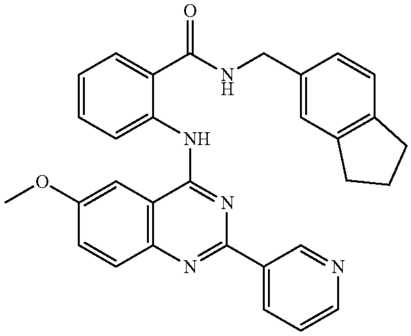 [SMILES: COc1ccc2nc(-c3cccnc3)nc(Nc3ccccc3C(=O)NCc3ccc4c(c3)CCC4)c2c1] | 501 | 502 | Methods Y, Z |

TABLE 7-continued
| Number | Product | Exact Mass | LCMS (M + 1) | Method of Coupling |
|---|---|---|---|---|
| 901 | 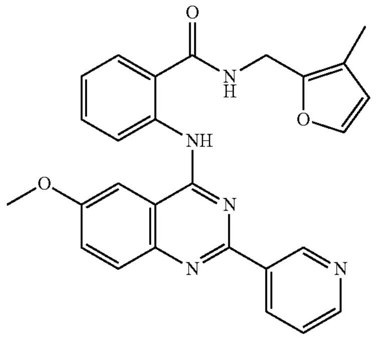 [SMILES: COc1ccc2nc(-c3cccnc3)nc(Nc3ccccc3C(=O)NCc3occc3C)c2c1] | 465 | 466 | Methods Y, Z |
| 902 | 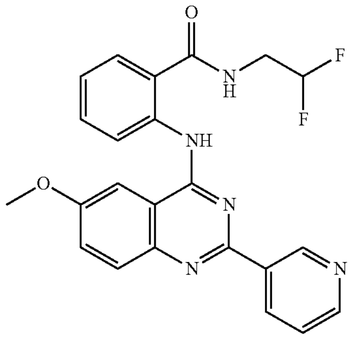 [SMILES: COc1ccc2nc(-c3cccnc3)nc(Nc3ccccc3C(=O)NCC(F)F)c2c1] | 435 | 436 | Methods Y, Z |
| 903 | 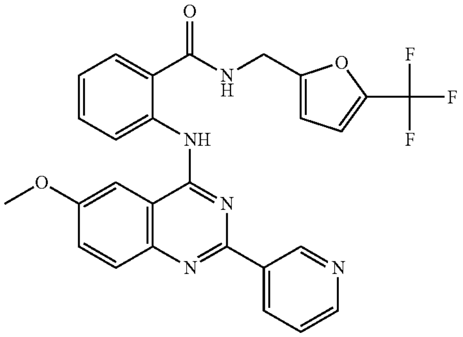 [SMILES: COc1ccc2nc(-c3cccnc3)nc(Nc3ccccc3C(=O)NCc3ccc(C(F)(F)F)o3)c2c1] | 519 | 520 | Methods Y, Z |
| 904 | 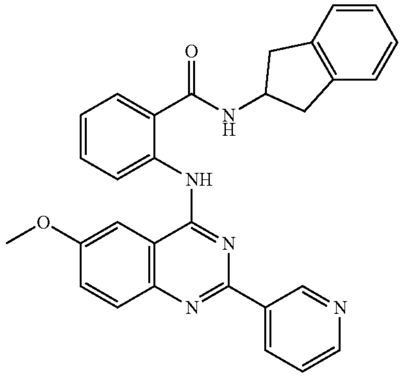 [SMILES: COc1ccc2nc(-c3cccnc3)nc(Nc3ccccc3C(=O)NC3Cc4ccccc4C3)c2c1] | 487 | 488 | Methods Y, Z |

TABLE 7-continued
| Number | Product | Exact Mass | LCMS (M + 1) | Method of Coupling |
|---|---|---|---|---|
| 905 | 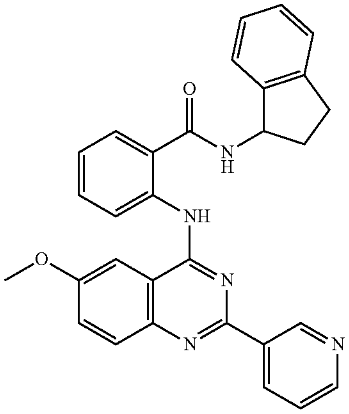 [SMILES: COc1ccc2nc(-c3cccnc3)nc(Nc3ccccc3C(=O)NC3CCc4ccccc43)c2c1] | 487 | 488 | Methods Y, Z |
| 906 | 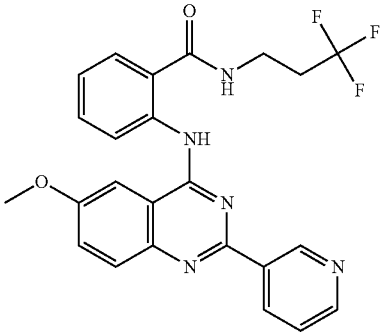 [SMILES: COc1ccc2nc(-c3cccnc3)nc(Nc3ccccc3C(=O)NCCC(F)(F)F)c2c1] | 467 | 468 | Methods Y, Z |
| 907 | 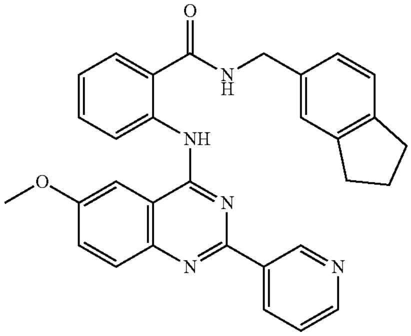 [SMILES: COc1ccc2nc(-c3cccnc3)nc(Nc3ccccc3C(=O)NCc3ccc4c(c3)CCC4)c2c1] | 501 | 502 | Methods Y, Z |
| 908 | 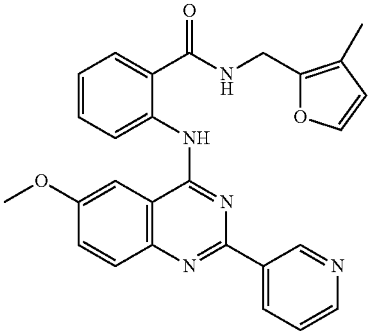 [SMILES: COc1ccc2nc(-c3cccnc3)nc(Nc3ccccc3C(=O)NCc3occc3C)c2c1] | 465 | 466 | Methods Y, Z |

TABLE 7-continued
| Number | Product | Exact Mass | LCMS (M + 1) | Method of Coupling |
|---|---|---|---|---|
| 909 | 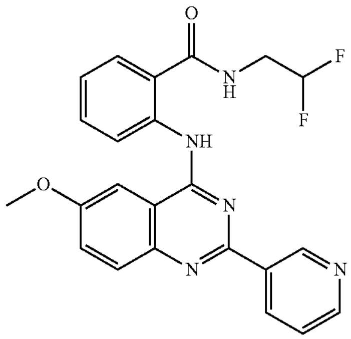 [SMILES: COc1ccc2nc(-c3cccnc3)nc(Nc3ccccc3C(=O)NCC(F)F)c2c1] | 435 | 436 | Methods Y, Z |
| 910 | 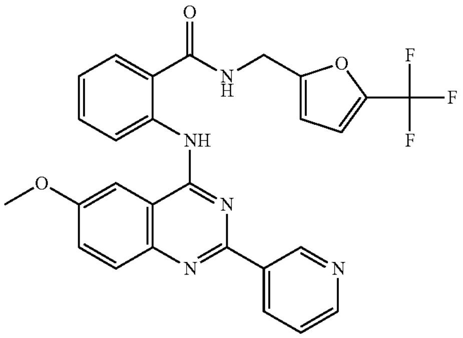 [SMILES: COc1ccc2nc(-c3cccnc3)nc(Nc3ccccc3C(=O)NCc3ccc(C(F)(F)F)o3)c2c1] | 519 | 520 | Methods Y, Z |
Scheme 29: General route for the synthesis of compounds with general formula vi
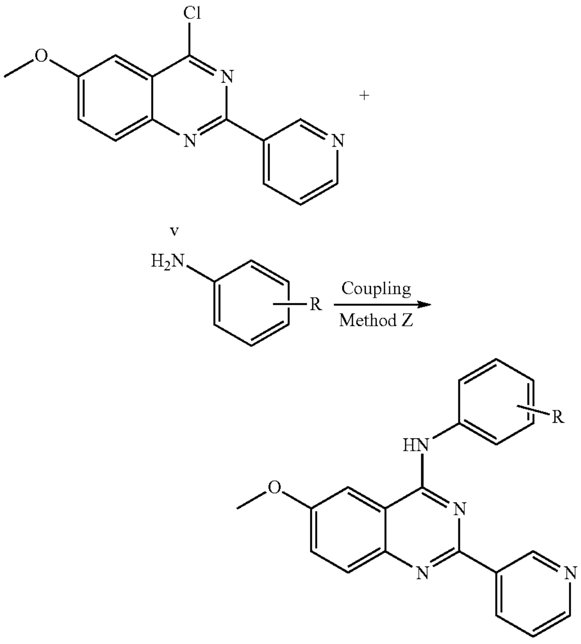
v
vi
Scheme 30: Representative synthesis of compounds of formula vi-b (see Scheme 29)
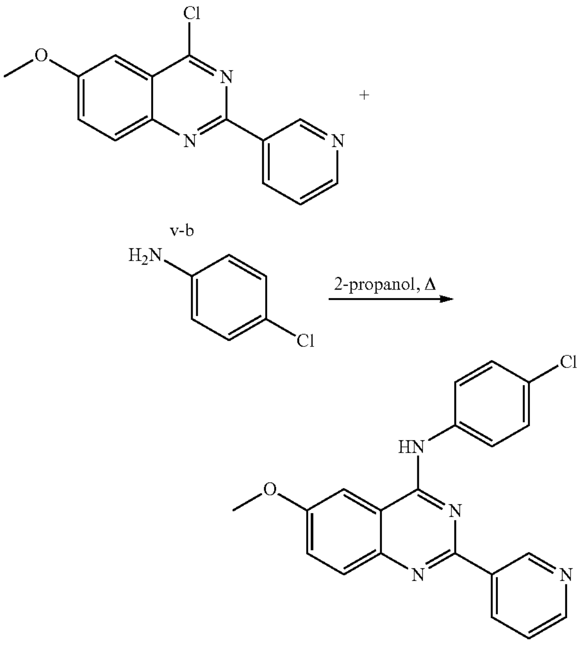
v-b
vi-k Method Z: Synthesis of N-(4-chlorophenyl)-6-methoxy-2-(pyridin-3-yl)quinazolin-4-amine (vi-k)

To 4-chloroaniline (24 μmol) was added the solution of 4-chloro-6-methoxy-2-pyridin-3-yl-quinazoline (20 mmol) in 2-propanol (200 μL). The mixture was refluxed for 8 h. After evaporation, the residue was dissolved in 5% TFA/MeOH-DMF (1:1) and purified by PREP-HPLC Condition D. The target fraction was lyophilized to afford the titled compound as the TFA salt whose structure was finally confirmed by LCMS using LCMS Method E.

The compounds in the following table were prepared in a manner analogous to that described in Scheme 29, replacing 4-chloroaniline with the appropriate aniline.

TABLE 8

| Number | Product | Exact Mass | LCMS (M + 1) | Method of Coupling |
|---|---|---|---|---|
| 911 | 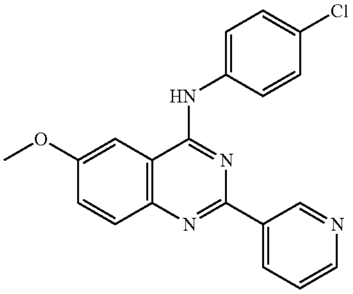 [SMILES: COc1ccc2nc(-c3cccnc3)nc(Nc3ccc(Cl)cc3)c2c1] | 362 | 363 | Method Z |
| 912 | 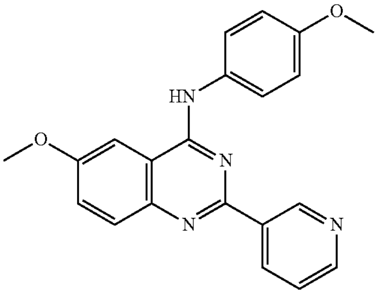 | 358 | 359 | Method Z |
| 913 | 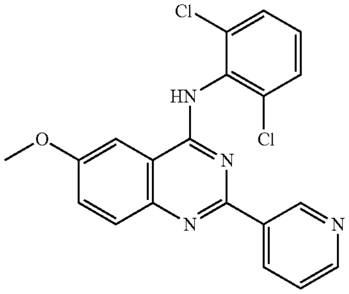 | 396 | 397 | Method Z |
| 914 | 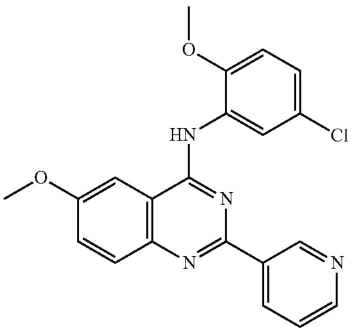 [SMILES: COc1ccc2nc(-c3cccnc3)nc(Nc3cc(Cl)ccc3OC)c2c1] | 392 | 393 | Method Z |

TABLE 8-continued
| Number | Product | Exact Mass | LCMS (M + 1) | Method of Coupling |
|---|---|---|---|---|
| 915 | 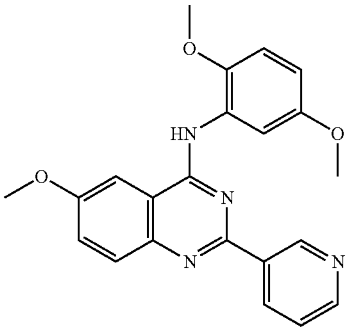 | 388 | 389 | Method Z |
| 916 | 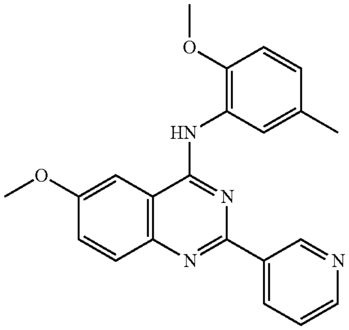 | 372 | 373 | Method Z |
| 917 | 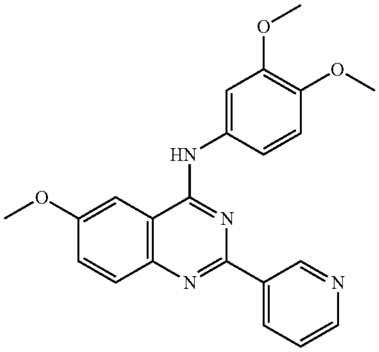 | 388 | 389 | Method Z |
| 918 | 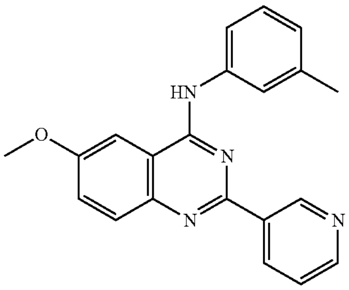 | 342 | 343 | Method Z |

TABLE 8-continued
| Number | Product | Exact Mass | LCMS (M + 1) | Method of Coupling |
|---|---|---|---|---|
| 919 | 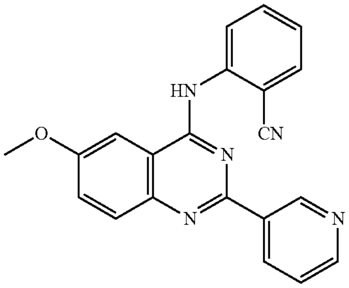 [SMILES: COc1ccc2nc(-c3cccnc3)nc(Nc3ccccc3C#N)c2c1] | 353 | 354 | Method Z |
| 920 | 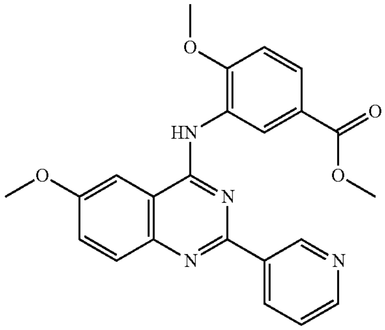 | 416 | 417 | Method Z |
| 921 | 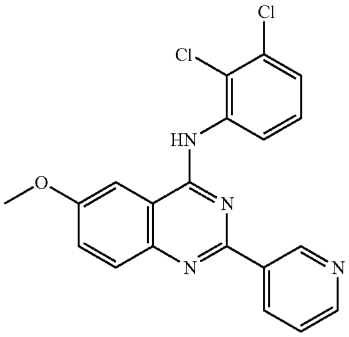 [SMILES: COc1ccc2nc(-c3cccnc3)nc(Nc3cccc(Cl)c3Cl)c2c1] | 396 | 397 | Method Z |
| 922 | 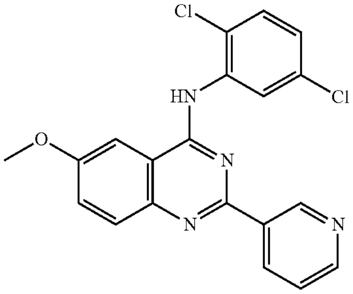 [SMILES: COc1ccc2nc(-c3cccnc3)nc(Nc3cc(Cl)ccc3Cl)c2c1] | 396 | 397 | Method Z |
| 923 | 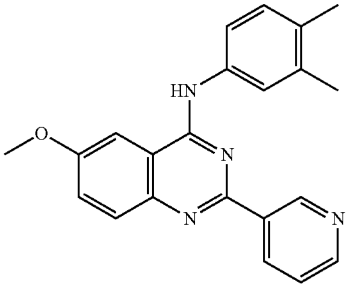 | 356 | 357 | Method Z |

TABLE 8-continued
| Number | Product | Exact Mass | LCMS (M + 1) | Method of Coupling |
|---|---|---|---|---|
| 924 | 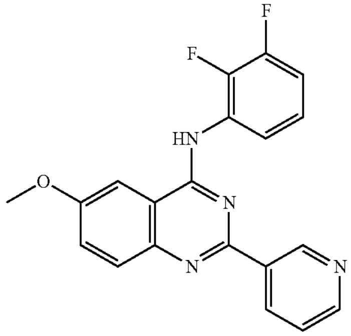 [SMILES: COc1ccc2nc(-c3cccnc3)nc(Nc3cccc(F)c3F)c2c1] | 364 | 365 | Method Z |
| 925 | 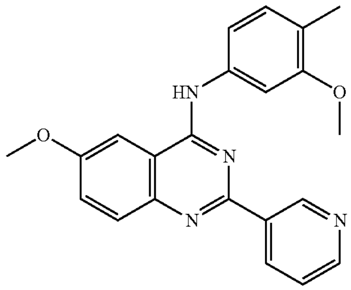 | 372 | 373 | Method Z |
| 926 | 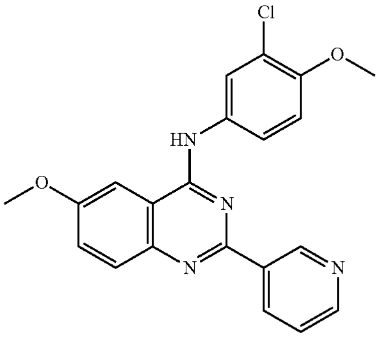 | 392 | 393 | Method Z |
| 927 | 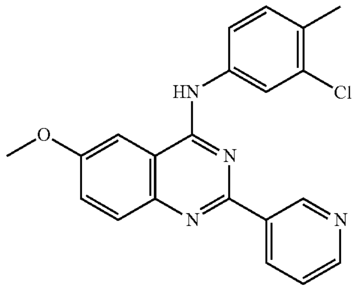 [SMILES: COc1ccc2nc(-c3cccnc3)nc(Nc3ccc(C)c(Cl)c3)c2c1] | 376 | 377 | Method Z |

TABLE 8-continued
| Number | Product | Exact Mass | LCMS (M + 1) | Method of Coupling |
|---|---|---|---|---|
| 928 | 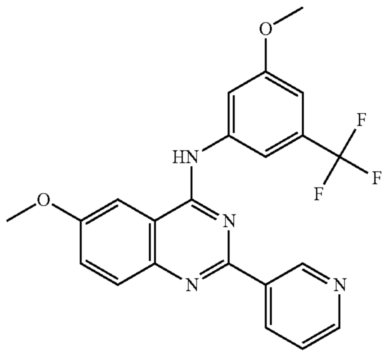 [SMILES: COc1cc(Nc2nc(-c3cccnc3)nc3ccc(OC)cc23)cc(C(F)(F)F)c1] | 426 | 427 | Method Z |
| 929 | 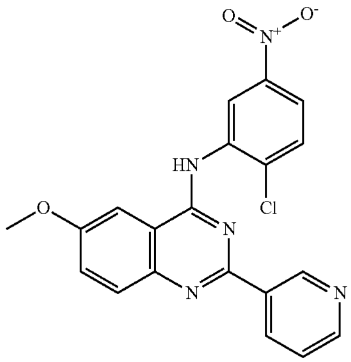 [SMILES: COc1ccc2nc(-c3cccnc3)nc(Nc3cc([N+](=O)[O-])ccc3Cl)c2c1] | 407 | 408 | Method Z |
| 930 | 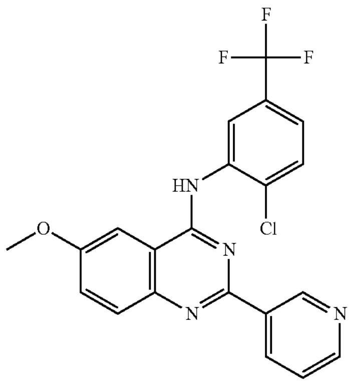 [SMILES: COc1ccc2nc(-c3cccnc3)nc(Nc3cc(C(F)(F)F)ccc3Cl)c2c1] | 430 | 431 | Method Z |
| 931 | 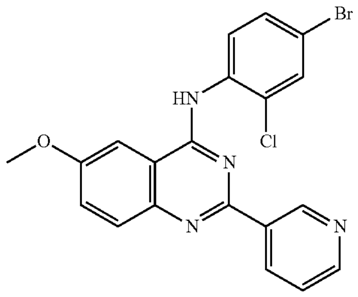 [SMILES: COc1ccc2nc(-c3cccnc3)nc(Nc3ccc(Br)cc3Cl)c2c1] | 440 | 441 | Method Z |

TABLE 8-continued
| Number | Product | Exact Mass | LCMS (M + 1) | Method of Coupling |
|---|---|---|---|---|
| 932 | 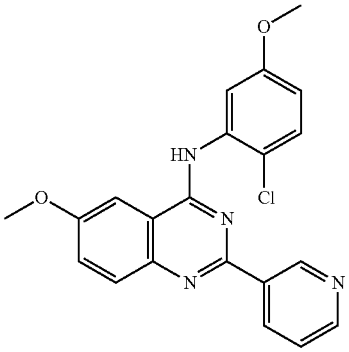 [SMILES: COc1ccc(Cl)c(Nc2nc(-c3cccnc3)nc3ccc(OC)cc23)c1] | 392 | 393 | Method Z |
| 933 | 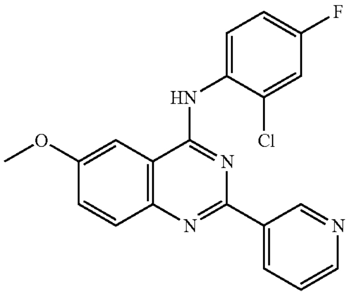 [SMILES: COc1ccc2nc(-c3cccnc3)nc(Nc3ccc(F)cc3Cl)c2c1] | 380 | 381 | Method Z |
| 934 | 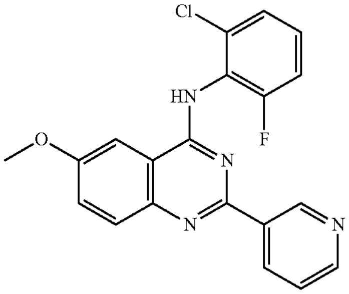 [SMILES: COc1ccc2nc(-c3cccnc3)nc(Nc3c(F)cccc3Cl)c2c1] | 380 | 381 | Method Z |
| 935 | 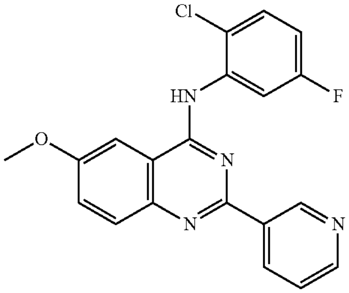 [SMILES: COc1ccc2nc(-c3cccnc3)nc(Nc3cc(F)ccc3Cl)c2c1] | 380 | 381 | Method Z |
| 936 | 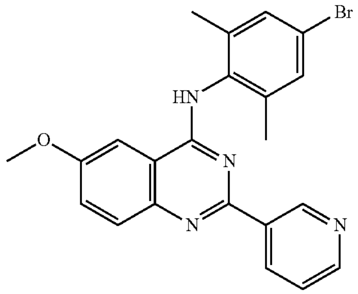 [SMILES: COc1ccc2nc(-c3cccnc3)nc(Nc3c(C)cc(Br)cc3C)c2c1] | 434 | 435 | Method Z |

TABLE 8-continued
| Number | Product | Exact Mass | LCMS (M + 1) | Method of Coupling |
|---|---|---|---|---|
| 937 | 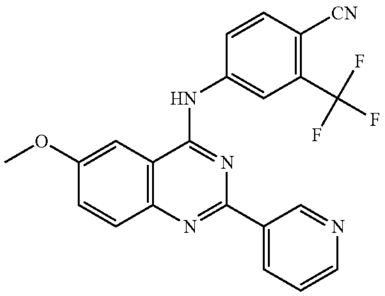 [SMILES: COc1ccc2nc(-c3cccnc3)nc(Nc3ccc(C#N)c(C(F)(F)F)c3)c2c1] | 421 | 422 | Method Z |
| 938 | 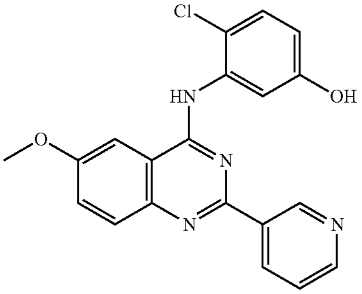 [SMILES: COc1ccc2nc(-c3cccnc3)nc(Nc3cc(O)ccc3Cl)c2c1] | 378 | 379 | Method Z |
| 939 | 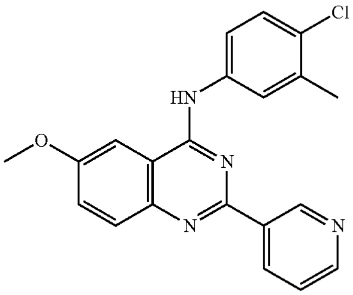 | 376 | 377 | Method Z |
| 940 | 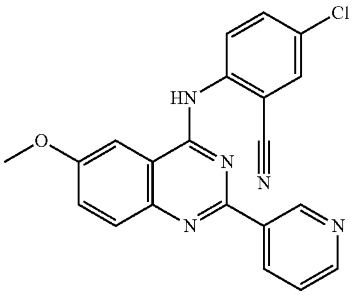 [SMILES: COc1ccc2nc(-c3cccnc3)nc(Nc3ccc(Cl)cc3C#N)c2c1] | 387 | 388 | Method Z |
| 941 | 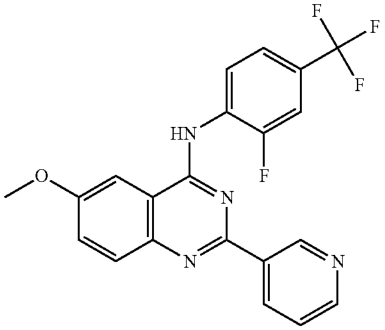 [SMILES: COc1ccc2nc(-c3cccnc3)nc(Nc3ccc(C(F)(F)F)cc3F)c2c1] | 414 | 415 | Method Z |

TABLE 8-continued
| Number | Product | Exact Mass | LCMS (M + 1) | Method of Coupling |
|---|---|---|---|---|
| 942 | 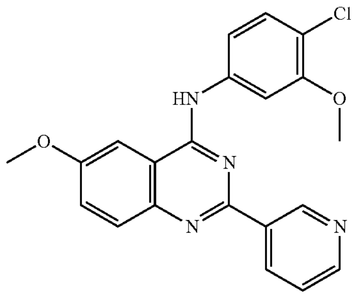 | 392 | 393 | Method Z |
| 943 | 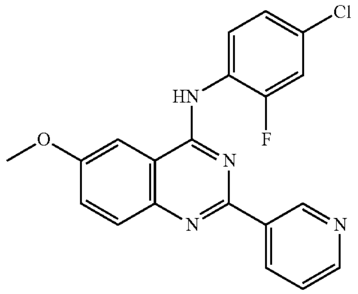 [SMILES: COc1ccc2nc(-c3cccnc3)nc(Nc3ccc(Cl)cc3F)c2c1] | 380 | 381 | Method Z |
| 944 | 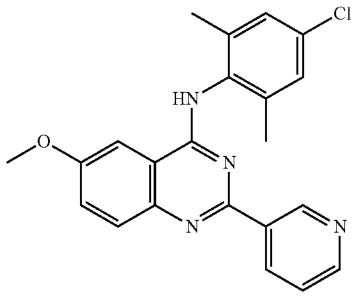 [SMILES: COc1ccc2nc(-c3cccnc3)nc(Nc3c(C)cc(Cl)cc3C)c2c1] | 390 | 391 | Method Z |
| 945 | 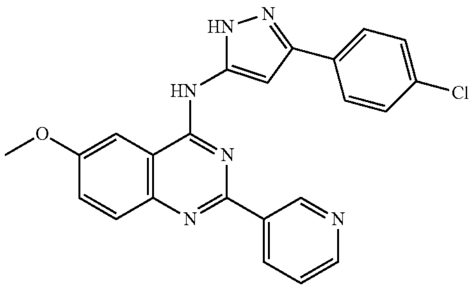 [SMILES: COc1ccc2nc(-c3cccnc3)nc(Nc3cc(-c4ccc(Cl)cc4)n[nH]3)c2c1] | 428 | 429 | Method Z |
| 946 | 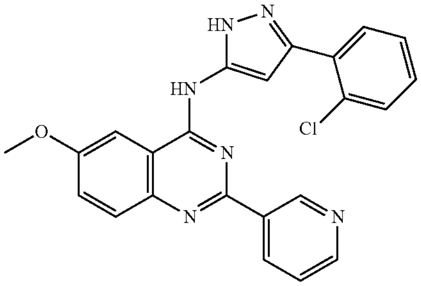 [SMILES: COc1ccc2nc(-c3cccnc3)nc(Nc3cc(-c4ccccc4Cl)n[nH]3)c2c1] | 428 | 429 | Method Z |

TABLE 8-continued
| Number | Product | Exact Mass | LCMS (M + 1) | Method of Coupling |
|---|---|---|---|---|
| 947 | 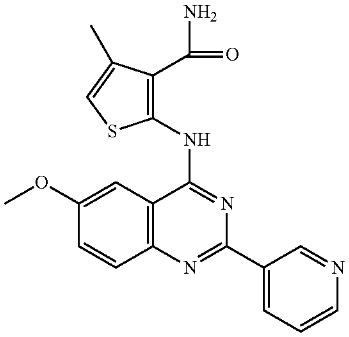 [SMILES: COc1ccc2nc(-c3cccnc3)nc(Nc3scc(C)c3C(N)=O)c2c1] | 391 | 392 | Method Z |
| 948 | 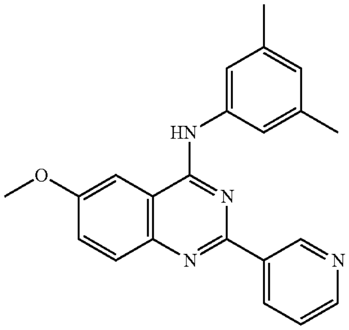 | 356 | 357 | Method Z |
| 949 | 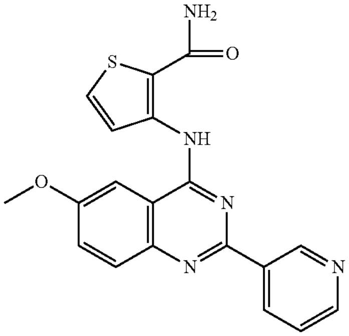 [SMILES: COc1ccc2nc(-c3cccnc3)nc(Nc3ccsc3C(N)=O)c2c1] | 377 | 378 | Method Z |
| 950 | 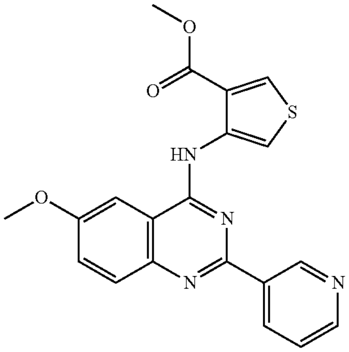 [SMILES: COC(=O)c1cscc1Nc1nc(-c2cccnc2)nc2ccc(OC)cc12] | 392 | 393 | Method Z |

TABLE 8-continued
| Number | Product | Exact Mass | LCMS (M + 1) | Method of Coupling |
|---|---|---|---|---|
| 951 | 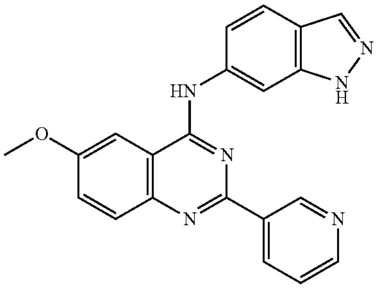 [SMILES: COc1ccc2nc(-c3cccnc3)nc(Nc3ccc4cn[nH]c4c3)c2c1] | 368 | 369 | Method Z |
| 952 | 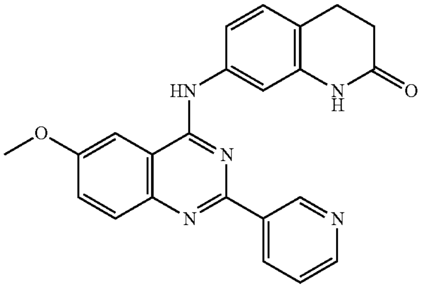 [SMILES: COc1ccc2nc(-c3cccnc3)nc(Nc3ccc4c(c3)NC(=O)CC4)c2c1] | 397 | 398 | Method Z |
| 953 | 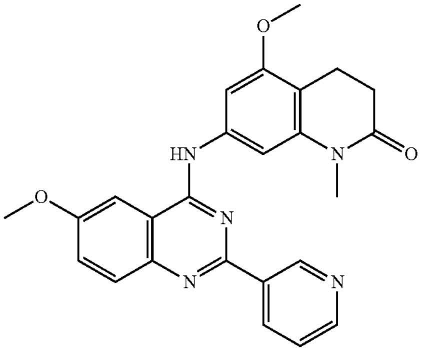 [SMILES: COc1ccc2nc(-c3cccnc3)nc(Nc3cc(OC)c4c(c3)N(C)C(=O)CC4)c2c1] | 441 | 442 | Method Z |
| 954 | 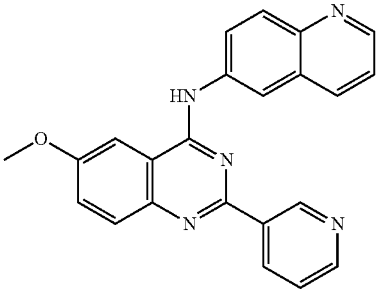 [SMILES: COc1ccc2nc(-c3cccnc3)nc(Nc3ccc4ncccc4c3)c2c1] | 379 | 380 | Method Z |
| 955 | 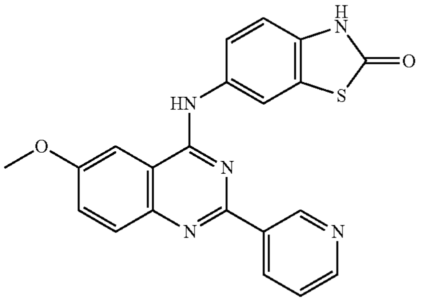 [SMILES: COc1ccc2nc(-c3cccnc3)nc(Nc3ccc4[nH]c(=O)sc4c3)c2c1] | 401 | 402 | Method Z |

TABLE 8-continued
| Number | Product | Exact Mass | LCMS (M + 1) | Method of Coupling |
|---|---|---|---|---|
| 956 | 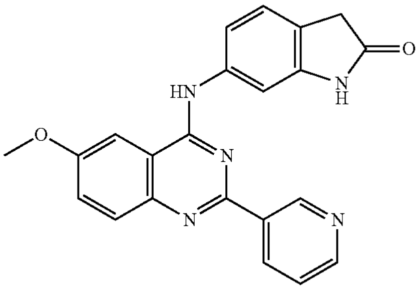 [SMILES: COc1ccc2nc(-c3cccnc3)nc(Nc3ccc4c(c3)NC(=O)C4)c2c1] | 383 | 384 | Method Z |
| 957 | 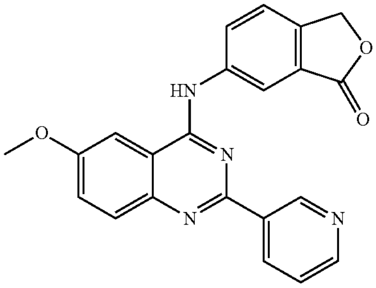 [SMILES: COc1ccc2nc(-c3cccnc3)nc(Nc3ccc4c(c3)C(=O)OC4)c2c1] | 382 | 383 | Method Z |
| 958 | 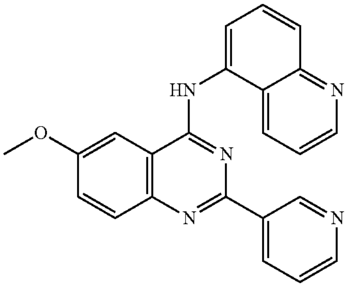 [SMILES: COc1ccc2nc(-c3cccnc3)nc(Nc3cccc4ncccc34)c2c1] | 379 | 380 | Method Z |
| 959 | 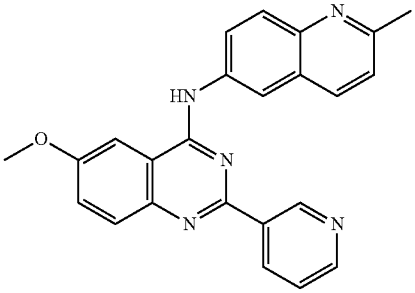 | 393 | 394 | Method Z |
| 960 | 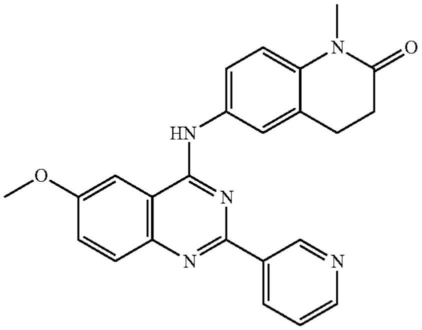 [SMILES: COc1ccc2nc(-c3cccnc3)nc(Nc3ccc4c(c3)CCC(=O)N4C)c2c1] | 411 | 412 | Method Z |

TABLE 8-continued
| Number | Product | Exact Mass | LCMS (M + 1) | Method of Coupling |
|---|---|---|---|---|
| 961 | 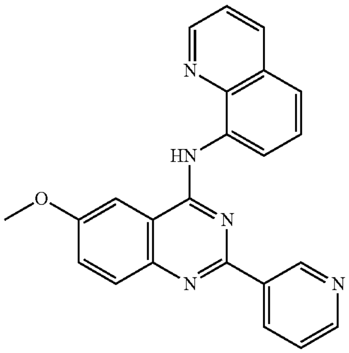 [SMILES: COc1ccc2nc(-c3cccnc3)nc(Nc3cccc4cccnc34)c2c1] | 379 | 380 | Method Z |
| 962 | 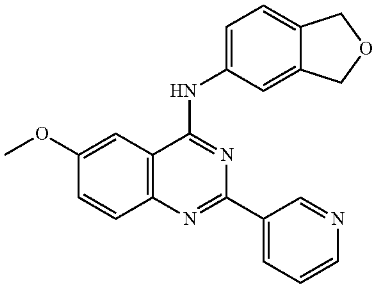 [SMILES: COc1ccc2nc(-c3cccnc3)nc(Nc3ccc4c(c3)COC4)c2c1] | 370 | 371 | Method Z |
| 963 | 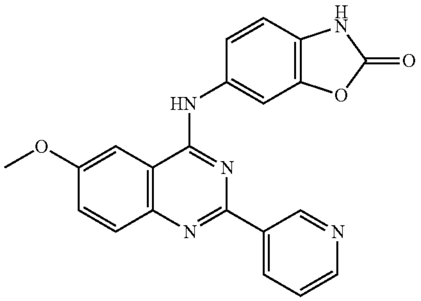 [SMILES: COc1ccc2nc(-c3cccnc3)nc(Nc3ccc4[nH]c(=O)oc4c3)c2c1] | 385 | 386 | Method Z |
| 964 | 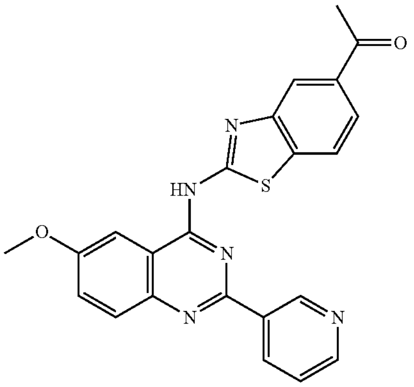 [SMILES: COc1ccc2nc(-c3cccnc3)nc(Nc3nc4cc(C(C)=O)ccc4s3)c2c1] | 427 | 428 | Method Z |

TABLE 8-continued
| Number | Product | Exact Mass | LCMS (M + 1) | Method of Coupling |
|---|---|---|---|---|
| 965 | 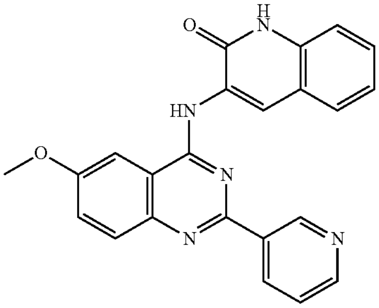 [SMILES: COc1ccc2nc(-c3cccnc3)nc(Nc3cc4ccccc4[nH]c3=O)c2c1] | 395 | 396 | Method Z |
| 966 | 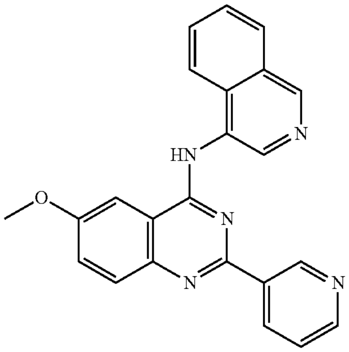 [SMILES: COc1ccc2nc(-c3cccnc3)nc(Nc3cncc4ccccc34)c2c1] | 379 | 380 | Method Z |
| 967 | 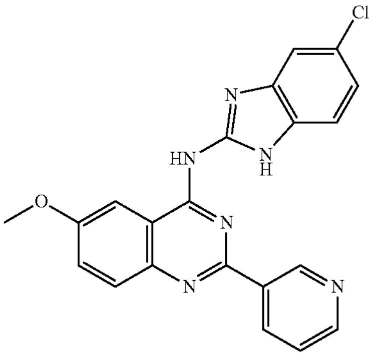 [SMILES: COc1ccc2nc(-c3cccnc3)nc(Nc3nc4cc(Cl)ccc4[nH]3)c2c1] | 402 | 403 | Method Z |
| 968 | 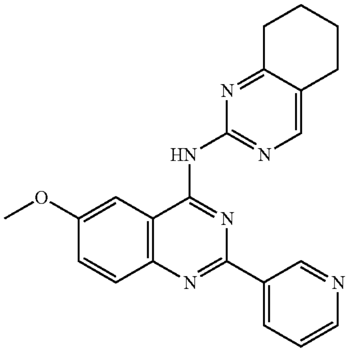 [SMILES: COc1ccc2nc(-c3cccnc3)nc(Nc3ncc4c(n3)CCCC4)c2c1] | 384 | 385 | Method Z |

Scheme 31: General route for the synthesis of compounds with general formula vi

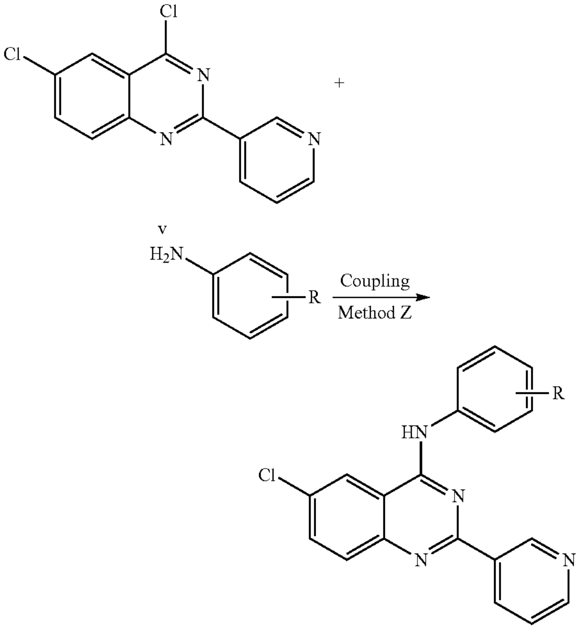

v vi

Scheme 32: Representative synthesis of compounds of formula vi (see Scheme 31)

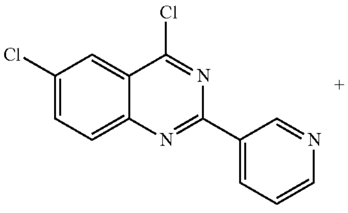

v-c

-continued

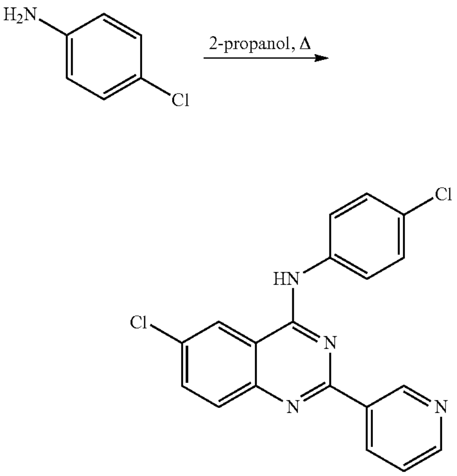

vi-h

Method Z: Synthesis of 6-chloro-N-(4-chlorophenyl)-2-(pyridin-3-yl)quinazolin-4-amine (vi-c)

To 4-chloroaniline (24 μmol) was added the solution of 4,6-dichloro-2-(pyridin-3-yl)quinazoline (20 μmol) in 2-propanol (200 μL). The mixture was refluxed for 8 h. After evaporation, the residue was dissolved in 5% TFA/MeOH-DMF (1:1) and purified by PREP-HPLC Condition D. The target fraction was lyophilized to afford the titled compound as the TFA salt whose structure was finally confirmed by LCMS using LCMS Method E.

The compounds in the following table were prepared in a manner analogous to that described in Scheme 31, replacing 4-chloroaniline with the appropriate aniline,

TABLE 9

| Number | Product | Exact Mass | LCMS (M + 1) | Method of Coupling |
|---|---|---|---|---|
| 969 | 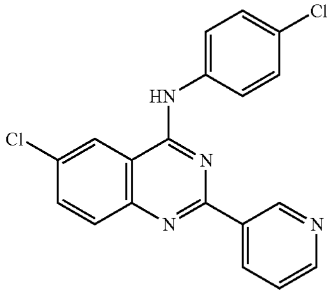 [SMILES: Clc1ccc(Nc2nc(-c3cccnc3)nc3ccc(Cl)cc23)cc1] | 366 | 367 | Method Z |

TABLE 9-continued
| Number | Product | Exact Mass | LCMS (M + 1) | Method of Coupling |
|---|---|---|---|---|
| 970 | 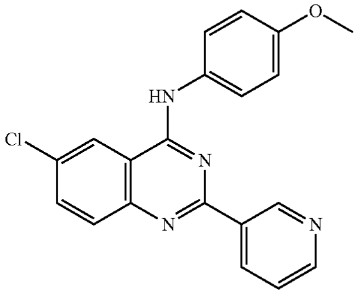 [SMILES: COc1ccc(Nc2nc(-c3cccnc3)nc3ccc(Cl)cc23)cc1] | 362 | 363 | Method Z |
| 971 | 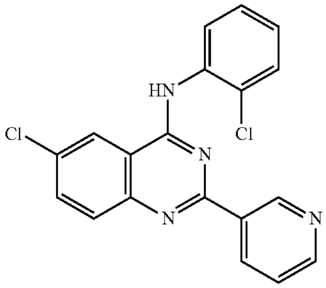 [SMILES: Clc1ccc2nc(-c3cccnc3)nc(Nc3ccccc3Cl)c2c1] | 366 | 367 | Method Z |
| 972 | 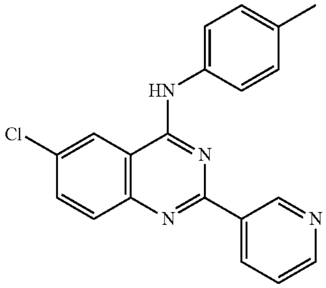 [SMILES: Cc1ccc(Nc2nc(-c3cccnc3)nc3ccc(Cl)cc23)cc1] | 346 | 347 | Method Z |
| 973 | 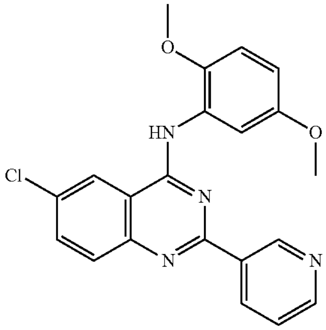 [SMILES: COc1ccc(OC)c(Nc2nc(-c3cccnc3)nc3ccc(Cl)cc23)c1] | 392 | 393 | Method Z |
| 974 | 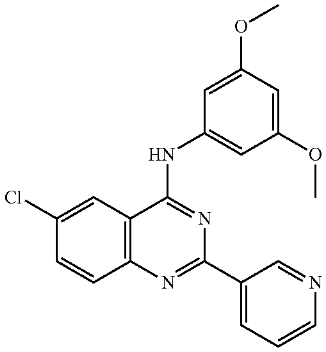 [SMILES: COc1cc(Nc2nc(-c3cccnc3)nc3ccc(Cl)cc23)cc(OC)c1] | 392 | 393 | Method Z |

TABLE 9-continued
| Number | Product | Exact Mass | LCMS (M + 1) | Method of Coupling |
|---|---|---|---|---|
| 975 | 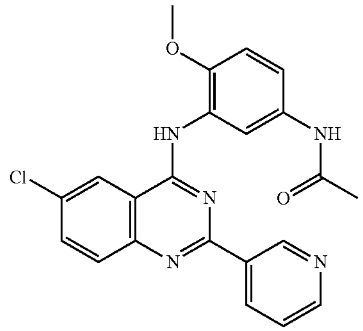 [SMILES: COc1ccc(NC(C)=O)cc1Nc1nc(-c2cccnc2)nc2ccc(Cl)cc12] | 419 | 420 | Method Z |
| 976 | 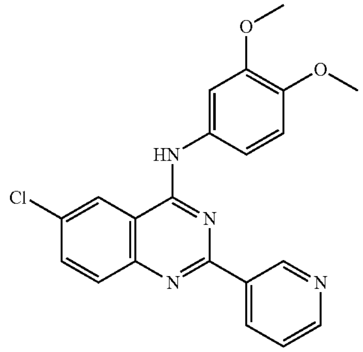 [SMILES: COc1ccc(Nc2nc(-c3cccnc3)nc3ccc(Cl)cc23)cc1OC] | 392 | 393 | Method Z |
| 977 | 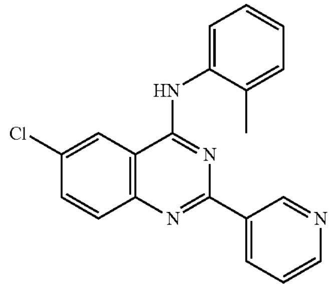 [SMILES: Cc1ccccc1Nc1nc(-c2cccnc2)nc2ccc(Cl)cc12] | 346 | 347 | Method Z |
| 978 | 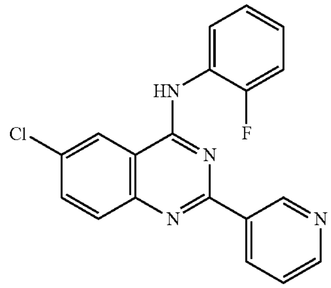 | 350 | 351 | Method Z |
| 979 | 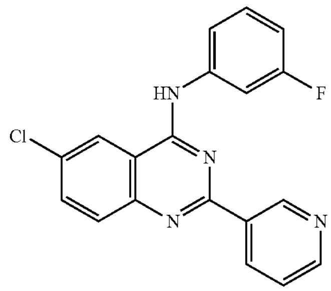 [SMILES: Fc1cccc(Nc2nc(-c3cccnc3)nc3ccc(Cl)cc23)c1] | 350 | 351 | Method Z |

TABLE 9-continued
| Number | Product | Exact Mass | LCMS (M + 1) | Method of Coupling |
|---|---|---|---|---|
| 980 | 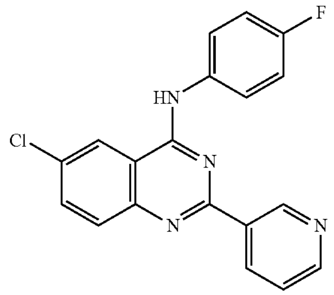 [SMILES: Fc1ccc(Nc2nc(-c3cccnc3)nc3ccc(Cl)cc23)cc1] | 350 | 351 | Method Z |
| 981 | 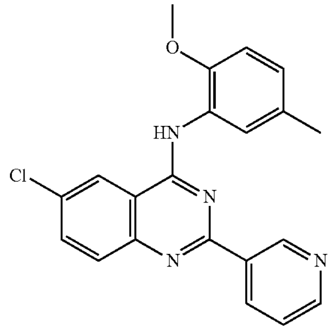 [SMILES: COc1ccc(C)cc1Nc1nc(-c2cccnc2)nc2ccc(Cl)cc12] | 376 | 377 | Method Z |
| 982 | 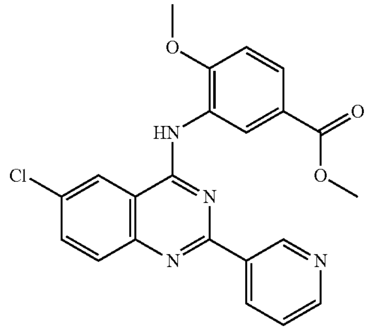 [SMILES: COC(=O)c1ccc(OC)c(Nc2nc(-c3cccnc3)nc3ccc(Cl)cc23)c1] | 420 | 421 | Method Z |
| 983 | 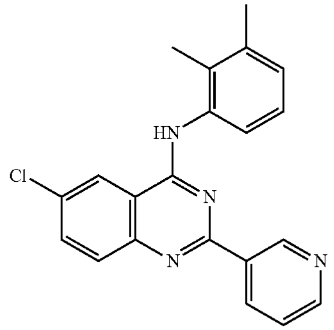 [SMILES: Cc1cccc(Nc2nc(-c3cccnc3)nc3ccc(Cl)cc23)c1C] | 360 | 361 | Method Z |

TABLE 9-continued
| Number | Product | Exact Mass | LCMS (M + 1) | Method of Coupling |
|---|---|---|---|---|
| 984 | 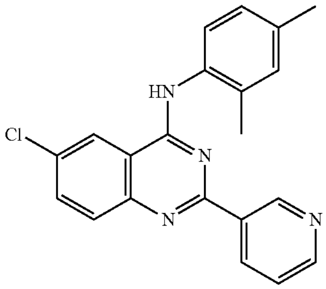 [SMILES: Cc1ccc(Nc2nc(-c3cccnc3)nc3ccc(Cl)cc23)c(C)c1] | 360 | 361 | Method Z |
| 985 | 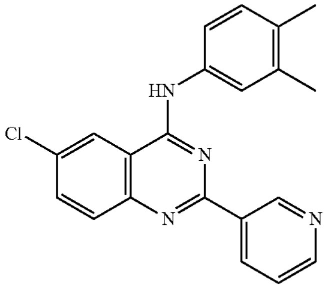 [SMILES: Cc1ccc(Nc2nc(-c3cccnc3)nc3ccc(Cl)cc23)cc1C] | 360 | 361 | Method Z |
| 986 | 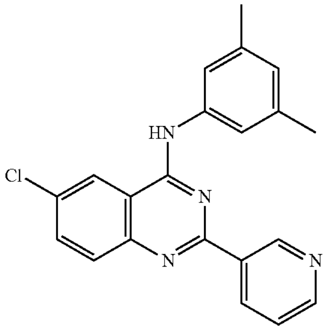 [SMILES: Cc1cc(C)cc(Nc2nc(-c3cccnc3)nc3ccc(Cl)cc23)c1] | 360 | 361 | Method Z |
| 987 | 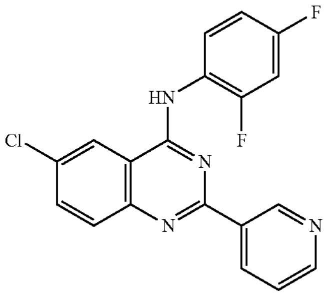 [SMILES: Fc1ccc(Nc2nc(-c3cccnc3)nc3ccc(Cl)cc23)c(F)c1] | 368 | 369 | Method Z |
| 988 | 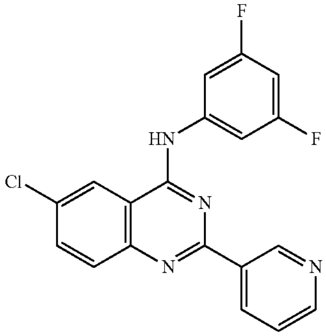 [SMILES: Fc1cc(F)cc(Nc2nc(-c3cccnc3)nc3ccc(Cl)cc23)c1] | 368 | 369 | Method Z |

TABLE 9-continued
| Number | Product | Exact Mass | LCMS (M + 1) | Method of Coupling |
|---|---|---|---|---|
| 989 | 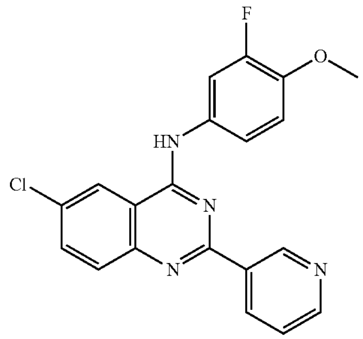 [SMILES: COc1ccc(Nc2nc(-c3cccnc3)nc3ccc(Cl)cc23)cc1F] | 380 | 381 | Method Z |
| 990 | 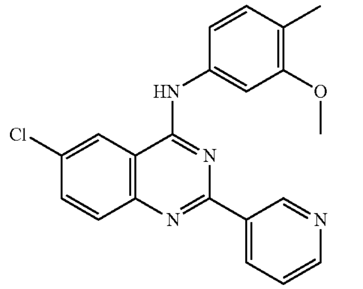 [SMILES: COc1cc(Nc2nc(-c3cccnc3)nc3ccc(Cl)cc23)ccc1C] | 376 | 377 | Method Z |
| 991 | 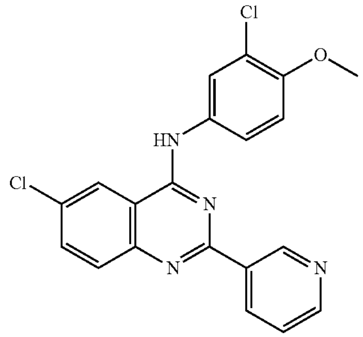 [SMILES: COc1ccc(Nc2nc(-c3cccnc3)nc3ccc(Cl)cc23)cc1Cl] | 396 | 397 | Method Z |
| 992 | 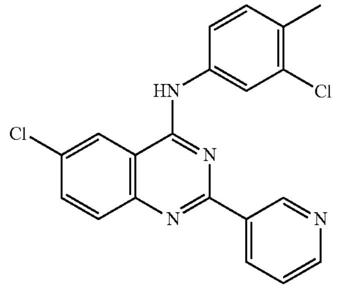 [SMILES: Cc1ccc(Nc2nc(-c3cccnc3)nc3ccc(Cl)cc23)cc1Cl] | 380 | 381 | Method Z |

TABLE 9-continued
| Number | Product | Exact Mass | LCMS (M + 1) | Method of Coupling |
|---|---|---|---|---|
| 993 | 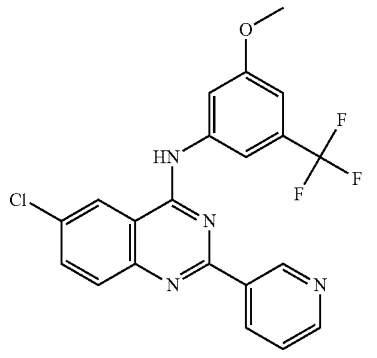 [SMILES: COc1cc(Nc2nc(-c3cccnc3)nc3ccc(Cl)cc23)cc(C(F)(F)F)c1] | 430 | 431 | Method Z |
| 994 | 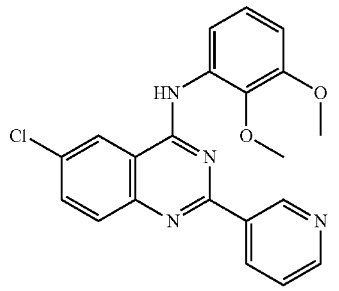 [SMILES: COc1cccc(Nc2nc(-c3cccnc3)nc3ccc(Cl)cc23)c1OC] | 392 | 393 | Method Z |
| 995 | 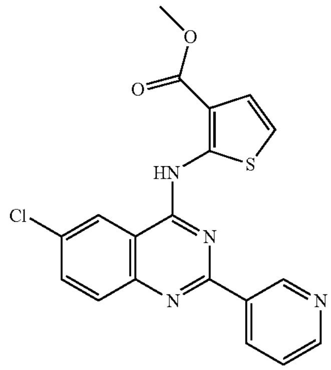 [SMILES: COC(=O)c1ccsc1Nc1nc(-c2cccnc2)nc2ccc(Cl)cc12] | 396 | 397 | Method Z |
| 996 | 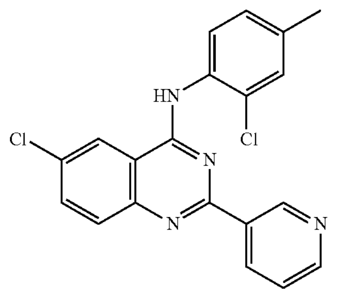 [SMILES: Cc1ccc(Nc2nc(-c3cccnc3)nc3ccc(Cl)cc23)c(Cl)c1] | 380 | 381 | Method Z |

TABLE 9-continued
| Number | Product | Exact Mass | LCMS (M + 1) | Method of Coupling |
| --- | --- | --- | --- | --- |
| 997 | 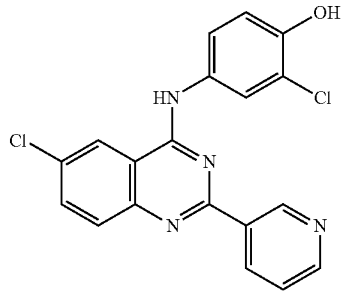 [SMILES: Oc1ccc(Nc2nc(-c3cccnc3)nc3ccc(Cl)cc23)cc1Cl] | 382 | 383 | Method Z |
| 998 | 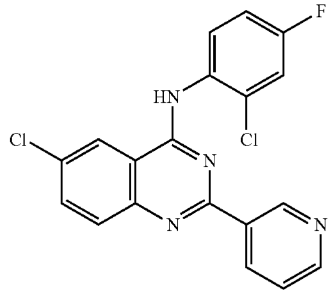 [SMILES: Fc1ccc(Nc2nc(-c3cccnc3)nc3ccc(Cl)cc23)c(Cl)c1] | 384 | 385 | Method Z |
| 999 | 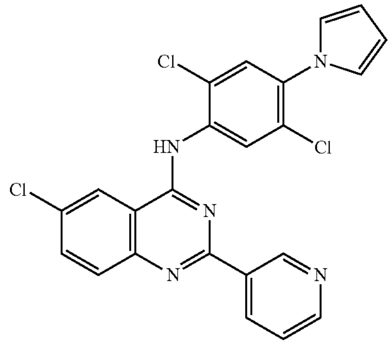 [SMILES: Clc1ccc2nc(-c3cccnc3)nc(Nc3cc(Cl)c(-n4cccc4)cc3Cl)c2c1] | 465 | 466 | Method Z |
| 1000 | 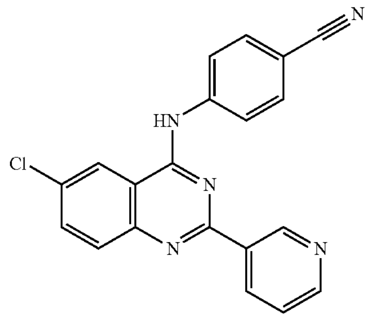 [SMILES: N#Cc1ccc(Nc2nc(-c3cccnc3)nc3ccc(Cl)cc23)cc1] | 357 | 358 | Method Z |
| 1001 | 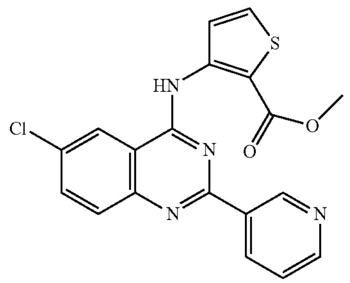 [SMILES: COC(=O)c1sccc1Nc1nc(-c2cccnc2)nc2ccc(Cl)cc12] | 396 | 397 | Method Z |

TABLE 9-continued
| Number | Product | Exact Mass | LCMS (M + 1) | Method of Coupling |
|---|---|---|---|---|
| 1002 | 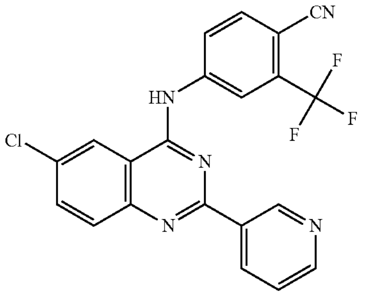 [SMILES: N#Cc1ccc(Nc2nc(-c3cccnc3)nc3ccc(Cl)cc23)cc1C(F)(F)F] | 425 | 426 | Method Z |
| 1003 | 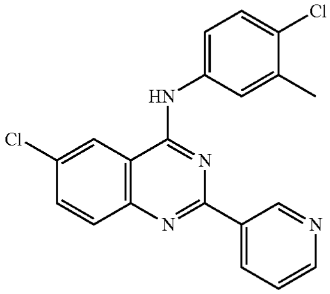 [SMILES: Cc1cc(Nc2nc(-c3cccnc3)nc3ccc(Cl)cc23)ccc1Cl] | 380 | 381 | Method Z |
| 1004 | 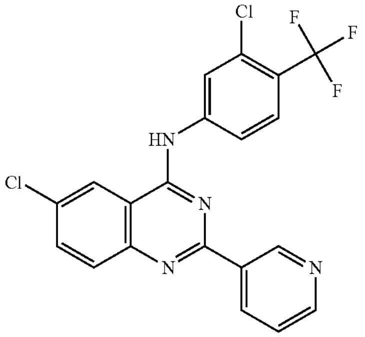 [SMILES: FC(F)(F)c1ccc(Nc2nc(-c3cccnc3)nc3ccc(Cl)cc23)cc1Cl] | 434 | 435 | Method Z |
| 1005 | 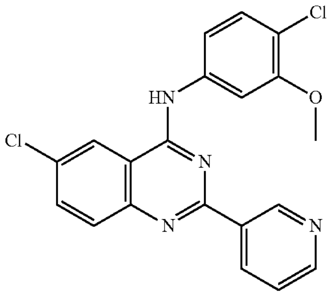 [SMILES: COc1cc(Nc2nc(-c3cccnc3)nc3ccc(Cl)cc23)ccc1Cl] | 396 | 397 | Method Z |
| 1006 | 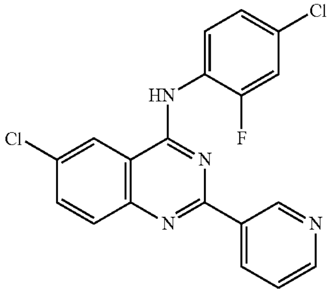 [SMILES: Fc1cc(Cl)ccc1Nc1nc(-c2cccnc2)nc2ccc(Cl)cc12] | 384 | 385 | Method Z |

TABLE 9-continued
| Number | Product | Exact Mass | LCMS (M + 1) | Method of Coupling |
|---|---|---|---|---|
| 1007 | 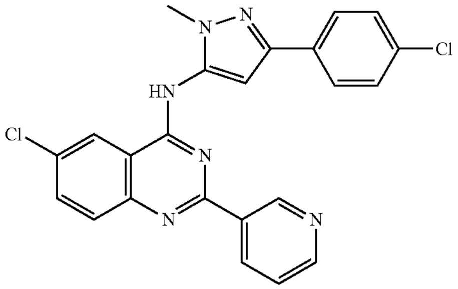 [SMILES: Cn1nc(-c2ccc(Cl)cc2)cc1Nc1nc(-c2cccnc2)nc2ccc(Cl)cc12] | 446 | 447 | Method Z |
| 1008 | 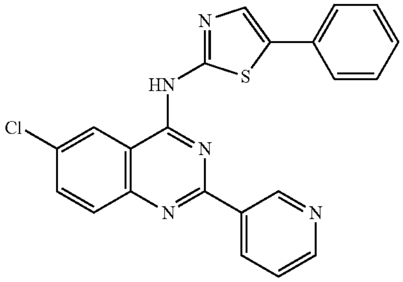 [SMILES: Clc1ccc2nc(-c3cccnc3)nc(Nc3ncc(-c4ccccc4)s3)c2c1] | 415 | 416 | Method Z |
| 1009 | 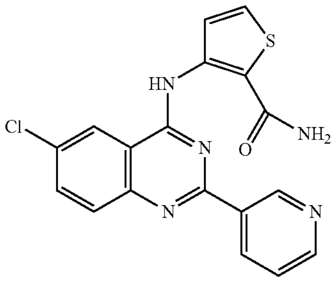 [SMILES: NC(=O)c1sccc1Nc1nc(-c2cccnc2)nc2ccc(Cl)cc12] | 381 | 382 | Method Z |
| 1010 | 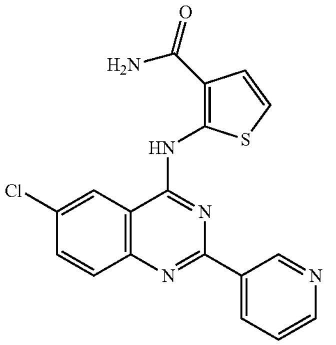 [SMILES: NC(=O)c1ccsc1Nc1nc(-c2cccnc2)nc2ccc(Cl)cc12] | 381 | 382 | Method Z |
| 1011 | 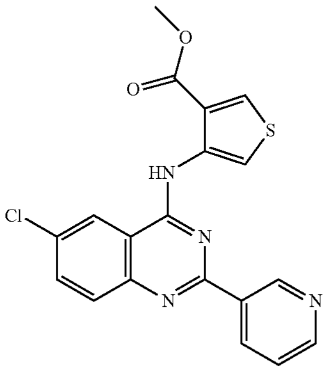 [SMILES: COC(=O)c1cscc1Nc1nc(-c2cccnc2)nc2ccc(Cl)cc12] | 396 | 397 | Method Z |

Scheme 33: Representative synthesis of thiophene analogs of formula vi (see Scheme 4)

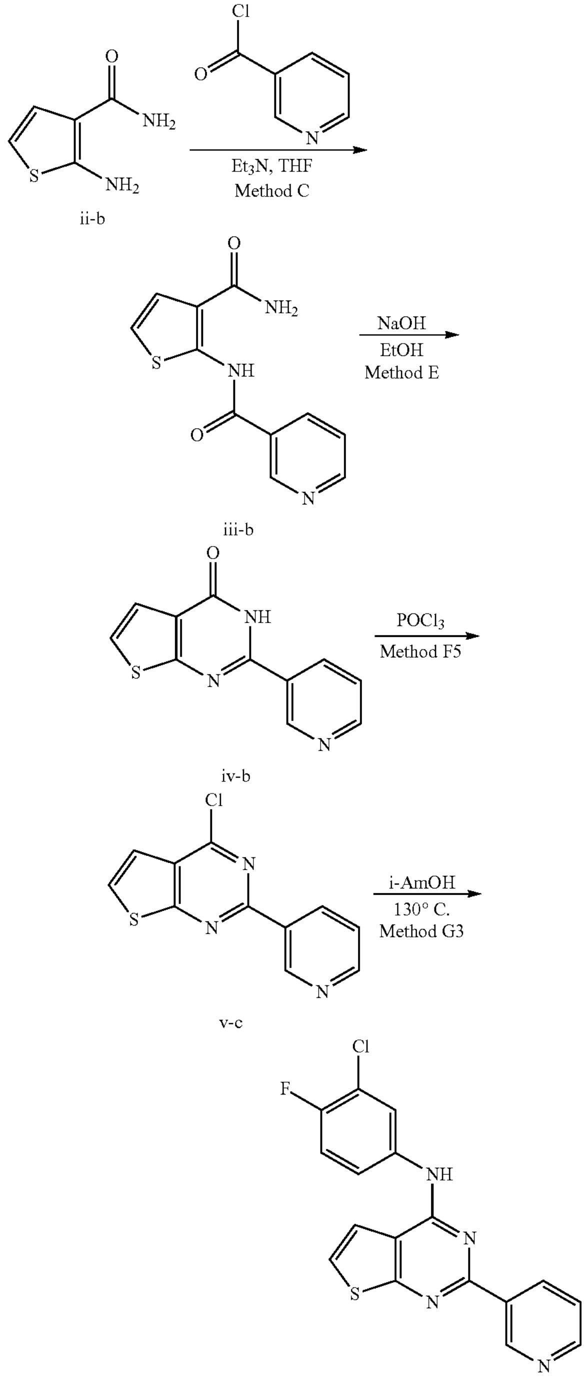

ii-b, iii-b, iv-b, v-c, vi-I

N-(3-Carbamoylthiophen-2-yl)nicotinamide (iii-b)

To a solution of 2-aminothiophene-3-carboxamide (800 mg, 5.63 mmol, 1.0 eq.) in THF (15 mL) and $Et_3N$ (626 mg, 6.19 mmol, 1.1 eq.) was added nicotinoyl chloride (795 mg, 5.63 mmol, 1.0 eq.) in anhydrous THF (15 mL) dropwise. The resulted mixture was stirred at room temperature overnight. After the reaction was completed, the volatiles were evaporated. The residue was washed with $CH_2Cl_2$ (20 mL). The resulting solid was collected and dried in vacuo to give 1.50 g of N-(3-carbamoylthiophen-2-yl)nicotinamide as a brown solid (quantitative yield). LCMS m/z=248.1 (M+1) (Method B) (retention time=1.34 min).

2-(Pyridin-3-yl)thieno[2,3-d]pyrimidin-4(3H)-one (iv-b)

A mixture of N-(3-carbamoylthiophen-2-yl)nicotinamide (1.50 g salt, 6.07 mmol, 1.0 eq.) in EtOH (300 mL) was added NaOH (1.50 g, 37.5 mmol, 6.18 eq.). The resulting mixture was stirred at 80° C. for 7 days. After the reaction was completed, the volatiles were removed in vacuo. Water (20 mL) was added to the residue and the pH1 was adjusted to around 2 by adding dilute HCl (2N in water). The solution was concentrated in vacuo to give 11.0 g of the HCl salt as a beige solid. LCMS m/z=230.0 (M+1) (Method B) (retention time=1.21 min). The crude product containing salts were used for the next step without further purification.

4-Chloro-2-(pyridin-3-yl)thieno[2,3-d]pyrimidine (v-c)

The suspension of 2-(pyridin-3-yl)thieno[2,3-d]pyrimidin-4(3H)-one (6.0 g, containing salts) in $POCl_3$ (30 ml.) was stirred at 120° C. for 10 h. After the reaction was completed, the mixture was added to ice-water slowly. The pH was adjusted to ~7 by slowly adding $NH_3.H_2O$ at 0° C., then a precipitate formed. The solid was collected and 540 mg of 4-chloro-2-(pyridin-3-yl)thieno[2,3-d]pyrimidine was obtained as a brown solid, LCMS m/z=247.9, 250.0 (M+1) (Method B) (retention time=1.85 min).

N-(3-Chloro-4-fluorophenyl)-2-(pyridin-3-yl)thieno[2,3-d]pyrimidin-4-amine (vi-l)

A mixture of 4-chloro-2-(pyridin-3-yl)thieno[2,3-d]pyrimidine (80 mg, 0.32 mmol, 1.0 eq.) and 3-chloro-4-fluorobenzenamine (93 mg, 0.64 mmol, 2.0 eq.) in i-AmOH (8 mL) was stirred at 130° C. overnight. A yellow precipitate formed and was collected and washed with MeOH (10 mL). The solid was suspended in $H_2O$ (10 mL) and $NH_3$—$H_2O$ (1 mL) was added. After filtration and drying in vacuo, 23.0 mg of the product was obtained as a yellow solid (20.0%). LCMS m/z=357.0, 359.0 (M+1) (Method B) (retention time=1.96 min). $^1$H-NMR (400 MHz, DMSO-d$_6$): δ 9.99 (s, 1H), 9.48 (d, J=1.6 Hz, 1H), 8.70-8.67 (m, 1H), 8.63 (d, J=8.0 Hz, 1H), 8.27 (dd, J=6.8, 2.6 Hz, 1H), 7.76-7.93 (m, 3H), 7.54-7.57 (m, 2H).

The compounds in the following table were prepared in a manner analogous to that described in Scheme 33, replacing 4-fluoro-3-chloroaniline with the appropriate aniline.

TABLE 10

| Number | PRODUCT | Salt type | Molecular Mass | $^1$H-NMR | $^1$H-NMR Solvent | LCMS | LCMS Protocol | Purity percent | Method for Coupling |
|---|---|---|---|---|---|---|---|---|---|
| 1012 | 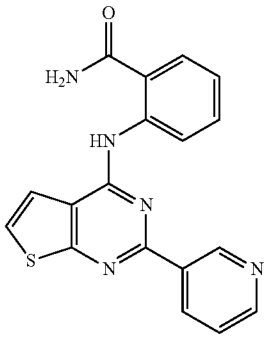 [SMILES: NC(=O)c1ccccc1Nc1nc(-c2cccnc2)nc2sccc12] | | 347.39 | 1H-NMR (400 MHz, DMSO-d6): δ 12.69 (s, 1H), 9.55 (d, J = 1.3 Hz, 1H), 9.00 (d, J = 8.0 Hz, 1H), 8.44 (s, 1H), 8.60-8.78 (m, 2H), 7.82-8.00 (m, 3H), 7.42-7.79 (m, 3H), 7.20 (t, J = 7.2 Hz, 1H). | DMSO | 348.1 (M + 1) | Method B (NH4HCO3) | 95 | Method C, G3 |
| 1013 | 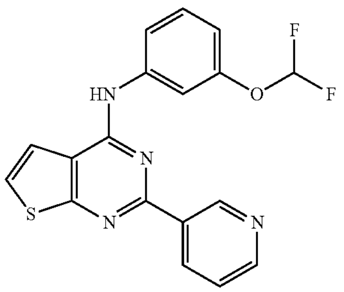 [SMILES: FC(F)Oc1cccc(Nc2nc(-c3cccnc3)nc3sccc23)c1] | | 370.38 | 1H-NMR (400 MHz, DMSO-d6): δ 9.96 (s, 1H), 9.51 (d, J = 1.2 Hz, 1H), 8.60-8.77 (m, 2H), 7.98-7.94 (m, 2H), 7.71-7.86 (m, 2H), 7.56-7.50 (m, 1H), 7.30 (t, J = 74.0 Hz, 1H), 6.96 (dd, J = 8.8, 2.0 Hz, 1H), | DMSO | 371.0 (M + 1) | Method B (NH4HCO3) | 95 | Method C, G3 |
| 1014 | 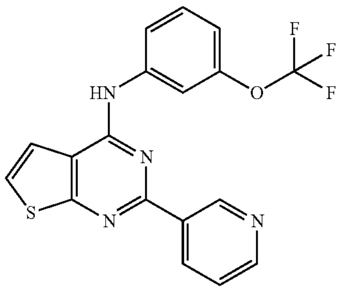 [SMILES: FC(F)(F)Oc1cccc(Nc2nc(-c3cccnc3)nc3sccc23)c1] | | 388.37 | 1H-NMR (400 MHz, DMSO-d6): δ 10.04 (s, 1H), 9.50 (d, J = 1.6 Hz, 1H), 8.58-8.75 (m, 2H), 8.18 (s, 1H), 7.77-8.00 (m, 3H), 7.50-7.65 (m, 2H), 7.08-7.18 (m, 1H) | DMSO | 389.0 (M + 1) | Method B (NH4HCO3) | 95 | Method C, G3 |
| 1015 | 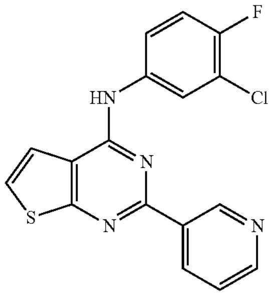 [SMILES: Fc1ccc(Nc2nc(-c3cccnc3)nc3sccc23)cc1Cl] | | 356.8 | 1H-NMR (400 MHz, DMSO-d6): δ 9.99 (s, 1H), 9.48 (d, J = 1.6 Hz, 1H), 8.70-8.67 (m, 1H), 8.63 (d, J = 8.0 Hz, 1H), 8.27 (dd, J = 6.8, 2.6 Hz, 1H), 7.76-7.93 (m, 3H), 7.54-7.57 (m, 2H). | DMSO | 357.0, 359.0 (M + 1) | Method B (NH4HCO3) | 95 | Method C, G3 |

Scheme 34: General route for the synthesis of compounds with general formula xiv

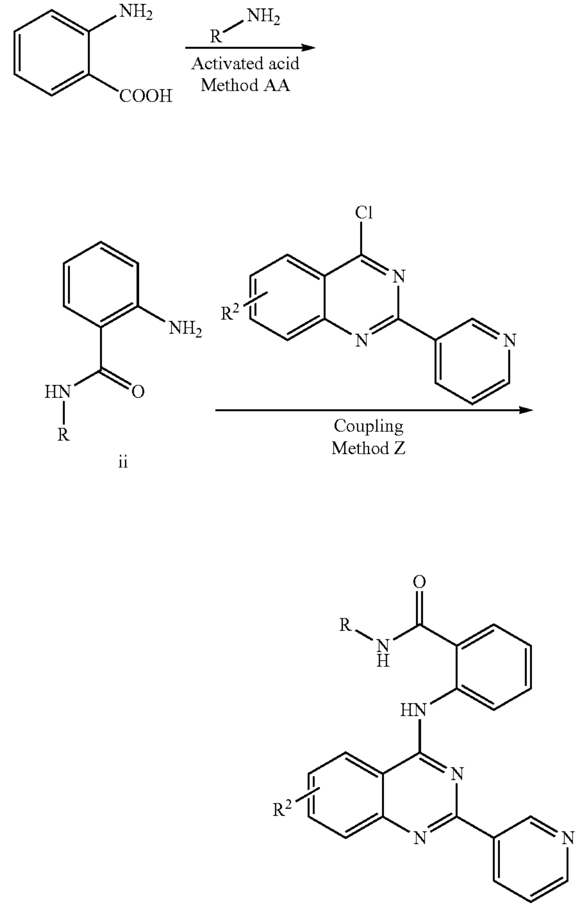

ii xiv

Scheme 35: Representative synthesis of compounds of formula xiv-g (see Scheme 34)

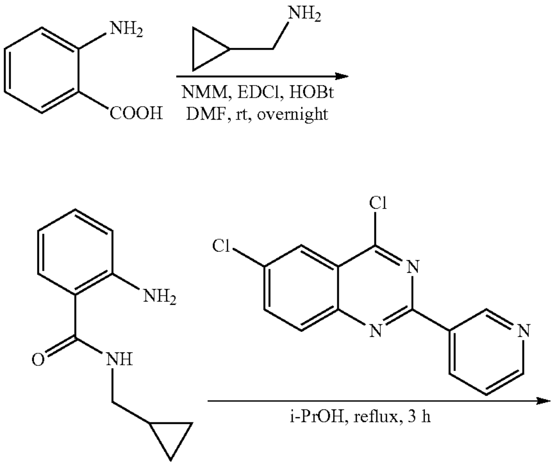

ii-c

-continued

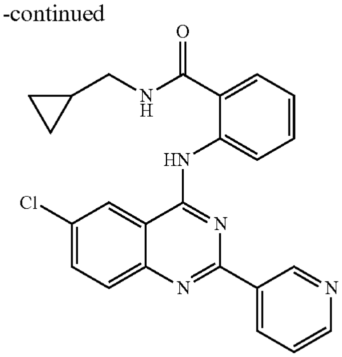

xiv-g

Method AA: 2-Amino-N-(cyclopropylmethyl)benzamide (ii-c)

A 100 ml, round bottom flask was charged with anthranilic acid (500 mg, 3.65 mmol), added DMF (15 mL) under nitrogen atmosphere and stirring. Then, added N-methylmorpholine (1 mL, 9.12 mmol), aminomethylcyclopropane (311 mg, 4.38 mmol), N-ethyl-N'-dimethylaminopropylcarbodiimide (EDCI) (840 mg, 4.38 mmol) and HOBt (670 mg, 4.38 mmol). The reaction mixture was stirred at room temperature overnight. The reaction mixture was quenched with water and extracted with diethyl ether (50 mL×2). The organic extracts were combined, washed with brine, dried over $MgSO_4$, filtered and concentrated to afford amorphous colorless 2-amino-N-(cyclopropylmethyl)benzamide (500 mg, 72% yield), which was checked by NMR and used for next step without further purification. $^1$H-NMR (Bruker 300 MHz, DMSO-$d_6$) δ 0.20-1.01 (m, 4H), 1.01-1.04 (m, 1H), 3.06-3.11 (m, 2H), 6.37-8.21 (m, 7H).

Method Z: 2-(6-chloro-2-(pyridin-3-yl)quinazolin-4-ylamino)-N-(cyclopropylmethyl)benzamide (xiv-g)

A 100 mL round bottom flask was charged with 4,6-dichloro-2-(pyridin-3-yl)quinazoline (synthesized as described in Scheme 1 and 4, substituting 5-chloro-2-nitrobenzoic acid for 2-nitro-5-propoxy-benzoic acid) (150 mg, 0.54 mmol) and 2-amino-N-(cyclopropylmethyl)benzamide) (310 mg, 1.63 mmol) and anhydrous i-PrOH (20 mL) was added and refluxed for 3 h. The reaction mixture was cooled to room temperature and $Et_3N$ (3 eq) was added. The solvent was removed in vacuo. To the crude product was added a water-methanol mixture (5:1, 50 mL), and then sonicated for 5 min. The solidified compound was collected by filtration, and the solid was recrystallized from hot methanol and washed with water. The product was dried at 50° C. to give 2-(6-chloro-2-(pyridin-3-yl)quinazolin-4-ylamino)-N-(cyclopropylmethyl)benzamide as a colorless cotton (220 mg, 94%). The structure was confirmed by NMR and elemental analysis. $^1$H NMR (Bruker 300 MHz, DMSO-$d_6$) ppm 0.20-0.98 (m, 5H), 3.07-3.21 (m, 2H), 7.24-8.26 (m, 7H), 8.68-9.55 (m, 5H), 12.22 (s, 1H). CHN Calcd. C, 67.05; H, 4.69; N, 16.29. Found C, 67.15; H, 4.89; N, 16.25

The compounds in the following table were prepared in a manner analogous to that described in Scheme 34, replacing aminomethylcyclopropane with the appropriate amine.

TABLE 11
| Number | Product | $^1$H-NMR | $^1$H-NMR Solvent | Purity percent | Method of Coupling |
|---|---|---|---|---|---|
| 1016 | 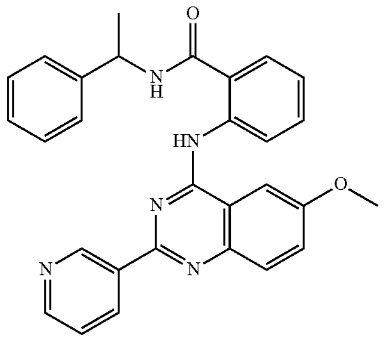 [SMILES: COc1ccc2nc(-c3cccnc3)nc(Nc3ccccc3C(=O)NC(C)c3ccccc3)c2c1] | $^1$H NMR (DMSO-$d_6$) ppm 1.46 (d, 3H, J = 6.7 Hz), 3.90 (s, 3H), 5.17-5.22 (m, 1H), 7.19-7.98 (m, 12H), 8.67-8.71 (m, 2H), 8.90 (d, 1H, J = 8.2 Hz), 9.22 (d, 1H, J = 8.3 Hz), 9.55 (s, 1H), 12.18 (s, 1H). | DMSO | >93 | Method Z |
| 1017 | 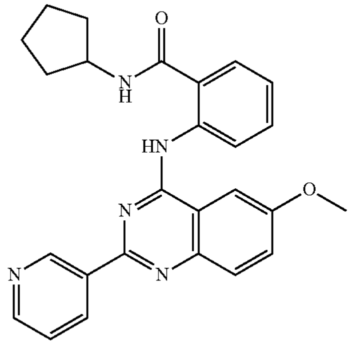 [SMILES: COc1ccc2nc(-c3cccnc3)nc(Nc3ccccc3C(=O)NC3CCCC3)c2c1] | $^1$H NMR (DMSO-$d_6$) ppm 1.49-1.62 (m, 8H), 3.99 (s, 3H), 4.24-4.26 (m, 1H), 7.24-7.71 (m, 7H), 8.65-9.55 (m, 5H), 12.19 (s, 1H). | DMSO | >98 | Method Z |

TABLE 11-continued
| | | | | | |
|---|---|---|---|---|---|
| 1018 | 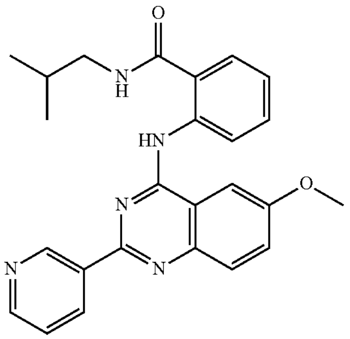 [SMILES: COc1ccc2nc(-c3cccnc3)nc(Nc3ccccc3C(=O)NCC(C)C)c2c1] | $^1H$ NMR (DMSO-$d_6$) ppm 0.88-1.99 (m, 7H), 3.14-3.16 (m, 2H), 3.02 (s, 3H), 7.57-7.91 (m, 7H), 8.68-9.55 (m, 5H), 12.19 (s, 1H). | DMSO | >98 | Method Z |
| 1019 | 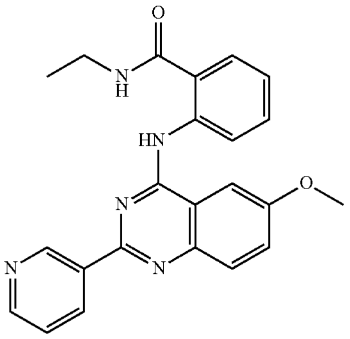 [SMILES: CCNC(=O)c1ccccc1Nc1nc(-c2cccnc2)nc2ccc(OC)cc12] | $^1H$ NMR (DMSO-$d_6$) ppm 1.07-1.12 (m, 3H), 3.44-3.52 (m, 2H), 4.01 (s, 3H), 7.24-786 (m, 8H), 8.68-9.55 (m, 5H), 12.19 (s, 1H). | DMSO | >98 | Method Z |
| 1020 | 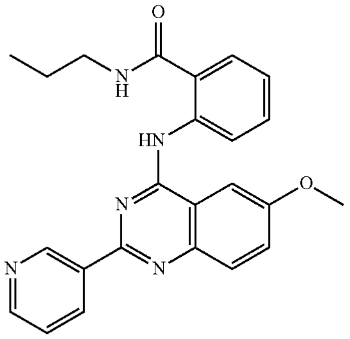 [SMILES: CCCNC(=O)c1ccccc1Nc1nc(-c2cccnc2)nc2ccc(OC)cc12] | 1H NMR (DMSO-$d_6$) ppm 0.87-0.92 (m, 3H), 1.53-1.62 (m, 2H, ), 3.30-3.32 (m, 2H), 3.98 (s, 3H), 7.21-7 89 (m 7H), 8.67-9.55 (m, 5H), 12.38 (s, 1H). | DMSO | >98 | Method Z |

TABLE 11-continued
| | | | | | |
|---|---|---|---|---|---|
| 1021 | 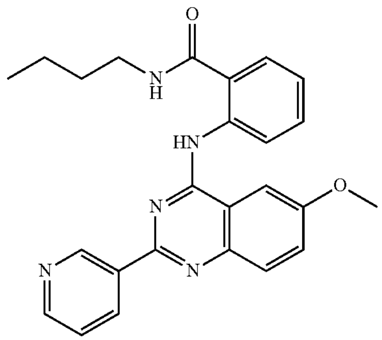 [SMILES: CCCCNC(=O)c1ccccc1Nc1nc(-c2cccnc2)nc2ccc(OC)cc12] | 1H NMR (DMSO-$d_6$) ppm 0.83-1.51 (m, 7H), 3.30-3.32 (m, 2H), 3.99 (s, 3H), 7.24-7.90 (m, 7H), 8.67-9.55 (m, 5H), 12.38 (s, 1H). | DMSO | >98 | Method Z |
| 1022 | 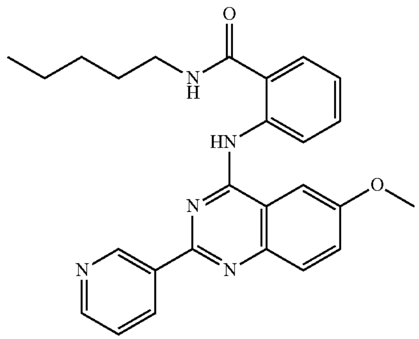 [SMILES: CCCCCNC(=O)c1ccccc1Nc1nc(-c2cccnc2)nc2ccc(OC)cc12] | 1H NMR (DMSO-$d_6$) ppm 0.79-1.52 (m, 9H), 3.25-3.30 (m, 2H), 3.98 (s, 3H), 7.21-7.88 (m, 7H), 8.68-9.55 (m, 5H), 12.30 (s, 1H). | DMSO | >98 | Method Z |
| 1023 | 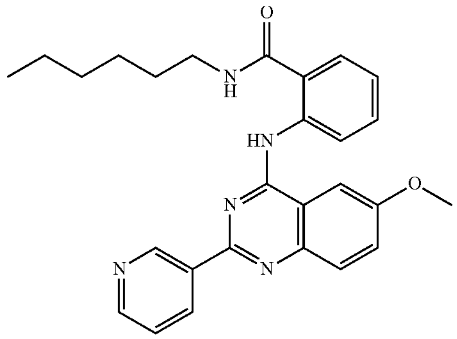 [SMILES: CCCCCCNC(=O)c1ccccc1Nc1nc(-c2cccnc2)nc2ccc(OC)cc12] | 1H NMR (DMSO-$d_6$) ppm 0.80-1.49 (m, 11H), 3.26-3.30 (m, 2H), 3.99 (s, 3H), 7.24-7.90 (m, 7H), 8.67-9.56 (m, 5H), 12.30 (s, 1H). | DMSO | >98 | Method Z |

TABLE 11-continued
| | | | | | |
|---|---|---|---|---|---|
| 1024 | 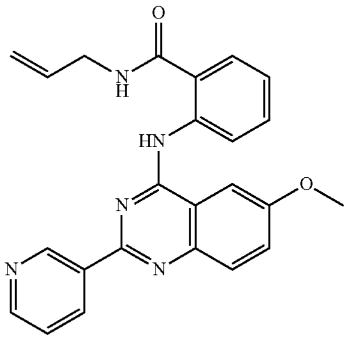 [SMILES: C=CCNC(=O)c1ccccc1Nc1nc(-c2cccnc2)nc2ccc(OC)cc12] | 1H NMR (DMSO-$d_6$) ppm 3.99-4.10 (m, 5H), 5.07-5.33 (m, 2H), 5.89-5.91(m, 1H), 7.24-7.90 (m, 7H), 8.68-9.55 (m, 5H), 12.30 (s, 1H). | DMSO | >98 | Method Z |
| 1025 | 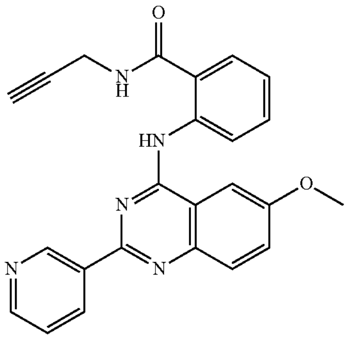 [SMILES: C#CCNC(=O)c1ccccc1Nc1nc(-c2cccnc2)nc2ccc(OC)cc12] | 1H NMR (DMSO-$d_6$) ppm 3.13 (s, 1H), 3.99-4.12 (m, 5H), 7.21-7.89 (m, 7H), 8.67-9.54 (m, 5H), 12.30 1H). | DMSO | >98 | Method Z |
| 1026 | 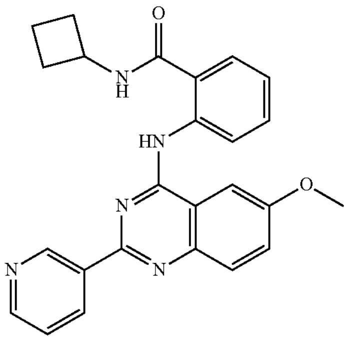 [SMILES: COc1ccc2nc(-c3cccnc3)nc(Nc3ccccc3C(=O)NC3CCC3)c2c1] | 1H NMR (DMSO-$d_6$) ppm 1.68-2.22 (m, 6H), 3.99 (s, 3H), 4.24-4.26 (m, 1H), 7.22-7.92 (m, 7H), 8.66-9.55 (m, 5H), 12.30 (s, 1H). | DMSO | >98 | Method Z |

TABLE 11-continued
| | | | | | |
|---|---|---|---|---|---|
| 1027 | 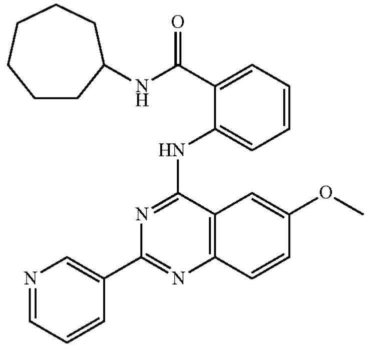 [SMILES: COc1ccc2nc(-c3cccnc3)nc(Nc3ccccc3C(=O)NC3CCCCCC3)c2c1] | 1H NMR (DMSO-$d_6$) ppm 1.41-1.86 (m, 12H), 3.90 (br s, 4H), 7.23-7.89 (m, 7H), 8.63-9.55 (m, 5H), 12.30 (s, 1H). | DMSO | >98 | Method Z |
| 1028 | 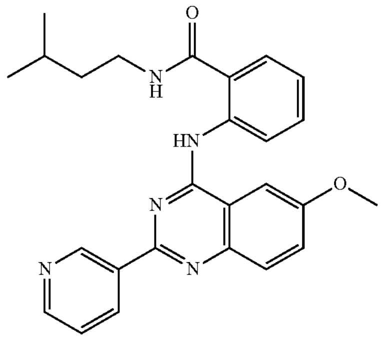 [SMILES: COc1ccc2nc(-c3cccnc3)nc(Nc3ccccc3C(=O)NCCC(C)C)c2c1] | 1H NMR (DMSO-$d_6$) ppm 0.85-1.60 (m, 9H), 3.27-3.33 (m, 2H), 3.99 (s, 3H), 7.21-7.91 (m, 7H), 8.68-9.55 (m, 5H), 12.19 (s, 1H). | DMSO | >98 | Method Z |
| 1029 | 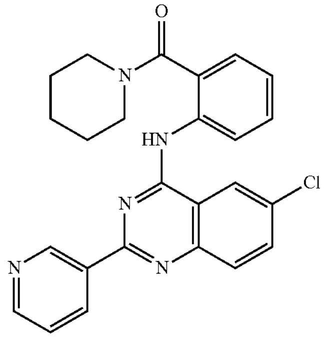 [SMILES: O=C(c1ccccc1Nc1nc(-c2cccnc2)nc2ccc(Cl)cc12)N1CCCCC1] | 1H NMR (DMSO-$d_6$) ppm 1.03-1.34 (m, 6H), 3.17-3.31 (m, 4H), 7.40-7.88 (m 7H), 8.55-10.03 (m, 5H), 12.32 (s, 1H). | DMSO | >98 | Method Z |

TABLE 11-continued
| | | | | | |
|---|---|---|---|---|---|
| 1030 | 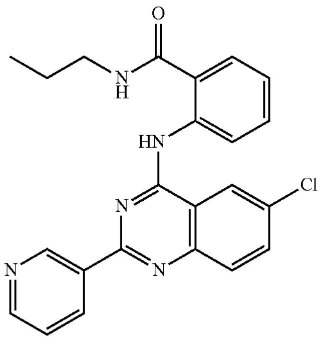 [SMILES: CCCNC(=O)c1ccccc1Nc1nc(-c2cccnc2)nc2ccc(Cl)cc12] | 1H NMR (DMSO-$d_6$) ppm 0.83-1.52 (m, 5H), 3.20-3.29 (m, 2H), 7.27-8.21 (m, 7H), 8.67-9.53 (m, 5H), 12.33 (s, 1H). | DMSO | >98 | Method Z |
| 1031 | 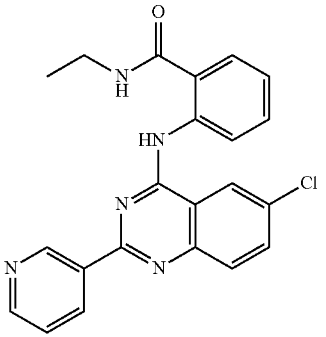 [SMILES: CCNC(=O)c1ccccc1Nc1nc(-c2cccnc2)nc2ccc(Cl)cc12] | 1H NMR (DMSO-$d_6$) ppm 1.02-1.07 (m, 3H), 3.24-3.32 (m, 2H), 7.27-8.22 (m, 7H), 8.67-9.53 (m, 5H), 12.34 (s, 1H). | DMSO | >98 | Method Z |
| 1032 | 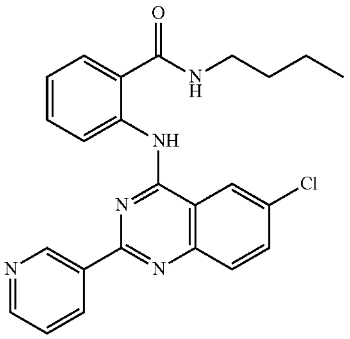 [SMILES: CCCCNC(=O)c1ccccc1Nc1nc(-c2cccnc2)nc2ccc(Cl)cc12] | 1H NMR (DMSO-$d_6$) ppm 0.75-1.37 (m, 7H), 3.18-3.20 (m, 2H) , 7.21-8.19 (m, 7H), 8.64-9.48 (m, 5H), 12.15 (s, 1H). | DMSO | >98 | Method Z |

TABLE 11-continued
| | | | | | |
|---|---|---|---|---|---|
| 1033 | 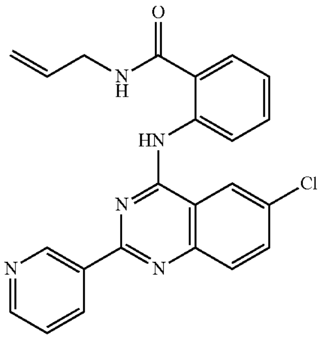 [SMILES: C=CCNC(=O)c1ccccc1Nc1nc(-c2cccnc2)nc2ccc(Cl)cc12] | 1H NMR (DMSO-$d_6$) ppm 3.90-3.92 (m, 2H), 5.02-5.17 (m, 2H), 5.81-5.86 (m, 1H), 7.27-8.23 (m, 7H), 8.68-9.55 (m, 5H), 12.25 (s, 1H). | DMSO | >98 | Method Z |
| 1034 | 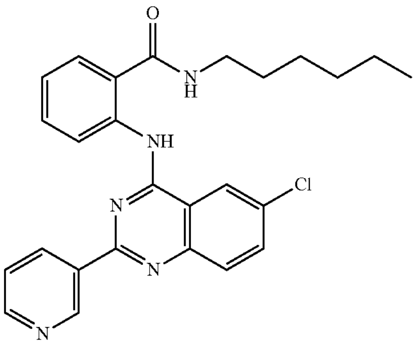 [SMILES: CCCCCCNC(=O)c1ccccc1Nc1nc(-c2cccnc2)nc2ccc(Cl)cc12] | 1H NMR (DMSO-$d_6$) ppm 0.78-1.42 (m, 11H), 3.20-3.29 (m, 2H), 7.25-7.91 (m, 7H), 8.23-9.53 (m, 5H), 12.17 (s, 1H). | DMSO | >98 | Method Z |
| 1035 | 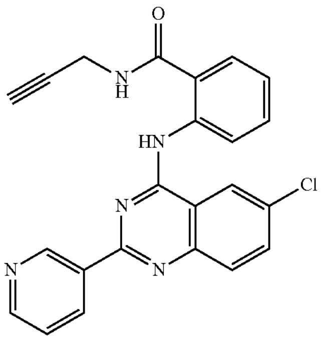 [SMILES: C#CCNC(=O)c1ccccc1Nc1nc(-c2cccnc2)nc2ccc(Cl)cc12] | $^1$H NMR (DMSO-$d_6$) ppm 3.06 (s, 1H), 4.05-4.08 (m, 2H), 7.28-8.22 (m, 7H), 8.65-9.51 (m, 5H), 12.12 (s, 1H). | DMSO | >98 | Method Z |

TABLE 11-continued
| | | | | | |
|---|---|---|---|---|---|
| 1036 | 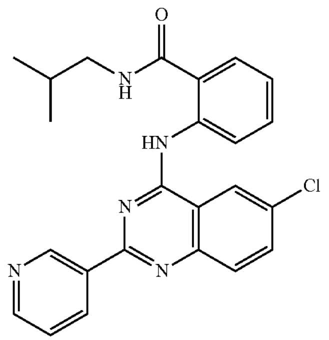 [SMILES: CC(C)CNC(=O)c1ccccc1Nc1nc(-c2cccnc2)nc2ccc(Cl)cc12] | 1H NMR (DMSO-$d_6$) ppm 0.88-1.92 (m, 7H), 3.05-3.16 (m, 2H), 7.23-7.94 (m, 7H), 8.22-9.54 (m, 5H), 12.21 (s, 1H). | DMSO | >98 | Method Z |
| 1037 | 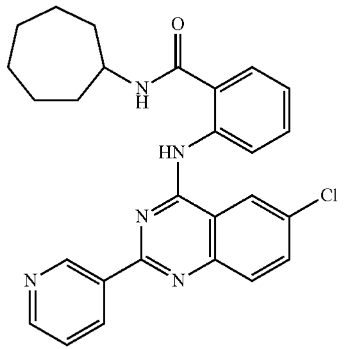 [SMILES: O=C(NC1CCCCCC1)c1ccccc1Nc1nc(-c2cccnc2)nc2ccc(Cl)cc12] | 1H NMR (DMSO-$d_6$) ppm 1.37-1.79 (m, 12H), 3.90-3.96 (m, 1H), 7.25-8.24 (m, 7H), 8.55-9.52 (m, 5H), 12.07 (s, 1H). | DMSO | >98 | Method Z |
| 1038 | 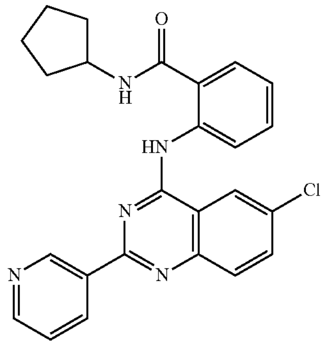 [SMILES: O=C(NC1CCCC1)c1ccccc1Nc1nc(-c2cccnc2)nc2ccc(Cl)cc12] | 1H NMR (DMSO-$d_6$) ppm 1.49-1.85 (m, 8H), 4.24-4.26 (m, 1H), 7.23-7.69 (m, 6H), 7.85-9.53 (m, 6H), 12.06 (s, 1H). | DMSO | >98 | Method Z |

TABLE 11-continued
| | | | | | |
|---|---|---|---|---|---|
| 1039 | 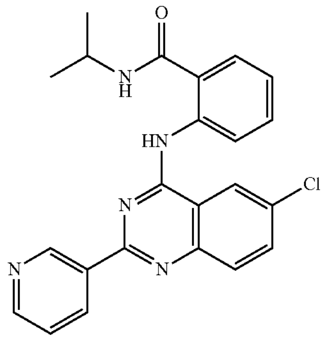 [SMILES: CC(C)NC(=O)c1ccccc1Nc1nc(-c2cccnc2)nc2ccc(Cl)cc12] | 1H NMR (DMSO-$d_6$) ppm 1.12-1.14 (m, 6H), 4.11-4.18 (m, 1H), 7.23-7.94 (m, 8H), 8.33-9.53 (m, 4H), 12.30 (s, 1H). | DMSO | >98 | Method Z |
| 1040 | 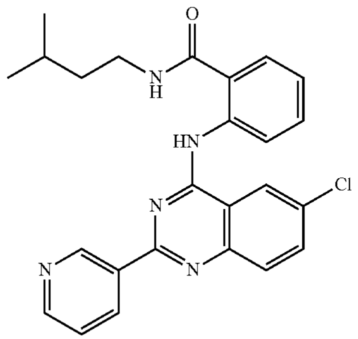 [SMILES: CC(C)CCNC(=O)c1ccccc1Nc1nc(-c2cccnc2)nc2ccc(Cl)cc12] | 1H NMR (DMSO-$d_6$) ppm 0.84-1.16 (m, 9H), 3.28-3.34 (m, 2H), 7.23-7.91 (m, 6H), 8.25-9.53 (m, 6H), 12.16 (s, 1H). | DMSO | >98 | Method Z |
| 1041 | 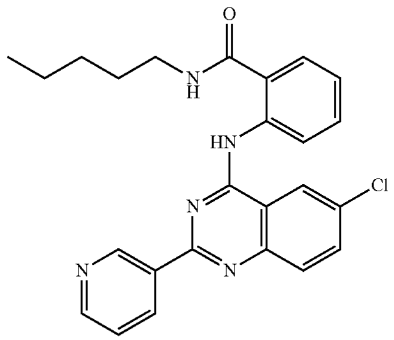 [SMILES: CCCCCNC(=O)c1ccccc1Nc1nc(-c2cccnc2)nc2ccc(Cl)cc12] | 1H NMR (DMSO-$d_6$) ppm 0.79-1.52 (m, 9H), 3.25-3.32 (m, 2H), 7.24-7.91 (m, 6H), 8.23-9.53 (m, 6H), 12.18 (s, 1H). | DMSO | >98 | Method Z |

TABLE 11-continued
| | | | | | |
|---|---|---|---|---|---|
| 1042 | 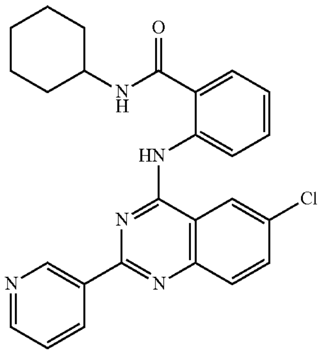 [SMILES: O=C(NC1CCCCC1)c1ccccc1Nc1nc(-c2cccnc2)nc2ccc(Cl)cc12] | 1H NMR (DMSO-$d_6$) ppm 1.04-1.81 (m, 10H), 3.77-3.82 (m, 1H), 7.21-8.05 (m, 8H), 8.65-9.52 (m, 4H), 11.96 (s, 1H). | DMSO | >98 | Method Z |
| 1043 | 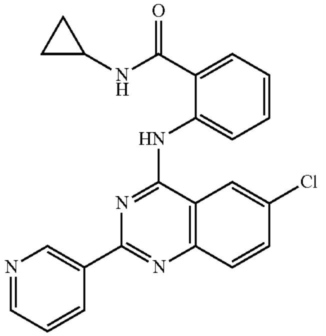 [SMILES: O=C(NC1CC1)c1ccccc1Nc1nc(-c2cccnc2)nc2ccc(Cl)cc12] | 1H NMR (DMSO-$d_6$) ppm 0.47-0.67 (m, 4H), 2.85-2.88 (m, 1H), 7.26-8.26 (m, 7H), 8.66-9.52 (m, 5H), 12.26 (s, 1H). | DMSO | >98 | Method Z |
| 1044 | 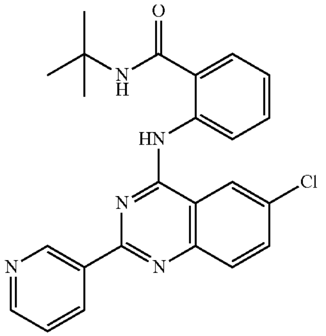 [SMILES: CC(C)(C)NC(=O)c1ccccc1Nc1nc(-c2cccnc2)nc2ccc(Cl)cc12] | 1H NMR (DMSO-$d_6$) ppm 1.14 (s, 9H), 7.30-7.93 (m, 7H), 8.21-9.50 (m, 5H), 12.22 (s, 1H). | DMSO | >98 | Method Z |

TABLE 11-continued
| | | | | | |
|---|---|---|---|---|---|
| 1045 | 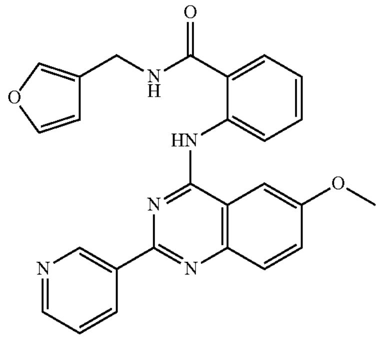 [SMILES: COc1ccc2nc(-c3cccnc3)nc(Nc3ccccc3C(=O)NCc3ccoc3)c2c1] | 1H NMR (DMSO-$d_6$) ppm 3.98 (s, 3H), 4.36 (s, 2H), 6.47 (s, 1H), 7.21-7.91 (m, 9H), 8.68-9.56 (m, 5H), 12.22 (s, 1H). | DMSO | >98 | Method Z |
| 1046 | 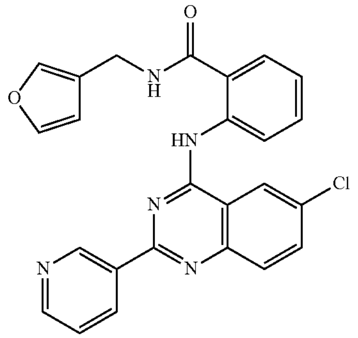 [SMILES: O=C(NCc1ccoc1)c1ccccc1Nc1nc(-c2cccnc2)nc2ccc(Cl)cc12] | 1H NMR (DMSO-$d_6$) ppm 4.30 (s, 2H), 6.42 (s, 1H), 7.28-8.24 (m, 9H), 8.70-9.53 (m, 5H), 12.22 (s, 1H). | DMSO | >98 | Method Z |
| 1047 | 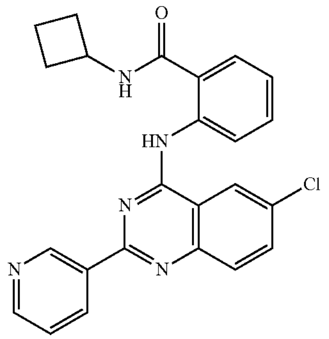 [SMILES: O=C(NC1CCC1)c1ccccc1Nc1nc(-c2cccnc2)nc2ccc(Cl)cc12] | 1H NMR (DMSO-$d_6$) ppm 1.69-2.55 (m, 6H), 4.41-4.44 (m, 1H), 7.23-8.24 (m, 7H), 8.65-9.54 (m, 5H), 12.06 (s, 1H). | DMSO | >98 | Method Z |

TABLE 11-continued
| | | | | | |
|---|---|---|---|---|---|
| 1048 | 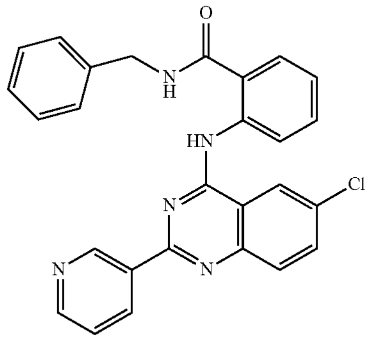 [SMILES: O=C(NCc1ccccc1)c1ccccc1Nc1nc(-c2cccnc2)nc2ccc(Cl)cc12] | 1H NMR (DMSO-$d_6$) ppm 4.55 (s, 2H), 7.17-8.21 (m, 12H), 8.65-9.54 (m, 5H), 12.06 (s, 1H). | DMSO | >98 | Method Z |
| 1049 | 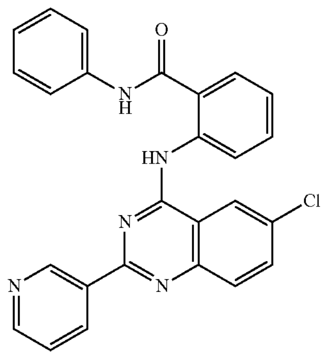 [SMILES: O=C(Nc1ccccc1)c1ccccc1Nc1nc(-c2cccnc2)nc2ccc(Cl)cc12] | 1H NMR (DMSO-$d_6$) ppm 7.02-8.67 (m, 15H), 9.47 (s, 1H), 10.04 (s, 1H), 12.06 (s, 1H). | DMSO | >98 | Method Z |
| 1050 | 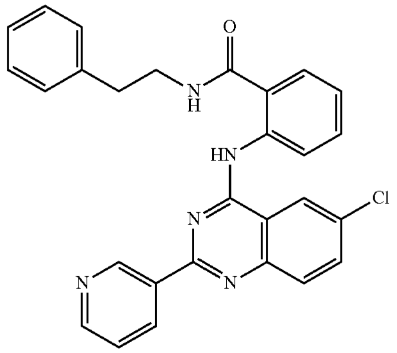 [SMILES: O=C(NCCc1ccccc1)c1ccccc1Nc1nc(-c2cccnc2)nc2ccc(Cl)cc12] | 1H NMR (DMSO-$d_6$) ppm 2.75-2.80 (m, 2H), 3.48-3.54 (m, 2H), 7.08-8.20 (m, 12H) 8.69-9.56 (m, 5H), 12.16 (s, 1H). | DMSO | >98 | Method Z |

TABLE 11-continued
| | | | | | |
|---|---|---|---|---|---|
| 1051 | 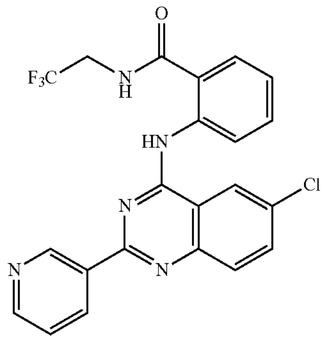 [SMILES: O=C(NCC(F)(F)F)c1ccccc1Nc1nc(-c2cccnc2)nc2ccc(Cl)cc12] | 1H NMR (DMSO-$d_6$) ppm 4.01-4.10 (m, 2H), 7.28-8.27 (m, 7H), 8.59-9.51 (m, 5H), 11.45 (s, 1H). | DMSO | >98 | Method Z |
| 1052 | 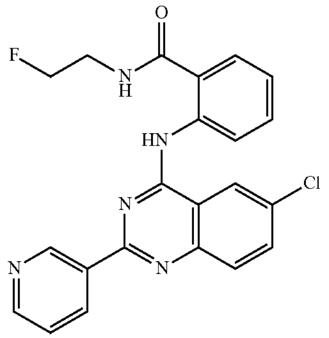 [SMILES: O=C(NCCF)c1ccccc1Nc1nc(-c2cccnc2)nc2ccc(Cl)cc12] | 1H NMR (DMSO-$d_6$) ppm 4.38-4.57 (m, 4H), 7.27-8.24 (m, 7H), 8.69-9.56 (m, 5H), 12.10 (s, 1H). | DMSO | >98 | Method Z |
| 1053 | 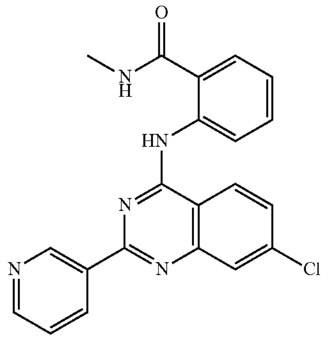 [SMILES: CNC(=O)c1ccccc1Nc1nc(-c2cccnc2)nc2cc(Cl)ccc12] | 1H NMR (DMSO-$d_6$) ppm 2.85-2.92 (br s, 3H), 7.20-8.22 (m, 7H), 8.67-9.56 (m, 5H), 12.61 (s, 1H). | DMSO | >98 | Method Z |

TABLE 11-continued
| | | | | | |
|---|---|---|---|---|---|
| 1054 | 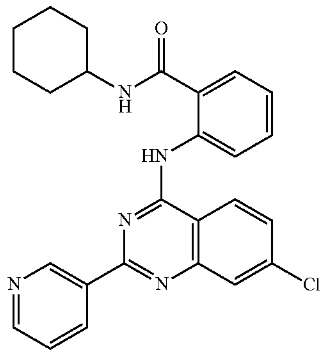 [SMILES: O=C(NC1CCCCC1)c1ccccc1Nc1nc(-c2cccnc2)nc2cc(Cl)ccc12] | 1H NMR (DMSO-$d_6$) ppm 1.04-1.81 (m, 10H), 3.77-3.82 (m, 1H), 7.24-8.05 (m, 8H), 8.65-9.52 (m, 4H), 12.27 (s, 1H). | DMSO | >98 | Method Z |
| 1055 | 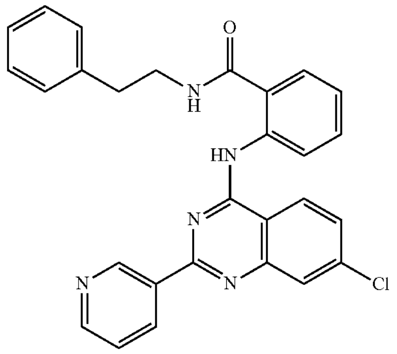 [SMILES: O=C(NCCc1ccccc1)c1ccccc1Nc1nc(-c2cccnc2)nc2cc(Cl)ccc12] | 1H NMR (DMSO-$d_6$) ppm 2.49-2.51 (m, 2H), 3.57-3.59 (m, 2H), 7.21-8.16 (m, 12H), 8.69-9.56 (m, 5H), 12.16 (s, 1H). | DMSO | >98 | Method Z |
| 1056 | 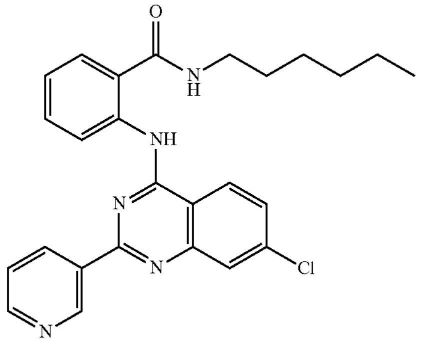 [SMILES: CCCCCCNC(=O)c1ccccc1Nc1nc(-c2cccnc2)nc2cc(Cl)ccc12] | 1H NMR (DMSO-$d_6$) ppm 0.79-1.44 (m, 11H), 3.26-3.30 (m, 2H), 7.24-7.92 (m, 7H), 8.67-9.52 (m, 5H), 12.45 (s, 1H). | DMSO | >98 | Method Z |

TABLE 11-continued
| | | | | | |
|---|---|---|---|---|---|
| 1057 | 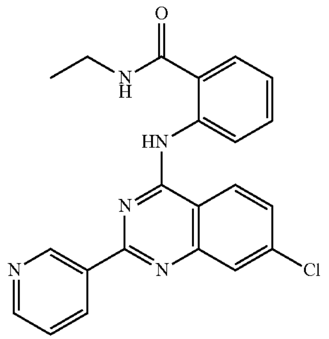 [SMILES: CCNC(=O)c1ccccc1Nc1nc(-c2cccnc2)nc2cc(Cl)ccc12] | 1H NMR (DMSO-$d_6$) ppm 1.04-1.16 (m, 3H), 3.33-3.38 (m, 2H), 7.20-8.22 (m, 7H), 8.60-9.53 (m, 5H), 12.34 (s, 1H). | DMSO | >98 | Method Z |
| 1058 | 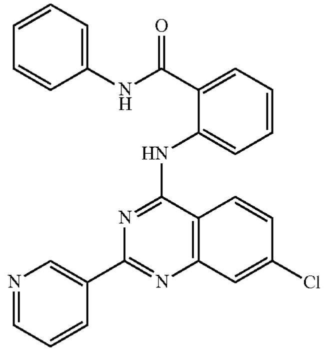 [SMILES: O=C(Nc1ccccc1)c1ccccc1Nc1nc(-c2cccnc2)nc2cc(Cl)ccc12] | 1H NMR (DMSO-$d_6$) ppm 7.09-8.68 (m, 15H), 9.51 (s, 1H), 10.34 (s, 1H), 12.06 (s, 1H). | DMSO | >98 | Method Z |
| 1059 | 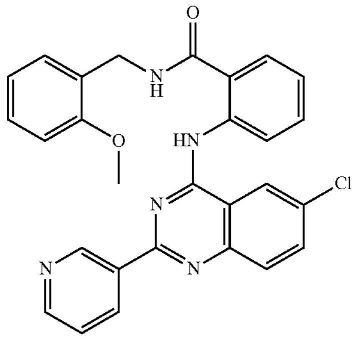 [SMILES: COc1ccccc1CNC(=O)c1ccccc1Nc1nc(-c2cccnc2)nc2ccc(Cl)cc12] | 1H NMR (DMSO-$d_6$) ppm 3.78 (s, 3H), 4.43 (s, 2H), 6.77-8.23 (m, 11H), 8.68-9.54 (m, 5H), 12.06 (s, 1H). | DMSO | >98 | Method Z |

TABLE 11-continued
| | | | | | |
|---|---|---|---|---|---|
| 1060 | 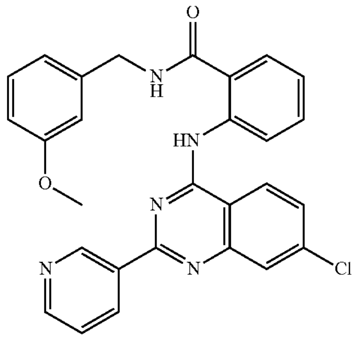 [SMILES: COc1cccc(CNC(=O)c2ccccc2Nc2nc(-c3cccnc3)nc3cc(Cl)ccc23)c1] | 1H NMR (DMSO-$d_6$) ppm 3.69 (s, 3H), 4.48 (s, 2H), 6.89-8.15 (m, 11H), 8.68-9.54 (m, 5H), 12.44 (s, 1H). | DMSO | >98 | Method Z |
| 1061 | 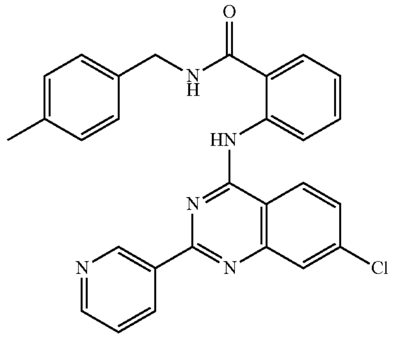 [SMILES: Cc1ccc(CNC(=O)c2ccccc2Nc2nc(-c3cccnc3)nc3cc(Cl)ccc23)cc1] | 1H NMR (DMSO-$d_6$) ppm 2.24 (s, 3H), 4.46 (s, 2H), 7.03-8.13 (m, 11H), 8.67-9.54 (m, 5H), 12.21 (s, 1H). | DMSO | >98 | Method Z |
| 1062 | 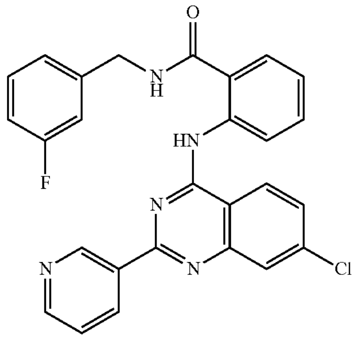 [SMILES: O=C(NCc1cccc(F)c1)c1ccccc1Nc1nc(-c2cccnc2)nc2cc(Cl)ccc12] | 1H NMR (DMSO-$d_6$) ppm 4.51 (s, 2H), 7.11-8.14 (m, 11H), 8.67-9.54 (m, 5H), 12.34 (s, 1H). | DMSO | >98 | Method Z |

TABLE 11-continued
| Number | Starting Material $R^1$ | Starting Material $R^3$ | Product | Salt Type | $^1H$ NMR | $^1H$ NMR Solvent | Purity percent | Method of Coupling |
|---|---|---|---|---|---|---|---|---|
| 1063 | | | 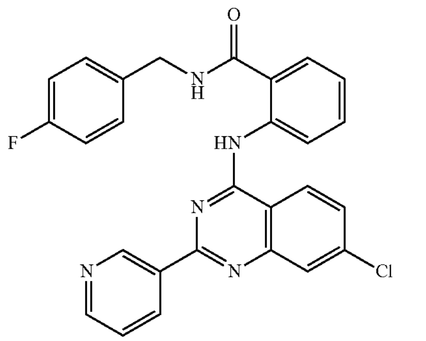 [SMILES: O=C(NCc1ccc(F)cc1)c1ccccc1Nc1nc(-c2cccnc2)nc2cc(Cl)ccc12] | | 1H NMR (DMSO-$d_6$) ppm 4.47 (s, 2H), 7.05-8.14 (m, 11H), 8.67-9.54 (m, 5H), 12.37 (s, 1H). | DMSO | >98 | Method Z |
| 1064 | | | 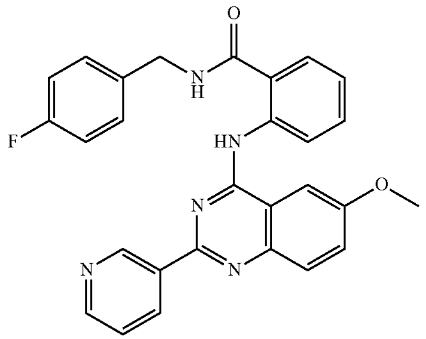 [SMILES: COc1ccc2nc(-c3cccnc3)nc(Nc3ccccc3C(=O)NCc3ccc(F)cc3)c2c1] | | 1H NMR (DMSO-$d_6$) ppm 3.95 (s, 3H), 4.47 (s, 2H), 7.05-8.14 (m, 11H), 8.67-9.54 (m, 5H), 12.32 (s, 1H). | DMSO | >98 | Method Z |
| 1065 | 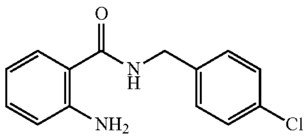 | 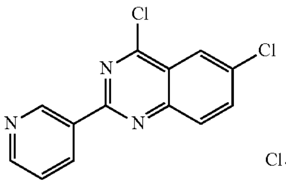 | 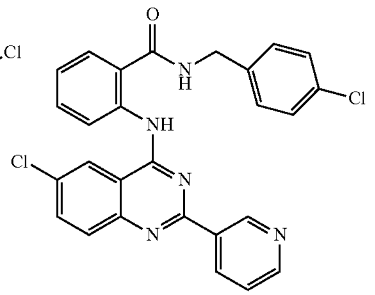 | | $^1H$ NMR (DMSO-$d_6$) ppm 4.52 (d, 2H, J = 5.8 Hz), 7.21-7.30 (m, 5H), 7.50 (t, J = 7.9 Hz, 1H), 7.68 (t, J = 7.8 Hz, 1H), 7.89-7.92 (m, 3H), 8.21 (d, J = 1.8 Hz, 1H), 8.65-8.70 (m, 3H), 8.99 (s, 1H), 9.52 (s, 1H), 11.88 (s, 1H) | DMSO | >98 | Method Y, Z |

TABLE 11-continued
| | | | | | | | |
|---|---|---|---|---|---|---|---|
| 1066 | 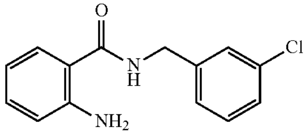 [SMILES: Nc1ccccc1C(=O)NCc1cccc(Cl)c1] | 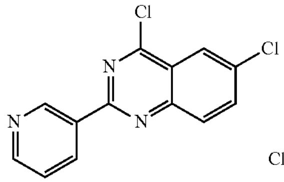 | 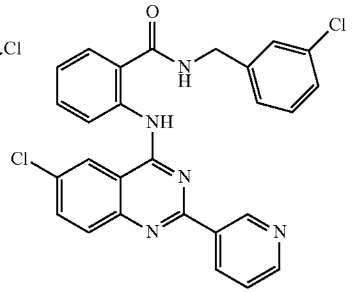 | $^1$H NMR (DMSO-$d_6$) ppm 4.49 (d, 2H, J = 5.6 Hz), 7.24-7.35 (m, 5H), 7.50 (t, J = 7.2 Hz, 1H), 7.70 (t, J = 7.6 Hz, 1H), 7.91-7.95 (m, 3H), 8.22 (d, J = 1.5 Hz, 1H), 8.67-8.73 (m, 3H), 9.19 (s, 1H), 9.53 (s, 1H), 11.98 (s, 1H) | DMSO | >98 | Meth-od Y, Z |
| 1067 | 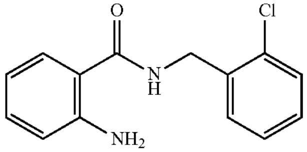 [SMILES: Nc1ccccc1C(=O)NCc1ccccc1Cl] | 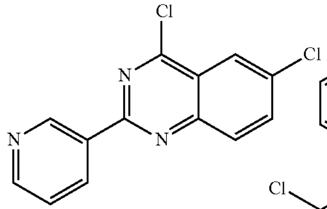 | 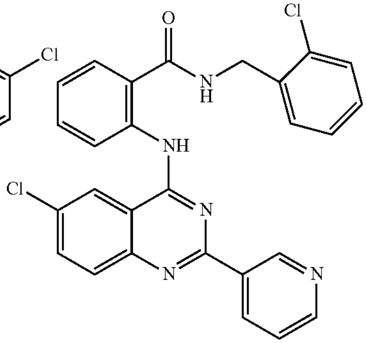 | $^1$H NMR (DMSO-$d_6$) ppm 4.58 (d, 2H, J = 5.7 Hz), 7.16-7.36 (m, 5H), 7.50 (t, J = 7.5 Hz, 1H), 7.69 (t, J = 7.5 Hz, 1H), 7.88-7.96 (m, 3H), 8.22 (d, J = 1.5 Hz, 1H), 8.65-8.69 (m, 3H), 8.98 (s, 1H), 9.52 (s, 1H), 11.87 (s, 1H) | DMSO | >98 | Meth-od Y, Z |
| 1068 | 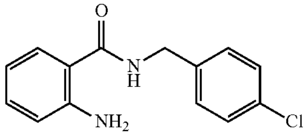 | 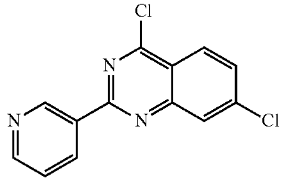 [SMILES: Clc1ccc2c(Cl)nc(-c3cccnc3)nc2c1] | 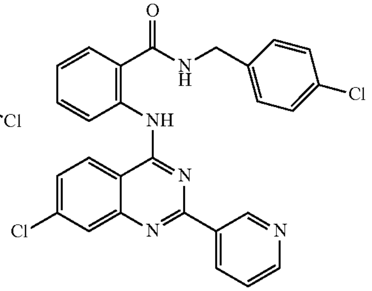 | $^1$H NMR (DMSO-$d_6$) ppm 4.47 (d, 2H, J = 5.6 Hz), 7.30 (br s, 5H), 7.54 (t, J = 7.7 Hz, 1H), 7.70 (t, J = 7.8 Hz, 1H), 7.88-7.96 (m, 3H), 8.15 (d, J = 1.5 Hz, 1H), 8.68-8.81 (m, 3H), 8.98 (s, 1H), 9.52 (s, 1H), 12.29 (s, 1H) | DMSO | >98 | Meth-od Y, Z |

TABLE 11-continued
| | | | | | | | |
|---|---|---|---|---|---|---|---|
| 1069 | 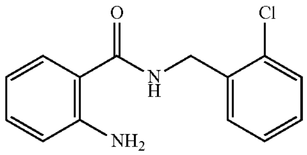 [SMILES: Nc1ccccc1C(=O)NCc1ccccc1Cl] | 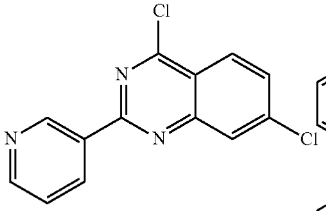 | 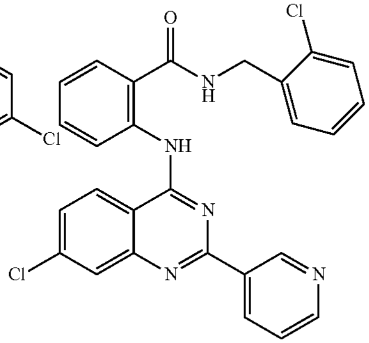 | $^1$H NMR (DMSO-$d_6$) ppm 4.57 (d, 2H, J = 5.6 Hz), 7.23-7.29 (m, 5H), 7.39 (t, J = 7.9 Hz, 1H), 7.71 (t, J = 7.9 Hz, 1H), 7.94-7.99 (m, 3H), 8.15 (d, J = 1.4 Hz, 1H), 8.68-8.84 (m, 3H), 9.24 (s, 1H), 9.55 (s, 1H), 12.23 (s, 1H) | DMSO | >98 | Meth-od Y, Z |
| 1070 | 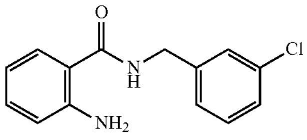 | 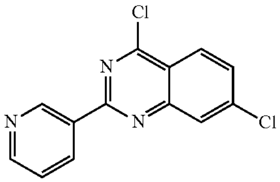 [SMILES: Clc1ccc2c(Cl)nc(-c3cccnc3)nc2c1] | 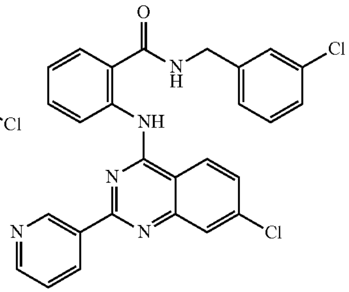 | $^1$H NMR (DMSO-$d_6$) ppm 4.50 (d, 2H, J = 5.5 Hz), 7.25-7.53 (m, 5H), 7.69 (t, J = 7.1 Hz, 1H), 7.73 (t, J = 7.0 Hz, 1H), 7.94-8.15 (m, 3H), 8.18 (d, J = 1.4 Hz, 1H), 8.68-8.82 (m, 3H), 9.24 (s, 1H), 9.54 (s, 1H), 12.21 (s, 1H) | DMSO | >98 | Meth-od Y, Z |
| 1071 | 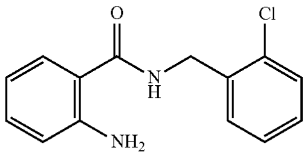 [SMILES: Nc1ccccc1C(=O)NCc1ccccc1Cl] | 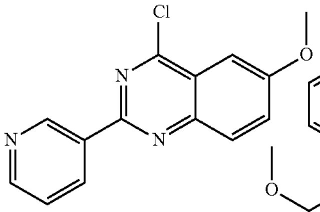 | 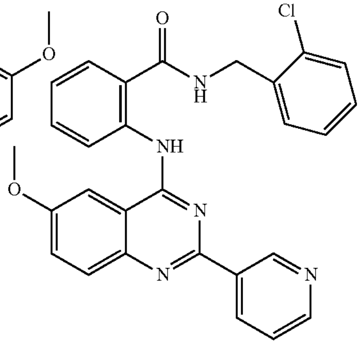 | $^1$H NMR (DMSO-$d_6$) ppm 3.90 (s, 3H), 4.56 (d, 2H, J = 5.6 Hz), 7.22-7.44 (m, 7H), 7.44 (t, J = 7.9 Hz, 1H), 7.74 (t, J = 7.9 Hz, 1H), 7.94-7.99 (m, 2H), 8.68-8.81 (m, 3H), 9.24 (s, 1H), 9.55 (s, 1H), 12.19 (s,1H) | DMSO | >98 | Meth-od Y, Z |

TABLE 11-continued
| | | | | | | |
|---|---|---|---|---|---|---|
| 1072 | 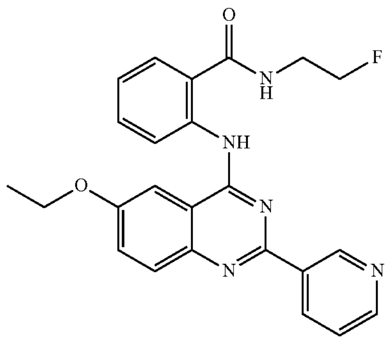 [SMILES: CCOc1ccc2nc(-c3cccnc3)nc(Nc3ccccc3C(=O)NCCF)c2c1] | HCl | $^1$H NMR (400 MHz, DMSO-$d_6$): δ 12.17 (s, 1H), 9.52 (s, 1H), 9.08 (s, 1H), 8.95 (d, J = 7.6 Hz, 1H), 8.85 (s, 1H), 8.66 (d, J = 7.8 Hz, 1H), 7.91 (t, J = 9.4 Hz, 2H), 7.84 (s, 1H), 7.75-7.67 (m, 1H), 7.65 (s, 1H), 7.59 (d, J = 8.1 Hz, 1H), 7.30 (t, J = 7.3 Hz, 1H), 4.47 (d, J = 47.3 Hz, 2H), 4.26 (d, J = 6.8 Hz, 2H), 3.58-3.50 (m, 2H), 1.47 (t, J = 6.7 Hz, 3H). | DMSO | 95 | Method Y, Z |

Scheme 36: General route for the synthesis of compounds with general formula xxxi
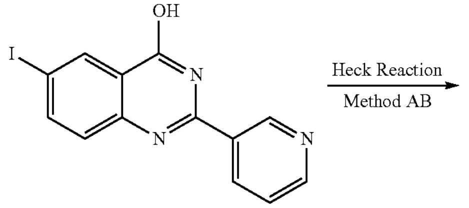
iv
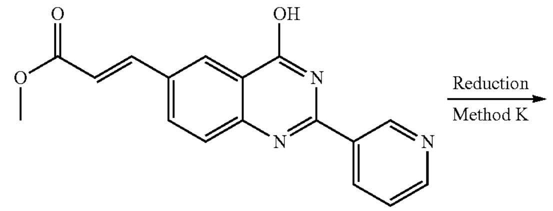
xxvi
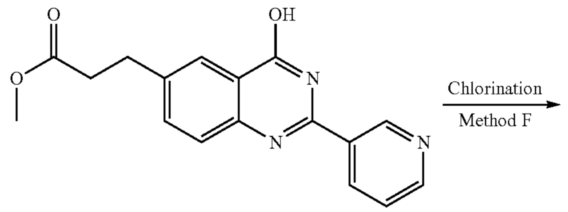
xxvii
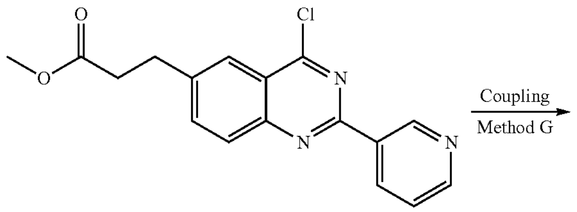
xxviii
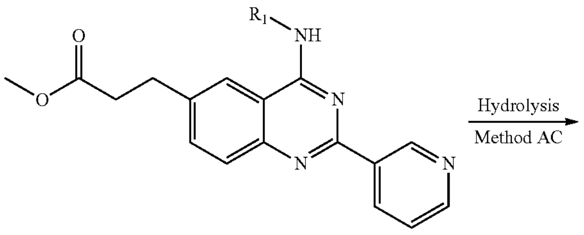
xxviv
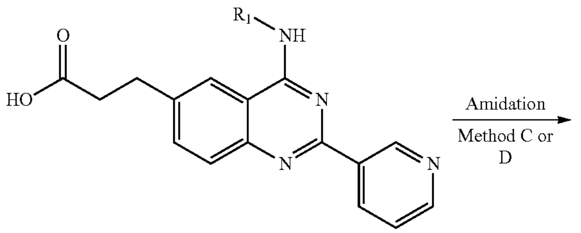
xxx
-continued
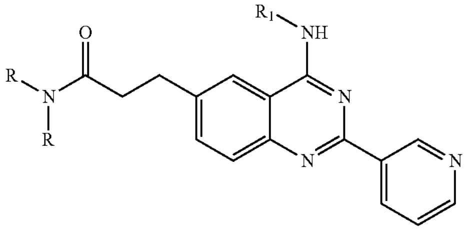
xxxi
Scheme 37: Representative synthesis of compounds of formula xxxi-a: (see Scheme 36)
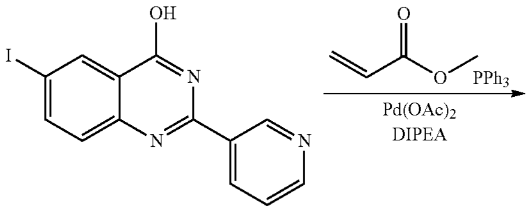
iv-c
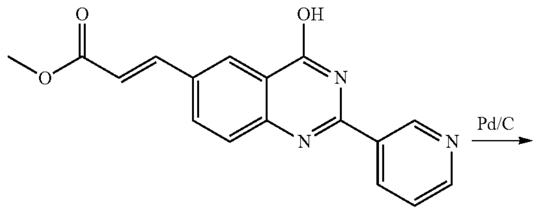
xxvi-a
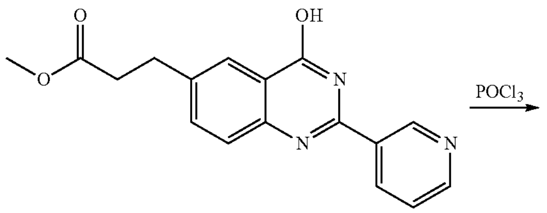
xxvii-a
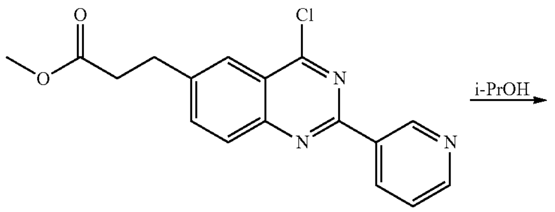
xxviii-a
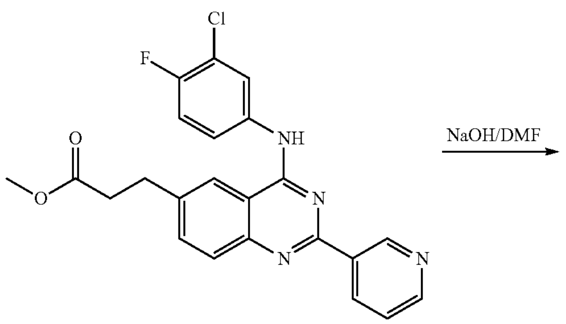
xxviv-a -continued

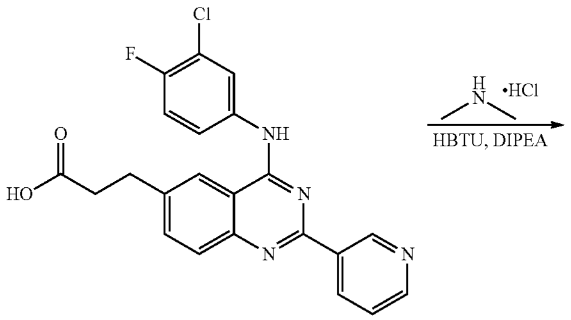

xxx-a

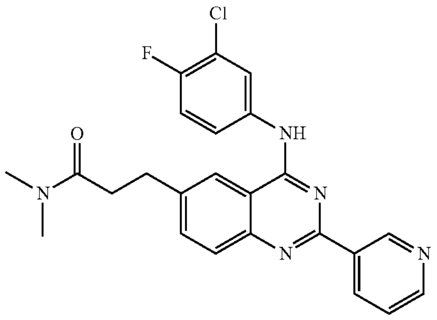

xxxi-a

Method AB: Methyl 3-(4-hydroxy-2-(pyridin-3-yl) quinazolin-6-yl)acrylate (xxvi-a)

To a solution of 6-iodo-2-(pyridin-3-yl) quinazolin-4-ol (synthesized as described in Scheme 1 and 4, substituting 5-iodo-2-nitrobenzoic acid for 2-nitro-5-propoxy-benzoic acid) (3.00 g, 8.6 mmol, 1.0 eq.), $Pd(OAc)_2$ (48 mg, 0.21 mmol, 0.025 eq.) and $PPh_3$ (113 mg, 0.43 mmol, 0.05 eq.) in DMF (8 mL) was added methyl acrylate (3.22 g, 25.8 mmol, 3.0 eq.) and DIPEA (1.22 g, 9.46 mmol, 1.1 eq.) under Ar atmosphere. The mixture was stirred at 110° C. overnight. After cooling, the mixture was filtered and the solid was washed with ethyl acetate three times to afford 1.30 g of xxxvi-a as green solid (yield 49%). LCMS m/z=308.0 (M+1) (Method B) (retention time=1.41 min).

Methyl 3-(4-hydroxy-2-(pyridin-3-yl)quinazolin-6-yl)propanoate (xxvii-a)

Methyl 3-(4-hydroxy-2-(pyridin-3-yl)quinazolin-6-yl) propanoate was prepared in a manner analogous to that described for 2-amino-5-methoxybenzoic acid in Method K, replacing 5-methoxy-2-nitrobenzoic acid with methyl 3-(4-hydroxy-2-(pyridin-3-yl)quinazolin-6-yl)acrylate to afford 1.40 g of xxvii-a in quantitative yield as a yellow solid. LCMS m/z=310.0 (M+1) (Method B) (retention time=1.42 min).

3-(4-Chloro-2-pyridin-3-yl-quinazolin-6-yl)-propionic acid methyl ester (xxviii-a)

3-(4-Chloro-2-pyridin-3-yl-quinazolin-6-yl)-propionic acid methyl ester (prepared in a manner analogous to that described for 4-chloro-6-propoxy-2-pyridin-3-yl-quinazoline using Method F, replacing 6-propoxy-2-pyridin-3-yl-1H-quinazolin-4-one with methyl 3-(4-hydroxy-2-(pyridin-3-yl)quinazolin-6-yl)propanoate) was obtained in quantitative yield to give 1.50 g of xxvii-a as a red solid. LCMS m/z=328.1, 330.0 (M+1) (Method B) (retention time=1.86 min).

3-[4-(3-Chloro-4-fluoro-phenylamino)-2-pyridin-3-yl-quinazolin-6-yl]-propionic acid methyl ester (xxviv-a)

3-[4-(3-Chloro-4-fluoro-phenylamino)-2-pyridin-3-yl-quinazolin-6-yl]-propionic acid methyl ester (prepared in a manner analogous to that described for 2-(6-propoxy-2-pyridin-3-yl-quinazolin-4-ylamino)-benzamide in Method G1, replacing 4,7-dichloro-2-(4-chlorophenyl)quinazoline and 2-aminobenzamide with 3-(4-chloro-2-pyridin-3-yl-quinazolin-6-yl)-propionic acid methyl ester and 3-chloro-4-fluoro-phenylamine) was obtained in a 43% yield to give 1.04 g of xxviv-a as a yellow solid. LCMS m/z=437.1, 439.1 (M+1) (Method B) (retention time=1.62 min).

Method AC: 3-(4-(3-Chloro-4-fluorophenylamino)-2-(pyridin-3-yl) quinazolin-6-yl)propanoic acid (xxx-a)

To a solution of 3-[4-(3-chloro-4-fluoro-phenylamino)-2-pyridin-3-yl-quinazolin-6-yl]-propionic acid methyl ester (1.04 g, 2.39 mmol, 1.0 eq.) in DMF (20 mL) was added a solution of NaOH (0.57 g, 14.3 mmol, 6.0 eq.) in $H_2O$ (8 mL). The mixture was stirred at room temperature for 2 h. 50 mL of water was added to the mixture. After filtration, the resulting filter cake was washed with water and dried in vacuo to give 933 mg of xxx-a as a yellow solid (yield 93%). LCMS m/z=423.1, 425.1 (M+1) (Method A) (retention time=1.51 min).

3-(4-(3-Chloro-4-fluorophenylamino)-2-(pyridin-3-yl)quinazolin-6-yl)-N,N-dimethyl propanamide (xxxi-a)

3-(4-(3-Chloro-4-fluorophenylamino)-2-(pyridin-3-yl) quinazolin-6-yl)-N,N-dimethyl propanamide (prepared in a manner analogous to that described for 2-benzamido-5-methoxy-3-methylbenzamide in Method D, replacing nicotinic acid and 2-amino-5-methoxy-3-methylbenzamide with 3-(4-(3-chloro-4-fluorophenylamino)-2-(pyridin-3-yl)quinazolin-6-yl)propanoic acid and dimethylamine hydrochloride) was obtained in 90% yield to give 891 mg of xxxi-a as a yellow solid. LCMS m/z=450.0, 452.0 (M+1) (Method B) (retention time=1.834 min). $^1$H-NMR (400 MHz, DMSO-$d_6$): δ 9.95 (s, 1H), 9.51 (d, J=1.6 Hz, 1H), 8.69-8.63 (m, 2H), 8.38 (s, 1H), 8.28 (dd, J=6.8, 2.4 Hz, 1H), 7.94-7.90 (m, 1H), 7.81 (s, 2H), 7.55-7.51 (m, 2H), 3.04 (t, J=7.6 Hz, 2H), 2.99 (s, 3H), 2.85 (s, 3H), 2.77 (t, J=8.0 Hz, 2H).

The compounds in the following table were prepared in a manner analogous to that described in Scheme 36, replacing dimethylamine with the appropriate amine and 4-fluoro, 3-chloro aniline with the appropriate aniline.

TABLE 12

| Number | PRODUCT | Salt type | Molecular Mass | $^1$H-NMR | $^1$H-NMR Solvent | LCMS | LCMS Protocol | Purity percent | Method for Coupling |
|---|---|---|---|---|---|---|---|---|---|
| 1073 | 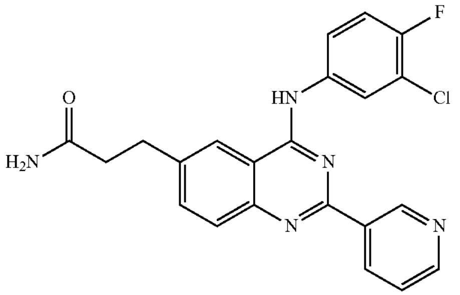 [SMILES: NC(=O)CCc1ccc2nc(-c3cccnc3)nc(Nc3ccc(F)c(Cl)c3)c2c1] | | 421.85 | $^1$H-NMR (400 MHz, DMSO-$d_6$): δ 10.01 (s, 1H), 9.52 (s, 1H), 8.65-8.69 (m, 2H), 8.39 (s, 1H), 8.28 (d, J = 5.2 Hz, 1H), 7.92-7.93 (m, 1H), 7.82 (q, J = 8.0 Hz, 2H), 7.52-7.57 (m, 2H), 7.35 (s, 1H), 6.84 (s, 1H), 3.05 (t, J = 7.2 Hz, 2H), 2.51-2.54 (m, 2H). | DMSO | 422.1 (M + 1) | Method B (NH4HCO3) | 95 | Method C |
| 1074 | 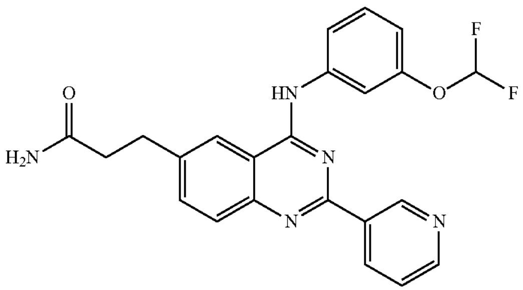 [SMILES: NC(=O)CCc1ccc2nc(-c3cccnc3)nc(Nc3cccc(OC(F)F)c3)c2c1] | | 435.43 | $^1$H-NMR (400 MHz, DMSO-$d_6$): δ 10.01 (s, 1H), 9.55 (d, J = 2.4 Hz, 1H), 8.68-8.70 (m, 2H), 8.47 (s, 1H), 7.97-7.99 (m, 1H), 7.79-7.36 (m, 3H), 7.50-7.55 (m, 2H), 7.36 (s, 1H), 7.30 (t, J = 73.6 Hz, 1H), 6.99 (dd, J = 8.4, 2.4 Hz, 1H), 6.82 (s, 1H), 3.05 (t, J = 8.0 Hz, 2H), 2.52 (t, J = 8.4 Hz, 2H). | DMSO | 436.2 (M + 1) | Method B (NH4HCO3) | 95 | Method C |
| 1075 | 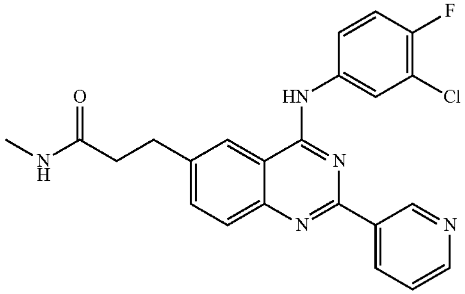 [SMILES: CNC(=O)CCc1ccc2nc(-c3cccnc3)nc(Nc3ccc(F)c(Cl)c3)c2c1] | | 435.88 | $^1$H-NMR (400 MHz, DMSO-$d_6$): δ 10.00 (s, 1H), 9.52 (s, 1H), 8.65-8.69 (m, 2H), 8.39 (s, 1H), 8.27-8.29 (m, 1H), 7.79 (dd, J = 9.2, 2.4 Hz, 1H), 7.76-7.85 (m, 3H), 7.52-7.57 (m, 2H), 3.05 (t, J = 7.6 Hz, 2H), 2.57 (d, J = 4.4 Hz, 3H), 2.52-2.54 (m, 2H). | DMSO | 436.1 (M + 1) | Method B (NH4HCO3) | 95 | Method D |

TABLE 12-continued
| Number | PRODUCT | Salt type | Molecular Mass | $^1$H-NMR | $^1$H-NMR Solvent | LCMS | LCMS Protocol | Purity percent | Method for Coupling |
|---|---|---|---|---|---|---|---|---|---|
| 1076 | 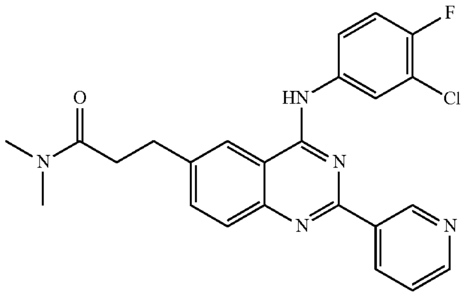 [SMILES: CN(C)C(=O)CCc1ccc2nc(-c3cccnc3)nc(Nc3ccc(F)c(Cl)c3)c2c1] | | 449.91 | $^1$H-NMR (400 MHz, DMSO-$d_6$): δ 9.95 (s, 1H), 9.51 (d, J = 1.6 Hz, 1H), 8.63-8.59 (m, 2H), 8.38 (s, 1H), 8.28 (dd, J = 6.8, 2.4 Hz, 1H), 7.90-7.94 (m, 1H), 7.81 (s, 2H), 7.51-7.55 (m, 2H), 3.04 (t, J = 7.6 Hz, 2H), 2.99 (s, 3H), 2.35 (s, 3H), 2.77 (t, J = 8.0 Hz, 2H). | DMSO | 450.0 (M + 1) | Method B (NH4HCO3) | 95 | Method D |
| 1077 | 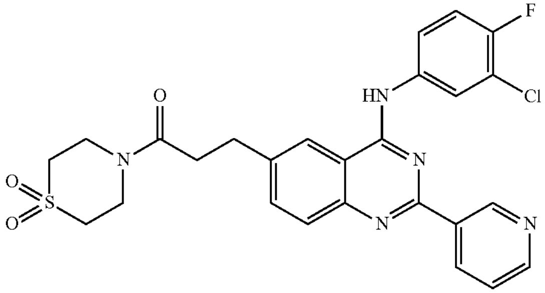 [SMILES: O=C(CCc1ccc2nc(-c3cccnc3)nc(Nc3ccc(F)c(Cl)c3)c2c1)N1CCS(=O)(=O)CC1] | | 540.01 | $^1$H-NMR (400 MHz, DMSO-$d_6$): δ 10.01 (s, 1H), 9.52 (d, J = 1.6 Hz, 1H), 8.61-8.74 (m, 2H), 8.41 (s, 1H), 8.28 (dd, J = 6.8, 2.6 Hz, 1H), 7.80-7.99 (m, 3H), 7.46-7.63 (m, 2H), 3.89 (s, 4H), 3.20 (s, 2H), 3.08 (t, J = 7.4 Hz, 4H), 2.90 (t, J = 7.6 Hz, 2H). | DMSO | 540.2, 542.2 (M + 1) | Method B (NH4HCO3) | 95 | Method D |

Scheme 38: General route for the synthesis of compounds with general formula xxxv:
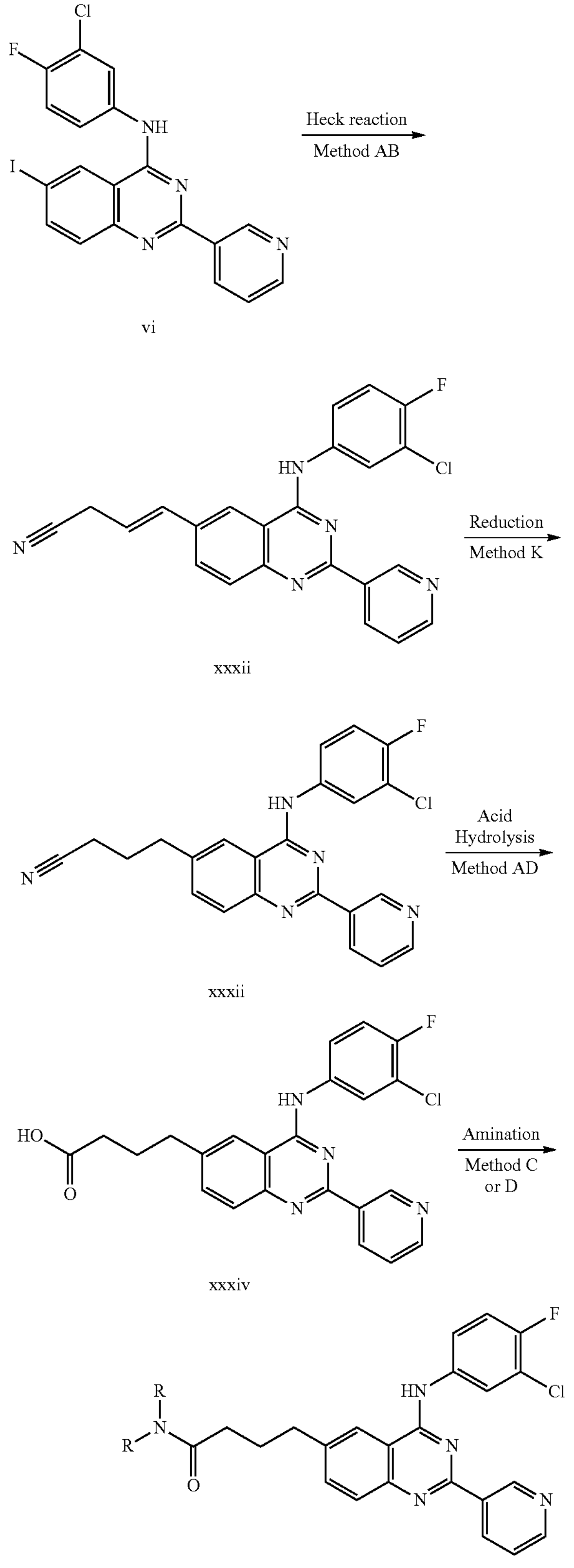
vi
xxxii
xxxii
xxxiv
xxxv
Scheme 39: Representative synthesis of compounds of formula xxxv-a: (see Scheme 38)
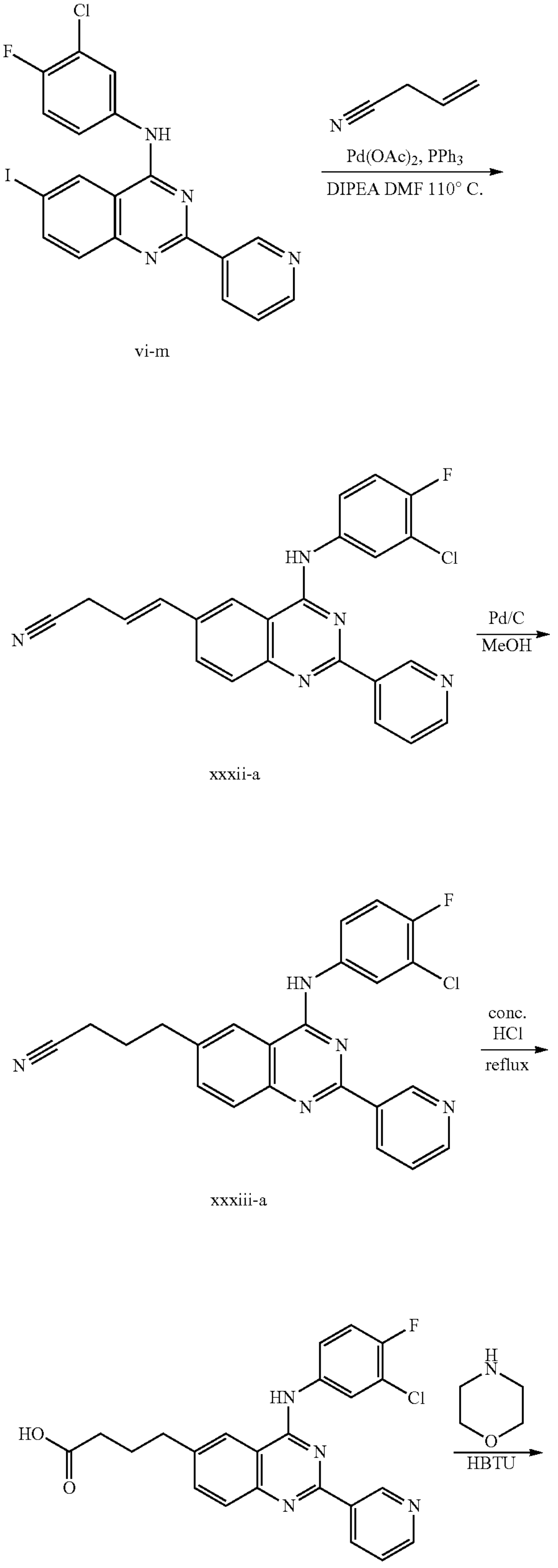
vi-m
xxxii-a
xxxiii-a
xxxiv-a -continued

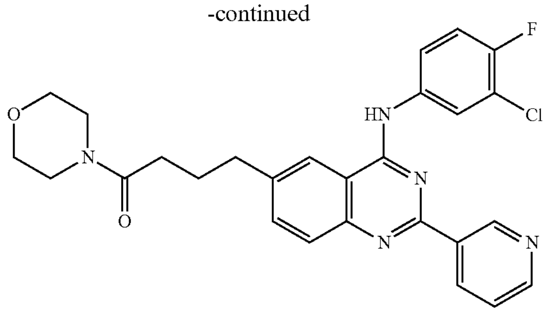

xxxv-a (Compound 1078)

(E)-4-[4-(3-Chloro-4-fluoro-phenylamino)-2-pyridin-3-yl-quinazolin-6-yl]-but-3-enenitrile (xxxii-a)

(E)-4-[4-(3-Chloro-4-fluoro-phenylamino)-2-pyridin-3-yl-quinazolin-6-yl]-but-3-enenitrile (prepared in a manner analogous to that described for (E)-methyl 3-(4-hydroxy-2-(pyridin-3-yl)quinazolin-6-yl)acrylate using Method AB, replacing 6-iodo-2-(pyridin-3-yl)quinazolin-4-ol and methyl acrylate with N-(3-chloro-4-fluorophenyl)-6-iodo-2-(pyridin-3-yl)quinazolin-4-amine and but-3-enenitrile) was obtained in a 48% yield to give 400 mg of xxii-a as grey solid. LCMS m/z=416.0 (M+1) (Method B) (retention time=1.99 min).

4-[4-(3-Chloro-4-fluoro-phenylamino)-2-pyridin-3-yl-quinazolin-6-yl]-butyronitrile (xxxiii-a)

4-[4-(3-Chloro-4-fluoro-phenylamino)-2-pyridin-3-yl-quinazolin-6-yl]-butyronitrile (prepared in a manner analogous to that described for 2-amino-5-methoxybenzoic acid in Method K, replacing 5-methoxy-2-nitrobenzoic acid with (E)-4-(4-(3-chloro-4-fluorophenylamino)-2-(pyridin-3-yl) quinazolin-6-yl)but-3-enenitrile) was obtained in a 95% yield to give 190 mg of xxxiii-a as a brown solid. LCMS m/z=418.1 (M+1) (Method B) (retention time=1.95 min).

Method AD: 4-(4-(3-chloro-4-fluorophenylamino)-2-(pyridin-3-yl)quinazolin-6-yl)butanoic acid (xxxiv-a)

4-[4-(3-Chloro-4-fluoro-phenylamino)-2-pyridin-3-yl-quinazolin-6-yl]-butyronitrile (190 mg, 046 mmol, 1.0 eq.) was treated with concentrated HCl (8 mL). The mixture was stirred at 100° C. for 2 days. The volatiles were removed in vacuo, and the residue was washed with water to afford 70 mg of xxxiv-a in a 35% yield as a yellow solid. LCMS m/z=437.1, 439.1 (M+1) (Method B) (retention time=1.46 min).

4-(4-(3-Chloro-4-fluorophenylamino)-2-(pyridin-3-yl)quinazolin-6-yl)-1-morpholino butan-1-one (xxxv-a)

4-(4-(3-chloro-4-fluorophenylamino)-2-(pyridin-3-yl) quinazolin-6-yl)-1-morpholinobutan-1-one was prepared in a manner analogous to that described for 2-benzamido-5-methoxy-3-methylbenzamide in Method D, replacing nicotinic acid and 2-amino-5-methoxy-3-methylbenzamide with 4-(4-(3-chloro-4-fluorophenylamino)-2-(pyridin-3-yl) quinazolin-6-yl) butanoic acid and morpholine to give 32 mg of xxxv-a in a 40% yield as a beige solid. LCMS m/z=506.2, 508.1 (M+1) (Method 1) (retention time=1.85 min). $^1$H NMR (400 MHz, DMSO-$d_6$): δ 10.04 (s, 1H), 9.52 (d, J=1.6 Hz, 1H), 8.69-8.65 (m, 2H), 8.39-8.38 (m, 1H), 8.27 (dd, J=6.8, 2.8 Hz, 1H), 7.94-7.90 (m, 1H), 7.86-7.84 (m, 1H), 7.80-7.77 (m, 1H), 7.57-7.52 (m, 2H), 3.56-3.53 (m, 4H), 3.46-3.41 (m, 4H), 2.85 (t, J=8.0 Hz, 2H), 2.40 (t, J=7.6 Hz, 2H), 1.97 (t, J=7.6 Hz, 2H).

Scheme 40: Representative synthesis of compounds of formula I-a

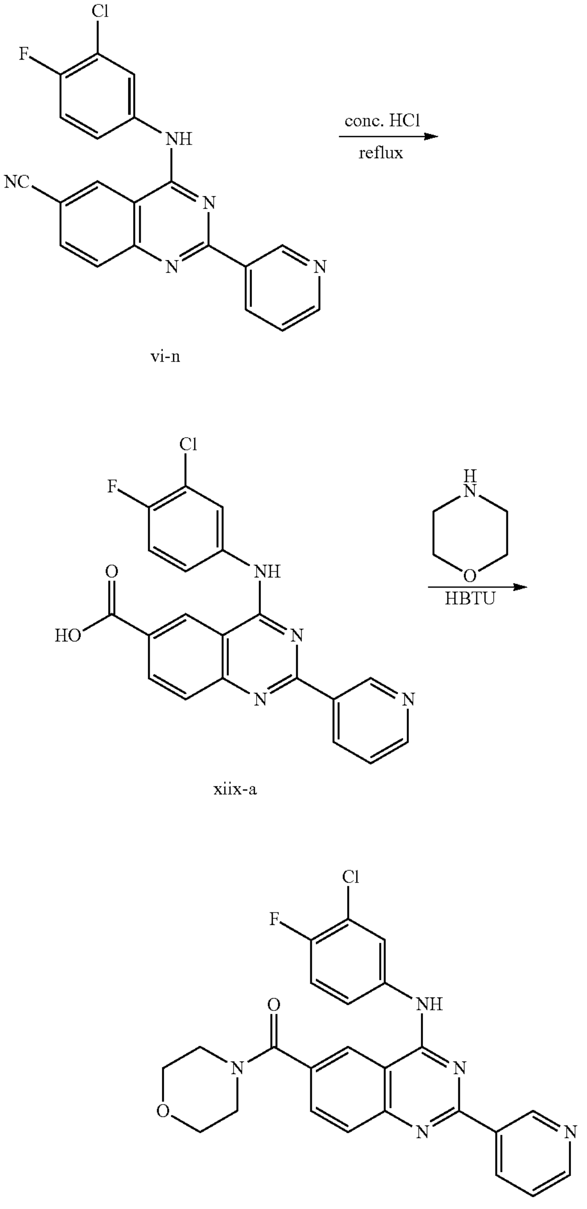

The compounds in the following table were prepared in a manner analogous to that described in Scheme 38 in the synthesis of 4-(4-(3-Chloro-4-fluorophenyl amino)-2-(pyridin-3-yl) quinazolin-6-yl)-1-morpholino butan-1-one, replacing (E)-4-[4-(3-Chloro-4-fluoro-phenylamino)-2-pyridin-3-yl-quinazolin-6-yl]-but-3-enenitrile with 4-(3-chloro-4-fluorophenylamino)-2-(pyridin-3-yl)quinazoline-6-carbonitrile.

TABLE 13

| Number | PRODUCT | Salt type | Molecular Mass | $^1$H-NMR | $^1$H-NMR Solvent | LCMS | LCMS Protocol | Purity percent | Method for Coupling |
|---|---|---|---|---|---|---|---|---|---|
| 1078 | 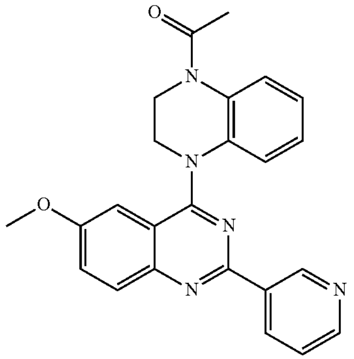 [SMILES: COc1ccc2nc(-c3cccnc3)nc(N3CCN(C(C)=O)c4ccccc43)c2c1] | | 411.46 | $^1$H-NMR (400 MHz, DMSO-$d_6$): δ 9.64 (d, J = 1.6 Hz, 1H), 8.78 (td, J = 7.9, 1.8 Hz, 1H), 8.71 (dd, J = 4.7, 1.6 Hz, 1H), 7.94 (d, J = 9.2 Hz, 1H), 7.59 (brs, 1H), 7.58 (dd. J = 7.6, 4.8 Hz, 1H). 7.52 (dd, J = 9.2. 2.8 Hz, 1H), 7.16 (t, J = 7.6 Hz, 1H), 7.08 (d, J = 6.4 Hz, 1H), 6.84 (dd, J = 8.0, 1.1 Hz, 1H), 6.69 (s, 1H), 4.36 (t, J = 6.5 Hz, 2H), 4.09 (t, J = 6.4 Hz, 2H), 3.46 (s, 3H), 2.30 (s, 3H). | DMSO | 412.2 (M + 1) | Method B (NH4HCO3) | 95 | Method C, G |
| 1079 | 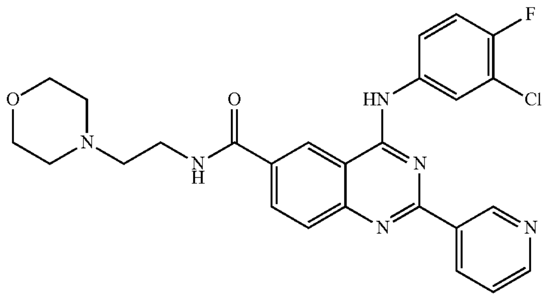 [SMILES: O=C(NCCN1CCOCC1)c1ccc2nc(-c3cccnc3)nc(Nc3ccc(F)c(Cl)c3)c2c1] | | 506.96 | $^1$H NMR (400 MHz, DMSO-$d_6$): δ 10.42 (s, 1H), 9.54 (d, J = 1.6 Hz, 1H), 9.08 (d, J = 1.2 Hz, 1H), 8.73-8.65 (m, 3H), 8.28 (dd, J = 6.8, 2.4 Hz, 1H), 7.97-7.93 (m, 2H), 7.60-7.53 (m, 2H), 3.60-3.58 (m, 4H), 3.51-3.46 (m, 2H), 2.55-2.53 (m, 2H), 2.41-2.48 (m, 4H), | DMSO | 508.1 (M + 1) 254.1 254.9 (M/2 + 1) | Method B (NH4HCO3) | 95 | Method C, G, C |
| 1080 | 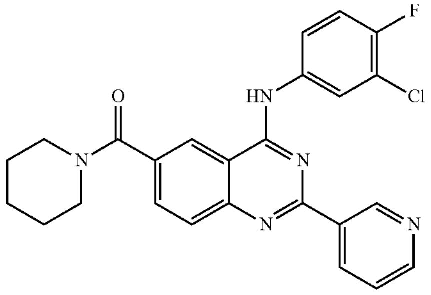 [SMILES: O=C(c1ccc2nc(-c3cccnc3)nc(Nc3ccc(F)c(Cl)c3)c2c1)N1CCCCC1] | | 461.92 | $^1$H NMR (400 MHz, DMSO-$d_6$): δ 10.21 (s, 1H), 9.54 (d, J = 1.6 Hz, 1H), 8.72-8.67 (m, 2H), 8.64 (d, J = 1.2 Hz, 1H), 8.28 (dd, J = 7.0, 2.6 Hz, 1H), 7.95-7.86 (m, 3H), 7.60-7.53 (m, 2H), 3.68 (d, J = 2.4 Hz, 2H), 3.37-3.34 (m, 2H), 1.65-1.51 (m, 6H). | DMSO | 462.0 464.0 (M + 1) 232.3 (M/2 + 1) | Method A (TFA) | 95 | Method C, G, C |

TABLE 13-continued

| Number | PRODUCT | Salt type | Molecular Mass | $^1$H-NMR | $^1$H-NMR Solvent | LCMS | LCMS Protocol | Purity percent | Method for Coupling |
|---|---|---|---|---|---|---|---|---|---|
| 1081 | 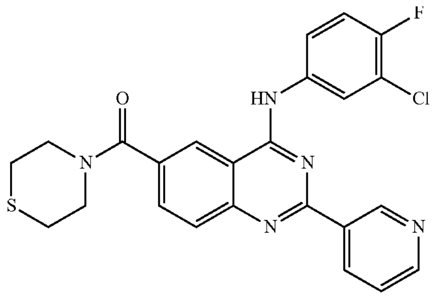 [SMILES: O=C(c1ccc2nc(-c3cccnc3)nc(Nc3ccc(F)c(Cl)c3)c2c1)N1CCSCC1] | | 479.96 | $^1$H NMR (400 MHz, DMSO-$d_6$): δ 10.20 (s, 1H), 9.53 (d, J = 1.6 Hz, 1H), 8.72-8.67 (m, 2H), 8.54 (d, J = 1.2 Hz, 1H), 8.28 (dd, J = 6.8, 2.8 Hz, 1H), 7.97-7.90 (m, 3H), 7.60-7.54 (m, 2H), 3.97-3.94 (m, 2H), 3.66-3.60 (m, 2H), 2.77-2.67 (m, 4H). | DMSO | 480.0 482.0 (M + 1) 240.6 (M/2 + 1) | Method A (TFA) | 95 | Method C, G, C |
| 1082 | 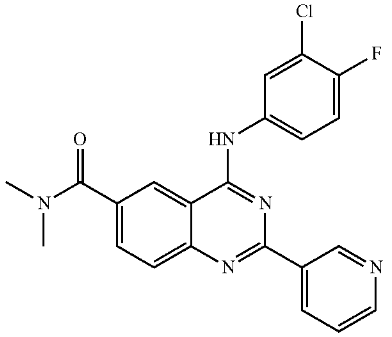 [SMILES: CN(C)C(=O)c1ccc2nc(-c3cccnc3)nc(Nc3ccc(F)c(Cl)c3)c2c1] | | 421.85 | $^1$H-NMR (400 MHz, DMSO-$d_6$): δ 10.20 (s, 1H), 9.55 (d, J = 1.6 Hz, 1H), 8.79-8.64 (m, 3H), 8.29 (dd, J = 6.8, 2.6 Hz, 1H), 8.01-7.87 (m, 3H), 7.53-7 .60 (m, 2H), 3.15-3.05 (m, 3H), 3.02 (s, 3H). | DMSO | 422.1, 424.1 (M + 1) | Method B ($NH_4HCO_3$) | 95 | Method C, G, D |
| 1083 | 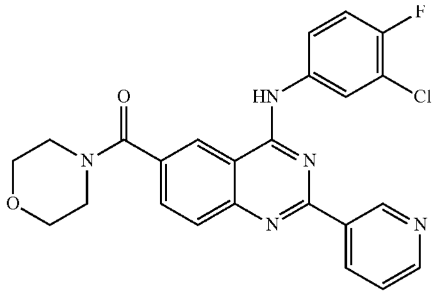 [SMILES: O=C(c1ccc2nc(-c3cccnc3)nc(Nc3ccc(F)c(Cl)c3)c2c1)N1CCOCC1] | | 463.89 | $^1$H-NMR (400 MHz, DMSO-$d_6$): δ 10.22 (s, 1H), 9.55 (d, J = 1.4 Hz, 1H), 8.77-8.65 (m, 3H), 8.02-7 .87 (m, 3H), 7.60-7.54 (m, 2H), 3.56-3.39 (m, 2H), 3.82-3.55 (m, 6H). | DMSO | 464.1, 466.1 (M + 1) | Method B ($NH_4HCO_3$) | 95 | Method C, G, D |

TABLE 13-continued

| Number | PRODUCT | Salt type | Molecular Mass | $^1$H-NMR | $^1$H-NMR Solvent | LCMS | LCMS Protocol | Purity percent | Method for Coupling |
|---|---|---|---|---|---|---|---|---|---|
| 1084 | 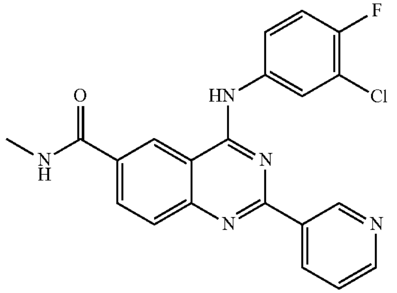 [SMILES: CNC(=O)c1ccc2nc(-c3cccnc3)nc(Nc3ccc(F)c(Cl)c3)c2c1] | | 407.83 | $^1$H-NMR (400 MHz, DMSO-$d_6$): δ 10.41 (s, 1H), 9.54 (d, J = 1.5 Hz, 1H), 9.08 (d, J = 1.3 Hz, 1H), 8.76-8.63 (m, 3H), 8.32-8.20 (m, 2H), 7.96-7.93 (m, 2H), 7.63-7.50 (m, 2H), 2.88 (d, J = 4.5 Hz, 3H). | DMSO | 408.0, 410.0 (M + 1) | Method B ($NH_4HCO_3$) | 95 | Method C, G, D |
| 1085 | 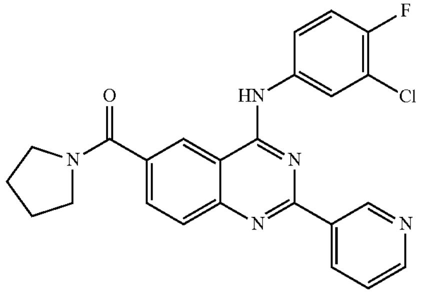 [SMILES: O=C(c1ccc2nc(-c3cccnc3)nc(Nc3ccc(F)c(Cl)c3)c2c1)N1CCCC1] | | 447.89 | $^1$H-NMR (400 MHz, DMSO-$d_6$): δ 10.23 (s, 1H), 9.55 (d, J = 1.5 Hz, 1H), 8.68-8.77 (m, 3H), 8.28 (dd, J = 6.9, 2.6 Hz, 1H), 8.02 (dd, J = 8.6, 1.6 Hz, 1H), 7.99-7.90 (m, 2H), 7.53-7.58 (m, 2H), 3.57 (t, J = 6.8 Hz, 2H), 3.51 (t, J = 6.4 Hz, 2H), 1.85-1.95 (m, 4H). | DMSO | 448.1, 420.1 (M + 1) | Method B ($NH_4HCO_3$) | 95 | Method C, G, D |
| 1086 | 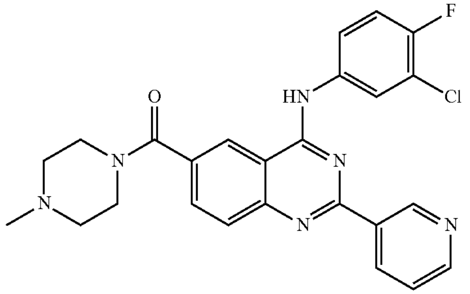 [SMILES: CN1CCN(C(=O)c2ccc3nc(-c4cccnc4)nc(Nc4ccc(F)c(Cl)c4)c3c2)CC1] | | 476.93 | $^1$H-NMR (400 MHz, DMSO-$d_6$): δ 10.22 (s, 1H), 9.54 (d, J = 1.5 Hz, 1H), 8.75-8.63 (m, 3H), 8.29 (dd, J = 6.8, 2.6 Hz, 1H), 8.01-7.84 (m, 3H), 7.60-7.53 (m, 2H), 3.72 (d, J = 2.2 Hz, 2H), 3.51-3.39 (m, 2H), 2.48-2.40 (m, 2H), 2.33 (d, J = 1.3 Hz, 2H), 2.24 (s, 3H). | DMSO | 477.1, 479.1 (M + 1) 239.1, 239.9 (M/2 + 1) | Method B ($NH_4HCO_3$) | 95 | Method C, G, D |

TABLE 13-continued

| Number | PRODUCT | Salt type | Molecular Mass | $^1$H-NMR | $^1$H-NMR Solvent | LCMS | LCMS Protocol | Purity percent | Method for Coupling |
|---|---|---|---|---|---|---|---|---|---|
| 1087 | 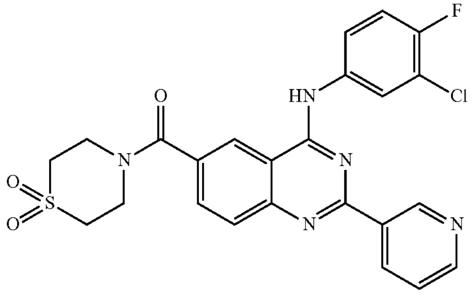 [SMILES: O=C(c1ccc2nc(-c3cccnc3)nc(Nc3ccc(F)c(Cl)c3)c2c1)N1CCS(=O)(=O)CC1] | | 511.96 | $^1$H-NMR (400 MHz, DMSO-$d_6$): δ 10.19 (s, 1H), 9.53 (d, J = 1.6 Hz, 1H), 8.59-8.82 (m, 3H), 8.26 (dd, J = 6.8, 2.6 Hz, 1H), 7.81-8.14 (m, 3H), 7.57 (m, 2H), 3.83-4.10 (m, ,4H), 3.33-3.35 (m, 4H). | DMSO | 512.1, 514.1 (M + 1) | Method B (NH4HCO3) | 95 | Method C, G, D |
| 1088 | 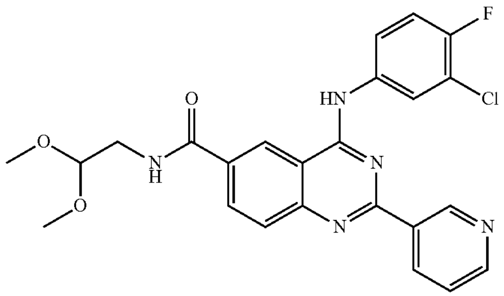 [SMILES: COC(CNC(=O)c1ccc2nc(-c3cccnc3)nc(Nc3ccc(F)c(Cl)c3)c2c1)OC] | | 481.91 | $^1$H-NMR (400 MHz, DMSO-$d_6$): δ 10.47 (s, 1H), 9.54 (d, J = 1.6 Hz, 1H), 9.23 (d, J = 1.2 Hz, 1H), 8.72-8.74 (m, 3H), 8.22-8.42 (m, 2H), 7.85-8.12 (m, 2H), 7.55-7.59 (m, 2H), 4.61 (t, J = 5.4 Hz, 1H), 3.47 (t, J = 5.2 Hz, 2H), 3.37 (s, 6H), | DMSO | 482.1, 484.2 (M + 1) | Method B (NH4HCO3) | 95 | Method C, G, D |
| 1089 | 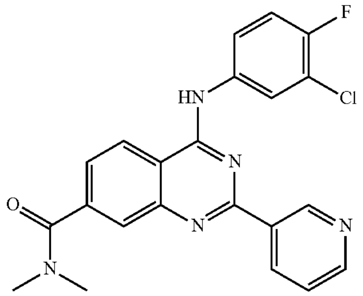 [SMILES: CN(C)C(=O)c1ccc2c(Nc3ccc(F)c(Cl)c3)nc(-c3cccnc3)nc2c1] | | 421.85 | $^1$H-NMR (400 MHz, DMSO-$d_6$): δ 10.23 (s, 1H), 9.59 (d, J = 1.2 Hz, 1H), 8.72-8.77 (m, 2H), 8.68 (d, J = 8.4 Hz, 1H), 8.34 (dd, J = 7.2, 2.0 Hz, 1H), 7.96-8.00 (m, 1H), 7.92 (m, 1H), 7.72-7.74 (m, 1H), 7.58-7.65 (m, 2H), 3.13 (s, 3H), 3.03 (s, 3H). | DMSO | 422.0 (M + 1) | Method A (TFA) | 95 | Method C, G, D |

TABLE 13-continued

| Number | PRODUCT | Salt type | Molecular Mass | $^1$H-NMR | $^1$H-NMR Solvent | LCMS | LCMS Protocol | Purity percent | Method for Coupling |
|---|---|---|---|---|---|---|---|---|---|
| 1090 | 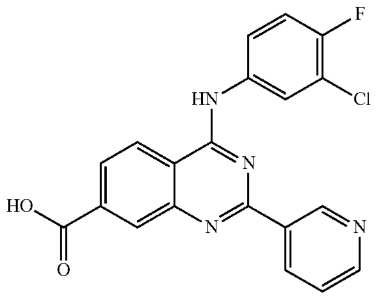 [SMILES: O=C(O)c1ccc2c(Nc3ccc(F)c(Cl)c3)nc(-c3cccnc3)nc2c1] | | 394.79 | $^1$H-NMR (400 MHz, DMSO-$d_6$): δ 10.25 (s, 1H), 9.54 (s, 1H), 8.68-8.70 (m, 2H), 8.60 (d, J = 8.4 Hz, 1H), 8.37 (s, 1H), 8.32 (dd, J = 7.2, 2.8 Hz, 1H), 8.11 (d, J = 7.2 Hz, 1H), 7.93-7.97 (m, 1H), 7.51-7.58 (m, 2H). | DMSO | 395.0 (M + 1) | Method A (TFA) | 95 | Method C, G, D |
| 1091 | 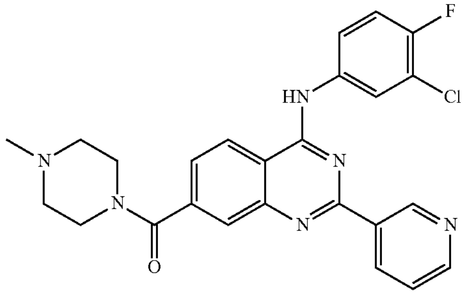 [SMILES: CN1CCN(C(=O)c2ccc3c(Nc4ccc(F)c(Cl)c4)nc(-c4cccnc4)nc3c2)CC1] | | 476.93 | $^1$H-NMR (400 MHz, DMSO-$d_6$): δ 10.19 (s, 1H), 9.53 (s, 1H), 8.62-8.72 (m, 3H), 8.29 (dd, J = 6.8, 2.4 Hz, 1H), 7.91-7.94 (m, 1H), 7.83 (s, 1H), 7.66 (d, J = 8.8 Hz, 1H), 7.53-7.59 (m, 2H), 3.69-3.71 (s, 2H), 3.36-3.38 (s, 2H), 2.42-2.44 (s, 2H), 2.30-2.32 (s, 2H), 2.23 (s, 3H). | DMSO | 477.2 (M + 1) 239.1 (1/2M +1) | Method B (NH4HCO3) | 95 | Method C, G, D |
| 1092 | 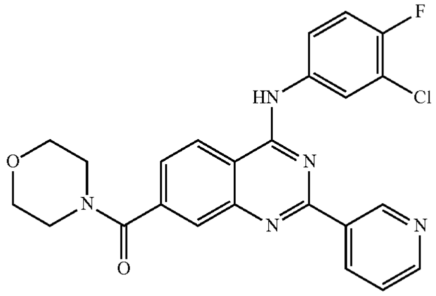 [SMILES: O=C(c1ccc2c(Nc3ccc(F)c(Cl)c3)nc(-c3cccnc3)nc2c1)N1CCOCC1] | | 463.89 | $^1$H-NMR (400 MHz, DMSO-$d_6$): δ 10.18 (s, 1H), 9.52 (s, 1H), 8.H)-8.71 (m, 3H), 8.28 (d, J = 4.8 Hz, 1H), 7.87-7.96 (m, 2H), 7.68 (d, J = 8.0 Hz, 1H), 7.52-7.58 (m, 2H), 3.61-3.71 (m, 6H), 3.40 (m, 2H). | DMSO | 464.1 (M + 1) | Method B (NH4HCO3) | 95 | Method G, D |

TABLE 13-continued

| Number | PRODUCT | Salt type | Molecular Mass | $^1$H-NMR | $^1$H-NMR Solvent | LCMS | LCMS Protocol | Purity percent | Method for Coupling |
|---|---|---|---|---|---|---|---|---|---|
| 1093 | 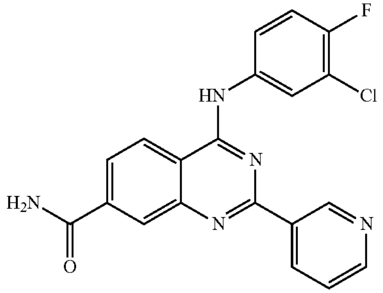 [SMILES: NC(=O)c1ccc2c(Nc3ccc(F)c(Cl)c3)nc(-c3cccnc3)nc2c1] | | 393.8 | $^1$H-NMR (400 MHz, DMSO-$d_6$): δ 10.20 (s, 1H), 9.54 (d, J = 1.6 Hz, 1H), 8.62-8.72 (m, 3H), 8.42 (d, J = 1.2 Hz, 1H), 8.37 (s, 1H), 8.30 (dd, J = 7.2, 2.8 Hz, 1H), 8.08 (dd, J = 8.4, 1.2 Hz, 1H), 7.91-7.95 (m, 1H), 7.71 (s, 1H), 7.53-7.60 (m, 2H). | DMSO | 394.1 (M + 1) | Method B (NH4HCO3) | 95 | Method G, D |
| 1094 | 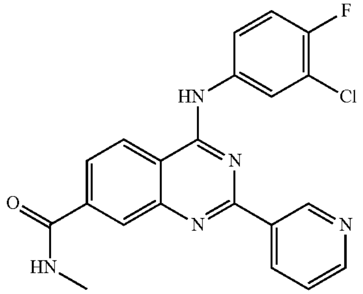 [SMILES: CNC(=O)c1ccc2c(Nc3ccc(F)c(Cl)c3)nc(-c3cccnc3)nc2c1] | | 407.83 | $^1$H-NMR (400 MHz, DMSO-$d_6$): δ 10.19 (s, 1H), 9.53 (s, 1H), 8.84 (d, J = 4.0 Hz, 1H), 8.60-8.72 (m, 3H), 8.35 (s, 1H), 8.29 (dd, J = 6.8, 2.8 Hz, 1H), 8.05 (d, J = 8.4 Hz, 1H), 7.90-7.93 (m, 1H), 7.52-7.59 (m, 2H), 2.87 (d, J = 4.8 Hz, 3H). | DMSO | 408.1 (M + 1) | Method B (NH4HCO3) | 95 | Method G, D |
| 1095 | 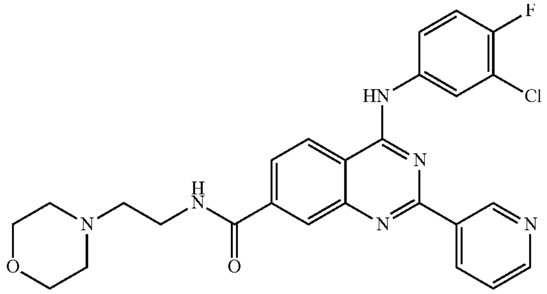 [SMILES: O=C(NCCN1CCOCC1)c1ccc2c(Nc3ccc(F)c(Cl)c3)nc(-c3cccnc3)nc2c1] | HCl | 506.96 | $^1$H-NMR (400 MHz, DMSO-$d_6$): δ 10.20 (s, 1H), 9.53 (d, J = 1.6 Hz, 1H), 8.85 (t, J = 5.6 Hz, 1H), 8.61-8.72 (m, 3H), 8.36 (d, J = 1.2 Hz, 1H), 7.93 (dd, J = 6.4, 2.4 Hz, 1H), 8.03 (dd, J = 8.8, 1.6 Hz, 1H), 7.91-7.95 (m, 1H), 7.52-7.59 (m, 2H), 3.60 (t, J = 4.4 Hz, 4H), 3.46-3.48 (q, J = 6.4 Hz, 2H), 2.51-2.54 (m, 2H), 2.42-2.48 (m, 4H). | DMSO | 507.1 (M + 1) 254.1 (M/2 +1) | Method B (NH4HCO3) | 95 | Method G, C |

TABLE 13-continued
| Number | PRODUCT | Salt type | Molecular Mass | $^1$H-NMR | $^1$H-NMR Solvent | LCMS | LCMS Protocol | Purity percent | Method for Coupling |
|---|---|---|---|---|---|---|---|---|---|
| 1096 | 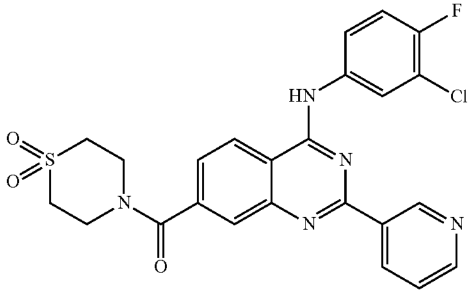 [SMILES: O=C(c1ccc2c(Nc3ccc(F)c(Cl)c3)nc(-c3cccnc3)nc2c1)N1CCS(=O)(=O)CC1] | | 511.96 | $^1$H-NMR (400 MHz, DMSO-$d_6$): δ 10.22 (s, 1H), 9.56 (d, J = 1.8 Hz, 1H), 8.61-8.79 (m, 3H), 8.31 (dd, J = 6.8, 2.6 Hz, 1H), 7.88-8.11 (m, 2H), 7.78 (dd, J = 8.4, 1.4 Hz, 1H), 7.51-7.66 (m, 2H), 4.12 (brs, 2H), 3.76 (brs, 2H), 3.30-3.33 (m, 4H). | DMSO | 512.1, 514.2 (M + 1) | Method B (NH4HCO3) | 95 | Method G, D |
| 1097 | 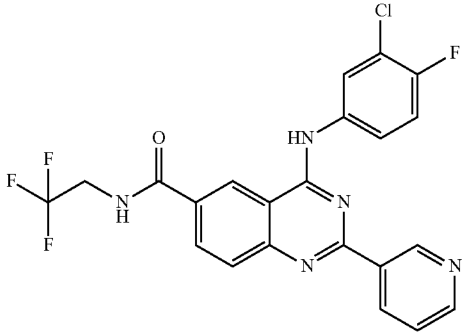 [SMILES: O=C(NCC(F)(F)F)c1ccc2nc(-c3cccnc3)nc(Nc3ccc(F)c(Cl)c3)c2c1] | | 474 | $^1$H-NMR (400 MHz, DMSO-$d_6$): δ 10.64 (brs, 1H), 9.53 (s, 1H), 9.44 (t, J = 6.4 Hz, 1H), 9.35 (s, 1H), 8.90 (d, J = 8.0 Hz, 1H), 8.85 (d, J = 4.8 Hz, 1H), 8.35 (dd, J = 8.4, 1.2 Hz, 1H), 8.27 (dd, J = 6.8, 2.4 Hz, 1H), 8.00-7.97 (m, 2H), 7.82 (dt, J = 13.2, 5.2 Hz, 1H), 7.55 (t, J = 8.8 Hz, 1H), 4.22-4.18 (m, 2H). | DMSO | 475.7, 476.6 (M + 1) | Method B (NH4HCO3) | 95 | Method C, G, D |

Scheme 41: General route for the synthesis of compounds with general formula xxxvi

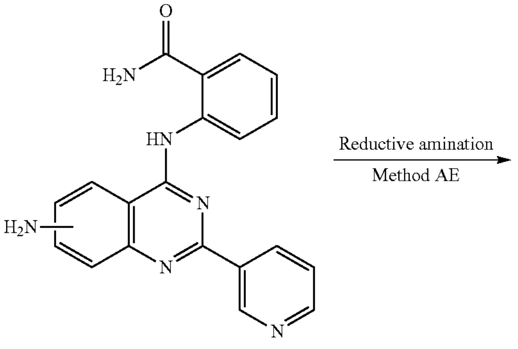

vi

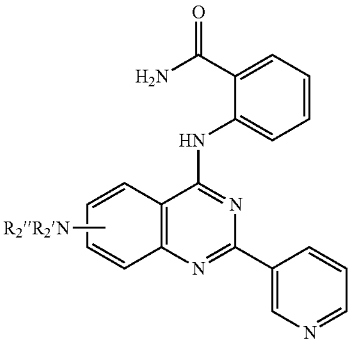

xxxvi

Scheme 42: Representative synthesis of compounds of formula xxxvi-a: (see Scheme 41)

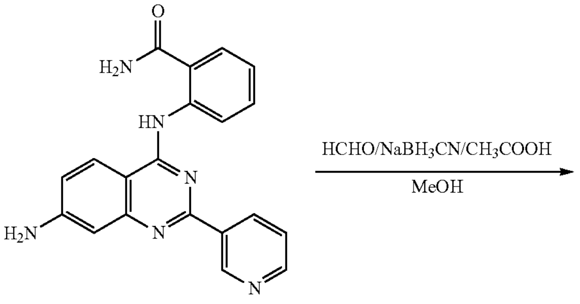

vi-o

-continued

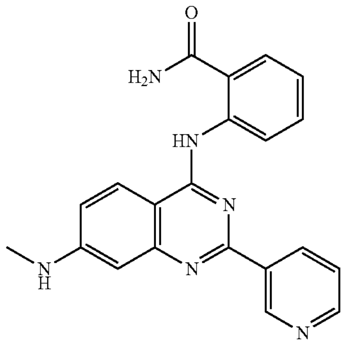

xxxvi-a

Method AE: 2-(7-(Methylamino)-2-(pyridin-3-yl)quinazolin-4-ylamino)benzamide (xxxvi-a)

A mixture of 2-(7-amino-2-(pyridin-3-yl)quinazolin-4-ylamino)benzamide (160 mg, 0.449 mmol, 1.0 eq.) and HCHO (40%, 37 mg, 0.494 mmol, 1.1 eq.), acetic acid (2 drops) were stirred at room temperature for 0.5 h. $NaBH_3CN$ (34 mg, 0.449 mmol, 1.0 eq.) was added and the mixture was stirred at room temperature overnight. After filtration, the filtrate was concentrated to give the crude product, which was purified by reverse phase chromatography ($MeOH/H_2O$=3:7) to afford 28 mg of xxxvi-a as a white solid (17%). LCMS m/z=371.1 (M+1), 372.1 (M+2) (Method B) (retention time=1.60 min). $^1H$ NMR (400 MHz, DMSO-$d_6$): δ 12.71 (s, 1H), 9.58 (d, J=1.6 Hz, 1H), 9.14-9.12 (m, 1H), 8.74-8.69 (m, 2H), 8.45 (s, 1H), 7.93-7.91 (m, 1H), 7.85 (d, J=9.2 Hz, 2H), 7.67-7.71 (m, 1H), 7.59-7.55 (m, 1H), 7.12-7.16 (m, 1H), 7.06-7.03 (m, 1H), 6.82-6.81 (m, 1H), 6.70 (d, J=2.4 Hz, 1H), 2.84 (d, J=4.8 Hz, 3H).

The compounds in the following table were prepared in a manner analogous to that described in Scheme 41, replacing formaldehyde with the appropriate aldehyde and 2-aminobenzamide with the appropriate aniline.

TABLE 14

| Number | PRODUCT | Salt type | Molecular Mass | $^1$H-NMR | $^1$H-NMR Solvent | LCMS | LCMS Protocol | Purity percent | Method for Coupling |
|---|---|---|---|---|---|---|---|---|---|
| 1098 | 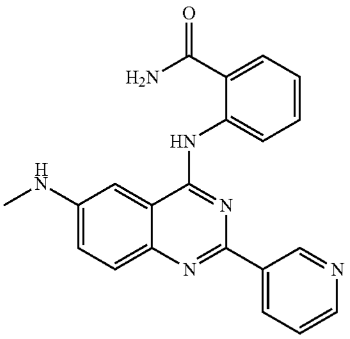 [SMILES: CNc1ccc2nc(-c3cccnc3)nc(Nc3ccccc3C(N)=O)c2c1] | | 370.41 | $^1$H-NMR (400 MHz, DMSO-$d_6$): δ 12.87 (s, 1H), 9.57 (d, J = 1.2 Hz, 1H), 9.25 (d, J = 8.8 Hz, 1H), 8.65-8.71 (m, 2H), 8.47 (s, 1H), 7.95-7.99 (m, 2H), 7.69-7.74 (m, 2H), 7.56 (dd, J = 7.7, 5.0 Hz, 1H), 7.33 (dd, J = 9.1, 1.9 Hz, 1H), 7.16 (t, J = 7.2 Hz, 1H), 6.90 (d, J = 1.2 Hz, 1H), 6.62 (d, J = 4.8 Hz, 1H), 2.88 (d, J = 4.8 Hz, 3H). | DMSO | 371.1 (M + 1) | Method B ($NH_4HCO_3$) | 95 | Method AE |
| 1099 | 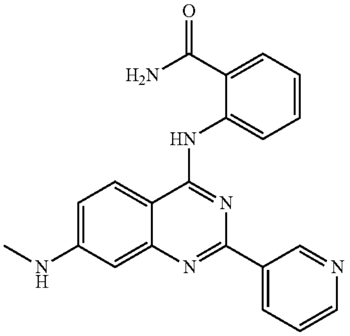 [SMILES: CNc1ccc2c(Nc3ccccc3C(N)=O)nc(-c3cccnc3)nc2c1] | | 370.41 | $^1$H-NMR (400 MHz, DMSO-$d_6$): δ 12.71 (s, 1H), 9.58 (d, J = 1.4 Hz, 1H), 9.13 (d, J = 7.7 Hz, 1H), 8.80-8.64 (m, 2H), 8.45 (s, 1H), 7.92 (dd, J = 7.9, 1.4 Hz, 1H), 7.85 (d, J = 9.2 Hz, 2H), 7.76-7.62 (m, 1H), 7.57 (dd, J = 7.9, 4.8 Hz, 1H), 7.15 (dd, J = 11.2, 4.0 Hz, 1H), 7.04 (dd, J = 9.0, 2.3 Hz, 1H), 6.81 (q, J = 4.8 Hz, 1H), 6.70 (d, J = 2.2 Hz, 1H), 2.85 (d, J = 4.9 Hz, 3H). | DMSO | 371.1 (M + 1) | Method B ($NH_4HCO_3$) | 95 | Method AE |

Scheme 43: General route for the synthesis of compounds with general formula xxxxi:

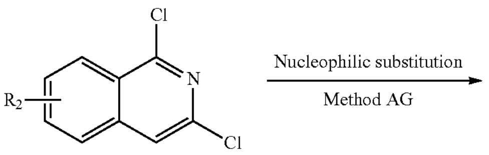

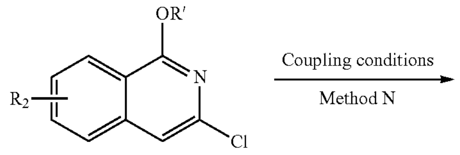

xxxvii

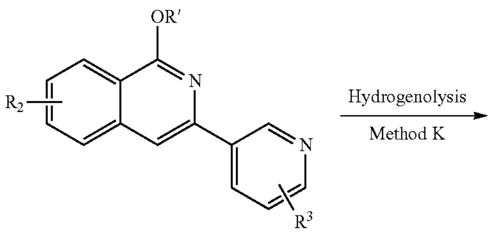

xxxviii

-continued

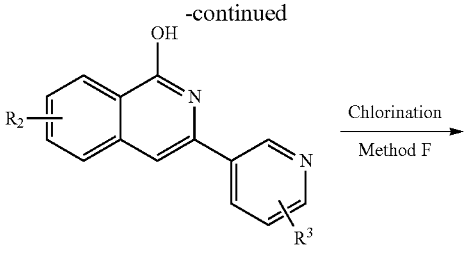

xxxviv

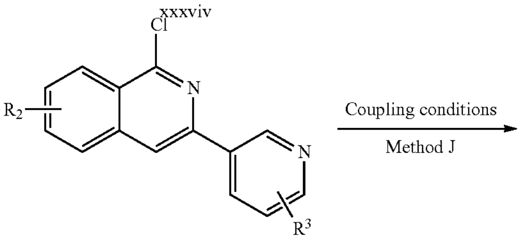

xl

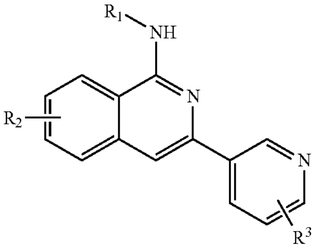

xli

Scheme 44: Representative synthesis of compounds of formula xli-a: (see Scheme 43)

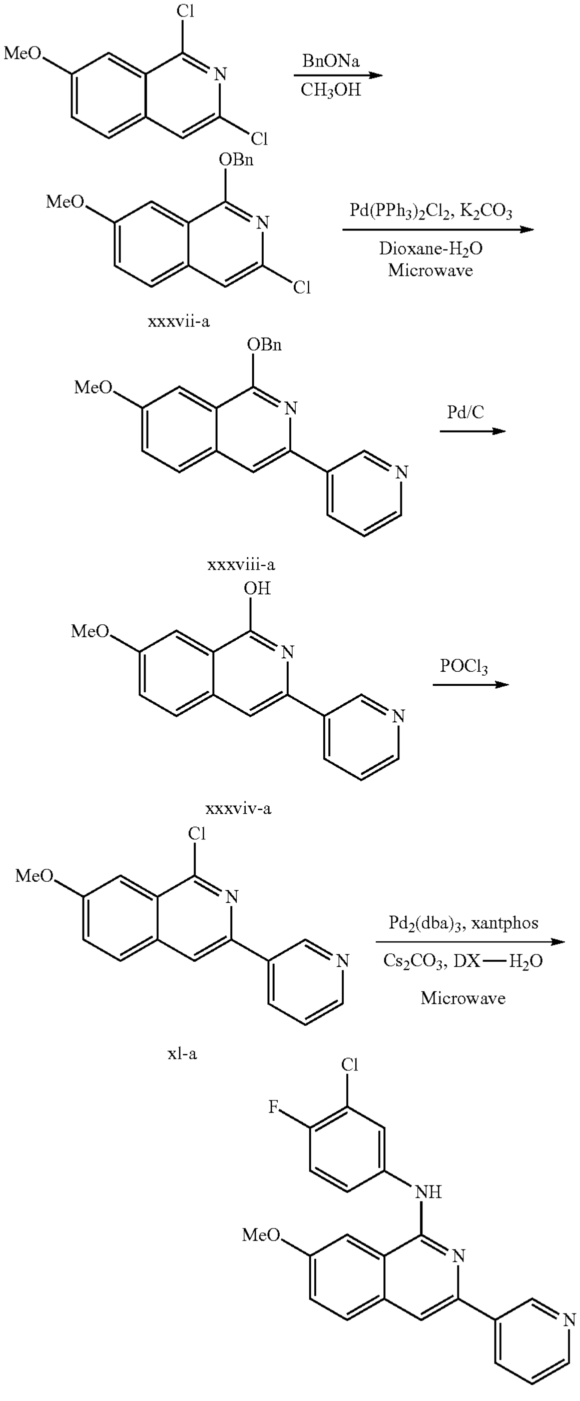

xxxvii-a xxxviii-a xxxviv-a xl-a xli-a

Method AG: 1-(Benzyloxy)-3-chloro-7-methoxyisoquinoline (xxxvii-a)

1,3-dichloro-7-methoxyisoquinoline (2.00 g, 8.8 mmol, 1.0 eq.) was dissolved in 30 mL anhydrous toluene and sodium benzyloxide (2.30 g, 17.6 mmol, 2.0 eq.) was added. The mixture was heated to 80° C. for 18 h. TLC indicated the reaction was complete. The mixture was concentrated to give the crude product, which was purified by chromatography on silica gel (eluted with petroleum ether) to give 2.20 g of xxxvii-a as a white solid (84.6%). LCMS m/z=300.1, 302.0 (M+1) (Method B) (retention time=2.23 min).

1-(Benzyloxy)-7-methoxy-3-(pyridin-3-yl)isoquinoline (xxxviii-a)

1-(Benzyloxy)-7-methoxy-3-(pyridin-3-yl)isoquinoline was prepared using Method N2. 1-(Benzyloxy)-3-chloro-7-methoxyisoquinoline (93 mg, 0.5 mmol, 1.0 eq.), potassium carbonate (357 mg, 2.5 mmol, 5.0 eq.), and $Pd(PPh_3)_2Cl_2$ (18 mg, 0.026 mmol, 0.05 eq.) was dissolved in the mixed solvent of 1,4-dioxane (3 mL) and water (1 mL). The resulting mixture was stirred at 120° C. for 30 min under the microwave condition. The solid was filtrated off and the filtrate was concentrated. The residue was partitioned between ethyl acetate and water. The combined organic layers were washed with brine, dried over anhydrous sodium sulfate. After filtration and evaporation, the residue was purified by silica gel chromatography (petroleum ether/ethyl acetate=1:10) to afford 100 mg of xxxviii-a as a yellow solid (84.7%).

7-Methoxy-3-(pyridin-3-yl)isoquinolin-1-ol (xxxviv-a)

7-Methoxy-3-(pyridin-3-yl)isoquinolin-1-ol (prepared in a manner analogous to that described for 2-amino-5-methoxybenzoic acid in Method K, replacing 5-methoxy-2-nitrobenzoic acid with 1-(benzyloxy)-7-methoxy-3-(pyridin-3-yl) isoquinoline) was obtained in a 63.6% yield to give 280 mg of xxxviv-a as a yellow solid. This was carried on without further purification, 1-Chloro-7-methoxy-3-(pyridin-3-yl)isoquinoline (xl-a)

1-Chloro-7-methoxy-3-(pyridin-3-yl)isoquinoline (prepared in a manner analogous to that described for 4-chloro-6-propoxy-2-pyridin-3-yl-quinazoline in Method F1, replacing 6-propoxy-2-pyridin-3-yl-1H-quinazolin-4-one with 3-(pyridin-3-yl)isoquinolin-1-ol) was obtained in a 73.0% yield to give 60 mg of xl-a as a brown solid. MS m/z=241.1 (M+1) (Method A) (retention time=1.34 min).

N-(3-Chloro-4-fluorophenyl)-7-methoxy-3-(pyridin-3-yl)isoquinolin-1-amine (xli-a)

N—(N-(3-chloro-4-fluorophenyl)-7-methoxy-3-(pyridin-3-yl)isoquinolin-1-amine was prepared using Method J. A mixture of 1-chloro-7-methoxy-3-(pyridin-3-yl)isoquinoline (40 mg, 0.17 mmol, 1.0 eq.), 3-chloro-4-fluoro aniline (30 mg, 0.21 mmol, 1.2 eq.), $Pd_2(dba)_3$ (10 mg, 0.011 mmol, 0.06 eq.), Xantphos (15 mg, 0.026 mmol, 0.15 eq.), cesium carbonate (167 mg, 0.52 mmol, 3.0 eq.) was suspended in the mixed solvent of 1,4-dioxane (4 mL) and water (1 mL). The resulting mixture was stirred at 120° C. for 30 min under the microwave conditions. After cooling, the resulting mixture was partitioned between water and ethyl acetate. The combined organic layers were washed with water and brine, dried over anhydrous sodium sulfate. After filtration and evaporation, the residue was purified by prep-HPLC to afford 3 mg of xli-a as a yellow solid (yield 5.2%). LCMS m/z=380.1 (M+1) (Method B). $^1H$ NMR (400 MHz, DMSO-$d_6$): δ 9.35 (s, 1H), 9.30 (d, J=2.0 Hz, 1H), 8.57 (dd, J=4.7, 1.5 Hz, 1H), 8.41 (td, J=8.0, 1.8 Hz, 1H), 8.30 (dd, J=6.9, 2.6 Hz, 1H), 7.94-7.87 (m, 4H), 7.43-7.49 (m, 3H), 3.99 (s, 3H).

The compounds in the following table were prepared in a manner analogous to that described in Scheme 43, replacing with the appropriate isoquinoline and aniline.

TABLE 15

| Number | PRODUCT | Salt type | Molecular Mass | $^1$H-NMR | $^1$H-NMR Solvent | LCMS | LCMS Protocol | Purity percent | Method for Coupling |
|---|---|---|---|---|---|---|---|---|---|
| 1100 | 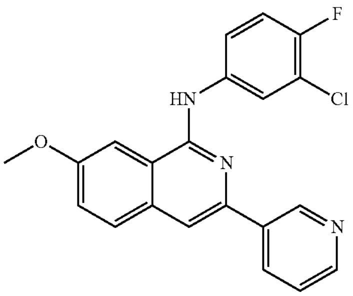 [SMILES: COc1ccc2cc(-c3cccnc3)nc(Nc3ccc(F)c(Cl)c3)c2c1] | | 379.81 | $^1$H-NMR (400 MHz, DMSO-$d_6$): δ 9.35 (s, 1H), 9.30 (d, J = 2.0 Hz, 1H), 8.57 (dd, J = 4.7, 1.5 Hz, 1H), 8.41 (td, J = 8.0, 1.8 Hz, 1H), 8.30 (dd, J = 6.9, 2.6 Hz, 1H), 7.94-7.87 (m, 4H), 7.43-7.49 (m, 3H), 3.99 (s, 3H). | DMSO | 380.1, 382.0 (M + 1) | Method B (NH4HCO3) | 95 | Method J |
| 1101 | 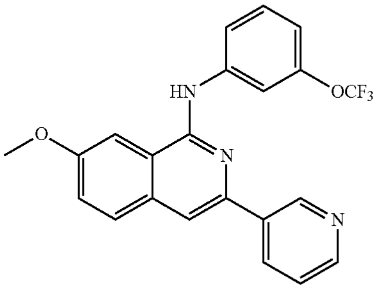 [SMILES: COc1ccc2cc(-c3cccnc3)nc(Nc3cccc(OC(F)(F)F)c3)c2c1] | | 411.38 | $^1$H-NMR (400 MHz, DMSO-$d_6$): δ 9.46 (s, 1H), 9.31 (d, J = 1.75 Hz, 1H), 8.57 (dd, J = 4.6, 1.3 Hz, 1H), 8.45-8.41 (m, 1H), 8.19 (s, 1H), 7.99-7.94 (m, 2H), 7.91-7.86 (m, 2H), 7.54-7.44 (m, 3H), 7.01 (d, J = 8.1 Hz, 1H), 4.00 (s, 3H). | DMSO | 412.1 (M + 1) | Method B (NH4HCO3) | 95 | Method J |
| 1102 | 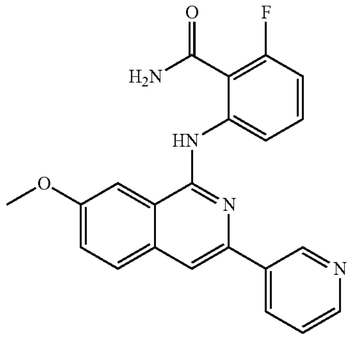 | | 388.39 | $^1$H-NMR (400 MHz, DMSO-$d_6$): δ 11.35 (s, 1H), 9.34 (d, J = 1.9 Hz, 1H), 8.80 (d, J = 8.4 Hz, 1H), 8.59 (dd, J = 4.7, 1.48 Hz, 1H), 8.49-8.45 (m, 1H), 8.26 (s, 1H), 8.13 (s, 1H), 8.02 (s, 1H), 7.97-7.92 (m, 1H), 7.61 (td, J = 14.9, 7.5 Hz, 1H), 7.56-7.48 (m, 3H), 6.95 (dd, J = 10.3, 8.3 Hz, 1H), 3.98 (s, 3H). | DMSO | 389.1 (M + 1) | Method B (NH4HCO3) | 95 | Method J |
| 1103 | 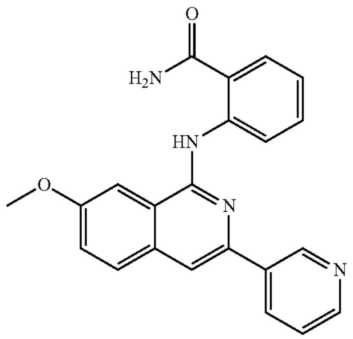 [SMILES: COc1ccc2cc(-c3cccnc3)nc(Nc3ccccc3C(N)=O)c2c1] | | 370.4 | $^1$H-NMR (400 MHz, CDCl3): δ 11.89 (s, 1H), 9.39 (s, 1H), 9.29 (s, 1H), 8.63-8.59 (m, 1H), 8.42-8.37 (m, 1H), 7.75 (d, J = 8.8 Hz, 1H), 7.60-7.62 (m, 4H), 7.44-7.33 (m, 3H), 7.05-7.00 (m, 1H), 4.06 (s, 3H). | CDCl3 | 371.1 (M + 1) | Method B (NH4HCO3) | 95 | Method J |

TABLE 15-continued

| Number | PRODUCT | Salt type | Molecular Mass | $^1$H-NMR | $^1$H-NMR Solvent | LCMS | LCMS Protocol | Purity percent | Method for Coupling |
|---|---|---|---|---|---|---|---|---|---|
| 1104 | 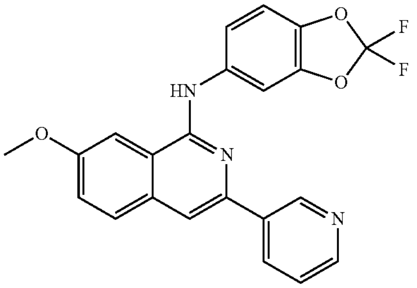 [SMILES: COc1ccc2cc(-c3cccnc3)nc(Nc3ccc4c(c3)OC(F)(F)O4)c2c1] | | 407.37 | $^1$H-NMR (400 MHz, CDCl3): δ 9.28 (s, 1H), 8.60 (d, J = 4.6 Hz, 1H), 8.34 (d, J = 7.8 Hz, 1H), 7.85 (s, 1H), 7.79 (d, J = 8.9 Hz, 1H), 7.63 (s, 1H), 7.43-7.35 (m, 2H), 7.22 (d, J = 8.6 Hz, 1H), 7.17 (s, 1H), 7.09-7.03 (m, 2H), 4.00 (s, 3H). | CDCl3 | 408.1 (M + 1) | Method B (NH4HCO3) | 95 | Method J |
| 1105 | 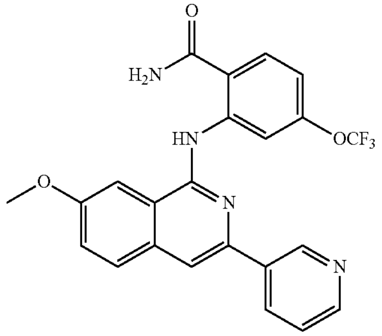 [SMILES: COc1ccc2cc(-c3cccnc3)nc(Nc3cc(OC(F)(F)F)ccc3C(N)=O)c2c1] | | 454.4 | $^1$H-NMR (400 MHz, DMSO-$d_6$): δ 13.00 (s, 1H), 9.43 (d, J = 1.2 Hz, 1H), 9.35 (s, 1H), 8.63 (d, J = 3.7 Hz, 1H), 8.53 (s, 1H), 8.48-8.44 (m, 1H), 8.03-8.09 (m, 3H), 7.97 (d, J = 8.9 Hz, 1H), 7.65 (d, J = 1.8 Hz, 1H), 7.56-7.50 (m, 2H), 7.05 (dd, J = 8.6, 1.93 Hz, 1H), 4.01 (s, 3H). | DMSO | 455.1 (M + 1) | Method B (NH4HCO3) | 95 | Method J |
| 1106 | 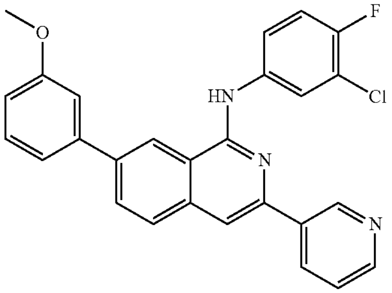 [SMILES: COc1cccc(-c2ccc3cc(-c4cccnc4)nc(Nc4ccc(F)c(Cl)c4)c3c2)c1] | | 455.91 | 1H-NMR (400 MHz, DMSO-$d_6$): δ 9.65 (s, 1H), 9.37 (d, J = 1.7 Hz, 1H), 8.83 (s, 1H), 8.63 (dd, J = 4.7, 1.3 Hz, 1H), 8.54-8.43 (m, 1H), 8.35 (dd, J = 6.9, 2.6 Hz, 1H), 8.15 (dd, J = 8.5, 1.4 Hz, 1H), 8.03 (t, J = 4.3 Hz, 2H), 7.91-7.95 (m, 1H), 7.46-7.55 (m, 5H), 7.11-7.01 (m, 1H), 3.91 (s, 3H). | DMSO | 456.1, 458.1 (M + 1) | Method B ($NH_4HCO_3$) | 95 | Method J |
| 1107 | 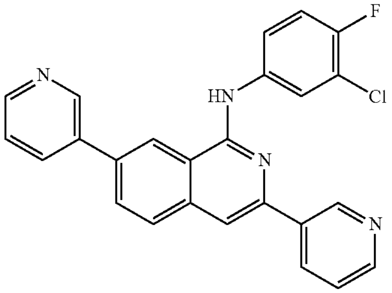 | | | $^1$H-NMR (400 MHz, DMSO-$d_6$): δ 9.63 (s, 1H), 9.36 (d, J = 1.9 Hz, 1H), 9.19 (d, J = 1.9 Hz, 1H), 8.91 (s, 1H), 8.67 (dd, J = 4.8, 1.5 Hz, 1H), 8.62 (dd, J = 4.7, 1.5 Hz, 1H), 8.53-8.44 (m, 1H), 8.35-8.32 (m, 2H), 8.19 (dd, J = 8.5, 1.5 Hz, 1H), 8.13-8.01 (m, 2H), 7.92 (ddd, J = 9.1, 4.3, 2.7 Hz, 1H), 7.61 (dd, J = 7.9, 4.8 Hz, 1H), 7.55 (dd, J = 8.0, 4.8 Hz, 1H), 7.50 (t, J = 9.1 Hz, 1H). | DMSO | 426.7 428.7 (M + 1) | Method B (NH4HCO3) | 95 | Method J |

Scheme 45: General route for the synthesis of compounds with general formula xxxv-a:

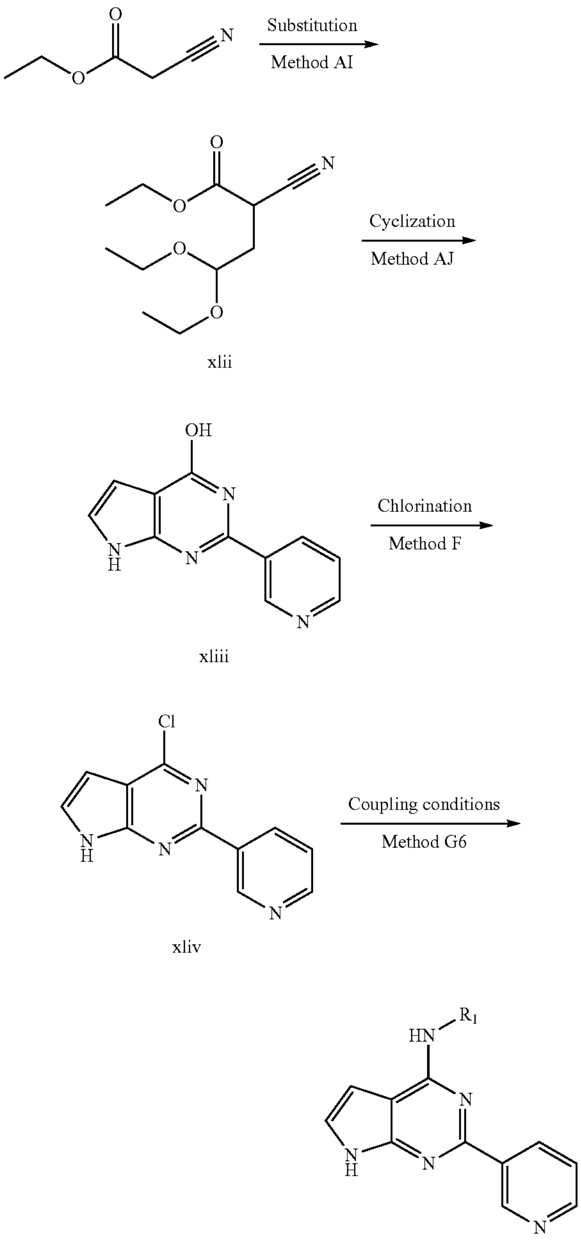

Scheme 46: Representative synthesis of compounds of formula xxxv-a: (see Scheme 45)

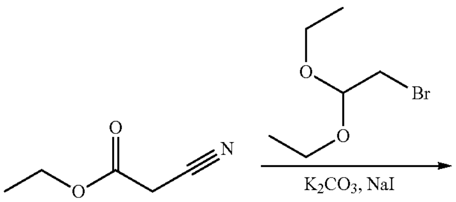

-continued

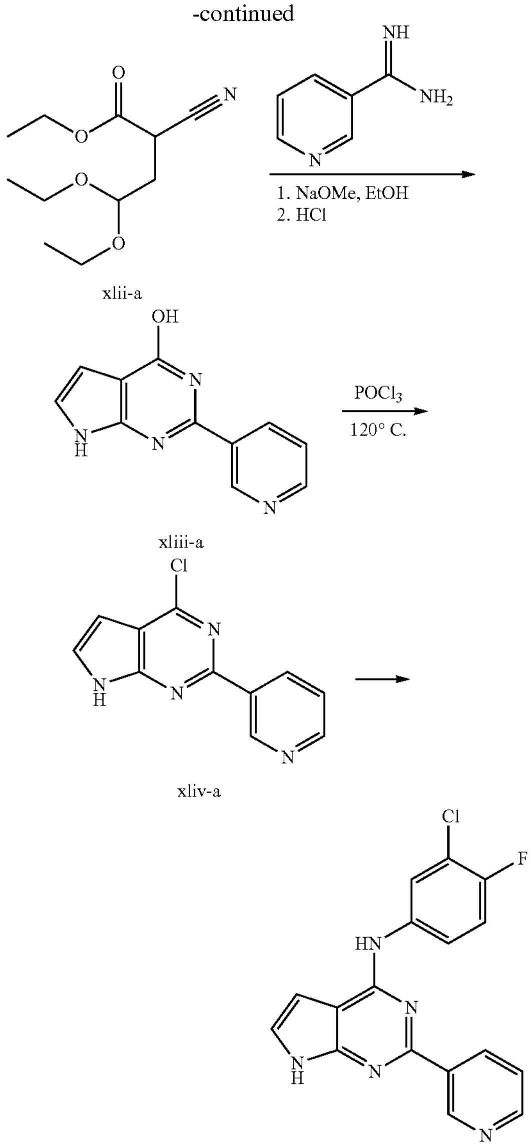

Method AI: Ethyl 2-cyano-4,4-diethoxybutanoate (xlii-a)

2-Bromo-1,1-diethoxyethane (4 g, 20 mmol, 1.0 eq.) was added to a mixture of ethyl 2 cyanoacetate (11.4 g, 101 mmol, 5.0 eq.), $K_2CO_3$ (2.8 g, 20 mmol, 1.0 eq.) and NaI (200 mg, 1.3 mmol, 0.06 eq.), as described in J. Chem. Soc., 1960, 131-138. The reaction mixture was refluxed for 4 h at 145° C. After cooling, the reaction mixture was purified by chromatography on silica gel (eluted with petroleum ether/ethyl acetate (80:1→40:1→10:1) to give 3.57 g of xlii-a as a colorless oil (78%). $^1H$ NMR (400 MHz, $CDCl_3$): δ 4.70 (t, J=5.6 Hz, 1H), 4.26 (q, J=7.2 Hz, 2H), 3.78-3.64 (m, 3H), 3.62-3.45 (m, 2H), 2.35-2.14 (m, 2H), 1.34 (q, J=7.2 Hz, 3H), 1.25-1.16 (m, 6H).

Method AJ: 2-(Pyridin-3-yl)-7H-pyrrolo[2,3-d]pyrimidin-4-ol (xliii)

To a solution of nicotinimidamide (5.03 g, 41.6 mmol, 1.2 eq.) in EtOH (100 mL), was added NaOMe (4.8 g, 88.8 mmol, 2.5 eq.). The mixture was stirred at room temperature for 4 h. The reaction mixture was added to ethyl 2-cyano-4,4-diethoxybutanoate (8.00 g, 34.9 mmol, 1 eq.). This mixture was stirred at 105° C. overnight. After cooling, the reaction mixture was acidified with conc. HCl and stirred at room temperature for 2 h. A precipitate formed and was collected and washed with $H_2O$ (20 mL×2). After lyophilization, 3.10 g of product: was obtained as a gray yellow solid (yield 41.8%). LCMS=213.1 (M+1) (Method B) (retention time=1.07 min) $^1$H NMR (400 MHz, DMSO-$d_6$): δ 12.26 (s, 1H), 12.04 (s, 1H), 9.23 (d, J=1.6 Hz, 1H), 8.70 (dd, J=4.8, 1.2 Hz, 1H), 8.43-8.40 (m, 1H), 7.55 (dd, J=8.0, 4.8 Hz, 1H), 7.12 (d, J=1.6 Hz, 1H), 6.51 (d, J=2.8 Hz, 1H).

4-Chloro-2-(pyridin-3-yl)-7H-pyrrolo[2,3-d]pyrimidine (xlv-a)

4-Chloro-2-(pyridin-3-yl)-7H-pyrrolo[2,3-d]pyrimidine (prepared in a manner analogous to that described for 4-chloro-6-propoxy-2-pyridin-3-yl-quinazoline in Method F1 replacing 6-propoxy-2-pyridin-3-yl-1H-quinazolin-4-one with 2-(pyridin-3-yl)-7H-pyrrolo[2,3-d]pyrimidin-4-ol) to give 450 mg of xliv-a in a 69.0% yield as a brown solid. LCMS m/z=231.0, 233.0 (M+1) (Method B) (retention time=1.60 min).

N-(3-chloro-4-fluorophenyl)-2-(pyridin-3-yl)-7H-pyrrolo[2,3-d]pyrimidin-4-amine (xlv-a)

N-(3-chloro-4-fluorophenyl)-2-(pyridin-3-yl)-7H-pyrrolo[2,3-d]pyrimidin-4-amine (prepared in a manner analogous to that described for N-(3-chloro-4-fluorophenyl)-6-(3-(dimethylamino)propyl)-2-(pyridin-3-yl)quinazolin-4-amine using Method G6, replacing 3-(4-(3-chloro-4-fluorophenylamino)-2-(pyridin-3-yl)quinazolin-6-yl)propyl methanesulfonate with 4-chloro-2-(pyridin-3-yl)-7H-pyrrolo[2,3-d]pyrimidine) to give a 11.3% yield, 10 Mg of xlv-a as brown solid. LCMS m/z=340.1, 342.0 (M+1) (Method B) (retention time=1.814 min). $^1$H NMR (400 MHz, DMSO-$d_6$): δ 9.48 (d, J=1.6 Hz, 1H), 8.62 (dd, J=4.8, 1.6 Hz, 1H), 8.60-8.56 (m, 1H), 8.27 (dd, J=6.4, 2.4 Hz, 1H), 8.06 (ddd, J=8.8, 4.0, 2.8 Hz, 1H), 7.71 (d, J=3.6 Hz, 1H), 7.66 (t, J=9.2 Hz, 1H), 7.50 (dd, J=8.0, 4.8 Hz, 1H), 7.41 (br s, 2H), 6.85 (d, J=3.6 Hz, 1H).

The compounds in the following table were prepared in a manner analogous to that described in Scheme 45, replacing with the appropriate aniline.

TABLE 16

| Number | PRODUCT | Salt type | Molecular Mass | $^1$H-NMR | $^1$H-NMR Solvent | LCMS | LCMS Protocol | Purity percent | Method for Coupling |
|---|---|---|---|---|---|---|---|---|---|
| 1108 | 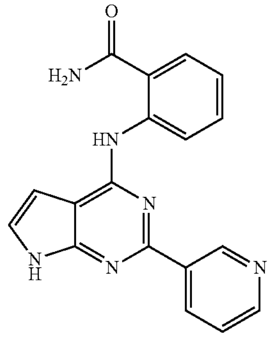 [SMILES: NC(=O)c1ccccc1Nc1nc(-c2cccnc2)nc2[nH]ccc12] | | 330.34 | $^1$H-NMR (400 MHz, DMSO-$d_6$): δ 12.29 (s, 1H), 12.09 (s, 1H), 9.54 (d, J = 1.2 Hz, 1H), 9.11 (d, J = 8.4 Hz, 1H), 8.65-8.68 (m, 1H), 8.35 (s, 1H), 7.89 (dd, J = 8.0, 1.2 Hz, 1H), 7.79 (s, 1H), 7.67 (td, J = 8.8, 1.2 Hz, 1H), 7.55 (dd, J = 7.2, 4.8 Hz, 1H), 7.43-7.41 (m, 1H), 7.10 (td, J = 8.0, 1.2 Hz, 1H), 6.49 (d, J = 3.6 Hz, 1H). | DMSO | 331.1 (M + 1) | Method B (NH4HCO3) | 95 | Method AJ, F, G6 |
| 1109 | 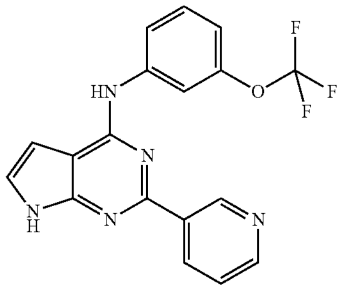 [SMILES: FC(F)(F)Oc1cccc(Nc2nc(-c3cccnc3)nc3[nH]ccc23)c1] | | 371.32 | $^1$H-NMR (400 MHz, DMSO-$d_6$): δ 12.02 (d, J = 1.3 Hz, 1H), 9.75 (s, 1H), 9.50 (d, J = 1.5 Hz, 1H), 8.68-8.53 (m, 2H), 8.29 (s, 1H), 7.94-7.75 (m, 1H), 7.61-7.44 (m, 2H), 7.41-7.29 (m, 1H), 7.04 (s, 1H), 6.88 (dd, J = 3.4, 1.9 Hz, 1H). | DMSO | 372.0 (M + 1) | Method A (TFA) | 95 | Method AJ, F, G6 |

TABLE 16-continued

| Number | PRODUCT | Salt type | Molecular Mass | $^1$H-NMR | $^1$H-NMR Solvent | LCMS | LCMS Protocol | Purity percent | Method for Coupling |
|---|---|---|---|---|---|---|---|---|---|
| 1110 | 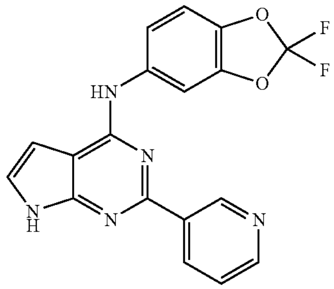 [SMILES: FC1(F)Oc2ccc(Nc3nc(-c4cccnc4)nc4[nH]ccc34)cc2O1] | | 366.32 | 1H-NMR (400 MHz, DMSO-d6): δ 11.98 (s, 1H), 9.69 (s, 1H), 9.48 (d, J = 1.8 Hz, 1H), 8.64-8.59 (m, 2H), 8.19 (d, J = 2.0 Hz, 1H), 7.63 (dd, J = 8.8, 2.0 Hz, 1H), 7.54 (dd, J = 7.9, 4.8 Hz, 1H), 7.45 (d, J = 8.8 Hz, 1H), 7.34 (d, J = 3.0 Hz, 1H), 6. | DMSO | 368.1 (M + 1) | Method A (TFA) | 95 | Method AJ, F, G6 |
| 1111 | 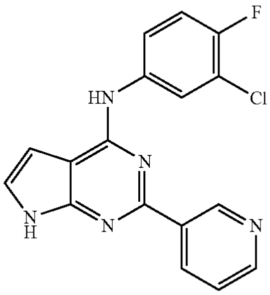 [SMILES: Fc1ccc(Nc2nc(-c3cccnc3)nc3[nH]ccc23)cc1Cl] | | 339.75 | $^1$H-NMR (400 MHz, DMSO-$d_6$): δ 11.51 (s, 1H), 8.78 (d, J = 8.0 Hz, 2H), 8.17 (d, J = 9.2 Hz, 1H), 7.80 (dd, J = 9.2, 2.8 Hz, 1H), 7.70-7.64 (m, 1H), 7.46 (d, J = 2.8 Hz, 1H), 7.41 (d, J = 8.0 Hz, 1H), 7.20 (d, J = 4.0 Hz, 2H), 7.16-7.08 (m, 1H). | DMSO | 340.1, 342.0 (M + 1) | Method B (NH4HCO3) | 95 | Method AJ, F, G6 |

Scheme 47: General route for the synthesis of compounds with general formula xxxxvii:

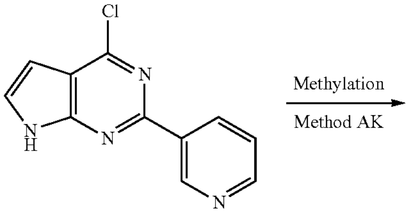

xliv

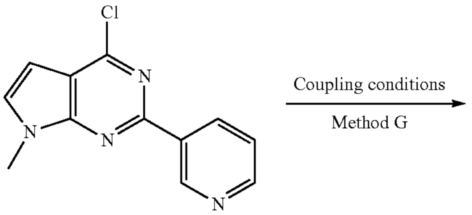

xlvi

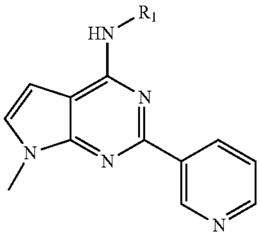

xlvii

Scheme 48: Representative synthesis of compound of formula xxxxvii-a: (see Scheme 47)

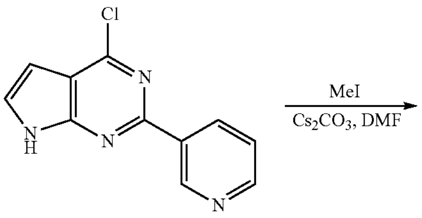

xliv-a

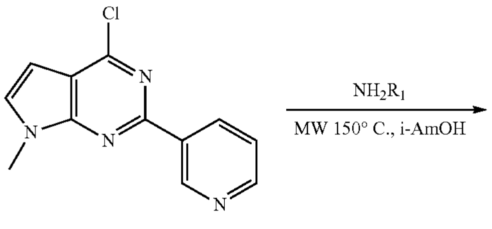

xlvi-a

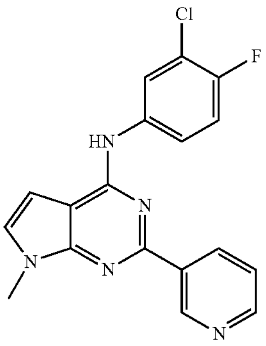

xlvii-a

Method AK: 4-Chloro-7-methyl-2-(pyridin-3-yl)-7H-pyrrolo[2,3-d]pyrimidine (xliv-a)

To a solution of 4-chloro-2-(pyridin-3-yl)-7H-pyrrolo[2,3-d]pyrimidine (80 mg, 0.34 mmol, 1.0 eq.) in dry DMF (20 mL) was added $Cs_2CO_3$ (221 mg, 0.68 mmol, 2.0 eq.) and iodomethane (54.3 mg, 0.38 mmol, 1.1 eq.) at 0° C. The reaction mixture was warmed to room temperature and stirred for 2.5 h. The reaction mixture was poured into ice water and extracted with EtOAc (20 mL×3). The combined organic layers were dried over anhydrous $Na_2SO_4$. After filtration and concentration, the residue was purified by chromatography on silica gel (petroleum ether/ethyl acetate 8:1) to give 65 mg of xlvi-a as brown solid (56.7%).

N-(3-chloro-4-fluorophenyl)-7-methyl-2-(pyridin-3-yl)-7H-pyrrolo[2,3-d]pyrimidin-4-amine (xlvii-a)

N-(3-chloro-4-fluorophenyl)-7-methyl-2-(pyridin-3-yl)-7H-pyrrolo[2,3-d]pyrimidin-4-amine (prepared in a manner analogous to that described for N-(3-chloro-4-fluorophenyl)-6-(3-(dimethylamino)propyl)-2-(pyridin-3-yl)quinazolin-4-amine using Method G6, replacing 3-(4-(3-chloro-4-fluorophenylamino)-2-(pyridin-3-yl)quinazolin-6-yl)propyl methanesulfonate with 4-chloro-7-methyl-2-(pyridin-3-yl)-7H-pyrrolo[2,3-d]pyrimidine) to give a 70.0% yield, 30 mg of xlvii-a as a brown solid. LCMS m/z=354.1, 356.1 (M+1) (Method B) (retention time=1.94 min). $^1H$ NMR (400 MHz, DMSO-$d_6$): δ 9.97 (s, 1H), 9.53 (s, 1H), 9.15 (d, J=8.0 Hz, 1H), 8.91 (d, J=5.2 Hz, 1H), 8.25 (dd, J=6.8, 2.4 Hz, 1H), 8.04 (dd, J=7.6, 5.6 Hz, 1H), 7.94-7.90 (m, 1H), 7.48-7.43 (m, 2H), 6.95 (d, J=3.2 Hz, 1H), 3.88 (s, 3H).

The compounds in the following table were prepared in a manner analogous to that described in Scheme 46, replacing with the appropriate aniline.

TABLE 17

| Number | PRODUCT | Salt type | Molecular Mass | $^1H$-NMR | $^1H$-NMR Solvent | LCMS | LCMS Protocol | Purity percent | Method for Coupling |
|---|---|---|---|---|---|---|---|---|---|
| 1112 | 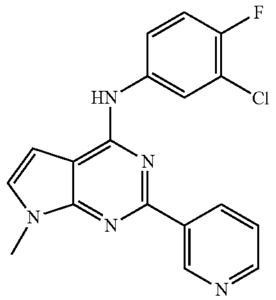 [SMILES: Cn1ccc2c(Nc3ccc(F)c(Cl)c3)nc(-c3cccnc3)nc21] | HCl | 353.78 | $^1H$ NMR (400 MHz, DMSO-$d_6$): δ 9.97 (s, 1H), 9.53 (s, 1H), 9.15 (d, J = 8.0 Hz, 1H), 8.91 (d, J = 5.2 Hz, 1H), 8.25 (dd, J = 6.8, 2.4 Hz, 1H), 8.04 (dd, J = 7.6, 5.6 Hz, 1H), 7.94-7.90 (m, 1H), 7.48-7.43 (m, 2H), 6.95 (d, J = 3.2 Hz, 1H), 3.88 (s, 3H). | DMSO | 354.1, 356.1 (M + 1) | Method B (NH4HCO3) | 95 | Method AK, G6 |
| 1113 | 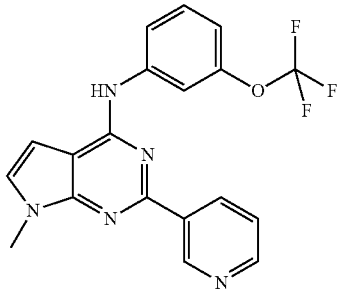 [SMILES: Cn1ccc2c(Nc3cccc(OC(F)(F)F)c3)nc(-c3cccnc3)nc21] | | 385.34 | $^1H$ NMR (400 MHz, DMSO-$d_6$): δ 9.81 (s, 1H), 9.56 (d, J = 1.6 Hz, 1H), 8.69-8.64 (m, 2H), 8.29 (s, 1H), 7.87 (d, J = 8.8 Hz, 1H), 7.55-7.51 (m, 2H), 7.41 (d, J = 3.6 Hz, 1H), 7.04 (d, J = 8.0 Hz, 1H), 6.90 (d, J = 3.6 Hz, 1H), 3.87 (s, 3H). | DMSO | 386.1 (M + 1) | Method B (NH4HCO3) | 95 | Method AK, G6 |
| 1114 | 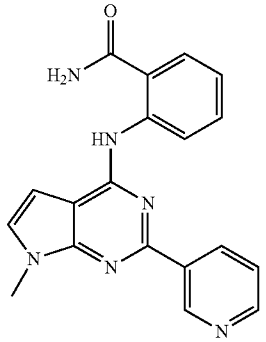 [SMILES: Cn1ccc2c(Nc3ccccc3C(N)=O)nc(-c3cccnc3)nc21] | | | 1H-NMR (400 MHz, DMSO-d6): δ 12.32 (s, 1H), 9.61 (s, 1H), 9.11 (d, J = 7.6 Hz, 1H), 9.11 (d, J = 7.6 Hz, 1H), 8.74 (dt, J = 8.0, 1.9 Hz, 1H), 8.67 (d, J = 3.6 Hz, 1H), 8.38 (s, 1H), 8.38 (s, 1H), 7.90 (dd, J = 7.9, 1.4 Hz, 1H), 7.82 (s, 1H), 7.68 (dd | DMSO | 344.9 (M + 1) | Method B (NH4HCO3) | 95 | Method AK, G6 |

Scheme 49: General route for the synthesis of compounds with general formula xlviii:

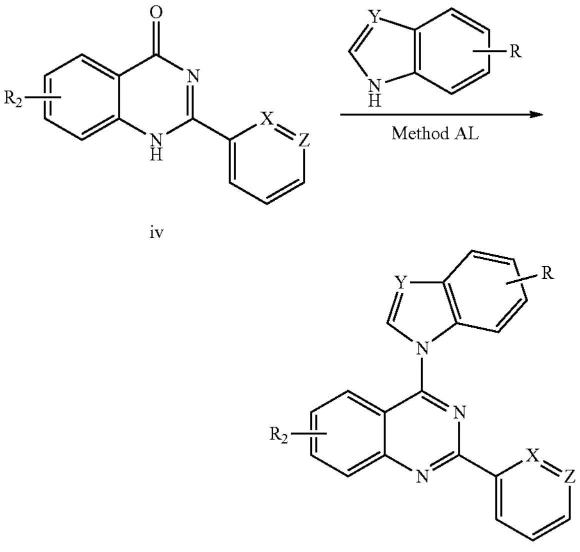

iv xlviii

X, Y and Z = CH or N

Scheme 50: Representative synthesis of compounds of formula xlviii-a (See Scheme 49)

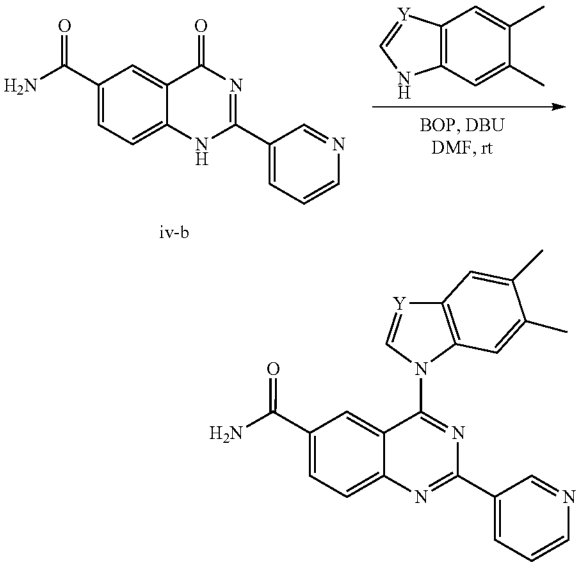

iv-b xlviii-a (Compound 1115)

Method AL: 4-(5,6-dimethyl-1H-benzo[d]imidazol-1-yl)-2-(pyridin-3-yl)quinazoline-6-carboxamide (xlviii-a)

To a suspension of 4-oxo-2-(pyridin-3-yl)-1,4-dihydroquinazoline-6-carboxamide (prepared as described in scheme 4) (100 mg, 0.376 mmol, 1.0 eq.) in dry DMF (20 mL) was added benzotriazole-1-yl-oxy-tris-(dimethylamino)-phosphonium hexafluorophosphate (216 mg, 0.488 mmol, 1.3 eq.) and diaza(1,3)bicyclo[5.4.0]undecene (114.5 mg, 0.752 mmol, 2.0 eq.) following a procedure outlined in *J. Org. Chem.,* 2007, 72, 1019440210. To the clear solution was then added 5,6-dimethyl-1H-benzo[d]imidazole (165.2 mg, 1.13 mmol, 3.0 eq.) and the mixture was stirred overnight at room temperature. The resultant precipitate was then collected by filtration and washed with dichloromethane, water, and ether. The product was dried in vacuo to give 26.3 mg of the desired product: (xlviii-a) as an off-white solid (6.7%). LCMS m/z=395.1 (M+1) (Method C) (retention time=1.68 min). $^1$H NMR (300 MHz, DMSO) δ 9.69 (s, 1H), 8.90 (s, 1H), 8.82 (d, J=15.2 Hz, 2H), 8.66 (s, 1H), 8.54 (d, j=8.6 Hz, 1H), 8.42 (s, 1H), 8.30 (d, J=8.5 Hz, 1H), 7.79 (s, 1H), 7.68 (s, 3H), 2.39 (s, 3H), 2.36 (s, 3H).

Scheme 51: General route for the synthesis of compounds with general formula xlviv

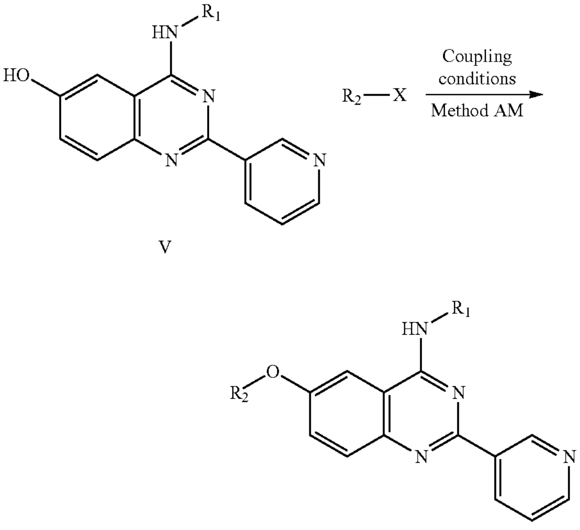

v xlviv

Scheme 52: Representative synthesis of compounds of formula xlviv (see Scheme 51)

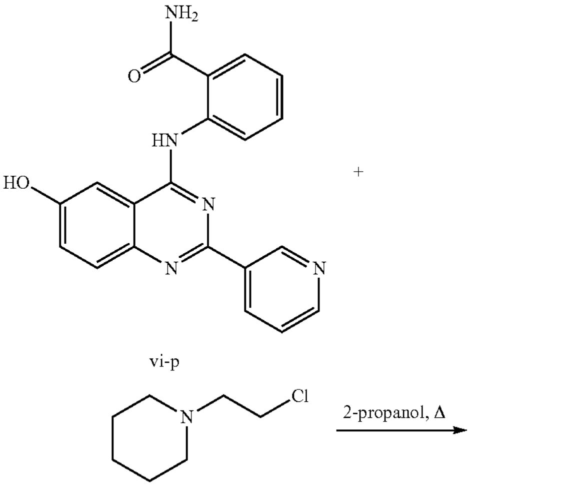

vi-p

-continued

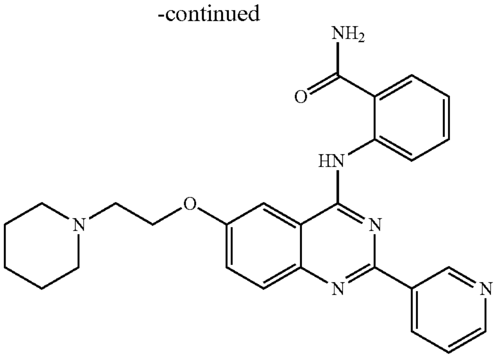

xlviv-a

Method AM: Synthesis of 2-(6-(2-(piperidin-1-yl)ethoxy)-2-(pyridin-3-yl)quinazolin-4-ylamino)benzamide (xlviv-a)

To 1-(2-chloroethyl)piperidine (45 μmol) was added the solution of 2-(6-hydroxy-2-(pyridin-3-yl)quinazolin-4-ylamino)benzamide (30 μmol) in NMP (200 μL) PS-BEMP (90 μmol) was added to the vials by resin dispenser. After the reaction mixture was heated at 90° C. for 12 h, the residue was diluted with methanol and purified by mass triggered PREP-HPLC Condition D. The target fraction was lyophilized to afford the titled compound whose structure was finally confirmed by LCMS using LCMS Method E.

The compounds in the following table were prepared in a manner analogous to that described in Scheme 51, replacing 1-(2-chloroethyl)piperidine with the appropriate alkyl halide.

TABLE 18

| Number | Starting Material 1 | Starting Material 2 | Product | Salt Type | Exact Mass | Mass Found (M + 1) | Purity (%) |
|---|---|---|---|---|---|---|---|
| 1116 | 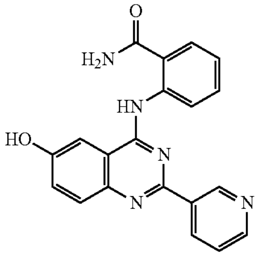 [SMILES: NC(=O)c1ccccc1Nc1nc(-c2cccnc2)nc2ccc(O)cc12] | 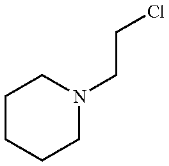 | 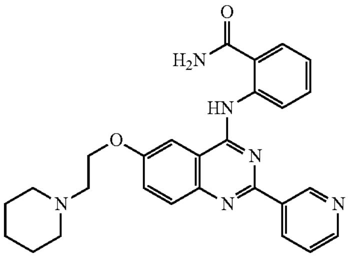 [SMILES: NC(=O)c1ccccc1Nc1nc(-c2cccnc2)nc2ccc(OCCN3CCCCC3)cc12] | | 468 | 469 | 98 |
| 1117 | 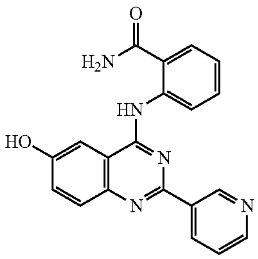 | 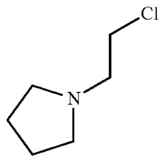 | 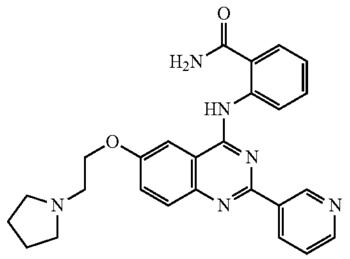 [SMILES: NC(=O)c1ccccc1Nc1nc(-c2cccnc2)nc2ccc(OCCN3CCCC3)cc12] | | 454 | 455 | 98 |
| 1118 | 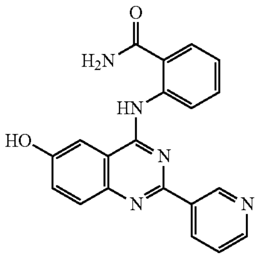 [SMILES: NC(=O)c1ccccc1Nc1nc(-c2cccnc2)nc2ccc(O)cc12] | 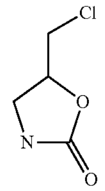 | 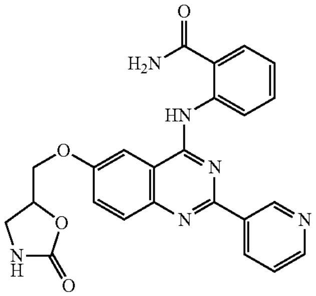 [SMILES: NC(=O)c1ccccc1Nc1nc(-c2cccnc2)nc2ccc(OCC3CNC(=O)O3)cc12] | | 456 | 457 | 98 |
| 1119 | 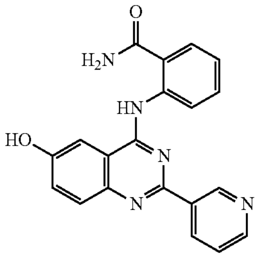 [SMILES: NC(=O)c1ccccc1Nc1nc(-c2cccnc2)nc2ccc(O)cc12] | 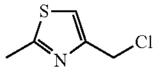 | 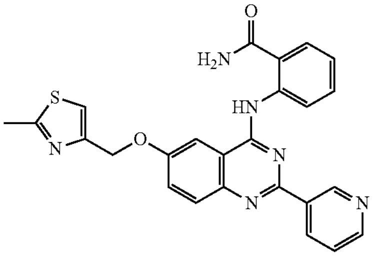 [SMILES: Cc1nc(COc2ccc3nc(-c4cccnc4)nc(Nc4ccccc4C(N)=O)c3c2)cs1] | | 468 | 469 | 98 |

TABLE 18-continued
| Number | Starting Material 1 | Starting Material 2 | Product | Salt Type | Exact Mass | Mass Found (M + 1) | Purity (%) |
|---|---|---|---|---|---|---|---|
| 1120 | 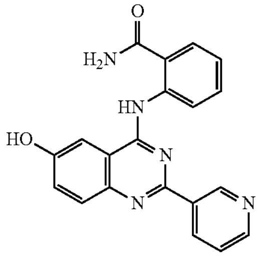 [SMILES: NC(=O)c1ccccc1Nc1nc(-c2cccnc2)nc2ccc(O)cc12] | 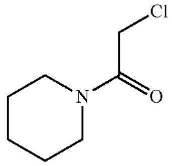 | 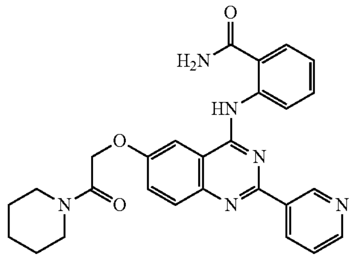 [SMILES: NC(=O)c1ccccc1Nc1nc(-c2cccnc2)nc2ccc(OCC(=O)N3CCCCC3)cc12] | | 482 | 483 | 98 |
| 1121 | 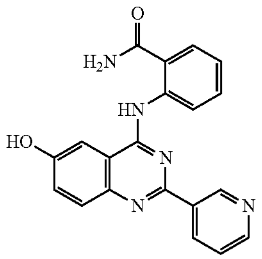 [SMILES: NC(=O)c1ccccc1Nc1nc(-c2cccnc2)nc2ccc(O)cc12] | 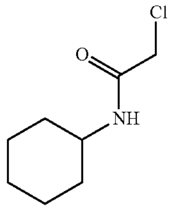 [SMILES: O=C(CCl)NC1CCCCC1] | 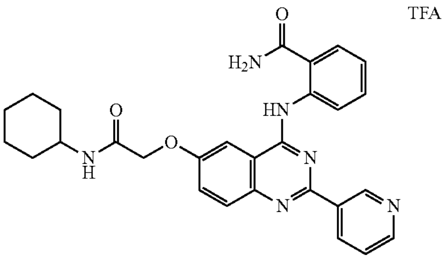 | TFA | 496 | 497 | 98 |
| 1122 | 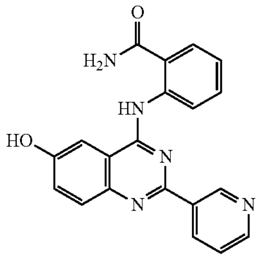 [SMILES: NC(=O)c1ccccc1Nc1nc(-c2cccnc2)nc2ccc(O)cc12] | 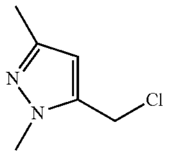 | 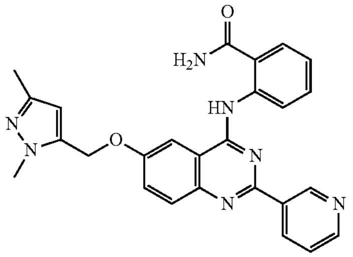 [SMILES: Cc1cc(COc2ccc3nc(-c4cccnc4)nc(Nc4ccccc4C(N)=O)c3c2)n(C)n1] | | 465 | 466 | 98 |
| 1123 | 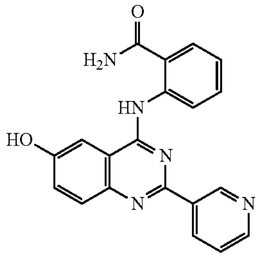 [SMILES: NC(=O)c1ccccc1Nc1nc(-c2cccnc2)nc2ccc(O)cc12] | 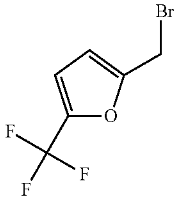 [SMILES: FC(F)(F)c1ccc(CBr)o1] | 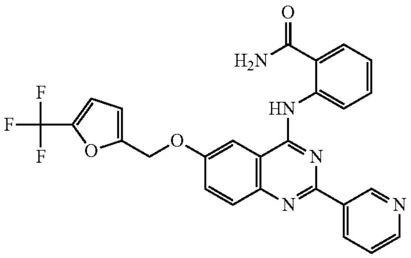 [SMILES: NC(=O)c1ccccc1Nc1nc(-c2cccnc2)nc2ccc(OCc3ccc(C(F)(F)F)o3)cc12] | | 505 | 506 | 98 |
Scheme 53: Synthesis of 2-(6-methoxy-2-(pyridin-3-yl)quinazolin-4-ylamino)-N-methyl-4-phenylthiazole-5-carboxamide dihydrochloride (Compound 1124)
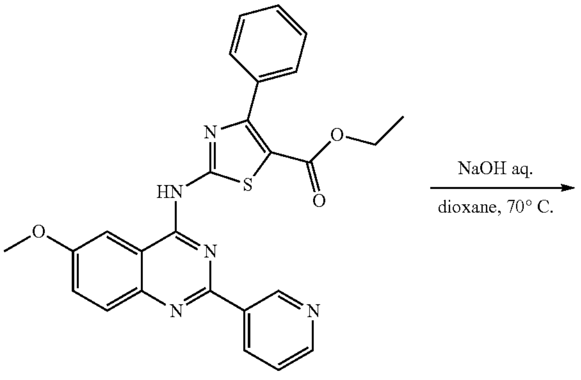
-continued
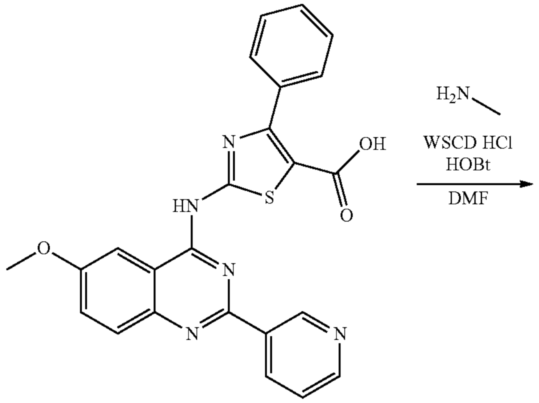

-continued

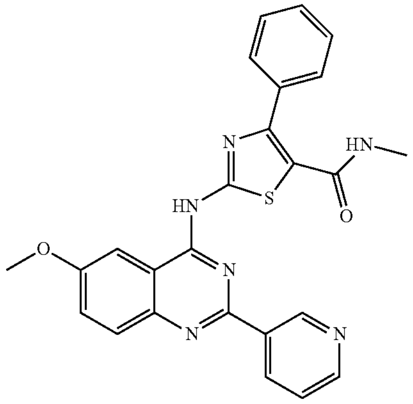

(Compound 1124)

To a suspension of ethyl 2-(6-methoxy-2-(pyridin-3-yl) quinazolin-4-ylamino)-4-phenylthiazole-5-carboxylate (1.3956 g, 2.89 mmol) in dioxane (40 mL) was added 1N NaOH (20 ml, 20.00 mmol) at room temperature to give a clear solution. The reaction mixture was stirred at room temperature for 1 h and then warmed to 50° C. overnight, however starting material remained. An additional 20 mL of 1N NaOH was added and heating was continued at 50° C. for 1 h and at 70° C. for 5 h 30 min. The reaction mixture was cooled to room temperature and diluted with water and ethyl acetate. The water phase was removed and adjusted to an acidic pH with 1N HCl (40 mL). A precipitate formed and was collected and washed with water. The product was dried in vacuo to give 1.20 g of a brown solid in a 91% yield, $^1$H NMR (DMSO-$d_6$) ppm 12.88 (hr, 2H), 9.77 (dd, J=2.12, 0.6 Hz, 1H), 8.92-8.89 (m, 1H), 8.78 (dd, J=4.8, 1.68 Hz, 1H), 8.32 (br, 1H), 7.96 (d, J=9.12 Hz, 1H), 7.82-7.80 (m, 2H), 7.70-7.67 (m, 1H), 7.63 (dd, J=9.12, 2.68 Hz, 1H), 7.50-7.44 (m, 3H), 3.98 (s, 3H).

Method AN: 2-(6-methoxy-2-(pyridin-3-yl)quinazolin-4-ylamino)-N-methyl-4-phenylthiazole-5-carboxamide To a suspension of 2-(6-methoxy-2-(pyridin-3-yl)quinazolin-4-ylamino)-4-phenylthiazole-5-carboxylic acid (291.8 mg, 0.641 mmol) in DMF (20 mL) under nitrogen atmosphere was added N-(3-dimethylaminopropyl)-N'-ethylcarbodiimide hydrochloride (189 mg, 0.986 mmol) and 1-hydroxybenzotriazole hydrate (147 mg, 0.961 mmol) at room temperature. The reaction mixture was stirred at room temperature for 10 min to give a clear solution and methylamine in a methanol solution (4 mL) was added at room temperature. The reaction mixture was stirred at room temperature for 2 h 15 min. Additional methyl amine in a methanol solution (4 mL) was added at room temperature and then heated to 50° C. for 1 h followed by room temperature for 2 days. The reaction mixture was partitioned between water and ethyl acetate. The water phase was collected and a solid precipitated from the water phase. The solid was filtered and dried in an oven at 60° C. to give 107.9 mg (0.23 mmol) as the parent compound. The parent compound was suspended in methanol and 4N HCl in ethyl acetate (ca. 2 mL) was added to give a clear solution which precipitated over time. The solid was collected by filtration and dried in oven at 60° C. for 2 days to give 82.4 mg of the HCl salt as a yellow solid in 24% yield. $^1$H NMR (DMSO-$d_c$) δ 12.77 (brs, 1H), 9.76 (d, J=1.72. Hz, 1H), 9.18 (d, J=7.88 Hz, 1H), 8.92 (d J=5.04 Hz, 1H), 8.35 (brs, 1H), 8.27 (brd, J=4.56 Hz, 1H), 7.99-7.965 (m, 2H), 7.79 (brd, J=7.16 Hz, 2H), 7.65 (dd, J=9.12, 2.56 Hz, 1H), 7.50-7.41 (m, 3H), 4.00 (s, 3H), 2.76 (d, J=4.56 Hz, 3H). The 1H of 2HCl was not observed.

The compounds in the following table were prepared in a manner analogous to that described in Scheme 53, replacing N-methyl amine with the appropriate alkyl amine.

TABLE 19

| Number | Starting Material 1 | Starting Material 2 | Product | Salt Type |
|---|---|---|---|---|
| 1124 | 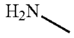 | 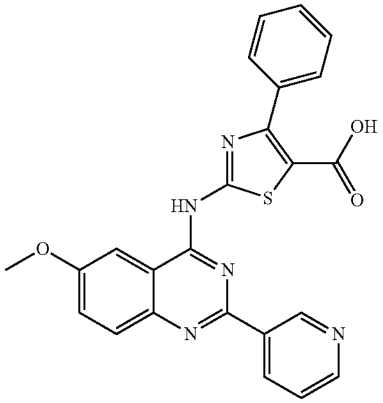 [SMILES: COc1ccc2nc(-c3cccnc3)nc(Nc3nc(-c4ccccc4)c(C(=O)O)s3)c2c1] | 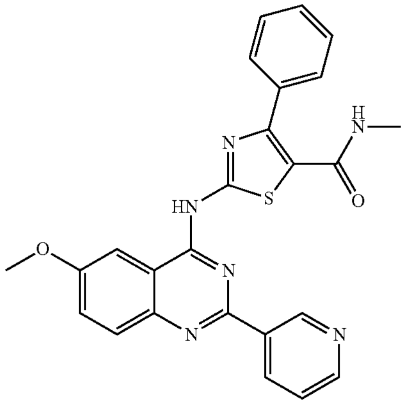 | 2 HCl |

TABLE 19-continued

| | | | | |
|---|---|---|---|---|
| 1125 | $NH_3$ | 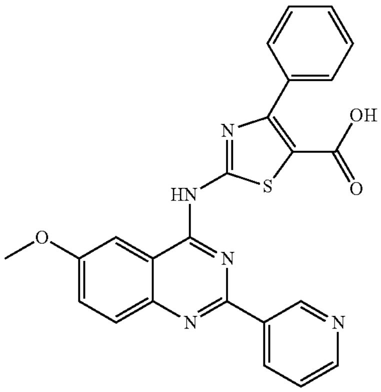 [SMILES: COc1ccc2nc(-c3cccnc3)nc(Nc3nc(-c4ccccc4)c(C(=O)O)s3)c2c1] | 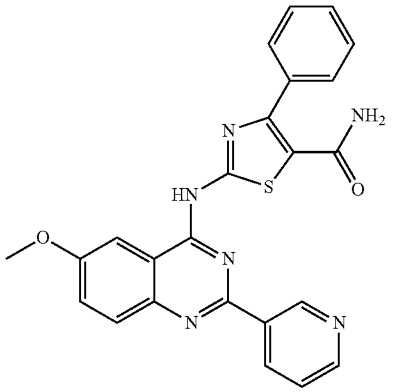 [SMILES: COc1ccc2nc(-c3cccnc3)nc(Nc3nc(-c4ccccc4)c(C(N)=O)s3)c2c1] | 2 HCl |
| 1126 | 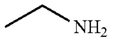 | 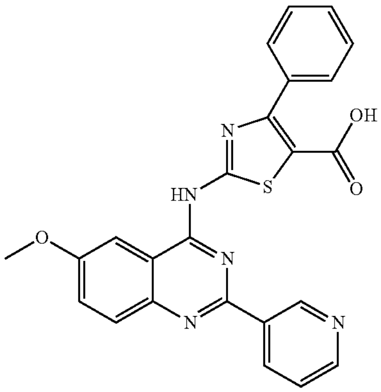 [SMILES: COc1ccc2nc(-c3cccnc3)nc(Nc3nc(-c4ccccc4)c(C(=O)O)s3)c2c1] | 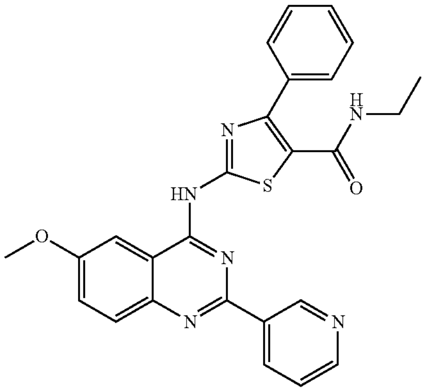 [SMILES: CCNC(=O)c1sc(Nc2nc(-c3cccnc3)nc3ccc(OC)cc23)nc1-c1ccccc1] | |

| Number | $^1$H NMR | $^1$H NMR Solvent | Purity percent | Method of Coupling |
|---|---|---|---|---|
| 1124 | 1H NMR (DMSO-d6) ppm 12.77 (brs, 1H), 9.76 (d, J = 1.72 Hz, 1H), 9.18 (d, J = 7.88 Hz, 1H), 8.92 (d J = 5.04 Hz, 1H), 8.35 (brs, 1H), 8.27 (brd, J = 4.56 Hz, 1H), 7.99-7.965 (m, 2H), 7.79 (brd, J = 7.16 Hz, 2H), 7.65 (dd, J = 9.12, 2.56 Hz, 1H), 7.50-7.41 (m, 3H), 4.00 (s, 3H), 2.76 (d, J = 4.56 Hz, 3H). The 1H of 2HCl was not observed. | DMSO | >98 | Method AN |
| 1125 | 1H NMR (DMSO-d6) ppm 12.75 (brs, 1H), 9.77 (d, J = 1.52 Hz, 1H), 9.13 (brs, 1H), 8.88 (brd, J = 5.08 Hz, 1H), 8.34 (d, J = 2.04 Hz, 1H), 7.98 (d, J = 9.12 HZ, 1H), 7.90 (brm, 1H), 7.83-7.80 (m, 2H), 7.66-7.53 (brm, 3H), 7.51-7.42 (m, 3H), 4.00 (s, 3H). The 1H of 2HCl was not observed. | DMSO | >98 | Method AN |
| 1126 | 1H NMR (DMSO-d6) ppm 12.66 (s, 1H), 9.76 (s, 1H), 8.88 (d, J = 7.76 HZ, 1H), 8.75 (d, J = 3.68 Hz, 1H), 8.40-8.20 (br, 2H), 7.94 (br, 1H), 7.80 (d, J = 7.16 Hz, 2H), 7.63 (m, 2H), 7.49-7.41 (m, 3H), 3.99 (s, 3H), 3.24 (q, J = 7.24 Hz, 2H), 1.07 (t, J = 7.24 Hz, 3H) | DMSO | >98 | Method AN |

Scheme 54: General route for the synthesis of compounds with general formula I

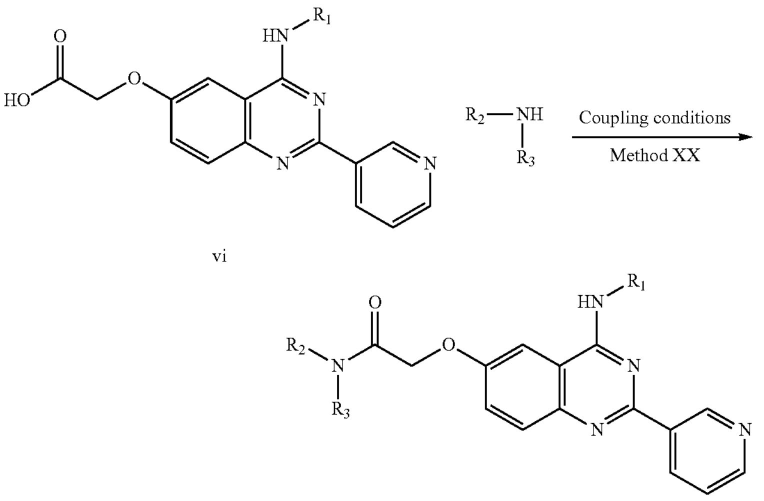

vi

I

Scheme 55: Representative synthesis of compounds of formula I-a: (see Scheme 54)

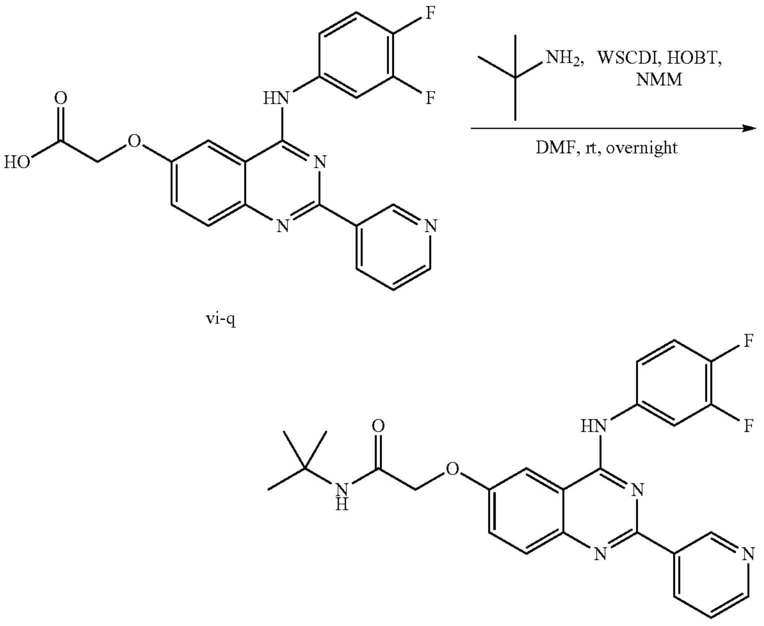

vi-q

I

Method AO: N-tert-butyl-2-(4-(3,4-difluorophenylamino)-2-(pyridin-3-yl)quinazolin-6-yloxy)acetamide To a solution of carboxylic acid derivative (500 mg, 1.2 mmol) in UMP was added 2-aminoisobutane (134 mg, 1.8 mmol), NMM (0.4 mL, 3.6 mmol), WSCDI (282 mg, 1.4 mmol) and HOBT (22.5 mg, 1.4 mmol). The reaction mixture was stirred at room temperature overnight. The resulting solution was poured into ice-water and the precipitate formed and was filtered off. The solid was washed with water and dried to give 350 mg (62% yield) of desired product, $^1$H NMR (400 MHz, DMSO) δ 9.86 (s, 1H), 9.49 (d, J=1.5 Hz, 1H), 8.71-8.57 (m, 2H), 8.11 (ddd, J=13.3, 7.5, 2.5 Hz, 1H), 8.00-7.93 (m, 1H), 7.87 (d, J=9.1 Hz, 1H), 7.67 (ddd, J=11.7, 7.1, 2.1 Hz, 2H), 7.59-7.47 (m, 3H), 4.61 (s, 2H), 1.35 (s, 9H).

The compounds in the following table were prepared in a manner analogous to that described in Scheme 54, replacing 2-aminoisobutane with the appropriate alkyl amine.

TABLE 20

| Number | Starting Material $R^1$ | Starting Material $R^3$ | Product |
|---|---|---|---|
| 1127 | 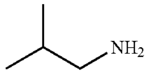 | 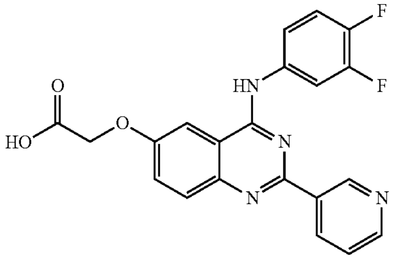 [SMILES: O=C(O)COc1ccc2nc(-c3cccnc3)nc(Nc3ccc(F)c(F)c3)c2c1] | 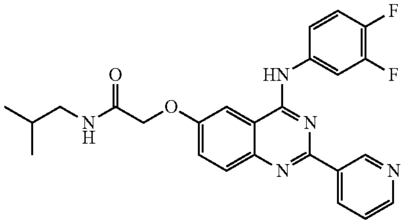 [SMILES: CC(C)CNC(=O)COc1ccc2nc(-c3cccnc3)nc(Nc3ccc(F)c(F)c3)c2c1] |
| 1128 | 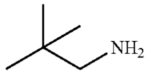 | 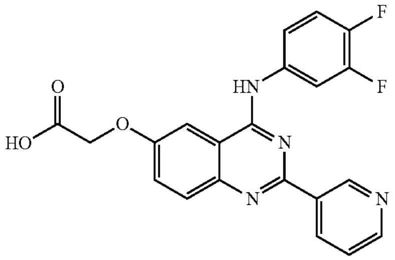 [SMILES: O=C(O)COc1ccc2nc(-c3cccnc3)nc(Nc3ccc(F)c(F)c3)c2c1] | 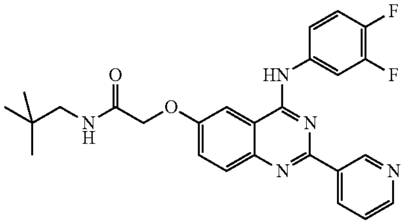 [SMILES: CC(C)(C)CNC(=O)COc1ccc2nc(-c3cccnc3)nc(Nc3ccc(F)c(F)c3)c2c1] |
| 1129 | 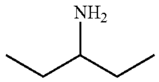 | 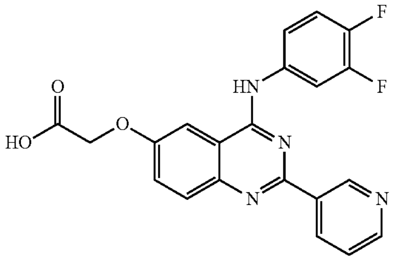 [SMILES: O=C(O)COc1ccc2nc(-c3cccnc3)nc(Nc3ccc(F)c(F)c3)c2c1] | 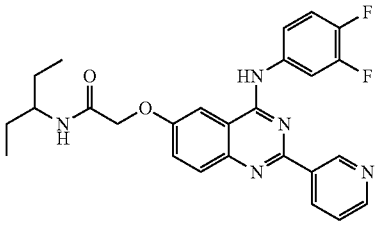 [SMILES: CCC(CC)NC(=O)COc1ccc2nc(-c3cccnc3)nc(Nc3ccc(F)c(F)c3)c2c1] |

| Number | Salt Type | $^1$H NMR | $^1$H NMR Solvent | Purity percent | Method of Coupling |
|---|---|---|---|---|---|
| 1127 | 3 HCl | $^1$H NMR (400 MHz, DMSO) δ 10.60 (s, 1H), 9.48 (d, J = 1.9 Hz, 1H), 9.14 (dt, J = 8.2, 1.6 Hz, 1H), 8.96 (dd, J = 5.5, 1.3 Hz, 1H), 8.37 (t, J = 6.0 Hz, 1H), 8.24 (d, J = 2.6 Hz, 1H), 8.11-7.97 (m, 3H), 7.74 (ddd, J = 11.8, 7.4, 3.3 Hz, 2H), 7.55 (dt, J = 10.5, 9.1 Hz, 1H), 4.79 (s, 2H), 3.01 (t, J = 6.5 Hz, 2H), 1.86-1.59 (m, 1H), 0.85 (d, J = 6.7 Hz, 6H). | DMSO | >98 | Method AO |
| 1128 | 3 HCl | $^1$H NMR (400 MHz, DMSO) δ 10.81 (s, 1H), 9.50 (d, J = 1.9 Hz, 1H), 9.16 (d, J = 8.2 Hz, 1H), 8.98 (dd, J = 5.5, 1.3 Hz, 1H), 8.40 (d, J = 2.5 Hz, 1H), 8.29 (t, J = 6.4 Hz, 1H), 8.18-7.95 (m, 3H), 7.83-7.67 (m, 2H), 7.55 (dt, J = 10.5, 9.1 Hz, 1H), 4.88 (s, 2H), 2.98 (d, J = 6.4 Hz, 1H), 0.84 (s, 9H). | DMSO | >98 | Method AO |
| 1129 | 2 HCl | $^1$H NMR (400 MHz, DMSO) δ 10.87 (s, 1H), 9.50 (d, J = 1.9 Hz, 1H), 9.16 (d, J = 8.2 Hz, 1H), 8.98 (dd, J = 5.5, 1.3 Hz, 1H), 8.41 (d, J = 2.5 Hz, 1H), 8.23-7.96 (m, 4H), 7.85-7.66 (m, 2H), 7.55 (dt, J = 10.5, 9.1 Hz, 1H), 4.85 (s, 2H), 3.80-3.43 (m, 1H), 1.65-1.21 (m, 4H), 0.81 (t, J = 7.4 Hz, 6H). | DMSO | >98 | Method AO |

Scheme 56: Synthesis of N-(1H-benzo[d]imidazol-2-yl)-6-methoxy-2-(pyridin-3-yl)quinazolin-4-amine dihydrochloride (Compound 1130)

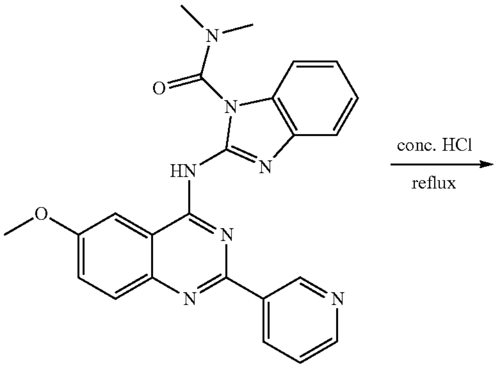

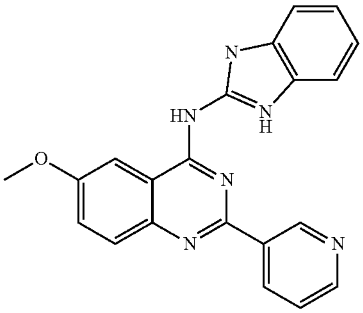

Compound 1130

2-(6-methoxy-2-(pyridin-3-yl)quinazolin-4-ylamino)-1,N-dimethyl-1H-benzo[d]imidazole-1-carboxamide (334.1 mg, 0.760 mmol) was dissolved in concentrated HCl (0.063 ml, 0.760 mmol). The solution was stirred at room temperature overnight and then at 50° C. for 3 h 30 min followed by 100° C. for 3 h. The solid was collected and dried in vacuo to give 116.2 mg of a yellow solid in a yield 35%. $^1$H NMR (DMSO-$d_6$) δ 13.22 (br, 1H), 9.55 (s, 1H), 8.92 (dd, J=4.96, 1.36 Hz, 1H), 8.88 (br, 1H), 8.01 (d, J=9.12 Hz, 1H), 7.92 (br, 1H), 7.83 (br, 1H), 7.67 (dd, J=9.12, 2.80 Hz, 1H), 7.61 (m, 2H), 7.38 (m, 2H), 3.97 (s, 3H). The 1H of 2HCl and NH— were not observed.

Scheme 57: Synthesis of N-(4-(4-chlorophenyl)-1H-imidazol-2-yl)-6-methoxy-2-(pyridin-3-yl)quinazolin-4-amine dihydrochloride (Compound 1131)

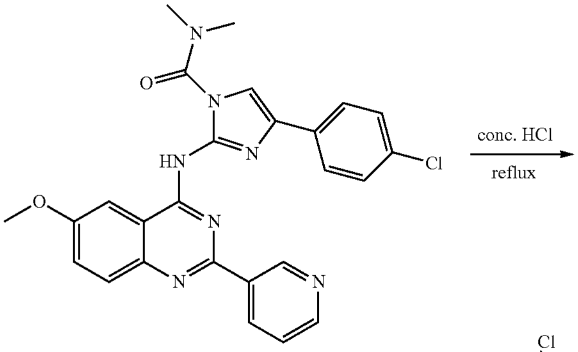

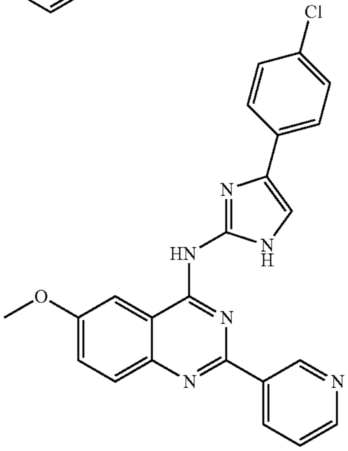

Compound 1131

4-(4-chlorophenyl)-2-(6-methoxy-2-(pyridin-3-yl)quinazolin-4-ylamino)-N,N-dimethyl-1H-imidazole-1-carboxamide and concentrated $HCl_{(aq)}$ (10 mL) were added to a round bottom flask, a precipitate appeared upon refluxing the mixture for 3 h. The solid was collected (373.4 mg) and tritiated with $CH_2Cl_2$/methanol overnight. The product was filtered and dried to give 261.7 mg of a solid. A suspension of the product in methanol was added to a 1N solution of $NaOH_{(aq.)}$ (5 nit) followed by $CH_2Cl_2$ and $H_2O$. The solid was collected and washed with methanol to give 255.7 mg (0.596 mmol) of the parent product. The free parent was suspended in $CH_2Cl_2$/methanol and converted to the HCl salt by addition of a 0.3 ml solution of 4N HCl in ethyl acetate. The HCl salt was collected and dried in vacuo to give 248.4 mg as brown solid in a 26% yield. $^1$H NMR (DMSO-$d_6$) δ 13.61 (br, 1H), 12.81 (br, 1H), 9.46 (s, 1H), 8.87 (d, J=5.24 Hz, 1H), 8.70 (br, 1H), 7.91-7.87 (m, 5H), 7.75 (m, 1H), 7.62-7.56 (m, 3H), 3.95 (s, 3H). The 1H ref 2HCl was not observed.

Scheme 58: Synthesis of 4-(4-(4-chlorophenyl)thiazol-2-ylamino)-2-(pyridin-3-yl)quinazolin-6-ol (Compound 1132)

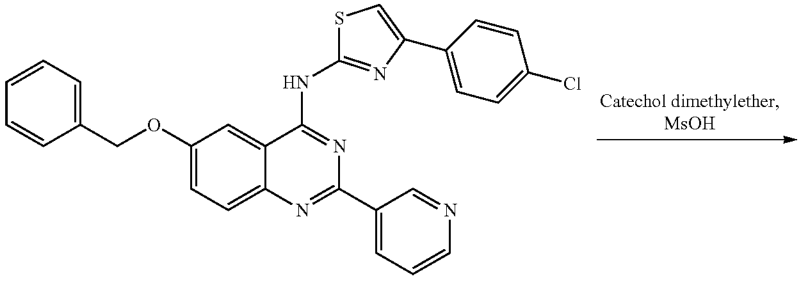

-continued

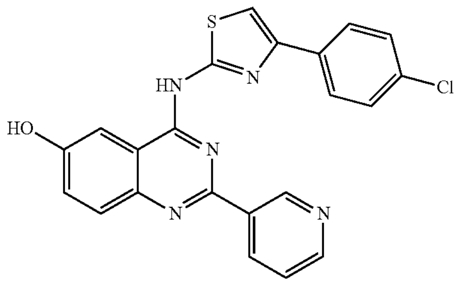

(Compound 1132)

To a mixture of N-(6-(benzyloxy)-2-(pyridin-3-yl)quinazolin-4-yl)-4-(4-chlorophenyl)thiazol-2-amine and catechol, dimethyl ether (0.16 g, 1.15 mmol) was added methanesulfonic acid (4.0 mL). The mixture was stirred for 1 hr and was then poured into water. The slurry was added to a stirring sat. $NaHCO_{3(aq)}$, solution slowly and allowed to stir for 30 min. The precipitate was filtered to give a brown solid which was washed with methanol to give 4-(4-(4-chlorophenyl)thiazol-2-ylamino)-2-(pyridin-3-yl)quinazolin-6-ol (0.23 g, 91.0%).

Scheme 59: Synthesis of 4-(4-phenylthiazol-2-ylamino)-2-(pyridin-3-34)quinazolin-6-ol (Compound 1133)

Synthesis of 4-(4-phenylthiazol-2-ylamino)-2-(pyridin-3-yl)quinazolin-6-ol was performed in a similar manner to that described for 4-(4-(4-chlorophenyl)thiazol-2-ylamino)-2-(pyridin-3-yl)quinazolin-6-ol substituting for 4-(4-phenylthiazol-2-ylamino)-2-(pyridin-3-yl)quinazolin-6-ol for the N-(6-(benzyloxy)-2-(pyridin-3-yl)quinazolin-4-yl)-4-(4-chlorophenyl)thiazol-2-amine giving 4-(4-phenylthiazol-2-ylamino)-2-(pyridin-3-yl)quinazolin-6-ol. $^1H$ NMR (300 MHz, DMSO) δ 10.06-9.22 (m, 2H), 8.95 (dt, J=7.9, 1.6 Hz, 1H), 8.62 (dd, J=4.7, 1.4 Hz, 1H), 7.99 (d, J=7.5 Hz, 2H), 7.87 (d, J=2.8 Hz, 1H), 7.59-7.47 (m, 2H), 7.45-7.32 (m, 3H), 7.30-7.09 (m, 2H).

Scheme 60: Synthesis of 2-(5-fluoro-2-(6-methoxy-2-(pyridin-3-yl)quinazolin-4-ylamino)phenyl)-1,3-dioxolane-2-carboxylic acid (Compound 1134)

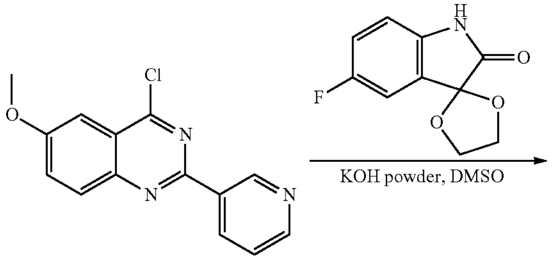

v-c

-continued

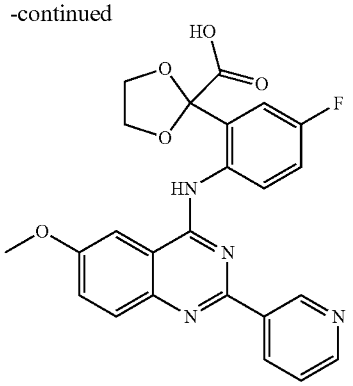

(Compound 1134)

To a mixture of 4-chloro-6-methoxy-2-(pyridin-3-yl)quinazoline (0.50 g, 1.84 mmol) and 5'-fluorospiro[[1,3]-dioxolane-2,3'-indolin]-2'-one (0.42 g, 2.02 mmol) in dry DMSO (4 mL) was added KOH powder (0.11 g, 2.02 mmol). The reaction mixture was stirred for 15 h at room temperature and then the reaction mixture was poured into water. The aqueous layer was washed with ethyl acetate 20 mL) and the resulting aqueous layer was acidified with 5N HCl to give a precipitate. The solid was filtered to give 2-(5-fluoro-2-(6-methoxy-2-(pyridin-3-yl)quinazolin-4-ylamino)phenyl)-1,3-dioxolane-2-carboxylic acid as a light yellow powder (0.27 g, 0.58 mmol, 32%). LCMS m/z=432 (M+1) (Method C) $^1H$ NMR (300 MHz, DMSO) δ 9.50-9.38 (m, 2H), 8.69-8.59 (m, 2H), 8.42 (dd, J=9.7, 5.3 Hz, 1H), 7.86 (d, J=9.1 Hz, 1H), 7.64 (d, J=2.6 Hz, 1H), 7.61-7.41 (m, 4H), 4.25-4.11 (m, 4H), 3.98 (s, 3H).

Scheme 61: N-(3-chloro-4-fluorophenyl)-6-(3-(dimethylamino)prop-1-ynyl)-2-(pyridin-3-yl)quinazolin-4-amine (compound 1135)

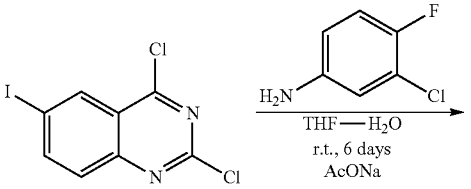

-continued

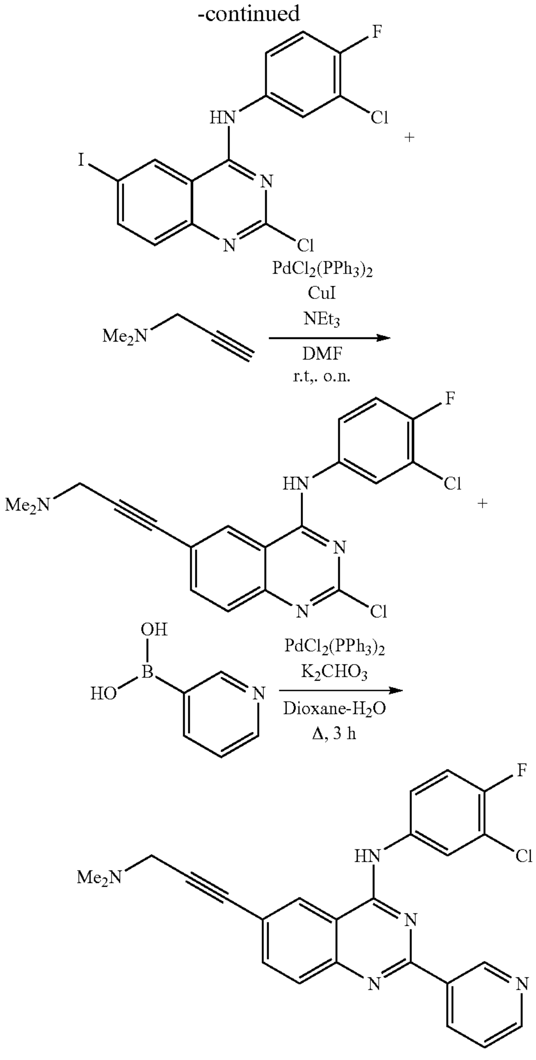

(Compound 1135)

In a 50 mL round-bottomed flask was added 2,4-dichloro-6-iodoquinazoline (0.52 g, 1.6 mmol), 3-chloro-4-fluoroaniline (0.30 g, 2.1 mmol), and sodium acetate (0.20 g, 2.4 mmol) in THF (6 mL) and water (2 mL) to give a brown suspension. After being stirred at room temperature for 6 days, the reaction mixture was diluted with water (15 mL) and extracted with ethyl acetate (2×10 mL). The organic layers were combined and washed with brine (1×20 mL), dried over $Na_2SO_4$, filtered and concentrated. The resulting product, was washed with $CH_2Cl_2$ and dried to give 0.51 g of 2-chloro-N-(3-chloro-4-fluorophenyl)-6-iodoquinazolin-4-amine as a tight brown solid in a 73% yield, $^1H$ NMR (300 MHz, DMSO) δ 10.29 (s, 1H), 8.95 (s, 1H), 8.14 (dd, J=1.5, 9.0 Hz, 1H), 8.06 (dd, J=2.7, 6.6 Hz, 1H), 7.81-7.76 (m, 1H), 7.52-7.46 (m, 2H).

In a 50 mL round-bottomed flask was added 2-chloro-N-(3-chloro-4-fluorophenyl)-6-iodoquinazolin-4-amine (200 mg, 0.46 mmol), N,N-dimethylpropargylamine (99 mL, 0.92 mmol), $NEt_3$ (0.26 mL, 1.84 mmol), CuI (0.88 mg, 4.6 mmol) and $PdCl_2(PPh_3)_2$ (6.5 mg, 9.2 mmol) in DMF (3 mL) to give a light yellow suspension. The mixture was stirred at room temperature overnight under an argon atmosphere. The reaction mixture was diluted with water (10 mL) and ethyl acetate (10 mL) and then a precipitate formed. The resulting precipitate was removed by filtration through Celite. The filtrate was extracted with ethyl acetate (2×10 mL). The combined organic layer was washed with water (1×15 mL) and brine (1×15 mL) and was dried over $Na_2SO_4$, filtered and concentrated. The residue was purified by column chromatography on silica gel (eluted with $CH_2Cl_2$/MeOH 1:0 to 9:1). The desired product was washed with $CH_2Cl_2$ to give 61 mg of 2-chloro-N-(3-chloro-4-fluorophenyl)-6-(3-(dimethylamino)prop-1-ynyl)quinazolin-4-amine, as pale yellow solid in a 34% yield. LCMS m/z=389 (M+1) (Method C) (retention time=2.2.4 min). $^1H$ NMR (300 MHz, DMSO) δ 10.30 (s, 1H), 8.68 (s, 1H), 8.07 (dd, J=2.7, 6.9 Hz, 1H), 7.86 (dd, J=1.8, 8.7 Hz, 1H), 7.81-7.70 (m, 1H), 7.68 (d, J=8.4 Hz, 1H), 7.49 (t, J=9.2 Hz, 1H), 3.52 (s, 2H), 2.28 (s, 6H).

In a 50 mL round-bottomed flask was added 2-chloro-N-(3-chloro-4-fluorophenyl)-6-(3-(dimethylamino)prop-1-ynyl)quinazolin-4-amine, (61 mg, 0.16 mmol), 3-pyridineboronic acid (25 mg, 0.20 mmol), $K_2CO_3$ (0.11 mg, 0.78 mmol) and $PdCl_2(PPh_3)_2$, (5.5 mg, 7.8 mM) in dioxane (2 mL) to give a yellow suspension. The mixture was heated at reflux for 3 h under argon. After cooling to room temperature, water (10 mL) and ethyl acetate (10 mL) were added to the mixture to form a precipitate. The resulting precipitate was filtered through Celite. The filtrate was extracted with ethyl acetate (2×10 mL) and the combined organic layers were washed with water (1×15 mL) and brine (1×15 mL) and then dried over $Na_2SO_4$, filtered and concentrated. The residue was purified by column chromatography on silica gel (eluted with AcOEt/MeOH 1:0 to 9:1). The desired product was washed with $CH_2Cl_2$ to give 25 mg of N-(3-chloro-4-fluorophenyl)-6-(3-(dimethylamino)prop-1-ynyl)-2-(pyridin-3-yl)quinazolin-4-amine as a light brown solid in 37% yield. LCMS m/z=432 (M+1) (Method C) (retention time=1.86 ruin). $^1H$ NMR (300 MHz, DMSO) δ 10.13 (s, 1H), 9.51 (s, 1H), 8.77-8.56 (m, 3H), 8.26 (dd, J=6.9, 2.5 Hz, 1H), 8.02-7.78 (m, 3H), 7.64-7.47 (m, 2H), 3.54 (s, 2H), 2.30 (s, 6H).

Scheme 62: Synthesis of 4-(2-carbamoylphenylamino)-2-(pyridin-3-yl)quinazolin-6-yl benzylcarbamate (compound 1756)

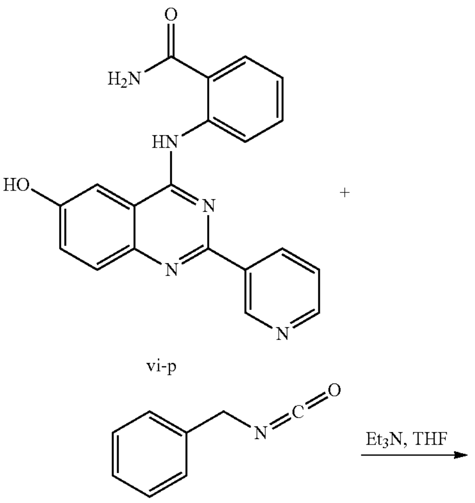

vi-p

-continued

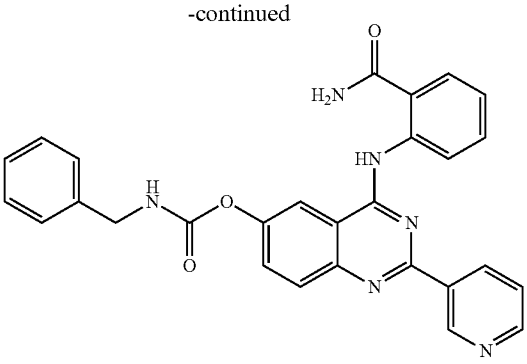

(Compound 1756)

A mixture of 2-(6-hydroxy-2-(pyridin-3-yl)quinazolin-4-ylamino)benzamide (200 mg, 0.283 mmol), (isocyanatomethyl)benzene (5 mL) and $Et_3N$ (57 mg, 0.283 mmol) in tetrahydrofuran (THF) (10 in T) was stirred at room temperature overnight. Water (10 mL) was added to the above mixture and the mixture was concentrated in vacuo. The precipitate was collected by filtration and washed with water (6 mL×2) to afford 72 mg of the desired product as a white solid in a yield 26.0%. LCMS: rt=1.829 min, $[MH]^+$=491.1 $^1$H-NMR (400 MHz, DMSO-$d_6$): δ 13.05 (s, 1H), 9.63 (s, 1H), 9.07 (d, J=8.5 Hz, 1H), 8.87 (d, J=8.0 Hz, 1H), 8.79 (d, J=3.7 Hz, 1H), 8.59 (t, J=6.1 Hz, 1H), 8.49 (s, 1H), 8.02-7.89 (m, 4H), 7.82-7.68 (m, 3H), 7.46-7.22 (m, 6H), 4.35 (d, J=6.1 Hz, 2H).

Scheme 63: Synthesis of 4-(2-carbamoylphenylamino)-2-(pyridin-3-yl)quinazolin-6-yl ethylcarbamate (compound 1136)

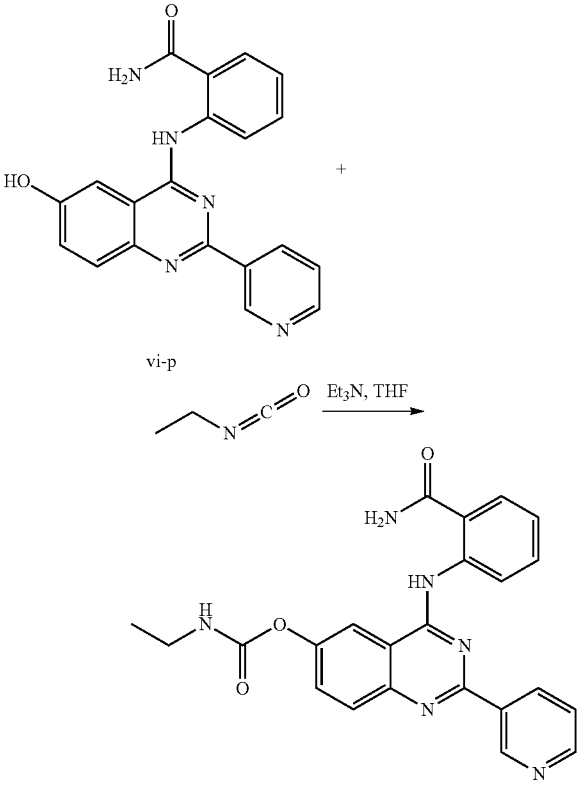

(Compound 1136)

4-(2-carbamoylphenylamino)-2-(pyridin-3-yl)quinazolin-6-yl ethylcarbamate was synthesized in a similar manner to that described for 4-(2-carbamoylphenylamino)-2-(pyridin-3-yl)quinazolin-6-yl benzylcarbamate substituting isocyanatoethane for (isocyanatomethyl)benzene. The resulting product was analyzed by LCMS: rt=1.11 min, $[M+1]^+$=429.0, $^1$H-NMR (400 MHz, DMSO-$d_6$): δ 13.06 (s, 1H), 9.66 (s, 1H), 9.10 (d, J=8.3 Hz, 1H), 8.87-8.80 (m, 2H), 8.51 (s, 1H), 8.06-7.94 (m, 4H), 7.88 (s, 1H), 7.79-7.63 (m, 3H), 7.24 (t, J=7.6 Hz, 1H), 3.22-3.11 (m, 2H), 1.14 (t, J=7.2 Hz, 3H).

Scheme 64: 4-(3-chloro-4-fluorophenylamino)-N-methyl-2-(pyridin-3-yl)-N-(2,2,2-trifluorethyl)quinazoline-6-carboxamide (compound 1137) and N-(3-chloro-4-fluorophenyl)-6-((methyl(2,2,2-trifluoroethyl)amino)methyl)-2-(pyridin-3-yl)quinazolin-4-amine (compound 1138)

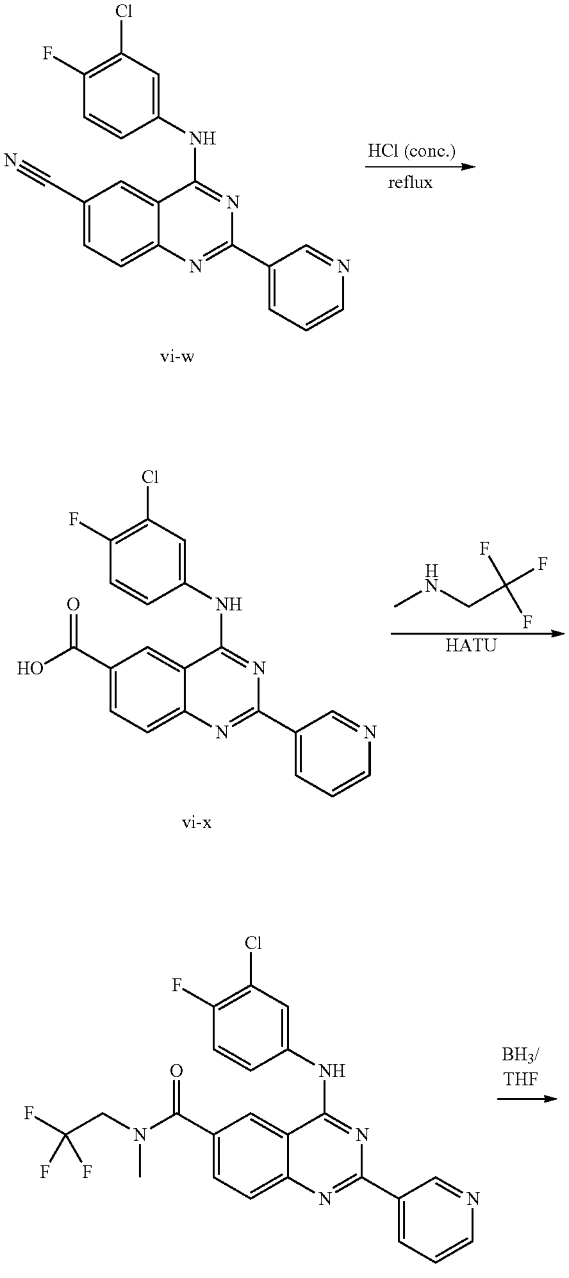

(Compound 1137)

-continued

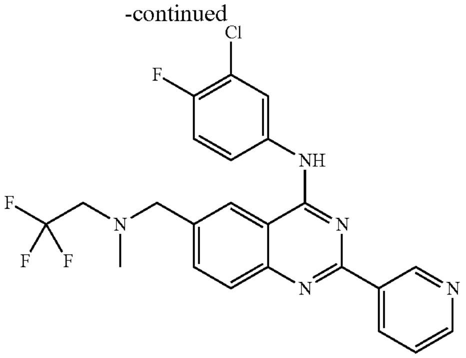

(Compound 1138)

A mixture of 4-(3-chloro-4-fluorophenylamino)-2-(pyridin-3-yl)quinazoline-carbonitrile (1.5 g, 4.0 mmol) in HCl (conc, 25 mL) was heated to 100° C. and stirred overnight. After cooling and filtration, the solid was washed with water (10 mL) twice to give 1.4 g of the desired product 4-(3-chloro-4-fluorophenylamino)-2-(pyridin-3-yl)quinazoline-6-carboxylic acid as a yellow solid in a 89.0% yield. LCMS: r.t=1.271 min, $[M+H]^+$=394.9

A mixture of 4-(3-chloro-4-fluorophenylamino)-2-(pyridin-3-yl)quinazoline-6-carboxylic acid (900 mg, 2.4 mmol), DIPEA (620 mg, 4.8 mmol) and HATU (1.4 g, 3.6 mmol) in DMF (10 mL) was pre-stirred for 20 min, and 2,2,2-trifluoro-N-methylethanamine (360 mg, 2.4 mmol) was added in one portion. The resulting mixture was stirred at room temperature overnight. Water (80 mL) was added and a precipitate formed which was collected and purified by prep-HPLC to afford 490 mg of the desired product 4-(3-chloro-4-fluorophenylamino)-N-methyl-2-(pyridin-3-yl)-N-(2,2,2-trifluoroethyl)quinazoline-6-carboxamide as a white solid in 42.0% yield. LCMS: r.t=1.970 min, 490.0 $^1$H-NMR (400 MHz, DMSO-$d_6$): δ 10.79 (brs, 1H), 9.59 (s, 1H), 9.19 (d, J=7.6 Hz, 1H), 9.04 (d, J=4.8 Hz, 1H), 8.90 (s, 1H), 8.22-8.00 (m, 5H), 7.62 (t, J=9.2 Hz, 1H), 4.55-4.52 (m, 2H), 3.22 (s, 3H).

To a mixture of 4-(3-chloro-4-fluorophenylamino)-N-methyl-2-(pyridin-3-yl)-N-(2,2,2-trifluoroethyl)quinazoline-6-carboxamide (60 mg, 0.12 mmol) THF (1 mL) was added $BH_3$-THF (2 mol/L, 1 mL). The mixture was stirred at room temperature overnight. Methanol (0.2 mL) was added to quench the reaction mixture. The mixture was purified by prep-HPLC to give the desired product N-(3-chloro-4-fluorophenyl)-6-((methyl(2,2,2-trifluoroethyl)amino)methyl)-2-(pyridin-3-yl)quinazolin-4-amine (GL0001H-3309) as a white solid 15 mg in a yield of 26.0%. LCMS: r.t=2.154 min, $[MH]^+$=476.1. $^1$H-NMR (400 MHz, DMSO-$d_6$): δ 10.09 (s, 1H), 9.53 (s, 1H), 8.70-8.66 (m, 2H), 8.44 (s, 1H), 8.27-8.25 (m, 1H), 7.93-7.91 (m, 3H), 7.57-7.55 (m, 2H), 3.93 (s, 2H), 3.39-3.32 (m, 2H), 2.40 (s, 3H).

Synthesis of 4-(3-chloro-4-fluorophenylamino)-2-(pyridin-3-yl)-N-(2,2,2-trifluoroethyl)quinazoline-6-carboxamide (compound 1139)

4-(3-chloro-4-fluorophenylamino)-2-(pyridin-3-yl)-N-(2,2,2-trifluoroethyl)quinazoline-6-carboxamide was synthesized in a similar manner to that described for 4-(3-chloro-4-fluorophenylamino)-N-methyl-2-(pyridin-3-yl)-N-(2,2,2-trifluoroethyl)quinazoline-6-carboxamide substituting 2,2,2-trifluoroethylamine for 2,2,2-trifluoro-N-methylethylamine. The resulting product was analyzed. LCMS: r.t=1.934 min, $[M+1]^+$=476.0. $^1$H-NMR (400 MHz, DMSO-$d_6$): δ 10.43 (s, 1H), 9.54 (s, 1H), 9.32 (t, J=6.1 Hz, 1H), 9.14 (s, 1H), 8.72 (d, J=4.6 Hz, 1H), 8.68 (d, J=8.0 Hz, 1H), 8.32 (d, J=8.7 Hz, 1H), 8.27 (dd, J=6.7, 2.2 Hz, 1H), 7.98 (d, J=8.7 Hz, 1H), 7.96-7.90 (m, 1H), 7.62-7.51 (m, 2H), 4.27-4.14 (m, 2H).

Scheme 65: General route for the synthesis of compounds with general formula vi

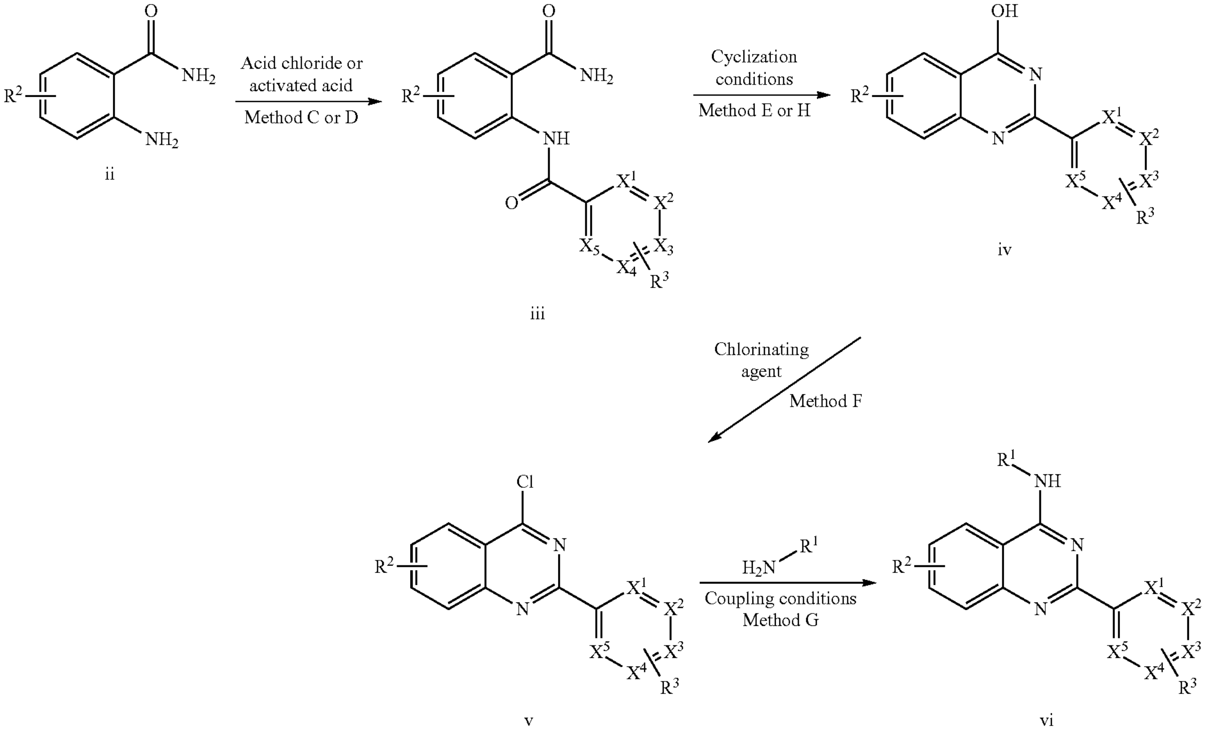

$X^1$, $X^2$, $X^3$, $X^4$ or $X^5$ = CH or N, at least two of $X^1$, $X^2$, $X^3$, $X^4$ or $X^5$ must be N Method E for Cyclization
E1: Sodium methoxide/Toluene
E2: NaOH/EtOH
Method G for Coupling Conditions
G1: i-PrOH/85-100° C.
G2: THF/reflux
G3: i-AmOH/100-130° C.
G4: MeOH/microwave/150° C.
G5: i-AmOH/microwave/150° C.
G6: THF/$Et_3N$/reflux Scheme 66: Representative synthesis of compounds of formula vi-a with a pyridazine (see Scheme 65)

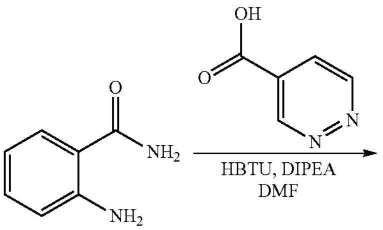

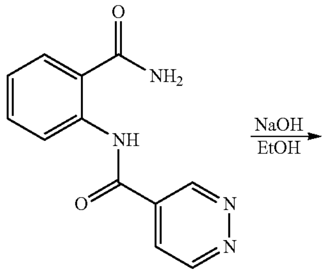

iii-c

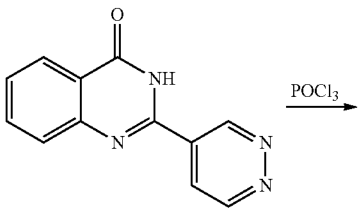

iv-f

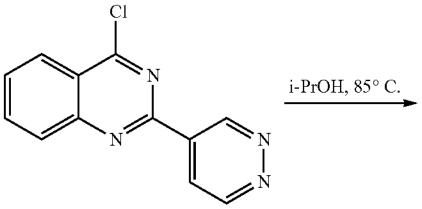

v-f

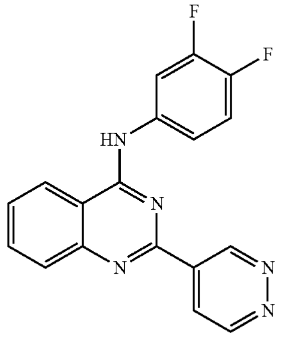

vi-r

Method D: N-(2-carbamoylphenyl)pyridazine-4-carboxamide (iii-c)

A mixture of pyridazine-4-carboxylic acid (500 mg, 4.0 mmol, 1.0 eq.), 2-aminobenzamide (603 mg, 4.4 mmol, 1.1 eq.) and HBTU (3.0 g, 8.0 mmol, 2.0 eq.) was suspended in 15 mL of DMF. DIPEA (2.0 mL, 1.56 g, 12.0 mmol, 3.0 eq.) was added dropwise at room temperature and was stirred over night. After quenching with water, the resulting precipitate was collected and washed with a small amount of DCM. A white solid (388 mg) was obtained, LCMS m/z=243.1 (M+1) (Method B) (retention time=0.99 min) was used in the next step without further purification.

Method E1: 2-(pyridazin-4-yl)quinazolin-4(3H)-one (iv-f)

A 100 mL round-bottom flask equipped with a Dean-Stark trap was charged with a mixture of N-(2-carbamoylphenyl) pyridazine-4-carboxamide (300 mg, 1.0 eq.), sodium methoxide (401 mg, 7.4 mmol, 6.0 eq.) and 10 mL of anhydrous toluene. The reaction mixture was heated to 110° C. and refluxed overnight. After cooling, the volatiles were removed in vacuo and the residue was quenched with a saturated aqueous solution of $NH_4Cl$ (10 mL). The pH of the mixture was adjusted to 3 with 10% HCl in water. The solution was extracted with DCM (50 ml×3). The combined organic layers were washed with brine, dried over $Na_2SO_4$. After filtration and evaporation, 88 mg of a yellow solid was obtained, LCMS m/z=225.1 (M+1) (Method A) (retention time=1.10 min) which was used in the next step without further purification.

Method F5: 4-chloro-2-(pyridazin-4-yl)quinazoline (v-f)

A 100-mL round-bottom flask was charged with 2-(pyridazin-4-yl) quinazolin-4(3H)-one (30 mg) which was suspended in 3 mL of $POCl_3$. The reaction mixture was heated to reflux for 1 h. The reaction mixture turned to a clear brown solution. After cooling, 50 mL of ice/water was carefully added. An aqueous ammonia solution (25% by weight in water) was added dropwise to the mixture with stirring until the pH of the mixture was adjusted to 7~8. An internal temperature of 0° C. was maintained by the addition of ice. The mixture was warmed to room temperature and extracted with DCM (50 ml×3). The combined organic layers were washed with brine, dried over $Na_2SO_4$. After filtration and evaporation, 32 mg was obtained as a light brown solid. LCMS m/z=242.9 (M+1) (Method B) (retention time=1.65 min). The solid was used directly in the next step without further purification.

Method G1: N-(3,4-difluorophenyl)-2-(pyridazin-4-yl)quinazolin-4-amine (vi-r)

(This method is representative of method G1, G2, and G3. These three methods can be implemented in a similar way except for substitution of the appropriate solvent and temperature) The mixture of 4-chloro-2-(pyridazin-4-yl) quinazoline (10 mg, 0.041 mmol, 1 eq.) and 3,4-difluorobenzenamine (11 mg, 0.082 mmol, 2 eq.) was suspended in i-PrOH. The mixture was heated at 85° C. overnight. After cooling, the resulting precipitate was filtered and purified on HPLC (Condition C). 7.3 mg of N-(3,4-difluorophenyl)-2-(pyridazin-4-yl)quinazolin-4-amine was obtained (yield 53%). LCMS m/z=336.0 (M+1) (Method B) (retention time=1.731 min). $^1H$-NMR (400 MHz, DMSO-$d_6$): δ 10.23

(s, 1H), 10.00 (dd, J=2.2, 1.3 Hz, 1H), 9.44 (dd, J=5.4, 1.2 Hz, 1H), 8.59 (d, J=8.1 Hz, 1H), 8.39 (dd, J=5.4, 2.4 Hz, 1H), 8.05-8.13 (m, 1H), 7.99 (s, 1H), 7.97 (d, J=3.6 Hz, 1H), 7.72-7.79 (m, 2H), 7.51-7.61 (m, 1H).

The compounds in the following table were prepared in a manner analogous to that described in Scheme 1 and 64 (prepared according to method procedure A-G as designated).

TABLE 21

| Number | PRODUCT | Salt type | Molecular Mass | $^1$H-NMR | $^1$H-NMR Solvent | LCMS | LCMS Protocol | Purity percent | Method for Coupling |
|---|---|---|---|---|---|---|---|---|---|
| 1140 | 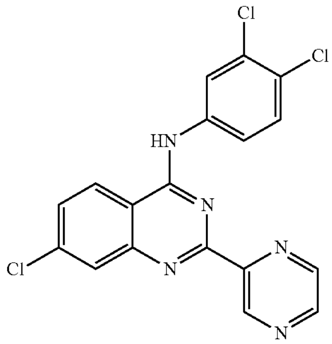 [SMILES: Clc1ccc2c(Nc3ccc(Cl)c(Cl)c3)nc(-c3cnccn3)nc2c1] | | 402.66 | 1H-NMR (400 MHz, CD3OD): δ 9.40 (s, 1H), 9.84-9.86 (m, 2H), 8.52 (d, J = 8.4 Hz, 1H), 8.15 (s, 1H), 8.02 (s, 1H), 7.84 (dd, J = 9.2, 2.4 Hz, 1H), 7.66-7.67 (m, 2H). | CD3OD | 402.0, 404.0, 405.9 (M + 1) | Method B (NH4HCO3) | 95 | Method C, G1 |
| 1141 | 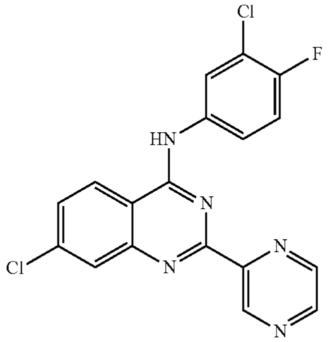 [SMILES: Fc1ccc(Nc2nc(-c3cnccn3)nc3cc(Cl)ccc23)cc1Cl] | | 386.21 | 1H-NMR (400 MHz, DMSO-d6): δ 10.78 (s, 1H), 9.49 (s, 1H), 8.89 (d, J = 10.8 Hz, 2H), 8.75 (d, J = 8.8 Hz, 1H), 8.44 (dd, J = 6.8, 2.4 Hz, 1H), 8.12 (d, J = 2.0 Hz, 1H), 7.94-7.99 (m, 1H), 7.87 (dd, J = 8.8, 2.0 Hz, 1H), 7.56 (t, J = 9.2 Hz, 1H). | DMSO | 386.0, 388.0 (M + 1) | Method B (NH4HCO3) | 95 | Method C, G1 |
| 1142 | 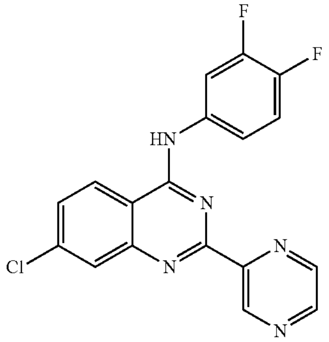 [SMILES: Fc1ccc(Nc2nc(-c3cnccn3)nc3cc(Cl)ccc23)cc1F] | | 369.76 | 1H-NMR (400 MHz, CD3OD): δ 9.40 (s, 1H), 8.76 (d, J = 10.8 Hz, 2H), 8.40 (d, J = 8.8 Hz, 1H), 8.02 (d, J = 2.0 Hz, 1H), 7.80-7.86 (m, 1H), 7.68 (dd, J = 8.8, 1.6 Hz, 1H), 7.52 (d, J = 9.2 Hz, 1H), 7.33 (q, J = 9.2 Hz, 1H). | CD3OD | 370.0, 372.1 (M + 1) | Method B (NH4HCO3) | 95 | Method C, G1 |
| 1143 | 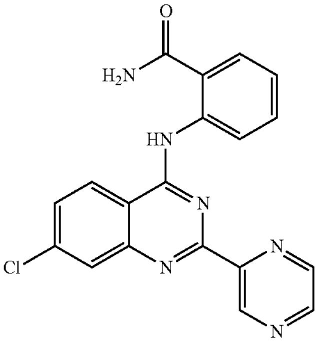 [SMILES: NC(=O)c1ccccc1Nc1nc(-c2cnccn2)nc2cc(Cl)ccc12] | | 376.8 | 1H-NMR (400 MHz, CD3OD): δ 9.55 (s, 1H), 8.80 (d, J = 7.2 Hz, 3H), 8.26 (d, J = 8.8 Hz, 1H), 8.04 (s, 1H), 7.85 (d, J = 6.8 Hz, 1H), 7.72 (d, J = 8.4 Hz, 1H), 7.66 (t, J = 7.2 Hz, 1H), 7.28 (t, J = 7.6 Hz, 1H). | CD3OD | 377.1, 379.0 (M + 1) | Method B (NH4HCO3) | 95 | Method C, G1 |

TABLE 21-continued

| Number | PRODUCT | Salt type | Molecular Mass | $^1$H-NMR | $^1$H-NMR Solvent | LCMS | LCMS Protocol | Purity percent | Method for Coupling |
|---|---|---|---|---|---|---|---|---|---|
| 1144 | 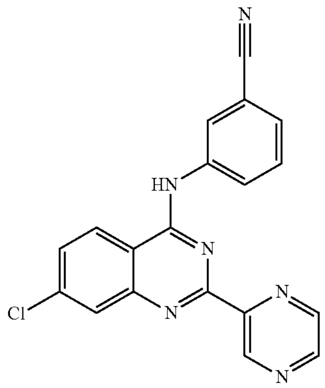 [SMILES: N#Cc1cccc(Nc2nc(-c3cnccn3)nc3cc(Cl)ccc23)c1] | | 358.78 | 1H-NMR (400 MHz, CD3OD): δ 9.39 (d, J = 1.6 Hz, 1H), 8.79 (d, J = 6.8 Hz, 2H), 8.47 (d, J = 9.2 Hz, 1H), 8.20 (s, 1H), 8.05-8.10 (m, 2H), 7.77 (dd, J = 8.8, 2.0 Hz, 1H), 7.63-7.66 (m, 2H). | CD3OD | 359.0, 361.0 (M + 1) | Method B (NH4HCO3) | 95 | Method C, G1 |
| 1145 | 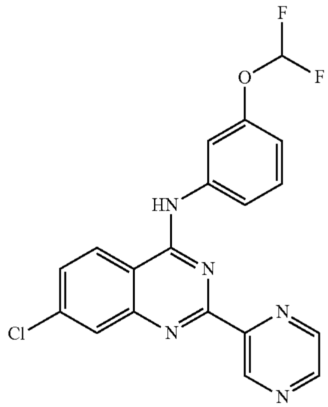 [SMILES: FC(F)Oc1cccc(Nc2nc(-c3cnccn3)nc3cc(Cl)ccc23)c1] | | 399.78 | 1H-NMR (400 MHz, DMSO-d6): δ 10.63 (s, 1H), 9.52 (d, J = 1.2 Hz, 1H), 8.86 (t, J = 6.0 Hz, 2H), 8.77 (d, J = 8.4 Hz, 1H), 8.12 (d, J = 15.6 Hz, 2H), 7.85 (d, J = 8.8 Hz, 2H), 7.53 (t, J = 8.0 Hz, 1H), 7.32 (t, J = 74.0 Hz, 1H), 7.04 (dd, J = 8.0, 1.6 Hz, 1H). | DMSO | 400.0, 402.0 (M + 1) | Method B (NH4HCO3) | 95 | Method C, G1 |
| 1146 | 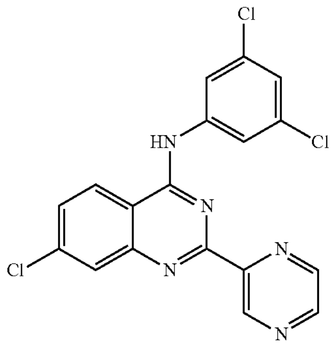 [SMILES: Clc1cc(Cl)cc(Nc2nc(-c3cnccn3)nc3cc(Cl)ccc23)c1] | | 402.66 | 1H-NMR (400 MHz, CD3OD): δ 9.40 (s, 1H), 8.85-8.88 (m, 2H), 8.53 (d, J = 9.2 Hz, 1H), 8.17 (d, J = 2.0 Hz, 1H), 7.80-7.88 (m, 3H), 7.46 (s, 1H). | CD3OD | 401.9, 403.9, 405.9 (M + 1) | Method B (NH4HCO3) | 95 | Method C, G1 |
| 1147 | 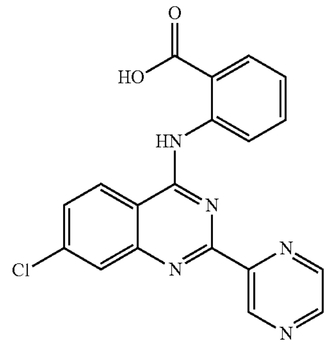 [SMILES: O=C(O)c1ccccc1Nc1nc(-c2cnccn2)nc2cc(Cl)ccc12] | | 377.78 | 1H-NMR (400 MHz, DMSO-d6): δ 12.28 (s, 1H), 9.58 (s, 1H), 9.14 (d, J = 8.4 Hz, 1H), 8.87 (s, 1H), 8.80 (d, J = 2.0 Hz, 1H), 8.28 (d, J = 9.2 Hz, 1H), 8.07-8.12 (m, 2H), 7.86 (dd, J = 8.8, 2.0 Hz, 1H), 7.77 (t, J = 8.8 Hz, 1H), 7.26 (t, J = 7.6 Hz, 1H). | DMSO | 378.1, 380.0 (M + 1) | Method B (NH4HCO3) | 95 | Method C, G1 |

TABLE 21-continued

| Number | PRODUCT | Salt type | Molecular Mass | $^1$H-NMR | $^1$H-NMR Solvent | LCMS | LCMS Protocol | Purity percent | Method for Coupling |
|---|---|---|---|---|---|---|---|---|---|
| 1148 | 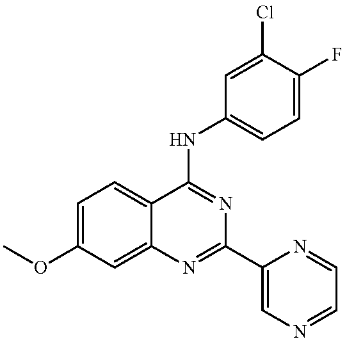 [SMILES: COc1ccc2c(Nc3ccc(F)c(Cl)c3)nc(-c3cnccn3)nc2c1] | | 381.79 | 1H-NMR (400 MHz, DMSO-d6): δ 11.69-11.49 (m, 1H), 9.40 (d, J = 1.2 Hz, 1H), 9.00-8.86 (m, 3H), 8.24 (dd, J = 6.6, 2.1 Hz, 1H), 7.91 (ddd, J = 8.9, 4.2, 2.6 Hz, 1H), 7.71 (d, J = 1.4 Hz, 1H), 7.61 (t, J = 9.0 Hz, 1H), 7.49 (dd, J = 9.2, 2.3 Hz, 1H), 4.00 (s, 3H). | DMSO | 382.1, 384.1 (M + 1) | Method B (NH4HCO3) | 95 | Method C, G1 |
| 1149 | 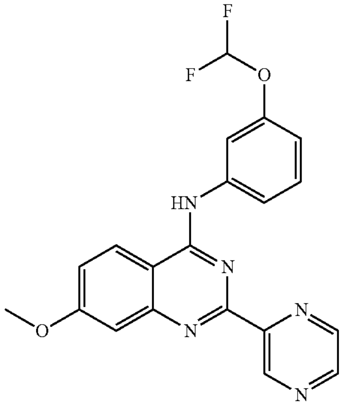 [SMILES: COc1ccc2c(Nc3cccc(OC(F)F)c3)nc(-c3cnccn3)nc2c1] | | 395.36 | 1H-NMR (400 MHz, DMSO-d6): δ 9.96 (s, 1H), 9.57 (d, J = 1.4 Hz, 1H), 8.83-8.74 (m, 2H), 8.57 (d, J = 9.1 Hz, 1H), 8.28 (t, J = 2.0 Hz, 1H), 7.86 (dd, J = 8.2, 1.2 Hz, 1H), 7.50-7.32 (m, 3H), 7.31 (t, J = 74.0 Hz, 1H), 6.94 (dd, J = 8.0, 2.2 Hz, 1H), 3.98 (s, 3H). | DMSO | 396.1, (M + 1), 397.2 (M + 2) | Method B (NH4HCO3) | 95 | Method C, G1 |
| 1150 | 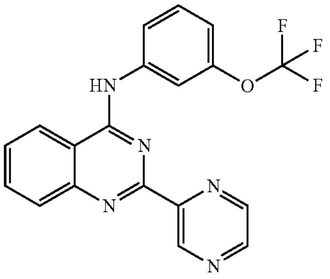 [SMILES: FC(F)(F)Oc1cccc(Nc2nc(-c3cnccn3)nc3ccccc23)c1] | | 383.33 | 1H-NMR (400 MHz, DMSO-d6): δ 10.27 (s, 1H), 9.57 (s, 1H), 8.80 (dd, J = 19.8, 1.7 Hz, 2H), 8.72-8.66 (m, 1H), 8.50 (s, 1H), 8.07-7.94 (m, 3H), 7.75 (t, J = 7.2 Hz, 1H), 7.57 (t, J = 8.2 Hz, 1H), 7.14 (d, J = 8.8 Hz, 1H). | DMSO | 384.1 (M + 1) | Method B (NH4HCO3) | 95 | Method C, G1 |
| 1151 | 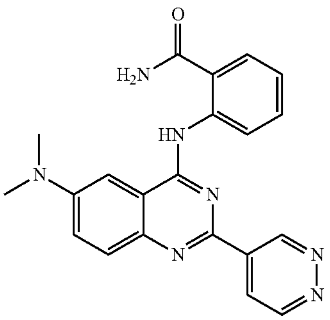 [SMILES: CN(C)c1ccc2nc(-c3ccnnc3)nc(Nc3ccccc3C(N)=O)c2c1] | | 385.42 | 1H-NMR (400 MHz, DMSO-d6): δ 13.01 (s, 1H), 10.04 (s, 1H), 9.40 (d, J = 5.4 Hz, 1H), 9.20 (d, J = 8.4 Hz, 1H), 8.48 (s, 1H), 8.42 (dd, J = 5.3, 1.9 Hz, 1H), 8.04-7.94 (m, 2H), 7.84 (d, J = 9.2 Hz, 1H), 7.75 (t, J = 7.9 Hz, 1H), 7.58 (d, J = 9.2 Hz, 1H), 7.20 (t, J = 7.5 Hz, 1H), 7.13 (s, 1H), 3.15 (s, 6H). | DMSO | 386.0 (M + 1) | Method A (TFA) | 95 | Method D, G1 |

TABLE 21-continued

| Number | PRODUCT | Salt type | Molecular Mass | $^1$H-NMR | $^1$H-NMR Solvent | LCMS | LCMS Protocol | Purity percent | Method for Coupling |
|---|---|---|---|---|---|---|---|---|---|
| 1152 | 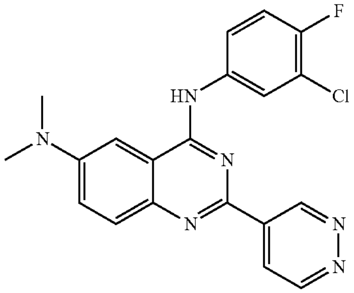 [SMILES: CN(C)c1ccc2nc(-c3ccnnc3)nc(Nc3ccc(F)c(Cl)c3)c2c1] | | HCl | 1H-NMR (400 MHz, DMSO-d6): δ 10.96 (s, 1H), 9.97 (d, J = 1.1 Hz, 1H), 9.55 (d, J = 5.5 Hz, 1H), 8.61 (dd, J = 5.5, 2.2 Hz, 1H), 8.15 (dd, J = 6.8, 2.6 Hz, 1H), 8.08 (d, J = 9.3 Hz, 1H), 7.94 (ddd, J = 8.9, 4.3, 2.6 Hz, 1H), 7.74 (s, 1H), 7.62 (dd, J = 9.4, 2.5 Hz, 1H), 7.56 (t, J = 9.1 Hz, 1H), 3.16 (s, 6H). | DMSO | 395.1, 397.1 (M + 1) | Method A (TFA) | 95 | Method D, G1 |
| 1153 | 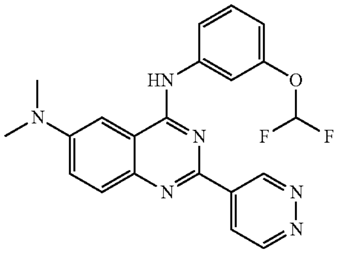 [SMILES: CN(C)c1ccc2nc(-c3ccnnc3)nc(Nc3cccc(OC(F)F)c3)c2c1] | HCl | 408.4 | 1H-NMR (400 MHz, DMSO-d6): δ 10.71 (brs, 1H), 10.01-9.99 (m, 1H), 9.52 (dd, J = 5.5, 1.0 Hz, 1H), 8.60 (dd, J = 5.5, 2.3 Hz, 1H), 8.07 ((d, J = 9.2 Hz 1H), 7.85-7.78 (m, 2H), 7.71 (s, 1H), 7.65 (dd, J = 9.3, 2.5 Hz, 1H), 7.56 (t, J = 8.2 Hz, 1H), 7.33 (t, J = 74.0 Hz, 1H), 7.09 (dd, J = 8.1, 2.1 Hz, 1H), 3.17 (s, 6H). | DMSO | 409.1 (M + 1) | Method A (TFA) | 95 | Method D, G1 |
| 1154 | 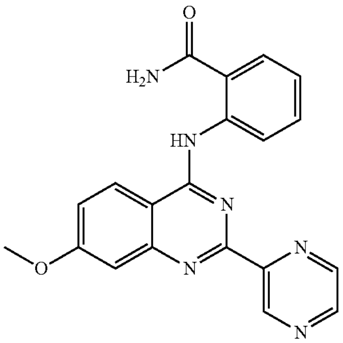 [SMILES: COc1ccc2c(Nc3ccccc3C(N)=O)nc(-c3cnccn3)nc2c1] | | 372.38 | 1H-NMR (400 MHz, DMSO-d6): δ 13.13 (s, 1H), 9.63 (d, J = 1.2 Hz, 1H), 9.34 (d, J = 7.6 Hz, 1H), 8.91-8.84 (m, 1H), 8.79 (d, J = 2.4 Hz, 1H), 8.49 (s, 1H), 8.12 (d, J = 9.6 Hz, 1H), 8.03-7.85 (m, 2H), 7.75-7.61 (m, 1H), 7.48-7.30 (m, 2H), 7.28-7.06 (m, 1H), 3.99 (s, 3H). | DMSO | 373.1 (M + 1) | Method B (NH4HCO3) | 95 | Method C, G1 |
| 1155 | 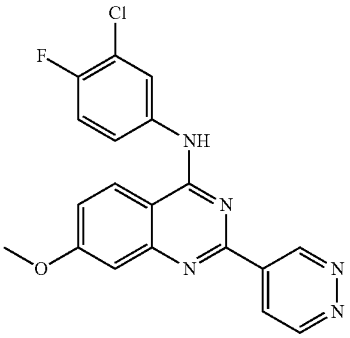 [SMILES: COc1ccc2c(Nc3ccc(F)c(Cl)c3)nc(-c3ccnnc3)nc2c1] | | 381.79 | 1H-NMR (400 MHz, DMSO-d6): δ 10.16 (s, 1H), 9.99-9.95 (m, 1H), 9.42 (dd, J = 5.2, 1.2 Hz, 1H), 8.58-8.51 (m, 1H), 8.35 (dd, J = 5.2, 2.4 Hz, 1H), 8.21 (dd, J = 6.8, 2.4 Hz, 1H), 7.93 (ddd, J = 8.8, 4.2, 2.7 Hz, 1H), 7.53 (dd, J = 11.7, 6.4 Hz, 1H), 7.32 (dd, J = 6.6, 2.6 Hz, 2H), 3.97 (s, 3H). | DMSO | 382.0, 384.0 (M + 1) | Method B (NH4HCO3) | 95 | Method D, G1 |

TABLE 21-continued

| Number | PRODUCT | Salt type | Molecular Mass | $^1$H-NMR | $^1$H-NMR Solvent | LCMS | LCMS Protocol | Purity percent | Method for Coupling |
|---|---|---|---|---|---|---|---|---|---|
| 1156 | 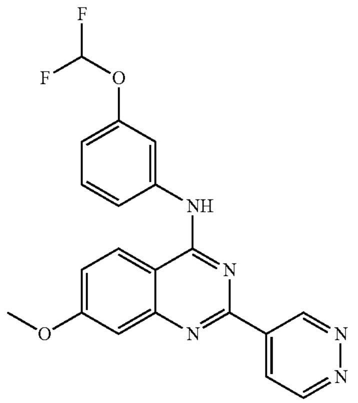 [SMILES: COc1ccc2c(Nc3cccc(OC(F)F)c3)nc(-c3ccnnc3)nc2c1] | | 395.36 | 1H-NMR (400 MHz, DMSO-d6) δ 10.07 (s, 1H), 10.01 (d, J = 1.3 Hz, 1H), 9.43 (dd, J = 5.2, 1.2 Hz, 1H), 8.55 (d, J = 10.0 Hz, 1H), 8.40 (dd, J = 5.2, 2.0 Hz, 1H), 7.91 (d, J = 2.0 Hz, 1H), 7.86-7.77 (m, 1H), 7.55-7.35 (m, 3H), 7.32 (t, J = 74.0 Hz, 1H), 7.01 (dd, J = 8.0, 2.0 Hz, 1H), 3.99 (s, 3H). | DMSO | 396.1 (M + 1) | Method B (NH4HCO3) | 95 | Method D, G1 |
| 1157 | 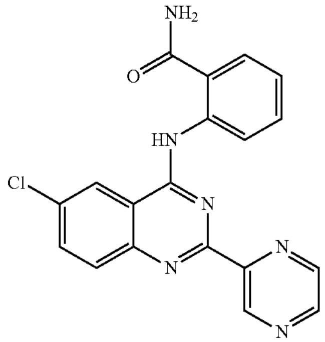 [SMILES: NC(=O)c1ccccc1Nc1nc(-c2cnccn2)nc2ccc(Cl)cc12] | | 376.80 | 1H-NMR (400 MHz, DMSO-d6): δ 13.34 (s, 1H), 9.61 (d, 1H), 9.28 (d, J = 8.4 Hz, 1H), 8.87 (s, 1H), 8.80 (s, 1H), 8.53 (s, 1H), 8.25 (s, 1H), 7.94-8.06 (m, 4H), 7.70 (t, J = 8.0 Hz, 1H), 7.23 (t, J = 7.6 Hz, 1H). | DMSO | 377.0, 379.0 (M + 1) | Method B (NH4HCO3) | 95 | Method C, G1 |
| 1158 | 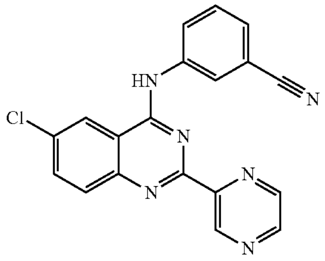 [SMILES: N#Cc1cccc(Nc2nc(-c3cnccn3)nc3ccc(Cl)cc23)c1] | | 358.78 | 1H-NMR (400 MHz, DMSO-d6): δ 10.35 (s, 1H), 9.54 (s, 1H), 8.77-8.84 (m, 4H), 8.32 (d, J = 8.0 Hz, 1H), 8.00-8.03 (m, 2H), 7.62-7.70 (m, 2H). | DMSO | 359.0, 361.0 (M + 1) | Method B (NH4HCO3) | 95 | Method C, G1 |
| 1159 | 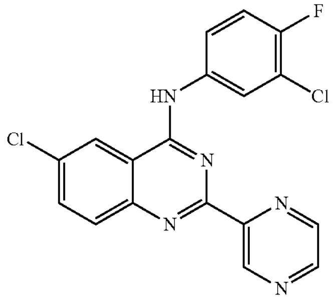 [SMILES: Fc1ccc(Nc2nc(-c3cnccn3)nc3ccc(Cl)cc23)cc1Cl] | | 386.21 | 1H-NMR (400 MHz, DMSO-d6): δ 10.55 (s, 1H), 9.50 (s, 1H), 8.83 8.87 (m, 3H), 8.47-8.49 (m, 1H), 7.96-8.06 (m, 3H), 7.54 (t, J = 9.2 Hz, 1H). | DMSO | 386.0, 388.0, 390.0 (M + 1) | Method B (NH4HCO3) | 95 | Method C, G1 |

TABLE 21-continued

| Number | PRODUCT | Salt type | Molecular Mass | $^1$H-NMR | $^1$H-NMR Solvent | LCMS | LCMS Protocol | Purity percent | Method for Coupling |
|---|---|---|---|---|---|---|---|---|---|
| 1160 | 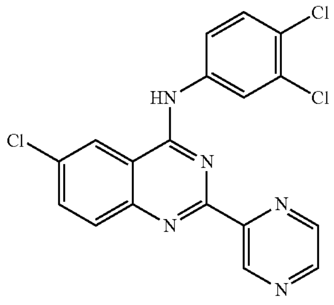 | | 402.66 | 1H-NMR (400 MHz, DMSO-d6): δ 10.54 (s, 1H), 9.53 (s, 1H), 8.84-8.88 (m, 3H), 8.62 (d, J = 2.0 Hz, 1H), 8.01-8.07 (m, 3H), 7.73 (d, J = 8.8 Hz, 1H). | DMSO | 401.9, 403.9, 406.0 (M + 1) | Method B (NH4HCO3) | 95 | Method C, G1 |
| 1161 | 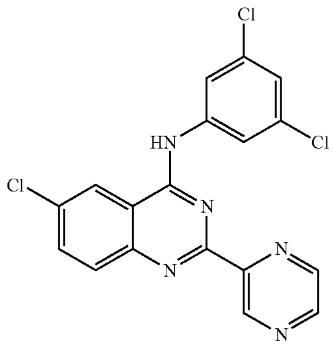 [SMILES: Clc1cc(Cl)cc(Nc2nc(-c3cnccn3)nc3ccc(Cl)cc23)c1] | | 402.66 | 1H-NMR (400 MHz, DMSO-d6): δ 10.42 (s, 1H), 9.55 (d, J = 1.6 Hz, 1H), 8.87-8.88 (m, 1H), 8.82 (d, J = 2.4 Hz, 1H), 8.36 (d, J = 2.0 Hz, 2H), 8.00-8.07 (m, 2H), 7.40 (t, J = 1.6 Hz, 1H). | DMSO | 401.9, 403.8, 405.8 (M + 1) | Method B (NH4HCO3) | 95 | Method C, G1 |
| 1162 | 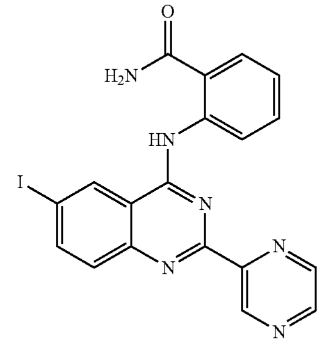 [SMILES: NC(=O)c1ccccc1Nc1nc(-c2cnccn2)nc2ccc(I)cc12] | | 468.25 | 1H-NMR (400 MHz, DMSO-d6): δ 13.36 (s, 1H), 9.59 (d, J = 1.2 Hz, 1H), 9.15-9.12 (m, 1H), 8.90-8.85 (m, 2H), 8.68 (d, J = 1.2 Hz, 1H), 8.52 (s, 1H), 8.28-8.25 (m, 1H), 8.07 (s, 1H), 7.99-7.96 (m, 1H), 7.83 (d, J = 8.8 Hz, 1H), 7.74-7.70 (m, 1H), 7.28 (t, J = 7.6 Hz, 1H). | DMSO | 469.0 (M + 1) | Method B (NH4HCO3) | 90 | Method C, G1 |
| 1163 | 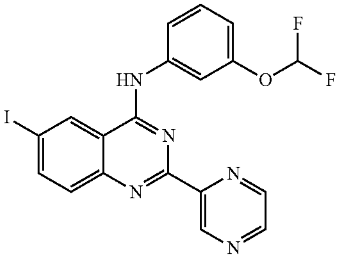 [SMILES: FC(F)Oc1cccc(Nc2nc(-c3cnccn3)nc3ccc(I)cc23)c1] | | 491.23 | 1H-NMR (400 MHz, DMSO-d6): δ 10.83 (s, 1H), 9.32 (s, 1H), 9.07 (s, 1H), 8.74 (s, 2H), 8.16 (dd, J = 8.0, 1.6 Hz, 1H), 7.87 (s, 1H), 7.74-7.64 (m, 2H), 7.39 (t, J = 8.0 Hz, 1H), 7.16 (t, J = 74.0 Hz, 1H), 6.96-6.92 (m, 1H). | DMSO | 492.0 (M + 1) | Method B (NH4HCO3) | 90 | Method C, G1 |

TABLE 21-continued

| Number | PRODUCT | Salt type | Molecular Mass | $^1$H-NMR | $^1$H-NMR Solvent | LCMS | LCMS Protocol | Purity percent | Method for Coupling |
|---|---|---|---|---|---|---|---|---|---|
| 1164 | 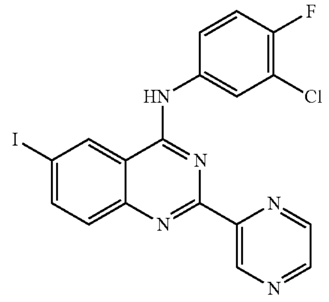 [SMILES: Fc1ccc(Nc2nc(-c3cnccn3)nc3ccc(I)cc23)cc1Cl] | | 477.66 | 1H-NMR (400 MHz, DMSO-d6): δ 11.48 (s, 1H), 9.42 (s, 1H), 9.34 (s, 1H), 8.95-8.93 (m, 2H), 8.35-8.30 (m, 2H), 7.97-7.90 (m, 2H), 7.60 (t, J = 9.0 Hz, 1H). | DMSO | 478.0, 480.0 (M + 1) | Method B (NH4HCO3) | 90 | Method C, G1 |
| 1165 | 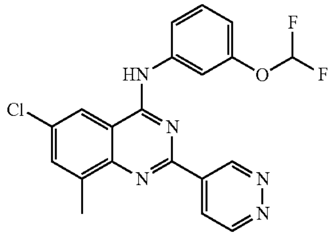 [SMILES: Cc1cc(Cl)cc2c(Nc3cccc(OC(F)F)c3)nc(-c3ccnnc3)nc12] | | 413.81 | 1H-NMR (400 MHz, DMSO-d6): δ 10.07 (s, 1H), 9.99 (s, 1H), 9.40 (d, J = 5.6 Hz, 1H), 8.56 (d, J = 1.6 Hz, 1H), 8.36 (dd, J = 5.2, 2.0 Hz, 1H), 7.87 (m, 1H), 7.81 (m, 1H), 7.53 (t, J = 7.8 Hz, 1H), 7.30 (t, J = 74.0 Hz, 1H), 8.36 (dd, J = 8.4, 2.0 Hz, 1H), 2.70 (s, 3H). | DMSO | 414.1, 416.0 (M + 1) | Method B (NH4HCO3) | 95 | Method D, G1 |
| 1166 | 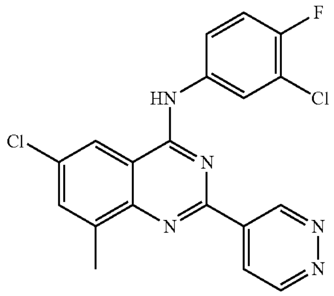 [SMILES: Cc1cc(Cl)cc2c(Nc3ccc(F)c(Cl)c3)nc(-c3ccnnc3)nc12] | | 400.24 | 1H-NMR (400 MHz, DMSO-d6): δ 10.16 (s, 1H), 10.01 (s, 1H), 9.46 (d, J = 5.2 Hz, 1H), 8.56 (d, J = 1.6 Hz, 1H), 8.39 (dd, J = 5.4, 2.2 Hz, 1H), 8.20 (dd, J = 7.2, 2.6 Hz, 1H), 7.95-7.91 (m, 1H), 7.89 (s, 1H), 7.57 (t, J = 9.0 Hz, 1H), 2.75 (s, 3H). | DMSO | 400.0, 402.0 (M + 1) | Method B (NH4HCO3) | 95 | Method D, G1 |
| 1167 | 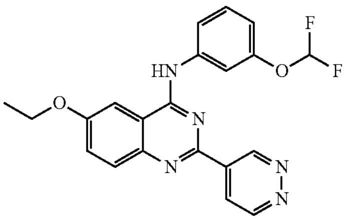 [SMILES: CCOc1ccc2nc(-c3ccnnc3)nc(Nc3cccc(OC(F)F)c3)c2c1] | | 409.39 | 1H-NMR (400 MHz, DMSO-d6): δ 10.05-10.3 (m, 2H), 9.45 (dd, J = 5.2, 1.2 Hz, 1H), 8.42 (dd, J = 5.2, 1.2 Hz, 1H), 8.06 (d, J = 2.8 Hz, 1H), 7.97-7.94 (m, 2H), 7.86 (dd, J= 8.0, 1.2 Hz, 1H), 7.66-7.60 (m, 2H), 7.38 (t, J = 74.0 Hz, 1H), 7.10-7.08 (m, 1H), 4.32 (q, J = 6.8 Hz, 2H), 1.51 (t, J = 7.0 Hz, 3H). | DMSO | 410.1 (M + 1) | Method B (NH4HCO3) | 95 | Method D, G1 |

TABLE 21-continued

| Number | PRODUCT | Salt type | Molecular Mass | $^1$H-NMR | $^1$H-NMR Solvent | LCMS | LCMS Protocol | Purity percent | Method for Coupling |
|---|---|---|---|---|---|---|---|---|---|
| 1168 | 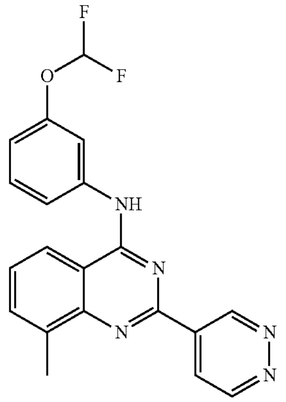 [SMILES: Cc1cccc2c(Nc3cccc(OC(F)F)c3)nc(-c3ccnnc3)nc12] | | 379.36 | 1H-NMR (400 MHz, DMSO-d6): δ 10.13 (s, 1H), 10.07 (d, J = 2.0 Hz, 1H), 9.44 (dd, J = 5.2, 2.4 Hz, 1H), 8.48-8.44 (m, 2H), 7.93 (t, J = 2.0 Hz, 1H), 7.86-7.84 (m, 2H), 7.66-7.62 (m, 1H), 7.54 (t, J = 8.4 Hz, 1H), 7.32 (t, J = 74.0 Hz, 1H), 7.02 (dd, J = 8.0, 2.4 Hz, 1H), 2.77 (s, 3H). | DMSO | 380.1 (M + 1) | Method B (NH4HCO3) | 95 | Method D, G1 |
| 1169 | 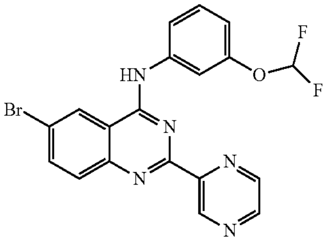 [SMILES: FC(F)Oc1cccc(Nc2nc(-c3cnccn3)nc3ccc(Br)cc23)c1] | | 444.23 | 1H-NMR (400 MHz, DMSO-d6): δ 10.17 (s, 1H), 9.55 (s, 1H), 8.98 (s, 1H), 8.79 (d, J = 12.8 Hz, 2H), 8.26 (s, 1H), 8.08 (d, J = 9.2 Hz, 1H), 7.92-7.88 (m, 2H), 7.52-7.50 (m, 1H), 7.32 (t, J = 71.6 Hz, 1H), 6.99 (d, J = 7.6 Hz, 1H). | DMSO | 444.0, 446.0 (M + 1) | Method B (NH4HCO3) | 95 | Method C, G1 |
| 1170 | 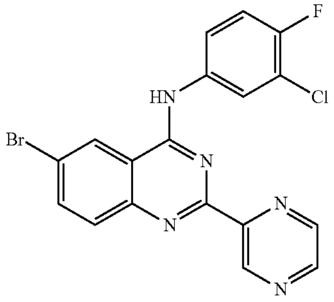 | | 430.66 | 1H-NMR (400 MHz, DMSO-d6): δ 10.11 (s, 1H), 9.52 (s, 1H), 8.89 (d, J = 1.2 Hz, 1H), 8.83 (s, 1H), 8.77 (d, J = 2.4 Hz, 1H), 8.56 (dd, J = 6.8, 2.4 Hz, 1H), 8.05 (dd, J = 9.2, 2.0 Hz, 1H), 8.02-7.96 (m, 1H), 7.88 (d, J = 8.8 Hz, 1H), 7.49 (t, J = 9.2 Hz, 1H). | DMSO | 430.0, 432.0, 434.0 (M + 1) | Method B (NH4HCO3) | 95 | Method C, G1 |
| 1171 | 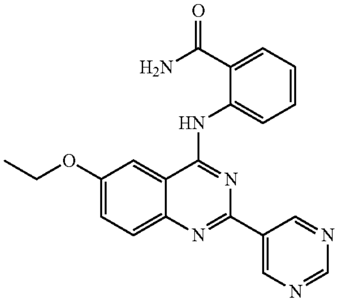 [SMILES: CCOc1ccc2nc(-c3cncnc3)nc(Nc3ccccc3C(N)=O)c2c1] | | 386.41 | 1H-NMR (400 MHz, DMSO-d6): δ 13.07 (s, 1H), 9.63 (s, 2H), 9.33 (s, 1H), 8.95 (d, J = 8.0 Hz, 1H), 8.50 (s, 1H), 7.99-7.94 (m, 3H), 7.76-7.71 (m, 1H), 7.62-7.59 (m, 2H), 7.24 (t, J = 7.4 Hz, 1H), 4.23 (q, J = 7.0 Hz, 2H), 1.46 (t, J = 7.0 Hz, 3H). | DMSO | 387.1 (M + 1) | Method B (NH4HCO3) | 95 | Method C, G1 |

TABLE 21-continued

| Number | PRODUCT | Salt type | Molecular Mass | $^1$H-NMR | $^1$H-NMR Solvent | LCMS | LCMS Protocol | Purity percent | Method for Coupling |
|---|---|---|---|---|---|---|---|---|---|
| 1172 | 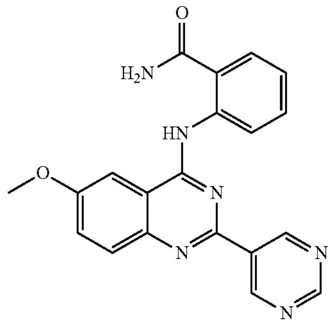 [SMILES: COc1ccc2nc(-c3cncnc3)nc(Nc3ccccc3C(N)=O)c2c1] | | 372.38 | 1H-NMR (400 MHz, DMSO-d6): δ 13.11 (s, 1H), 9.61 (s, 2H), 9.34 (s, 1H), 8.91 (d, J = 8.0 Hz, 1H), 8.49 (s, 1H), 7.98-7.95 (m, 3H), 7.72 (t, J = 8.0 Hz, 1H), 7.62-7.60 (m, 2H), 7.24 (t, J = 7.6 Hz, 1H), 3.97 (s, 3H). | DMSO | 373.1 (M + 1) | Method B (NH4HCO3) | 95 | Method C, G1 |
| 1173 | 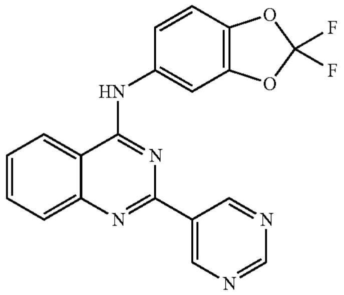 [SMILES: FC1(F)Oc2ccc(Nc3nc(-c4cncnc4)nc4ccccc34)cc2O1] | HCl | 379.32 | 1H-NMR (400 MHz, DMSO-d6): δ 10.55 (brs, 1H), 9.59 (s, 2H), 9.35 (s, 1H), 8.68 (d, J = 8.4 Hz, 1H), 8.09-8.07 (m, 1H), 8.00-7.96 (m, 2H), 7.76-7.72 (m, 1H), 7.67 (dd, J = 8.8, 2.0 Hz, 1H), 7.53 (d, J = 8.8 Hz, 1H). | DMSO | 380.0 (M + 1) | Method B (NH4HCO3) | 95 | Method C, G1 |
| 1174 | 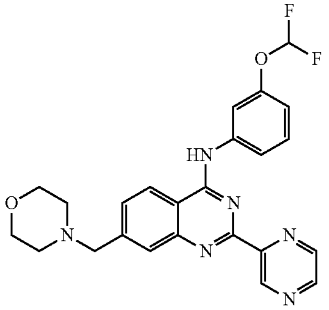 [SMILES: FC(F)Oc1cccc(Nc2nc(-c3cnccn3)nc3cc(CN4CCOCC4)ccc23)c1] | HCl | 464.47 | 1H-NMR (400 MHz, DMSO-d6): δ 10.14 (s, 1H), 9.59 (s, 1H), 8.80 (m, 2H), 8.62 (d, J = 7.6 Hz, 1H), 8.30 (s, 1H), 7.90 (s, 2H), 7.70 (d, J = 7.6 Hz, 1H), 7.53-7.45 (m, 1H), 7.39-6.86 (m, 1H), 7.30 (t, J = 74.1 Hz, 1H), 3.73 (s, 2H), 3.63-3.58 (m, 4H), 2.48-2.43 (m, 4H). | DMSO | 465.1 (M + 1) | Method B (NH4HCO3) | 95 | Method C, G1 |
| 1175 | 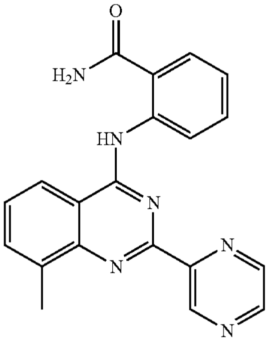 [SMILES: Cc1cccc2c(Nc3ccccc3C(N)=O)nc(-c3cnccn3)nc12] | | 357.37 | 1H-NMR (400 MHz, DMSO-d6): δ 9.70 (s, 1H), 9.43 (d, J = 8.4 Hz, 1H), 8.90 (s, 1H), 8.78 (d, J = 2.0 Hz, 1H), 8.22 (d, J = 8.0 Hz, 1H), 8.11 (d, J = 8.0 Hz, 1H), 7.80 (d, J = 2.8 Hz, 1H), 7.60-7.65 (m, 2H), 7.09-7.13 (m, 3H), 2.76 (s, 3H). | DMSO | 358.0 (M + 1) | Method B (NH4HCO3) | 95 | Method C, G1 |

TABLE 21-continued

| Number | PRODUCT | Salt type | Molecular Mass | $^1$H-NMR | $^1$H-NMR Solvent | LCMS | LCMS Protocol | Purity percent | Method for Coupling |
|---|---|---|---|---|---|---|---|---|---|
| 1176 | 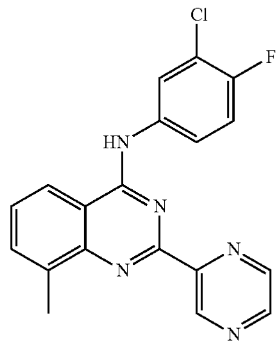 | | 365.79 | 1H-NMR (400 MHz, DMSO-d6): δ 10.02 (s, 1H), 9.62 (s, 1H), 8.85 (s, 1H), 8.76 (d, J = 2.4 Hz, 1H), 8.45 (d, J = 8.0 Hz, 1H), 8.03-8.07 (m, 1H), 7.81 (d, J = 6.8 Hz, 1H), 7.61 (t, J = 7.6 Hz, 1H), 7.49 (t, J = 9.2 Hz, 1H), 2.75 (s, 3H). | DMSO | 366.0, 368.0 (M + 1) | Method B (NH4HCO3) | 95 | Method C, G1 |
| 1177 | 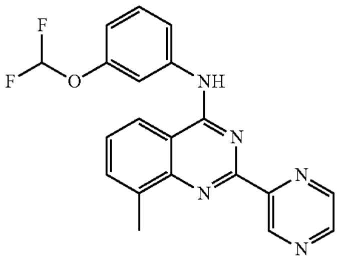 [SMILES: Cc1cccc2c(Nc3cccc(OC(F)F)c3)nc(-c3cnccn3)nc12] | | 379.36 | 1H-NMR (400 MHz, DMSO-d6): δ 10.02 (s, 1H), 9.64 (s, 1H), 8.83 (s, 1H), 8.76 (d, J = 2.0 Hz, 1H), 8.50 (d, J = 8.0 Hz, 1H), 8.38 (s, 1H), 7.92 (d, J = 8.4 Hz, 1H), 7.81 (d, J = 6.8 Hz, 1H), 7.61 (t, J = 7.8 Hz, 1H), 7.49 (t, J = 8.4 Hz, 1H), 7.32 (t, J = 74.0 Hz, 1H), 6.95 (d, J = 7.2 Hz, 1H), 2.75 (s, 3H). | DMSO | 380.0 (M + 1) | Method B (NH4HCO3) | 95 | Method C, G1 |
| 1178 | 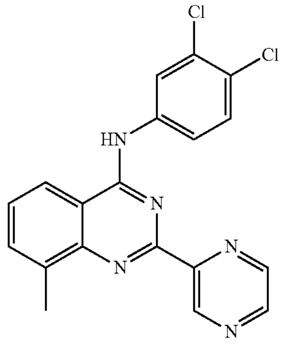 [SMILES: Cc1cccc2c(Nc3ccc(Cl)c(Cl)c3)nc(-c3cnccn3)nc12] | | 382.25 | 1H-NMR (400 MHz, DMSO-d6): δ 10.21 (s, 1H), 9.62 (s, 1H), 8.86 (t, J = 2.4 Hz, 1H), 8.78 (t, J = 3.2 Hz, 2H), 8.52 (d, J = 8.4 Hz, 1H), 8.10-8.13 (m, 1H), 7.83 (d, J = 7.2 Hz, 1H), 7.68 (d, J = 9.2 Hz, 1H), 7.63 (t, J = 7.6 Hz, 1H), 2.75 (s, 3H). | DMSO | 381.9, 383.9 (M + 1) | Method B (NH4HCO3) | 95 | Method C, G1 |
| 1179 | 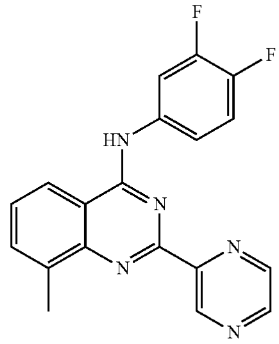 [SMILES: Cc1cccc2c(Nc3ccc(F)c(F)c3)nc(-c3cnccn3)nc12] | | 349.34 | 1H-NMR (400 MHz, DMSO-d6): δ 10.21 (s, 1H), 9.60 (s, 1H), 8.87 (s, 1H), 8.78 (d, J = 2.4 Hz, 1H), 8.50-8.60 (m, 2H), 7.80-7.85 (m, 2H), 7.61 (t, J = 7.8 Hz, 1H), 7.46-7.54 (m, 1H), 2.74 (s, 3H). | DMSO | 350.0 (M + 1) | Method B (NH4HCO3) | 95 | Method C, G1 |

TABLE 21-continued

| Number | PRODUCT | Salt type | Molecular Mass | $^1$H-NMR | $^1$H-NMR Solvent | LCMS | LCMS Protocol | Purity percent | Method for Coupling |
|---|---|---|---|---|---|---|---|---|---|
| 1180 | 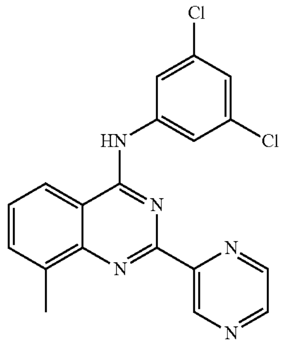 [SMILES: Cc1cccc2c(Nc3cc(Cl)cc(Cl)c3)nc(-c3cnccn3)nc12] | | 382.25 | 1H-NMR (400 MHz, DMSO-d6), δ 10.20 (s, 1H), 9.62 (s, 1H), 8.85 (s, 1H), 8.77 (d, J = 2.8 Hz, 1H), 8.47-8.52 (m, 3H), 7.81 (d, J = 3.2 Hz, 1H), 7.60 (t, J = 7.8 Hz, 1H), 7.31 (t, J = 1.6 Hz, 1H), 2.51 (s, 3H). | DMSO | 381.9, 383.9 (M + 1) | Method B (NH4HCO3) | 95 | Method C, G1 |
| 1181 | 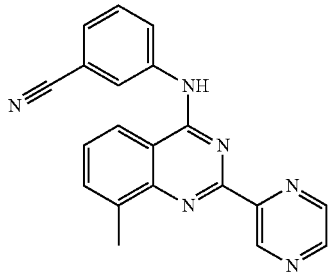 [SMILES: Cc1cccc2c(Nc3cccc(C#N)c3)nc(-c3cnccn3)nc12] | | 338.37 | 1H-NMR (400 MHz, DMSO-d6): δ 10.21 (s, 1H), 9.64 (s, 1H), 8.86 (d, J = 9.2 Hz, 2H), 8.78 (d, J = 8.0 Hz, 1H), 8.51 (d, J = 8.0 Hz, 1H), 8.38 (d, J = 8.4 Hz, 1H), 7.84 (d, J = 7.2 Hz, 1H), 7.61-7.65 (m, 3H), 2.76 (s, 3H). | DMSO | 339.0 (M + 1) | Method B (NH4HCO3) | 95 | Method C, G1 |
| 1182 | 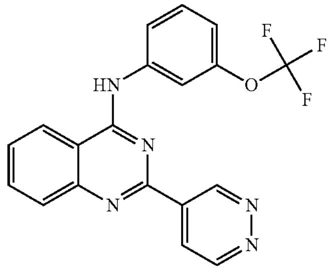 [SMILES: FC(F)(F)Oc1cccc(Nc2nc(-c3ccnnc3)nc3ccccc23)c1] | | 383.33 | 1H-NMR (400 MHz, DMSO-d6): δ 10.24 (s, 1H), 9.99 (s, 1H), 9.41 (d, J = 5.2 Hz, 1H), 8.62 (d, J = 8.4 Hz, 1H), 8.36-8.38 (m, 1H) 8.10 (s, 1H), 7.95-7.98 (m, 3H), 7.73-7.74 (m, 1H), 7.62 (t, J = 8.0 Hz, 1H), 7.20 (d, J = 8.0 Hz, 1H). | DMSO | 384.2 (M + 1) | Method B (NH4HCO3) | 95 | Method D, G1 |
| 1183 | 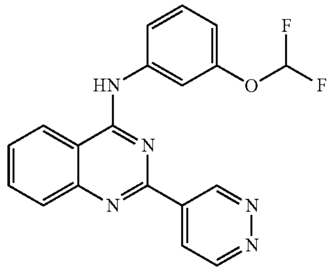 [SMILES: FC(F)Oc1cccc(Nc2nc(-c3ccnnc3)nc3ccccc23)c1] | | 365.34 | 1H-NMR (400 MHz, DMSO-d6): δ 10.19 (s, 1H), 10.01 (s, 1H), 9.41-9.43 (m, 1H), 8.63 (d, J = 8.0 Hz, 1H), 8.39-8.41 (m, 1H), 7.93-7.97 (m, 3H), 7.84 (d, J = 8.4 Hz, 1H), 7.74 (m, 1H), 7.54-7 56 (m, 1H), 7.32 (t, J = 74.0 Hz, 1H), 7.02-7.04 (m, 1H). | DMSO | 366.2 (M + 1) | Method B (NH4HCO3) | 95 | Method D, G1 |
| 1184 | 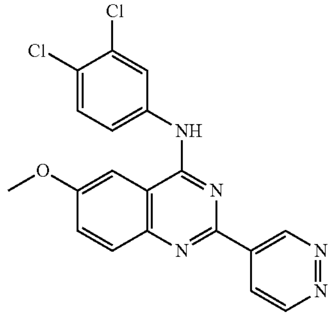 [SMILES: COc1ccc2nc(-c3ccnnc3)nc(Nc3ccc(Cl)c(Cl)c3)c2c1] | | 398.25 | 1H-NMR (400 MHz, DMSO-d6): δ 10.27 (s, 1H), 9.96 (s, 1H), 9.44 (d, J = 4.8 Hz, 1H), 8.40-8.41 (m, 1H), 8.29 (d, J = 2.0 Hz, 1H), 8.06 (d, J = 2.4 Hz, 1H), 7.99-8.02 (m, 1H), 7.89 (d, J = 8.8 Hz, 1H), 7.71 (d, J = 8.8 Hz, 1H), 7.56-7.58 (m, 1H), 3.99 (s, 3H). | DMSO | 398.0, 400.0, 402.0 (M + 1) | Method B (NH4HCO3) | 95 | Method D, G1 |

TABLE 21-continued

| Number | PRODUCT | Salt type | Molecular Mass | $^1$H-NMR | $^1$H-NMR Solvent | LCMS | LCMS Protocol | Purity percent | Method for Coupling |
|---|---|---|---|---|---|---|---|---|---|
| 1185 | 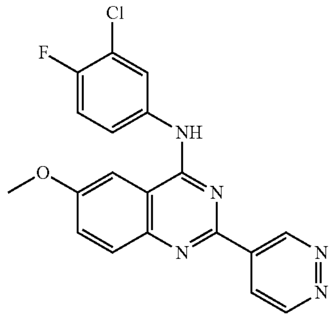 | | 381.79 | 1H-NMR (400 MHz, DMSO-d6): δ 9.92 (s, 1H), 9.36-9.38 (m, 1H), 8.27-8.29 (m, 1H), 8.14-8.16 (m, 1H), 7.51 (s, 1H), 7.83-7.91 (m, 3H), 7.51-7.56 (m, 2H), 3.97 (s, 3H). | DMSO | 382.1, 384.1 (M + 1) | Method B (NH4HCO3) | 95 | Method D, G1 |
| 1186 | 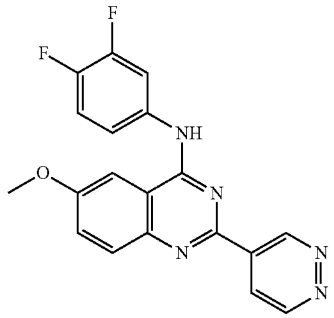 | | 365.34 | 1H-NMR (400 MHz, DMSO-d6): δ 9.95-10.00 (m, 2H), 9.40 (d, J = 5.6 Hz, 1H), 8.32-8.33 (m, 1H), 8.06 (m, 1H), 7.96 (s, 1H), 7.89 (d, J = 9.2 Hz, 1H), 7.69 (m, 1H), 7.54-7.59 (m, 2H), 3.98 (s, 3H). | DMSO | 366.1 (M + 1) | Method B (NH4HCO3) | 95 | Method D, G1 |
| 1187 | 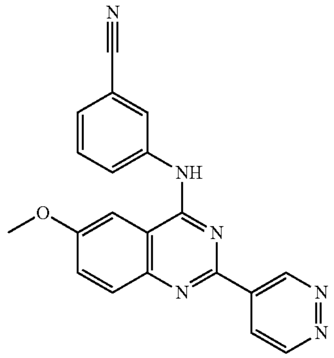 [SMILES: COc1ccc2nc(-c3ccnnc3)nc(Nc3cccc(C#N)c3)c2c1] | | 354.36 | 1H-NMR (400 MHz, DMSO-d6): δ 10.00 (s, 1H), 9.90 (m, 1H), 9.35-9.36 (m, 1H), 8.23-8.30 (m, 3H), 7.84-7.90 (m, 2H), 7.62-7.71 (m, 2H), 7.54-7.57 (m, 1H), 3.96 (s, 3H). | DMSO | 355.1 (M + 1) | Method B (NH4HCO3) | 95 | Method D, G1 |
| 1188 | 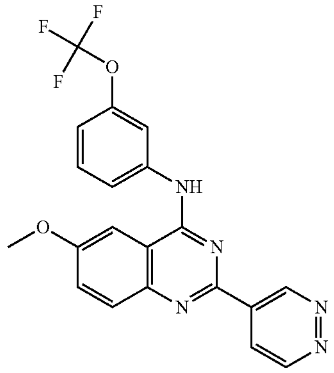 [SMILES: COc1ccc2nc(-c3ccnnc3)nc(Nc3cccc(OC(F)(F)F)c3)c2c1] | | 413.35 | 1H-NMR (400 MHz, DMSO-d6): δ 9.96-10.0 (m, 2H), 8.39-8.40 (m, 1H), 8.31-8.33 (m, 1H), 8.07 (s, 1H), 7.88-7.96 (m, 3H), 7.57-7.67 (m, 2H), 7.22 (d, J = 8.0 Hz, 1H), 4.01 (s, 3H). | DMSO | 414.1 (M + 1) | Method B (NH4HCO3) | 95 | Method D, G1 |

TABLE 21-continued

| Number | PRODUCT | Salt type | Molecular Mass | $^1$H-NMR | $^1$H-NMR Solvent | LCMS | LCMS Protocol | Purity percent | Method for Coupling |
|---|---|---|---|---|---|---|---|---|---|
| 1189 | 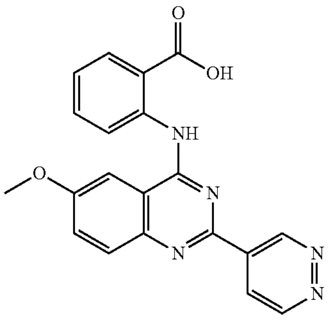 [SMILES: COc1ccc2nc(-c3ccnnc3)nc(Nc3ccccc3C(=O)O)c2c1] | | 373.36 | 1H-NMR (400 MHz, DMSO-d6): 12.15 (s, 1H), 10.02 (s, 1H), 9.41 (d, J = 5.2 Hz, 1H), 8.94 (d, J = 7.6 Hz, 1H), 8.41 (m, 1H), 8.09 (d, J = 7.6 Hz, 1H), 7.93 (d, J = 8.8 Hz, 1H), 7.80 (t, J = 8.4 Hz, 1H), 7.60-7.62 (m, 2H), 7.25 (t, J = 7.6 Hz, 1H), 4.01 (s, 3H). | DMSO | 374.1, 376.1 (M + 1) | Method B (NH4HCO3) | 95 | Method D, G1 |
| 1190 | 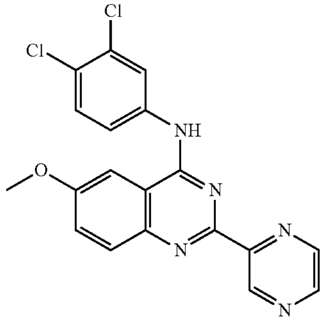 [SMILES: COc1ccc2nc(-c3cnccn3)nc(Nc3ccc(Cl)c(Cl)c3)c2c1] | | 398.25 | 1H-NMR (400 MHz, DMSO-d6): δ 9.95 (s, 1H), 9.54 (s, 1H), 8.81-8.32 (m, 1H), 8.74 (d, J = 2.0 Hz, 1H), 8.66 (d, J = 2.4 Hz, 1H), 8.06 (dd, J = 8.8, 2.4 Hz, 1H), 8.00 (d, J = 2.4 Hz, 1H), 7.92 (d, J = 8.8 Hz, 1H), 7.70 (d, J = 8.8 Hz, 1H), 7.60 (dd, J = 8.8, 2.4 Hz, 1H), 3.40 (s, 3H). | DMSO | 397.9, 400.0, 401.9 (M + 1) | Method B (NH4HCO3) | 95 | Method D, G6 |
| 1191 | 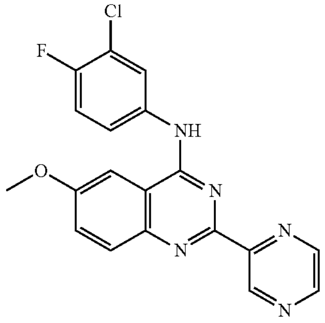 [SMILES: COc1ccc2nc(-c3cnccn3)nc(Nc3ccc(F)c(Cl)c3)c2c1] | | 381.79 | 1H-NMR (400 MHz, DMSO-d6): δ 9.90 (s, 1H), 9.52 (s, 1H), 8.81 (m, 1H), 8.73 (d, J = 2.4 Hz, 1H), 8.53 (dd, J = 6.8, 2.4 Hz, 1H, 7.98-8.03 (m, 2H), 7.91 (d, J = 9.2 Hz, 1H), 7.59 (dd, J = 5.2, 2.4 Hz, 1H), 7.51 (t, J = 8.8 Hz, 1H), 3.40 (s, 3H). | DMSO | 382.0, 384.0 (M + 1) | Method B (NH4HCO3) | 95 | Method D, G6 |
| 1192 | 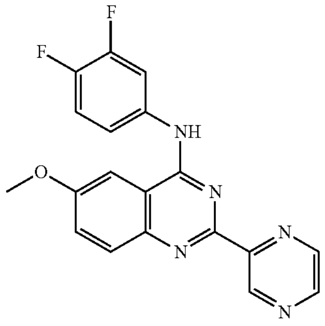 [SMILES: COc1ccc2nc(-c3cnccn3)nc(Nc3ccc(F)c(F)c3)c2c1] | | 365.34 | 1H-NMR (400 MHz, DMSO-d6): δ 9.89 (s, 1H), 9.52-9.53 (m, 1H), 8.81-8.82 (m, 1H), 8.73 (d, J = 2.4 Hz, 1H), 8.45-8.51 (m, 1H), 7.98 (m, 1H), 7.90 (d, J = 9.2 Hz, 1H), 7.75-7.78 (m, 1H), 7.47-7.59 (m, 2H), 3.40 (s, 3H). | DMSO | 366.0 (M + 1) | Method B (NH4HCO3) | 95 | Method D, G6 |

TABLE 21-continued

| Number | PRODUCT | Salt type | Molecular Mass | $^{1}$H-NMR | $^{1}$H-NMR Solvent | LCMS | LCMS Protocol | Purity percent | Method for Coupling |
|---|---|---|---|---|---|---|---|---|---|
| 1193 | 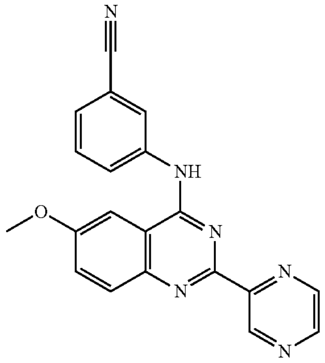 [SMILES: COc1ccc2nc(-c3cnccn3)nc(Nc3cccc(C#N)c3)c2c1] | | 354.36 | 1H-NMR (400 MHz, DMSO-d6): δ 10.06 (s, 1H), 9.54 (s, 1H), 8.74-8.81 (m, 3H), 8.35 (d, J = 8.4 Hz, 1H), 8.04 (m, 1H), 7.92-7.95 (m, 1H), 7.59-7.69 (m, 3H), 3.40 (s, 3H). | DMSO | 355.0 (M + 1) | Method B (NH4HCO3) | 95 | Method D, G6 |
| 1194 | 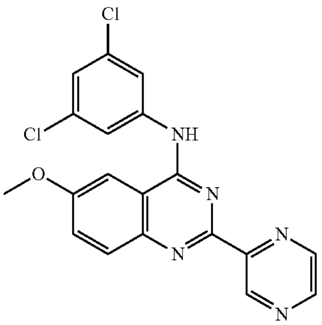 [SMILES: COc1ccc2nc(-c3cnccn3)nc(Nc3cc(Cl)cc(Cl)c3)c2c1] | | 398.25 | 1H-NMR (400 MHz, DMSO-d6): δ 9.91 (s, 1H), 9.55 (d, J = 1.2 Hz, 1H), 8.81 (t, J = 2.0 Hz, 1H), 8.74 (d, J = 2.4 Hz, 1H), 8.39 (d, J = 1.6 Hz, 1H), 7.97 (d, J = 2.8 Hz, 1H), 7.92 (d, J = 8.8 Hz, 1H), 7.59 (dd, J = 8.8, 2.4 Hz, 1H), 7.32 (t, J = 1.6 Hz, 1H), 3.40 (s, 3H). | DMSO | 398.0, 399.9, 402.0 (M + 1) | Method B (NH4HCO3) | 95 | Method D, G6 |
| 1195 | 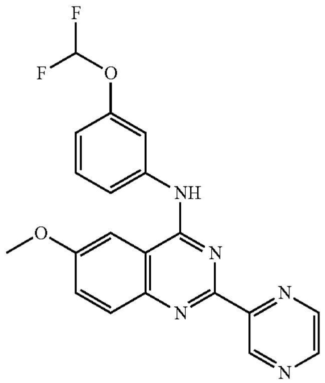 [SMILES: COc1ccc2nc(-c3cnccn3)nc(Nc3cccc(OC(F)F)c3)c2c1] | | 395.36 | 1H-NMR (400 MHz, DMSO-d6): δ 9.91 (s, 1H), 9.55 (m, 1H), 8.74-8.79 (m, 2H), 8.25 (s, 1H), 8.03 (d, J = 2.4 Hz, 1H), 7.92 (d, J = 9.2 Hz, 1H), 7.86 (d, J = 8.4 Hz, 1H), 7.60 (dd, J = 9.2, 2.4 Hz, 1H), 7.48-7.52 (m, 1H), 7.34 (t, J = 74.0 Hz, 1H), 6.96-6.98 (m, 1H), 3.40 (s, 3H). | DMSO | 396.1 (M + 1) | Method B (NH4HCO3) | 95 | Method D, G6 |
| 1196 | 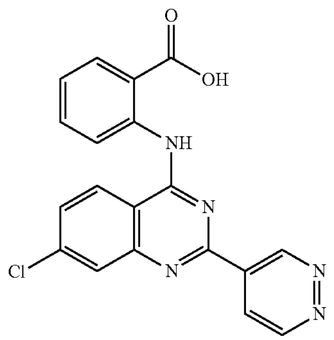 [SMILES: O=C(O)c1ccccc1Nc1nc(-c2ccnnc2)nc2cc(Cl)ccc12] | | 377.78 | 1H-NMR (400 MHz, DMSO-d6): δ 12.26 (s, 1H), 9.94 (s, 1H), 9.41-9.42 (m, 1H), 8.75 (d, J = 8.0 Hz, 1H), 8.33-8.34 (m, 1H), 8.19 (d, J = 8.4 Hz, 1H), 8.05 (d, J = 7.6 Hz, 1H), 7.93 (m, 1H), 7.75-7.77 (m, 2H), 7.05-7.30 (m, 2H). | DMSO | 378.0, 380.0 (M + 1) | Method B (NH4HCO3) | 95 | Method D, G6 |

TABLE 21-continued

| Number | PRODUCT | Salt type | Molecular Mass | $^1$H-NMR | $^1$H-NMR Solvent | LCMS | LCMS Protocol | Purity percent | Method for Coupling |
|---|---|---|---|---|---|---|---|---|---|
| 1197 | 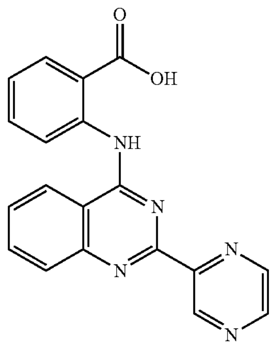 [SMILES: O=C(O)c1ccccc1Nc1nc(-c2cnccn2)nc2ccccc12] | | 343.34 | 1H-NMR (400 MHz, DMSO-d6): δ 13.86 (s, 1H), 12.39 (s, 1H), 9.62 (d, J = 0.8 Hz, 1H), 9.29 (d, J = 8.0 Hz, 1H), 8.87 (s, 1H), 8.80 (d, J = 2.4 Hz, 1H), 8.27 (d, J = 8.0 Hz, 1H), 8.12 (dd, J = 8.0, 1.6 Hz, 1H), 7.97-8.05 (m, 3H), 7.75-7.79 (m, 2H), 7.24 (t, J = 7.6 Hz, 1H). | DMSO | 344.0 (M + 1) | Method B (NH4HCO3) | 95 | Method D, G6 |
| 1198 | 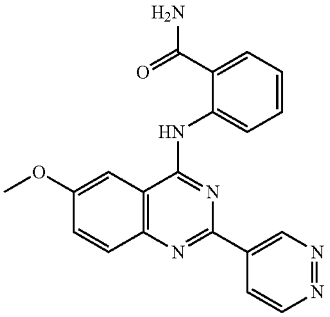 [SMILES: COc1ccc2nc(-c3ccnnc3)nc(Nc3ccccc3C(N)=O)c2c1] | | 372.38 | 1H-NMR (400 MHz, DMSO-d6): δ 13.05 (s, 1H), 9.99 (s, 1H), 9.39 (d, J = 5.2 Hz, 1H), 9.05 (d, J = 8.4 Hz, 1H), 8.47 (s, 1H), 8.36-8.38 (m, 1H), 7.85-7.98 (m, 3H), 7.71 (t, J = 7.6 Hz, 1H), 7.46-7.60 (m, 2H), 7.20 (t, J = 7.6 Hz, 1H), 3.95 (s, 3H). | DMSO | 373.0 (M + 1) | Method B (NH4HCO3) | 95 | Method D, G1 |
| 1199 | 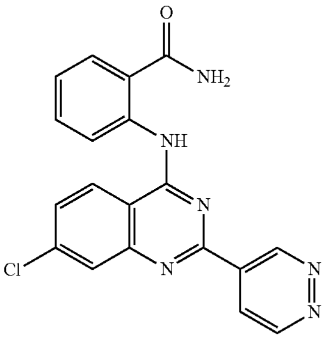 | | 376.8 | 1H-NMR (400 MHz, DMSO-d6): δ 13.15 (s, 1H), 10.00 (s, 1H), 9.44 (d, J = 4.2 Hz, 1H), 8.95 (d, J = 8.4 Hz, 1H), 8.49 (s, 1H), 8.40-8.42 (m, 1H), 8.15 (d, J = 9.2 Hz, 1H), 7.91-7.97 (m, 3H), 7.80 (t, J = 7.6 Hz, 1H), 7.73 (t, J = 7.6 Hz, 1H), 7.25 (t, J = 7.2 Hz, 1H). | DMSO | 377.0, 379.0 (M + 1) | Method B (NH4HCO3) | 95 | Method D, G1 |
| 1200 | 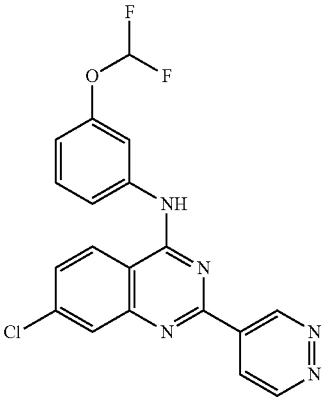 [SMILES: FC(F)Oc1cccc(Nc2nc(-c3ccnnc3)nc3cc(Cl)ccc23)c1] | | 399.78 | 1H-NMR (400 MHz, DMSO-d6): δ 12.29 (s, 1H), 9.98 (s, 1H), 9.42 (d, J = 5.2 Hz, 1H), 8.66 (d, J = 9.2 Hz, 1H), 8.36-8.38 (m, 1H), 8.00 (d, J = 1.5 Hz, 1H), 7.89 (s, 1H), 7.79-7.81 (m, 2H), 7.49-7.57 (m, 1H), 7.31 (t, J = 74.0 Hz, 1H), 7.04 (dd, J = 8.0, 1.2 Hz, 1H). | DMSO | 400.0, 401.9 (M + 1) | Method A (TFA) | 95 | Method D, G1 |

TABLE 21-continued

| Number | PRODUCT | Salt type | Molecular Mass | $^1$H-NMR | $^1$H-NMR Solvent | LCMS | LCMS Protocol | Purity percent | Method for Coupling |
|---|---|---|---|---|---|---|---|---|---|
| 1201 | 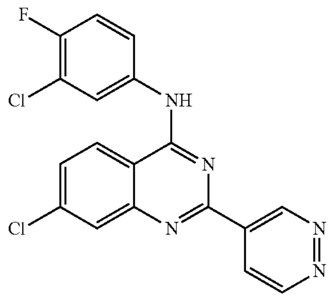 | | 386.21 | 1H-NMR (400 MHz, DMSO-d6): δ 9.94 (s, 1H), 9.43 (d, J = 5.2 Hz, 1H), 8.72 (d, J = 8.8 Hz, 1H), 8.33 (dd, J = 5.6, 2.4 Hz, 1H), 8.21 (dd, J = 6.4, 1.6 Hz, 1H), 7.93-7.98 (m, 2H), 7.78 (dd, J = 8.8, 2.0 Hz, 1H), 7.54 (t, J = 9.2 Hz, 2H). | DMSO | 386.0 387.8 (M + 1) | Method A (TFA) | 95 | Method D, G1 |
| 1202 | 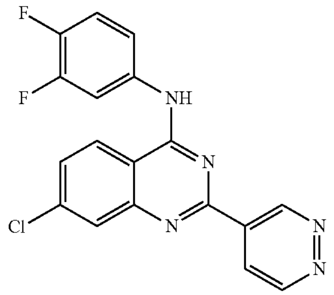 [SMILES: Fc1ccc(Nc2nc(-c3ccnnc3)nc3cc(Cl)ccc23)cc1F] | | 369.76 | 1H-NMR (400 MHz, DMSO-d6): δ 10.28 (s, 1H), 9.95 (m, 1H), 9.44-9.45 (m, 1H), 8.60 (d, J = 8.8 Hz, 1H), 8.32-8.34 (m, 1H), 8.02-8.08 (m, 1H), 7.98 (d, J = 6.4 Hz, 1H), 7.79 (dd, J = 9.2, 2.4 Hz, 1H), 7.70-7.72 (m, 1H), 7.56 (q, J = 9.2 Hz, 1H). | DMSO | 369.9, 371.0 (M + 1) | Method A (TFA) | 95 | Method D, G1 |
| 1203 | 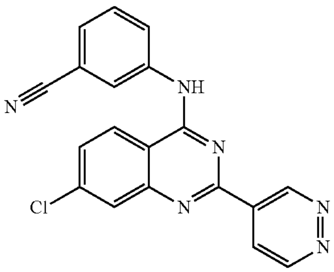 [SMILES: N#Cc1cccc(Nc2nc(-c3ccnnc3)nc3cc(Cl)ccc23)c1] | | 358.78 | 1H-NMR (400 MHz, DMSO-d6): δ 10.36 (s, 1H), 9.92 (s, 1H), 9.42 (d, J = 4.8 Hz, 1H), 8.59 (d, J = 8.4 Hz, 1H), 8.23-8.33 (m, 3H), 7.96 (d, J = 1.6 Hz, 1H), 7.65-7.79 (m, 3H). | DMSO | 359.0, 361.0 (M + 1) | Method B (NH4HCO3) | 95 | Method D, G1 |
| 1204 | 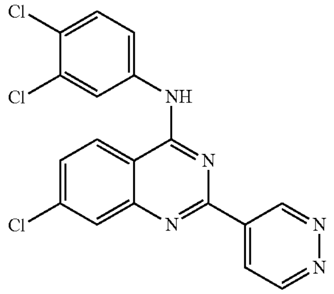 [SMILES: Clc1ccc2c(Nc3ccc(Cl)c(Cl)c3)nc(-c3ccnnc3)nc2c1] | | 402.66 | 1H-NMR (400 MHz, DMSO-d6): δ 10.32 (s, 1H), 9.96 (s, 1H), 9.44 (d, J = 5.2 Hz, 1H), 8.60 (d, J = 8.4 Hz, 1H), 8.28-8.35 (m, 2H), 7.94-7.99 (m, 2H), 7.79 (d, J = 8.8 Hz, 1H), 7.73 (d, J = 8.8 Hz, 1H). | DMSO | 401.9, 403.9, 405.9 (M + 1) | Method B (NH4HCO3) | 95 | Method D, G1 |
| 1205 | 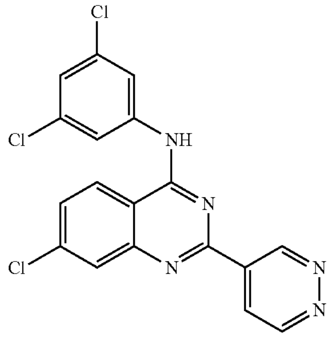 [SMILES: Clc1cc(Cl)cc(Nc2nc(-c3ccnnc3)nc3cc(Cl)ccc23)c1] | | 402.66 | 1H-NMR (400 MHz, DMSO-d6): δ 9.90 (s, 1H), 9.42 (d, J = 4.8 Hz, 1H), 8.58 (d, J = 8.8 Hz, 1H), 8.27 (s, 1H), 8.07 (s, 2H), 7.92 (s, 1H), 7.73 (d, J = 8.0 Hz, 1H), 7.36 (s, 1H). | DMSO | 401.9, 403.9, 405.9 (M + 1) | Method B (NH4HCO3) | 95 | Method D, G1 |

TABLE 21-continued

| Number | PRODUCT | Salt type | Molecular Mass | $^1$H-NMR | $^1$H-NMR Solvent | LCMS | LCMS Protocol | Purity percent | Method for Coupling |
|---|---|---|---|---|---|---|---|---|---|
| 1206 | 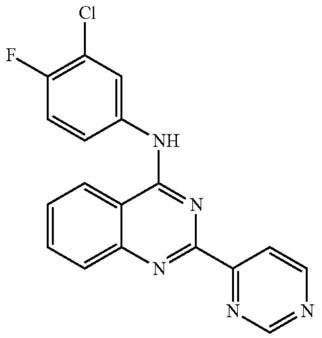 [SMILES: Fc1ccc(Nc2nc(-c3ccncn3)nc3ccccc23)cc1Cl] | | 351.76 | 1H-NMR (400 MHz, DMSO-d6): δ 10.59 (s, 1H), 9.43 (m, 1H), 9.07 (d, J = 5.2 Hz, 1H), 8.71 (d, J = 8.4 Hz, 1H), 8.50 (dd, J = 6.4, 2.0 Hz, 1H), 8.31 (dd, J = 5.2, 0.8 Hz, 1H), 8.00-8.09 (m, 3H), 7.80 (t, J = 7.2 Hz, 1H), 7.53 (t, J = 9.2 Hz, 1H). | DMSO | 352.0, 354.0 (M + 1) | Method B (NH4HCO3) | 95 | Method D, G1 |
| 1207 | 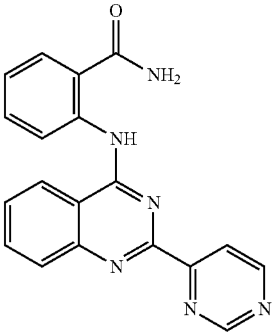 [SMILES: NC(=O)c1ccccc1Nc1nc(-c2ccncn2)nc2ccccc12] | | 342.35 | 1H-NMR (400 MHz, DMSO-d6): δ 13.31 (s, 1H), 9.38-9.43 (m, 2H), 9.05 (d, J = 5.2 Hz, 1H), 8.52 (s, 1H), 8.47 (d, J = 5.2 Hz, 1H), 8.25 (d, J = 8.0 Hz, 1H), 7.95-8.04 (m, 4H), 7.82 (t, J = 7.2 Hz, 1H), 7.70 (t, J = 7.6 Hz, 1H), 7.22 (t, J = 7.6 Hz, 1H). | DMSO | 343.1 (M + 1) | Method B (NH4HCO3) | 95 | Method D, G1 |
| 1208 | 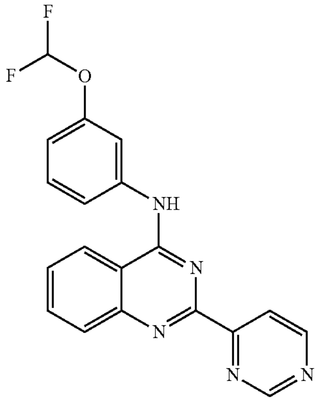 [SMILES: FC(F)Oc1cccc(Nc2nc(-c3ccncn3)nc3ccccc23)c1] | | 365.34 | 1H-NMR (400 MHz, DMSO-d6): δ 10.13 (s, 1H), 9.37 (d, J = 1.2 Hz, 1H), 9.01 (d, J = 5.2 Hz, 1H), 8.68 (d, J = 8.4 Hz, 1H), 8.40 (dd, J = 5.2, 1.2 Hz, 1H), 8.28 (t, J = 1.2 Hz, 1H), 7.92-8.00 (m, 3H), 7.77-7.79 (m, 1H), 7.47-7.52 (m, 1H), 7.34 (t, J = 74.0 Hz, 1H), 6.97 (dd, J = 8.4, 2.4 Hz, 1H). | DMSO | 366.1 (M + 1) | Method B (NH4HCO3) | 95 | Method D, G1 |
| 1209 | 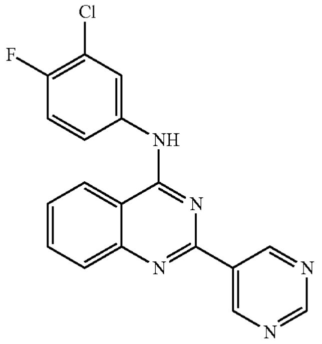 [SMILES: Fc1ccc(Nc2nc(-c3cncnc3)nc3ccccc23)cc1Cl] | HCl (batch 02) | 351.76 | 1H-NMR (400 MHz, DMSO-d6): δ 10.82 (s, 1H), 9.59 (s, 2H), 9.36 (s, 1H), 8.74 (d, J = 8.4 Hz, 1H), 8.22 (dd, J = 6.8, 2.4 Hz, 1H), 8.07 (d, J = 8.4 Hz, 1H), 8.00 (t, J = 7.6 Hz, 1H), 7.90-7.94 (m, 1H), 7.75 (t, J = 7.2 Hz, 1H), 7.56 (t, J = 9.2 Hz, 1H). | DMSO | 352.0, 354.1 (M + 1) | Method B (NH4HCO3) | 95 | Method D, G1 |

TABLE 21-continued

| Number | PRODUCT | Salt type | Molecular Mass | $^1$H-NMR | $^1$H-NMR Solvent | LCMS | LCMS Protocol | Purity percent | Method for Coupling |
|---|---|---|---|---|---|---|---|---|---|
| 1210 | 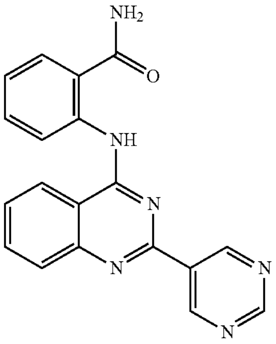 [SMILES: NC(=O)c1ccccc1Nc1nc(-c2cncnc2)nc2ccccc12] | | 342.35 | 1H-NMR (400 MHz, DMSO-d6): δ 13.17 (s, 1H), 9.65 (s, 2H), 9.36 (s, 1H), 8.93 (d, J = 8.0 Hz, 1H), 8.51 (s, 1H), 8.23 (d, J = 8.4 Hz, 1H), 7.92-8.02 (m, 4H), 7.72-7.79 (m, 2H), 7.26 (t, J = 7.6 Hz, 1H). | DMSO | 343.1 (M + 1) | Method B (NH4HCO3) | 95 | Method D, G4 |
| 1211 | 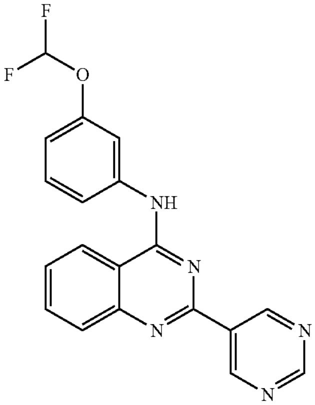 [SMILES: FC(F)Oc1cccc(Nc2nc(-c3cncnc3)nc3ccccc23)c1] | | 365.34 | 1H-NMR (400 MHz, DMSO-d6): δ 10.15 (s, 1H), 9.62 (s, 2H), 9.32 (s, 1H), 8.63 (d, J = 8.0 Hz, 1H), 7.94-7.97 (m, 3H), 7.81 (dd, J = 8.4, 1.2 Hz, 1H), 7.69-7.74 (m, 1H), 7.50-7.55 (m, 1H), 7.31 (t, J = 74.0 Hz, 1H), 7.01 (dd, J = 8.4, 2.4 Hz, 1H). | DMSO | 366.1 (M + 1) | Method B (NH4HCO3) | 95 | Method D, G6 |
| 1212 | 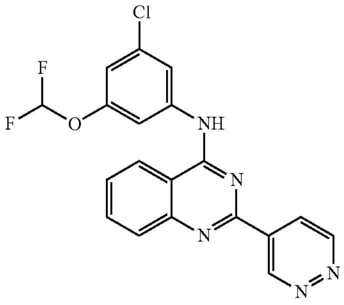 [SMILES: FC(F)Oc1cc(Cl)cc(Nc2nc(-c3ccnnc3)nc3ccccc23)c1] | | 399.78 | 1H-NMR (400 MHz, DMSO-d6): δ 10.27 (s, 1H), 10.01-10.02 (m, 1H), 9.44-9.46 (m, 1H), 8.62 (d, J = 8.4 Hz, 1H), 8.40 (dd, J = 5.2, 2.0 Hz, 1H), 8.04 (t, J = 1.6 Hz, 1H), 8.00 (d, J = 3.2 Hz, 2H), 7.94 (m, 1H), 7.76-7.80 (m, 1H), 7.38 (t, J = 73.8 Hz, 1H), 7.16 (t, J = 2.0 Hz, 1H). | DMSO | 400.0, 402.0 (M + 1) | Method B (NH4HCO3) | 95 | Method D, G6 |
| 1213 | 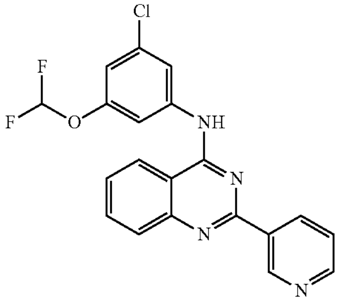 [SMILES: FC(F)Oc1cc(Cl)cc(Nc2nc(-c3cccnc3)nc3ccccc23)c1] | | 398.79 | 1H-NMR (400 MHz, DMSO-d6): δ 10.16 (s, 1H), 9.56 (m, 1H), 8.69-8.72 (m, 2H), 8.59 (d, J = 8.0 Hz, 1H), 8.08 (d, J = 1.6 Hz, 1H), 7.94-7.97 (m, 2H), 7.69-7.73 (m, 1H), 7.55-7.58 (m, 1H), 7.36 (t, J = 73.6 Hz, 1H), 7.13 (t, J = 2.0 Hz, 1H). | DMSO | 399.0, 401.1 (M + 1) | Method B (NH4HCO3) | 95 | Method D, G6 |

TABLE 21-continued

| Number | PRODUCT | Salt type | Molecular Mass | $^1$H-NMR | $^1$H-NMR Solvent | LCMS | LCMS Protocol | Purity percent | Method for Coupling |
|---|---|---|---|---|---|---|---|---|---|
| 1214 | 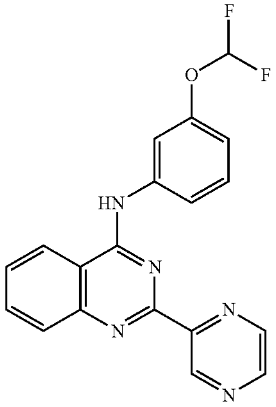 [SMILES: FC(F)Oc1cccc(Nc2nc(-c3cnccn3)nc3ccccc23)c1] | | 365.34 | 1H-NMR (400 MHz, DMSO-d6): δ 11.17 (s, 1H), 9.49 (s, 1H), 8.88-8.92 (m, 3H), 8.16 (d, J = 8.0 Hz, 1H), 8.07 (t, J = 7.6 Hz, 2H), 7.84 (t, J = 8.0 Hz, 2H), 7.57 (t, J = 8.0 Hz, 1H), 7.36 (t, J = 74.0 Hz, 1H), 7.10-7.12 (m, 1H). | DMSO | 366.1 (M + 1) | Method B (NH4HCO3) | 95 | Method D, G6 |
| 1215 | 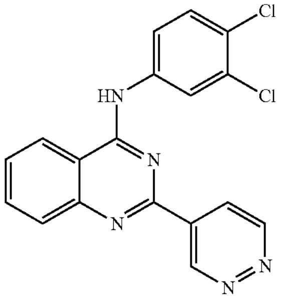 | | 368.22 | 1H-NMR (400 MHz, DMSO-d6): δ 10.23 (s, 1H), 10.00 (s, 1H), 9.44 (d, J = 5.2 Hz, 1H), 8.58 (d, J = 8.0 Hz, 1H), 8.38 (dd, J = 2.4, 5.2 Hz, 1H), 8.32 (d, J = 2.0 Hz, 1H), 7.96-8.00 (m, 3H) 7.73-7.77 (m, 2H). | DMSO | 367.8, 369.8, 371.8 (M + 1) | Method B (NH4HCO3) | 95 | Method D, G1 |
| 1216 | 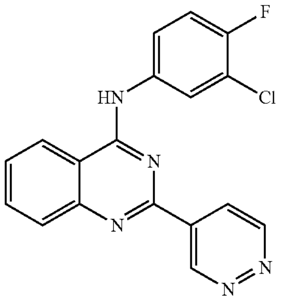 [SMILES: Fc1ccc(Nc2nc(-c3ccnnc3)nc3ccccc23)cc1Cl] | | 351.76 | 1H-NMR (400 MHz, DMSO-d6): δ 10.21 (s, 1H), 9.99 (s, 1H), 9.43 (d, J = 5.2 Hz, 1H), 8.58 (d, J = 8.4 Hz, 1H), 8.38 (dd, J = 5.2, 2.0 Hz, 1H), 8.22 (dd, J = 7.0, 2.6 Hz, 1H), 7.89-7.93 (m, 3H), 7.68-7.72 (m, 1H), 7.55 (t, J = 8.6 Hz, 1H). | DMSO | 351.9, 353.8 (M + 1) | Method B (NH4HCO3) | 95 | Method D, G1 |
| 1217 | 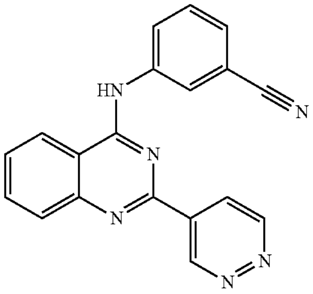 [SMILES: N#Cc1cccc(Nc2nc(-c3ccnnc3)nc3ccccc23)c1] | | 324.34 | 1H-NMR (400 MHz, DMSO-d6): δ 10.32 (s, 1H), 9.99 (dd, J = 2.0, 1.2 Hz, 1H), 9.44 (dd, J = 5.2, 0.8 Hz, 1H), 8.61 (d, J = 8.4 Hz, 1H), 8.38-8.40 (m, 2H), 8.28-8.31 (m, 1H), 7.99 (s, 1H), 7.97 (d, J = 3.6 Hz, 1H), 7.66-7.80 (m, 3H). | DMSO | 325.0 (M + 1) | Method B (NH4HCO3) | 95 | Method D, G1 |

TABLE 21-continued

| Number | PRODUCT | Salt type | Molecular Mass | $^1$H-NMR | $^1$H-NMR Solvent | LCMS | LCMS Protocol | Purity percent | Method for Coupling |
|---|---|---|---|---|---|---|---|---|---|
| 1218 | 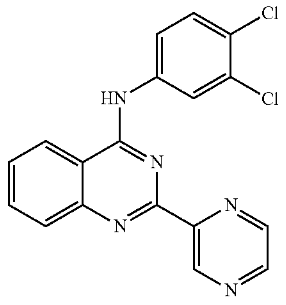 [SMILES: Clc1ccc(Nc2nc(-c3cnccn3)nc3ccccc23)cc1Cl] | | 368.22 | 1H-NMR (400 MHz, DMSO-d6): δ 11.94 (s, 1H), 9.44 (d, J = 0.8 Hz, 1H), 9.06 (d, J = 8.0 Hz, 1H), 9.00 (d, J = 2.4 Hz, 1H), 8.97 (t, J = 1.8 Hz, 1H), 8.38 (d, J = 2.4 Hz, 1H), 8.38 (d, J = 2.4 Hz, 1H), 8.12 (t, J = 7.4 Hz, 1H), 8.00 (dd, J = 8.6, 2.2 Hz, 1H), 7.86 (t, J = 7.6 Hz, 1H), 7.82 (d, J = 8.8 Hz, 1H). | DMSO | 367.9, 369.9, 371.8 (M + 1) | Method B (NH4HCO3) | 95 | Method D, G6 |
| 1219 | 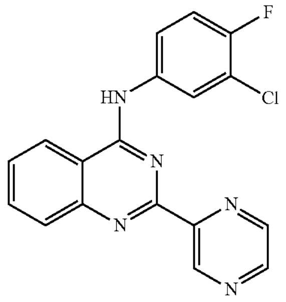 [SMILES: Fc1ccc(Nc2nc(-c3cnccn3)nc3ccccc23)cc1Cl] | | 351.76 | 1H-NMR (400 MHz, DMSO-d6): δ 11.62 (s, 1H), 9.40 (d, J = 0.8 Hz, 1H), 8.60-8.83 (m, 3H), 8.32 (dd, J = 6.6, 2.2 Hz, 1H), 8.20 (d, J = 8.8 Hz, 1H), 8.09 (t, J = 7.4 Hz, 1H), 7.95-8.00 (m, 1H), 7.85 (t, J = 7.8 Hz, 1H), 7.61 (t, J = 9.2 Hz, 1H). | DMSO | 352.0, 354.0 (M + 1) | Method B (NH4HCO3) | 95 | Method D, G6 |
| 1220 | 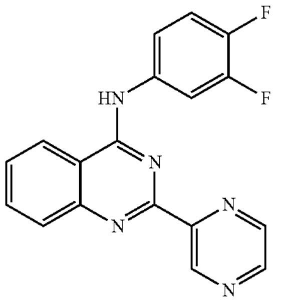 [SMILES: Fc1ccc(Nc2nc(-c3cnccn3)nc3ccccc23)cc1F] | | 335.31 | 1H-NMR (400 MHz, DMSO-d6): δ 11.05 (s, 1H), 9.48 (d, J = 0.8 Hz, 1H), 8.91-8.93 (m, 2H), 8.81 (d, J = 8.4 Hz, 1H), 8.28-8.33 (m, 1H), 8.14 (d, J = 8.4 Hz, 1H), 8.06 (t, J = 7.6 Hz, 1H), 7.77-7.85 (m, 2H), 7.56-7.63 (m, 1H) | DMSO | 336.1 (M + 1) | Method B (NH4HCO3) | 95 | Method D, G6 |
| 1221 | 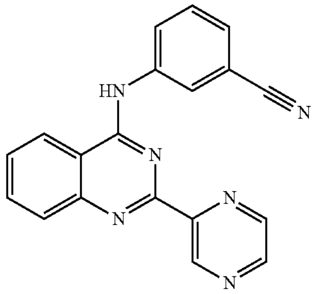 [SMILES: N#Cc1cccc(Nc2nc(-c3cnccn3)nc3ccccc23)c1] | | 324.34 | 1H-NMR (400 MHz, DMSO-d6): δ 12.09 (s, 1H), 9.40 (d, J = 1.6 Hz, 1H), 9.10 (d, J = 8.4 Hz, 1H), 9.00 (d, J = 2.0 Hz, 1H), 8.97 (t, J = 2.0 Hz, 1H), 8.49 (s, 1H), 8.26-8.30 (m, 2H), 8.12-8.06 (m, 1H), 7.87-7.91 (m, 1H), 7.76-7.84 (m, 2H) | DMSO | 324.9 (M + 1) | Method B (NH4HCO3) | 95 | Method D, G6 |

TABLE 21-continued

| Number | PRODUCT | Salt type | Molecular Mass | $^1$H-NMR | $^1$H-NMR Solvent | LCMS | LCMS Protocol | Purity percent | Method for Coupling |
|---|---|---|---|---|---|---|---|---|---|
| 1222 | 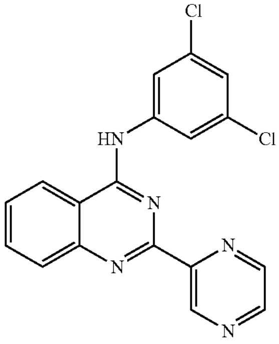 [SMILES: Clc1cc(Cl)cc(Nc2nc(-c3cnccn3)nc3ccccc23)c1] | | 368.22 | 1H-NMR (400 MHz, DMSO-d6): δ 10.21 (s, 1H), 9.59 (d, J = 1.2 Hz, 1H), 8.85 (t, J = 1.8 Hz, 1H), 8.78 (d, J = 2.0 Hz, 1H), 8.64 (d, J = 8.4 Hz, 1H), 8.42 (d, J = 1.6 Hz, 2H), 7.96-8.02 (m, 2H), 7.74-7.78 (m, 1H), 7.35 (d, J = 1.6 Hz, 1H). | DMSO | 368.0, 370.0, 372.0 (M + 1) | Method B (NH4HCO3) | 95 | Method D, G6 |
| 1223 | 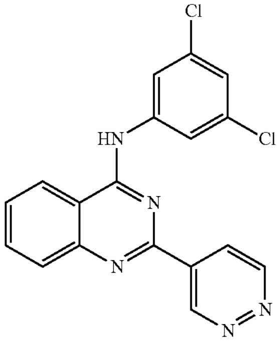 [SMILES: Clc1cc(Cl)cc(Nc2nc(-c3ccnnc3)nc3ccccc23)c1] | | 368.22 | 1H-NMR (400 MHz, DMSO-d6): δ 10.26 (s, 1H), 10.00 (s, 1H), 9.45 (d, J = 5.2 Hz, 1H), 8.56 (d, J = 8.4 Hz, 1H), 8.38 (dd, J = 5.0, 1.8 Hz, 1H), 8.09 (s, 2H), 7.94 (s, 1H), 7.92 (d, J = 9.2 Hz, 1H), 7.70-7.74 (m, 1H), 7.35 (s, 1H). | DMSO | 368.1, 370.1 (M + 1) | Method B (NH4HCO3) | 95 | Method D, G1 |
| 1224 | 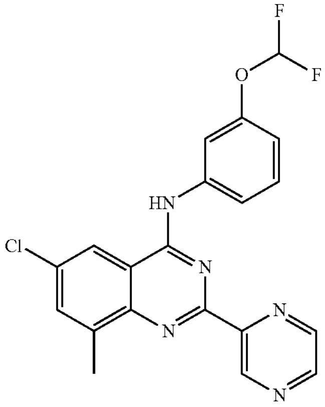 [SMILES: Cc1cc(Cl)cc2c(Nc3cccc(OC(F)F)c3)nc(-c3cnccn3)nc12] | | 413.81 | 1H-NMR (400 MHz, DMSO-d6): δ 10.05 (s, 1H), 9.63 (s, 1H), 8.82 (s, 1H), 8.78 (s, 1H), 8.66 (s, 1H), 8.31 (s, 1H), 7.89-7.91 (m, 2H), 7.49 (d, J = 8.0 Hz, 1H), 7.31 (t, J = 73.6 Hz, 1H), 6.96 (d, J = 7.6 Hz, 1H), 2.74 (s, 3H). | DMSO | 414.0 416.0 (M + 1) | Method B (NH4HCO3) | 95 | Method C, G3 |
| 1225 | 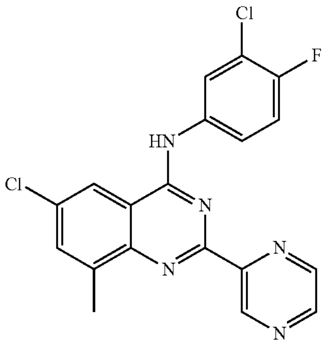 [SMILES: Cc1cc(Cl)cc2c(Nc3ccc(F)c(Cl)c3)nc(-c3cnccn3)nc12] | | 400.24 | 1H NMR (400 MHz, DMSO-d6): δ 9.90 (s, 1H), 9.54 (s, 1H), 8.77-8.80 (m, 2H), 8.60 (s, 1H), 8.50 (s, 1H), 7.99 (s, 1H), 7.76 (8, 1H), 7.44 (s, 1H), 2.67 (s, 3H). | DMSO | 400.0 401.9 (M + 1) | Method B (NH4HCO3) | 95 | Method C, G3 |

TABLE 21-continued

| Number | PRODUCT | Salt type | Molecular Mass | $^1$H-NMR | $^1$H-NMR Solvent | LCMS | LCMS Protocol | Purity percent | Method for Coupling |
|---|---|---|---|---|---|---|---|---|---|
| 1226 | 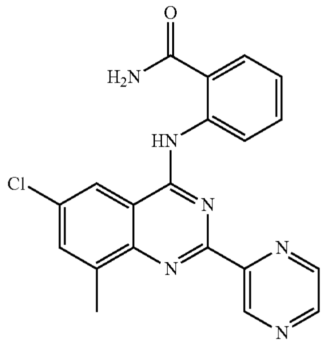 [SMILES: Cc1cc(Cl)cc2c(Nc3ccccc3C(N)=O)nc(-c3cnccn3)nc12] | | 390.83 | 1H-NMR (400 MHz, DMSO-d6): δ 13.33 (s, 1H), 9.67 (s, 1H), 9.38 (d, J = 8.0 Hz, 1H), 8.88 (s, 1H), 8.79 (s, 1H), 8.52 (s, 1H), 8.08 (s, 1H), 8.04 (s, 1H), 7.97 (d, J = 7.2 Hz, 1H), 7.88 (s, 1H), 7.69 (d, J = 7.2 Hz, 1H), 7.21 (t, J = 7.6 Hz, 1H), 2.75 (s, 3H). | DMSO | 391.0 392.0 (M + 1) | Method A (TFA) | 95 | Method C, G3 |
| 1227 | 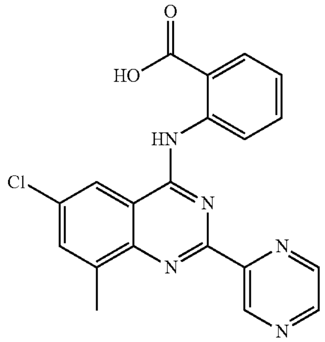 [SMILES: Cc1cc(Cl)cc2c(Nc3ccccc3C(=O)O)nc(-c3cnccn3)nc12] | | 391.81 | 1H-NMR (400 MHz, DMSO-d6): δ 16.00 (s, 1H), 9.69 (s, 1H), 9.39 (d, J = 8.4 Hz, 1H), 8.90 (s, 1H), 8.79 (s, 1H), 8.29 (s, 1H), 8.13 (d, J = 7.6 Hz, 1H), 7.82 (s, 1H), 7.50 (s, J = 7.6 Hz, 1H), 7.06 (t, J = 7.2 Hz, 1H), 2.73 (s, 3H). | DMSO | 392.0 393.1 (M + 1) | Method A (TFA) | 95 | Method C, G3 |
| 1228 | 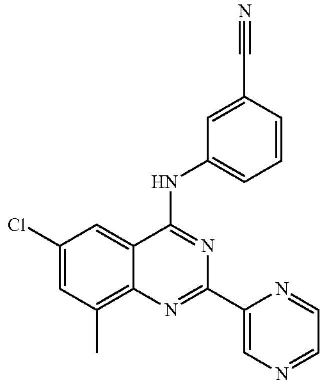 [SMILES: Cc1cc(Cl)cc2c(Nc3cccc(C#N)c3)nc(-c3cnccn3)nc12] | | 372.81 | 1H-NMR (400 MHz, DMSO-d6): δ 10.07 (s, 1H), 9.57 (s, 1H), 8.82 (s, 2H), 8.76 (s, 1H), 8.57 (s, 1H), 8.32 (d, J = 7.6 Hz, 1H), 7.81 (s, 1H), 7.57-7.63 (m, 2H), 2.70 (s, 3H). | DMSO | 373.0 374.0 (M + 1) | Method B (NH4HCO3) | 95 | Method C, G3 |
| 1229 | 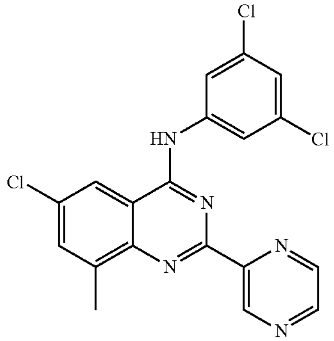 [SMILES: Cc1cc(Cl)cc2c(Nc3cc(Cl)cc(Cl)c3)nc(-c3cnccn3)nc12] | | 416.69 | 1H-NMR (400 MHz, DMSO-d6): δ 10.09 (s, 1H), 9.63 (d, J = 1.2 Hz, 1H), 8.85 (dd, J = 2.4, 1.6 Hz, 1H), 8.78 (d, J = 2.4 Hz, 2H), 8.63 (d, J = 1.6 Hz, 1H), 8.45 (s, 2H), 7.34 (t, J = 2.0 Hz, 1H), 2.74 (s, 3H). | DMSO | 416.9 417.9 (M + 1) | Method B (NH4HCO3) | 95 | Method C, G3 |

TABLE 21-continued

| Number | PRODUCT | Salt type | Molecular Mass | $^1$H-NMR | $^1$H-NMR Solvent | LCMS | LCMS Protocol | Purity percent | Method for Coupling |
|---|---|---|---|---|---|---|---|---|---|
| 1230 | 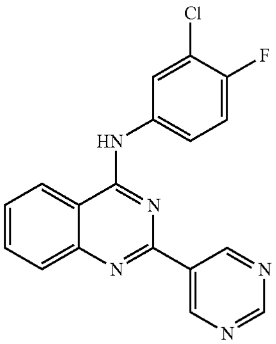 [SMILES: Fc1ccc(Nc2nc(-c3cncnc3)nc3ccccc23)cc1Cl] | HCl | 351.76 | 1H-NMR (400 MHz, DMSO-d6): δ 10.42 (s, 1H), 9.60 (s, 2H), 9.34 (s, 1H), 8.64 (d, J = 8.4 Hz, 1H), 8.24 (dd, J = 8.4, 2.4 Hz, 1H), 7.98-7.92 (m, 3H), 7.76-7.71 (m, 1H), 7.56 (t, J = 8.8 Hz, 1H). | DMSO | 352.0, 354.0 (M + 1) | Method B (NH4HCO3) | 95 | Method C, G1 |
| 1231 | 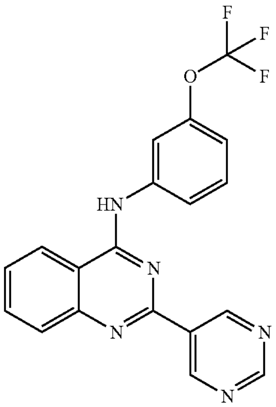 [SMILES: FC(F)(F)Oc1cccc(Nc2nc(-c3cncnc3)nc3ccccc23)c1] | HCl | 383.33 | 1H-NMR (400 MHz, DMSO-d6): δ 10.58 (s, 1H), 9.61 (s, 2H), 9.34 (s, 1H), 8.71 (d, J = 8.4 Hz, 1H), 8.13 (s, 1H), 8.04-7.93 (m, 3H), 7.78-7.73 (m, 1H), 7.62 (t, J = 8.4 Hz, 1H), 7.21 (d, J = 8.0 Hz, 1H). | DMSO | 384.1 (M + 1) | Method B (NH4HCO3) | 95 | Method C, G1 |
| 1232 | 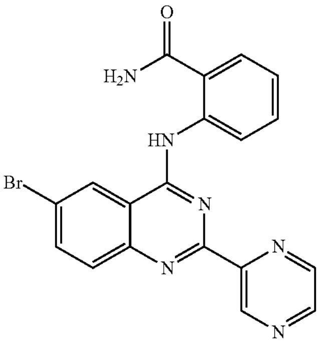 [SMILES: NC(=O)c1ccccc1Nc1nc(-c2cnccn2)nc2ccc(Br)cc12] | | 421.25 | 1H-NMR (400 MHz, DMSO-d6): δ 10.34 (s, 1H), 9.58 (s, 1H), 9.27-9.25 (m, 1H), 8.84-8.77 (m, 2H), 9.52 (s, 1H), 8.35 (s, 1H), 8.07-7.67 (m, 5H), 7.20 (t, J = 7.5 Hz, 1H). | DMSO | 421.0, 423.0 (M + 1) | Method B (NH4HCO3) | 95 | Method C, G6 |
| 1233 | 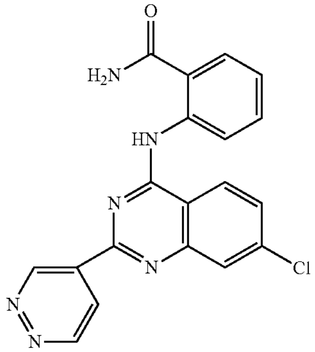 [SMILES: NC(=O)c1ccccc1Nc1nc(-c2ccnnc2)nc2cc(Cl)ccc12] | | | 1H-NMR (400 MHz, DMSO-d6): δ 13.15 (s, 1H), 10.00 (s, 1H), 9.44 (d, J = 5.2 Hz, 1H), 8.95 (d, J = 8.4 Hz, 1H), 8.48 (s, 1H), 8.42-8.40 (m, 1H), 8.16 (d, J = 9.2 Hz, 1H), 7.97-7.91 (m, 3H), 7.81-7.73 (m, 2H), 7.25 (t, J = 2.4 Hz, 1H). | DMSO | 377.0 (M + 1) | Method B (NH4HCO3) | 95 | Method G |

TABLE 21-continued

| Number | PRODUCT | Salt type | Molecular Mass | $^1$H-NMR | $^1$H-NMR Solvent | LCMS | LCMS Protocol | Purity percent | Method for Coupling |
|---|---|---|---|---|---|---|---|---|---|
| 1234 | 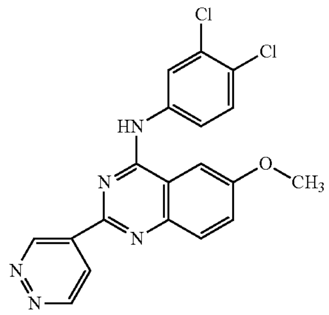 [SMILES: COc1ccc2nc(-c3ccnnc3)nc(Nc3ccc(Cl)c(Cl)c3)c2c1] | | | 1H-NMR (400 MHz, DMSO-d6): δ 9.95 (s, 1H), 9.54 (s, 1H), 8.82 (s, 1H), 8.74 (d, J = 2.0 Hz, 1H), 8.66 (d, J = 2.4 Hz, 1H), 8.07 (dd, J = 8.8, 2.4 Hz, 1H), 8.00 (d, J = 2.4 Hz, 1H), 7.92 (d, J = 8.8 Hz, 1H), 7.70 (d, J = 8.8 Hz, 1H), 7.60 (dd, J = 8.8, 2.4 Hz, 1H), 4.00 (s, 3H). | DMSO | 397.9, 400.0 (M + 1) | Method B (NH4HCO3) | 95 | Method G |

Scheme 67: Representative synthesis of compounds of formula with a pyrazine liii-a (see Scheme 65)

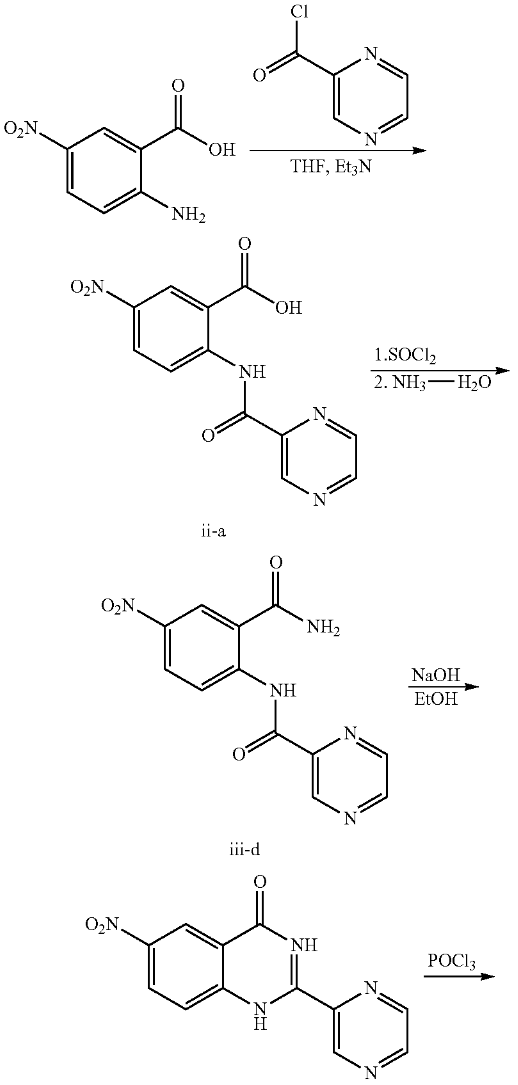

ii-a iii-d iv-g

-continued

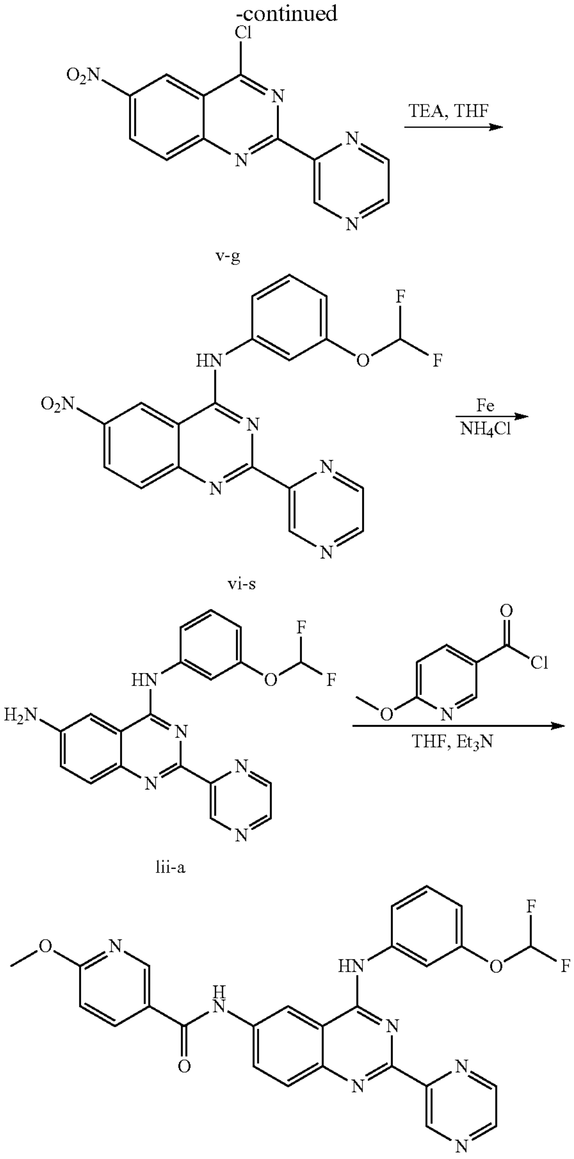

v-g vi-s lii-a liii-a

Method C: 5-Nitro-2-(pyrazine-2-carboxamido)benzoic acid (Ii-a)

To a solution of pyrazine-2-carboxylic acid (1.36 g, 10.9 mmol, 1 eq.) in $SOCl_2$ (20 mL) was added DMF (2 drops). The mixture was stirred at 60° C. for 2.0 min. The volatiles were removed in vacuo to give crude pyrazine-2-carbonyl chloride, which was used in the next step directly. TO a suspension of 2-amino-5-nitrobenzoic acid (2.00 g, 10.9 mmol, 1.0 eq.) in THF (50 mL) was added $Et_3N$ (1.09 g) and pyrazine-2-carbonyl chloride in anhydrous THF (50 mL) dropwise. The resulting mixture was stirred at room temperature for 18 h. After the reaction was completed, the volatiles were removed. The residue was suspended in $H_2O$ (10 mL) and the pH was adjusted to 5 by slow addition of 2N HCl in water. The resulting solid was collected and dried in vacuo to give 3.12 g of 5-nitro-2-(pyrazine-2-carboxamido)benzoic acid as a brown solid (99%). LCMS m/z=289.0 (M+1) (Method B) (retention time=1.24 min), Method A: N-(2-carbamoyl-4-nitrophenyl)pyrazine-2-carboxamide (iii-d)

A mixture of 5-nitro-2-(pyrazine-2-carboxamido)benzoic acid (3.12 g, 10.8 mmol) in $SOCl_2$ (20 mL) was stirred at 80° C. for 2 h. After cooling, the volatiles were removed and the residue was suspended in DCM (150 mL), and a solution of $NH_3.H_2O$ (25% by weight water, 40 mL) was added and stirred for 4 h. The resulting precipitate was collected and dried in vacuo to give 2.42 g of N-(2-carbamoyl-4-nitrophenyl)pyrazine-2-carboxamide as a dark red solid (74.6). LCMS m/z=288.0 (M+1) (Method B) (retention time=1.11 min).

Method E2: 6-nitro-2-(pyrazin-2-yl)quinazolin-4 (1H)-one (iv-g)

To a mixture of N-(2-carbamoyl-4-nitrophenyl)pyrazine-2-carboxamide (2.42 g, 8.43 mmol, 1.0 eq.) in EtOH (60 mL) was added NaOH (198 g, 49.5 mmol, 5.0 eq.). The resulting mixture was stirred at room temperature for 18 h. After the reaction was completed, the volatiles were removed in vacuo. The residue was partitioned between $H_2O$ (50 mL) and ethyl acetate (50 mL). The aqueous layer was neutralized to pH 5 by slow addition of aqueous citric acid. The resulting precipitate was collected and dried to give 2.00 g of 6-nitro-2-(pyrazin-2-yl)quinazolin-4(3H)-one as a yellow solid (88%), LCMS m/z=270.1 (M+1) (Method A) (retention time=1.36 min).

Method F2: 4-Chloro-6-nitro-2-(pyrazin-2-yl) quinazoline (v-g)

To a mixture of 6-nitro-2-(pyrazin-2-yl)quinazolin-4(3H)-one (1.00 g, 3.7 mmol) in $POCl_3$ (10 mL) was added N,N-dimethylbenzenamine (0.1 mL). The resulting mixture was stirred at 120° C. for 2 h. After the reaction was completed, $POCl_3$ was removed in vacuo, and the residue was co-evaporated with toluene twice to give a dark crude product, which was used for the next step without further purification.

Method G6: N-(3-(difluoromethoxy)phenyl)-6-nitro-2-(pyrazin-2-yl)quinazolin-4-amine (vi-s)

A mixture of 4-chloro-6-nitro-2-(pyrazin-2-yl)quinazoline (1.00 g, crude, 3.7 mmol, 1.0 eq.), 3-(difluoromethoxy)benzenamine (600 mg, 3.7 mmol, 1.0 eq.) and $Et_3N$ (1.00 g, 10 mmol, 3.0 eq) in THF (80 mL) was stirred at 75° C. for 18 h. After cooling, the volatiles were removed in vacuo and the residue was washed with $H_2O$ (100 mL×2). The solid was dried in vacuo to afford 1.40 g of N-(3-(difluoromethoxy) phenyl)-6-nitro-2-(pyrazin-2-yl)quinazolin-4-amine as a black solid (90.2% of two steps). LCMS m' z=411.0 (M+1) (Method A) (retention time=1.61 min).

Method B: $N^4$-(3-(difluoromethoxy)phenyl)-2-(pyrazin-2-yl)quinazoline-4,6-diamine (Iii-a)

To a mixture of N-(3-(difluoromethoxy)phenyl)-6-nitro-2-(pyrazin-2-yl) quinazolin-4-amine (1.40 g, 3.4 mmol, 1.0 eq.) in MeOH-$H_2O$ (v/v, 3:1, 110 mL) was added $NH_4Cl$ (1.80 g, 34 mmol, 10.0 eq.) and Fe (1.91 g, 34 mmol, 10.0 eq.). The resulting mixture was stirred at 60° C. for 3 h. After the reaction was completed, the mixture was cooled to room temperature, and the iron was filtered off. The filtrate was concentrated to 15 ml, and a precipitate formed and was collected and dried in vacuo to give 1.13 g of $N^4$-(3-(difluoromethoxy)phenyl)-2-(pyrazin-2-yl)quinazoline-4,6-diamine as a pale yellow solid (87.5%). LCMS m/z=381.1 (M+1) (Method B) (retention time=1.60 min), $^1$H-NMR (400 MHz, DMSO-$d_6$): δ 9.69 (s, 1H), 9.52 (d, J=1.2 Hz, 1H), 8.75 (d, J=2.4 Hz, 1H), 8.69 (d, J=2.4 Hz, 1H), 8.30 (s, 1H), 7.87 (dd, J=8.4, 0.8 Hz, 1H), 7.72 (d, J=8.8 Hz, 1H), 7.49-7.42 (m, 2H), 7.33-7.32 (m, 1H), 7.31 (t, J=7.4 Hz, 1H), 5.85 (s, 2H).

Method C: N-(4-(3-(difluoromethoxy)phenylamino)-2-(pyrazin-2-yl)quinazolin-6-yl)-6-methoxynicotinamide (Iiii-a)

To a solution of 6-methoxynicotinic acid (100 mg, 0.65 mmol) in SOCK, (2 mL) was added DMF (1 drop). The mixture was stirred at 60° C. for 20 min. The volatiles were removed in vacuo to give 6-methoxynicotinoyl chloride, which was used for the next step directly. To a suspension of $N^4$-(3-(difluoromethoxy)phenyl)-2-(pyrazin-2-yl)quinazoline-4,6-diamine (130 mg, 0.34 mmol, 0.5 eq.) in THF (5 mL) and $Et_3N$ (101 mg, 1 mmol, 3.0 eq) was added 6-methoxynicotinoyl chloride in anhydrous THF (5 mL) dropwise. The resulting mixture was stirred at room temperature for 18 h. The volatiles were removed in vacuo. The residue was washed with MeOH and re-crystallized from THF/MeOH twice, and purified by reverse phase chromatography PREP-HPLC (A=$NH_4HCO_3$—$H_2O$, 10 mmol/L, B=MeOH) to afford 33 mg of N-(4-(3-(difluoromethoxy)phenylamino)-2-(pyrazin-2-yl)quinazolin-6-yl)-6-methoxynicotinamide as a pale yellow solid (18.8%). LCMS m/z=516.1 (M+1), 258.6 (M/2+1) (Method A) (retention time=1.57 min), $^1$H-NMR (400 MHz, DMSO-($d_6$): δ 10.71 (s, 1H), 10.18 (s, 1H), 9.57 (d, J=1.6 Hz, 1H), 9.01 (d, J=1.6 Hz, 1H), 8.91 (d, J=2.4 Hz, 1H), 8.81 (t, J=2.0 Hz, 1H), 8.76 (d, J=2.4 Hz, 1H), 8.34 (dd, J=8.8, 2.8 Hz, 1H), 8.23 (s, 1H), 8.08 (dd, J=8.8, 2.0 Hz, 1H), 8.00 (d, J=9.2 Hz, 1H), 7.90 (d, J=9.2 Hz, 1H), 7.46-7.50 (m, 1H), 7.32 (t, J=74.4 Hz 1H), 7.02 (d, J=8.8 Hz, 1H), 6.95 (dd, J=8.0, 2.0 Hz, 1H), 3.97 (s, 3H).

The compounds in the following table were prepared in a manner analogous to that described in Scheme 67 (prepared according to method procedure A-G as designated).

TABLE 22
| Number | PRODUCT | Salt type | Molecular Mass | $^1$H-NMR |
|---|---|---|---|---|
| 1242 | 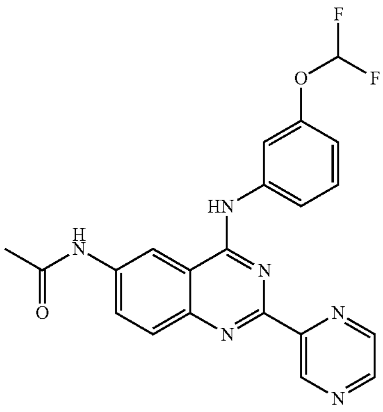 [SMILES: CC(=O)Nc1ccc2nc(-c3cnccn3)nc(Nc3cccc(OC(F)F)c3)c2c1] | | 422.39 | $^1$H-NMR (400 MHz, DMSO-$d_6$): δ 10.10-10.45 (m, 2H), 9.68 (s, 1H), 8.45-9.10 (m, 2H), 7.68-8.37 (m, 4H), 7.36-7.52 (m, 2H), 7.02-7.08 (m, 1H), 2.21 (s, 3H). |
| 1243 | 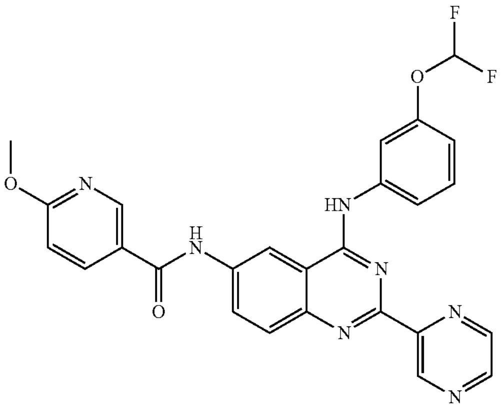 [SMILES: COc1ccc(C(=O)Nc2ccc3nc(-c4cnccn4)nc(Nc4cccc(OC(F)F)c4)c3c2)cn1] | | 515.47 | $^1$H-NMR (400 MHz, DMSO-$d_6$): δ 10.71 (s, 1H), 10.18 (s, 1H), 9.57 (d, J = 1.6 Hz, 1H), 9.01 (d, J = 1.6 Hz, 1H), 8.91 (d, J = 2.4 Hz, 1H), 8.81 (t, J = 2.0 Hz, 1H), 8.76 (d, J = 2.4 Hz, 1H), 8.34 (dd, J = 8.8, 2.8 Hz, 1H), 8.23 (s, 1H), 8.08 (dd, J = 8.8, 2.0 Hz, 1H), 8.00 (d, J = 9.2 Hz, 1H), 7.90 (d, J = 9.2 Hz, 1H), 7.46-7.50 (m, 1H), 7.32 (t, J = 74.4 Hz, 1H), 7.02 (d, J = 8.8 Hz, 1H), 6.95 (dd, J = 8.0, 2.0 Hz, 1H), 3.97 (s, 3H). |
| 1244 | 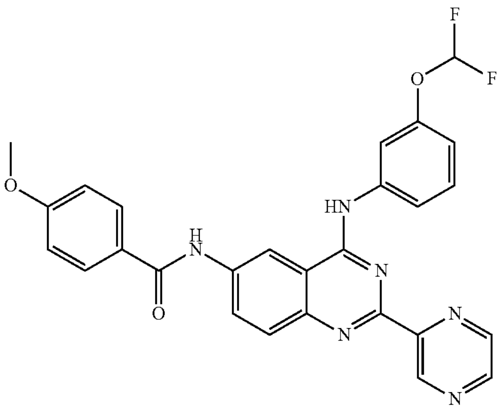 [SMILES: COc1ccc(C(=O)Nc2ccc3nc(-c4cnccn4)nc(Nc4cccc(OC(F)F)c4)c3c2)cc1] | | 514.48 | $^1$H-NMR (400 MHz, DMSO-$d_6$): δ 10.56 (s, 1H), 10.16 (s, 1H), 9.57 (s, 1H), 9.00 (d, J = 1.6 Hz, 1H), 8.81(d, J = 2.4 Hz, 1H), 8.76 (d, J = 2.8 Hz, 1H), 8.23 (s, 1H), 8.07-8.12 (m, 3H), 7.99 (d, J = 9.2 Hz, 1H), 7.89 (d, J = 9.2 Hz, 1H), 7.46-7.50 (m, 1H), 7.32 (t, J = 72.8 Hz, 1H), 7.11-7.13 (m, 2H), 6.95 (dd, J = 8.4, 2.4 Hz, 1H), 3.87 (s, 3H). |

TABLE 22-continued

| | | | |
|---|---|---|---|
| 1245 | 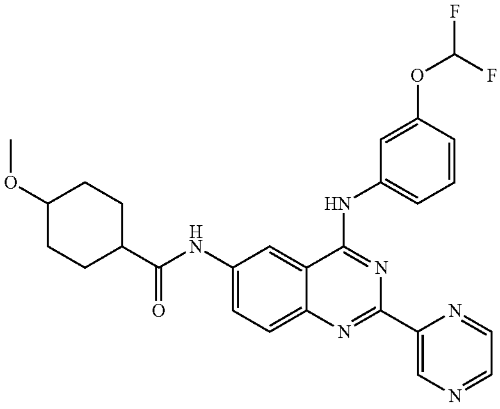 [SMILES: COC1CCC(C(=O)Nc2ccc3nc(-c4cnccn4)nc(Nc4cccc(OC(F)F)c4)c3c2)CC1] | 520.53 | $^1$H-NMR (400 MHz, DMSO-$d_6$): δ 10.30 (s, 1H), 10.16 (s, 1H), 9.54 (s, 1H), 8.89 (s, 1H), 8.79 (t, J = 2.4 Hz, 1H), 8.74 (d, J = 2.8 Hz, 1H), 8.20 (s, 1H), 7.93 (s, 2H), 7.87 (d, J = 8.4 Hz, 1H), 7.48 (dd, J = 10.0, 2.0 Hz, 1H), 7.31 (t, J = 74.0 Hz, 1H), 6.94 (dd, J = 8.4, 2.0 Hz, 1H), 3.26 (s, 3H), 3.18-3.22 (m, 1H), 1.91-1.96 (m, 2H), 1.66-1.78 (m, 2H), 1.53-1.63 (m, 2H), 1.38-1.49 (m, 2H). |
| 1246 | 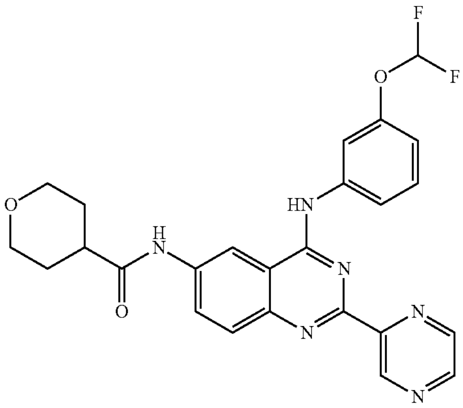 [SMILES: O=C(Nc1ccc2nc(-c3cnccn3)nc(Nc3cccc(OC(F)F)c3)c2c1)C1CCOCC1] | 492.48 | $^1$H-NMR (400 MHz, DMSO-$d_6$): δ 10.35 (s, 1H), 10.15 (s, 1H), 9.54 (s, 1H), 8.90 (d, J = 2.0 Hz, 1H), 8.80 (dd, J = 2.4, 1.2 Hz, 1H), 8.75 (d, J = 2.4 Hz, 1H), 8.19 (s, 1H), 7.95 (d, J = 8.8 Hz, 1H), 7.86-7.91 (m, 2H), 7.48 (dd, J = 10.8, 2.8 Hz, 1H), 7.31 (t, J = 74.4 Hz, 1H), 6.94 (dd, J = 7.6, 2.0 Hz, 1H), 3.94-3.97 (m, 2H), 3.40-3.43 (m, 2H), 2.70-2.73 (m, 1H), 1.65-1.78 (m, 4H). |

| Number | $^1$H-NMR Solvent | LCMS | LCMS Protocol | Purity percent | Method for Coupling |
|---|---|---|---|---|---|
| 1242 | DMSO | 423.0 (M + 1) | Method A (TFA) | 95 | Method C, G4, C |
| 1243 | DMSO | 516.2 (M + 1) | Method B (NH4HCO3) | 95 | Method C, G4, C |
| 1244 | DMSO | 515.2 (M + 1) | Method B (NH4HCO3) | 95 | Method C, G4, C |
| 1245 | DMSO | 521.2 (M + 1) | Method B (NH4HCO3) | 95 | Method C, G4, C |
| 1246 | DMSO | 493.2 (M + 1) | Method B (NH4HCO3) | 95 | Method C, G4, C |

Scheme 68: Synthesis of 6-(3-methoxyphenyl)-N-methyl-2-(pyrimidin-5-yl)quinazolin-4-amine (Compound 1247)

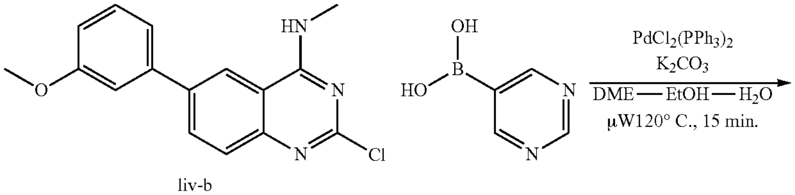

liv-b

-continued

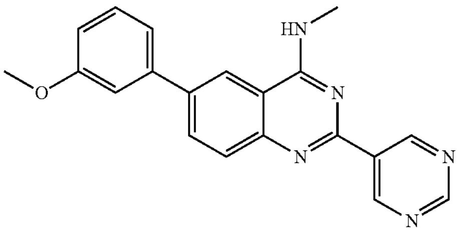

(Compound 1247)

Method BF: 6-(3-methoxyphenyl)-N-methy-2-(pyrimidin-5-yl)quinazolin-4-amine (compound 1247)

In a 10 mL microwave vial was added 2-chloro-6-(3-methoxyphenyl)-N-methylquinazolin-4-amine (0.080 g, 0.267 mmol), pyrimidine-5-boronic acid (0.099 g, 0.801 mmol), dichlorobis(triphenylphosphine)palladium (II) ($Pd(PPh_3)_2Cl_2$) (9.37 mg, 0.013 mmol), and potassium carbonate (0.111 g, 0.801 mmol) in DME (3 mL), EtOH (1.286 mL), and water (0.857 mL) to give a yellow suspension. The vial was irradiated at 120° C. for 15 min under argon. Water (10 rill) was added to the mixture and extracted with ethyl acetate (2×10 mL). The organic layers were combined and washed with brine (1×20 mL) and then dried over $MgSO_4$, filtered and concentrated. The residue was washed with $MeOH-CH_2Cl_2$ and dried to give 35 mg of 6-(3-methoxyphenyl)-N-methyl-2-(pyrimidin-5-yl)quinazolin-4-amine as a white solid (38%). LCMS m/z=344 (M+1) (Method D) (retention time=1.78 min) $^1H$ NMR (300 MHz, DMSO) δ 9.79-9.59 (m, 2H), 9.30 (s, 1H), 8.72 (d, J=4.6 Hz, 1H), 8.59 (s, 1H), 8.16 (d, J=8.6 Hz, 1H), 7.85 (d, J=8.7 Hz, 1H), 7.53-7.28 (m, 3H), 7.00 (d, J=6.8 Hz, 1H), 3.86 (s, 3H), 3.18 (d, J=3.9 Hz, 3H).

Scheme 69: Synthesis of 6-(3-methoxyphenyl)-N-methyl-2-(pyridin-3-yl)quinazolin-4-amine (Compound 1235)

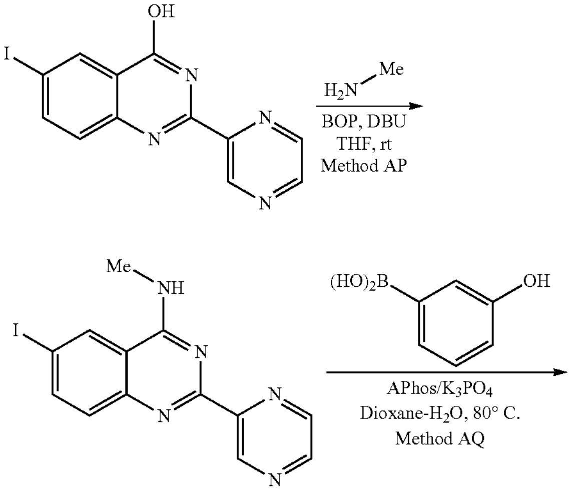

-continued

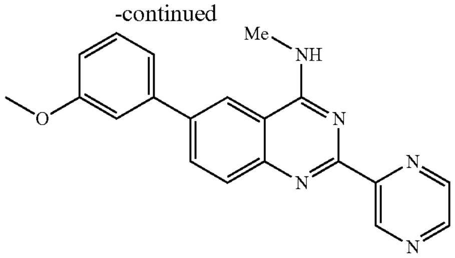

(Compound 1235)

In a 100 mL round-bottomed flask was added 6-iodo-2-(pyrazin-2-yl)quinazolin-4(3H)-one (0.500 g, 1.428 mmol), BOP (0.821 g, 1.857 mmol), and 1,8-diazabicyclo[5.4.0]undec-7-ene (0.426 ml, 2.86 mmol) in DMT (10 mL) to give a colorless solution. Methylamine, 2M in THF (2.142 ml, 4.28 mmol) was added and stirred at room temperature overnight. The reaction mixture was diluted with water (50 mL) and then a precipitate formed. The resulting solid was collected by filtration and dried to give 0.515 g of 6-iodo-N-methyl-2-(pyrazin-2-yl)quinazolin-4-amine as a pale brown solid in a 99% yield. LCMS m/z=364 (M+1) (Method D) (retention time=1.25 min). $^1H$ NMR (300 MHz, DMSO) δ 9.60 (s, 1H), 8.89-8.65 (m, 3H), 8.65-8.48 (m, 1H), 8.06 (d, J=8.7 Hz, 1H), 7.59 (d, J=8.7 Hz, 1H), 3.11 (d, J=4.2 Hz, 3H).

In a 50 ml, round-bottomed flask was added 6-iodo-N-methyl-2-(pyrazin-2-yl)quinazolin-4-amine (0.100 g, 0.275 mmol), 3-methoxyphenylboronic acid (0.063 g, 0.413 mmol), bis(di-tert-butyl(4-dimethylaminophenyl)phosphine) dichloropalladium(II) (0.016 g, 0.022 mmol), and potassium phosphate tribasic monohydrate (0.190 g, 0.826 mmol) in dioxane (5 mL) and water (0.5 mL) to give a brown suspension. The reaction mixture was heated at 80° C. overnight under argon. After cooling to room temperature, the reaction mixture was diluted with water (10 mL) and then a precipitate formed. The resulting solid was collected by filtration and washed with ethyl acetate and dried to give 25 mg of 6-(3-methoxyphenyl)-N-methyl-2-(pyrazin-2-yl)quinazolin-4-amine as a pale yellow solid in a 26% yield. LCMS m/z=344 (M+1) (Method D) (retention time=1.43 ruin). $^1H$ NMR (300 MHz, DMSO) δ 9.64 (s, 1H), 8.85-8.78 (m, 1H), 8.77-8.71 (m, 1H), 8.70-8.63 (m, 1H), 8.63-8.55 (m, 1H), 8.18 (d, J=8.8 Hz, 1H), 7.89 (d, J=8.9 Hz, 1H), 7.53-7.31 (m, 3H), 7.09-6.92 (m, 1H), 3.86 (5, 3H), 3.17 (d, J=3.6 Hz, 3H).

The compounds in the following table were prepared in a manner analogous to that described in Scheme 69 (prepared according to method described for 6-(3-methoxyphenyl)-N-methyl-2-(pyridin-3-yl)quinazolin-4-amine).

TABLE 23

| Number | PRODUCT | Salt type | Molecular Mass | $^1$H-NMR |
|---|---|---|---|---|
| 1235 | 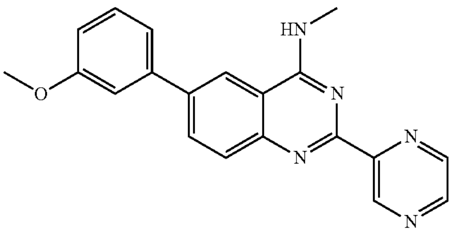 [SMILES: CNc1nc(-c2cnccn2)nc2ccc(-c3cccc(OC)c3)cc12] | | 343.38 | 1H NMR (300 MHz, DMSO) δ 9.64 (s, 1H), 8.85-8.78 (m, 1H), 8.77-8.71 (m, 1H), 8.70-8.63 (m, 1H), 8.63-8.55 (m, 1H), 8.18 (d, J = 0.8 Hz, 1H), 7.89 (d, J = 8.9 Hz, 1H), 7.53-7.31 (m, 3H), 7.09-6.92 (m, 1H), 3.86 (s, 3H), 3.17 (d, J = 3.6 Hz, 3H). |
| 1236 | 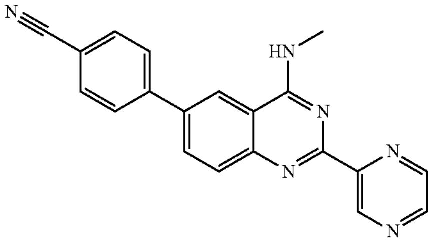 [SMILES: CNc1nc(-c2cnccn2)nc2ccc(-c3ccc(C#N)cc3)cc12] | | 338.37 | 1H NMR (300 MHz, DMSO) δ 9.64 (s, 1H), 8.87-8.61 (m, 4H), 8.24 (d, J = 8.8 Hz, 1H), 8.15-7.98 (m, 4H), 7.92 (d, J = 8.7 Hz, 1H), 3.17 (d, J = 4.0 Hz, 3H). |
| 1237 | 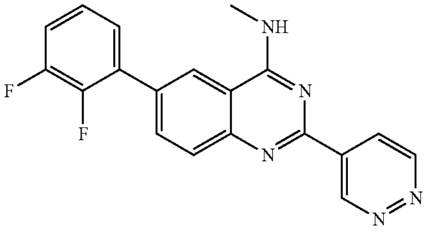 [SMILES: CNc1nc(-c2ccnnc2)nc2ccc(-c3cccc(F)c3F)cc12] | 2HCl | | $^1$H-NMR (400 MHz, DMSO-$d_6$): δ 10.17 (s, 1H), 9.54 (d, J = 5.2 Hz, 1H), 9.36 (s, 1H), 8.63 (s, 2H), 8.13-8.06 (m, 2H), 7.58-7.51 (m, 2H), 7.43-7.38 (m, 1H), 3.23 (d, J = 4.0 Hz, 3H). |
| 1238 | 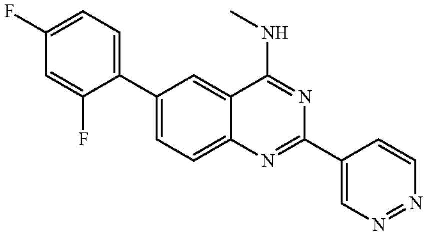 [SMILES: CNc1nc(-c2ccnnc2)nc2ccc(-c3ccc(F)cc3F)cc12] | 2HCl | | $^1$H-NMR (400 MHz, DMSO-10.14 (s, 1H), 9.50 (d, J = 5.2 Hz, 1H), 9.24 (s, 1H), 8.60 (dd, J = 5.4, 1.8 Hz, 1H), 8.55 (s, 1H), 8.04 (q, J = 8.8 Hz, 2H), 7.76 (dd, J = 15.4, 9.0 Hz, 1H), 7.51-7.45 (m, 1H), 7.32 (dt, J = 8.4, 2.0 Hz, 1H), 3.23 (d, J = 4.4 Hz, 3H). |
| 1239 | 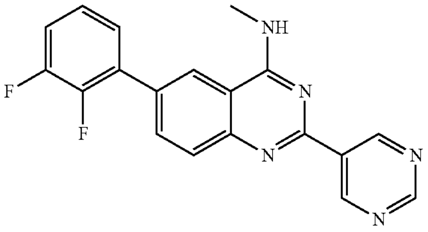 [SMILES: CNc1nc(-c2cncnc2)nc2ccc(-c3cccc(F)c3F)cc12] | | | $^1$H-NMR (400 MHz, DMSO-$d_6$): δ 9.73 (s, 1H), 9.32 (s, 1H), 8.74 (d, J = 4.4 Hz, 1H), 8.51 (s, 1H), 8.03 (d, J = 8.7 Hz, 1H), 7.92 (d, J = 8.6 Hz, 1H), 7.54-7.49 (m, 2H), 7.42-7.37 (m, 1H), 4.12 (q, J = 5.2 Hz, 1H), 3.17 (t, J = 4.5 Hz, 3H). |
| 1240 | 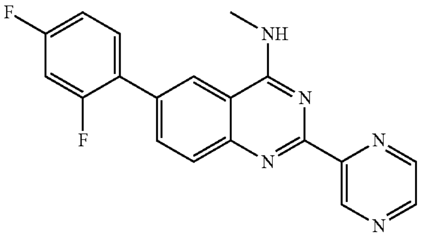 [SMILES: CNc1nc(-c2cnccn2)nc2ccc(-c3ccc(F)cc3F)cc12] | 2HCl | | $^1$H-NMR (400 MHz, CD3OD): δ 9.77 (s, 1H), 8.85 (d, J = 11.4 Hz, 2H), 8.42 (s, 1H), 8.19-8.03 (m, 2H), 7.60 (dd, J = 15.6, 7.8 Hz, 1H), 7.10 (t, J = 8.4 Hz, 2H), 3.38 (s, 3H). |

TABLE 23-continued

| | | | |
|---|---|---|---|
| 1241 | 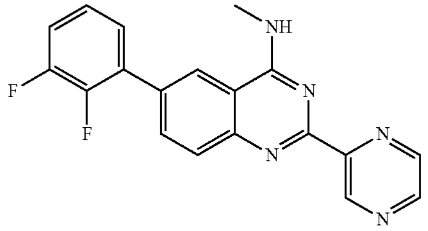 [SMILES: CNc1nc(-c2cnccn2)nc2ccc(-c3cccc(F)c3F)cc12] | 2HCl | $^1$H-NMR (400 MHz, DMSO): δ 10.84 (d, J = 1.8 Hz, 1H), 9.87 (s, 1H), 9.06 (d, J = 13.6 Hz, 2H), 8.90 (s, 1H), 8.32 (t, J = 9.8 Hz, 2H), 7.67-7.35 (m, 3H), 3.39 (s, 3H). |

| Number | $^1$H-NMR Solvent | LCMS | LCMS Protocol | Purity percent | Method for Coupling |
|---|---|---|---|---|---|
| 1235 | DMSO | 344 (M + 1) | Method D | 100 | Method AP/AQ |
| 1236 | DMSO | 339 (M + 1) | Method D | 100 | Method C, G1 |
| 1237 | DMSO | 350.1, 351.1, (M + 1) | Method B ($NH_4HCO_3$) | 95 | Method C, G1 |
| 1238 | DMSO | 350.1, 351.1, (M + 1) | Method B ($NH_4HCO_3$) | 95 | Method C, G1 |
| 1239 | DMSO | 350.1 (M + 1) | Method B ($NH_4HCO_3$) | 95 | Method C, G1 |
| 1240 | CD3OD | 350.1 (M + 1) | Method B ($NH_4HCO_3$) | 95 | Method C, G1 |
| 1241 | DMSO | 349.9 (M + 1) | Method B ($NH_4HCO_3$) | 95 | Method C, G1 |

Scheme 70: General route for the synthesis of compounds with general formula ii

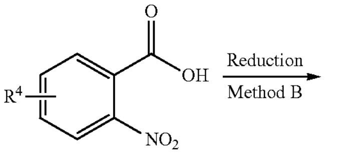

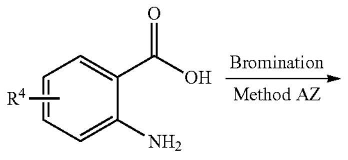

lv

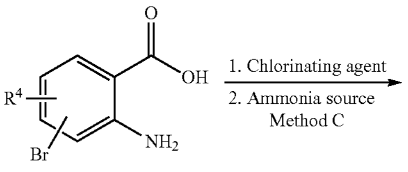

lvi

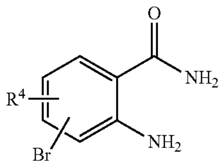

ii

Scheme 71: Representative synthesis of compounds of formula ii (see Scheme 70)

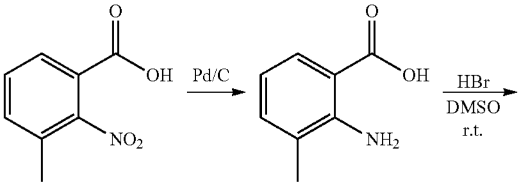

lv-a

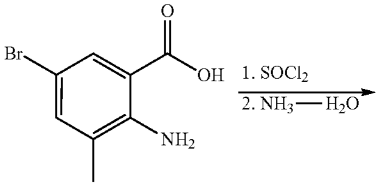

lvi-a

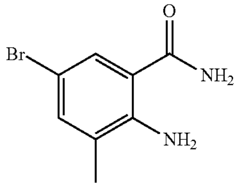

ii-c

Method B2: 2-Amino-3-methylbenzoic acid (Iv-a)

Pd/C catalyst (ISO mg) was suspended in a solution of 3-methyl-2-nitrobenzoic acid (1.50 g, 8.28 mmol, 1.0 eq) in THF (60 mL), the mixture was stirred under $H_2$ atmosphere at room temperature overnight. The Pd/C was removed by filtration over Celite and the THF was removed in vacuo to give 1.23 g of Iv-a as a white solid (yield 98%). LCMS m/z=152.1

(M+1) (Method B) (retention time=0.73 min). The product was used further without purification.

Method AZ: 2-Amino-5-bromo-3-methylbenzoic acid (Ivi-a)

To a solution of 2-amino-3-methylbenzoic acid (1.23 g, 8.14 mmol, 1.0 eq) in 15 mL of DMSO was added 40% HBr (6.00 mL, 44.7 mmol, 5 eq). The resulting mixture was stirred at room temperature overnight. A white precipitate formed during the course of the reaction. The reaction mixture was quenched with saturated aqueous $NaHCO_3$ resulting in a white solid that was filtered and dried in vacuo to yield 950 mg in 51% yield of Ivi-a as white solid. LCMS m/z=229.9 (M+1) (Method B) (retention time=1.20 min), Method C: 2-Amino-5-bromo-3-methylbenzamide (ii-e)

A mixture of 2-amino-5-bromo-3-methylbenzoic acid (950 mg, 4.15 mmol) and $SOCl_2$ (20 mL) was stirred at 80° C. for 2 h. After the reaction was completed, the mixture was cooled to room temperature. The $SOCl_2$ was removed in vacuo and the residue was dissolved in anhydrous THF (10 mL). The THF solution was then added dropwise to a 28% by weight solution of $NH_3$—$H_2O$ (10 mL). After 1 h, the resulting precipitate was collected and dried in vacuo to give 82.0 mg of ii-c as a yellow solid (87%). LCMS m/z=288.9, 230.9 (M+1) (Method B) (retention time=1.49 min).

Scheme 72: General route for the synthesis of compounds with general formula lvii and lviii

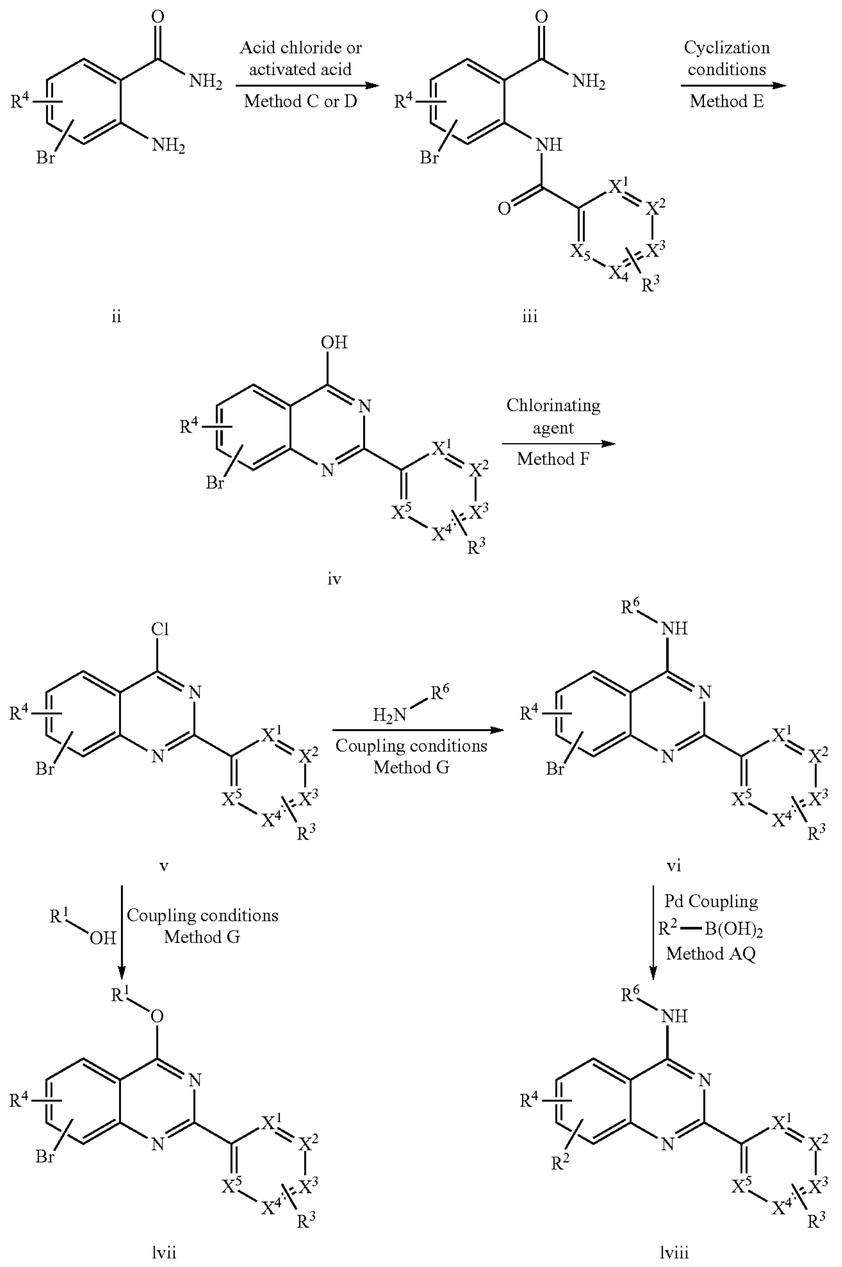

ii iii iv v vi lvii lviii $X^1$, $X^2$, $X^3$, $X^4$ or $X^5$ = CH or N, at least one $X^1$, $X^2$, $X^3$, $X^4$ or $X^5$ must be N Method G for Coupling Conditions
G1: i-PrOH/85-100° C.
G2: THF/heat
G3: i-AmOH/100-130° C.
G4: MeOH/microwave/150° C.
G5: i-AmOH/microwave/150° C.
G6: THF/$Et_3N$/reflux
G7: THF-$H_2O$/NaOAc/rt-60° C.
G8: NaH/THF
G9: n-BuLi/THF
G10: LHMDS/THF
G11: LDA/THF
G13: $Cs_2CO_3$/DMA/80° C.
G14: NaOtBu/DMF/Microwave/100° C.
Method AQ for Coupling Conditions
AQ1: $Pd(PPh_3)_2Cl_2/K_2CO_3$/Dioxane-$H_2O$
AQ2: $Pd_2(APhos)_2Cl_2/K_3PO_4$/Dioxane-$H_2O$
AQ3: $Pd(PPh_3)_4/K_3PO_4$/Dioxane-$H_2O$
AQ4: $Pd(dppf)Cl_2—CH_2Cl_2/K_3PO_4$/Dioxane-$H_2O$
AQ5: $Pd(OAc)_2Cl_2$/S-Phos/$K_3PO_4$/Dioxane-$H_2O$
AQ6: $Pd(dppf)Cl_2—CH_2Cl_2/Na_2CO_3$/Dioxane-$H_2O$ Scheme 73: Representative synthesis of compounds of formula lvii and lviii (see Scheme 72)

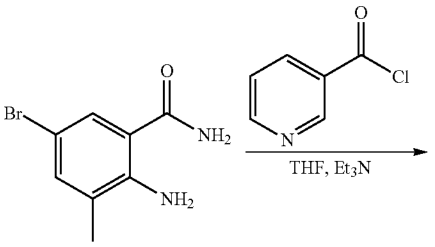

ii-c

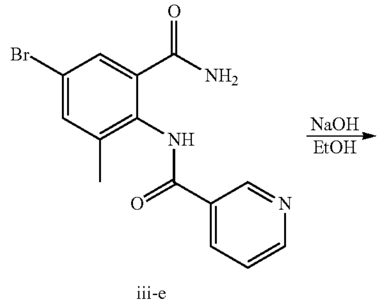

iii-e

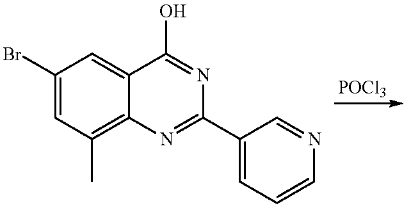

iv-h

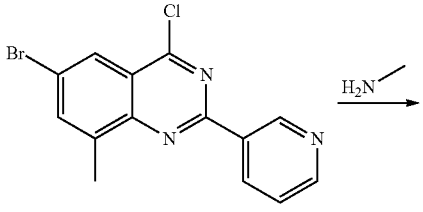

v-h

-continued

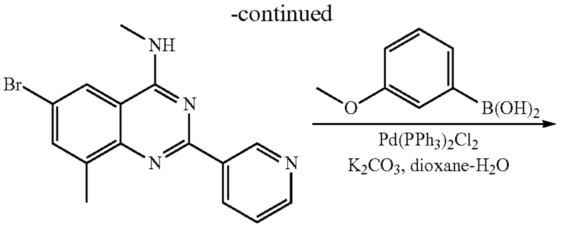

vi-t

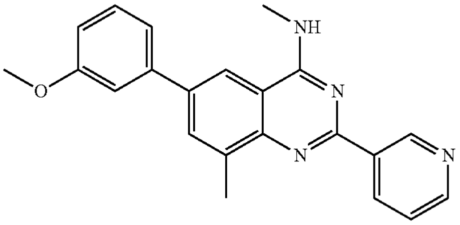

lviii-a

Method C: N-(4-bromo-2-carbamoyl-6-methylphenyl)nicotinamide (iii-e)

To a solution of 2-amino-5-bromo-3-methylbenzamide (820 mg, 3.55 mmol, 1.0 eq.) in THF (15 mL) and $Et_3N$ (0.7 nit) was added nicotinoyl chloride (551 mg, 3.91 mmol, 1.1 eq.) in anhydrous THF (15 mL) dropwise. The resulting mixture was stirred at room temperature overnight. After the reaction was completed, the resultant precipitate was filtered and dried in vacuo to give 1.74 g of crude iii-e as a yellow solid. LCMS m/z=333.8, 335.8 (M+1) (Method B) (retention time=1.42 min).

Method E: 6-Bromo-8-methyl-2-(pyridin-3-yl) quinazolin-4-ol (iv-h)

A mixture of N-(4-bromo-2-carbamoyl-6-methylphenyl) nicotinamide (1.74 g salt, 5.22 mmol, 1.0 eq) in EtOH (50 mL) was treated with NaOH (1.04 g, 26.1 mmol, 5.0 eq). The resulting mixture was stirred at room temperature overnight. After the reaction was completed, the volatiles were removed in vacuo. Water (30 mL) was added to the residue and the mixture was adjusted to pH~1 or 2 by slow addition of aqueous HCl. The resultant precipitate was collected and dried to give 870 mg of iv-h as a yellow solid (77% yield after two steps), LCMS m/z=315.7, 317.7 (M+1) (Method B) (retention time=1.74 min).

Method F5: 6-Bromo-4-chloro-8-methyl-2-(pyridin-3-yl)quinazoline (v-h)

6-Bromo-8-methyl-2-(pyridin-3-yl)quinazolin-4-ol (870 mg, 2.76 mmol) was added $POCl_3$ (10 mL). The resulting mixture was stirred at 120° C. overnight. After the reaction was completed, the mixture was carefully poured into ice-water. The pH was adjusted to 7 by slow addition of $NH_4OH$ at 0° C. The resultant solid was collected to give 1.00 g of v-h as a beige solid (quantitative yield). LCMS m/z=333.9, 335.9 (M+1) (Method B) (retention time=2.23 min).

Method G6: 6-Bromo-N, 8-dimethyl-2-(pyridin-3-yl) quinazolin-4-amine (vi-t)

A mixture of 6-bromo-4-chloro-8-methyl-2-(pyridin-3-yl) quinazoline (200 mg, 0.60 mmol, 1.0 eq.), methylamine (81 mg, 1.20 mmol, 2.0 eq.) and $Et_3N$ (0.2 mL) in i-PrOH (10 mL) was stirred at 85° C. overnight. The resultant yellow precipitate was collected to afford 125 mg of vi-t as a beige solid (63.4%). LCMS m/z=328.8, 330.8 (M+1-1) (Method B) (retention time=1.95 min).

Method G2: 7-bromo-N-methyl-2-(pyridin-3-yl) quinazolin-4-amine (vi-u)

To a suspension of 7-bronco-4-chloro-2-(pyridin-3-yl) quinazoline (5.0 g, 0.0156 mol) in THF (100 mL) was added dropwise a methylamine solution (40 wt. % in $H_2O$) (24 ml, 0.272 mmol) with cooling. The suspension was stirred at 60° C. for 3 h, cooled, filtered, and dried to give the title compound. (3.62 g, 73.5%)

Method AQ1: 6-(3-Methoxyphenyl)-N,8-dimethyl-2-(pyridin-3-yl)quinazolin-4-amine (Iviii-a)

(This method is representative of method AQ2 and can be implemented in a similar way except for substitution of the appropriate catalyst and base) To a mixture of 6-bronco-N,8-dimethyl-2-(pyridin-3-yl)quinazolin-4-amine (130 mg, 0.396 mmol, 1.0 eq), 3-methoxyphenylboronic acid (60 mg, 0.396 mmol, 1.0 eq), $K_2CO_3$ (295 mg, 2.14 mmol, 5.4 eq.) in dioxane (8 mL) and $H_2O$ (4 mL) was added $Pd(PPh_3)_2Cl_2$ (15 mg, 0.021 mmol, 0.054 eq) under $N_2$ atmosphere. The resulting mixture was stirred at 120° C. under $N_2$ atmosphere overnight. After the reaction was completed, the mixture was filtered, and the filtrate was concentrated in vacuo. The residue was purified by reverse phase HPLC column to afford 11 mg of Iviii-a as a white solid (yield 7.8%). LCMS m/z=357.2, (M+1) (Method B (retention time=2.11 min), $^1H$ NMR (400 MHz, DMSO-$d_6$): δ 9.68 (d, J=1.2 Hz, 1H), 8.75 (d, J=8.0 Hz, 1H), 8.62 (d, J=4.6 Hz, 1H), 8.49 (d, J=4.4 Hz, 1H), 8.35 (s, 1H), 7.97 (s, 1H), 7.49 (dd, J=7.8, 4.8 Hz, 1H), 7.44-7.29 (m, 3H), 6.93 (dd, J=6.8, 2.4 Hz, 1H), 3.81 (s, 3H), 3.12 (d, J=4.4 Hz, 3H), 2.68 (s, 3H).

Method AQ3: 6-(4-Fluorophenyl)-N,8-dimethyl-2-(pyridin-3-yl)quinazolin-4-amine dihydrochloride (Iviii-h)

6-Bromo-N,8-dimethyl-2-(pyridin-3-yl)quinazolin-4-amine (340 mg, 1.03 mmol), 3-fluorobenzeneboronic acid (217 mg, 1.55 mmol), $K_2PO_4$ (658 mg, 3.10 mmol) and $Pd(PPh_3)_4$ (59.7 mg, 0.052 mmol) were dissolved in the mixed solvent of 1,4-dioxane (10 mL) and water (1 mL). The resulting mixture was stirred at 90° C. for 6 hours under a nitrogen atmosphere. After the reaction was completed, water was added to the mixture and stirred for 30 minutes. The resulting precipitate was collected by filtration and purified by column chromatography on NH-silica gel (eluted with THF) to give a yellow powder. The solid was suspended in ethanol and 5N HCl (1 mL) was added to the mixture. The mixture was sonicated for 10 min and the resulting precipitate was collected by filtration and dried to give 304 mg of 6-(3-fluorophenyl)-N,8-dimethyl-2-(pyridin-3-yl)quinazolin-4 amine dihydrochloride as a yellow powder in 71% yield.

Method AQ4: 6-(2,4-Difluorophenyl)-N,5-dimethyl-2-(pyridin-3-yl)quinazolin-4-amine(Iviii-c)

6-Bromo-N,5-dimethyl-2-(pyridin-3-yl)quinazolin-4-amine (350 mg, 1.06 mmol), 2,4-difluorophenylboronic acid (252 mg, 1.595 mmol), $K_3PO_4$ (677 mg, 3.19 mmol) and $Pd(dppf)Cl_2—CH_2Cl_2$ (87 mg, 0.106 mmol) were dissolved in the mixed solvent of 1,4-dioxane (10 mL) and water (1 mL). The resulting mixture was stirred at 90° C. for 2.5 hours under $N_2$. After the reaction was completed, water was added to the mixture and extracted with ethyl acetate. The combined organic layers were washed with water and brine, dried over $Na_2SO_4$. After filtration and evaporation, the crude product was purified by column chromatography on NH-silica gel (eluted with isocratic 33% ethyl acetate/67% hexane) to give a white powder. The solid was suspended in ethanol and 5N HCl (1.0 mL) was added to the mixture. The mixture was sonicated for 10 min and the resultant precipitate was collected by filtration and dried to give 139 mg of 6-(2,4-difluorophenyl)-N,5-dimethyl-2-(pyridin-3-yl)quinazolin-4-amine dihydrochloride as a pale yellow powder in a 30% yield.

Method AQ5: 7-(3-fluorophenyl)-N,6-dimethyl-2-(pyridin-3-yl)quinazolin-4-amine dihydrochloride (Iviii-d)

A mixture of 7-chloro-N,6-dimethyl-2-(pyridin-3-yl) quinazolin-4-amine (400 mg, 1.40 mmol), 3-fluorophenylboronic acid (294 g, 2.10 mmol), Pd(OAc) (15.8 mg, 0.070 mmol), 2-dicyclohexylphosphino-2',6'-dimethoxybiphenyl (86.7 mg, 0.211 mmol), $K_3PO_4$ (900 mg, 4.23 mmol) in dioxane (10 mL) and water (2 mL) was stirred under reflux for 2.5 h. Ethyl acetate (20 mL) was added to the cooled mixture and a precipitate formed and was filtered. The solid was recrystallized from DMF and water to give the title compound as free form. The solid was suspended in ethyl acetate (10 mL) and 4N HCl in ethyl acetate (1.0 mL) was added. The resulting solid was subjected to sonication for 20 min, filtered and dried to give the title compound as the bis-110 salt (0.10 g, 18.7%).

Method AQ6:7-(3,4-difluorophenyl)-N,8-dimethyl-2-(pyridin-3-yl)quinazolin-4-amine dihydrochloride (Iviii-e)

To a suspension of 3,4-difluorophenylboronic acid (389 mg, 2.46 mmol) and 7-bromo-N,8-dimethyl-2-(pyridin-3-yl) quinazolin-4-amine (395.4 mg, 1.201 mmol) in dioxane/$H_2O$ (2/1) (30 mL) under a nitrogen atmosphere was added $Na_2CO_3$ (633.2 mg, 5.97 mmol) and (1,1'-bis(diphenylphosphino)ferrocene)-dichloropalladium(II) (98 mg, 0.120 mmol) at room temperature. The mixture was stirred at 100° C. for 1.5 h. Water was added to the reaction mixture and then a precipitate formed. The solid was filtered and washed with water and dried. The dried solid was then heated in a methanol/dioxane mixture to give a clear solution and filtered through Celite. The filtrate was concentrated to give the crude product. The crude product was sonicated in methanol/$CH_2Cl_2$ for ca. 15 min and filtered to give 305.2 mg of a pale brown solid as the parent compound. To a suspension of parent compound in methanol was added 4N HCl in ethyl acetate (ca. 4 mL) to give a clear solution. The solution was concentrated and recrystallized from ethanol to give the HCl salt. The salt was collected and dried in an oven at 60° C. to give 231.3 mg in a 44% yield as pale yellow solid. $^1H$ NMR (DMSO-$d_6$) δ 9.73 (s, 1H), 9.37 (brd, J=8.08 Hz, 1H), 8.97 (brd, J=5.24 Hz, 1H), 8.77 (brs, 1H), 8.20 (d, J=8.48 Hz, 1H), 8.10-8.07 (brm, 1H), 7.63-7.55 (brm, 2H), 7.47 (d, J=8.48 Hz, 1H), 7.32 (brm, 1H), 3.20 (d, J=4.20 Hz, 3H), 2.65 (s, 3H). The 1H of 2HCl was not observed.

Scheme 74: General route for the synthesis of compounds with general formula lviii
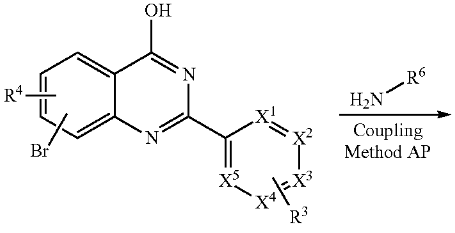
iv
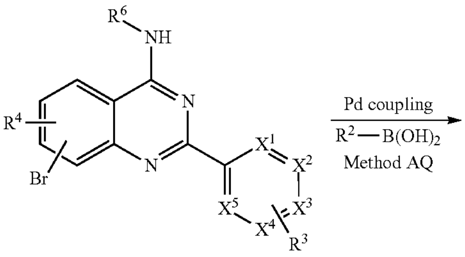
vi
-continued
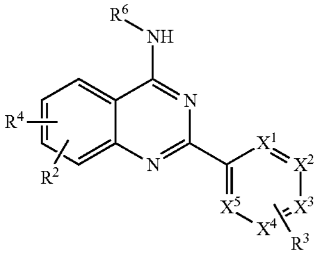
lviii
$X^1$, $X^2$, $X^3$, $X^4$ or $X^5$ = CH or N, at least one $X^1$, $X^2$, $X^3$, $X^4$ or $X^5$ must be N
Scheme 75: Representative synthesis of compounds of formula lviii (see Scheme 74)
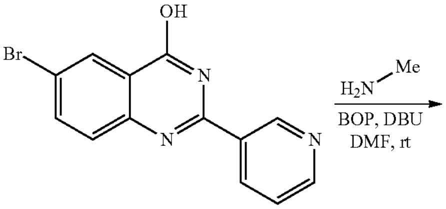
iv-i
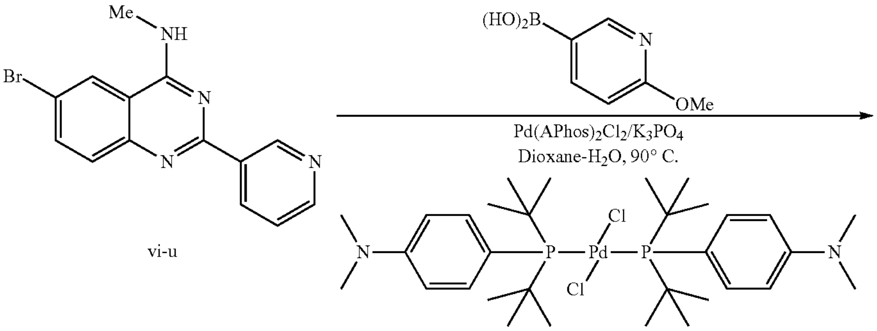
vi-u
Pd(APhos)$_2$Cl$_2$
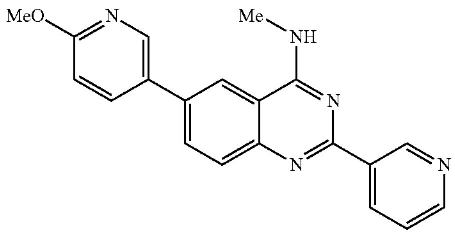
lviii-f Method AP: 6-bromo-N-methyl-2-(pyridine-3-yl) quinazoline-4-amine (vi-u)

To a solution of 6-promo-2-(pyridin-3-yl)quinazolin-4(3H)-one (5.00 g, 16.6 mmol), (benzotriazol-1-yloxy)tris(dimethylamino)phosphonium hexafluorophosphate (BOP) (9.52 g, 21.5 mmol), and 1,8-diazabicyclo[5.4.0]undec-7-ene (DBU) (4.94 ml, 33.1 mmol) in DMF (50 mL) was added methylamine, 2M in THF (16.6 mL, 33.1 mmol). The mixture was stirred overnight at room temperature. Water (100 mL) was added to the mixture and stirred. The resultant precipitate was collected by filtration and dried to give 5.15 g of 6-bromo-N-methyl-2-(pyridin-3-yl)quinazolin-4-amine as pale yellow solid (99%) LCMS m/z=315 (M+1) (Method D) (retention time=1.34 min). $^1$H NMR (300 MHz, DMSO) δ 9.60 (dd, J=2.1, 0.8 Hz, 1H), 8.79-8.70 (m, 1H), 8.67 (dd, J=4.8, 1.7 Hz, 1H), 8.57 (s, 1H), 8.51 (d, J=2.0 Hz, 1H), 7.90 (dd, J=8.9, 2.1 Hz, 1H), 7.71 (d, J=8.9 Hz, 1H) 7.52 (ddd, J=7.9, 4.8, 0.9 Hz, 1H), 3.13 (d, J=4.5 Hz, 3H).

Method AQ2: 6-(6-methoxypyridin-3-yl)-N-methyl-2-(pyridine-3-yl)quinazoline-4-amine (Iviii-f)

To a 1 dram reaction vial was added 6-bromo-N-methyl-2-(pyridine-3-yl)quinazoline-4-amine (35 mg, 0.111 mmol), 6-methoxypyridin-3-ylboronic acid (20.4 mg, 0.133 mmol), $Pd(APhos)_2Cl_2$ (3.2 mg, 0.0041 mmol) and potassium phosphate monohydrate (77 mg, 0.33 mmol) in a mixture of dioxane-water (9:1, 2 mL). The reaction mixture was heated to 90° C. for 14 h after which it was cooled to room temperature and diluted with water (5 mL). The resultant precipitate was collected by filtration and recrystallized from methanol to give 6-(6-methoxypyridin-3-yl)-N-methyl-2-(pyridine-3-yl) quinazoline-4-amine as a pale yellow solid (19.1 mg, 51%). LCMS m/z=344 (M+1) (Method C) (retention time=2.01 min) $^1$H NMR (300 MHz, DMSO) δ 9.64 (d, J=1.3 Hz, 1H), 8.84-8.74 (m, 1H), 8.68 (dd, J=6.2, 1.7 Hz, 2H), 8.57 (d, J=1.6 Hz, 2H), 8.16 (ddd, J=14.4, 8.7, 2.2 Hz, 2H), 7.85 (d, J=8.7 Hz, 1H), 7.54 (dd, J=7.9, 4.8 Hz, 1H), 7.00 (d, J=8.7 Hz, 1H), 3.93 (s, 3H), 3.18 (d, J=4.3 Hz, 3H).

The compounds in the following table were prepared in a manner analogous to that described in Scheme 72 or 74, replacing methylamine with the appropriate amine and 6-methoxypyridin-3-ylboronic acid with the appropriate boronic acid.

TABLE 24

| Number | Product | Salt | Molecular Mass | $^1$H-NMR | $^1$H-NMR Solvent | LCMS | Retention Time | LCMS Protocol | Purity percent | Method for Coupling |
|---|---|---|---|---|---|---|---|---|---|---|
| 1248 | 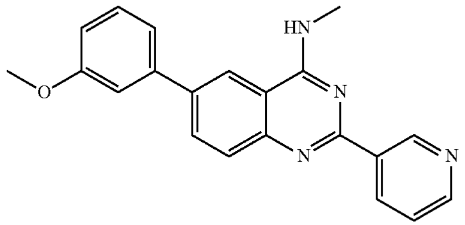 [SMILES: CNc1nc(-c2cccnc2)nc2ccc(-c3cccc(OC)c3)cc12] | HCl | 342.4 | $^1$H-NMR (400 MHz, DMSO-$d_6$): δ 9.66 (s, 1H), 8.50-8.89 (m, 3H), 8.16 (d, J = 8.2 Hz, 1H), 7.86 (d, J = 8.6 Hz, 1H), 7.30-7.61 (m, 4H), 7.01 (d, J = 6.4 Hz, 1H), 3.88 (s, 3H), 3.32 (brs, 1H), 3.19 (s, 3H). | DMSO | 343.1 (M + 1) | | Method B (NH4HCO3) | 95 | Method AQ1 |
| 1249 | 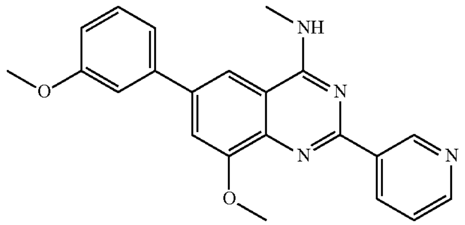 [SMILES: CNc1nc(-c2cccnc2)nc2c(OC)cc(-c3cccc(OC)c3)cc12] | | 372.4 | 1H-NMR (400 MHz, DMSO-d6): δ 9.63 (s, 1H), 8.77 (d, J = 7.9 Hz, 1H), 8.67 (d, J = 3.7 Hz, 1H), 8.50 (s, 1H), 8.11 (s, 1H), 7.56-7.53 (m, 2H), 7.48-7.40 (m, 3H), 7.01 (d, J = 3.9 Hz, 1H), 4.07 (s, 3H), 3.88 (s, 3H), 3.17 (d, J = 4.0 Hz, 3H). | DMSO | 372.9 (M + 1) | | Method B (NH4HCO3) | 95 | Method AQ1 |
| 1250 | 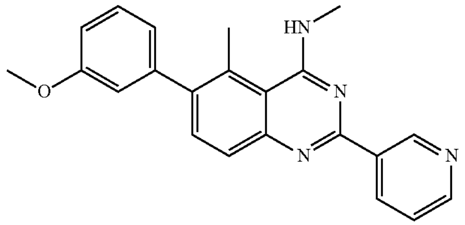 [SMILES: CNc1nc(-c2cccnc2)nc2ccc(-c3cccc(OC)c3)c(C)c12] | | 356.4 | 1H-NMR (400 MHz, DMSO-d6): δ 9.63 (s, 1H), 8.79-8.74 (m, 1H), 8.69 (d, J = 4.0 Hz, 1H), 7.67 (d, J = 8.4 Hz, 1H), 7.60 (d, J = 8.8 Hz, 1H), 7.57-7.51 (m, 1H), 7.42 (t, J = 8.0 Hz, 1H), 7.37-7.30 (m, 1H), 7.02-6.92 (m, 3H), 3.82 (s, 3H), 3.18 (d, J = 4.0 Hz, 3H), 2.69 (s, 3H). | DMSO | 357.1 (M + 1) | | Method B (NH4HCO3) | 95 | Method AQ1 |
| 1251 | 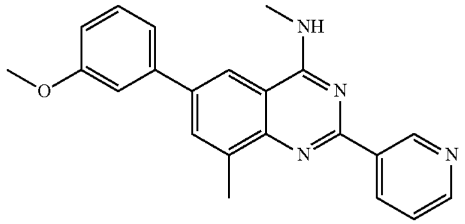 [SMILES: CNc1nc(-c2cccnc2)nc2c(C)cc(-c3cccc(OC)c3)cc12] | | 356.4 | 1H-NMR (400 MHz, DMSO-d6): δ 9.68 (d, J = 1.2 Hz, 1H), 8.75 (d, J = 8.0 Hz, 1H), 8.62 (d, J = 4.6 Hz, 1H), 8.49 (d, J = 4.4 Hz, 1H), 8.35 (s, 1H), 7.97 (s, 1H), 7.49 (dd, J = 7.8, 4.8 Hz, 1H), 7.44-7.29 (m, 3H), 6.93 (dd, J = 6.8, 2.4 Hz, 1H), 3.81 (s, 3H), 3.12 (d, J = 4.4 Hz, 3H), 2.68 (s, 3H). | DMSO | 357.2 (M + 1) | | Method B (NH4HCO3) | 95 | Method AQ1 |

TABLE 24-continued
| | | | | | | | | | | |
|---|---|---|---|---|---|---|---|---|---|---|
| 1252 | 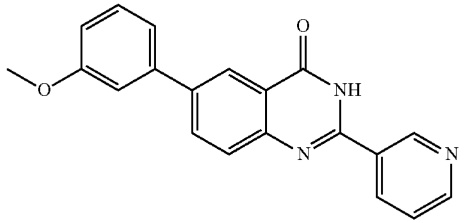 [SMILES: COc1cccc(-c2ccc3nc(-c4cccnc4)[nH]c(=O)c3c2)c1] | | 329.3 | 1H NMR (300 MHz, DMSO) δ 9.31 (s, 1H), 8.76 (d, J = 4.7 Hz, 1H), 8.51 (d, J = 8.0 Hz, 1H), 8.37 (d, J = 2.0 Hz, 1H), 8.18 (dd, J = 8.5, 2.2 Hz, 1H), 7.84 (d, J = 8.4 Hz, 1H), 7.59 (dd, J = 7.9, 4.8 Hz, 1H), 7.49-7.23 (m, 3H), 6.99 (d, J = 6.7 Hz, 1H), 3.85 (s, 3H). | DMSO | 330 (M + 1) | 1.76 | Method D | 100 | |
| 1253 | 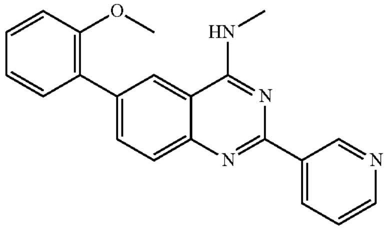 [SMILES: CNc1nc(-c2cccnc2)nc2ccc(-c3ccccc3OC)cc12] | HCl | 342.4 | 1H NMR (300 MHz, DMSO) δ 10.11 (s, 1H), 9.63 (s, 1H), 9.07-8.86 (m, 2H), 8.58 (s, 1H), 8.16 (s, 2H), 7.92-7.77 (m, 1H), 7.54-7.36 (m, 2H), 7.20 (d, J = 8.6 Hz, 1H), 7.16-7.07 (m, 1H), 3.81 (s, 3H), 3.29 (d, J = 3.9 Hz, 3H). | DMSO | 343 (M + 1) | 1.47 | Method D | 100 | Method AQ2 |
| 1254 | 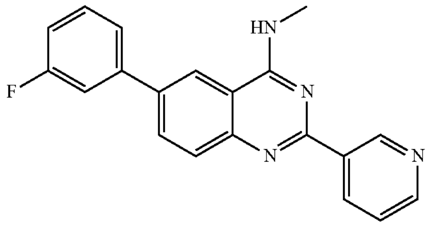 [SMILES: CNc1nc(-c2cccnc2)nc2ccc(-c3cccc(F)c3)cc12] | | 330.3 | 1H NMR (300 MHz, DMSO) δ 9.59 (s, 1H), 8.73 (d, J = 8.3 Hz, 1H), 8.65 (d, J = 4.7 Hz, 1H), 8.37-8.22 (m, 1H), 8.18-8.05 (m, 1H), 7.76 (d, J = 9.0 Hz, 1H), 7.71 (s, 1H), 7.56-7.43 (m, 2H), 4.58 (s, 2H), 3.14 (d, J = 4.4 Hz, 3H), 2.69 (d, J = 4.6 Hz, 3H). | DMSO | 331 (M + 1) | 1.52 | Method D | 100 | Method AQ2 |
| 1255 | 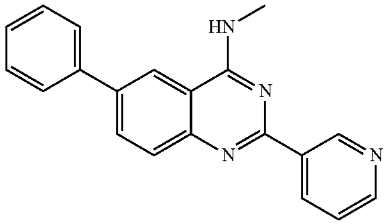 [SMILES: CNc1nc(-c2cccnc2)nc2ccc(-c3ccccc3)cc12] | | 312.4 | 1H NMR (300 MHz, DMSO) δ 9.64 (s, 1H), 8.88-8.47 (m, 4H), 8.25-8.05 (m, 1H), 7.97-7.72 (m, 3H), 7.67-7.35 (m, 4H), 3.18 (d, J = 4.4 Hz, 3H). | DMSO | 313 (M + 1) | 1.48 | Method D | 100 | Method AQ2 |

TABLE 24-continued
| | | | | | | | | | | |
|---|---|---|---|---|---|---|---|---|---|---|
| 1256 | 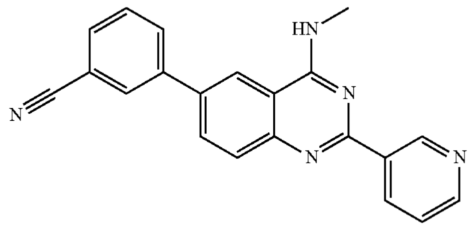 [SMILES: CNc1nc(-c2cccnc2)nc2ccc(-c3cccc(C#N)c3)cc12] | HCl | 337.4 | 1H NMR (300 MHz, DMSO) δ 9.93 (s, 1H), 9.63 (s, 1H), 9.00 (d, J = 8.3 Hz, 1H), 8.95-8.82 (m, 2H), 8.46-8.32 (m, 2H), 8.25 (d, J = 7.0 Hz, 1H), 8.13 (d, J = 8.4 Hz, 1H), 7.92 (d, J = 7.2 Hz, 1H), 7.88-7.70 (m, 2H), 3.29 (d, J = 4.2 Hz, 3H). | DMSO | 338 (M + 1) | 1.50 | Method D | 100 | Method AQ2 |
| 1257 | 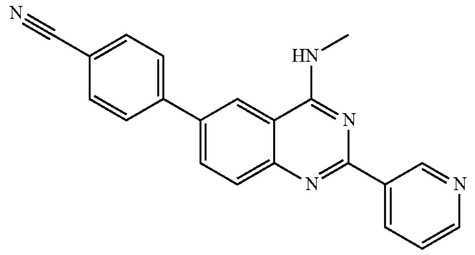 [SMILES: CNc1nc(-c2cccnc2)nc2ccc(-c3ccc(C#N)cc3)cc12] | | 337.4 | 1H NMR (300 MHz, DMSO) δ 9.64 (s, 1H), 8.77 (d, J = 7.9 Hz, 1H), 8.73-8.59 (m, 3H), 8.21 (d, J = 8.8 Hz, 1H), 8.11-7.94 (m, 4H), 7.87 (d, J = 8.7 Hz, 1H), 7.54 (dd, J = 7.9, 4.8 Hz, 1H), 3.18 (d, J = 4.0 Hz, 3H). | DMSO | 338 (M + 1) | 1.50 | Method D | 100 | Method AQ2 |
| 1258 | 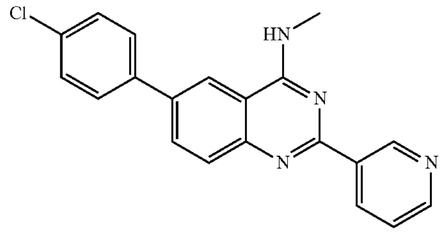 [SMILES: CNc1nc(-c2cccnc2)nc2ccc(-c3ccc(Cl)cc3)cc12] | | 346.8 | 1H NMR (300 MHz, DMSO) δ 9.64 (s, 1H), 8.77 (d, J = 7.9 Hz, 1H), 8.72-8.52 (m, 3H), 8.14 (d, J = 8.7 Hz, 1H), 7.97-7.74 (m, 3H), 7.68-7.45 (m, 3H), 3.18 (d, J = 4.0 Hz, 3H). | DMSO | 347 (M + 1) | 1.60 | Method D | 100 | Method AQ2 |
| 1259 | 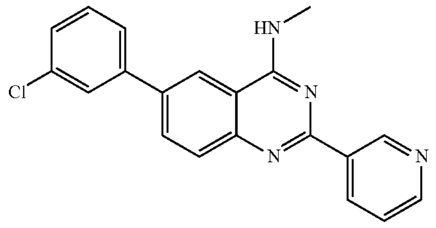 [SMILES: CNc1nc(-c2cccnc2)nc2ccc(-c3cccc(Cl)c3)cc12] | | 346.8 | 1H NMR (300 MHz, DMSO) δ 9.64 (s, 1H), 8.78 (d, J = 8.0 Hz, 1H), 8.72-8.54 (m, 3H), 8.17 (d, J = 8.7 Hz, 1H), 7.94 (s, 1H), 7.90-7.78 (m, 2H), 7.61-7.42 (m, 3H), 3.19 (d, J = 4.4 Hz, 3H). | DMSO | 347 (M + 1) | 1.66 | Method D | 100 | Method AQ2 |

TABLE 24-continued

| | | | | | | | | | |
|---|---|---|---|---|---|---|---|---|---|
| 1260 | 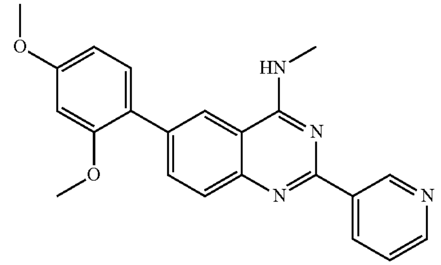 [SMILES: CNc1nc(-c2cccnc2)nc2ccc(-c3ccc(OC)cc3OC)cc12] | 372.4 | 1H NMR (300 MHz, DMSO) δ 9.63 (s, 1H), 8.77 (dd, J = 7.9, 1.8 Hz, 1H), 8.67 (d, J = 4.7 Hz, 1H), 8.46 (d, J = 4.4 Hz, 1H), 8.26 (s, 1H), 7.95-7.84 (m, 1H), 7.75 (d, J = 8.6 Hz, 1H), 7.53 (dd, J = 7.9, 4.8 Hz, 1H), 7.35 (d, J = 8.3 Hz, 1H), 6.77-6.60 (m, 2H), 3.80 (ss, 6H), 3.14 (d, J = 4.3 Hz, 3H). | DMSO | 373 (M + 1) | 1.49 | Method D | 100 | Method AQ2 |
| 1261 | 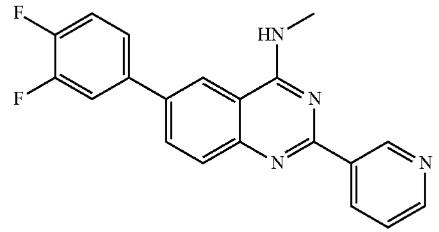 [SMILES: CNc1nc(-c2cccnc2)nc2ccc(-c3ccc(F)c(F)c3)cc12] | 348.3 | 1H NMR (300 MHz, DMSO) δ 9.63 (s, 1H), 8.77 (dd, J = 8.0, 1.9 Hz, 1H), 8.68 (d, J = 4.6 Hz, 1H), 8.59 (s, 2H), 8.21-8.09 (m, 1H), 8.02-7.88 (m, 1H), 7.84 (d, J = 8.7 Hz, 1H), 7.71 (s, 1H), 7.67-7.58 (m, 1H), 7.53 (dd, J = 7.6, 5.1 Hz, 1H), 3.18 (d, J = 4.4 Hz, 3H). | DMSO | 349 (M + 1) | 1.61 | Method D | 100 | Method AQ2 |
| 1262 | 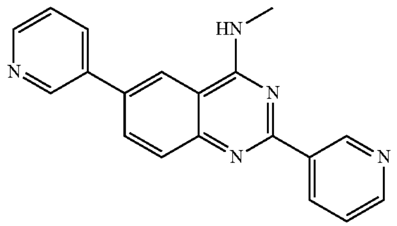 [SMILES: CNc1nc(-c2cccnc2)nc2ccc(-c3cccnc3)cc12] | 313.4 | 1H NMR (300 MHz, DMSO) δ 9.65 (s, 1H), 9.09 (s, 1H), 8.78 (d, J = 8.0 Hz, 1H), 8.73-8.55 (m, 4H), 8.30-8.14 (m, 2H), 7.89 (d, J = 8.6 Hz, 1H), 7.63-7.47 (m, 2H), 3.19 (d, J = 4.3 Hz, 3H). | DMSO | 314 (M + 1) | 1.70 | Method C | 96 | Method AQ2 |
| 1263 | 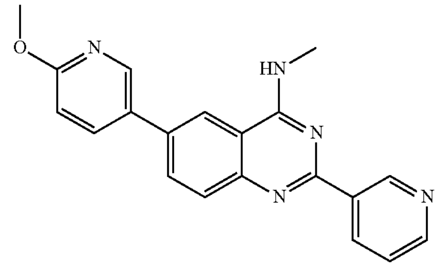 [SMILES: CNc1nc(-c2cccnc2)nc2ccc(-c3ccc(OC)nc3)cc12] | 343.4 | 1H NMR (300 MHz, DMSO) δ 9.64 (d, J = 1.3 Hz, 1H), 8.84-8.74 (m, 1H), 8.68 (dd, J = 6.2, 1.7 Hz, 2H), 8.57 (d, J = 1.6 Hz, 2H), 8.16 (ddd, J = 14.4, 8.7, 2.2 Hz, 2H), 7.85 (d, J = 8.7 Hz, 1H), 7.54 (dd, J = 7.9, 4.8 Hz, 1H), 7.00 (d, J = 8.7 Hz, 1H), 3.93 (s, 3H), 3.18 (d, J = 4.3 Hz, 3H). | DMSO | 344.1 (M + 1) | 1.94 | Method C | 95 | Method AQ2 |

TABLE 24-continued

| | | | | | | | | | |
|---|---|---|---|---|---|---|---|---|---|
| 1264 | 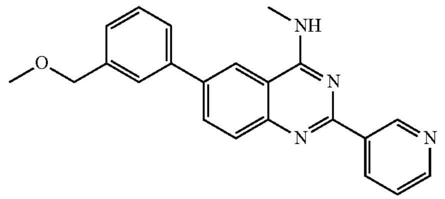 [SMILES: CNc1nc(-c2cccnc2)nc2ccc(-c3cccc(COC)c3)cc12] | 356.4 | 1H NMR (300 MHz, DMSO) δ 10.76 (s, 1H), 9.75 (d, J = 1.6 Hz, 1H), 9.23 (d, J = 8.2 Hz, 1H), 9.05-8.86 (m, 2H), 8.41-8.24 (m, 2H), 8.24-8.05 (m, 2H), 7.96 (dd, J = 8.1, 5.2 Hz, 1H), 6.56 (d, J = 9.5 Hz, 1H), 4.81 (s, 2H), 3.34 (s, 3H), 3.29 (d, J = 4.3 Hz, 3H). | DMSO | 357.1 (M + 1) | 2.13 | Method C | 100 | Method AQ2 |
| 1265 | 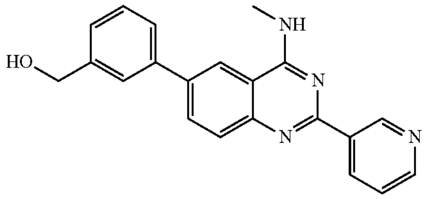 [SMILES: CNc1nc(-c2cccnc2)nc2ccc(-c3cccc(CO)c3)cc12] | 342.4 | 1H NMR (300 MHz, DMSO) δ 9.64 (s, 1H), 8.78 (dd, J = 8.0, 1.9 Hz, 1H), 8.67 (dd, J = 6.3, 4.7 Hz, 2H), 8.58 (s, 1H), 8.17-8.06 (m, 1H), 7.86 (d, J = 8.7 Hz, 1H), 7.79 (s, 1H), 7.72 (d, J = 7.6 Hz, 1H), 7.60-7.44 (m, 2H), 7.37 (d, J = 7.5 Hz, 1H), 5.31 (t, J = 5.4 Hz, 1H), 4.62 (d, J = 4.9 Hz, 2H), 3.18 (d, J = 4.4 Hz, 3H). | DMSO | 343.1 (M + 1) | 1.78 | Method C | 99 | Method AQ2 |
| 1266 | 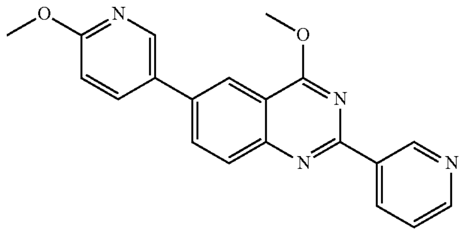 [SMILES: COc1ccc(-c2ccc3nc(-c4cccnc4)nc(OC)c3c2)cn1] | 344.4 | 1H NMR (300 MHz, DMSO) δ 9.65 (d, J = 2.1 Hz, 1H), 8.92-8.59 (m, 3H), 8.59-8.47 (m, 1H), 8.40-8.11 (m, 2H), 8.04 (d, J = 8.5 Hz, 1H), 7.58 (dd, J = 7.9, 4.8 Hz, 1H), 6.95 (d, J = 8.6 Hz, 1H), 4.29 (s, 3H), 3.93 (s, 3H). | DMSO | 345.1 (M + 1) | 2.32 | Method C | 100 | Method AQ2 |
| 1267 | 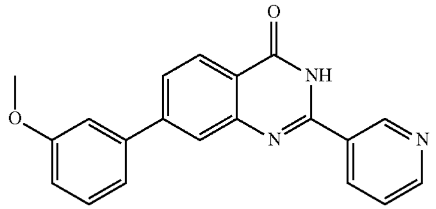 [SMILES: COc1cccc(-c2ccc3c(=O)[nH]c(-c4cccnc4)nc3c2)c1] | 329.4 | 1H NMR (300 MHz, DMSO) δ 12.77 (s, 1H), 9.33 (d, J = 1.7 Hz, 1H), 8.77 (dd, J = 4.7, 1.5 Hz, 1H), 8.60-8.46 (m, 1H), 8.23 (d, J = 8.3 Hz, 1H), 8.04 (d, J = 1.5 Hz, 1H), 7.87 (dd, J = 8.3, 1.8 Hz, 1H), 7.67-7.53 (m, 1H), 7.52-7.29 (m, 3H), 7.04 (ddd, J = 7.7, 2.4, 1.5 Hz, 1H), 3.57 (s, 3H). | DMSO | 330 (M + 1) | 1.78 | Method C | 100 | Method AQ2 |

TABLE 24-continued

| | | | | | | | | | | |
|---|---|---|---|---|---|---|---|---|---|---|
| 1268 | 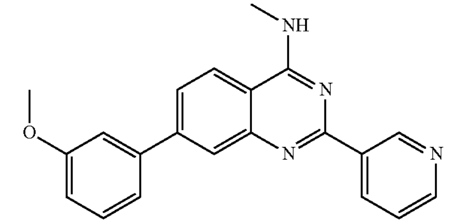 | | 342.4 | 1H NMR (300 MHz, DMSO) δ 9.65 (dd, J = 2.1, 0.8 Hz, 1H), 8.84-8.74 (m, 1H), 8.68 (dd, J = 4.7, 1.7 Hz, 1H), 8.52 (d, J = 4.4 Hz, 1H), 8.30 (d, J = 8.6 Hz, 1H), 8.03 (d, J = 1.7 Hz, 1H), 7.85 (dd, J = 8.5, 1.8 Hz, 1H), 7.54 (ddd, J = 8.0, 4.8, 0.8 Hz, 1H), 7.47-7.34 (m, 3H), 7.08-6.96 (m, 1H), 3.34 (s, 3H), 3.17 (d, J = 4.4 Hz, 3H). | DMSO | 343.3 (M + 1) | 2.09 | Method C | | Method AQ2 |
| 1269 | 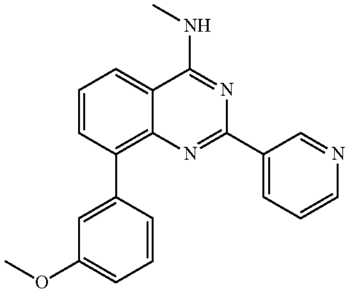 [SMILES: CNc1nc(-c2cccnc2)nc2c(-c3cccc(OC)c3)cccc12] | | 342.4 | 1H NMR (300 MHz, DMSO) δ 9.53 (d, J = 2.0 Hz, 1H), 8.65 (dd, J = 5.9, 3.5 Hz, 2H), 8.51 (d, J = 4.2 Hz, 1H), 8.23 (d, J = 8.3 Hz, 1H), 7.84 (d, J = 7.3 Hz, 1H), 7.65-7.25 (m, 5H), 7.00 (dd, J = 8.1, 2.6 Hz, 1H), 3.33 (s, 3H), 3.17 (d, J = 4.2 Hz, 3H). | DMSO | 343.3 (M + 1) | 2.16 | Method C | 100 | Method AQ2 |
| 1270 | 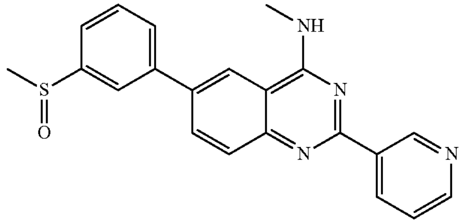 [SMILES: CNc1nc(-c2cccnc2)nc2ccc(-c3cccc(S(C)=O)c3)cc12] | 2HCl | 374.5 | 1H NMR (300 MHz, DMSO) δ 10.67 (s, 1H), 9.69 (s, 1H), 9.12 (d, J = 11.6 Hz, 2H), 8.97 (d, J = 5.0 Hz, 1H), 8.43 (d, J = 7.4 Hz, 1H), 8.31 (d, J = 8.6 Hz, 1H), 8.20 (s, 1H), 8.07 (s, 1H) 7.98-7.86 (m, 1H), 7.77 (s, 2H), 3.31 (d, J = 3.9 Hz, 3H), 2.90 (s, 3H). | DMSO | 375.1 (M + 1) | 1.67 | Method C | 95 | Method AQ2 |
| 1271 | 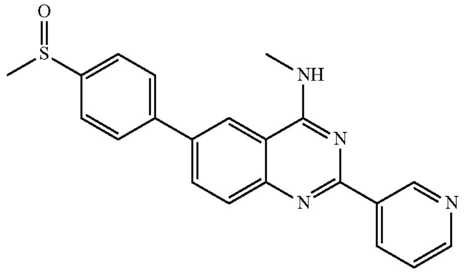 [SMILES: CNc1nc(-c2cccnc2)nc2ccc(-c3ccc(S(C)=O)cc3)cc12] | | 374.5 | 1H NMR (300 MHz, DMSO) δ 9.70-9.57 (m, 1H), 8.84-8.72 (m, 1H), 8.73-8.62 (m, 3H), 8.19 (dd, J = 8.7, 1.9 Hz, 1H), 8.06 (d, J = 8.4 Hz, 2H), 7.86 (dd, J = 10.6, 8.5 Hz, 3H), 7.60-7.49 (m, 1H), 3.19 (d, J = 4.4 Hz, 2H), 2.81 (s, 3H). | DMSO | 375.1 (M + 1) | 1.64 | Method C | 95 | Method AQ2 |

TABLE 24-continued

| | | | | | | | | | | |
|---|---|---|---|---|---|---|---|---|---|---|
| 1272 | 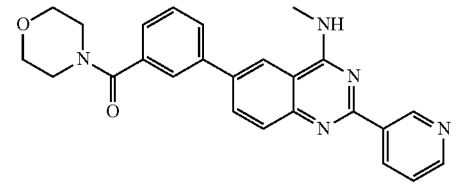 [SMILES: CNc1nc(-c2cccnc2)nc2ccc(-c3cccc(C(=O)N4CCOCC4)c3)cc12] | 2HCl | 425.5 | 1H NMR (300 MHz, DMSO) δ 10.54 (s, 1H), 9.70 (d, J = 1.7 Hz, 1H), 9.12 (d, J = 8.1 Hz, 1H), 8.98 (dd, J = 5.5, 4.0 Hz, 2H), 8.37 (dd, J = 26.8, 7.9 Hz, 2H), 8.09-7.84 (m, 3H), 7.63 (t, J = 7.7 Hz, 1H), 7.49 (d, J = 7.6 Hz, 1H), 3.67 (bs, 8H), 3.31 (d, J = 4.3 Hz, 3H). | DMSO | 426.2 (M + 1) | 1.72 | Method C | 95 | Method AQ2 |
| 1273 | 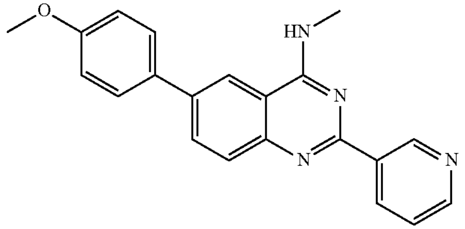 [SMILES: CNc1nc(-c2cccnc2)nc2ccc(-c3ccc(OC)cc3)cc12] | HCl | 342.4 | 1H NMR (300 MHz, DMSO) δ 9.64 (s, 1H), 8.77 (d, J = 7.9 Hz, 1H), 8.71-8.65 (m, 1H), 8.60 (s, 1H), 8.53 (s, 1H), 8.10 (d, J = 8.7 Hz, 1H), 7.87-7.77 (m, 3H), 7.59-7.49 (m, 1H), 7.10 (d, J = 8.7 Hz, 2H), 3.83 (d, J = 0.9 Hz, 3H), 3.19 (s, 3H). | DMSO | 343.1 (M + 1) | 2.06 | Method C | 100 | Method AQ2 |
| 1274 | 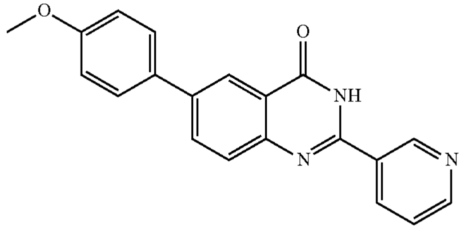 [SMILES: COc1ccc(-c2ccc3nc(-c4cccnc4)[nH]c(=O)c3c2)cc1] | | 329.4 | 1H NMR (300 MHz, DMSO) δ 9.34 (d, J = 1.5 Hz, 1H), 8.74 (dd, J = 4.8, 1.6 Hz, 1H), 8.53 (d, J = 8.0 Hz, 1H), 8.32 (d, J = 2.1 Hz, 1H), 8.10 (dd, J = 8.5, 2.3 Hz, 1H), 7.79 (d, J = 8.6 Hz, 1H), 7.76 (s, 1H), 7.73 (s, 1H), 7.58 (dd, J = 8.0, 4.8 Hz, 1H), 7.07 (d, J = 8.8 Hz, 2H), 3.82 (s, 3H). | DMSO | 330.0 (M + 1) | 1.75 | Method C | 100 | Method AQ2 |
| 1275 | 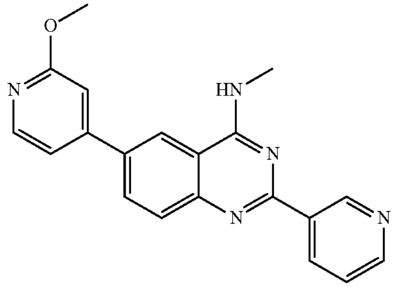 [SMILES: CNc1nc(-c2cccnc2)nc2ccc(-c3ccnc(OC)c3)cc12] | | 343.4 | 1H NMR (300 MHz, DMSO) δ 9.65 (d, J = 1.5 Hz, 1H), 8.84-8.65 (m, 4H), 8.31 (d, J = 5.4 Hz, 1H), 8.24 (dd, J = 8.7, 1.9 Hz, 1H), 7.87 (d, J = 8.7 Hz, 1H), 7.59-7.46 (m, 2H), 7.33 (d, J = 0.9 Hz, 1H), 3.93 (s, 3H), 3.20 (d, J = 4.4 Hz, 3H). | DMSO | 344.1 (M + 1) | 1.95 | Method C | 95 | Method AQ2 |

TABLE 24-continued

| | | | | | | | | | |
|---|---|---|---|---|---|---|---|---|---|
| 1276 | 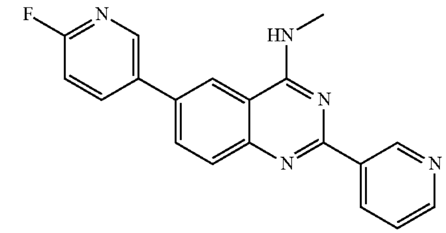 [SMILES: CNc1nc(-c2cccnc2)nc2ccc(-c3ccc(F)nc3)cc12] | 331.3 | 1H NMR (300 MHz, DMSO) δ 9.63 (d, J = 1.4 Hz, 1H), 8.81-8.74 (m, 1H), 8.73 (d, J = 2.3 Hz, 1H), 8.68 (dd, J = 4.7, 1.7 Hz, 1H), 8.66-8.56 (m, 2H), 8.44 (td, J = 8.2, 2.6 Hz, 1H), 8.18 (dd, J = 8.7, 2.0 Hz, 1H), 7.87 (d, J = 8.7 Hz, 1H), 7.54 (dd, J = 7.9, 4.8 Hz, 1H), 7.38 (dd, J = 8.5, 2.9 Hz, 1H), 3.18 (d, J = 4.4 Hz, 3H). | DMSO | 332.1 (M + 1) | 1.89 | Method C | 100 | Method AQ2 |
| 1277 | 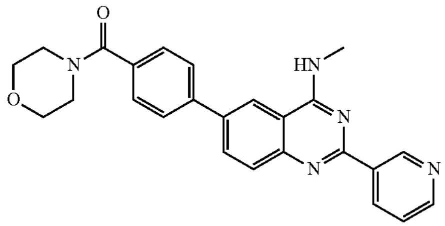 [SMILES: CNc1nc(-c2cccnc2)nc2ccc(-c3ccc(C(=O)N4CCOCC4)cc3)cc12] | 425.5 | 1H NMR (300 MHz, DMSO) δ 9.63 (d, J = 1.4 Hz, 1H), 8.77 (d, J = 8.0 Hz, 1H), 8.70-8.59 (m, 3H), 8.15 (dd, J = 8.7, 1.6 Hz, 1H), 7.92 (d, J = 8.2 Hz, 2H), 7.85 (d, J = 8.7 Hz, 1H), 7.62-7.48 (m, 3H), 3.62 (s, J = 54.7 Hz, 8H), 3.17 (d, J = 4.2 Hz, 3H). | DMSO | 426.2 (M + 1) | 1.69 | Method C | 100 | Method AQ2 |
| 1278 | 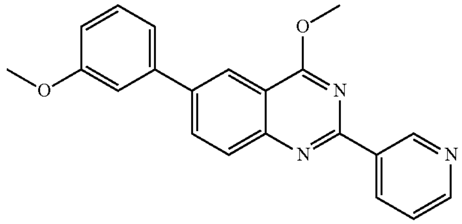 [SMILES: COc1cccc(-c2ccc3nc(-c4cccnc4)nc(OC)c3c2)c1] | 343.4 | 1H NMR (300 MHz, DMSO) δ 9.67 (d, J = 1.5 Hz, 1H), 8.86-8.77 (m, 1H), 8.74 (dd, J = 4.7, 1.6 Hz, 1H), 8.37-8.25 (m, 2H), 8.06 (d, J = 8.7 Hz, 1H), 7.60 (dd, J = 7.9, 4.1 Hz, 1H), 7.50-7.30 (m, 3H), 7.02 (dd, J = 7.9, 1.4 Hz, 1H), 4.31 (s, 3H), 3.87 (s, 3H). | DMSO | 344.2 (M + 1) | 2.47 | Method C | 100 | Method AQ2 |

| Number | Starting Material 1 | Starting Material 2 | Product |
|---|---|---|---|
| 1279 | 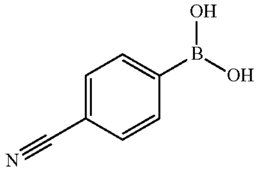 [SMILES: N#Cc1ccc(B(O)O)cc1] | 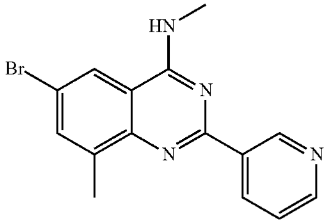 [SMILES: CNc1nc(-c2cccnc2)nc2c(C)cc(Br)cc12] | 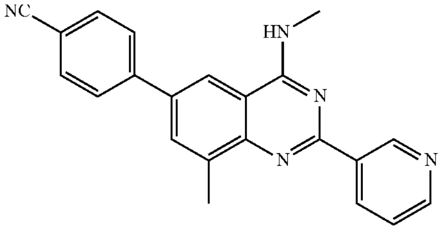 [SMILES: CNc1nc(-c2cccnc2)nc2c(C)cc(-c3ccc(C#N)cc3)cc12] |

TABLE 24-continued
| | | | |
|---|---|---|---|
| 1280 | 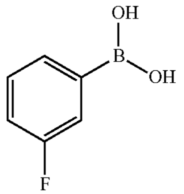 | 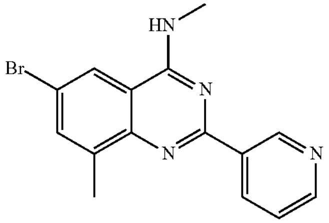 [SMILES: CNc1nc(-c2cccnc2)nc2c(C)cc(Br)cc12] | 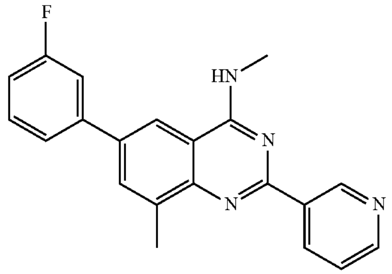 [SMILES: CNc1nc(-c2cccnc2)nc2c(C)cc(-c3cccc(F)c3)cc12] |
| 1281 | 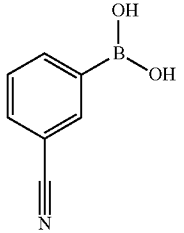 [SMILES: N#Cc1cccc(B(O)O)c1] | 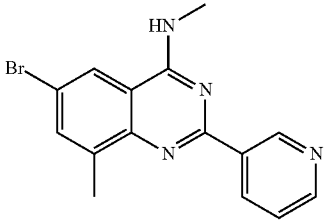 [SMILES: CNc1nc(-c2cccnc2)nc2c(C)cc(Br)cc12] | 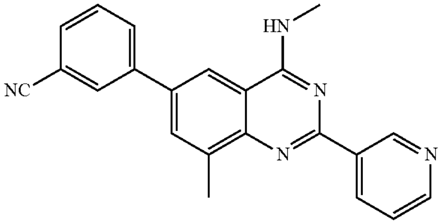 [SMILES: CNc1nc(-c2cccnc2)nc2c(C)cc(-c3cccc(C#N)c3)cc12] |
| 1282 | 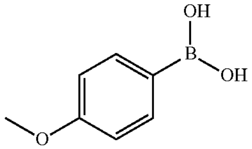 | 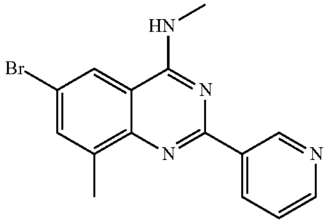 | 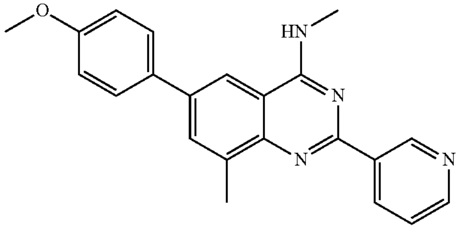 |
| 1283 | 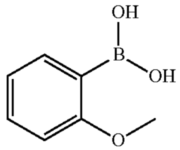 | 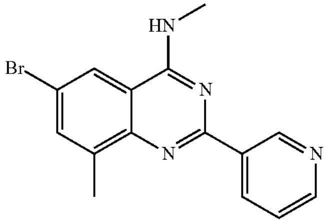 [SMILES: CNc1nc(-c2cccnc2)nc2c(C)cc(Br)cc12] | 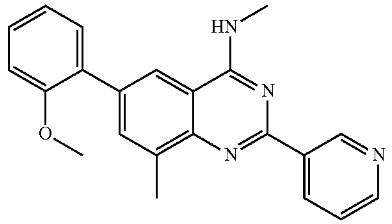 [SMILES: CNc1nc(-c2cccnc2)nc2c(C)cc(-c3ccccc3OC)cc12] |

TABLE 24-continued
| | | | |
|---|---|---|---|
| 1284 | 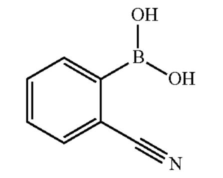 [SMILES: N#Cc1ccccc1B(O)O] | 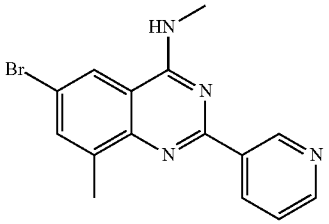 [SMILES: CNc1nc(-c2cccnc2)nc2c(C)cc(Br)cc12] | 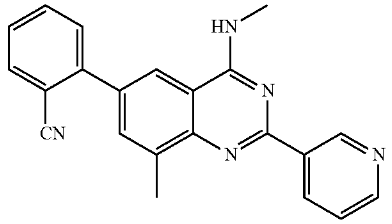 [SMILES: CNc1nc(-c2cccnc2)nc2c(C)cc(-c3ccccc3C#N)cc12] |
| 1285 | 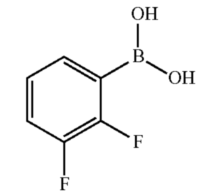 [SMILES: OB(O)c1cccc(F)c1F] | 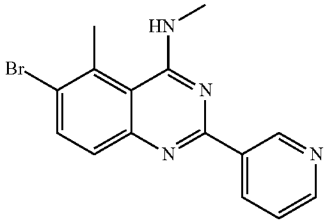 [SMILES: CNc1nc(-c2cccnc2)nc2ccc(Br)c(C)c12] | 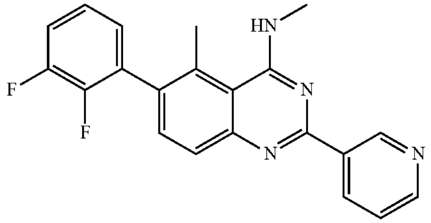 [SMILES: CNc1nc(-c2cccnc2)nc2ccc(-c3cccc(F)c3F)c(C)c12] |
| 1286 | 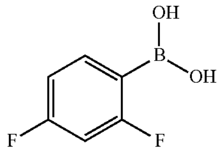 | 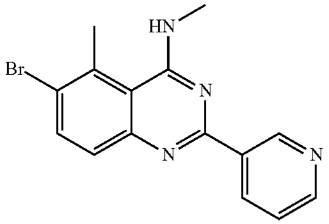 [SMILES: CNc1nc(-c2cccnc2)nc2ccc(Br)c(C)c12] | 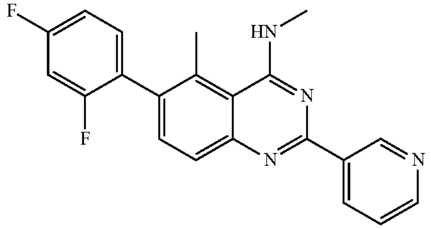 [SMILES: CNc1nc(-c2cccnc2)nc2ccc(-c3ccc(F)cc3F)c(C)c12] |
| 1287 | 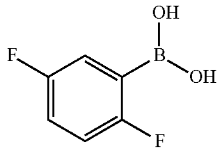 | 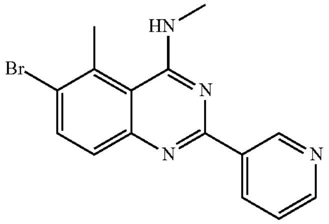 [SMILES: CNc1nc(-c2cccnc2)nc2ccc(Br)c(C)c12] | 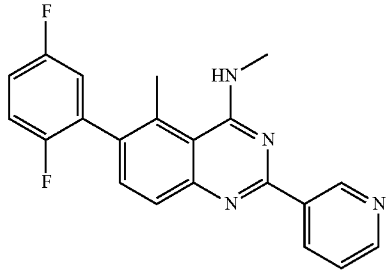 [SMILES: CNc1nc(-c2cccnc2)nc2ccc(-c3cc(F)ccc3F)c(C)c12] |

TABLE 24-continued
| | | | |
|---|---|---|---|
| 1288 | 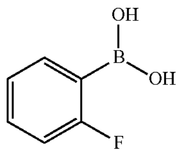 | 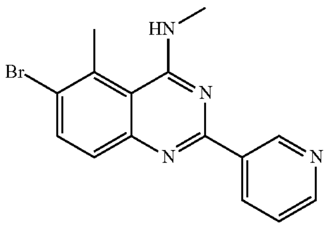 [SMILES: CNc1nc(-c2cccnc2)nc2ccc(Br)c(C)c12] | 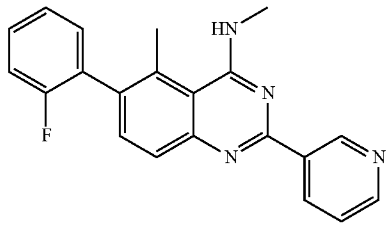 [SMILES: CNc1nc(-c2cccnc2)nc2ccc(-c3ccccc3F)c(C)c12] |
| 1289 | 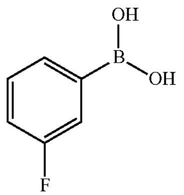 | 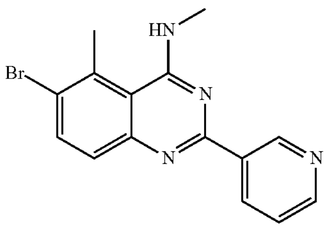 [SMILES: CNc1nc(-c2cccnc2)nc2ccc(Br)c(C)c12] | 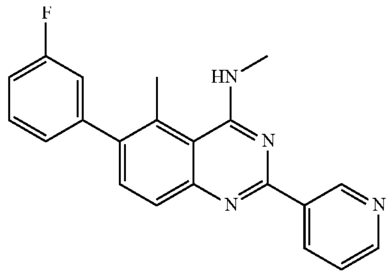 [SMILES: CNc1nc(-c2cccnc2)nc2ccc(-c3cccc(F)c3)c(C)c12] |
| 1290 | 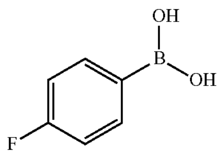 | 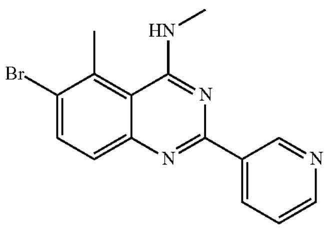 [SMILES: CNc1nc(-c2cccnc2)nc2ccc(Br)c(C)c12] | 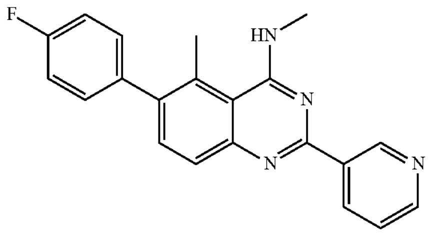 [SMILES: CNc1nc(-c2cccnc2)nc2ccc(-c3ccc(F)cc3)c(C)c12] |
| 1291 | 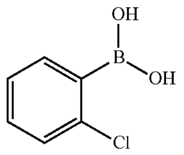 | 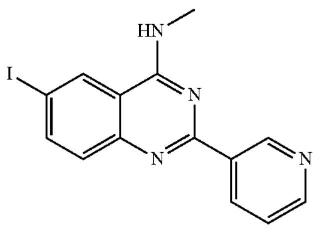 [SMILES: CNc1nc(-c2cccnc2)nc2ccc(I)cc12] | 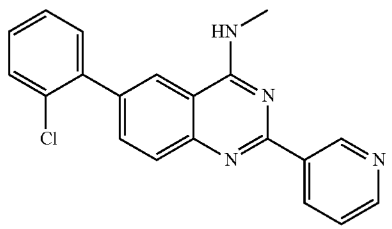 |

TABLE 24-continued
| | | | |
|---|---|---|---|
| 1292 | 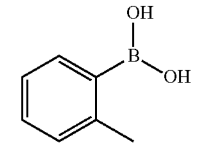 | 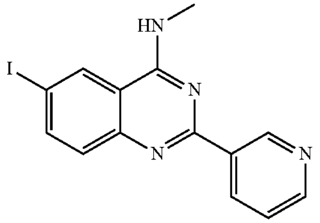 [SMILES: CNc1nc(-c2cccnc2)nc2ccc(I)cc12] | 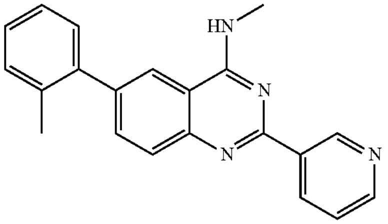 [SMILES: CNc1nc(-c2cccnc2)nc2ccc(-c3ccccc3C)cc12] |
| 1293 | 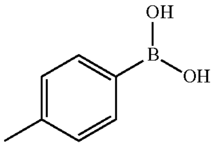 | 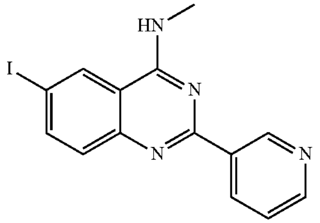 [SMILES: CNc1nc(-c2cccnc2)nc2ccc(I)cc12] | 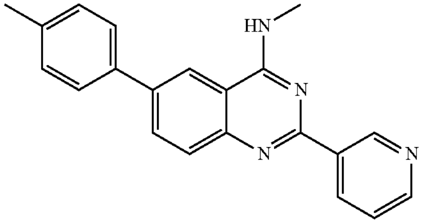 [SMILES: CNc1nc(-c2cccnc2)nc2ccc(-c3ccc(C)cc3)cc12] |
| 1294 | 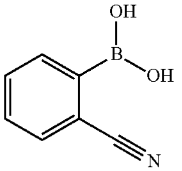 [SMILES: N#Cc1ccccc1B(O)O] | 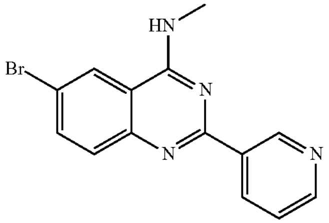 [SMILES: CNc1nc(-c2cccnc2)nc2ccc(Br)cc12] | 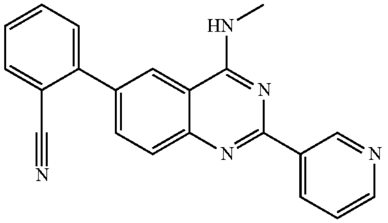 [SMILES: CNc1nc(-c2cccnc2)nc2ccc(-c3ccccc3C#N)cc12] |
| 1295 | 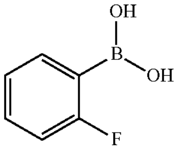 | 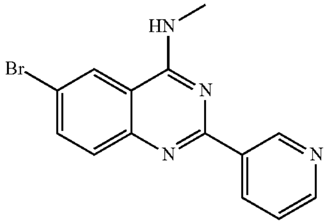 [SMILES: CNc1nc(-c2cccnc2)nc2ccc(Br)cc12] | 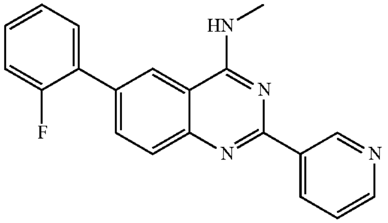 [SMILES: CNc1nc(-c2cccnc2)nc2ccc(-c3ccccc3F)cc12] |

TABLE 24-continued
| | | | |
|---|---|---|---|
| 1296 | 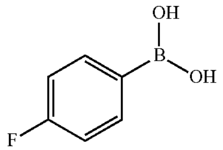 | 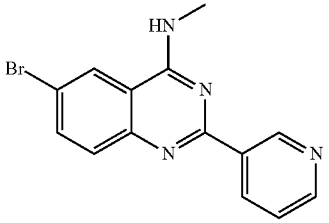 [SMILES: CNc1nc(-c2cccnc2)nc2ccc(Br)cc12] | 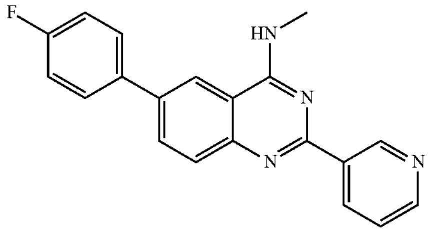 [SMILES: CNc1nc(-c2cccnc2)nc2ccc(-c3ccc(F)cc3)cc12] |
| 1297 | 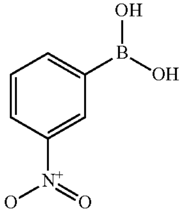 | 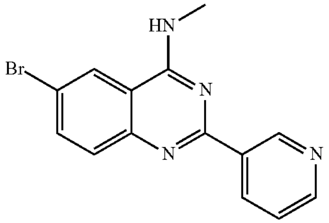 | 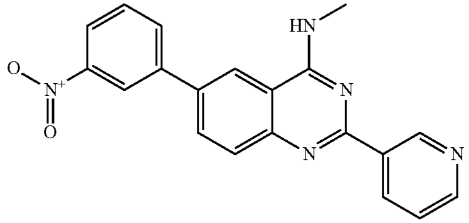 |
| 1298 | 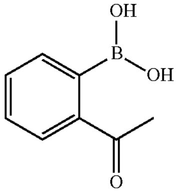 | 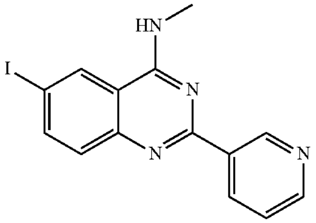 [SMILES: CNc1nc(-c2cccnc2)nc2ccc(I)cc12] | 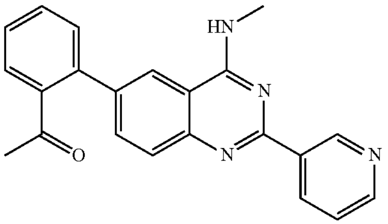 [SMILES: CNc1nc(-c2cccnc2)nc2ccc(-c3ccccc3C(C)=O)cc12] |
| 1299 | 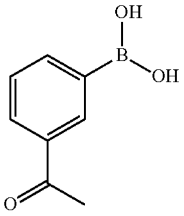 | 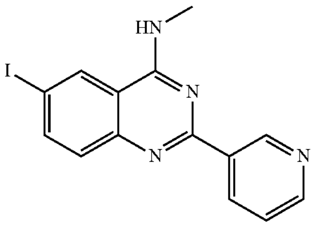 [SMILES: CNc1nc(-c2cccnc2)nc2ccc(I)cc12] | 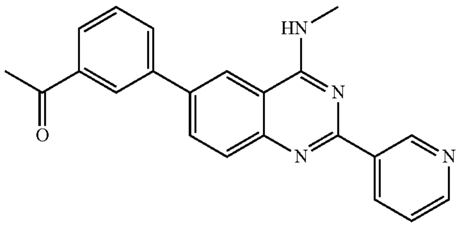 [SMILES: CNc1nc(-c2cccnc2)nc2ccc(-c3cccc(C(C)=O)c3)cc12] |

TABLE 24-continued
| | | | |
|---|---|---|---|
| 1300 | 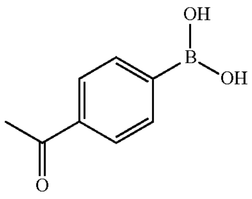 | 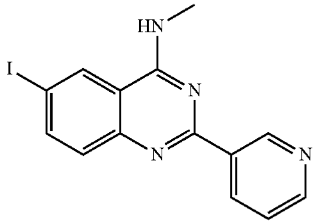 [SMILES: CNc1nc(-c2cccnc2)nc2ccc(I)cc12] | 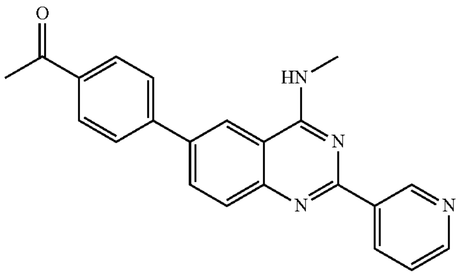 [SMILES: CNc1nc(-c2cccnc2)nc2ccc(-c3ccc(C(C)=O)cc3)cc12] |
| 1301 | 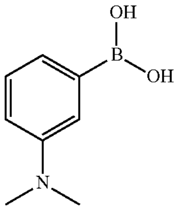 | 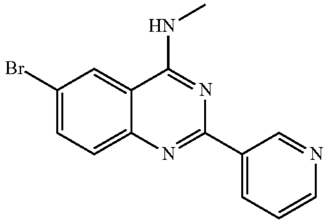 [SMILES: CNc1nc(-c2cccnc2)nc2ccc(Br)cc12] | 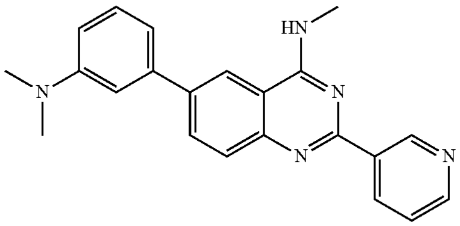 [SMILES: CNc1nc(-c2cccnc2)nc2ccc(-c3cccc(N(C)C)c3)cc12] |
| 1302 | 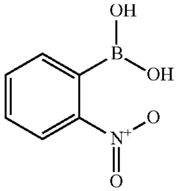 | 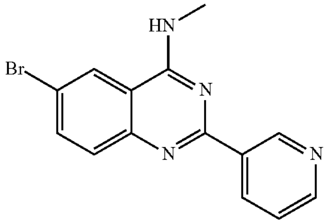 [SMILES: CNc1nc(-c2cccnc2)nc2ccc(Br)cc12] | 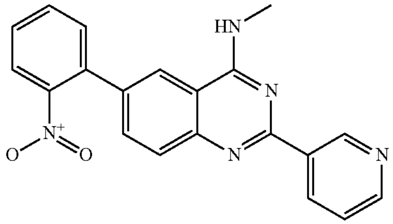 |
| 1303 | 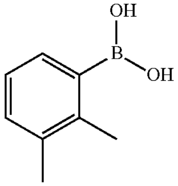 | 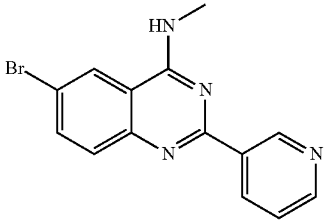 [SMILES: CNc1nc(-c2cccnc2)nc2ccc(Br)cc12] | 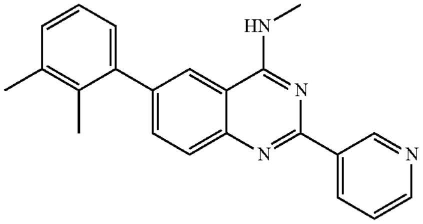 [SMILES: CNc1nc(-c2cccnc2)nc2ccc(-c3cccc(C)c3C)cc12] |

TABLE 24-continued
| | | | |
|---|---|---|---|
| 1304 | 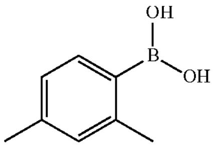 | 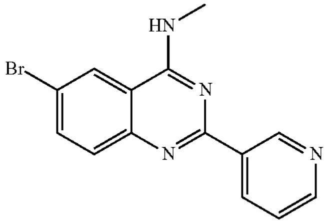 [SMILES: CNc1nc(-c2cccnc2)nc2ccc(Br)cc12] | 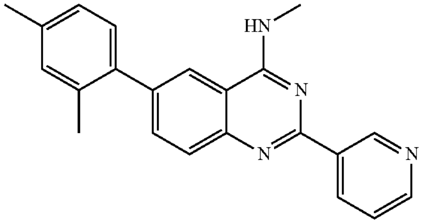 [SMILES: CNc1nc(-c2cccnc2)nc2ccc(-c3ccc(C)cc3C)cc12] |
| 1305 | 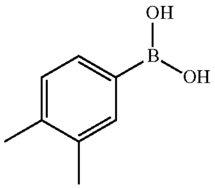 | 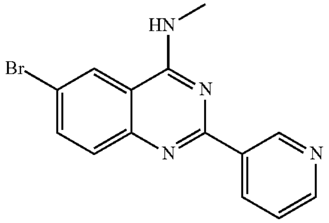 [SMILES: CNc1nc(-c2cccnc2)nc2ccc(Br)cc12] | 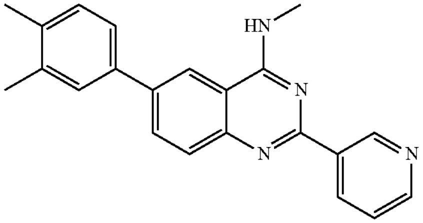 [SMILES: CNc1nc(-c2cccnc2)nc2ccc(-c3ccc(C)c(C)c3)cc12] |
| 1306 | 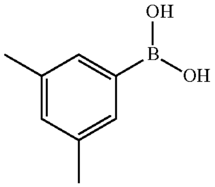 | 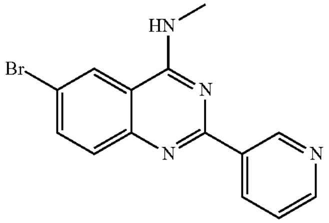 [SMILES: CNc1nc(-c2cccnc2)nc2ccc(Br)cc12] | 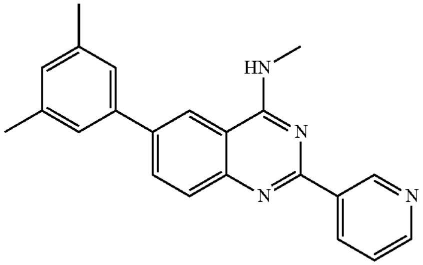 [SMILES: CNc1nc(-c2cccnc2)nc2ccc(-c3cc(C)cc(C)c3)cc12] |
| 1307 | 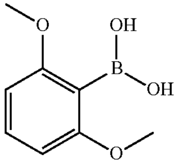 | 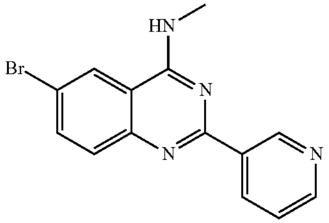 [SMILES: CNc1nc(-c2cccnc2)nc2ccc(Br)cc12] | 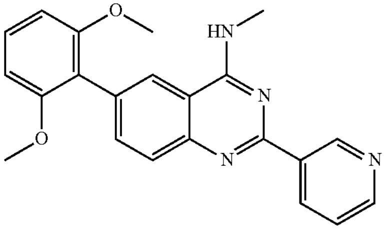 [SMILES: CNc1nc(-c2cccnc2)nc2ccc(-c3c(OC)cccc3OC)cc12] |

TABLE 24-continued
| | | | |
|---|---|---|---|
| 1308 | 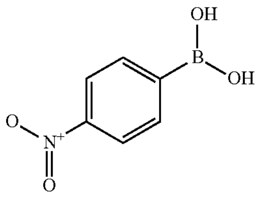 | 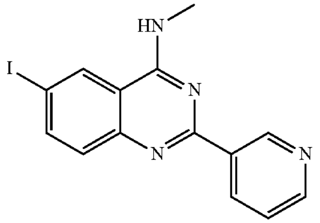 [SMILES: CNc1nc(-c2cccnc2)nc2ccc(I)cc12] | 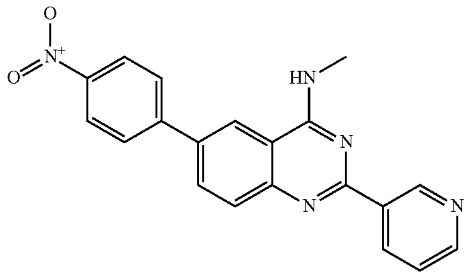 |
| 1309 | 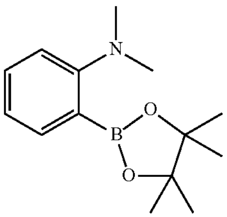 [SMILES: CN(C)c1ccccc1B1OC(C)(C)C(C)(C)O1] | 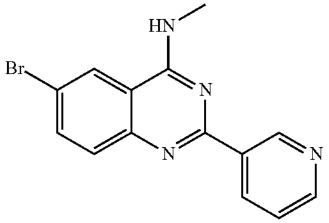 [SMILES: CNc1nc(-c2cccnc2)nc2ccc(Br)cc12] | 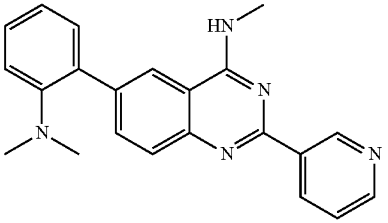 [SMILES: CNc1nc(-c2cccnc2)nc2ccc(-c3ccccc3N(C)C)cc12] |
| 1310 | 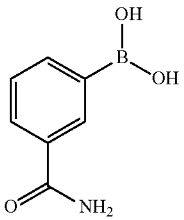 [SMILES: NC(=O)c1cccc(B(O)O)c1] | 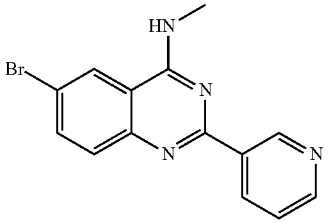 [SMILES: CNc1nc(-c2cccnc2)nc2ccc(Br)cc12] | 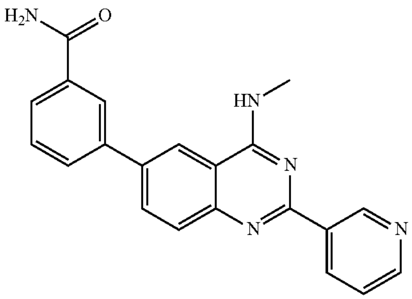 [SMILES: CNc1nc(-c2cccnc2)nc2ccc(-c3cccc(C(N)=O)c3)cc12] |
| 1311 | 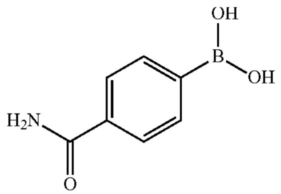 [SMILES: NC(=O)c1ccc(B(O)O)cc1] | 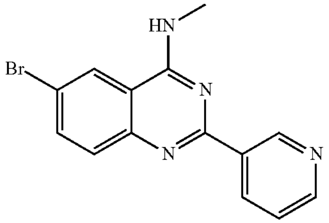 [SMILES: CNc1nc(-c2cccnc2)nc2ccc(Br)cc12] | 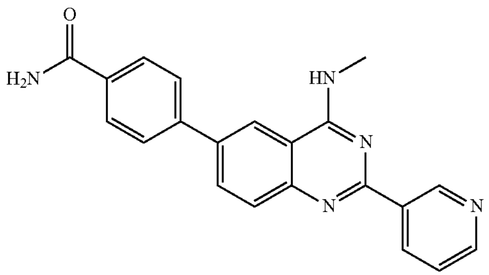 [SMILES: CNc1nc(-c2cccnc2)nc2ccc(-c3ccc(C(N)=O)cc3)cc12] |

TABLE 24-continued
| | | | |
|---|---|---|---|
| 1312 | 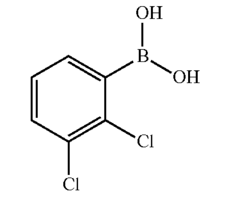 [SMILES: OB(O)c1cccc(Cl)c1Cl] | 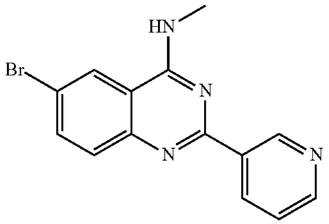 [SMILES: CNc1nc(-c2cccnc2)nc2ccc(Br)cc12] | 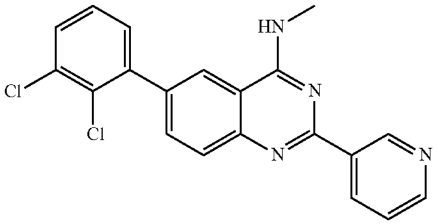 [SMILES: CNc1nc(-c2cccnc2)nc2ccc(-c3cccc(Cl)c3Cl)cc12] |
| 1313 | 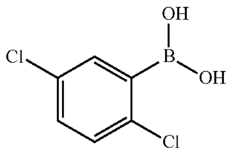 | 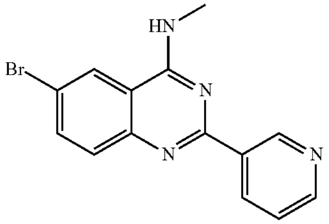 [SMILES: CNc1nc(-c2cccnc2)nc2ccc(Br)cc12] | 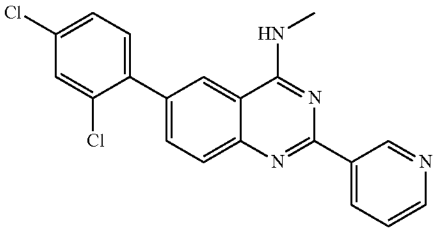 [SMILES: CNc1nc(-c2cccnc2)nc2ccc(-c3ccc(Cl)cc3Cl)cc12] |
| 1314 | 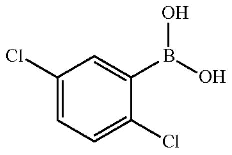 | 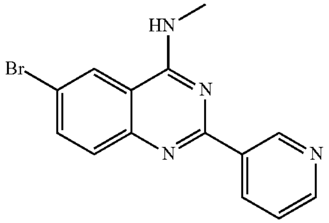 [SMILES: CNc1nc(-c2cccnc2)nc2ccc(Br)cc12] | 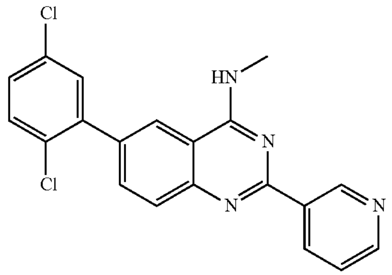 [SMILES: CNc1nc(-c2cccnc2)nc2ccc(-c3cc(Cl)ccc3Cl)cc12] |
| 1315 | 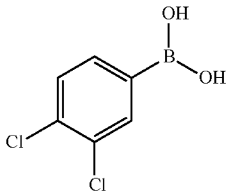 [SMILES: OB(O)c1ccc(Cl)c(Cl)c1] | 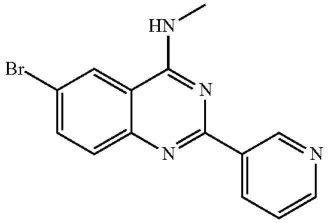 [SMILES: CNc1nc(-c2cccnc2)nc2ccc(Br)cc12] | 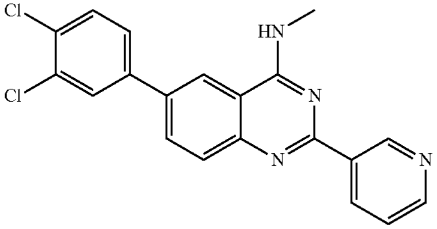 [SMILES: CNc1nc(-c2cccnc2)nc2ccc(-c3ccc(Cl)c(Cl)c3)cc12] |

TABLE 24-continued
| | | | |
|---|---|---|---|
| 1316 | 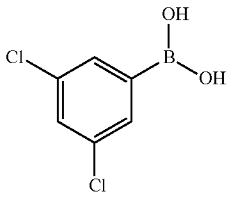 [SMILES: OB(O)c1cc(Cl)cc(Cl)c1] | 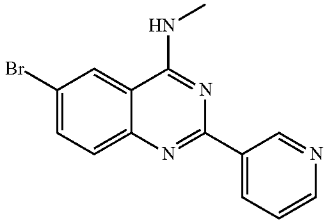 [SMILES: CNc1nc(-c2cccnc2)nc2ccc(Br)cc12] | 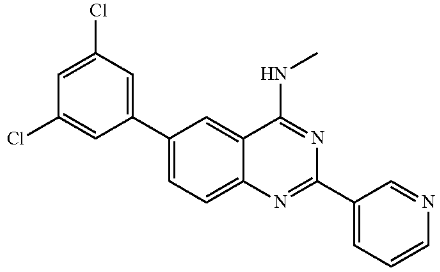 [SMILES: CNc1nc(-c2cccnc2)nc2ccc(-c3cc(Cl)cc(Cl)c3)cc12] |
| 1317 | 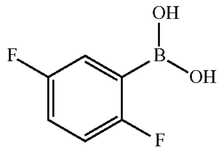 | 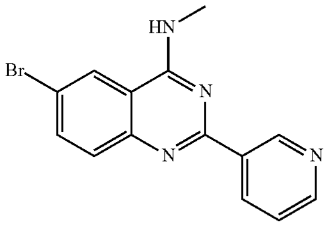 [SMILES: CNc1nc(-c2cccnc2)nc2ccc(Br)cc12] | 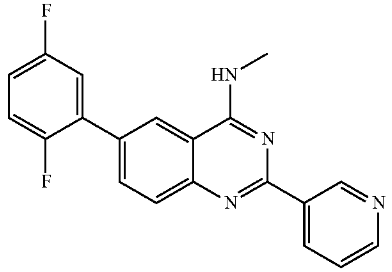 [SMILES: CNc1nc(-c2cccnc2)nc2ccc(-c3cc(F)ccc3F)cc12] |
| 1318 | 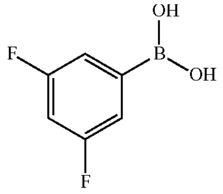 [SMILES: OB(O)c1cc(F)cc(F)c1] | 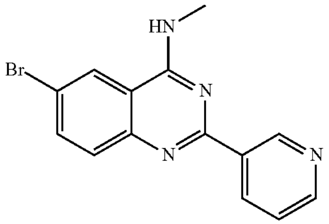 [SMILES: CNc1nc(-c2cccnc2)nc2ccc(Br)cc12] | 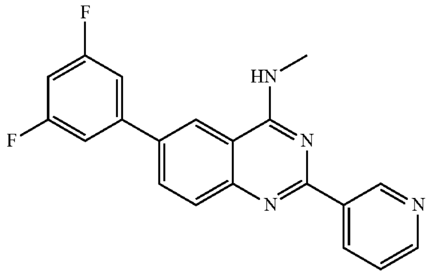 [SMILES: CNc1nc(-c2cccnc2)nc2ccc(-c3cc(F)cc(F)c3)cc12] |
| 1319 | 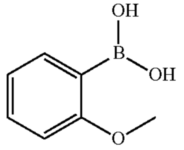 | 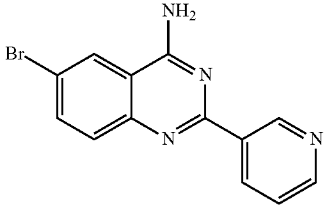 [SMILES: Nc1nc(-c2cccnc2)nc2ccc(Br)cc12] | 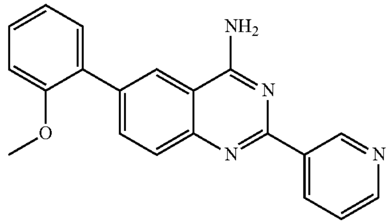 [SMILES: COc1ccccc1-c1ccc2nc(-c3cccnc3)nc(N)c2c1] |

TABLE 24-continued
| | | | |
|---|---|---|---|
| 1320 | 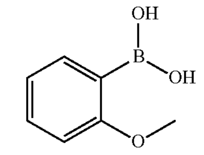 | 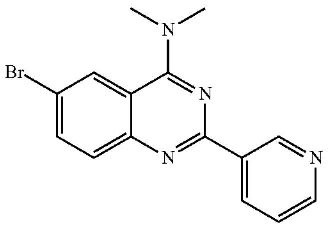 [SMILES: CN(C)c1nc(-c2cccnc2)nc2ccc(Br)cc12] | 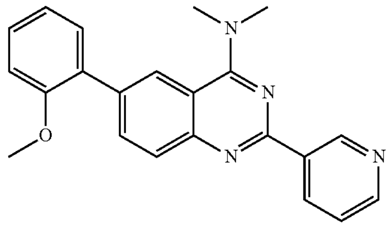 [SMILES: COc1ccccc1-c1ccc2nc(-c3cccnc3)nc(N(C)C)c2c1] |
| 1321 | 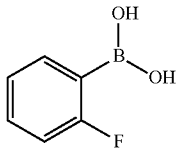 | 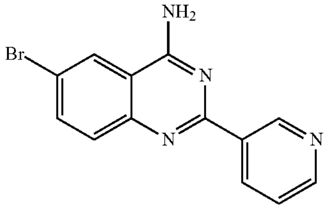 [SMILES: Nc1nc(-c2cccnc2)nc2ccc(Br)cc12] | 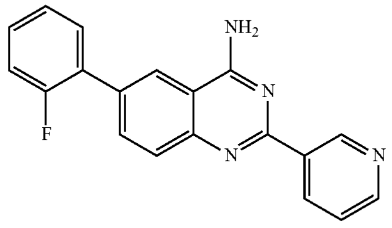 [SMILES: Nc1nc(-c2cccnc2)nc2ccc(-c3ccccc3F)cc12] |
| 1322 | 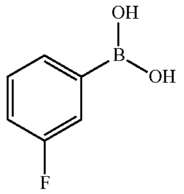 | 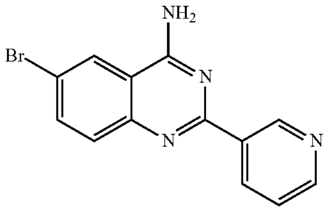 [SMILES: Nc1nc(-c2cccnc2)nc2ccc(Br)cc12] | 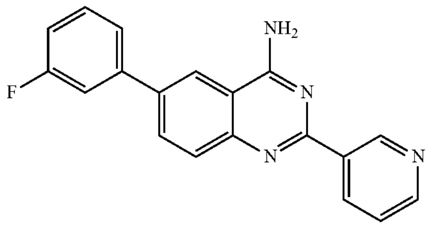 [SMILES: Nc1nc(-c2cccnc2)nc2ccc(-c3cccc(F)c3)cc12] |
| 1323 | 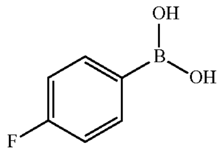 | 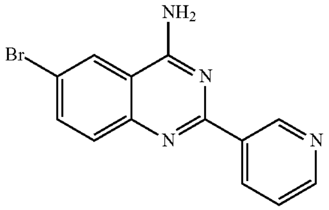 [SMILES: Nc1nc(-c2cccnc2)nc2ccc(Br)cc12] | 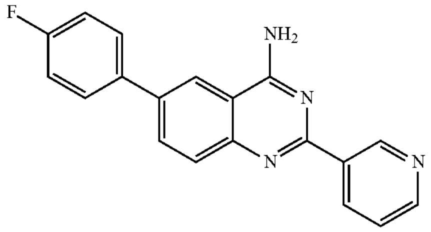 [SMILES: Nc1nc(-c2cccnc2)nc2ccc(-c3ccc(F)cc3)cc12] |

TABLE 24-continued
| | | | |
|---|---|---|---|
| 1324 | 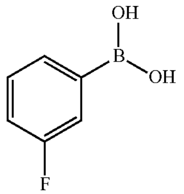 | 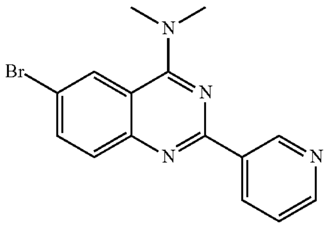 [SMILES: CN(C)c1nc(-c2cccnc2)nc2ccc(Br)cc12] | 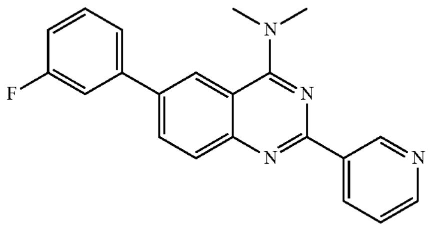 [SMILES: CN(C)c1nc(-c2cccnc2)nc2ccc(-c3cccc(F)c3)cc12] |
| 1325 | 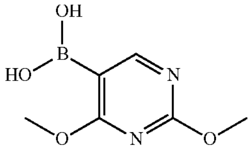 | 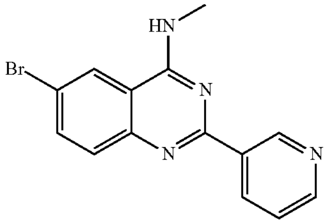 [SMILES: CNc1nc(-c2cccnc2)nc2ccc(Br)cc12] | 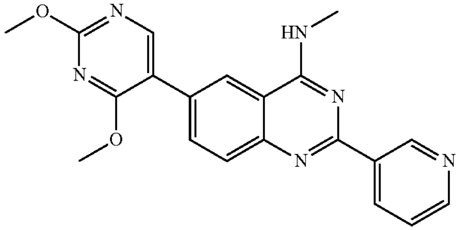 [SMILES: CNc1nc(-c2cccnc2)nc2ccc(-c3cnc(OC)nc3OC)cc12] |
| 1326 | 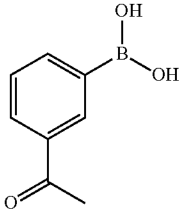 | 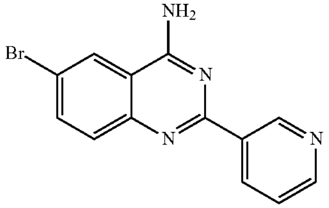 [SMILES: Nc1nc(-c2cccnc2)nc2ccc(Br)cc12] | 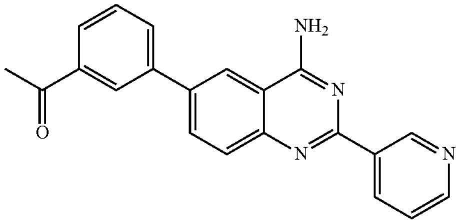 [SMILES: CC(=O)c1cccc(-c2ccc3nc(-c4cccnc4)nc(N)c3c2)c1] |
| 1327 | 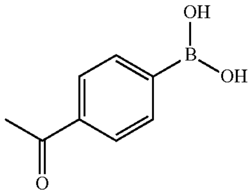 | 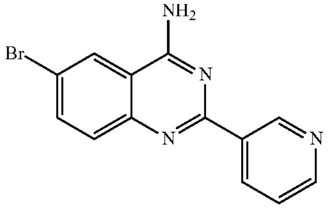 [SMILES: Nc1nc(-c2cccnc2)nc2ccc(Br)cc12] | 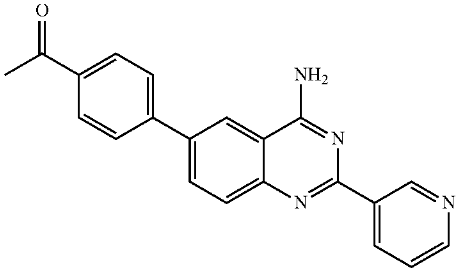 [SMILES: CC(=O)c1ccc(-c2ccc3nc(-c4cccnc4)nc(N)c3c2)cc1] |

TABLE 24-continued
| | | | |
|---|---|---|---|
| 1328 | 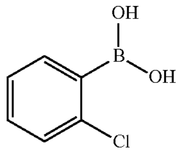 | 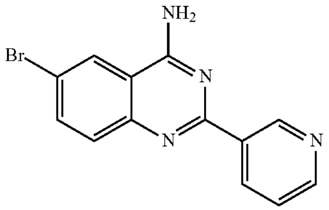 [SMILES: Nc1nc(-c2cccnc2)nc2ccc(Br)cc12] | 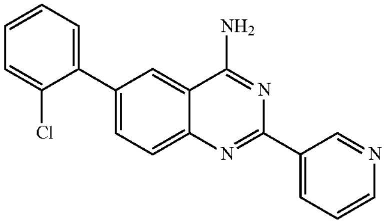 [SMILES: Nc1nc(-c2cccnc2)nc2ccc(-c3ccccc3Cl)cc12] |
| 1329 | 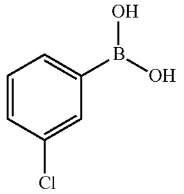 | 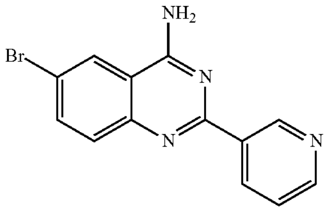 [SMILES: Nc1nc(-c2cccnc2)nc2ccc(Br)cc12] | 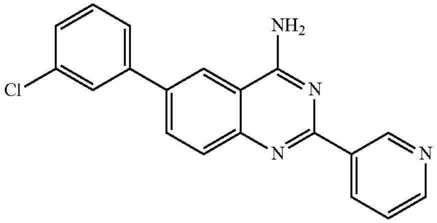 [SMILES: Nc1nc(-c2cccnc2)nc2ccc(-c3cccc(Cl)c3)cc12] |
| 1330 | 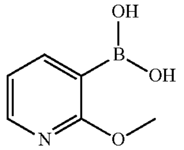 | 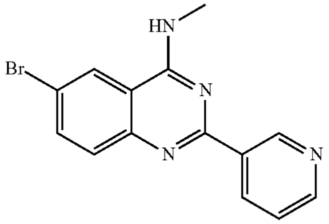 [SMILES: CNc1nc(-c2cccnc2)nc2ccc(Br)cc12] | 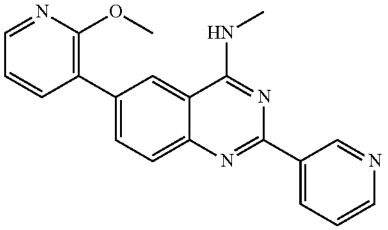 [SMILES: CNc1nc(-c2cccnc2)nc2ccc(-c3cccnc3OC)cc12] |
| 1331 | 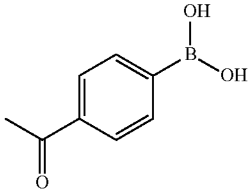 | 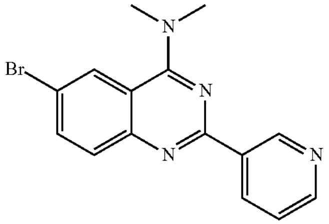 [SMILES: CN(C)c1nc(-c2cccnc2)nc2ccc(Br)cc12] | 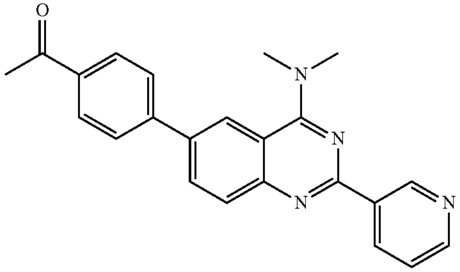 [SMILES: CC(=O)c1ccc(-c2ccc3nc(-c4cccnc4)nc(N(C)C)c3c2)cc1] |

TABLE 24-continued
| | | | |
|---|---|---|---|
| 1332 | 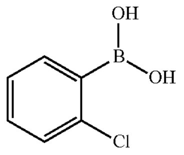 | 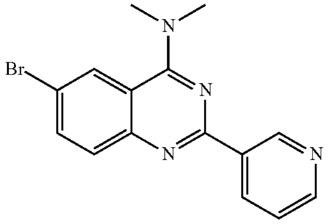 [SMILES: CN(C)c1nc(-c2cccnc2)nc2ccc(Br)cc12] | 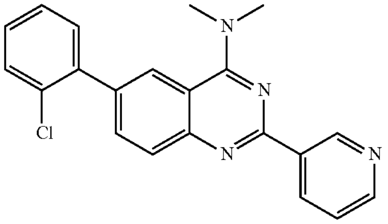 [SMILES: CN(C)c1nc(-c2cccnc2)nc2ccc(-c3ccccc3Cl)cc12] |
| 1333 | 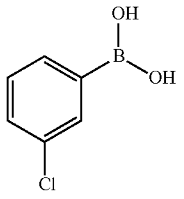 | 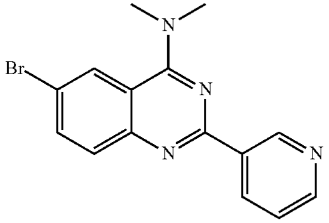 [SMILES: CN(C)c1nc(-c2cccnc2)nc2ccc(Br)cc12] | 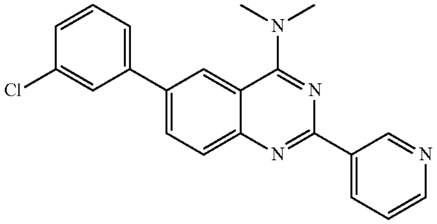 [SMILES: CN(C)c1nc(-c2cccnc2)nc2ccc(-c3cccc(Cl)c3)cc12] |
| 1334 | 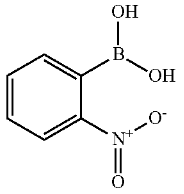 | 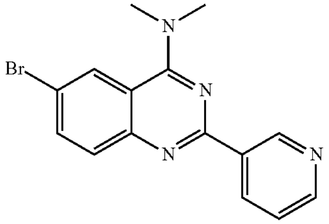 [SMILES: CN(C)c1nc(-c2cccnc2)nc2ccc(Br)cc12] | 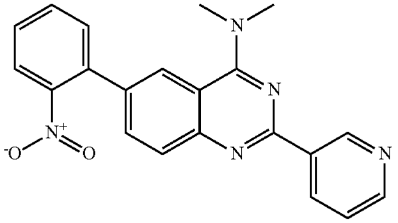 |
| 1335 | 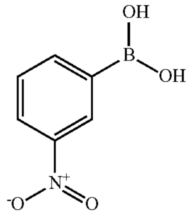 | 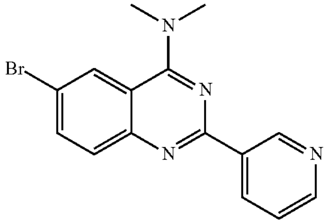 [SMILES: CN(C)c1nc(-c2cccnc2)nc2ccc(Br)cc12] | 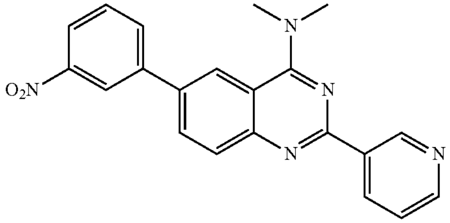 [SMILES: CN(C)c1nc(-c2cccnc2)nc2ccc(-c3cccc([N+](=O)[O-])c3)cc12] |

TABLE 24-continued
| | | | |
|---|---|---|---|
| 1336 | 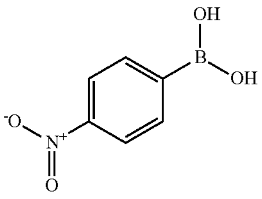 | 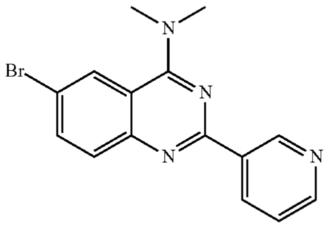 [SMILES: CN(C)c1nc(-c2cccnc2)nc2ccc(Br)cc12] | 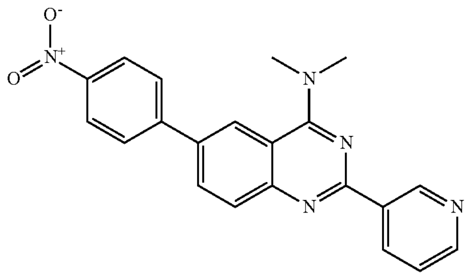 [SMILES: CN(C)c1nc(-c2cccnc2)nc2ccc(-c3ccc([N+](=O)[O-])cc3)cc12] |
| 1337 | 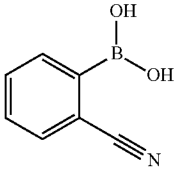 [SMILES: N#Cc1ccccc1B(O)O] | 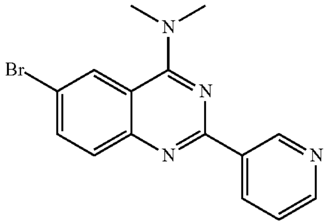 [SMILES: CN(C)c1nc(-c2cccnc2)nc2ccc(Br)cc12] | 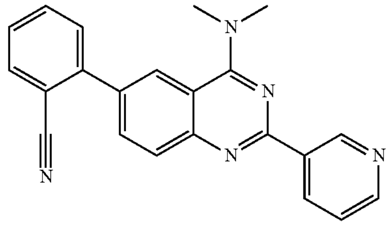 [SMILES: CN(C)c1nc(-c2cccnc2)nc2ccc(-c3ccccc3C#N)cc12] |
| 1338 | 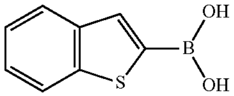 [SMILES: OB(O)c1cc2ccccc2s1] | 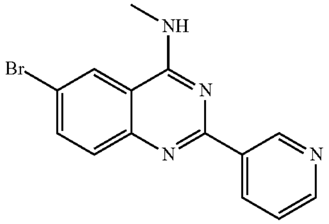 [SMILES: CNc1nc(-c2cccnc2)nc2ccc(Br)cc12] | 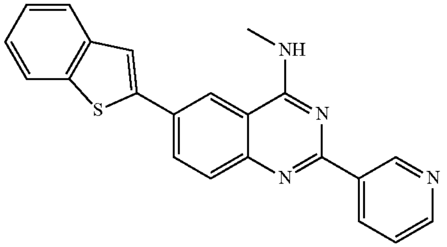 [SMILES: CNc1nc(-c2cccnc2)nc2ccc(-c3cc4ccccc4s3)cc12] |
| 1339 | 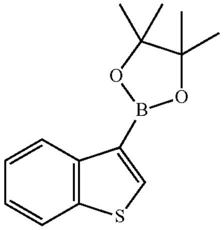 [SMILES: CC1(C)OB(c2csc3ccccc23)OC1(C)C] | 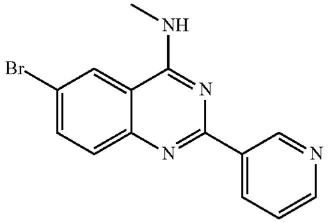 [SMILES: CNc1nc(-c2cccnc2)nc2ccc(Br)cc12] | 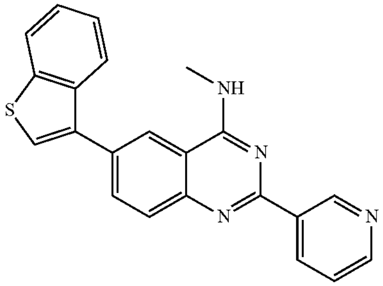 [SMILES: CNc1nc(-c2cccnc2)nc2ccc(-c3csc4ccccc34)cc12] |

TABLE 24-continued
| | | | |
|---|---|---|---|
| 1340 | 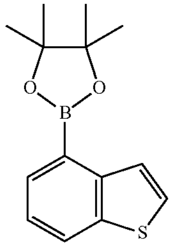 [SMILES: CC1(C)OB(c2cccc3sccc23)OC1(C)C] | 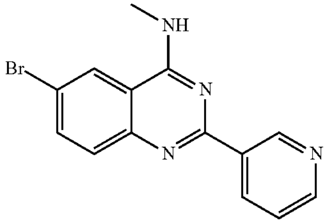 [SMILES: CNc1nc(-c2cccnc2)nc2ccc(Br)cc12] | 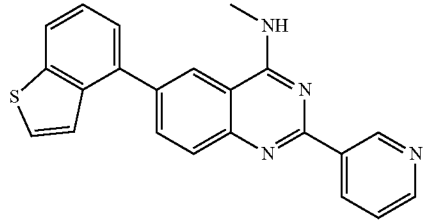 [SMILES: CNc1nc(-c2cccnc2)nc2ccc(-c3cccc4sccc34)cc12] |
| 1341 | 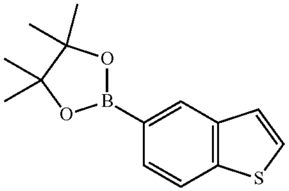 [SMILES: CC1(C)OB(c2ccc3sccc3c2)OC1(C)C] | 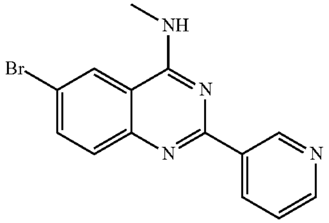 [SMILES: CNc1nc(-c2cccnc2)nc2ccc(Br)cc12] | 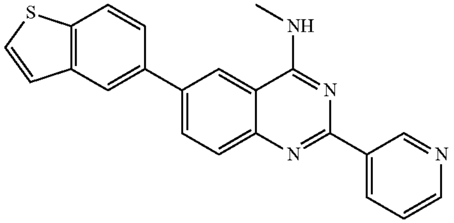 [SMILES: CNc1nc(-c2cccnc2)nc2ccc(-c3ccc4sccc4c3)cc12] |
| 1342 | 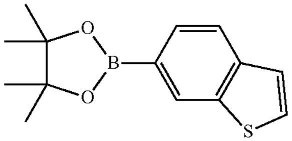 [SMILES: CC1(C)OB(c2ccc3ccsc3c2)OC1(C)C] | 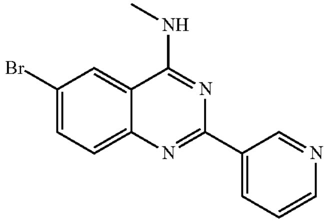 [SMILES: CNc1nc(-c2cccnc2)nc2ccc(Br)cc12] | 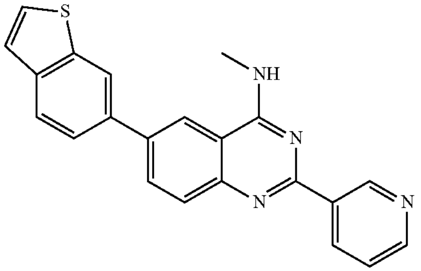 [SMILES: CNc1nc(-c2cccnc2)nc2ccc(-c3ccc4ccsc4c3)cc12] |
| 1343 | 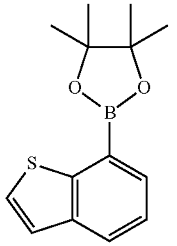 [SMILES: CC1(C)OB(c2cccc3ccsc23)OC1(C)C] | 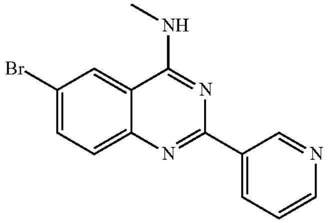 | 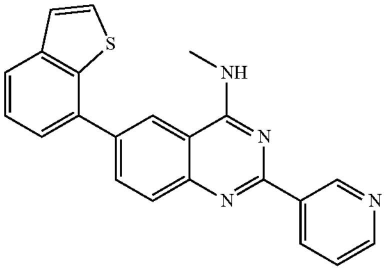 [SMILES: CNc1nc(-c2cccnc2)nc2ccc(-c3cccc4ccsc34)cc12] |

TABLE 24-continued
| | | | |
|---|---|---|---|
| 1344 | 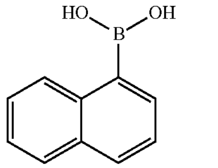 [SMILES: OB(O)c1cccc2ccccc12] | 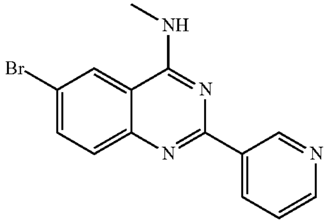 [SMILES: CNc1nc(-c2cccnc2)nc2ccc(Br)cc12] | 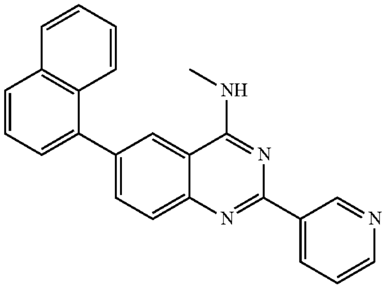 [SMILES: CNc1nc(-c2cccnc2)nc2ccc(-c3cccc4ccccc34)cc12] |
| 1345 | 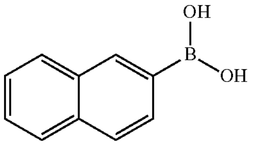 [SMILES: OB(O)c1ccc2ccccc2c1] | 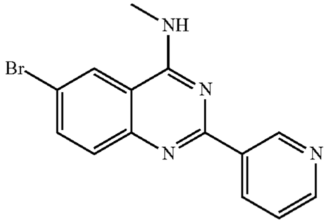 [SMILES: CNc1nc(-c2cccnc2)nc2ccc(Br)cc12] | 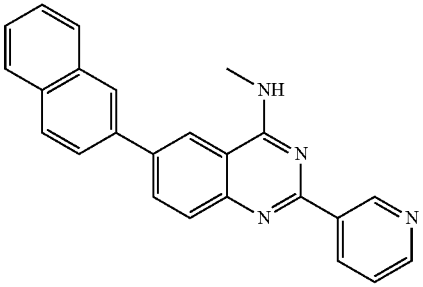 [SMILES: CNc1nc(-c2cccnc2)nc2ccc(-c3ccc4ccccc4c3)cc12] |
| 1346 | 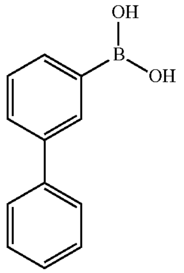 [SMILES: OB(O)c1cccc(-c2ccccc2)c1] | 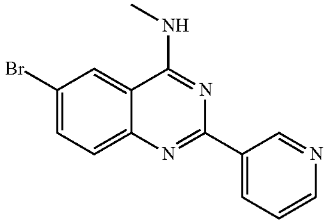 [SMILES: CNc1nc(-c2cccnc2)nc2ccc(Br)cc12] | 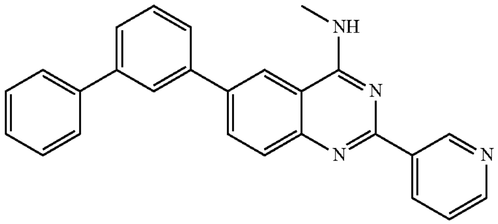 [SMILES: CNc1nc(-c2cccnc2)nc2ccc(-c3cccc(-c4ccccc4)c3)cc12] |

TABLE 24-continued
| | | | |
|---|---|---|---|
| 1347 | 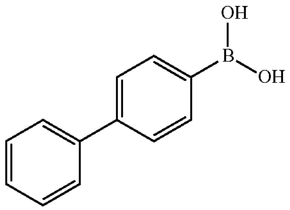 [SMILES: OB(O)c1ccc(-c2ccccc2)cc1] | 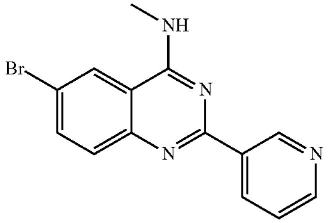 [SMILES: CNc1nc(-c2cccnc2)nc2ccc(Br)cc12] | 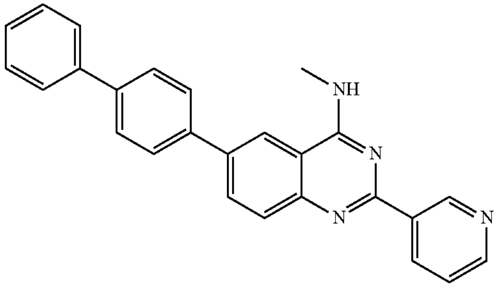 [SMILES: CNc1nc(-c2cccnc2)nc2ccc(-c3ccc(-c4ccccc4)cc3)cc12] |
| 1348 | 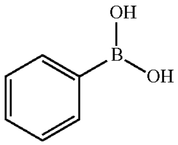 | 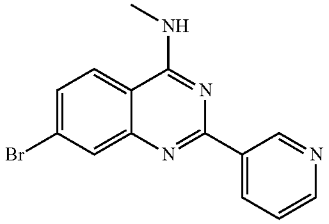 [SMILES: CNc1nc(-c2cccnc2)nc2cc(Br)ccc12] | 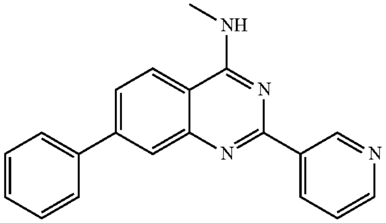 [SMILES: CNc1nc(-c2cccnc2)nc2cc(-c3ccccc3)ccc12] |
| 1349 | 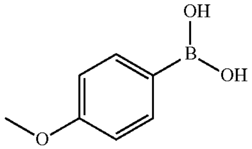 | 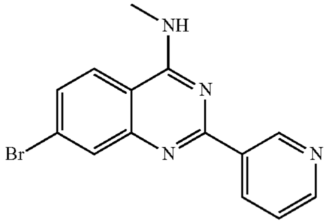 [SMILES: CNc1nc(-c2cccnc2)nc2cc(Br)ccc12] | 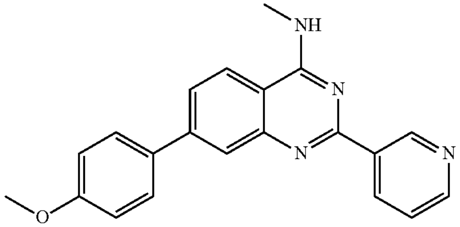 [SMILES: CNc1nc(-c2cccnc2)nc2cc(-c3ccc(OC)cc3)ccc12] |
| 1350 | 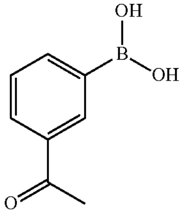 | 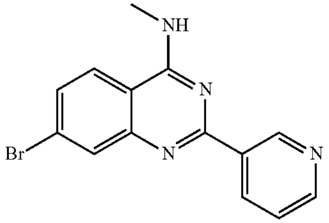 [SMILES: CNc1nc(-c2cccnc2)nc2cc(Br)ccc12] | 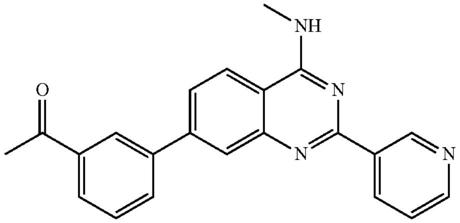 [SMILES: CNc1nc(-c2cccnc2)nc2cc(-c3cccc(C(C)=O)c3)ccc12] |

TABLE 24-continued
| | | | |
|---|---|---|---|
| 1351 | 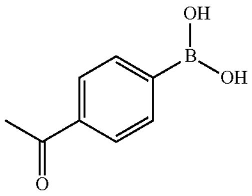 | 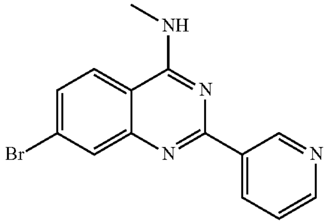 [SMILES: CNc1nc(-c2cccnc2)nc2cc(Br)ccc12] | 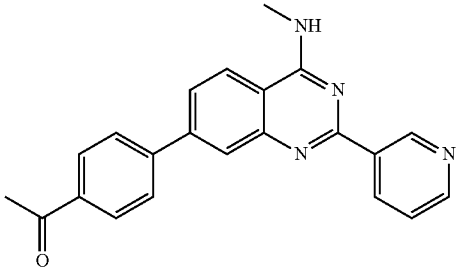 [SMILES: CNc1nc(-c2cccnc2)nc2cc(-c3ccc(C(C)=O)cc3)ccc12] |
| 1352 | 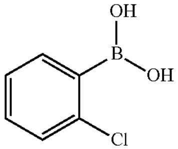 | 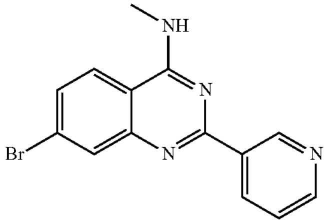 [SMILES: CNc1nc(-c2cccnc2)nc2cc(Br)ccc12] | 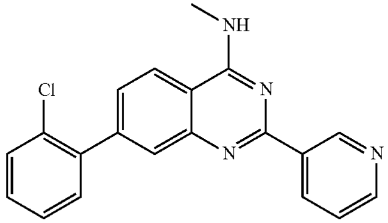 [SMILES: CNc1nc(-c2cccnc2)nc2cc(-c3ccccc3Cl)ccc12] |
| 1353 | 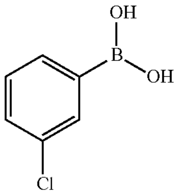 | 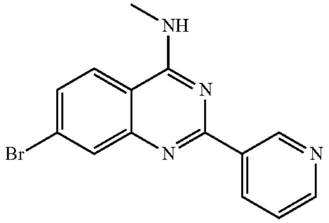 [SMILES: CNc1nc(-c2cccnc2)nc2cc(Br)ccc12] | 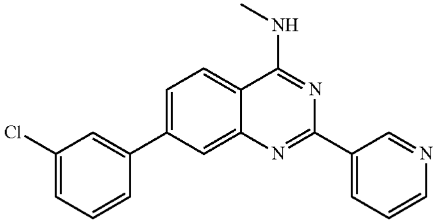 [SMILES: CNc1nc(-c2cccnc2)nc2cc(-c3cccc(Cl)c3)ccc12] |
| 1354 | 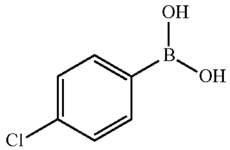 | 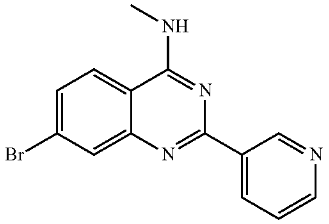 [SMILES: CNc1nc(-c2cccnc2)nc2cc(Br)ccc12] | 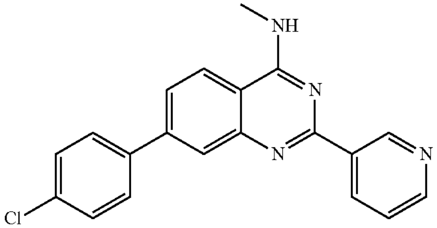 [SMILES: CNc1nc(-c2cccnc2)nc2cc(-c3ccc(Cl)cc3)ccc12] |

TABLE 24-continued
| | | | |
|---|---|---|---|
| 1355 | 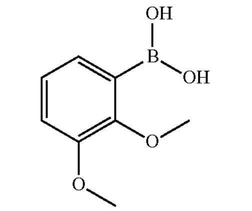 | 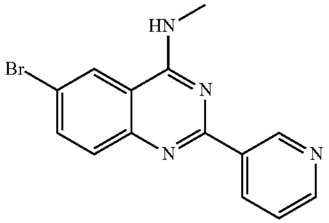 [SMILES: CNc1nc(-c2cccnc2)nc2ccc(Br)cc12] | 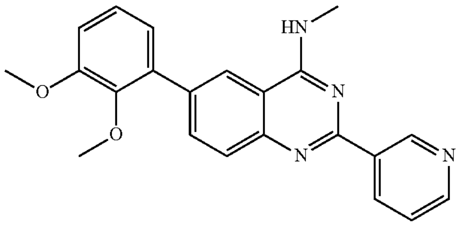 [SMILES: CNc1nc(-c2cccnc2)nc2ccc(-c3cccc(OC)c3OC)cc12] |
| 1356 | 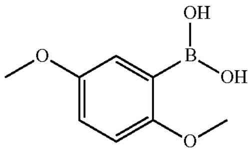 | 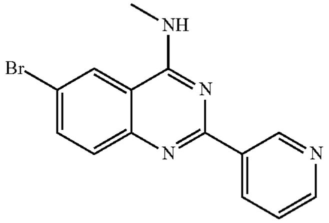 [SMILES: CNc1nc(-c2cccnc2)nc2ccc(Br)cc12] | 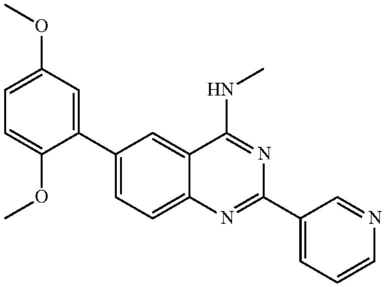 [SMILES: CNc1nc(-c2cccnc2)nc2ccc(-c3cc(OC)ccc3OC)cc12] |
| 1357 | 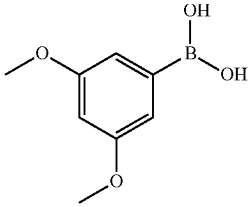 | 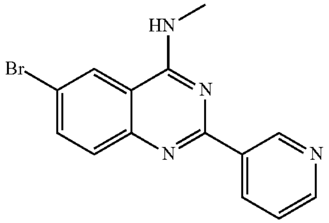 [SMILES: CNc1nc(-c2cccnc2)nc2ccc(Br)cc12] | 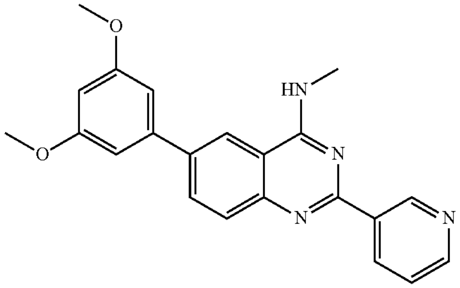 [SMILES: CNc1nc(-c2cccnc2)nc2ccc(-c3cc(OC)cc(OC)c3)cc12] |
| 1358 | 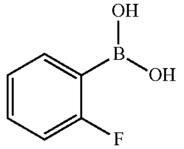 | 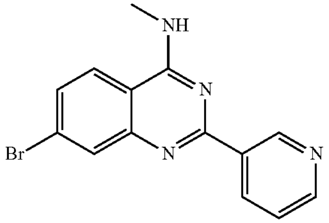 [SMILES: CNc1nc(-c2cccnc2)nc2cc(Br)ccc12] | 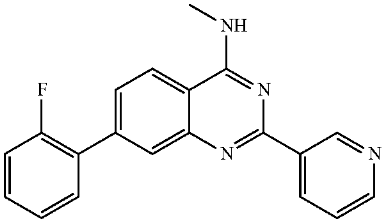 |

TABLE 24-continued
| | | | |
|---|---|---|---|
| 1359 | 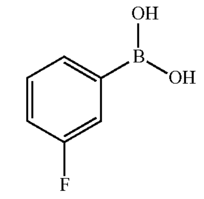 | 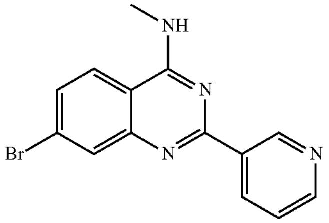 [SMILES: CNc1nc(-c2cccnc2)nc2cc(Br)ccc12] | 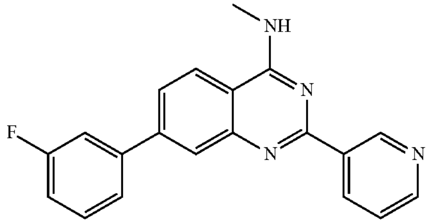 [SMILES: CNc1nc(-c2cccnc2)nc2cc(-c3cccc(F)c3)ccc12] |
| 1360 | 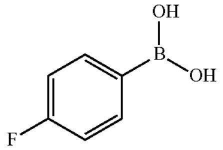 | 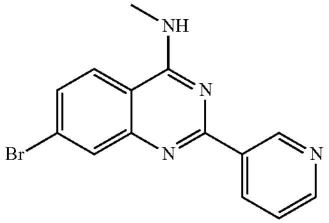 [SMILES: CNc1nc(-c2cccnc2)nc2cc(Br)ccc12] | 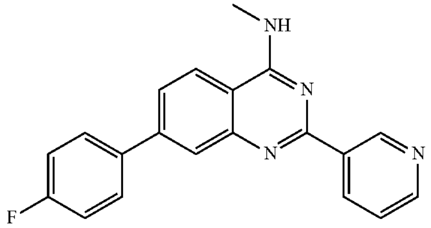 [SMILES: CNc1nc(-c2cccnc2)nc2cc(-c3ccc(F)cc3)ccc12] |
| 1361 | 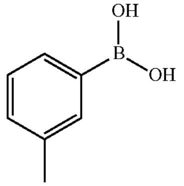 | 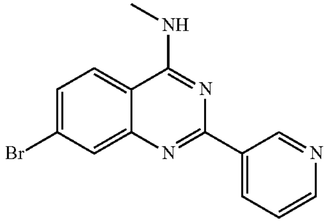 [SMILES: CNc1nc(-c2cccnc2)nc2cc(Br)ccc12] | 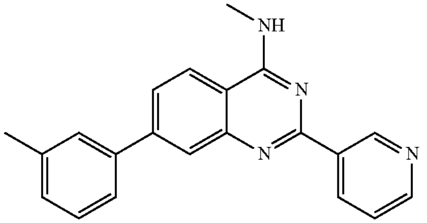 [SMILES: CNc1nc(-c2cccnc2)nc2cc(-c3cccc(C)c3)ccc12] |
| 1362 | 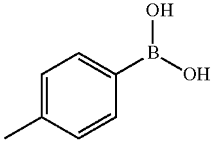 | 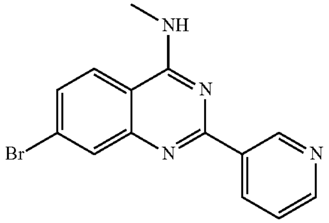 [SMILES: CNc1nc(-c2cccnc2)nc2cc(Br)ccc12] | 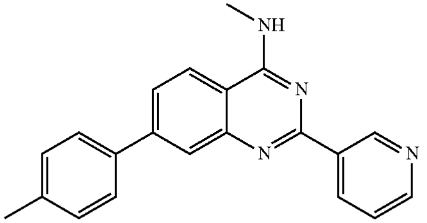 [SMILES: CNc1nc(-c2cccnc2)nc2cc(-c3ccc(C)cc3)ccc12] |

TABLE 24-continued
| | | | |
|---|---|---|---|
| 1363 | 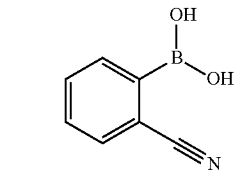 [SMILES: N#Cc1ccccc1B(O)O] | 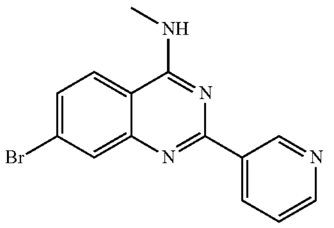 [SMILES: CNc1nc(-c2cccnc2)nc2cc(Br)ccc12] | 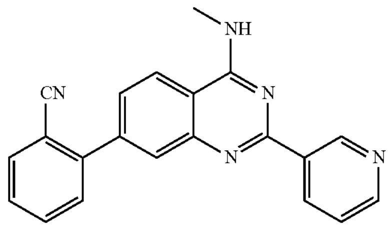 [SMILES: CNc1nc(-c2cccnc2)nc2cc(-c3ccccc3C#N)ccc12] |
| 1364 | 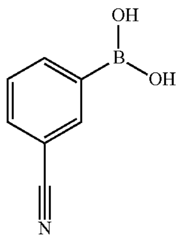 [SMILES: N#Cc1cccc(B(O)O)c1] | 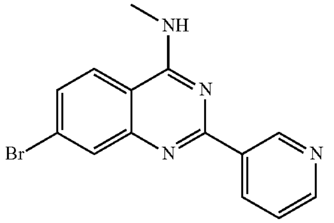 [SMILES: CNc1nc(-c2cccnc2)nc2cc(Br)ccc12] | 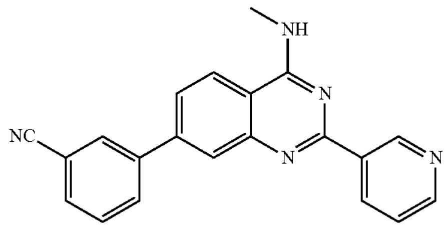 [SMILES: CNc1nc(-c2cccnc2)nc2cc(-c3cccc(C#N)c3)ccc12] |
| 1365 | 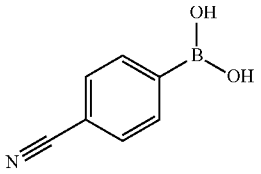 [SMILES: N#Cc1ccc(B(O)O)cc1] | 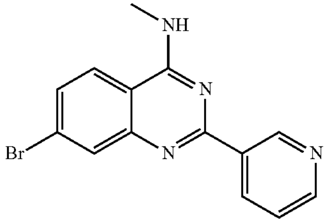 [SMILES: CNc1nc(-c2cccnc2)nc2cc(Br)ccc12] | 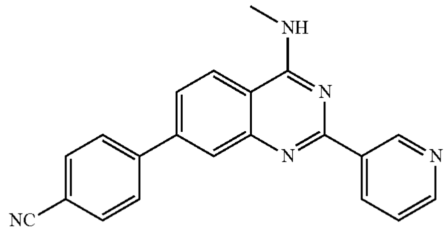 [SMILES: CNc1nc(-c2cccnc2)nc2cc(-c3ccc(C#N)cc3)ccc12] |
| 1366 | 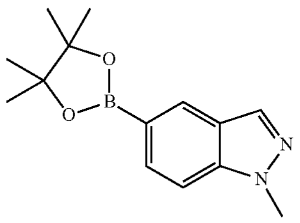 [SMILES: Cn1ncc2cc(B3OC(C)(C)C(C)(C)O3)ccc21] | 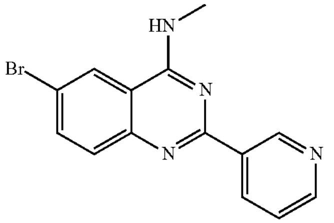 [SMILES: CNc1nc(-c2cccnc2)nc2ccc(Br)cc12] | 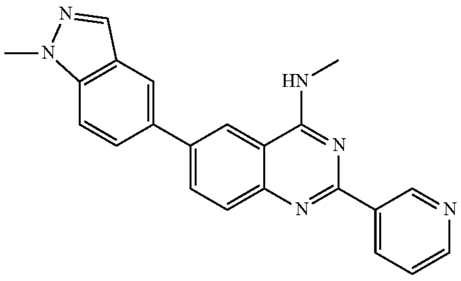 [SMILES: CNc1nc(-c2cccnc2)nc2ccc(-c3ccc4c(cnn4C)c3)cc12] |

TABLE 24-continued
| | | | |
|---|---|---|---|
| 1367 | 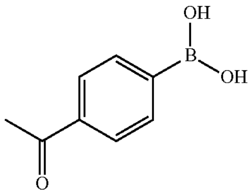 | 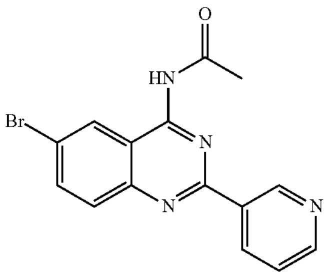 [SMILES: CC(=O)Nc1nc(-c2cccnc2)nc2ccc(Br)cc12] | 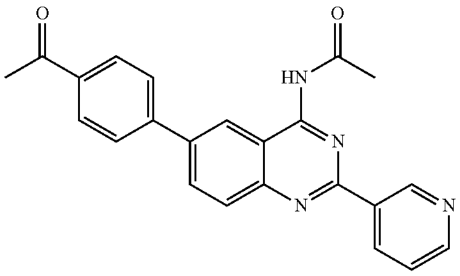 [SMILES: CC(=O)Nc1nc(-c2cccnc2)nc2ccc(-c3ccc(C(C)=O)cc3)cc12] |
| 1368 | 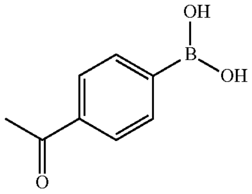 | 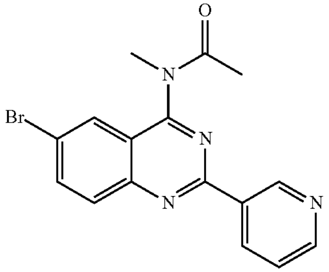 [SMILES: CC(=O)N(C)c1nc(-c2cccnc2)nc2ccc(Br)cc12] | 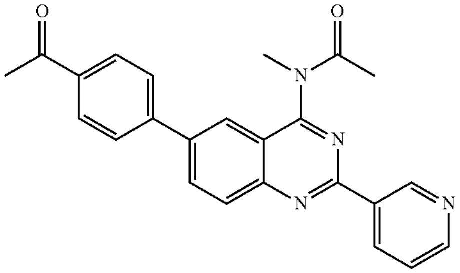 [SMILES: CC(=O)c1ccc(-c2ccc3nc(-c4cccnc4)nc(N(C)C(C)=O)c3c2)cc1] |
| 1369 | 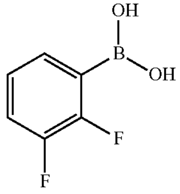 [SMILES: OB(O)c1cccc(F)c1F] | 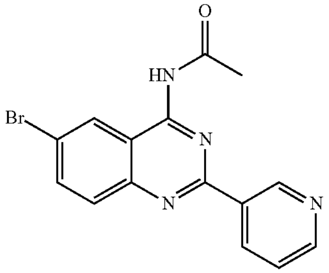 [SMILES: CC(=O)Nc1nc(-c2cccnc2)nc2ccc(Br)cc12] | 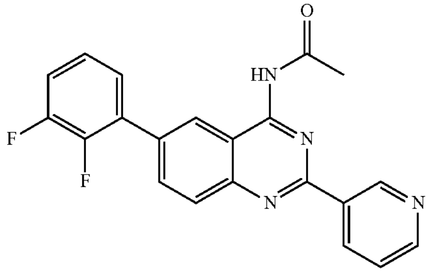 [SMILES: CC(=O)Nc1nc(-c2cccnc2)nc2ccc(-c3cccc(F)c3F)cc12] |

TABLE 24-continued
| | | | |
|---|---|---|---|
| 1370 | 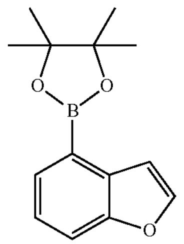 [SMILES: CC1(C)OB(c2cccc3occc23)OC1(C)C] | 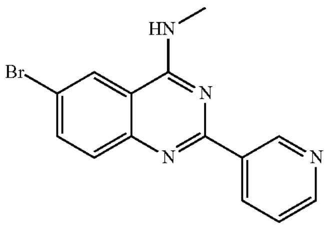 [SMILES: CNc1nc(-c2cccnc2)nc2ccc(Br)cc12] | 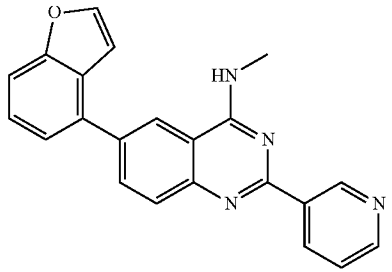 [SMILES: CNc1nc(-c2cccnc2)nc2ccc(-c3cccc4occc34)cc12] |
| 1371 | 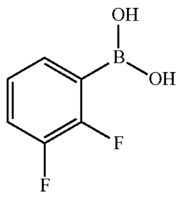 [SMILES: OB(O)c1cccc(F)c1F] | 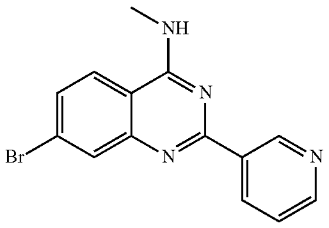 [SMILES: CNc1nc(-c2cccnc2)nc2cc(Br)ccc12] | 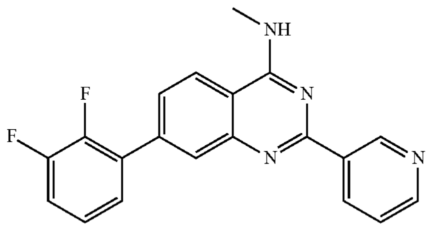 [SMILES: CNc1nc(-c2cccnc2)nc2cc(-c3cccc(F)c3F)ccc12] |
| 1372 | 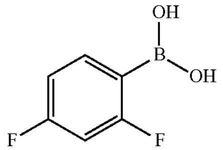 | 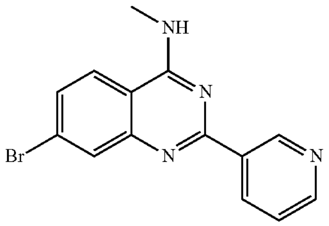 [SMILES: CNc1nc(-c2cccnc2)nc2cc(Br)ccc12] | 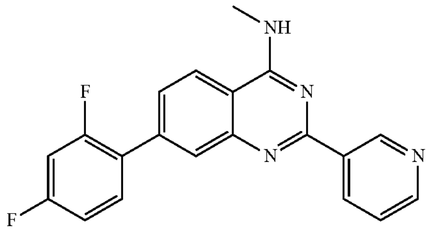 [SMILES: CNc1nc(-c2cccnc2)nc2cc(-c3ccc(F)cc3F)ccc12] |
| 1373 | 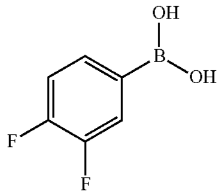 | 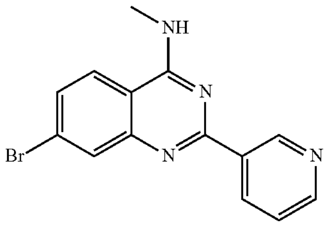 [SMILES: CNc1nc(-c2cccnc2)nc2cc(Br)ccc12] | 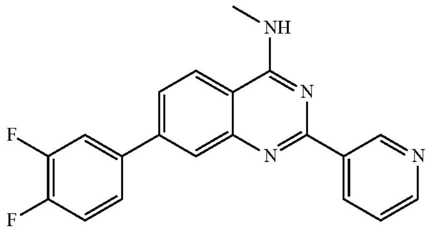 [SMILES: CNc1nc(-c2cccnc2)nc2cc(-c3ccc(F)c(F)c3)ccc12] |

TABLE 24-continued
| | | | |
|---|---|---|---|
| 1374 | 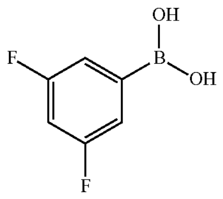 | 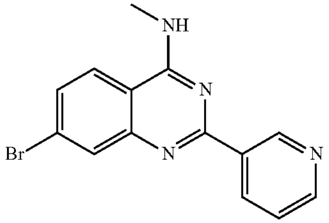 [SMILES: CNc1nc(-c2cccnc2)nc2cc(Br)ccc12] | 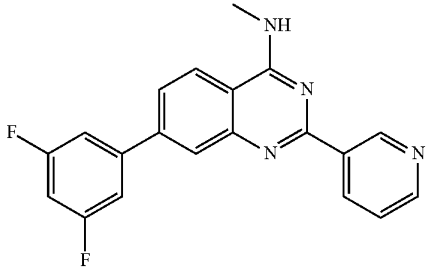 [SMILES: CNc1nc(-c2cccnc2)nc2cc(-c3cc(F)cc(F)c3)ccc12] |
| 1375 | 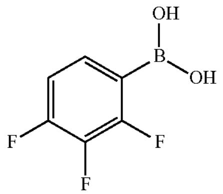 [SMILES: OB(O)c1ccc(F)c(F)c1F] | 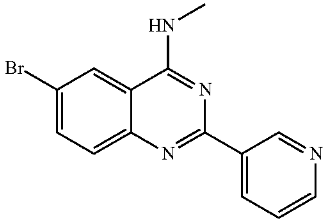 [SMILES: CNc1nc(-c2cccnc2)nc2ccc(Br)cc12] | 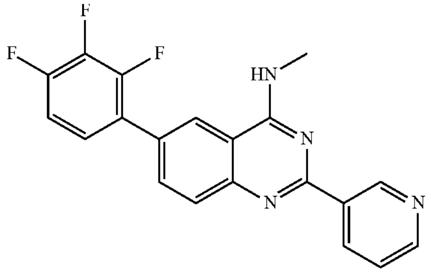 [SMILES: CNc1nc(-c2cccnc2)nc2ccc(-c3ccc(F)c(F)c3F)cc12] |
| 1376 | 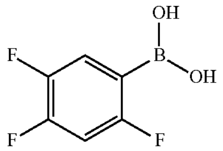 | 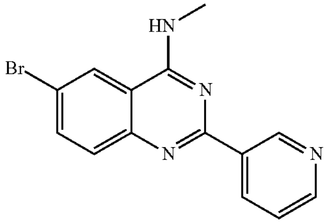 [SMILES: CNc1nc(-c2cccnc2)nc2ccc(Br)cc12] | 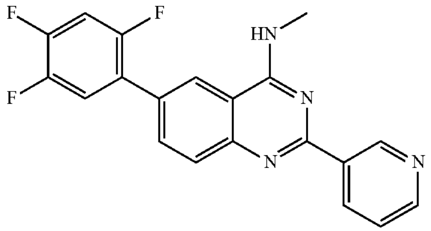 [SMILES: CNc1nc(-c2cccnc2)nc2ccc(-c3cc(F)c(F)cc3F)cc12] |
| 1377 | 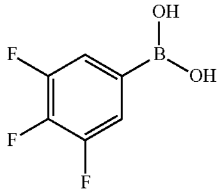 | 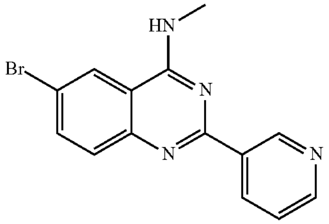 [SMILES: CNc1nc(-c2cccnc2)nc2ccc(Br)cc12] | 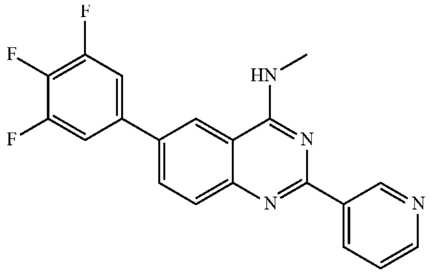 [SMILES: CNc1nc(-c2cccnc2)nc2ccc(-c3cc(F)c(F)c(F)c3)cc12] |

TABLE 24-continued
| | | | |
|---|---|---|---|
| 1378 | 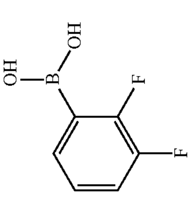 | 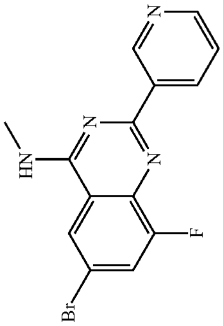 | 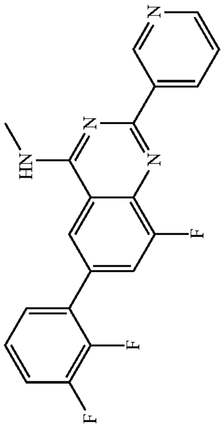 |
| 1379 | 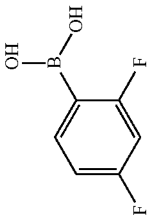 | 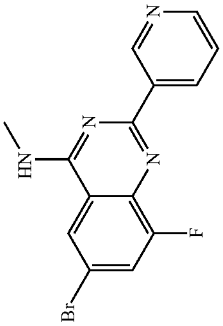 | 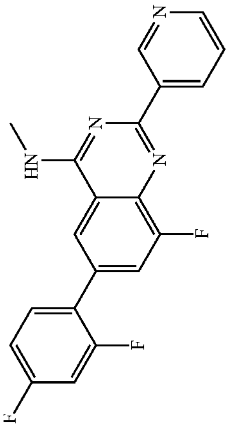 |
| 1380 | 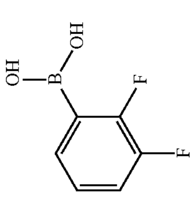 | 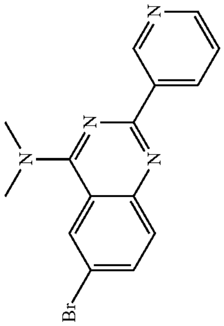 | 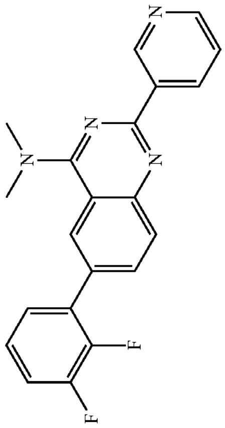 |
| 1381 | 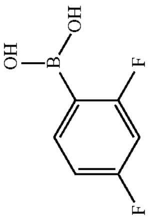 | 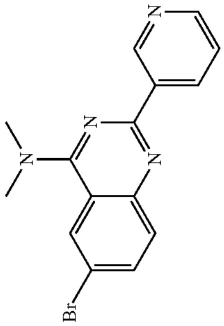 | 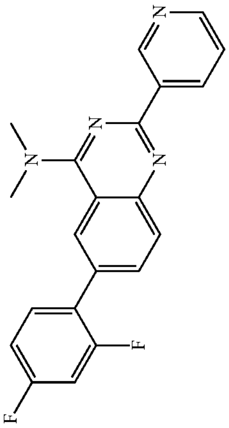 |

TABLE 24-continued
| | | | |
|---|---|---|---|
| 1382 | 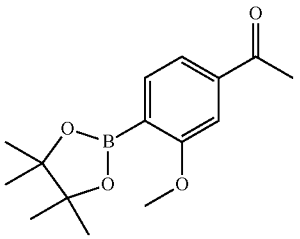 [SMILES: COc1cc(C(C)=O)ccc1B1OC(C)(C)C(C)(C)O1] | 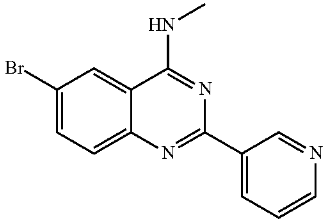 [SMILES: CNc1nc(-c2cccnc2)nc2ccc(Br)cc12] | 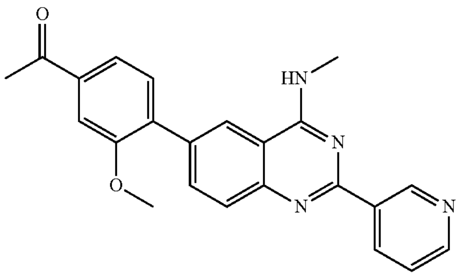 [SMILES: CNc1nc(-c2cccnc2)nc2ccc(-c3ccc(C(C)=O)cc3OC)cc12] |
| 1383 | 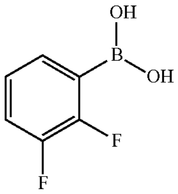 [SMILES: OB(O)c1cccc(F)c1F] | 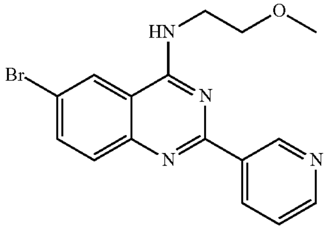 [SMILES: COCCNc1nc(-c2cccnc2)nc2ccc(Br)cc12] | 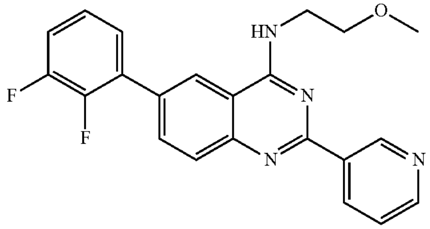 [SMILES: COCCNc1nc(-c2cccnc2)nc2ccc(-c3cccc(F)c3F)cc12] |
| 1384 | 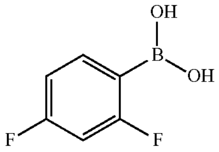 | 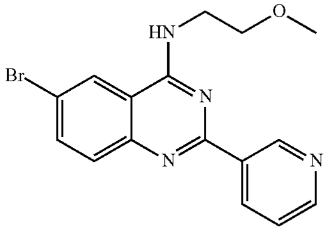 | 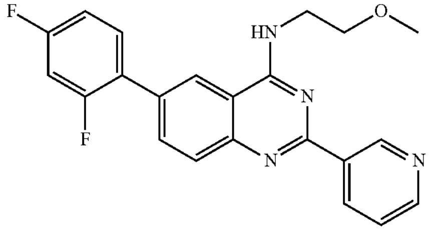 [SMILES: COCCNc1nc(-c2cccnc2)nc2ccc(-c3ccc(F)cc3F)cc12] |
| 1385 | 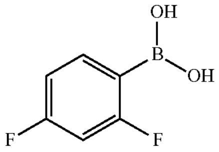 | 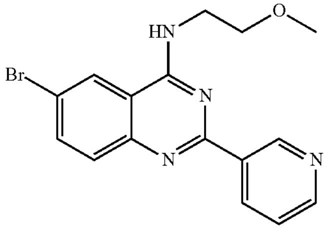 [SMILES: COCCNc1nc(-c2cccnc2)nc2ccc(Br)cc12] | 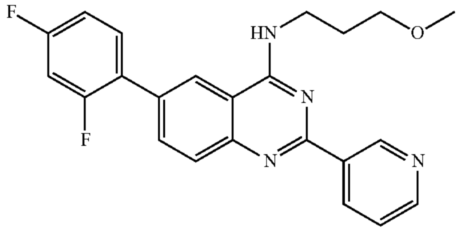 [SMILES: COCCCNc1nc(-c2cccnc2)nc2ccc(-c3ccc(F)cc3F)cc12] |

TABLE 24-continued
| | | | |
|---|---|---|---|
| 1386 | 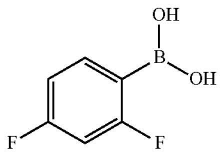 | 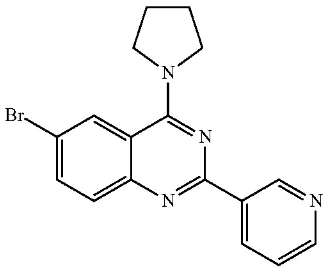 [SMILES: Brc1ccc2nc(-c3cccnc3)nc(N3CCCC3)c2c1] | 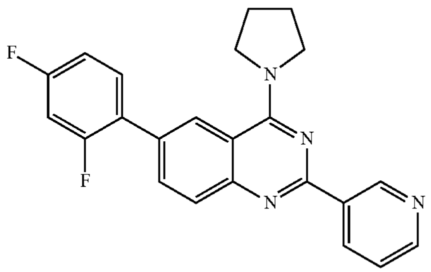 [SMILES: Fc1ccc(-c2ccc3nc(-c4cccnc4)nc(N4CCCC4)c3c2)c(F)c1] |
| 1387 | 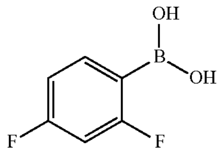 | 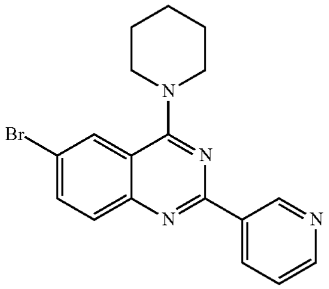 [SMILES: Brc1ccc2nc(-c3cccnc3)nc(N3CCCCC3)c2c1] | 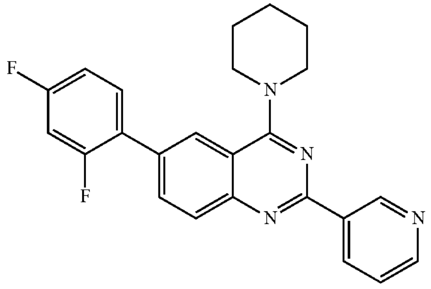 [SMILES: Fc1ccc(-c2ccc3nc(-c4cccnc4)nc(N4CCCCC4)c3c2)c(F)c1] |
| 1388 | 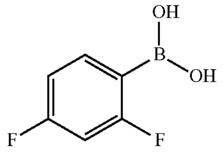 | 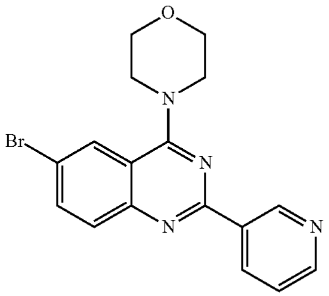 [SMILES: Brc1ccc2nc(-c3cccnc3)nc(N3CCOCC3)c2c1] | 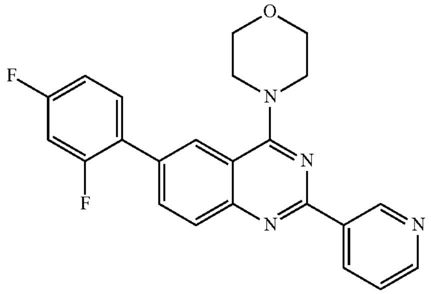 [SMILES: Fc1ccc(-c2ccc3nc(-c4cccnc4)nc(N4CCOCC4)c3c2)c(F)c1] |

TABLE 24-continued
| | | | |
|---|---|---|---|
| 1389 | 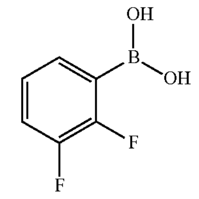 [SMILES: OB(O)c1cccc(F)c1F] | 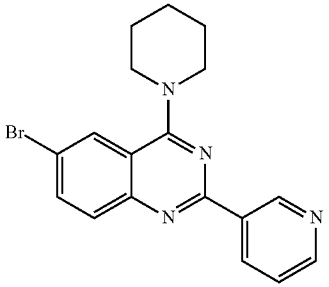 [SMILES: Brc1ccc2nc(-c3cccnc3)nc(N3CCCCC3)c2c1] | 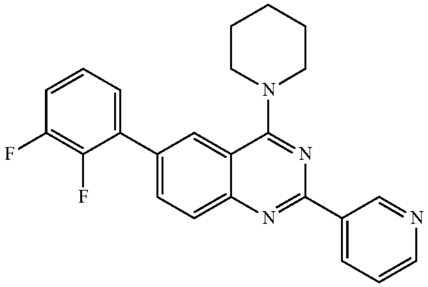 [SMILES: Fc1cccc(-c2ccc3nc(-c4cccnc4)nc(N4CCCCC4)c3c2)c1F] |
| 1390 | 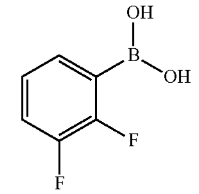 [SMILES: OB(O)c1cccc(F)c1F] | 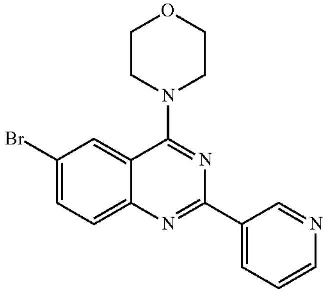 [SMILES: Brc1ccc2nc(-c3cccnc3)nc(N3CCOCC3)c2c1] | 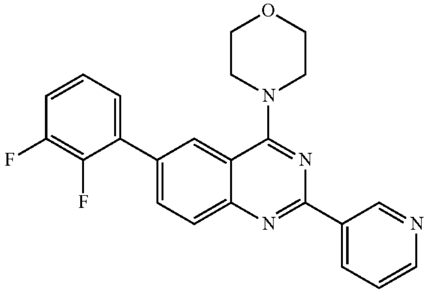 [SMILES: Fc1cccc(-c2ccc3nc(-c4cccnc4)nc(N4CCOCC4)c3c2)c1F] |
| 1391 | 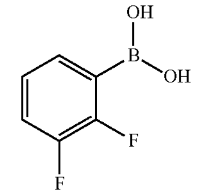 [SMILES: OB(O)c1cccc(F)c1F] | 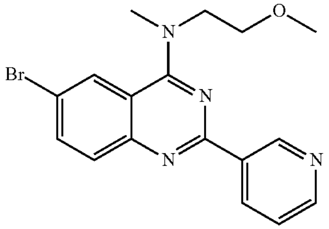 [SMILES: COCCN(C)c1nc(-c2cccnc2)nc2ccc(Br)cc12] | 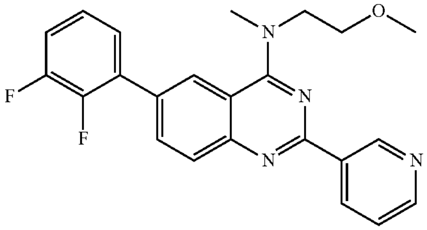 [SMILES: COCCN(C)c1nc(-c2cccnc2)nc2ccc(-c3cccc(F)c3F)cc12] |
| 1392 | 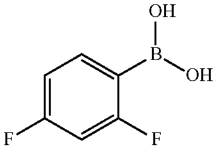 | 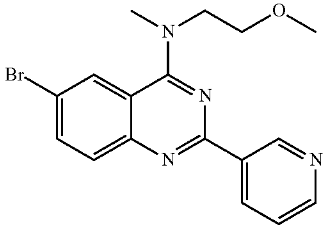 [SMILES: COCCN(C)c1nc(-c2cccnc2)nc2ccc(Br)cc12] | 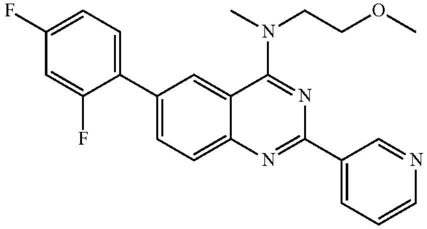 [SMILES: COCCN(C)c1nc(-c2cccnc2)nc2ccc(-c3ccc(F)cc3F)cc12] |

TABLE 24-continued
| | | | |
|---|---|---|---|
| 1393 | 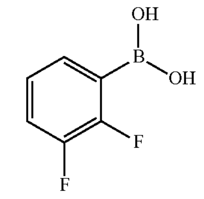 [SMILES: OB(O)c1cccc(F)c1F] | 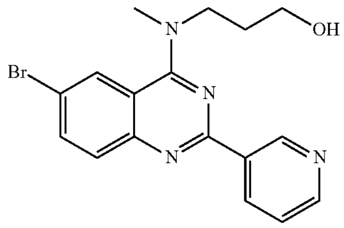 [SMILES: CN(CCCO)c1nc(-c2cccnc2)nc2ccc(Br)cc12] | 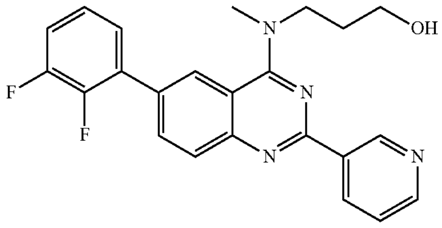 [SMILES: CN(CCCO)c1nc(-c2cccnc2)nc2ccc(-c3cccc(F)c3F)cc12] |
| 1394 | 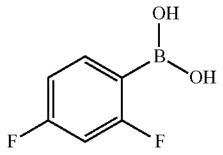 | 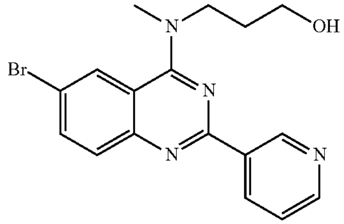 [SMILES: CN(CCCO)c1nc(-c2cccnc2)nc2ccc(Br)cc12] | 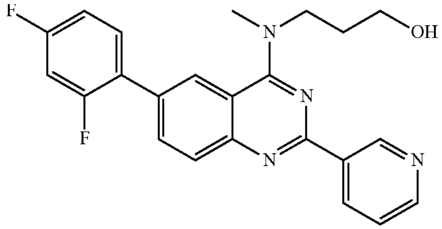 [SMILES: CN(CCCO)c1nc(-c2cccnc2)nc2ccc(-c3ccc(F)cc3F)cc12] |
| 1395 | 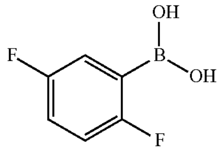 | 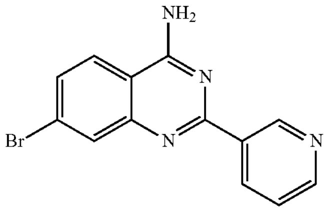 [SMILES: Nc1nc(-c2cccnc2)nc2cc(Br)ccc12] | 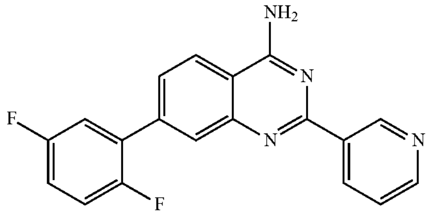 [SMILES: Nc1nc(-c2cccnc2)nc2cc(-c3cc(F)ccc3F)ccc12] |
| 1396 | 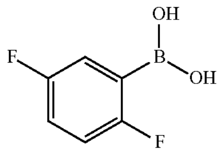 | 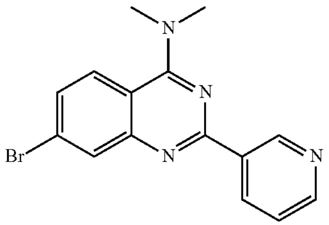 [SMILES: CN(C)c1nc(-c2cccnc2)nc2cc(Br)ccc12] | 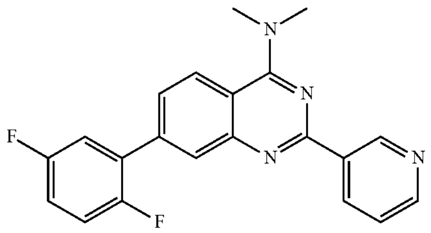 [SMILES: CN(C)c1nc(-c2cccnc2)nc2cc(-c3cc(F)ccc3F)ccc12] |

TABLE 24-continued
| | | | |
|---|---|---|---|
| 1397 | 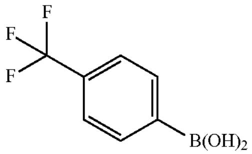 | 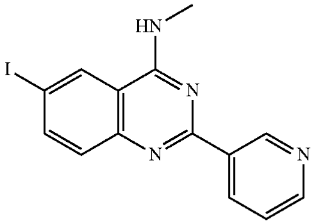 [SMILES: CNc1nc(-c2cccnc2)nc2ccc(I)cc12] | 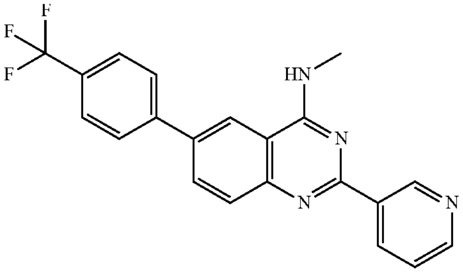 [SMILES: CNc1nc(-c2cccnc2)nc2ccc(-c3ccc(C(F)(F)F)cc3)cc12] |
| 1398 | 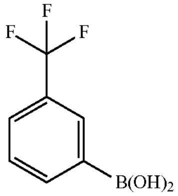 | 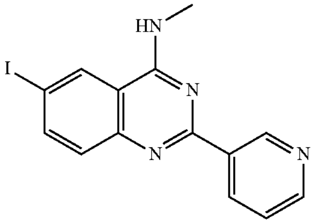 [SMILES: CNc1nc(-c2cccnc2)nc2ccc(I)cc12] | 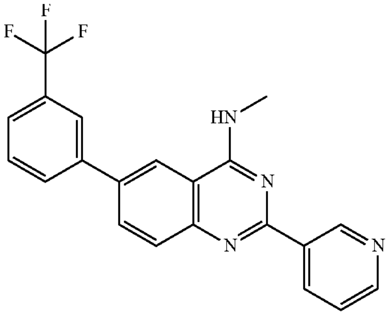 [SMILES: CNc1nc(-c2cccnc2)nc2ccc(-c3cccc(C(F)(F)F)c3)cc12] |
| 1399 | 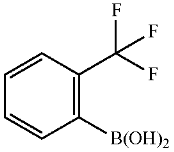 | 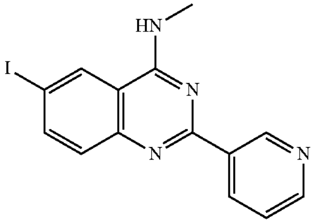 [SMILES: CNc1nc(-c2cccnc2)nc2ccc(I)cc12] | 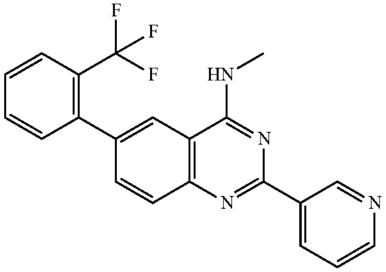 [SMILES: CNc1nc(-c2cccnc2)nc2ccc(-c3ccccc3C(F)(F)F)cc12] |
| 1400 | 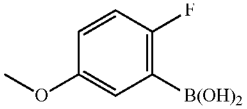 | 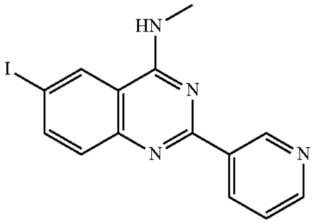 [SMILES: CNc1nc(-c2cccnc2)nc2ccc(I)cc12] | 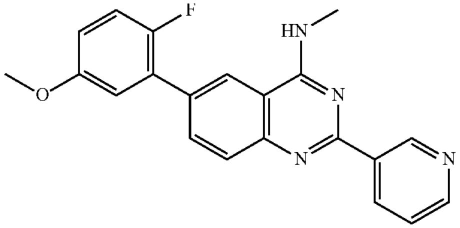 [SMILES: CNc1nc(-c2cccnc2)nc2ccc(-c3cc(OC)ccc3F)cc12] |

TABLE 24-continued
| | | | |
|---|---|---|---|
| 1401 | 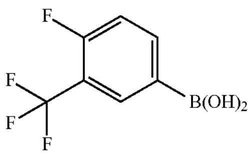 [SMILES: OB(O)c1ccc(F)c(C(F)(F)F)c1] | 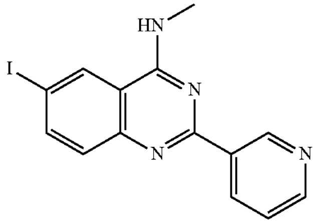 [SMILES: CNc1nc(-c2cccnc2)nc2ccc(I)cc12] | 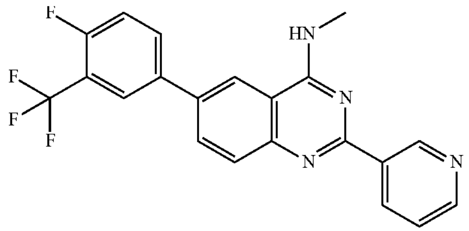 [SMILES: CNc1nc(-c2cccnc2)nc2ccc(-c3ccc(F)c(C(F)(F)F)c3)cc12] |
| 1402 | 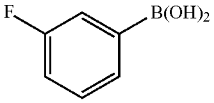 | 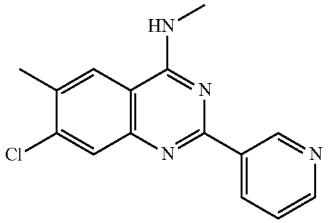 [SMILES: CNc1nc(-c2cccnc2)nc2cc(Cl)c(C)cc12] | 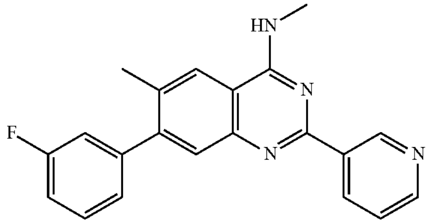 [SMILES: CNc1nc(-c2cccnc2)nc2cc(-c3cccc(F)c3)c(C)cc12] |
| 1403 | 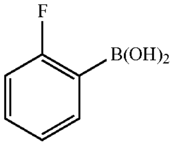 | 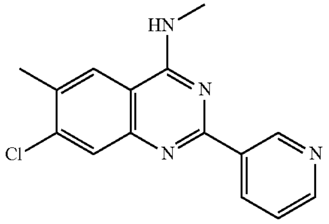 [SMILES: CNc1nc(-c2cccnc2)nc2cc(Cl)c(C)cc12] | 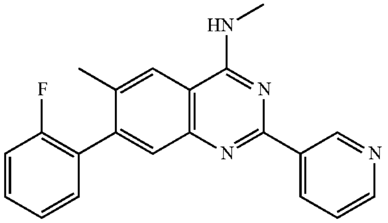 [SMILES: CNc1nc(-c2cccnc2)nc2cc(-c3ccccc3F)c(C)cc12] |
| 1404 | 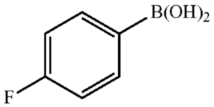 | 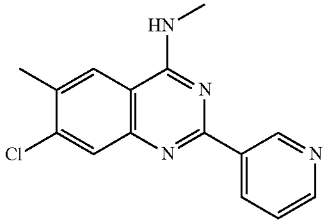 [SMILES: CNc1nc(-c2cccnc2)nc2cc(Cl)c(C)cc12] | 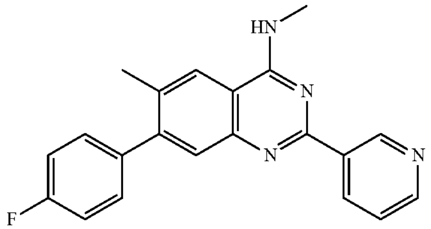 [SMILES: CNc1nc(-c2cccnc2)nc2cc(-c3ccc(F)cc3)c(C)cc12] |

TABLE 24-continued
| | | | |
|---|---|---|---|
| 1405 | 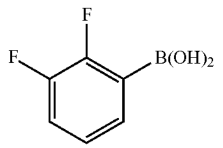 | 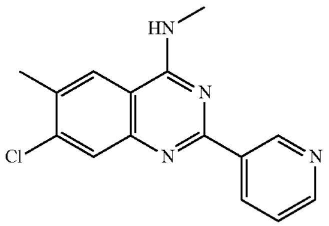 [SMILES: CNc1nc(-c2cccnc2)nc2cc(Cl)c(C)cc12] | 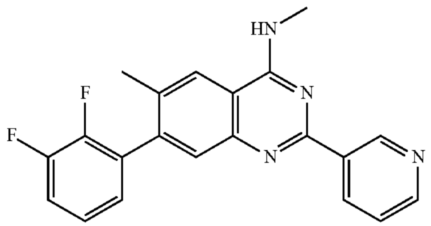 [SMILES: CNc1nc(-c2cccnc2)nc2cc(-c3cccc(F)c3F)c(C)cc12] |
| 1406 | 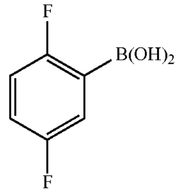 [SMILES: OB(O)c1cc(F)ccc1F] | 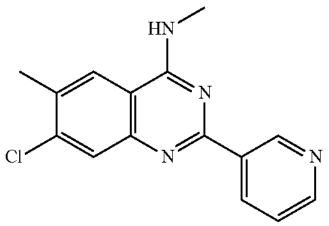 [SMILES: CNc1nc(-c2cccnc2)nc2cc(Cl)c(C)cc12] | 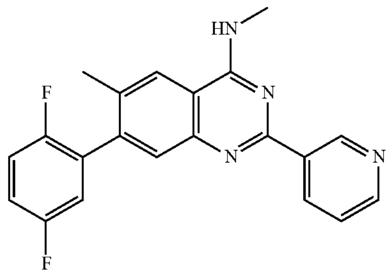 [SMILES: CNc1nc(-c2cccnc2)nc2cc(-c3cc(F)ccc3F)c(C)cc12] |
| 1407 | 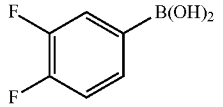 | 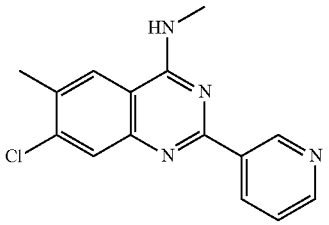 [SMILES: CNc1nc(-c2cccnc2)nc2cc(Cl)c(C)cc12] | 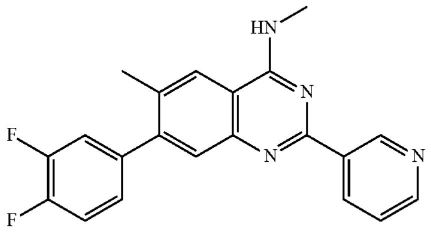 [SMILES: CNc1nc(-c2cccnc2)nc2cc(-c3ccc(F)c(F)c3)c(C)cc12] |
| 1408 | 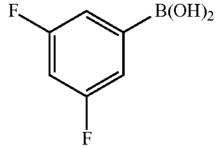 | 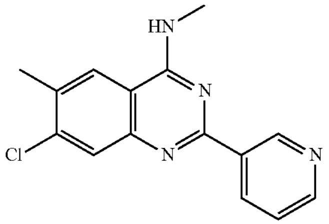 [SMILES: CNc1nc(-c2cccnc2)nc2cc(Cl)c(C)cc12] | 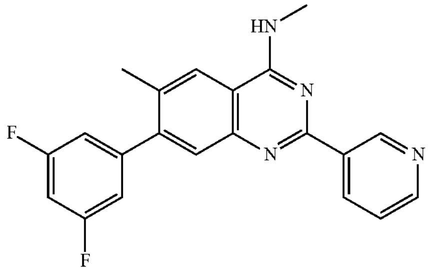 [SMILES: CNc1nc(-c2cccnc2)nc2cc(-c3cc(F)cc(F)c3)c(C)cc12] |

TABLE 24-continued
| | | | |
|---|---|---|---|
| 1409 | 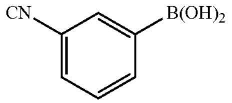 | 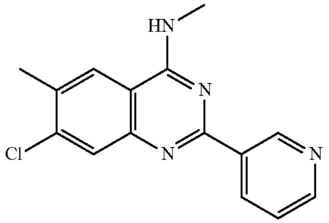 [SMILES: CNc1nc(-c2cccnc2)nc2cc(Cl)c(C)cc12] | 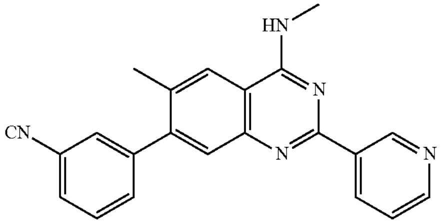 |
| 1410 | 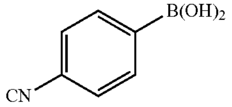 | 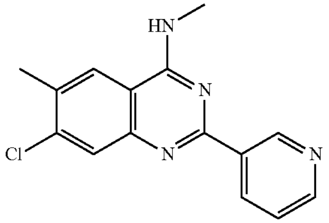 [SMILES: CNc1nc(-c2cccnc2)nc2cc(Cl)c(C)cc12] | 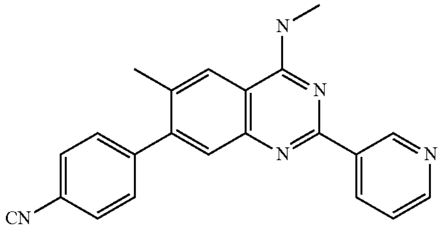 |
| 1411 | 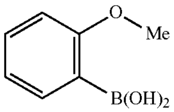 | 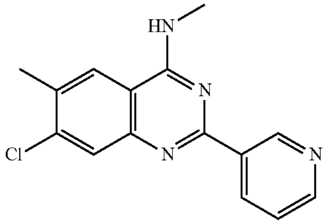 [SMILES: CNc1nc(-c2cccnc2)nc2cc(Cl)c(C)cc12] | 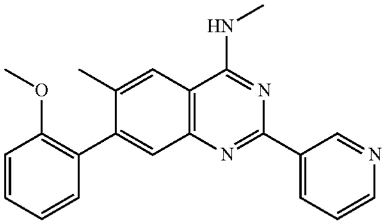 [SMILES: CNc1nc(-c2cccnc2)nc2cc(-c3ccccc3OC)c(C)cc12] |
| 1412 | 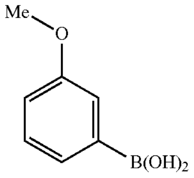 | 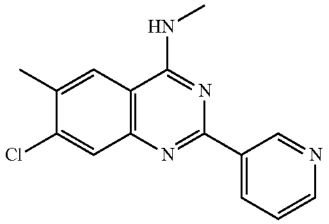 [SMILES: CNc1nc(-c2cccnc2)nc2cc(Cl)c(C)cc12] | 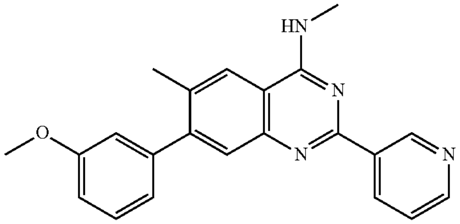 [SMILES: CNc1nc(-c2cccnc2)nc2cc(-c3cccc(OC)c3)c(C)cc12] |

TABLE 24-continued
| | | | |
|---|---|---|---|
| 1413 | 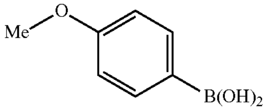 | 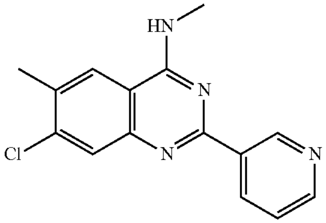 [SMILES: CNc1nc(-c2cccnc2)nc2cc(Cl)c(C)cc12] | 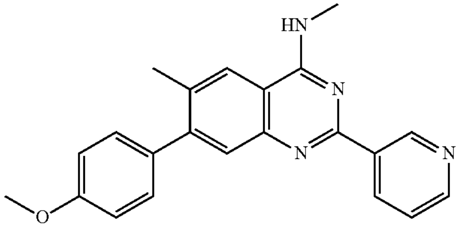 [SMILES: CNc1nc(-c2cccnc2)nc2cc(-c3ccc(OC)cc3)c(C)cc12] |
| 1414 | 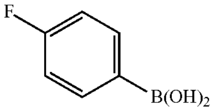 | 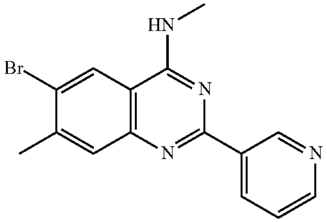 [SMILES: CNc1nc(-c2cccnc2)nc2cc(C)c(Br)cc12] | 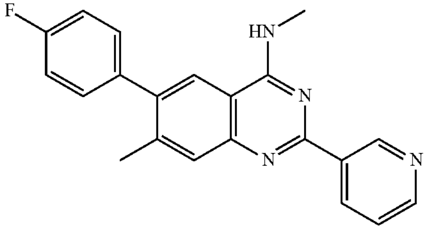 [SMILES: CNc1nc(-c2cccnc2)nc2cc(C)c(-c3ccc(F)cc3)cc12] |
| 1415 | 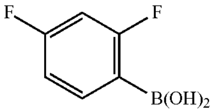 | 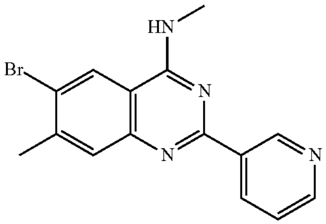 [SMILES: CNc1nc(-c2cccnc2)nc2cc(C)c(Br)cc12] | 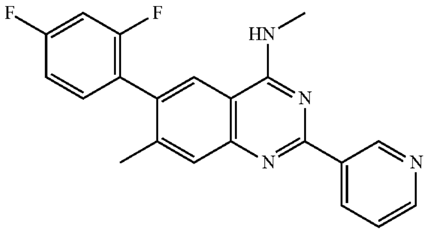 [SMILES: CNc1nc(-c2cccnc2)nc2cc(C)c(-c3ccc(F)cc3F)cc12] |
| 1416 | 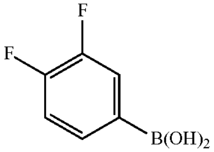 | 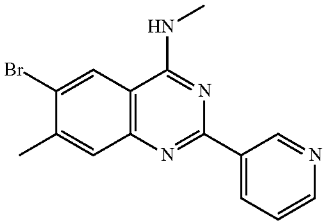 [SMILES: CNc1nc(-c2cccnc2)nc2cc(C)c(Br)cc12] | 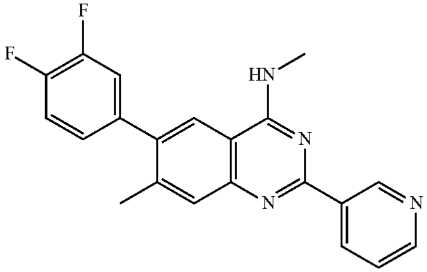 [SMILES: CNc1nc(-c2cccnc2)nc2cc(C)c(-c3ccc(F)c(F)c3)cc12] |

TABLE 24-continued
| | | | |
|---|---|---|---|
| 1417 | 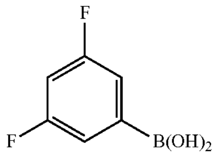 | 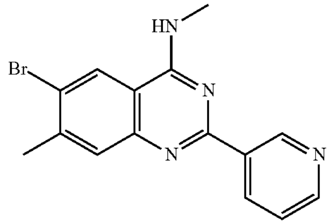 [SMILES: CNc1nc(-c2cccnc2)nc2cc(C)c(Br)cc12] | 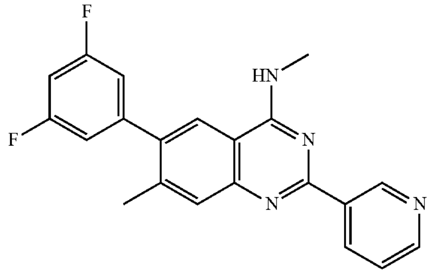 [SMILES: CNc1nc(-c2cccnc2)nc2cc(C)c(-c3cc(F)cc(F)c3)cc12] |
| 1418 | 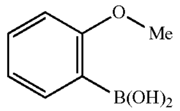 | 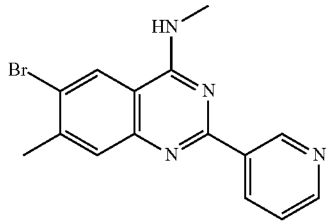 [SMILES: CNc1nc(-c2cccnc2)nc2cc(C)c(Br)cc12] | 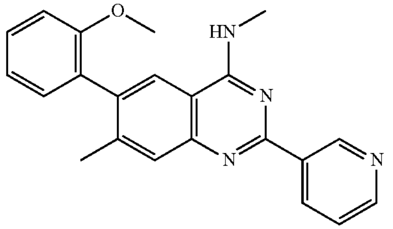 [SMILES: CNc1nc(-c2cccnc2)nc2cc(C)c(-c3ccccc3OC)cc12] |
| 1419 | 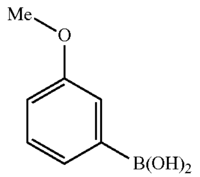 | 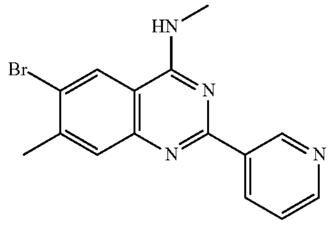 [SMILES: CNc1nc(-c2cccnc2)nc2cc(C)c(Br)cc12] | 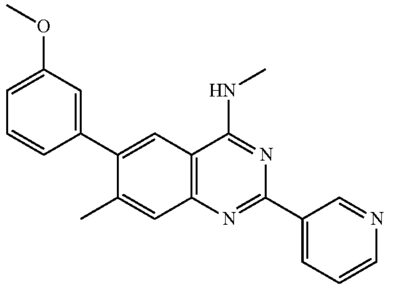 [SMILES: CNc1nc(-c2cccnc2)nc2cc(C)c(-c3cccc(OC)c3)cc12] |
| 1420 | 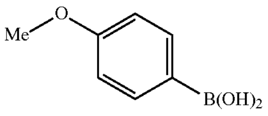 | 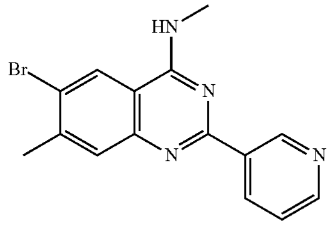 [SMILES: CNc1nc(-c2cccnc2)nc2cc(C)c(Br)cc12] | 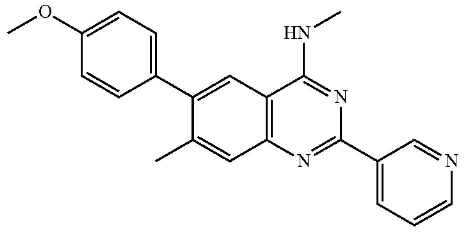 [SMILES: CNc1nc(-c2cccnc2)nc2cc(C)c(-c3ccc(OC)cc3)cc12] |

TABLE 24-continued
| | | | |
|---|---|---|---|
| 1421 | 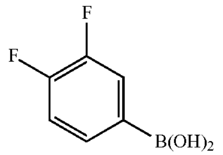 | 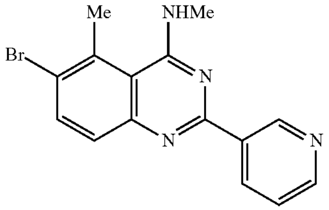 [SMILES: CNc1nc(-c2cccnc2)nc2ccc(Br)c(C)c12] | 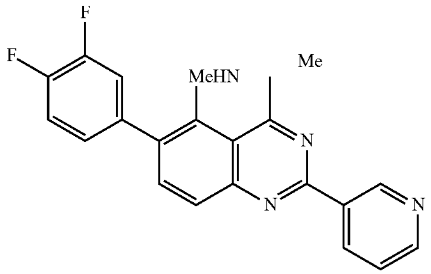 [SMILES: CNc1c(-c2ccc(F)c(F)c2)ccc2nc(-c3cccnc3)nc(C)c12] |
| 1422 | 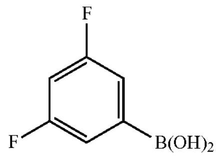 | 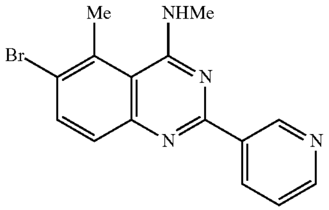 [SMILES: CNc1nc(-c2cccnc2)nc2ccc(Br)c(C)c12] | 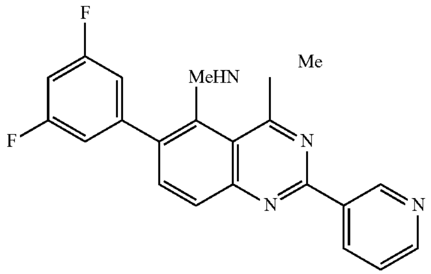 [SMILES: CNc1c(-c2cc(F)cc(F)c2)ccc2nc(-c3cccnc3)nc(C)c12] |
| 1423 | 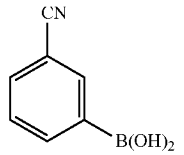 [SMILES: N#Cc1cccc(B(O)O)c1] | 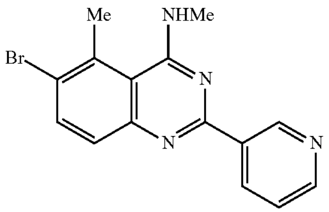 [SMILES: CNc1nc(-c2cccnc2)nc2ccc(Br)c(C)c12] | 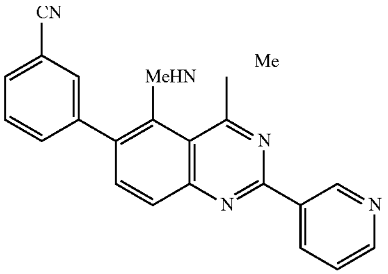 [SMILES: CNc1c(-c2cccc(C#N)c2)ccc2nc(-c3cccnc3)nc(C)c12] |
| 1424 | 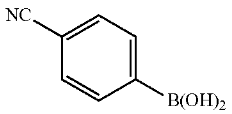 | 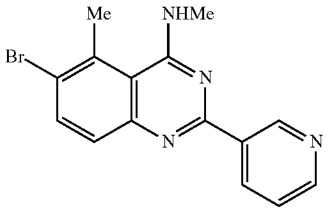 [SMILES: CNc1nc(-c2cccnc2)nc2ccc(Br)c(C)c12] | 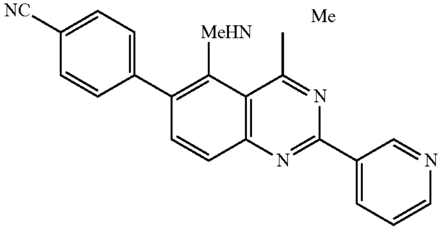 [SMILES: CNc1c(-c2ccc(C#N)cc2)ccc2nc(-c3cccnc3)nc(C)c12] |

TABLE 24-continued
| | | | |
|---|---|---|---|
| 1425 | 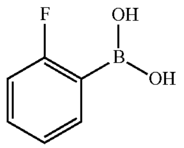 | 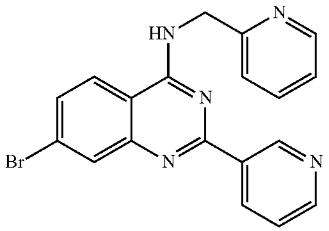 [SMILES: Brc1ccc2c(NCc3ccccn3)nc(-c3cccnc3)nc2c1] | 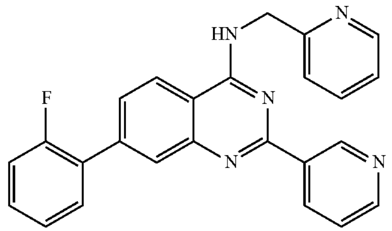 [SMILES: Fc1ccccc1-c1ccc2c(NCc3ccccn3)nc(-c3cccnc3)nc2c1] |
| 1426 | 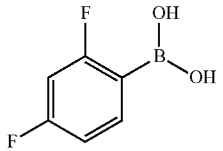 | 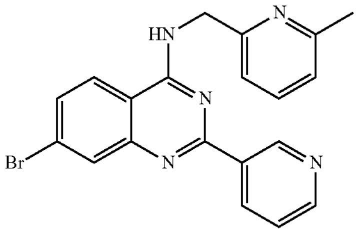 [SMILES: Cc1cccc(CNc2nc(-c3cccnc3)nc3cc(Br)ccc23)n1] | 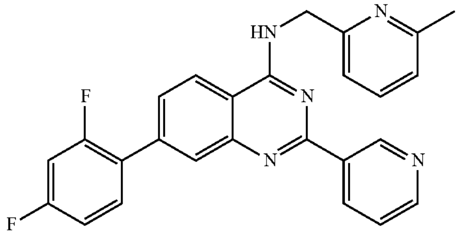 [SMILES: Cc1cccc(CNc2nc(-c3cccnc3)nc3cc(-c4ccc(F)cc4F)ccc23)n1] |
| 1427 | 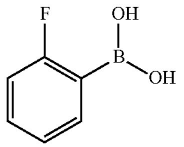 | 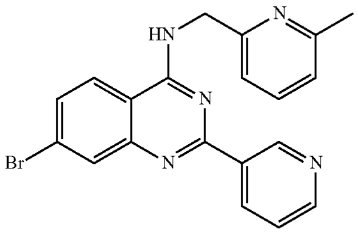 [SMILES: Cc1cccc(CNc2nc(-c3cccnc3)nc3cc(Br)ccc23)n1] | 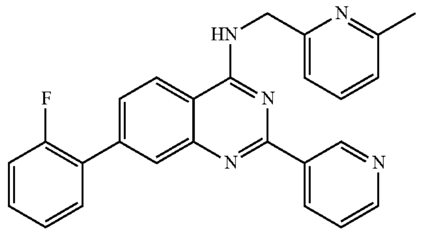 [SMILES: Cc1cccc(CNc2nc(-c3cccnc3)nc3cc(-c4ccccc4F)ccc23)n1] |
| 1428 | 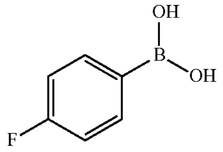 | 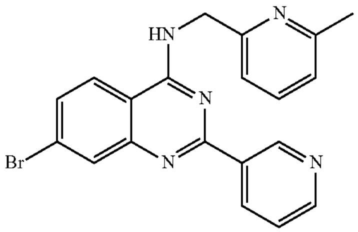 [SMILES: Cc1cccc(CNc2nc(-c3cccnc3)nc3cc(Br)ccc23)n1] | 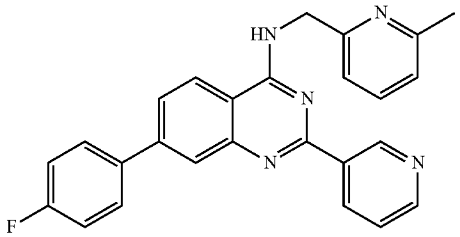 |

TABLE 24-continued
| | | | |
|---|---|---|---|
| 1429 | 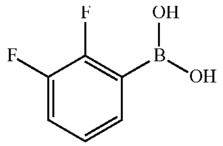 | 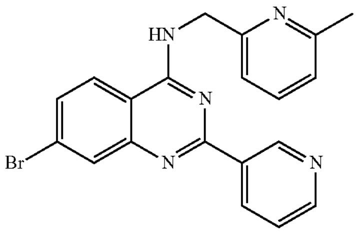 [SMILES: Cc1cccc(CNc2nc(-c3cccnc3)nc3cc(Br)ccc23)n1] | 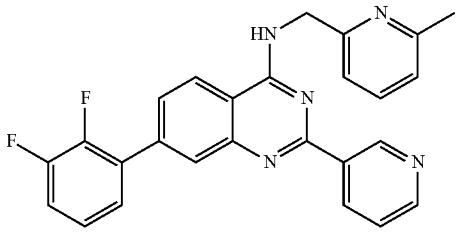 [SMILES: Cc1cccc(CNc2nc(-c3cccnc3)nc3cc(-c4cccc(F)c4F)ccc23)n1] |
| 1430 | 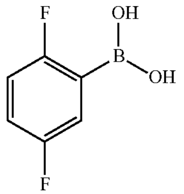 [SMILES: OB(O)c1cc(F)ccc1F] | 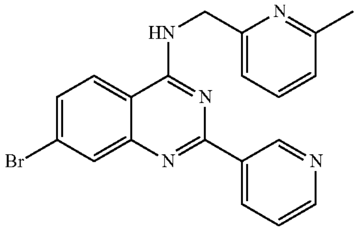 [SMILES: Cc1cccc(CNc2nc(-c3cccnc3)nc3cc(Br)ccc23)n1] | 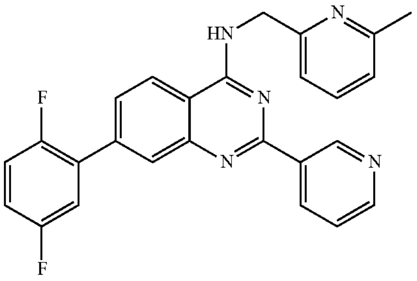 [SMILES: Cc1cccc(CNc2nc(-c3cccnc3)nc3cc(-c4cc(F)ccc4F)ccc23)n1] |
| 1431 | 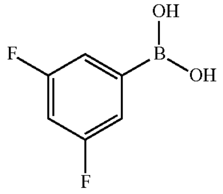 | 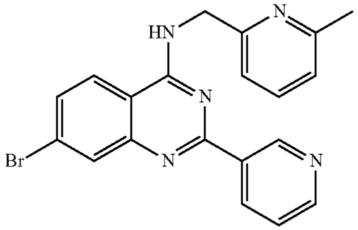 [SMILES: Cc1cccc(CNc2nc(-c3cccnc3)nc3cc(Br)ccc23)n1] | 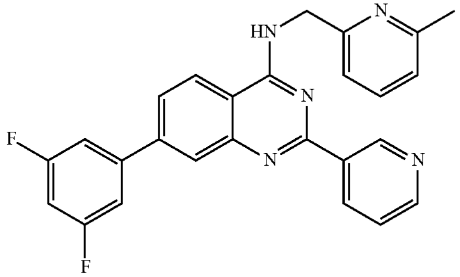 [SMILES: Cc1cccc(CNc2nc(-c3cccnc3)nc3cc(-c4cc(F)cc(F)c4)ccc23)n1] |
| 1432 | 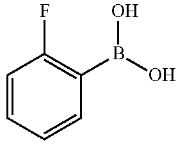 | 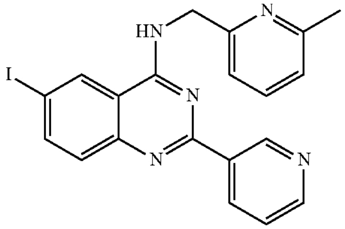 [SMILES: Cc1cccc(CNc2nc(-c3cccnc3)nc3ccc(I)cc23)n1] | 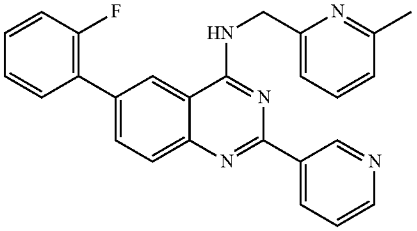 [SMILES: Cc1cccc(CNc2nc(-c3cccnc3)nc3ccc(-c4ccccc4F)cc23)n1] |

TABLE 24-continued
| | | | |
|---|---|---|---|
| 1433 | 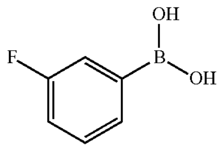 | 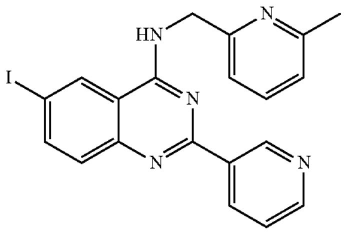 [SMILES: Cc1cccc(CNc2nc(-c3cccnc3)nc3ccc(I)cc23)n1] | 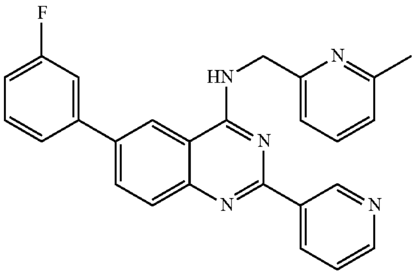 [SMILES: Cc1cccc(CNc2nc(-c3cccnc3)nc3ccc(-c4cccc(F)c4)cc23)n1] |
| 1434 | 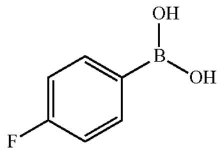 | 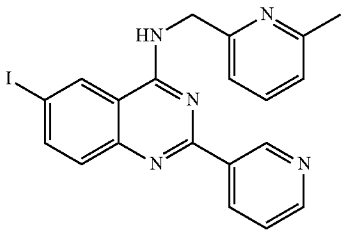 [SMILES: Cc1cccc(CNc2nc(-c3cccnc3)nc3ccc(I)cc23)n1] | 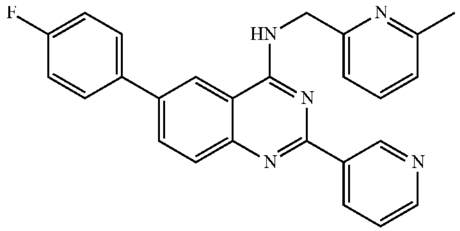 [SMILES: Cc1cccc(CNc2nc(-c3cccnc3)nc3ccc(-c4ccc(F)cc4)cc23)n1] |
| 1435 | 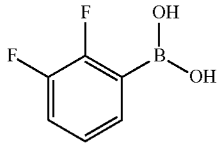 | 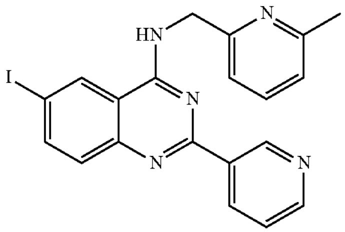 | 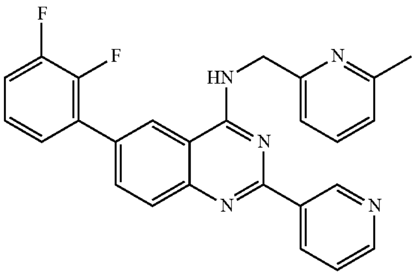 [SMILES: Cc1cccc(CNc2nc(-c3cccnc3)nc3ccc(-c4cccc(F)c4F)cc23)n1] |
| 1436 | 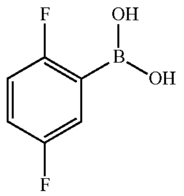 [SMILES: OB(O)c1cc(F)ccc1F] | 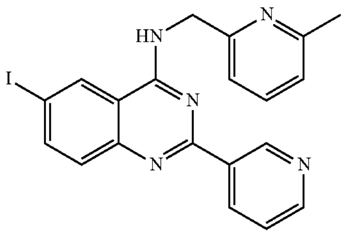 [SMILES: Cc1cccc(CNc2nc(-c3cccnc3)nc3ccc(I)cc23)n1] | 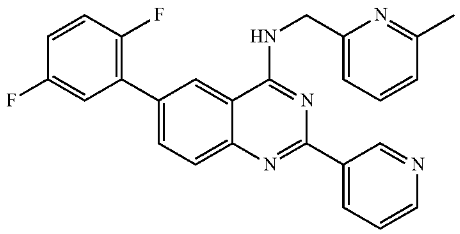 [SMILES: Cc1cccc(CNc2nc(-c3cccnc3)nc3ccc(-c4cc(F)ccc4F)cc23)n1] |

TABLE 24-continued
| | | | |
|---|---|---|---|
| 1437 | 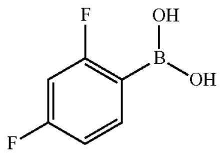 | 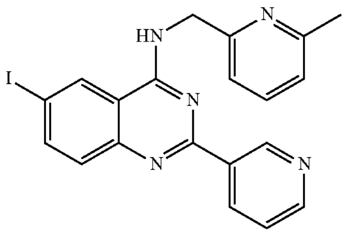 [SMILES: Cc1cccc(CNc2nc(-c3cccnc3)nc3ccc(I)cc23)n1] | 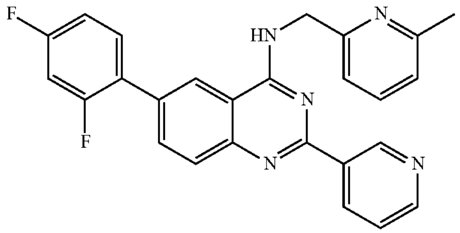 [SMILES: Cc1cccc(CNc2nc(-c3cccnc3)nc3ccc(-c4ccc(F)cc4F)cc23)n1] |
| 1438 | 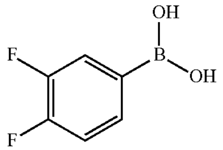 | 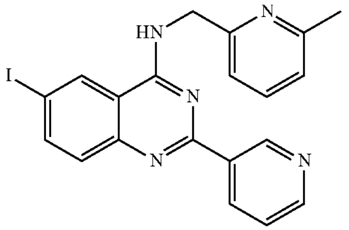 [SMILES: Cc1cccc(CNc2nc(-c3cccnc3)nc3ccc(I)cc23)n1] | 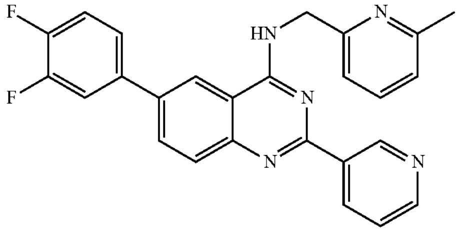 |
| 1439 | 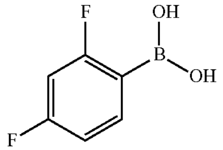 | 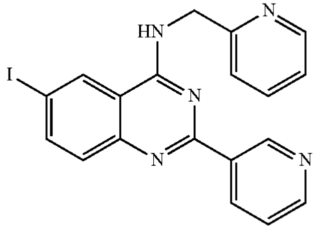 [SMILES: Ic1ccc2nc(-c3cccnc3)nc(NCc3ccccn3)c2c1] | 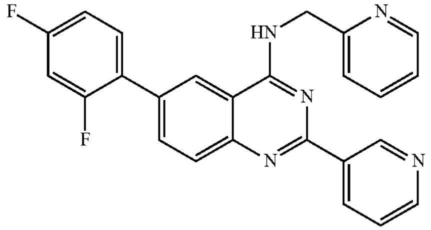 [SMILES: Fc1ccc(-c2ccc3nc(-c4cccnc4)nc(NCc4ccccn4)c3c2)c(F)c1] |
| 1440 | 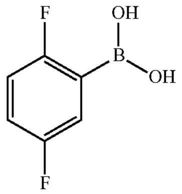 [SMILES: OB(O)c1cc(F)ccc1F] | 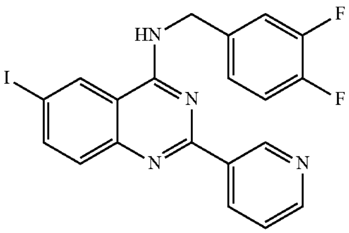 [SMILES: Fc1ccc(CNc2nc(-c3cccnc3)nc3ccc(I)cc23)cc1F] | 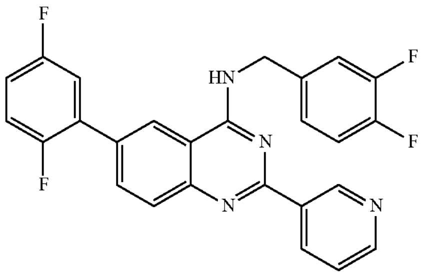 [SMILES: Fc1ccc(F)c(-c2ccc3nc(-c4cccnc4)nc(NCc4ccc(F)c(F)c4)c3c2)c1] |

TABLE 24-continued
| | | | |
|---|---|---|---|
| 1441 | 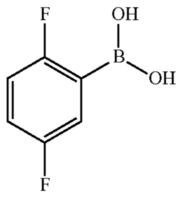 [SMILES: OB(O)c1cc(F)ccc1F] | 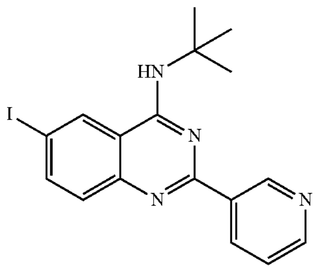 [SMILES: CC(C)(C)Nc1nc(-c2cccnc2)nc2ccc(I)cc12] | 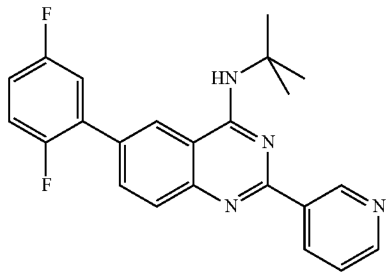 [SMILES: CC(C)(C)Nc1nc(-c2cccnc2)nc2ccc(-c3cc(F)ccc3F)cc12] |
| 1442 | 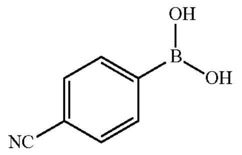 [SMILES: N#Cc1ccc(B(O)O)cc1] | 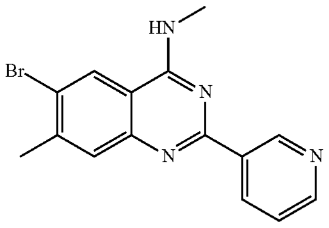 [SMILES: CNc1nc(-c2cccnc2)nc2cc(C)c(Br)cc12] | 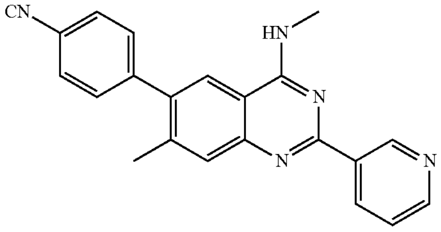 |
| 1443 | 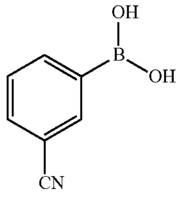 [SMILES: N#Cc1cccc(B(O)O)c1] | 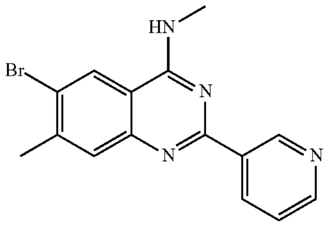 [SMILES: CNc1nc(-c2cccnc2)nc2cc(C)c(Br)cc12] | 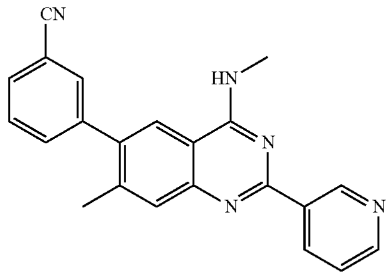 [SMILES: CNc1nc(-c2cccnc2)nc2cc(C)c(-c3cccc(C#N)c3)cc12] |
| 1444 | 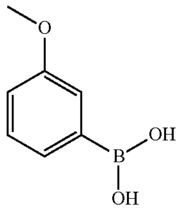 | 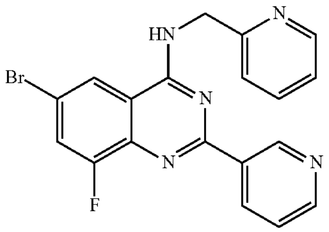 [SMILES: Fc1cc(Br)cc2c(NCc3ccccn3)nc(-c3cccnc3)nc12] | 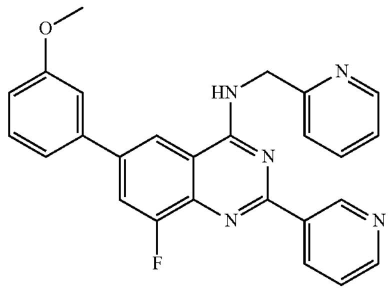 [SMILES: COc1cccc(-c2cc(F)c3nc(-c4cccnc4)nc(NCc4ccccn4)c3c2)c1] |

TABLE 24-continued
| | | | |
|---|---|---|---|
| 1445 | 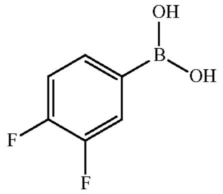 [SMILES: OB(O)c1ccc(F)c(F)c1] | 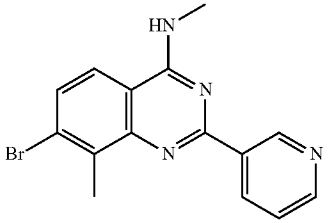 [SMILES: CNc1nc(-c2cccnc2)nc2c(C)c(Br)ccc12] | 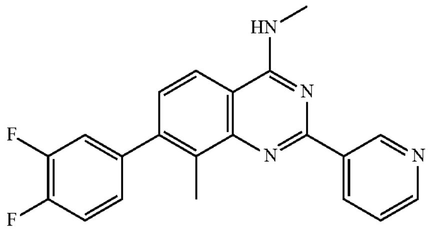 [SMILES: CNc1nc(-c2cccnc2)nc2c(C)c(-c3ccc(F)c(F)c3)ccc12] |
| 1446 | 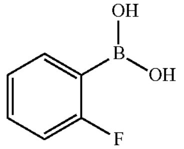 | 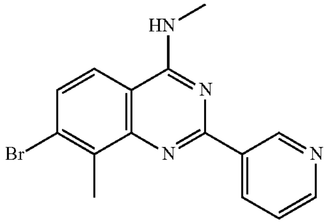 [SMILES: CNc1nc(-c2cccnc2)nc2c(C)c(Br)ccc12] | 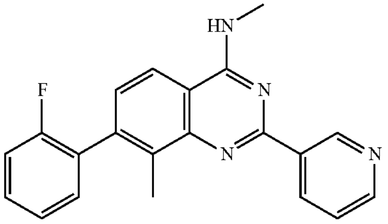 [SMILES: CNc1nc(-c2cccnc2)nc2c(C)c(-c3ccccc3F)ccc12] |
| 1447 | 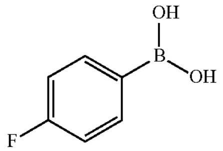 | 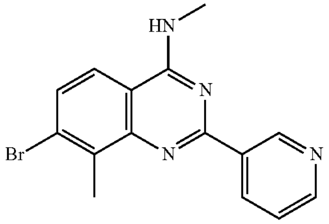 [SMILES: CNc1nc(-c2cccnc2)nc2c(C)c(Br)ccc12] | 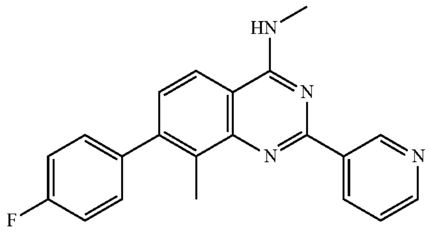 [SMILES: CNc1nc(-c2cccnc2)nc2c(C)c(-c3ccc(F)cc3)ccc12] |
| 1448 | 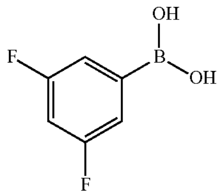 | 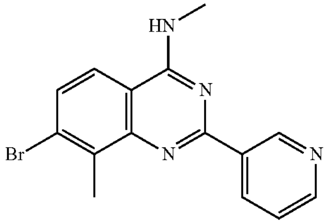 [SMILES: CNc1nc(-c2cccnc2)nc2c(C)c(Br)ccc12] | 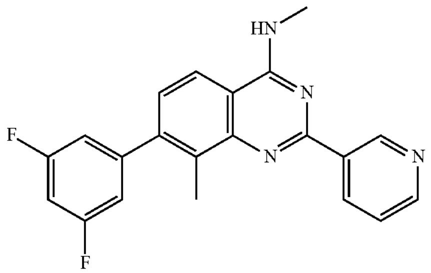 [SMILES: CNc1nc(-c2cccnc2)nc2c(C)c(-c3cc(F)cc(F)c3)ccc12] |

TABLE 24-continued
| | | | |
|---|---|---|---|
| 1449 | 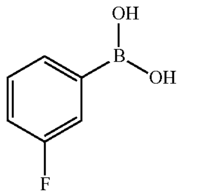 | 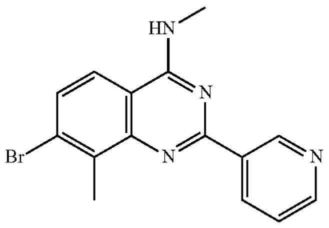 [SMILES: CNc1nc(-c2cccnc2)nc2c(C)c(Br)ccc12] | 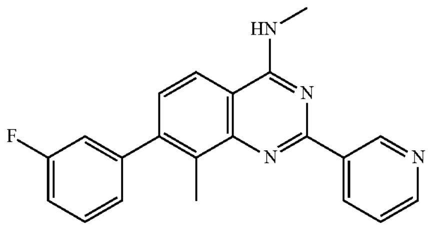 [SMILES: CNc1nc(-c2cccnc2)nc2c(C)c(-c3cccc(F)c3)ccc12] |
| 1450 | 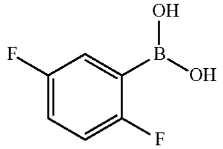 | 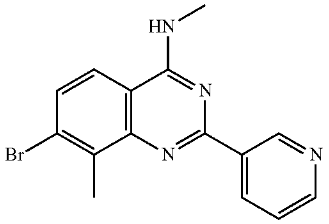 [SMILES: CNc1nc(-c2cccnc2)nc2c(C)c(Br)ccc12] | 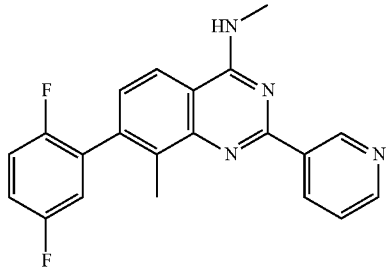 [SMILES: CNc1nc(-c2cccnc2)nc2c(C)c(-c3cc(F)ccc3F)ccc12] |
| 1451 | 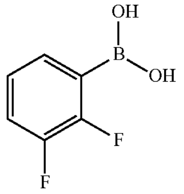 [SMILES: OB(O)c1cccc(F)c1F] | 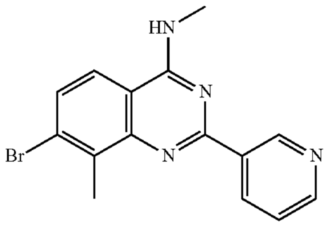 [SMILES: CNc1nc(-c2cccnc2)nc2c(C)c(Br)ccc12] | 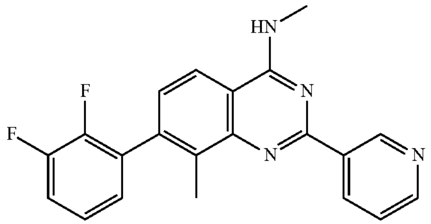 [SMILES: CNc1nc(-c2cccnc2)nc2c(C)c(-c3cccc(F)c3F)ccc12] |
| 1452 | 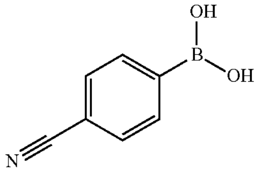 [SMILES: N#Cc1ccc(B(O)O)cc1] | 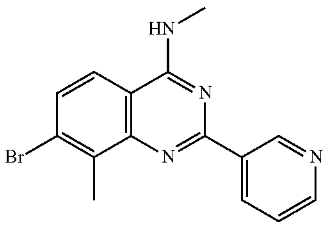 [SMILES: CNc1nc(-c2cccnc2)nc2c(C)c(Br)ccc12] | 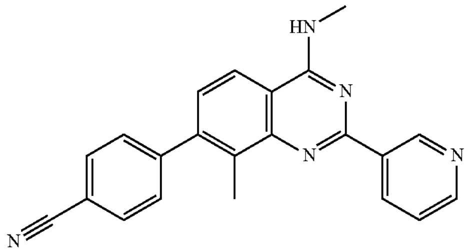 [SMILES: CNc1nc(-c2cccnc2)nc2c(C)c(-c3ccc(C#N)cc3)ccc12] |

TABLE 24-continued
| | | | |
|---|---|---|---|
| 1453 | 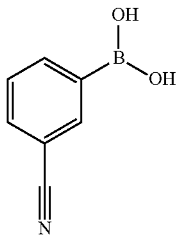 [SMILES: N#Cc1cccc(B(O)O)c1] | 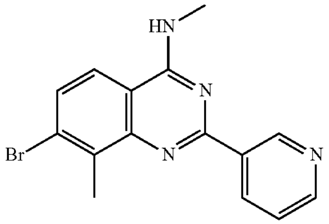 [SMILES: CNc1nc(-c2cccnc2)nc2c(C)c(Br)ccc12] | 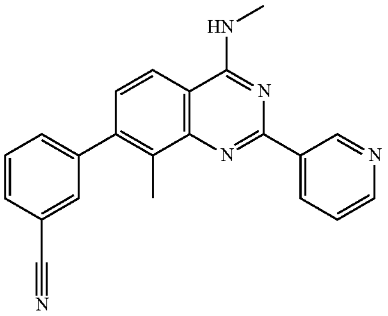 [SMILES: CNc1nc(-c2cccnc2)nc2c(C)c(-c3cccc(C#N)c3)ccc12] |
| 1454 | 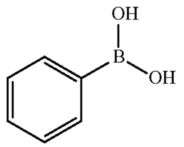 | 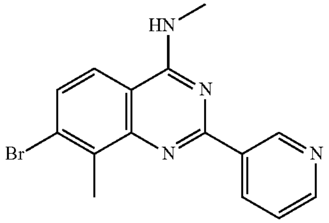 [SMILES: CNc1nc(-c2cccnc2)nc2c(C)c(Br)ccc12] | 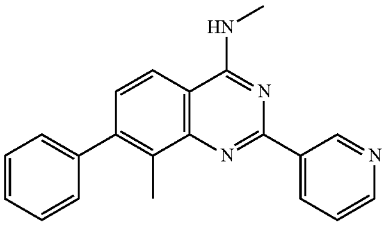 [SMILES: CNc1nc(-c2cccnc2)nc2c(C)c(-c3ccccc3)ccc12] |
| 1455 | 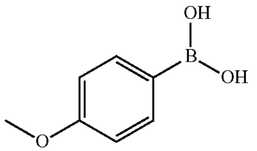 | 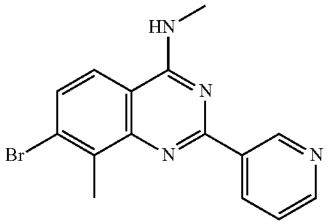 [SMILES: CNc1nc(-c2cccnc2)nc2c(C)c(Br)ccc12] | 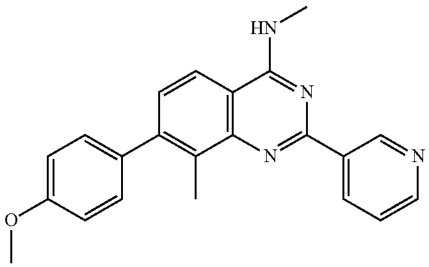 [SMILES: CNc1nc(-c2cccnc2)nc2c(C)c(-c3ccc(OC)cc3)ccc12] |

TABLE 24-continued
| | | | |
|---|---|---|---|
| 1456 | 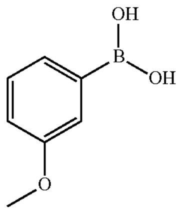 | 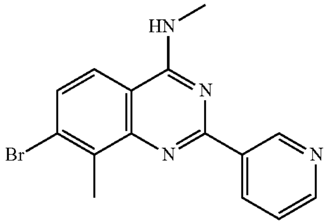 [SMILES: CNc1nc(-c2cccnc2)nc2c(C)c(Br)ccc12] | 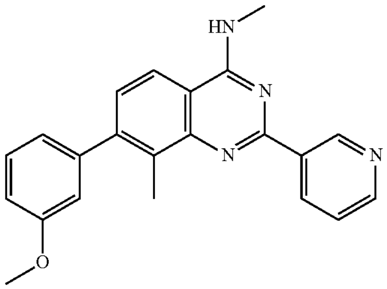 [SMILES: CNc1nc(-c2cccnc2)nc2c(C)c(-c3cccc(OC)c3)ccc12] |
| 1457 | 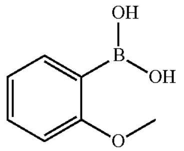 | 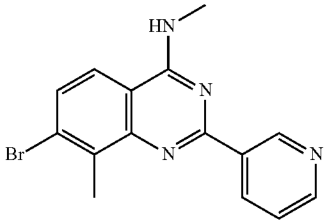 [SMILES: CNc1nc(-c2cccnc2)nc2c(C)c(Br)ccc12] | 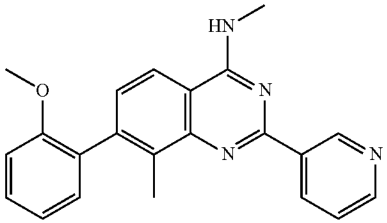 [SMILES: CNc1nc(-c2cccnc2)nc2c(C)c(-c3ccccc3OC)ccc12] |
| 1458 | 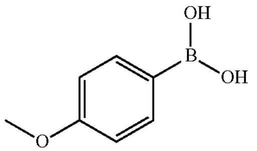 | 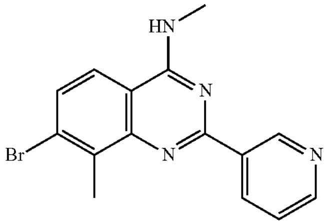 [SMILES: CNc1nc(-c2cccnc2)nc2c(C)c(Br)ccc12] | 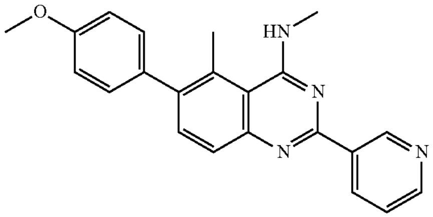 [SMILES: CNc1nc(-c2cccnc2)nc2ccc(-c3ccc(OC)cc3)c(C)c12] |
| 1459 | 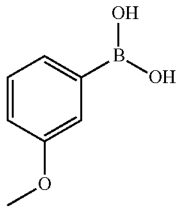 | 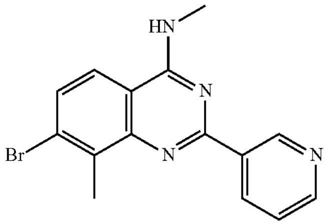 [SMILES: CNc1nc(-c2cccnc2)nc2c(C)c(Br)ccc12] | 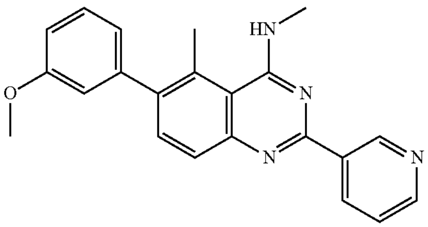 [SMILES: CNc1nc(-c2cccnc2)nc2ccc(-c3cccc(OC)c3)c(C)c12] |

TABLE 24-continued
| | | | |
|---|---|---|---|
| 1460 | 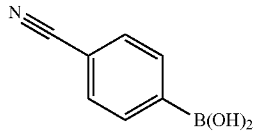 | 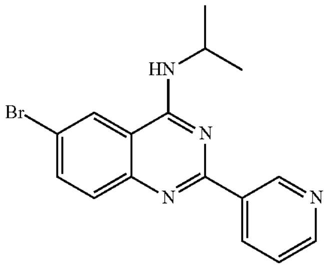 [SMILES: CC(C)Nc1nc(-c2cccnc2)nc2ccc(Br)cc12] | 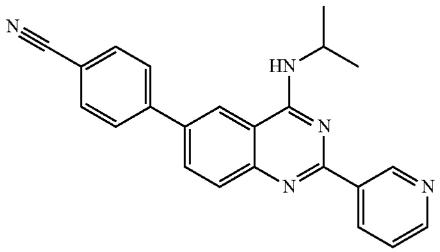 [SMILES: CC(C)Nc1nc(-c2cccnc2)nc2ccc(-c3ccc(C#N)cc3)cc12] |
| 1461 | 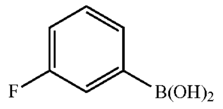 | 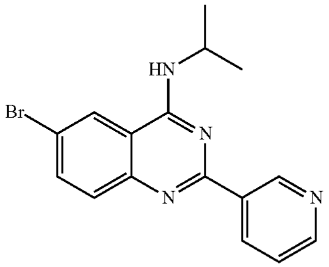 [SMILES: CC(C)Nc1nc(-c2cccnc2)nc2ccc(Br)cc12] | 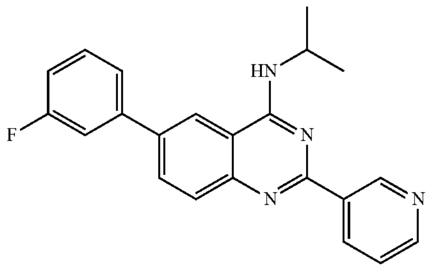 [SMILES: CC(C)Nc1nc(-c2cccnc2)nc2ccc(-c3cccc(F)c3)cc12] |
| 1462 | 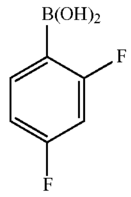 [SMILES: OB(O)c1ccc(F)cc1F] | 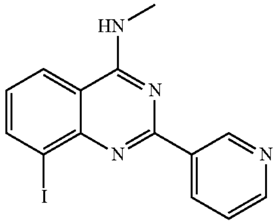 [SMILES: CNc1nc(-c2cccnc2)nc2c(I)cccc12] | 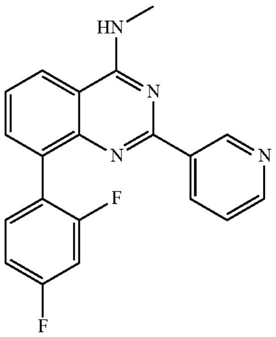 [SMILES: CNc1nc(-c2cccnc2)nc2c(-c3ccc(F)cc3F)cccc12] |

TABLE 24-continued
| | |
|---|---|
| 1463 | 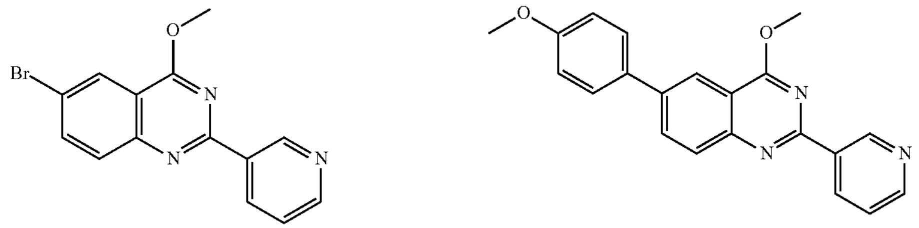 |
| 1464 | 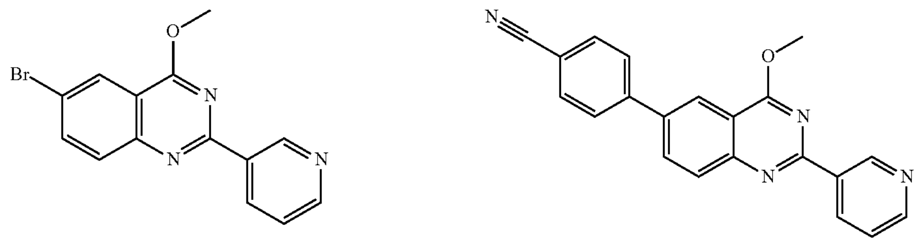 |
| 1465 | 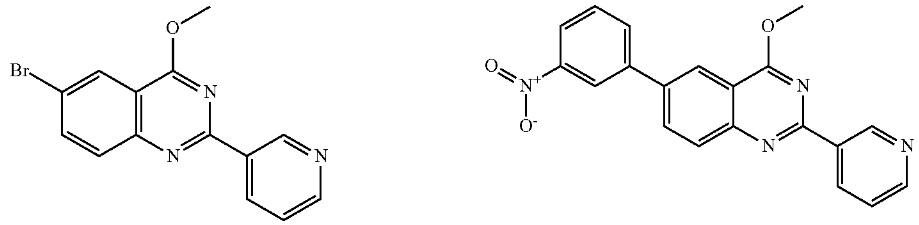 |
| 1466 | 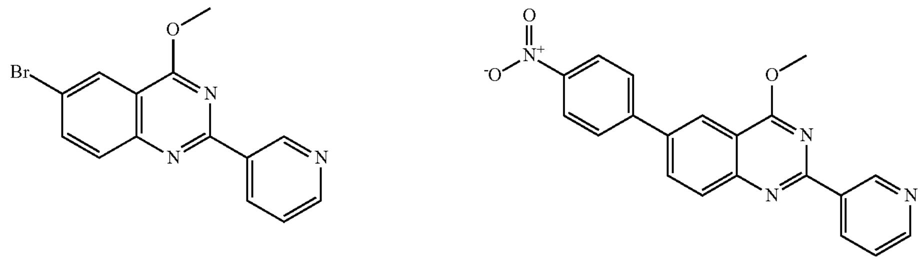 |

TABLE 24-continued
| | | |
|---|---|---|
| 1467 | 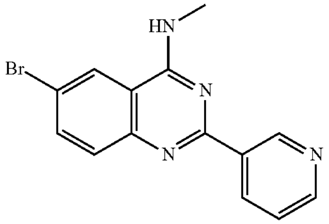 [SMILES: CNc1nc(-c2cccnc2)nc2ccc(Br)cc12] | 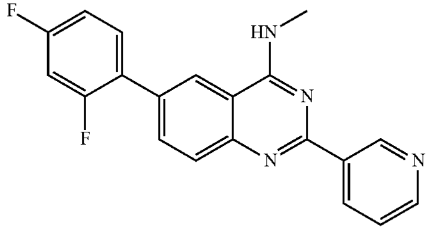 [SMILES: CNc1nc(-c2cccnc2)nc2ccc(-c3ccc(F)cc3F)cc12] |
| 1468 | 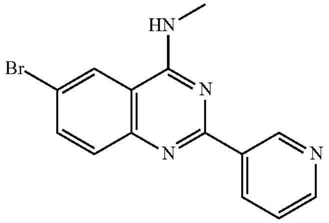 [SMILES: CNc1nc(-c2cccnc2)nc2ccc(Br)cc12] | 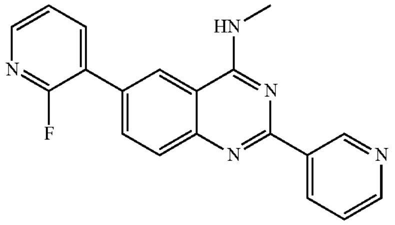 [SMILES: CNc1nc(-c2cccnc2)nc2ccc(-c3cccnc3F)cc12] |
| 1469 | 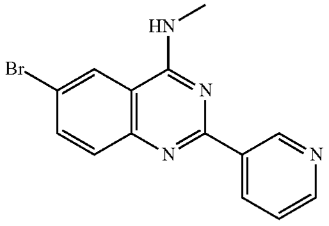 [SMILES: CNc1nc(-c2cccnc2)nc2ccc(Br)cc12] | 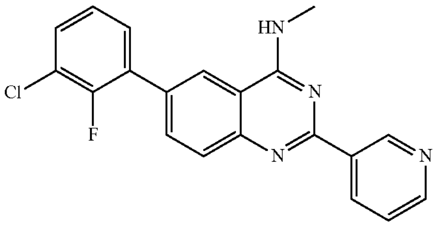 [SMILES: CNc1nc(-c2cccnc2)nc2ccc(-c3cccc(Cl)c3F)cc12] |
| 1470 | 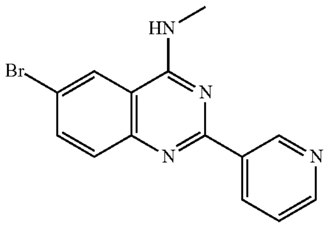 | 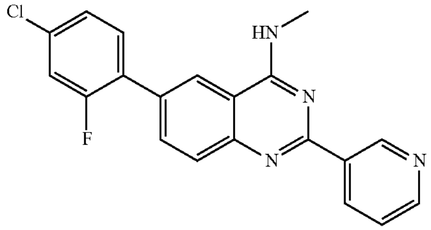 [SMILES: CNc1nc(-c2cccnc2)nc2ccc(-c3ccc(Cl)cc3F)cc12] |

TABLE 24-continued
| | | |
|---|---|---|
| 1471 | 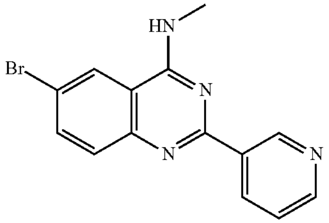 [SMILES: CNc1nc(-c2cccnc2)nc2ccc(Br)cc12] | 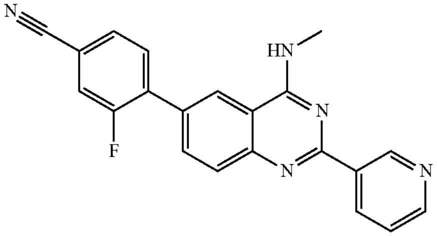 [SMILES: CNc1nc(-c2cccnc2)nc2ccc(-c3ccc(C#N)cc3F)cc12] |
| 1472 | 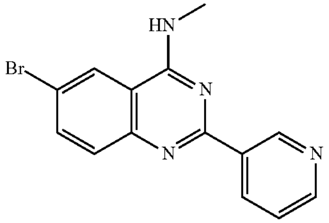 [SMILES: CNc1nc(-c2cccnc2)nc2ccc(Br)cc12] | 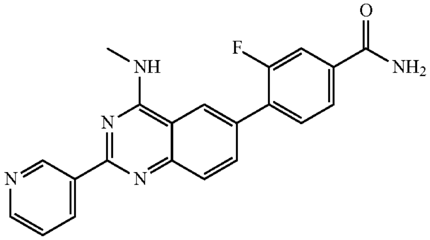 [SMILES: CNc1nc(-c2cccnc2)nc2ccc(-c3ccc(C(N)=O)cc3F)cc12] |
| 1473 | 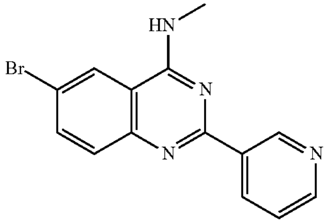 [SMILES: CNc1nc(-c2cccnc2)nc2ccc(Br)cc12] | 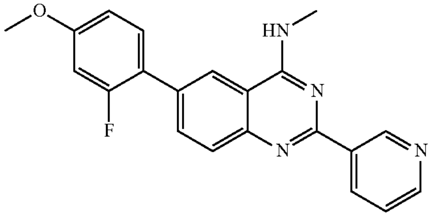 [SMILES: CNc1nc(-c2cccnc2)nc2ccc(-c3ccc(OC)cc3F)cc12] |
| 1474 | 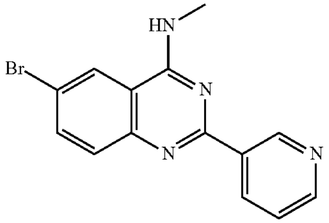 [SMILES: CNc1nc(-c2cccnc2)nc2ccc(Br)cc12] | 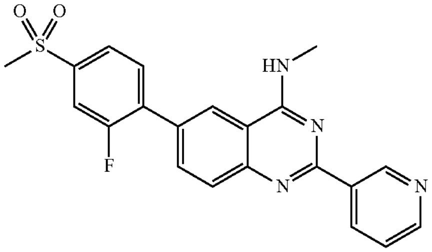 [SMILES: CNc1nc(-c2cccnc2)nc2ccc(-c3ccc(S(C)(=O)=O)cc3F)cc12] |

TABLE 24-continued
| | | |
|---|---|---|
| 1475 | 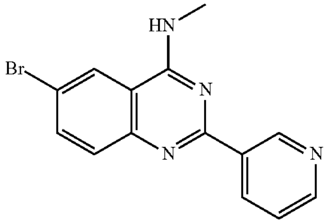 [SMILES: CNc1nc(-c2cccnc2)nc2ccc(Br)cc12] | 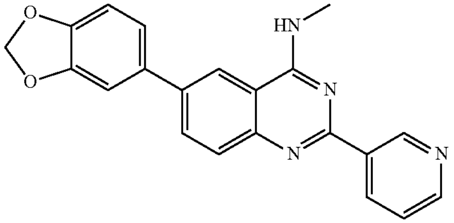 [SMILES: CNc1nc(-c2cccnc2)nc2ccc(-c3ccc4c(c3)OCO4)cc12] |
| 1476 | 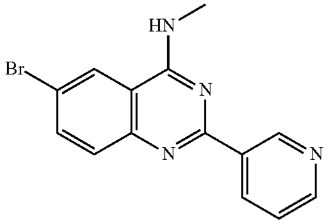 [SMILES: CNc1nc(-c2cccnc2)nc2ccc(Br)cc12] | 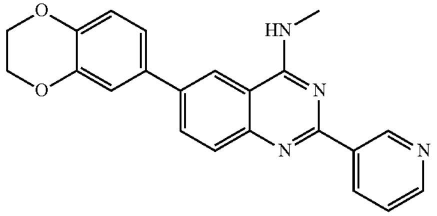 [SMILES: CNc1nc(-c2cccnc2)nc2ccc(-c3ccc4c(c3)OCCO4)cc12] |
| 1477 | 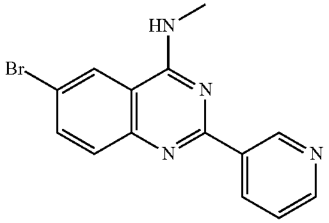 [SMILES: CNc1nc(-c2cccnc2)nc2ccc(Br)cc12] | 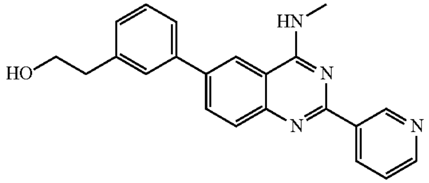 [SMILES: CNc1nc(-c2cccnc2)nc2ccc(-c3cccc(CCO)c3)cc12] |
| 1478 | 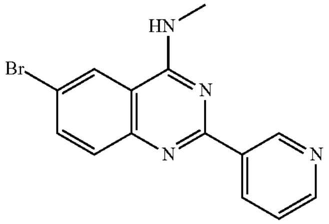 [SMILES: CNc1nc(-c2cccnc2)nc2ccc(Br)cc12] | 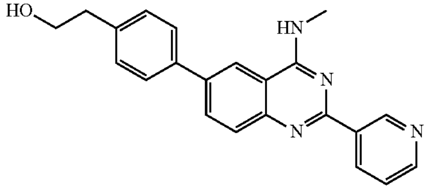 [SMILES: CNc1nc(-c2cccnc2)nc2ccc(-c3ccc(CCO)cc3)cc12] |

TABLE 24-continued
| | | | |
|---|---|---|---|
| 1479 | | 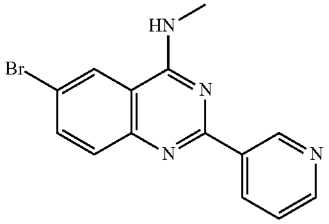 [SMILES: CNc1nc(-c2cccnc2)nc2ccc(Br)cc12] | 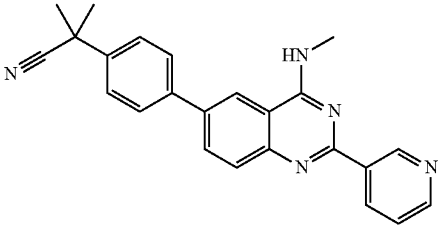 [SMILES: CNc1nc(-c2cccnc2)nc2ccc(-c3ccc(C(C)(C)C#N)cc3)cc12] |
| 1480 | | 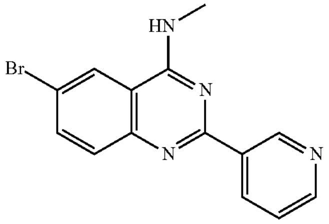 [SMILES: CNc1nc(-c2cccnc2)nc2ccc(Br)cc12] | 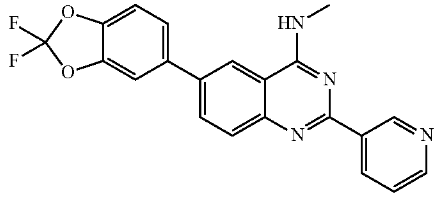 [SMILES: CNc1nc(-c2cccnc2)nc2ccc(-c3ccc4c(c3)OC(F)(F)O4)cc12] |
| 1481 | 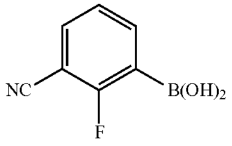 [SMILES: N#Cc1cccc(B(O)O)c1F] | 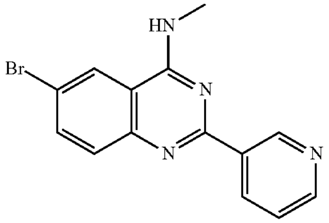 [SMILES: CNc1nc(-c2cccnc2)nc2ccc(Br)cc12] | 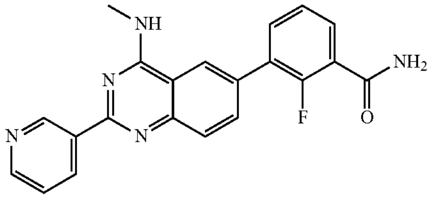 [SMILES: CNc1nc(-c2cccnc2)nc2ccc(-c3cccc(C(N)=O)c3F)cc12] |
| 1482 | | | 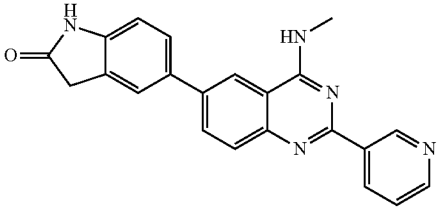 [SMILES: CNc1nc(-c2cccnc2)nc2ccc(-c3ccc4c(c3)CC(=O)N4)cc12] |

TABLE 24-continued
| | |
|---|---|
| 1483 | 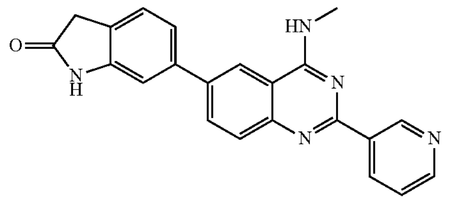 [SMILES: CNc1nc(-c2cccnc2)nc2ccc(-c3ccc4c(c3)NC(=O)C4)cc12] |
| 1484 | 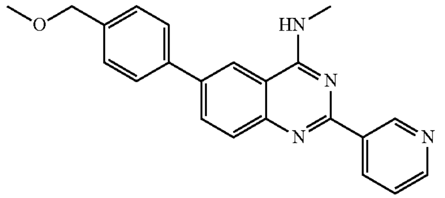 [SMILES: CNc1nc(-c2cccnc2)nc2ccc(-c3ccc(COC)cc3)cc12] |
| 1485 | 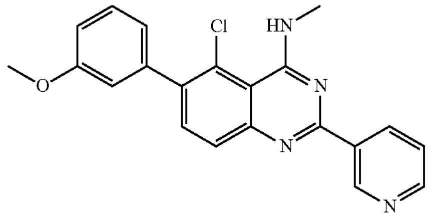 [SMILES: CNc1nc(-c2cccnc2)nc2ccc(-c3cccc(OC)c3)c(Cl)c12] |
| 1486 | 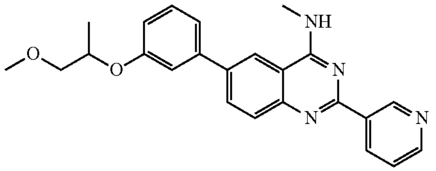 [SMILES: CNc1nc(-c2cccnc2)nc2ccc(-c3cccc(OC(C)COC)c3)cc12] |
| 1487 | 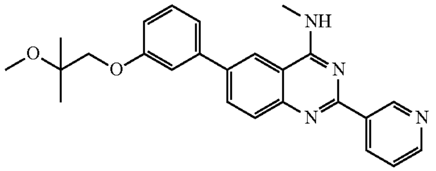 [SMILES: CNc1nc(-c2cccnc2)nc2ccc(-c3cccc(OCC(C)(C)OC)c3)cc12] |

TABLE 24-continued
| | |
|---|---|
| 1488 | 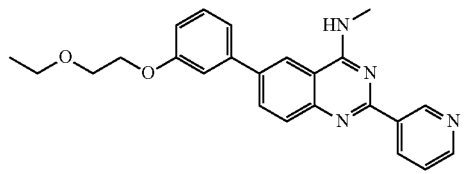 [SMILES: CCOCCOc1cccc(-c2ccc3nc(-c4cccnc4)nc(NC)c3c2)c1] |
| 1489 | 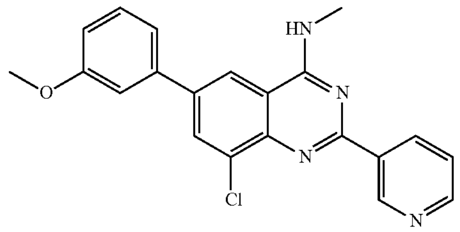 [SMILES: CNc1nc(-c2cccnc2)nc2c(Cl)cc(-c3cccc(OC)c3)cc12] |
| 1490 | 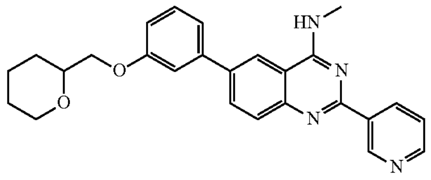 [SMILES: CNc1nc(-c2cccnc2)nc2ccc(-c3cccc(OCC4CCCCO4)c3)cc12] |
| 1492 | 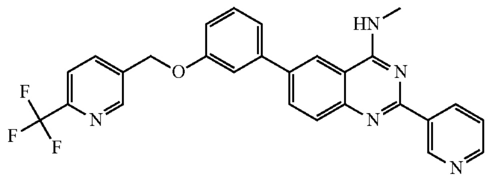 [SMILES: CNc1nc(-c2cccnc2)nc2ccc(-c3cccc(OCc4ccc(C(F)(F)F)nc4)c3)cc12] |
| 1493 | 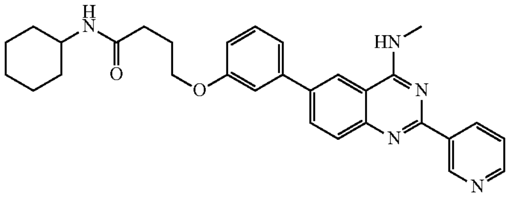 [SMILES: CNc1nc(-c2cccnc2)nc2ccc(-c3cccc(OCCCC(=O)NC4CCCCC4)c3)cc12] |

TABLE 24-continued
| | |
|---|---|
| 1494 | 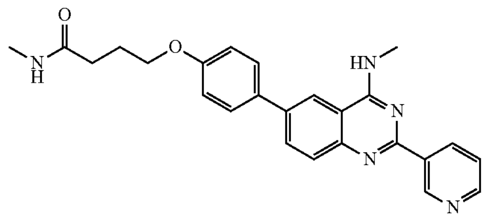 [SMILES: CNC(=O)CCCOc1ccc(-c2ccc3nc(-c4cccnc4)nc(NC)c3c2)cc1] |
| 1495 | 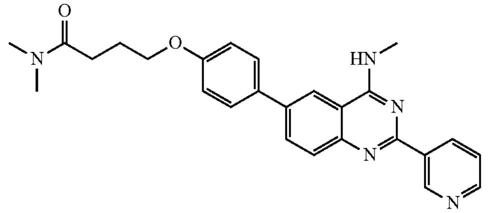 [SMILES: CNc1nc(-c2cccnc2)nc2ccc(-c3ccc(OCCCC(=O)N(C)C)cc3)cc12] |
| 1496 | 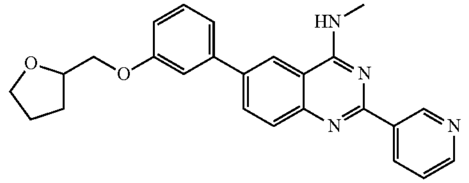 [SMILES: CNc1nc(-c2cccnc2)nc2ccc(-c3cccc(OCC4CCCO4)c3)cc12] |
| 1497 | 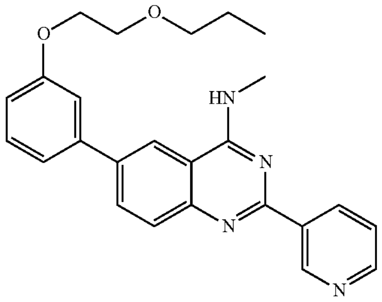 [SMILES: CCCOCCOc1cccc(-c2ccc3nc(-c4cccnc4)nc(NC)c3c2)c1] |

TABLE 24-continued
| | |
|---|---|
| 1498 | 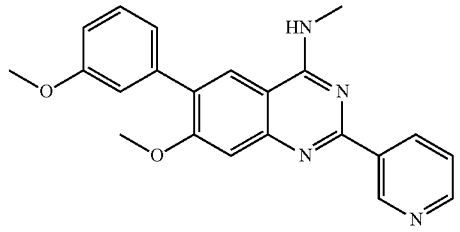 [SMILES: CNc1nc(-c2cccnc2)nc2cc(OC)c(-c3cccc(OC)c3)cc12] |
| 1499 | 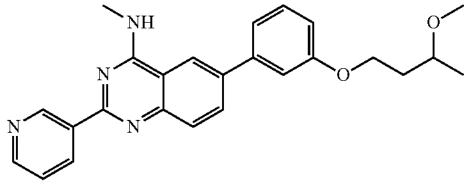 [SMILES: CNc1nc(-c2cccnc2)nc2ccc(-c3cccc(OCCC(C)OC)c3)cc12] |
| 1500 | 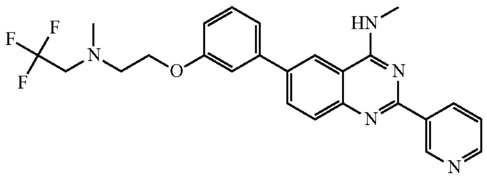 [SMILES: CNc1nc(-c2cccnc2)nc2ccc(-c3cccc(OCCN(C)CC(F)(F)F)c3)cc12] |
| 1501 | 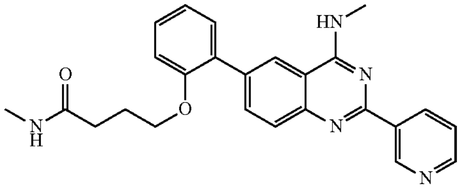 [SMILES: CNC(=O)CCCOc1ccccc1-c1ccc2nc(-c3cccnc3)nc(NC)c2c1] |
| 1502 | 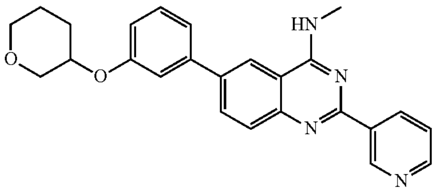 [SMILES: CNc1nc(-c2cccnc2)nc2ccc(-c3cccc(OC4CCCOC4)c3)cc12] |

TABLE 24-continued
| | |
|---|---|
| 1503 | 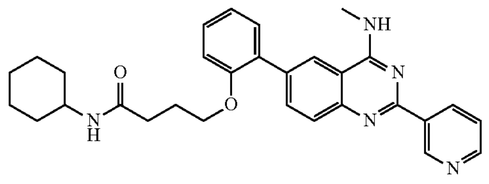 [SMILES: CNc1nc(-c2cccnc2)nc2ccc(-c3ccccc3OCCCC(=O)NC3CCCCC3)cc12] |
| 1504 | 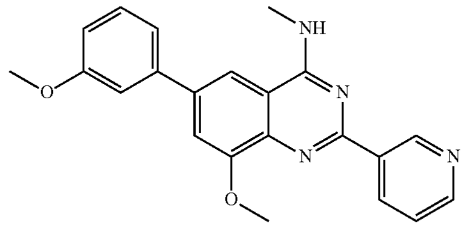 [SMILES: CNc1nc(-c2cccnc2)nc2c(OC)cc(-c3cccc(OC)c3)cc12] |
| 1505 | 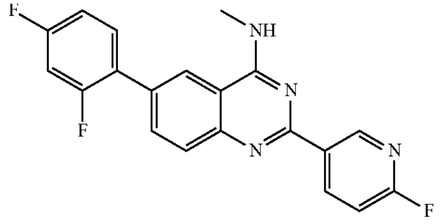 [SMILES: CNc1nc(-c2ccc(F)nc2)nc2ccc(-c3ccc(F)cc3F)cc12] |
| 1506 | 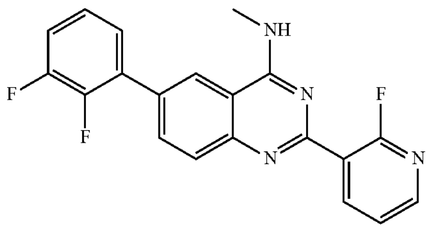 |
| 1507 | 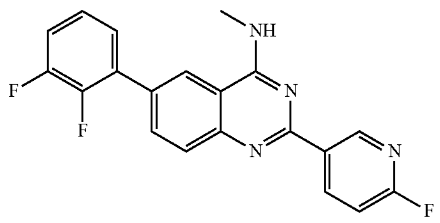 [SMILES: CNc1nc(-c2ccc(F)nc2)nc2ccc(-c3cccc(F)c3F)cc12] |

TABLE 24-continued
| | |
|---|---|
| 1508 | 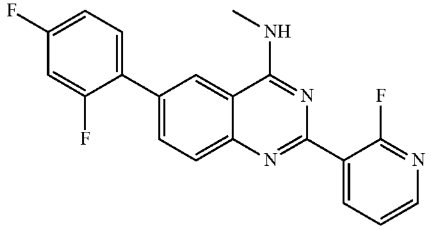 [SMILES: CNc1nc(-c2cccnc2F)nc2ccc(-c3ccc(F)cc3F)cc12] |
| 1509 | 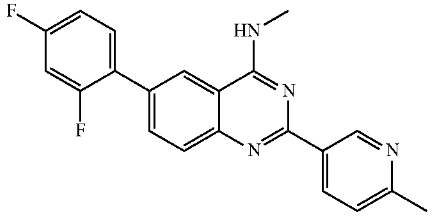 [SMILES: CNc1nc(-c2ccc(C)nc2)nc2ccc(-c3ccc(F)cc3F)cc12] |
| 1510 | 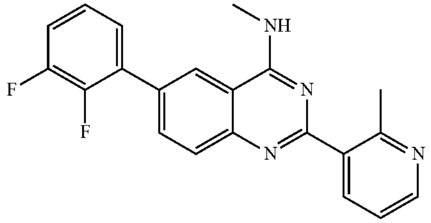 [SMILES: CNc1nc(-c2cccnc2C)nc2ccc(-c3cccc(F)c3F)cc12] |
| 1511 | 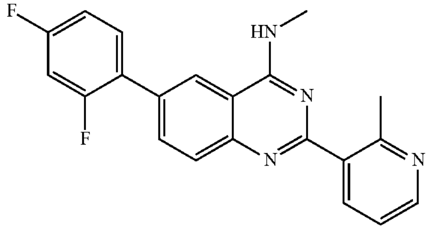 [SMILES: CNc1nc(-c2cccnc2C)nc2ccc(-c3ccc(F)cc3F)cc12] |

TABLE 24-continued
| | |
|---|---|
| 1512 | 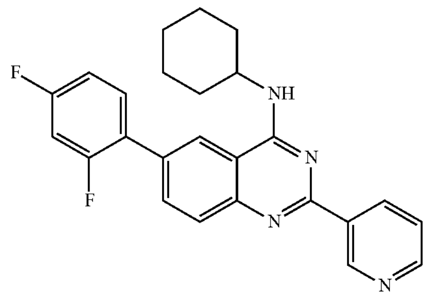 [SMILES: Fc1ccc(-c2ccc3nc(-c4cccnc4)nc(NC4CCCCC4)c3c2)c(F)c1] |
| 1513 | 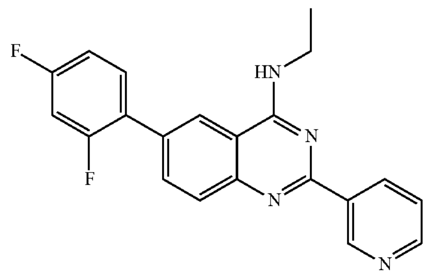 [SMILES: CCNc1nc(-c2cccnc2)nc2ccc(-c3ccc(F)cc3F)cc12] |
| 1514 | 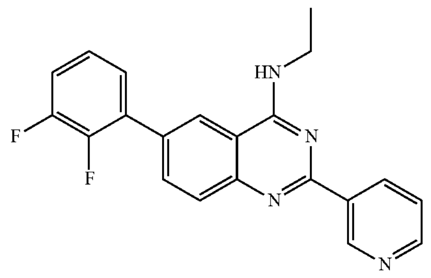 [SMILES: CCNc1nc(-c2cccnc2)nc2ccc(-c3cccc(F)c3F)cc12] |

TABLE 24-continued
| | |
|---|---|
| 1515 | 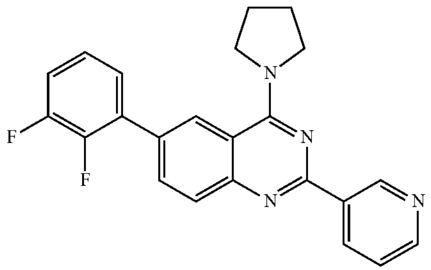 [SMILES: Fc1cccc(-c2ccc3nc(-c4cccnc4)nc(N4CCCC4)c3c2)c1F] |
| 1516 | 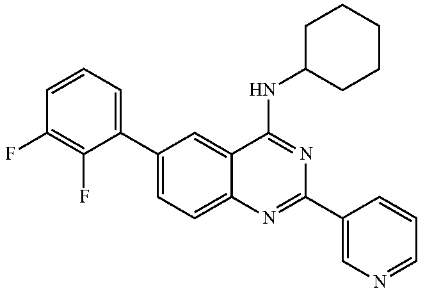 [SMILES: Fc1cccc(-c2ccc3nc(-c4cccnc4)nc(NC4CCCCC4)c3c2)c1F] |
| 1517 | 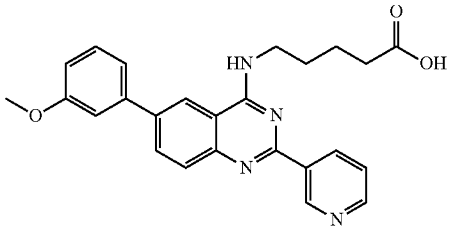 [SMILES: COc1cccc(-c2ccc3nc(-c4cccnc4)nc(NCCCCC(=O)O)c3c2)c1] |
| 1518 | 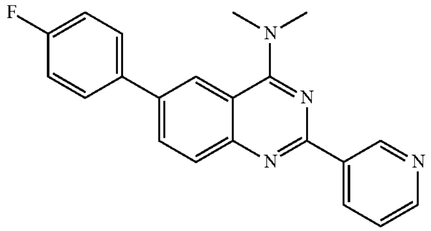 [SMILES: CN(C)c1nc(-c2cccnc2)nc2ccc(-c3ccc(F)cc3)cc12] |

TABLE 24-continued
| | |
|---|---|
| 1519 | 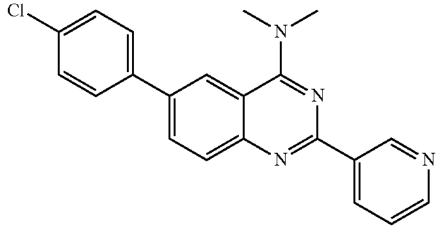 [SMILES: CN(C)c1nc(-c2cccnc2)nc2ccc(-c3ccc(Cl)cc3)cc12] |
| 1520 | 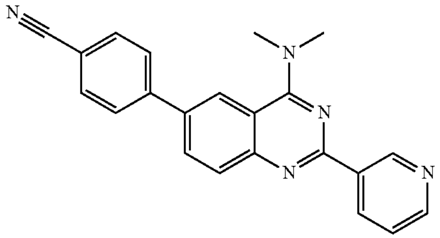 [SMILES: CN(C)c1nc(-c2cccnc2)nc2ccc(-c3ccc(C#N)cc3)cc12] |
| 1521 | 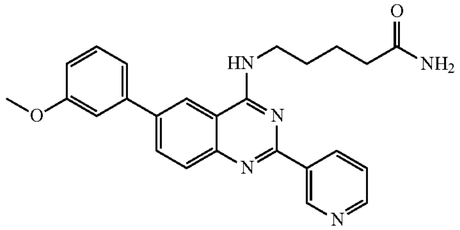 [SMILES: COc1cccc(-c2ccc3nc(-c4cccnc4)nc(NCCCCC(N)=O)c3c2)c1] |
| 1522 | 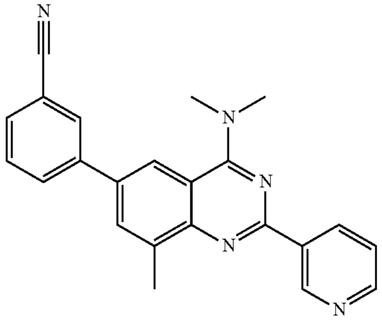 [SMILES: Cc1cc(-c2cccc(C#N)c2)cc2c(N(C)C)nc(-c3cccnc3)nc12] |

TABLE 24-continued
| | |
|---|---|
| 1523 | 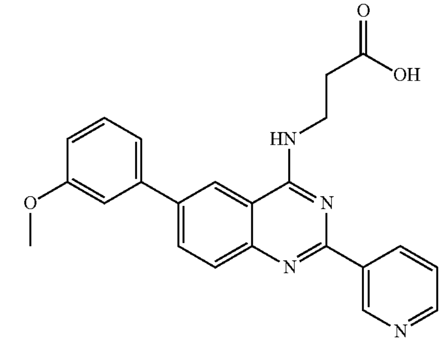 [SMILES: COc1cccc(-c2ccc3nc(-c4cccnc4)nc(NCCC(=O)O)c3c2)c1] |
| 1524 | 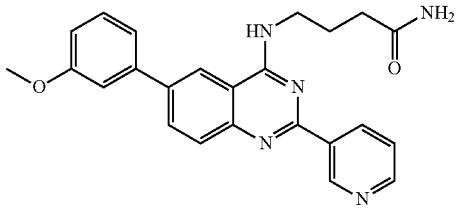 [SMILES: COc1cccc(-c2ccc3nc(-c4cccnc4)nc(NCCCC(N)=O)c3c2)c1] |
| 1525 | 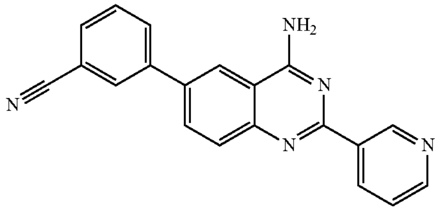 [SMILES: N#Cc1cccc(-c2ccc3nc(-c4cccnc4)nc(N)c3c2)c1] |
| 1526 | 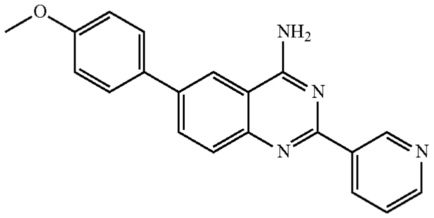 [SMILES: COc1ccc(-c2ccc3nc(-c4cccnc4)nc(N)c3c2)cc1] |

TABLE 24-continued
| | |
|---|---|
| 1527 | 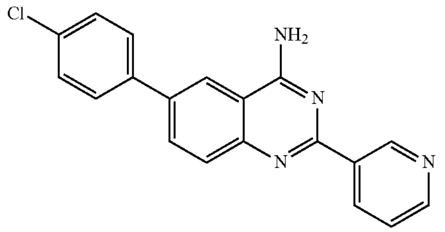 [SMILES: Nc1nc(-c2cccnc2)nc2ccc(-c3ccc(Cl)cc3)cc12] |
| 1528 | 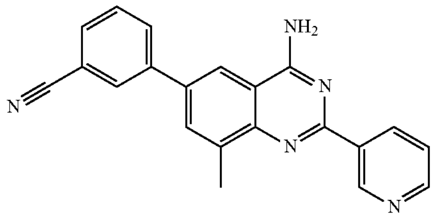 [SMILES: Cc1cc(-c2cccc(C#N)c2)cc2c(N)nc(-c3cccnc3)nc12] |
| 1529 | 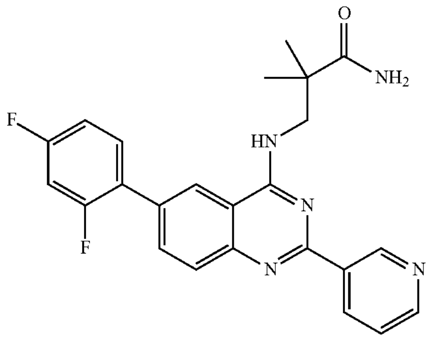 [SMILES: CC(C)(CNc1nc(-c2cccnc2)nc2ccc(-c3ccc(F)cc3F)cc12)C(N)=O] |
| 1530 | 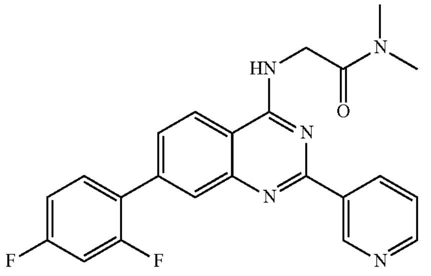 [SMILES: CN(C)C(=O)CNc1nc(-c2cccnc2)nc2cc(-c3ccc(F)cc3F)ccc12] |

TABLE 24-continued
| | |
|---|---|
| 1531 | 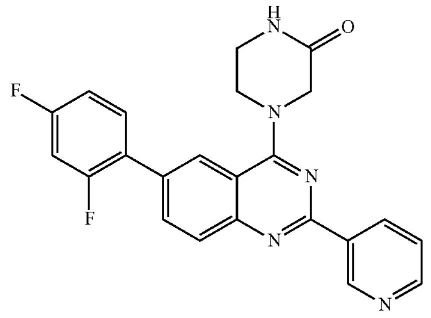 [SMILES: O=C1CN(c2nc(-c3cccnc3)nc3ccc(-c4ccc(F)cc4F)cc23)CCN1] |
| 1532 | 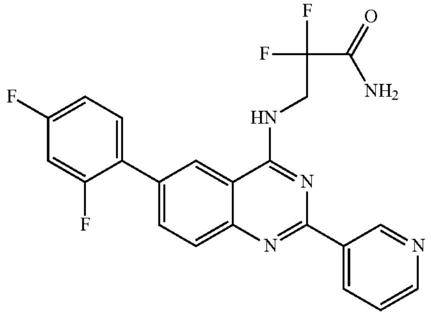 [SMILES: NC(=O)C(F)(F)CNc1nc(-c2cccnc2)nc2ccc(-c3ccc(F)cc3F)cc12] |
| 1533 | 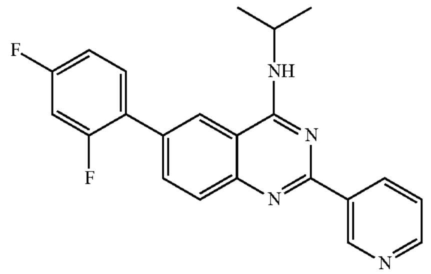 [SMILES: CC(C)Nc1nc(-c2cccnc2)nc2ccc(-c3ccc(F)cc3F)cc12] |

TABLE 24-continued
| | |
|---|---|
| 1534 | 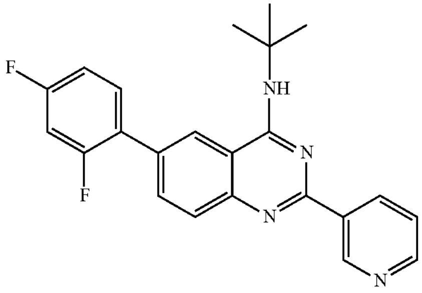 [SMILES: CC(C)(C)Nc1nc(-c2cccnc2)nc2ccc(-c3ccc(F)cc3F)cc12] |
| 1535 | 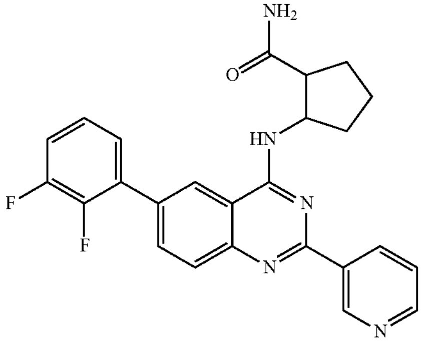 [SMILES: NC(=O)C1CCCC1Nc1nc(-c2cccnc2)nc2ccc(-c3cccc(F)c3F)cc12] |
| 1536 | 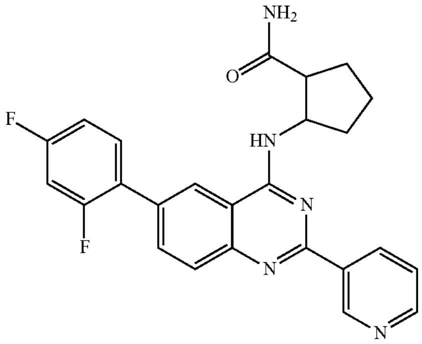 [SMILES: NC(=O)C1CCCC1Nc1nc(-c2cccnc2)nc2ccc(-c3ccc(F)cc3F)cc12] |

TABLE 24-continued
| | |
|---|---|
| 1537 | 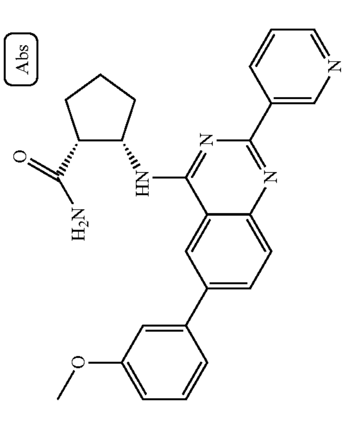 |
| 1538 | 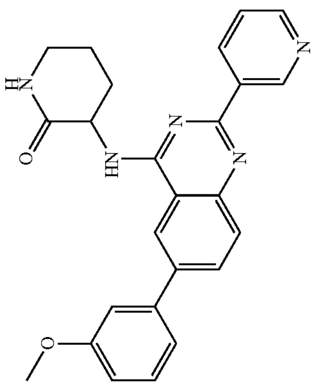 |
| 1539 | 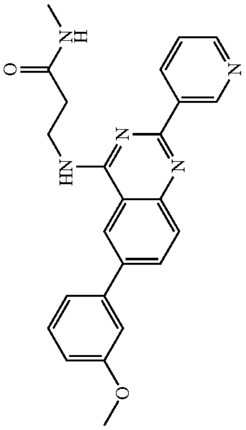 |

TABLE 24-continued
| | |
|---|---|
| 1540 | 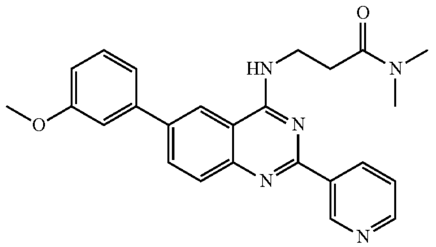 |
| 1541 | 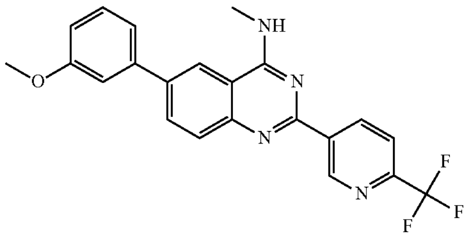 [SMILES: CNc1nc(-c2ccc(C(F)(F)F)nc2)nc2ccc(-c3cccc(OC)c3)cc12] |
| 1542 | 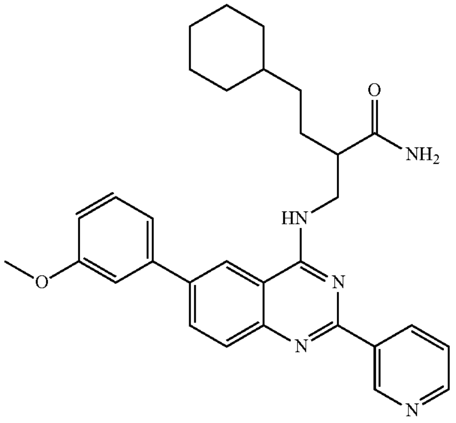 [SMILES: COc1cccc(-c2ccc3nc(-c4cccnc4)nc(NCC(CCC4CCCCC4)C(N)=O)c3c2)c1] |

TABLE 24-continued
| | |
|---|---|
| 1543 | 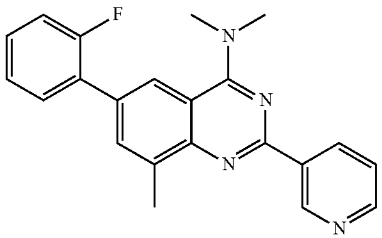 [SMILES: Cc1cc(-c2ccccc2F)cc2c(N(C)C)nc(-c3cccnc3)nc12] |
| 1544 | 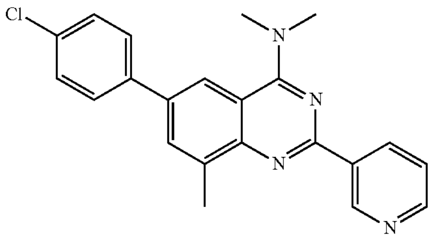 [SMILES: Cc1cc(-c2ccc(Cl)cc2)cc2c(N(C)C)nc(-c3cccnc3)nc12] |
| 1545 | 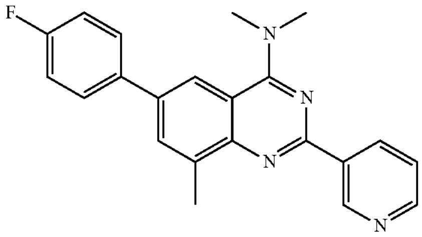 [SMILES: Cc1cc(-c2ccc(F)cc2)cc2c(N(C)C)nc(-c3cccnc3)nc12] |
| 1546 | 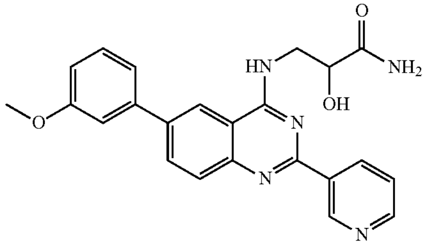 [SMILES: COc1cccc(-c2ccc3nc(-c4cccnc4)nc(NCC(O)C(N)=O)c3c2)c1] |

TABLE 24-continued
| | |
|---|---|
| 1547 | 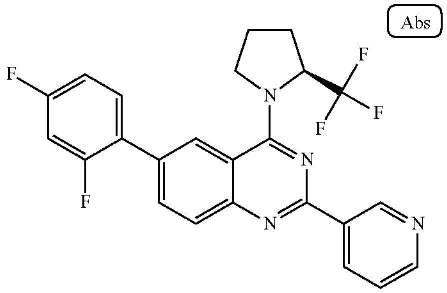 [SMILES: Fc1ccc(-c2ccc3nc(-c4cccnc4)nc(N4CCC[C@H]4C(F)(F)F)c3c2)c(F)c1] |
| 1548 | 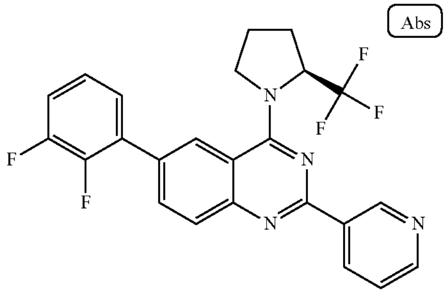 [SMILES: Fc1cccc(-c2ccc3nc(-c4cccnc4)nc(N4CCC[C@H]4C(F)(F)F)c3c2)c1F] |
| 1549 | 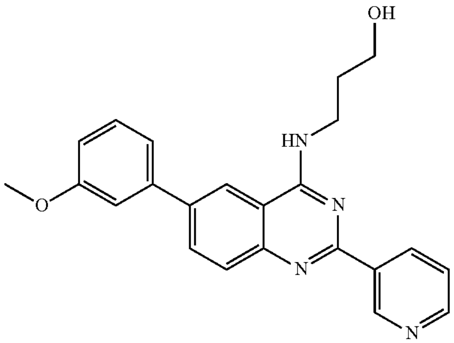 [SMILES: COc1cccc(-c2ccc3nc(-c4cccnc4)nc(NCCCO)c3c2)c1] |

TABLE 24-continued
| | |
|---|---|
| 1550 | 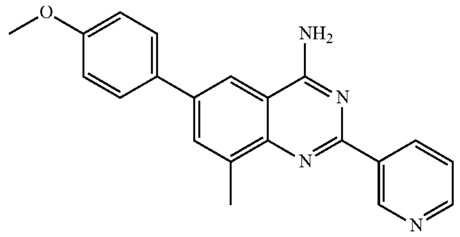 [SMILES: COc1ccc(-c2cc(C)c3nc(-c4cccnc4)nc(N)c3c2)cc1] |
| 1551 | 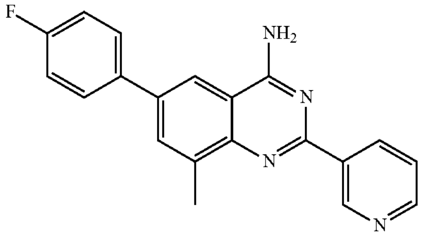 [SMILES: Cc1cc(-c2ccc(F)cc2)cc2c(N)nc(-c3cccnc3)nc12] |
| 1552 | 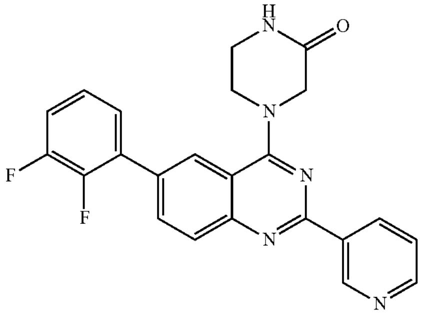 [SMILES: O=C1CN(c2nc(-c3cccnc3)nc3ccc(-c4cccc(F)c4F)cc23)CCN1] |

TABLE 24-continued
| | |
|---|---|
| 1553 | 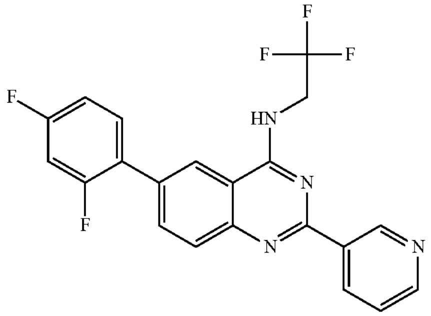 [SMILES: Fc1ccc(-c2ccc3nc(-c4cccnc4)nc(NCC(F)(F)F)c3c2)c(F)c1] |
| 1554 | 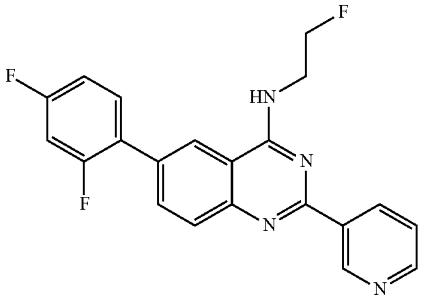 [SMILES: FCCNc1nc(-c2cccnc2)nc2ccc(-c3ccc(F)cc3F)cc12] |
| 1555 | 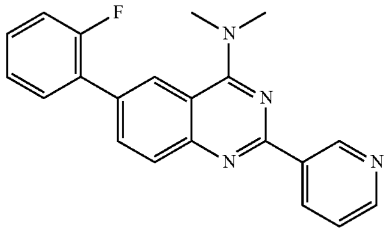 [SMILES: CN(C)c1nc(-c2cccnc2)nc2ccc(-c3ccccc3F)cc12] |

TABLE 24-continued
| | |
|---|---|
| 1556 | 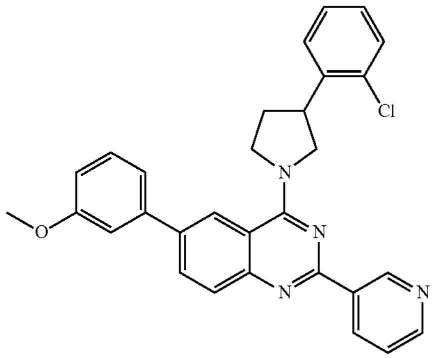 [SMILES: COc1cccc(-c2ccc3nc(-c4cccnc4)nc(N4CCC(c5ccccc5Cl)C4)c3c2)c1] |
| 1557 | 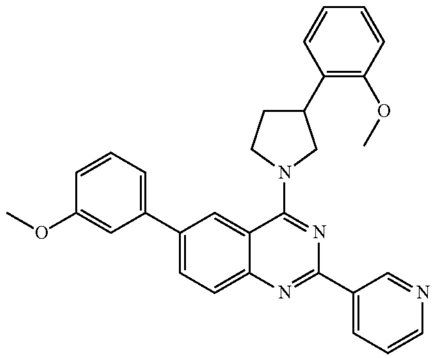 [SMILES: COc1cccc(-c2ccc3nc(-c4cccnc4)nc(N4CCC(c5ccccc5OC)C4)c3c2)c1] |
| 1558 | 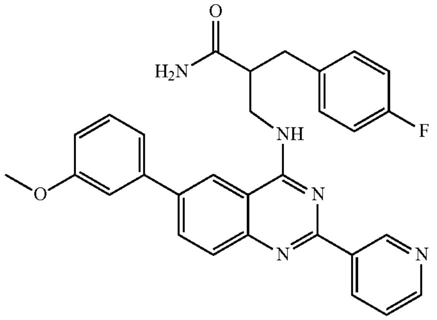 [SMILES: COc1cccc(-c2ccc3nc(-c4cccnc4)nc(NCC(Cc4ccc(F)cc4)C(N)=O)c3c2)c1] |

TABLE 24-continued
| | |
|---|---|
| 1559 | 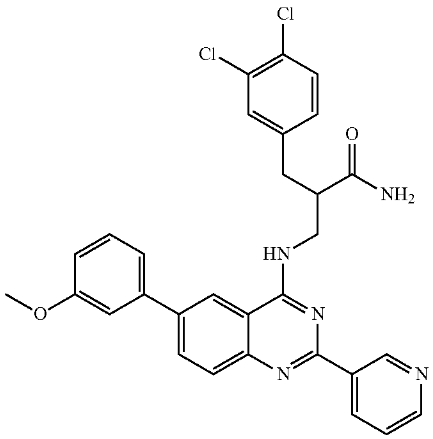 [SMILES: COc1cccc(-c2ccc3nc(-c4cccnc4)nc(NCC(Cc4ccc(Cl)c(Cl)c4)C(N)=O)c3c2)c1] |
| 1560 | 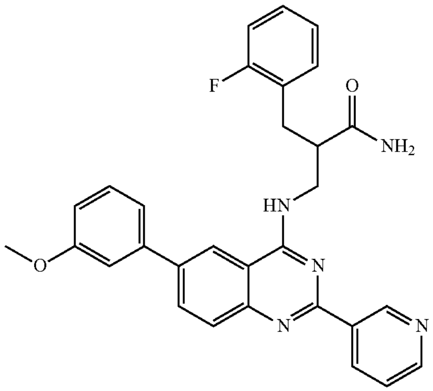 [SMILES: COc1cccc(-c2ccc3nc(-c4cccnc4)nc(NCC(Cc4ccccc4F)C(N)=O)c3c2)c1] |

TABLE 24-continued
| | |
|---|---|
| 1561 | 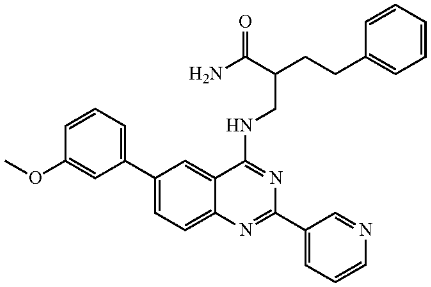 [SMILES: COc1cccc(-c2ccc3nc(-c4cccnc4)nc(NCC(CCc4ccccc4)C(N)=O)c3c2)c1] |
| 1562 | 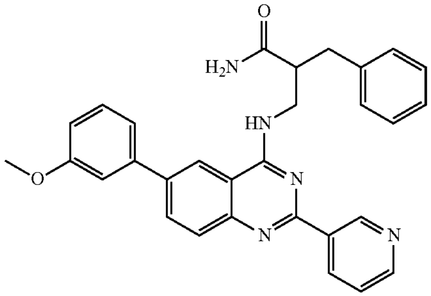 [SMILES: COc1cccc(-c2ccc3nc(-c4cccnc4)nc(NCC(Cc4ccccc4)C(N)=O)c3c2)c1] |
| 1563 | 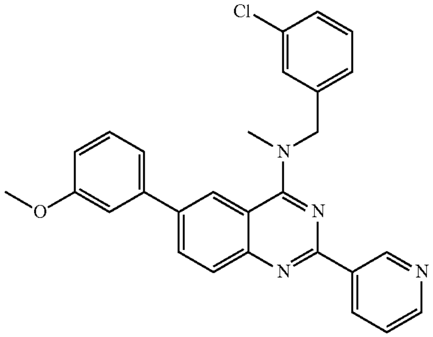 [SMILES: COc1cccc(-c2ccc3nc(-c4cccnc4)nc(N(C)Cc4cccc(Cl)c4)c3c2)c1] |

TABLE 24-continued
| | |
|---|---|
| 1564 | 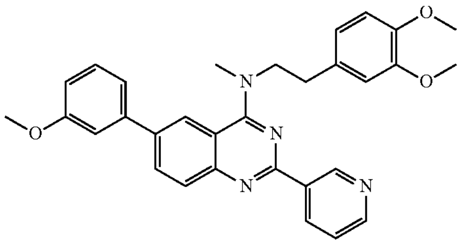 |
| 1565 | 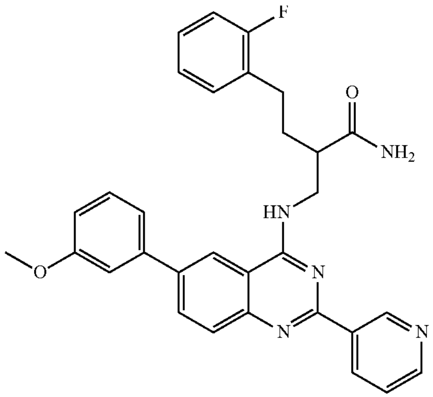 [SMILES: COc1cccc(-c2ccc3nc(-c4cccnc4)nc(NCC(CCc4ccccc4F)C(N)=O)c3c2)c1] |
| 1566 | 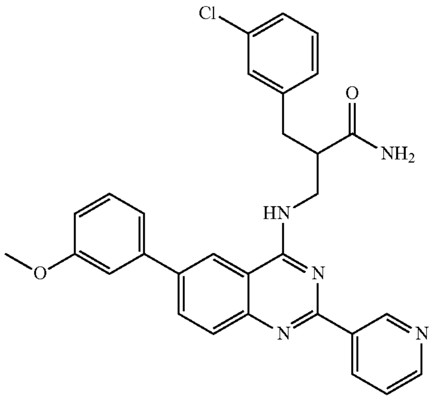 [SMILES: COc1cccc(-c2ccc3nc(-c4cccnc4)nc(NCC(Cc4cccc(Cl)c4)C(N)=O)c3c2)c1] |

TABLE 24-continued
| | |
|---|---|
| 1567 | 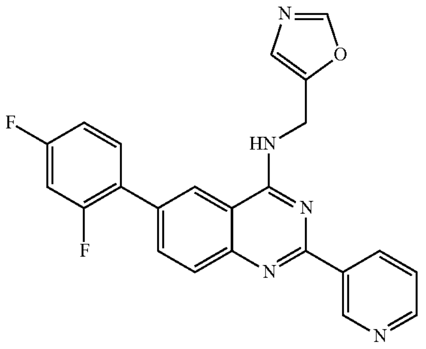 [SMILES: Fc1ccc(-c2ccc3nc(-c4cccnc4)nc(NCc4cnco4)c3c2)c(F)c1] |
| 1568 | 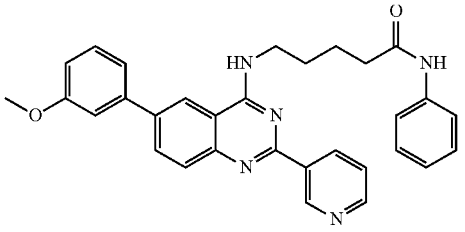 [SMILES: COc1cccc(-c2ccc3nc(-c4cccnc4)nc(NCCCCC(=O)Nc4ccccc4)c3c2)c1] |
| 1569 | 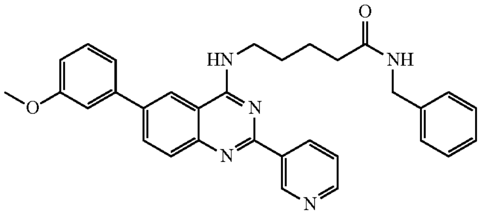 [SMILES: COc1cccc(-c2ccc3nc(-c4cccnc4)nc(NCCCCC(=O)NCc4ccccc4)c3c2)c1] |

TABLE 24-continued
| | |
|---|---|
| 1570 | 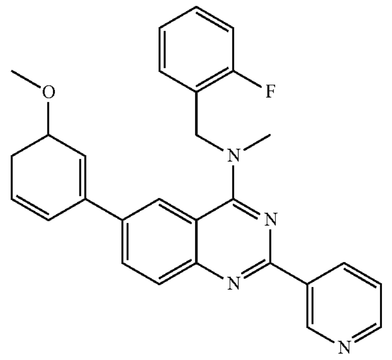 [SMILES: COC1C=C(c2ccc3nc(-c4cccnc4)nc(N(C)Cc4ccccc4F)c3c2)C=CC1] |
| 1571 | 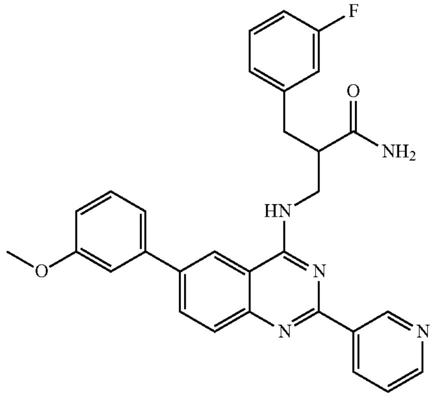 [SMILES: COc1cccc(-c2ccc3nc(-c4cccnc4)nc(NCC(Cc4cccc(F)c4)C(N)=O)c3c2)c1] |

TABLE 24-continued
| | |
|---|---|
| 1572 | 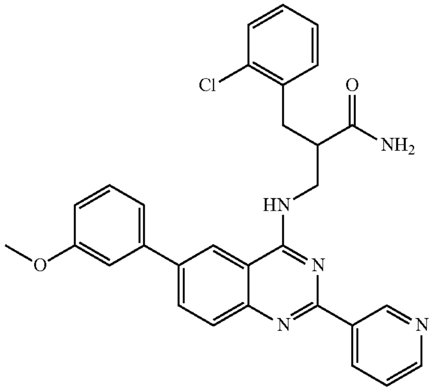 [SMILES: COc1cccc(-c2ccc3nc(-c4cccnc4)nc(NCC(Cc4ccccc4Cl)C(N)=O)c3c2)c1] |
| 1573 | 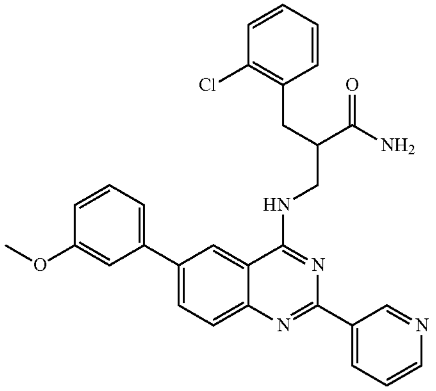 [SMILES: COc1cccc(-c2ccc3nc(-c4cccnc4)nc(NCC(Cc4ccccc4Cl)C(N)=O)c3c2)c1] |

TABLE 24-continued
| | |
|---|---|
| 1574 | 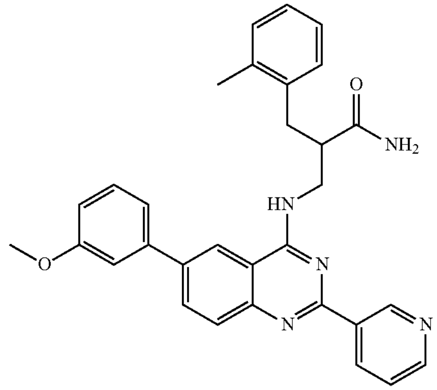 [SMILES: COc1cccc(-c2ccc3nc(-c4cccnc4)nc(NCC(Cc4ccccc4C)C(N)=O)c3c2)c1] |
| 1575 | 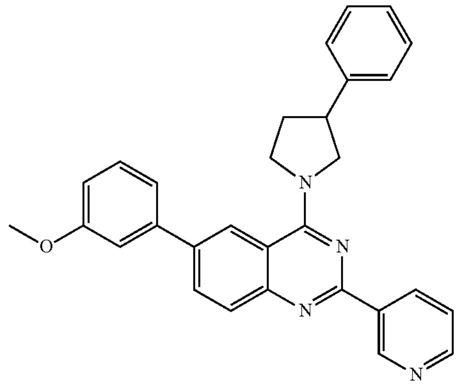 [SMILES: COc1cccc(-c2ccc3nc(-c4cccnc4)nc(N4CCC(c5ccccc5)C4)c3c2)c1] |

TABLE 24-continued
| | |
|---|---|
| 1576 | 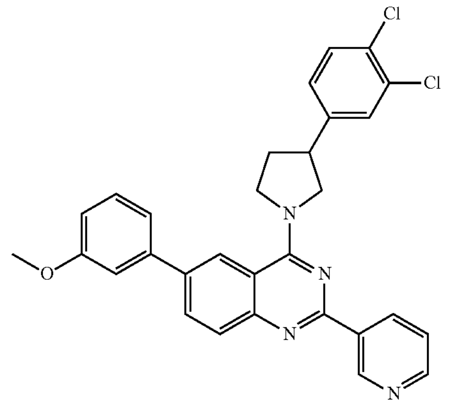 [SMILES: COc1cccc(-c2ccc3nc(-c4cccnc4)nc(N4CCC(c5ccc(Cl)c(Cl)c5)C4)c3c2)c1] |
| 1577 | 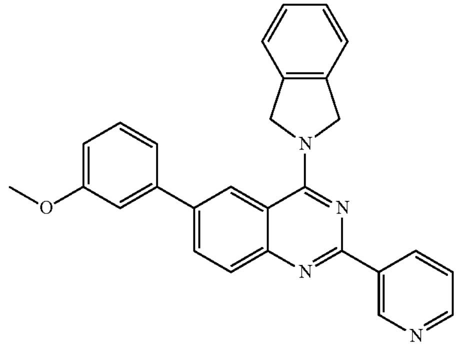 [SMILES: COc1cccc(-c2ccc3nc(-c4cccnc4)nc(N4Cc5ccccc5C4)c3c2)c1] |

TABLE 24-continued
| | |
|---|---|
| 1578 | 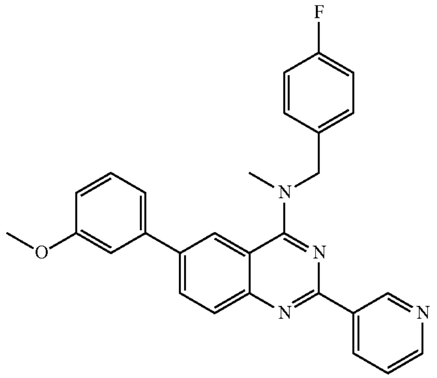 [SMILES: COc1cccc(-c2ccc3nc(-c4cccnc4)nc(N(C)Cc4ccc(F)cc4)c3c2)c1] |
| 1579 | 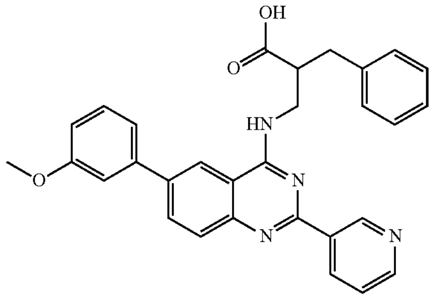 [SMILES: COc1cccc(-c2ccc3nc(-c4cccnc4)nc(NCC(Cc4ccccc4)C(=O)O)c3c2)c1] |
| 1580 | 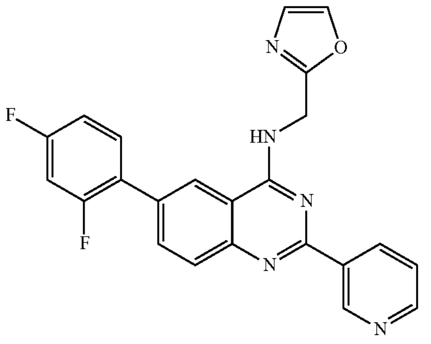 [SMILES: Fc1ccc(-c2ccc3nc(-c4cccnc4)nc(NCc4ncco4)c3c2)c(F)c1] |

TABLE 24-continued
| | |
|---|---|
| 1581 | 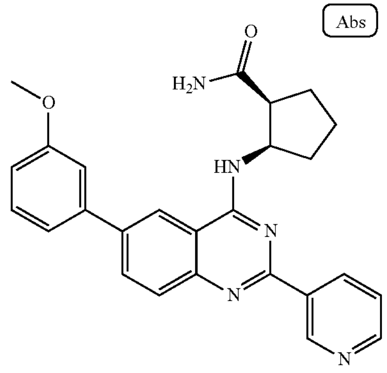 [SMILES: COc1cccc(-c2ccc3nc(-c4cccnc4)nc(N[C@@H]4CCC[C@@H]4C(N)=O)c3c2)c1] |
| 1583 | 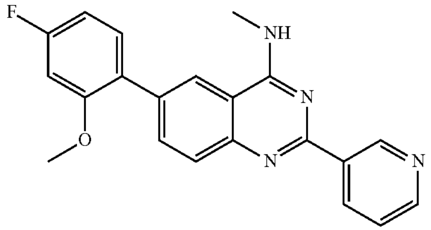 [SMILES: CNc1nc(-c2cccnc2)nc2ccc(-c3ccc(F)cc3OC)cc12] |
| 1584 | 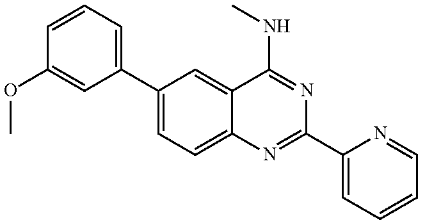 [SMILES: CNc1nc(-c2ccccn2)nc2ccc(-c3cccc(OC)c3)cc12] |
| 1585 | 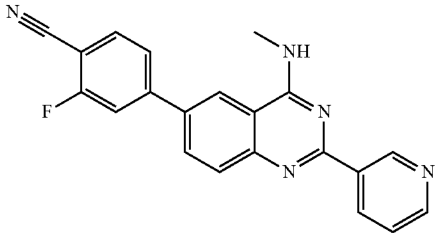 [SMILES: CNc1nc(-c2cccnc2)nc2ccc(-c3ccc(C#N)c(F)c3)cc12] |

TABLE 24-continued
| | |
|---|---|
| 1586 | 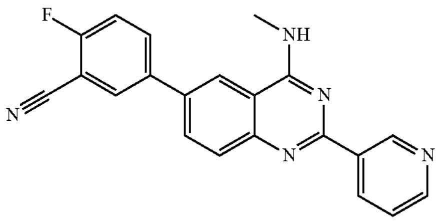 [SMILES: CNc1nc(-c2cccnc2)nc2ccc(-c3ccc(F)c(C#N)c3)cc12] |
| 1587 | 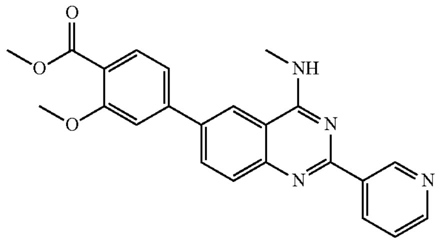 [SMILES: CNc1nc(-c2cccnc2)nc2ccc(-c3ccc(C(=O)OC)c(OC)c3)cc12] |
| 1588 | 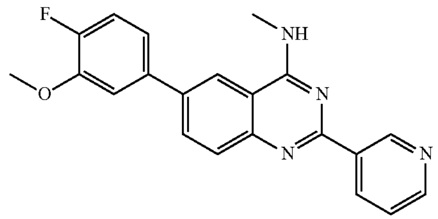 [SMILES: CNc1nc(-c2cccnc2)nc2ccc(-c3ccc(F)c(OC)c3)cc12] |
| 1589 | 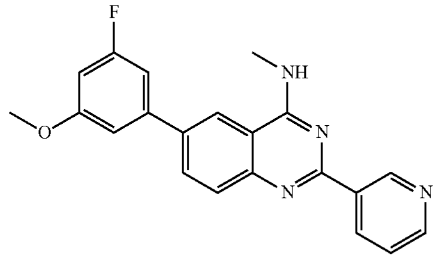 [SMILES: CNc1nc(-c2cccnc2)nc2ccc(-c3cc(F)cc(OC)c3)cc12] |

TABLE 24-continued
| | |
|---|---|
| 1590 | 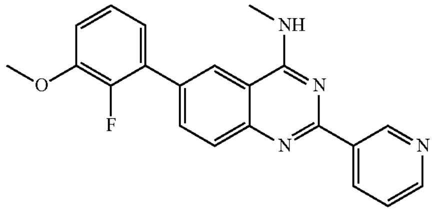 [SMILES: CNc1nc(-c2cccnc2)nc2ccc(-c3cccc(OC)c3F)cc12] |
| 1591 | 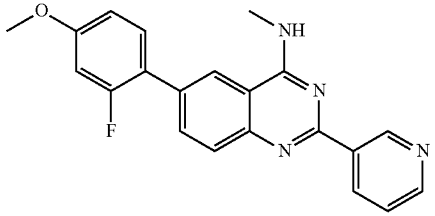 [SMILES: CNc1nc(-c2cccnc2)nc2ccc(-c3ccc(OC)cc3F)cc12] |
| 1592 | 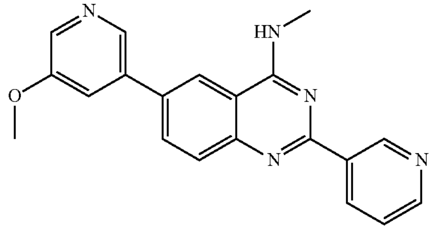 [SMILES: CNc1nc(-c2cccnc2)nc2ccc(-c3cncc(OC)c3)cc12] |
| 1593 | 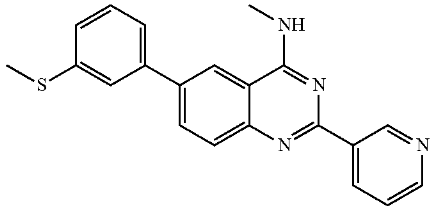 [SMILES: CNc1nc(-c2cccnc2)nc2ccc(-c3cccc(SC)c3)cc12] |
| 1594 | 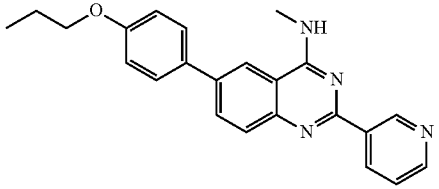 [SMILES: CCCOc1ccc(-c2ccc3nc(-c4cccnc4)nc(NC)c3c2)cc1] |

TABLE 24-continued
| | |
|---|---|
| 1595 | 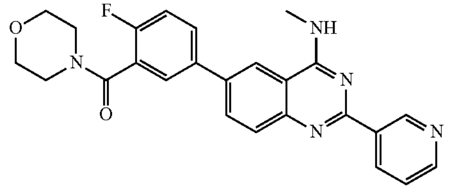 [SMILES: CNc1nc(-c2cccnc2)nc2ccc(-c3ccc(F)c(C(=O)N4CCOCC4)c3)cc12] |
| 1596 | 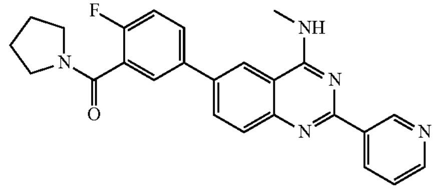 [SMILES: CNc1nc(-c2cccnc2)nc2ccc(-c3ccc(F)c(C(=O)N4CCCC4)c3)cc12] |
| 1597 | 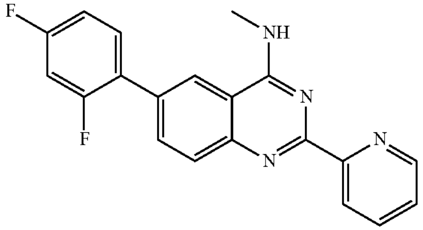 [SMILES: CNc1nc(-c2ccccn2)nc2ccc(-c3ccc(F)cc3F)cc12] |
| 1598 | 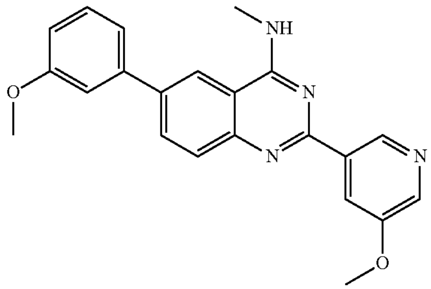 [SMILES: CNc1nc(-c2cncc(OC)c2)nc2ccc(-c3cccc(OC)c3)cc12] |

TABLE 24-continued
| | | | |
|---|---|---|---|
| 1599 | | | 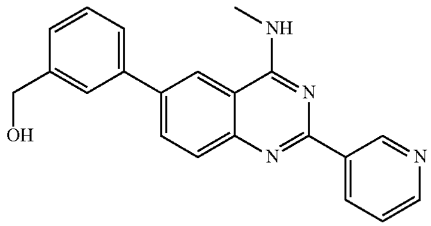 [SMILES: CNc1nc(-c2cccnc2)nc2ccc(-c3cccc(CO)c3)cc12] |
| 1600 | | | 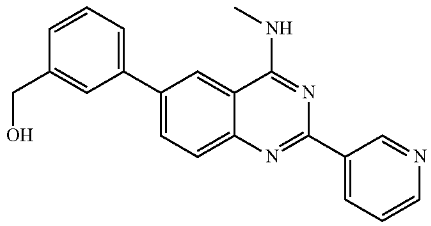 [SMILES: CNc1nc(-c2cccnc2)nc2ccc(-c3cccc(CO)c3)cc12] |
| 1601 | 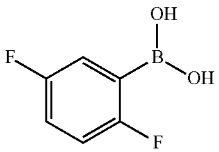 | 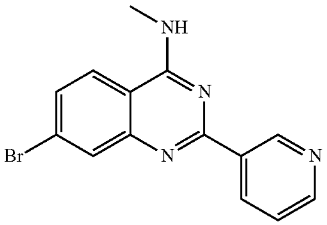 [SMILES: CNc1nc(-c2cccnc2)nc2cc(Br)ccc12] | 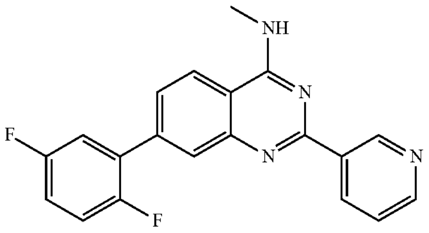 [SMILES: CNc1nc(-c2cccnc2)nc2cc(-c3cc(F)ccc3F)ccc12] |
| 1602 | 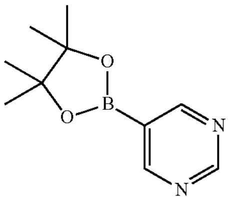 | 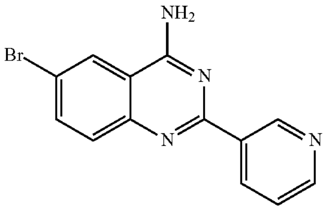 [SMILES: Nc1nc(-c2cccnc2)nc2ccc(Br)cc12] | 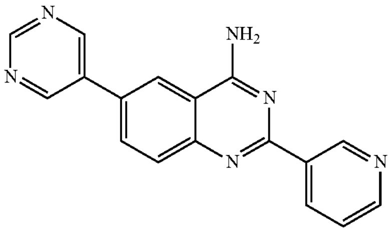 [SMILES: Nc1nc(-c2cccnc2)nc2ccc(-c3cncnc3)cc12] |

TABLE 24-continued
| | | | |
|---|---|---|---|
| 1603 | 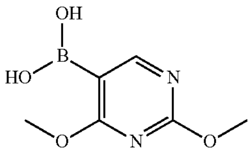 | 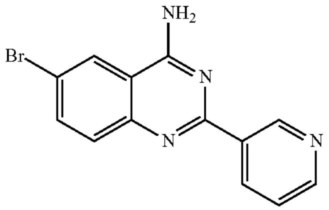 [SMILES: Nc1nc(-c2cccnc2)nc2ccc(Br)cc12] | 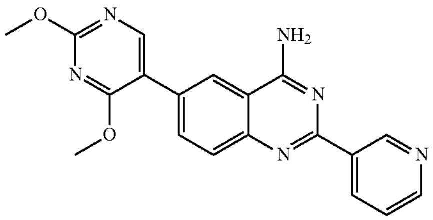 [SMILES: COc1ncc(-c2ccc3nc(-c4cccnc4)nc(N)c3c2)c(OC)n1] |
| 1604 | 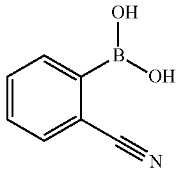 [SMILES: N#Cc1ccccc1B(O)O] | 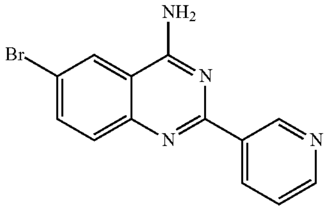 [SMILES: Nc1nc(-c2cccnc2)nc2ccc(Br)cc12] | 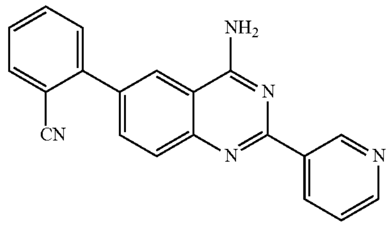 [SMILES: N#Cc1ccccc1-c1ccc2nc(-c3cccnc3)nc(N)c2c1] |
| 1605 | 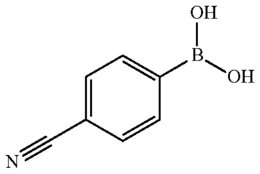 [SMILES: N#Cc1ccc(B(O)O)cc1] | 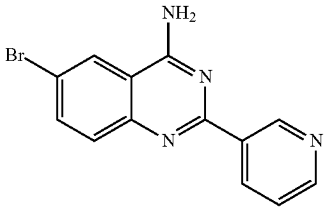 [SMILES: Nc1nc(-c2cccnc2)nc2ccc(Br)cc12] | 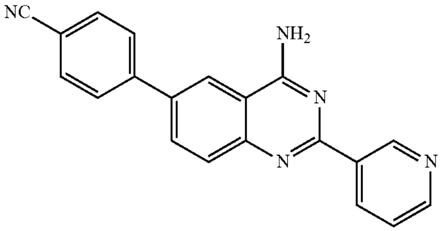 [SMILES: N#Cc1ccc(-c2ccc3nc(-c4cccnc4)nc(N)c3c2)cc1] |
| 1606 | 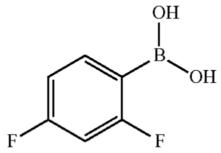 | 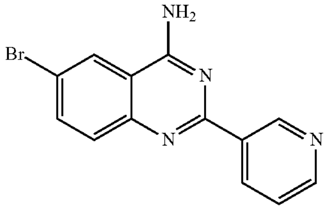 [SMILES: Nc1nc(-c2cccnc2)nc2ccc(Br)cc12] | 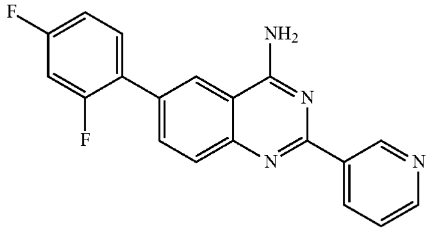 |

TABLE 24-continued
| | | | |
|---|---|---|---|
| 1607 | 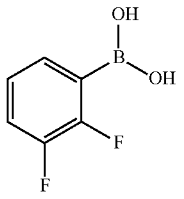 [SMILES: OB(O)c1cccc(F)c1F] | 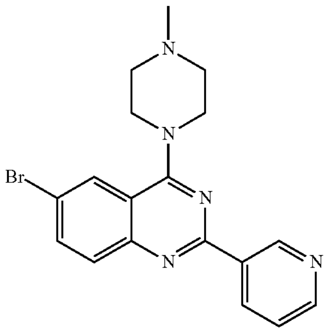 [SMILES: CN1CCN(c2nc(-c3cccnc3)nc3ccc(Br)cc23)CC1] | 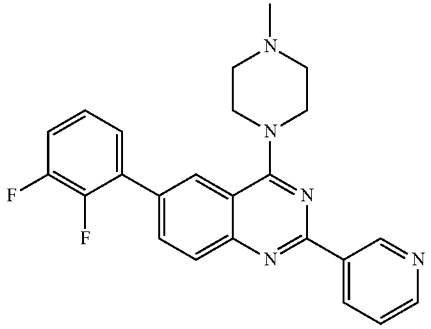 [SMILES: CN1CCN(c2nc(-c3cccnc3)nc3ccc(-c4cccc(F)c4F)cc23)CC1] |
| 1608 | 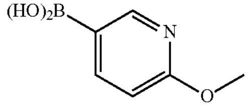 | 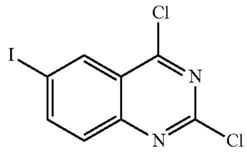 [SMILES: Clc1nc(Cl)c2cc(I)ccc2n1] | 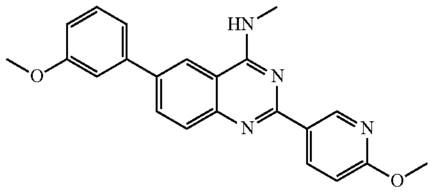 |
| 1609 | 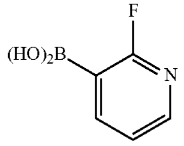 | 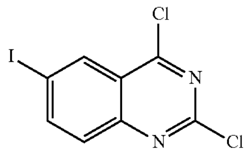 [SMILES: Clc1nc(Cl)c2cc(I)ccc2n1] | 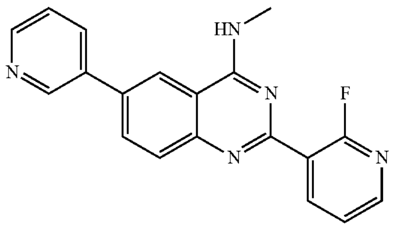 [SMILES: CNc1nc(-c2cccnc2F)nc2ccc(-c3cccnc3)cc12] |
| 1610 | 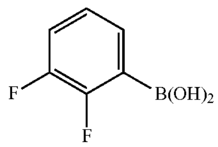 | 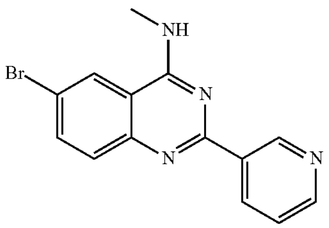 [SMILES: CNc1nc(-c2cccnc2)nc2ccc(Br)cc12] | 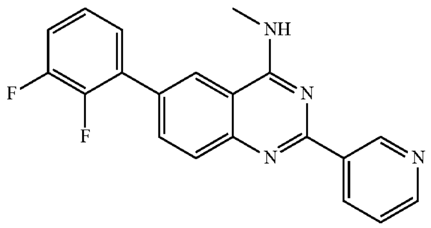 [SMILES: CNc1nc(-c2cccnc2)nc2ccc(-c3cccc(F)c3F)cc12] |

TABLE 24-continued
| | | | |
|---|---|---|---|
| 1611 | 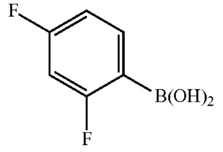 | 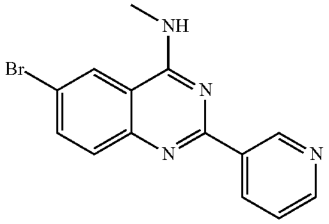 [SMILES: CNc1nc(-c2cccnc2)nc2ccc(Br)cc12] | 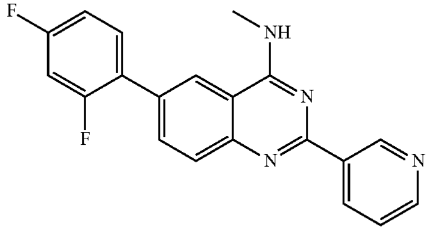 [SMILES: CNc1nc(-c2cccnc2)nc2ccc(-c3ccc(F)cc3F)cc12] |
| 1612 | 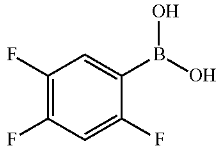 | 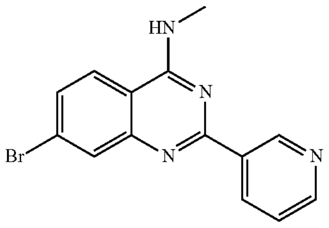 [SMILES: CNc1nc(-c2cccnc2)nc2cc(Br)ccc12] | 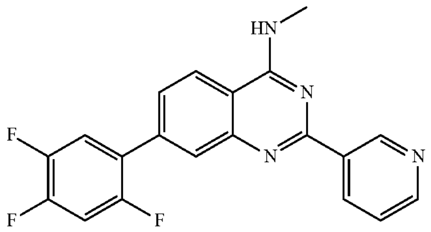 [SMILES: CNc1nc(-c2cccnc2)nc2cc(-c3cc(F)c(F)cc3F)ccc12] |
| 1613 | 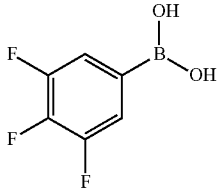 [SMILES: OB(O)c1cc(F)c(F)c(F)c1] | 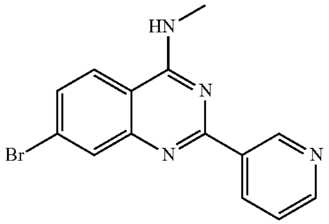 [SMILES: CNc1nc(-c2cccnc2)nc2cc(Br)ccc12] | 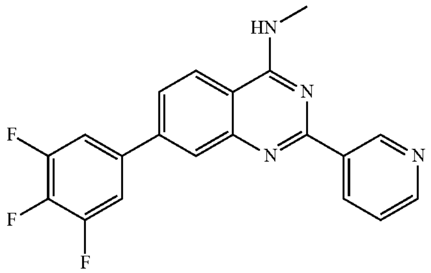 [SMILES: CNc1nc(-c2cccnc2)nc2cc(-c3cc(F)c(F)c(F)c3)ccc12] |
| 1614 | 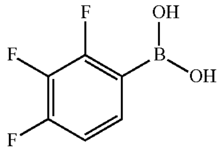 | 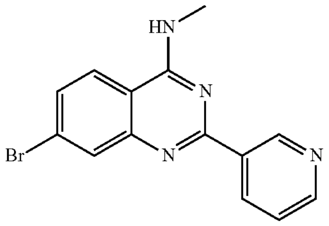 [SMILES: CNc1nc(-c2cccnc2)nc2cc(Br)ccc12] | 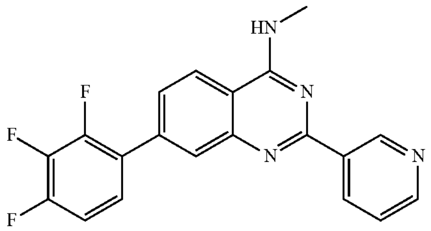 [SMILES: CNc1nc(-c2cccnc2)nc2cc(-c3ccc(F)c(F)c3F)ccc12] |

TABLE 24-continued
| | | | |
|---|---|---|---|
| 1615 | 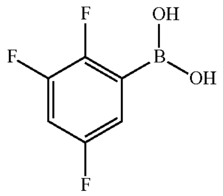 | 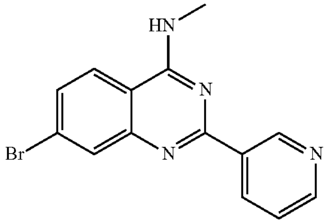 [SMILES: CNc1nc(-c2cccnc2)nc2cc(Br)ccc12] | 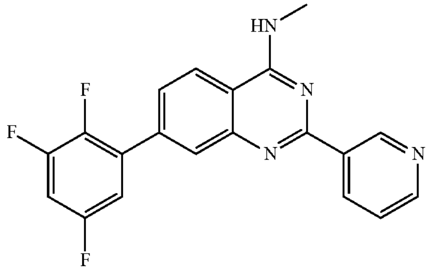 [SMILES: CNc1nc(-c2cccnc2)nc2cc(-c3cc(F)cc(F)c3F)ccc12] |
| 1760 | 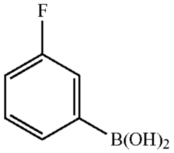 | 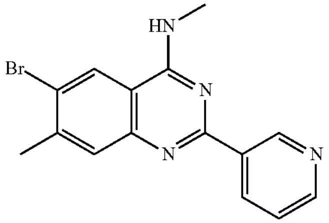 [SMILES: CNc1nc(-c2cccnc2)nc2cc(C)c(Br)cc12] | 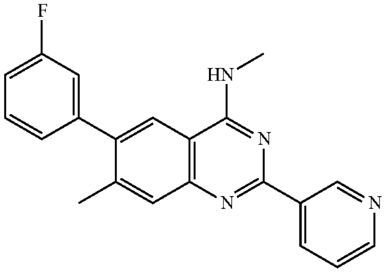 [SMILES: CNc1nc(-c2cccnc2)nc2cc(C)c(-c3cccc(F)c3)cc12] |
| Number | Salt type | $^1$H NMR | $^1$H NMR Solvent | Purity percent | Method of Coupling | LCMS | LCMS Method |
|---|---|---|---|---|---|---|---|
| 1279 | 2 HCl | $^1$H NMR (400 MHz, DMSO) δ 9.69 (d, J = 1.8 Hz, 1H), 9.40-9.33 (m, 1H), 9.03-8.93 (m, 2H), 8.64-8.59 (m, 1H), 8.18-8.14 (m, 1H), 8.13-8.05 (m, 3H), 8.04-7.97 (m, 2H), 3.21 (d, J = 4.4 Hz, 3H), 2.77 (s, 3H). | DMSO | >98 | AQ3 | | |
| 1280 | 2 HCl | $^1$H NMR (400 MHz, DMSO) δ 9.71-9.65 (m, 1H), 9.44-9.36 (m, 1H), 9.06-8.94 (m, 2H), 8.59-8.54 (m, 1H), 8.19-8.10 (m, 2H), 7.79-7.71 (m, 2H), 7.61-7.54 (m, 1H), 7.29-7.22 (m, 1H), 3.21 (d, J = 3.9 Hz, 3H), 2.76 (s, 3H). | DMSO | >98 | AQ3 | | |
| 1281 | 2 HCl | $^1$H NMR (400 MHz, DMSO) δ 9.72-9.65 (m, 1H), 9.43-9.36 (m, 1H), 9.04-8.91 (m, 2H), 8.63-8.55 (m, 1H), 8.36-8.31 (m, 1H), 8.26-8.20 (m, 1H), 8.20-8.11 (m, 2H), 7.91-7.85 (m, 1H), 7.78-7.70 (m, 1H), 3.22 (d, J = 4.2 Hz, 3H), 2.76 (s, 3H). | DMSO | >98 | AQ3 | | |

TABLE 24-continued

| | | | | | |
|---|---|---|---|---|---|
| 1282 | 2 HCl | $^{1}$H NMR (400 MHz, DMSO) δ 9.70-9.65 (m, 1H), 9.37 (d, J = 8.2 Hz, 1H), 9.03-8.90 (m, 2H), 8.49-8.42 (m, 1H), 8.12 (dd, J = 8.1, 5.6 Hz, 1H), 8.08-8.03 (m, 1H), 7.88-7.78 (m, 2H), 7.15-7.04 (m, 2H), 3.84 (s, 3H), 3.21 (d, J = 3.9 Hz, 3H), 2.76 (s, 3H). | DMSO | >98 | AQ3 |
| 1283 | 2 HCl | $^{1}$H NMR (400 MHz, DMSO) δ 9.73-9.67 (m, 1H), 9.36 (d, J = 7.4 Hz, 1H), 9.02-8.96 (m, 1H), 8.82 (s, 1H), 8.26-8.19 (m, 1H), 8.15-8.07 (m, 1H), 7.89-7.83 (m, 1H), 7.47-7.38 (m, 2H), 7.21-7.15 (m, 1H), 7.14-7.06 (m, 1H), 3.81 (s, 3H), 3.19 (d, J = 4.5 Hz, 3H), 2.77 (s, 3H). | DMSO | >98 | AQ3 |
| 1284 | 2 HCl | $^{1}$H NMR (400 MHz, DMSO) δ 9.72 (d, J = 1.8 Hz, 1H), 9.34-9.28 (m, 1H), 8.95 (dd, J = 5.4, 1.4 Hz, 1H), 8.88-8.78 (m, 1H), 8.38 (d, J = 1.5 Hz, 1H), 8.07-8.00 (m, 2H), 7.95-7.90 (m, 1H), 7.90-7.83 (m, 1H), 7.76 (dd, J = 7.8, 0.7 Hz, 1H), 7.68-7.63 (m, 1H), 3.19 (d, J = 4.5 Hz, 3H), 2.77 (s, 3H). | DMSO | >98 | AQ3 |
| 1285 | | $^{1}$H NMR (400 MHz, DMSO) δ 9.63 (dd, J = 2.1, 0.8 Hz, 1H), 8.80-8.75 (m, 1H), 8.69 (dd, J = 3.7, 1.8 Hz, 1H), 7.72 (d, J = 8.5 Hz, 1H), 7.61 (d, J = 8.5 Hz, 1H), 7.58-7.49 (m, 2H), 7.46-7.40 (m, 1H), 7.39-7.32 (m, 1H), 7.28-7.18 (m, 1H), 3.18 (d, J = 4.4 Hz, 3H), 2.64 (s, 3H). | DMSO | >98 | AQ4 |
| 1286 | 2 HCl | $^{1}$H NMR (400 MHz, DMSO) δ 9.67-9.60 (m, 1H), 9.06-8.88 (m, 3H), 8.12 (d, J = 8.8 Hz, 1H), 7.91-7.79 (m, 2H), 7.53-7.40 (m, 2H), 7.34-7.24 (m, 1H), 3.34 (d, J = 4.6 Hz, 3H), 2.66 (s, 3H). | DMSO | >98 | AQ4 |
| 1287 | HCl | $^{1}$H NMR (400 MHz, DMSO) δ 9.62-9.57 (m, 1H), 8.94-8.86 (m, 2H), 8.62 (s, 1H), 7.95 (d, J = 8.5 Hz, 1H), 7.86-7.75 (m, 2H), 7.52-7.36 (m, 2H), 7.35-7.28 (m, 1H), 3.31 (d, J = 4.5 Hz, 3H), 2.67 (s, 3H). | DMSO | >98 | AQ4 |

TABLE 24-continued

| | | | | | |
|---|---|---|---|---|---|
| 1288 | HCl | $^1H$ NMR (400 MHz, DMSO) δ 9.63-9.58 (m, 1H), 8.95-8.86 (m, 2H), 8.73 (s, 1H), 8.01 (d, J = 8.5 Hz, 1H), 7.87-7.75 (m, 2H), 7.61-7.50 (m, 1H), 7.45-7.33 (m, 3H), 3.32 (d, J = 4.5 Hz, 3H), 2.66 (s, 3H). | DMSO | >98 | AQ4 |
| 1289 | 2 HCl | $^1H$ NMR (400 MHz, DMSO) δ 9.64-9.60 (m, 1H), 9.00-8.86 (m, 3H), 8.06 (d, J = 8.5 Hz, 1H), 7.91-7.79 (m, 2H), 7.65-7.55 (m, 1H), 7.37-7.29 (m, 1H), 7.29-7.22 (m, 2H), 3.35 (d, J = 4.6 Hz, 3H), 2.72 (s, 3H). | DMSO | >98 | AQ4 |
| 1290 | 2 HCl | $^1H$ NMR (400 MHz, DMSO) δ 9.69-9.64 (m, 1H), 9.14-8.99 (m, 2H), 8.96 (dd, J = 5.0, 1.5 Hz, 1H), 8.15 (d, J = 8.6 Hz, 1H), 7.90-7.81 (m, 2H), 7.50-7.34 (m, 4H), 3.35 (d, J = 4.6 Hz, 3H), 2.72 (s, 3H). | DMSO | >98 | AQ4 |
| 1291 | HCl | $^1H$ NMR (300 MHz, $CDCl_3$) δ 9.63 (s, 2H), 8.96 (d, J = 8.2 Hz, 1H), 8.90 (d, J = 5.0 Hz, 1H), 8.50 (s, 1H), 8.16-7.99 (m, 2H), 7.82 (dd, J = 8.0, 4.9 Hz, 1H), 7.71-7.62 (m, 1H), 7.61-7.47 (m, 3H), 3.26 (d, J = 4.5 Hz, 3H). | DMSO | >98 | G2/AQ3 |
| 1292 | 2 HCl | $^1H$ NMR (300 MHz, $CDCl_3$) δ 10.27 (s, 1H), 9.69 (s, 1H), 9.09 (d, J = 8.1 Hz, 1H), 8.97 (d, J = 5.0 Hz, 1H), 8.56 (s, 1H), 8.32 (d, J = 8.6 Hz, 1H), 8.04 (d, J = 8.7 Hz, 1H), 7.89 (dd, J = 8.0, 5.1 Hz, 1H), 7.45-7.26 (m, 4H), 3.29 (d, J = 4.2 Hz, 3H), 2.32 (s, 3H). | DMSO | >98 | G2/AQ3 |
| 1293 | 2 HCl | $^1H$ NMR (300 MHz, DMSO) δ 10.40 (s, 1H), 9.73 (s, 1H), 9.15 (d, J = 7.9 Hz, 1H), 8.98 (d, J = 5.1 Hz, 1H), 8.67 (s, 1H), 8.33 (d, J = 8.6 Hz, 1H), 8.18 (d, J = 8.7 Hz, 1H), 7.91 (dd, J = 7.9, 5.2 Hz, 1H), 7.45 (m, 2H), 7.20 (d, J = 8.2 Hz, 1H), 7.12 (t, J = 7.5 Hz, 1H), 3.82 (s, 3H), 3.29 (d, J = 4.1 Hz, 3H). | DMSO | >98 | G2/AQ3 |

TABLE 24-continued

| | | | | | |
|---|---|---|---|---|---|
| 1294 | | $^{1}$H NMR (300 MHz, $CDCl_3$) δ 9.66 (s, 1H), 8.80 (d, J = 7.9 Hz, 1H), 8.74-8.67 (m, 1H), 8.60 (m, 1H), 8.49 (s, 1H), 8.00 (dd, J = 18.5, 10.4 Hz, 2H), 7.96-7.81 (m, 2H), 7.76 (d, J = 7.6 Hz, 1H), 7.65 (t, J = 7.6 Hz, 1H), 7.56 (dd, J = 7.6, 5.0 Hz, 1H), 3.18 (d, J = 4.2 Hz, 3H). | DMSO | >98 | G2/AQ3 |
| 1295 | 2 HCl | $^{1}$H NMR (300 MHz, $CDCl_3$) δ 9.88 (s, 1H), 9.66 (s, 1H), 9.01 (d, J = 8.3 Hz, 1H), 8.90 (d, J = 4.2 Hz, 1H), 8.70 (s, 1H), 8.27-8.08 (m, 2H), 7.81 (dd, J = 8.0, 5.1 Hz, 1H), 7.72 (t, J = 7.6 Hz, 1H), 7.60-7.48 (m, 1H), 7.48-7.27 (m, 2H), 3.27 (d, J = 4.3 Hz, 3H). | DMSO | >98 | G2/AQ3 |
| 1296 | 2 HCl | $^{1}$H NMR (300 MHz, $CDCl_3$) δ 9.63 (m, 2H), 8.93 (d, J = 7.7 Hz, 1H), 8.88 (d, J = 4.1 Hz, 1H), 8.76 (s, 1H), 8.29 (d, J = 8.4 Hz, 1H), 8.07 (d, J = 8.6 Hz, 1H), 7.94 (dd, J = 8.6, 5.5 Hz, 2H), 7.82-7.73 (m, 1H), 7.41 (t, J = 8.7 Hz, 2H), 3.28 (d, J = 4.3 Hz, 3H). | DMSO | >98 | G2/AQ3 |
| 1297 | 2 HCl | $^{1}$H NMR (300 MHz, DMSO) δ 9.82 (s, 1H), 9.64 (d, J = 1.7 Hz, 1H), 9.00 (d, J = 8.0 Hz, 1H), 8.95-8.86 (m, 2H), 8.69 (t, J = 1.9 Hz, 1H), 8.51-8.34 (m, 2H), 8.30 (dd, J = 7.9, 1.8 Hz, 1H), 8.13 (d, J = 8.7 Hz, 1H), 7.93-7.76 (m, 2H), 3.30 (d, J = 4.5 Hz, 3H). | DMSO | >98 | G2/AQ3 |
| 1298 | 2 HCl | $^{1}$H NMR (300 MHz, DMSO) δ 10.30 (s, 1H), 9.70 (d, J = 2.1 Hz, 1H), 9.11 (d, J = 8.2 Hz, 1H), 9.04-8.83 (m, 1H), 8.56 (s, 1H), 8.26 (d, J = 8.6 Hz, 1H), 8.01-7.80 (m, 3H), 7.78-7.64 (m, 1H), 7.60 (t, J = 7.2 Hz, 1H), 7.54 (d, J = 7.2 Hz, 1H), 3.29 (d, J = 4.4 Hz, 3H), 2.44 (s, 3H). | DMSO | >98 | G2/AQ3 |
| 1299 | | $^{1}$H NMR (300 MHz, DMSO) δ 10.50 (s, 1H), 9.66 (s, 1H), 9.09 (d, J = 8.2 Hz, 1H), 9.01 (s, 1H), 8.94 (d, J = 5.0 Hz, 1H), 8.40 (d, J = 8.7 Hz, 1H), 8.28 (d, J = 8.3 Hz, 1H), 8.13-8.00 (m, 4H), 7.88 (dd, J = 8.0, 5.2 Hz, 1H), 3.30 (d, J = 4.1 Hz, 3H), 2.62 (s, 3H). | DMSO | >98 | G2/AQ3 |

TABLE 24-continued

| | | | | | |
|---|---|---|---|---|---|
| 1300 | 2 HCl | $^1$H NMR (300 MHz, DMSO) δ 10.49 (s, 1H), 9.66 (s, 1H), 9.09 (d, J = 7.9 Hz, 1H), 9.01 (s, 1H), 8.95 (d, J = 5.0 Hz, 1H), 8.40 (d, J = 8.6 Hz, 1H), 8.29 (d, J = 8.7 Hz, 1H), 8.15-7.94 (m, 4H), 7.88 (dd, J = 7.9, 5.2 Hz, 1H), 3.31 (d, J = 4.1 Hz, 3H), 2.63 (s, 3H). | DMSO | >98 | G2/AQ3 |
| 1301 | 2 HCl | $^1$H NMR (300 MHz, DMSO) δ 10.97 (s, 1H), 9.71 (d, J = 2.0 Hz, 1H), 9.29 (s, 1H), 9.15 (d, J = 8.0 Hz, 1H), 8.98 (dd, J = 5.0, 1.3 Hz, 1H), 8.49-8.38 (m, 1H), 8.34 (d, J = 8.8 Hz, 1H), 8.21 (s, 1H), 7.92 (dd, J = 8.1, 5.1 Hz, 1H), 7.84 (s, 1H), 7.69-7.52 (m, 2H), 3.31 (d, J = 4.3 Hz, 3H), 3.23 (s, 6H). | DMSO | >98 | G2/AQ3 |
| 1302 | 2 HCl | $^1$H NMR (300 MHz, DMSO) δ 10.33 (s, 1H), 9.73 (d, J = 1.7 Hz, 1H), 9.20 (d, J = 8.0 Hz, 1H), 9.00 (d, J = 4.2 Hz, 1H), 8.68 (s, 1H), 8.32 (d, J = 8.6 Hz, 1H), 8.16 (d, J = 7.9 Hz, 1H), 8.01-7.93 (m, 2H), 7.90 (t, J = 7.2 Hz, 1H), 7.74 (dd, J = 15.4, 7.7 Hz, 2H), 3.24 (t, J = 18.2 Hz, 3H). | DMSO | >98 | G2/AQ3 |
| 1303 | HCl | $^1$H NMR (300 MHz, DMSO) δ 10.46 (s, 1H), 9.76 (d, J = 2.1 Hz, 1H), 9.21 (d, J = 8.2 Hz, 1H), 9.00 (dd, J = 5.1, 1.2 Hz, 1H), 8.58 (d, J = 1.3 Hz, 1H), 8.41 (d, J = 8.6 Hz, 1H), 8.08-7.86 (m, 2H), 7.36-7.09 (m, 3H), 3.29 (d, J = 4.3 Hz, 3H), 2.33 (s, 3H), 2.17 (s, 3H). | DMSO | >98 | G2/AQ3 |
| 1304 | | $^1$H NMR (300 MHz, DMSO) δ 9.65 (d, J = 2.1 Hz, 1H), 8.79 (dt, J = 8.0, 1.9 Hz, 1H), 8.69 (dd, J = 4.7, 1.6 Hz, 1H), 8.46 (d, J = 4.5 Hz, 1H), 8.20 (d, J = 1.7 Hz, 1H), 7.83 (d, J = 8.5 Hz, 1H), 7.75 (dd, J = 8.5, 1.6 Hz, 1H), 7.54 (dd, J = 7.9, 4.8 Hz, 1H), 7.28-7.02 (m, 3H), 3.33 (s, 6H), 3.15 (d, J = 4.4 Hz, 3H), 2.51 (dt, J = 3.6, 1.7 Hz, 1H), 2.35 (s, 3H), 2.27 (s, 3H). | DMSO | >98 | G2/AQ3 |

TABLE 24-continued

| | | | | | |
|---|---|---|---|---|---|
| 1305 | HCl | $^1$H NMR (300 MHz, DMSO) δ 10.48 (s, 1H), 9.70 (s, 1H), 9.11 (d, J = 7.8 Hz, 1H), 8.97 (d, J = 4.7 Hz, 1H), 8.90 (s, 1H), 8.36 (d, J = 8.6 Hz, 1H), 8.29 (d, J = 8.7 Hz, 1H), 7.98-7.80 (m, 1H), 7.74 (s, 1H), 7.65 (d, J = 7.5 Hz, 1H), 7.30 (d, J = 7.8 Hz, 1H), 3.32 (d, J = 4.0 Hz, 3H), 2.33 (d, J = 10.0 Hz, 3H), 2.29 (s, 3H). | DMSO | >98 | G2/AQ3 |
| 1306 | HCl | $^1$H NMR (300 MHz, DMSO) δ 10.45-10.35 (m, 1H), 9.69 (s, 1H), 9.09 (s, 1H), 8.99 (s, 1H), 8.88 (s, 1H), 8.37 (d, J = 8.6 Hz 1H), 8.28 (d, J = 8.7 Hz, 1H), 7.94 (s, 1H), 7.54 (s, 1H), 7.11 (s, 1H), 3.34 (d, J = 4.3 Hz, 3H), 2.40 (s, 3H). | DMSO | >98 | G2/AQ3 |
| 1307 | 2 HCl | $^1$H NMR (300 MHz, DMSO) δ 10.28 (s, 1H), 9.84-9.66 (m, 1H), 9.17 (d, J = 8.1 Hz, 1H), 8.99 (d, J = 5.0 Hz, 1H), 8.46 (s, 1H), 8.36 (d, J = 8.6 Hz, 1H), 7.98-7.80 (m, 2H), 7.41 (t, J = 8.4 Hz, 1H), 6.83 (d, J = 8.4 Hz, 2H), 3.71 (s, 6H), 3.29 (d, J = 4.2 Hz, 3H). | DMSO | >98 | G2/AQ3 |
| 1308 | HCl | $^1$H NMR (300 MHz, DMSO) δ 9.64 (s, 1H), 8.96-8.91 (m, 1H), 8.89-8.83 (m, 2H), 8.41 (d, J = 9.1 Hz, 2H), 8.38-8.32 (m, 1H), 8.16 (d, J = 9.0 Hz, 2H), 8.02 (d, J = 9.1 Hz, 1H), 7.81-7.73 (m, 1H), 3.27 (d, J = 4.3 Hz, 3H). | DMSO | >98 | G2/AQ3 |
| 1309 | | $^1$H NMR (300 MHz, DMSO) δ 9.64 (d, J = 2.0 Hz, 1H), 8.78 (ddd, J = 14.6, 8.2, 6.5 Hz, 1H), 8.70 (dd, J = 4.7, 1.4 Hz, 1H), 8.56 (d, J = 4.3 Hz, 1H), 8.33 (d, J = 1.5 Hz, 1H), 8.06 (dd, J = 8.6, 1.4 Hz, 1H), 7.81 (d, J = 8.6 Hz, 1H), 7.56 (dd, J = 7.9, 4.8 Hz, 1H), 7.34 (t, J = 7.5 Hz, 2H), 7.20-7.00 (m, 2H), 3.16 (d, J = 4.4 Hz, 3H). | DMSO | >98 | G2/AQ3 |
| 1310 | 2 HCl | $^1$H NMR (300 MHz, DMSO) δ 10.63 (s, 1H), 9.69 (s, 1H), 9.16 (s, 1H), 9.10 (d, J = 7.9 Hz, 1H), 8.97 (d, J = 5.0 Hz, 1H), 8.52 (s, 1H), 8.45 (d, J = 8.7 Hz, 1H), 8.29 (d, J = 8.7 Hz, 2H), 8.07 (d, J = 7.8 Hz, 1H), 8.01-7.84 (m, 2H), 7.63 (t, J = 7.8 Hz, 1H), 7.54 (s, 1H), 3.31 (d, J = 4.3 Hz, 3H). | DMSO | >98 | G2/AQ3 |

TABLE 24-continued

| | | | | | |
|---|---|---|---|---|---|
| 1311 | HCl | $^{1}H$ NMR (300 MHz, DMSO) δ 10.20 (s, 1H), 9.65 (s, 1H), 9.02 (s, 1H), 8.95 (s, 2H), 8.43 (d, J = 8.7 Hz, 1H), 8.26-8.14 (m, 1H), 8.04 (dd, J = 18.8, 8.1 Hz, 4H), 7.88 (s, 1H), 7.47 (s, 1H), 3.32 (s, 3H), 3.17 (d, J = 1.8 Hz, 9H). | DMSO | >98 | G2/AQ3 |
| 1312 | HCl | $^{1}H$ NMR (300 MHz, DMSO) δ 9.79 (s, 1H), 9.66 (d, J = 1.7 Hz, 1H), 9.02 (d, J = 8.1 Hz, 1H), 8.96-8.86 (m, 1H), 8.57 (s, 1H), 8.18 (d, J = 8.7 Hz, 1H), 8.05 (dd, J = 8.7, 1.4 Hz, 1H), 7.82 (dd, J = 8.1, 5.0 Hz, 1H), 7.79-7.72 (m, 1H), 7.64-7.45 (m, 2H), 3.25 (d, J = 4.4 Hz, 3H). | DMSO | >98 | G2/AQ3 |
| 1313 | 2 HCl | $^{1}H$ NMR (300 MHz, DMSO) δ 10.01 (s, 1H), 9.65 (s, 1H), 9.06 (d, J = 7.8 Hz, 1H), 8.95 (d, J = 4.8 Hz, 1H), 8.59 (s, 1H), 8.21 (d, J = 8.6 Hz, 1H), 8.07 (d, J = 9.1 Hz, 1H), 7.95-7.77 (m, 2H), 7.66-7.52 (m, 2H), 3.27 (d, J = 4.3 Hz, 3H), 3.17 (d, J = 0.7 Hz, 1H). | DMSO | >98 | G2/AQ3 |
| 1314 | HCl | $^{1}H$ NMR (300 MHz, DMSO) δ 10.10 (s, 1H), 9.69 (s, 1H), 9.13 (d, J = 8.0 Hz, 1H), 8.98 (d, J = 5.1 Hz, 1H), 8.62 (s, 1H), 8.27 (d, J = 8.6 Hz, 1H), 8.13 (d, J = 8.3 Hz, 1H), 8.02-7.83 (m, 1H), 7.77-7.65 (m, 2H), 7.60 (d, J = 8.5 Hz, 1H), 3.29 (d, J = 3.9 Hz, 3H). | DMSO | >98 | G2/AQ3 |
| 1315 | HCl | $^{1}H$ NMR (300 MHz, DMSO) δ 9.62 (s, 1H), 9.02-8.93 (m, 1H), 8.89 (d, J = 4.5 Hz, 1H), 8.80 (s, 1H), 8.35 (d, J = 8.7 Hz, 1H), 8.18 (s, 1H), 8.04 (d, J = 8.7 Hz, 1H), 7.96-7.75 (m, 2H), 3.29 (d, J = 4.2 Hz, 3H). | DMSO | >98 | G2/AQ3 |
| 1316 | 2 HCl | $^{1}H$ NMR (300 MHz, DMSO) δ 10.36 (s, 1H), 9.67 (s, 1H), 9.13 (d, J = 8.2 Hz, 1H), 9.01-8.82 (m, 2H), 8.40 (d, J = 9.1 Hz, 1H), 8.26 (d, J = 8.7 Hz, 1H), 7.97 (s, 2H), 7.90 (dd, J = 8.0, 5.2 Hz, 1H), 7.65 (s, 1H), 3.31 (d, J = 4.3 Hz, 3H). | DMSO | >98 | G2/AQ3 |

TABLE 24-continued

| | | | | | |
|---|---|---|---|---|---|
| 1317 | | $^1$H NMR (300 MHz, DMSO) δ 9.65 (d, J = 1.9 Hz, 1H), 8.89-8.75 (m, 1H), 8.74-8.67 (m, 1H), 8.67-8.56 (m, 1H), 8.48 (s, 1H), 8.06-7.94 (m, 1H), 7.87 (d, J = 8.7 Hz, 1H), 7.68-7.51 (m, 2H), 7.46 (td, J = 9.6, 4.7 Hz, 1H), 7.39-7.21 (m, 1H), 3.18 (d, J = 4.4 Hz, 3H). | DMSO | >98 | G2/AQ3 |
| 1318 | HCl | $^1$H NMR (300 MHz, DMSO) δ 10.57 (s, 1H), 9.69 (d, J = 2.0 Hz, 1H), 9.15 (d, J = 8.0 Hz, 1H), 9.02 (s, 1H), 8.97 (d, J = 4.4 Hz, 1H), 8.40 (d, J = 8.8 Hz, 1H), 8.29 (d, J = 8.7 Hz, 1H), 7.91 (dd, J = 8.0, 5.2 Hz, 1H), 7.77-7.63 (m, 2H), 7.37-7.18 (m, 1H), 3.29 (d, J = 4.3 Hz, 3H). | DMSO | >98 | G2/AQ3 |
| 1319 | | $^1$H NMR (300 MHz, $CDCl_3$) δ 9.58 (d, J = 2.0 Hz, 1H), 8.78-8.60 (m, 2H), 8.35 (d, J = 1.7 Hz, 1H), 8.11-7.84 (m, 3H), 7.78 (d, J = 8.6 Hz, 1H), 7.54 (dd, J = 7.9, 4.8 Hz, 1H), 7.48-7.34 (m, 2H), 7.17 (d, J = 8.1 Hz, 1H), 7.10 (t, J = 7.4 Hz, 1H), 3.81 (s, 3H). | DMSO | >98 | G2/AQ3 |
| 1320 | | $^1$H NMR (300 MHz, $CDCl_3$) δ 9.62 (d, J = 2.1 Hz, 1H), 8.82-8.72 (m, 1H), 8.72-8.66 (m, 1H), 8.30 (s, 1H), 7.93 (dd, J = 8.7, 1.2 Hz, 1H), 7.86 (d, J = 8.6 Hz, 1H), 7.54 (dd, J = 7.9, 4.8 Hz, 1H), 7.50-7.33 (m, 2H), 7.18 (d, J = 8.3 Hz, 1H), 7.09 (t, J = 7.5 Hz, 1H), 3.82 (s, 3H), 3.46 (s, 6H). | DMSO | >98 | G2/AQ3 |
| 1321 | | $^1$H NMR (300 MHz, $CDCl_3$) δ 9.59 (d, J = 2.1 Hz, 1H), 8.76-8.66 (m, 2H), 8.50 (s, 2H), 8.06 (brs, 1H), 7.99 (dt, J = 8.6, 1.7 Hz, 1H), 7.86 (d, J = 8.7 Hz, 1H), 7.75-7.63 (m, 1H), 7.54 (dd, J = 7.9, 4.8 Hz, 1H), 7.52-7.44 (m, 1H), 7.44-7.32 (m, 2H). | DMSO | >98 | G2/AQ3 |
| 1322 | | $^1$H NMR (300 MHz, $CDCl_3$) δ 9.59 (d, J = 2.1 Hz, 1H), 8.79-8.62 (m, 3H), 8.21 (dd, J = 8.8, 1.9 Hz, 1H), 8.10 (brs, 2H), 7.86 (d, J = 8.7 Hz, 1H), 7.80-7.69 (m, 2H), 7.68-7.49 (m, 2H), 7.32-7.20 (m, 1H). | DMSO | >98 | G2/AQ3 |

TABLE 24-continued

| | | | | |
|---|---|---|---|---|
| 1323 | $^1$H NMR (300 MHz, $CDCl_3$) δ 9.58 (d, J = 2.0 Hz, 1H), 8.80-8.64 (m, 2H), 8.62 (d, J = 1.8 Hz, 1H), 8.14 (dd, J = 8.7, 1.9 Hz, 1H), 8.07 (brs, 2H), 7.98-7.87 (m, 2H), 7.85 (d, J = 8.7 Hz, 1H), 7.54 (dd, J = 7.9, 4.8 Hz, 1H), 7.38 (t, J = 8.8 Hz, 2H). | DMSO | >98 | G2/AQ3 |
| 1324 | $^1$H NMR (300 MHz, $CDCl_3$) δ 9.65-9.57 (m, 1H), 8.82-8.70 (m, 1H), 8.70-8.63 (m, 1H), 8.36 (d, J = 1.8 Hz, 1H), 8.11 (dd, J = 8.7, 1.7 Hz, 1H), 7.89 (d, J = 8.7 Hz, 1H), 7.72-7.60 (m, 2H), 7.60-7.47 (m, 2H), 7.32-7.18 (m, 1H), 3.49 (s, 6H). | DMSO | >98 | G2/AQ3 |
| 1325 | $^1$H NMR (400 MHz, DMSO) δ 9.64 (d, J = 1.4 Hz, 1H), 8.78 (dt, J = 8.3, 1.8 Hz, 1H), 8.69 (dd, J = 4.7, 1.8 Hz, 1H), 8.61-8.46 (m, 2H), 8.40 (d, J = 1.6 Hz, 1H), 7.99 (dd, J = 9.0, 1.8 Hz, 1H), 7.83 (d, J = 9.0 Hz, 1H), 7.54 (dd, J = 8.4, 4.5 Hz, 1H), 3.99 (d, J = 8.9 Hz, 6H), 3.17 (d, J = 4.6 Hz, 3H). | DMSO | >98 | G2/AQ3 |
| 1326 | $^1$H NMR (300 MHz, DMSO) δ 9.64-9.55 (m, 1H), 8.81-8.62 (m, 3H), 8.40 (s, 1H), 8.23 (dd, J = 8.8, 1.4 Hz, 1H), 8.13 (d, J = 7.7 Hz, 1H), 8.00 (d, J = 7.7 Hz, 2H), 7.89 (d, J = 8.7 Hz, 1H), 7.69 (t, J = 7.7 Hz, 1H), 7.54 (dd, J = 7.9, 4.8 Hz, 1H), 2.71 (s, 3H). | DMSO | >98 | G2/AQ3 |
| 1327 | $^1$H NMR (300 MHz, DMSO) δ 9.58 (d, J = 2.1 Hz, 1H), 8.76-8.65 (m, 3H), 8.24 (dd, J = 8.7, 1.8 Hz, 1H), 8.19-7.93 (m, 6H), 7.88 (d, J = 8.8 Hz, 1H), 7.54 (dd, J = 7.9, 4.8 Hz, 1HH), 2.65 (s, 3H). | DMSO | >98 | G2/AQ3 |
| 1328 | $^1$H NMR (300 MHz, DMSO) δ 9.60 (d, J = 1.8 Hz, 1H), 8.73 (dt, J = 8.0, 1.8 Hz, 1H), 8.69 (dd, J = 4.8, 1.6 Hz, 1H), 8.37 (s, 1H), 7.99 (brs, 2H), 7.92-7.81 (m, 2H), 7.67-7.60 (m, 1H), 7.60-7.52 (m, 2H), 7.52-7.43 (m, 2H). | DMSO | >98 | G2/AQ3 |

TABLE 24-continued

| | | | | | |
|---|---|---|---|---|---|
| 1329 | | $^1$H NMR (300 MHz, DMSO) δ 9.60 (d, J = 2.0 Hz, 1H), 8.77-8.65 (m, 3H), 8.19 (dd, J = 8.7, 1.8 Hz, 1H), 8.09 (brs, 2H), 7.99-7.94 (m, 1H), 7.90-7.79 (m, 2H), 7.63-7.51 (m, 2H), 7.48 (d, J = 8.1 Hz, 1H). | DMSO | >98 | G2/AQ3 |
| 1330 | | $^1$H NMR (300 MHz, DMSO) δ 9.65 (s, 1H), 8.87-8.75 (m, 1H), 8.70 (s, 1H), 8.55 (s, 1H), 8.41 (s, 1H), 8.25 (s, 1H), 8.09-7.76 (m, 3H), 7.62-7.44 (m, 1H), 7.18 (s, 1H), 3.93 (s, 3H), 3.17 (s, 3H). | DMSO | >98 | G2/AQ3 |
| 1331 | | $^1$H NMR (300 MHz, DMSO) δ 9.61 (s, 1H), 8.75 (d, J = 7.6 Hz, 1H), 8.68 (s, 1H), 8.45 (s, 1H), 8.18 (d, J = 9.2 Hz, 1H), 8.07 (d, J = 8.2 Hz, 2H), 8.01-7.87 (m, 3H), 7.55 (s, 1H), 3.51 (s, 6H), 2.63 (s, 3H). | DMSO | >98 | G2/AQ3 |
| 1332 | | $^1$H NMR (300 MHz, DMSO) δ 9.63 (s, 1H), 8.83-8.72 (m, 1H), 8.70 (d, J = 3.3 Hz, 1H), 8.21 (s, 1H), 7.89 (q, J = 8.6 Hz, 2H), 7.74-7.41 (m, 5H), 3.47 (s, 6H). | DMSO | >98 | G2/AQ3 |
| 1333 | | $^1$H NMR (300 MHz, DMSO) δ 9.62 (d, J = 2.0 Hz, 1H), 8.76 (dt, J = 7.9, 1.8 Hz, 1H), 8.70 (dd, J = 4.8, 1.6 Hz, 1H), 8.38 (d, J = 1.9 Hz, 1H), 8.13 (dd, J = 8.7, 1.9 Hz, 1H), 7.98-7.84 (m, 2H), 7.78 (d, J = 7.6 Hz, 1H), 7.66-7.41 (m, 3H), 3.51 (s, 6H). | DMSO | >98 | G2/AQ3 |
| 1334 | 2 HCl | $^1$H NMR (300 MHz, DMSO) δ 9.81-9.63 (m, 1H), 9.18 (d, J = 8.4 Hz, 1H), 9.07-8.89 (m, 1H), 8.39 (d, J = 8.7 Hz, 1H), 8.31 (d, J = 1.7 Hz, 1H), 8.22-8.07 (m, 1H), 8.02 (dd, J = 8.7, 1.7 Hz, 1H), 7.98-7.91 (m, 1H), 7.91-7.83 (m, 1H), 7.80-7.68 (m, 2H), 3.65 (s, 6H). | DMSO | >98 | G2/AQ3 |
| 1335 | | $^1$H NMR (300 MHz, DMSO) δ 9.65-9.62 (m, 1H), 8.82-8.75 (m, 1H), 8.73-8.68 (m, 1H), 8.61-8.56 (m, 1H), 8.50 (d, J = 2.0 Hz, 1H), 8.34-8.20 (m, 3H), 7.97 (d, J = 8.7 Hz, 1H), 7.82 (t, J = 8.0 Hz, 1H), 7.57 (dd, J = 8.3, 5.2 Hz, 1H), 3.54 (s, 6H). | DMSO | >98 | G2/AQ3 |

TABLE 24-continued

| | | | | | |
|---|---|---|---|---|---|
| 1336 | | $^1H$ NMR (300 MHz, DMSO) δ 9.61 (d, J = 1.8 Hz, 1H), 8.80-8.72 (m, 1H), 8.72-8.67 (m, 1H), 8.47 (d, J = 1.6 Hz, 1H), 8.39-8.29 (m, 2H), 8.19 (dd, J = 8.7, 1.8 Hz, 1H), 8.14-8.07 (m, 2H), 7.94 (d, J = 8.7 Hz, 1H), 7.55 (dd, J = 7.9, 4.8 Hz, 1H), 3.52 (s, 6H). | DMSO | >98 | G2/AQ3 |
| 1337 | 2 HCl | $^1H$ NMR (300 MHz, DMSO) δ 9.67-9.61 (m, 1H), 8.82-8.73 (m, 1H), 8.73-8.65 (m, 1H), 8.39 (s, 1H), 8.03-7.96 (m, 3H), 7.90-7.72 (m, 2H), 7.72-7.60 (m, 1H), 7.56 (dd, J = 7.6, 5.1 Hz, 1H), 3.53 (s, 6H). | DMSO | >98 | G2/AQ3 |
| 1338 | | $^1H$ NMR (300 MHz, DMSO) δ 9.65 (d, J = 2.1 Hz, 1H), 8.78 (dt, J = 8.1, 1.8 Hz, 1H), 8.71-8.59 (m, 3H), 8.19 (dd, J = 8.6, 1.7 Hz, 1H), 8.07-7.95 (m, 2H), 7.93-7.81 (m, 2H), 7.54 (dd, J = 7.9, 4.7 Hz, 1H), 7.47-7.34 (m, 2H), 3.23-3.20 (m, 3H). | DMSO | >98 | G2/AQ3 |
| 1339 | | $^1H$ NMR (300 MHz, DMSO) δ 9.68-9.64 (m, 1H), 8.83-8.75 (m, 1H), 8.69 (d, J = 4.7 Hz, 1H), 8.56-8.45 (m, 2H), 8.17-8.05 (m, 1H), 8.05-7.87 (m, 4H), 7.58-7.40 (m, 3H), 3.18 (d, J = 4.1 Hz, 3H). | DMSO | >98 | G2/AQ3 |
| 1340 | | $^1H$ NMR (300 MHz, DMSO) δ 9.67 (d, J = 1.5 Hz, 1H), 8.80 (dt, J = 7.9, 1.9 Hz, 1H), 8.69 (dd, J = 4.8, 1.7 Hz, 1H), 8.57-8.41 (m, 2H), 8.08 (dd, J = 6.1, 2.6 Hz, 1H), 7.99 (dd, J = 8.6, 1.8 Hz, 1H), 7.92 (d, J = 8.6 Hz, 1H), 7.84 (d, J = 5.6 Hz, 1H), 7.62-7.44 (m, 4H), 3.17 (d, J = 4.5 Hz, 3H). | DMSO | >98 | G2/AQ3 |
| 1341 | | $^1H$ NMR (300 MHz, DMSO) δ 9.66 (d, J = 1.5 Hz, 1H), 8.79 (dt, J = 7.9, 1.9 Hz, 1H), 8.68 (dd, J = 4.8, 1.7 Hz, 1H), 8.65 (d, J = 1.9 Hz, 1H), 8.61-8.53 (m, 1H), 8.35 (d, J = 1.6 Hz, 1H), 8.21 (dd, J = 8.7, 2.0 Hz, 1H), 8.16 (d, J = 8.4 Hz, 1H), 7.92-7.80 (m, 3H), 7.59-7.48 (m, 2H), 3.21 (d, J = 4.5 Hz, 3H). | DMSO | >98 | G2/AQ3 |

TABLE 24-continued

| | | | | | |
|---|---|---|---|---|---|
| 1342 | | $^{1}$H NMR (300 MHz, DMSO) δ 9.66 (d, J = 1.6 Hz, 1H), 8.79 (dt, J = 8.0, 1.9 Hz, 1H), 8.73-8.61 (m, 3H), 8.50 (s, 1H), 8.24 (dd, J = 8.7, 1.9 Hz, 1H), 8.04 (d, J = 8.4 Hz, 1H), 7.96-7.82 (m, 3H), 7.60-7.50 (m, 2H), 3.21 (d, J = 4.4 Hz, 3H). | DMSO | >98 | G2/AQ3 |
| 1343 | 2 HCl | $^{1}$H NMR (300 MHz, DMSO) δ 10.41 (brs, 1H), 9.75 (d, J = 1.7 Hz, 1H), 9.24-9.19 (m, 1H), 9.01 (dd, J = 5.2, 1.5 Hz, 1H), 8.90 (d, J = 1.5 Hz, 1H), 8.46 (d, J = 8.7 Hz, 1H), 8.39 (dd, J = 8.7, 1.7 Hz, 1H), 8.06-7.91 (m, 2H), 7.86 (d, J = 5.5 Hz, 1H), 7.66-7.52 (m, 3H), 3.29 (d, J = 4.5 Hz, 3H). | DMSO | >98 | G2/AQ3 |
| 1344 | HCl | $^{1}$H NMR (300 MHz, DMSO) δ 10.33 (brs, 1H), 9.78 (d, J = 2.0 Hz, 1H), 9.23 (d, J = 8.1 Hz, 1H), 9.01 (d, J = 5.0 Hz, 1H), 8.73 (s, 1H), 8.48 (d, J = 8.6 Hz, 1H), 8.14 (d, J = 8.6 Hz, 1H), 8.05 (d, J = 8.0 Hz, 2H), 7.95 (dd, J = 8.1, 5.2 Hz, 1H), 7.79 (d, J = 8.1 Hz, 1H), 7.72-7.50 (m, 4H), 3.27 (d, J = 4.3 Hz, 3H). | DMSO | >98 | G2/AQ3 |
| 1345 | | $^{1}$H NMR (300 MHz, DMSO) δ 9.68 (d, J = 1.4 Hz, 1H), 8.85-8.77 (m, 1H), 8.77-8.62 (m, 3H), 8.40 (s, 1H), 8.30 (dd, J = 8.7, 1.6 Hz, 1H), 8.14-7.95 (m, 4H), 7.91 (d, J = 8.7 Hz, 1H), 7.63-7.50 (m, 3H), 3.22 (d, J = 4.3 Hz, 3H). | DMSO | >98 | G2/AQ3 |
| 1346 | | $^{1}$H NMR (300 MHz, DMSO) δ 9.67 (d, J = 2.0 Hz, 1H), 8.80 (dt, J = 8.0, 1.9 Hz, 1H), 8.69 (dd, J = 4.7, 1.7 Hz, 1H), 8.67-8.55 (m, 2H), 8.25 (dd, J = 8.7, 1.8 Hz, 1H), 8.13-8.09 (m, 1H), 7.92-7.77 (m, 4H), 7.71 (d, J = 7.8 Hz, 1H), 7.67-7.47 (m, 4H), 7.47-7.37 (m, 1H), 3.20 (d, J = 4.4 Hz, 3H). | DMSO | >98 | G2/AQ3 |

TABLE 24-continued

| | | | | | |
|---|---|---|---|---|---|
| 1347 | | $^1H$ NMR (300 MHz, DMSO) δ 9.68-9.65 (m, 1H), 8.79 (dt, J = 8.0, 1.9 Hz, 1H), 8.69 (dd, J = 4.8, 1.7 Hz, 1H), 8.68-8.60 (m, 2H), 8.20 (dd, J = 8.7, 1.9 Hz, 1H), 7.99-7.95 (m, 2H), 7.92-7.81 (m, 3H), 7.80-7.73 (m, 2H), 7.61-7.46 (m, 3H), 7.46-7.36 (m, 1H), 3.20 (d, J = 4.4 Hz, 3H). | DMSO | >98 | G2/AQ3 |
| 1348 | | $^1H$ NMR (300 MHz, DMSO) δ 9.66 (d, J = 1.5 Hz, 1H), 8.80 (dt, J = 7.9, 1.9 Hz, 1H), 8.70 (dd, J = 4.7, 1.7 Hz, 1H), 8.55 (d, J = 4.6 Hz, 1H), 8.32 (d, J = 8.6 Hz, 1H), 8.04 (d, J = 1.8 Hz, 1H), 7.92-7.84 (m, 3H), 7.60-7.50 (m, 3H), 7.50-7.42 (m, 1H), 3.18 (d, J = 4.5 Hz, 3H). | DMSO | >98 | G2/AQ3 |
| 1349 | 2 HCl | $^1H$ NMR (300 MHz, DMSO) δ 10.23 (brs, 1H), 9.67 (d, J = 2.1 Hz, 1H), 9.04 (d, J = 7.7 Hz, 1H), 8.98-8.91 (m, 1H), 8.57 (d, J = 8.7 Hz, 1H), 8.43 (s, 1H), 8.08 (d, J = 8.3 Hz, 1H), 7.91-7.76 (m, 3H), 7.22-7.10 (m, 2H), 3.85 (s, 3H), 3.31 (d, J = 4.4 Hz, 3H). | DMSO | >98 | G2/AQ3 |
| 1350 | 2 HCl | $^1H$ NMR (300 MHz, DMSO) δ 10.48 (brs, 1H), 9.74 (d, J = 1.9 Hz, 1H), 9.19 (d, J = 8.3 Hz, 1H), 9.07-8.97 (m, 1H), 8.71 (d, J = 8.8 Hz, 1H), 8.64 (s, 1H), 8.36 (s, 1H), 8.19 (d, J = 7.6 Hz, 1H), 8.16-8.06 (m, 2H), 7.95 (dd, J = 8.1, 5.0 Hz, 1H), 7.75 (t, J = 7.7 Hz, 1H), 3.31 (d, J = 4.4 Hz, 3H), 2.71 (s, 3H). | DMSO | >98 | G2/AQ3 |
| 1351 | 2 HCl | $^1H$ NMR (300 MHz, DMSO) δ 10.47 (brs, 1H), 9.73 (d, J = 1.3 Hz, 1H), 9.19 (d, J = 8.3 Hz, 1H), 9.03-8.94 (m, 1H), 8.69-8.62 (m, 2H), 8.15-8.07 (m, 3H), 8.02-7.77 (m, 3H), 3.29 (d, J = 4.3 Hz, 3H), 2.65 (s, 3H). | DMSO | >98 | G2/AQ3 |
| 1352 | 2 HCl | $^1H$ NMR (300 MHz, DMSO) δ 10.44 (brs, 1H), 9.74 (s, 1H), 9.19 (d, J = 7.3 Hz, 1H), 8.99 (d, J = 5.2 Hz, 1H), 8.68 (d, J = 8.4 Hz, 1H), 8.37 (s, 1H), 8.03-7.90 (m, 1H), 7.83 (d, J = 8.2 Hz, 1H), 7.72-7.62 (m, 1H), 7.53 (d, J = 9.6 Hz, 3H), 3.32 (d, J = 4.0 Hz, 3H). | DMSO | >98 | G2/AQ3 |

TABLE 24-continued

| | | | | | |
|---|---|---|---|---|---|
| 1353 | 2 HCl | $^1$H NMR (300 MHz, DMSO) δ 10.48 (brs, 1H), 9.77 (s, 1H), 9.29-9.23 (m, 1H), 9.05-8.97 (m, 1H), 8.74-8.59 (m, 2H), 8.20-8.08 (m, 1H), 8.02-7.95 (m, 1H), 7.90 (s, 1H), 7.84-7.79 (m, 1H), 7.68-7.57 (m, 2H), 3.35-3.29 (m, 3H). | DMSO | >98 | G2/AQ3 |
| 1354 | 2 HCl | $^1$H NMR (300 MHz, DMSO) δ 10.35 (brs, 1H), 9.72 (d, J = 2.0 Hz, 1H), 9.21-9.11 (m, 1H), 8.98 (dd, J = 5.1, 1.4 Hz, 1H), 8.65 (d, J = 8.7 Hz, 1H), 8.59 (s, 1H), 8.09 (dd, J = 8.8, 1.7 Hz, 1H), 7.95-7.82 (m, 3H), 7.70-7.60 (m, 2H), 3.30 (d, J = 4.4 Hz, 3H). | DMSO | >98 | G2/AQ3 |
| 1355 | 2 HCl | $^1$H NMR (300 MHz, DMSO) δ 10.51 (brs, 1H), 9.77 (d, J = 1.9 Hz, 1H), 9.22 (d, J = 8.2 Hz, 1H), 9.01 (dd, J = 5.1, 1.4 Hz, 1H), 8.69 (s, 1H), 8.40 (d, J = 8.7 Hz, 1H), 8.17 (dd, J = 8.7, 1.6 Hz, 1H), 7.96 (dd, J = 8.1, 5.2 Hz, 1H), 7.30-7.15 (m, 2H), 7.10 (dd, J = 7.3, 1.9 Hz, 1H), 3.89 (s, 3H), 3.59 (s, 3H), 3.30 (d, J = 4.5 Hz, 3H). | DMSO | >98 | G2/AQ3 |
| 1356 | 2 HCl | $^1$H NMR (300 MHz, DMSO) δ 10.42 (s, 1H), 9.71 (d, J = 1.8 Hz, 1H), 9.12 (d, J = 8.1 Hz, 1H), 8.97 (dd, J = 5.1, 1.5 Hz, 1H), 8.71 (s, 1H), 8.30 (d, J = 8.7 Hz, 1H), 8.19 (dd, J = 8.7, 1.6 Hz, 1H), 7.90 (dd, J = 7.9, 5.1 Hz, 1H), 7.18-7.06 (m, 2H), 7.01 (dd, J = 8.9, 3.1 Hz, 1H), 3.81 (s, 3H), 3.76 (s, 3H), 3.30 (d, J = 4.4 Hz, 3H). | DMSO | >98 | G2/AQ3 |
| 1357 | HCl | $^1$H NMR (300 MHz, DMSO) δ 10.21 (brs, 1H), 9.63 (s, 1H), 8.99 (d, J = 8.0 Hz, 1H), 8.93 (d, J = 3.7 Hz, 1H), 8.87 (s, 1H), 8.37 (d, J = 8.9 Hz, 1H), 8.15 (d, J = 8.2 Hz, 1H), 7.91-7.78 (m, 1H), 7.05 (d, J = 2.1 Hz, 2H), 6.66-6.58 (m, 1H), 3.87 (s, 6H), 3.31 (d, J = 4.2 Hz, 3H). | DMSO | >98 | G2/AQ3 |

TABLE 24-continued

| | | | | | |
|---|---|---|---|---|---|
| 1358 | 2 HCl | $^1$H NMR (300 MHz, DMSO) δ 10.43 (brs, 1H), 9.73 (d, J = 1.8 Hz, 1H), 9.17 (d, J = 8.2 Hz, 1H), 8.99 (dd, J = 5.0, 1.3 Hz, 1H), 8.69 (d, J = 8.6 Hz, 1H), 8.49 (s, 1H), 8.05-7.88 (m, 2H), 7.71 (t, J = 7.9 Hz, 1H), 7.64-7.50 (m, 1H), 7.50-7.33 (m, 2H), 3.32 (d, J = 4.3 Hz, 3H). | DMSO | >98 | G2/AQ3 |
| 1359 | 2 HCl | $^1$H NMR (300 MHz, DMSO) δ 10.29 (s, 1H), 9.70 (d, J = 1.7 Hz, 1H), 9.14 (d, J = 8.3 Hz, 1H), 8.97 (dd, J = 5.1, 1.3 Hz, 1H), 8.63 (d, J = 8.7 Hz, 1H), 8.58 (s, 1H), 8.15-8.04 (m, 1H), 7.90 (dd, J = 8.0, 5.1 Hz, 1H), 7.75-7.57 (m, 3H), 7.43-7.30 (m, 1H), 3.30 (d, J = 4.3 Hz, 3H). | DMSO | >98 | G2/AQ3 |
| 1360 | 2 HCl | $^1$H NMR (300 MHz, DMSO) δ 10.41 (brs, 1H), 9.73 (d, J = 1.9 Hz, 1H), 9.16 (d, J = 8.3 Hz, 1H), 8.98 (dd, J = 5.1, 1.4 Hz, 1H), 8.65 (d, J = 8.8 Hz, 1H), 8.60 (s, 1H), 8.12-8.02 (m, 1H), 8.00-7.84 (m, 3H), 7.49-7.33 (m, 2H), 3.30 (d, J = 4.4 Hz, 3H). | DMSO | >98 | G2/AQ3 |
| 1361 | 2 HCl | $^1$H NMR (300 MHz, DMSO) δ 10.39 (s, 1H), 9.71 (d, J = 1.8 Hz, 1H), 9.17-9.08 (m, 1H), 8.97 (dd, J = 5.1, 1.5 Hz, 1H), 8.64 (d, J = 8.7 Hz, 1H), 8.58 (s, 1H), 8.07 (dd, J = 8.6, 1.7 Hz, 1H), 7.88 (dd, J = 8.1, 5.2 Hz, 1H), 7.70-7.58 (m, 2H), 7.46 (t, J = 7.6 Hz, 1H), 7.33 (d, J = 7.4 Hz, 1H), 3.30 (d, J = 4.4 Hz, 3H), 2.43 (s, 3H). | DMSO | >98 | G2/AQ3 |
| 1362 | 2 HCl | $^1$H NMR (300 MHz, DMSO) δ 10.37 (brs, 1H), 9.70 (d, J = 1.7 Hz, 1H), 9.10 (d, J = 8.1 Hz, 1H), 8.96 (dd, J = 5.0, 1.4 Hz, 1H), 8.62 (d, J = 8.7 Hz, 1H), 8.58 (s, 1H), 8.08 (dd, J = 8.6, 1.6 Hz, 1H), 7.87 (dd, J = 7.9, 5.0 Hz, 1H), 7.74 (d, J = 8.2 Hz, 2H), 7.39 (d, J = 8.0 Hz, 2H), 3.30 (d, J = 4.4 Hz, 3H), 2.40 (s, 3H). | DMSO | >98 | G2/AQ3 |
| 1363 | 2 HCl | $^1$H NMR (300 MHz, DMSO) δ 9.82 (brs, 1H), 9.65 (s, 1H), 9.14-9.02 (m, 1H), 9.02-8.90 (m, 1H), 8.64-8.51 (m, 1H), 8.20 (s, 1H), 8.07 (d, J = 7.8 Hz, 1H), 8.00-7.85 (m, 3H), 7.85-7.66 (m, 2H), 3.30 (s, 3H). | DMSO | >98 | G2/AQ3 |

TABLE 24-continued

| | | | | | |
|---|---|---|---|---|---|
| 1364 | HCl | $^1$H NMR (300 MHz, DMSO) δ 9.83 (brs, 1H), 9.68-9.63 (m, 1H), 9.12-9.02 (m, 1H), 9.01-8.91 (m, 1H), 8.56 (d, J = 9.2 Hz, 1H), 8.42 (s, 1H), 8.35 (s, 1H), 8.19 (d, J = 8.7 Hz, 1H), 8.13 (d, J = 9.3 Hz, 1H), 7.97 (d, J = 7.8 Hz, 1H), 7.93-7.84 (m, 1H), 7.79 (t, J = 8.2 Hz, 1H), 3.28 (d, 4.5 Hz, 3H). | DMSO | >98 | G2/AQ3 |
| 1365 | 2 HCl | $^1$H NMR (300 MHz, DMSO) δ 10.27 (brs, 1H), 9.72 (s, 1H), 9.23-9.10 (m, 1H), 8.98 (s, 1H), 8.77-8.55 (m, 2H), 8.18-7.86 (m, 6H), 3.34-3.27 (m, 3H). | DMSO | >98 | G2/AQ3 |
| 1366 | | $^1$H NMR (300 MHz, DMSO) δ 9.66 (d, J = 2.0 Hz, 1H), 8.79 (dt, J = 7.9, 1.9 Hz, 1H), 8.69 (dd, J = 4.7, 1.6 Hz, 1H), 8.65-8.53 (m, 2H), 8.22-8.12 (m, 3H), 7.92 (dd, J = 8.8, 1.5 Hz, 1H), 7.86 (d, J = 8.7 Hz, 1H), 7.80 (d, J = 8.8 Hz, 1H), 7.54 (dd, J = 7.9, 4.8 Hz, 1H), 4.11 (s, 3H), 3.20 (d, J = 4.4 Hz, 3H). | DMSO | >98 | G2/AQ3 |
| 1367 | | $^1$H NMR (300 MHz, DMSO) δ 11.10 (s, 1H), 9.63 (d, J = 2.0 Hz, 1H), 8.85 (d, J = 1.7 Hz, 1H), 8.81-8.70 (m, 2H), 8.39 (dd, J = 8.9, 1.9 Hz, 1H), 8.15-8.02 (m, 5H), 7.60 (dd, J = 8.0, 4.8 Hz, 1H), 2.65 (s, 3H), 2.61 (s, 3H). | | | |
| 1368 | HCl | $^1$H NMR (300 MHz, DMSO) δ 9.72 (d, J = 1.8 Hz, 1H), 9.27-9.21 (m, 1H), 8.97 (dd, J = 5.3, 1.4 Hz, 1H), 8.50 (dd, J = 8.8, 2.1 Hz, 1H), 8.34 (d, J = 1.9 Hz, 1H), 8.30 (d, J = 8.8 Hz, 1H), 8.15-8.09 (m, 2H), 8.09-7.98 (m, 3H), 3.55 (s, 3H), 2.65 (s, 3H), 2.22 (s, 3H). | DMSO | >98 | G2/AQ3 |
| 1369 | HCl | $^1$H NMR (300 MHz, DMSO) δ 11.16 (s, 1H), 9.67 (s, 1H), 9.20 (d, J = 8.2 Hz, 1H), 8.97 (d, J = 4.3 Hz, 1H), 8.75 (s, 1H), 8.23 (d, J = 8.7 Hz, 1H), 8.14 (d, J = 8.8 Hz, 1H), 8.02 (dd, J = 8.0, 5.5 Hz, 1H), 7.66-7.47 (m, 2H), 7.47-7.34 (m, 1H), 2.56 (s, 3H). | DMSO | >98 | G2/AQ3 |

TABLE 24-continued

| | | | | | |
|---|---|---|---|---|---|
| 1370 | 2 HCl | $^1$H NMR (300 MHz, DMSO) δ 10.17 (brs, 1H), 9.68 (d, J = 2.0 Hz, 1H), 9.06 (d, J = 8.0 Hz, 1H), 8.95 (dd, J = 5.0, 1.4 Hz, 1H), 8.77 (s, 1H), 8.31 (s, 2H), 8.16 (d, J = 2.1 Hz, 1H), 7.87 (dd, J = 7.8, 5.2 Hz, 1H), 7.72 (d, J = 7.8 Hz, 1H), 7.61-7.47 (m, 2H), 7.19 (d, J = 1.4 Hz, 1H), 3.31 (d, J = 4.4 Hz, 3H). | DMSO | >98 | G2/AQ3 |
| 1371 | 2 HCl | $^1$H NMR (300 MHz, DMSO) δ 10.28 (brs, 1H), 9.71 (s, 1H), 9.16 (d, J = 7.9 Hz, 1H), 8.98 (d, J = 4.2 Hz, 1H), 8.67 (d, J = 8.9 Hz, 1H), 8.45 (s, 1H), 8.01-7.83 (m, 2H), 7.68-7.50 (m, 2H), 7.50-7.35 (m, 1H), 3.31 (d, J = 4.1 Hz, 3H). | DMSO | >98 | G2/AQ3 |
| 1372 | HCl | $^1$H NMR (300 MHz, DMSO) δ 9.72-9.45 (m, 2H), 8.95 (d, J = 7.6 Hz, 1H), 8.88 (d, J = 3.8 Hz, 1H), 8.49 (d, J = 8.5 Hz, 1H), 8.13 (s, 1H), 7.91-7.75 (m, 3H), 7.53-7.43 (m, 1H), 7.36-7.25 (m, 1H), 3.27 (d, J = 4.3 Hz, 3H). | DMSO | >98 | G2/AQ3 |
| 1373 | 2 HCl | $^1$H NMR (300 MHz, DMSO) δ 10.04 (brs, 1H), 9.70 (s, 1H), 9.22-9.07 (m, 1H), 8.93 (s, 1H), 8.62 (d, J = 7.6 Hz, 1H), 8.55 (s, 1H), 8.06 (d, J = 8.9 Hz, 1H), 7.99-7.79 (m, 2H), 7.79-7.55 (m, 2H), 3.33-3.27 (m, 3H). | DMSO | >98 | G2/AQ3 |
| 1374 | 2 HCl | $^1$H NMR (300 MHz, DMSO) δ 9.64 (s, 1H), 9.34 (brs, 1H), 9.06-8.92 (m, 1H), 8.86 (s, 1H), 8.50-8.37 (m, 1H), 8.25 (s, 1H), 8.11-7.95 (m, 1H), 7.85-7.74 (m, 1H), 7.74-7.57 (m, 2H), 7.43-7.29 (m, 1H), 3.28-3.21 (m, 3H). | DMSO | >98 | G2/AQ3 |
| 1375 | HCl | $^1$H NMR (300 MHz, DMSO) δ 9.63 (d, J = 1.6 Hz, 1H), 9.38 (brs, 1H), 9.01-8.91 (m, 1H), 8.84 (dd, J = 5.0, 1.6 Hz, 1H), 8.60 (s, 1H), 8.08 (s, 2H), 7.76 (dd, J = 7.9, 5.1 Hz, 1H), 7.64-7.38 (m, 2H), 3.26 (d, J = 3.7 Hz, 3H). | DMSO | >98 | G2/AQ3 |
| 1376 | HCl | $^1$H NMR (300 MHz, DMSO) δ 9.88 (brs, 1H), 9.65 (s, 1H), 9.18-8.99 (m, 1H), 8.90 (s, 1H), 8.70 (s, 1H), 8.31-8.03 (m, 2H), 7.94-7.77 (m, 2H), 7.77-7.57 (m, 1H), 3.28 (s, 3H). | DMSO | >98 | G2/AQ3 |

TABLE 24-continued

| | | | | | |
|---|---|---|---|---|---|
| 1377 | 2 HCl | $^1$H NMR (300 MHz, DMSO) δ 10.33 (s, 1H), 9.67 (s, 1H), 9.10 (d, J = 7.8 Hz, 1H), 9.02 (s, 1H), 8.92 (d, J = 5.0 Hz, 1H), 8.35 (d, J = 8.8 Hz, 1H), 8.25 (d, J = 8.8 Hz, 1H), 8.03-7.76 (m, 3H), 3.31 (s, 3H). | DMSO | >98 | G2/AQ3 |
| 1378 | 2 HCl | $^1$H NMR (300 MHz, DMSO) δ 9.66 (d, J = 1.7 Hz, 1H), 9.56-9.34 (m, 1H), 9.26-9.10 (m, 1H), 9.05 (d, J = 4.7 Hz, 1H), 8.44 (s, 1H), 8.19 (dd, J = 8.1, 5.7 Hz, 1H), 7.95 (d, J = 11.5 Hz, 1H), 7.63-7.45 (m, 2H), 7.45-7.26 (m, 1H), 3.19 (d, J = 4.4 Hz, 3H). | DMSO | >98 | G2/AQ3 |
| 1379 | HCl | $^1$H NMR (300 MHz, DMSO) δ 9.67-9.59 (m, 1H), 9.38 (d, J = 8.3 Hz, 1H), 9.22-9.10 (m, 1H), 9.03 (d, J = 4.9 Hz, 1H), 8.37 (s, 1H), 8.16 (dd, J = 8.1, 5.6 Hz, 1H), 7.89 (d, J = 11.6 Hz, 1H), 7.78 (td, J = 8.9, 6.6 Hz, 1H), 7.54-7.36 (m, 1H), 7.30 (td, J = 8.3, 2.0 Hz, 1H), 3.18 (d, J = 4.4 Hz, 3H). | DMSO | >98 | G2/AQ3 |
| 1380 | 2 HCl | $^1$H NMR (300 MHz, DMSO) δ 9.72 (d, J = 1.6 Hz, 1H), 9.25-9.14 (m, 1H), 8.99 (dd, J = 5.2, 1.5 Hz, 1H), 8.51 (s, 1H), 8.44 (d, J = 8.7 Hz, 1H), 8.26-8.11 (m, 1H), 7.94 (dd, J = 8.0, 5.2 Hz, 1H), 7.65-7.49 (m, 2H), 7.49-7.29 (m, 1H), 3.69 (s, 6H). | DMSO | >98 | G2/AQ3 |
| 1381 | 2 HCl | $^1$H NMR (300 MHz, DMSO) δ 9.71 (s, 1H), 9.18 (d, J = 8.0 Hz, 1H), 8.98 (d, J = 5.1 Hz, 1H), 8.49-8.36 (m, 2H), 8.16 (d, J = 8.8 Hz, 1H), 7.99-7.86 (m, 1H), 7.86-7.72 (m, 1H), 7.46 (t, J = 10.2 Hz, 1H), 7.29 (t, J = 8.5 Hz, 1H), 3.69 (s, 6H). | DMSO | >98 | G2/AQ3 |
| 1382 | HCl | $^1$H NMR (300 MHz, DMSO) δ 10.25 (brs, 1H), 9.66 (d, J = 1.6 Hz, 1H), 9.04 (d, J = 3.2 Hz, 1H), 8.94 (dd, J = 5.0, 1.6 Hz, 1H), 8.70 (s, 1H), 8.23 (d, J = 8.8 Hz, 1H), 8.16 (dd, J = 8.7, 1.5 Hz, 1H), 7.84 (dd, J = 8.0, 5.1 Hz, 1H), 7.71 (dd, J = 8.0, 1.4 Hz, 1H), 7.65-7.55 (m, 2H), 3.90 (s, 3H), 3.29 (d, J = 4.5 Hz, 3H), 2.64 (s, 3H). | DMSO | >98 | G2/AQ3 |

TABLE 24-continued

| | | | | | |
|---|---|---|---|---|---|
| 1383 | 2 HCl | $^1$H NMR (300 MHz, DMSO) δ 10.18 (brs, 1H), 9.68 (d, J = 1.8 Hz, 1H), 9.17 (d, J = 8.0 Hz, 1H), 8.99 (dd, J = 5.2, 1.4 Hz, 1H), 8.86 (s, 1H), 8.31 (d, J = 8.7 Hz, 1H), 8.22 (d, J = 8.8 Hz, 1H), 7.97 (dd, J = 8.0, 5.3 Hz, 1H), 7.64-7.49 (m, 2H), 7.49-7.34 (m, 1H), 4.06-3.92 (m, 2H), 3.73 (t, J = 5.5 Hz, 2H), 3.33 (s, 3H). | DMSO | >98 | G2/AQ3 |
| 1384 | 2 HCl | $^1$H NMR (300 MHz, DMSO) δ 10.18 (brs, 1H), 9.67 (d, J = 1.6 Hz, 1H), 9.14 (d, J = 3.1 Hz, 1H), 8.99 (dd, J = 5.2, 1.5 Hz, 1H), 8.80 (s, 1H), 8.29 (d, J = 8.7 Hz, 1H), 8.18 (d, J = 8.7 Hz, 1H), 7.95 (dd, J = 8.2, 5.2 Hz, 1H), 7.79 (td, J = 8.9, 6.6 Hz, 1H), 7.50 (ddd, J = 11.6, 9.3, 2.6 Hz, 1H), 7.33 (td, J = 8.3, 2.3 Hz, 1H), 4.08-3.94 (m, 3H), 3.73 (t, J = 5.5 Hz, 3H), 3.32 (s, 3H). | DMSO | >98 | G2/AQ3 |
| 1385 | 2 HCl | $^1$H NMR (300 MHz, DMSO) δ 10.33 (brs, 1H), 9.70 (d, J = 1.7 Hz, 1H), 9.15 (d, J = 8.2 Hz, 1H), 8.99 (dd, J = 5.2, 1.5 Hz, 1H), 8.81 (s, 1H), 8.33 (d, J = 8.7 Hz, 1H), 8.18 (d, J = 8.7 Hz, 1H), 7.95 (dd, J = 8.1, 5.2 Hz, 1H), 7.81 (td, J = 8.9, 6.6 Hz, 1H), 7.49 (ddd, J = 11.5, 9.3, 2.5 Hz, 1H), 7.32 (td, J = 8.5, 2.2 Hz, 1H), 3.96-3.78 (m, 2H), 3.48 (t, J = 6.1 Hz, 2H), 3.27 (s, 3H), 2.14-1.93 (m, 2H). | DMSO | >98 | G2/AQ3 |
| 1386 | 2 HCl | $^1$H NMR (300 MHz, DMSO) δ 9.73 (s, 1H), 9.17 (d, J = 8.4 Hz, 1H), 8.99 (s, 1H), 8.52 (s, 1H), 8.43 (d, J = 8.8 Hz, 1H), 8.21 (d, J = 9.0 Hz, 1H), 8.02-7.90 (m, 1H), 7.87-7.78 (m, 1H), 7.57-7.38 (m, 1H), 7.38-7.24 (m, 1H), 4.31-4.18 (m, 4H), 2.08 (s, 4H). | DMSO | >98 | G2/AQ3 |
| 1387 | 2 HCl | $^1$H NMR (300 MHz, DMSO) δ 9.68 (d, J = 1.7 Hz, 1H), 9.17 (d, J = 8.3 Hz, 1H), 8.99 (dd, J = 5.2, 1.5 Hz, 1H), 8.34 (d, J = 8.6 Hz, 1H), 8.24-8.12 (m, 2H), 7.97 (dd, J = 8.0, 5.2 Hz, 1H), 7.81 (td, J = 8.9, 6.6 Hz, 1H), 7.49 (ddd, J = 11.6, 9.3, 2.5 Hz, 1H), 7.30 (td, J = 8.4, 2.1 Hz, 1H), 4.16 (brs, 4H), 1.80 (brs, 6H). | DMSO | >98 | G2/AQ3 |

TABLE 24-continued

| | | | | | |
|---|---|---|---|---|---|
| 1388 | 2 HCl | $^1$H NMR (300 MHz, DMSO) δ 9.70 (d, J = 1.7 Hz, 1H), 9.26 (d, J = 8.3 Hz, 1H), 9.01 (dd, J = 5.3, 1.4 Hz, 1H), 8.37-8.19 (m, 2H), 8.15 (d, J = 8.7 Hz, 1H), 8.02 (dd, J = 8.1, 5.3 Hz, 1H), 7.81 (td, J = 8.9, 6.5 Hz, 1H), 7.48 (ddd, J = 11.6, 9.3, 2.6 Hz, 1H), 7.30 (td, J = 8.4, 2.3 Hz, 1H), 4.23-4.12 (m, 4H), 3.90-3.80 (m, 4H). | DMSO | >98 | G2/AQ3 |
| 1389 | 2 HCl | $^1$H NMR (300 MHz, DMSO) δ 9.68 (d, J = 1.7 Hz, 1H), 9.17 (d, J = 8.2 Hz, 1H), 8.99 (dd, J = 5.2, 1.5 Hz, 1H), 8.34 (d, J = 8.7 Hz, 1H), 8.27-8.13 (m, 2H), 7.97 (dd, J = 8.1, 5.4 Hz, 1H), 7.67-7.48 (m, 2H), 7.41 (ddd, J = 14.7, 9.9, 4.9 Hz, 1H), 4.16 (brs, 4H), 1.80 (brs, 6H). | DMSO | >98 | G2/AQ3 |
| 1390 | 2 HCl | $^1$H NMR (300 MHz, DMSO) δ 9.70 (d, J = 1.8 Hz, 1H), 9.26 (d, J = 8.3 Hz, 1H), 9.01 (dd, J = 5.3, 1.4 Hz, 1H), 8.36-8.23 (m, 2H), 8.18 (d, J = 8.7 Hz, 1H), 8.03 (dd, J = 8.0, 5.4 Hz, 1H), 7.64-7.46 (m, 2H), 7.46-7.29 (m, 1H), 4.23-4.16 (m, 4H), 3.35 (d, J = 4.7 Hz, 4H). | DMSO | >98 | G2/AQ3 |
| 1391 | 2 HCl | $^1$H NMR (300 MHz, DMSO) δ 9.68 (d, J = 1.7 Hz, 1H), 9.18 (d, J = 8.2 Hz, 1H), 9.00 (dd, J = 5.2, 1.2 Hz, 1H), 8.62 (s, 1H), 8.39 (d, J = 8.7 Hz, 1H), 8.21 (d, J = 8.8 Hz, 1H), 7.98 (dd, J = 8.0, 5.2 Hz, 1H), 7.64-7.47 (m, 2H), 7.46-7.27 (m, 1H), 4.26 (t, J = 5.2 Hz, 2H), 3.85 (t, J = 5.3 Hz, 2H), 3.72 (s, 3H), 3.33 (s, 3H). | DMSO | >98 | G2/AQ3 |
| 1392 | 2 HCl | $^1$H NMR (300 MHz, DMSO) δ 9.67 (d, J = 1.7 Hz, 1H), 9.15 (d, J = 8.1 Hz, 1H), 8.99 (d, J = 4.1 Hz, 1H), 8.56 (s, 1H), 8.36 (d, J = 8.7 Hz, 1H), 8.17 (d, J = 8.7 Hz, 1H), 7.96 (dd, J = 8.1, 5.2 Hz, 1H), 7.86-7.70 (m, 1H), 7.55-7.40 (m, 1H), 7.30 (td, J = 8.5, 2.2 Hz, 1H), 4.36-4.18 (m, 2H), 3.88-3.77 (m, 2H), 3.72 (s, 3H), 3.33 (s, 3H). | DMSO | >98 | G2/AQ3 |

TABLE 24-continued

| | | | | | |
|---|---|---|---|---|---|
| 1393 | 2 HCl | $^1$H NMR (300 MHz, DMSO) δ 9.70 (d, J = 3.7 Hz, 1H), 9.24-9.06 (m, 1H), 8.99 (dd, J = 5.1, 1.5 Hz, 1H), 8.52 (s, 1H), 8.40 (d, J = 8.7 Hz, 1H), 8.30-8.14 (m, 1H), 7.93 (dd, J = 8.0, 5.2 Hz, 1H), 7.63-7.46 (m, 2H), 7.46-7.25 (m, 1H), 4.22-4.11 (m, 2H), 3.73 (s, 3H), 3.59 (t, J = 5.9 Hz, 2H), 2.10-1.92 (m, 2H). | DMSO | >98 | G2/AQ3 |
| 1394 | 2 HCl | $^1$H NMR (300 MHz, DMSO) δ 9.68 (d, J = 1.7 Hz, 1H), 9.11 (d, J = 8.3 Hz, 1H), 8.97 (dd, J = 5.1, 1.5 Hz, 1H), 8.46 (s, 1H), 8.36 (d, J = 8.7 Hz, 1H), 8.17 (d, J = 8.8 Hz, 1H), 7.90 (dd, J = 8.1, 5.2 Hz, 1H), 7.80 (td, J = 8.9, 6.6 Hz, 1H), 7.47 (ddd, J = 11.6, 9.3, 2.6 Hz, 1H), 7.29 (td, J = 8.4, 2.1 Hz, 1H), 4.22-4.08 (m, 2H), 3.72 (s, 3H), 3.59 (t, J = 5.9 Hz, 2H), 2.10-1.94 (m, 2H). | DMSO | >98 | G2/AQ3 |
| 1395 | HCl | $^1$H NMR (300 MHz, DMSO) δ 9.97-9.66 (m, 2H), 9.66-9.58 (m, 1H), 9.17-9.05 (m, 1H), 8.99 (dd, J = 5.2, 1.5 Hz, 1H), 8.66 (d, J = 8.6 Hz, 1H), 8.50 (s, 1H), 8.01-7.88 (m, 2H), 7.62 (ddd, J = 9.1, 6.1, 3.1 Hz, 1H), 7.58-7.36 (m, 2H). | DMSO | >98 | G2/AQ3 |
| 1396 | HCl | $^1$H NMR (300 MHz, DMSO) δ 9.70 (d, J = 1.8 Hz, 1H), 9.16 (d, J = 8.3 Hz, 1H), 8.98 (d, J = 3.9 Hz, 1H), 8.58-8.42 (m, 2H), 8.00-7.82 (m, 2H), 7.69-7.38 (m, 3H), 3.69 (s, 6H). | DMSO | >98 | G2/AQ3 |
| 1397 | HCl | $^1$H NMR (400 MHz, DMSO) δ 10.47 (s, 1H), 9.63 (d, J = 1.8 Hz, 1H), 9.11 (d, J = 3.0 Hz, 1H), 9.04 (s, 1H), 8.96 (dd, J = 5.1, 1.4 Hz, 1H), 8.41 (dd, J = 8.8, 1.6 Hz, 1H), 8.30 (d, J = 8.7 Hz, 1H), 8.14 (d, J = 3.2 Hz, 2H), 7.90 (d, J = 8.4 Hz, 3H), 3.34 (t, J = 17.1 Hz, 3H). | DMSO | >98 | AQ4 |
| 1398 | HCl | $^1$H NMR (400 MHz, DMSO) δ 10.15 (s, 1H), 9.65 (d, J = 1.7 Hz, 1H), 9.06 (d, J = 7.9 Hz, 1H), 8.99-8.90 (m, 2H), 8.44 (d, J = 7.2 Hz, 1H), 8.23-8.17 (m, 3H), 7.94-7.76 (m, 3H), 3.32 (d, J = 4.5 Hz, 3H). | DMSO | >98 | AQ4 |

TABLE 24-continued

| | | | | | |
|---|---|---|---|---|---|
| 1399 | HCl | $^1$H NMR (400 MHz, DMSO) δ 10.05 (s, 1H), 9.65 (d, J = 2.1 Hz, 1H), 9.10-9.00 (m, 1H), 8.96 (dd, J = 5.1, 1.5 Hz, 1H), 8.65 (s, 1H), 8.26-8.17 (m, 1H), 8.16-8.07 (m, 1H), 7.90 (dd, J = 7.8, 5.3 Hz, 1H), 7.77-7.69 (m, 1H), 7.68-7.55 (m, 3H), 3.29 (d, J = 4.6 Hz, 3H). | DMSO | >98 | AQ4 |
| 1400 | HCl | $^1$H NMR (400 MHz, DMSO) δ 9.77 (s, 1H), 9.63 (d, J = 1.7 Hz, 1H), 9.04-8.85 (m, 2H), 8.63 (s, 1H), 8.12 (q, J = 8.7 Hz, 2H), 7.83 (dd, J = 7.8, 4.9 Hz, 1H), 7.38-7.25 (m, 2H), 7.25-7.17 (m, 1H), 3.92 (s, 3H). | DMSO | >98 | AQ4 |
| 1401 | HCl | $^1$H NMR (400 MHz, DMSO) δ 10.05 (s, 1H), 9.64 (d, J = 1.7 Hz, 1H), 9.04 (d, J = 7.6 Hz, 1H), 8.99-8.92 (m, 1H), 8.89 (s, 1H), 8.41 (d, J = 8.8 Hz, 1H), 8.33-8.20 (m, 2H), 8.16 (d, J = 3.6 Hz, 1H), 7.94-7.84 (m, 1H), 7.81-7.68 (m, 1H), 3.32 (d, J = 4.5 Hz, 3H). | DMSO | >98 | AQ4 |
| 1402 | 2 HCl | $^1$H NMR (400 MHz, DMSO) δ 10.30 (s, 1H), 9.68 (d, J = 1.8 Hz, 1H), 9.15-9.05 (m, 1H), 8.97 (dd, J = 5.1, 1.4 Hz, 1H), 8.52 (s, 1H), 8.10 (s, 1H), 7.96-7.82 (m, 1H), 7.67-7.55 (m, 1H), 7.42-7.26 (m, 3H), 3.31 (d, J = 4.5 Hz, 3H), 2.40 (s, 3H). | DMSO | >98 | AQ5 |
| 1403 | 2 HCl | $^1$H NMR (400 MHz, DMSO) δ 9.87 (s, 1H), 9.59 (d, J = 1.5 Hz, 1H), 9.00-8.89 (m, 2H), 8.42 (s, 1H), 7.93-7.80 (m, 2H), 7.62-7.54 (m, 1H), 7.49-7.36 (m, 3H), 3.30 (d, J = 4.6 Hz, 3H), 2.32 (s, 3H). | DMSO | >98 | AQ5 |
| 1404 | 2 HCl | $^1$H NMR (400 MHz, DMSO) δ 10.19 (s, 1H), 9.68-9.61 (m, 1H), 9.05-8.98 (m, 1H), 8.94 (dd, J = 5.0, 1.6 Hz, 1H), 8.48 (d, J = 5.7 Hz, 1H), 8.02 (s, 1H), 7.91-7.82 (m, 1H), 7.59-7.50 (m, 2H), 7.43-7.36 (m, 2H), 3.31 (d, J = 4.6 Hz, 3H), 2.40 (s, 3H). | DMSO | >98 | AQ5 |

TABLE 24-continued

| | | | | | |
|---|---|---|---|---|---|
| 1405 | 2 HCl | $^1$H NMR (400 MHz, DMSO) δ 10.11 (s, 1H), 9.69-9.61 (m, 1H), 9.11-9.02 (m, 1H), 8.95 (dd, J = 5.1, 1.5 Hz, 1H), 8.52 (s, 1H), 8.05 (s, 1H), 7.89 (dd, J = 8.1, 5.1 Hz, 1H), 7.68-7.56 (m, 1H), 7.48-7.38 (m, 1H), 7.33-7.25 (m, 1H), 3.31 (d, J = 4.6 Hz, 3H), 2.33 (s, 3H). | DMSO | >98 | AQ5 |
| 1406 | 2 HCl | $^1$H NMR (400 MHz, DMSO) δ 10.03 (s, 1H), 9.63 (dd, J = 2.2, 0.7 Hz, 1H), 9.09-9.00 (m, 1H), 8.95 (dd, J = 5.1, 1.6 Hz, 1H), 8.48 (s, 1H), 8.00 (s, 1H), 7.89 (dd, J = 7.9, 5.2 Hz, 1H), 7.54-7.35 (m, 3H), 3.30 (d, J = 4.6 Hz, 3H), 2.33 (s, 3H). | DMSO | >98 | AQ5 |
| 1407 | 2 HCl | $^1$H NMR (400 MHz, DMSO) δ 10.09 (s, 1H), 9.63 (d, J = 1.6 Hz, 1H), 9.08-8.98 (m, 1H), 8.95 (dd, J = 5.1, 1.5 Hz, 1H), 8.46 (s, 1H), 7.98 (s, 1H), 7.87 (dd, J = 8.1, 5.1 Hz, 1H), 7.64 (ddt, J = 16.8, 14.3, 5.3 Hz, 2H), 7.40-7.30 (m, 1H), 3.30 (d, J = 4.6 Hz, 3H), 2.41 (s, 3H). | DMSO | >98 | AQ5 |
| 1408 | 2 HCl | $^1$H NMR (400 MHz, DMSO) δ 9.92 (s, 1H), 9.61 (d, J = 1.6 Hz, 1H), 9.03-8.97 (m, 1H), 8.94 (dd, J = 5.1, 1.5 Hz, 1H), 8.42 (s, 1H), 7.93 (s, 1H), 7.87 (dd, J = 8.1, 5.0 Hz, 1H), 7.44-7.36 (m, 1H), 7.33-7.23 (m, 2H), 3.29 (d, J = 4.6 Hz, 3H), 2.41 (s, 3H). | DMSO | >98 | AQ5 |
| 1409 | 2 HCl | $^1$H NMR (400 MHz, DMSO) δ 10.11 (s, 1H), 9.64 (d, J = 2.2 Hz, 1H), 9.10-9.03 (m, 1H), 8.96 (dd, J = 5.1, 1.5 Hz, 1H), 8.49 (s, 1H), 8.05-7.94 (m, 3H), 7.94-7.88 (m, 1H), 7.88-7.82 (m, 1H), 7.77 (t, J = 7.7 Hz, 1H), 3.31 (d, J = 4.5 Hz, 3H), 2.40 (s, 3H). | DMSO | >98 | AQ5 |
| 1410 | 3 HCl | $^1$H NMR (400 MHz, DMSO) δ 10.22 (s, 1H), 9.67 (d, J = 1.6 Hz, 1H), 9.14-9.07 (m, 1H), 8.97 (dd, J = 5.1, 1.5 Hz, 1H), 8.52 (s, 1H), 8.10-8.00 (m, 3H), 7.91 (dd, J = 7.9, 5.3 Hz, 1H), 7.75-7.67 (m, 2H), 3.31 (d, J = 4.5 Hz, 3H), 2.39 (s, 3H). | DMSO | >98 | AQ5 |

TABLE 24-continued

| | | | | | |
|---|---|---|---|---|---|
| 1411 | 2 HCl | $^1$H NMR (400 MHz, DMSO) δ 10.20-9.85 (m, 1H), 9.58 (s, 1H), 8.94-8.85 (m, 2H), 8.38 (s, 1H), 7.88-7.76 (m, 2H), 7.54-7.44 (m, 1H), 7.24-7.16 (m, 2H), 7.12 (td, J = 7.4, 0.9 Hz, 1H), 3.76 (s, 3H), 3.31 (d, J = 4.5 Hz, 3H), 2.24 (s, 3H). | DMSO | >98% | AQ5 |
| 1412 | 2 HCl | $^1$H NMR (400 MHz, DMSO) δ 10.20 (s, 1H), 9.69-9.61 (m, 1H), 9.01 (d, J = 7.8 Hz, 1H), 8.93 (dd, J = 5.0, 1.6 Hz, 1H), 8.49 (s, 1H), 8.06 (s, 1H), 7.83 (dd, J = 8.0, 5.1 Hz, 1H), 7.51-7.41 (m, 1H), 7.13-7.05 (m, 1H), 7.05-6.95 (m, 2H), 3.81 (d, J = 10.8 Hz, 3H), 3.31 (d, J = 4.6 Hz, 3H), 2.41 (s, 3H). | DMSO | >98% | AQ5 |
| 1413 | 2 HCl | $^1$H NMR (400 MHz, DMSO) δ 10.09 (s, 1H), 9.60 (s, 1H), 9.00-8.88 (m, 2H), 8.42 (s, 1H), 7.94 (s, 1H), 7.86-7.78 (m, 1H), 7.48-7.39 (m, 2H), 7.16-7.06 (m, 2H), 3.85 (s, 3H), 3.31 (d, J = 4.6 Hz, 3H), 2.43 (s, 3H). | DMSO | >98% | AQ5 |
| 1414 | 2 HCl | $^1$H NMR (400 MHz, DMSO) δ 10.02 (s, 1H), 9.63 (s, 1H), 9.05-8.91 (m, 2H), 8.36 (s, 1H), 8.10-7.99 (m, 1H), 7.91-7.80 (m, 1H), 7.59-7.50 (m, 2H), 7.44-7.32 (m, 2H), 3.27 (d, J = 4.5 Hz, 3H), 2.45 (s, 3H). | DMSO | >98 | AQ5 |
| 1415 | 2 HCl | $^1$H NMR (400 MHz, DMSO) δ 10.01 (s, 1H), 9.65 (s, 1H), 9.10-8.99 (m, 1H), 8.97 (d, J = 5.0 Hz, 1H), 8.41 (s, 1H), 8.09 (s, 1H), 7.97-7.83 (m, 1H), 7.61-7.41 (m, 2H), 7.31 (td, J = 8.4, 2.2 Hz, 1H), 3.26 (d, J = 4.5 Hz, 3H), 2.35 (s, 3H). | DMSO | >98 | AQ5 |
| 1416 | 2 HCl | $^1$H NMR (400 MHz, DMSO) δ 10.01-9.69 (m, 1H), 9.61 (s, 1H), 8.94 (m, J = 5.0 Hz, 2H), 8.36 (s, 1H), 7.99 (s, 1H), 7.92-7.81 (m, 1H), 7.71-7.57 (m, 2H), 7.41-7.31 (m, 1H), 3.26 (d, J = 4.5 Hz, 3H), 2.47 (s, 3H). | DMSO | >98 | AQ5 |
| 1417 | 2 HCl | $^1$H NMR (400 MHz, DMSO) δ 9.90 (s, 1H), 9.63 (d, J = 1.8 Hz, 1H), 9.08-8.89 (m, 2H), 8.40 (s, 1H), 8.02 (s, 1H), 7.92-7.81 (m, 1H), 7.44-7.25 (m, 3H), 3.27 (d, J = 4.5 Hz, 3H), 2.49 (s, 3H). | DMSO | >98 | AQ5 |

TABLE 24-continued

| | | | | | |
|---|---|---|---|---|---|
| 1418 | 2 HCl | $^{1}H$ NMR (400 MHz, DMSO) δ 9.99 (s, 1H), 9.62 (s, 1H), 8.95 (d, J = 5.0 Hz, 2H), 8.27 (s, 1H), 8.11-7.99 (m, 1H), 7.89-7.80 (m, 1H), 7.53-7.45 (m, 1H), 7.24 (dd, J = 7.4, 1.7 Hz, 1H), 7.19 (d, J = 8.0 Hz, 1H), 7.12 (td, J = 7.4, 0.9 Hz, 1H), 3.74 (d, J = 8.9 Hz, 3H), 3.26 (d, J = 4.6 Hz, 3H), 2.28 (s, 3H). | DMSO | >98 | AQ5 |
| 1419 | 2 HCl | $^{1}H$ NMR (400 MHz, DMSO) δ 10.30 (s, 1H), 9.72 (d, J = 1.6 Hz, 1H), 9.20-9.10 (m, 1H), 8.98 (dd, J = 5.1, 1.5 Hz, 1H), 8.45 (s, 1H), 8.21 (s, 1H), 7.91 (dd, J = 8.0, 5.1 Hz, 1H), 7.48-7.40 (m, 1H), 7.08-7.01 (m, 3H), 3.84 (s, 3H), 3.26 (d, J = 4.5 Hz, 3H), 2.45 (s, 3H). | DMSO | >98 | AQ5 |
| 1420 | 2 HCl | $^{1}H$ NMR (400 MHz, DMSO) δ 10.08-9.71 (m, 1H), 9.58 (d, J = 2.0 Hz, 1H), 8.96-8.83 (m, 2H), 8.31 (s, 1H), 7.91 (s, 1H), 7.87-7.79 (m, 1H), 7.47-7.39 (m, 2H), 7.10 (d, J = 8.8 Hz, 2H), 3.84 (s, 3H), 3.27 (d, J = 4.5 Hz, 3H), 2.47 (s, 3H). | DMSO | >98 | AQ5 |
| 1421 | 2 HCl | 1H NMR (400 MHz, DMSO) δ 9.69-9.63 (m, 1H), 9.10-8.93 (m, 3H), 8.12 (d, J = 8.4 Hz, 1H), 7.90-7.82 (m, 2H), 7.63-7.58 (m, 1H), 7.56-7.43 (m, 1H), 7.30-7.22 (m, 1H), 3.35 (d, j = 4.6 Hz, 3H), 2.73 (s, 3H). | DMSO | >98 | AQ4 |
| 1422 | 2 HCl | 1H NMR (400 MHz, DMSO) δ 9.62 (s, 1H), 8.95 (d, J = 5.0 Hz, 3H), 8.03 (s, 1H), 7.85 (t, J = 9.9 Hz, 2H), 7.44-7.34 (m, 1H), 7.17 (dd, J = 8.2, 2.2 Hz, 2H), 3.34 (d, J = 4.5 Hz, 3H), 2.73 (s, 3H). | DMSO | >98 | AQ4 |
| 1423 | 2 HCl | 1H NMR (400 MHz, DMSO) δ 9.62 (d, J = 2.1 Hz, 1H), 9.00-8.75 (m, 3H), 8.08-7.99 (m, 1H), 7.99-7.93 (m, 1H), 7.93-7.79 (m, 3H), 7.79-7.73 (m, 2H), 3.34 (d, J = 4.5 Hz, 3H), 2.70 (s, 3H). | DMSO | >98 | AQ4 |
| 1424 | 2 HCl | 1H NMR (400 MHz, DMSO) δ 9.61 (s, 1H), 8.99-8.63 (m, 3H), 8.07-7.98 (m, 3H), 7.89-7.78 (m, 2H), 7.65-7.59 (m, 2H), 3.33 (d, J = 4.5 Hz, 3H), 2.70 (s, 3H). | DMSO | >98 | AQ4 |

TABLE 24-continued

| | | | | | |
|---|---|---|---|---|---|
| 1425 | 3 HCl | $^1$H NMR (400 MHz, DMSO) δ 10.49 (s, 1H), 9.56 (s, 1H), 9.19 (s, 1H), 8.95 (d, J = 5.3 Hz, 1H), 8.83 (d, J = 5.5 Hz, 1H), 8.73 (d, J = 6.4 Hz, 1H), 8.41 (d, J = 5.6 Hz, 1H), 8.26 (s, 1H), 8.09 (s, 1H), 8.02-7.91 (m, 2H), 7.85 (s, 1H), 7.78-7.68 (m, 1H), 7.61-7.51 (m, 1H), 7.48-7.36 (m, 2H), 5.36 (s, 2H). | DMSO | >98 | Method AQ3 |
| 1426 | 3 HCl | $^1$H NMR (400 MHz, DMSO) δ 10.53 (s, 1H), 9.67 (d, J = 1.8 Hz, 1H), 9.32 (dd, J = 5.8, 4.1 Hz, 1H), 8.97 (dd, J = 5.4, 1.4 Hz, 1H), 8.75 (d, J = 8.7 Hz, 1H), 8.35 (t, J = 7.9 Hz, 1H), 8.24 (d, J = 13.5 Hz, 1H), 8.03 (dd, J = 8.1, 5.4 Hz, 1H), 7.92 (dd, J = 13.5, 4.8 Hz, 2H), 7.85-7.73 (m, 2H), 7.53-7.43 (m, 1H), 7.36-7.25 (m, 1H), 5.40 (d, J = 5.6 Hz, 2H), 2.85 (s, 3H). | DMSO | >98 | Method AQ3 |
| 1427 | 3 HCl | $^1$H NMR (400 MHz, DMSO) δ 10.42 (s, 1H), 9.64 (d, J = 1.7 Hz, 1H), 9.26 (d,.J = 8.1 Hz, 1H), 8.95 (dd, J = 5.3, 1.4 Hz, 1H), 8.71 (d, J = 8.7 Hz, 1H), 8.30 (d, J = 18.0 Hz, 2H), 8.04-7.84 (m, 3H), 7.74 (dd, J = 7.8, 6.0 Hz, 2H), 7.62-7.33 (m, 3H), 5.38 (d, J = 5.5 Hz, 2H), 2.84 (s, 3H). | DMSO | >98 | Method AQ3 |
| 1428 | 3 HCl | $^1$H NMR (400 MHz, DMSO) δ 10.40 (s, 1H), 9.63 (d, J = 1.6 Hz, 1H), 9.24 (d, J = 8.1 Hz, 1H), 8.95 (dd, J = 5.3, 1.4 Hz, 1H), 8.69 (d, J = 3.7 Hz, 1H), 8.41-8.22 (m, 2H), 8.09 (dd, J = 8.7, 1.8 Hz, 1H), 8.01-7.84 (m, 4H), 7.74 (d, J = 7.8 Hz, 1H), 7.46-7.33 (m, 2H), 5.36 (d, J = 5.5 Hz, 2H), 2.83 (s, 3H). | DMSO | >98 | Method AQ3 |
| 1429 | 3 HCl | $^1$H NMR (400 MHz, DMSO) δ 10.21 (s, 1H), 9.62 (s, 1H), 9.19 (d, J = 7.8 Hz, 1H), 8.93 (d, J = 4.6 Hz, 1H), 8.68 (d, J = 8.6 Hz, 1H), 8.26 (dd, J = 28.0, 20.1 Hz, 2H), 8.04-7.80 (m, 3H), 7.72 (d, J = 7.8 Hz, 1H), 7.64-7.50 (m, 2H), 7.46-7.33 (m, 1H), 5.33 (d, J = 5.3 Hz, 2H), 2.81 (s, 3H). | DMSO | >98 | Method AQ3 |

TABLE 24-continued

| | | | | | |
|---|---|---|---|---|---|
| 1430 | 3 HCl | $^1$H NMR (400 MHz, DMSO) δ 10.40 (s, 1H), 9.66 (d, J = 1.8 Hz, 1H), 9.31 (d, J = 8.2 Hz, 1H), 8.96 (dd, J = 5.4, 1.4 Hz, 1H), 8.73 (d, J = 8.7 Hz, 1H), 8.33 (t, J = 7.9 Hz, 1H), 8.23 (s, 1H), 8.03 (dd, J = 8.1, 5.4 Hz, 1H), 7.93 (dd, J = 11.7, 8.3 Hz, 2H), 7.76 (d, J = 7.9 Hz, 1H), 7.70-7.60 (m, 1H), 7.54-7.35 (m, 2H), 5.38 (d, J = 5.5 Hz, 2H), 2.85 (s, 3H). | DMSO | >98 | Method AQ3 |
| 1431 | 3 HCl | $^1$H NMR (400 MHz, DMSO) δ 10.15 (s, 1H), 9.61 (s, 1H), 9.22 (t, J = 7.3 Hz, 1H), 8.98-8.90 (m, 1H), 8.65 (dd, J = 8.6, 3.0 Hz, 1H), 8.36-8.26 (m, 2H), 8.13 (dd, J = 8.7, 1.9 Hz, 1H), 8.05-7.95 (m, 1H), 7.88 (d, J = 7.9 Hz, 1H), 7.76-7.64 (m, 3H), 7.43-7.33 (m, 1H), 5.33 (s, 2H), 2.82 (s, 3H). | DMSO | >98 | Method AQ3 |
| 1432 | 3 HCl | $^1$H NMR (400 MHz, DMSO) δ 10.26 (s, 1H), 9.62 (d, J = 1.8 Hz, 1H), 9.23 (d, J = 8.2 Hz, 1H), 8.94 (dd, J = 5.4, 1.5 Hz, 1H), 8.78 (s, 1H), 8.30 (t, J = 7.9 Hz, 1H), 8.20-8.15 (m, 1H), 8.10 (d, J = 8.7 Hz, 1H), 8.00 (dd, J = 7.9, 5.3 Hz, 1H), 7.88 (d, J = 7.9 Hz, 1H), 7.80-7.71 (m, 2H), 7.59-7.50 (m, 1H), 7.47-7.35 (m, 2H), 5.35 (d, J = 5.5 Hz, 2H), 2.82 (s, 3H). | DMSO | >98 | Method AQ3 |
| 1433 | 3 HCl | $^1$H NMR (400 MHz, DMSO) δ 10.39 (s, 1H), 9.61 (d, J = 1.7 Hz, 1H), 9.19 (d, J = 8.2 Hz, 1H), 9.01 (d, J = 1.8 Hz, 1H), 8.93 (dd, J = 5.3, 1.5 Hz, 1H), 8.38 (dd, J = 8.8, 1.9 Hz, 1H), 8.29 (t, J = 7.9 Hz, 1H), 8.09 (d, J = 8.7 Hz, 1H), 7.97 (dd, J = 8.1, 5.3 Hz, 1H), 7.92-7.80 (m, 3H), 7.72 (d, J = 7.3 Hz, 1H), 7.66-7.57 (m, 1H), 7.35-7.26 (m, 1H), 5.36 (d, J = 5.5 Hz, 2H), 2.81 (s, 3H). | DMSO | >98 | Method AQ3 |

TABLE 24-continued

| | | | | | |
|---|---|---|---|---|---|
| 1434 | 3 HCl | $^{1}$H NMR (400 MHz, DMSO) δ 10.45 (s, 1H), 9.60 (d, J = 1.9 Hz, 1H), 9.19 (d, J = 8.2 Hz, 1H), 9.01-8.89 (m, 2H), 8.36-8.25 (m, 2H), 8.10 (d, J = 8.7 Hz, 1H), 8.05-7.94 (m, 3H), 7.88 (dd, J = 12.8, 3.4 Hz, 1H), 7.72 (d, J = 7.8 Hz, 1H), 7.46-7.35 (m, 2H), 5.36 (d, J = 5.5 Hz, 2H), 2.32 (s, 3H). | DMSO | >98 | Method AQ3 |
| 1435 | 3 HCl | $^{1}$H NMR (400 MHz, DMSO) δ 10.28 (s, 1H), 9.63 (d, J = 1.8 Hz, 1H), 9.24 (d, J = 8.2 Hz, 1H), 8.95 (d, 1H), 8.83 (s, 1H), 8.30 (t, J = 7.9 Hz, 1H), 8.19 (dd, J = 8.7, 1.8 Hz, 1H), 8.11 (d, J = 8.7 Hz, 1H), 8.00 (dd, J = 8.1, 5.4 Hz, 1H), 7.88 (d, J = 8.0 Hz, 1H), 7.73 (d, J = 7.8 Hz, 1H), 7.64-7.51 (m, 2H), 7.46-7.37 (m, 1H), 5.36 (d, J = 5.5 Hz, 2H), 2.82 (s, 3H). | DMSO | >98 | Method AQ3 |
| 1436 | 3 HCl | $^{1}$H NMR (400 MHz, DMSO) δ 10.02 (s, 1H), 9.56 (d, J = 1.6 Hz, 1H), 9.06 (d, J = 8.0 Hz, 1H), 8.88 (dd, J = 5.2, 1.5 Hz, 1H), 8.75 (s, 1H), 8.25-8.13 (m, 2H), 8.04 (d, J = 8.7 Hz, 1H), 7.89 (dd, J = 7.8, 5.3 Hz, 1H), 7.79 (d, J = 8.0 Hz, 1H), 7.70-7.60 (m, 2H), 7.53-7.44 (m, 1H), 7.38 (ddd, J = 12.2, 8.4, 3.5 Hz, 1H), 5.27 (d, J = 5.3 Hz, 2H), 2.77 (s, 3H). | DMSO | >98 | Method AQ3 |
| 1437 | 3 HCl | $^{1}$H NMR (400 MHz, DMSO) δ 10.20 (s, 1H), 9.60 (d, J = 1.7 Hz, 1H), 9.19 (d, J = 8.1 Hz, 1H), 8.93 (dd, J = 5.4, 1.5 Hz, 1H), 8.75 (s, 1H), 8.29 (t, J = 7.9 Hz, 1H), 8.17-8.05 (m, 2H), 7.98 (dd, J = 8.0, 5.4 Hz, 1H), 7.83 (ddd, J = 15.5, 8.4, 6.0 Hz, 2H), 7.72 (d, J = 7.8 Hz, 1H), 7.54-7.44 (m, 1H), 7.38-7.28 (m, 1H), 5.33 (d, J = 5.5 Hz, 2H), 2.81 (s, 3H). | DMSO | >98 | Method AQ3 |

TABLE 24-continued

| | | | | | |
|---|---|---|---|---|---|
| 1438 | 4 HCl | $^1$H NMR (400 MHz, DMSO) δ 10.45 (s, 1H), 9.62 (d, J = 1.7 Hz, 1H), 9.21 (d, J = 8.1 Hz, 1H), 9.03 (d, J = 1.7 Hz, 1H), 8.93 (dd, J = 5.3, 1.4 Hz, 1H), 8.39-8.26 (m, 2H), 8.15-8.04 (m, 2H), 8.00-7.81 (m, 3H), 7.76-7.59 (m, 2H), 5.36 (d, J = 5.5 Hz, 2H), 2.82 (s, 3H). | DMSO | >98 | Method AQ3 |
| 1439 | 3 HCl | $^1$H NMR (400 MHz, DMSO) δ 10.29 (s, 1H), 9.53 (d, J = 1.8 Hz, 1H), 9.12 (d, J = 8.0 Hz, 1H), 8.93 (dd, J = 5.3, 1.4 Hz, 1H), 8.78 (d, J = 2.5 Hz, 2H), 8.31 (t, J = 7.8 Hz, 1H), 8.13 (q, J = 8.7 Hz, 2H), 8.04-7.89 (m, 2H), 7.87-7.68 (m, 2H), 7.50 (ddd, J = 11.6, 9.3, 2.6 Hz, 1H), 7.33 (td, J = 8.3, 1.9 Hz, 1H), 5.30 (d, J = 5.4 Hz, 2H). | DMSO | >98 | Method AQ3 |
| 1440 | 2 HCl | $^1$H NMR (400 MHz, DMSO) 10.41 (s, 1H), 9.63 (d, J = 1.7 Hz, 1H), 9.15 (d, J = 8.1 Hz, 1H), 8.97 (dd, J = 5.2, 1.4 Hz, 1H), 8.83 (s, 1H), 8.20 (s, 2H), 7.97 (dd, J = 8.0, 5.3 Hz, 1H), 7.73-7.56 (m, 2H), 7.54-7.28 (m, 4H), 5.03 (d, J = 5.7 Hz, 2H). | DMSO | >98 | Method AQ3 |
| 1441 | 2 HCl | $^1$H NMR (400 MHz, DMSO) δ 9.59 (d, J = 1.6 Hz, 1H), 9.07-8.94 (m, 2H), 8.84 (s, 1H), 8.76 (s, 1H), 8.22-8.13 (m, 2H), 7.96 (dd, J = 8.0, 5.3 Hz, 1H), 7.66 (ddd, J = 9.2, 6.1, 3.2 Hz, 1H), 7.53-7.32 (m, 2H), 1.69 (s, 9H). | DMSO | >98 | Method AQ3 |
| 1442 | 2 HCl | $^1$H NMR (400 MHz, DMSO) δ 9.93 (s, 1H), 9.62 (d, J = 1.6 Hz, 1H), 9.06-8.87 (m, 2H), 8.39 (s, 1H), 8.06-7.98 (m, 3H), 7.87 (dd, J = 8.0, 5.1 Hz, 1H), 7.77--7.67 (m, 2H), 3.26 (d, J = 4.6 Hz, 3H), 2.45 (s, 3H). | DMSO | >98 | Method AQ3 |
| 1443 | 2 HCl | $^1$H NMR (400 MHz, DMSO) δ 9.98 (s, 1H), 9.64 (s, 1H), 8.99 (dd, J = 27.3, 6.4 Hz, 2H), 8.41 (s, 1H), 8.10-7.93 (m, 3H), 7.88 (dd, J = 7.7, 6.0 Hz, 2H), 7.76 (t, J = 7.8 Hz, 1H), 3.27 (d, J = 4.5 Hz, 3H), 2.46 (s, 3H). | DMSO | >98 | Method AQ3 |

TABLE 24-continued

| | | | | | |
|---|---|---|---|---|---|
| 1444 | 2 HCl | $^1$H NMR (400 MHz, DMSO) δ 9.76-9.69 (m, 1H), 9.37 (t, J = 5.4 Hz, 1H), 8.99 (dd, J = 11.7, 7.5 Hz, 1H), 8.81 (dt, J = 7.9, 4.0 Hz, 1H), 8.70 (t, J = 7.3 Hz, 1H), 8.52 (d, J = 9.2 Hz, 1H), 8.35-8.27 (m, 1H), 8.10 (dd, J = 12.8, 7.3 Hz, 1H), 8.01-7.90 (m, 2H), 7.77-7.71 (m, 1H), 7.50-7.37 (m, 3H), 7.06-7.01 (m, 1H), 5.19 (t, J = 17.9 Hz, 2H), 3.88 (s, 3H). | DMSO | >98 | Method AQ3, F, G2 (reflux) |
| 1445 | 2 HCl | 1H NMR (DMSO-d6) ppm 9.73 (s, 1H), 9.37 (brd, J = 8.08 Hz, 1H), 8.97 (brd, J = 5.24 Hz, 1H), 8.77 (brs, 1H), 8.20 (d, J = 8.48 Hz, 1H), 8.10-8.07 (brm, 1H), 7.63-7.55 (brm, 2H), 7.47 (d, J = 8.48 Hz, 1H), 7.32 (brm, 1H), 3.20 (d, J = 4.20 Hz, 3H), 2.65 (s, 3H). The 1H of 2HCl was not observed. | DMSO | >98 | AQ6 |
| 1446 | 3 HCl | 1H NMR (DMSO-d6) ppm 9.73 (d, J = 1.76 Hz, zH), 9.39 (brd, J = 8.16 Hz, 1H), 8.98 (dd, J = 5.44, 1.20 Hz, 1H), 8.80 (brs, 1H), 8.22 (d, J = 8.48 Hz, 1H), 8.12-8.08 (brm, 1H), 7.57-7.51 (m, 1H), 7.46-7.35 (m, 4H), 3.21 (d, J = 4.32 Hz, 3H), 2.55 (s, 3H). The 1H of 3HCl was not observed. | DMSO | >98 | AQ6 |
| 1447 | 3 HCl | 1H NMR (DMSO-d6) ppm 9.72 (d, J = 1.68 Hz, 1H), 9.26 (brd, J = 8.48 Hz, 1H), 8.91 (dd, J = 5.28, 1.40 Hz, 1H), 8.69 (brs, 1H), 8.18 (d, J = 8.56 Hz, 1H), 8.00-7.96 (brm, 1H), 7.53-7.49 (m, 2H), 7.44 (d, J = 8.56 Hz, 1H), 7.38-7.33 (m, 2H), 3.20 (d, J = 4.40 Hz, 3H), 2.63 (s, 3H). The 1H of 3HCl was not observed. | DMSO | >98 | AQ6 |
| 1448 | 2 HCl | 1H NMR (DMSO-d6) ppm 9.73 (d, J = 1.44 Hz, 1H), 9.36 (brd, J = 7.88 Hz, 1H), 8.96 (d, J = 5.04 Hz, 1H), 8.77 (brs, 1H), 8.21 (d, J = 8.56 Hz, 1H), 8.07 (brm, 1H), 7.48 (d, J = 8.56 Hz, 1H), 7.38-7.32 (m, 1H), 7.27-7.22 (m, 2H), 3.20 (d, J = 4.4 Hz, 3H), 2.65 (s, 3H). The 1H of 2HCl was not observed. | DMSO | >98 | AQ6 |

TABLE 24-continued

| | | | | | |
|---|---|---|---|---|---|
| 1449 | 3 HCl | 1H NMR (DMSO-d6) ppm 9.73 (d, J = 1.72 Hz, 1H), 9.32 (brd, J = 7.56 Hz, 1H), 8.94 (brd, J = 5.48 Hz, 1H), 8.74 (brs, 1H), 8.20 (d, J = 8.56 Hz, 1H), 8.08-8.02 (m, 1H), 7.60-7.54 (m, 1H), 7.47 (d, J = 7.35-7.27 (m, 3H), 3.20 (d, J = 4.4 Hz, 3H), 2.65 (s, 3H). The 1H of 3HCl was not observed. | DMSO | >98 | AQ6 |
| 1450 | 2 HCl | 1H NMR (DMSO-d6) ppm 9.74 (d, J = 1.76 Hz, 1H), 9.37 (brd, J = 8.16 Hz, 1H), 8.97 (brdd, J = 5.44, 1.24 Hz, 1H), 8.79 (brs, 1H), 8.22 (d, J = 8.52 Hz, 1H), 8.10-8.06 (brm, 1H), 7.48-7.35 (m, 4H), 3.21 (d, J = 4.36 Hz, 3H), 2.56 (brs, 3H). The 1H of 2HCl was not observed. | DMSO | >98 | AQ6 |
| 1451 | 3 HCl | 1H NMR (DMSO-d6) ppm 9.74 (d, J = 1.52 Hz, 1H), 9.37 (d, J = 8.08 Hz, 1H), 8.97 (dd, J = 5.54, 1.16 Hz, 1H), 8.80 (brs, 1H), 8.23 (d, J = 8.52 Hz, 1H), 8.10-8.07 (m, 1H), 7.60-7.53 (m, 1H), 7.48 (d, J = 8.52 Hz, 1H), 7.41-7.36 (m, 1H), 7.30-7.26 (m, 1H), 3.21 (d, J = 4.36 Hz, 3H), 2.56 (s, 3H). The 1H of 3HCl was not observed. | DMSO | >98 | AQ6 |
| 1452 | 3 HCl | 1H NMR (DMSO-d6) ppm 9.73 (d, J = 1.68 Hz, 1H), 9.26 (brd, J = 7.8 Hz, 1H), 8.91 (brdd, J = 5.28, 1.36 Hz, 1H), 8.71 (brs, 1H), 8.21 (d, J = 8.52 Hz, 1H), 8.00 (d, J = 8.4 Hz, 2H), 7.99-7.95 (m, 1H), 7.69 (d, 8.4 Hz, 2H), 7.46 (d, J = 8.52 Hz, 1H), 3.20 (d, J = 4.4 Hz, 3H), 2.63 (s, 3H). The 1H of 3HCl was not observed. | DMSO | >98 | AQ6 |
| 1453 | 2 HCl | 1H NMR (DMSO-d6) ppm 9.73 (d, J = 1.72 Hz, 1H), 9.33 (brd, J = 7.64 Hz, 1H), 8.95 (brd, J = 5.28 Hz, 1H), 8.76 (brs, 1H), 8.22 (d, J = 8.48 Hz, 1H), 8.05 (brm, J = 7.64, 5.28 Hz, 1H), 7.98-7.93 (m, 2 H), 7.84-7.81 (m, 1H), 7.74 (dd, J = 7.84, 7.76 Hz, 1H), 7.49 (d, J = 8.84 Hz, 1H), 3.21 (d, J = 4.4 Hz, 3H), 2.63 (s, 3H). The 1H of 2HCl was not observed. | DMSO | >98 | AQ6 |

TABLE 24-continued

| | | | | | |
|---|---|---|---|---|---|
| 1454 | 2 HCl | $^1$H NMR (DMSO-$d_6$) ppm 9.72 (d, J = 1.76 Hz, 1H), 9.42 (brd, J = 8.00 Hz, 1H), 9.00 (d, J = 5.52 Hz, 1H), 8.83 (bsr, 1H), 8.22 (d, J = 8.56 Hz, 1H), 8.13 (brm, 1H), 7.55-7.51 (m, 2H), 7.48-7.43 (m, 4H), 3.21 (brd, J = 4.16 Hz, 3H), 2.64 (s, 3H). The 1H of 2HCl was not observed. | DMSO | >98 | AQ6 |
| 1455 | 2 HCl | $^1$H NMR (DMSO-$d_6$) ppm 9.72 (s, 1H), 9.33 (d, J = 8.24 Hz, 1H), 8.96 (d, J = 5.40 Hz, 1H), 8.75 (brs, 1H), 8.17 (d, J = 8.60 Hz, 1H), 8.06 (brm, 1H), 7.45 (d, J = 8.80 Hz, 1H), 7.40 (d, J = 8.64 Hz, 2H), 7.08 (d, J = 8.64 Hz, 2H), 3.84 (s, 3H), 3.20 (d, J = 4.20 Hz, 3H), 2.66 (s, 3H). The 1H of 2HCl was not observed. | DMSO | >98 | AQ6 |
| 1456 | 2 HCl | $^1$H NMR (DMSO-$d_6$) ppm 9.72 (d, J = 1.64 Hz, 1H), 9.38 (d, J = 8.04 Hz, 1H), 8.98 (dd, J = 5.48, 1.24 Hz, 1H), 8.79 (brs, 1H), 8.20 (d, J = 8.52 Hz, 1H), 8.12-8.09 (m, 1H), 7.48-7.42 (m, 2H), 7.04-6.97 (m, 3H), 3.82 (s, 3H), 3.21 (d, J = 4.28 Hz, 3H), 2.65 (s, 3H). The 1H of 2HCl was not observed. | DMSO | >98 | AQ6 |
| 1457 | 2 HCl | $^1$H NMR (DMSO-$d_6$) ppm 9.71 (d, J = 1.32 Hz, 1H), 9.40 (d, J = 7.64 Hz, 1H), 8.99 (dd, J = 5.52, 1.16 Hz, 1H), 3.32 (brs, 1H), 8.17 (d, J = 8.48 Hz, 1H), 8.13 (m, 1H), 7.47-7.43 (m, 1H), 7.37 (d, J = 8.48 Hz, 1H), 7.22-7.16 (m, 2H), 7.11-7.07 (m, 1H), 3.73 (s, 3H), 3.21 (d, J = 4.12 Hz, 3H), 2.47 (s, 3H). The 1H of 2HCl was not observed. | DMSO | >98 | AQ6 |
| 1458 | 2 HCl | $^1$H NMR (DMSO-$d_6$) ppm 9.57 (d, J = 1.88 Hz, 1H), 8.93 (dd, J = 4.88, 1.56 Hz, 1H), 8.87 (brd, J = 6.52 Hz, 1H), 7.95 (d, J = 8.36 Hz, 1H), 7.84 (d, J = 8.36 Hz, 1H), 7.81 (m, 1H), 7.34 (d, J = 8.72 Hz, 2H), 7.11 (d, J = 8.72 Hz, 2H), 3.84 (s, 3H), 3.34 (d, J = 4.56 Hz, 3H), 2.72 (s, 3H). The 1H of 2HCl and NH— were not observed. | DMSO | >98 | AQ6 |

TABLE 24-continued

| | | | | | | | |
|---|---|---|---|---|---|---|---|
| 1459 | 2 HCl | $^1$H NMR (DMSO-$d_6$) ppm 9.59 (s, 1H), 8.94 (dd, J = 4.92, 1.48 Hz, 1H), 8.89 (br, 1H), 7.98 (d, J = 8.48 Hz, 1H), 7.86 (d, J = 8.48 Hz, 1H), 7.82 (m, 1H), 7.46 (t, J = 7.96 Hz, 1H), 7.06-7.03 (m, 1H), 6.98-6.94 (m, 2H), 3.83 (s, 3H), 3.34 (d, J = 4.56 Hz, 3H), 2.72 (s, 3H). The 1H of 2HCl and NH— were not observed. | DMSO | >98 | AQ6 | | |
| 1460 | | $^1$H NMR (300 MHz, DMSO) δ 9.60 (s, 1H), 8.84-8.57 (m, 3H), 8.30 (d, J = 7.0 Hz, 1H), 8.18 (d, J = 8.8 Hz, 1H), 8.12-7.93 (m, 4H), 7.85 (dd, J = 8.7, 1.5 Hz, 1H), 7.60-7.46 (m, 1H), 4.85-4.58 (m, 1H), 1.37 (d, J = 6.5 Hz, 6H). | DMSO | 100 | AQ1 | 366 (M + 1) | Method A (Formic acid) |
| 1461 | HCl | 1H NMR (300 MHz, DMSO) δ 9.81 (s, 1H), 9.60 (s, 1H), 8.95 (s, 3H), 8.39 (d, J = 3.9 Hz, 1H), 8.19 (s, 1H), 7.96-7.73 (m, 3H), 7.68-7.55 (m, 1H), 7.39-7.25 (m, 1H), 4.99-4.81 (m, 1H), 1.42 (d, J = 6.5 Hz, 6H). | DMSO | 100 | AQ1 | 359 (M + 1) | Method A (Formic acid) |
| 1462 | | $^1$H NMR (300 MHz, DMSO) δ 9.43 (s, 1H), 8.75-8.47 (m, 3H), 8.29 (d, J = 7.2 Hz, 1H), 7.79 (d, J = 7.1 Hz, 1H), 7.72-7.54 (m, 2H), 7.48 (dd, J = 7.8, 4.9 Hz, 1H), 7.44-7.32 (m, 1H), 7.30-7.12 (m, 1H), 3.32 (s, 3H), 3.16 (d, J = 4.3 Hz, 3H). | DMSO | 100 | AQ1 | 349 (M + 1) | Method A (Formic acid) |
| 1463 | | 1H NMR (300 MHz, DMSO) δ 9.68 (dd, J = 2.1, 0.8 Hz, 1H), 8.86-8.78 (m, 1H), 8.74 (dd, J = 4.8, 1.7 Hz, 1H), 8.34-8.25 (m, 2H), 8.09-8.02 (m, 1H), 7.80 (d, J = 8.9 Hz, 2H), 7.60 (ddd, J = 8.0, 4.8, 0.8 Hz, 1H), 7.09 (d, J = 8.9 Hz, 2H), 4.31 (s, 3H), 3.83 (s, 3H). | DMSO | 99 | Method AQ2 | 344.0 (M + 1) | Method C |
| 1464 | | 1H NMR (300 MHz, DMSO) δ 9.67 (d, J = 2.1 Hz, 1H), 8.82 (d, J = 7.9 Hz, 1H), 8.74 (dd, J = 4.8, 1.7 Hz, 1H), 8.46 (d, J = 1.7 Hz, 1H), 8.36 (dd, J = 8.8, 2.2 Hz, 1H), 8.15-7.94 (m, 5H), 7.60 (ddd, J = 8.0, 4.8, 0.8 Hz, 1H), 4.31 (s, 3H). | DMSO | 99 | Method AQ2 | 338.9 (M + 1) | Method C |

TABLE 24-continued

| | | | | | | | |
|---|---|---|---|---|---|---|---|
| 1465 | 2 HCl | 1H NMR (300 MHz, DMSO) δ 9.71 (d, J = 1.8 Hz, 1H), 9.15 (d, J = 8.0 Hz, 1H), 8.90 (dd, J = 5.2, 1.4 Hz, 1H), 8.58 (s, J = 1.8 Hz, 1H), 8.48 (d, J = 1.6 Hz, 1H), 8.43 (dd, J = 8.7, 2.2 Hz, 1H), 8.32 (dd, J = 7.8, 0.9 Hz, 1H), 8.28 (dd, J = 8.2, 2.2 Hz, 1H), 8.14 (d, J = 8.7 Hz, 1H), 7.92 (dd, J = 8.0, 5.2 Hz, 1H), 7.81 (t, J = 8.0 Hz, 1H), 4.34 (s, 3H). | DMSO | 99 | Method AQ2 | 359.0 (M + 1) | Method C |
| 1466 | 2 HCl | 1H NMR (300 MHz, DMSO) δ 9.71 (d, J = 2.0 Hz, 1H), 9.12 (dd, J = 8.0, 1.4 Hz, 1H), 8.89 (dd, J = 5.2, 1.5 Hz, 1H), 8.49 (d, J = 1.6 Hz, 1H), 8.42 (dd, J = 8.8, 2.2 Hz, 1H), 8.34 (d, J = 9.0 Hz, 2H), 8.14 (dd, J = 9.2, 2.4 Hz, 3H), 7.88 (dd, J = 7.8, 5.5 Hz, 1H), 4.34 (s, 3H). | DMSO | 99 | Method AQ2 | 359.0 (M + 1) | Method C |
| 1467 | 2 HCl | 1H NMR (300 MHz, DMSO) δ 9.36 (s, 1H), 9.00 (d, J = 6.5 Hz, 2H), 8.78 (d, J = 4.5 Hz, 2H), 8.58 (s, 1H), 8.06 (s, 2H), 7.75 (dd, J = 15.6, 8.9 Hz, 1H), 7.47 (ddd, J = 11.7, 9.4, 2.6 Hz, 1H), 7.31 (td, J = 8.4, 2.7 Hz, 1H), 3.22 (d, J = 4.2 Hz, 3H). | DMSO | 99 | Method AQ2 | 349.6 (M + 1) | Method C |
| 1468 | 3 HCl | 1H NMR (300 MHz, DMSO) δ 9.97 (s, 1H), 9.63 (d, J = 1.6 Hz, 1H), 9.04 (d, J = 7.0 Hz, 1H), 8.94 (dd, J = 5.1, 1.5 Hz, 1H), 8.76 (d, J = 0.7 Hz, 1H), 8.41-8.05 (m, 4H), 7.89 (dd, J = 7.1, 4.8 Hz, 1H), 7.59 (ddd, J = 7.1, 4.9, 1.8 Hz, 1H), 3.27 (d, J = 4.3 Hz, 3H). | DMSO | 99 | Method AQ2 | 332.4 (M + 1) | Method C |
| 1469 | 2 HCl | 1H NMR (300 MHz, DMSO) δ 10.04 (s, 1H), 9.65 (d, J = 1.5 Hz, 1H), 9.06 (d, J = 7.3 Hz, 1H), 8.95 (dd, J = 5.1, 1.5 Hz, 1H), 8.71 (s, 1H), 8.19 (s, 2H), 7.89 (dd, J = 7.6, 5.1 Hz, 1H), 7.76-7.61 (m, 2H), 7.42 (td, J = 7.9, 0.9 Hz, 1H), 3.27 (d, J = 4.4 Hz, 3H). | DMSO | 95 | Method AQ2 | 365.3 (M + 1) | Method C |

TABLE 24-continued

| | | | | | | | |
|---|---|---|---|---|---|---|---|
| 1470 | 2 HCl | 1H NMR (300 MHz, DMSO) δ 10.03 (s, 1H), 9.63 (d, J = 1.5 Hz, 1H), 9.04 (d, J = 7.9 Hz, 1H), 8.94 (dd, J = 5.1, 1.5 Hz, 1H), 8.68 (s, 1H), 8.16 (s, 2H), 7.88 (dd, J = 7.6, 5.1 Hz, 1H), 7.74 (t, J = 8.5 Hz, 1H), 7.67 (dd, J = 10.8, 2.0 Hz, 1H), 7.51 (dd, J = 8.3, 1.6 Hz, 1H), 3.27 (d, J = 4.4 Hz, 3H). | DMSO | 94 | Method AQ2 | 365.3 (M + 1) | Method C |
| 1471 | 2 HCl | 1H NMR (300 MHz, DMSO) δ 9.95 (s, 1H), 9.64 (d, J = 1.6 Hz, 1H), 9.07 (d, J = 7.9 Hz, 1H), 8.94 (dd, J = 5.1, 1.5 Hz, 1H), 8.75 (s, 1H), 8.18 (s, 2H), 8.09 (d, J = 11.1 Hz, 1H), 7.92 (d, J = 4.0 Hz, 3H), 3.27 (d, J = 4.4 Hz, 3H). | DMSO | 96 | Method AQ2 | 356.4 (M + 1) | Method C |
| 1472 | 2 HCl | 1H NMR (300 MHz, DMSO) δ 10.01 (s, 1H), 9.63 (d, J = 1.5 Hz, 1H), 9.03 (d, J = 7.8 Hz, 1H), 8.94 (dd, J = 5.1, 1.5 Hz, 1H), 8.73 (s, 1H), 8.25-8.12 (m, 3H), 7.93-7.76 (m, 4H), 7.63 (d, J = 0.8 Hz, 1H), 3.28 (d, J = 4.4 Hz, 3H). | DMSO | 95 | Method AQ2 | 374.4 (M + 1) | Method C |
| 1473 | 2 HCl | 1H NMR (300 MHz, DMSO) δ 9.97 (s, 1H), 9.61 (d, J = 2.1 Hz, 1H), 8.98 (d, J = 4.6 Hz, 1H), 8.93 (dd, J = 5.1, 1.5 Hz, 1H), 8.68-8.60 (m, 1H), 8.13 (d, J = 6.1 Hz, 2H), 7.85 (dd, J = 7.7, 5.2 Hz, 1H), 7.63 (t, J = 8.3 Hz, 1H), 7.37-7.23 (m, 2H), 3.27 (d, J = 4.5 Hz, 3H), 2.56 (s, J = 5.2 Hz, 3H). | DMSO | 95 | Method AQ2 | 377.5 (M + 1) | Method C |
| 1474 | 2 HCl | 1H NMR (300 MHz, DMSO) δ 9.98 (s, 1H), 9.64 (d, J = 1.6 Hz, 1H), 9.06 (d, J = 8.8 Hz, 1H), 8.94 (dd, J = 5.1, 1.5 Hz, 1H), 8.75 (s, 1H), 8.26-8.11 (m, 2H), 8.04-7.85 (m, 5H), 3.35 (s, 3H), 3.27 (d, J = 4.1 Hz, 3H). | DMSO | 96 | Method AQ2 | 409.5 (M + 1) | Method C |
| 1475 | 2 HCl | 1H NMR (300 MHz, DMSO) δ 10.25 (s, 1H), 9.63 (d, J = 1.6 Hz, 1H), 9.00 (d, J = 7.1 Hz, 1H), 8.93 (dd, J = 5.0, 1.5 Hz, 1H), 8.79 (s, 1H), 8.31 (dd, J = 8.8, 1.5 Hz, 1H), 8.17 (d, J = 8.5 Hz, 1H), 7.84 (dd, J = 7.5, 4.3 Hz, 1H), 7.51 (d, J = 1.8 Hz, 1H), 7.40 (dd, J = 8.2, 1.9 Hz, 1H), 7.09 (d, J = 3.1 Hz, 1H), 6.10 (s, 2H), 3.29 (d, J = 4.3 Hz, 3H). | DMSO | 99 | Method AQ2 | 357.5 (M + 1) | Method C |

TABLE 24-continued

| | | | | | | | |
|---|---|---|---|---|---|---|---|
| 1476 | 2 HCl | 1H NMR (300 MHz, DMSO) δ 10.26 (s, 1H), 9.63 (d, J = 1.6 Hz, 1H), 9.01 (d, J = 3.6 Hz, 1H), 8.93 (dd, J = 5.0, 1.5 Hz, 1H), 8.77 (s, 1H), 8.31 (dd, J = 8.8, 1.4 Hz, 1H), 8.18 (d, J = 8.6 Hz, 1H), 7.84 (dd, J = 6.9, 5.8 Hz, 1H), 7.44 (d, J = 2.2 Hz, 1H), 7.39 (dd, J = 8.4, 2.3 Hz, 1H), 7.01 (d, J = 8.4 Hz, 1H), 4.30 (s, 4H), 3.29 (d, J = 4.4 Hz, 3H). | DMSO | 99 | Method AQ2 | 371.5 (M + 1) | Method C |
| 1477 | 2 HCl | 1H NMR (300 MHz, DMSO) δ 10.19 (s, 1H), 9.61 (d, J = 1.6 Hz, 1H), 8.98 (d, J = 8.8 Hz, 1H), 8.93 (dd, J = 5.0, 1.5 Hz, 1H), 8.82 (s, 1H), 8.35 (dd, J = 8.8, 1.3 Hz, 1H), 8.16 (d, J = 8.5 Hz, 1H), 7.85 (dd, J = 8.1, 5.2 Hz, 1H), 7.76-7.66 (m, 2H), 7.46 (t, J = 7.6 Hz, 1H), 7.31 (d, J = 7.7 Hz, 1H), 3.69 (t, J = 7.0 Hz, 2H), 3.31 (d, J = 4.4 Hz, 3H), 2.84 (t, J = 7.0 Hz, 2H). | DMSO | 99 | Method AQ2 | 357.5 (M + 1) | Method C |
| 1478 | 2 HCl | 1H NMR (300 MHz, DMSO) δ 10.11 (s, 1H), 9.60 (d, J = 1.9 Hz, 1H), 8.93 (dd, J = 10.3, 5.4 Hz, 2H), 8.80 (d, J = 0.6 Hz, 1H), 8.34 (dd, J = 8.0, 0.5 Hz, 1H), 8.10 (d, J = 8.3 Hz, 1H), 7.88-7.75 (m, 3H), 7.40 (d, J = 8.3 Hz, 2H), 3.65 (t, J = 6.9 Hz, 2H), 3.30 (d, J = 4.4 Hz, 3H), 2.79 (t, J = 6.9 Hz, 2H). | DMSO | 99 | Method AQ2 | 357.5 (M + 1) | Method C |
| 1479 | 2 HCl | 1H NMR (300 MHz, DMSO) δ 10.27 (s, 1H), 9.62 (d, J = 1.5 Hz, 1H), 8.99 (s, 1H), 8.96-8.33 (m, 2H), 8.37 (d, J = 8.9 Hz, 1H), 8.18 (d, J = 8.6 Hz, 1H), 7.96 (d, J = 8.5 Hz, 2H), 7.85 (s, 1H), 7.70 (d, J = 8.5 Hz, 2H), 3.30 (d, J = 4.3 Hz, 3H), 1.74 (s, 6H). | DMSO | 99 | Method AQ2 | 380.5 (M + 1) | Method C |
| 1480 | 2 HCl | 1H NMR (300 MHz, DMSO) δ 10.23 (s, 1H), 9.62 (d, J = 1.8 Hz, 1H), 9.02 (d, J = 6.6 Hz, 1H), 8.93 (dd, J = 5.0, 1.5 Hz, 1H), 8.88 (d, J = 0.5 Hz, 1H), 8.33 (d, J = 8.5 Hz, 1H), 8.16 (d, J = 8.5 Hz, 1H), 7.99 (d, J = 1.7 Hz, 1H), 7.86 (dd, J = 7.4, 5.1 Hz, 1H), 7.75 (dd, J = 8.5, 1.8 Hz, 1H), 7.60 (d, J = 8.5 Hz, 1H), 3.29 (d, J = 4.3 Hz, 3H). | DMSO | 99 | Method AQ2 | 393.4 (M + 1) | Method C |

TABLE 24-continued

| | | | | | | | |
|---|---|---|---|---|---|---|---|
| 1481 | | 1H NMR (300 MHz, DMSO) δ 9.63 (d, J = 1.4 Hz, 1H), 8.81-8.73 (m, 1H), 3.68 (dd, J = 4.7, 1.7 Hz, 1H), 8.61 (d, J = 4.3 Hz, 1H), 8.45 (s, 1H), 7.97 (d, J = 8.6 Hz, 1H), 7.86 (d, J = 8.7 Hz, 2H), 7.77-7.61 (m, 3H), 7.53 (dd, J = 7.9, 4.8 Hz, 1H), 7.40 (t, J = 7.6 Hz, 1H), 3.15 (d, J = 4.3 Hz, 3H). | DMSO | 99 | Method AQ2, followed by hydrolysis with 30% $H_2O_2$ and NaOH in ethanol | 374.5 (M + 1) | Method C |
| 1482 | 2 HCl | 1H NMR (300 MHz, DMSO) δ 10.60 (s, 1H), 10.29 (s, 1H), 9.62 (d, J = 1.5 Hz, 1H), 9.00 (d, J = 7.1 Hz 1H), 8.92 (dd, J = 4.9, 1.4 Hz, 1H), 8.76 (s, 1H), 8.29 (d, J = 8.9 Hz, 1H), 8.20 (d, J = 8.4 Hz, 1H), 7.84 (dd, J = 7.8, 4.8 Hz, 1H), 7.79-7.68 (m, 2H), 6.95 (d, J = 8.0 Hz, 1H), 3.57 (s, 2H), 3.29 (d, J = 4.3 Hz, 3H). | DMSO | 94 | Method AQ1, except that dioxane water was replaced with DME/water/EtOH in the microwave at 120° C. for 10 min | 368.5 (M + 1) | Method C |
| 1483 | 2 HCl | 1H NMR (300 MHz, DMSO) δ 10.67 (s, 1H), 9.60 (d, J = 2.4 Hz, 1H), 8.99-8.88 (m, 2H), 8.73 (d, J = 1.0 Hz, 1H), 8.27 (d, J = 9.2 Hz, 1H), 8.10 (d, J = 7.5 Hz, 1H), 7.83 (dd, J = 6.9, 4.3 Hz, 1H), 7.40 (q, J = 3.3 Hz, 2H), 7.20 (s, 1H), 3.56 (s, 2H), 3.29 (d, J = 4.1 Hz, 3H). | DMSO | 99 | Method AQ1, except that dioxane water was replaced with DME/water/EtOH in the microwave at 120° C. for 10 min | 368.5 (M + 1) | Method C |
| 1484 | 2 HCl | 1H NMR (300 MHz, DMSO) δ 10.12 (s, 1H), 9.61 (d, J = 1.9 Hz, 1H), 9.04-8.89 (m, 2H), 8.84 (d, J = 1.2 Hz, 1H), 8.36 (dd, J = 8.7, 1.3 Hz, 1H), 8.14 (d, J = 8.1 Hz, 1H), 7.94-7.78 (m, 3H), 7.50 (d, J = 8.3 Hz, 2H), 4.49 (s, 2H), 3.39-3.23 (m, 6H). | DMSO | 99 | Method AQ1, except that dioxane water was replaced with DME/water/EtOH in the microwave at 120° C. for 10 min | 357.5 (M + 1) | Method C |
| 1485 | | 1H-NMR (400 MHz, DMSO-d6): δ 9.63 (s, 1H), 8.76 (td, J = 8.0, 1.6 Hz, 1H), 871 (dd, J = 4.8, 1.6 Hz, 1H), 8.37 (s, 1H), 7.81 (d, J = 8.8 Hz, 1H), 7.72 (d, J = 8.8 Hz, 1H), 7.59-7.54 (m, 1H), 7.43 (t, J = 8.0 Hz, 1H), 7.06-6.98 (m, 3H), 3.82 (s, 3H). | DMSO | 95 | Method G1, AQ1 | 377.0 379.0 (M + 1) | Method B ($NH_4HCO_3$) |

TABLE 24-continued

| | | | | | | | |
|---|---|---|---|---|---|---|---|
| 1486 | 2HCl | 1H-NMR (400 MHz, DMSO-d6): δ 9.81 (s, 1H), 9.38 (d, J = 8.4 Hz, 1H), 9.15 (d, J = 5.2 Hz, 1H), 8.69 (d, J = 1.6 Hz, 1H), 8.41 (dd, J = 8.8, 2.0 Hz, 1H), 8.29-8.26 (m, 1H), 8.14 (d, J = 8.8 Hz, 1H), 7.50-7.41 (m, 3H), 7.11-7.08 (m, 1H), 4.80-4.76 (m, 1H), 3.66-3.57 (m, 2H), 3.50 (s, 3H), 3.44 (s, 3H), 1.35 (d, J = 6.4 Hz, 3H). | DMSO | 95 | Method G1, AQ1 | 401.1 (M + 1) | Method B ($NH_4HCO_3$) |
| 1487 | 2HCl | 1H-NMR (400 MHz, CD3OD): δ 9.55 (s, 1H), 8.92 (d, J = 4.9 Hz, 1H), 8.89 (dt, J = 8.2, 1.8 Hz, 1H), 8.62 (s, 1H), 8.37 (d, J = 8.8 Hz, 1H), 8.03 (d, J = 8.7 Hz, 1H), 7.83 (dd, J = 8.0, 5.0 Hz, 1H), 7.49 (t, J = 8.1 Hz, 1H), 7.43 (s, 2H), 7.10 (d, J = 7.6 Hz, 1H), 4.01 (s, 2H), 3.46 (s, 3H), 3.35 (s, 3H), 1.37 (s, 6H). | MeOD | 95 | Method G1, AQ1 | 415.1 (M + 1) | Method B ($NH_4HCO_3$) |
| 1488 | 2HCl | 1H-NMR (400 MHz, DMSO-d6): δ 10.34 (s, 1H), 9.65 (s, 1H), 9.04 (d, J = 6.9 Hz, 1H), 8.99-8.87 (m, 2H), 8.39 (d, J = 9.2 Hz, 1H), 8.24 (d, J = 8.2 Hz, 1H), 7.86 (s, 1H), 7.47-7.43 (m, 3H), 7.05 (d, J = 6.8 Hz, 1H), 4.26-4.22 (m, 2H), 3.77-3.73 (m, 2H), 3.56-3.50 (m, 2H), 3.32 (d, J = 4.3 Hz, 3H), 1.15 (t, J = 7.0 Hz, 3H). | DMSO | 95 | Method G1, AQ1 | 400.9 (M + 1) | Method B ($NH_4HCO_3$) |
| 1489 | | 1H-NMR (400 MHz, DMSO-d6): δ 9.68 (s, 1H), 8.81-8.78 (m, 2H), 8.71 (d, J = 3.6 Hz, 1H), 8.54 (s, 1H), 8.32 (d, J = 1.2 Hz, 1H), 7.57 (dd, J = 7.6, 4.8 Hz, 1H), 7.46-7.42 (m, 3H), 7.04-7.01 (m, 1H), 3.88 (s, 3H), 3.19 (d, J = 4.0 Hz, 3H). | DMSO | 95 | Method G1, AQ1 | 377.1, 379.1 (M + 1) | Method B ($NH_4HCO_3$) |
| 1490 | 2HCl | 1H-NMR (400 MHz, DMSO-d6): δ 10.50 (brs, 1H), 9.68 (d, J = 2.0 Hz, 1H), 9.09 (d, J = 8.0 Hz, 1H), 8.96 (dd, J = 5.2, 1.2 Hz, 1H), 8.94 (s, 1H), 8.40 (d, J = 9.2 Hz, 1H), 8.29 (d, J = 8.8 Hz, 1H), 7.89 (dd, J = 8.0, 1.6 Hz, 1H), 7.48-7.43 (m, 3H), 7.03 (d, J = 7.2 Hz, 1H), 4.06-4.05 (m, 2H), 3.92 (d, J = 11.6 Hz, 1H), 3.69-3.66 (m, 1H), 3.42-3.39 (m, 1H), 3.32 (d, J = 4.4 Hz, 3H), 1.86-1.83 (m, 1H), 1.69 (d, J = 12.4 Hz, 1H), 1.52-1.51 (m, 3H), 1.38-1.35 (m, 1H). | DMSO | 95 | Method G1, AQ1 | 427.2 (M + 1) | Method B ($NH_4HCO_3$) |

TABLE 24-continued

| | | | | | | | |
|---|---|---|---|---|---|---|---|
| 1492 | 3HCl | 1H-NMR (400 MHz, DMSO-d6): δ 10.80 (s, 1H), 9.70 (s, 1H), 9.13 (d, J = 8.0 Hz, 1H), 9.07 (s, 1H), 8.97 (d, J = 4.4 Hz, 1H), 8.94 (s, 1H), 8.39 (d, J = 8.8 Hz, 1H), 8.32 (d, J = 8.8 Hz, 1H), 8.23 (d, J = 8.0 Hz, 1H), 7.98 (t, J = 8.0 Hz, 1H), 7.90 (t, J = 6.2 Hz, 1H), 7.68 (s, 1H), 7.53 (d, J = 8.0 Hz, 1H), 7.45 (d, J = 7.8 Hz, 1H), 7.12 (d, J = 8.0 Hz, 1H), 5.50 (s, 2H), 3.30 (d, J = 2.4 Hz, 3H). | DMSO | 95 | Method G1, AQ1 | 488.0 (M + 1) | Method B ($NH_4HCO_3$) |
| 1493 | 2HCl | 1H-NMR (400 MHz, DMSO-d6): δ 10.58 (s, 1H), 9.71 (s, 1H), 9.14 (d, J = 7.6 Hz, 1H), 8.98 (d, J = 8.0 Hz, 2H), 8.40 (d, J = 8.8 Hz, 1H), 8.31 (d, J = 8.8 Hz, 1H), 7.92 (t, J = 6.2 Hz, 1H), 7.81 (t, J = 7.6 Hz, 1H), 7.47-7.43 (m, 3H), 7.02 (d, J = 7.2 Hz, 1H), 4.10 (t, J = 6.0 Hz, 2H), 3.53 (d, J = 6.4 Hz, 1H), 3.32 (d, J = 2.4 Hz, 3H), 2.26 (t, J = 7.0 Hz, 2H), 2.00-1.93 (m, 2H), 1.73-1.63 (m, 4H), 1.55-1.51 (m, 1H), 1.28-1.02 (m, 5H). | DMSO | 95 | Method G1, AQ1 | 496.2 (M + 1) | Method B ($NH_4HCO_3$) |
| 1494 | 2HCl | 1H-NMR (400 MHz, DMSO-d6): δ 10.07 (s, 1H), 9.60 (s, 1H), 8.92 (d, J = 4.4 Hz, 2H), 876 (s, 1H), 8.32 (d, J = 8.4 Hz, 1H), 8.10 (d, J = 8.0 Hz, 1H), 7.85-7.83 (m, 4H), 7.11 (d, J = 8.8 Hz, 2H), 4.04 (t, J = 6.4 Hz, 2H), 3.30 (d, J = 4.0 Hz, 3H), 2.58 (d, J = 4.0 Hz, 3H), 2.26 (t, J = 7.4 Hz, 2H), 2.00-1.93 (m, 2H). | DMSO | 95 | Method G1, AQ1 | 428.1, 429.1, (M + 1) | Method B ($NH_4HCO_3$) |
| 1495 | 2HCl | 1H-NMR (400 MHz, DMSO-d6): δ 10.63 (s, 1H), 9.73 (s, 1H), 9.17 (d, J = 7.6 Hz, 1H), 8.99 (s, 1H), 8.91 (s, 1H), 8.34 (s, 2H), 7.93 (t, J = 6.0 Hz, 1H), 7.88 (d, J = 7.2 Hz, 2H), 7.09 (d, J = 7.6 Hz, 2H), 4.08-4.06 (m, 2H), 3.32 (s, 3H), 2.98 (s, 3H), 2.84 (s, 3H), 2.47-2.46 (m, 2H), 1.98-1.94 (m, 2H). | DMSO | 95 | Method G1, AQ1 | 442.1, 443.1, (M + 1) | Method B ($NH_4HCO_3$) |

TABLE 24-continued

| | | | | | | | |
|---|---|---|---|---|---|---|---|
| 1496 | 2HCl | 1H-NMR (400 MHz, DMSO-d6): δ 10.26 (s, 1H), 9.64 (s, 1H), 9.01 (d, J = 7.0 Hz, 1H), 8.94 (s, 1H), 8.89 (s, 1H), 8.39 (d, J = 8.2 Hz, 1H), 8.19 (d, J = 8.1 Hz, 1H), 7.85 (s, 1H), 7.47 (d, J = 5.8 Hz, 3H), 7.05 (d, J = 3.4 Hz, 1H), 4.21 (dt, J = 10.8, 5.5 Hz, 1H), 4.08 (qd, J = 10.1, 5.2 Hz, 2H), 3.82 (dd, J = 14.4, 7.0 Hz, 1H), 3.71 (dd, J = 14.1, 7.4 Hz, 1H), 3.31 (d, J = 4.2 Hz, 3H), 2.08-2.00 (m, 1H), 1.98-1.79 (m, 2H), 1.72-1.68 (m, 1H). | DMSO | 95 | Method G1, AQ1 | 413.1, 414.1, (M + 1) | Method B ($NH_4HCO_3$) |
| 1497 | 2HCl | 1H-NMR (400 MHz, DMSO-d6): δ 10.53 (s, 1H), 9.68 (s, 1H), 9.09 (d, J = 7.7 Hz, 1H), 8.96 (d, J = 5.9 Hz, 2H), 8.39 (d, J = 8.7 Hz, 1H), 8.30 (d, J = 8.3 Hz, 1H), 7.94-7.79 (m, 1H), 7.48-7.45 (m, 3H), 7.04 (d, J = 7.5 Hz, 1H), 4.30-4.18 (m, 2H), 3.80-3.70 (m, 2H), 3.44 (t, J = 6.6 Hz, 2H), 3.31 (d, J = 4.2 Hz, 3H), 1.56-1.54 (m, 2H), 0.89 (t, J = 7.4 Hz, 3H). | DMSO-$d_6$ | 95 | Method G1, AQ1 | 415.1 (M + 1) | Method B ($NH_4HCO_3$) |
| 1498 | 2HCl | 1H-NMR (400 MHz, DMSO-d6): δ 10.07 (s, 1H), 9.67 (s, 1H), 9.03 (d, J = 8.0 Hz, 1H), 8.95 (d, J = 4.5 Hz, 1H), 8.51 (s, 1H), 7.85 (s, 2H), 7.41 (t, J = 7.9 Hz, 1H), 7.18 (dd, J = 7.8, 5.1 Hz, 2H), 7.02 (dd, J = 8.2, 2.3 Hz, 1H), 3.97 (s, 3H), 3.84 (s, 3H). | DMSO | 95 | Method G1, AQ1 | 373.1 (M + 1) | Method B ($NH_4HCO_3$) |
| 1499 | 2HCl | 1H-NMR (400 MHz, DMSO-d6): δ 10.06 (s, 1H), 9.66 (s, 1H), 9.02 (d, J = 7.5 Hz, 1H), 8.95 (s, 1H), 8.89 (s, 1H), 8.39 (d, J = 8.5 Hz, 1H), 8.22 (d, J = 8.6 Hz, 1H), 7.85 (dd, J = 7.0, 5.4 Hz, 1H), 7.52-7.43 (m, 3H), 7.09-7.01 (m, 1H), 4.17-4.15 (m, 2H), 3.32-3.30 (m, 4H), 3.25 (s, 3H), 1.98-1.82 (m, 2H), 1.17 (d, J = 6.1 Hz, 3H). | DMSO | 95 | Method G1, AQ1 | 415.1 (M + 1) | Method B ($NH_4HCO_3$) |

TABLE 24-continued

| | | | | | | | |
|---|---|---|---|---|---|---|---|
| 1500 | 2HCl | 1H-NMR (400 MHz, CD3OD): δ 9.80 (s, 1H), 9.37 (d, J = 8.2 Hz, 1H), 9.13 (d, J = 5.3 Hz, 1H), 8.90 (s, 1H), 8.45 (d, J = 8.4 Hz, 1H), 8.25 (dd, J = 7.9, 5.6 Hz, 1H), 8.17 (d, J = 8.7 Hz, 1H), 7.64 (s, 1H), 7.54 (d, J = 5.1 Hz, 2H), 7.17 (dd, J = 7.5, 3.6 Hz, 1H), 4.70-4.62 (m, 2H), 4.42 (q, J = 9.0 Hz, 2H), 3.93-3.86 (m, 2H), 3.51 (s, 3H), 3.24 (s, 3H). | $CD_3OD$ | 95 | Method G1, AQ1 | 468.1 (M + 1) | Method B ($NH_4HCO_3$) |
| 1501 | 2HCl | 1H-NMR (400 MHz, DMSO): δ 10.45 (brs, 1H), 9.72 (s, 1H), 9.12 (d, J = 7.6 Hz, 1H), 8.97 (d, J = 4.0 Hz, 1H), 8.70 (s, 1H), 8.35 (d, J = 8.8 Hz, 1H), 8.23 (d, J = 8.4 Hz, 1H), 7.90-7.87 (m, 2H), 7.49 (d, J = 7.2 Hz, 1H), 7.43 (t, J = 7.2 Hz, 1H), 7.18 (d, J = 8.4 Hz, 1H), 7.11 (t, J = 7.2 Hz, 1H), 4.03 (t, J = 6.4 Hz, 2H), 3.30 (d, J = 4.4 Hz, 3H), 2.54 (d, J = 4.0 Hz, 3H), 2.19 (t, J = 7.4 Hz, 2H), 1.93-1.86 (m, 2H). | DMSO | 95 | Method G1, AQ1 | 428.1 (M + 1) | Method B ($NH_4HCO_3$) |
| 1502 | | 1H-NMR (400 MHz, DMSO-d6): δ 9.65 (s, 1H). 8.88 (s, 1H), 8.81 (d, J = 8 Hz, 1H), 8.73 (s, 1H), 8.62 (s, 1H), 8.19 (d, J = 8 Hz, 1H), 7.88 (d, J = 9.2 Hz, 1H), 7.61-7.58 (m, 1H), 7.47-7.44 (m, 3H), 7.06-7.04 (m, 1H), 4.56-4.54 (m, 1H), 3.87 (dd, J = 11.2, 2.0 Hz, 1H), 3.68-3.64 (m, 1H), 3.56-3.53 (m, 2H), 3.21 (d, J = 4.4 Hz, 3H), 2.09-2.05 (m, 1H), 1.83-1.72 (m, 2H), 1.61-1.55 (m, 1H). | DMSO | 95 | Method G1, AQ1 | 413.1 (M + 1) | Method B ($NH_4HCO_3$) |
| 1503 | 2HCl | 1H-NMR (400 MHz, CD3OD): δ 9.77 (s, 1H), 9.43 (d, J = 8.1 Hz, 1H), 9.08 (d, J = 5.6 Hz, 1H), 8.46 (s, 1H), 8.34-8.25 (m, 1H), 8.20 (d, J = 8.7 Hz, 1H), 8.02 (d, J = 8.7 Hz, 1H), 7.37 (d, J = 7.5 Hz, 1H), 7.32 (t, J = 7.4 Hz, 1H), 7.05 (d, J = 8.3 Hz, 1H), 7.00 (t, J = 7.5 Hz, 1H), 3.98 (t, J = 6.1 Hz, 2H), 3.44 (t, J = 11.1 Hz, 1H), 3.35 (s, 3H), 2.17 (t, J = 7.3 Hz, 2H), 1.93-1.89 (m, 2H), 1.70-1.53 (m, 4H), 1.48 (d, J = 12.5 Hz, 1H), 1.22-1.12 (m, 2H), 1.08-1.02 (m, 3H). | $CD_3OD$ | 95 | Method G1, AQ1 | 496.2 (M + 1) | Method B ($NH_4HCO_3$) |

TABLE 24-continued

| | | | | | | | |
|---|---|---|---|---|---|---|---|
| 1504 | | 1H-NMR (400 MHz, DMSO-d6): δ 9.63 (s, 1H), 8.76 (d, J = 8.0 Hz, 1H), 8.67 (d, J = 3.6 Hz, 1H), 8.50 (d, J = 4.0 Hz, 1H), 8.10 (s, 1H), 7.56-7.53 (m, 2H), 7.46-7.42 (m, 3H), 7.03-7.01 (m, 1H), 4.07 (s, 3H), 3.88 (s, 3H), 3.17 (d, J = 4.0 Hz, 1H). | DMSO | 95 | Method G1, AQ1 | 372.9 (M + 1) | Method B ($NH_4HCO_3$) |
| 1505 | | 1H-NMR (400 MHz, DMSO): δ 9.28 (s, 1H), 8.94 (t, J = 7.6 Hz, 1H), 8.62 (d, J = 4.2 Hz, 1H), 8.42 (s, 1H), 7.94 (d, J = 8.8 Hz, 1H), 7.84 (d, J = 8.8 Hz, 1H), 7.73-7.71 (m, 1H), 7.46 (t, J = 10.0 Hz, 1H), 7.33-7.27 (m, 2H), 3.16 (d, J = 4.4 Hz, 3H). | DMSO | 95 | Method G1, AQ1 | 367.0 (M + 1) | Method B ($NH_4HCO_3$) |
| 1506 | | 1H-NMR (400 MHz, DMSO): δ 8.77 (s, 1H), 8.66 (t, J = 8.6 Hz, 1H), 8.52 (s, 1H), 8.44-8.31 (m, 1H), 8.03 (d, J= 8.6 Hz, 1H), 7.88 (d, J = 8.6 Hz, 1H), 7.62-7.49 (m, 3H), 7.42-7.37 (m, 1H), 3.12 (d, J = 3.0 Hz, 3H). | DMSO | 95 | Method G1, AQ1 | 366.9 (M + 1) | Method B ($NH_4HCO_3$) |
| 1507 | | 1H-NMR (400 MHz, DMSO): δ 9.29 (d, J = 2.0 Hz, 1H), 8.95 (dt, J = 8.4, 2.4 Hz, 1H), 8.65 (d, J = 4.4 Hz, 1H), 8.49 (s, 1H), 7.94-7.93 (m, 2H), 7.60-7.26 (m, 4H), 3.16 (d, J = 4.4 Hz, 3H). | DMSO | 95 | Method G1, AQ1 | 367.1 (M + 1) | Method B ($NH_4HCO_3$) |
| 1508 | 2HCl | $^1$H-NMR (400 MHz, DMSO-$d_6$): δ 10.46 (s, 1H), 8.77 (s, 1H), 8.65 (t, J = 8.5 Hz, 1H), 8.55 (s, 1H), 8.19 (d, J = 8.7 Hz, 1H), 8.07 (d, J = 8.6 Hz, 1H), 7.79 (dd, J = 15.8, 7.8 Hz, 1H), 7.71-7.66 (m, 1H), 7.51 (t, J = 10.2 Hz, 1H), 7.34 (t, J = 8.5 Hz, 1H), 3.23 (d, J = 3.3 Hz, 3H). | DMSO | 95 | Method G1, AQ1 | 367.0 (M + 1) | Method B ($NH_4HCO_3$) |
| 1509 | 2HCl | $^1$H-NMR (400 MHz, DMSO-$d_6$): δ 9.98 (s, 1H), 9.55 (d, J = 1.3 Hz, 1H), 9.07 (d, J = 7.2 Hz, 1H), 8.67 (s, 1H), 8.16 (dd, J = 18.0. 8.4 Hz, 2H), 7.84 (d, J = 8.3 Hz, 1H), 7.78 (td, J = 8.9, 6.6 Hz, 1H), 7.55-7.45 (m, 1H), 7.33 (td, J = 8.4, 2.0 Hz, 1H), 3.28 (d, J = 4.4 Hz, 3H), 2.74 (s, 3H). | DMSO | 95 | Method G1, AQ1 | 363.1 (M + 1) | Method B ($NH_4HCO_3$) |

TABLE 24-continued

| | | | | | | | |
|---|---|---|---|---|---|---|---|
| 1510 | 2HCl | $^1$H-NMR (400 MHz, DMSO-$d_6$): δ 10.17 (s, 1H), 8.82 (dd, J = 7.9, 6.7 Hz, 2H), 8.65 (s, 1H), 8.21 (d, J = 8.5 Hz, 1H), 8.07 (d, J = 8.6 Hz, 1H), 7.80 (s, 1H), 7.65-7.50 (m, 2H), 7.42 (dd, J = 12.7, 7.6 Hz, 1H), 3.20 (d, J = 4.4 Hz, 3H), 2.94 (s, 3H). | DMSO | 95 | Method G1, AQ1 | 363.0 (M + 1) | Method B ($NH_4HCO_3$) |
| 1511 | 2HCl | $^1$H-NMR (400 MHz, DMSO-$d_6$): δ 10.24 (s, 1H), 8.84 (d, J = 4.0 Hz, 1H), 8.77 (s, 1H), 8.64 (s, 1H), 8.18 (d, J = 8.6 Hz, 1H), 8.08 (d, J = 8.6 Hz, 1H), 7.79 (td, J = 8.9, 6.6 Hz, 2H), 7.57-7.46 (m, 1H), 7.34 (td, J = 8.5, 2.2 Hz, 1H), 3.20 (d, J = 4.5 Hz, 3H), 2.93 (s, 3H). | DMSO | 95 | Method G1, AQ1 | 362.9 (M + 1) | Method B ($NH_4HCO_3$) |
| 1512 | 2HCl | $^1$H-NMR (400 MHz, DMSO-$d_6$): δ 9.57 (s, 1H), 8.83 (dd, J = 8.0, 1.6 Hz, 1H), 8.63 (dd, J = 4.8, 2.0 Hz, 1H), 8.38 (s, 1H), 7.95-7.86 (m, 2H), 7.67-7.57 (m, 2H), 7.15-7.09 (m, 2H), 4.44 (brs, 1H), 2.17 (t, J = 7.6 Hz, 1H), 1.91-1.89 (m, 1H), 1.78 (d, J = 12.0 Hz, 1H), 1.56-1.48 (m, 4H), 1.32-1.28 (m, 1H). | DMSO | 95 | Method G1, AQ1 | 417.1 (M + 1) | Method B ($NH_4HCO_3$) |
| 1513 | 2HCl | $^1$H-NMR (400 MHz, DMSO-$d_6$): δ 9.55 (s, 1H), 8.94-8.89 (m, 2H), 8.58 (s, 1H), 8.23 (d, J = 8.8 Hz, 1H), 8.04 (d, J = 8.8 Hz, 1H), 7.85 (t, J = 6.8 Hz, 1H), 7.73 (dd, J = 14.4, 8.0 Hz, 1H), 7.25-7.19 (m, 2H), 4.01 (q, J = 7.2 Hz, 2H), 1.48 (t, J = 7.2 Hz, 3H). | DMSO | 95 | Method G1, AQ1 | 363.1 (M + 1) | Method B ($NH_4HCO_3$) |
| 1514 | 2HCl | $^1$H-NMR (400 MHz, DMSO-$d_6$): δ 9.71 (s, 1H), 9.21 (d, J = 8.4 Hz, 1H), 9.08 (d, J = 4.4 Hz, 1H), 8.68 (s, 1H), 8.30 (d, J = 8.8 Hz, 1H), 8.15-8.12 (m, 2H), 7.50-7.38 (m, 3H), 4.04 (q, J = 7.2 Hz, 2H), 1.49 (t, J = 7.2 Hz, 3H). | DMSO | 95 | Method G1, AQ1 | 363.1 (M + 1) | Method B ($NH_4HCO_3$) |
| 1515 | 2HCl | $^1$H-NMR (400 MHz, DMSO-$d_6$): δ 9.67 (s, 1H), 9.25 (d, J = 8.0 Hz, 1H), 9.03 (d, J = 5.2 Hz, 1H), 8.60 (s, 1H), 8.21-8.14 (m, 2H), 8.06 (d, J = 8.4 Hz, 1H), 7.40-7.26 (m, 3H), 4.26 (brs, 4H), 2.14 (brs, 4H). | DMSO-$d_6$ | 95 | Method G1, AQ1 | 389.1 (M + 1) | Method B ($NH_4HCO_3$) |

TABLE 24-continued

| | | | | | | | |
|---|---|---|---|---|---|---|---|
| 1516 | 2HCl | $^1$H-NMR (400 MHz, DMSO-$d_6$): δ 9.60 (s, 1H), 9.14 (d, J = 8.0 Hz, 1H), 9.10 (d, J = 5.2 Hz, 1H), 8.69 (s, 1H), 8.19 (d, J = 8.4 Hz, 1H), 8.09 (dd, J = 8.0, 5.2 Hz, 1H), 8.03 (d, J = 8.8 Hz, 1H), 7.39-7.27 (m, 3H), 4.60-4.50 (m, 1H), 2.08 (d, J = 11.6 Hz, 2H), 1.84 (d, J = 12.0 Hz, 2H), 1.69 (d, J = 8.4 Hz, 1H), 1.57-1.45 (m, 4H), 1.18-1.10 (m, 1H). | DMSO | 95 | Method G1, AQ1 | 417.1 (M + 1) | Method B ($NH_4HCO_3$) |
| 1517 | | $^1$H-NMR (400 MHz, DMSO-$d_6$): δ 12.04 (brs, 1H), 9.58 (s, 1H), 9.38 (brs, 1H), 8.84 (d, J = 5.6 Hz, 2H), 8.72 (s, 1H), 8.28 (d, J = 9.2 Hz, 1H), 7.75 (t, J = 6.8 Hz, 1H), 7.51-7.41 (m, 3H), 7.07-7.03 (m, 1H), 3.88 (s, 3H), 3.80 (q, J = 5.6 Hz, 2H), 2.32 (t, J = 72 Hz, 2H), 1.86-1.74 (m, 2H), 1.73-1.64 (m, 2H). | DMSO | 95 | Method G1, AQ1 | 428.9 (M + 1) | Method B ($NH_4HCO_3$) |
| 1518 | | $^1$H-NMR (400 MHz, DMSO-$d_6$): δ 9.61 (s, 1H), 8.74 (td, J = 8.0, 1.6 Hz, 1H), 8.71-8.66 (m, 1H), 8.31 (d, J = 1.6 Hz, 1H), 8.08 (dd, J = 8.8, 2.0 Hz, 1H), 7.90 (d, J = 8.8 Hz, 1H), 7.87-7.81 (m, 2H), 7.58-7.49 (m, 1H), 7.39-7.30 (m, 2H), 3.49 (s, 6H). | DMSO | 95 | Method G1, AQ1 | 345.1 (M + 1) | Method B ($NH_4HCO_3$) |
| 1519 | | $^1$H NMR (400 MHz, DMSO-$d_6$): δ 9.61 (s, 1H), 8.74 (d, J = 7.2 Hz, 1H), 8.69 (d, J = 3.6 Hz, 1H), 8.32 (s, 1H), 8.08 (d, J = 8.4 Hz, 1H), 7.39 (d, J = 8.4 Hz, 1H), 7.82 (d, J = 7.6 Hz, 2H), 7.62-7.48 (m, 3H), 3.48 (s, 6H). | DMSO | 95 | Method G1, AQ1 | 361.1 363.1 (M + 1) | Method B ($NH_4HCO_3$) |
| 1520 | | $^1$H-NMR (400 MHz, DMSO-$d_6$): δ 9.61 (s, 1H), 8.74 (td, J = 8.0, 1.6 Hz, 1H), 8.69 (dd, J = 4.8, 1.6 Hz, 1H), 8.42 (d, J = 2.0 Hz, 1H), 8.16 (dd, J = 8.8, 2.0 Hz, 1H), 8.04-7.89 (m, 5H), 7.54 (q, J = 5.2 Hz, 1H), 3.51 (s, 6H). | DMSO | 95 | Method G1, AQ1 | 352.1 (M + 1) | Method B ($NH_4HCO_3$) |
| 1521 | | $^1$H-NMR (400 MHz, DMSO-$d_6$): δ 9.61 (s, 1H), 8.76 (d, J = 8.0 Hz, 1H), 8.68-8.60 (m, 2H), 8.15 (d, J = 8.8 Hz, 1H), 7.85 (d, J = 8.8 Hz, 1H), 7.56 (q, J = 4.8 Hz, 1H), 7.49-7.40 (m, 3H), 7.30 (s, 1H), 7.06-6.97 (m, 1H), 6.73 (s, 1H), 3.87 (s, 5H), 2.14 (t, J = 7.2 Hz, 2H), 1.80-1.71 (m, 2H), 1.71-1.62 (m, 2H). | DMSO | 95 | Method G1, AQ1 | 428.1 (M + 1) | Method B ($NH_4HCO_3$) |

TABLE 24-continued

| | | | | | | | |
|---|---|---|---|---|---|---|---|
| 1522 | 2 HCl | $^1$H-NMR (400 MHz, DMSO-$d_6$): δ 9.67 (s, 1H), 9.39 (d, J = 8.2 Hz, 1H), 9.02 (d, J = 5.3 Hz, 1H), 8.31 (d, J = 9.3 Hz, 2H), 8.24-8.10 (m, 3H), 7.88 (d, J = 7.7 Hz, 1H), 7.72 (t, J = 7.8 Hz, 1H), 3.54 (s, 6H), 2.78 (s, 3H). | DMSO | 95 | Method G1, AQ1 | 366.1 (M + 1) | Method B ($NH_4HCO_3$) |
| 1523 | | $^1$H-NMR (400 MHz, DMSO-$d_6$): δ 9.63 (d, J = 1.7 Hz, 1H), 8.88-8.32 (m, 4H), 8.16 (dd, J = 8.7, 1.8 Hz, 1H), 7.86 (t, J = 9.2 Hz, 1H), 7.55 (dd, J = 7.9, 4.8 Hz, 1H), 7.50-7.34 (m, 3H), 7.01 (dt, J = 7.3, 2.1 Hz, 1H), 3.96-3.84 (m, 5H), 2.78 (t, J = 6.9 Hz, 2H). | DMSO | 95 | Method G1, AQ1 | 400.9 (M + 1) | Method B ($NH_4HCO_3$) |
| 1524 | | $^1$H-NMR (400 MHz, DMSO-$d_6$): 9.63 (s, 1H), 8.77 (d, J = 8 Hz, 1H), 8.66-8.63 (m, 3H), 8.15 (d, J = 8.8 Hz, 1H), 7.85 (d, J = 8.8 Hz, 1H), 7.45-7.41 (m, 3H), 7.33 (s, 1H), 7.01 (d, J = 7.0 Hz, 1H), 6.79 (s, 1H), 3.88 (s, 3H), 3.72 (d, J = 6.0 Hz, 2H), 2.24 (t, J = 7.2 Hz, 2H), 2.04-1.94 (m, 2H). | DMSO | 95 | Method G1, AQ1 | 414.1 (M + 1) | Method B ($NH_4HCO_3$) |
| 1525 | | $^1$H-NMR (400 MHz, DMSO-$d_6$): δ 9.58 (d, J = 1.2 Hz, 1H), 8.73-8.68 (m, 3H), 8.37 (s, 1H), 8.27-8.22 (m, 4H), 7.89-7.87 (m, 2H), 7.75 (t, J = 8.0 Hz, 1H), 7.55 (dd, J = 8.0, 5.2 Hz, 1H). | DMSO | 95 | Method G1, AQ1 | 324.1 (M + 1) | Method B ($NH_4HCO_3$) |
| 1526 | | $^1$H-NMR (400 MHz, DMSO-$d_6$): δ 9.57 (d, J = 1.6 Hz, 1H), 8.72-8.66 (m, 2H), 8.57 (d, J = 1.6 Hz, 1H), 8.19-7.91 (m, 3H), 7.83 (d, J = 8.0 Hz, 3H), 7.54 (dd, J = 7.6, 4.8 Hz, 1H), 7.10 (d, J = 8.4 Hz, 2H), 3.83 (s, 3H). | DMSO | 95 | Method G1, AQ1 | 329.1 (M + 1) | Method B ($NH_4HCO_3$) |
| 1527 | | $^1$H-NMR (400 MHz, DMSO-$d_6$): δ 9.58 (s, 1H), 8.72-8.66 (m, 3H), 8.16 (d, J = 8.4 Hz, 3H), 7.91 (d, J = 8.4 Hz, 2H), 7.85 (d, J = 8.8 Hz, 1H), 7.60 (d, J = 8.4 Hz, 2H), 7.54 (dd, J = 7.6, 4.3 Hz, 1H). | DMSO | 95 | Method G1, AQ1 | 333.1, 335.0 (M + 1) | Method B ($NH_4HCO_3$) |
| 1528 | 2HCl | $^1$H-NMR (400 MHz, DMSO-$d_6$): δ 9.59 (s, 1H), 9.28 (d, J = 8.0 Hz, 1H), 9.01 (d, J = 5.6 Hz, 2H), 8.65 (s, 2H), 8.37 (s, 2H), 8.25 (d, J = 8.0 Hz, 1H), 8.22 (s, 1H), 8.13 (t, J = 6.8 Hz, 1H), 7.88 (d, J = 7.6 Hz, 1H), 7.74 (t, J = 8.0 Hz, 1H), 2.77 (s, 3H). | DMSO | 95 | Method G1, AQ1 | 338.1 (M + 1) | Method B ($NH_4HCO_3$) |

TABLE 24-continued

| | | | | | | | |
|---|---|---|---|---|---|---|---|
| 1529 | 2HCl | $^1$H-NMR (400 MHz, DMSO-$d_6$): δ 9.78 (s, 1H), 9.72 (d, J = 1.8 Hz, 1H), 9.18 (d, J = 8.1 Hz, 1H), 8.98 (dd, J = 5.1, 1.2 Hz, 1H), 8.78 (s, 1H), 8.29 (d, J = 8.6 Hz, 1H), 8,17 (d, J = 8.6 Hz, 1H), 7.95 (dd, J = 7.9, 5.3 Hz, 1H), 7.80 (td, J = 8.9, 6.6 Hz, 1H), 7.55-7.45 (m, 1H), 7.34 (td, J = 8.4, 2.3 Hz, 1H), 7.26 (s, 1H), 6.96 (s, 1H), 3.98 (d, J = 6.1 Hz, 2H), 1.24 (s, 6H). | DMSO | 95 | Method G1, AQ1 | 434.1 (M + 1) | Method B ($NH_4HCO_3$) |
| 1530 | 2HCl | $^1$H-NMR (400 MHz, DMSO-$d_6$): δ 9.58 (s, 1H), 9.04-8.89 (m, 2H), 8.71-8.66 (m, 1H), 8.15-8.11 (m, 2H), 7.82-7.76 (m, 2H), 7.51 (t, J = 9.2 Hz, 1H), 7.34 (t, J = 8.8 Hz, 1H), 4.64 (s, 2H), 3.19 (s, 3H), 2.91 (s, 3H). | DMSO | 95 | Method G1, AQ1 | 420.1 (M + 1) | Method B ($NH_4HCO_3$) |
| 1531 | | $^1$H-NMR (400 MHz, DMSO-$d_6$): δ 9.63 (s, 1H), 8.78 (d, J = 7.9 Hz, 1H), 8.72 (d, J = 3.2 Hz, 1H), 8.19 (s, 2H), 8.08-7.97 (m, 2H), 7.80 (dd, J = 15.5, 8.9 Hz, 1H), 7.58 (dd, J = 7.6, 4.9 Hz, 1H), 7.52-7.41 (m, 1H), 7.29 (td, J = 8.3, 1.9 Hz, 1H), 4.48 (s, 2H), 4.15 (s, 2H), 3.48 (s, 2H). | DMSO | 95 | Method G1, AQ1 | 418.1 (M + 1) | Method B ($NH_4HCO_3$) |
| 1532 | | $^1$H-NMR (400 MHz, DMSO-$d_6$): δ 9.65 (s, 1H), 8.87 (s, 1H), 8.79 (d, J = 7.7 Hz, 1H), 8.70 (s, 1H), 8.59 (s, 1H), 8.23 (s, 1H), 8.05-7.89 (m, 3H), 7.75 (dd, J = 15.1, 7.6 Hz, 1H), 7.56 (s, 1H), 7.48 (t, J = 9.9 Hz, 1H), 7.32 (t, J = 8.1 Hz, 1H), 4.46 (t, J = 13.4 Hz, 2H). | DMSO | 95 | Method G1, AQ1 | 442.0 (M + 1) | Method B ($NH_4HCO_3$) |
| 1533 | 2HCl | $^1$H-NMR (400 MHz, DMSO-$d_6$): δ 9.63 (s, 1H), 8.95-9.03 (m, 2H), 8.78 (s, 1H), 8.14-8.24 (m, 2H), 7.88 (t, J = 6.0 Hz, 1H), 7.79 (d, J = 8.8 Hz, 1H), 7.54-7.48 (m, 1H), 7.35-7.32 (m, 1H), 4.89 (m, 1H), 1.39 (d, J = 1.2 Hz, 6H). | DMSO | 95 | Method G1, AQ1 | 377.1 (M + 1) | Method B ($NH_4HCO_3$) |
| 1534 | 2HCl | $^1$H-NMR (400 MHz, DMSO-$d_6$): δ 9.61 (s, 1H), 8.69-8.74 (m, 2H), 8.59 (s, 1H), 7.92 (d, J = 8.0 Hz, 1H), 7.84 (d, J = 8.4 Hz, 1H), 7.71-7.77 (m, 1H), 7.66 (s, 1H), 7.56-7.60 (m, 1H), 7.42-7.48 (m, 1H), 7.27-7.32 (m, 1H), 1.66 (s, 9H). | DMSO | 95 | Method G1, AQ1 | 391.1 (M + 1) | Method B ($NH_4HCO_3$) |

TABLE 24-continued

| | | | | | | | |
|---|---|---|---|---|---|---|---|
| 1535 | 2HCl | $^1$H-NMR (400 MHz, DMSO-$d_6$): δ 9.74 (s, 1H), 9.66 (s, 1H), 9.22 (d, J = 7.6 Hz, 1H), 8.99 (d, J = 4.8 Hz, 1H), 8.83 (s, 1H), 8.33 (d, J = 8.4 Hz, 1H), 8.20 (d, J = 8.8 Hz, 1H), 7.95 (t, J = 6.2 Hz, 1H), 7.58 (q, J = 8.6 Hz, 1H), 7.51 (t, J = 7.0 Hz, 1H), 7.46-7.41 (m, 1H), 7.25 (s, 1H), 6.72 (s, 1H), 5.13-5.06 (m, 1H), 3.21 (q, J = 7.3 Hz, 1H), 2.22-1.92 (m, 5H), 1.68-1.57 (m, 1H). | DMSO | 95 | Method G1, AQ1 | 446.0 (M + 1) | Method B ($NH_4HCO_3$) |
| 1536 | 2HCl | $^1$H-NMR (400 MHz, DMSO-$d_6$): δ 9.81 (s, 2H), 9.32 (d, J = 8.0 Hz, 1H), 9.02 (d, J = 5.2 Hz, 1H), 8.81 (s, 1H), 8.42 (d, J = 8.4 Hz, 1H), 8.18 (d, J = 8.4 Hz, 1H), 8.00 (dd, J = 7.8, 5.8 Hz, 1H), 7.76 (dd, J = 15.4, 3.6 Hz, 1H), 7.51 (t, J = 10.0 Hz, 1H), 7.35 (t, J = 8.2 Hz, 1H), 7.29 (s, 1H), 6.73 (s, 1H), 5.15-5.07 (m, 1H), 3.21 (q, J = 7.3 Hz, 1H), 2.23-1.87 (m, 5H), 1.68-1.57 (m, 1H). | DMSO | 95 | Method G1, AQ1 | 446.1 (M + 1) | Method B ($NH_4HCO_3$) |
| 1537 | | $^1$H-NMR (400 MHz, DMSO-$d_6$): δ 9.66 (s, 1H), 8.79 (d, J = 7.6 Hz, 1H), 8.69 (dd, J = 4.4, 1.2 Hz, 1H), 8.61 (d, J = 1.6 Hz, 1H), 8.40 (d, J = 7.2 Hz, 1H), 8.13 (dd, J = 8.6, 1.4 Hz, 1H), 7.85 (d, J = 8.4 Hz, 1H), 7.55 (dd, J = 7.6, 4.8 Hz, 1H), 7.49-7.40 (m, 3H), 7.11 (s, 1H), 7.02 (d, J = 7.2 Hz, 1H), 6.69 (s, 1H), 5.03-4.96 (m, 1H), 3.87 (s, 3H), 3.20 (dd, J = 15.0, 7.4 Hz, 1H), 2.22-1.88 (m, 5H), 1.70-1.56 (m, 1H). | DMSO | 95 | Method G1, AQ1 | | Method B ($NH_4HCO_3$) |
| 1538 | | $^1$H-NMR (400 MHz, DMSO-$d_6$): δ 9.60 (s, 1H), 8.86 (d, J = 7.7 Hz, 1H), 8.74 (d, J = 8.0 Hz, 1H), 8.69 (d, J = 3.3 Hz, 1H), 8.65 (s, 1H), 8.19 (d, J = 7.4 Hz, 1H), 7.87 (d, J = 8.8 Hz, 2H), 7.54 (dd, J = 7.8, 4.8 Hz, 1H), 7.50-7.40 (m, 3H), 7.01 (dd, J = 7.3, 3.9 Hz, 1H), 4.85 (dd, J = 16.9, 8.7 Hz, 1H), 3.88 (s, 3H), 2.16 (s, 2H), 1.96 (s, 2H). | DMSO | 95 | Method G1, AQ1 | 426.1, 427.1 (M + 1) | Method B ($NH_4HCO_3$) |

TABLE 24-continued

| | | | | | | | |
|---|---|---|---|---|---|---|---|
| 1539 | 2HCl | $^1$H-NMR (400 MHz, DMSO-$d_6$): δ 10.34 (s, 1H), 9.67 (s, 1H), 9.07 (s, 1H), 8.97 (d, J = 5.0 Hz, 1H), 8.92 (s, 1H), 8.39 (d, J = 8.8 Hz, 1H), 8.25 (d, J = 7.4 Hz, 1H), 7.99 (s, 1H), 7.90 (s, 1H), 7.48 (d, J = 5.8 Hz, 3H), 7.09-6.99 (m, 1H), 4.03 (d, J = 6.1 Hz, 2H), 3.89 (s, 3H), 2.65 (t, J = 6.8 Hz, 2H), 2.56 (d, J = 4.4 Hz, 3H). | DMSO | 95 | Method G1, AQ1 | 414.0, 415.0 (M + 1) | Method B ($NH_4HCO_3$) |
| 1540 | 2HCl | $^1$H-NMR (400 MHz, DMSO-$d_6$): δ 10.48 (s, 1H), 9.64 (s, 1H), 9.05 (d, J = 7.9 Hz, 1H), 9.01-8.92 (m, 2H), 8.38 (d, J = 8.8 Hz, 1H), 8.28 (d, J = 8.6 Hz, 1H), 7.93-7.83 (m, 1H), 7.55-7.43 (m, 3H), 7.08-6.98 (m, 1H), 4.04 (dd, J = 12.4, 6.6 Hz, 2H), 3.89 (s, 3H), 2.98 (s, 3H), 2.89 (t, J = 7.0 Hz, 2H), 2.34 (s, 3H). | DMSO | 95 | Method G1, AQ1 | 428.1, 429.1 (M + 1) | Method B ($NH_4HCO_3$) |
| 1541 | 2HCl | $^1$H-NMR (400 MHz, DMSO-$d_6$): δ 10.02 (brs, 1H), 9.75 (d, J = 1.6 Hz, 1H), 9.07 (dd, J = 8.0, 1.6 Hz, 1H), 8.83 (s, 1H), 8.35 (d, J = 9.2 Hz, 1H), 8.19 (d, J = 8.6 Hz, 1H), 8.14 (d, J = 8.8 Hz, 1H), 7.48-7.46 (m, 3H), 7.06-7.03 (m, 1H), 3.89 (s, 3H), 3.30 (d, J = 4.0 Hz, 3H). | DMSO | 95 | Method G1, AQ1 | 411.1 (M + 1) | Method B ($NH_4HCO_3$) |
| 1542 | 2HCl | $^1$H-NMR (400 MHz, DMSO-$d_6$): δ 10.22 (brs, 1H), 9.64 (s, 1H), 9.01 (d, J = 6.4 Hz, 1H), 8.95 (d, J = 4.0 Hz, 1H), 8.89 (s, 1H), 8.39 (d, J = 8.4 Hz, 1H), 8.23 (d, J = 8.0 Hz, 1H), 7.85 (t, J = 5.2 Hz, 1H), 7.52-7.42 (m, 4H), 7.08-7.05 (m, 1H), 6.89 (s, 1H), 3.89 (s, 4H), 3.83-3.76 (m, 2H), 2.83-2.79 (m, 1H), 1.65-1.56 (m, 7H), 1.24-1.07 (m, 6H), 0.89-0.81 (m, 2H). | DMSO | 95 | Method G1, AQ1 | 510.2 (M + 1) | Method B ($NH_4HCO_3$) |
| 1543 | | $^1$H-NMR (400 MHz, DMSO-$d_6$): δ 9.67 (d, J = 1.6 Hz, 1H), 8.80 (dt, J = 8.0, 2.0 Hz, 1H), 8.70 (dd, J = 4.4, 2.0 Hz, 1H), 8.15 (s, 1H), 7.87 (s, 1H), 7.71-7.67 (m, 1H), 7.58-7.55 (m, 1H), 7.47 (d, J = 2.4 Hz, 1H), 7.34 (m, 2H), 3.45 (s, 6H), 2.76 (s, 3H). | DMSO | 95 | Method G1, AQ1 | 359.1 (M + 1) | Method B ($NH_4HCO_3$) |

TABLE 24-continued

| | | | | | | | |
|---|---|---|---|---|---|---|---|
| 1544 | | $^1$H-NMR (400 MHz, DMSO-$d_6$): δ 9.66 (s, 1H), 8.82-8.79 (m, 1H), 8.70 (d, J = 4.0 Hz, 1H), 8.20 (d, J = 1.6 Hz, 1H), 8.02 (s, 1H), 7.86-7.84 (m, 2H), 7.58-7.55 (m, 3H), 3.48 (s, 6H), 2.77 (s, 3H). | DMSO | 95 | Method G1, AQ1 | 375.1 (M + 1) | Method B ($NH_4HCO_3$) |
| 1545 | | $^1$H-NMR (400 MHz, DMSO-$d_6$): δ 9.68 (s, 1H), 9.01 (d, J = 8.0 Hz, 1H), 8.82 (d, J = 4.4 Hz, 1H), 8.18 (d, J = 1.6 Hz, 1H), 8.03 (s, 1H), 7.88-7.84 (m, 2H), 7.80-7.77 (m, 1H), 7.37-7.33 (m, 2H), 3.50 (s, 6H), 2.78 (s, 3H). | DMSO | 95 | Method G1, AQ1 | 359.1 (M + 1) | Method B ($NH_4HCO_3$) |
| 1546 | | $^1$H-NMR (400 MHz, $CD_3OD$): δ 9.51 (s, 1H), 8.81 (d, J = 7.3 Hz, 1H), 8.54 (s, 1H), 8.35 (s, 1H), 8.02 (d, J = 8.3 Hz, 1H), 7.83 (d, J = 8.8 Hz, 1H), 7.50 (d, J = 7.2 Hz, 1H), 7.29 (dt, J = 11.2, 4.8 Hz, 3H), 6.88 (d, J = 7.5 Hz, 1H), 4.43 (dd, J = 7.1, 4.0 Hz, 1H), 4.16 (dd, J = 13.8, 4.0 Hz, 1H), 3.86 (dd, J = 13.7, 7.4 Hz, 1H), 3.80 (s, 3H). | CD3OD | 95 | Method G1, AQ1 | 416.1 (M + 1) | Method B ($NH_4HCO_3$) |
| 1547 | 2HCl | $^1$H-NMR (400 MHz, $CD_3OD$): δ 9.74 (s, 1H), 9.44 (d, J = 8.2 Hz, 1H), 9.02 (d, J = 5.5 Hz, 1H), 8.50 (s, 1H), 8.24 (dd, J = 8.0, 5.9 Hz, 1H), 8.16 (q, J = 8.7 Hz, 2H), 7.70-7.58 (m, 1H), 7.12-7.00 (m, 2H), 6.13 (s, 1H), 4.44-4.41 (m, 1H), 4.29-4.27 (m, 1H), 2.37-2.16 (m, 3H), 2.09-2.07 (m, 1H). | $CD_3OD$ | 95 | Method G1, AQ1 | 457.0 (M + 1) | Method B ($NH_4HCO_3$) |
| 1548 | 2HCl | $^1$H-NMR (400 MHz, $CD_3OD$): δ 9.85 (s, 1H), 9.57 (d, J = 8.0 Hz, 1H), 9.10 (d, J = 4.8 Hz, 1H), 8.64 (s, 1H), 8.34-8.22 (m, 3H), 7.51 (t, J = 6.9 Hz, 1H), 7.47-7.33 (m, 2H), 6.23 (s, 1H), 4.53-4.51 (m, 1H), 4.38-4.36 (m, 1H), 2.51-2.30 (m, 3H), 2.19-2.18 (m, 1H). | $CD_3OD$ | 95 | Method G1, AQ1 | 457.1 (M + 1) | Method B ($NH_4HCO_3$) |
| 1549 | 2HCl | $^1$H-NMR (400 MHz, DMSO): δ 10.38 (brs, 1H), 9.63 (d, J = 1.6 Hz, 1H), 9.00 (d, J = 8.0 Hz, 1H), 8.95-8.94 (m, 2H), 8.39 (d, J = 9.2 Hz, 1H), 8.23 (d, J = 8.4 Hz, 1 H), 7.88-7.85 (m, 1 H), 7.49-7.48 (m, 3H), 7.07-7.04 (m, 1H), 3.94-3.89 (m, 5H), 3.60-3.57 (m, 2H), 1.96-1.93 (m, 2H). | DMSO | 95 | Method G1, AQ1 | 387.1 (M + 1) | Method B ($NH_4HCO_3$) |

TABLE 24-continued

| | | | | | | | |
|---|---|---|---|---|---|---|---|
| 1550 | | $^1$H-NMR (400 MHz, DMSO): δ 9.62 (s, 1H), 8.72-8.70 (m, 2H), 8.40 (s, 1H), 8.11-7.94 (m, 2H), 7.91-7.74 (m, 3H), 7.54 (dd, J = 7.6, 4.8 Hz, 1H), 7.09 (d, J = 8.6 Hz, 2H), 3.83 (s, 3H), 2.74 (s, 3H). | DMSO | 95 | Method G1, AQ1 | 343.1 (M + 1) | Method B ($NH_4HCO_3$) |
| 1551 | | $^1$H-NMR (400 MHz, DMSO): δ 9.64 (s, 1H), 8.76 (d, J = 8.0 Hz, 1H), 8.70 (d, J = 4.4 Hz, 1H), 8.46 (s, 1H), 8.12-7.83 (m, 5H), 7.57 (dd, J = 7.8, 4.8 Hz, 1H), 7.39 (t, J = 8.7 Hz, 2H), 2.84 (s, 3H). | DMSO | 95 | Method G1, AQ1 | 331.1 (M + 1) | Method B ($NH_4HCO_3$) |
| 1552 | | 1H-NMR (400 MHz, DMSO): δ 9.62 (s, 1H), 8.77 (d, J = 8.0 Hz, 1H), 8.71 (d, J = 4.4 Hz, 1H), 8.23 (s, 1H), 8.20 (s, 1H), 8.07-8.00 (m, 2H), 7.60-7.50 (m, 3H), 7.40-7.37 (m, 1H), 4.48 (s, 2H), 4.12-4.10 (m, 2H), 3.48-3.46 (m, 2H). | DMSO | 95 | Method G1, AQ1 | 418.1 (M + 1) | Method B ($NH_4HCO_3$) |
| 1553 | 2HCl | $^1$H-NMR (400 MHz, DMSO-$d_6$): δ 9.74 (s, 1H), 9.45 (s, 1H), 9.27 (d, J = 8.8 Hz, 1H), 8.97 (s, 1H), 8.69 (s, 1H), 8.12-8.00 (m, 3H), 7.83-7.76 (m, 1H), 7.51-7.32 (m, 2H), 480-4.64 (m, 2H). | DMSO | 95 | Method G1, AQ1 | 417.1 (M + 1) | Method B ($NH_4HCO_3$) |
| 1554 | 2HCl | $^1$H-NMR (400 MHz, CD3OD): δ 9.86 (s, 1H), 9.48 (d, J = 8.8 Hz, 1H), 9.18 (d, J = 5.2 Hz, 1H), 8.72 (s1H), 8.92 (s, 1H), 8.37-8.31 (m, 2H), 8.22 (d, J = 8.8 Hz, 1H), 7.80-7.55 (m, 1H), 7.26-7.20 (m, 2H), 4.92 (d, J = 4.8 Hz, 1H), 4.81 (t, J = 4.8 Hz, 1H), 4.39-4.30 (m, 2H). | CD3OD | 95 | Method G1, AQ1 | 380.9 (M + 1) | Method B ($NH_4HCO_3$) |
| 1555 | | $^1$H-NMR (400 MHz, DMSO-$d_6$): δ 9.62 (s, 1H), 8.7-8.68 (m, 2H), 8.32 (s, 1H), 7.97-7.93 (m, 2H), 7.91-7.36 (m, 5H), 347 (s, 6H). | DMSO | 95 | Method G1, AQ1 | 345.1 (M + 1) | Method B ($NH_4HCO_3$) |
| 1556 | | $^1$H-NMR (400 MHz, DMSO-$d_6$): δ 9.61 (s, 1H), 8.75 (d, J = 8.0 Hz, 1H), 8.67 (d, J = 3.6 Hz, 2H), 8.48 (s, 1H), 8.13 (d, J = 8.8 Hz, 1H), 7.91 (d, J = 8.8 Hz, 1H), 7.59-7.49 (m, 3H), 7.45-7.30 (m, 5H), 7.02-6.92 (m, 1H), 4.50 (q, J = 3.2 Hz, 1H), 4.39-4.20 (m, 2H), 4.14-4.09 (m, 1H), 3.98-3.83 (m, 1H), 3.38 (s, 3H), 2.49-2.40 (m, 1H), 2.35-2.18 (m, 1H). | DMSO | 95 | Method G1, AQ1 | 493.0 495.0 (M + 1) | Method B ($NH_4HCO_3$) |

TABLE 24-continued

| | | | | | | | |
|---|---|---|---|---|---|---|---|
| 1557 | | $^1$H-NMR (400 MHz, DMSO-$d_6$): δ 9.60 (s, 1H), 8.73 (dd, J = 7.6, 1.2 Hz, 1H), 8.67 (dd, J = 8.4, 1.2 Hz, 1H), 8.47 (s, 1H), 8.11 (dd, J = 8.4, 1.6 Hz, 1H), 7.89 (d, J = 8.8 Hz, 1H), 7.54-7.50 (m, 1H), 7.42 (t, J = 8.0 Hz, 1H), 7.38-7.32 (m, 2H), 7.32-7.23 (m, 2H), 7.05 (d, J = 8.4 Hz, 1H), 7.00-6.92 (m, 2H), 4.45 (t, J = 8.4 Hz, 1H), 4.24 (s, 2H), 4.08-3.95 (m, 1H), 3.88-3.80 (m, 7H), 2.44-2.33 (m, 1H), 2.29-2.15 (m, 1H). | DMSO | 95 | Method G1, AQ1 | 489.1 (M + 1) | Method B ($NH_4HCO_3$) |
| 1558 | | $^1$H-NMR (400 MHz, DMSO-$d_6$): δ 9.56 (s, 1H), 9.02 (s, 1H), 8.19 (d, J = 7.5 Hz, 1H), 7.86 (d, J = 8.7 Hz, 1H), 7.58 (dd, J = 7.7, 4.9 Hz, 1H), 7.52-7.37 (m, 3H), 7.37-7.24 (m, 3H), 7.12 (t, J = 8.8 Hz, 2H), 7.02 (d, J = 7.5 Hz, 1H), 6.84 (s, 1H), 3.89-3.78 (m, 4H), 3.72-3.66 (m, 1H), 3.13 (s, 1H), 2.97-2.90 (m, 1H), 2.86-2.78 (m, 1H). | DMSO | 95 | Method G1, AQ1 | 506.1 (M + 1) | Method B ($NH_4HCO_3$) |
| 1559 | 2 HCl | $^1$H-NMR (400 MHz, DMSO-$d_6$): δ 10.48-10.00 (m, 1H), 9.70 (s, 1H), 9.12-8.77 (m, 3H), 8.42-8.32 (m, 1H), 8.30-8.17 (m, 1H), 7.95-7.79 (m, 1H), 7.55-7.44 (m, 6H), 7.26 (d, J = 7.2 Hz, 1H), 7.05 (s, 1H), 6.94 (S, 1H), 3.89 (s, 5H), 3.22 (s, 1H), 2.97-2.81 (m, 2H). | DMSO | 95 | Method G1, AQ1 | 558.1 560.0 562.0 (M + 1) | Method B ($NH_4HCO_3$) |
| 1560 | 2 HCl | $^1$H-NMR (400 MHz, DMSO-$d_6$): δ 10.25 (s, 1H), 9.61 (d, J = 1.5 Hz, 1H), 8.96 (d, J = 4.0 Hz, 1H), 8.87 (s, 1H), 8.39 (d, J = 8.5 Hz, 1H), 8.25 (d, J = 7.7 Hz, 1H), 7.87 (s, 1H), 7.52-7.44 (m, 4H), 7.36 (t, J = 7.6 Hz, 1H), 7.28 (dd, J = 13.5, 6.0 Hz, 1H), 7.22-7.10 (m, 2H), 7.06 (d, J = 7.5 Hz, 1H), 6.89 (s, 1H), 3.95-3.81 (m, 5H), 3.21 (d, J = 9.0 Hz, 1H), 2.94 (d, J = 7.3 Hz, 2H). | DMSO | 95 | Method G1, AQ1 | 508.2 (M + 1) | Method B ($NH_4HCO_3$) |

TABLE 24-continued

| | | | | | | |
|---|---|---|---|---|---|---|
| 1561 | $^1$H-NMR (400 MHz, DMSO-$d_6$): δ 9.64 (s, 1H), 8.71 (m, 2H), 8.69 (d, J = 3.5 Hz, 1H), 8.64 (s, 1H), 8.15 (d, J = 8.4 Hz, 1H), 7.85 (d, J = 8.7 Hz, 1H), 7.58-7.49 (m, 1H), 7.43 (m, 4H), 7.28-7.18 (m, 4H), 7.15 (m, 1H), 7.01 (d, J = 7.2 Hz, 1H), 6.94 (s, 1H), 3.82-3.73 (m, 5H), 2.90-2.87 (m. 1H), 2.68-2.65 (m, 2H), 1.89-1.86 (m, 2H). | DMSO | 95 | Method G1, AQ1 | 503.9 (M + 1) | Method B ($NH_4HCO_3$) |
| 1562 | $^1$H-NMR (400 MHz, DMSO-$d_6$): 9.85 (s, 1H), 8.76 (s, 1H), 8.65 (d, J = 3.6 Hz, 1H), 8.64 (s, 1H), 8.53 (d, J = 8.0 Hz, 1H), 8.14 (d, J = 8.6 Hz, 1H), 7.83 (d, J = 8.7 Hz, 1H), 7.51 (dd, J = 8.0, 4.7 Hz, 1H), 7.45 (d, J = 6.7 Hz, 2H), 7.40 (s, 1H), 7.31-7.27 (m, 5H), 7.24 (d, J = 6.6 Hz, 1H), 7.00 (d, J = 6.9 Hz, 1H), 6.80 (s, 1H), 3.77-3.70 (m, 5H), 3.17-3.15 (m, 1H), 2.98-2.81 (m, 2H). | DMSO | 95 | Method G1, AQ1 | 489.9 (M + 1) | Method B ($NH_4HCO_3$) |
| 1563 | $^1$H-NMR (400 MHz, DMSO-$d_6$): δ 9.57 (s, 1H), 8.74-8.68 (m, 2H), 8.21 (s, 1H), 8.15 (dd, J = 8.7, 1.6 Hz, 1H), 7.95 (d, J = 8.7 Hz, 1H), 7.56-7.52 (m, 2H), 7.46-7.31 (m, 4H), 7.12 (d, J = 6.5 Hz, 2H), 6.95-6.93 (m, 1H), 5.16 (s, 2H), 3.78 (s, 3H), 3.53 (s, 3H). | DMSO | 95 | Method G1, AQ1 | 467.1, 469.1 (M + 1) | Method B ($NH_4HCO_3$) |
| 1564 | $^1$H-NMR (400 MHz, DMSO-$d_6$): δ 9.64 (d, J = 1.4 Hz, 1H), 8.75 (d, J = 7.9 Hz, 1H), 8.70 (d, J = 4.6 Hz, 1H), 8.32 (s, 1H), 8.12 (d, J = 8.7 Hz, 1H), 7.91 (d, J = 8.7 Hz, 1H), 7.55 (dd, J = 7.9, 4.8 Hz, 1H), 7.43 (t, J = 7.9 Hz, 1H), 7.36-7.29 (m, 2H), 7.01-6.98 (m, 1H), 6.88 (s, 1H), 6.83 (s, 2H), 4.12-4.03 (m, 2H), 3.85 (s, 3H), 3.69 (s, 3H), 3.62 (s, 3H), 3.56 (d, J = 8.0 Hz, 3H), 3.15-3.02 (m, 2H). | DMSO | 95 | Method G1, AQ1 | 507.2 (M + 1) | Method B ($NH_4HCO_3$) |

TABLE 24-continued

| | | | | | | | |
|---|---|---|---|---|---|---|---|
| 1565 | | $^1$H-NMR (400 MHz, DMSO-$d_6$): δ 9.64 (d, J = 2.0 Hz, 1H), 8.77-8.69 (m, 2H), 8.68 (d, J = 1.6 Hz, 1H), 8.64 (d, J = 1.6 Hz, 1H), 8.16 (dd, J = 3.8, 1.6 Hz, 1H), 7.85 (d, J = 8.8 Hz, 1H), 7.55-7.52 (m, 1H ), 7.46-7.41 (m, 4H), 7.29 (t, J = 7.2 Hz, 1H), 7.23-7.19 (m, 1H), 7.14-7.06 (m, 2H), 7.01 (dt, J = 9.2 , 2.0 Hz, 1H), 6.96 (s, 1H), 3.87-3.76 (m, 5H), 2.94-2.93 (m, 1H), 2.68 (t, J = 7.8 Hz, 2H), 1.89-1.83 (m, 2H). | DMSO | 95 | Method G1, AQ1 | 522.3 (M + 1) | Method B ($NH_4HCO_3$) |
| 1566 | | $^1$H-NMR (400 MHz, DMSO-$d_6$): δ 9.59 (s, 1H), 8.76 (t, J = 5.2 Hz, 1H), 8.69 (dd, J = 4.4, 1.2 Hz, 1H), 8.63 (s, 1H), 8.56 (d, J = 8.4 Hz, 1H), 8.15 (dd, J = 8.8, 1.4 Hz, 1H), 7.84 (d, J = 8.4 Hz, 1H), 7.53-7.50 (m, 1H), 7.48-7.40 (m, 3H), 7.36-7.32 (m, 3H), 7.30-7.24 (m, 2H), 7.02-7.00 (m, 1H), 6.85 (s, 1H), 3.92-3.83 (m, 4H), 3.72-3.69 (m, 1H), 3.18-3.14 (m, 1H), 2.96-2.84 (m, 2H). | DMSO | 95 | Method G1, AQ1 | 524.2, 526.2 (M + 1) | Method B ($NH_4HCO_3$) |
| 1567 | | $^1$H-NMR (400 MHz, DMSO-$d_6$): δ 9.64 (s, 1H), 9.08 (s, 1H), 8.79-8.69 (m, 2H), 8.51 (s, 1H), 8.31 (s, 1H), 8.00-7.89 (m, 2H), 7.85-7.69 (m, 1H), 7.67-7.42 (m, 2H), 7.30-7.21 (m, 2H), 5.00 (d, J = 5.1 Hz, 2H). | DMSO | 95 | Method G1, AQ1 | 416.0 (M + 1) | Method B ($NH_4HCO_3$) |
| 1568 | 2HCl | $^1$H-NMR (400 MHz, DMSO-$d_6$): δ 10.58 (s, 1H), 10.09 (d, J = 4.4 Hz, 1H), 9.65 (s, 1H), 9.05-9.02 (m, 2H), 8.95 (d, J = 4.4 Hz, 1H), 8.37 (d, J = 8.4 Hz, 1H), 8.30-8.27 (m, 1H), 7.85 (t, J = 6.2 Hz, 1H), 7.59 (d, J = 8.0 Hz, 2H), 7.49-7.43 (m, 3H), 7.24 (t, J = 7.8 Hz, 2H), 7.03-6.97 (m, 2H), 3.89 (s, 3H), 3.86-3.84 (m, 2H), 2.44 (t, J = 7.0 Hz, 2H), 1.87-1.77 (m, 4H). | DMSO | 95 | Method G1, AQ1 | 504.1 (M + 1) | Method B ($NH_4HCO_3$) |

TABLE 24-continued

| | | | | | | | |
|---|---|---|---|---|---|---|---|
| 1569 | 2HCl | $^1$H-NMR (400 MHz, DMSO-$d_6$): δ 10.62 (s, 1H), 9.67 (s, 1H), 9.08 (d, J = 7.2 Hz, 1H), 9.03 (s, 1H), 8.97 (d, J = 5.2 Hz, 1H), 8.44 (t, J = 5.6 Hz, 1H), 8.40 (dd, J = 8.8, 0.8 Hz, 1H), 8.32 (dd, J = 9.2, 2.8 Hz, 1H), 7.89 (t, J = 6.4 Hz, 1H), 7.50-7.44 (m, 3H), 7.25-7.14 (m, 5H), 7.03 (d, J = 7.2 Hz, 1H), 4.24 (d, J = 6.0 Hz , 2H), 3.89 (s, 3H), 3.87-3.82 (m, 2H), 2.26 (t, J = 7.0 Hz, 2H), 1.84-1.69 (m, 4H). | DMSO | 95 | Method G1, AQ1 | 518.1 (M + 1) | Method B ($NH_4HCO_3$) |
| 1570 | | $^1$H-NMR (400 MHz, DMSO-$d_6$): δ 9.55 (s, 1H), 8.69 (dd, J = 11.3, 6.2 Hz, 2H), 8.23 (s, 1H), 8.15 (d, J = 8.7 Hz, 1H), 7.95 (d, J = 8.7 Hz, 1H), 7.59-7.50 (m, 2H), 7.44-7.26 (m, 3H), 7.23 (t, J = 7.5 Hz, 1H), 7.15 (s, 1H), 7.12 (d, J = 7.7 Hz, 1H), 6.95 (d, J = 8.1 Hz, 1H), 5.18 (s, 2H), 3.79 (s, 3H), 3.54 (s, 3H). | DMSO | 95 | Method G1, AQ1 | 451.2, 452.2, 453.2 (M + 1) | Method B ($NH_4HCO_3$) |
| 1571 | 2HCl | $^1$H-NMR (400 MHz, DMSO-$d_6$): δ 9.62 (s, 1H), 9.60 (s, 1H), 8.88 (d, J = 4.3 Hz, 1H), 8.82 (s, 1H), 8.78 (d, J = 8.1 Hz, 1H), 8.31 (d, J = 8.6 Hz, 1H), 8.12 (d, J = 7.9 Hz, 1H), 7.75 (dd, J = 7.8, 5.1 Hz, 1H), 7.53-7.39 (m, 4H), 7.33 (dd, J = 14.3, 7.9 Hz, 1H), 7.12 (t, J = 7.8 Hz, 2H), 7.03 (dd, J = 11.0, 6.3 Hz, 2H), 6.90 (s, 1H), 3.97-3.90 (m, 4H), 3.82 (dd, J = 18.0, 9.5 Hz, 1H), 3.19 (dd, J = 13.4, 7.5 Hz, 1H), 2.98 (dd, J = 13.6, 7.9 Hz, 1H), 2.87 (dd, J = 13.6, 6.7 Hz, 1H). | DMSO | 95 | Method G1, AQ1 | 508.1, 509.1, 510.1 (M + 1) | Method B ($NH_4HCO_3$) |
| 1572 | 2HCl | $^1$H-NMR (400 MHz, DMSO-$d_6$): δ 10.20 (s, 1H), 9.61 (s, 1H), 8.94 (d, J = 4.8 Hz, 1H), 8.86 (s, 2H), 8.37 (d, J = 8.4 Hz, 1H), 8.22 (s, 1H), 7.83 (s, 1H), 7.56-7.32 (m, 6H), 7.31-7.19 (m, 2H), 7.06 (d, J = 7.2 Hz, 1H), 6.89 (s, 1H), 4.03-3.93 (m, 1H), 3.88 (s, 3H), 3.82 (dd, J = 14.4, 5.5 Hz, 1H), 3.22 (s, 1H), 3.02 (d, J = 7.2 Hz, 2H). | DMSO | 95 | Method G1, AQ1 | 524.1, 525.1, 526.0 (M + 1) | Method B ($NH_4HCO_3$) |

TABLE 24-continued

| | | | | | | | |
|---|---|---|---|---|---|---|---|
| 1573 | 2HCl | $^{1}$H-NMR (400 MHz, DMSO-$d_6$): δ 10.31 (s, 1H), 9.63 (s, 1H), 8.96 (d, J = 4.4 Hz, 1H), 8.90 (s, 1H), 8.84 (d, J = 7.7 Hz, 1H), 8.39 (d, J = 8.7 Hz, 1H), 8.27 (d, J = 8.0 Hz, 1H), 7.91-7.80 (m, 1H), 7.48 (dd, J = 15.6, 7.7 Hz, 3H), 7.36 (s, 1H), 7.24-7.03 (m, 5H), 6.85 (s, 1H), 4.03-3.93 (m, 1H), 3.88 (s, 3H), 3.83 (dd, J = 14.7, 7.6 Hz, 1H), 3.15 (s, 1H), 2.94 (dd, J = 13.8, 8.0 Hz, 1H), 2.84 (dd, J = 13.8, 6.6 Hz, 1H), 2.29 (s, 3H). | DMSO | 95 | Method G1, AQ1 | 504.1, 505.2, 506.1 (M + 1) | Method B ($NH_4HCO_3$) |
| 1574 | 2HCl | $^{1}$H-NMR (400 MHz, DMSO-$d_6$): δ 10.43 (s, 1H), 9.71 (s, 1H), 9.05 (d, J = 4.7 Hz, 1H), 9.01 (d, J = 7.6 Hz, 1H), 8.96 (s, 1H), 8.45 (d, J = 8.6 Hz, 1H), 8.38 (d, J = 8.4 Hz, 1H), 7.99-7.89 (m, 1H), 7.61-7.41 (m, 4H), 7.23 (d, J = 7.8 Hz, 2H), 7.13 (d, J = 7.6 Hz, 3H), 6.93 (s, 1H), 4.01-3.84 (m, 5H), 3.31-3.21 (m, 1H), 3.02-2.97 (m, 7.5 Hz, 1H), 2.87-2.81 (m, 1H), 2.29 (s, 3H). | DMSO | 95 | Method G1, AQ1 | 504.1 (M + 1) | Method B ($NH_4HCO_3$) |
| 1575 | | $^{1}$H-NMR (400 MHz, $CD_3OD$): δ 9.39 (s, 1H), 8.69 (d, J = 8.0 Hz, 1H), 8.65 (s, 1H), 8.38 (s, 1H), 8.07 (d, J = 7.9 Hz, 1H), 7.85 (d, J = 8.6 Hz, 1H), 7.60-7.53 (m, 1H), 7.35-7.25 (m, 5H), 7.18 (dd, J = 13.6, 7.2 Hz, 2H), 7.12 (s, 1H), 6.88 (dd, J = 7.9, 2.1 Hz, 1H), 4.49 (dd, J = 11.3, 7.9 Hz, 1H), 4.36-4.17 (m, 2H), 4.04 (t, J = 10.4 Hz, 1H), 3.74 (s, 3H), 3.60-3.49 (m, 1H), 2.50-2.39 (m, 1H), 2.27-2.14 (m, 1H). | CD3OD | 95 | Method G1, AQ1 | 459.0 (M + 1) | Method B ($NH_4HCO_3$) |
| 1576 | | $^{1}$H-NMR (400 MHz, DMSO-$d_6$): δ 9.67 (d, J = 1.7 Hz, 1H), 9.05 (s, 1H), 8.94 (d, J = 3.7 Hz, 1H), 8.59 (s, 1H), 8.40-8.22 (m, 2H), 7.85 (s, 1H), 7.79 (d, J = 1.9 Hz, 1H), 7.66 (d, J = 8.3 Hz, 1H), 7.52-7.36 (m, 4H), 7.04 (d, J = 7.6 Hz, 1H), 4.74-4.72 (m, 2H), 4.48-4.43 (m, 3H), 3.85 (s, 3H), 3.74-3.60 (m, 1H), 2.25-2.23 (m, 1H). | DMSO | 95 | Method G1, AQ1 | 527.0, 529.0 (M + 1) | Method B ($NH_4HCO_3$) |

TABLE 24-continued

| | | | | | | | |
|---|---|---|---|---|---|---|---|
| 1577 | 2HCl | $^1$H-NMR (400 MHz, DMSO): δ 9.69 (d, J = 1.6 Hz, 1H), 8.89 (d, J = 8.0 Hz, 1H), 8.79 (d, J = 1.6 Hz, 1H), 8.73 (s, 1H), 8.21 (d, J = 9.2 Hz, 1H), 8.01 (d, J = 8.8 Hz, 1H), 7.67 (dd, J = 7.6, 4.8 Hz, 1H), 7.56-7.38 (m, 7H), 7.05-7.02 (m, 1H), 5.59 (s, 4H), 3.89 (s, 3H). | DMSO | 95 | Method G1, AQ1 | 431.1 (M + 1) | Method B ($NH_4HCO_3$) |
| 1578 | | $^1$H-NMR (400 MHz, DMSO): δ 9.59 (d, J = 1.6 Hz, 1H), 8.81-8.64 (m, 2H), 8.28-8.10 (m, 2H), 7.96 (d, J = 8.6 Hz, 1H), 7.55 (td, J = 8.5, 5.0 Hz, 3H), 7.40-7.06 (m, 5H), 6.94 (dd, J = 8.2, 2.0 Hz, 1H), 5.15 (s, 2H), 3.78 (s, 3H), 3.51 (s, 3H). | DMSO | 95 | Method G1, AQ1 | 451.2 (M + 1) | Method B ($NH_4HCO_3$) |
| 1579 | 2HCl | $^1$H-NMR (400 MHz, DMSO-$d_6$): δ 10.61 (s, 1H), 9.66 (s, 1H), 9.00 (d, J = 13.5 Hz, 3H), 8.43-8.31 (m, 2H), 7.89 (s, 1H), 7.48 (dd, J = 14.6, 7.2 Hz, 3H), 7.33-7.22 (m, 4H), 7.21-7.14 (m, 1H), 7.05 (d, J = 7.2 Hz, 1H), 4.10-3.85 (m, 2H), 3.90 (s, 3H), 3.37-3.27 (m, 1H), 3.07-2.91 (m, 2H). | DMSO | 95 | Method G1, AQ1 | 491.2 (M + 1) | Method B ($NH_4HCO_3$) |
| 1580 | 2HCl | $^1$H-NMR (400 MHz, DMSO-$d_6$): δ 9.91 (s, 1H), 9.60 (s, 1H), 9.11 (s, 1H), 9.95 (s, 1H), 8.66 (s, 1H), 8.20-8.02 (m, 3H), 7.97 (s, 1H), 7.78 (dd, J = 13.3, 6.5 Hz, 1H), 7.50 (t, J = 11.3 Hz, 1H), 7.33 (t, J = 8.1 Hz, 1H), 7.21 (s, 1H), 5.08 (d, J = 3.8 Hz, 2H). | DMSO | 95 | Method G1, AQ1 | 416.0 (M + 1) | Method B ($NH_4HCO_3$) |
| 1581 | 2HCl | $^1$H-NMR (400 MHz, DMSO-$d_6$): δ 9.84 (s, 1H), 9.71 (s, 1H), 9.12 (d, J = 6.2 Hz, 1H), 8.96 (d, J = 4.8 Hz, 1H), 8.91 (s, 1H), 8.37 (d, J = 8.4 Hz, 1H), 8.30 (s, 1H), 7.88 (s, 1H), 7.57-7.38 (m, 3H), 7.24 (s, 1H), 7.08 (d, J = 7.9 Hz, 1H), 6.73 (s, 1H), 5.18-5.05 (m, 1H), 3.88 (s, 3H), 3.23 (dd, J = 14.8, 7.4 Hz, 1H), 2.31-2.17 (m, 1H), 2.15-1.89 (m, 4H), 1.71-1.57 (m, 1H). | DMSO | 95 | Method G1, AQ1 | 440.2 (M + 1) | Method B ($NH_4HCO_3$) |

TABLE 24-continued

| | | | | | | | |
|---|---|---|---|---|---|---|---|
| 1583 | 2HCl | 1H-NMR (300 MHz, DMSO): δ 10.39 (s, 1H), 9.71 (s, 1H), 9.14 (d, J = 8.1 Hz, 1H), 8.98 (d, J = 4.0 Hz, 1H), 8.71 (s, 1H), 8.31 (d, J = 8.8 Hz, 1H), 8.25-8.19 (m, 1H), 7.96-7.89 (m, 1H), 7.38 (dd, J = 9.2, 3.0 Hz, 1H), 7.34-7.14 (m, 2H), 3.81 (s, 4H), 3.30 (d, J = 4.4 Hz, 4H). | DMSO | 95 | Method AQ2, AP | 361.7 (M + 1) | Method C |
| 1584 | 2HCl | 1H-NMR (300 MHz, DMSO): δ 10.84 (s, 1H), 9.01 (s, 1H), 8.95 (d, J = 3.9 Hz, 1H), 8.72 (d, J = 7.8 Hz, 1H), 8.50-8.40 (m, 1H), 8.33 (d, J = 8.8 Hz, 1H), 8.24 (td, J = 7.8, 1.7 Hz, 1H), 7.85 (dd, J = 6.5, 4.8 Hz, 1H), 7.57-7.43 (m, 3H), 7.09-7.02 (m, 1H), 3.90 (s, 3H), 3.38 (s, 3H) | DMSO | 95 | Method AQ2, AP | 343.5 (M + 1) | Method C |
| 1585 | 2HCl | 1H-NMR (300 MHz, DMSO): δ 10.44-10.13 (m, 1H), 9.66 (s, 1H), 9.08 (d, J = 10.1 Hz, 2H), 8.96 (d, J = 3.7 Hz, 1H), 8.44 (d, J = 8.9 Hz, 1H), 8.22 (d, J = 8.4 Hz, 1H), 8.13 (dd, J = 13.3, 5.3 Hz, 2H), 8.00 (d, J = 8.2 Hz, 1H), 7.91 (s, 1H), 3.30 (d, J = 4.4 Hz, 3H). | DMSO | 95 | Method AQ2, AP | 356.4 (M + 1) | Method C |
| 1586 | | 1H-NMR (300 MHz, DMSO): δ 9.64 (s, 1H), 8.78 (d, J = 8.0 Hz, 1H), 8.73-8.69 (m, 1H), 8.63 (s, 2H), 8.47-8.37 (m, 1H), 8.32-8.25 (m, 1H), 8.23-8.12 (m, 1H), 7.87 (d, J = 8.6 Hz, 1H), 7.73 (t, J = 9.0 Hz, 1H), 7.55 (dd, J = 7.9, 4.7 Hz, 1H), 3.20 (d, J = 4.3 Hz, 3H). | DMSO | 95 | Method AQ2, AP | 356.4 (M + 1) | Method C |
| 1587 | | 1H-NMR (300 MHz, DMSO): δ 9.65 (s, 1H), 8.79 (d, J = 8.0 Hz, 1H), 8.72-8.57 (m, 2H), 8.24 (d, J = 8.7 Hz, 1H), 7.88 (d, J = 8.7 Hz, 1H), 7.82 (d, J = 3.0 Hz, 1H), 7.76 (d, J = 8.0 Hz, 1H), 7.53 (t, J = 10.9 Hz, 2H), 7.45-7.36 (m, 1H), 3.99 (s, 3H), 3.94 (s, 3H), 3.21 (d, J = 4.1 Hz, 3H). | DMSO | 95 | Method AQ2, AP | 401.5 (M + 1) | Method C |
| 1588 | 2HCl | 1H-NMR (300 MHz, DMSO): δ 10.77 (s, 1H), 9.66 (s, 1H), 9.06 (s, 2H), 8.95 (d, J = 3.8 Hz, 1H), 8.38 (d, J = 8.8 Hz, 1H), 8.26 (d, J = 8.8 Hz, 1H), 7.87 (s, 1H), 7.71 (d, J = 8.1 Hz, 1H), 7.38 (dd, J = 22.8, 11.6 Hz, 2H), 4.03 (s, 3H), 3.31 (d, J = 4.1 Hz, 3H). | DMSO | 95 | Method AQ2, AP | 361.5 (M + 1) | Method C |

TABLE 24-continued

| | | | | | | | |
|---|---|---|---|---|---|---|---|
| 1589 | 2HCl | 1H-NMR (300 MHz, DMSO): δ 10.23-10.05 (m, 1H), 9.64 (s, 1H), 9.00 (s, 1H), 8.94 (s, 1H), 8.89 (s, 1H), 8.38 (d, J = 8.6 Hz, 1H), 8.14 (d, J = 8.5 Hz, 1H), 7.85 (s, 1H), 7.36 (d, J = 8.7 Hz, 2H), 6.95 (d, J = 10.9 Hz, 1H), 3.90 (s, 1H), 3.30 (d, J = 4.3 Hz, 3H). | DMSO | 95 | Method AQ2, AP | 361.5 (M + 1) | Method C |
| 1590 | 2HCl | 1H-NMR (300 MHz, DMSO): δ 10.34 (s, 1H), 9.70 (s, 1H), 9.14 (d, J = 7.4 Hz, 1H), 8.98 (d, J = 3.9 Hz, 1H), 8.75 (s, 1H), 8.32 (d, J = 8.8 Hz, 1H), 8.17 (d, J = 8.8 Hz, 1H), 7.93 (d, J = 4.8 Hz, 1H), 7.27 (dd, J = 19.5, 6.3 Hz, 3H), 3.88 (s, 3H), 3.28 (d, J = 4.1 Hz, 3H). | DMSO | 95 | Method AQ2, AP | 361.3 (M + 1) | Method C |
| 1591 | 2HCl | 1H-NMR (300 MHz, DMSO): δ 10.21 (s, 1H), 9.66 (d, J = 1.6 Hz, 1H), 9.04 (d, J = 7.3 Hz, 1H), 8.96 (d, J = 3.5 Hz, 1H), 8.67 (s, 1H), 8.28-8.12 (m, 2H), 7.88 (s, 1H), 7.66 (t, J = 8.8 Hz, 1H), 7.11-6.97 (m, 2H), 3.86 (s, 3H), 3.30 (d, J = 4.4 Hz, 3H). | DMSO | 95 | Method AQ2, AP | 361.3 (M + 1) | Method C |
| 1592 | 3HCl | 1H-NMR (300 MHz, DMSO): δ 10.77 (s, 1H), 9.69 (s, 1H), 9.39 (s, 1H), 9.16 (d, J = 7.8 Hz, 1H), 9.04 (s, 1H), 8.97 (d, J = 3.6 Hz, 1H), 8.63 (d, J = 2.5 Hz, 1H), 8.53 (s, 2H), 8.31 (d, J = 8.5 Hz, 1H), 7.91 (d, J = 5.4 Hz, 1H), 4.11 (s, 3H), 3.30 (d, J = 4.4 Hz, 3H). | DMSO | 95 | Method AQ2, AP | 343.1 (M + 1) | Method C |
| 1593 | 2HCl | | DMSO | 95 | Method AQ2, AP | 359.1 (M + 1) | Method C |
| 1594 | | 1H-NMR (300 MHz, DMSO): δ 9.64 (d, J = 1.3 Hz, 1H), 8.82-8.75 (m, 1H), 8.68 (dd, J = 4.8, 1.7 Hz, 1H), 8.60 (s, 1H), 8.53 (d, J = 1.7 Hz, 1H), 8.10 (dd, J = 8.7, 1.9 Hz, 1H), 7.86-7.77 (m, 4H), 7.58-7.48 (m, 2H), 7.09 (d, J = 8.8 Hz, 2H), 6.97 (d, J = 8.8 Hz, 1H), 3.99 (d, J = 6.0 Hz, 2H), 3.18 (d, J = 4.4 Hz, 3H), 1.82-1.69 (m, 2H), 1.07 (d, J = 6.7 Hz, 3H). | DMSO | 95 | Method AQ2, AP | 371.1 (M + 1) | Method C |

TABLE 24-continued

| | | | | | | | |
|---|---|---|---|---|---|---|---|
| 1595 | 2HCl | 1H-NMR (300 MHz, DMSO): δ 10.24-10.10 (bs, 1H), 9.65 (s, 1H), 9.02 (s, 1H), 8.96 (d, J = 3.8 Hz, 1H), 8.90 (s, 1H), 8.39 (s, 1H), 8.20 (s, 1H), 8.07 (s, 1H), 7.98 (s, 1H), 7.89 (s, 1H), 7.54 (t, J = 9.1 Hz, 1H), 3.70 (bs, 4H), 3.59 (bs, 4H), 3.32 (d, J = 4.4 Hz, 3H). | DMSO | 95 | Method AQ2, AP | 443.5 (M + 1) | Method C |
| 1596 | 2HCl | 1H-NMR (300 MHz, DMSO): δ 10.37 (s, 1H), 9.69 (d, J = 1.7 Hz, 1H), 9.10 (d, J = 7.0 Hz, 1H), 9.03-8.93 (m, 2H), 8.42 (d, J = 8.6 Hz, 1H), 8.28 (d, J = 9.3 Hz, 1H), 8.05 (d, J = 3.5 Hz, 1H), 7.99 (dd, J = 6.2, 2.4 Hz, 2H), 7.52 (t, J = 9.1 Hz, 1H), 3.54-3.43 (m, 4H), 3.30 (t, J = 10.4 Hz, 3H), 1.98-1.81 (m, 4H). | DMSO | 95 | Method AQ2, AP | 428.5 (M + 1) | Method C |
| 1597 | 2HCl | 1H-NMR (300 MHz, DMSO): δ 10.71 (s, 1H), 8.96 (d, J = 3.9 Hz, 1H), 8.81 (s, 1H), 8.74 (d, J = 7.9 Hz, 1H), 8.36 (d, J = 8.7 Hz, 1H), 8.29-8.19 (m, 2H), 7.87 (dd, J = 6.5, 4.7 Hz, 1H), 7.80 (dd, J = 15.5, 8.9 Hz, 1H), 7.61-7.50 (m, 1H), 7.36 (d, J = 8.1 Hz, 1H), 3.37 (d, J = 4.5 Hz, 3H). | DMSO | 95 | Method AQ2, AP | 349.4 (M + 1) | Method C |
| 1598 | | 1H-NMR (300 MHz, DMSO): δ 9.27 (d, J = 1.5 Hz, 1H), 8.61 (dd, J = 12.6, 3.0 Hz, 2H), 8.41 (d, J = 2.9 Hz, 1H), 8.34-8.27 (m, 1H), 8.16 (dd, J = 8.7, 1.9 Hz, 1H), 7.86 (d, J = 8.7 Hz, 1H), 7.45 (dd, J = 16.0, 9.2 Hz, 3H), 7.05-6.97 (m, 1H), 3.96 (s, 3H), 3.87 (s, 3H), 3.19 (d, J = 4.3 Hz, 3H). | DMSO | 95 | Method AQ2, AP | 373.4 (M + 1) | Method C |
| 1599 | 2HCl | 1H-NMR (300 MHz, DMSO): δ 10.44-10.13 (m, 1H), 9.65 (s, 1H), 9.02 (s, 1H), 8.96 (d, J = 3.5 Hz, 1H), 8.87 (s, 1H), 8.37 (d, J = 9.1 Hz, 1H), 8.24 (s, 1H), 7.86 (s, 2H), 7.78 (d, J = 7.9 Hz, 1H), 7.54 (d, J = 7.6 Hz, 1H), 7.43 (d, J = 7.5 Hz, 1H), 4.64 (s, 2H), 3.33 (d, J = 4.2 Hz, 3H), 3.17 (s, 1H). | DMSO | 95 | Method AQ2, AP | 343.5 (M + 1) | Method C |

TABLE 24-continued

| | | | | | | | |
|---|---|---|---|---|---|---|---|
| 1600 | MSA | 1H-NMR (300 MHz, DMSO): δ 9.90 (s, 1H), 9.57 (d, J = 1.6 Hz, 1H), 8.93 (dd, J = 5.0, 1.5 Hz, 2H), 8.73 (s, 1H), 8.32 (d, J = 8.7 Hz, 1H), 8.01 (d, J = 8.8 Hz, 1H), 7.85 (dd, J = 10.1, 7.0 Hz, 2H), 7.73 (d, J = 7.5 Hz, 1H), 7.52 (t, J = 7.6 Hz, 1H), 7.42 (d, J = 7.5 Hz, 1H), 4.63 (s, 2H), 3.30 (d, J = 4.3 Hz, 3H), 2.32 (s, 3H). | DMSO | 95 | Method AQ2, AP | 343.5 (M + 1) | Method C |
| 1601 | MsOH | $^1$H NMR (300 MHz, DMSO) δ 9.72 (brs, 1H), 9.58 (d, J = 1.6 Hz, 1H), 9.03-8.89 (m, 2H), 8.45 (d, J = 8.7 Hz, 1H), 8.11 (s, 1H), 7.99-7.84 (m, 2H), 7.64 (ddd, J = 9.2, 6.1, 3.1 Hz, 1H), 7.58-7.31 (m, 2H), 3.28 (d, J = 4.5 Hz, 3H), 2.39 (s, 3H). | DMSO | 98 | G2/AQ3 | | |
| 1602 | | $^1$H NMR (300 MHz, DMSO) δ 9.59 (d, J = 2.0 Hz, 1H), 9.33 (s, 2H), 9.24 (s, 1H), 8.79 (d, J = 1.5 Hz, 1H), 8.76-8.64 (m, 2H), 8.30 (dd, J = 8.7, 1.5 Hz, 1H), 8.12 (brs, 2H), 7.91 (d, J = 8.7 Hz, 1H), 7.55 (dd, J = 7.9, 4.8 Hz, 1H). | DMSO | 98 | G2/AQ3 | | |
| 1603 | | $^1$H NMR (300 MHz, DMSO) δ 9.64-9.53 (m, 1H), 8.77-8.53 (m, 2H), 8.53 (s, 1H), 8.43 (d, J = 1.5 Hz, 1H), 8.11 - 7.90 (m, 3H), 7.82 (d, J = 8.7 Hz, 1H), 7.54 (dd, J = 7.9, 4.8 Hz, 1H), 4.00 (s, 3H), 3.98 (s, 3H). | DMSO | 98 | G2/AQ3 | | |
| 1604 | | $^1$H NMR (300 MHz, DMSO) δ 9.59 (d, J = 2.0 Hz, 1H), 8.83-8.66 (m, 2H), 8.55 (s, 1H), 8.27-7.99 (m, 4H), 7.99-7.82 (m, 2H), 7.77 (d, J = 7.7 Hz, 1H), 7.66 (t, J = 7.6 Hz, 1H), 7.56 (dd, J = 7.9, 4.8 Hz, 1H). | DMSO | 98 | G2/AQ3 | | |
| 1605 | | 1H NMR (300 MHz, DMSO) δ 9.58 (d, J = 2.1 Hz, 1H), 8.80-8.64 (m, 2H), 8.25 (dd, J = 8.7, 1.6 Hz, 1H), 8.10 (d, J = 8.3 Hz, 2H), 8.02 (d, J = 8.3 Hz, 2H), 7.88 (d, J = 8.7 Hz, 1H), 7.55 (dd, J = 7.9, 4.8 Hz, 1H). | DMSO | 98 | G2/AQ3 | | |

TABLE 24-continued

| | | | | | | |
|---|---|---|---|---|---|---|
| 1606 | 2HCl | $^1$H NMR (300 MHz, DMSO) δ 9.95-9.43 (m, 3H), 9.05 (d, J = 8.2 Hz, 1H), 8.99 (dd, J = 5.1, 1.5 Hz, 1H), 8.74 (s, 1H), 8.33 (d, J = 8.7 Hz, 1H), 8.21 (d, J = 8.7 Hz, 1H), 7.93 (dd, J = 8.0, 5.1 Hz, 1H), 7.79 (td, J = 8.9, 6.6 Hz, 1H), 7.51 (ddd, J = 11.5, 9.3, 2.6 Hz, 1H), 7.33 (td, J = 8.3, 1.9 Hz, 1H). | DMSO | 98 | G2/AQ3 | |
| 1607 | 3HCl | $^1$H NMR (300 MHz, DMSO) δ 11.88 (s, 1H), 9.77 (d, J = 1.7 Hz, 1H), 9.56-9.28 (m, 1H), 9.19-9.01 (m, 1H), 8.31-8.11 (m, 4H), 7.75-7.47 (m, 2H), 7.47-7.23 (m, 1H), 4.83-4.67 (m, 2H), 3.96 (t, J = 12.2 Hz, 2H), 3.57 (d, J = 11.9 Hz, 2H), 3.46-3.19 (m, 2H), 2.83 (d, J = 3.1 Hz, 3H). | DMSO | 98 | G2/AQ3 | |
| 1608 | HCl | $^1$H NMR (300 MHz, DMSO) δ 14.45 (s, 1H), 10.36 (s, 1H), 9.31 (d, J = 2.2 Hz, 1H), 8.82 (s, 1H), 8.73 (ddd, J = 8.8, 2.5, 0.9 Hz, 1H), 8.36 (d, J = 9.0 Hz, 1H), 8.16 (d, J = 3.4 Hz, 1H), 7.56-7.36 (m, 3H), 7.11 (d, J = 8.4 Hz, 1H), 7.03 (d, J = 7.1 Hz, 1H), 3.99 (s, 3H), 3.87 (s, 3H), 3.30 (d, J = 3.9 Hz, 3H). | DMSO | 100 | Method AQ2/BF | |
| 1609 | HCl | $^1$H NMR (300 MHz, DMSO) δ 10.97 (s, 1H), 9.56-9.35 (m, 2H), 9.04-8.81 (m, 2H), 8.66 (t, J = 7.7 Hz, 1H), 8.61-8.45 (m, 2H), 8.15 (d, J = 8.6 Hz, 1H), 8.10-7.96 (m, 1H), 7.77-7.58 (m, 1H), 3.25 (d, J = 4.1 Hz, 3H). | DMSO | 100 | Method AQ2/BF | |
| 1610 | 2 MsOH | $^1$H NMR (300 MHz, $CDCl_3$) δ 9.93 (brs, 1H), 9.61 (d, J = 1.8 Hz, 1H), 9.10-8.96 (m, 2H), 8.64 (s, 1H), 8.21 (d, J = 8.7 Hz, 1H), 8.06 (d, J = 8.7 Hz, 1H), 7.99 (dd, J = 8.0, 5.3 Hz, 1H), 7.69-7.47 (m, 2H), 7.47-7.34 (m, 1H), 3.30 (d, J = 4.5 Hz, 3H), 2.42 (s, 6H). | DMSO | >98 | G2/AQ3 | Method 3 |

TABLE 24-continued

| | | | | | | | |
|---|---|---|---|---|---|---|---|
| 1611 | 2HCl | $^1$H NMR (300 MHz, $CDCl_3$) δ 10.42 (brs, 1H), 9.71 (d, J = 1.9 Hz, 1H), 9.17 (d, J = 8.1 Hz, 1H), 8.99 (dd, J = 5.1, 1.3 Hz, 1H), 8.78 (s, 1H), 8.33 (d, J = 8.7 Hz, 1H), 8.17 (d, J = 8.7 Hz, 1H), 7.94 (dd, J = 8.1, 5.2 Hz, 1H), 7.79 (td, J = 8.9, 6.7 Hz, 1H), 7.55-7.37 (m, 1H), 7.31 (td, J = 3.4, 2.2 Hz, 1H), 3.29 (d, J = 4.4 Hz, 3H). | DMSO | >98 | G2/AQ3 | | |
| 1612 | HCl | $^1$H NMR (300 MHz, DMSO) δ 9.95 (brs, 1H), 9.65 (s, 1H), 9.18-9.02 (m, 1H), 8.95 (d, J = 4.7 Hz, 1H), 8.58 (d, J = 8.7 Hz, 1H), 8.28 (s, 1H), 8.09-7.70 (m, 4H), 3.29 (d, J = 4.4 Hz, 3H). | DMSO | >98 | G2/AQ3 | | |
| 1613 | | $^1$H NMR (300 MHz, DMSO) δ 9.64 (d, J = 1.5 Hz, 1H), 8.77 (dt, J = 7.9, 1.9 Hz, 1H), 8.69 (dd, J = 4.8, 1.7 Hz, 1H), 8.61-8.48 (m, 1H), 8.31 (d, J = 8.7 Hz, 1H), 8.11 (d, J = 1.8 Hz, 1H), 8.00-7.83 (m, 3H), 7.55 (dd, J = 7.9, 4.8 Hz, 1H), 3.17 (d, J = 4.4 Hz, 3H). | DMSO | >98 | G2/AQ3 | | |
| 1614 | | $^1$H NMR (300 MHz, DMSO) δ 9.65 (dd, J = 2.1, 0.8 Hz, 1H), 8.78 (dt, J = 8.0, 1.9 Hz, 1H), 8.69 (dd, J = 4.8, 1.7 Hz, 1H), 8.65-8.50 (m, 1H), 8.33 (d, J = 8.6 Hz, 1H), 8.04-7.85 (m, 1H), 7.69 (dt, J = 8.5, 1.8 Hz, 1H), 7.65-7.37 (m, 3H), 3.18 (d, J = 4.5 Hz, 3H). | DMSO | >98 | G2/AQ3 | Method 3 | |
| 1615 | | $^1$H NMR (300 MHz, DMSO) δ 9.65 (d, J = 1.7 Hz, 1H), 8.84-8.74 (m, 1H), 8.69 (dd, J = 4.7, 1.5 Hz, 1H), 8.65-8.52 (m, 1H), 8.34 (d, J = 8.6 Hz, 1H), 7.98 (s, 1H), 7.72 (d, J = 8.5 Hz, 1H), 7.69-7.43 (m, 3H), 3.18 (d, J = 4.3 Hz, 3H). | DMSO | >98 | G2/AQ3 | Method 3 | |
| 1760 | 2 HCl | $^1$H NMR (400 MHz, DMSO) δ 10.04 (s, 1H), 9.65 (s, 1H), 9.11-8.99 (m, 1H), 8.96 (dd, J = 5.0, 1.4 Hz, 1H), 8.41 (s, 1H), 8.13-8.05 (m, 1H), 7.92-7.82 (m, 1H), 7.64-7.55 (m, 1H), 7.44-7.26 (m, 3H), 3.27 (d, J = 4.6 Hz, 3H), 2.47 (s, 3H). | DMSO | >98 | AQ5 | ND | 4 |

Scheme 76: General route for the synthesis of compounds with general formula lviii and lx

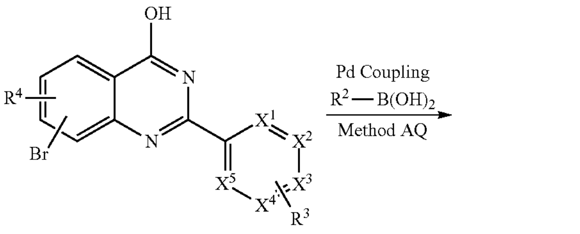

iv

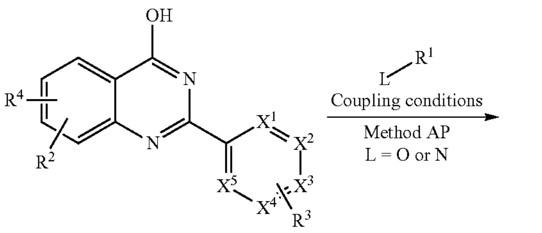

lix

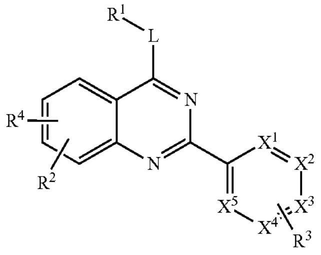

lviii or ix $X^1$, $X^2$, $X^3$, $X^4$ or $X^5$ = CH or N, at least one $X^1$, $X^2$, $X^3$, $X^4$ or $X^5$ must be N Scheme 77: Representative synthesis of compounds of formula lviii (see Scheme 76)

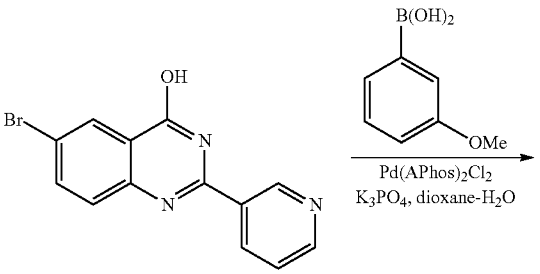

iv-j

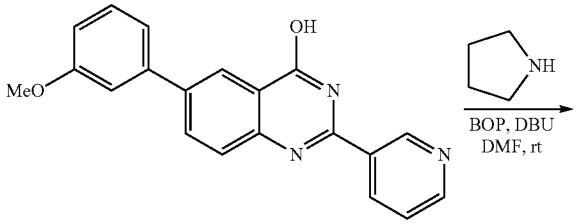

lix-a

-continued

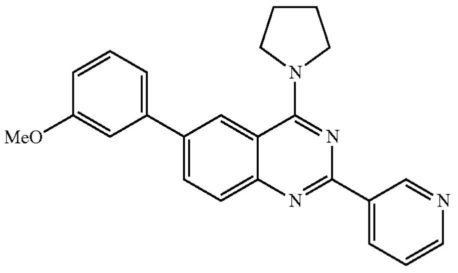

lviii-g 6-(3-methoxyphenyl)-2-(pyridine-3-yl)quinazoline-4-ol (lix-a)

6-(3-methoxyphenyl)-2-(pyridine-3-yl)quinazoline-4-ol was prepared from 6-bromo-2-(pyridin-3-yl)quinazolin-4-ol (synthesized following Scheme 70 substituting 2-amino-5-bromobenzamide for 2-amino-5-bromo-3-methylbenzamide) and 3-methoxylphenylboronic acid as described in Scheme 72 using method AQ2. The resultant product, 6-(6-methoxypyridin-3-yl)-N-methyl-2-(pyridine-3-yl)quinazoline-4-amine, was a pale yellow solid (19.1 mg, 51%). LCMS m/z=344 (M+1) (Method C) (retention time=2.01 min). $^1$H NMR (300 MHz, DMSO) δ 9.64 (d, J=1.3 Hz, 1H), 8.84-8.74 (m, 1H), 8.68 (dd, J=6.2, 1.7 Hz, 2H), 8.57 (d, J=1.6 Hz, 2H), 8.16 (ddd, J=14.4, 8.7, 2.2 Hz, 2H), 7.85 (d, J=8.7 Hz, 1H), 7.54 (dd, J=7.9, 4.8 Hz, 1H), 7.00 (d, J=8.7 Hz, 1H), 3.93 (s, 3H), 3.18 (d, J=4.3 Hz, 3H).

Method AP: 6-(3-methoxyphenyl)-2-(pyridine-3-yl)-4-(pyrrolidin-1-yl)quinazoline (Iviii-g)

6-(3-methoxyphenyl)-2-(pyridine-3-yl)-4-(pyrrolidin-1-yl)quinazoline was prepared from 6-(3-methoxyphenyl)-2-(pyridine-3-yl)quinazoline-4-01 and pyrrolidine in a manner analogous to that described for 6-bromo-N-methyl-2-(pyridine-3-yl)quinazoline-4-amine using Method AP in Scheme 72. 6-(3-methoxyphenyl)-2-(pyridine-3-yl)-4-(pyrrolidin-1-yl)quinazoline was a pale yellow solid (43 mg, 31%), LCMS m/z=383 (M+1) (Method C) (retention time=2.49 ruin). $^1$H NMR (300 MHz, DMSO) δ 9.62 (s, 1H), 8.94 (d, J=5.0 Hz, 2H), 8.56 (s, 1H), 8.32 (dd, J=19.9, 8.5 Hz, 2H), 7.83 (s, 1H), 7.56-7.30 (m, 3H), 7.04 (d, J=6.8 Hz, 1H), 4.2.7 (s, 4H), 3.86 (s, 3H), 2.08 (s, 4H).

The compounds in the following table were prepared in a manner analogous to that described in Scheme 76, replacing pyrrolidine with the appropriate amine and 3-methoxyphenylboronic acid with the appropriate boronic acid.

TABLE 25

| Number | Product | Salt | $^1$H-NMR | $^1$H-NMR Solvent | LCMS | Retention Time | LCMS Protocol | Purity Percent | Method for Coupling |
|---|---|---|---|---|---|---|---|---|---|
| 1616 | 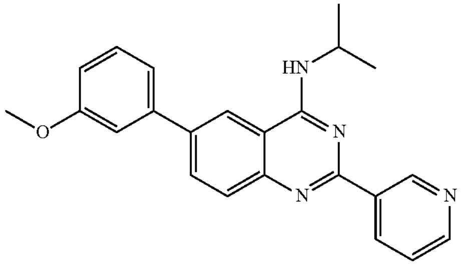 [SMILES: COc1cccc(-c2ccc3nc(-c4cccnc4)nc(NC(C)C)c3c2)c1] | HCl | 1H NMR (300 MHz, DMSO) δ 9.82 (s, 1H), 9.59 (s, 1H), 9.08-8.81 (m, 3H), 8.36 (d, J = 8.8 Hz, 1H), 8.17 (d, J = 8.6 Hz, 1H), 7.95-7.77 (rn, 1H), 7.58-7.37 (m, 3H), 7.05 (d, J = 6.5 Hz, 1 H), 5.01-4.79 (m, 1H), 3.87 (s, 3H), 1.42 (d, J = 6.5 Hz, 6H). | DMSO | 371 (M + 1) | 2.36 | Method C | 100 | Method AP |
| 1617 | 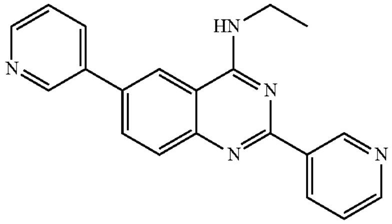 [SMILES: CCNc1nc(-c2cccnc2)nc2ccc(-c3cccnc3)cc12] | HCl | 1H NMR (300 MHz, DMSO) δ 10.38 (s, 1H), 9.64 (s. 1H), 9.43 (s, 1H), 9.28 (s, 1H), 9.07 (d. J = 7.9 Hz, 1H), 9.00-8.76 (m, 3H), 8.48 (d, J = 7.5 Hz, 1H), 8.27 (d, J = 8.4 Hz, 1H), 8.08-7.95 (m, 1H), 7.94-7.81 (m, 1H), 3.97-3.74 (m, 2H), 1.38 (t, J = 7.2 Hz, 3H). | DMSO | 328 (M + 1) | 1.82 | Method C | 100 | Method AP |
| 1618 | 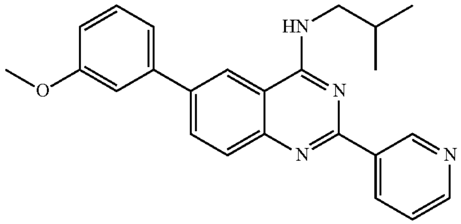 [SMILES: COc1cccc(-c2ccc3nc(-c4cccnc4)nc(NCC(C)C)c3c2)c1] | HCl | 1H NMR (300 MHz, DMSO) δ 10.11 (s, 1H), 9.58 (s, 1H), 9.03-8.79 (m, 3H), 8.35 (d, J = 8.7 Hz, 1H), 8.23-8.09 (m, 1H), 7.90-7.75 (m, 1H), 7.58-7.36 (m, 3H), 7.04 (d, J = 3.3 Hz, 1H), 3.88 (s, 3H), 3.65 (t, J = 6.0 Hz, 2H), 2.29-2.09 (m, 1H), 1.02 (d, J = 6.7 Hz, 6H). | DMSO | 385 (M + 1) | 1.76 | Method D | 100 | Method AP |

TABLE 25-continued
| | | | | | | | | | |
|---|---|---|---|---|---|---|---|---|---|
| 1619 | 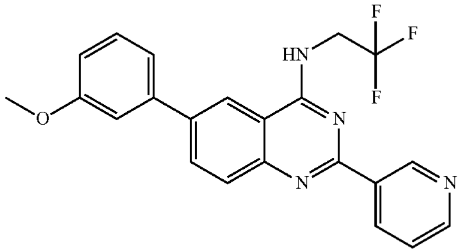 [SMILES: COc1cccc(-c2ccc3nc(-c4cccnc4)nc(NCC(F)(F)F)c3c2)c1] | HCl | 1H NMR (300 MHz, DMSO) δ 9.83-9.52 (m, 2H), 9.27 (d, J = 7.1 Hz, 1H), 8.95 (d, J = 5.1 Hz, 1H), 8.87 (s, 1H), 8.32 (d, J = 8.9 Hz, 1H), 8.15-7.92 (m, 2H), 7.59-7.33 (m, 3H), 7 04 (d, J = 3.4 Hz, 1H), 4.86-4.57 (m, 2H), 3.88 (s, 3H). | DMSO | 411 (M + 1) | 1.99 | Method D | 100 | Meth-od AP |
| 1620 | 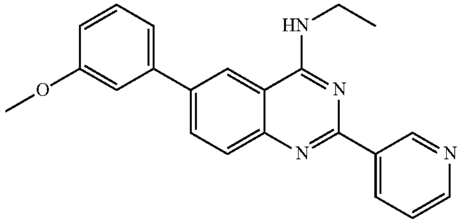 [SMILES: CCNc1nc(-c2cccnc2)nc2ccc(-c3cccc(OC)c3)cc12] | HCl | 1H NMR (300 MHz, DMSO) δ 10.50 (s, 1H), 9.64 (d, J = 1.4 Hz, 1H), 9.12-8.85 (m, 3H), 8.46-8.33 (m, 1H), 8.27 (d, J = 8.9 Hz, 1H), 7.88 (dd, J = 7.9, 5.1 Hz, 1H), 7.57-7.37 (m, 3H), 7.11-6.94 (m, 1H), 4.00-3.76 (m, 5H), 1.37 (t, J = 7.2 Hz, 3H). | DMSO | MS not work | 1.56 | Method D | 100 | Meth-od AP |
| 1621 | 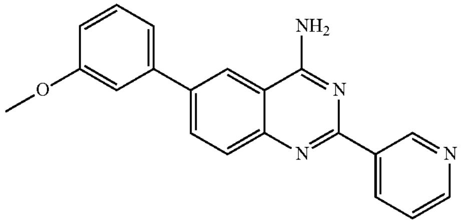 [SMILES: COc1cccc(-c2ccc3nc(-c4cccnc4)nc(N)c3c2)c1] | | 1H NMR (300 MHz, DMSO) δ 9.57 (s, 1H), 8.78-8.50 (m, 3H), 8.33-7.89 (m, 3H), 7.83 (d, J = 8.7 Hz, 1H), 7.53 (dd, J = 7.9, 4.8 Hz, 1H), 7.47-7.32 (m, 3H), 7.04-6.91 (m, 1H), 3.86 (s, 3H). | DMSO | 329 (M + 1) | 1.47 | Method D | 100 | Meth-od AP |
| 1622 | 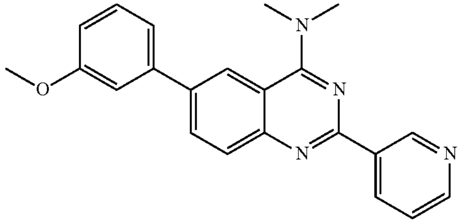 [SMILES: COc1cccc(-c2ccc3nc(-c4cccnc4)nc(N(C)C)c3c2)c1] | HCl | 1H NMR (300 MHz, DMSO) δ 9.65 (s, 1H), 9.14-8.87 (m, 2H), 8.50 (s, 1H), 8.33 (s, 2H), 7.94-7.77 (m, 1H), 7.52-7.25 (m, 3H), 7.02 (d, J = 7.9 Hz, 1H), 3.84 (s, 3H), 3.71 (s, 6H). | DMSO | 357 (M + 1) | 1.55 | Method D | 100 | Meth-od AP |

TABLE 25-continued

| | | | | | | | | | |
|---|---|---|---|---|---|---|---|---|---|
| 1623 | 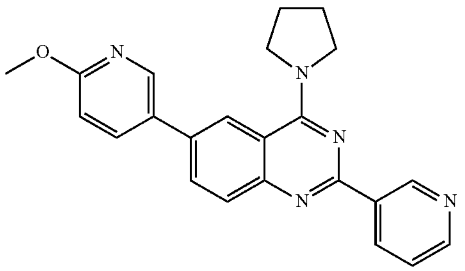 [SMILES: COc1ccc(-c2ccc3nc(-c4cccnc4)nc(N4CCCC4)c3c2)cn1] | | 1H NMR (300 MHz, DMSO) δ 9.60 (d, J = 1.4 Hz, 1H), 8.81-8.55 (m, 3H), 8.42 (d, J = 1.8 Hz, 1H), 8.11 (ddd, J = 18.8, 8.7, 2.2 Hz, 2H), 7.86 (d, J = 8.7 Hz, 1H), 7.52 (dd, J = 7.9, 4.8 Hz, 1H), 6.95 (d, J = 8.6 Hz, 1H), 4.27 (s, 4H), 3.92 (s, 3H), 2.08 (s, 4H). | DMSO | 384.1 (M + 1) | 2.33 | Method C | 100 | Meth-od AP |
| 1624 | 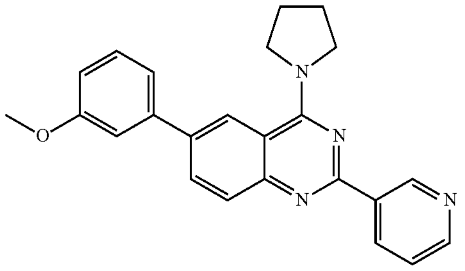 [SMILES: COc1cccc(-c2ccc3nc(-c4cccnc4)nc(N4CCCC4)c3c2)c1] | 2HCl | 1H NMR (300 MHz, DMSO) δ 9.62 (s, 1H), 8.94 (d, J = 5.0 Hz, 2H), 8.56 (s, 1H), 8.32 (dd, J = 19.9, 8.5 Hz, 2H), 7.83 (s, 1H), 7.56-7.30 (m, 3H), 7.04 (d, J = 6.8 Hz, 1H), 4.27 (s, 4H), 3.86 (s, 3H), 2.08 (s, 4H). | DMSO | 383.2 (M + 1) | 2.47 | Method C | 95 | Meth-od AP |
| 1625 | 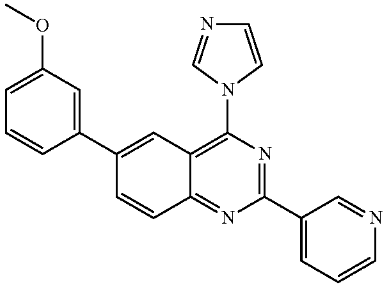 [SMILES: COc1cccc(-c2ccc3nc(-c4cccnc4)nc(-n4ccnc4)c3c2)c1] | | 1H NMR (300 MHz, DMSO) δ 9.70 (d, J = 1.4 Hz, 1H), 8.35 (d, J = 7.9 Hz, 1H), 8.80-8.72 (m, 2H), 8.45 (d, J = 8.7 Hz, 1H), 8.27 (dd J = 14.9, 5.9 Hz. 3H), 7.63 (dd. J = 7.3, 4.8 Hz, 1H), 7.52-7.33 (m, 4H), 7.04 (d, J = 7.1 Hz, 1H), 3.88 (s, 3H). | DMSO | 380.1 (M + 1) | 2.01 | Method C | 100 | Meth-od AP |
| 1626 | 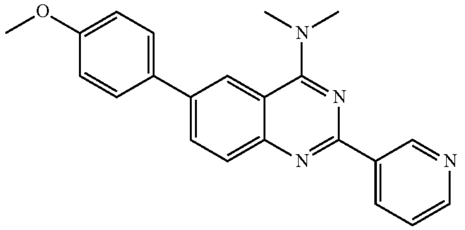 | HCl | 1H NMR (300 MHz, DMSO) δ 9.61 (s, 1H), 8.75 (d, J = 7.7 Hz, 1H), 8.68 (d, J = 4.6 Hz, 1H), 8.30 (s, 1H), 8.08 (d, J = 8.6 Hz, 1H), 7.89 (d, J = 8.8 Hz, 1H), 7.75 (d, J = 8.7 Hz, 2H), 7.54 (dd, J = 7.6, 5.0 Hz, 1H), 7.07 (d, J = 8.7 Hz, 2H), 3.82 (s, 4H), 3.49 (s, 7H). | DMSO | 358.0 (M + 1) | 2.25 | Method C | 100 | Meth-od AP |

TABLE 25-continued
| | | | | | | | | | |
|---|---|---|---|---|---|---|---|---|---|
| 1627 | 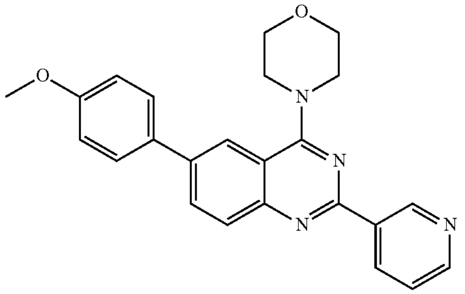 [SMILES: COc1ccc(-c2ccc3nc(-c4cccnc4)nc(N4CCOCC4)c3c2)cc1] | HCl | 1H NMR (300 MHz, DMSO) δ 9.52 (s, 1H), 8.76 (d, J = 7.9 Hz, 1H), 8.73-8.66 (m, 1H), 8.19-8.09 (m, 2H), 7.97 (d, J = 8.6 Hz, 1H), 7.82-7.73 (m, 2H), 7.61-7.52 (m, 1H), 7.14-7.05 (m, 2H), 3.94 (s, 5H), 3.89-3.80 (m, 9H). | DMSO | 399.2 (M + 1) | 2.19 | Method C | 100 | Meth-od AP |
| 1628 | 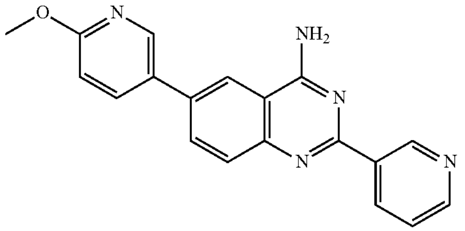 [SMILES: COc1ccc(-c2ccc3nc(-c4cccnc4)nc(N)c3c2)cn1] | | 1H NMR (300 MHz, DMSO) δ 9.55 (dd, J = 2.1, 0.8 Hz, 1H), 8.76-8.62 (m, 3H), 8.60 (d, J = 1.7 Hz, 1H), 8.24-8.10 (m, 2H), 8.02 (s, 2H), 7.83 (d, J = 8.7 Hz, 1H), 7.58-7.46 (m, 1H), 6.98 (d, J = 9.2 Hz, 1H), 3.91 (s, 3H). | DMSO | 330.1 (M + 1) | 1.72 | Method C | 100 | Meth-od AP |
| 1629 | 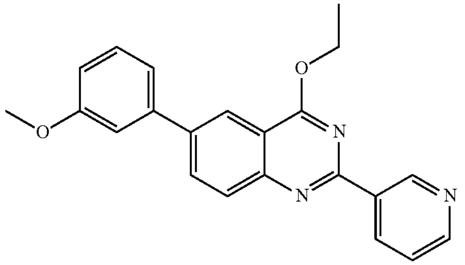 [SMILES: CCOc1nc(-c2cccnc2)nc2ccc(-c3cccc(OC)c3)cc12] | | 1H NMR (300 MHz, DMSO) δ 9.65 (d, J = 2.1 Hz, 1H), 8.79 (d, J = 8.0 Hz, 1H), 8.73 (dd, J = 4.7, 1.6 Hz, 1H), 8.36-8.25 (m, 2H), 8.06 (d, J = 8.7 Hz, 1H), 7.59 (dd, J = 7.6, 4.4 Hz, 1H), 7.48-7.40 (m, 1H), 7.41-7.29 (m, 2H), 7.01 (dd, J = 8.0, 2.4 Hz, 1H), 4.80 (q, J = 7.1 Hz, 2H), 3.85 (s, 3H), 1.53 (t, J = 7.0 Hz, 3H). | DMSO | 358 (M + 1) | | Method C | 99 | Meth-od AP |

TABLE 25-continued
| | | | | | | | | |
|---|---|---|---|---|---|---|---|---|
| 1630 | 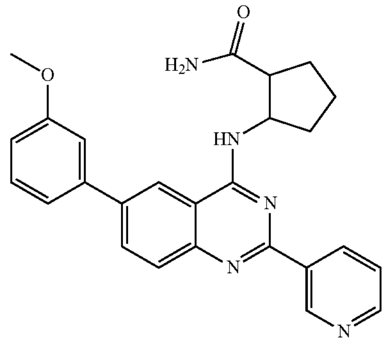 [SMILES: COc1cccc(-c2ccc3nc(-c4cccnc4)nc(NC4CCCC4C(N)=O)c3c2)c1] | 2 HCl | 1H NMR (300 MHz, DMSO) δ 9.68 (d, J = 1.8 Hz, 1H), S.07 (d, J = 5.5 Hz, 1H), 8.96 (d, J = 3.5 Hz, 1H), 8.30 (s, 1H), 8.37 (d, J = 7.5 Hz, 1H), 8.22 (d, J = 8.3 Hz, 1H), 7.94-7.83 (m, 1H), 7.57-7,39 (m, 3H), 7.22 (d, J = 1.0 Hz, 1H), 7.08 (d, J = 7.3 Hz, 1H), 6.72 (s, 1H), 5.18-5.04 (m, 1H), 3.88 (s, J = 2.7 Hz, 3H), 3.23 (dd, J = 13.7, 6.1 Hz, 1H), 2.31-2.17 (m, 1H), 2.17-1.88 (m, 4H), 1.74-1.55 (m, 1H). | DMSO | 440.6 (M + 1) | Method C | 99 | Meth-od AP |
| 1631 | 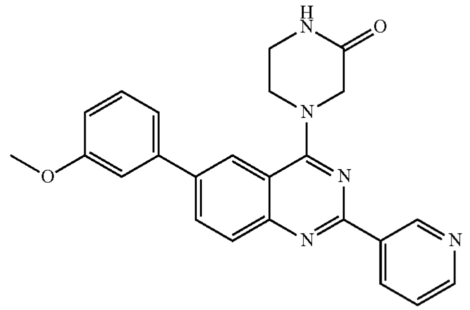 [SMILES: COc1cccc(-c2ccc3nc(-c4cccnc4)nc(N4CCNC(=O)C4)c3c2)c1] | 2 HCl | 1H NMR (300 MHz, DMSO) δ 9.70 (d, J = 1.6 Hz, 1H), 9.24 (d, J = 7.4 Hz, 1H), 8.99 (dd, J = 5.3, 1.4 Hz, 1H), 8.34 (dd, J = 15.7, 6.1 Hz, 3H), 8.21 (d, J = 8.4 Hz, 1H), 8.01 (dd, J = 7.7, 5.1 Hz, 1H), 7.51-7.33 (m, 3H), 7.04 (dd, J = 7.8, 2.4 Hz, 1H), 4.67 (s, 2H), 4.33 (s, 2H), 3.87 (s, J = 3.6 Hz, 3H), 3.50 (s, 2H). | DMSO | 412.4 (M + 1) | Method C | 99 | Meth-od AP |
| 1632 | 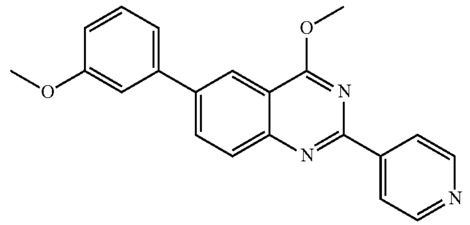 [SMILES: COc1cccc(-c2ccc3nc(-c4ccncc4)nc(OC)c3c2)c1] | 2 HCl | 1H NMR (300 MHz, DMSO) δ 9.00 (d, J = 6.5 Hz, 2H), 8.78 (d, J = 6.5 Hz, 2H), 8.46-8.32 (m, 2H), 8.15 (d, J = 8.4 Hz, 1H), 7.53-7.30 (m, 3H), 7.02 (d, J = 7.8 Hz, 1H), 4.34 (s, J = 2.4 Hz. 3H), 3.86 (s, J = 2.5 Hz, 3H). | DMSO | 344.4 (M + 1) | Method C | 99 | Meth-od AP |

TABLE 25-continued
| | | | | | | | |
|---|---|---|---|---|---|---|---|
| 1633 | 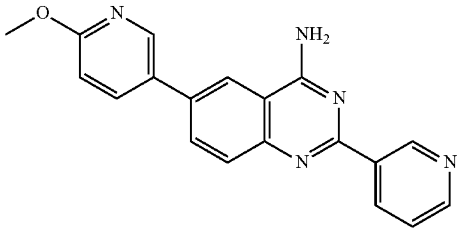 [SMILES: COc1ccc(-c2ccc3nc(-c4cccnc4)nc(N)c3c2)cn1] | 1H NMR (300 MHz, DMSO) δ 9.55 (dd, J = 2.1, 0.8 Hz, 1H), 8.76-8.62 (m, 3H), 8.60 (d, J = 1.7 Hz, 1H), 8.24-8.10 (m, 2H), 8.02 (s, 2H), 7.83 (d, J = 8.7 Hz, 1H), 7.56-7.46 (m, 1H), 6.98 (d, J = 9.2 Hz, 1H), 3.91 (s, 3H). | DMSO | 330.1 (M + 1) | Method C | 99 | Meth-od AP |
| Num-ber | Starting Material $R^1$ | Starting Material $R^3$ | Product | Salt Type | $^1H$ NMR | $^1H$ NMR Solvent |
|---|---|---|---|---|---|---|
| 1634 | 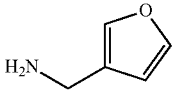 | 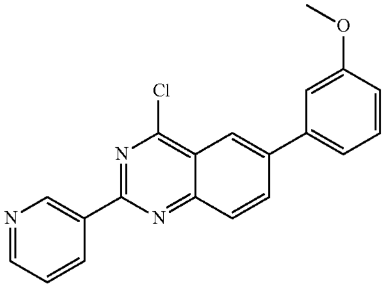 [SMILES: COc1cccc(-c2ccc3nc(-c4cccnc4)nc(Cl)c3c2)c1] | 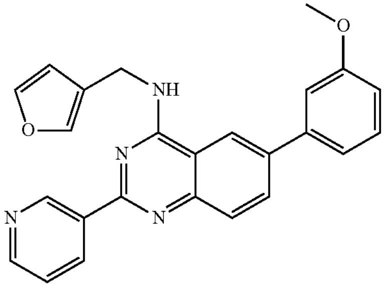 [SMILES: COc1cccc(-c2ccc3nc(-c4cccnc4)nc(NCc4ccoc4)c3c2)c1] | | $^1H$ NMR (DMSO-$d_6$) ppm 3.87 (s, 3H), 4.76 (d, 2H, J = 5.4 Hz), 6.58 (d, 1H, J = 1.1 Hz), 7.00-7.75 (m, 8H), 7.85 (d, 1H, J = 8.6 Hz), 8.64-8.97 (m, 4H), 9.64 (s, 1H) | DMSO |

TABLE 25-continued
| | | | | | |
|---|---|---|---|---|---|
| 1635 | 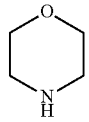 | 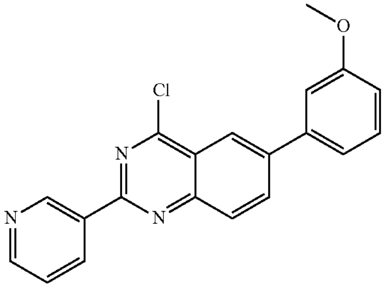 [SMILES: COc1cccc(-c2ccc3nc(-c4cccnc4)nc(Cl)c3c2)c1] | 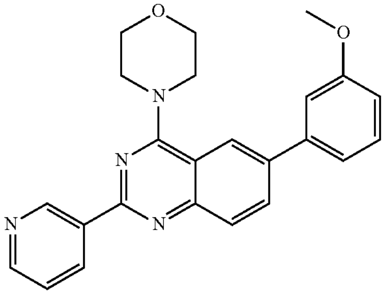 [SMILES: COc1cccc(-c2ccc3nc(-c4cccnc4)nc(N4CCOCC4)c3c2)c1] | $^1$H NMR (DMSO-$d_6$) ppm 3.34-3.95 (m, 11H), 7.01 (d, 1H, J = 8.1 Hz), 7.32-7.45 (m, 3H), 7.56 (dd, 1H, J = 6.1, 8.1 Hz), 7.97 (d, 1H, J = 8.2 Hz), 8.16-8.76 (m, 4H), 9.61 (s, 1H) | DMSO |
| 1636 | 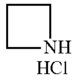 | 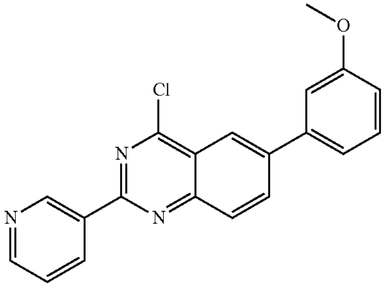 [SMILES: COc1cccc(-c2ccc3nc(-c4cccnc4)nc(Cl)c3c2)c1] | 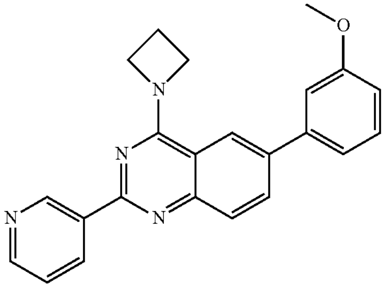 [SMILES: COc1cccc(-c2ccc3nc(-c4cccnc4)nc(N4CCC4)c3c2)c1] | $^1$H NMR (DMSO-$d_6$) ppm 2.23 (m, 2H), 3.85 (s, 3H), 4.71 (br s, 4H), 6.98 (dd, 1H, J = 2.1, 8.0 Hz), 7.31-7.55 (m, 4H), 7.87 (d, 1H, J = 8.2 Hz), 8.12-8.74 (m, 4H), 9.59 (s, 1H) | DMSO |

TABLE 25-continued
| | | | | | |
|---|---|---|---|---|---|
| 1637 | 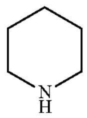 | 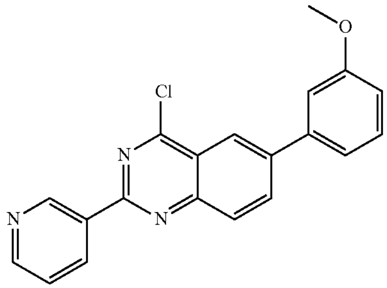 [SMILES: COc1cccc(-c2ccc3nc(-c4cccnc4)nc(Cl)c3c2)c1] | 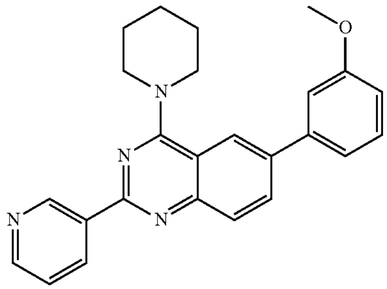 [SMILES: COc1cccc(-c2ccc3nc(-c4cccnc4)nc(N4CCCCC4)c3c2)c1] | 1H NMR (DMSO-d6) ppm 1.77 (br s, 6H), 3.86-3.89 (br m, 7H), 6.99 (dd, 1H, J = 1.4, 8.6 Hz), 7.31-7.57 (m, 4H), 7.93 (d, 1H, J = 1.4, 8.6 Hz), 8.11-8.16 (m, 2H), 8.69-8.76 (m, 2H), 9.61 (s, 1H) | DMSO |
| 1638 | 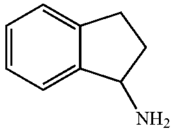 | 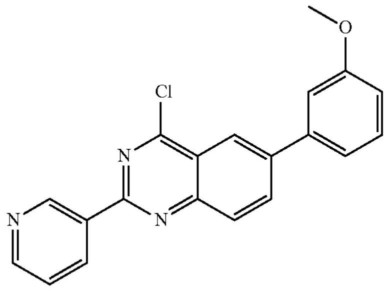 [SMILES: COc1cccc(-c2ccc3nc(-c4cccnc4)nc(Cl)c3c2)c1] | 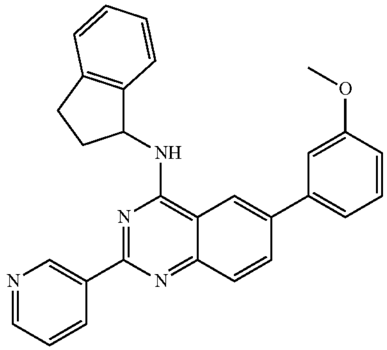 [SMILES: COc1cccc(-c2ccc3nc(-c4cccnc4)nc(NC4CCc5ccccc54)c3c2)c1] | 1H NMR (DMSO-d6) ppm 2.18-2.22 (m, 1H), 3.00-3.09 (m, 1H), 3.11-3.22 (m, 2H), 3.31-3.34 (m, 1H), 3.86 (s, 3H), 6.29-6.31 (m, 1H), 7.17-8.82 (m, 14H), 9.63 (s, 1H) | DMSO |

TABLE 25-continued
| | | | | | |
|---|---|---|---|---|---|
| 1639 | 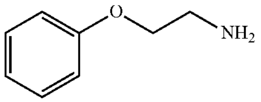 | 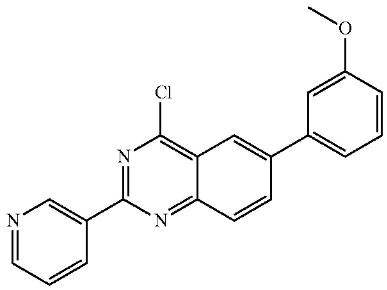 [SMILES: COc1cccc(-c2ccc3nc(-c4cccnc4)nc(Cl)c3c2)c1] | 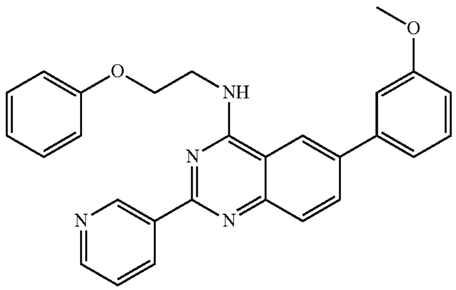 [SMILES: COc1cccc(-c2ccc3nc(-c4cccnc4)nc(NCCOc4ccccc4)c3c2)c1] | 1H NMR (DMSO-d6) ppm 3.87 (s, 3H), 4.10-4.13 (m, 2H), 4.35-4.38 (m, 2H), 6.92-7.46 (m, 10H), 7.85 (d, 1H, J = 8.6 Hz), 8.16 (d, 1H, J = 8.6 Hz), 8.66-8.75 (m, 4H), 3.61 (s, 1H) | DMSO |
| 1640 | 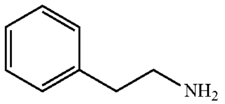 | 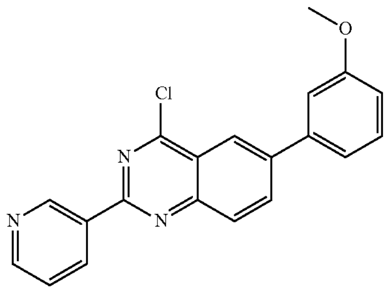 [SMILES: COc1cccc(-c2ccc3nc(-c4cccnc4)nc(Cl)c3c2)c1] | 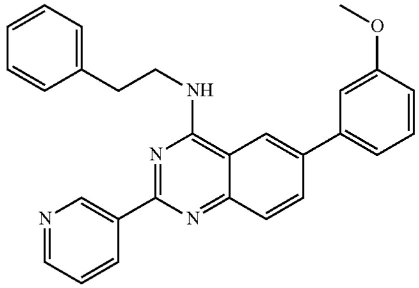 [SMILES: COc1cccc(-c2ccc3nc(-c4cccnc4)nc(NCCc4ccccc4)c3c2)c1] | 1H NMR (DMSO-d6) ppm 3.07 (t, 2H, J = 6.9 Hz), 3.87 (s, 3H), 3.92-3.96 (m, 2H), 7.00-7.58 (m, 10H), 7.84 (d, 1H, J = 8.6 Hz), 8.14 (d, 1H, J = 8.6 Hz), 8.59-8.78 (m, 4H), 9.64 (s, 1H) | DMSO |

TABLE 25-continued
| | | | | | |
|---|---|---|---|---|---|
| 1641 | 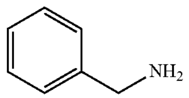 | 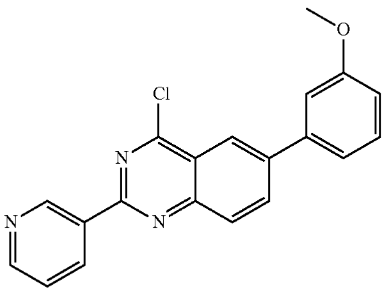 [SMILES: COc1cccc(-c2ccc3nc(-c4cccnc4)nc(Cl)c3c2)c1] | 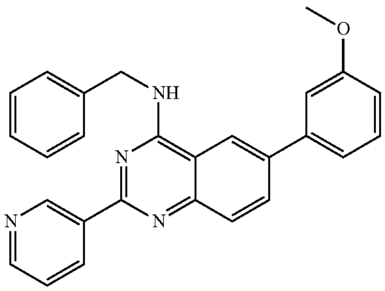 | 1H NMR (DMSO-d6) ppm 3.37 (s, 3H), 4.95 (d, 2H, J = 5.6 Hz), 7.01-7.51 (m, 10H), 7.85 (d, 1H, J = 8.6 Hz), 8.16 (d, 1H, J = 8.6 Hz), 8.65-8.73 (m, 4H), 956 (s, 1H) | DMSO |
| 1642 | 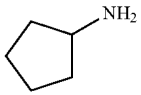 | 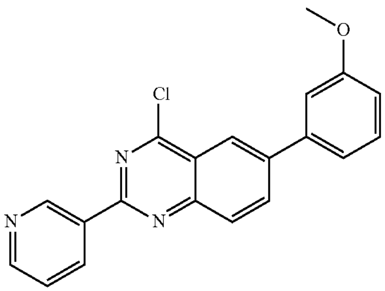 [SMILES: COc1cccc(-c2ccc3nc(-c4cccnc4)nc(Cl)c3c2)c1] | 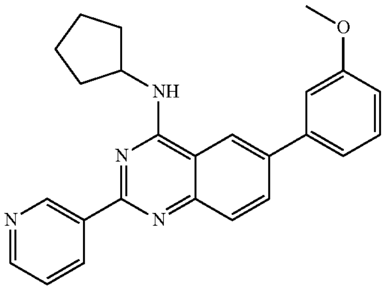 [SMILES: COc1cccc(-c2ccc3nc(-c4cccnc4)nc(NC4CCCC4)c3c2)c1] | 1H NMR (DMSO-d6) ppm 1.66-1.781 (m, 6H), 2.16-2.19 (m, 2H), 3.87 (s, 3H), 4.78 (br s, 1H), 7.00-7.55 (m, 5H), 7.83 (d, 1H, J = 8.6 Hz), 8.12 (d, 1H, J = 8.6 Hz), 8.29 (s, 1H), 8.67-8.77 (m, 3H), 9.62 (s, 1H) | DMSO |

TABLE 25-continued
| | | | | | | |
|---|---|---|---|---|---|---|
| 1643 | 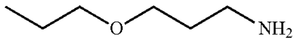 | 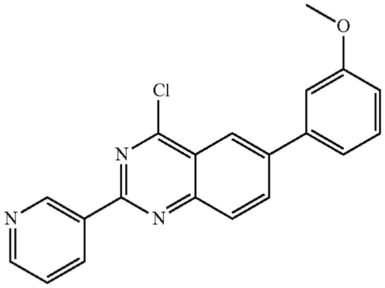 [SMILES: COc1cccc(-c2ccc3nc(-c4cccnc4)nc(Cl)c3c2)c1] | 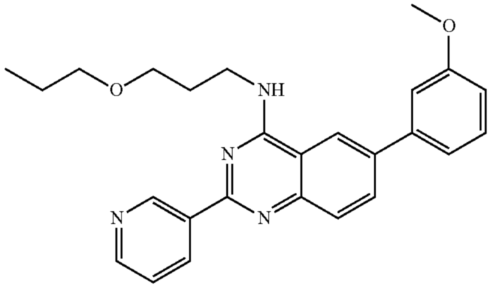 [SMILES: CCCOCCCNc1nc(-c2cccnc2)nc2ccc(-c3cccc(OC)c3)cc12] | HCl | 1H NMR (DMSO-d6) ppm 0.81 (t, 3H, J = 7.4 Hz), 1.47-1.54 (m, 2H), 2.00-2.05 (m, 2H), 3.32-3.37 (m, 4H), 3.86-3.91 (m, 5H), 7.03-7.80 (m, 5H), 8.16 (d, 1H, J = 8.7 Hz), 8.34 (d, 1H, J = 8.7 Hz), 8.86-8.96 (m, 3H), 9.61 (s, 1H), 10.03 (s, 1H) | DMSO |
| 1644 | 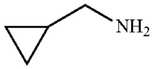 | 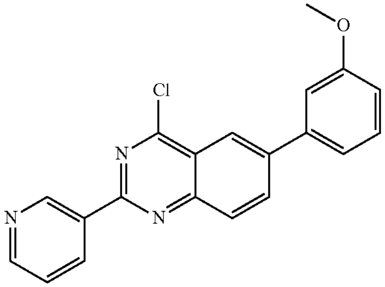 [SMILES: COc1cccc(-c2ccc3nc(-c4cccnc4)nc(Cl)c3c2)c1] | 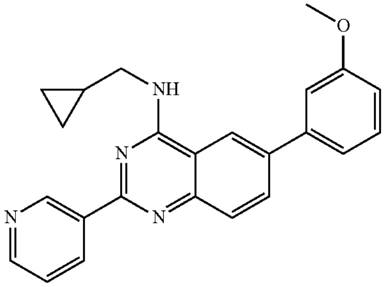 [SMILES: COc1cccc(-c2ccc3nc(-c4cccnc4)nc(NCC4CC4)c3c2)c1] | | 1H NMR (DMSO-d6) ppm 0.38-0.54 (m, 4H), 1.30-1.32 (m, 1H), 3.58-3.62 (m, 2H), 3.87 (s, 3H), 7.00-7.54 (m, 5H), 7.86 (d, 1H, J = 8.6 Hz), 8.14 (d, 1H, J = 8.6 Hz), 8.64-8.76 (m, 4H), 9.62 (s, 1H) | DMSO |

TABLE 25-continued
| | | | | | |
|---|---|---|---|---|---|
| 1645 | 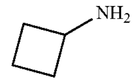 | 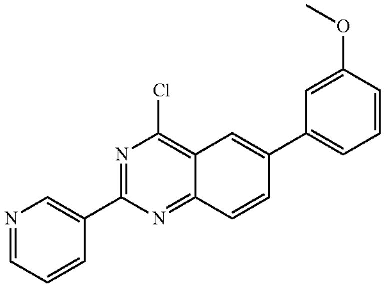 [SMILES: COc1cccc(-c2ccc3nc(-c4cccnc4)nc(Cl)c3c2)c1] | 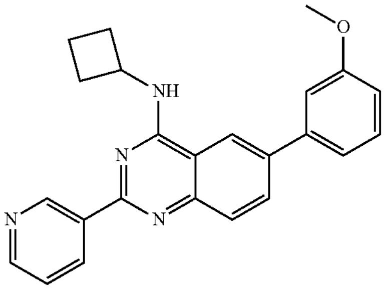 [SMILES: COc1cccc(-c2ccc3nc(-c4cccnc4)nc(NC4CCC4)c3c2)c1] | 1H NMR (DMSO-d6) ppm 1.83-1.88 (m, 2H), 2.21-2.27 (m, 2H), 2.43 (br s, 2H), 3.87 (s, 3H), 4.88-4.91 (m, 1H), 7.03-7.57 (m, 5H), 7.83 (d, 1H, J = 8.6 Hz), 8.13 (d, 1H, J = 8.6 Hz), 8.62-8.77 (m, 4H), 9.63 (s, 1H) | DMSO |
| 1646 | 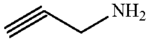 | 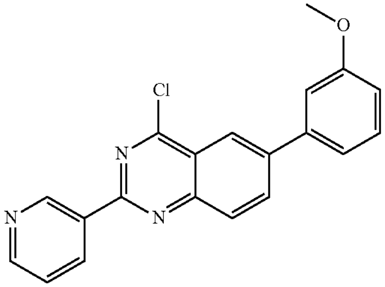 [SMILES: COc1cccc(-c2ccc3nc(-c4cccnc4)nc(Cl)c3c2)c1] | 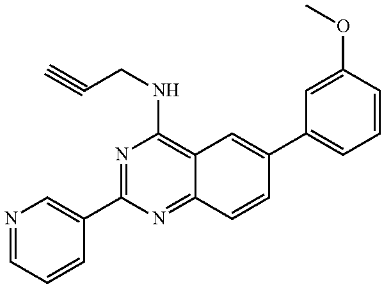 [SMILES: C#CCNc1nc(-c2cccnc2)nc2ccc(-c3cccc(OC)c3)cc12] | 1H NMR (DMSO-d6) ppm 3.21 (s, 1H), 3.88 (s, 3H), 4.52 (dd, 2H, J = 2.2, 5.2 Hz), 7.01-7.58 (m, 5H), 7.88 (d, 1H, J = 8.7 Hz), 8.19 (d, 1H, J = 8.6 Hz), 8.64-9.01 (m, 4H), 9.66 (s, 1H) | DMSO |

TABLE 25-continued
| | | | | | |
|---|---|---|---|---|---|
| 1647 | 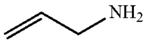 | 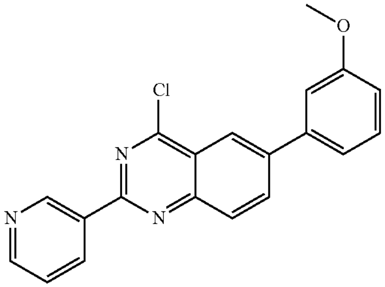 [SMILES: COc1cccc(-c2ccc3nc(-c4cccnc4)nc(Cl)c3c2)c1] | 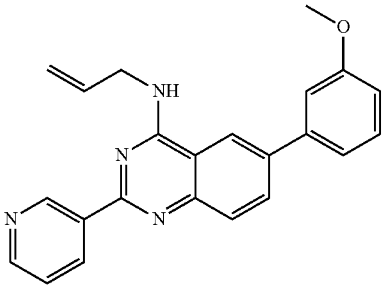 [SMILES: C=CCNc1nc(-c2cccnc2)nc2ccc(-c3cccc(OC)c3)cc12] | 1H NMR (DMSO-d6) ppm 3.87 (s, 3H), 4.37 (br s, 2H), 5.19 (dd, 1H, J = 1.5, 10.2 Hz), 5.31 (dd, 1H, J = 1.5, 17.2 Hz), 6.01-6.22 (m, 1H), 7.00-7.56 (m, 5H), 7.85 (d, 1H, J = 8.6 Hz), 8.16 (d, 1H, J = 8.6 Hz), 8.67-8.82 (m, 4H), 9.61 (s, 1H) | DMSO |
| 1648 | 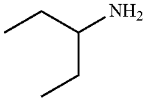 | 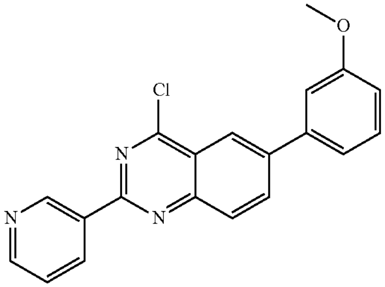 [SMILES: COc1cccc(-c2ccc3nc(-c4cccnc4)nc(Cl)c3c2)c1] | 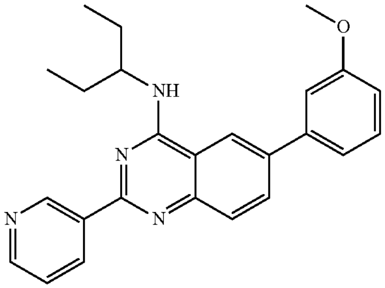 [SMILES: CCC(CC)Nc1nc(-c2cccnc2)nc2ccc(-c3cccc(OC)c3)cc12] | 1H NMR (DMSO-d6) ppm 0.94-0.99 (t, 6H, J = 7.4 Hz), 1.68-1.80 (m, 4H), 3.87 (s, 3H), 4.49-4.52 (m, 1H), 7.01-7.47 (m, 5H), 7.83 (d, 1H, J = 8.6 Hz), 8.11-8.15 (m, 2H), 8.67-8.75 (m, 3H), 9.63 (s, 1H) | DMSO |

TABLE 25-continued
| | | | | | |
|---|---|---|---|---|---|
| 1649 | 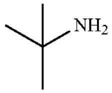 | 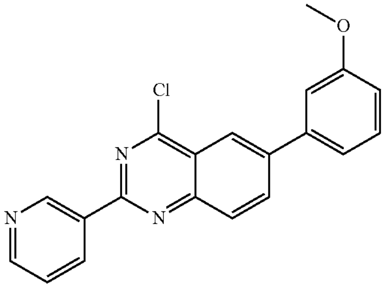 [SMILES: COc1cccc(-c2ccc3nc(-c4cccnc4)nc(Cl)c3c2)c1] | 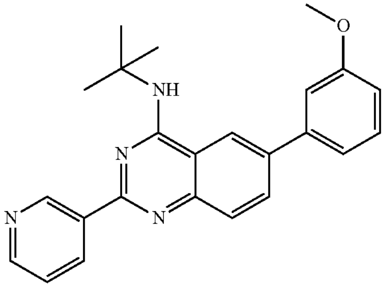 [SMILES: COc1cccc(-c2ccc3nc(-c4cccnc4)nc(NC(C)(C)C)c3c2)c1] | 1H NMR (DMSO-d6) ppm 1.68 (s, 9H), 3.87 (s, 3H), 7.01-7.70 (m, 6H), 7.82 (d, 1H, J = 8.6 Hz), 8.11 (d, 1H, J = 8.6 Hz), 8.67-8.74 (m, 3H), 9.60 (s, 1H) | DMSO |
| 1650 | 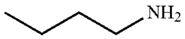 | 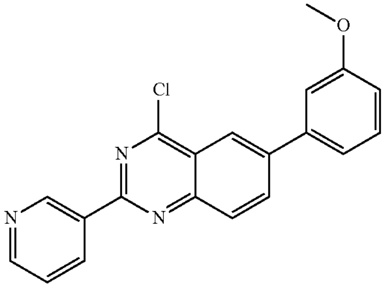 [SMILES: COc1cccc(-c2ccc3nc(-c4cccnc4)nc(Cl)c3c2)c1] | 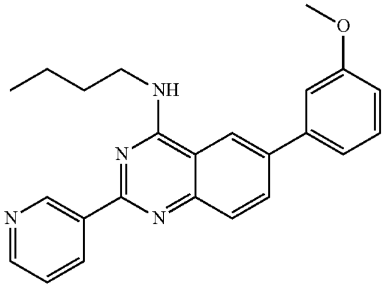 [SMILES: CCCCNc1nc(-c2cccnc2)nc2ccc(-c3cccc(OC)c3)cc12] | 1H NMR (DMSO-d6) ppm 0.97 (t, 3H, J = 7.2 Hz), 1.44-1.48 (m, 2H), 1.74-1.78 (m, 2H), 3.71-3.75 (m, 2H), 3.89 (s, 3H), 7.00-7.56 (m, 5H), 7.83 (d, 1H, J = 8.6 Hz), 8.15 (d, 1H, J = 8.6 Hz), 8.59-8.76 (m, 4H), 9.62 (s, 1H) | DMSO |

TABLE 25-continued
| | | | | | |
|---|---|---|---|---|---|
| 1651 | 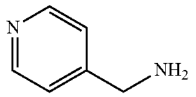 | 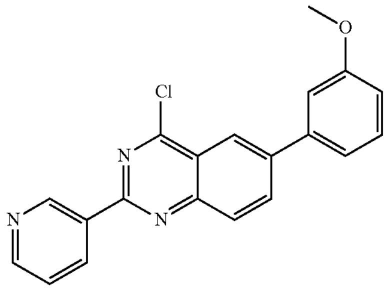 [SMILES: COc1cccc(-c2ccc3nc(-c4cccnc4)nc(Cl)c3c2)c1] | 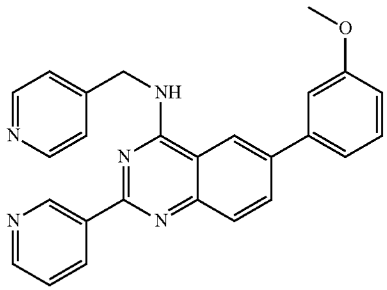 [SMILES: COc1cccc(-c2ccc3nc(-c4cccnc4)nc(NCc4ccncc4)c3c2)c1] | 1H NMR (DMSO-d6) ppm 3.87 (s, 3H), 4.98 (d, 2H, J = 5.6 Hz), 7.02-7.46 (m, 7H), 7.87 (d, 1H, J = 8.7 Hz), 8.51 (dd, 1H, J = 1.5, 4.5 Hz), 8.50-8.71 (m, 5H), 9.26 (s, 1H), 9.48 (s, 1H) | DMSO |
| 1652 | 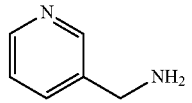 | 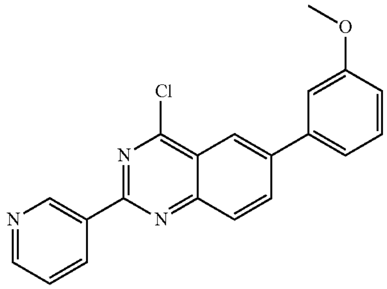 [SMILES: COc1cccc(-c2ccc3nc(-c4cccnc4)nc(Cl)c3c2)c1] | 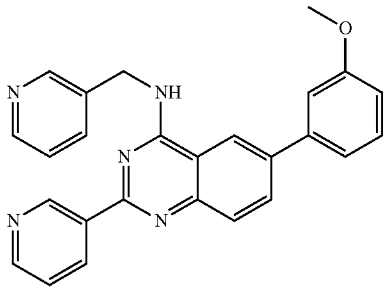 | 1H NMR (DMSO-d6) ppm 3.87 (s, 3H), 4.93 (d, 2H, J = 5.5 Hz), 7.00-7.46 (m, 6H), 7.86-7.90 (m, 2H), 8.16 (d, 1H, J = 1.7 Hz), 8.46 (d, 1H, J = 1.7 Hz), 8.66-8.76 (m, 4H), 9.22 (s, 1H), 9.56 (s, 1H) | DMSO |

TABLE 25-continued
| | | | | | |
|---|---|---|---|---|---|
| 1653 | 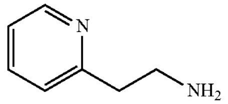 | 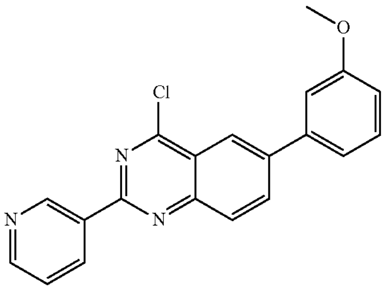 [SMILES: COc1cccc(-c2ccc3nc(-c4cccnc4)nc(Cl)c3c2)c1] | 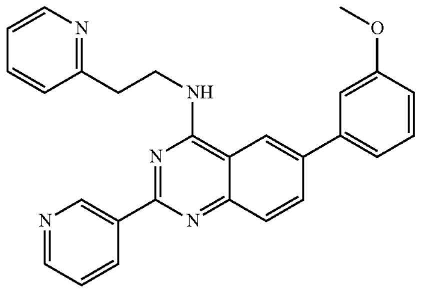 [SMILES: COc1cccc(-c2ccc3nc(-c4cccnc4)nc(NCCc4ccccn4)c3c2)c1] | 1H NMR (DMSO-d6) ppm 3.22-3.27 (m, 2H), 3.87 (s, 3H). 4.04-4.11 (m, 2H), 7.02-7.46 (m, 8H), 7.83 (d, 1H, J = 8.6 Hz), 8.13 (d, 1H, J = 1.6 Hz), 8.67-8.78 (m, 5H), 9.64 (s, 1H) | DMSO |
| 1654 | 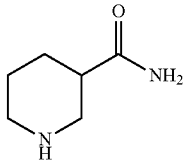 | 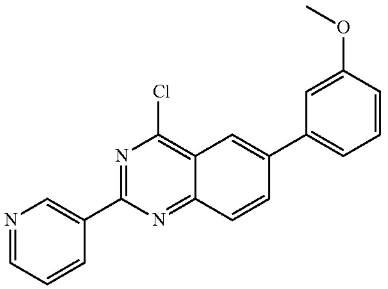 [SMILES: COc1cccc(-c2ccc3nc(-c4cccnc4)nc(Cl)c3c2)c1] | 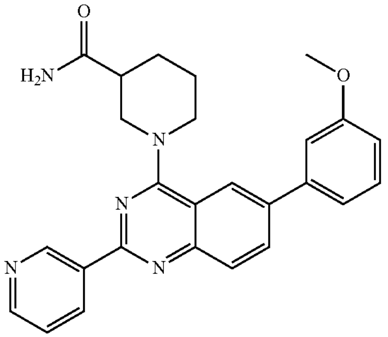 [SMILES: COc1cccc(-c2ccc3nc(-c4cccnc4)nc(N4CCCC(C(N)=O)C4)c3c2)c1] | 1H NMR (DMSO-d6) ppm 1.76-1.88 (m, 4H), 2.66 (br s, 1H), 3.37-3.48 (m, 2H), 3.86 (s, 3H), 4.39-4.47 (m, 2H), 6.95-7.57 (m, 7H), 7.95 (d, 1H, J = 8.7 Hz), 8.15-8.19 (m, 2H), 8.69-8.76 (m, 2H), 9,61 (s, 1H) | DMSO |

TABLE 25-continued
| | | | | | |
|---|---|---|---|---|---|
| 1655 | 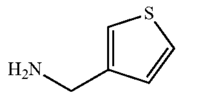 | 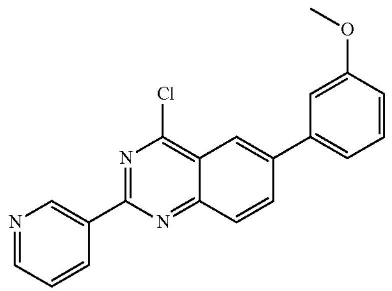 [SMILES: COc1cccc(-c2ccc3nc(-c4cccnc4)nc(Cl)c3c2)c1] | 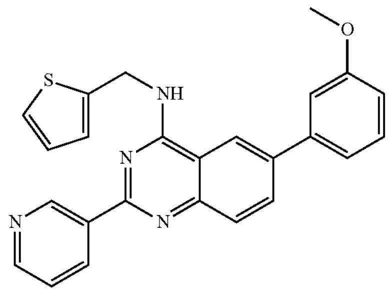 [SMILES: COc1cccc(-c2ccc3nc(-c4cccnc4)nc(NCc4cccs4)c3c2)c1] | $^1$H NMR (DMSO-$d_6$) ppm 3.87 (s, 3H), 4.97 (d, 2H, J = 5.6 Hz), 7.00-7.50 (m, 8H), 7.85 (d, 1H, J = 8.7 Hz), 8.16 (s, 1H), 8.66-8.77 (m, 3H), 9.11 (s, 1H), 9.61 (s, 1H) | DMSO |
| 1656 | 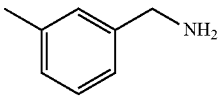 | 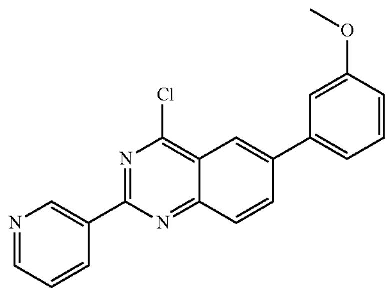 [SMILES: COc1cccc(-c2ccc3nc(-c4cccnc4)nc(Cl)c3c2)c1] | 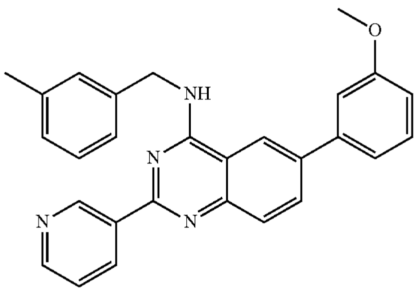 [SMILES: COc1cccc(-c2ccc3nc(-c4cccnc4)nc(NCc4cccc(C)c4)c3c2)c1] | $^1$H NMR (DMSO-$d_6$) ppm 2.28 (s, 3H), 3.87 (s, 3H), 4.91 (d, 2H, J = 5.5 Hz), 7.00-7.52 (m, 9H), 7.86 (d, 1H, J = 8.6 Hz), 8.17 (dd, 1H, J = 8.6, 1.8 Hz), 8.66-9.16 (m, 3H), 9.18-9.16 (m, 1H), 9.57 (s, 1H) | DMSO |

TABLE 25-continued
| | | | | | |
|---|---|---|---|---|---|
| 1657 | 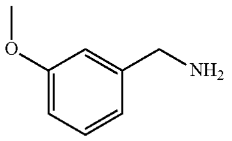 | 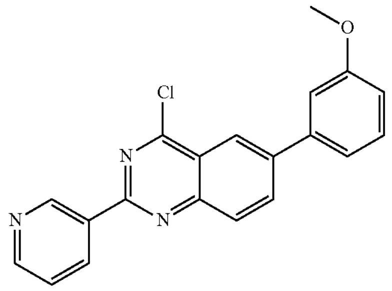 [SMILES: COc1cccc(-c2ccc3nc(-c4cccnc4)nc(Cl)c3c2)c1] | 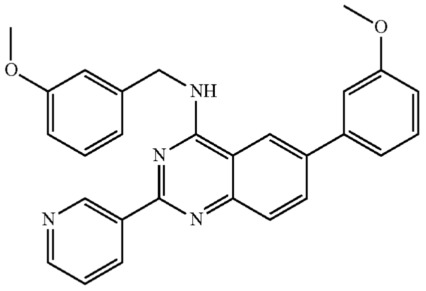 [SMILES: COc1cccc(CNc2nc(-c3cccnc3)nc3ccc(-c4cccc(OC)c4)cc23)c1] | $^1$H NMR (DMSO-$d_6$) ppm 3.71 (s, 3H), 3.87 (s, 3H), 4.91 (d, 2H, J = 5.7 Hz), 6.82-7.52 (m, 9H), 7.86 (d, 1H, J = 8.7 Hz), 8.17 (dd, 1H, J = 8.7, 1.8 Hz), 8.66-9.15 (m, 3H), 9.17-9.19 (m, 1H), 9.57 (s, 1H) | DMSO |
| 1658 | 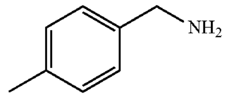 | 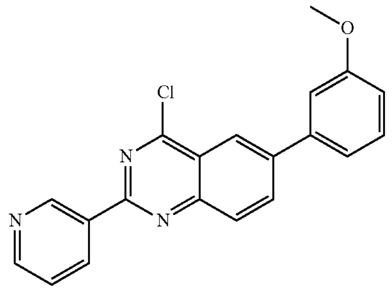 [SMILES: COc1cccc(-c2ccc3nc(-c4cccnc4)nc(Cl)c3c2)c1] | 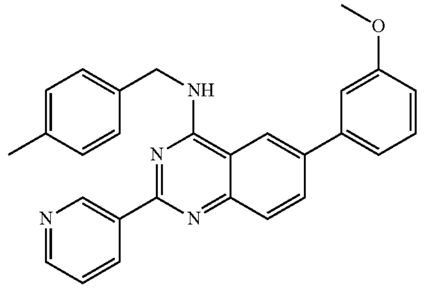 [SMILES: COc1cccc(-c2ccc3nc(-c4cccnc4)nc(NCc4ccc(C)cc4)c3c2)c1] | $^1$H NMR (DMSO-$d_6$) ppm 2.25 (s, 3H), 3.87 (s, 3H), 4.91 (d, 2H, J = 5.7 Hz), 7.00-7.53 (m, 9H), 7.86 (d, 1H, J = 8.6 Hz), 8.17 (dd, 1H, J = 8.6, 1.8 Hz), 8.66-9.15 (m, 3H), 9.17-9.19 (m, 1H), 9.57 (s, 1H) | DMSO |

TABLE 25-continued
| | | | | | |
|---|---|---|---|---|---|
| 1659 | 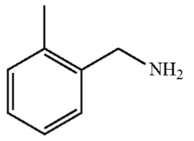 | 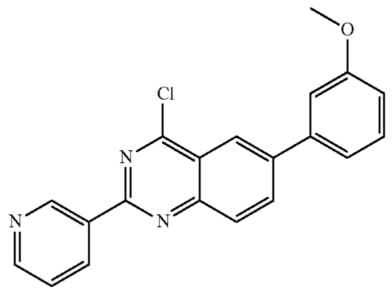 [SMILES: COc1cccc(-c2ccc3nc(-c4cccnc4)nc(Cl)c3c2)c1] | 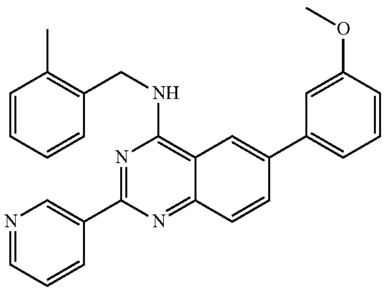 [SMILES: COc1cccc(-c2ccc3nc(-c4cccnc4)nc(NCc4ccccc4C)c3c2)c1] | $^1H$ NMR (DMSO-$d_6$) ppm 2.44 (s, 3H), 3.86 (s, 3H), 4.95 (d, 2H, J = 5.7 Hz), 7.01-7.53 (m, 9H), 7.86 (d, 1H, J = 8.6 Hz), 8.17 (dd, 1H, J = 8.6, 1.8 Hz), 8.65-9.02 (m, 3H), 9.50-9.52 (m, 1H), 9.54 (s, 1H) | DMSO |
| 1660 | 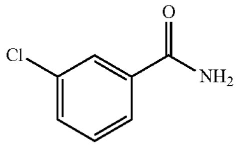 | 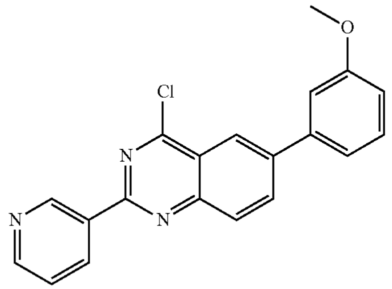 [SMILES: COc1cccc(-c2ccc3nc(-c4cccnc4)nc(Cl)c3c2)c1] | 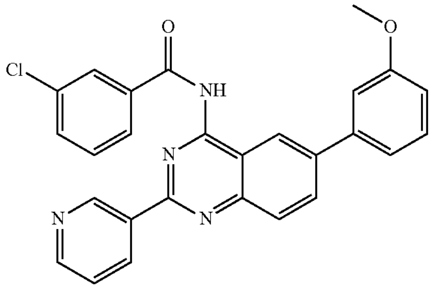 [SMILES: COc1cccc(-c2ccc3nc(-c4cccnc4)nc(NC(=O)c4cccc(Cl)c4)c3c2)c1] | $^1H$ NMR (DMSO-$d_6$) ppm 3.87 (s, 3H), 7.03 (s, 1H), 7.44-7.94 (m, 10H), 8.07-8.70 (m, 4H), 9.41 (s, 1H) | DMSO |

TABLE 25-continued
| | | | | | |
|---|---|---|---|---|---|
| 1661 | 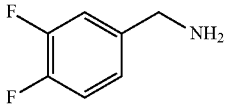 | 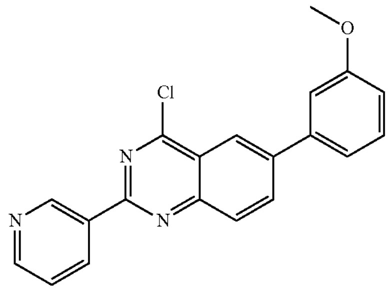 [SMILES: COc1cccc(-c2ccc3nc(-c4cccnc4)nc(Cl)c3c2)c1] | 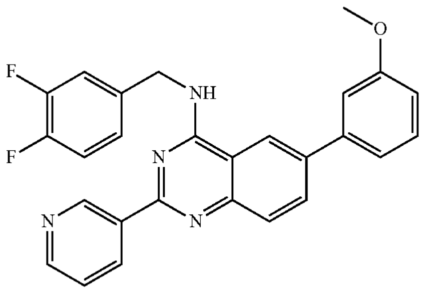 | $^1H$ NMR (DMSO-$d_6$) ppm 3.87 (s, 3H), 4.91 (d, 2H, J = 5.5 Hz), 7.00-7.04 (m, 1H), 7.04-7.55 (m, 7H), 7.87 (d, 1H, J = 8.6 Hz), 8.18 (dd, 1H, J = 8.6, 1.8 Hz), 8.66-9.18 (m, 3H), 9.18-9.21 (m, 1H), 9.55 (s, 1H) | DMSO |
| 1662 | 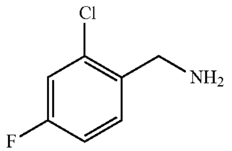 | 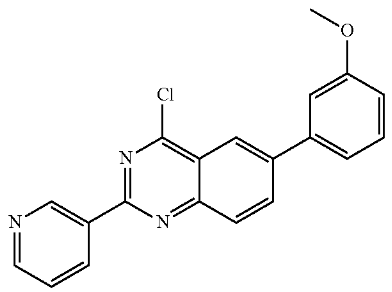 [SMILES: COc1cccc(-c2ccc3nc(-c4cccnc4)nc(Cl)c3c2)c1] | 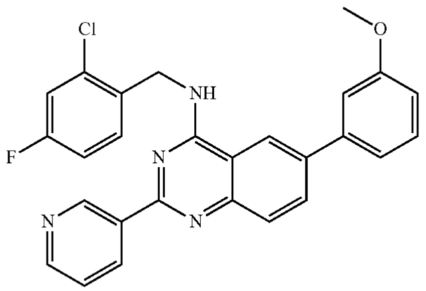 [SMILES: COc1cccc(-c2ccc3nc(-c4cccnc4)nc(NCc4ccc(F)cc4Cl)c3c2)c1] | $^1H$ NMR (DMSO-$d_6$) ppm 3.87 (s, 3H), 4.99 (d, 2H, J = 5.5 Hz), 7.01-7.05 (m, 2H), 7.15-7.56 (m, 6H), 7.88 (d, 1H, J = 8.6 Hz), 8.20 (dd, 1H, J = 8.6, 1.8 Hz), 8.64-9.18 (m, 3H), 9.19-9.21 (m, 1H), 9.50 (s, 1H) | DMSO |

TABLE 25-continued
| | | | | | |
|---|---|---|---|---|---|
| 1663 | 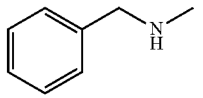 | 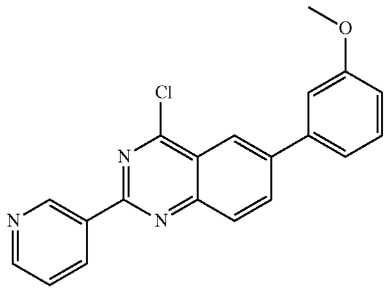 [SMILES: COc1cccc(-c2ccc3nc(-c4cccnc4)nc(Cl)c3c2)c1] | 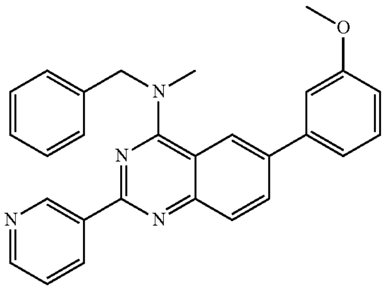 [SMILES: COc1cccc(-c2ccc3nc(-c4cccnc4)nc(N(C)Cc4ccccc4)c3c2)c1] | $^1H$ NMR (DMSO-$d_6$) ppm 3.49 (s, 3H), 3.74 (s, 3H), 5.15 (s, 2H), 6.90 (d, J = 8.2 Hz, 1H), 7.04-7.29 (m, 2H), 7 33-7.54 (m, 7H), 7.93 (d, 1H, J = 8.6 Hz), 8.15 (dd, 1H, J = 8.6, 1.8 Hz), 8.21 (s, 1H), 8.68-8.75 (m, 2H), 9.59 (s, 1H) | DMSO |
| 1664 | 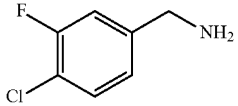 | 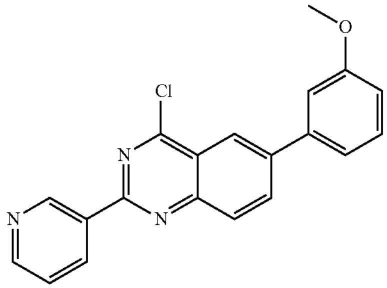 [SMILES: COc1cccc(-c2ccc3nc(-c4cccnc4)nc(Cl)c3c2)c1] | 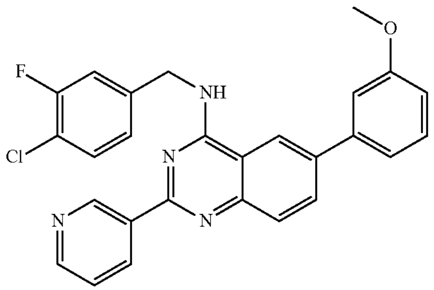 | $^1H$ NMR (DMSO-$d_6$) ppm 3.87 (s, 3H), 4.94 (d, 2H, J = 5.5 Hz), 7.01-7.03 (m, 1H), 7.35-7.57 (m, 7H), 7.88 (d, 1H, J = 8.6 Hz), 8.20 (dd, 1H, J = 8.6, 1.8 Hz), 8.66-9.22 (m, 3H), 9.19-9.21 (m, 1H), 9.50 (s, 1H) | DMSO |

TABLE 25-continued
| | | | | | |
|---|---|---|---|---|---|
| 1665 | 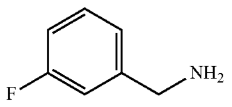 | 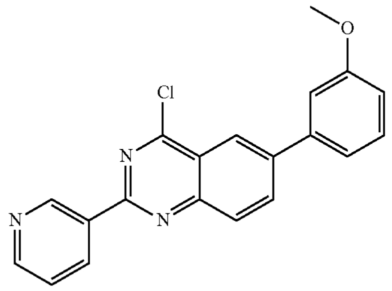 [SMILES: COc1cccc(-c2ccc3nc(-c4cccnc4)nc(Cl)c3c2)c1] | 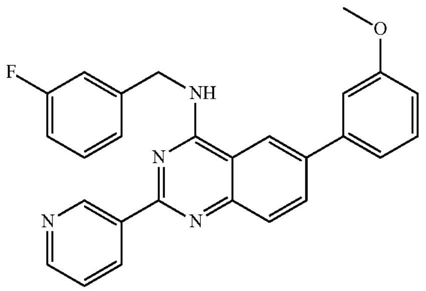 [SMILES: COc1cccc(-c2ccc3nc(-c4cccnc4)nc(NCc4cccc(F)c4)c3c2)c1] | $^1$H NMR (DMSO-$d_6$) ppm 3.87 (s, 3H), 4.96 (d, 2H, J = 5.5 Hz), 7.00-7.03 (m, 2H), 7.33-7.52 (m, 7H), 7.88 (d, 1H, J = 8.6 Hz), 8.19 (dd, 1H, J = 8.6, 1.8 Hz), 8.65-9.20 (m, 3H), 9.19-9.21 (m, 1H), 9.54 (s, 1H) | DMSO |
| 1666 | 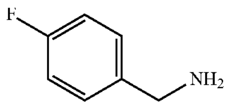 | 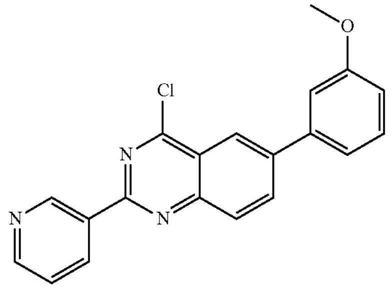 [SMILES: COc1cccc(-c2ccc3nc(-c4cccnc4)nc(Cl)c3c2)c1] | 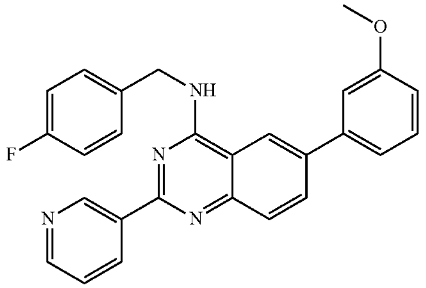 [SMILES: COc1cccc(-c2ccc3nc(-c4cccnc4)nc(NCc4ccc(F)cc4)c3c2)c1] | $^1$H NMR (DMSO-$d_6$) ppm 3.87 (s, 3H), 4.93 (d, 2H, J = 5.5 Hz), 7.00-7.19 (m, 3H), 7.41-7.55 (m, 6H), 7.88 (d, 1H, J = 8.6 Hz), 8.17 (dd, 1H, J = 8.6, 1.8 Hz), 8.65-9.18 (m, 3H), 9.13-9.21 (m, 1H), 9.57 (s, 1H) | DMSO |

TABLE 25-continued
| | | | | | |
|---|---|---|---|---|---|
| 1667 | 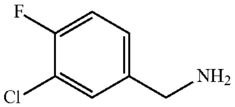 | 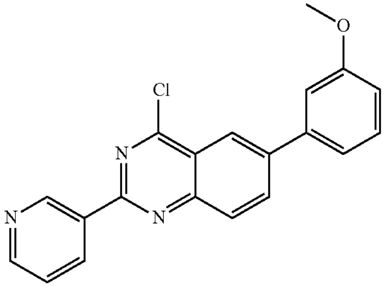 [SMILES: COc1cccc(-c2ccc3nc(-c4cccnc4)nc(Cl)c3c2)c1] | 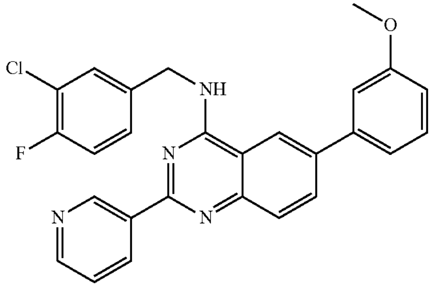 [SMILES: COc1cccc(-c2ccc3nc(-c4cccnc4)nc(NCc4ccc(F)c(Cl)c4)c3c2)c1] | $^1$H NMR (DMSO-$d_6$) ppm 3.87 (s, 3H), 4.92 (d, 2H, J = 5.5 Hz), 7.01-7.03 (d, 1H, J = 7.0 Hz), 7.37-7.53 (m, 6H), 7.72 (d, 1H, J = 8.6 Hz), 8.18 (dd, 1H, J = 8.6, 1.8 Hz), 8.66-9.19 (m, 3H), 9.20-9.23 (m, 1H), 9.56 (s, 1H) | DMSO |
| 1668 | 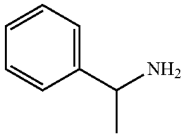 | 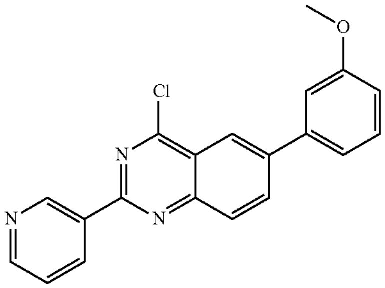 [SMILES: COc1cccc(-c2ccc3nc(-c4cccnc4)nc(Cl)c3c2)c1] | 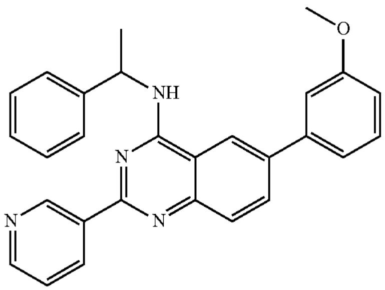 | $^1$H NMR (DMSO-$d_6$) ppm 1.68 (d, 3H, J = 7.0 Hz), 3.87 (s, 3H), 4.92 (d, 2H, J = 5.5 Hz), 5.75-5.78 (m, 1H), 7.02 (d, 1H, J = 7.0 Hz), 7.32-7.56 (m, 9H), 7.84 (d, 1H, J = 8.6 Hz), 8.15 (dd, 1H, J = 8.6, 1.8 Hz), 8.64-8.84 (m, 4H), 9.51 (s, 1H) | DMSO |

TABLE 25-continued
| | | | | | |
|---|---|---|---|---|---|
| 1669 | 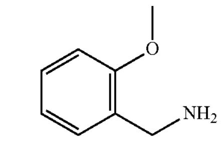 | 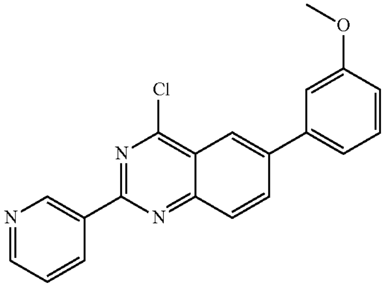 [SMILES: COc1cccc(-c2ccc3nc(-c4cccnc4)nc(Cl)c3c2)c1] | 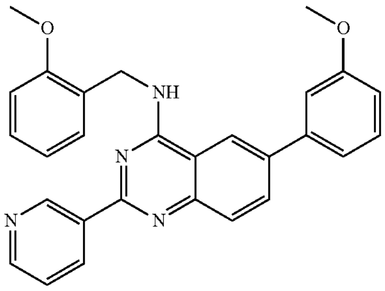 [SMILES: COc1cccc(-c2ccc3nc(-c4cccnc4)nc(NCc4ccccc4OC)c3c2)c1] | $^1H$ NMR (DMSO-$d_6$) ppm 3.70 (s, 3H), 3.86 (s, 3H), 4.92 (d, J = 5.1 Hz, 2H), 6.89-7.01 (m, 3H), 7.41-7.54 (m, 6H), 7.85 (d, J = 8.6 Hz, 1H), 7.85 (d, J = 8.6 Hz, 1H), 8.67-8.75 (m, 3H), 9.19 (s, 1H), 9.56 (s, 1H) | DMSO |
| 1670 | 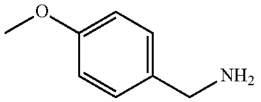 | 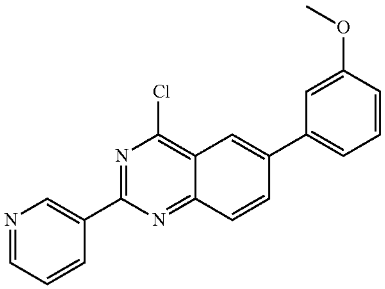 [SMILES: COc1cccc(-c2ccc3nc(-c4cccnc4)nc(Cl)c3c2)c1] | 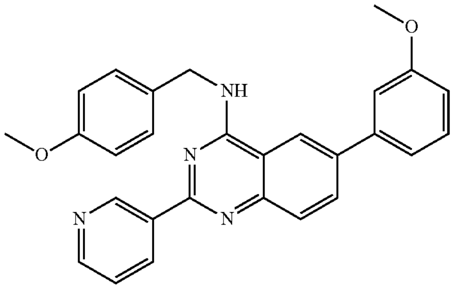 [SMILES: COc1ccc(CNc2nc(-c3cccnc3)nc3ccc(-c4cccc(OC)c4)cc23)cc1] | $^1H$ NMR (DMSO-$d_6$) ppm 3.87 (s, 3H), 3.91 (s, 3H), 4.92 (d, J = 5.0 Hz, 2H), 6.87-7.52 (m, 9H), 7.85 (d, J = 8.5 Hz, 1H), 8.17 (d, J = 8.5 Hz, 1H), 8.64-8.73 (m, 3H), 9.05 (s, 1H), 9.52 (s, 1H) | DMSO |

TABLE 25-continued
| | | | | | |
|---|---|---|---|---|---|
| 1671 | 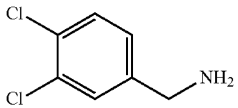 | 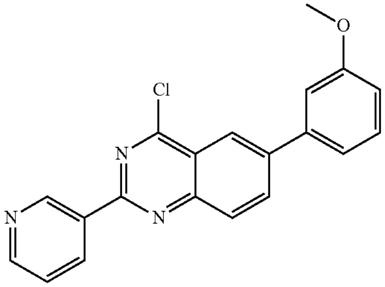 [SMILES: COc1cccc(-c2ccc3nc(-c4cccnc4)nc(Cl)c3c2)c1] | 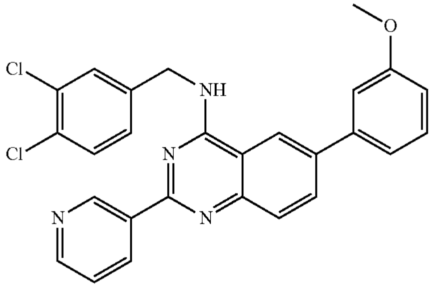 | $^1$H NMR (DMSO-$d_6$) ppm 3.87 (s, 3H), 4.93 (d, J = 5.6 Hz, 2H), 7.02 (s, 1H), 7.41-7.61 (m, 7H), 7.83 (d, J = 8.9 Hz, 1H), 8.18 (d, J = 8.9 Hz, 1H), 8.66-8.71 (m, 3H), 9.21 (s, 1H), 9.54 (s, 1H) | DMSO |
| 1672 | 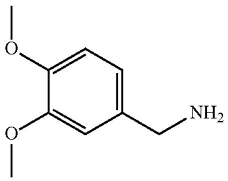 | 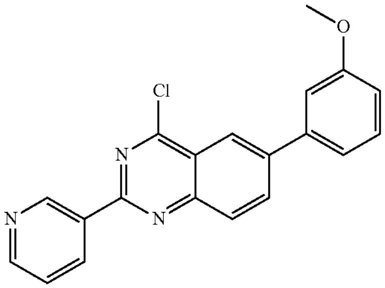 [SMILES: COc1cccc(-c2ccc3nc(-c4cccnc4)nc(Cl)c3c2)c1] | 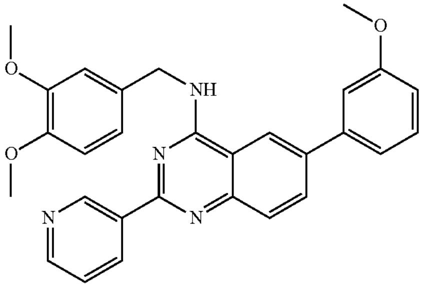 [SMILES: COc1cccc(-c2ccc3nc(-c4cccnc4)nc(NCc4ccc(OC)c(OC)c4)c3c2)c1] | $^1$H NMR (DMSO-$d_6$) ppm 3.69 (s, 6H), 3.87 (s, 3H), 4.93 (d, J = 5.6 Hz, 2H), 6.90 (s, 1H), 7.00-7.54 (m, 7H), 7.85 (d, J = 8.6 Hz, 1H), 8.17 (d, J = 8.6 Hz, 1H), 8.66-8.78 (m, 3H), 9.14 (s, 1H), 9.63 (s, 1H) | DMSO |

TABLE 25-continued
| | | | | |
|---|---|---|---|---|
| 1673 | 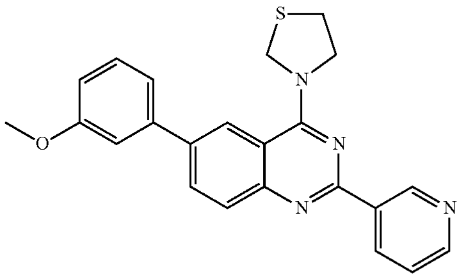 [SMILES: COc1cccc(-c2ccc3nc(-c4cccnc4)nc(N4CCSC4)c3c2)c1] | | — | DMSO |
| 1674 | 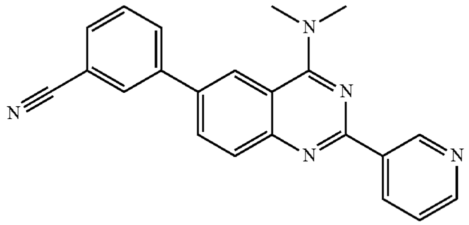 [SMILES: CN(C)c1nc(-c2cccnc2)nc2ccc(-c3cccc(C#N)c3)cc12] | 2HCl | 1H—NMR (300 MHz, DMSO): δ 9.71 (d, J = 1.6 Hz, 1H), 9.16 (d, J = 8.2 Hz, 1H), 8.98 (dd, J = 5.1, 1,5 Hz, 1H), 8.58 (s, 1H), 8 48-8.34 (m, 3H), 8.20 (ds J = 8.0 Hz, 1H), 7.98-7.87 (m, 2H), 7.75 (t, J = 7.8 Hz, 1H), 3.73 (s, 6H). | DMSO |

TABLE 25-continued
| | | | |
|---|---|---|---|
| 1675 | 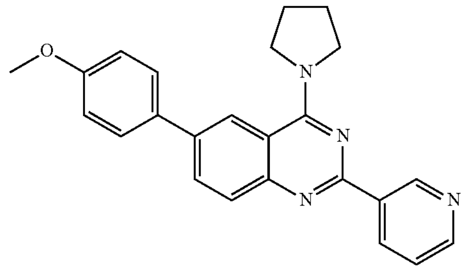 [SMILES: COc1ccc(-c2ccc3nc(-c4cccnc4)nc(N4CCCC4)c3c2)cc1] | 1H—NMR (300 MHz, DMSO): δ 9.59 (s, 1H), 8.78-8.62 (m, 2H), 8.38 (s, 1H), 8.05 (dd, J = 8.6, 1.3 Hz, 1H), 7.34 (d, J = 8.7 Hz, 1H), 7.73 (d, J = 8.7 Hz, 2H), 7.52 (dd, J = 7.8, 4.7 Hz, 1H), 7.07 (d, J = 8.8 Hz, 2H), 4.04 (s, 4H), 3.82 (s, 3H), 2.02 (3, 4H). | DMSO |

TABLE 25-continued
| | | | | |
|---|---|---|---|---|
| 1676 | 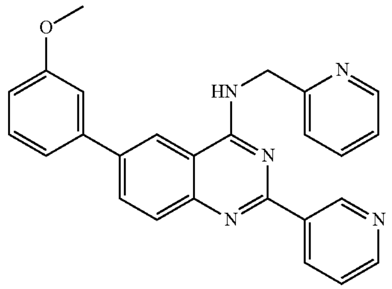 [SMILES: COc1cccc(-c2ccc3nc(-c4cccnc4)nc(NCc4ccccn4)c3c2)c1] | 3HCl | 1H—NMR (300 MHz, DMSO): δ 10.40 (s, 1H), 9.48 (d, J = 2.0 Hz, 1H), 8.95 (s, 2H), 3.88 (d, J = 5.2 Hz, 1H), 8.72 (d, J = 4.3 Hz, 1H), 8.35 (d, J = 8.9 Hz, 1H), 8.18 (s, 1H), 8.08 (d, J = 8.8 Hz, 1H), 7.94-7.81 (m, 2H), 7.64 (s, 1H), 7.54-7.45 (m, 3H), 7.06-7.00 (m, 1H), 5.25 (d, J = 5.1 Hz, 2H), 3.88 (s, 3H). | DMSO |

TABLE 25-continued
| | | | |
|---|---|---|---|
| 1677 | 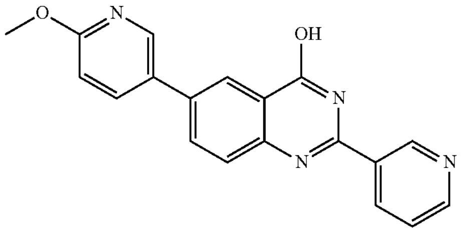 [SMILES: COc1ccc(-c2ccc3nc(-c4cccnc4)nc(O)c3c2)cn1] | 1H—NMR (300 MHz, DMSO): δ 12.83 (s, 1H), 9.32 (d, J = 2.2 Hz, 1H), 8.77 (dd, J = 4.8, 1.5 Hz, 1H), 8.63 (d, J = 2.5 Hz, 1H), 8.56-8.49 (m, 1H), 8.37 (d, J = 2.2 Hz, 1H), 8.23-8.14 (m, 2H), 7.85 (d, J = 8.5 Hz, 1H), 7.60 (dd, J = 3.0, 4.8 Hz, 1H), 6.96 (d, J = 8.7 Hz, 1H), 3.92 (s, 3H). | DMSO |

TABLE 25-continued
| | | | | | |
|---|---|---|---|---|---|
| 1678 | NH3 | 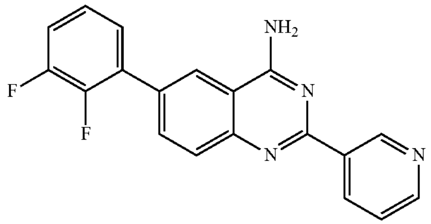 [SMILES: Nc1nc(-c2cccnc2)nc2ccc(-c3cccc(F)c3F)cc12] | 2HCl | 1H NMR (300 MHz, DMSO) δ 9.79 (brs, 1H), 9,60 (s, 2H), 9.07 (d, J = 7.4 Hz, 1H), 9.00 (d, J = 4.5 Hz, 1H), 8.80 (s, 1H), 3.35 (d, J = 8.7 Hz, 1H), 8.26 (d, J = 8.6 Hz, 1H), 8.02-7.88 (m, 1H), 7.67-7.48 (m, 2H), 7.43-7.37 (m, 1H). | DMSO |
| Number | Purity percent | Method of Coupling |
|---|---|---|
| 1634 | >98 | Method AQ3, F5, G2 (reflux) |
| 1635 | >98 | Method AQ3, F5, G2 (reflux) |
| 1636 | >98 | Method AQ3, F5, G2 (reflux) |

TABLE 25-continued

| | | |
|---|---|---|
| 1637 | >98 | Method AQ3, F5, G2 (reflux) |
| 1638 | >98 | Method AQ3, F5, G2 (reflux) |
| 1639 | >98 | Method AQ3, F5, G2 (reflux) |
| 1640 | >98 | Method AQ3, F5, G2 (reflux) |
| 1641 | >98 | Method AQ3, F5, G2 (reflux) |
| 1642 | >98 | Method AQ3, F5, G2 (reflux) |
| 1643 | >98 | Method AQ3, F5, G2 (reflux) |

TABLE 25-continued

| | | | |
|---|---|---|---|
| | 1644 | >98 | Method AQ3, F5, G2 (reflux) |
| | 1645 | >98 | Method AQ3, F5, G2 (reflux) |
| | 1646 | >98 | Method AQ3, F5, G2 (reflux) |
| | 1647 | >98 | Method AQ3, F5, G2 (reflux) |
| | 1648 | >98 | Method AQ3, F5, G2 (reflux) |
| | 1649 | >98 | Method AQ3, F5, G2 (reflux) |
| | 1650 | >98 | Method AQ3, F5, G2 (reflux) |

TABLE 25-continued

| | | |
|---|---|---|
| 1651 | >98 | Method AQ3, F5, G2 (reflux) |
| 1652 | >98 | Method AQ3, F5, G2 (reflux) |
| 1653 | >98 | Method AQ3, F5, G2 (reflux) |
| 1654 | >98 | Method AQ3, F5, G2 (reflux) |
| 1655 | >98 | Method AQ3, F5, G2 (reflux) |
| 1656 | >98 | Method AQ3, F5, G2 (reflux) |
| 1657 | >98 | Method AQ3, F5, G2 (reflux) |

TABLE 25-continued

| | | | |
|---|---|---|---|
| | 1658 | >98 | Method AQ3, F5, G2 (reflux) |
| | 1659 | >98 | Method AQ3, F5, G2 (reflux) |
| | 1660 | >98 | Method AQ3, F5, G2 (reflux) |
| | 1661 | >98 | Method AQ3, F5, G2 (reflux) |
| | 1662 | >98 | Method AQ3, F5, G2 (reflux) |
| | 1663 | >98 | Method AQ3, F5, G2 (reflux) |
| | 1664 | >98 | Method AQ3, F5, G2 (reflux) |

TABLE 25-continued

| | | | |
|---|---|---|---|
| | 1665 | >98 | Method AQ3, F5, G2 (reflux) |
| | 1666 | >98 | Method AQ3, F5, G2 (reflux) |
| | 1667 | >98 | Method AQ3, F5, G2 (reflux) |
| | 1668 | >98 | Method AQ3, F5, G2 (reflux) |
| | 1669 | >98 | Method AQ3, F5, G2 (reflux) |
| | 1670 | >98 | Method AQ3, F5, G2 (reflux) |
| | 1671 | >98 | Method AQ3, F5, G2 (reflux) |

TABLE 25-continued

| | | |
|---|---|---|
| 1672 | >98 | Method AQ3, F5, G2 (reflux) |
| 1673 | 95 | Method AQ3, AP |
| 1674 | 95 | Method AQ3, AP |
| 1675 | 95 | Method AQ3, AP |
| 1676 | 95 | Method AQ3, AP |
| 1677 | 95 | Method AQ3, AP |
| 1678 | >98 | Method AQ3, F5, G2 (reflux) |

Scheme 78: General route for the synthesis of compounds with general formula lxiii

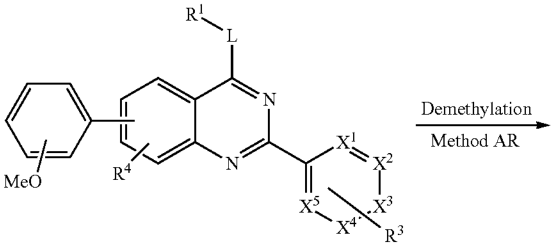

lviii

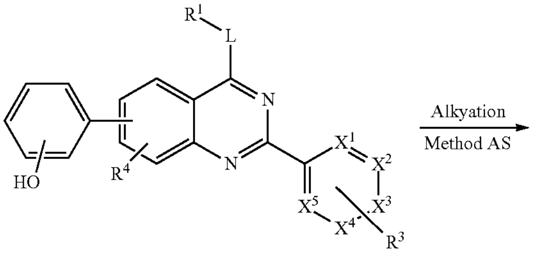

lxi

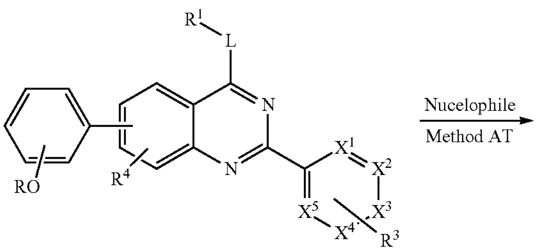

lxii

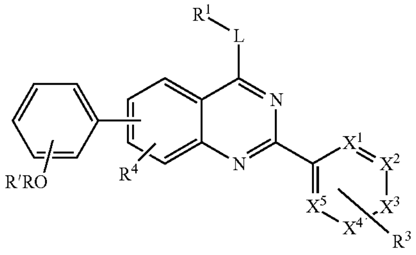

lxiii $X^1$, $X^2$, $X^3$, $X^4$ or $X^5$ = CH or N, at least one $X^1$, $X^2$, $X^3$, $X^4$ or $X^5$ must be N Method AT for Alkylation:

Method AT1: NaOMe/MeOH/microwave/150° C.

Method AT2: MeOH/microwave/150° C.

Method AT3: DIPEA/KI/DMF/microwave/150° C.

Scheme 79: Representative synthesis of compounds of formula lxiii (see Scheme 76)

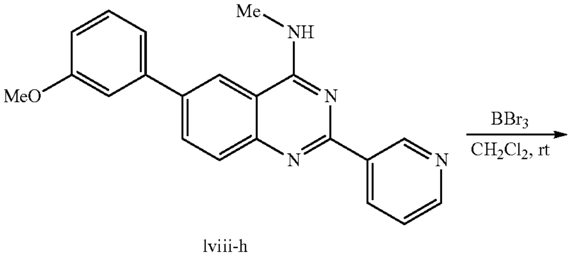

lviii-h

-continued

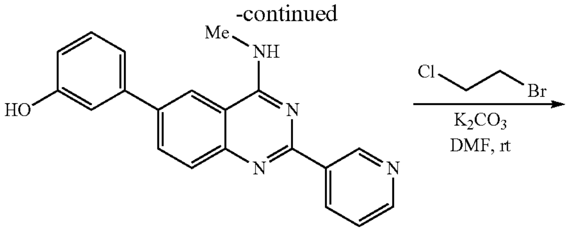

lxi-a

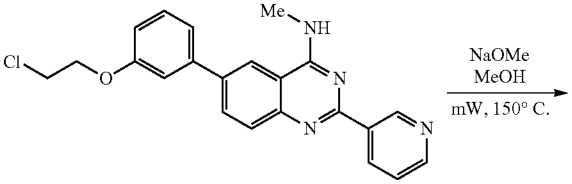

lxii-a

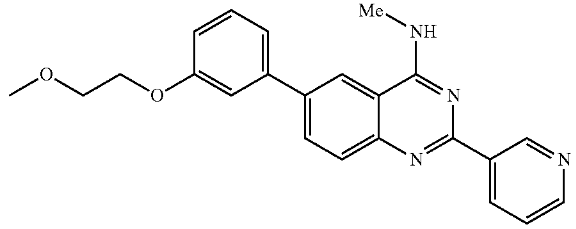

lxiii-a

Method AR: 3-(4-(methylamino)-2-(pyridin-3-yl) quinazolin-6-yl)phenol (lxi-a)

To a suspension of 6-(3-methoxyphenyl)-N-methyl-2-(pyridin-3-yl)quinazolin-4-amine (prepared in a similar method described for 6-(3-methoxy phenyl)-2-(pyridine-3-yl)-4-(pyrrolidin-1-yl)quinazoline using Scheme 74, substituting N-methylamine for pyrrolidine) (1.00 g, 2.9 mmol) in $CH_2Cl_2$ (15 mL) and boron tribromide 1M solution in dichloromethane (8.76 ml, 8.76 mmol) was added at 0° C. The reaction mixture was stirred overnight at room temperature after which it was carefully poured into a vigorously stirring mixture of ice and saturated aqueous solution of $NaHCO_3$. The resultant solid was collected by filtration, dried and then dissolved in a mixture of $K_2CO_3$ (2 g) and methanol (50 mL). The solution was then acidified using aqueous $NH_4Cl$ solution. (50 mL) and the precipitate which formed was collected by filtration and dried to give 0.95 g of 3-(4-(methylamino)-2-(pyridin-3-yl)quinazolin-6-yl)phenol as pale yellow solid (99%). LCMS m/z=329 (M+1) (Method D) (retention time=1.30 min). $^1H$ NMR (300 MHz, DMSO) δ 9.63 (s, 1H), 9.60 (s, 1H), 8.77 (d, J=8.0 Hz, 1H), 8.74-8.59 (m, 2H), 8.54 (s, 1H), 8.05 (d, J=8.7 Hz, 1H), 7.83 (d, J=8.7 Hz, 1H), 7.54 (dd, J=7.9, 4.8 Hz, 1H), 7.38-7.12 (m, 3H), 6.82 (d, J=7.8 Hz, 1H), 3.17 (d, J=4.3 Hz, 3H).

Method AS: 6-(3-(2-chloroethoxy)phenyl)-N-methyl-2-(pyridin-3-yl)quinazolin-4-amine (lxii-a)

A suspension of 3-(4-(methylamino)-2-(pyridin-3-yl) quinazolin-6-yl)phenol (0.30 g, 0.914 mmol), 1-bromo-2-chloroethane (0.38 ml, 4.57 mmol), and potassium carbonate (0.38 g, 2.74 mmol) in DMF (10 mL) was stirred for 2 days at room temperature. Water (10 mL) and ethyl acetate (10 mL) were added to the mixture and extracted. The organic layer was separated and concentrated in vacuo to leave a solid, which was collected by filtration and washed with hexane and dried to give 0.30 g of 6-(3-(2-chloroethoxy)phenyl)-N-methyl-2-(pyridin-3-yl)quinazolin-4-amine as brown solid (83%). The product was used without further purification.

Method AT1: 6-(3-(2-methoxyethoxy)phenyl)-N-methyl-2-(pyridin-3-yl)quinazolin-4-amine (lxiii-a)

A solution of 6-(3-(2-chloroethoxy)phenyl)-N-methyl-2-(pyridin-3-yl)quinazolin-4-amine (70 mg, 0.18 mmol) and sodium methoxide (97 mg, 1.8 mmol) in methanol (3 mL) was placed in a microwave reaction vial. The mixture was heated under microwave irradiation conditions at 150° C. for 30 minutes after which the solvent was removed in vacuo. The crude product was obtained, which was purified by column chromatography on basic silica gel (eluted with hexane/ethyl acetate 3:1→1:4) to give 20 mg of 6-(3-(2-methoxyethoxy)phenyl)-N-methyl-2-(pyridin-3-yl)quinazolin-4-amine as an off-white powder (29%). LCMS m/z=387 (M+1) (Method D) (retention time=1.49 min). $^{1}$H NMR (300 MHz, DMSO) δ 9.64 (s, 1H), 8.77 (d, J=8.2 Hz, 1H), 8.73-8.51 (m, 3H), 8.16 (d, J=8.7 Hz, 1H), 7.84 (d, J=8.3 Hz, 1H), 7.60-7.32 (m, 4H), 7.01 (s, 1H), 4.21 (s, 2H), 3.70 (s, 2H), 3.33 (s, 3H), 3.19 (s, 3H), Method AT2: N-Methyl-6-(4-(2-morpholinoethoxy)phenyl)-2-(pyridin-3-yl)quinazolin-4-amine (lxiii-b)

In a 10 mL microwave vial 6-(4-(2-chloroethoxy)phenyl)-N-methyl-2-(pyridin-3-yl)quinazolin-4-amine (70.0 mg, 0.179 mmol) and morpholine (0.155 ml, 1.791 mmol) were added in methanol (3 mL) to give a yellow suspension. The vial was irradiated at 150° C. in the microwave for 30 min. The volatiles were evaporated in vacuo. Water (10 mL) was added to the reaction mixture and extracted with ethyl acetate (2×10 mL). The organic layers were combined and washed with brine (1×20 mL), then dried over $MgSO_4$, filtered and concentrated. The residue was purified by column chromatography on basic silica gel (eluted with hexane/ethyl acetate 3:2 to 0:1). The product was obtained as the parent and converted to the HCl salt by addition of 4 M HCl-dioxane, then crystallized from EtOH-H2O to give 55 mg of N-methyl-6-(4-(2-morpholinoethoxy)phenyl)-2-(pyridin-3-yl)quinazolin-4-amine as a yellow powder (60% yield), LCMS m/z=442 (M+1) (Method D) (retention time=1.12 min). $^{1}$H NMR (300 MHz, DMSO) δ 11.31 (s, 1H), 10.41 (s, 1H), 9.63 (s, 1H), 9.10-8.79 (m, 3H), 8.34 (d, J=8.2 Hz, 1H), 8.28-8.12 (m, 1H), 7.92 (d, J=8.0 Hz, 2H), 7.87-7.74 (m, 1H), 7.18 (d, J=8.0 Hz, 2H), 4.60-4.46 (m, 2H), 4.06-3.91 (m, 2H), 3.91-3.74 (m, 2H), 3.67-3.41 (m, 4H), 3.38-3.09 (m, J=10.1 Hz, 5H).

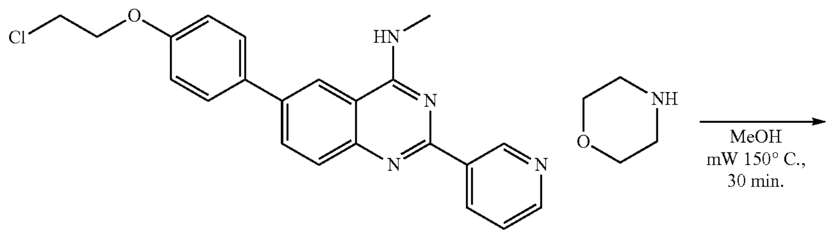

lxii-b

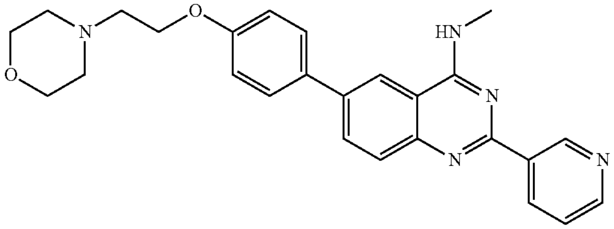

lxiii-b

Method AT3: N-methyl-2-(pyridin-3-yl)-6-(3-(2-(2, 2,2trifluoroethylamino)ethoxy)phenyl)quinazolin-4-amine (lxiii-c)

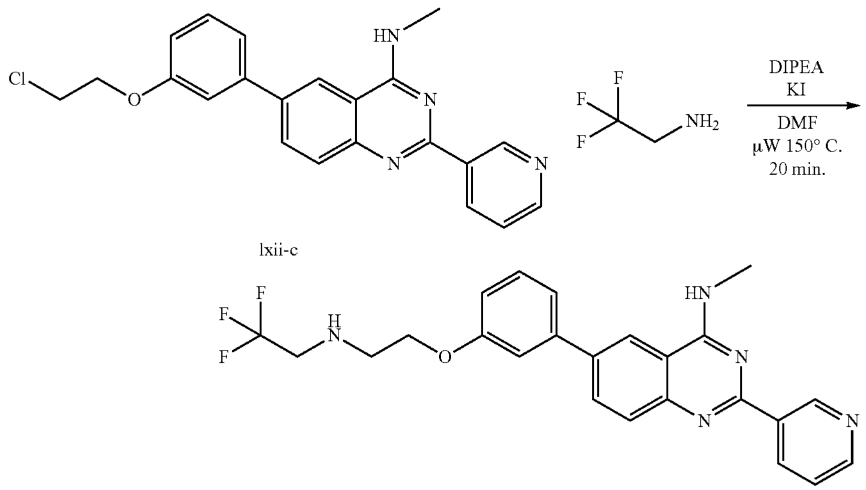

lxii-c lxiii-c

In a 10 mL microwave vial was added 6-(3-(2-chloroethoxy)phenyl)-N-methyl-2-(pyridin-3-yl)quinazolin-4-amine (50.0 mg, 0.128 mmol), 2,2,2-trifluoroethylamine (0.100 ml, 1.279 mmol), potassium iodide (42.5 mg, 0.256 mmol), and N,N'-diisopropylethylamine (0.045 ml, 0.256 mmol) in DMF (3 mL) to give a yellow suspension. The vial was irradiated at 150° C. in the microwave for 20 min. Water (10 mL) was added to the mixture and extracted with ethyl acetate (2×20 mL). The organic layers were combined and washed with water (1×20 mL) and brine (1×20 mL), dried over $MgSO_4$, filtered and concentrated. The residue was purified by column chromatography on silica gel (eluted with ($CH_2Cl_2$/$CH_2Cl_2$-MeOH-$NH_4OH$=100:20:1 1:0 to 0:1). The product was converted to the HCl salt by addition of 4 M HCl-dioxane, then crystallization from IPA-H2O to give 30 mg of N-methyl-2-(pyridin-3-yl)-6-(3-(2-(2,2,2-trifluoroethylamino)ethoxy)phenyl)quinazolin-4-amine as a yellow powder (42%). LCMS m/z=454 (M+1) (Method C) (retention time=2.26 min). $^1$H NMR (300 MHz, DMSO) δ 10.73-10.36 (m, 1H), 9.65 (s, 1H), 9.13-8.98 (m, 2H), 8.93 (d, J=5.0 Hz, 1H), 8.38 (d, J=8.4 Hz, 1H), 8.24 (d, J=7.7 Hz, 1H), 7.94-7.75 (m, 1H), 7.69-7.41 (m, 3H), 7.09 (d, J=8.1 Hz, 1H), 4.61-4.43 (m, 2H), 4.28-4.07 (m, 2H), 3.59-3.39 (m, 2H), 3.30 (d, J=2.8 Hz, 3H).

Scheme 80: Method AU: N-(2-(4-(4-(methylamino)-2-(pyridin-3-yl)quinazolin-6-yl)phenoxy)ethyl) acetamide (lxiv-a)

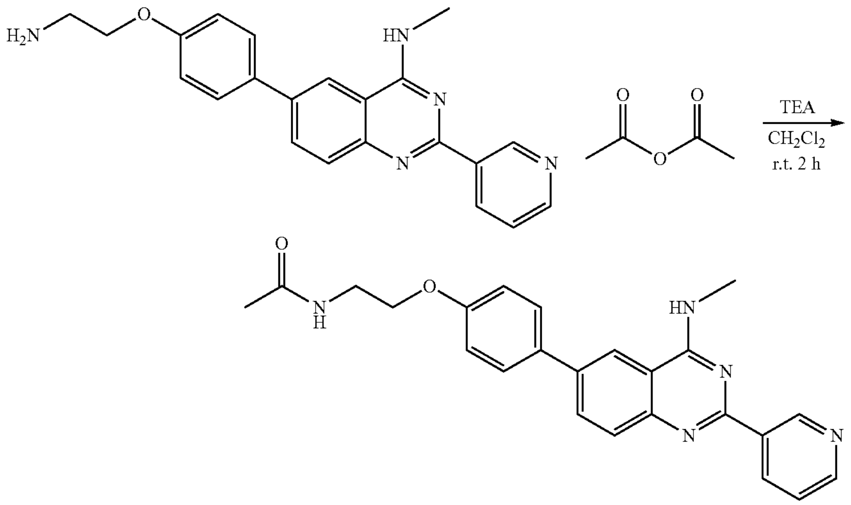

lxiv-a

In a 50 mL round-bottomed flask was added 6-(4-(2-aminoethoxy)phenyl)-N-methyl-2-(pyridin-3-yl)quinazolin-4-amine (15.0 mg, 0.040 mmol) and triethylamine (0.017 ml, 0.121 mmol) in $CH_2Cl_2$ (5 mL) to give a yellow solution.

Acetic anhydride (4.58 μl, 0.048 mmol) was added and the mixture was stirred for 2 h at room temperature. Water (10 mL) was added to the mixture and extracted with ethyl acetate (2×10 mL). The organic layers were combined and washed with brine (1×20 mL), dried over $Mg_2SO_4$, filtered and concentrated. The residue was purified by column chromatography on silica gel (eluted with $CH_2Cl_2$/MeOH 1:0 to 9:1). The product was converted to the HCl salt by addition of 4 M HCl-dioxane, then dissolved in a small amount of methanol, followed by ethyl acetate. The resulting solid was filtered and dried to give 10 mg of N-(2-(4-(4-(methylamino)-2-(pyridin-3-yl)quinazolin-6-yl)phenoxy)ethyl)acetamide as a HCl salt as a yellow solid in a 51% yield. LCMS m/z=414 (M+1) (Method C) (retention time=1.28 min). $^1$H NMR (300 MHz, DMSO) δ 10.26 (s, 1H), 9.62 (s, 1H), 9.06-8.90 (m, 2H), 8.81 (s, 1H), 8.34 (d, J=9.0 Hz, 1H), 8.17 (d, J=6.6 Hz, 2H), 7.86 (d, J=8.0 Hz, 3H), 7.13 (d, J=7.91 Hz, 2H), 4.06 (t, J=5.4 Hz, 2H), 3.52-3.38 (m, 2H), 3.30 (d, J=4.1 Hz, 3H), 1.84 (s, 3H).

The compounds in the following table were prepared in a manner analogous to that described in Scheme 78, replacing 1-bromo-2-chloroethane with the corresponding alkyl halide.

TABLE 26

| Number | PRODUCT | Salt | $^1$H-NMR | $^1$H-NMR Solvent | LCMS | Retention Time | LCMS Protocol | Purity percent | Method for Coupling |
|---|---|---|---|---|---|---|---|---|---|
| 1679 | 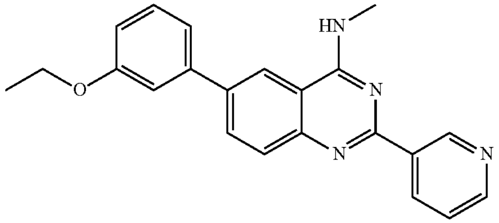 [SMILES: CCOc1cccc(-c2ccc3nc(-c4cccnc4)nc(NC)c3c2)c1] | HCl | 1H NMR (300 MHz, DMSO) δ 10.36 (s, 1H), 9.65 (s, 1H), 9.13-8.99 (m, 1H), 8.99-8.83 (m, 2H), 8.38 (d, J = 8.8 Hz, 1H), 8.30-8.16 (m, 1H), 7.94-7.80 (m, 1H), 7.55-7.35 (m, 3H), 7.09-6.97 (m, 1H), 4.16 (q, J = 7.0 Hz, 2H), 3.31 (d, J = 4.3 Hz, 3H), 1.37 (t, J = 6.9 Hz, 3H). | DMSO | 357 (M + 1) | 1.62 | Method D | 100 | Method AR/AS/AT1 |
| 1680 | 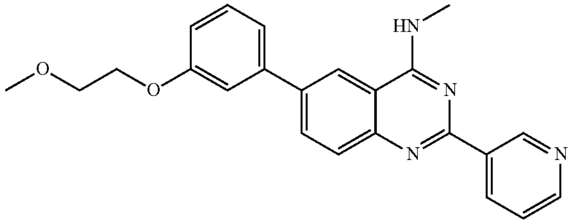 [SMILES: CNc1nc(-c2cccnc2)nc2ccc(-c3cccc(OCCOC)c3)cc12] | | 1H NMR (300 MHz, DMSO) δ 9.64 (s, 1H), 8.77 (d, J = 8.2 Hz, 1H), 8.73-8.51 (m, 3H), 8.16 (d, J = 8.7 Hz, 1H), 7.84 (d, J = 8.3 Hz, 1H), 7.60-7.32 (m, 4H), 7.01 (s, 1H), 4.21 (s, 2H), 3.70 (s, 2H), 3.33 (s, 3H), 3.19 (s, 3H). | DMSO | 387 (M + 1) | 1.49 | Method D | 100 | Method AR/AS/ATI |
| 1681 | 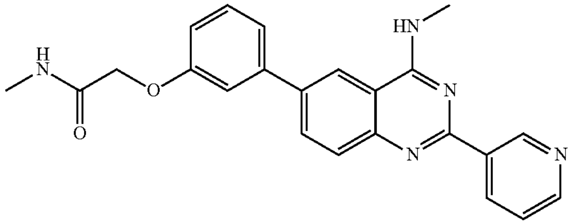 [SMILES: CNC(=O)COc1cccc(-c2ccc3nc(-c4cccnc4)nc(NC)c3c2)c1] | | 1H NMR (300 MHz, DMSO) δ 9.64 (s, 1H), 8.78 (d, J = 7.9 Hz, 1H), 8.72-8.49 (m, 3H), 8.22-8.01 (m, 2H), 7.85 (d, J = 8.6 Hz, 1H), 7.62-7.36 (m, 4H), 7.01 (s, 1H), 4.59 (s, 2H), 3.19 (d, J = 4.0 Hz, 3H), 2.68 (d, J = 4.5 Hz, 3H). | DMSO | 400 (M + 1) | 1.31 | Method D | 100 | Method AR/W with KI |
| 1682 | 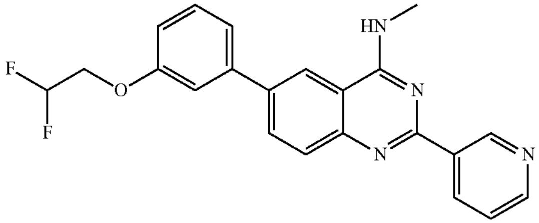 [SMILES: CNc1nc(-c2cccnc2)nc2ccc(-c3cccc(OCC(F)F)c3)cc12] | 2HCl | 1H NMR (300 MHz, DMSO) δ 10.47 (s, 1H), 9.65 (d, J = 1.7 Hz, 1H), 9.05 (d, J = 7.9 Hz, 1H), 9.01-8.88 (m, 2H), 8.39 (m, 1H), 8.23 (d, J = 8.8 Hz, 1H), 7.87 (dd, J = 8.0, 5.3 Hz, 1H), 7.65-7.39 (m, 3H), 7.09 (m, 1H), 6.44 (m, 1H), 4.47 (td, J = 14.7, 3.4 Hz, 2H), 3.29 (d, J = 4.5 Hz, 3H). | DMSO | 393.4 (M + 1) | | Method C (NH4HCO3) | 100 | Method AR/AS (K2CO3, DMF-THF (1:1), 60° C.) then Method AT |

TABLE 26-continued

| Number | PRODUCT | Salt | $^1$H-NMR | $^1$H-NMR Solvent | LCMS | Retention Time | LCMS Protocol | Purity percent | Method for Coupling |
|---|---|---|---|---|---|---|---|---|---|
| 1683 | 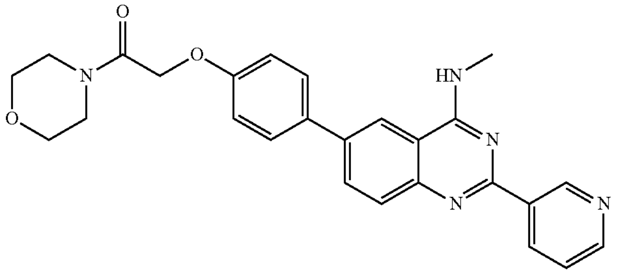 [SMILES: CNc1nc(-c2cccnc2)nc2ccc(-c3ccc(OCC(=O)N4CCOCC4)cc3)cc12] | HCl | $^1$H NMR (300 MHz, DMSO) δ 10.12 (s, 1H), 9.60 (s, 1H), 9.03-8.87 (m, 2H), 8.77 (s, 1H), 8.32 (d, J = 8.5 Hz, 1H), 8.21-8.02 (m, 1H), 7.92-7.69 (m, 3H), 7.20-7.02 (m, 2H), 4.93 (s, 2H), 3.70-3.40 (m, 8H), 3.29 (d, J = 3.5 Hz, 3H). | DMSO | 456 (M + 1) | 1.73 | Method B (Ammonium formate) | 100 | Method AR/W with KI |
| 1684 | 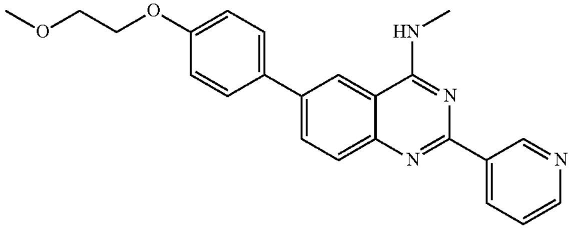 [SMILES: CNc1nc(-c2cccnc2)nc2ccc(-c3ccc(OCCOC)cc3)cc12] | HCl | $^1$H NMR (300 MHz, DMSO) δ 10.38 (s, 1H), 9.64 (s, 1H), 9.02 (d, J = 6.7 Hz, 1H), 8.93 (d, J = 4.9 Hz, 1H), 8.84 (s, 1H), 8.34 (d, J = 9.0 Hz, 1H), 8.22 (d, J = 8.7 Hz, 1H), 7.98-7.70 (m, 3H), 7.11 (d, J = 7.3 Hz, 2H), 4.26-4.05 (m, 2H), 3.78-3.57 (m, 2H), 3.45-3.19 (m, 6H). | DMSO | 387 (M + 1) | 1.47 | Method A (Formic acid) | 100 | Method AR/AS/ AT1 |
| 1685 | 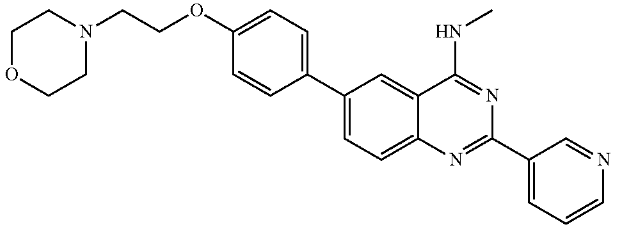 [SMILES: CNc1nc(-c2cccnc2)nc2ccc(-c3ccc(OCCN4CCOCC4)cc3)cc12] | HCl | $^1$H NMR (300 MHz, DMSO) δ 11.31 (s, 1H), 10.41 (s, 1H), 9.63 (s, 1H), 9.10-8.79 (m, 3H), 8.34 (d, J = 8.2 Hz, 1H), 8.28-8.12 (m, 1H), 7.92 (d, J = 8.0 Hz, 2H), 7.87-7.74 (m, 1H), 7.18 (d, J = 8.0 Hz, 2H), 4.60-4.46 (m, 2H), 4.06-3.91 (m, 2H), 3.91-3.74 (m, 2H), 3.67-3.41 (m, 4H), 3.38-3.09 (m, J = 10.1 Hz, 5H). | DMSO | 442 (M + 1) | 1.22 | Method A (Formic acid) | 100 | Method AR/AS/ AT2 |
| 1686 | 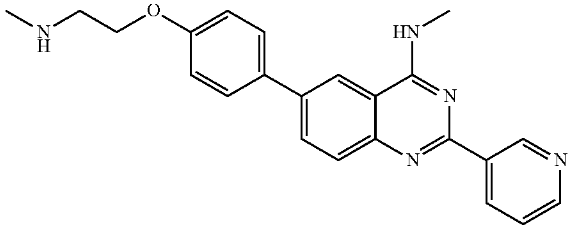 [SMILES: CNCCOc1ccc(-c2ccc3nc(-c4cccnc4)nc(NC)c3c2)cc1] | HCl | $^1$H NMR (300 MHz, DMSO) δ 10.32-9.70 (m, 1H), 9.61 (s, 1H), 9.13-8.70 (m, 5H), 8.29 (d, J = 8.5 Hz, 1H), 8.20-8.01 (m, 1H), 7.89 (d, J = 8.6 Hz, 2H), 7.83-7.67 (m, 1H), 7.16 (d, J = 8.8 Hz, 2H), 4.38-4.27 (m, 2H), 3.43-3.32 (m, 2H), 3.27 (d, J = 3.7 Hz, 3H), 2.63 (t, J = 4.8 Hz, 3H). | DMSO | 386 (M + 1) | 1.46 | Method B (Ammonium formate) | 100 | Method AR/AS/ AT2 |

TABLE 26-continued

| Number | PRODUCT | Salt | $^1$H-NMR | $^1$H-NMR Solvent | LCMS | Retention Time | LCMS Protocol | Purity percent | Method for Coupling |
|---|---|---|---|---|---|---|---|---|---|
| 1687 | 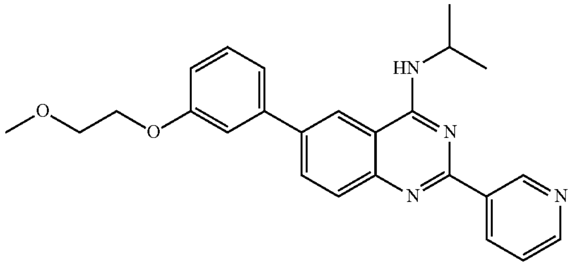 [SMILES: COCCOc1cccc(-c2ccc3nc(-c4cccnc4)nc(NC(C)C)c3c2)c1] | HCl | $^1$H NMR (300 MHz, DMSO) δ 9.95 (s, 1H), 9.62 (s, 1H), 9.13-8.86 (m, J = 5.2 Hz, 3H), 8.39 (d, J = 8.7 Hz, 1H), 8.26 (s, 1H), 7.97-7.80 (m, 1H), 7.61-7.37 (m, 3H), 7.14-6.98 (m, 1H), 5.01-4.81 (m, 1H), 4.31-4.13 (m, 2H), 3.79-3.63 (m, 2H), 1.42 (d, J = 6.5 Hz, 6H). | DMSO | 415 (M + 1) | 1.65 | Method A (Formic acid) | 100 | Method AR/AS/AT1 |
| 1688 | 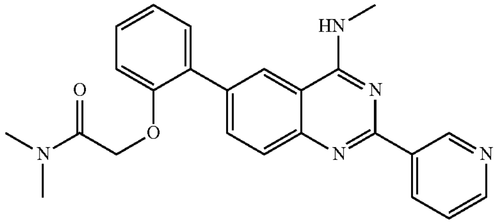 [SMILES: CNc1nc(-c2cccnc2)nc2ccc(-c3ccccc3OCC(=O)N(C)C)cc12] | HCl | $^1$H NMR (300 MHz, DMSO) δ 10.12 (s, 1H), 9.63 (s, 1H), 9.10-8.88 (m, 2H), 8.72 (s, 1H), 8.44 (d, J = 8.3 Hz, 1H), 8.14 (d, J = 8.3 Hz, 1H), 7.85 (dd, J = 7.6, 4.8 Hz, 1H), 7.52 (d, J = 6.3 Hz, 1H), 7.39 (t, J = 7.9 Hz, 1H), 7.22-7.04 (m, 2H), 4.97 (s, 2H), 3.30 (d, J = 4.1 Hz, 3H). 2.97 (s, 3H), 2.85 (s, 3H). | DMSO | 414 (M + 1) | 1.28 | Method A (Formic acid) | 100 | Method AR/W with KI |
| 1689 | 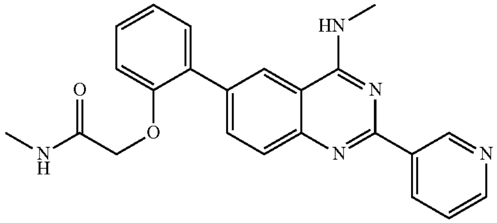 [SMILES: CNC(=O)COc1ccccc1-c1ccc2nc(-c3cccnc3)nc(NC)c2c1] | HCl | $^1$H NMR (300 MHz, DMSO) δ 10.22 (s, 1H), 9.63 (s, 1H), 9.10-8.87 (m, 2H), 8.75 (s, 1H), 8.35 (d, J = 8.8 Hz, 1H), 8.15 (d, J = 8.7 Hz, 1H), 8.01 (d, J = 4.2 Hz, 1H), 7.93-7.77 (m, 1H), 7.51 (d, J = 7.3 Hz, 1H), 7.43 (t, J = 7.8 Hz, 1H), 7.16 (t, J = 7.5 Hz, 1H), 7.07 (d, J = 8.5 Hz, 1H), 4.54 (s, 2H), 3.29 (d, J = 3.9 Hz, 3H), 2.64 (d, J = 4.4 Hz, 3H). | DMSO | 400 (M + 1) | 1.33 | Method A (Formic acid) | 100 | Method AR/W with KI |
| 1690 | 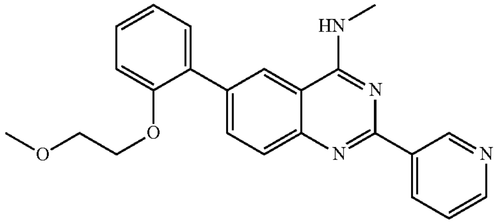 [SMILES: CNc1nc(-c2cccnc2)nc2ccc(-c3ccccc3OCCOC)cc12] | HCl | $^1$H NMR (300 MHz, DMSO) δ 10.09 (s, 1H), 9.62 (s, 1H), 9.05-8.87 (m, 2H), 8.60 (s, 1H), 8.26 (d, J = 8.6 Hz, 1H), 8.13 (d, J = 3.8 Hz, 1H), 7.90-7.77 (m, 1H), 7.54-7.36 (m, 2H), 7.26-7.06 (m, 2H), 4.23-4.11 (m, 2H), 3.70-3.58 (m, 2H), 3.29 (d, J = 4.4 Hz, 3H), 3.24 (s, 3H). | DMSO | 387 (M + 1) | 1.51 | Method A (Formic acid) | 100 | Method AR/AS/AT1 |

TABLE 26-continued

| Number | PRODUCT | Salt | $^1$H-NMR | $^1$H-NMR Solvent | LCMS | Retention Time | LCMS Protocol | Purity percent | Method for Coupling |
|---|---|---|---|---|---|---|---|---|---|
| 1691 | 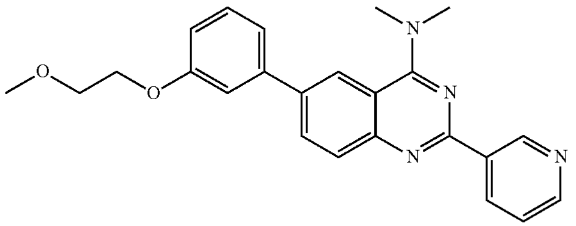 [SMILES: COCCOc1cccc(-c2ccc3nc(-c4cccnc4)nc(N(C)C)c3c2)c1] | HCl | $^1$H NMR (300 MHz, DMSO) δ 9.65 (s, 1H), 9.04 (d, J = 7.8 Hz, 1H), 8.94 (d, J = 5.0 Hz, 1H), 8.50 (s,1H), 8.39-8.22 (m, 2H), 7.97-7.80 (m, 1H), 7.53-7.31 (m, 3H), 7.03 (d, J = 6.8 Hz, 1H), 4.26-4.13 (m, 2H), 3.82-3.59 (m, 8H), 3.32 (s, 3H). | DMSO | 401 (M + 1) | 1.47 | Method A (Formic acid) | 100 | Method AR/AS/ AT1 |
| 1692 | 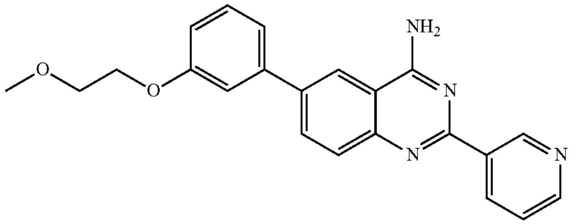 [SMILES: COCCOc1cccc(-c2ccc3nc(-c4cccnc4)nc(N)c3c2)c1] | HCl | $^1$H NMR (300 MHz, DMS0) δ 9.83-9.26 (m, 3H), 9.00-8.76 (m, 3H), 8.40 (d, J = 8.8 Hz, 1H), 8.18 (d, J = 8.6 Hz, 1H), 7.89-7.72 (m, 1H), 7.58-7.36 (m, 3H), 7.04 (d, J = 3.4 Hz, 1H), 4.30-4.18 (m, 2H), 3.79-3.66 (m, 2H), 3.33 (s, 3H). | DMSO | 373 (M + 1) | 1.42 | Method A (Formic acid) | 100 | Method AR/AS/ AT1 |
| 1693 | 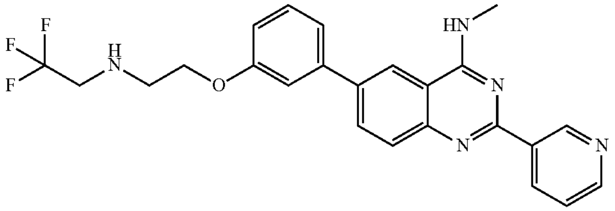 [SMILES: CNc1nc(-c2cccnc2)nc2ccc(-c3cccc(OCCNCC(F)(F)F)c3)cc12] | HCl | $^1$H NMR (300 MHz, DMSO) δ 10.73-10.36 (m, 1H), 9.65 (s, 1H), 9.13-8.98 (m, 2H), 8.93 (d, J = 5.0 Hz, 1H), 8.38 (d, J = 3.4 Hz, 1H), 8.24 (d, J = 7.7 Hz, 1H), 7.94-7.75 (m, 1H), 7.69-7.41 (m, 3H), 7.09 (d, J = 8.1 Hz, 1H), 4.61-4.43 (m, 2H), 4.28-4.07 (m, 2H), 3.59-3.39 (m, 2H), 3.30 (d, J = 2.8 Hz, 3H). | DMSO | 454 (M + 1) | 2.26 | Method B (Ammonium formate) | 100 | Method AR/AS/ AT3 |

TABLE 26-continued

| Number | PRODUCT | Salt | $^1H$-NMR | $^1H$-NMR Solvent | LCMS | Retention Time | LCMS Protocol | Purity percent | Method for Coupling |
|---|---|---|---|---|---|---|---|---|---|
| 1694 | 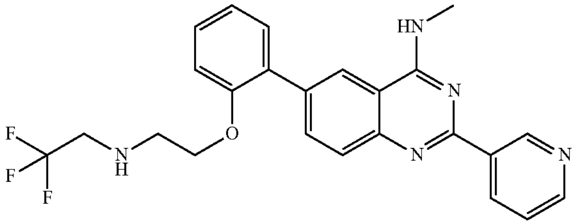 [SMILES: CNc1nc(-c2cccnc2)nc2ccc(-c3ccccc3OCCNCC(F)(F)F)cc12] | HCl | $^1H$ NMR (300 MHz, DMSO) δ 10.35 (s, 1H), 9.67 (s, 1H), 9.04 (d, J = 7.3 Hz, 1H), 8.94 (d, J = 5.0 Hz, 1H), 8.78 (s, 1H), 8.24 (s, 2H), 7.96-7.77 (m, 1H), 7.60-7.40 (m, 2H), 7.33-7.10 (m, 2H), 4.50-4.36 (m, 2H), 4.05-3.85 (m, 2H), 3.53-3.37 (m, 2H), 3.28 (d, J = 3.6 Hz, 3H), | DMSO | 454 (M + 1) | 2.11 | Method B (Ammonium formate) | 100 | Method AR/AS/AT3 |
| 1695 | 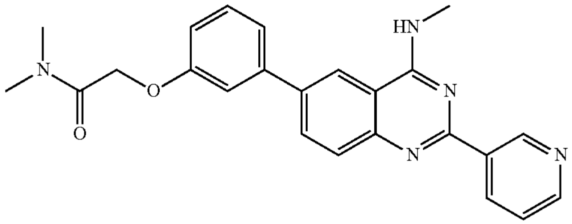 [SMILES: CNc1nc(-c2cccnc2)nc2ccc(-c3cccc(OCC(=O)N(C)C)c3)cc12] | | $^1H$ NMR (300 MHz, DMSO) δ 9.64 (s, 1H), 8.77 (d, J = 8.0 Hz, 1H), 8.73-8.50 (m, 3H), 8.14 (d, J = 8.7 Hz, 1H), 7.84 (d, J = 8.7 Hz, 1H), 7.54 (dd, J = 7.9, 4.8 Hz, 1H), 7.48-7.34 (m, 3H), 6.96 (d, J = 3.2 Hz, 1H), 4.91 (s, 2H), 3.18 (d, J = 4.3 Hz, 3H), 3.03 (s, 3H), 2.86 (s, 3H). | DMSO | 414 (M + 1) | 1.30 | Method A (Formic acid) | 100 | Method AR/W with KI |

Scheme 81: General route for the synthesis of compounds with general formula lxx
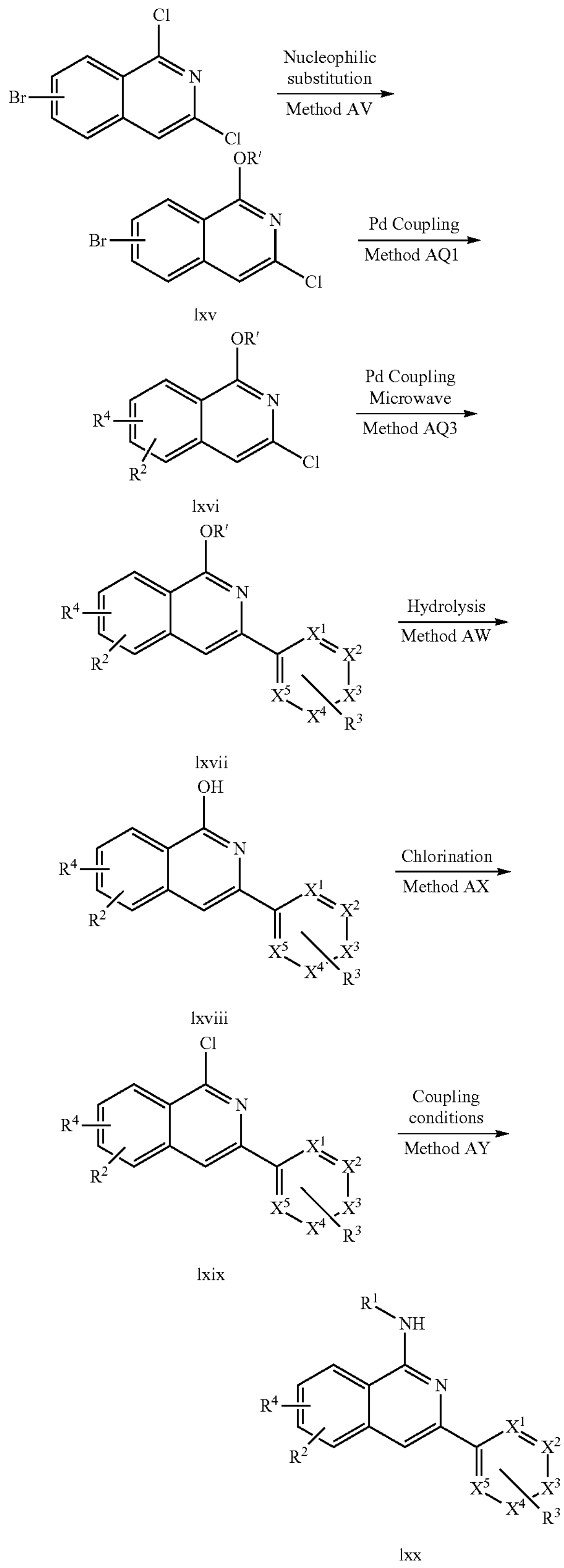
lxv
lxvi
lxvii
lxviii
lxix
lxx
$X^1$, $X^2$, $X^3$, $X^4$ or $X^5$ = CH or N, at least one $X^1$, $X^2$, $X^3$, $X^4$ or $X^5$ must be N
Scheme 82: Representative synthesis of compounds of formula lxx-a: (see Scheme 81)
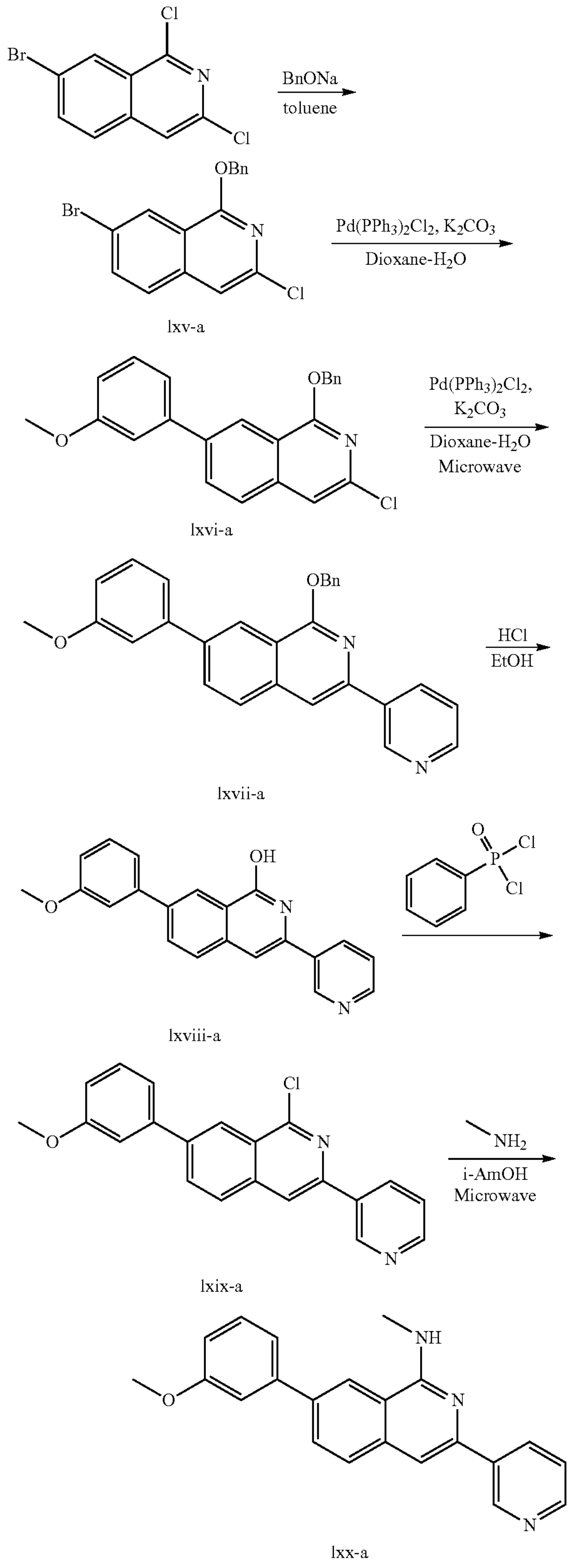
lxv-a
lxvi-a
lxvii-a
lxviii-a
lxix-a
lxx-a Method AV: 1-(Benzyloxy)-7-bromo-3-chloroisoquinoline (lxv-a)

To 20 mL of benzylalcohol was slowly added Na (2.00 g, 86.9 mmol) at 0° C., the mixture was then stirred at room temperature for 4 h. 7-bromo-1,3-dichloroisoquinoline (2.00 g, 7.2 mmol) in toluene (50 mL) was added to the mixture with stirring. The reaction mixture was heated at 80° C. overnight. The solvent was removed under reduced pressure, the residue was purified with chromatography on silica gel (petroleum ether) to give 2.00 g xiv-a as a white solid (yield 80%) LCMS m/z=257.9, 259.9 (M+1) (Method B) (retention time=1.62 min).

Method AQ1: 1-(Benzyloxy)-3-chloro-7-(3-methoxyphenyl)isoquinoline (lxvi-a)

To a mixture of 1-(benzyloxy)-7-bromo-3-chloroisoquinoline (1.00 g, 2.86 mmol, 1.0 eq), 3-methoxyphenylboronic acid (435 mg, 2.86 mmol, 1.0 eq), $K_2CO_3$ (2.13 g, 15.4 mmol, 5.4 eq) in dioxane (10 mL) and $H_2O$ (5 mL) was added $Pd(PPh_3)_2Cl_2$ (100 mg, 0.15 mmol, 0.05 eq) under $N_2$ atmosphere. The resulting mixture was stirred at 110° C. under $N_2$ atmosphere overnight. The solvent was removed in vacuo and the residue was purified with chromatography on silica gel (hexane/ethyl acetate 250:1) to give 550 mg of lxvi-a as white solid (yield 37%). LCMS m/z=376.0 (M+1) (Method B) (retention time=2.43 min).

Method AQ3: 1-(Benzyloxy)-7-(3-methoxyphenyl)-3-(pyridin-3-yl)isoquinoline (lxvii-a)

To a mixture of 1-(benzyloxy)-3-chloro-7-(3-methoxyphenyl)isoquinoline (150 mg, 0.40 mmol, 1.0 eq), pyridin-3-ylboronic acid (74 mg, 0.60 mmol, 1.5 eq), $K_2CO_3$ (166 mg, 1.20 mmol, 3.0 eq) in dioxane (2 ml) and $H_2O$ (1 mL) was added $Pd(PPh_3)_2Cl_2$ (14 mg, 0.02 mmol, 0.05 eq) under $N_2$ atmosphere. The sealed tube was irradiated in the CEM microwave at 130° C. for 1 h. After the reaction was completed, the volatiles were removed in vacuo and the residue was purified with chromatography on silica gel (hexane/ethyl acetate 50:1) to give 200 mg of crude lxvii-a as a brown oil, which was used directly in the next step without purification, LCMS m/z=419.0 (M+1) (Method B) (retention time=2.25 min).

Method AW: 7-(3-Methoxyphenyl)-3-(pyridin-3-yl)isoquinolin-1-ol (lxviii-a)

A mixture of 1-(benzyloxy)-7-(3-methoxyphenyl)-3-(pyridin-3-yl)isoquinoline (200 mg, 0.48 mmol), and concentrated HCl (10 mL) in ethanol (20 mL) was stirred at room temperature overnight. After the reaction was completed, the mixture was filtered and concentrated to afford 130 mg of lxviii-a as a yellow solid (yield 90% for two steps). LCMS m/z=329.0 (M+1) (Method B) (retention time=1.66 min).

Method AX: 1-Chloro-7-(3-methoxyphenyl)-3-(pyridin-3-yl)isoquinoline (lxix-a)

To a mixture of 7-(3-methoxyphenyl)-3-(pyridin-3-yl)isoquinolin-1-ol (130 mg, 0.395 mmol) in phenylphosphonic dichloride (5 mL) was stirred at 120° C. overnight. After the reaction was completed, the mixture was added to ice-water slowly. The pH was adjusted to 7 by slow addition of $NH_3H_2O$ at 0° C. Then the mixture was extracted with dichloromethane (100 mL×3). The combined organic layer were dried over $MgSO_4$, filtered and concentrated in vacuo to give 130 mg of crude lxix-a as a white solid, which was used directly in the next step without purification. LCMS m/z=346.9 (M+1) (Method B) (retention time=1.80 min).

Method AY: 7-(3-Methoxyphenyl)-N-methyl-3-(pyridin-3-yl)isoquinolin-1-amine (lxx-a)

A mixture of 1-chloro-7-(3-methoxyphenyl)-3-(pyridin-3-yl)isoquinoline (90 mg, 0.26 mmol), methylamine hydrochloride (200 mg, 2.96 mmol, 10.0 eq) and $Et_3N$ (0.5 mL) was added to a sealed tube with i-AmOH (2 mL). The sealed tube was irradiated in the CEM microwave at 160° C. for 1 h. After the reaction was completed, the i-AmOH was removed in vacuo and the residue was dissolved in 10 mL of water and dichloromethane, the mixture was extracted with dichloromethane (3×50 mL). The combined organic layers were dried over $MgSO_4$, filtered and concentrated in vacuo and the residue was washed with MeOH to give 5 mg of lxx-a as a brown solid (yield 6%). LCMS m/z=342.1 (M+1) (Method B) (retention time=2.02 min). $^1H$ NMR (400 MHz, DMSO-$d_6$): δ 9.40 (d, J=0.9 Hz, 1H), 8.67-8.47 (m, 3H), 8.08-7.95 (m, 1H), 7.89-7.84 (m, 2H), 7.66 (s, 1H), 7.57-7.49 (m, 1H), 7.46-7.42 (m, 3H), 7.08-6.95 (m, 1H), 3.88 (s, 3H), 3.14 (d, J=4.3 Hz, 3H).

The compounds in the following table were prepared in a manner analogous to that described in Scheme 81, replacing with the appropriate isoquinoline and aniline.

TABLE 27

| Number | PRODUCT | Salt type | Molecular Mass | $^1$H-NMR | $^1$H-NMR Solvent | LCMS | LCMS Protocol | Purity percent | Method for Coupling |
|---|---|---|---|---|---|---|---|---|---|
| 1697 | 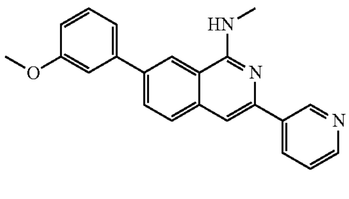 [SMILES: CNc1nc(-c2cccnc2)cc2ccc(-c3cccc(OC)c3)cc12] | | 341.41 | 1H-NMR (400 MHz, DMSO-d6): δ 9.40 (d, J = 0.9 Hz, 1H), 8.67-8.47 (m, 3H), 8.08-7.95 (m, 1H), 7.89-7.84 (m, 2H), 7.66 (s, 1H), 7.57-7.49 (m, 1H), 7.46-7.42 (m, 3H), 7.08-6.95 (m, 1H), 3.88 (s, 3H), 3.14 (d, J = 4.3 Hz, 3H). | DMSO | 342.1 (M + 1) | Method B (NH4HCO3) | 95 | Method AX, H1 |

TABLE 27-continued

| Number | PRODUCT | Salt type | Molecular Mass | $^1$H-NMR | $^1$H-NMR Solvent | LCMS | LCMS Protocol | Purity percent | Method for Coupling |
|---|---|---|---|---|---|---|---|---|---|
| 1698 | 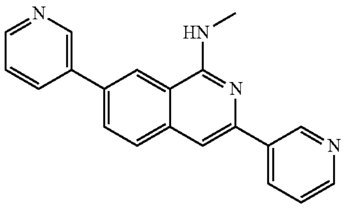 [SMILES: CNc1nc(-c2cccnc2)cc2ccc(-c3cccnc3)cc12] | | 312.37 | 1H-NMR (400 MHz, DMSO-d6): δ 9.40 (d, J = 1.8 Hz, 1H), 9.12 (d, J = 2.1 Hz, 1H), 8.66 (s, 1H), 8.60 (m, 2H), 8.54 (dt, J = 8.0, 1.9 Hz, 1H), 8.29-8.23 (m, 1H), 8.08 (dd, J = 8.5, 1.6 Hz, 1H), 7.92 (d, J = 8.5 Hz, 1H), 7.87 (d, J = 4.5 Hz, 1H), 7.68 (s, 1H), 7.56 (dd, J = 7.8, 4.8 Hz, 1H), 7.51 (dd, J = 7.8, 4.8 Hz, 1H), 3.14 (d, J = 4.4 Hz, 3H). | DMSO | 312.9 (M + 1) | Method B (NH4HCO3) | 95 | Method AX, H1 |

Scheme 83: General route for the synthesis of compounds with general formula lxxi

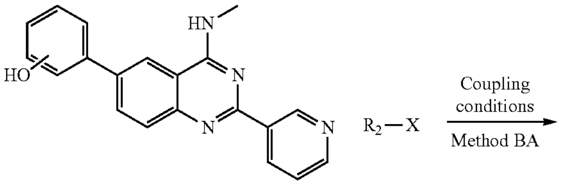

vi

-continued

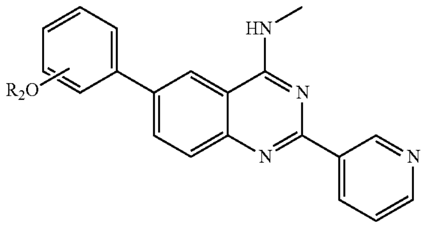

lxxi

Scheme 84: Representative synthesis of compounds of formula lxxi-a (see Scheme 81)

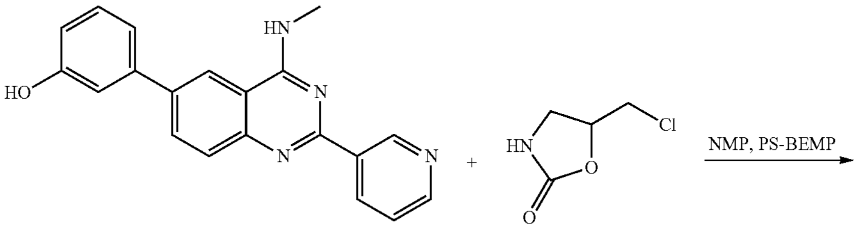

vi-v

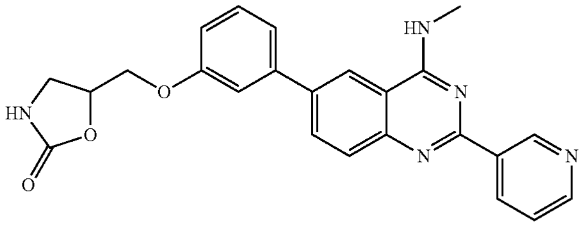

lxxi-a

Method BA: Synthesis of 5-[3-(4-Methylamino-2-pyridin-3-yl-quinazolin-6-yl)-phenoxymethyl]-oxazolidin-2-one (lxxi-a)

To 5-(chloromethyl)oxazolidin-2-one (45 μmol) was added the solution of 3-(4-(methylamino)-2-(pyridin-3-yl)quinazolin-6-yl)phenol (30 μmol) in NMP (200 μL). PS-BEMP (90 μmol) was added to the vials by resin dispenser. After the reaction mixture was heated at 90° C. for 12 h, the residue was diluted with methanol and purified by PREP-HPLC Condition D. The target fraction was lyophilized to afford the titled compound whose structure was finally confirmed by LCMS using LCMS Method E.

The compounds in the following table were prepared in a manner analogous to that described in Scheme 80, replacing 5-(chloromethyl)oxazolidin-2-one with the appropriate alkyl halide.

TABLE 28

| Number | Starting Material 1 | Starting Material 2 |
|---|---|---|
| 1699 | 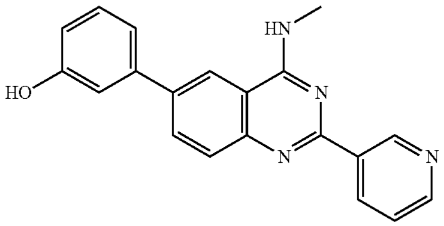 [SMILES: CNc1nc(-c2cccnc2)nc2ccc(-c3cccc(O)c3)cc12] | 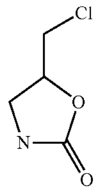 |
| 1700 | 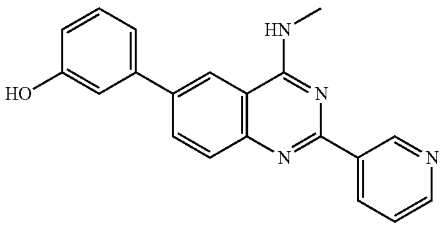 [SMILES: CNc1nc(-c2cccnc2)nc2ccc(-c3cccc(O)c3)cc12] | 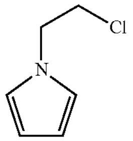 |
| 1701 | 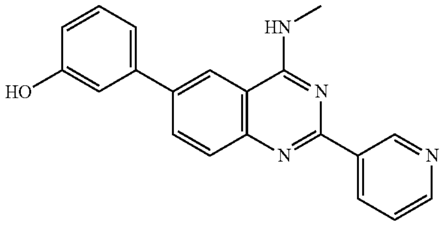 [SMILES: CNc1nc(-c2cccnc2)nc2ccc(-c3cccc(O)c3)cc12] | 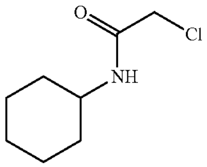 [SMILES: O=C(CCl)NC1CCCCC1] |
| 1702 | 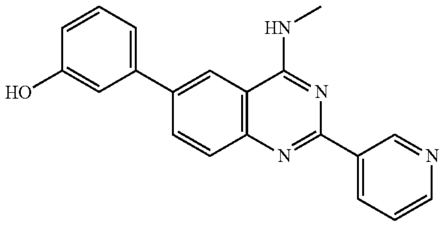 [SMILES: CNc1nc(-c2cccnc2)nc2ccc(-c3cccc(O)c3)cc12] | 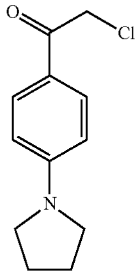 [SMILES: O=C(CCl)c1ccc(N2CCCC2)cc1] |
| 1703 | 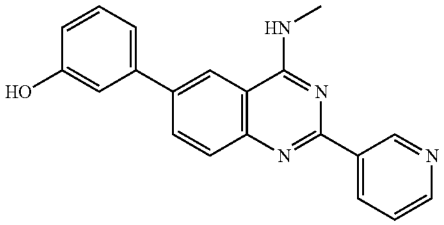 [SMILES: CNc1nc(-c2cccnc2)nc2ccc(-c3cccc(O)c3)cc12] | 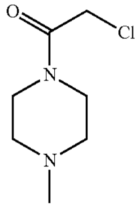 |

TABLE 28-continued
| | | |
|---|---|---|
| 1704 | 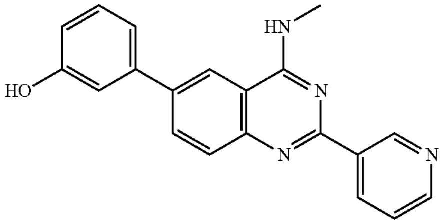 [SMILES: CNc1nc(-c2cccnc2)nc2ccc(-c3cccc(O)c3)cc12] | 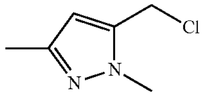 |
| 1705 | 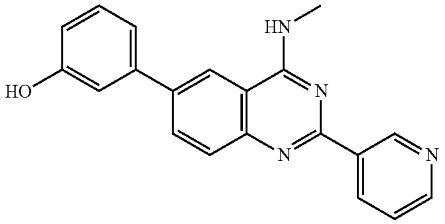 [SMILES: CNc1nc(-c2cccnc2)nc2ccc(-c3cccc(O)c3)cc12] | 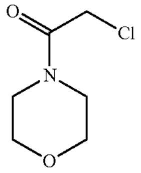 |
| 1706 | 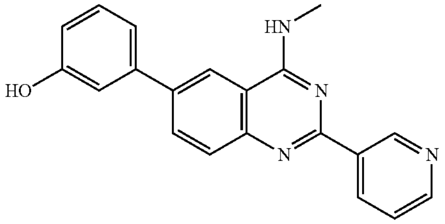 [SMILES: CNc1nc(-c2cccnc2)nc2ccc(-c3cccc(O)c3)cc12] | 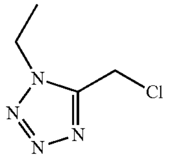 |
| 1707 | 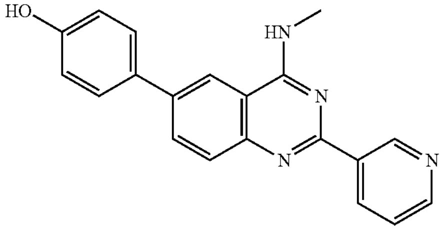 [SMILES: CNc1nc(-c2cccnc2)nc2ccc(-c3ccc(O)cc3)cc12] | 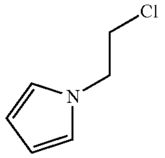 |
| 1708 | 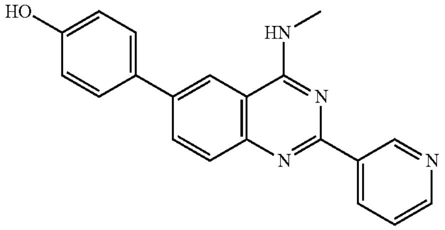 [SMILES: CNc1nc(-c2cccnc2)nc2ccc(-c3ccc(O)cc3)cc12] | 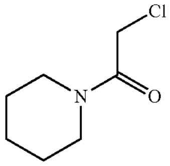 |
| 1709 | 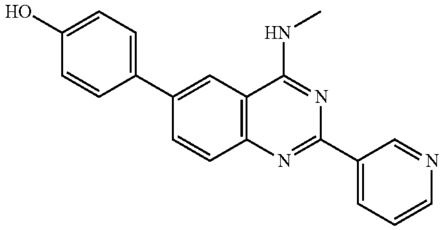 [SMILES: CNc1nc(-c2cccnc2)nc2ccc(-c3ccc(O)cc3)cc12] | 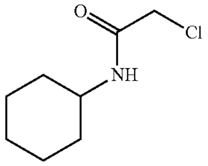 [SMILES: O=C(CCl)NC1CCCCC1] |
| 1710 | 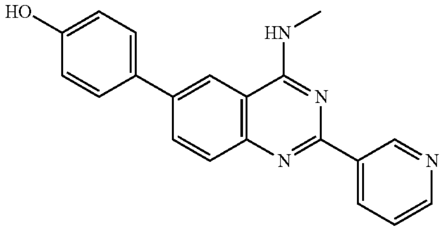 [SMILES: CNc1nc(-c2cccnc2)nc2ccc(-c3ccc(O)cc3)cc12] | 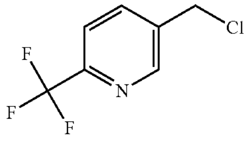 [SMILES: FC(F)(F)c1ccc(CCl)cn1] |

TABLE 28-continued
| | | |
|---|---|---|
| 1711 | 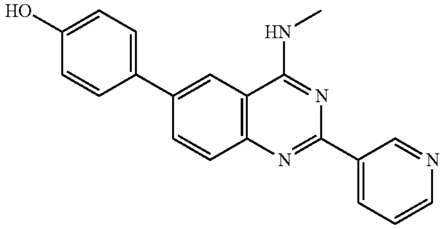 [SMILES: CNc1nc(-c2cccnc2)nc2ccc(-c3ccc(O)cc3)cc12] | 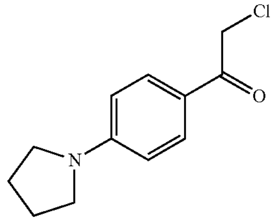 [SMILES: O=C(CCl)c1ccc(N2CCCC2)cc1] |
| 1712 | 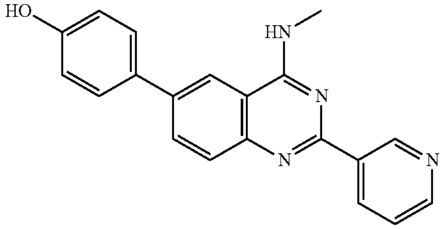 [SMILES: CNc1nc(-c2cccnc2)nc2ccc(-c3ccc(O)cc3)cc12] | 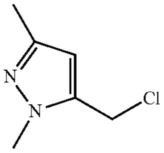 |
| 1713 | 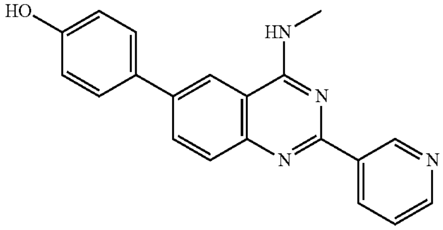 [SMILES: CNc1nc(-c2cccnc2)nc2ccc(-c3ccc(O)cc3)cc12] | 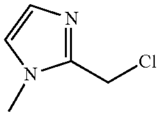 |
| 1714 | 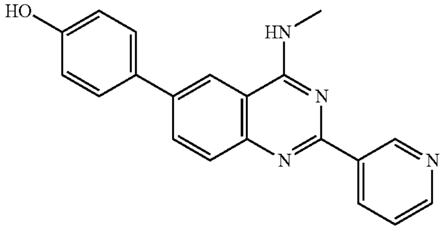 [SMILES: CNc1nc(-c2cccnc2)nc2ccc(-c3ccc(O)cc3)cc12] | 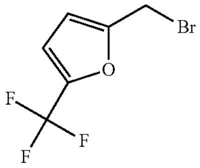 [SMILES: FC(F)(F)c1ccc(CBr)o1] |
| 1715 | 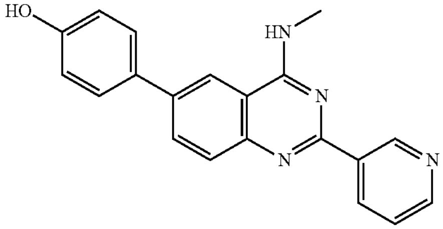 [SMILES: CNc1nc(-c2cccnc2)nc2ccc(-c3ccc(O)cc3)cc12] | 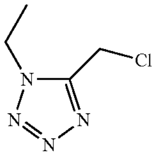 |
| Number | Product |
|---|---|
| 1699 | 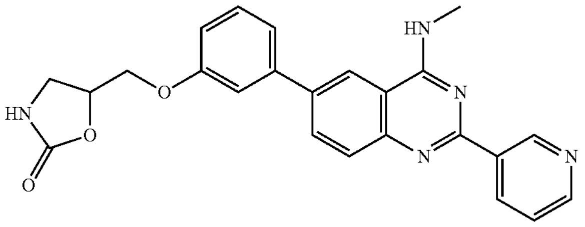 [SMILES: CNc1nc(-c2cccnc2)nc2ccc(-c3cccc(OCC4CNC(=O)O4)c3)cc12] |

TABLE 28-continued
1700
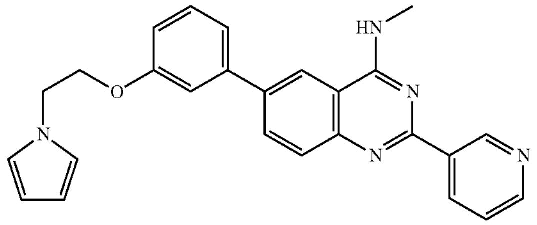 [SMILES: CNc1nc(-c2cccnc2)nc2ccc(-c3cccc(OCCn4cccc4)c3)cc12]
1701
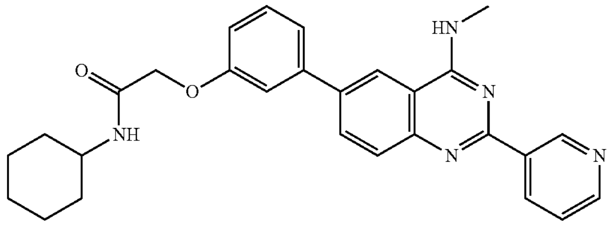 [SMILES: CNc1nc(-c2cccnc2)nc2ccc(-c3cccc(OCC(=O)NC4CCCCC4)c3)cc12]
1702
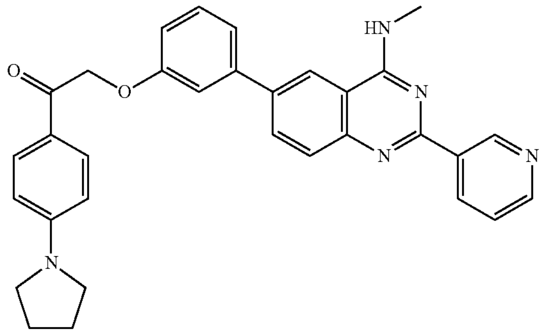 [SMILES: CNc1nc(-c2cccnc2)nc2ccc(-c3cccc(OCC(=O)c4ccc(N5CCCC5)cc4)c3)cc12]
1703
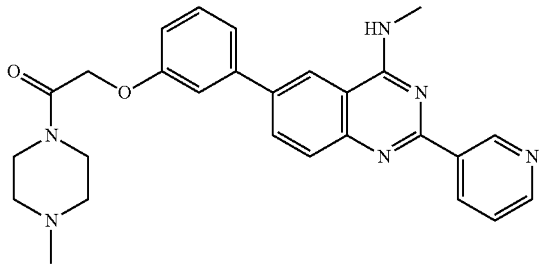 [SMILES: CNc1nc(-c2cccnc2)nc2ccc(-c3cccc(OCC(=O)N4CCN(C)CC4)c3)cc12]
1704
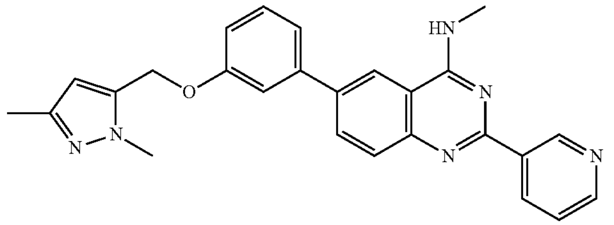 [SMILES: CNc1nc(-c2cccnc2)nc2ccc(-c3cccc(OCc4cc(C)nn4C)c3)cc12]
1705
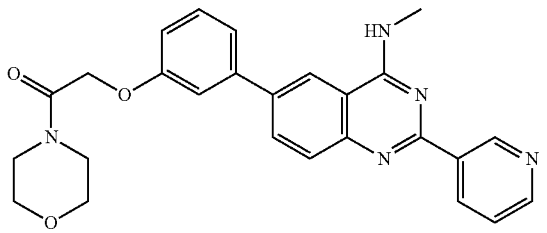 [SMILES: CNc1nc(-c2cccnc2)nc2ccc(-c3cccc(OCC(=O)N4CCOCC4)c3)cc12]

TABLE 28-continued
1706
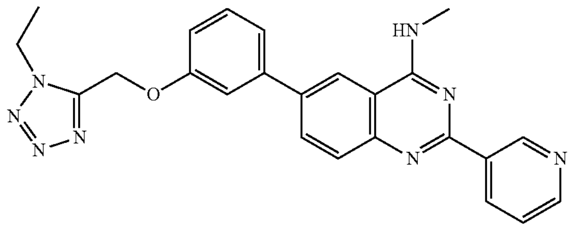 [SMILES: CCn1nnnc1COc1cccc(-c2ccc3nc(-c4cccnc4)nc(NC)c3c2)c1]
1707
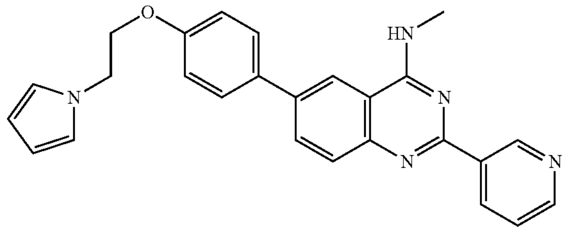 [SMILES: CNc1nc(-c2cccnc2)nc2ccc(-c3ccc(OCCn4cccc4)cc3)cc12]
1708
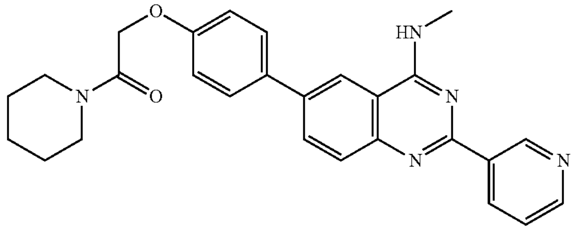 [SMILES: CNc1nc(-c2cccnc2)nc2ccc(-c3ccc(OCC(=O)N4CCCCC4)cc3)cc12]
1709
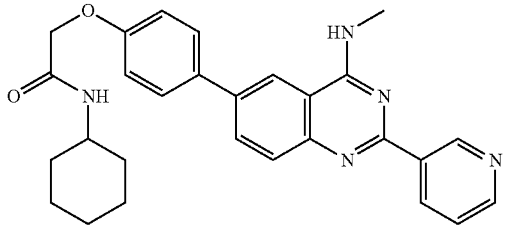 [SMILES: CNc1nc(-c2cccnc2)nc2ccc(-c3ccc(OCC(=O)NC4CCCCC4)cc3)cc12]
1710
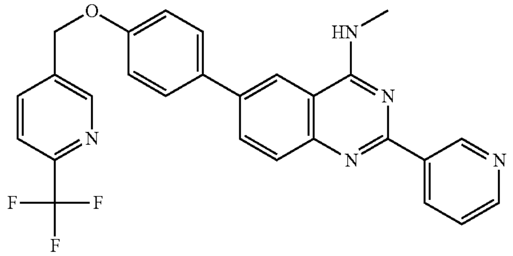 [SMILES: CNc1nc(-c2cccnc2)nc2ccc(-c3ccc(OCc4ccc(C(F)(F)F)nc4)cc3)cc12]
1711
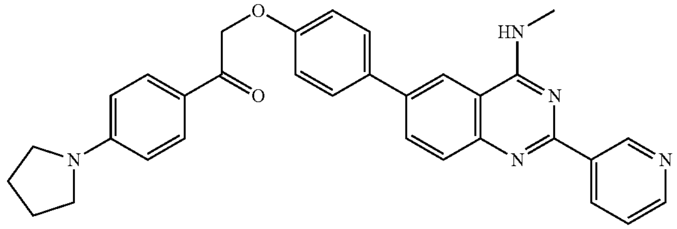 [SMILES: CNc1nc(-c2cccnc2)nc2ccc(-c3ccc(OCC(=O)c4ccc(N5CCCC5)cc4)cc3)cc12]

TABLE 28-continued
1712 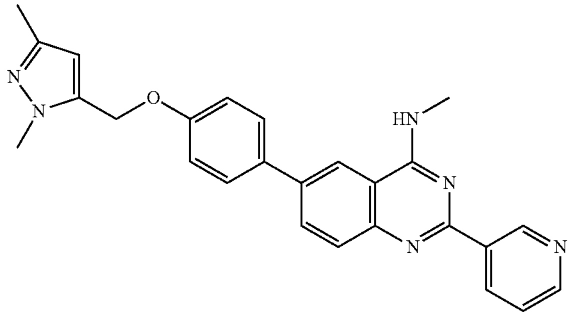 [SMILES: CNc1nc(-c2cccnc2)nc2ccc(-c3ccc(OCc4cc(C)nn4C)cc3)cc12]
1713 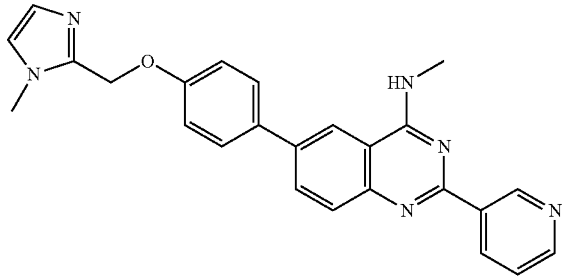 [SMILES: CNc1nc(-c2cccnc2)nc2ccc(-c3ccc(OCc4nccn4C)cc3)cc12]
1714 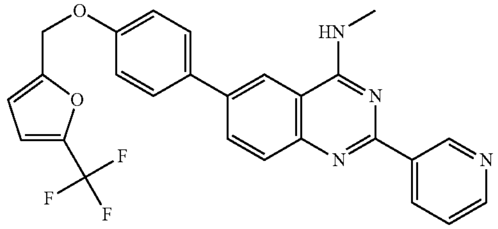 [SMILES: CNc1nc(-c2cccnc2)nc2ccc(-c3ccc(OCc4ccc(C(F)(F)F)o4)cc3)cc12]
1715 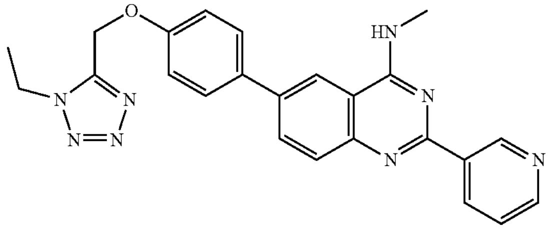 [SMILES: CCn1nnnc1COc1ccc(-c2ccc3nc(-c4cccnc4)nc(NC)c3c2)cc1]
| Number | Salt Type | Exact Mass | Mass Found (M + 1) | Purity (%) |
|---|---|---|---|---|
| 1699 | | 427 | 428 | 98 |
| 1700 | | 421 | 422 | 98 |
| 1701 | TFA | 467 | 468 | 98 |
| 1702 | | 515 | 516 | 98 |
| 1703 | 2TFA | 468 | 469 | 98 |
| 1704 | TFA | 436 | 437 | 98 |
| 1705 | | 455 | 456 | 98 |
| 1706 | | 438 | 439 | 98 |
| 1707 | | 421 | 422 | 98 |
| 1708 | | 453 | 454 | 98 |
| 1709 | TFA | 467 | 468 | 98 |
| 1710 | | 487 | 488 | 98 |
| 1711 | TFA | 515 | 516 | 98 |
| 1712 | TFA | 436 | 437 | 98 |
| 1713 | TFA | 422 | 423 | 98 |
| 1714 | TFA | 476 | 477 | 98 |
| 1715 | 2TFA | 438 | 439 | 98 |

Scheme 85: General route for the synthesis of compounds with general formula lxxi

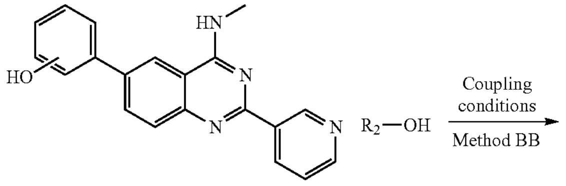

vi

-continued

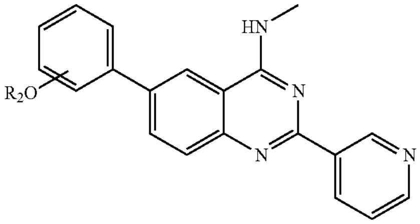

lxxi

Scheme 86: Representative synthesis of compounds of formula lxxi (see Scheme 85)

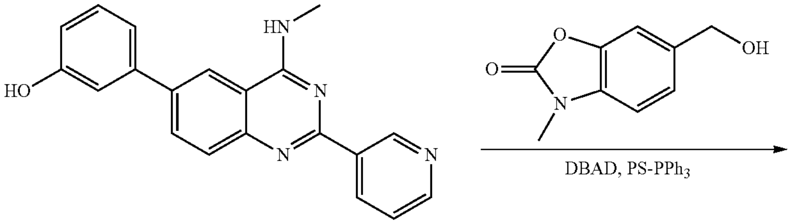

vi-v

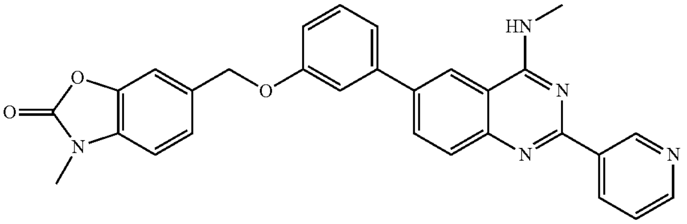

lxxi-b

Method BB: Synthesis of 3-methyl-6-((3-(4-(methylamino)-2-(pyridin-3-yl)quinazolin 6-yl)phenoxy)methyl)benzo[d]oxazol-2(3H)-one (lxxi-b)

To 6-(hydroxymethyl)-3-methylbenzo[d]oxazol-2(3H)-one (45.1 μmol) was added the solution of 3-(4-(methylamino)-2-(pyridin-3-yl)quinazolin-6-yl)phenol (30 μmol) in THF (400 μL). After PS-triphenylphosphine (60 μmol) was added, the solution of DBAD (di-tert-butyl azodicarboxylate, 66 mmol) in THF was dispensed to the vials. The mixture was heated at 50° C. for 8 h. After the solvent was removed, the residue was diluted with methanol and purified by Mass triggered PREP-HPLC Condition D. The target fraction was lyophilized to afford the titled compound whose structure was finally confirmed by LCMS using LCMS Method E.

The compounds in the following table were prepared in a manner analogous to that described in Scheme 85, replacing 6-(hydroxymethyl)-3-methylbenzo[d]oxazol-2(3H)-one with the appropriate alkyl alcohol.

TABLE 29

| Number | Starting Material 1 | Starting Material 2 |
|---|---|---|
| 1716 | 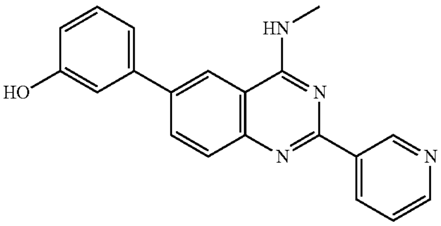 [SMILES: CNc1nc(-c2cccnc2)nc2ccc(-c3cccc(O)c3)cc12] | 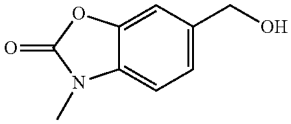 |

TABLE 29-continued
| | | |
|---|---|---|
| 1717 | 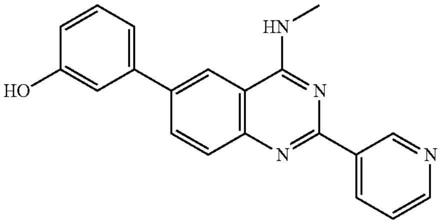 [SMILES: CNc1nc(-c2cccnc2)nc2ccc(-c3cccc(O)c3)cc12] | 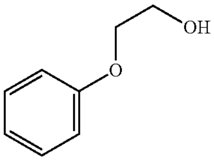 |
| 1718 | 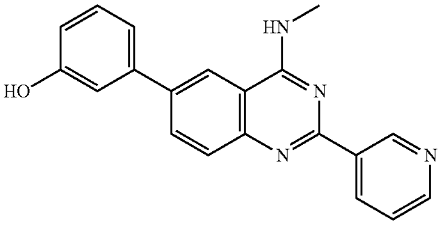 [SMILES: CNc1nc(-c2cccnc2)nc2ccc(-c3cccc(O)c3)cc12] | 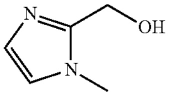 |
| 1719 | 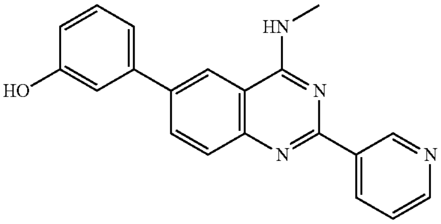 [SMILES: CNc1nc(-c2cccnc2)nc2ccc(-c3cccc(O)c3)cc12] | 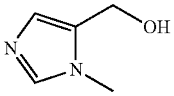 |
| 1720 | 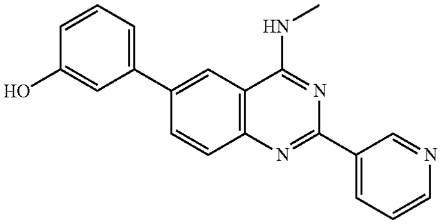 [SMILES: CNc1nc(-c2cccnc2)nc2ccc(-c3cccc(O)c3)cc12] | 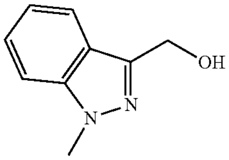 |
| 1721 | 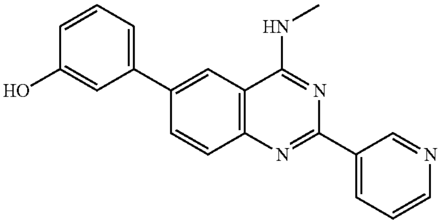 [SMILES: CNc1nc(-c2cccnc2)nc2ccc(-c3cccc(O)c3)cc12] | 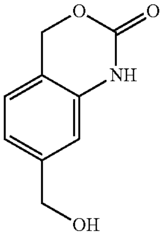 [SMILES: O=C1Nc2cc(CO)ccc2CO1] |
| 1722 | 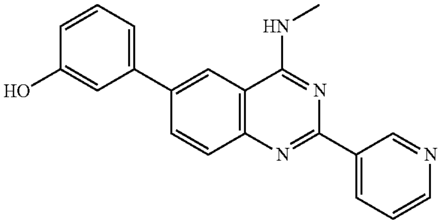 [SMILES: CNc1nc(-c2cccnc2)nc2ccc(-c3cccc(O)c3)cc12] | 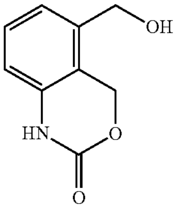 [SMILES: O=C1Nc2cccc(CO)c2CO1] |

TABLE 29-continued
| | | |
|---|---|---|
| 1723 | 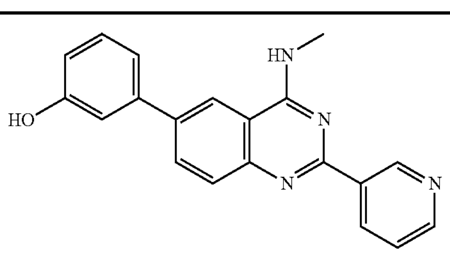 | 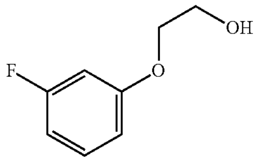 [SMILES: OCCOc1cccc(F)c1] |
| 1724 | 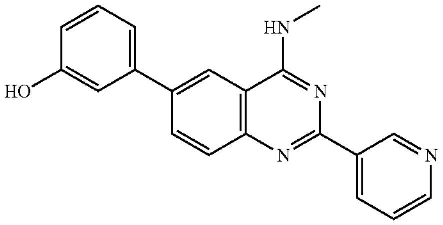 [SMILES: CNc1nc(-c2cccnc2)nc2ccc(-c3cccc(O)c3)cc12] | 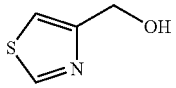 |
| 1725 | 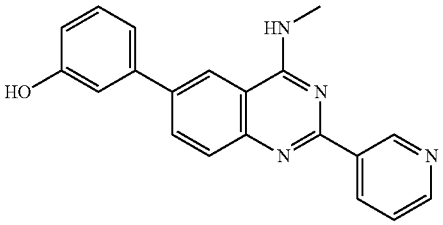 [SMILES: CNc1nc(-c2cccnc2)nc2ccc(-c3cccc(O)c3)cc12] | 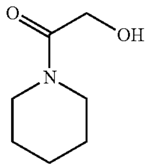 |
| 1726 | 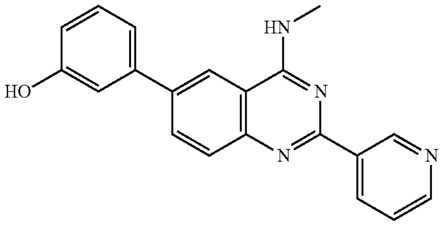 [SMILES: CNc1nc(-c2cccnc2)nc2ccc(-c3cccc(O)c3)cc12] | 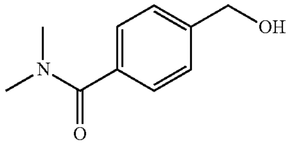 |
| 1727 | 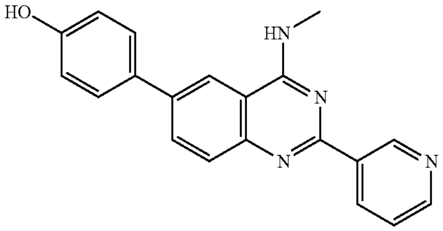 [SMILES: CNc1nc(-c2cccnc2)nc2ccc(-c3ccc(O)cc3)cc12] | 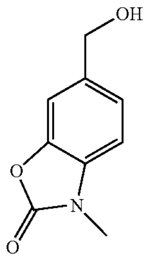 |
| 1728 | 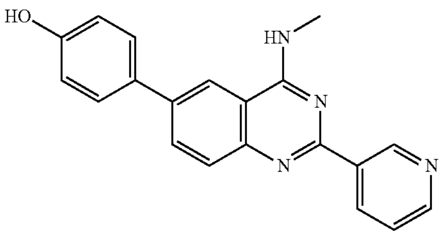 [SMILES: CNc1nc(-c2cccnc2)nc2ccc(-c3ccc(O)cc3)cc12] | 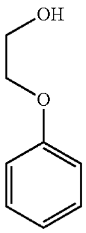 |

TABLE 29-continued
| | | |
|---|---|---|
| 1729 | 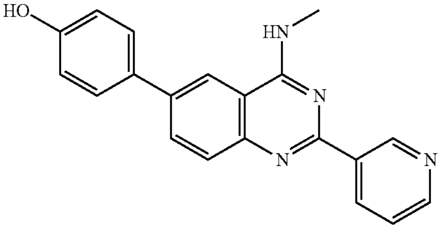 [SMILES: CNc1nc(-c2cccnc2)nc2ccc(-c3ccc(O)cc3)cc12] | 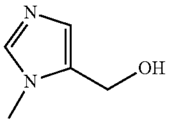 |
| 1730 | 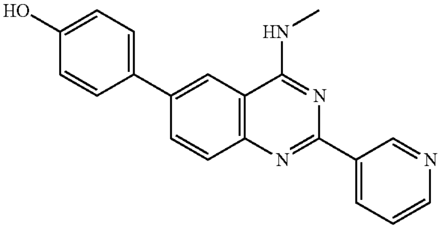 [SMILES: CNc1nc(-c2cccnc2)nc2ccc(-c3ccc(O)cc3)cc12] | 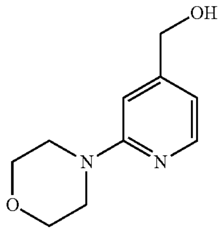 [SMILES: OCc1ccnc(N2CCOCC2)c1] |
| 1731 | 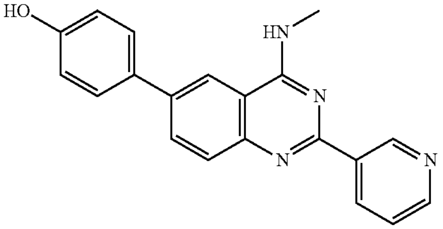 [SMILES: CNc1nc(-c2cccnc2)nc2ccc(-c3ccc(O)cc3)cc12] | 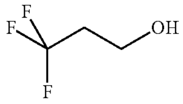 |
| 1732 | 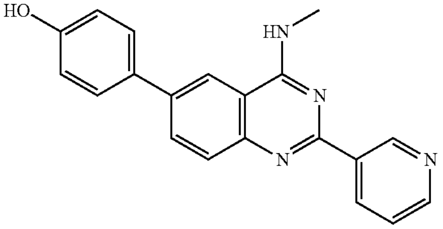 [SMILES: CNc1nc(-c2cccnc2)nc2ccc(-c3ccc(O)cc3)cc12] | 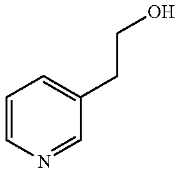 |
| 1733 | 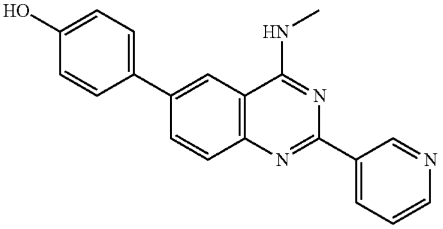 [SMILES: CNc1nc(-c2cccnc2)nc2ccc(-c3ccc(O)cc3)cc12] | 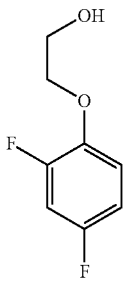 |
| 1734 | 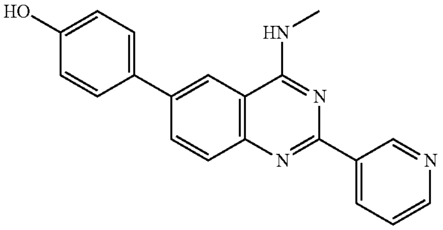 [SMILES: CNc1nc(-c2cccnc2)nc2ccc(-c3ccc(O)cc3)cc12] | 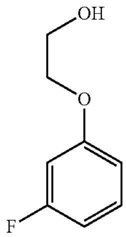 |

TABLE 29-continued
| | | |
|---|---|---|
| 1735 | 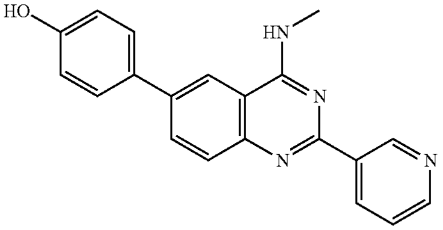 [SMILES: CNc1nc(-c2cccnc2)nc2ccc(-c3ccc(O)cc3)cc12] | 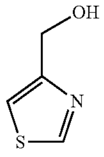 |
| 1736 | 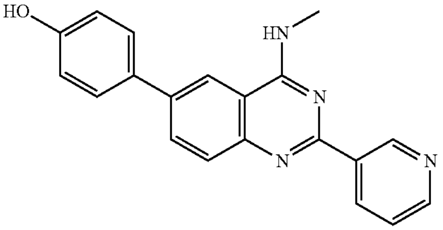 [SMILES: CNc1nc(-c2cccnc2)nc2ccc(-c3ccc(O)cc3)cc12] | 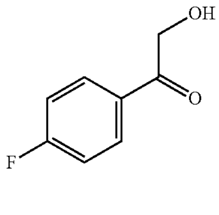 |
| 1737 | 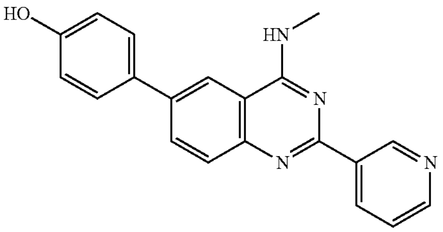 [SMILES: CNc1nc(-c2cccnc2)nc2ccc(-c3ccc(O)cc3)cc12] | 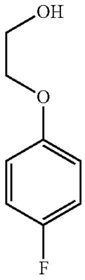 [SMILES: OCCOc1ccc(F)cc1] |
| 1738 | 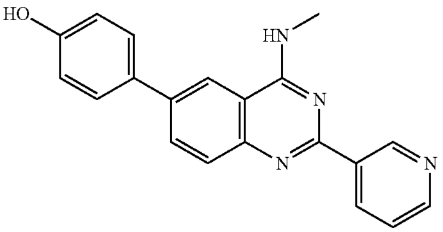 [SMILES: CNc1nc(-c2cccnc2)nc2ccc(-c3ccc(O)cc3)cc12] | 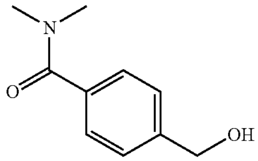 |
| Number | Product |
|---|---|
| 1716 | 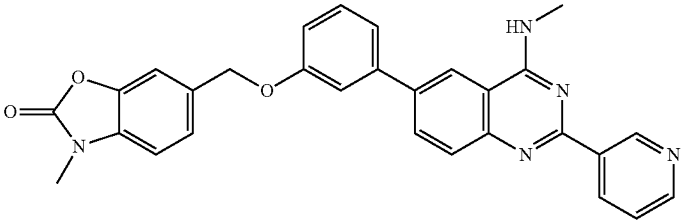 [SMILES: CNc1nc(-c2cccnc2)nc2ccc(-c3cccc(OCc4ccc5c(c4)oc(=O)n5C)c3)cc12] |
| 1717 | 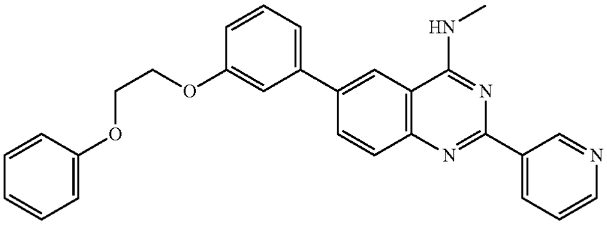 [SMILES: CNc1nc(-c2cccnc2)nc2ccc(-c3cccc(OCCOc4ccccc4)c3)cc12] |

TABLE 29-continued
1718
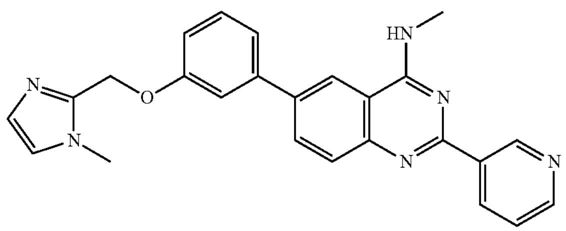 [SMILES: CNc1nc(-c2cccnc2)nc2ccc(-c3cccc(OCc4nccn4C)c3)cc12]
1719
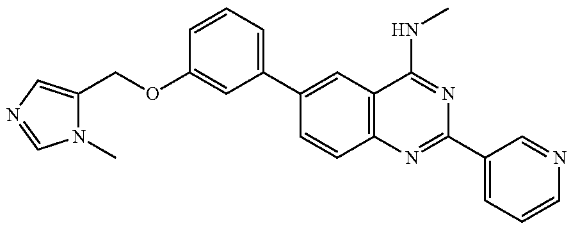 [SMILES: CNc1nc(-c2cccnc2)nc2ccc(-c3cccc(OCc4cncn4C)c3)cc12]
1720
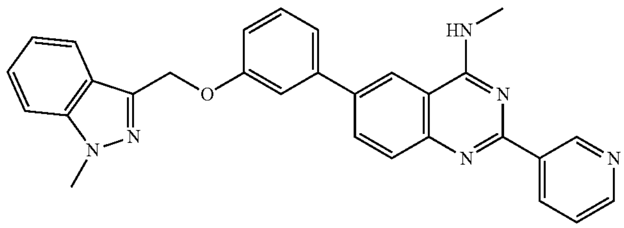 [SMILES: CNc1nc(-c2cccnc2)nc2ccc(-c3cccc(OCc4nn(C)c5ccccc45)c3)cc12]
1721
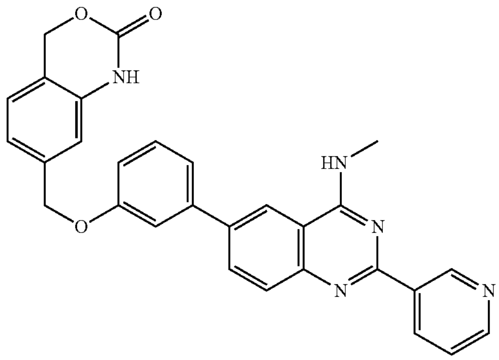 [SMILES: CNc1nc(-c2cccnc2)nc2ccc(-c3cccc(OCc4ccc5c(c4)NC(=O)OC5)c3)cc12]
1722
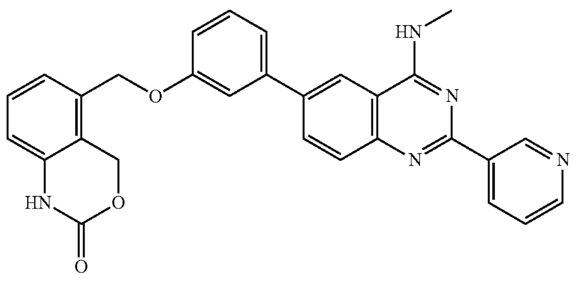 [SMILES: CNc1nc(-c2cccnc2)nc2ccc(-c3cccc(OCc4cccc5c4COC(=O)N5)c3)cc12]
1723
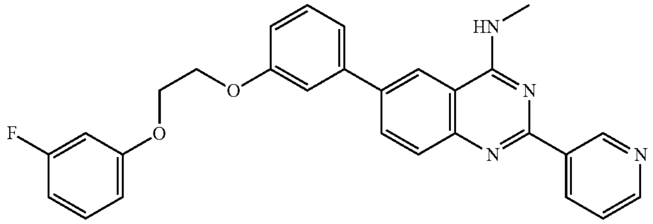 [SMILES: CNc1nc(-c2cccnc2)nc2ccc(-c3cccc(OCCOc4cccc(F)c4)c3)cc12]

TABLE 29-continued
1724
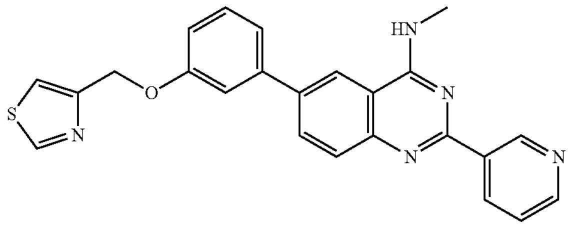 [SMILES: CNc1nc(-c2cccnc2)nc2ccc(-c3cccc(OCc4cscn4)c3)cc12]
1725
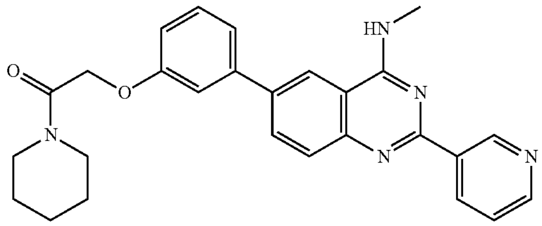 [SMILES: CNc1nc(-c2cccnc2)nc2ccc(-c3cccc(OCC(=O)N4CCCCC4)c3)cc12]
1726
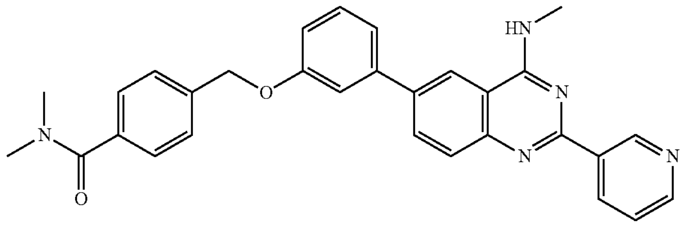 [SMILES: CNc1nc(-c2cccnc2)nc2ccc(-c3cccc(OCc4ccc(C(=O)N(C)C)cc4)c3)cc12]
1727
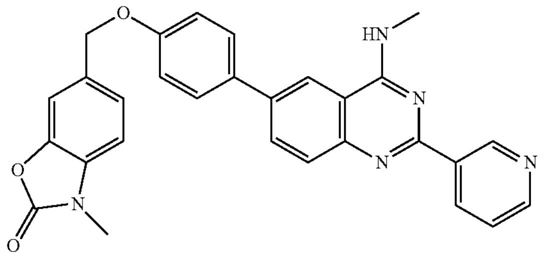 [SMILES: CNc1nc(-c2cccnc2)nc2ccc(-c3ccc(OCc4ccc5c(c4)oc(=O)n5C)cc3)cc12]
1728
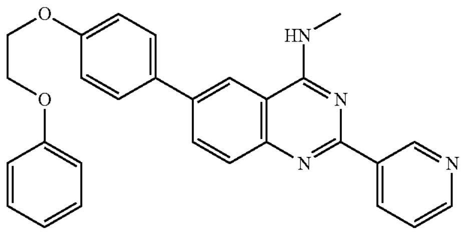 [SMILES: CNc1nc(-c2cccnc2)nc2ccc(-c3ccc(OCCOc4ccccc4)cc3)cc12]
1729
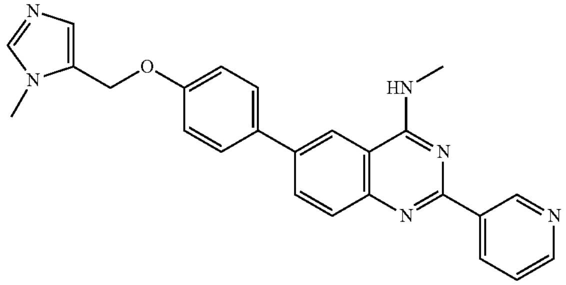 [SMILES: CNc1nc(-c2cccnc2)nc2ccc(-c3ccc(OCc4cncn4C)cc3)cc12]

TABLE 29-continued
1730 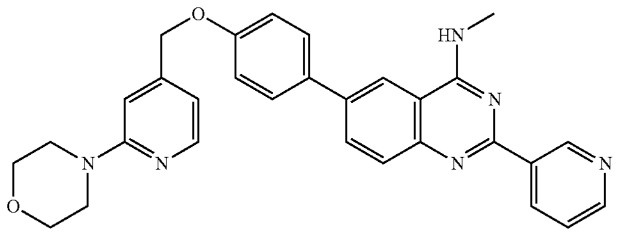 [SMILES: CNc1nc(-c2cccnc2)nc2ccc(-c3ccc(OCc4ccnc(N5CCOCC5)c4)cc3)cc12]
1731 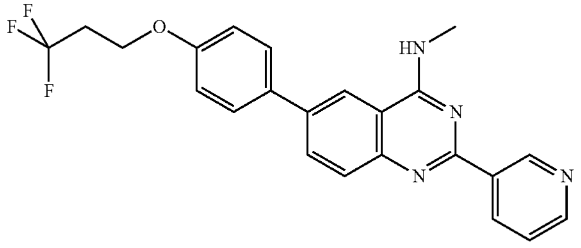 [SMILES: CNc1nc(-c2cccnc2)nc2ccc(-c3ccc(OCCC(F)(F)F)cc3)cc12]
1732 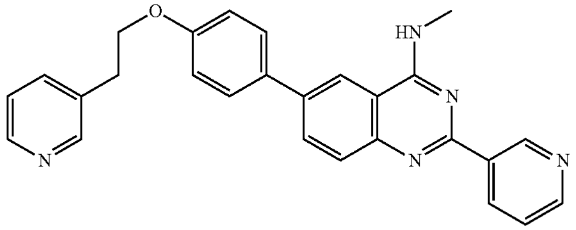 [SMILES: CNc1nc(-c2cccnc2)nc2ccc(-c3ccc(OCCc4cccnc4)cc3)cc12]
1733 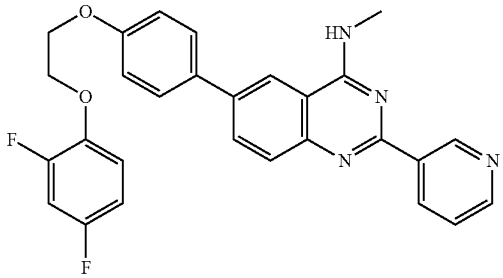 [SMILES: CNc1nc(-c2cccnc2)nc2ccc(-c3ccc(OCCOc4ccc(F)cc4F)cc3)cc12]
1734 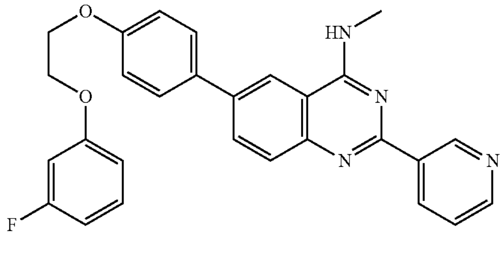 [SMILES: CNc1nc(-c2cccnc2)nc2ccc(-c3ccc(OCCOc4cccc(F)c4)cc3)cc12]
1735 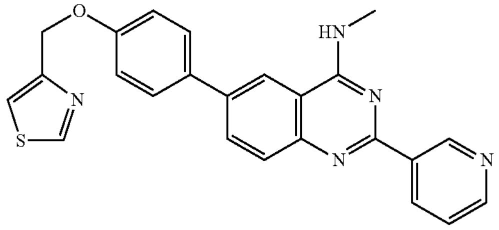 [SMILES: CNc1nc(-c2cccnc2)nc2ccc(-c3ccc(OCc4cscn4)cc3)cc12]

TABLE 29-continued
1736
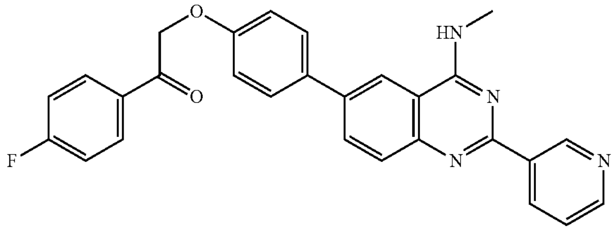 [SMILES: CNc1nc(-c2cccnc2)nc2ccc(-c3ccc(OCC(=O)c4ccc(F)cc4)cc3)cc12]
1737
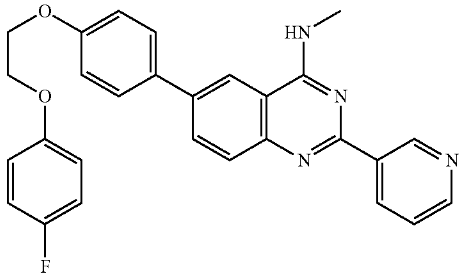 [SMILES: CNc1nc(-c2cccnc2)nc2ccc(-c3ccc(OCCOc4ccc(F)cc4)cc3)cc12]
1738
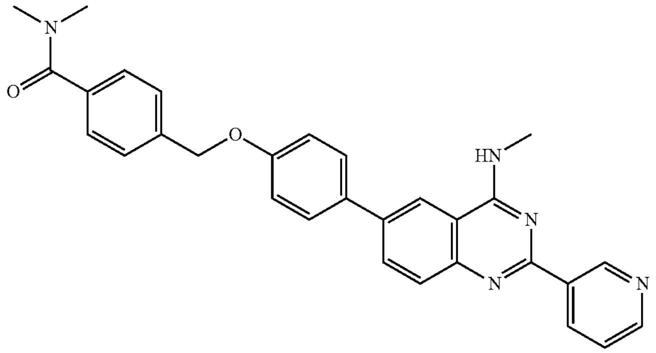 [SMILES: CNc1nc(-c2cccnc2)nc2ccc(-c3ccc(OCc4ccc(C(=O)N(C)C)cc4)cc3)cc12]
| Number | Salt Type | Exact Mass | Mass Found (M + 1) | Purity (%) |
|---|---|---|---|---|
| 1716 | TFA | 489 | 490 | 100 |
| 1717 | TFA | 448 | 449 | 100 |
| 1718 | TFA | 422 | 423 | 100 |
| 1719 | TFA | 422 | 423 | 100 |
| 1720 | TFA | 472 | 473 | 100 |
| 1721 | TFA | 489 | 490 | 100 |
| 1722 | TFA | 489 | 490 | 100 |
| 1723 | TFA | 466 | 467 | 100 |
| 1724 | TFA | 425 | 426 | 94 |
| 1725 | TFA | 453 | 454 | 100 |
| 1726 | TFA | 489 | 490 | 100 |
| 1727 | TFA | 489 | 490 | 100 |
| 1728 | TFA | 448 | 449 | 100 |
| 1729 | TFA | 422 | 423 | 100 |
| 1730 | TFA | 504 | 505 | 100 |
| 1731 | TFA | 424 | 425 | 100 |
| 1732 | TFA | 433 | 434 | 100 |
| 1733 | TFA | 484 | 485 | 100 |
| 1734 | TFA | 466 | 467 | 100 |
| 1735 | TFA | 425 | 426 | 100 |
| 1736 | TFA | 464 | 465 | 95 |
| 1737 | TFA | 466 | 467 | 100 |
| 1738 | TFA | 489 | 490 | 100 |

Scheme 87: Synthesis of N-(6-bromo-2-(pyridin-3-yl)quinazolin-4-yl) acetamide with formula lxxii (Compound 1739)

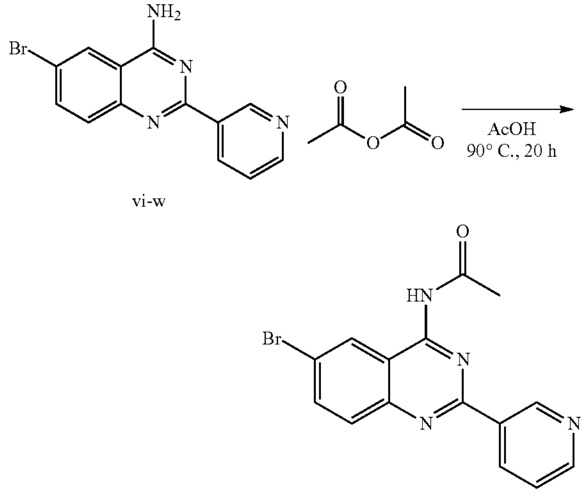

vi-w lxxii-a

Synthesis of N-(6-bromo-2-(pyridin-3-yl)quinazolin-4-yl)acetamide (lxxii-a)

A 100 mL round bottom flask was fitted with a reflux condenser and charged with 6-bromo-2-(pyridin-3-yl) quinazolin-4-amine (2.45 g, 8.14 mmol), acetic anhydride (5.81 g, 57.0 mmol) and acetic acid (30 mL). The reaction mixture was stirred at 90° C. for 20 min and then cooled to room temperature. A precipitate formed during the reaction and was collected by filtration and washed with water (100 mL). The solid was dried at 60° C. to give N-(6-bromo-2-(pyridin-3-yl)quinazolin-4-yl)acetamide as a white powder (1.83 g, 66%). $^1$H NMR (300 MHz, $CDCl_3$) δ 9.72 (s, 1H), 8.84-8.69 (m, 3H), 8.22 (s, 1H), 8.02-7.90 (m, 2H), 7.53-7.41 (m, 1H), 2.83 (s, 3H).

Scheme 88: Synthesis of N-(6-bromo-2-(pyridin-3-yl)quinazolin-4-yl)-N-methylacetamide with formula lxxiii (Compound 1740)

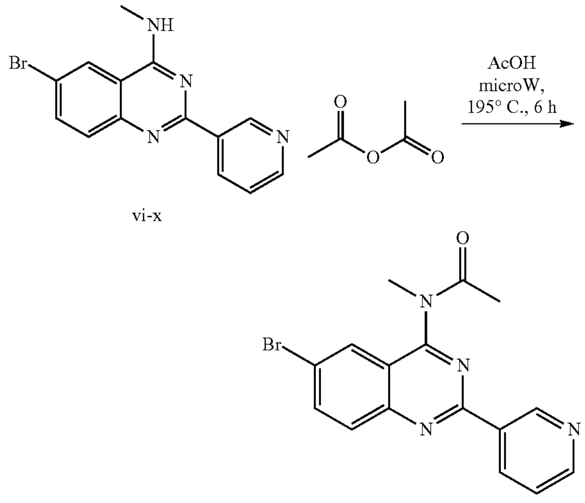

vi-x lxxiii-a

Synthesis of N-(6-bromo-2-(pyridin-3-yl)quinazolin-4-yl)-N-methylacetamide (lxxiii-a)

To a solution of 6-bromo-N-methyl-2-(pyridin-3-yl) quinazolin-4-amine (1.20 g, 3.81 mmol) in acetic acid (10 mL) was added acetic anhydride (1.94 g, 19.0 mmol) and stirred at 195° C. using microwave for 6 h. The reaction mixture was checked by LC-MS, no starting material was observed, ice was added into the reaction. The precipitate was collected by filtration and washed with water. The product was dried at 60° C. to give N-(6-bromo-2-(pyridin-3-yl) quinazolin-4-yl)-N-methylacetamide (711 mg, 52%) as a light brown powder. $^1$H NMR (300 MHz, $CDCl_3$) δ 9.76 (dd, J=2.2, 0.8 Hz, 1H), 8.85-8.79 (m, 1H), 8.76 (dd, J=4.8, 1.7 Hz, 1H), 8.09 (dd, J=1.8, 0.8 Hz, 1H), 8.05-8.01 (m, 2H), 7.46 (ddd, J=8.0, 4.8, 0.8 Hz, 1H), 3.52 (s, 3H), 2.11 (s, 3H).

Scheme 89: Synthesis of compounds of formula lxxv

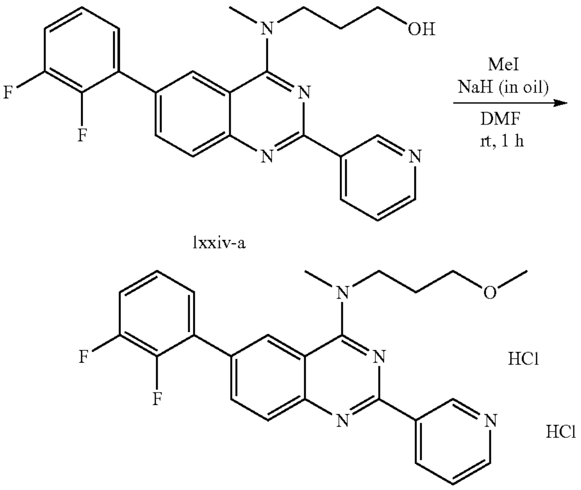

lxxiv-a lxxv-a

Method BC: Synthesis of 6-(2,3-difluorophenyl)-N-(3-methoxypropyl)-N-methyl-2-(pyridin-3-yl) quinazolin-4-amine dihydrochloride (lxxv-a) (Compound 1742)

To a solution of the hydroxyl derivative (520 mg, 1.27 mmol) in DMF (20 mL) was added methyl iodide (262 mg, 1.84 mmol) and NaH (55% in oil; 69 mg, 1.9 mmol) at 0° C. The reaction mixture was stirred at room temperature for 1 h and the ice water was added into the reaction mixture. The resulting solution was extracted with ethyl acetate (3 times), dried over $Na_2SO_4$, concentrated and purified by column chromatography (NH-silica gel, 50% hexane/50% ethyl acetate). The resulting product was dissolved in isopropyl alcohol and 1N—HCl (5 mL) was added and a precipitate formed which was collected by filtration and dried at 60° C. to give 6-(2,3-difluorophenyl)-N-(3-methoxypropyl)-N-methyl-2-(pyridin-3-yl)quinazolin-4-amine dihydrochloride as an orange powder (130 mg, 21%). $^1$H NMR (300 MHz, DMSO) δ 9.66 (d, J=1.6 Hz, 1H), 9.09 (d, J=8.1 Hz, 1H), 8.96 (dd, J=5.1, 1.5 Hz, 1H), 8.51 (s, 1H), 8.33 (d, J=8.7 Hz, 1H), 8.20 (d, J=8.8 z, 1H), 7.90 (dd, J=8.1, 5.1 Hz, 1H), 7.66-7.47 (m, 2H), 7.47-7.32 (m, 1H), 4.22-4.07 (m, 2H), 3.70 (s, 3H), 3.48 (t, J=5.8 Hz, 2H), 3.22 (s, 3H), 2.19-2.01 (m, 2H).

Scheme 90: Synthesis of 2-(3-(4-(dimethylamino)-2-(pyridin-3-yl)quinazolin-6-yl)phenyl)ethanol of formula lxxvi (Compound 1743)

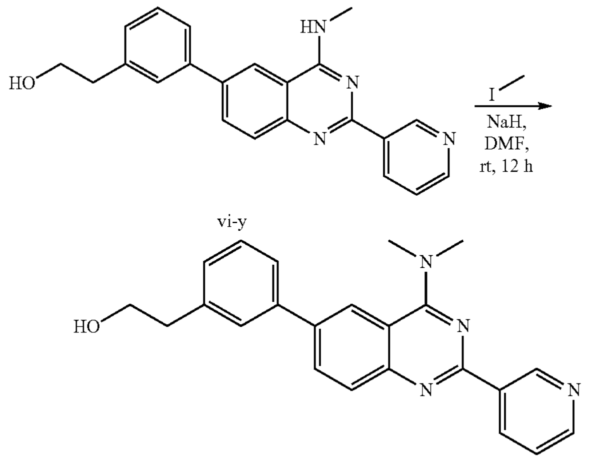

vi-y lxxvi-a

Method BD: 2-(3-(4-(dimethylamino)-2-(pyridin-3-yl)quinazolin-6-yl)phenyl)ethanol, 2HCl (lxxvi-a)

To a reaction vial containing 2-(3-(4-(methylamino)-2-(pyridin-3-yl)quinazolin-6-yl)phenyl)ethanol (89.0 mg, 0.25 mmol) in DMF (1 ml) was added 60% sodium hydride (13 mg, 0.325 mmol) and iodomethane (0.02 mL, 0.325 mmol). The reaction mixture was allowed to stir at ambient temperature for 12 h. Water (20 ml) was added to the reaction mixture, and the crude product was extracted with ethyl acetate (4×15 mL). The crude material was purified via ISCO (silica, 4 g column, 95% $CH_2Cl_2$-5% MeOH-0.1% $NH_4OH$) to give the product as an off-white solid. The free base was then converted to the HCl salt to yield the final product as a yellow solid (24.6 mg, 0.055 mmol, 22%). LC-MS m/z=371.5 (M+1) (retention time=1.86) $^1$H NMR (300 MHz, DMSO) δ 9.61 (d, J=211 Hz, 1H), 8.99 (d, J=7.5 Hz, 1H), 8.93 (dd, J=5.0, 1.5 Hz, 1H), 8.48 (d, J=1.0 Hz, 1H), 8.28 (dd, J=17.4, 9.4 Hz, 2H), 7.84 (dd, J=7.7, 5.1 Hz, 1H), 7.69-7.60 (m, 2H), 7.44 (t, J=7.5 Hz, 1H), 7.30 (d, J=7.3 Hz, 1H), 3.78-3.61 (m, 9H), 2.82 (t, J=7.0 Hz, 2H).

Synthesis of 6-(2,4-difluorophenyl)-N-(3-methoxypropyl)-N-methyl-2-(pyridin-3-yl)quinazolin-4-amine dihydrochloride (lxxvii-a) (Compound 1744)

6-(2,4-difluorophenyl)-N-(3-methoxypropyl)-N-methyl-2-(pyridin-3-yl)quinazolin-4-amine dihydrochloride was synthesized in a similar manner to that described for 6-(2,3-difluorophenyl)-N-(3-methoxypropyl)-N-methyl-2-(pyridin-3-yl)quinazolin-4-amine dihydrochloride substituting the appropriate hydroxyl derivative. 6-(2,4-difluorophenyl)-N-(3-methoxypropyl)-N-methyl-2-(pyridin-3-yl)quinazolin-4-amine was obtained as the dihydrochloride salt $^1$H NMR (300 MHz, DMSO) δ 9.69 (d, J=2.0 Hz, 1H), 9.14 (d, J=8.3 Hz, 1H), 8.97 (dd, J=5.1, 1.2 Hz, 1H), 8.45 (s, 1H), 8.39 (d, J=8.6 Hz, 1H), 8.17 (d, J=8.8 Hz, 1H), 7.92 (dd, J=8.0, 5.2 Hz, 1H), 7.86-7.73 (m, 1H), 7.57-7.38 (m, 1H), 7.36-7.23 (m, 1H), 4.19-4.04 (m, 2H), 3.71 (s, 3H), 3.48 (t, J=5.7 Hz, 2H), 3.23 (s, 3H), 2.21-1.96 (m, 2H).

Scheme 91: Synthesis of compounds of formula lxxviii

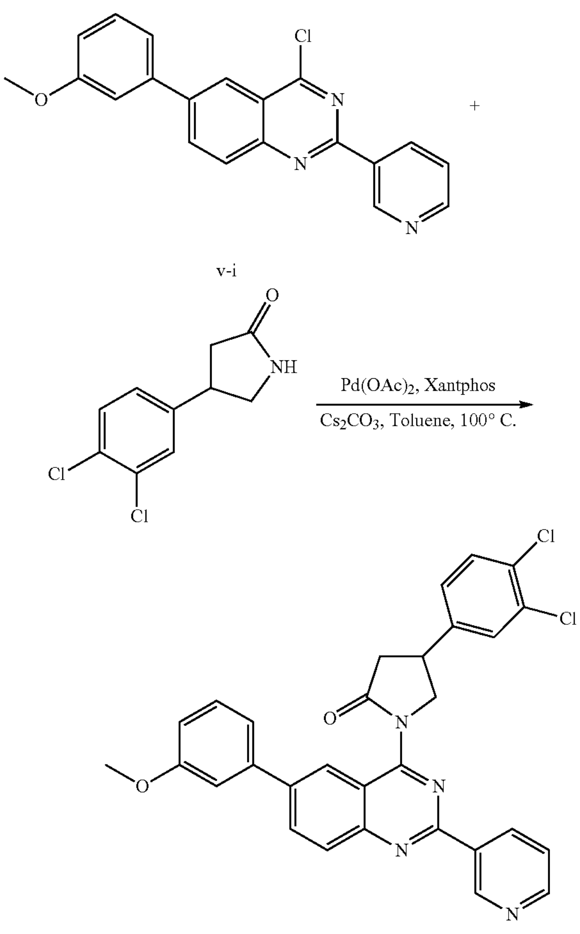

v-i lxxviii-a

Method BE: 4-(3,4-dichlorophenyl)-1-(6-(3-methoxyphenyl)-2-(pyridin-3-yl)quinazolin-4-yl)pyrrolidin-2-one (lxxviii-a)

To a mixture of 4-chloro-6-(3-methoxyphenyl)-2-(pyridin-3-yl)quinazoline (40 mg, 0.12 mmol), 4-(3,4-dichlorophenyl)pyrrolidin-2-one (100 mg, 0.437 mmol) and $Cs_2CO_3$ (42 mg, 0.127 mmol) in dry toluene (6 mL) was added $Pd(OAc)_2$ (3 mg, 0.01 mmol) and Xantphos (10 mg, 0.02 mmol) under a nitrogen atmosphere. The resulting mixture was stirred at 100° C. for 12 h. After cooling, the mixture was filtered through a pad of celite. The residue was purified by silica gel chromatography, eluted with petroleum ether/ethyl acetate (5:4) to give the desired product as a yellow solid. 14 mg of the desired product was obtained in a 22.5% yield, LCMS: retention time=1.802 min, $[MH]^+$=541.0, 543.0. $^1$H-NMR (400 MHz, DMSO-$d_6$): δ 9.73 (s, 1H), 9.05-9.04 (m, 1H), 8.86-8.85 (m, 1H), 8.42-8.38 (m, 2H), 8.19 (d, J=8.8 Hz, 1H), 7.89 (d, J=1.6 Hz, 1H), 7.82-7.81 (m, 1H), 7.69 (d, J=8.0 Hz, 1H), 7.58 (dd, J=8.0, 1.6 Hz, 1H), 7.50 (t, J=8.0 Hz, 1H), 7.41-7.36 (m, 2H), 7.07 (dd, J=8.0, 2.0 Hz, 1H), 4.57-4.46 (m, 2H), 4.06-4.03 (m, 1H), 3.20-3.01 (m, 2H), 3.88 (s, 3H).

The compounds in the following table were prepared in a manner analogous to that described in Scheme 91, replacing 4-(3,4-dichlorophenyl)pyrrolidin-2-one with the appropriate amide TABLE 30
| Number | Product | Salt type | $^1$H NMR | $^1$H NMR Solvent | Purity percent | Method of Coupling | LCMS | LCMS Method |
|---|---|---|---|---|---|---|---|---|
| 1745 | 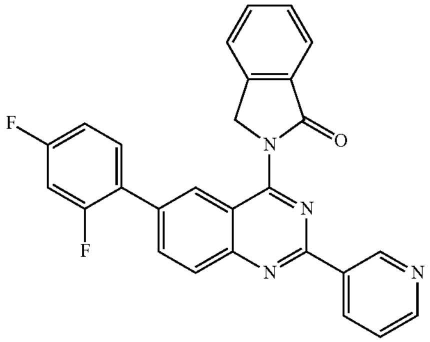 [SMILES: O=C1c2ccccc2CN1c1nc(-c2cccnc2)nc2ccc(-c3ccc(F)cc3F)cc12] | | $^1$H-NMR (400 MHz, DMSO-$d_6$): δ 9.75 (s, 1H), 8.90 (d, J = 8.0 Hz, 1H), 8.78 (d, J = 4.0 Hz, 1H), 8.35 (s, 1H), 8.28-8.19 (m, 2H), 7.92 (d, J = 7.6 Hz, 1H), 7.82 (d, J = 5.0 Hz, 2H), 7.73-7.70 (m, 1H), 7.68-7.61 (m, 2H), 7.52-7.42 (m, 1H), 7.29 (t, J = 8.4 Hz, 1H), 5.61 (s, 2H). | DMSO | 95 | Method BE | 451.0 (M + 1) | Method B ($NH_4HCO_3$) |
| 1746 | 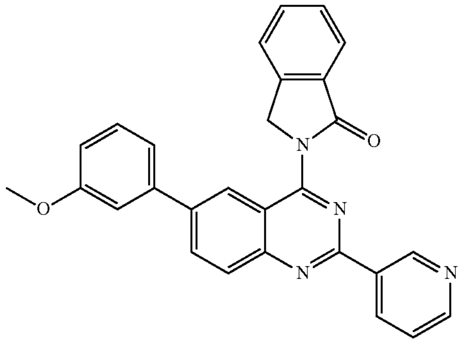 [SMILES: COc1cccc(-c2ccc3nc(-c4cccnc4)nc(N4Cc5ccccc5C4=O)c3c2)c1] | | $^1$H-NMR (400 MHz, DMSO-$d_6$): δ 9.74 (s, 1H), 8.89 (d, J = 8.0 Hz, 1H), 8.77 (d, J = 3.8 Hz, 1H), 8.45 (s, 1H), 8.39 (d, J = 8.7 Hz, 1H), 8.18 (d, J = 8.7 Hz, 1H), 7.94 (d, J = 7.6 Hz, 1H), 7.83 (s, 2H), 7.72-7.56 (m, 2H), 7.52-7.27 (m, 3H), 7.03 (d, J = 7.9 Hz, 1H), 5.60 (s, 2H), 3.85 (s, 3H). | DMSO | 95 | Method BE | 445.1 (M + 1) | Method B ($NH_4HCO_3$) |

TABLE 30-continued
| Number | Product | Salt type | $^{1}H$ NMR | $^{1}H$ NMR Solvent | Purity percent | Method of Coupling | LCMS | LCMS Method |
|---|---|---|---|---|---|---|---|---|
| 1747 | 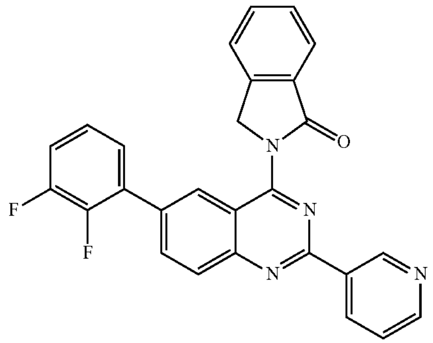 [SMILES: O=C1c2ccccc2CN1c1nc(-c2cccnc2)nc2ccc(-c3cccc(F)c3F)cc12] | | $^{1}H$-NMR (400 MHz, DMSO-$d_6$): δ 9.76 (s, 1H), 8.91 (d, J = 6.4 Hz, 1H), 8.79 (s, 1H), 8.41 (s, 1H), 8.30-8.23 (m, 2H), 7.92 (d, J = 8.0 Hz, 1H), 7.83 (s, 2H), 7.65 (d, J = 3.6 Hz, 2H), 7.55-7.49 (m, 2H), 7.40 (s, 1H), 5.61 (s, 2H). | DMSO | 95 | Method BE | 451.0, 452.0, (M + 1) | Method B ($NH_4HCO_3$) |
| 1748 | 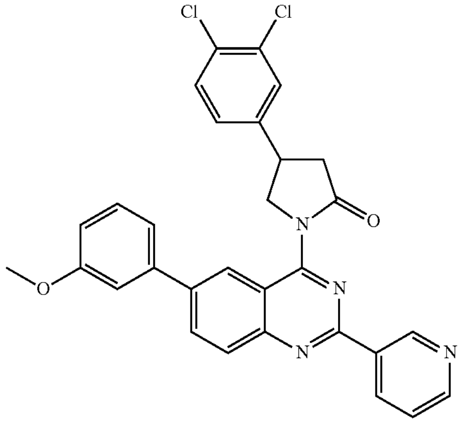 [SMILES: COc1cccc(-c2ccc3nc(-c4cccnc4)nc(N4CC(c5ccc(Cl)c(Cl)c5)CC4=O)c3c2)c1] | 2HCl | $^{1}H$-NMR (400 MHz, DMSO-$d_6$): δ 9.73 (s, 1H), 9.05-9.04 (m, 1H), 8.36-8.85 (m, 1H), 8.42-8.38 (m, 2H), 8.19 (d, J = 8.8 Hz, 1H), 7.89 (d, J = 1.6 Hz, 1H), 7.82-7.81 (m, 1H), 7.69 (d, J = 8.0 Hz, 1H), 7.58 (dd, J = 8.0, 1.6 Hz, 1H), 7.50 (t, J = 8.0 Hz, 1H), 7.41-7.36 (m, 2H), 7.07 (dd, J = 8.0, 2.0 Hz, 1H), 4.57-4.46 (m, 2H), 4.06-4.03 (m, 1H), 3.20-3.01 (m, 2H), 3.88 (s, 3H), | DMSO | 95 | Method BE | 541.0, 543.0 (M + 1) | Method B ($NH_4HCO_3$) |

TABLE 30-continued
| Number | Product | Salt type | $^1$H NMR | $^1$H NMR Solvent | Purity percent | Method of Coupling | LCMS | LCMS Method |
|---|---|---|---|---|---|---|---|---|
| 1749 | 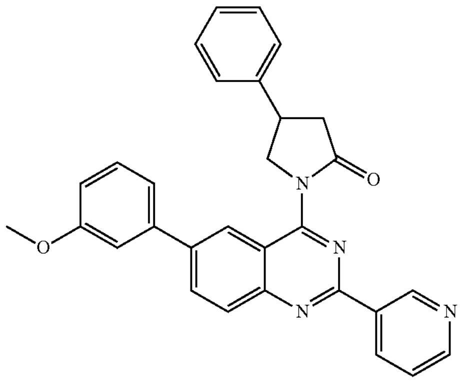 [SMILES: COc1cccc(-c2ccc3nc(-c4cccnc4)nc(N4CC(c5ccccc5)CC4=O)c3c2)c1] | 2HCl | $^1$H-NMR (400 MHz, DMSO-$d_6$): δ 9.68 (s, 1H), 8.83 (d, J = 8.0 Hz, 1H), 8.76 (s, 1H), 8.39-8.37 (m, 2H), 8.17 (d, J = 10.0 Hz, 1H), 7.63-7.31 (m, 9H), 7.06 (dd, J = 8.4, 2.0 Hz, 1H), 4.56-4.45 (m, 2H), 4.03-3.99 (m, 1H), 3.88 (s, 3H), 3.19-2.97 (m, 2H). | DMSO | 95 | Method BE | 472.9 (M + 1) | Method B ($NH_4HCO_3$) |
| 1750 | 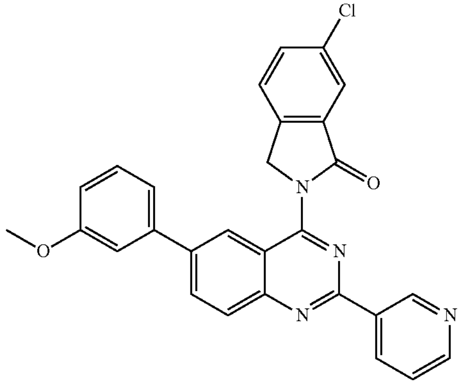 [SMILES: COc1cccc(-c2ccc3nc(-c4cccnc4)nc(N4Cc5ccc(Cl)cc5C4=O)c3c2)c1] | | $^1$H-NMR (400 MHz, DMSO-$d_6$): δ 9.74 (d, J = 8.4 Hz, 1H), 8.89 (dt, J = 8.4, 1.6 Hz, 1H), 8.78 (dd, J = 4.4,1.2 Hz, 1H), 8.46 (d, J = 1.6 Hz, 1H), 8.41. (dd, J = 8.8, 1.6 Hz, 1H), 8.20 (d, J = 8.4 Hz, 1H), 7.97 (s, 1H), 7.88 (s, 2H), 7.65-7.62 (m, 1H), 7.48-7.44 (m, 1H),7.41-7.37 (m, 2H), 7.04 (dd, J = 8.0, 1.6 Hz, 1H), 5.59 (s, 2H), 3.86 (s, 3H). | DMSO | 95 | Method BE | 479.0 (M + 1) | Method B ($NH_4HCO_3$) |

TABLE 30-continued
| Number | Product | Salt type | $^1$H NMR | $^1$H NMR Solvent | Purity percent | Method of Coupling | LCMS | LCMS Method |
|---|---|---|---|---|---|---|---|---|
| 1751 | 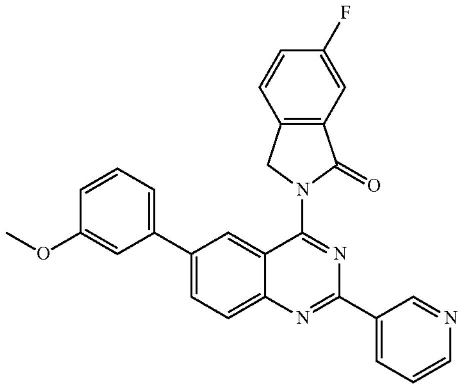 [SMILES: COc1cccc(-c2ccc3nc(-c4cccnc4)nc(N4Cc5ccc(F)cc5C4=O)c3c2)c1] | | $^1$H-NMR (400 MHz, DMSO-$d_6$): δ 9.74 (s, 1H), 8.89 (d, J = 8.4 Hz, 1H), 8.78 (d, J = 4.4 Hz, 1H), 8.46 (s, 1H), 8.41 (d, J = 9.2 Hz, 1H), 8.20 (d, J = 8.8 Hz, 1H), 7.91-7.87 (m, 1H), 7.77-7.62 (m, 3H), 7.48-7.37 (m, 3H), 7.03 (d, J = 6.4 Hz, 1H), 5.58 (s, 2H), 3.86 (s, 3H). | DMSO | 95 | Method BE | 463.1 (M + 1) | Method B ($NH_4HCO_3$) |

Scheme 91: Synthesis of N-tert-butyl-6-(2,4-difluorophenyl)-2-(pyridin-3-yl)quinazolin-4-amine methanesulfonate (lxxix-a) (Compound 1752)

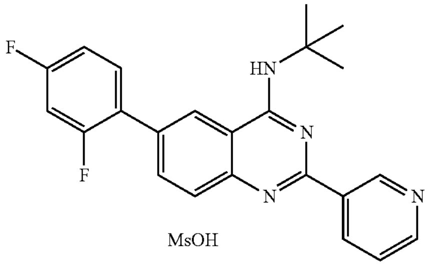

lxxix-a
(Compound 1752)

N-tert-butyl-6-(2,4-difluorophenyl)-2-(pyridin-3-yl) quinazolin-4-amine (1.51 g, 3.87 mmol) was dissolved in $CH_2Cl_2$/MeOH (20 mL/20 mL). Methanesulfonic acid (0.251 mL, 3.87 mmol) was added to the solution. The volatiles were evaporated in vacuo. The resultant residue was crystallized from EtOH (30 mL) to give 1.35 g of N-tert-butyl-6-(2,4-difluorophenyl)-2-(pyridin-3-yl)quinazolin-4-amine methanesulfonate as a light yellow powder (72%), LCMS m/z=391 (M+1) (Method D) (Retention time=1.91 min). $^1$H NMR (300 MHz, DMSO) δ 9.52 (s, 1H), 9.01-8.83 (m, 2H), 8.75 (s, 1H), 8.58 (s, 1H), 8.09 (d, J=7.2 Hz, 1H), 8.03-7.85 (m, 2H), 7.83-7.68 (m, 1H), 7.59-7.43 (m, 1H), 7.33 (t, J=7.91 Hz, 1H), 2.31 (s, 3H), 1.66 (s, 9H).

Scheme 92: Synthesis of N-tert-butyl-6-(2,4-difluorophenyl)-2-(pyridin-3-yl)quinazolin-4-amine fumarate (lxxx) (Compound 1753)

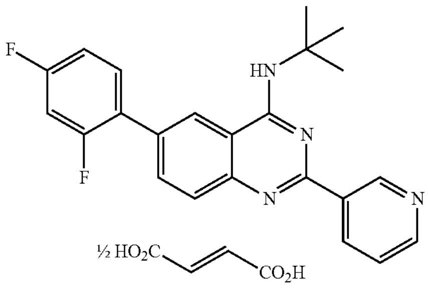

lxxx-a
(Compound 1753)

N-tert-butyl-6-(2,4-difluorophenyl)-2-(pyridin-3-yl) quinazolin-4-amine (1.22 g, 3.12 mmol) was dissolved in $CH_2Cl_2$ 1/MeOH (20 mL/20 mL). Fumaric acid (0.363 g, 3.12 mmol) was added to the solution. The mixture was sonicated until fumaric acid was dissolved. Then, the volatiles were evaporated in vacuo. The resultant solid was washed with MeOH and dried to give 1.28 g of N-tert-butyl-6-(2,4-difluorophenyl)-2-(pyridin-3-yl)quinazolin-4-amine ½ fumarate as a light yellow powder (91%). LCMS m/z=391 (M+1) (Method D) (Retention time=1.95 min). $^1$H NMR (300 MHz, DMSO) δ 13.14 (s, 1H), 9.59 (s, 1H), 8.82-8.65 (m, 2H), 8.57 (s, 1H), 7.89 (d, J=8.7 Hz, 1H), 7.82 (d, J=8.7 Hz, 1H), 7.79-7.62 (m, 2H), 7.61-7.52 (m, 1H), 7.51-7.38 (m, 1H), 7.28 (t, J=8.61 Hz, 1H), 6.61 (s, 1H), 1.64 (s, 9H).

Scheme 93: Synthesis of N-methyl-6-(3-(2-propoxyethoxy)phenyl)-2-(pyridin-3-yl)quinazolin-4-amine fumarate (lxxxi) (Compound 1754)

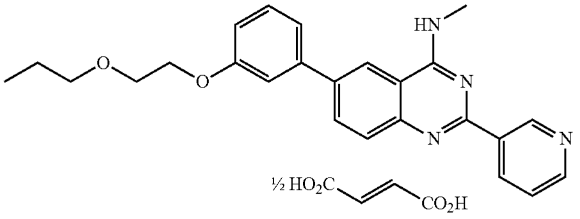

lxxxi-a
(Compound 1754)

N-methyl-6-(3-(2-propoxyethoxy)phenyl)-2-(pyridin-3-yl)quinazolin-4-amine fumarate was synthesized in a similar manner to that described N-tert-butyl-6-(2,4-difluorophenyl)-2-(pyridin-3-yl)quinazolin-4-amine fumarate. LCMS m/z=415.5 (M+1) (Method C($NH_4HCO_3$) (Retention time=2.43 min). $^1$H NMR (300 MHz, $CD_3OD$) δ 9.57 (s, 1H), 8.84 (m, 1H), 8.63 (s, 1H), 8.35 (m, 1H), 8.07 (m, 1H), 7.88 (d, J=8.7 Hz, 1H), 7.58 (m, 1H), 7.48-7.24 (m, 4H), 7.00 (m, 1H), 6.74 (s, 1H), 4.36-4.05 (m, 2H), 4.00-3.70 (m, 2H), 3.53 (t, J=6.6 Hz, 2H), 3.29-3.13 (m, 3H), 1.75-1.51 (m, 2H), 0.95 (t, J=7.4 Hz, 3H).

Scheme 94: Synthesis of N-methyl-6-(3-(2-propoxyethoxy)phenyl)-2-(pyridin-3-yl)quinazolin-4-amine methanesulfonate (lxxxii-a) (Compound 1755)

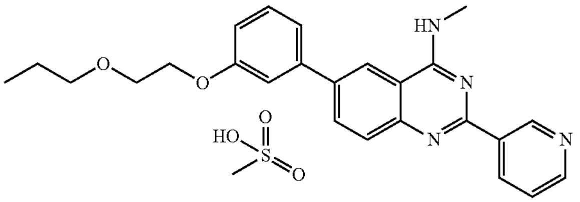

lxxxii-a
(Compound 1755)

N-methyl-6-(3-(2-propoxyethoxy)phenyl)-2-(pyridin-3-yl)quinazolin-4-amine methanesulfonate was synthesized in a similar manner to that described N-tert-butyl-6-(2,4-difluorophenyl)-2-(pyridin-3-yl)quinazolin-4-amine methanesulfonate. LCMS m/z=415.5 (M+1) (Method C($NH_4HCO_3$) (Retention time=2.43 min). $^1$H NMR (300 MHz, $CD_3OD$) δ 9.49 (s, 1H), 9.00-8.72 (m, 1H), 8.53 (s, 1H), 8.29 (m, 1H), 7.99 (d, J=8.7 Hz, 1H), 7.80 (dd, J=8.0, 5.1 Hz, 1H), 7.52-7.25 (m, 3H), 7.02 (m, 1H), 4.38-4.06 (m, 2H), 3.98-3.72 (m, 2H), 3.61-3.48 (m, 2H), 3.42 (d, J=0.6 Hz, 3H), 3.34-3.26 (m, 2H), 2.71 (s, 3H), 1.80-1.47 (m, 2H), 0.96 (t, J=7.4 Hz, 3H).

Biological Testing:

STEP46 Biochemical Assays

Serial dilutions of compounds were performed in 100% DMSO and 1 uL of compounds were dispensed into 384-well black polystyrene plates (Corning, N.Y.). Compounds were incubated with 24 uL of buffer containing 50 mM Hepes, 1 mM DTT, 0.02% Brij35, 1 ng/well purified STEP46 enzyme for 30 nm in at room temperature. The reaction was initiated by addition of 25 uL of DiFMUP (6,8-difluoro-4-methylumbelliferyl phosphate) (InVitrogen, CA) with a final concentration of 10 μM and incubated at 27° C. for 90 min. Final DMSO concentration is 2%. Plates were read with florescence intensity at excitation/emission of 360/460 nm using a PheraStar plate reader (BMG Labtech, NC).

Data Analysis

Data were expressed as percentage (%) inhibition of enzyme activity. 0% inhibition is defined as the RFUs (relative fluorescence units) in the absence of compounds and 100% inhibition is defined as RFUs in the absence of STEP46 enzyme. $IC_{50}$ values of compounds with inhibitory activity against STEP46 were determined by GraphPad Prism (version 4.03) using four parameter logistic equation. Some compounds act as activators. For compounds showing STEP46 enzymatic activation, data are represented as percentage of inhibition but with negative values at three representative concentrations (25, 50 and 100 uM).

Compounds 1-1760 show either inhibition or activation>50% at 100 uM, 50 or 25 uM.

| Number | STEP IC50 (μM) |
|---|---|
| 73 | ++ |
| 296 | ++ |
| 297 | + |
| 300 | + |
| 303 | ++ |
| 306 | + |
| 309 | ++ |
| 312 | +++ |
| 313 | +++ |
| 314 | ++ |
| 315 | ++ |
| 316 | +++ |
| 317 | ++ |
| 318 | ++ |
| 320 | ++ |
| 322 | + |
| 325 | +++ |
| 326 | ++ |
| 327 | ++ |
| 329 | +++ |
| 330 | ++ |
| 332 | +++ |
| 333 | +++ |
| 334 | ++ |
| 335 | +++ |
| 336 | +++ |
| 337 | +++ |
| 339 | ++ |
| 341 | ++ |
| 342 | ++ |
| 343 | + |
| 344 | ++ |
| 346 | ++ |
| 348 | ++ |
| 352 | ++ |
| 390 | ++ |
| 391 | ++ |
| 392 | ++ |
| 393 | ++ |
| 396 | ++ |
| 399 | +++ |
| 400 | ++ |
| 403 | ++ |
| 407 | ++ |
| 412 | +++ |
| 415 | ++ |
| 416 | +++ |
| 418 | ++ |
| 419 | +++ |
| 421 | + |
| 423 | ++ |
| 424 | ++ |
| 425 | ++ |
| 426 | + |
| 427 | ++ |
| 428 | ++ |
| 429 | +++ |
| 430 | +++ |
| 431 | +++ |
| 433 | ++ |

-continued

| Number | STEP IC50 (μM) |
|---|---|
| 434 | ++ |
| 435 | +++ |
| 436 | ++ |
| 437 | ++ |
| 439 | +++ |
| 440 | ++ |
| 441 | ++ |
| 442 | +++ |
| 443 | +++ |
| 444 | +++ |
| 445 | +++ |
| 446 | ++ |
| 447 | ++ |
| 448 | +++ |
| 449 | ++ |
| 451 | +++ |
| 452 | +++ |
| 453 | +++ |
| 454 | ++ |
| 455 | ++ |
| 456 | +++ |
| 457 | ++ |
| 458 | +++ |
| 459 | +++ |
| 460 | ++ |
| 461 | ++ |
| 463 | ++ |
| 466 | ++ |
| 467 | ++ |
| 468 | +++ |
| 470 | ++ |
| 471 | ++ |
| 472 | ++ |
| 473 | ++ |
| 474 | ++ |
| 629 | ++ |
| 630 | ++ |
| 631 | ++ |
| 632 | +++ |
| 633 | ++ |
| 634 | ++ |
| 635 | +++ |
| 636 | + |
| 637 | ++ |
| 638 | ++ |
| 639 | +++ |
| 640 | ++ |
| 641 | +++ |
| 642 | +++ |
| 643 | +++ |
| 644 | ++ |
| 645 | ++ |
| 647 | ++ |
| 648 | ++ |
| 649 | ++ |
| 650 | +++ |
| 651 | +++ |
| 652 | +++ |
| 653 | +++ |
| 655 | +++ |
| 656 | +++ |
| 657 | +++ |
| 658 | ++ |
| 660 | +++ |
| 661 | +++ |
| 662 | +++ |
| 663 | +++ |
| 664 | ++ |
| 665 | ++ |
| 666 | +++ |
| 667 | +++ |
| 668 | +++ |
| 669 | +++ |
| 670 | +++ |
| 671 | ++ |
| 672 | ++ |

-continued

| Number | STEP IC50 (μM) |
|---|---|
| 673 | ++ |
| 674 | ++ |
| 675 | +++ |
| 676 | +++ |
| 677 | + |
| 678 | ++ |
| 679 | +++ |
| 680 | ++ |
| 681 | ++ |
| 682 | ++ |
| 683 | ++ |
| 684 | ++ |
| 685 | +++ |
| 686 | +++ |
| 687 | +++ |
| 688 | +++ |
| 689 | +++ |
| 690 | ++ |
| 691 | +++ |
| 692 | +++ |
| 693 | +++ |
| 694 | +++ |
| 695 | +++ |
| 696 | +++ |
| 697 | ++ |
| 698 | +++ |
| 699 | +++ |
| 700 | +++ |
| 701 | ++ |
| 702 | +++ |
| 703 | +++ |
| 704 | +++ |
| 705 | +++ |
| 706 | +++ |
| 707 | +++ |
| 708 | ++ |
| 709 | +++ |
| 846 | ++ |
| 847 | +++ |
| 884 | + |
| 888 | + |
| 889 | ++ |
| 896 | + |
| 899 | ++ |
| 900 | ++ |
| 901 | ++ |
| 923 | ++ |
| 932 | ++ |
| 933 | ++ |
| 934 | +++ |
| 962 | +++ |
| 1124 | +++ |
| 1125 | ++ |
| 1126 | ++ |
| 1140 | +++ |
| 1141 | +++ |
| 1142 | ++ |
| 1143 | ++ |
| 1144 | ++ |
| 1145 | ++ |
| 1146 | ++ |
| 1148 | ++ |
| 1150 | + |
| 1151 | ++ |
| 1152 | ++ |
| 1153 | ++ |
| 1155 | ++ |
| 1157 | ++ |
| 1158 | ++ |
| 1159 | ++ |
| 1160 | ++ |
| 1161 | ++ |
| 1165 | +++ |
| 1167 | ++ |
| 1168 | ++ |
| 1171 | ++ |
| 1172 | ++ |
| 1173 | + |
| 1176 | ++ |
| 1178 | ++ |
| 1180 | ++ |
| 1181 | ++ |
| 1182 | ++ |
| 1183 | ++ |
| 1184 | ++ |
| 1185 | ++ |
| 1186 | ++ |
| 1187 | +++ |
| 1188 | ++ |
| 1191 | ++ |
| 1192 | ++ |
| 1193 | ++ |
| 1194 | +++ |
| 1198 | ++ |
| 1200 | ++ |
| 1201 | ++ |
| 1202 | ++ |
| 1203 | ++ |
| 1204 | + |
| 1205 | ++ |
| 1206 | ++ |
| 1208 | + |
| 1211 | + |
| 1212 | ++ |
| 1213 | ++ |
| 1214 | ++ |
| 1215 | +++ |
| 1216 | +++ |
| 1217 | ++ |
| 1218 | ++ |
| 1219 | ++ |
| 1220 | + |
| 1221 | + |
| 1222 | ++ |
| 1223 | +++ |
| 1225 | ++ |
| 1226 | ++ |
| 1227 | ++ |
| 1228 | ++ |
| 1229 | ++ |
| 1230 | ++ |
| 1234 | ++ |
| 1237 | ++ |
| 1238 | ++ |
| 1239 | ++ |
| 1248 | ++ |
| 1279 | ++ |
| 1280 | ++ |
| 1281 | +++ |
| 1282 | ++ |
| 1283 | + |
| 1284 | ++ |
| 1285 | + |
| 1286 | ++ |
| 1324 | ++ |
| 1327 | + |
| 1328 | + |
| 1330 | + |
| 1332 | ++ |
| 1333 | + |
| 1334 | + |
| 1335 | ++ |
| 1336 | ++ |
| 1337 | ++ |
| 1339 | ++ |
| 1340 | ++ |
| 1341 | ++ |
| 1346 | ++ |
| 1348 | + |
| 1350 | ++ |
| 1351 | ++ |
| 1352 | + |

-continued

| Number | STEP IC50 (μM) |
|---|---|
| 1353 | ++ |
| 1354 | ++ |
| 1356 | ++ |
| 1357 | ++ |
| 1358 | ++ |
| 1359 | ++ |
| 1360 | ++ |
| 1361 | + |
| 1362 | ++ |
| 1363 | ++ |
| 1364 | ++ |
| 1365 | ++ |
| 1366 | ++ |
| 1369 | ++ |
| 1370 | ++ |
| 1371 | ++ |
| 1372 | ++ |
| 1373 | ++ |
| 1374 | ++ |
| 1375 | ++ |
| 1376 | ++ |
| 1380 | ++ |
| 1381 | ++ |
| 1382 | +++ |
| 1391 | + |
| 1395 | ++ |
| 1396 | ++ |
| 1400 | ++ |
| 1401 | ++ |
| 1402 | ++ |
| 1403 | + |
| 1404 | + |
| 1406 | ++ |
| 1407 | ++ |
| 1408 | ++ |
| 1409 | ++ |
| 1410 | ++ |
| 1411 | + |
| 1412 | ++ |
| 1413 | ++ |
| 1414 | ++ |
| 1415 | + |
| 1416 | ++ |
| 1419 | ++ |
| 1420 | ++ |
| 1422 | ++ |
| 1423 | + |
| 1424 | + |
| 1425 | ++ |
| 1430 | ++ |
| 1437 | ++ |
| 1445 | ++ |
| 1446 | ++ |
| 1447 | + |
| 1448 | ++ |
| 1449 | + |
| 1450 | ++ |
| 1451 | ++ |
| 1452 | +++ |
| 1453 | ++ |
| 1454 | + |
| 1455 | ++ |
| 1456 | ++ |
| 1458 | + |
| 1467 | ++ |
| 1497 | ++ |
| 1516 | + |
| 1601 | ++ |
| 1611 | ++ |
| 1680 | ++ |

Key
+ $IC_{50}$ > 10 uM
++ $IC_{50}$ 1-10 uM
+++ $IC_{50}$ < 1 uM

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A compound of formula (I):

(I)

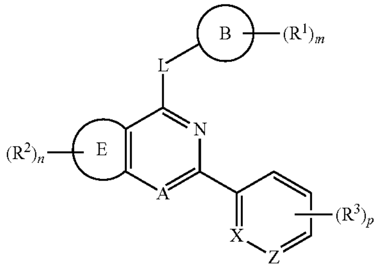

or a salt thereof, wherein:

A is CH or N;

B is phenyl, dihydroindenyl, dihydrobenzoxazinyl, dihydrobenzodioxinyl, chromenyl, tetrahydroisoquinolyl, tetrahydroquinolinyl, dihydroquinolyl, quinolyl, tetrahydroquinazolinyl, indolinyl, dihydrobenzothiazolyl, dihydrobenzimidazolyl, dihydrobenzoxazolyl, isoindolinyl, benzofuryl, benzothienyl, benzodioxolyl, indolyl, indazolyl, benzoimidazolyl, benzotriazolyl, benzisoxazolyl, benzoxazolyl, benzothiazolyl, benzoxadiazolyl, tetrahydrobenzothienyl, thienyl, thiazolyl, imidazolyl, pyrazolyl, thiadiazolyl or pyridyl;

m is 0, 1, 2, 3, or 4;

E is phenyl, thienyl, or pyrrolyl;

when E is phenyl, n is 1 or 2; and when E is thienyl or pyrrolyl, n is 0 or 1;

L is $NR^5$;

one of X and Z is N and the other is CH;

p is 0, 1, or 2;

each $R^1$ is independently $C_1$-$C_8$ alkyl, halo, haloalkyl, haloalkoxy, alkoxyalkyl, —CN, oxo, —$NO_2$, —C(Y)$NR^bR^{b'}$, —$NR^cC(Y)R^{c'}$, —$SO_2NR^bR^{b'}$, —$OR^d$, or —$S(O)_qR^f$;

each $R^2$ is independently $C_1$-$C_8$ alkyl, $C_3$-$C_8$ cycloalkyl, thiomorpholinylalkyl, pyrrolidinylalkyl, morpholinylalkyl, haloalkyl, haloalkoxy, aminoalkyl, alkylaminoalkyl, dialkylaminoalkyl, hydroxyalkyl, alkoxyalkyl, silyloxyalkyl, —CN, —$NO_2$, —C(O)$OR^a$, —C(Y)$NR^bR^{b'}$, —$NR^bR^{b'}$, —$OR^d$, —C(Y)$R^e$ or —$S(O)_qR^f$;

each $R^3$ is independently $C_1$-$C_8$ alkyl, halo, haloalkyl, —$NR^bR^{b'}$ or —$OR^d$;

$R^5$ is hydrogen; or when m is not 0, $R^5$ and one $R^1$ may be taken together with the atoms to which they are attached to form an optionally substituted heteroaryl or heterocyclyl ring;

Y is O or S;

q is 1 or 2; and each $R^a$, $R^b$, $R^{b'}$, $R^c$, $R^{c'}$, $R^d$, $R^e$, and $R^f$ is independently hydrogen, $C_1$-$C_8$ alkyl, $C_2$-$C_8$ alkenyl, $C_2$-$C_8$ alkynyl, $C_3$-$C_8$ cycloalkyl, phenyl, dihydroindenyl, morpholinyl, tetrahydropyranyl, piperidyl, pyrrolidinyl, thiomorpholinyl, phenylalkyl, thienylalkyl, pyridylalkyl, tetrahydropyranylalkyl, dihydroindenylalkyl, tetrahydrofurylalkyl, hydroxyalkyl, morpholinylalkyl, pyrrolidinylalkyl, dialkylaminoalkyl, piperidylalkyl, benzodioxolilalkyl, dihydrobenzodioxinylalkyl, $C_3$-$C_8$ cycloalkylalkyl, haloalkyl or alkoxyalkyl.

2. The compound according to claim 1 or a salt thereof, wherein:

A is N;

B is phenyl or pyridyl;

m is 1, 2 or 3;

E is phenyl;

n is 1 or 2;

p is 0 or 1; and $R^5$ is hydrogen.

3. The compound according to claim 2 or a salt thereof, wherein:

m is 1 or 2;

p is 0;

$R^1$ is $C_1$-$C_8$ alkyl, halo, haloalkyl, haloalkoxy, —CN, —$NO_2$, —C(Y)$NR^bR^{b'}$, —$NR^cC(Y)R^{c'}$, —$SO_2NR^bR^{b'}$, —$OR^d$, or —$S(O)_qR^f$; and $R^2$ is —$OR^d$.

4. The compound according to claim 3 or a salt thereof, wherein:

$R^2$ is —$OR^d$, in which $R^d$ is $C_1$-$C_8$ alkyl; and each $R^b$, $R^{b'}$, $R^c$, $R^{c'}$, $R^d$ and $R^f$ is independently hydrogen, $C_1$-$C_8$ alkyl, $C_2$-$C_8$ alkenyl, $C_2$-$C_8$ alkynyl, $C_3$-$C_8$ cycloalkyl, phenyl, dihydroindenyl, tetrahydropyranyl, phenylalkyl, thienylalkyl, tetrahydropyranylalkyl, dihydroindenylalkyl, or haloalkyl.

5. The compound according to claim 4 or a salt thereof, wherein:

$R^1$ is $C_1$-$C_8$ alkyl, halo, haloalkyl, haloalkoxy, —C(Y)$NR^bR^{b'}$ or —$OR^d$; and each $R^b$, $R^{b'}$, $R^d$ and $R^f$ is independently hydrogen, $C_1$-$C_8$ alkyl, $C_3$-$C_8$ cycloalkyl or haloalkyl.

6. The compound according to claim 1 or a salt thereof, wherein the compound of formula (I) is a compound selected from the group consisting of:

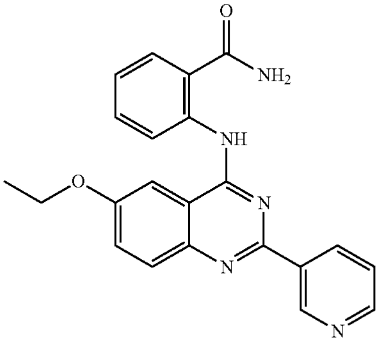
,

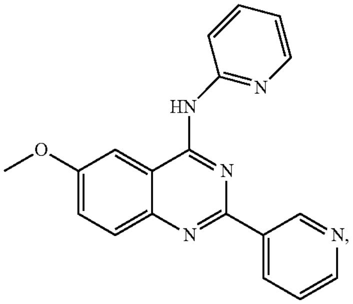
,

-continued

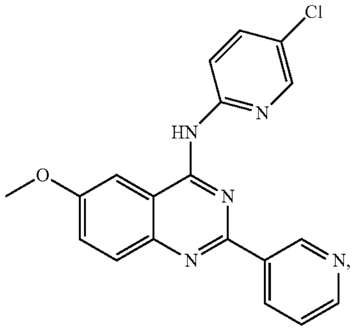
,

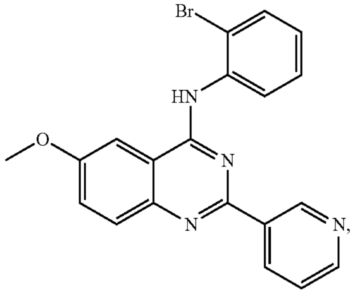
,

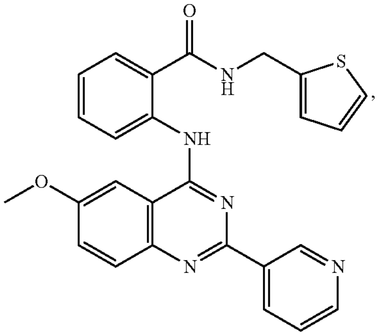
,

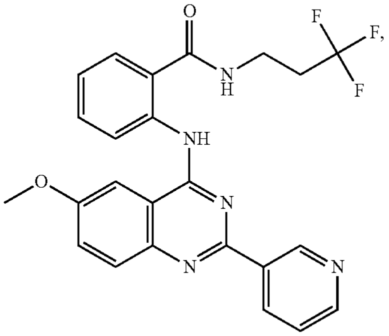
,

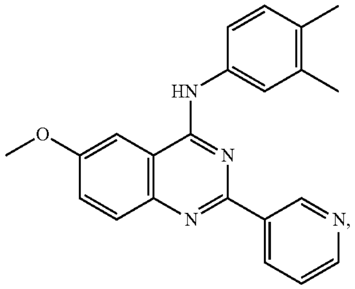
,

-continued
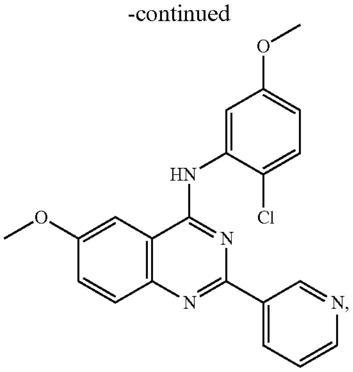
and
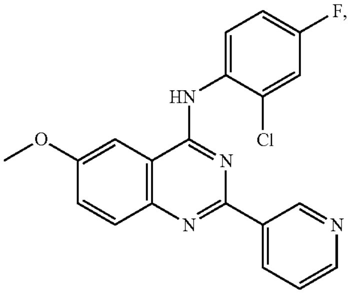
-continued
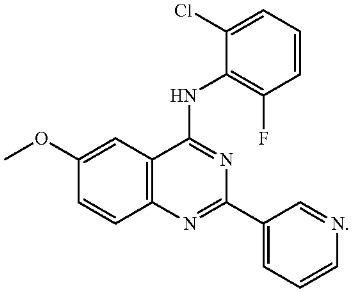
7. A pharmaceutical composition comprising the compound according to any one of claim 1 or claims 1-6 or a salt thereof as an active ingredient and a pharmaceutically acceptable carrier.
* * * * *